US012582726B1

(12) United States Patent
Wodziak et al.

(10) Patent No.: US 12,582,726 B1
(45) Date of Patent: Mar. 24, 2026

(54) SYNTHETIC CANCER-SPECIFIC PROMOTERS

(71) Applicant: EARLI Inc., Redwood City, CA (US)

(72) Inventors: Dariusz Wodziak, Redwood City, CA (US); Shireen Rudina, Redwood City, CA (US); Maggie C. Louie, Redwood City, CA (US); Yue Zhang, Redwood City, CA (US); Elizabeth Stroebele, Redwood City, CA (US); Albert Park, Redwood City, CA (US); David Suhy, Redwood City, CA (US); Paul Escarpe, San Ramon, CA (US); Cyriac Roeding, Portola Valley, CA (US); Justin Lin, Simi Valley, CA (US); Alex Harwig, South San Francisco, CA (US); Leland Harrison Hartwell, Seattle, WA (US)

(73) Assignee: EARLI Inc., Redwood City, CA (US)

( * ) Notice: Subject to any disclaimer, the term of this patent is extended or adjusted under 35 U.S.C. 154(b) by 0 days.

(21) Appl. No.: 19/218,156

(22) Filed: May 23, 2025

Related U.S. Application Data

(63) Continuation-in-part of application No. 18/455,209, filed on Aug. 24, 2023, which is a continuation of application No. 17/219,666, filed on Mar. 31, 2021, now Pat. No. 12,060,613, which is a continuation-in-part of application No. PCT/US2020/026758, filed on Apr. 4, 2020.

(60) Provisional application No. 63/834,389, filed on Jan. 22, 2025, provisional application No. 62/955,925, filed on Dec. 31, 2019, provisional application No. 62/830,279, filed on Apr. 5, 2019.

(51) Int. Cl.
| | |
|---|---|
| *A61K 48/00* | (2006.01) |
| *C12N 15/67* | (2006.01) |
| *C12N 15/85* | (2006.01) |

(52) U.S. Cl.
CPC .......... *A61K 48/0058* (2013.01); *C12N 15/67* (2013.01); *C12N 15/85* (2013.01); *C12N 2830/008* (2013.01)

(58) Field of Classification Search
None
See application file for complete search history.

(56) References Cited

U.S. PATENT DOCUMENTS

| | | | |
|---|---|---|---|
| 5,210,015 | A | 5/1993 | Gelfand et al. |
| 5,480,792 | A | 1/1996 | Buechler et al. |
| 5,525,524 | A | 6/1996 | Buechler et al. |
| 5,538,848 | A | 7/1996 | Livak et al. |
| 5,679,526 | A | 10/1997 | Buechler et al. |
| 5,824,799 | A | 10/1998 | Buechler et al. |
| 5,851,776 | A | 12/1998 | Valkirs |
| 5,863,736 | A | 1/1999 | Haaland |
| 5,874,304 | A | 2/1999 | Zolotukhin et al. |
| 5,885,527 | A | 3/1999 | Buechler |
| 5,922,615 | A | 7/1999 | Nowakowski et al. |
| 5,939,272 | A | 8/1999 | Buechler et al. |
| 5,947,124 | A | 9/1999 | Buechler et al. |
| 5,968,750 | A | 10/1999 | Zolotukhin et al. |
| 5,985,579 | A | 11/1999 | Buechler et al. |
| 6,019,944 | A | 2/2000 | Buechler |
| 6,020,192 | A | 2/2000 | Muzyczka et al. |
| 6,113,855 | A | 9/2000 | Buechler |
| 6,143,576 | A | 11/2000 | Buechler |
| 6,737,523 | B1 | 5/2004 | Fisher et al. |
| 6,977,174 | B2 | 12/2005 | Crouzet et al. |
| 7,268,229 | B2 | 9/2007 | Wood et al. |
| 7,897,380 | B2 | 3/2011 | Kay et al. |
| 9,534,248 | B2 | 1/2017 | Gambhir et al. |
| 9,737,620 | B2 | 8/2017 | Williams |
| 11,060,087 | B2 | 7/2021 | Brunicardi et al. |
| 12,060,613 | B2 | 8/2024 | Suhy et al. |
| 2004/0167381 | A1 | 8/2004 | Lichter et al. |
| 2004/0214329 | A1 | 10/2004 | Kay et al. |
| 2005/0059044 | A1 | 3/2005 | Graham et al. |
| 2009/0311664 | A1 | 12/2009 | Fong et al. |
| 2010/0076062 | A1 | 3/2010 | Thompson et al. |
| 2010/0158931 | A1 | 6/2010 | Weinschenk et al. |
| 2011/0104125 | A1 | 5/2011 | Yu |
| 2011/0117608 | A1 | 5/2011 | Graham et al. |
| 2012/0053080 | A1 | 3/2012 | Cui et al. |
| 2012/0058562 | A1 | 3/2012 | Thomson et al. |
| 2013/0171726 | A1 | 7/2013 | Roelvink et al. |
| 2013/0323301 | A1 | 12/2013 | Gruber et al. |
| 2014/0127326 | A1 | 5/2014 | Sood et al. |
| 2014/0140959 | A1 | 5/2014 | Szalay et al. |

(Continued)

FOREIGN PATENT DOCUMENTS

| | | |
|---|---|---|
| CN | 102191245 A | 9/2011 |
| CN | 103038343 A | 4/2013 |

(Continued)

OTHER PUBLICATIONS

Cejas et al., "Chromatin immunoprecipitation from fixed clinical tissues reveals tumor-specific enhancer profiles" 22(6) Nature Medicine 685-691, Online Methods (Year: 2016).*
Williams et al., "CpG-island fragments from the HNRPA2B1/CBX3 genomic locus reduce silencing and enhance transgene expression from the hCMV promoter/enhancer in mammalian cells" 5 BMC Biotechnology 17, 1-9 (Year: 2005).*
U.S. Appl. No. 14/480,861 Notice of Allowance dated Sep. 1, 2016.
U.S. Appl. No. 17/219,666 Notice of Allowance dated Apr. 30, 2024.
U.S. Appl. No. 17/219,666 Notice of Allowance dated Mar. 5, 2024.
U.S. Appl. No. 18/452,504 Notice of Allowance dated Jun. 25, 2025.

(Continued)

*Primary Examiner* — Nancy J Leith
(74) *Attorney, Agent, or Firm* — Wilson Sonsini Goodrich & Rosati

(57) ABSTRACT

Described herein are synthetic promoters and/or enhancers that are specific for cancer cells and methods of engineering synthetic cancer-specific promoters.

47 Claims, 93 Drawing Sheets

Specification includes a Sequence Listing.

(56) References Cited

U.S. PATENT DOCUMENTS

| | | | |
|---|---|---|---|
| 2015/0071859 | A1 | 3/2015 | Gambhir et al. |
| 2015/0275221 | A1 | 10/2015 | Williams |
| 2016/0051704 | A1 | 2/2016 | Morse et al. |
| 2016/0145582 | A1 | 5/2016 | Yu |
| 2016/0215296 | A1 | 7/2016 | Williams |
| 2016/0331845 | A1 | 11/2016 | Mao et al. |
| 2017/0211066 | A1 | 7/2017 | Croce et al. |
| 2017/0356903 | A1 | 12/2017 | Domenyuk et al. |
| 2018/0009864 | A1 | 1/2018 | Brunicardi et al. |
| 2018/0080013 | A1 | 3/2018 | Loew et al. |
| 2018/0171337 | A1 | 6/2018 | O'Neill et al. |
| 2018/0222961 | A1 | 8/2018 | Schuster et al. |
| 2018/0303952 | A1 | 10/2018 | Sagert et al. |
| 2019/0010190 | A1 | 1/2019 | Weinschenk et al. |
| 2019/0032083 | A1 | 1/2019 | Kotin et al. |
| 2019/0211089 | A1 | 7/2019 | Daugherty et al. |
| 2019/0309323 | A1 | 10/2019 | Aguillon Gutierrez et al. |
| 2021/0011006 | A1 | 1/2021 | Aalipour et al. |
| 2021/0277474 | A1 | 9/2021 | Suhy et al. |
| 2022/0275451 | A1 | 9/2022 | Suhy et al. |
| 2023/0321238 | A1 | 10/2023 | Hu et al. |
| 2025/0060367 | A1 | 2/2025 | Suhy et al. |
| 2025/0064973 | A1 | 2/2025 | Suhy et al. |
| 2025/0144249 | A1 | 5/2025 | Harwig et al. |
| 2025/0161496 | A1 | 5/2025 | Wodziak et al. |

FOREIGN PATENT DOCUMENTS

| | | | | |
|---|---|---|---|---|
| WO | WO-2012058522 | A2 | 5/2012 | |
| WO | WO-2014017941 | A1 | 1/2014 | |
| WO | WO-2014035457 | A1 | 3/2014 | |
| WO | WO-2014172452 | A1 | 10/2014 | |
| WO | WO-2014172542 | A1 | 10/2014 | |
| WO | WO 2015/143029 | A1 * | 9/2015 | ............. C12N 15/86 |
| WO | WO-2018112365 | A2 | 6/2018 | |
| WO | WO-2018187688 | A1 | 10/2018 | |
| WO | WO-2019168948 | A1 | 9/2019 | |
| WO | WO-2020206385 | A1 | 10/2020 | |
| WO | WO-2022212547 | A1 | 10/2022 | |
| WO | WO-2023215416 | A1 | 11/2023 | |
| WO | WO-2025019712 | A1 | 1/2025 | |
| WO | WO-2025049606 | A1 | 3/2025 | |

OTHER PUBLICATIONS

Williams et al. Improving cell and gene therapy safety and performance using next-generation Nanoplasmid vectors. Molecular Therapy: Nucleic Acids 35: 494-503 (2023).

Abe, Miyako, and Donald Kufe. Characterization of cis-acting elements regulating transcription of the human DF3 breast carcinoma-associated antigen (MUCI) gene 90:282-286 (1993).

Adams, Jason Y. et al. Visualization of Advanced Human Prostate Cancer Lesions in Living Mice by a Targeted Gene Transfer Vector and Optical Imaging. Nature Medicine 8(8):891-897 (2002).

Ahn, B-C et al. Potent, tumor-specific gene expression in an orthotopic hepatoma rat model using a Survivin-targeted, amplifiable adenoviral vector. Gene Ther. 18(6): 606-612 (2011).

Akamatsu et al. Common variants at 11q12, 10q26 and 3p11.2 are associated with prostate cancer susceptibility in Japanese. Nature Genetics 44(4):426-430 (2012).

Almond, B. et al. GenBank Accession No. AY738224. Version No. AY738224.1. Firefly luciferase reporter vector pGL4.12[luc2CP], complete sequence: pp. 1-3. Record created Nov. 8, 2004. Retrieved Dec. 30, 2024. Retrieved from: https://www.ncbi.nlm.nih.gov/nuccore/AY738224.1?report=genbank&log$=seqview.

Ansel, Howard C. et al. Pharmaceutical Dosage Forms and Drug Delivery System, Seventh Edition. Lippincott Wiliams (1999).

Aoyama, Akira et al. Expression of αB-crystallin in human brain tumors. International journal of cancer 55(5):760-764 (1993).

Ausubel, Frederick et al. Short protocols in molecular biology, 3rd edition. Wiley & Sons (1995).

Bachtarzi, Houria et al. Cancer gene therapy with targeted adenoviruses. Expert opinion on drug delivery 5(11):1231-1240 (2008).

Baczynska, Dagmara et al. The tumorigenic potential of human CX-1 colon adenocarcinoma cells depends on carcinoembryonic antigen (CEACAM5) expression. Cellular and Molecular Biology Letters 8(2):471-486 (2003).

Bahce, I. et al., Pilot study of (89)Zr-bevacizumab positron emission tomography in patients with advanced non-small cell lung cancer. EJNMMI Res. 4(1):35 (2014).

Ballester, et al. Idiopathic Pulmonary Fibrosis and Lung Cancer: Mechanisms and Molecular Targets. International Journal of Molecular Sciences 20(3):593, 1-28 (2019).

Bao, Rudi et al. Activation of Cancer-specific Gene Expression by the Survivin Promoter. Journal of the National Cancer Institute 94)7):522-528 (2002).

Basset, Paul. et al. A novel metalloproteinase gene specifically expressed in stromal cells of breast carcinomas. Nature 348(6303):699-704 (1990).

Berger, Joel et al. Secreted Placental Alkaline Phosphatase: a Powerful New Quantitative Indicator of Gene Expression in Eukaryotic Cells. Gene vol. 66,1: 1-10 (1988).

Bhang, Hyo-eun C. et al. Tumor-Specific Imaging Through Progression Elevated Gene-3 Promoter-Driven Gene Expression. Nature Medicine 17(1):123-129 (2011).

Bode, Jürgen et al. Architecture and utilization of highly expressed genomic sites. New comprehensive biochemistry 38:551-572 (2003).

Bois-Joyeux B. et al. Members of the CAAT/enhancer-binding protein, hepatocyte nuclear factor-1 and nuclear factor-1 families can differentially modulate the activities of the rat alpha- fetoprotein promoter and enhancer. Biochemical Journal 301(1):49-55 (1994).

Bombardieri, E. et al. Somatostatin receptor imaging of small cell lung cancer (SCLC) by means of 111In-DTPA octreotide scintigraphy. European Journal of Cancer 31(2):184-188 (1995).

Bonnet, Marie-Elise et al. Systemic Delivery of DNA or siRNA Mediated by Linear Polyethylenimine (L-PEI) does not Induce an Inflammatory Response. Pharmaceutical Research vol. 25,12: 2972-2982 (2008).

Branchini, et al. Red-emitting luciferases for bioluminescence reporter and imaging applications. Anal Biochem. 396(2):290-7 (2010).

Bronstein, I. et al. Chemiluminescent reporter gene assays: sensitive detection of the GUS and SEAP gene products. BioTechniques 17(1):172-4, 176-7 (1994).

Brown, Patricia A. et al. Delivery of DNA into skeletal muscle in large animals. Electroporation Protocols: Preclinical and Clinical Gene Medicine 423:215-224 (2008).

Browne, Andrew W et al. Cancer Screening by Systemic Administration of a Gene Delivery Vector Encoding Tumor-selective Secretable Biomarker Expression. PLoS One vol. 6,5:e19530, 1-9 (2011).

Buddingh, Bastiaan C, and Jan C M van Hest. Artificial Cells: Synthetic Compartments with Life-like Functionality and Adaptivity. Accounts of chemical research 50(4):769-777 (2017).

Caplen, Natasha J. et al. Liposome-mediated CFTR gene transfer to the nasal epithelium of patients with cystic fibrosis. Nature Medicine 1(1):39-46 (1995).

Cawood, Ryan et al. Use of tissue-specific microRNA to control pathology of wild-type adenovirus without attenuation of its ability to kill cancer cells. PLoS pathogens 5(5):e1000440, 1-10 (2009).

Chaudhuri, Tandra R et al. Blood-Based Screening and Light Based Imaging for the Early Detection and Monitoring of Ovarian Cancer Xenografts. Technology in Cancer Research & Treatment vol. 2,2: 171-180 (2003).

Chen, Chao et al. Promoter-Operating Targeted Expression of Gene Therapy in Cancer: Current Stage and Prospect. Molecular Therapy Nucleic Acids 11:508-514 (2018).

Chen, Jin-Shing et al. Cancer-Specific Activation of the Survivin Promoter and Its Potential Use in Gene Therapy. Cancer Gene Therapy vol. 11,11: 740-747 (2004).

Chen, Yu et al. Use of the XRCC2 Promoter for in Vivo Cancer Diagnosis and Therapy. Cell Death and Disease vol. 9(4):420, 1-12 (2018).

(56)                    References Cited

OTHER PUBLICATIONS

Chen, Z Y et al. Silencing of Episomal Transgene Expression by Plasmid Bacterial DNA Elements in Vivo. Gene Therapy vol. 11,10: 856-864 (2004).

Chen, Zhi-Ying et al. Minicircle DNA Vectors Devoid of Bacterial DNA result in Persistent and High-Level Transgene Expression in Vivo. Molecular Therapy 8(3):495-500 (2003).

Chisholm, Edward J. et al. Cancer-specific transgene expression mediated by systemic injection of nanoparticles. Cancer research 69(6):2655-2662 (2009).

Crystal, Ronald G. The gene as the drug. Nature Medicine 1(1):15-17 (1995).

Curtin et al., Short Communication: Bidirectional promoter interference between two widely used internal heterologous promoters. Gene Therapy, 15:84-390 (2008).

Darquet, A M et al. A New DNA Vehicle for Nonviral Gene Delivery: Supercoiled Minicircle. Gene Therapy vol. 4, 12: 1341-1349 (1997).

Darquet, A M et al. Minicircle: an Improved DNA Molecule for in Vitro and in Vivo Gene Transfer. Gene Therapy 6(2):209-218 (1999).

Daughtry, et al. Tailoring encodable lanthanide-binding tags as MRI contrast agents. Chembiochem. 13(17):2567-74 (2012).

Dent et al., Exhaled breath analysis for lung cancer. J Thorac Dis. 5(Suppl 5):S540-S550 (Oct. 2013).

Diamandis, Eleftherios P. Cancer biomarkers: can we turn recent failures into success ?. Journal of the National Cancer Institute 102(19):1462-1467 (2010).

Dragulescu-Andrasi, Anca et al. Bioluminescence resonance energy transfer (BRET) imaging of protein-protein interactions within deep tissues of living subjects. Proceedings of the National Academy of Sciences 108(29):12060-12065 (2011).

Eisenberg, D. et al., Analysis of Membrane and Surface Protein Sequences with the Hydrophobic Moment Plot. Journal of Molecular Biology 179:25-142 (1984).

EP20785373.0 European Partial Exam Report dated Dec. 20, 2022.

EP20785373.0 Extended European Search Report dated Apr. 26, 2023.

EP20785373.0 Extended European Search Report dated Apr. 4, 2023.

EP20785373.0 Partial Supplementary European Search Report dated Dec. 20, 2022.

EP22782118.8 Supplementary European Search Report dated Apr. 22, 2025.

European Patent Application No. 20785373.0 Communication pursuant to Article 94(3) EPC dated Mar. 28, 2024.

Fernandez-Retana, J. et al., Gene signature based on degradome-related genes can predict distal metastasis in cervical cancer patients. Tumour Biol. 39(6):1010428317711895 (2017).

Forss-Petter, Sonja et al. Transgenic mice expressing β-galactosidase in mature neurons under neuron-specific enolase promoter control. Neuron 5(2):187-197 (1990).

Franch, Thomas, and Kenn Gerdes. U-turns and Regulatory RNAs. Current Opinion in Microbiology 3(2):159-164 (2000).

Fukazawa, Takuya et al. Development of a Cancer-Targeted Tissue-Specific Promoter System. Cancer Research 64(1):363-369 (2004).

Gao, Xiang, and Leaf Huang. A novel cationic liposome reagent for efficient transfection of mammalian cells. Biochemical and Biophysical Research Communications 179(1):280-285 (1991).

GARVER Jr, R. I. et al. Strategy for achieving selective killing of carcinomas. Gene therapy 1(1):46-50 (1994).

Gazit, Gadi et al. Use of the stress-inducible grp78/BiP promoter in targeting high level gene expression in fibrosarcoma in vivo. Cancer research 55(8):1660-1663 (1995).

GenBank Accession No. NG_029069. Version No. NG_029069.1. *Homo sapiens* baculoviral IAP repeat containing 5 (BIRC5), RefSeqGene on chromosome 17: pp. 1-7. Record created Jun. 8, 2011. Retrieved May 9, 2025. Retrieved from: https://www.ncbi.nlm.nih.gov/nuccore/NG_029069.1.

Gervais, François G. et al. Involvement of caspases in proteolytic cleavage of Alzheimer's amyloid-β precursor protein and amyloidogenic AB peptide formation. Cell 97(3):395-406 (1999).

Giang, Irene et al. Prodrug applications for targeted cancer therapy. The AAPS journal 16:899-913 (2014).

Gibson, Ursula E. et al. A novel method for real time quantitative RT-PCR. Genome research 6(10):995-1001 (1996).

Goryawala, Mohammed et al. Abstract # 4151 Development of a Cancer-Activated Biologic Imaging Platform for Early Lung Cancer Diagnosis. Poster EARLI Inc. (Mar. 22, 2024).

Griffiths, et al., Reagents and Methods for PET Using Bispecific Antibody Pretargeting and 68Ga-Radiolabeled Bivalent Hapten-Peptide-Chelate Conjugates. The Journal of Nuclear Medicine 45(1):30-39 (2004).

Guidance for Industry Estimating the Maximum Safe Starting Dose in Initial Clinical Trials for Therapeutics in Adult Healthy Volunteers. U.S. Department of Health and Human Services Food and Drug Administration Center for Drug Evaluation and Research (CDER). Jul. 2005.

Harrington et al., New Therapies, Cancer Gene Therapy: Part 1. Vector Development and Regulation of Gene Expression. Clinical Oncology 14: 3-16 (2002).

Harrington, Kevin J et al. Cancer Gene Therapy: Part 2. Candidate Transgenes and their Clinical Development. Clinical Oncology vol. 14,2: 148-169 (2002).

Haun, Jered B. et al. Micro-NMR for rapid molecular analysis of human tumor samples. Science translational medicine 3(71):71ra16, 1-13 (2011).

Heid, Christian A. et al. Real time quantitative PCR. Genome research 6(10):986-994 (1996).

Holland, Pamela M. et al. Detection of specific polymerase chain reaction product by utilizing the 5'—3'exonuclease activity of Thermus aquaticus DNA polymerase. Proceedings of the National Academy of Sciences 88(16):7276-7280 (1991).

Hori, Sharon S. and Sanjiv S. Gambhir. Mathematical model identifies blood biomarker-based early cancer detection strategies and limitations. Science translational medicine 3(109):109ra116, 1-9 (2011).

Hrstka, Roman et al. The pro-metastatic protein anterior gradient-2 predicts poor prognosis in tamoxifen-treated breast cancers. Oncogene 29(34):4838-4847 (2010).

Huber et al. Retroviral-Mediated Gene Therapy for the Treatment of Hepatocellular Carcinoma: An Innovative Approach for Cancer Therapy. PNAS USA 88:8039-8043 (1991).

Hum, N.R. et al. Comparative molecular analysis of cancer behavior cultured in vitro, in vivo, and ex vivo. Cancers. 12(3):690 (2020).

Huston, James S. et al. Protein Engineering of Antibody Binding Sites: Recovery of Specific Activity in an Anti-digoxin Single-chain Fv Analogue Produced in *Escherichia Coli*. PNAS USA 85(16):5879-5883 (1988).

Huyn, Steven T. et al. A potent, imaging adenoviral vector driven by the cancer-selective mucin-1 promoter that targets breast cancer metastasis. Clinical Cancer Research 15(9):3126-3134 (2009).

Ikhuoria, Ebosetale Blessing, and Christian Bach. Introduction to Breast Carcinogenesis Symptoms, Risks Factors, Treatment and Management. European Journal of Engineering and Technology Research 3(7):58-66 (2018).

Inouye, Satoshi, and Osamu Shimomura. The Use of Renil-laLuciferase, OplophorusLuciferase, and Apoaequorin as Bioluminescent Reporter Protein in the Presence of Coelenterazine Analogues as Substrate. Biochemical and biophysical research communications 233(2):349-353 (1997).

Ito, Takeshi et al. Survivin promotes cell proliferation in human hepatocellular carcinoma. Hepatology 31(5):1080-1085 (2000).

Iyer, M et al. Non-invasive Imaging of a Transgenic Mouse Model Using a Prostate-specific Two-step Transcriptional Amplification Strategy. Transgenic Research vol. 14,1: 47-55 (2005).

Iyer, Meera et al. Bioluminescence Imaging of Systemic Tumor Targeting Using a Prostate-Specific Lentiviral Vector. Human Gene Therapy vol. 17,1: 125-132 (2006).

(56)             References Cited

OTHER PUBLICATIONS

Iyer, Meera et al. Noninvasive Imaging of Enhanced Prostate-specific Gene Expression Using a Two-step Transcriptional Amplification-based Lentivirus Vector. Molecular Therapy vol. 10,3: 545-552 (2004).

Jacobs, A et al. Positron-Emission Tomography of Vector-Mediated Gene Expression in Gene Therapy for Gliomas. Lancet 358(9283): 727-729 (2001).

Jansen, et al., Molecular Drug Imaging: 89Zr-Bevacizumab PET in Children with Diffuse Intrinsic Pontine Glioma. J Nucl Med 58:711-716 (2017).

Jemal et al., Higher Lung Cancer Incidence in Young Women Than Young Men in the United States. N Engl J Med 378:1999-2009 (2018).

Johansen, Jens et al. Increased in Vitro and in Vivo Transgene Expression Levels Mediated Through Cis-acting Elements. The Journal of Gene Medicine 5(12):1080-1089 (2003).

Johnson, Leisa et al. Selectively Replicating Adenoviruses Targeting Deregulated E2F Activity are Potent, Systemic Antitumor Agents. Cancer Cell 1(4):325-337 (2002).

Kabat, Elvin A. et al. Sequences of Proteins of Immunological Interest, 5th Edition. U.S. Department of Health and Human Services NIH Publication No. 91-3242 (1991).

Kaczkowski, B. et al., Transcriptome Analysis of Recurrently Deregulated Genes across Multiple Cancers Identifies New Pan-Cancer Biomarkers. Cancer Res 76(2): 216-226 (2016).

Kang, Joo Hyun et al. Molecular-Genetic Imaging Based on Reporter Gene Expression. Journal of Nuclear Medicine 49(6):164S-179S (2008).

Kashkin, et al. Cancer Specificity of Promoters of the Genes Controlling Cell proliferation. Journal of Cellular Biochemistry 116(2):299-309 (2015).

Katsunori, and Osamu Shimomura. Coelenterazine analogs as chemiluminescent probe for superoxide anion. Analytical biochemistry 249(1):37-43 (1997).

Kawasaki, K. et al., FAM111B enhances proliferation of KRAS-driven lung adenocarcinoma by degrading p16. Cancer Sci. 111(7):2635-2646 (2020).

Kay, Mark A. et al. A robust system for production of minicircle DNA vectors. Nature biotechnology 28(12):1287-1289 (2010).

Kemp, Troy J et al. Evaluation of systemic and mucosal anti-HPV16 and anti-HPV18 antibody responses from vaccinated women. Vaccine 26(29-30):3608-3616 (2008).

Kern, Scott E. Why your new cancer biomarker may never work: recurrent patterns and remarkable diversity in biomarker failures. Cancer research 72(23):6097-6101 (2012).

Kikuchi, Eiji et al. Highly efficient gene delivery for bladder cancers by intravesically administered replication-competent retroviral vectors. Clinical Cancer Research 13(15):4511-4518 (2007).

Kim, Kyung-Jin et al. Two-promoter Vector is Highly Efficient for Overproduction of Protein Complexes. Protein Science vol. 13,6: 1698-1703 (2004).

Kitsis, R.N. et al. Discordance between gene regulation in vitro and in vivo. Gene Expression. 2(4):313-318 (1992).

Koh, Takashi et al. Alternative splicing of the neurofibromatosis 1 gene correlates with growth patterns and neuroendocrine properties of human small-cell lung-carcinoma cells. International journal of cancer 60(6):843-847 (1995).

Komata, T et al. Treatment of Malignant Glioma Cells With the Transfer of Constitutively Active Caspase-6 Using the Human Telomerase Catalytic Subunit (Human Telomerase Reverse Transcriptase) Gene Promoter. Cancer Research 61(15):5796-5802 (2001).

Kotterman, Melissa A. et al. Engineering adeno-associated viruses for clinical gene therapy. Nature reviews. Genetics 15(7):445-451 (2014).

Kyo, Satoru et al. Understanding and exploiting hTERT promoter regulation for diagnosis and treatment of human cancers. Cancer Sci. 99(8):1528-15338 (2008).

La Rocca, G. et al. Zymographic detection and clinical correlations of MMP-2 and MMP-9 in breast cancer sera. British journal of cancer 90(7):1414-1421 (2004).

Lan, K H et al. In Vivo Selective Gene Expression and Therapy Mediated by Adenoviral Vectors for Human Carcinoembryonic Antigen-producing Gastric Carcinoma. Cancer Research 57(19):4279-4284 (1997).

Le Fur, et al., Yttrium-86 PET imaging in rodents to better understand the biodistribution and clearance of gadolinium-based contrast agents used in MRI. Journal of Nuclear Medicine 60(supplement 1):346 (2019).

Ledwith, B. J. et al. Plasmid DNA vaccines: assay for integration into host genomic DNA. Developments in biologicals 104:33-43 (2000).

Ledwith, Brian J. et al. Plasmid DNA Vaccines: Investigation of Integration into Host Cellular DNA following Intramuscular Injection in Mice. Intervirology 43(4-6):258-272 (2000).

Lee et al. Enhancement of Anticancer Efficacy Using Modified Lipophilic Nanoparticle Drug Encapsulation. International Journal of Nanomedicine 7:731-737 (2012).

Lee, Hung-Yu H. et al. Abstract # 6176 Leveraging deep learning for fully automated analysis of pre-clinical mouse positron emission tomography. Poster EARLI Inc. (Apr. 1, 2024).

Lemm, Karsten. Turning Cancer Against Itself. DLD News. Dec. 26, 2025. [retrieved on Jun. 2, 2025]. Available at URL:https://dldnews.com/cancer-therapy-how-earli-aims-to-turn-cancer-against-itself/.

Lenzi et al., NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16 (2014).

Li, Binghua et al. A Survivin-mediated Oncolytic Adenovirus Induces Non-apoptotic Cell Death in Lung Cancer Cells and Shows Antitumoral Potential in Vivo. The Journal of Gene Medicine vol. 8,10: 1232-1242 (2006).

Li, Jian-Hua et al. Tumor-targeted Gene Therapy for Nasopharyngeal Carcinoma. Cancer Research vol. 62,1: 171-178 (2002).

Liberman, Herbert A. and Leon Lachman. Pharmaceutical Dosage Forms: Parental Medications. Marcel Decker, New York 1-7 (1980).

Liberzon, Arthur. et al. The molecular signatures database hallmark gene set collection. Cell systems 1(6):417-425 (2015).

Lisziewicz, Julianna. et al. Single DermaVir immunization: dose-dependent expansion of precursor/memory T cells against all HIV antigens in HIV-1 infected individuals. PloS one 7(5):e35416, 1-10 (2012).

Livak, Kenneth J. et al. Oligonucleotides with fluorescent dyes at opposite ends provide a quenched probe system useful for detecting PCR product and nucleic acid hybridization. Genome Research 4(6):357-362 (1995).

Louis, Irina Vlasova-st, and Calandra Sagarsky. Chapter 3:Mammalian Cis-acting RNA Sequence Elements. Gene Expression and Regulation in Mammalian Cells-transcription From General Aspects :35-66 (2018).

Lu, B et al. Evaluation of Tumor-specific Promoter Activities in Melanoma. Gene Therapy vol. 12,4: 330-338 (2005).

Lu et al.: A Mini-intronic Plasmid (Mip): A Novel Robust Transgene Expression Vector in vivo and in Vitro. Molecular Therapy, 21(5):954-963 (2013).

Luke, Jeremy et al. Novel Nonviral Plasmid Vectors With Minimalized Bacterial Backbones Dramatically Increase Transgene Expression Level in Vivo. Nature Technology 22:1 (2014).

Maccallum, Robert M. et al. Antibody-Antigen Interactions: Contact Analysis And Binding Site Topography. Journal of Molecular Biology 262(5):732-745 (1996).

Major, S. et al. Tuberculosis in CBA/J mice. Veterinary pathology 50(6):1016-1021 (2013).

Manuel, William S. et al. Transfection by polyethyleneimine-coated microspheres. Journal of Drug Targeting 9(1):15-22 (2001).

Marie, Corinne et al. pFARs, Plasmids free of antibiotic resistance markers, display high-level transgene expression in muscle, skin and tumour cells. The Journal of Gene Medicine: A cross-

(56)                    References Cited

OTHER PUBLICATIONS disciplinary journal for research on the science of gene transfer and its clinical applications 12(4):323-332 (2010).

Mariotti, Stefano et al. Assay of thyroglobulin in serum with thyroglobulin autoantibodies: an unobtainable goal?. The Journal of Clinical Endocrinology & Metabolism 80(2):468-472 (1995).

Mazzone et al., Diagnosis of lung cancer by the analysis of exhaled breath with a colorimetric sensor array. Thorax 62(7):565-8 (Jul. 2007).

Melling M, The influence of SUMOylation on the adenoviral early region 4 protein Orf6/7, (2018), Dissertation, Department of Biology of the University of Hamburg, Jul. 6, 2018.

Mercier, S. et al., FAM111B Mutation Is Associated With Pancreatic Cancer Predisposition. Pancreas 48(5):e41-e42 (May/Jun. 2019).

Milewski, David. et al. FOXM1 activates AGR2 and causes progression of lung adenomas into invasive mucinous adenocarcinomas. PLoS Genetics 13(12):e1007097, 1-21 (2017).

Munoz-Alvarez, et al. PET Imaging of Oncolytic VSV Expressing the Mutant HSV-1 Thymidine Kinase Transgene in a Preclinical HCC Rat Model. Molecular Therapy 23(4):728-736 (2015).

Na, Dokyun et al. Metabolic engineering of *Escherichia coli* using synthetic small regulatory RNAs. Nature biotechnology 31(2):170-174 (2013).

Nagrath, Sunitha. et al. Isolation of rare circulating tumour cells in cancer patients by microchip technology. Nature 450(7173):1235-1239 (2007).

Nichols, Warren W. et al. Potential DNA vaccine integration into host cell genome. Annals of the New York Academy of Sciences 772:30-39 (1995).

Nitta, Taizo et al. Selective expression of interleukin-10 gene within glioblastoma multiforme. Brain research 649(1-2):122-128 (1994).

Osborn, Mary et al. Villin, intestinal brush border hydrolases and keratin polypeptides in intestinal metaplasia and gastric cancer; an immunohistologic study emphasizing the different degrees of intestinal and gastric differentiation in signet ring cell carcinomas. Virchows Archiv A 413:303-312 (1988).

Patel, Yash D. et al. Control of Multigene Expression Stoichiometry in Mammalian Cells Using Synthetic Promoters. ACS Synth Biol 10(5): 1155-1165 (2021) (w/Supplemental Information).

PCT/US2020/026758 International Search Report and Written Opinion dated Jul. 9, 2020.

PCT/US2022/022603 International Search Report and Written Opinion dated Jul. 22, 2022.

PCT/US2024/038613 International Search Report and Written Opinion dated Dec. 18, 2024.

Penheiter, Alan R. et al. The sodium iodide symporter (NIS) as an imaging reporter for gene, viral, and cell-based therapies. Curr Gene Ther 12(1):33-47 (2012).

Perez-Torres, Carlos J. et al. In vitro and in vivo magnetic resonance imaging (MRI) detection of GFP through magnetization transfer contrast (MTC). NeuroImage 50(2):375-382 (2010).

Pethe, Manasi A. et al. Data-driven supervised learning of a viral protease specificity landscape from deep sequencing and molecular simulations. Proceedings of the National Academy of Sciences 116(1):168-176 (2019).

Porceddu, et al. Utility of Positron Emission Tomography For the Detection of Disease in Residual Neck Nodes After (Chemo) Radiotherapy in Neck and Head Cancer. Head and Neck: Journal for the Sciences and Specialties of the Head and Neck 27(3):175-181 (2005).

Positron emission tomography from Wikipedia. Printed on Oct. 12, 2023.

Qin, Chunxia. et al. Tyrosinase as a multifunctional reporter gene for Photoacoustic/MRI/PET triple modality molecular imaging. Scientific reports 3(1):1490, 1-8 (2013).

Quinn, C. M. et al. c-erbB-3 protein expression in human breast cancer: comparison with other tumour variables and survival. Histopathology 25(3):247-252 (1994).

Rajkumar, Thangarajan, and William John Gullick. The type I growth factor receptors in human breast. Breast cancer research and treatment 29(1):3-9 (1994).

Ray, Sunetra et al. Noninvasive Imaging of Therapeutic Gene Expression Using a Bidirectional Transcriptional Amplification Strategy. Molecular Theory 16(11):1848-1856 (2008).

Reddy, J. et al. Predicting master transcription factors from pan-cancer expression data. Sci Adv 7(48):eabf6123 (2021).

Richter, J R et al. A Dual-Reporter, Diagnostic Vector for Prostate Cancer Detection and Tumor Imaging. Gene Therapy 21(10):897-902 (2014).

Rojas-Solano, José R. et al. Robotic bronchoscopy for diagnosis of suspected lung cancer: a feasibility study. Journal of bronchology & interventional pulmonology 25(3):168-175 (2018).

Ronald J A et al. Artificial MicroRNAs as Novel Secreted Reporters for Cell Monitoring in Living Subjects. PLoS One 11(7):e0159369 (2016).

Ronald, John A et al. Detecting Cancers Through Tumor-activatable Minicircles That Lead to a Detectable Blood Biomarker. PNAS USA 112(10):3068-3073 (2015).

Ronald, John A. et al. MicroRNA-regulated non-viral vectors with improved tumor specificity in an orthotopic rat model of hepatocellular carcinoma. Gene therapy 20(10):1006-1013 (2013).

Schirmbeck, Reinhold. et al. The immunogenicity of adenovirus vectors limits the multispecificity of CD8 T-cell responses to vector-encoded transgenic antigens. Molecular Therapy 16(9):1609-1616 (2008).

Screen captures from YouTube video clip entitled A New Frontier in Cancer Treatment (Cyriac Roeding) | DLD25. Uploaded on Jan. 18, 2025 by user DLDconference: pp. 1-30. Retrieved from Internet: http://www.https://www.youtube.com/watch?v=eMDWz88L5Ew on Jun. 2, 2025.

Sharei, Armon. et al. Ex Vivo Cytosolic Delivery of Functional Macromolecules to Immune Cells. PLoS One 10(4):e0118803, 1-12 (2015).

Shearwin et al., Transcriptional interference—a crash course. Trends in Genetics, 21:339-345 (2005).

Shim et al., Nonviral Delivery Systems for Cancer Gene Therapy: Strategies and Challenges. Current Gene Therapy 18:3-20 (2018).

Shimomura, Osamu. et al. Semi-synthetic aequorins with improved sensitivity to Ca2+ ions. Biochemical Journal 261(3):913-920 (1989).

Shirley, Lawrence A. et al. Therapeutic Endoscopic Ultrasonography: Intratumoral Injection for Pancreatic Adenocarcinoma. Gastroenterology Research and Practice 2013(1):207129, 1-3 (2013).

Smith, Martin J. et al. Surfactant protein A-directed toxin gene kills lung cancer cells in vitro. Human Gene Therapy 5(1):29-35 (1994).

Stroebele, Elizabeth et al. Abstract #6128 Using high-throughput screening to identify DNA response elements that sense cancer dysregulated pathways. Poster EARLI Inc. (Apr. 3, 2024).

Sugio, Kumiko. et al. Enhanced safety profiles of the telomerase-specific replication-competent adenovirus by incorporation of normal cell-specific microRNA-targeted sequences. Clinical Cancer Research 17(9):2807-2818 (2011).

Sumida, Shawn M. et al. Neutralizing antibodies to adenovirus serotype 5 vaccine vectors are directed primarily against the adenovirus hexon protein. The Journal of Immunology 174(11):7179-7185 (2005).

Sun, H. et al., FAM111B, a direct target of p53, promotes the malignant process of lung adenocarcinoma. Onco Targets Ther. 12:2829-2842 (2019).

Sunshine, et al. Poly(β-Amino Ester)-Nanoparticle Mediated Transfection of Retinal Pigment Epithelial Cells In Vitro and In Vivo. PLoS One 7(5): e37543, 1-11 (2012).

Tada, Masaharu. et al. High vol. hydrodynamic injection of plasmid DNA via the hepatic artery results in a high level of gene expression in rat hepatocellular carcinoma induced by diethylnitrosamine. The Journal of Gene Medicine: A cross-disciplinary journal for research on the science of gene transfer and its clinical applications 8(8):1018-1026 (2006).

Tan, Yadi. et al. The inhibitory role of CpG immunostimulatory motifs in cationic lipid vector-mediated transgene expression in vivo. Human gene therapy 10(13):2153-2161 (1999).

(56)		References Cited

OTHER PUBLICATIONS

Tannous, Bakhos A et al. Gaussia Luciferase Reporter Assay for Monitoring Biological Processes in Culture and in Vivo. Nature protocols vol. 4,4: 582-591 (2009).
Tanyi et al., Janos L. Identification of Tissue- and Cancer-Selective Promoters for the Introduction of Genes into Human Ovarian Cancer Cells. Gynecol Oncol 85(30):451-458 (2002).
Tsuruta, Yuko. et al. A Fiber-Modified Mesothelin Promoter-Based Conditionally Replicating Adenovirus for Treatment of Ovarian Cancer. Clinical cancer research 14(11):3582-3588 (2008).
Tulchinsky, E. et al. Transcriptional analysis of the mts1 gene with specific reference to 5'flanking sequences. Proceedings of the National Academy of Sciences 89(19):9146-9150 (1992).
Ueki, Hideo et al. A Novel Gene Expression System for Detecting Viable Bladder Cancer Cells. International Journal of Oncology 41(1):135-140 (2012).
U.S. Pat. No. 12,060,613 B2 Listing of Claims (p. 133) issued on Aug. 13, 2024.
U.S. Appl. No. 18/325,809 Office Action dated May 9, 2025.
U.S. Appl. No. 18/452,504 Office Action dated Dec. 16, 2024.
U.S. Appl. No. 18/452,504 Office Action dated Jan. 9, 2024.
U.S. Appl. No. 18/452,504 Office Action dated May 20, 2024.
U.S. Appl. No. 18/452,504 Office Action dated May 6, 2025.
U.S. Appl. No. 18/455,209 Office Action dated Dec. 27, 2024.
U.S. Appl. No. 18/455,209 Office Action dated Jun. 18, 2024.
U.S. Appl. No. 18/455,209 Office Action dated May 13, 2025.
U.S. Appl. No. 16/223,294 Listing of Claims as of Jul. 25, 2024.
U.S. Appl. No. 17/494,465 Listing of Claims as of May 19, 2022.
U.S. Appl. No. 18/320,145 Listing of Claims as of Feb. 23, 2024.
U.S. Appl. No. 18/325,809 Listing of Claims as of May 30, 2023.
U.S. Appl. No. 18/452,504 Listing of Claims as of Nov. 20, 2024.
U.S. Appl. No. 18/455,209 Listing of Claims as of Mar. 25, 2025.
U.S. Appl. No. 18/936,497 Listing of Claims as of Nov. 19, 2024.
Van Houdt, Winan J et al. The Human Survivin Promoter: a Novel Transcriptional Targeting Strategy for Treatment of Glioma. Journal of Neurosurgery vol. 104,4: 583-592 (2006).
Vile, Richard. et al. A comparison of the properties of different retroviral vectors containing the murine tyrosinase promoter to achieve transcriptionally targeted expression of the HSVtk or IL-2 genes. Gene Therapy 1(5):307-316 (1994).
Wagner, E Gerhart H. et al. Antisense RNAs in Bacteria and their Genetic Elements. Advances in Genetics 46:361-398 (2002).
Wang, Manping et al. MUSEAP, a novel reporter gene for the study of long-term gene expression in immunocompetent mice. Gene 279(1):99-108 (2001).
Wang, TianDuo, et al. A Survivin-driven, Tumor-activatable Minicircle System for Prostate Cancer Theranostics. Molecular Therapy vol. 20: 209-219 (2021).
Wang, Z. et al. Detection of integration of plasmid DNA into host genomic DNA following intramuscular injection and electroporation. Gene therapy 11(8):711-721 (2004).
Wang, Zhao-Xia et al. Adenovirus-mediated Suicide Gene Therapy Under the Control of Cox-2 Promoter for Colorectal Cancer. Cancer Biology & Therapy 8(15):1480-1488 (2009).
Warram, J M et al., Systemic Delivery of a Breast Cancer-detecting Adenovirus Using Targeted Microbubbles. Cancer Gene Therapy vol. 19,8: 545-552 (2012).
Warram, Jason M. et al. A genetic strategy for combined screening and localized imaging of breast cancer. Molecular Imaging and Biology 13(3):452-461 (2011).
Weidle, Ulrich H. et al. Proteases as activators for cytotoxic prodrugs in antitumor therapy. Cancer genomics & proteomics 11(2):67-79 (2014).
Williams, et al. Plasmid DNA Vaccine Vector Design: Impact on Efficacy, Safety and Upstream Production. Biotechnology advances 27(4):353-370 (2009).
Wolff, Jon A. et al. Direct gene transfer into mouse muscle in vivo. Science 247(4949):1465-1468 (1990).
Wu, Lily et al. Transcriptionally Targeted Gene Therapy to Detect and Treat Cancer. Trends in Molecular Medicine 9(10):421-429 (2003).
Yaghoubi et al., PET imaging of herpes simplex virus type 1 thymidine kinase (HSV1-tk) or mutant HSV1-sr39tk reporter gene expression in mice and humans using [18F]FHBG. Nat Protoc. 1(6):3069-3075 (2006).
Yaghoubi et al., Positron Emission Tomography Reporter Genes and Reporter Probes: Gene and Cell Therapy Applications. Theranostics, 2(4):374-391 (2012).
Yang, Jian. et al. A nanoparticle formulation that selectively transfects metastatic tumors in mice. Proceedings of the National Academy of Sciences 110(36):14717-14722 (2013).
Yang, L. et al. Tumor-specific gene expression using the survivin promoter is further increased by hypoxia. Gene Therapy 11(15):1215-1223 (2004).
Ye, Xun et al. Insulation from viral transcriptional regulatory elements enables improvement to hepatoma-specific gene expression from adenovirus vectors. Biochemical and biophysical research communications 307(4):759-764 (2003).
Yu, et al. 3D Blob Brain Tumor Detection and Segmentation in MR Images. IEEE 11th International Symposium on Biomedical Imaging (ISBI):1192-1197 (2014).
Zali, Hakimeh et al. Gastric cancer: prevention, risk factors and treatment. Gastroenterology and Hepatology from bed to bench 4(4):175-185 (2011).
Zhang, Liqun et al. Interrogating Androgen Receptor Function in Recurrent Prostate Cancer. Cancer Research 63(15):4552-4560 (2003).
Zhang, Ying et al. AAV-mediated TRAIL gene expression driven by hTERT promoter suppressed human hepatocellular carcinoma growth in mice. Life sciences 82(23-24):1154-1161 (2008).
Zhang, Yue (Wendy) et al. Abstract # 4311 Using multi-omics analysis to identify dysregulated transcription factors in non-small cell lung cancer (NSCLC) to drive the expression of a cancer-activated synthetic biomarker. Poster EARLI Inc. (Mar. 22, 2023).
Zhong, Bao-yuan et al. Experimental study on FAK shRNA regulated by tumor-specific Surivivin promoter for targeted therapy of liver cancer. Chinese Medical Innovation 14(29):27-30 (Oct. 2017) (English Abstract).
Zhou, Jinfeng et al. Identification of CEACAM5 as a biomarker for prewarning and prognosis in gastric cancer. Journal of Histochemistry and Cytochemistry 63(12):922-930 (2015).
Zhou, Li et al. Viruses and neurodegeneration. Virology journal 10:172, 1-17 (2013).
Zugates, Gregory T. et al. Rapid optimization of gene delivery by parallel end-modification of poly (β-amino ester) s. Molecular Therapy 15(7):1306-1312 (2007).
Zuo, Yufang et al., Minicircle-oriP-IFNy: A Novel Targeted Gene Therapeutic System for EBV Positive Human Nasopharyngeal Carcinoma. PLoS One 6:e19407 (2011).
Zvibel, Isabel et al. Insulin-like growth factor II regulation of gene expression in rat and human hepatomas. Journal of cellular physiology 162(1):36-43 (1995).
Cohen, Paul A. et al. Cervical cancer. The Lancet 393(10167):169-182 (2019).
Elouahabi, Abdelatif and Jean-Marie Ruysschaert. Formation and intracellular trafficking of lipoplexes and polyplexes. Molecular Therapy 11(3):336-347 (2005).
EP25180204.7 Extended European Search Report dated Oct. 24, 2025.
Shi, Chao et al. Aberrantly activated Gli2-KIF20A axis is crucial for growth of hepatocellular carcinoma and predicts poor prognosis. Oncotarget 7(18):26206-26219 (2016).
Turning Tumors Against Themselves from the Inside. The Scientist. 7 pages. Jun. 12, 2025. [retrieved on Aug. 15, 2025]. Available at https://www.the-scientist.com/turning-tumors-against-themselves-from-the-inside-73085.
Wang, TianDuo et al. A novel approach for assessment of prostate cancer aggressiveness using surviving-driven tumour-activatable minicircles. Gene Therapy. 26: 177-186 (2019).

(56)  References Cited

OTHER PUBLICATIONS

Zhang, Weijing et al. High expression of KIF20A is associated with poor overall survival and tumor progression in early-stage cervical squamous cell carcinoma. PLOS ONE 11(12):e0167449, 1-21 (2016).

* cited by examiner

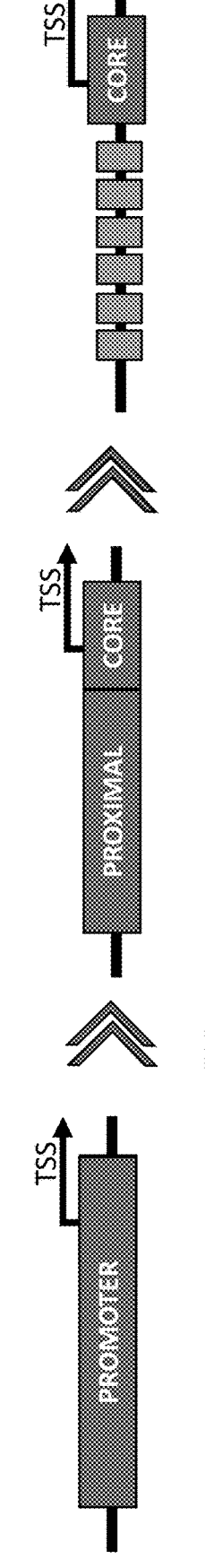
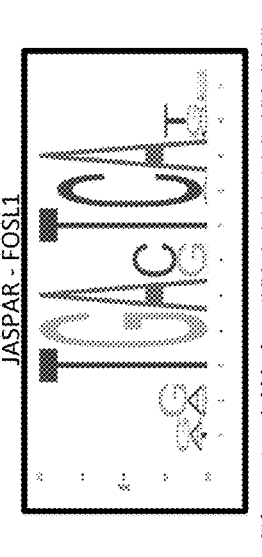
FIG. 1

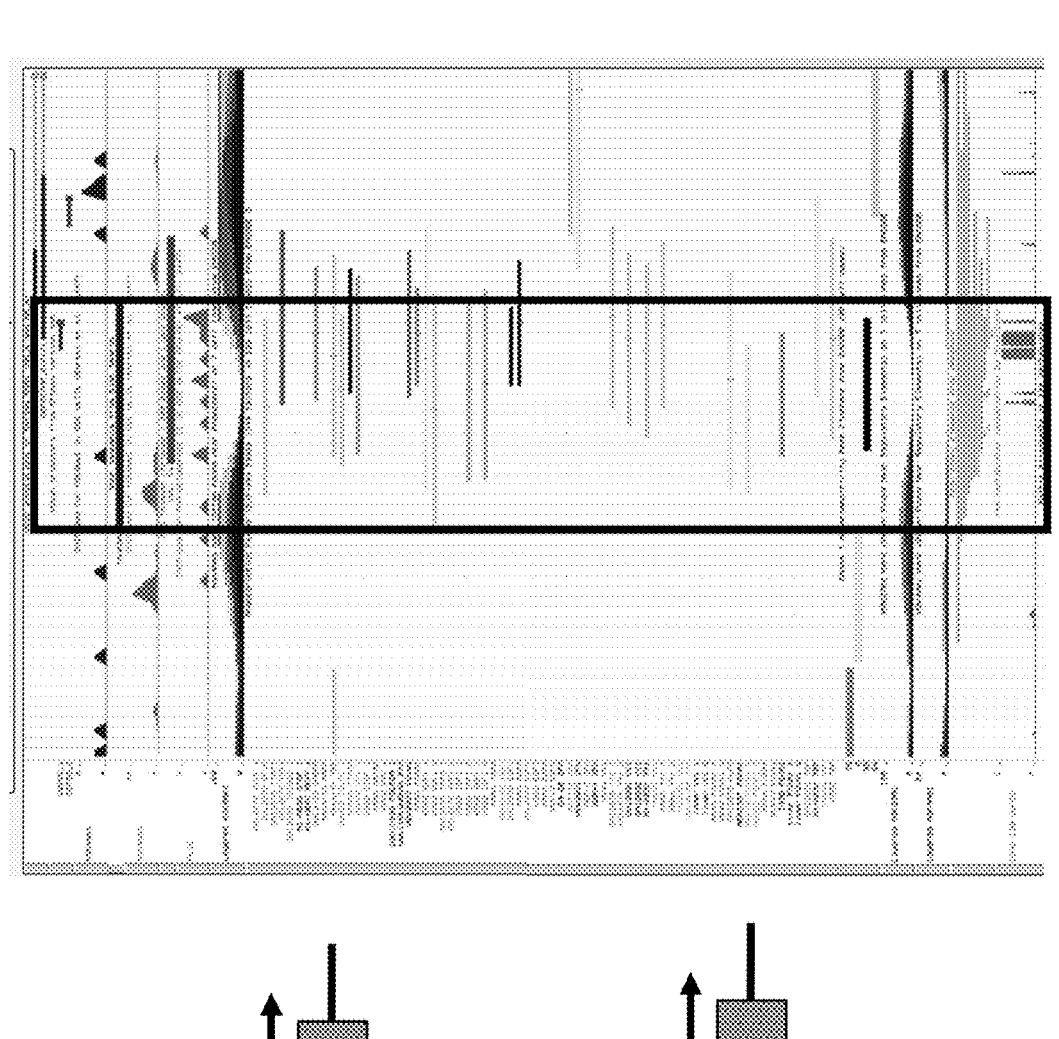
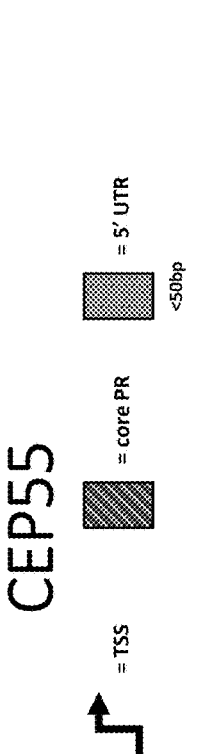
CEP55
= TSS
= core PR
= 5' UTR
<50bp
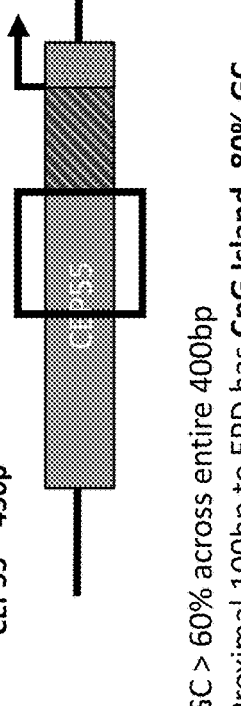
CEP55 ~ 450p
GC > 60% across entire 400bp
Proximal 100bp to EPD has CpG Island, 80% GC
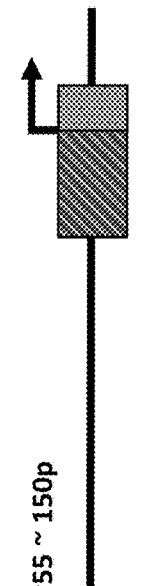
coreCEP55 ~ 150p
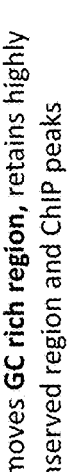
Removes GC rich region, retains highly
conserved region and ChIP peaks
FIG. 3

FIG. 4

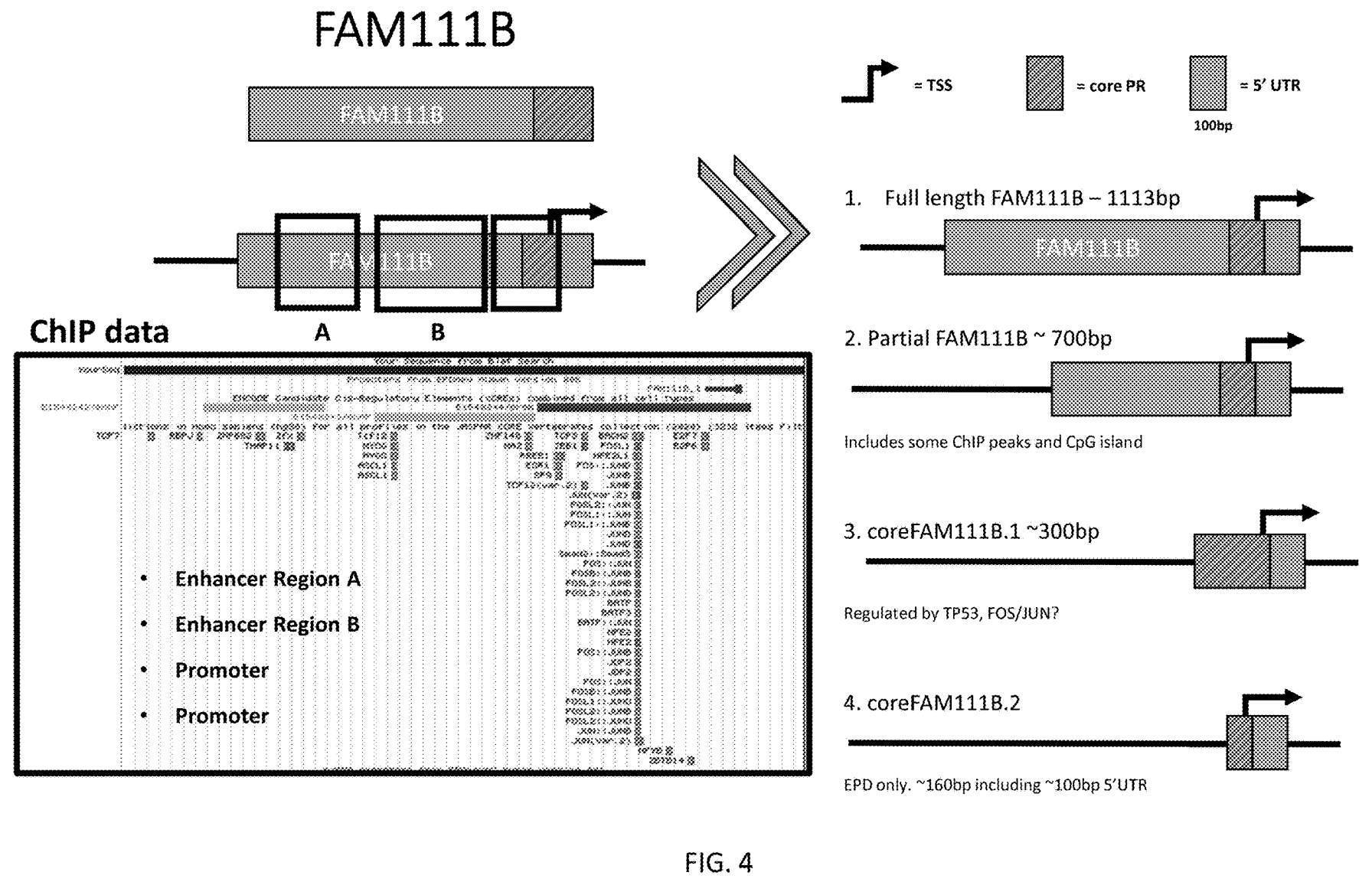

Performance in human PDX models

Synthetic promoters can drive specificity via minimal cancer-activated cores, and sensitivity via master-regulated TFs 1　Bioinformatic analysis to identify endogenous cancer-activated promoters, engineered into minimal cancer-activated sequences 2　Bioinformatic identification of Master Regulated TFs, tiled and tested with Massively Parallel Reporter Assays (MPRA) to identify optimal sequences, spacing and combinations.

3　Rationally designed or high-throughput screening (HTS) to identify enhancer elements to increase transcription and boost signal.

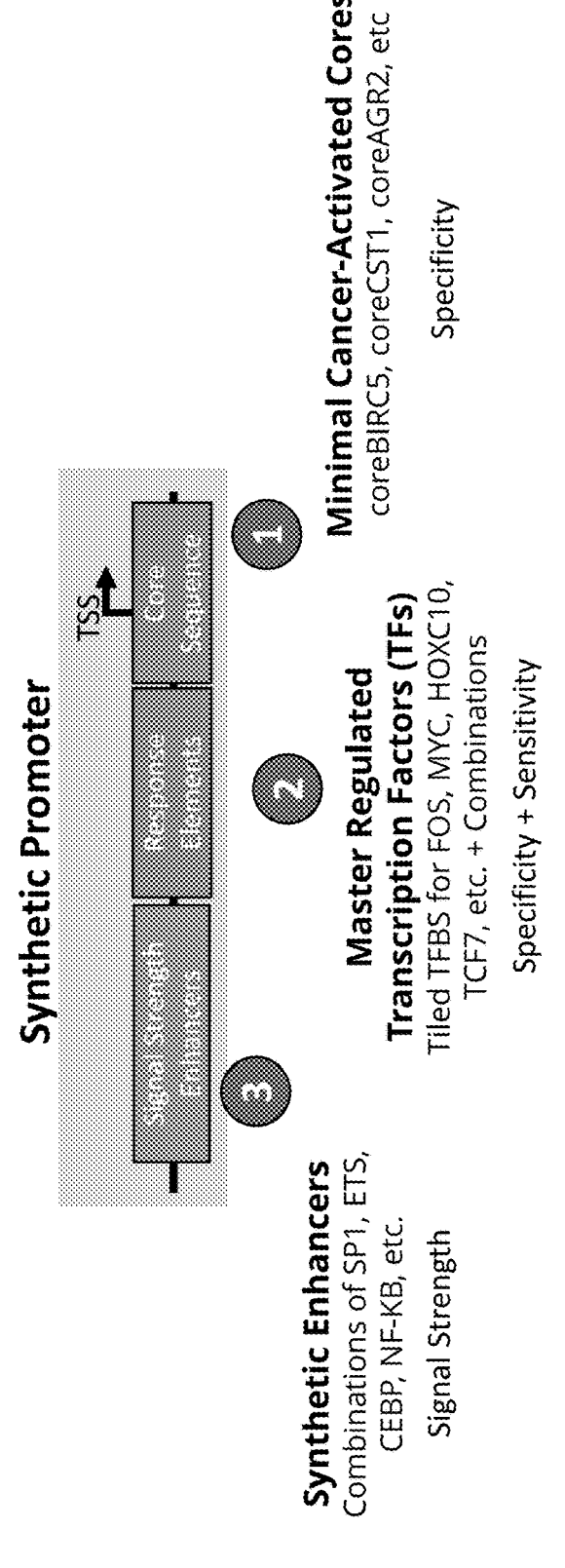

Synthetic Promoter

Minimal Cancer-Activated Cores
coreBIRC5, coreCST1, coreAGR2, etc

Specificity

Master Regulated Transcription Factors (TFs)
Tiled TFBS for FOS, MYC, HOXC10, TCF7, etc. + Combinations Specificity + Sensitivity

Synthetic Enhancers
Combinations of SP1, ETS, CEBP, NF-KB, etc.

Signal Strength

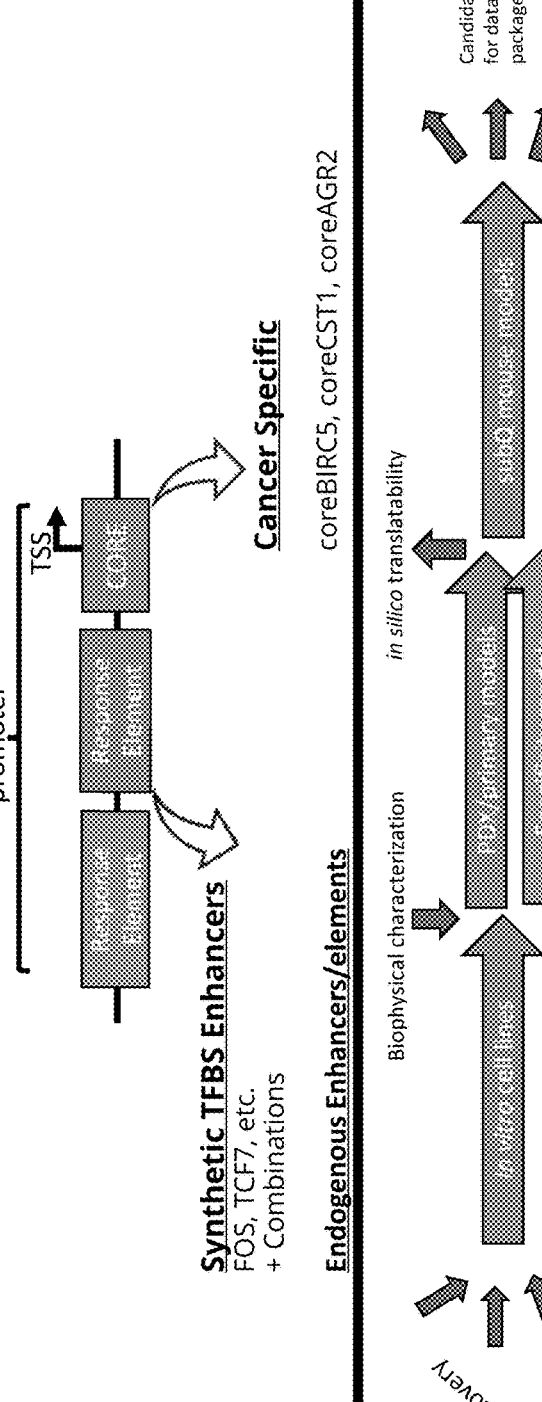
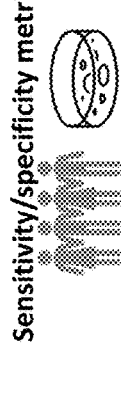
FIG. 12

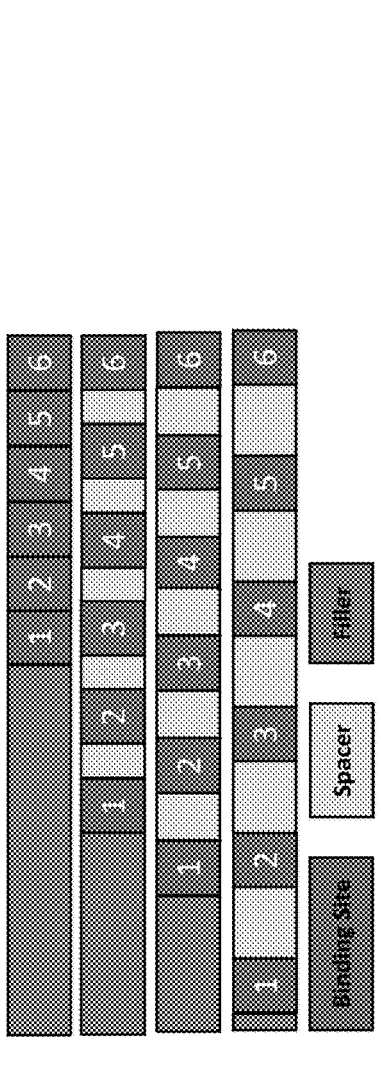
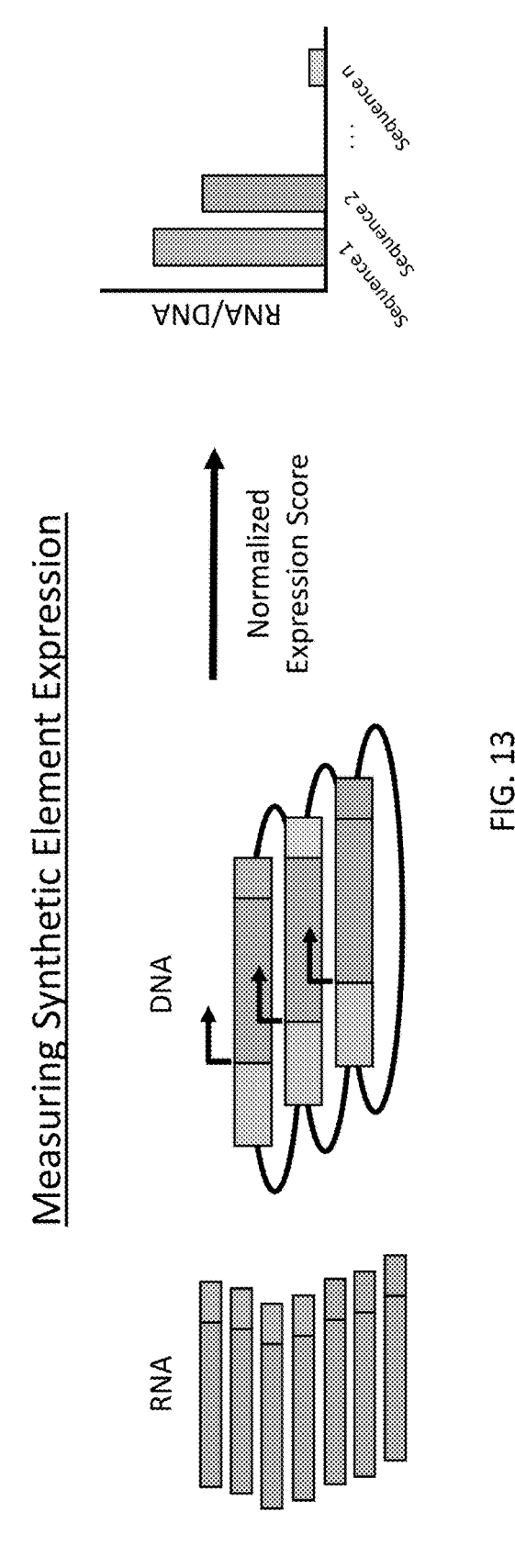
FIG. 13

Of the 1,800 unique synthetic promoters, some synthetic promoters drive expression at or near the baseline expression of the core promoter, and some synthetic promoters drive strong expression.

Figure 15:
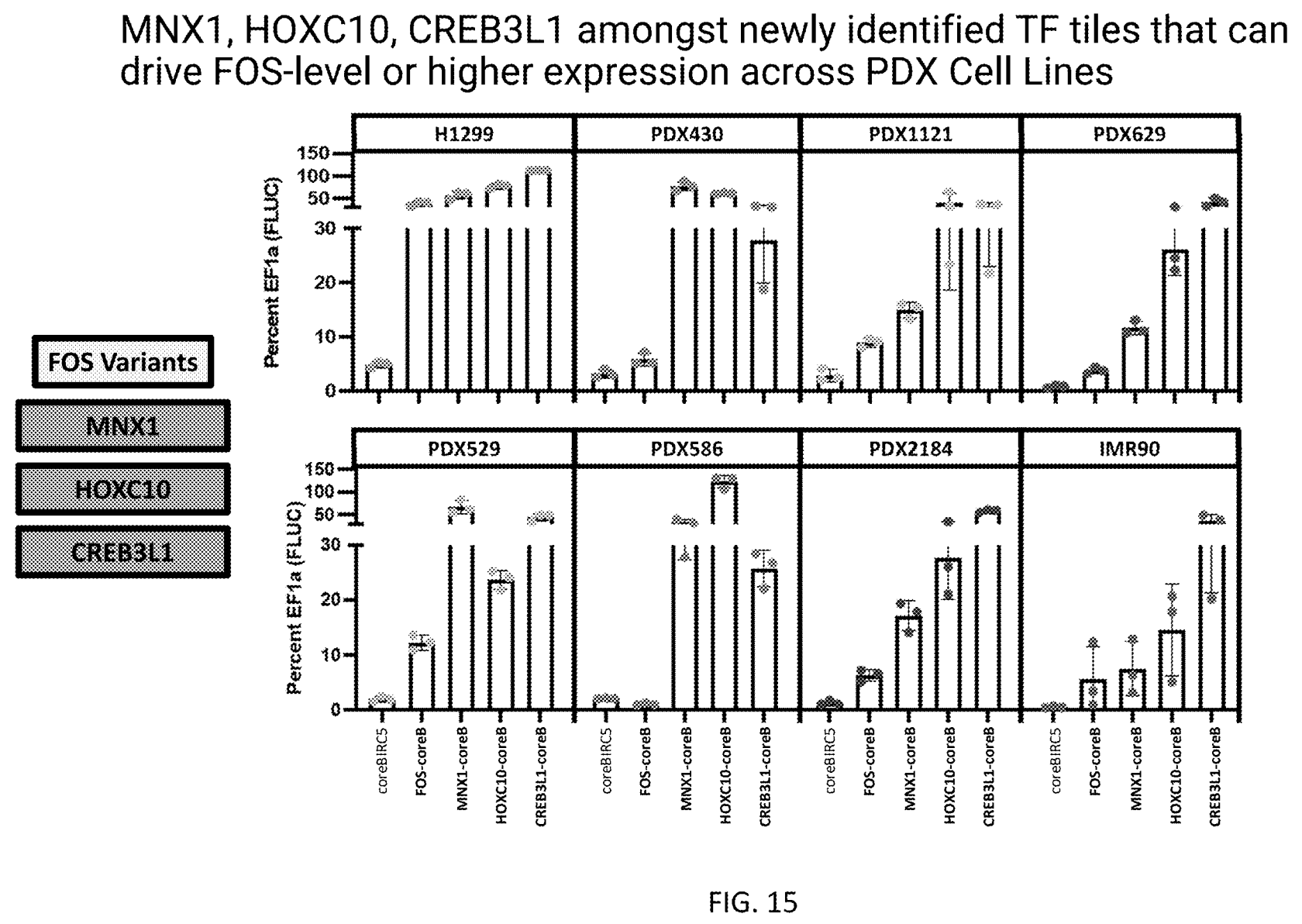

MNX1, HOXC10, CREB3L1 amongst newly identified TF tiles that can drive FOS-level or higher expression across PDX Cell Lines

TCF7L1 & TCF7 TF tiles are active in NCI-H520 and LK-2 cell lines as predicted by Bioinformatics

** New cell lines identified by Bioinformatics as Wnt+

Addition of TP53 elements to TATA-TSS core results in significantly increased expression in PDX586 as predicted by HTS-002

TP53 variants are highly expressed in A549s

Note: There are cancer cell lines which has TP63 high expression. Chose ACH-001113 which has TP53 mutation leading to loss of DNA binding.

| | One like S49 ( ) | One as negative control like H1299 ( ) | One has high Tp63 ( ) |
|---|---|---|---|
| P53 mutation status | WT | Mutated | Mutated |
| Key gene set expression | Up regulated | No change | No change |
| TP63 expression | low | low | high |

Mutation profile in CPTAC LUSC

Mutation profile in CPTAC LUAD

Tracking TP53 element across cell lines

HIGH > EF1A

MED < EF1A but higher than other TF tiles

LOW = off or lower than most TF tiles

| Cell Line | TP53 Status | Construct Expression |
|---|---|---|
| H1299 | NULL – deletion | LOW |
| PDX586 | WT, MUT verified by ES but functional? | HIGH |
| PDX430 | | MED |
| PDX629 | | LOW |
| H520 | WT** | LOW |
| H358 | MUT DEL | LOW |
| LK2 | MUT (V272M) in DBD, oncogenic, LOF | LOW |
| H1975 | MUT - p.R273H | LOW |
| A549 | WT | HIGH |
| BEAS-2B | WT | LOW/MED (high variability only v22 active) |
| H1944 | WT | HIGH |
| SAEC-2 | WT (verify by PCR) | HIGH |
| HepG2 | WT | HIGH |
| HEP3B | MUT | LOW |
| H460 | WT | ?? |

**The cells express greatly reduced levels of p53 mRNA relative to normal lung tissue, but exhibit no gross structural DNA abnormalities.

FIG. 23

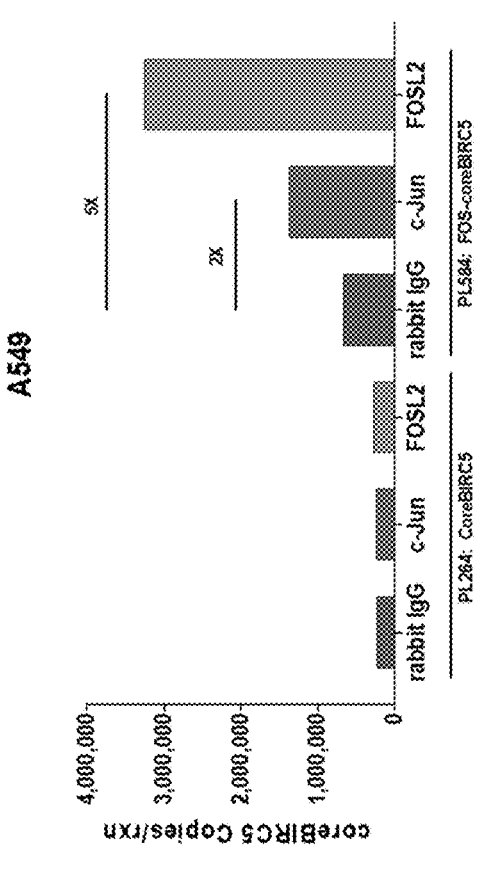
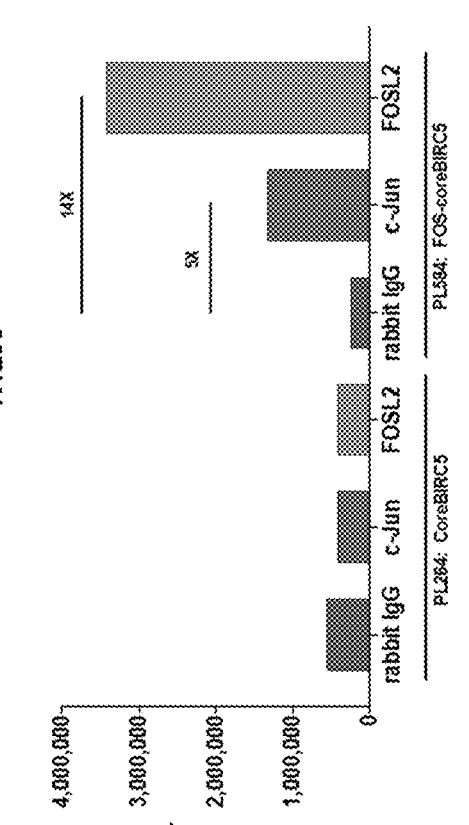
FIG. 33

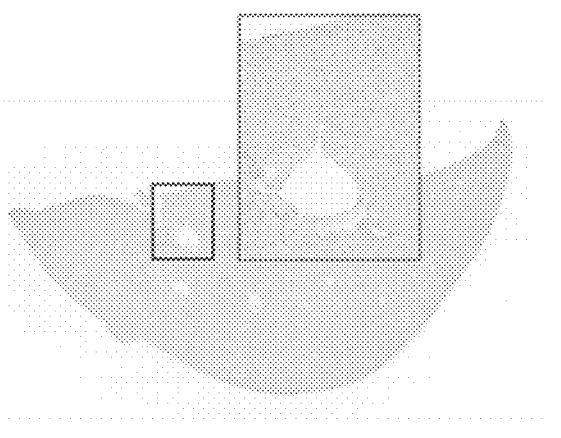
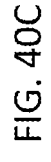
FIG. 40C
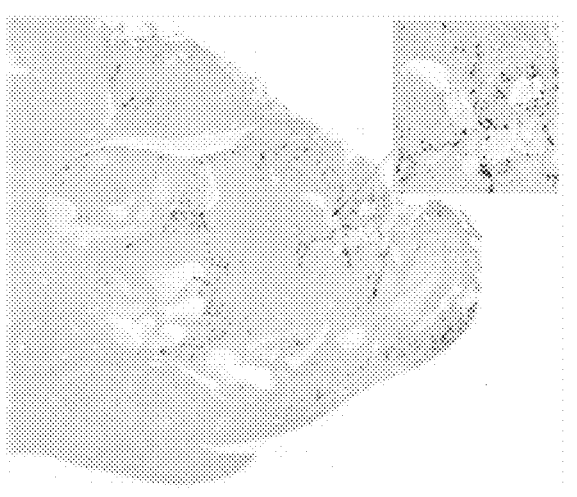
FIG. 40B
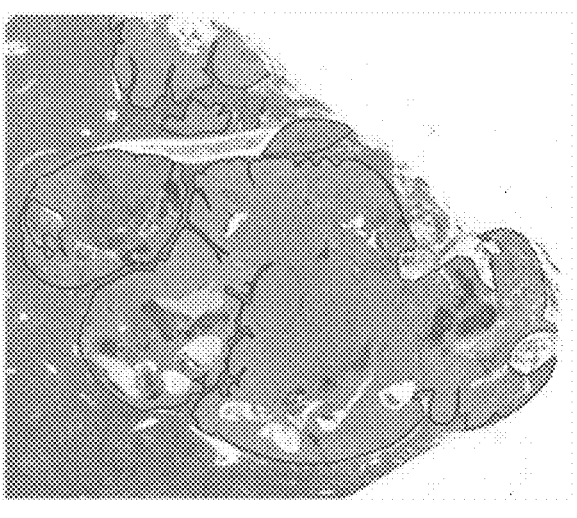
FIG. 40A

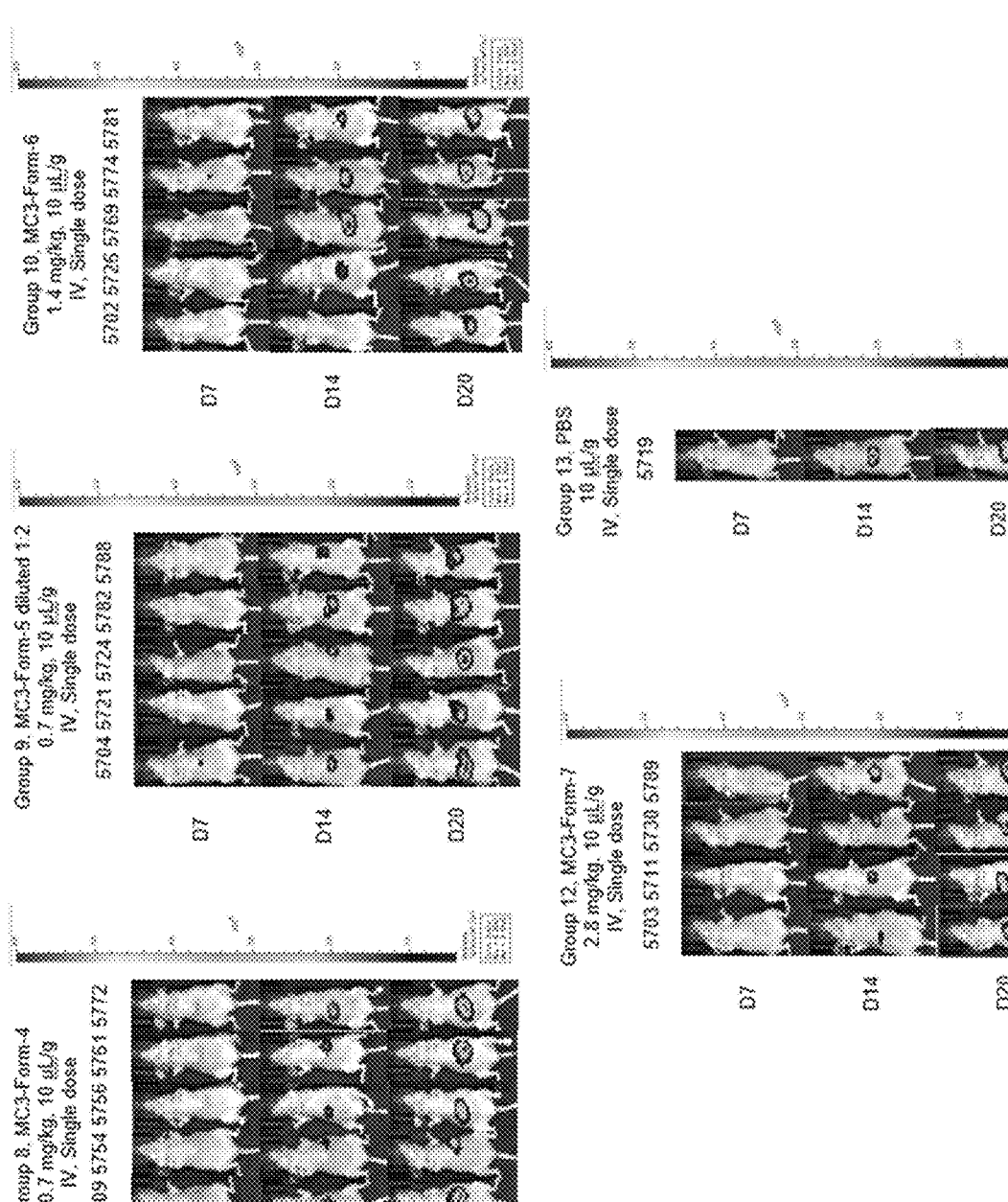
FIG. 42 – continued

Analysis via QPCR verified DNA delivery

| Groups | Mouse # | RGK DNA Distribution (copies/ml) | RGK DNA Distribution (copies/cell) |
|---|---|---|---|
| Group A – PBS + Test Compound | 1 | 91,651 | 0.26 |
| | 2 | 168,994 | 4.27 |
| | 3 | 55,958 | 0.15 |
| Group B – Infection + Test Compound | 1 | 55,801 | 0.17 |
| | 2 | 47,005 | 0.15 |
| | 3 | 117,565 | 0.27 |
| | 4 | 56,960 | 0.21 |

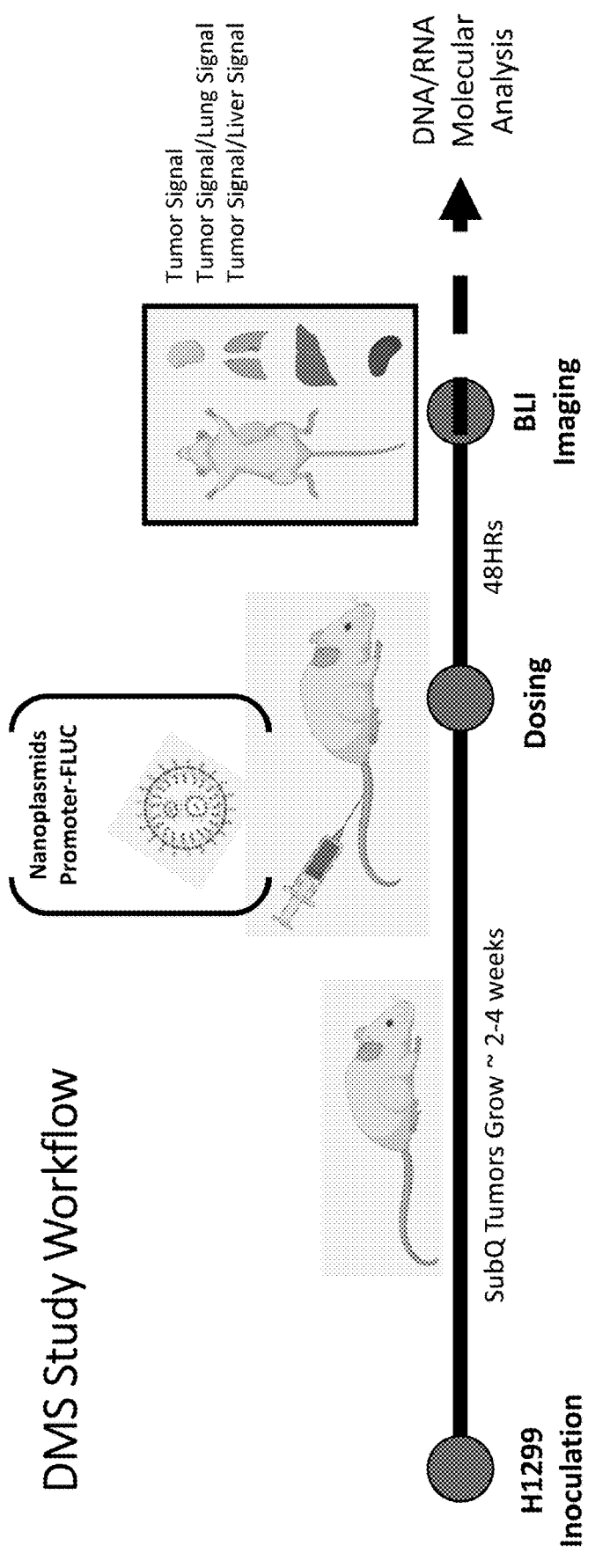

DMS Study Workflow

H1299 Inoculation

Nanoplasmids Promoter-FLUC

SubQ Tumors Grow ~ 2-4 weeks

Dosing

48HRs

BLI Imaging

Tumor Signal
Tumor Signal/Lung Signal
Tumor Signal/Liver Signal

DNA/RNA Molecular Analysis

Recent progress in increasing signal strength:

DMS65 Tested new promoters: CAG > FOS-TATA-TSS > FOS-coreBIRC5 ~ BIRC5

DMS69 Confirmed lower dose 1.4 mpk okay for strong promoters including FOS-TATA, HIGH-coreBIRC5

**Does addition of FOS element improve *in vivo* performance of core promoters?**

FIG. 47

Can we combine general activating elements with the new core promoters?

Addition of general TF/mediators

Low: 5'-EBS-C/EBP-EBS-3'
Medium: 5'-C/EBP-GCbox-ARE-DRE-EBS-NFkB-ARE
High: 5'-GCbox-ARE-NFkB-DRE-EBS-ARE-DRE-NFkB-GCbox-NFkb-ARE-3'

Can these LOW, MED, and HIGH elements boost expression with coreBIRC5?

Can we combine the HIGH element with new core promoters?

New Primary Models (PDX or primary tissue derived) provide diverse clinically relevant models Promoters with Wnt-related TFs show 6-10x more activation in EMT cell state vs. wildtype A549s Top 10 enhancer candidates following visual assessment of ~150 most promising hits

| Enhancer # | Linked Gene | Chromosome | Start | End |
|---|---|---|---|---|
| EN011 | UNC5CL | chr6 | 40807304 | 40807805 |
| EN012 | BOP1 | chr8 | 144788135 | 144788636 |
| EN013 | RTN4RL2 | chr11 | 57458633 | 57459134 |
| EN014 | ARNTL2 | chr12 | 27177638 | 27178139 |
| EN015 | ARNTL2 | chr12 | 27460331 | 27460832 |
| EN016 | AGR2 | chr7 | 16905133 | 16905634 |
| EN017 | LHX2 | chr9 | 124041590 | 124042091 |
| EN018 | TRNP1 | chr1 | 26991252 | 26991753 |
| EN019 | MUC5AC | chr11 | 1152306 | 1152807 |
| EN020 | DOK4 | chr16 | 57606885 | 57607386 |

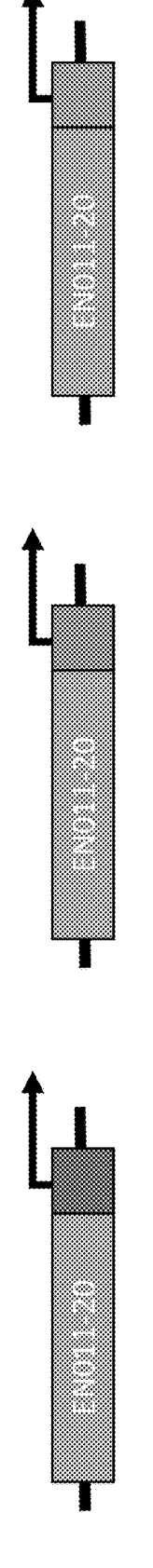

For PoC, cloned top 10 enhancers in front of 3x different core promoters...

...& tested across representative cell lines for indication of choice (LUAD).

FIG. 56

FLUC expression as % of EF1A for Enhancers Across Cancer Cell Lines
Enhancers 18 & 19 can drive strong expression, may also be more specific than FOS

| | H1299 | A549 | H1975 | LXFL 529 | LXFA 586 | LXFA 629 | LXFA 677 | LXFA 737 | LXFL 1121 | LXFA 2184 | IMR90 | SAEC-3 | NHBE-2 |
|---|---|---|---|---|---|---|---|---|---|---|---|---|---|
| coreBIRC5 | 8% | 14% | 5% | 11% | 3% | 1% | 1% | 9% | 2% | 3% | 5% | 2% | 17% |
| EN18+coreBIRC5 | 6% | 26% | 3% | 12% | 3% | 1% | 1% | 5% | 10% | 3% | 3% | 1% | 5% |
| EN19+coreBIRC5 | 12% | 18% | 5% | 19% | 3% | 2% | 1% | 3% | 5% | 3% | 3% | 0% | 5% |
| FOSL1-coreBIRC5 | | | 115% | 5% | 18% | 41% | | 20% | 25% | 11% | | 19% | 23% |
| TATA-TSS | 3% | 11% | 1% | 2% | 1% | 1% | 0% | 4% | 2% | 1% | 4% | 1% | 9% |
| EN18+TATA-TSS | 8% | 50% | 3% | 17% | 3% | 3% | 0% | 7% | 53% | 2% | 7% | 1% | 5% |
| EN19+TATA-TSS | 3% | 12% | 1% | 6% | 1% | 2% | 0% | 2% | 3% | 4% | 3% | 1% | 7% |
| FOSL1-TATA | | | 937% | 63% | 330% | 298% | | 381% | 149% | 229% | | 207% | 368% |
| Canscript | 5% | 6% | 2% | 3% | 1% | 8% | 2% | 4% | 2% | 1% | 7% | 53% | 26% |
| EN18+Canscript | 98% | 443% | 16% | 66% | 34% | 62% | 45% | 46% | 18% | 33% | 18% | 38% | 40% |
| EN19+Canscript | 84% | 240% | 33% | 38% | 36% | 48% | 74% | 48% | 12% | 29% | 89% | 97% | 68% |
| FOSL1-CS | | | 54% | 9% | 19% | 60% | | 13% | 18% | 18% | | 5% | 140% |

Next steps:
- Test EN18+Canscript and EN19+Canscript *in vivo*
- Deep dive into EN18 and EN19 – what is driving expression? How can we bash or engineer sequence?

FIG. 58

Two-Step Promoter Amplification Utilizing the Yeast GAL4-VP System

TSTA can result in significantly increased expression in lung cancer cell lines with BIRC5 or FOSL1-BIRC5core driving expression of GAL4 but not AFP3

TSTA can result in significantly increased expression in liver cancer cell lines with various promoters driving expression of GAL4

| Fold Change with TSTA compared to PR-FLUC | | | | | | | |
|---|---|---|---|---|---|---|---|
| Promoter | SNU-387 | SNU-423 | SNU-449 | SNU-475 | SK-HEP-1 | PLC/PRF/5 | C3A |
| BIRC5 | 15x | 1.1x | 7x | 6x | 15x | 5x | 10x |
| FOSL1 BIRC5core | 10x | 3x | 7x | 30x | 15x | 10x | 7x |
| AFP3 | 1.1x | 8x | 15x | 5x | 60x | 10x | 3x |

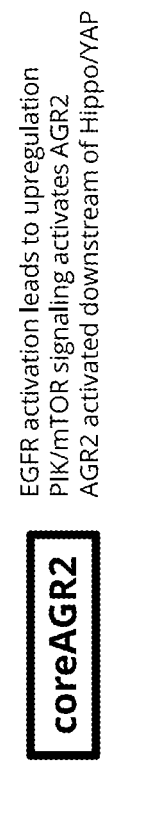
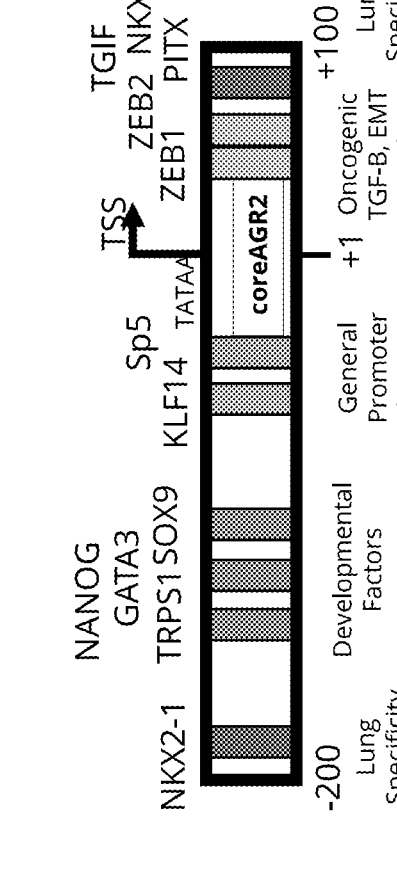
FIG. 63

Annotated core FAM111B promoter with predicted TF binding sites

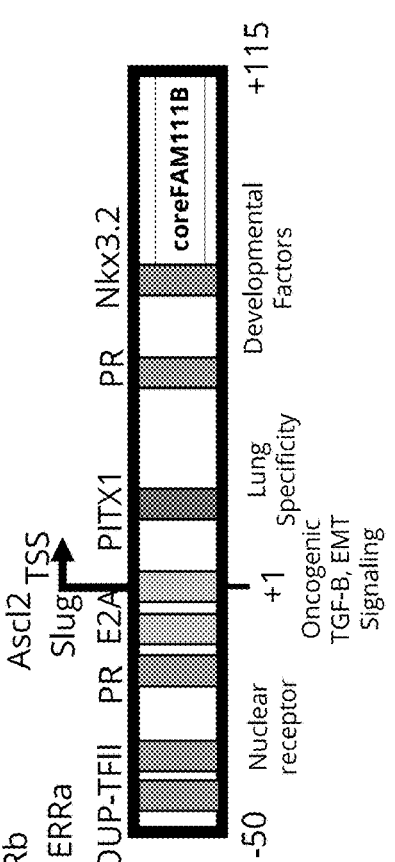

NR can have properties as agonists or antagonists depending on signaling condition
THRb – Thyroid Hormone Receptor
ERRa - Estrogen-related Receptor
PR – Progesterone Receptor EMT-related factors may regulate FAM111B expression (Slug, E2A, Ascl2)

NKX3-2 required for plasmid nuclear import in non-dividing smooth muscle cells

FIG. 64A

Preliminary results from core promoter element deletion studies identified activating and repressing elements within coreFAM111B NR can have properties as agonists or antagonists depending on signaling condition
THRb – Thyroid Hormone Receptor
ERRa - Estrogen-related Receptor
PR – Progesterone Receptor EMT-related factors may regulate FAM111B expression (Slug, E2A, Ascl2)

NKX3-2 required for plasmid nuclear import in non-dividing smooth muscle cells

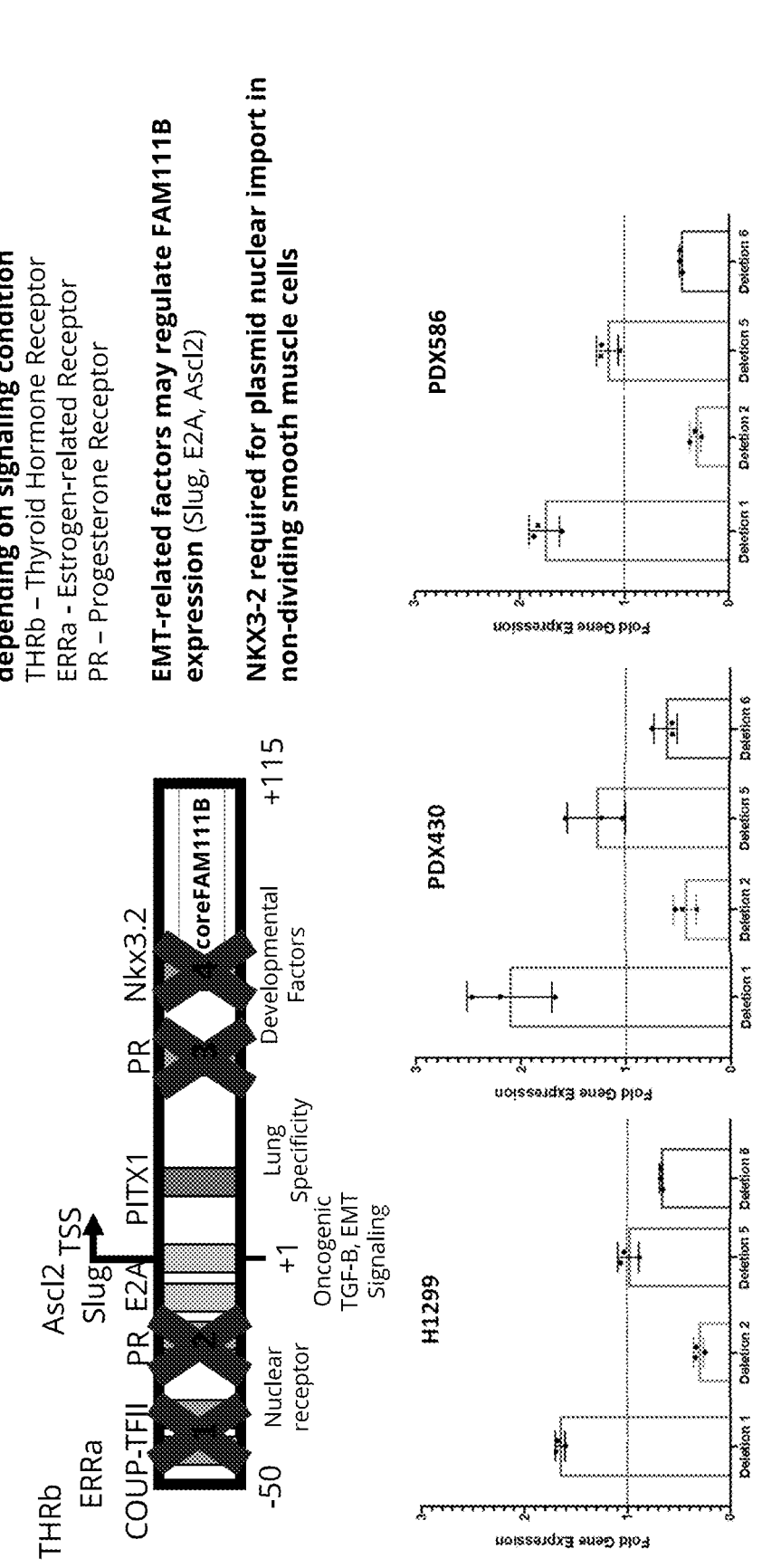

FIG. 64B

Top 10 Ranked Response Elements

| H1299 | | LXFA586 | | LXFL430 | |
|---|---|---|---|---|---|
| FOSL1_v1:CREB3L1-v6-2x2_v4 | 6.25 | NFKB1_v3 | 3.61 | TCF7_v2 | 6.62 |
| Control:FOSL1_v1 | 5.39 | TP53-v6:TCF7-v2-3x1_v3 | 2.85 | TCF7L1_v19 | 5.75 |
| Control:FOSL1-v1:CREB3L1-v6-3x1_v4 | 4.92 | HIF1A_v15 | 2.66 | TCF3_v14 | 5.25 |
| XBP1_v19 | 3.67 | TP53_v11 | 2.66 | TCF3_v9 | 4.40 |
| NFKB1_v3 | 3.17 | PROM1_v25 | 2.58 | MTF1_v9 | 4.22 |
| HIF1A_v15 | 2.95 | TCF12_v4 | 2.52 | TCF7-v6:TCF7L1-v19_v1 | 3.87 |
| CREB3L1-v6:Control:FOSL1-v4-2x2_v1 | 2.70 | ZFX_v3 | 2.44 | FOXO1::ELK3_v6 | 3.86 |
| FOXO1::ELK3_v15 | 2.57 | TP53_v6 | 2.44 | NFE2L2_v14 | 3.42 |
| XBP1_v13 | 2.47 | TP53-v6:HIF1A_v4 | 2.44 | Control:FOSL1-v1:CREB3L1-v6-3x1_v1 | 3.13 |
| XBP1_v10 | 2.42 | TP53_v6 | 2.44 | MTF1_v19 | 3.06 |

FOXO1 (Forkhead box protein O1) and ELK3 (ETS Transcription Factor ELK3)

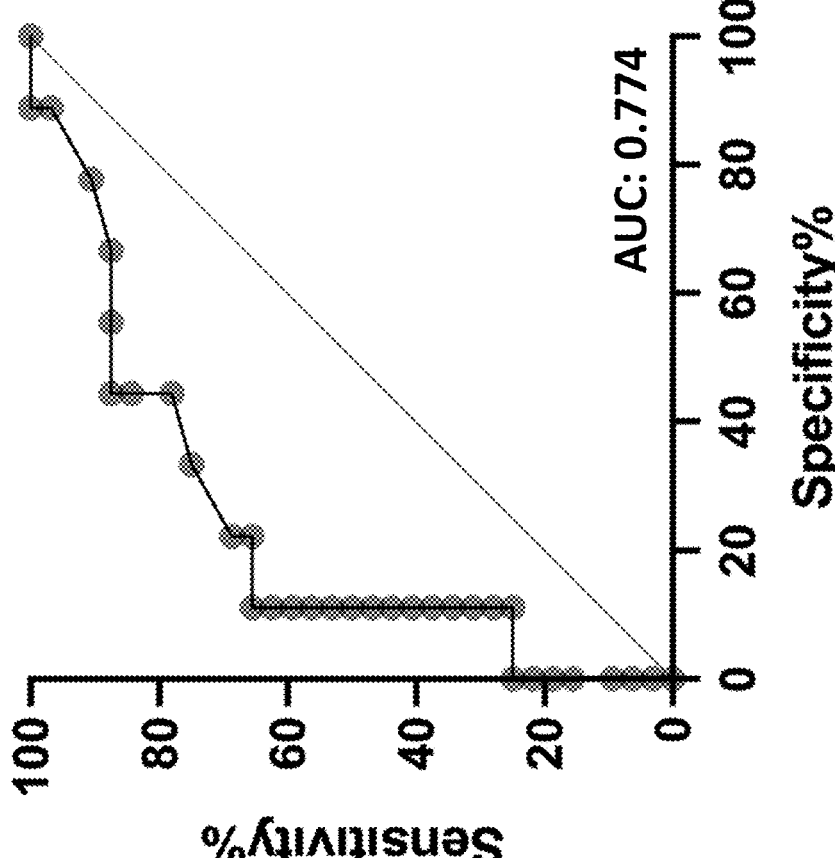
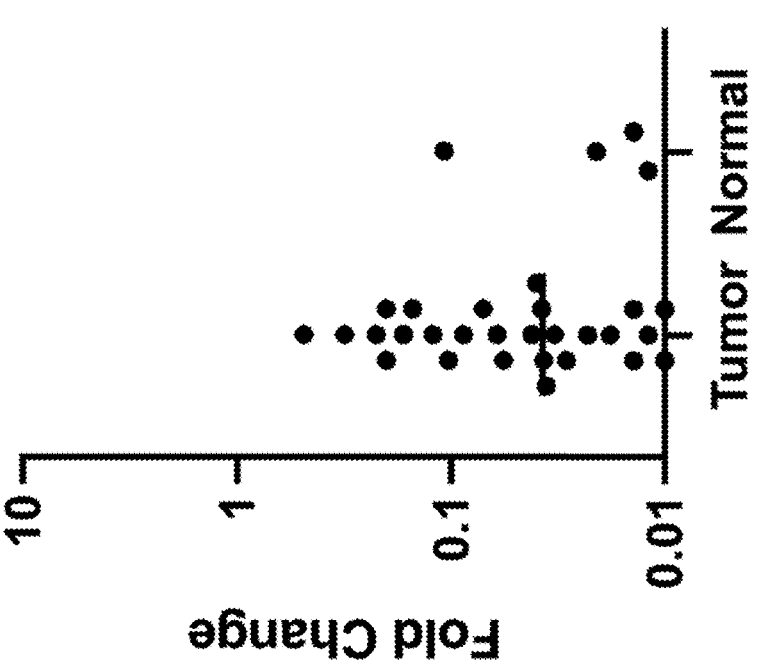
FIG. 74B

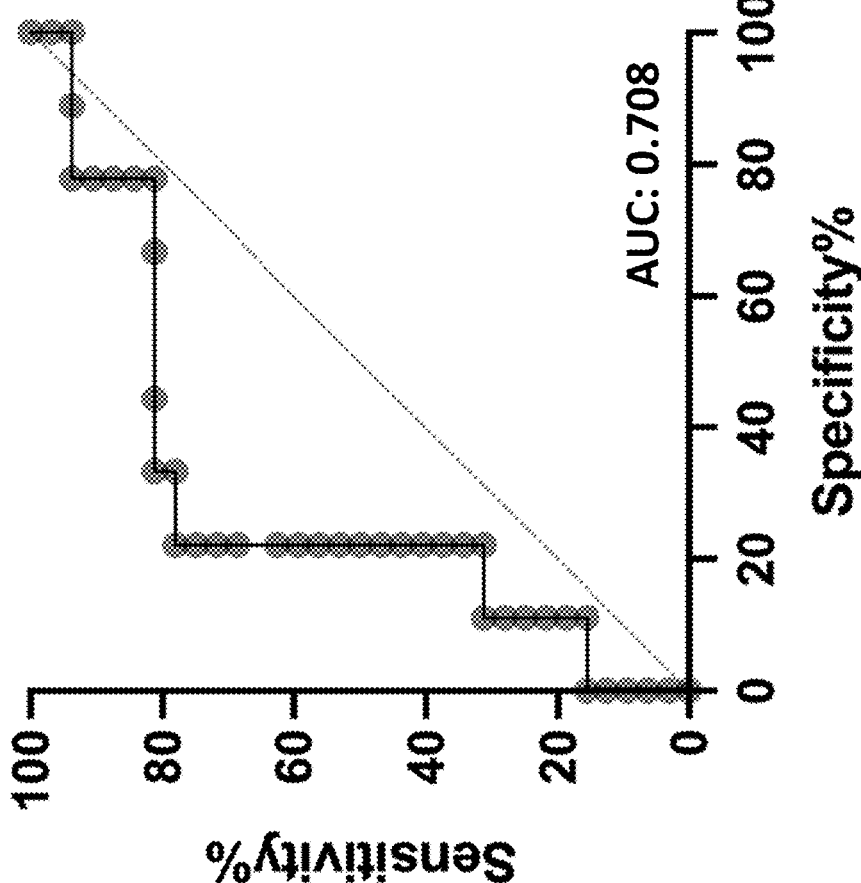
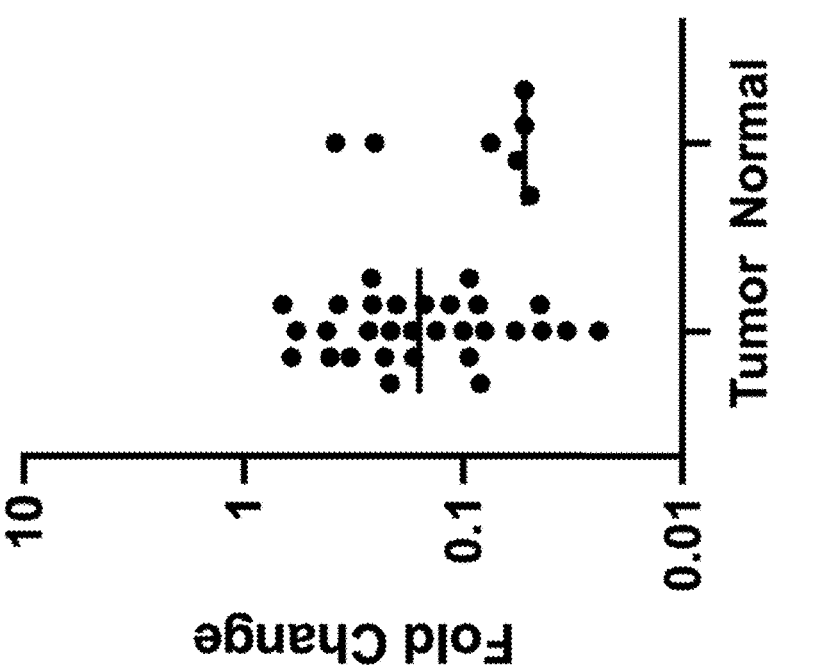
FIG. 74D

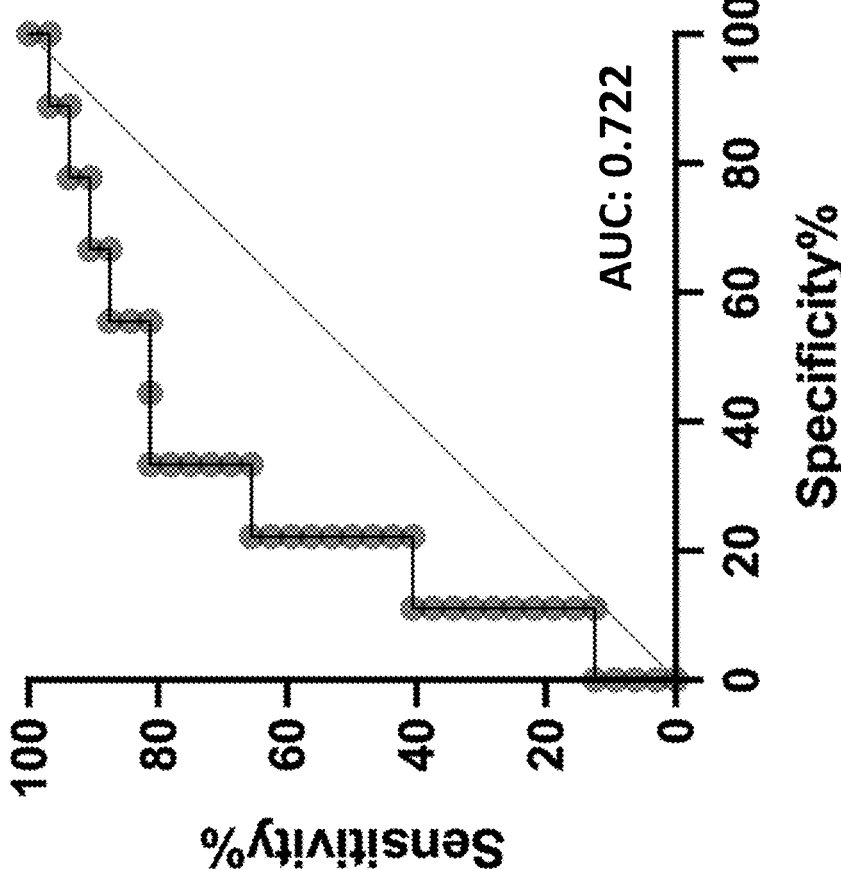
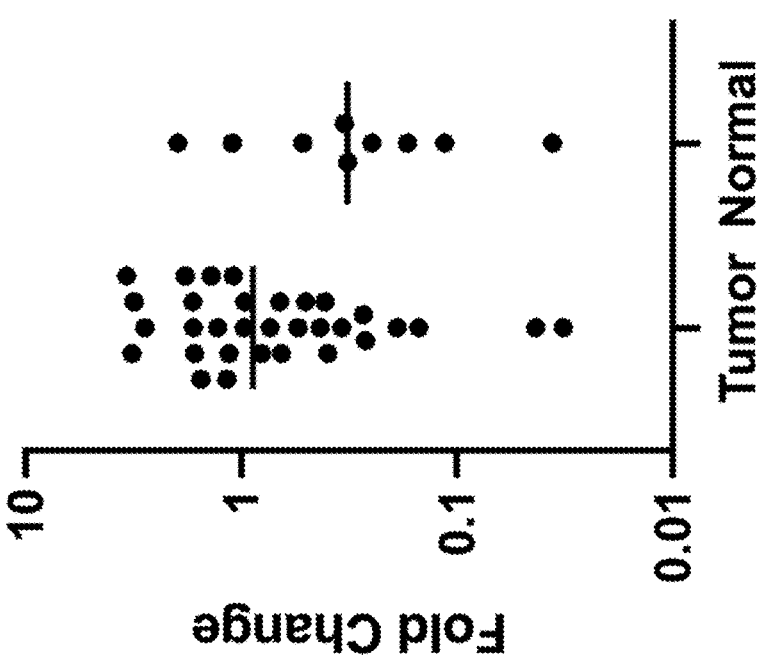
FIG. 74F

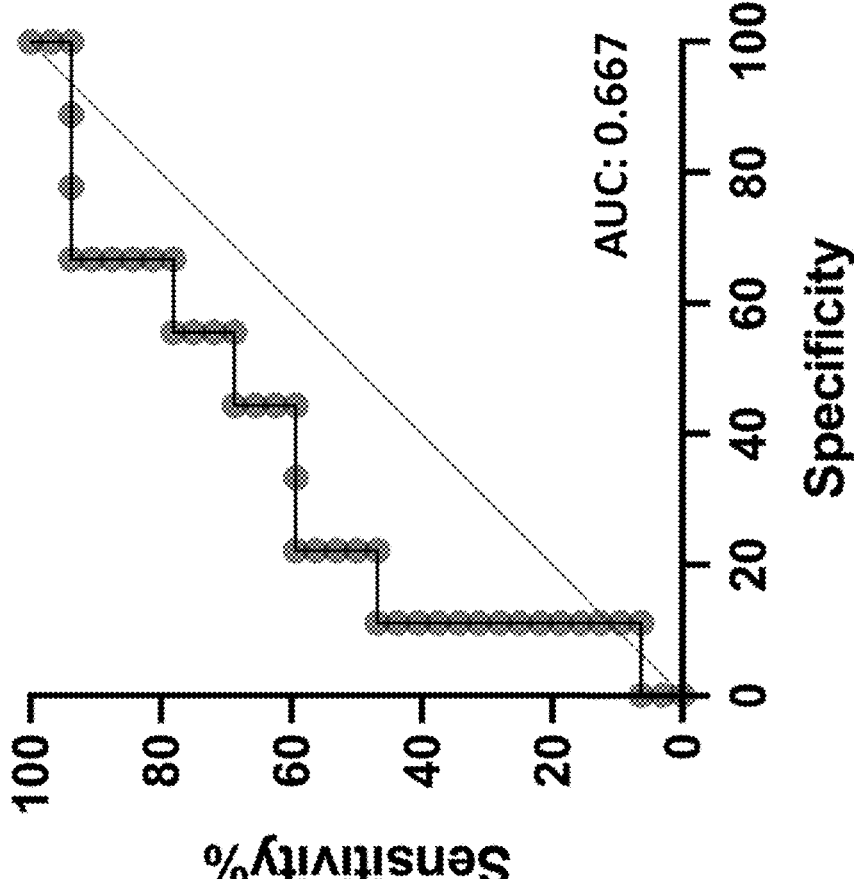
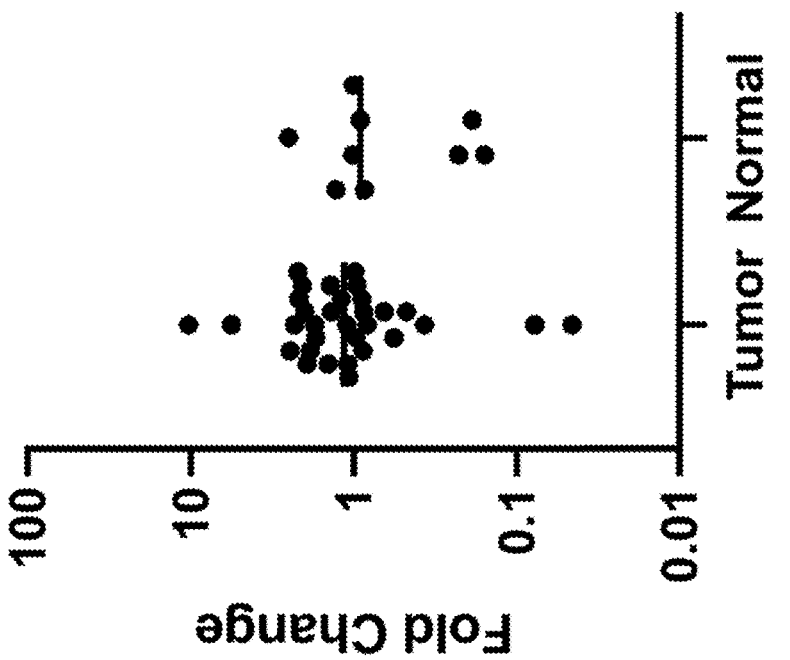
FIG. 74H

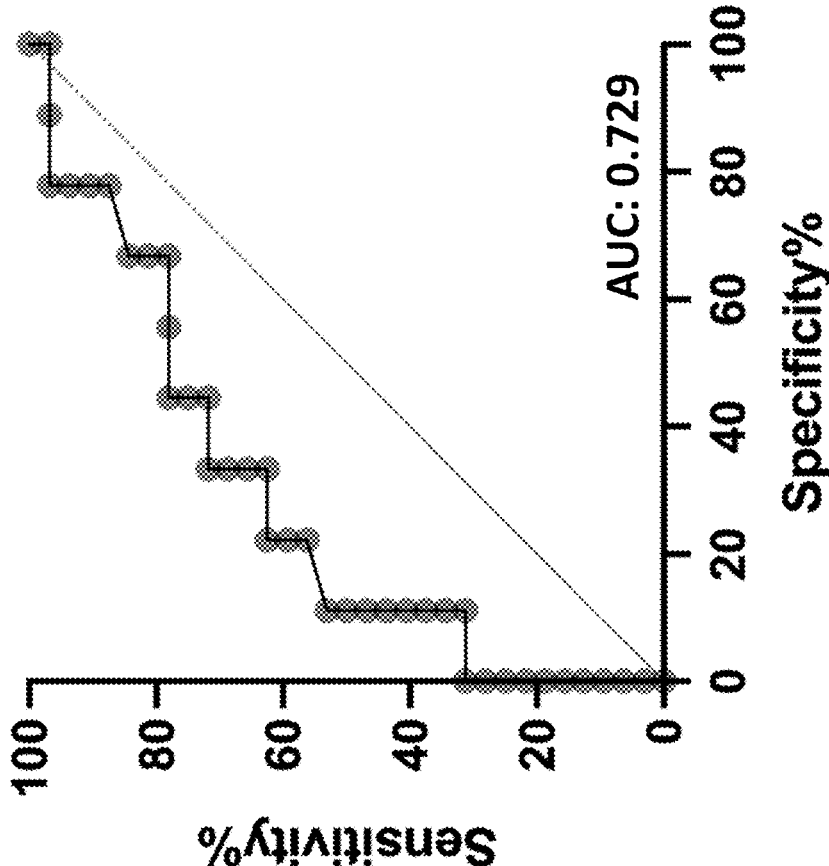
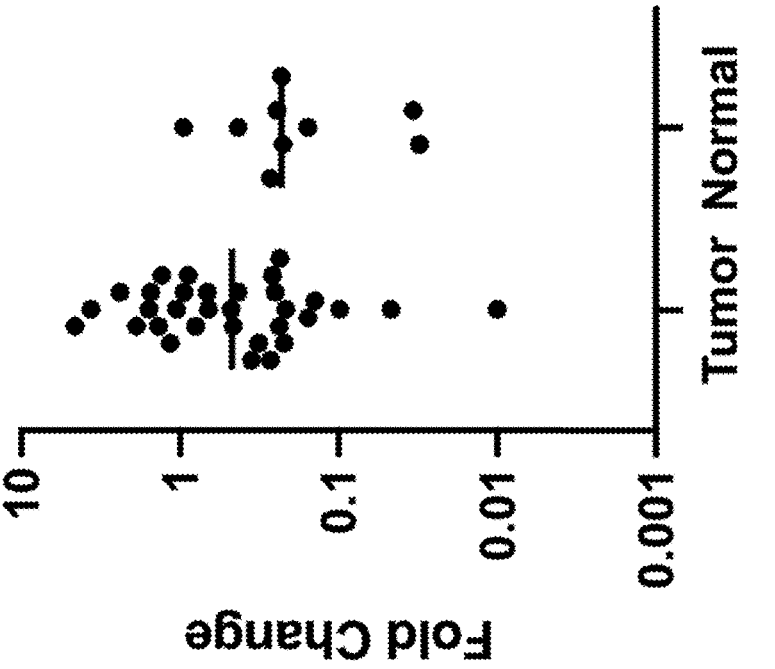
FIG. 74J

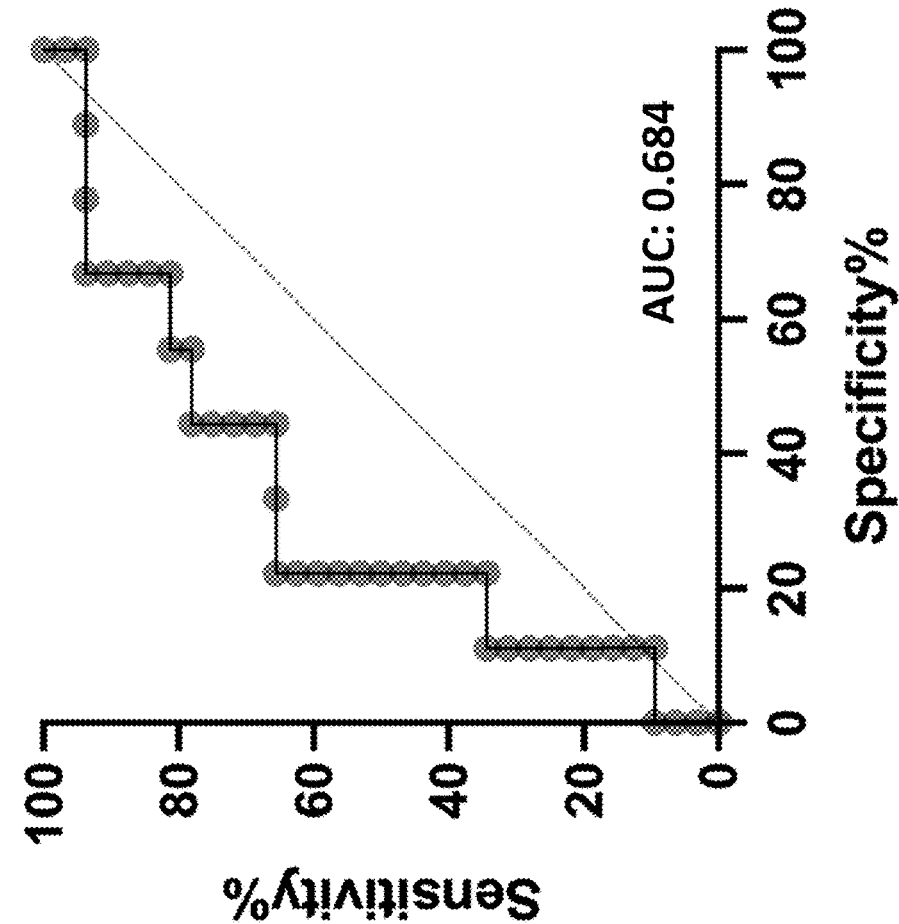
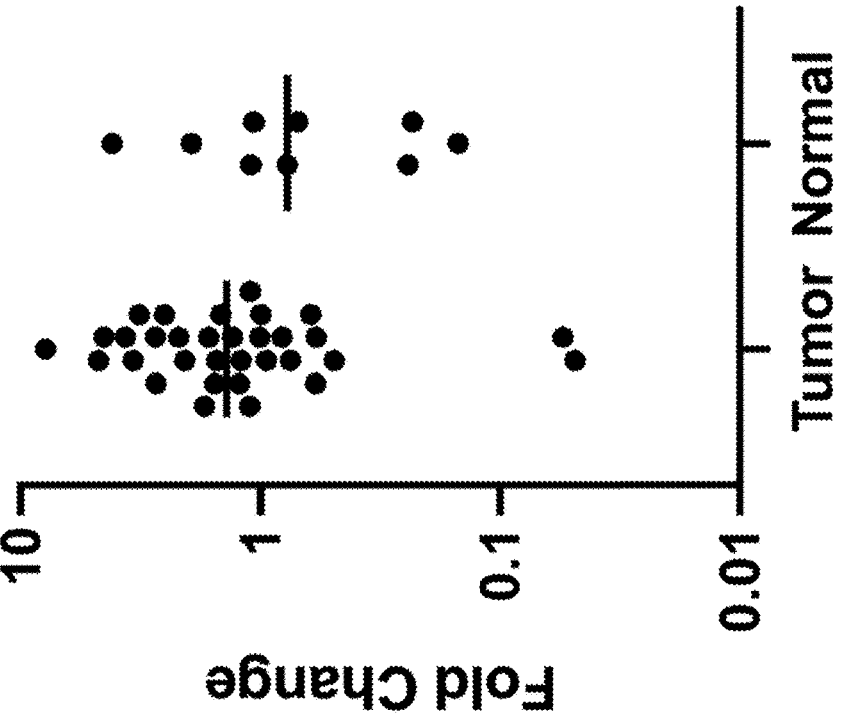
FIG. 74L

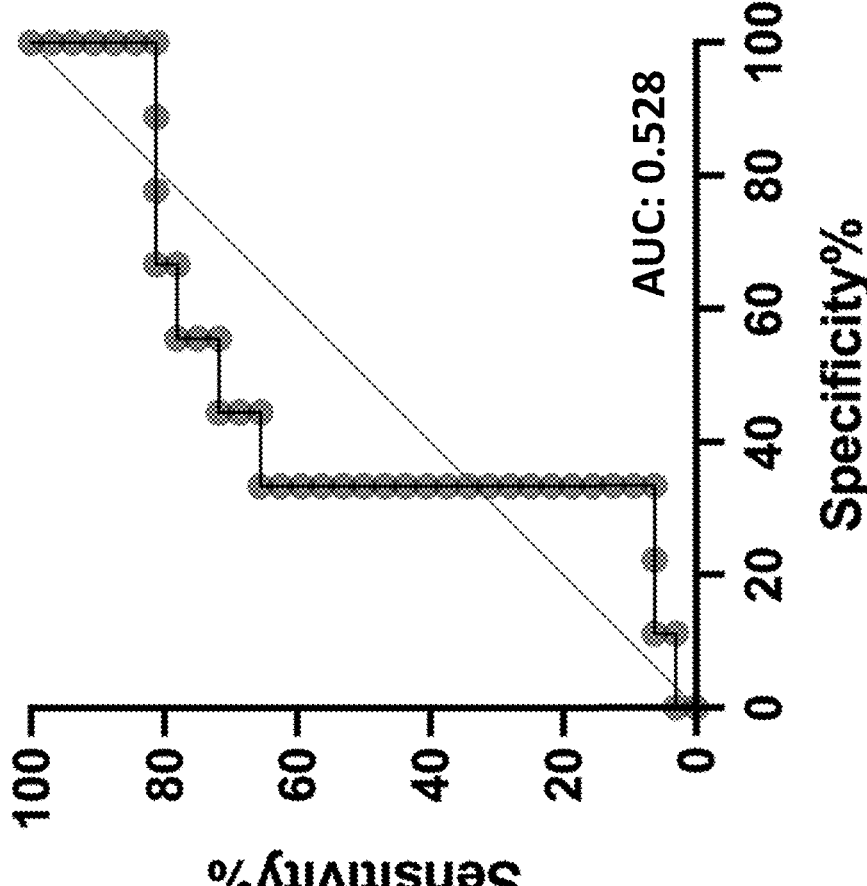
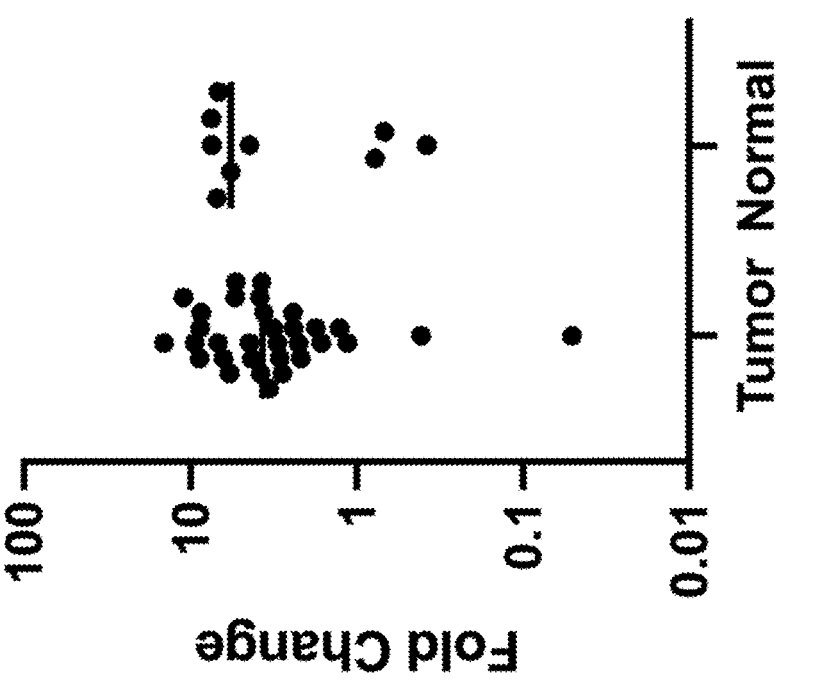
FIG. 75

SEQUENCE LISTING

```
Sequence total quantity: 587
SEQ ID NO: 1            moltype = DNA  length = 311
FEATURE                 Location/Qualifiers
source                  1..311
                        mol_type = other DNA
                        organism = synthetic construct
SEQUENCE: 1
ggcctaactg gccggtacca catcggctat gctgctgcta tgcgagcgtc agtattttat   60
ctttgatcag ctattttatc tttagtatcg tattttatct ttctcatcgt attttatctt  120
tatccgatta ttttatcttt cagcagttat tttatctttg gtacctgcgc tcccgacatg  180
ccccgcggcg cgccattaac cgccagattt gagtcgcggg acccgttggc agaggtgggc  240
tagcctcgag gatatcaaga tctggcctcg gcggccaagc ttggcaatcc ggtactgttg  300
gtaaagccac c                                                       311

SEQ ID NO: 2            moltype = DNA  length = 311
FEATURE                 Location/Qualifiers
source                  1..311
                        mol_type = other DNA
                        organism = synthetic construct
SEQUENCE: 2
ggcctaactg gccggtacca gctcatgcct atccgattag cttatctttt gaccagagct   60
agcttatctt tctaactcgc atagcttatc ttttgcaagc tactagctta tctttcgatg  120
ctcattagct tatctttaga cgtactctag cttatctttg gtacctgcgc tcccgacatg  180
ccccgcggcg cgccattaac cgccagattt gagtcgcggg acccgttggc agaggtgggc  240
tagcctcgag gatatcaaga tctggcctcg gcggccaagc ttggcaatcc ggtactgttg  300
gtaaagccac c                                                       311

SEQ ID NO: 3            moltype = DNA  length = 311
FEATURE                 Location/Qualifiers
source                  1..311
                        mol_type = other DNA
                        organism = synthetic construct
SEQUENCE: 3
ggcctaactg gccggtacca tcactgctga ggtacagatg cacgatgtag ctgagcgaca   60
gtatagtgca cagtgagtca ttatgatacg tgtcattatc accattgtca ttattagacg  120
tgtcattatc tgctatgtca ttatgctaca ggtcattatg gtacctgcgc tcccgacatg  180
```

```
cccccgcggcg cgccattaac cgccagattt gagtcgcggg acccgttggc agaggtgggc   240
tagcctcgag gatatcaaga tctggcctcg gcggccaagc ttggcaatcc ggtactgttg   300
gtaaagccac c                                                          311

SEQ ID NO: 4               moltype = DNA   length = 311
FEATURE                    Location/Qualifiers
source                     1..311
                           mol_type = other DNA
                           organism = synthetic construct
SEQUENCE: 4
ggcctaactg gccggtaccc agcagtcatt atacgtcgcc taaatcgaga tgctgtactg   60
atctatattc cagatgtttt caattccaga tgttttacat tccagatgtt ttacattcca   120
gatgtttctc attccagatg ttttgaattc cagatgtttg gtacctgcgc tcccgacatg   180
cccccgcggcg cgccattaac cgccagattt gagtcgcggg acccgttggc agaggtgggc   240
tagcctcgag gatatcaaga tctggcctcg gcggccaagc ttggcaatcc ggtactgttg   300
gtaaagccac c                                                          311

SEQ ID NO: 5               moltype = DNA   length = 311
FEATURE                    Location/Qualifiers
source                     1..311
                           mol_type = other DNA
                           organism = synthetic construct
SEQUENCE: 5
ggcctaactg gccggtaccc tgagcgacag tatagtgcac agtgacatta cagatgttta   60
cgacgaatta cagatgtttc tcatcgatta cagatgtttc agctcaatta cagatgtttg   120
ctgctgatta cagatgttta ccagagatta cagatgtttg gtacctgcgc tcccgacatg   180
cccccgcggcg cgccattaac cgccagattt gagtcgcggg acccgttggc agaggtgggc   240
tagcctcgag gatatcaaga tctggcctcg gcggccaagc ttggcaatcc ggtactgttg   300
gtaaagccac c                                                          311

SEQ ID NO: 6               moltype = DNA   length = 311
FEATURE                    Location/Qualifiers
source                     1..311
                           mol_type = other DNA
                           organism = synthetic construct
SEQUENCE: 6
ggcctaactg gccggtaccc gatgtagctg agcgacagta tagtgcacag tgactgcagc   60
agtcattata cgtcgcctaa atcgagatgc tgtactgatc tataaggatc ggtaatgacg   120
taatgacgta atgacgtaat gacgtaatga cgtacctgcgc tcccgacatg   180
cccccgcggcg cgccattaac cgccagattt gagtcgcggg acccgttggc agaggtgggc   240
tagcctcgag gatatcaaga tctggcctcg gcggccaagc ttggcaatcc ggtactgttg   300
gtaaagccac c                                                          311

SEQ ID NO: 7               moltype = DNA   length = 311
FEATURE                    Location/Qualifiers
source                     1..311
                           mol_type = other DNA
                           organism = synthetic construct
SEQUENCE: 7
ggcctaactg gccggtacca gctgagcgac agtatagtgc acagtgactg cagcagtcat   60
tatacgtcgc ctaaatcgag atgctgtact gatctataag tcgtaaactg tcgtaaactg   120
tcgtaaactg tcgtaaactg tcgtaaactg tcgtaaactg gtacctgcgc tcccgacatg   180
cccccgcggcg cgccattaac cgccagattt gagtcgcggg acccgttggc agaggtgggc   240
tagcctcgag gatatcaaga tctggcctcg gcggccaagc ttggcaatcc ggtactgttg   300
gtaaagccac c                                                          311

SEQ ID NO: 8               moltype = DNA   length = 311
FEATURE                    Location/Qualifiers
source                     1..311
                           mol_type = other DNA
                           organism = synthetic construct
SEQUENCE: 8
ggcctaactg gccggtacct gtagctgagc gacagtatag tgcacagtga ctgcagcagt   60
cattgtcgta aattgagtat cgtcgtaaat tgacgaacgt cgtaaattga cgacagtcgt   120
aaattagtac ctgtcgtaaa ttactctgcg tcgtaaattg gtacctgcgc tcccgacatg   180
cccccgcggcg cgccattaac cgccagattt gagtcgcggg acccgttggc agaggtgggc   240
tagcctcgag gatatcaaga tctggcctcg gcggccaagc ttggcaatcc ggtactgttg   300
gtaaagccac c                                                          311

SEQ ID NO: 9               moltype = DNA   length = 311
FEATURE                    Location/Qualifiers
source                     1..311
                           mol_type = other DNA
                           organism = synthetic construct
SEQUENCE: 9
ggcctaactg gccggtacca tccgatgtgc ctgacgaact catttctaat ctatcgatgt   60
agctttctaa tctatgcagt cattattcta atcattcgc aatctattct aatctatctt   120
ctaactcttc taatcattg ctacagcttt ctaatctatg gtacctgcgc tcccgacatg   180
cccccgcggcg cgccattaac cgccagattt gagtcgcggg acccgttggc agaggtgggc   240
```

```
tagcctcgag gatatcaaga tctggcctcg gcggccaagc ttggcaatcc ggtactgttg   300
gtaaagccac c                                                        311

SEQ ID NO: 10          moltype = DNA   length = 311
FEATURE                Location/Qualifiers
source                 1..311
                       mol_type = other DNA
                       organism = synthetic construct
SEQUENCE: 10
ggcctaactg gccggtaccg cacagtgact gcagcagtca ttatacgtcg cctaaatcga   60
gatgctgtac tgatctattt cttggcagat gattcttggc agatcgttct tggcagagca   120
ttcttggcag aggtttcttg gcagactctt cttggcagag gtacctgcgc tcccgacatg   180
ccccgcggcg cgccattaac cgccagattt gagtcgcggg accgttggc agaggtgggc    240
tagcctcgag gatatcaaga tctggcctcg gcggccaagc ttggcaatcc ggtactgttg   300
gtaaagccac c                                                        311

SEQ ID NO: 11          moltype = DNA   length = 311
FEATURE                Location/Qualifiers
source                 1..311
                       mol_type = other DNA
                       organism = synthetic construct
SEQUENCE: 11
ggcctaactg gccggtaccg tgcaccatta gtacctgatc agcgatgctc atctcgacct   60
gatcggtaca acttctcacg gaggcttcta actcgccgca attataacgc aattattccg   120
caattactac gcaattacct cgcaattaac tcgcaattag gtacctgcgc tcccgacatg   180
ccccgcggcg cgccattaac cgccagattt gagtcgcggg accgttggc agaggtgggc    240
tagcctcgag gatatcaaga tctggcctcg gcggccaagc ttggcaatcc ggtactgttg   300
gtaaagccac c                                                        311

SEQ ID NO: 12          moltype = DNA   length = 311
FEATURE                Location/Qualifiers
source                 1..311
                       mol_type = other DNA
                       organism = synthetic construct
SEQUENCE: 12
ggcctaactg gccggtacca catcggctat gctgctgcta atgccacgtc accacatcga   60
catgccacgt caccatcatg ccatgccacg tcaccactgc aagatgccac gtcaccacag   120
tataatgcca cgtcaccaag ttactatgcc acgtcaccag gtacctgcgc tcccgacatg   180
ccccgcggcg cgccattaac cgccagattt gagtcgcggg accgttggc agaggtgggc    240
tagcctcgag gatatcaaga tctggcctcg gcggccaagc ttggcaatcc ggtactgttg   300
gtaaagccac c                                                        311

SEQ ID NO: 13          moltype = DNA   length = 311
FEATURE                Location/Qualifiers
source                 1..311
                       mol_type = other DNA
                       organism = synthetic construct
SEQUENCE: 13
ggcctaactg gccggtaccc cccaaatcac cccccccca ccgtaaagtc cccaaatcac    60
cccccccca aggtaagacc cccaaatcac cccccccc gtcgcctaac cccaaatcac      120
ccccccct actctgctcc cccaaatcac cccccccc gtacctgcgc tcccgacatg       180
ccccgcggcg cgccattaac cgccagattt gagtcgcggg accgttggc agaggtgggc    240
tagcctcgag gatatcaaga tctggcctcg gcggccaagc ttggcaatcc ggtactgttg   300
gtaaagccac c                                                        311

SEQ ID NO: 14          moltype = DNA   length = 311
FEATURE                Location/Qualifiers
source                 1..311
                       mol_type = other DNA
                       organism = synthetic construct
SEQUENCE: 14
ggcctaactg gccggtaccg accgtaaagt ggtgtgcacc attgaaactt gagcttacac   60
catcgaaact tgagcgtatc gcatcgaaac ttgagcggta cagatggaaa cttgagcacc   120
attagtagaa acttgagcag cgacagtaga aacttgagcg gtacctgcgc tcccgacatg   180
ccccgcggcg cgccattaac cgccagattt gagtcgcggg accgttggc agaggtgggc    240
tagcctcgag gatatcaaga tctggcctcg gcggccaagc ttggcaatcc ggtactgttg   300
gtaaagccac c                                                        311

SEQ ID NO: 15          moltype = DNA   length = 311
FEATURE                Location/Qualifiers
source                 1..311
                       mol_type = other DNA
                       organism = synthetic construct
SEQUENCE: 15
ggcctaactg gccggtacct gcacagtgac tgcagcagtc gggcgtgcgc tcccgactag   60
cccagggcgt gcgctcccga ctagccccgg gcgtgcgctc cgactagccc ctgggcgtgc   120
gctcccgact agccccgggc gtgcgctccc gactagcccg gtacctgcgc tcccgacatg   180
ccccgcggcg cgccattaac cgccagattt gagtcgcggg accgttggc agaggtgggc    240
tagcctcgag gatatcaaga tctggcctcg gcggccaagc ttggcaatcc ggtactgttg   300
```

```
gtaaagccac c                                                            311

SEQ ID NO: 16              moltype = DNA   length = 311
FEATURE                    Location/Qualifiers
source                     1..311
                           mol_type = other DNA
                           organism = synthetic construct
SEQUENCE: 16
ggcctaactg gccggtacca ggatcgacta gaagtcgcag attagacgac gatacgtact       60
actctgctcc tagacgtatc ctttgatgta aatcctttga tgtcaatcct ttgatgttaa      120
tcctttgatg ttagtccttt gatgtctgtc ctttgatgtg gtacctgcgc tcccgacatg      180
ccccgcggcg cgccattaac cgccagattt gagtcgcggg acccgttggc agaggtgggc      240
tagcctcgag gatatcaaga tctggcctcg gcggccaagc ttggcaatcc ggtactgttg      300
gtaaagccac c                                                            311

SEQ ID NO: 17              moltype = DNA   length = 311
FEATURE                    Location/Qualifiers
source                     1..311
                           mol_type = other DNA
                           organism = synthetic construct
SEQUENCE: 17
ggcctaactg gccggtacct gagcgacagt atagtgcaca gtgactgcag cagtcattat       60
acgtcgccta aaagacatca aaggtccaga catcaaaggt acagacatca aaggggaaga      120
catcaaaggg acagacatca aaggtgcaga catcaaaggg gtacctgcgc tcccgacatg      180
ccccgcggcg cgccattaac cgccagattt gagtcgcggg acccgttggc agaggtgggc      240
tagcctcgag gatatcaaga tctggcctcg gcggccaagc ttggcaatcc ggtactgttg      300
gtaaagccac c                                                            311

SEQ ID NO: 18              moltype = DNA   length = 311
FEATURE                    Location/Qualifiers
source                     1..311
                           mol_type = other DNA
                           organism = synthetic construct
SEQUENCE: 18
ggcctaactg gccggtacca tgcacgatgt agctgagaaa catcaaagga cgcaacgcca       60
aacatcaaag gagcctacac gaaacatcaa agggacgctg ctaaaacatc aaaggctaca      120
cgaccaaaca tcaaagggcc ttacaccaaa catcaaaggg gtacctgcgc tcccgacatg      180
ccccgcggcg cgccattaac cgccagattt gagtcgcggg acccgttggc agaggtgggc      240
tagcctcgag gatatcaaga tctggcctcg gcggccaagc ttggcaatcc ggtactgttg      300
gtaaagccac c                                                            311

SEQ ID NO: 19              moltype = DNA   length = 298
FEATURE                    Location/Qualifiers
source                     1..298
                           mol_type = other DNA
                           organism = synthetic construct
SEQUENCE: 19
gaattctagt gcacagtgac tgcagcaatg ccacgtcaac atcatgccat gccacgtcaa       60
cacctacaca tgccacgtca acaaccagag atgccacgtc aacactagca tatgccacgt      120
caacataagg atatgccacg tcaacaggta cctgcgctcc cgacatgccc cgcggcgcgc      180
cattaaccgc cagatttgag tcgcgggacc cgttggcaga ggtgggctag cctcgaggat      240
atcaagatct ggcctcggcg gccaagcttg caatccggt actgttggta aagccacc         298

SEQ ID NO: 20              moltype = DNA   length = 298
FEATURE                    Location/Qualifiers
source                     1..298
                           mol_type = other DNA
                           organism = synthetic construct
SEQUENCE: 20
gaattcgtgc accattagta cctgatcagc gatgctcatc tcgacctgat cggtacaact       60
tctcacggag gcttctaact cgccgcaatt ataacgcaat tattccgcaa ttactacgca      120
attacctcgc aattaactcg caattaggta cctgcgctcc cgacatgccc cgcggcgcgc      180
cattaaccgc cagatttgag tcgcgggacc cgttggcaga ggtgggctag cctcgaggat      240
atcaagatct ggcctcggcg gccaagcttg caatccggt actgttggta aagccacc         298

SEQ ID NO: 21              moltype = DNA   length = 315
FEATURE                    Location/Qualifiers
source                     1..315
                           mol_type = other DNA
                           organism = synthetic construct
SEQUENCE: 21
ggcctaacga attcgacgct gctacagctc agcctacacg accgtaaagt ggtgtgcaca       60
ccggaaatga gtatagaccg gaaatggcct tacaccggaa atgcagctca accggaaatg      120
actgcagacc ggaaatgcgc tgctaccgga aatgggtacc tgcgctcccg acatgcccg      180
cggcgcgcca ttaaccgcca gatttgagtc gcgggacccg ttggcagagg tgggctagcc      240
tcgaggatat caagatctgg cctcggcggc caagcttggc aatccggtac tgttggtaaa      300
gccaccatgg tggcc                                                        315

SEQ ID NO: 22              moltype = DNA   length = 311
```

-continued

```
FEATURE            Location/Qualifiers
source             1..311
                   mol_type = other DNA
                   organism = synthetic construct
SEQUENCE: 22
ggcctaactg gccgaattct gagcgacagt atagtgcaca gtgactgcag cagtcattat    60
acgtaccgga agtgtgtgcc taccggaagt gctatgcgac cggaagtgta gacgaaccgg   120
aagtgcagat taaccggaag tggctgctaa ccggaagtgg gtacctgcgc tcccgacatg   180
ccccgcggcg cgccattaac cgccagattt gagtcgcggg acccgttggc agaggtgggc   240
tagcctcgag gatatcaaga tctggcctcg gcggccaagc ttggcaatcc ggtactgttg   300
gtaaagccac c                                                        311

SEQ ID NO: 23         moltype = DNA  length = 298
FEATURE            Location/Qualifiers
source             1..298
                   mol_type = other DNA
                   organism = synthetic construct
SEQUENCE: 23
gaattcgtgc accattagta cctgatcagc gatgctcatc tcgacctgat cggtacaact    60
tctcacggag gcttctaact cgccgcaatt ataacgcaat tattccgcaa ttactacgca   120
attacctcgc aattaactcg caattaggta cctgcgctcc cgacatgccc cgcggcgcgc   180
cattaaccgc cagatttgag tcgcgggacc cgttggcaga ggtgggctag cctcgaggat   240
atcaagatct ggcctcggcg gccaagcttg caatccggt actgttggta aagccacc      298

SEQ ID NO: 24         moltype = DNA  length = 298
FEATURE            Location/Qualifiers
source             1..298
                   mol_type = other DNA
                   organism = synthetic construct
SEQUENCE: 24
gaattcgtca ttatacgtcg cgtcatgcat gactgcctga gcggtcatgc atgactgcta    60
ctcaagtcat gcatgactgc gaccagagtc atgcatgact gccgcctaag tcatgcatga   120
ctgcctctgc tgtcatgcat gactgcggta cctgcgctcc cgacatgccc cgcggcgcgc   180
cattaaccgc cagatttgag tcgcgggacc cgttggcaga ggtgggctag cctcgaggat   240
atcaagatct ggcctcggcg gccaagcttg gcaatccggt actgttggta aagccacc     298

SEQ ID NO: 25         moltype = DNA  length = 298
FEATURE            Location/Qualifiers
source             1..298
                   mol_type = other DNA
                   organism = synthetic construct
SEQUENCE: 25
gaattcaagt cgcagattag acgacgatac gtactactct gctcctagac gtactcaagt    60
atattaatcc agtgaccatt aatccactca tgcttaatcc aataactgtt aatccagtat   120
cgcttaatcc actacagctt aatccaggta cctgcgctcc cgacatgccc cgcggcgcgc   180
cattaaccgc cagatttgag tcgcgggacc cgttggcaga ggtgggctag cctcgaggat   240
atcaagatct ggcctcggcg gccaagcttg gcaatccggt actgttggta aagccacc     298

SEQ ID NO: 26         moltype = DNA  length = 311
FEATURE            Location/Qualifiers
source             1..311
                   mol_type = other DNA
                   organism = synthetic construct
SEQUENCE: 26
ggcctaactg gccgaattcc agatgcacga tgtagctgag cgacagtaaa ctgtaacctg    60
atacagcaac tgtaacctga taccctaact gtaacctgat acgataactg taacctgata   120
caaaaactgt aacctgatac ggcaactgta acctgatacg gtacctgcgc tcccgacatg   180
ccccgcggcg cgccattaac cgccagattt gagtcgcggg acccgttggc agaggtgggc   240
tagcctcgag gatatcaaga tctggcctcg gcggccaagc ttggcaatcc ggtactgttg   300
gtaaagccac c                                                        311

SEQ ID NO: 27         moltype = DNA  length = 311
FEATURE            Location/Qualifiers
source             1..311
                   mol_type = other DNA
                   organism = synthetic construct
SEQUENCE: 27
ggcctaactg gccgaattcg actgcagcag tcattatacg tcgcctaaat cggagaacaa    60
aggatggtgt ggagaacaaa ggataactga gagaacaaag gaaggatcgg agaacaaagg   120
aactgctgga gaacaaagga tatagtggag aacaaaggag gtacctgcgc tcccgacatg   180
ccccgcggcg cgccattaac cgccagattt gagtcgcggg acccgttggc agaggtgggc   240
tagcctcgag gatatcaaga tctggcctcg gcggccaagc ttggcaatcc ggtactgttg   300
gtaaagccac c                                                        311

SEQ ID NO: 28         moltype = DNA  length = 311
FEATURE            Location/Qualifiers
source             1..311
                   mol_type = other DNA
                   organism = synthetic construct
```

```
SEQUENCE: 28
ggcctaactg gccgaattcc tgagcgacag tatagtgcac agtgactgca gcagtcattc     60
ctttgatgta cgcaactcct ttgatgtcta tgcgtccttt gatgttaagg attcctttga    120
tgtaggtaca tcctttgatg tccgtaaatc ctttgatgtg gtacctgcgc tcccgacatg    180
ccccgcggcg cgccattaac cgccagattt gagtcgcggg acccgttggc agaggtgggc    240
tagcctcgag gatatcaaga tctggcctcg gcggccaagc ttggcaatcc ggtactgttg    300
gtaaagccac c                                                          311

SEQ ID NO: 29           moltype = DNA  length = 298
FEATURE                 Location/Qualifiers
source                  1..298
                        mol_type = other DNA
                        organism = synthetic construct
SEQUENCE: 29
gaattcagga tcgactagaa gtcgcagatt agacgacgat acgtactact ctgctcctag     60
acgtatcctt tgatgtaaat cctttgatgt caatcctttg atgttaatcc tttgatgtta    120
gtcctttgat gtctgtcctt tgatgtggta cctgcgctcc cgacatgccc cgcggcgcgc    180
cattaaccgc cagatttgag tcgcgggacc cgttggcaga ggtgggctag cctcgaggat    240
atcaagatct ggcctcggcg gccaagcttg gcaatccggt actgttggta aagccacc      298

SEQ ID NO: 30           moltype = DNA  length = 311
FEATURE                 Location/Qualifiers
source                  1..311
                        mol_type = other DNA
                        organism = synthetic construct
SEQUENCE: 30
ggcctaactg gccgaattcc aagactgcaa gctacgtgtg accagagccg ataactgagg     60
gcgggaacgc gcaacggggc gggaacgatg ctgtgggcgg gaacgacagc tcgggcggga    120
acgctctgct gggcgggaac ggctcctagg gcgggaacgg gtacctgcgc tcccgacatg    180
ccccgcggcg cgccattaac cgccagattt gagtcgcggg acccgttggc agaggtgggc    240
tagcctcgag gatatcaaga tctggcctcg gcggccaagc ttggcaatcc ggtactgttg    300
gtaaagccac c                                                          311

SEQ ID NO: 31           moltype = DNA  length = 298
FEATURE                 Location/Qualifiers
source                  1..298
                        mol_type = other DNA
                        organism = synthetic construct
SEQUENCE: 31
gaattcagga tcgactagaa gtcgcagatt agacgacgat acgtactact ctgctcctag     60
acgtatcctt tgatgtaaat cctttgatgt caatcctttg atgttaatcc tttgatgtta    120
gtcctttgat gtctgtcctt tgatgtggta cctgcgctcc cgacatgccc cgcggcgcgc    180
cattaaccgc cagatttgag tcgcgggacc cgttggcaga ggtgggctag cctcgaggat    240
atcaagatct ggcctcggcg gccaagcttg gcaatccggt actgttggta aagccacc      298

SEQ ID NO: 32           moltype = DNA  length = 298
FEATURE                 Location/Qualifiers
source                  1..298
                        mol_type = other DNA
                        organism = synthetic construct
SEQUENCE: 32
gaattcaggt aagtttcccg ccaaaatgtg accagagttt cccgccaaaa tgacgaactc     60
gtttcccgcc aaaaatgtag ctgagtttcc cgccaaaaca tagttactgt ttcccgccaa    120
aacctaaatc gagtttcccg ccaaaaggta cctgcgctcc cgacatgccc cgcggcgcgc    180
cattaaccgc cagatttgag tcgcgggacc cgttggcaga ggtgggctag cctcgaggat    240
atcaagatct ggcctcggcg gccaagcttg gcaatccggt actgttggta aagccacc      298

SEQ ID NO: 33           moltype = DNA  length = 298
FEATURE                 Location/Qualifiers
source                  1..298
                        mol_type = other DNA
                        organism = synthetic construct
SEQUENCE: 33
gaattctgct atgcgagcgt cagctcatgc ctatccgatg tgcctatgta aacataagag     60
ccgatgtaaa catataagga tatgtaaaca tatagacgaa tgtaaacata gaggtacatg    120
taaacataac acgacatgta aacataggta cctgcgctcc cgacatgccc cgcggcgcgc    180
cattaaccgc cagatttgag tcgcgggacc cgttggcaga ggtgggctag cctcgaggat    240
atcaagatct ggcctcggcg gccaagcttg gcaatccggt actgttggta aagccacc      298

SEQ ID NO: 34           moltype = DNA  length = 298
FEATURE                 Location/Qualifiers
source                  1..298
                        mol_type = other DNA
                        organism = synthetic construct
SEQUENCE: 34
gaattctaca gctcagccta cacgaccgta aagtggtgtg caccattgac cccccacaaa     60
gcaggacccc ccacaaagcg agacccccca caaaggacga cccccacaa agcctgaccc    120
cccacaaaga gtgacccccc acaaagggta cctgcgctcc cgacatgccc cgcggcgcgc    180
cattaaccgc cagatttgag tcgcgggacc cgttggcaga ggtgggctag cctcgaggat    240
```

```
atcaagatct ggcctcggcg gccaagcttg gcaatccggt actgttggta aagccacc        298

SEQ ID NO: 35            moltype = DNA   length = 298
FEATURE                  Location/Qualifiers
source                   1..298
                         mol_type = other DNA
                         organism = synthetic construct
SEQUENCE: 35
gaattcaagg tagacccccc actaagctca agtatagacc ccccactaag atagtgcaca        60
gacccccac taagtatccg atgtgacccc ccactaagcg caacgcctga cccccactca        120
agtcctagac gtgaccccc actaagggta cctgcgctcc cgacatgccc cgcggcgcgc        180
cattaaccgc cagatttgag tcgcgggacc cgttggcaga ggtgggctag cctcgaggat        240
atcaagatct ggcctcggcg gccaagcttg gcaatccggt actgttggta aagccacc        298

SEQ ID NO: 36            moltype = DNA   length = 298
FEATURE                  Location/Qualifiers
source                   1..298
                         mol_type = other DNA
                         organism = synthetic construct
SEQUENCE: 36
gaattcaact gagtatcgca tcgctcaaga tcagtggtca taaattagca gtcattgtca        60
taaattcctg atcggtgtca taaattgcct aaatcggtca taaattcagc tcatgcgtca        120
taaattacgc tgctacgtca taaattggta cctgcgctcc cgacatgccc cgcggcgcgc        180
cattaaccgc cagatttgag tcgcgggacc cgttggcaga ggtgggctag cctcgaggat        240
atcaagatct ggcctcggcg gccaagcttg gcaatccggt actgttggta aagccacc        298

SEQ ID NO: 37            moltype = DNA   length = 298
FEATURE                  Location/Qualifiers
source                   1..298
                         mol_type = other DNA
                         organism = synthetic construct
SEQUENCE: 37
gaattcagta tagtgcacag tgactgcagc agtcattata cgtcgccggg gtcaaaggtc        60
accaggggtc aaaggtcatc tggggtcaaa ggtcattagg ggtcaaaggt catgggggt        120
caaaggtcac gagggggtcaa aggtcaggta cctgcgctcc cgacatgccc cgcggcgcgc        180
cattaaccgc cagatttgag tcgcgggacc cgttggcaga ggtgggctag cctcgaggat        240
atcaagatct ggcctcggcg gccaagcttg gcaatccggt actgttggta aagccacc        298

SEQ ID NO: 38            moltype = DNA   length = 297
FEATURE                  Location/Qualifiers
source                   1..297
                         mol_type = other DNA
                         organism = synthetic construct
SEQUENCE: 38
aattcacatc ggctatgctg ctgctacagg tcaaaggtca ttagacgcag gtcaaaggtc        60
acacagtgca ggtcaaaggt caaggtacac aggtcaaagg tcactgacga caggtcaaag        120
gtcactcatc tcaggtcaaa ggtcaggtac ctgcgctcc gacatgcccc gcggcgcgc        180
attaaccgcc agatttgagt cgcgggaccc gttggcagag gtgggctagc ctcgaggata        240
tcaagatctg gcctcggcgg ccaagcttgg caatccggta ctgttggtaa agccacc        297

SEQ ID NO: 39            moltype = DNA   length = 298
FEATURE                  Location/Qualifiers
source                   1..298
                         mol_type = other DNA
                         organism = synthetic construct
SEQUENCE: 39
gaattctgca ccattagtac ctgatcagcg atgctatttt ggcgcccaaa tcatattttg        60
gcgcccaaat gacatttggg cgcccaaata caattttggc gcccaaatac gattttggcg        120
cccaaatagc attttggcgc ccaaatggta cctgcgctcc cgacatgccc cgcggcgcgc        180
cattaaccgc cagatttgag tcgcgggacc cgttggcaga ggtgggctag cctcgaggat        240
atcaagatct ggcctcggcg gccaagcttg gcaatccggt actgttggta aagccacc        298

SEQ ID NO: 40            moltype = DNA   length = 298
FEATURE                  Location/Qualifiers
source                   1..298
                         mol_type = other DNA
                         organism = synthetic construct
SEQUENCE: 40
gaattcggta caacttctca cggaggcttt tggcgccatt tcgacgattt ttggcgccat        60
ttactcaagt tttggcgcca tttttagtgca tttttggcgcc atttcgcaat cttttggcgc        120
catttggagg cttttttggcg ccatttggta cctgcgctcc cgacatgccc cgcggcgcgc        180
cattaaccgc cagatttgag tcgcgggacc cgttggcaga ggtgggctag cctcgaggat        240
atcaagatct ggcctcggcg gccaagcttg gcaatccggt actgttggta aagccacc        298

SEQ ID NO: 41            moltype = DNA   length = 298
FEATURE                  Location/Qualifiers
source                   1..298
                         mol_type = other DNA
                         organism = synthetic construct
```

```
SEQUENCE: 41
gaattcacga tacgtactac tctgctccta gacgtactca agtataaggt aagacatagt   60
taccgcaatt ataagacacg caattactag aagcgcaatt aacgtcgccg caattagact  120
gcacgcaatt agaatctccg caattaggta cctgcgctcc cgacatgccc cgcggcgcgc  180
cattaaccgc cagatttgag tcgcgggacc cgttggcaga ggtgggctag cctcgaggat  240
atcaagatct ggcctcggcg gccaagcttg gcaatccggt actgttggta aagccacc    298

SEQ ID NO: 42            moltype = DNA   length = 298
FEATURE                  Location/Qualifiers
source                   1..298
                         mol_type = other DNA
                         organism = synthetic construct
SEQUENCE: 42
gaattcaagt ataatgtaaa cacggcagca tcgtccaatg taaacacggc aagacatagt   60
aatgtaaaca cggctctcac ggagaatgta aacacggcct agcatcgtaa tgtaaacacg  120
gcgatgctca tcaatgtaaa cacggcggta cctgcgctcc cgacatgccc cgcggcgcgc  180
cattaaccgc cagatttgag tcgcgggacc cgttggcaga ggtgggctag cctcgaggat  240
atcaagatct ggcctcggcg gccaagcttg gcaatccggt actgttggta aagccacc    298

SEQ ID NO: 43            moltype = DNA   length = 298
FEATURE                  Location/Qualifiers
source                   1..298
                         mol_type = other DNA
                         organism = synthetic construct
SEQUENCE: 43
gaattcaagt cgcagattag acgaaaaacc ggttatgacg tactcaaaaa ccggttatga   60
gatgctgtaa aaccggttat tccgacgcaa aaaaccggtt atacgaactc ataaaaccgg  120
ttatagctca gcctaaaacc ggttatggta cctgcgctcc cgacatgccc cgcggcgcgc  180
cattaaccgc cagatttgag tcgcgggacc cgttggcaga ggtgggctag cctcgaggat  240
atcaagatct ggcctcggcg gccaagcttg gcaatccggt actgttggta aagccacc    298

SEQ ID NO: 44            moltype = DNA   length = 298
FEATURE                  Location/Qualifiers
source                   1..298
                         mol_type = other DNA
                         organism = synthetic construct
SEQUENCE: 44
gaattctgac tgcagcagtc attatacgtc gcctaaatcg agatgctgta cgtcgtaaat   60
tcacgaccgt cgtaaattcg ataacgtcgt aaattctagc atgtcgtaaa tttgcagcag  120
tcgtaaatta gattaggtcg taaattggta cctgcgctcc cgacatgccc cgcggcgcgc  180
cattaaccgc cagatttgag tcgcgggacc cgttggcaga ggtgggctag cctcgaggat  240
atcaagatct ggcctcggcg gccaagcttg gcaatccggt actgttggta aagccacc    298

SEQ ID NO: 45            moltype = DNA   length = 298
FEATURE                  Location/Qualifiers
source                   1..298
                         mol_type = other DNA
                         organism = synthetic construct
SEQUENCE: 45
gaattcatta gacgacgata cgtactactc tgctcctaga cgtactcaag tataaggtaa   60
gacgcaatta ttgcacaggc aattattcag cctgcaatta tctacagcgc aattatctga  120
tcagcaatta tgatacgtgc aattatggta cctgcgctcc cgacatgccc cgcggcgcgc  180
cattaaccgc cagatttgag tcgcgggacc cgttggcaga ggtgggctag cctcgaggat  240
atcaagatct ggcctcggcg gccaagcttg gcaatccggt actgttggta aagccacc    298

SEQ ID NO: 46            moltype = DNA   length = 298
FEATURE                  Location/Qualifiers
source                   1..298
                         mol_type = other DNA
                         organism = synthetic construct
SEQUENCE: 46
gaattcactc tgctcctaga cgtactcaag tataaggtag gacacgtgcc cgatgcacgg   60
acacgtgccc ccgtaaagga cacgtgccct aaatcgggac acgtgcccta gacgtggaca  120
cgtgcccgac tagaggacac gtgcccggta cctgcgctcc cgacatgccc cgcggcgcgc  180
cattaaccgc cagatttgag tcgcgggacc cgttggcaga ggtgggctag cctcgaggat  240
atcaagatct ggcctcggcg gccaagcttg gcaatccggt actgttggta aagccacc    298

SEQ ID NO: 47            moltype = DNA   length = 298
FEATURE                  Location/Qualifiers
source                   1..298
                         mol_type = other DNA
                         organism = synthetic construct
SEQUENCE: 47
gaattccaca gtgactgcag cagtcattat acgtcgccta aatcgagatg ctgtactgat   60
ctattaagcc gcgtactctt aagccggtca ttattaagcc gctataagtt aagccgcaac  120
gccttaagcc gacgaccgtt aagccgggta cctgcgctcc cgacatgccc cgcggcgcgc  180
cattaaccgc cagatttgag tcgcgggacc cgttggcaga ggtgggctag cctcgaggat  240
atcaagatct ggcctcggcg gccaagcttg gcaatccggt actgttggta aagccacc    298
```

```
SEQ ID NO: 48            moltype = DNA   length = 298
FEATURE                  Location/Qualifiers
source                   1..298
                         mol_type = other DNA
                         organism = synthetic construct
SEQUENCE: 48
gaattctcgg ctatgctgct gctatgcgag cgtcagctca tgcctatccg atgtgcctga    60
cgaactcatc gacgctgcta cagctaatcc tatgctaatc ctaacctaat cctaccctaa   120
tcctagccta atccttgcct aatcctggta cctgcgctcc cgacatgccc cgcggcgcgc   180
cattaaccgc cagatttgag tcgcgggacc cgttggcaga ggtgggctag cctcgaggat   240
atcaagatct ggcctcggcg gccaagcttg gcaatccggt actgttggta aagccacc     298

SEQ ID NO: 49            moltype = DNA   length = 298
FEATURE                  Location/Qualifiers
source                   1..298
                         mol_type = other DNA
                         organism = synthetic construct
SEQUENCE: 49
gaattctgta ctgatctata aggatcgact agaagtcgca gattagtatg tggtttagta    60
cctgtatgtg gttttcgcaa tgtatgtggt ttatgctgcg tatgtggttt agcagtcgta   120
tgtggtttga gcgtcgtatg tggtttggta cctgcgctcc cgacatgccc cgcggcgcgc   180
cattaaccgc cagatttgag tcgcgggacc cgttggcaga ggtgggctag cctcgaggat   240
atcaagatct ggcctcggcg gccaagcttg gcaatccggt actgttggta aagccacc     298

SEQ ID NO: 50            moltype = DNA   length = 298
FEATURE                  Location/Qualifiers
source                   1..298
                         mol_type = other DNA
                         organism = synthetic construct
SEQUENCE: 50
gaattcctgc agcagtcatt atacgtcgcc taaatcgaga tgctgtactg atctataagg    60
atcgagtatg tggtttatcg tatgtggttt gtagtatgtg gtttctggta tgtggttttg   120
tgtatgtggt ttccagtatg tggtttggta cctgcgctcc cgacatgccc cgcggcgcgc   180
cattaaccgc cagatttgag tcgcgggacc cgttggcaga ggtgggctag cctcgaggat   240
atcaagatct ggcctcggcg gccaagcttg gcaatccggt actgttggta aagccacc     298

SEQ ID NO: 51            moltype = DNA   length = 298
FEATURE                  Location/Qualifiers
source                   1..298
                         mol_type = other DNA
                         organism = synthetic construct
SEQUENCE: 51
gaattccacg atgtagctga gcgacagtat agtgcacagt gactgcagcc aattaactga    60
cgaactccaa ttaaatcagt gatcccaatt aatgcaagct acccaattaa tatgctgctg   120
ccaattaaca tcggctatcc aattaaggta cctgcgctcc cgacatgccc cgcggcgcgc   180
cattaaccgc cagatttgag tcgcgggacc cgttggcaga ggtgggctag cctcgaggat   240
atcaagatct ggcctcggcg gccaagcttg gcaatccggt actgttggta aagccacc     298

SEQ ID NO: 52            moltype = DNA   length = 298
FEATURE                  Location/Qualifiers
source                   1..298
                         mol_type = other DNA
                         organism = synthetic construct
SEQUENCE: 52
gaattcttag tacctgatca gcgatgctca tctcgacctg atcggtactc aattaatgta    60
ctgatctcaa ttaagtcgcc taaatcaatt aacgtactac tctcaattaa gatcggtaca   120
tcaattaaaa gtcgcagatc aattaaggta cctgcgctcc cgacatgccc cgcggcgcgc   180
cattaaccgc cagatttgag tcgcgggacc cgttggcaga ggtgggctag cctcgaggat   240
atcaagatct ggcctcggcg gccaagcttg gcaatccggt actgttggta aagccacc     298

SEQ ID NO: 53            moltype = DNA   length = 298
FEATURE                  Location/Qualifiers
source                   1..298
                         mol_type = other DNA
                         organism = synthetic construct
SEQUENCE: 53
gaattcctac gtgtgaccag agccgataac tgagtatcgc atcgctcaag atcagtgatc    60
actgcgaaat ttgagccctg aaatttgagc cgagaaattt gagcgctgaa atttgagcca   120
cgaaatttga gcttagaaat ttgagcggta cctgcgctcc cgacatgccc cgcggcgcgc   180
cattaaccgc cagatttgag tcgcgggacc cgttggcaga ggtgggctag cctcgaggat   240
atcaagatct ggcctcggcg gccaagcttg gcaatccggt actgttggta aagccacc     298

SEQ ID NO: 54            moltype = DNA   length = 298
FEATURE                  Location/Qualifiers
source                   1..298
                         mol_type = other DNA
                         organism = synthetic construct
SEQUENCE: 54
gaattcgacc tgatcggtac aacttctcac ggaggcttct aactctcctt tgatataact    60
```

```
cgctcctttg atatagcagt ctcctttgat atctcatctt cctttgtatat ctgtacttcc      120
tttgatattg ctatgtcctt tgatatggta cctgcgctcc cgacatgccc cgcggcgcgc      180
cattaaccgc cagatttgag tcgcgggacc cgttggcaga ggtgggctag cctcgaggat      240
atcaagatct ggcctcggcg gccaagcttg gcaatccggt actgttggta aagccacc       298

SEQ ID NO: 55           moltype = DNA   length = 522
FEATURE                 Location/Qualifiers
source                  1..522
                        mol_type = other DNA
                        organism = synthetic construct
SEQUENCE: 55
ggcctaactg gccggtacca ctagtggtga ctcatgggtg actcatgggt gactcatggt      60
gatcatgcta gcctcgagga tatcaagatc ggtaccacct cttaacaata cgtttcacaa      120
atagttaaaa acatgcatac tgaaaagcat acttttgcaa tgttattttt aaaaacaagg      180
aactctttaa cccagggaag ataatcactt ggggaaagga aggttcgttt ctgagttagc      240
aacaagtaaa tgcagcacta gtgggtggga ttgaggtgtg ccctggtgca taaatagaga      300
ctcagctgtg ctggcacact cagaagcttg gaccgcatcc tagccgccga ctcacacaag      360
gcaggtgggt gaggaaatcc aggtaaggct cctgacagca gctttagaag ggtacttgct      420
ggagtgaatt cgggcctctg attaccggtg ctagcctcga ggatatcaag atctggcctc      480
ggcggccaag cttggcaatc cggtactgtt ggtaaagcca cc                        522

SEQ ID NO: 56           moltype = DNA   length = 588
FEATURE                 Location/Qualifiers
source                  1..588
                        mol_type = other DNA
                        organism = synthetic construct
SEQUENCE: 56
ggcctaactg gccggtaccg atcttgatat cctcgaggct agcatgatca ccatgagtca      60
cccatgagtc acccatgagt cacccatgag tcacccatga gtcacccatg agtcacccat      120
gagtcaccca tgagtcaccc actagtggta ccacctctta acaatacgtt              180
tcacaaatag ttaaaaacat gcatactgaa aagcatactt ttgcaatgtt attttttaaaa    240
acaaggaact ctttaaccca gggaagataa tcacttgggg aaaggaaggt cgtttctga      300
gttagcaaca agtaaatgca gcactagtgg gtgggattga ggtgtgccct ggtgcataaa     360
tagagactca gctgtgctgg cacactcaga agcttggacc gcatcctagc cgccgactca     420
cacaaggcag gtgggtgagg aaatccaggt aaggctcctg acagcagctt tagaagggta     480
cttgctggag tgaattcggg cctctgatta ccggtgctag cctcgaggat atcaagatct     540
ggcctcggcg gccaagcttg gcaatccggt actgttggta aagccacc                 588

SEQ ID NO: 57           moltype = DNA   length = 577
FEATURE                 Location/Qualifiers
source                  1..577
                        mol_type = other DNA
                        organism = synthetic construct
SEQUENCE: 57
ggcctaactg gccggtaccg attcttgata tcctcgaggc tagcatgatc accatgagtc      60
acccatgagt cacccatgag tcacccatga gtcacccatg agtcacccat gagtcaccca      120
tgagtcaccc atgagtcacc catgagtcac cactagtggt accgatcttg atatcctcga     180
ggctagcatg atcaccatga gtcacccatg agtcacccat gagtcaccca tgagtcaccc     240
atgagtcacc catgagtcac ccatgagtca cccatgagtc acccatgagt caccactagt     300
ggtaccagtc gtggggagt gaaaagagag atggagaaag aggggatggg cagaaagagg     360
aggagagtc aggggcaggg catggaggtg ggtgggggctg ggctgccaaa gcaggataaa    420
tgcacacctg cctgctggtc tgggctccct gcctcgggct ctcaccctcc tctcctgcag     480
ctccagcttt gtgcttctac cggtgctagc ctcgaggata tcaagatctg gcctcggcgg     540
ccaagcttgg caatccggta ctgttggtaa agccacc                            577

SEQ ID NO: 58           moltype = DNA   length = 401
FEATURE                 Location/Qualifiers
source                  1..401
                        mol_type = other DNA
                        organism = synthetic construct
SEQUENCE: 58
ggcctaactg gccggtacca ctagtgacgt caccggaagt aagaaccgga agtatcgacc      60
ggaagtagac accggaagta ctaaccggaa gtaactaccg gaagtatgca ccggaagtag     120
acgtctacgt aagtggtggg ggagtgaaaa gagagatgga aagagggga atgggcagaa     180
agagaggagg agtcaggggc agggcatgg aggtgggtgg ggctgggctg ccaaagcagg    240
ataaatgcac acctgcctgc tggtctgggc tccctgcctc gggctctcac cctcctctcc     300
tgcagctcca gctttgtgct ctaccggtgc tagcctcgag gatatcaaga tctggcctcg     360
gcggccaagc ttggcaatcc ggtactgttg gtaaagccac c                        401

SEQ ID NO: 59           moltype = DNA   length = 461
FEATURE                 Location/Qualifiers
source                  1..461
                        mol_type = other DNA
                        organism = synthetic construct
SEQUENCE: 59
ggcctaactg gccggtacca ctagtgacgt caccggaagt aagaaccgga agtatcgacc      60
ggaagtagac accggaagta ctaaccggaa gtaactaccg gaagtatgca ccggaagtag     120
acgtctacgt aggcccgccc cctttcctta cgcggattgg tagctgcagg cttccctatc     180
tgattggccg aacgaacgca gcgcgtaatt taaaatattg tatctgtaac aaagctgcac     240
```

```
ctcgtgggcg gagttgtgct ctgcggctgc gaaagtccag cttcggcgac taggtgtgag    300
taagccagta tcccaggagg agcaagtggc acgtcttcgg gtgagtgtgc ggctgtgctg    360
gagcccgggt taccagctct ttaccggtgc tagcctcgag gatatcaaga tctggcctcg    420
gcggccaagc ttggcaatcc ggtactgttg gtaaagccac c                        461

SEQ ID NO: 60          moltype = DNA   length = 511
FEATURE                Location/Qualifiers
source                 1..511
                       mol_type = other DNA
                       organism = synthetic construct
SEQUENCE: 60
ggcctaactg gccggtacac tagtgacgtc accggaagta agaaccggaa gtatcgaccg    60
gaagtagaca ccggaagtac taaccggaag taactaccgg aagtatgcac cggaagtaga    120
cgtctacgta catactgaaa agcatacttt tgcaatgtta tttttaaaaa caaggaactc    180
tttaacccag ggaagataat cacttgggga aaggaaggtt cgtttctgag ttagcaacaa    240
gtaaatgcag cactagtggg tgggattgag gtgtgccctg gtgcataaat agagactcag    300
ctgtgctggc acactcagaa gcttggaccg catcctagcc gccgactcac acaaggcagg    360
tgggtgagga aatccaggta aggctcctga cagcagctt agaagggtac ttgctggagt      420
gaattcgggc ctctgattac tagcctcgag gatatcaaga tctggcctcg gcggccaagc    480
ttggcaatcc ggtactgttg gtaaagccac c                                   511

SEQ ID NO: 61          moltype = DNA   length = 321
FEATURE                Location/Qualifiers
source                 1..321
                       mol_type = other DNA
                       organism = synthetic construct
SEQUENCE: 61
ggcctaactg gccggtacca ctagtgacgt caccggaagt aagaaccgga agtatcgacc    60
ggaagtagac accggaagta ctaaccggaa gtaactaccg gaagtatgca ccggaagtag    120
acgtctacgt aacccacgtg atgctgagaa gtactcctgc cctaggaaga gactcagggc    180
agagggagga aggacagcag accagacagt cacagcagcc ttgacaaaac gttcctggaa    240
ctaccggtgc tagcctcgag gatatcaaga tctggcctcg gcggccaagc ttggcaatcc    300
ggtactgttg gtaaagccac c                                              321

SEQ ID NO: 62          moltype = DNA   length = 376
FEATURE                Location/Qualifiers
source                 1..376
                       mol_type = other DNA
                       organism = synthetic construct
SEQUENCE: 62
ggcctaactg gccggtacca ctagtgacgt caccggaagt aagaaccgga agtatcgacc    60
ggaagtagac accggaagta ctaaccggaa gtaactaccg gaagtatgca ccggaagtag    120
acgtctacgt acgggaaaag ttcagctgag agatataaaa gagcagtctt tccagcacct    180
gcaaatccag agcggcgggc actgacgggc acttgcaccg tgtggacaga ctctccggtt    240
ctgtgagtgg ttttttcttt cccgggtcgg acctggagtt cttaggggga tggctgaacc    300
ggtgctagcc tcgaggatat caagatctgg cctcggcggc caagcttggc aatccggtac    360
tgttggtaaa gccacc                                                    376

SEQ ID NO: 63          moltype = DNA   length = 547
FEATURE                Location/Qualifiers
source                 1..547
                       mol_type = other DNA
                       organism = synthetic construct
SEQUENCE: 63
ggcctaactg gccggtacca ctagtgacgt caccggaagt aagaaccgga agtatcgacc    60
ggaagtagac accggaagta ctaaccggaa gtaactaccg gaagtatgca ccggaagtag    120
acgtctacgt actgagcgac agtatagtgc acagtgacat tacagatgtt tacgacgaat    180
tacagatgtt tctcatcgat tacagatgtt tcagctcaat tacagatgtt tgctgctgat    240
tacagatgtt taccagagat tacagatgtt ttacgtaagt ggtggggggag tgaaaagaa    300
gatggagaaa gaggggatgg gcagaaagag gaggaggagt caggggcagg gcatggaggt    360
gggtggggct gggctgccaa agcaggataa atgcacacct gcctgctggt ctgggctccc    420
tgcctcgggc tctcaccctc ctctcctgca gctccagctt tgtgctctac cggtgctagc    480
ctcgaggata tcaagatctg gcctcggcgg ccaagcttgg caatccggta ctgttggtaa    540
agccacc                                                              547

SEQ ID NO: 64          moltype = DNA   length = 588
FEATURE                Location/Qualifiers
source                 1..588
                       mol_type = other DNA
                       organism = synthetic construct
SEQUENCE: 64
actagtgacg tcaccggaag taagaaccgg aagtatcgac cggaagtaga caccggaagt    60
actaaccgga agtaactacc ggaagtatgc accggaagta gacgtctacg tactgagcga    120
cagtatagtg cacagtgaca ttacagatgt ttacgacgaa ttacagatgt ttctcatcga    180
ttacagatgt ttcagctcaa ttacagatgt ttgctgctga ttacagatgt ttaccagaga    240
ttacagatgt tttacgtagg cccgcccct ttccttacgc ggattggtag ctgcaggctt    300
ccctatctga ttggccgaac gaacgcacgc gtaatttaa aatattgtat ctgtaacaaa    360
gctgcacctc gtgggcggag ttgtgctctg cggctgcgaa agtccagctt cggcgactag    420
gtgtgagtaa gccagtatcc caggaggagc aagtggcacg tcttcgggtg agtgtgcggc    480
```

```
tgtgctggag cccgggttac cagctcttta ccggtgctag cctcgaggat atcaagatct   540
ggcctcggcg gccaagcttg gcaatccggt actgttggta aagccacc                588

SEQ ID NO: 65          moltype = DNA   length = 657
FEATURE                Location/Qualifiers
source                 1..657
                       mol_type = other DNA
                       organism = synthetic construct
SEQUENCE: 65
ggcctaactg gccggtacac tagtgacgtc accggaagta agaaccggaa gtatcgaccg   60
gaagtagaca ccggaagtac taaccggaag taactaccgg aagtatgcac cggaagtaga  120
cgtctacgta ctgagcgaca gtatagtgca cagtgacatt acagatgttt acgacgaatt  180
acagatgttt ctcatcgatt acagatgttt cagctcaatt acagatgttt gctgctgatt  240
acagatgttt accagagatt acagatgttt tacgtacata ctgaaaagca tacttttgca  300
atgttatttt taaaaacaag gaactcttta acccagggaa gataatcact tggggaaagg  360
aaggttcgtt tctgagttag caacaagtaa atgcagcact agtgggtggg attgaggtgt  420
gccctggtgc ataaatagag actcagctgt gctggcacac tcagaagctt ggaccgcatc  480
ctagccgccg actcacacaa ggcaggtggg tgaggaaatc caggtaaggc tcctgacagc  540
agctttagaa gggtacttgc tggagtgaat tcgggcctct gattactagc ctcgaggata  600
tcaagatctg gcctcggcgg ccaagcttgg caatccggta ctgttggtaa agccacc     657

SEQ ID NO: 66          moltype = DNA   length = 522
FEATURE                Location/Qualifiers
source                 1..522
                       mol_type = other DNA
                       organism = synthetic construct
SEQUENCE: 66
ggcctaactg gccggtacca ctagtgacgt caccggaagt aagaaccgga agtatcgacc   60
ggaagtagac accggaagta ctaaccggaa gtaactaccg gaagtatgca ccggaagtag  120
acgtctacgt actgagcgac agtatagtgc acagtgacat tacagatgtt tacgacgaat  180
tacagatgtt tctcatcgat tacagatgtt tcagctcaat tacagatgtt tgctgctgat  240
tacagatgtt taccagagat tacagatgtt ttacgtacgg gaaaagttca gctgagagat  300
ataaagagc agtctttcca gcacctgcaa atccagagcg gcgggcactg acgggcactt  360
gcaccgtgtg gacagactct ccggttctgt gagtggtttt tcttttcccg ggtcggacct  420
ggagttctta gggggatggc tgaaccggtg ctagcctcga ggatatcaag atctggcctc  480
ggcggccaag cttggcaatc cggtactgtt ggtaaagcca cc                     522

SEQ ID NO: 67          moltype = DNA   length = 467
FEATURE                Location/Qualifiers
source                 1..467
                       mol_type = other DNA
                       organism = synthetic construct
SEQUENCE: 67
ggcctaactg gccggtacca ctagtgacgt caccggaagt aagaaccgga agtatcgacc   60
ggaagtagac accggaagta ctaaccggaa gtaactaccg gaagtatgca ccggaagtag  120
acgtctacgt actgagcgac agtatagtgc acagtgacat tacagatgtt tacgacgaat  180
tacagatgtt tctcatcgat tacagatgtt tcagctcaat tacagatgtt tgctgctgat  240
tacagatgtt taccagagat tacagatgtt ttacgtaacc cacgtgatgc tgagaagtac  300
tcctgcccta ggaagagact cagggcagag ggaggaagga cagcagacca gacagtcaca  360
gcagccttga caaaacgttc ctggaactac cggtgctagc ctcgaggata tcaagatctg  420
gcctcggcgg ccaagcttgg caatccggta ctgttggtaa agccacc               467

SEQ ID NO: 68          moltype = DNA   length = 453
FEATURE                Location/Qualifiers
source                 1..453
                       mol_type = other DNA
                       organism = synthetic construct
SEQUENCE: 68
ggcctaactg gccggtacca ctagtgacgt ctacgtactg agcgacagta tagtgcacag   60
tgacattaca gatgtttacg acgaattaca gatgtttctc atcgattaca gatgtttcag  120
ctcaattaca gatgtttgct gctgattaca gatgtttacc agagattaca gatgttttac  180
gtaagtggtg ggggagtgaa aagagagatg gagaaagagg ggatgggcag aaagaggagg  240
aggagtcagg ggcagggcat ggaggtgggt ggggctgggc tgccaaagca ggataaatgc  300
acacctgcct gctggtctgg gctccctgcc tcgggctctc accctcctct cctgcagctc  360
cagctttgtg ctctaccggt gctagcctcg aggatatcaa gatctggcct cggcggccaa  420
gcttggcaat ccggtactgt tggtaaagcc acc                              453

SEQ ID NO: 69          moltype = DNA   length = 513
FEATURE                Location/Qualifiers
source                 1..513
                       mol_type = other DNA
                       organism = synthetic construct
SEQUENCE: 69
ggcctaactg gccggtacca ctagtgacgt ctacgtactg agcgacagta tagtgcacag   60
tgacattaca gatgtttacg acgaattaca gatgtttctc atcgattaca gatgtttcag  120
ctcaattaca gatgtttgct gctgattaca gatgtttacc agagattaca gatgttttac  180
gtaggcccgc ccccttttcct tacgcggatt ggtagctgca ggcttcccta tctgattggc  240
cgaacgaacg cagcgcgtaa tttaaaatat tgtatctgta acaaagctgc acctcgtggg  300
cggagttgtg ctctgcggct gcgaaagtcc agcttcggcg actaggtgtg agtaagccag  360
```

-continued

```
tatcccagga ggagcaagtg gcacgtcttc gggtgagtgt gcggctgtgc tggagcccgg   420
gttaccagct ctttaccggt gctagcctcg aggatatcaa gatctggcct cggcggccaa   480
gcttggcaat ccggtactgt tggtaaagcc acc                                 513

SEQ ID NO: 70          moltype = DNA   length = 565
FEATURE                Location/Qualifiers
source                 1..565
                       mol_type = other DNA
                       organism = synthetic construct
SEQUENCE: 70
ggcctaactg gccggtacca ctagtgacgt ctacgtactg agcgacagta tagtgcacag   60
tgacattaca gatgtttacg acgaattaca gatgtttctc atcgattaca gatgtttcag   120
ctcaattaca gatgtttgct gctgattaca gatgtttacc agagattaca gatgttttac   180
gtacatactg aaaagcatac ttttgcaatg ttatttttaa aaacaaggaa ctctttaacc   240
cagggaagat aatcacttgg ggaaaggaag gttcgtttct gagttagcaa caagtaaatg   300
cagcactagt gggtgggatt gaggtgtgcc ctggtgcata aatagagact cagctgtgct   360
ggcacactca gaagcttgga ccgcatccta gccgccgact cacacaaggc aggtgggtga   420
ggaaatccag gtaaggctcc tgacagcagc tttagaaggg tacttgctgg agtgaattcg   480
ggcctctgat tagctagcct cgaggatatc aagatctggc ctcggcggcc aagcttggca   540
atccggtact gttggtaaag ccacc                                          565

SEQ ID NO: 71          moltype = DNA   length = 513
FEATURE                Location/Qualifiers
source                 1..513
                       mol_type = other DNA
                       organism = synthetic construct
SEQUENCE: 71
ggcctaactg gccggtacca ctagtgacgt cctgagcgac agtatagtgc acagtgacat   60
tacagatgtt tacgacgaat tacagatgtt tctcatcgat tacagatgtt tcagctcaat   120
tacagatgtt tgctgctgat tacagatgtt taccagagat tacagatgtt tgacgtctac   180
gtaggcccgc cccctttcct tacgcggatt ggtagctgca ggcttcccta tctgattggc   240
cgaacgaacg cagcgcgtaa tttaaaatat tgtatctgta acaaagctgc acctcgtggg   300
cggagttgtg ctctgcggct gcgaaagtcc agcttcggcg actaggtgtg agtaagccag   360
tatcccagga ggagcaagtg gcacgtcttc gggtgagtgt gcggctgtgc tggagcccgg   420
gttaccagct ctttaccggt gctagcctcg aggatatcaa gatctggcct cggcggccaa   480
gcttggcaat ccggtactgt tggtaaagcc acc                                 513

SEQ ID NO: 72          moltype = DNA   length = 599
FEATURE                Location/Qualifiers
source                 1..599
                       mol_type = other DNA
                       organism = synthetic construct
SEQUENCE: 72
ggcctaactg gccggtacca ctagtgacgt cctgagcgac agtatagtgc acagtgacat   60
tacagatgtt tacgacgaat tacagatgtt tctcatcgat tacagatgtt tcagctcaat   120
tacagatgtt tgctgctgat tacagatgtt taccagagat tacagatgtt tgacgtctac   180
gtactgatca gcgatgctca tctcgacctg atcggtacaa cttctcacgg aggcttctaa   240
gtcattacat acgtagtcat tactatacgt gtcattacag atgctgtcat tacacgaact   300
gtcattacgt actcagtcat tactacgtaa gtggtggggg agtgaaaaga gagatggaga   360
aagaggggat gggcagaaag aggaggagga gtcaggggca gggcatggag gtgggtgggg   420
ctgggctgcc aaagcaggat aaatgcacac ctgcctgctg gtctgggctc cctgcctcgg   480
gctctcaccc tcctctcctg cagctccagc tttgtgctct accggtgcta gcctcgagga   540
tatcaagatc tggcctcggc ggccaagctt ggcaatccgg tactgttggt aaagccacc    599

SEQ ID NO: 73          moltype = DNA   length = 428
FEATURE                Location/Qualifiers
source                 1..428
                       mol_type = other DNA
                       organism = synthetic construct
SEQUENCE: 73
ggcctaactg gccggtacca ctagtgacgt ctacgtactg agcgacagta tagtgcacag   60
tgacattaca gatgtttacg acgaattaca gatgtttctc atcgattaca gatgtttcag   120
ctcaattaca gatgtttgct gctgattaca gatgtttacc agagattaca gatgttttac   180
gtacgggaaa agttcagctg agagatataa aagagcagtc tttccagcac ctgcaaatcc   240
agagcggcgg gcactgacgg gcacttcac cgtgtggaca gactctccgg ttctgtgagt   300
ggttttttctt ttcccgggtc ggaccttggag ttcttagggg gatggctgaa ccggtgctag   360
cctcgaggat atcaagatct ggcctcggcg gccaagcttg gcaatccggt actgttggta   420
aagccacc                                                            428

SEQ ID NO: 74          moltype = DNA   length = 373
FEATURE                Location/Qualifiers
source                 1..373
                       mol_type = other DNA
                       organism = synthetic construct
SEQUENCE: 74
ggcctaactg gccggtacca ctagtgacgt ctacgtactg agcgacagta tagtgcacag   60
tgacattaca gatgtttacg acgaattaca gatgtttctc atcgattaca gatgtttcag   120
ctcaattaca gatgtttgct gctgattaca gatgtttacc agagattaca gatgttttac   180
gtaacccacg tgatgctgag aagtactcct gccctaggaa gagactcagg gcagagggag   240
```

```
gaaggacagc agaccagaca gtcacagcag ccttgacaaa acgttcctgg aactaccggt   300
gctagcctcg aggatatcaa gatctggcct cggcggccaa gcttggcaat ccggtactgt   360
tggtaaagcc acc                                                       373

SEQ ID NO: 75           moltype = DNA   length = 565
FEATURE                 Location/Qualifiers
source                  1..565
                        mol_type = other DNA
                        organism = synthetic construct
SEQUENCE: 75
ggcctaactg gccggtacca ctagtgacgt cctgagcgac agtatagtgc acagtgacat   60
tacagatgtt tacgacgaat tacagatgtt tctcatcgat tacagatgtt tcagctcaat   120
tacagatgtt tgctgctgat tacagatgtt taccagagat tacagatgtt tgacgtctac   180
gtacatactg aaaagcatac ttttgcaatg ttatttttaa aaacaaggaa ctctttaacc   240
cagggaagat aatcacttgg ggaaaggaag gttcgtttct gagttagcaa caagtaaatg   300
cagcactagt gggtgggatt gaggtgtgcc ctggtgcata aatagagact cagctgtgct   360
ggcacactca gaagcttgga ccgcatccta gccgccgact cacacaaggc aggtgggtga   420
ggaaatccag gtaaggctcc tgacagcagc tttagaaggg tacttgctgg agtgaattcg   480
ggcctctgat tagctagcct cgaggatatc aagatctggc ctcggcggcc aagcttggca   540
atccggtact gttggtaaag ccacc                                         565

SEQ ID NO: 76           moltype = DNA   length = 373
FEATURE                 Location/Qualifiers
source                  1..373
                        mol_type = other DNA
                        organism = synthetic construct
SEQUENCE: 76
ggcctaactg gccggtacca ctagtgacgt cctgagcgac agtatagtgc acagtgacat   60
tacagatgtt tacgacgaat tacagatgtt tctcatcgat tacagatgtt tcagctcaat   120
tacagatgtt tgctgctgat tacagatgtt taccagagat tacagatgtt tgacgtctac   180
gtaacccacg tgatgctgag aagtactcct gccctaggaa gagactcagg gcagagggag   240
gaaggacagc agaccagaca gtcacagcag ccttgacaaa acgttcctgg aactaccggt   300
gctagcctcg aggatatcaa gatctggcct cggcggccaa gcttggcaat ccggtactgt   360
tggtaaagcc acc                                                       373

SEQ ID NO: 77           moltype = DNA   length = 428
FEATURE                 Location/Qualifiers
source                  1..428
                        mol_type = other DNA
                        organism = synthetic construct
SEQUENCE: 77
ggcctaactg gccggtacca ctagtgacgt cctgagcgac agtatagtgc acagtgacat   60
tacagatgtt tacgacgaat tacagatgtt tctcatcgat tacagatgtt tcagctcaat   120
tacagatgtt tgctgctgat tacagatgtt taccagagat tacagatgtt tgacgtctac   180
gtacgggaaa agttcagctg agagatataa aagagcagtc tttccagcac ctgcaaatcc   240
agagcggcgg gcactgacgg gcacttgcac cgtgtggaca gactctccgg ttctgtgagt   300
ggttttttctt ttcccgggtc ggacctggag ttcttagggg gatggctgaa ccggtgctag   360
cctcgaggat atcaagatct ggcctcggcg gccaagcttg gcaatccggt actgttggta   420
aagccacc                                                             428

SEQ ID NO: 78           moltype = DNA   length = 659
FEATURE                 Location/Qualifiers
source                  1..659
                        mol_type = other DNA
                        organism = synthetic construct
SEQUENCE: 78
ggcctaactg gccggtacca ctagtgacgt cctgagcgac agtatagtgc acagtgacat   60
tacagatgtt tacgacgaat tacagatgtt tctcatcgat tacagatgtt tcagctcaat   120
tacagatgtt tgctgctgat tacagatgtt taccagagat tacagatgtt tgacgtctac   180
gtactgatca gcgatgctca tctcgacctg atcggtacaa cttctcacg aggcttctaa   240
gtcattacat acgtagtcat tactatacgt gtcattacag atgctgtcat tacacgaact   300
gtcattacgt actcagtcat tactacgtag gcccgcccccc tttccttacg cggattggta   360
gctgcaggct tccctatctg attggccgaa cgaacgcagc gcgtaattta aaatattgta   420
tctgtaacaa agctgcacct cgtgggcgga gttgtgctct gcggcctgcga aagtccagct   480
tcggcgacta ggtgtgagta agccagtatc ccaggaggag caagtggcac gtcttcgggt   540
gagtgtgcgg ctgtgctgga gcccgggtta ccagctcttt accggtgcta gcctcgagga   600
tatcaagatc tggcctcggc ggccaagctt ggcaatccgg tactgttggt aaagccacc   659

SEQ ID NO: 79           moltype = DNA   length = 755
FEATURE                 Location/Qualifiers
source                  1..755
                        mol_type = other DNA
                        organism = synthetic construct
SEQUENCE: 79
ggcctaactg gccggtacca cactagtgac gtcctgagcg acagtatagt gcacagtgac   60
attacagatg tttacgacga attacagatg tttctcatcg attacagatg tttcagctca   120
attacagatg tttgctgctg attacagatg tttaccagag attacagatg tttgacgtct   180
acgtactgat cagcgatgct catctcgacc tgatcggtac aacttctcac ggaggcttct   240
aagtcattac atacgtagtc attactatac gtgtcattac agatgctgtc attacacgaa   300
```

```
ctgtcattac gtactcagtc attactacgt acatactgaa aagcatactt ttgcaatgtt   360
attttaaaa acaaggaact ctttaaccca gggaagataa tcacttgggg aaaggaaggt   420
tcgtttctga gttagcaaca agtaaatgca gcactagtgg gtgggattga ggtgtgccct   480
ggttaagtgg tggggagtg aaaagagaga tggagaaaga ggggatgggc agaaagagga    540
ggaggagtca ggggcagggc atggaggtgg gtggggctgg gctgccaaag caggataaat   600
gcacacctgc ctgctggtct gggctccctg cctcgggctc tcaccctcct ctcctgcagc   660
tccagctttg tgctctaccg gtgctagcct cgaggatatc aagatctggc ctcggcggcc   720
aagcttggca atccggtact gttggtaaag ccacc                              755
```

```
SEQ ID NO: 80              moltype = DNA   length = 683
FEATURE                    Location/Qualifiers
source                     1..683
                           mol_type = other DNA
                           organism = synthetic construct
SEQUENCE: 80
ggcctaactg gccggtacaa ctagtgactc ctttgatgta cgcaactcct ttgatgtcta   60
tgcgtccttt gatgttaagg attcctttga tgtaggtaca tcctttgatg tccgtaaatc   120
ctttgatgtg gtaccgtcta ctacctgatc aaacatgccc ggacatgtcg taagacataa   180
acatgcccgg acatgtcctc gcaatctaac atgcccggac atgtcctcgc aatctaacat   240
gcccggacat gtctgcaagc tacaaacatg ccggacatgt cgtactcagt cattactacg   300
tacatactga aaagcatact tttgcaatgt tattttaa aacaaggaac tctttaaccc     360
agggaagata atcacttggg gaaaggaagg ttcgtttctg agttagcaac aagtaaatgc   420
agcactagtg ggtgggattg aggtgtgccc tggtgcataa atagagactc agctgtgctg   480
gcacactcag aagcttggac cgcatcctag ccgccgactc acacaaggca ggtgggtgag   540
gaaatccagg taaggctcct gacagcagct ttagaagggt acttgctgga gtgaattcgg   600
gcctctgatt actagcctcg aggatatcaa gatctggcct cggcggccaa gcttggcaat   660
ccggtactgt tggtaaagcc acc                                          683
```

```
SEQ ID NO: 81              moltype = DNA   length = 519
FEATURE                    Location/Qualifiers
source                     1..519
                           mol_type = other DNA
                           organism = synthetic construct
SEQUENCE: 81
ggcctaactg gccggtacca ctagtgacgt cctgagcgac agtatagtgc acagtgacat   60
tacagatgtt tacgacgaat tacagatgtt tctcatcgat tacagatgtt tcagctcaat   120
tacagatgtt tgctgctgat tacagatgtt taccagagat tacagatgtt tgacgtctac   180
gtactgatca gcgatgctca tctcgacctg atcggtacaa cttctcacgg aggcttctaa   240
gtcattacat acgtagtcat tactatacgt gtcattacag atgctgtcat tacacgaact   300
gtcattacgt actcagtcat tactacgtaa cccacgtgat gctgagaagt actcctgccc   360
taggaagaga ctcagggcag agggaggaag gacagcagac cagacagtca cagcagcctt   420
gacaaaacgt tcctggaact accggtgcta gcctcgagga tatcaagatc tggcctcggc   480
ggccaagctt ggcaatccgg tactgttggt aaagccacc                          519
```

```
SEQ ID NO: 82              moltype = DNA   length = 574
FEATURE                    Location/Qualifiers
source                     1..574
                           mol_type = other DNA
                           organism = synthetic construct
SEQUENCE: 82
ggcctaactg gccggtacca ctagtgacgt cctgagcgac agtatagtgc acagtgacat   60
tacagatgtt tacgacgaat tacagatgtt tctcatcgat tacagatgtt tcagctcaat   120
tacagatgtt tgctgctgat tacagatgtt taccagagat tacagatgtt tgacgtctac   180
gtactgatca gcgatgctca tctcgacctg atcggtacaa cttctcacgg aggcttctaa   240
gtcattacat acgtagtcat tactatacgt gtcattacag atgctgtcat tacacgaact   300
gtcattacgt actcagtcat tactacgtac gggaaaagtt cagctgagag atataaaaga   360
gcagtctttc cagcacctgc aaatccagag cggcgggcac tgacgggcac ttgcaccgtg   420
tggacagact ctccggttct gtgagtggtt tttcttttcc cgggtcggac ctggagttct   480
taggggggatg gctgaaccgg tgctagcctc gaggatatca agatctggcc tcggcggcca   540
agcttggcaa tccggtactg ttggtaaagc cacc                              574
```

```
SEQ ID NO: 83              moltype = DNA   length = 512
FEATURE                    Location/Qualifiers
source                     1..512
                           mol_type = other DNA
                           organism = synthetic construct
SEQUENCE: 83
ggcctaactg gccggtacca ctagtgacgt ctgtagctga gcgacagtat agtgcacagt   60
gactgcagca gtcattgtcg taaattgagt atcgtcgtaa attgacgaac gtcgtaaatt   120
agcgacagtc gtaaattagt acctgtcgta aattactctg cgtcgtaaat tgacgtctac   180
gtaggcccgc cccctttcct tacgcggatt ggtagctgca ggcttcccta tctgattggc   240
cgaacgaacg cagcgcgtaa tttaaaatat tgtatctgta acaaagctgc acctcgtggg   300
cggagttgtg ctctgcggct gcgaaagtcc agcttcggcg actaggtgtg agtaagccag   360
tatcccagga ggagcaagtg gcacgtcttc gggtgagtgt gcggctgtgc tggagcccgg   420
gttaccagct ctttaccggt ctagcctcga ggatatcaag atctggcctc ggcggccaag   480
cttggcaatc cggtactgtt ggtaaagcca cc                                512
```

```
SEQ ID NO: 84              moltype = DNA   length = 453
FEATURE                    Location/Qualifiers
```

-continued

```
source                    1..453
                          mol_type = other DNA
                          organism = synthetic construct
SEQUENCE: 84
ggcctaactg gccggtacca ctagtgacgt ctacgtactg atcagcgatg ctcatctcga   60
cctgatcggt acaacttctc acggaggctt ctaagtcatt acatacgtag tcattactat  120
acgtgtcatt acagatgctg tcattacacg aactgtcatt acgtactcag tcattactac  180
gtaagtggtg ggggagtgaa aagagagatg gagaaagagg ggatgggcag aaagaggagg  240
aggagtcagg ggcagggcat ggaggtgggt ggggctgggc tgccaaagca ggataaatgc  300
acacctgcct gctggtctgg gctccctgcc tcgggctctc accctcctct cctgcagctc  360
cagctttgtg ctctaccggt gctagcctcg aggatatcaa gatctggcct cggcggccaa  420
gcttggcaat ccggtactgt tggtaaagcc acc                               453

SEQ ID NO: 85            moltype = DNA   length = 513
FEATURE                  Location/Qualifiers
source                   1..513
                         mol_type = other DNA
                         organism = synthetic construct
SEQUENCE: 85
ggcctaactg gccggtacca ctagtgacgt ctacgtactg atcagcgatg ctcatctcga   60
cctgatcggt acaacttctc acggaggctt ctaagtcatt acatacgtag tcattactat  120
acgtgtcatt acagatgctg tcattacacg aactgtcatt acgtactcag tcattactac  180
gtaggcccgc ccccttttcct tacgcggatt ggtagctgca ggcttcccta tctgattggc  240
cgaacgaacg cagcgcgtaa tttaaaatat tgtatctgta acaaagctgc acctcgtggg  300
cggagttgtg ctctgcggct gcgaaagtcc agcttcggcg actaggtgtg agtaagccag  360
tatcccagga ggagcaagtg gcacgtcttc gggtgagtgt gcggctgtgc tggagcccgg  420
gttaccagct ctttaccggt gctagcctcg aggatatcaa gatctggcct cggcggccaa  480
gcttggcaat ccggtactgt tggtaaagcc acc                               513

SEQ ID NO: 86            moltype = DNA   length = 373
FEATURE                  Location/Qualifiers
source                   1..373
                         mol_type = other DNA
                         organism = synthetic construct
SEQUENCE: 86
ggcctaactg gccggtacca ctagtgacgt ctacgtactg atcagcgatg ctcatctcga   60
cctgatcggt acaacttctc acggaggctt ctaagtcatt acatacgtag tcattactat  120
acgtgtcatt acagatgctg tcattacacg aactgtcatt acgtactcag tcattactac  180
gtaacccacg tgatgctgag aagtactcct gccctaggaa gagactcagg gcagagggag  240
gaaggacagc agaccagaca gtcacagcag ccttgacaaa acgttcctgg aactaccggt  300
gctagcctcg aggatatcaa gatctggcct cggcggccaa gcttggcaat ccggtactgt  360
tggtaaagcc acc                                                     373

SEQ ID NO: 87            moltype = DNA   length = 565
FEATURE                  Location/Qualifiers
source                   1..565
                         mol_type = other DNA
                         organism = synthetic construct
SEQUENCE: 87
ggcctaactg gccggtacca ctagtgacgt ctacgtactg atcagcgatg ctcatctcga   60
cctgatcggt acaacttctc acggaggctt ctaagtcatt acatacgtag tcattactac  120
acgtgtcatt acagatgctg tcattacacg aactgtcatt acgtactcag tcattactac  180
gtacatactg aaaagcatac ttttgcaatg ttatttttaa aaacaaggaa ctctttaacc  240
cagggaagat aatcacttgg ggaaaggaag gttcgtttct gagttagcaa caagtaaatg  300
cagcactagt gggtgggatt gaggtgtgcc ctggtgcata aatagagact cagctgtgct  360
ggcacactca gaagcttgga ccgcatccta gccgccgact cacacaaggc aggtgggtga  420
ggaaatccag gtaaggctcc tgacagcagc tttagaaggg tacttgctgg agtgaattcg  480
ggcctctgat tagctagcct cgaggatatc aagatctggc ctcggcggcc aagcttggca  540
atccggtact gttggtaaag ccacc                                        565

SEQ ID NO: 88            moltype = DNA   length = 453
FEATURE                  Location/Qualifiers
source                   1..453
                         mol_type = other DNA
                         organism = synthetic construct
SEQUENCE: 88
ggcctaactg gccggtacca ctagtgacgt ctgtagctga gcgacagtat agtgcacagt   60
gactgcagca gtcattgtcg taaattgagt atcgtcgtaa attgacgaac gtcgtaaatt  120
agcgacagtc gtaaattagt acctgtcgta aattactctg cgtcgtaaat tgacgtctac  180
gtaagtggtg ggggagtgaa aagagagatg gagaaagagg ggatgggcag aaagaggagg  240
aggagtcagg ggcagggcat ggaggtgggt ggggctgggc tgccaaagca ggataaatgc  300
acacctgcct gctggtctgg gctccctgcc tcgggctctc accctcctct cctgcagctc  360
cagctttgtg ctctaccggt gctagcctcg aggatatcaa gatctggcct cggcggccaa  420
gcttggcaat ccggtactgt tggtaaagcc acc                               453

SEQ ID NO: 89            moltype = DNA   length = 428
FEATURE                  Location/Qualifiers
source                   1..428
                         mol_type = other DNA
```

-continued

```
                             organism = synthetic construct
SEQUENCE: 89
ggcctaactg gccggtacca ctagtgacgt ctgtagctga gcgacagtat agtgcacagt   60
gactgcagca gtcattgtcg taaattgagt atcgtcgtaa attgacgaac gtcgtaaatt  120
agcgacagtc gtaaattagt acctgtcgta aattactctg cgtcgtaaat tgacgtctac  180
gtacgggaaa agttcagctg agagatataa aagagcagtc tttccagcac ctgcaaatcc  240
agagcggcgg gcactgacgg gcacttcac cgtgtggaca gactctccgg ttctgtgagt   300
ggttttcctt ttcccgggtc ggacctggag ttcttagggg gatggctgaa ccggtgctag  360
cctcgaggat atcaagatct ggcctcggcg gccaagcttg gcaatccggt actgttggta  420
aagccacc                                                          428

SEQ ID NO: 90        moltype = DNA   length = 564
FEATURE              Location/Qualifiers
source               1..564
                     mol_type = other DNA
                     organism = synthetic construct
SEQUENCE: 90
ggcctaactg gccggtacaa ctagtgacgt ctgtagctga gcgacagtat agtgcacagt   60
gactgcagca gtcattgtcg taaattgagt atcgtcgtaa attgacgaac gtcgtaaatt  120
agcgacagtc gtaaattagt acctgtcgta aattactctg cgtcgtaaat tgacgtctac  180
gtacatactg aaaagcatac ttttgcaatg ttatttttaa aaacaaggaa ctctttaacc  240
cagggaagat aatcacttgg ggaaaggaag gttcgtttct gagttagcaa caagtaaatg  300
cagcactagt gggtgggatt gaggtgtgcc ctggtgcata aatagagact cagctgtgct  360
ggcacactca gaagcttgga ccgcatccta gccgccgact cacacaaggc aggtgggtga  420
ggaaatccag gtaaggctcc tgacagcagc tttagaaggg tacttgctgg agtgaattcg  480
ggcctctgat tactagcctc gaggatatca agatctggcc tcggcggcca agcttggcaa  540
tccggtactg ttggtaaagc cacc                                         564

SEQ ID NO: 91        moltype = DNA   length = 373
FEATURE              Location/Qualifiers
source               1..373
                     mol_type = other DNA
                     organism = synthetic construct
SEQUENCE: 91
ggcctaactg gccggtacca ctagtgacgt ctgtagctga gcgacagtat agtgcacagt   60
gactgcagca gtcattgtcg taaattgagt atcgtcgtaa attgacgaac gtcgtaaatt  120
agcgacagtc gtaaattagt acctgtcgta aattactctg cgtcgtaaat tgacgtctac  180
gtaacccacg tgatgctgag aagtactcct gccctaggag agactcagg gcagagggag   240
gaaggacagc agaccagaca gtcacagcag ccttgacaaa acgttcctgg aactaccggt  300
gctagcctcg aggatatcaa gatctggcct cggcggccaa gcttggcaat ccggtactgt  360
tggtaaagcc acc                                                     373

SEQ ID NO: 92        moltype = DNA   length = 428
FEATURE              Location/Qualifiers
source               1..428
                     mol_type = other DNA
                     organism = synthetic construct
SEQUENCE: 92
ggcctaactg gccggtacca ctagtgacgt ctacgtactg atcagcgatg ctcatctcga   60
cctgatcggt acaacttctc acggaggctt ctaagtcatt acatacgtag tcattactat  120
acgtgtcatt acagatgctg tcattacacg aactgtcatt acgtactcag tcattactac  180
gtacgggaaa agttcagctg agagatataa aagagcagtc tttccagcac ctgcaaatcc  240
agagcggcgg gcactgacgg gcacttcac cgtgtggaca gactctccgg ttctgtgagt   300
ggttttcctt ttcccgggtc ggacctggag ttcttagggg gatggctgaa ccggtgctag  360
cctcgaggat atcaagatct ggcctcggcg gccaagcttg gcaatccggt actgttggta  420
aagccacc                                                          428

SEQ ID NO: 93        moltype = DNA   length = 605
FEATURE              Location/Qualifiers
source               1..605
                     mol_type = other DNA
                     organism = synthetic construct
SEQUENCE: 93
ggcctaactg gccggtacca ctagtgacgt ctgtagctga gcgacagtat agtgcacagt   60
gactgcagca gtcattgtcg taaattgagt atcgtcgtaa attgacgaac gtcgtaaatt  120
agcgacagtc gtaaattagt acctgtcgta aattactctg cgtcgtaaat tgacgtctac  180
gtaacatcgg ctatgctgct gctaatgcca cgtcaccaca tcgacatgcc acgtcaccat  240
catgccatgc cacgtcacca ctgcaagatg ccacgtcacc acagtataat gccacgtcac  300
caagttacta tgccacgtca ccaggtacct acgtaagtgg tgggggagtg aaaagagaga  360
tggagaaaga ggggatgggc agaaagagga ggaggagtca ggggcagggc atggaggtgg  420
gtggggctgg gctgccaaag caggataaat gcacacctgc ctgctggtct gggctccctg  480
cctcgggctc tcaccctcct ctcctgcagc tccagctttg tgctctaccg gtgctagcct  540
cgaggatatc aagatctggc ctcggcggcc aagcttggca atccggtact gttggtaaag  600
ccacc                                                             605

SEQ ID NO: 94        moltype = DNA   length = 663
FEATURE              Location/Qualifiers
source               1..663
                     mol_type = other DNA
```

```
                        organism = synthetic construct
SEQUENCE: 94
ggcctaactg gccggtacac tagtgacgtc tgtagctgag cgacagtata gtgcacagtg    60
actgcagcag tcattgtcgt aaattgagta tcgtcgtaaa ttgacgaacg tcgtaaatta   120
gcgacagtcg taaattagta cctgtcgtaa attactctgc gtcgtaaatt gacgtctacg   180
taacatcggc tatgctgctg ctaatgccac gtcaccacat cgacatgcca cgtcaccatc   240
atgccatgcc acgtcaccac tgcaagatgc cacgtcacca cagtataatg ccacgtcacc   300
aagttactat gccacgtcac caggtaccta cgtaggcccg cccccttttcc ttacgcggat   360
tggtagctgc aggcttccct atctgattgg ccgaacgaac gcagcgcgta atttaaaata   420
ttgtatctgt aacaaagctg cacctcgtgg gcggagttgt gctctgcggc tgcgaaagtc   480
cagcttcggc gactaggtgt gagtaagcca gtatcccagg aggagcaagt ggcacgtctt   540
cgggtgagtg tgcggctgtg ctggagcccg ggttaccagc tctttaccgg tctagcctcg   600
aggatatcaa gatctggcct cggcggccaa gcttggcaat ccggtactgt tggtaaagcc   660
acc                                                                 663

SEQ ID NO: 95         moltype = DNA  length = 716
FEATURE               Location/Qualifiers
source                1..716
                      mol_type = other DNA
                      organism = synthetic construct
SEQUENCE: 95
ggcctaactg gccggtacaa ctagtgacgt ctgtagctga gcgacagtat agtgcacagt    60
gactgcagca gtcattgtcg taaattgagt atcgtcgtaa attgacgaac gtcgtaaatt   120
agcgacagtc gtaaattagt acctgtcgta aattactctg cgtcgtaaat tgacgtctac   180
gtaacatcgg ctatgctgct gctaatgcca cgtcaccaca tcgacatgcc acgtcaccat   240
catgccatgc cacgtcacca ctgcaagatg ccacgtcacc acagtataat gccacgtcac   300
caagttacta tgccacgtca ccaggtacct acgtacatac tgaaaagcat acttttgcaa   360
tgttatttt aaaaacaagg aactctttaa cccagggaag ataatcactt ggggaaagga   420
aggttcgttt ctgagttagc aacaagtaaa tgcagcacta gtgggtggga ttgaggtgtg   480
ccctggtgca taaatagaga ctcagctgtg ctggcacact cagaagcttg gaccgcatcc   540
tagccgccga ctcacacaag gcaggtgggg gaggaaatcc aggtaaggct cctgacagca   600
gctttagaag ggtacttgct ggagtgaatt cgggcctctg attactagcc tcgaggatat   660
caagatctgg cctcggcggc caagcttggc aatccggtac tgttggtaaa gccacc      716

SEQ ID NO: 96         moltype = DNA  length = 525
FEATURE               Location/Qualifiers
source                1..525
                      mol_type = other DNA
                      organism = synthetic construct
SEQUENCE: 96
ggcctaactg gccggtacca ctagtgacgt ctgtagctga gcgacagtat agtgcacagt    60
gactgcagca gtcattgtcg taaattgagt atcgtcgtaa attgacgaac gtcgtaaatt   120
agcgacagtc gtaaattagt acctgtcgta aattactctg cgtcgtaaat tgacgtctac   180
gtaacatcgg ctatgctgct gctaatgcca cgtcaccaca tcgacatgcc acgtcaccat   240
catgccatgc cacgtcacca ctgcaagatg ccacgtcacc acagtataat gccacgtcac   300
caagttacta tgccacgtca ccaggtacct acgtaaccca cgtgatgctg agaagtactc   360
ctgccctagg aagagactca gggcagaggg aggaaggaca gaaccaga cagtcacagc   420
agccttgaca aaacgttcct ggaactaccg gtgctagcct cgaggatatc aagatctggc   480
ctcggcggcc aagcttggca atccggtact gttggtaaag ccacc                  525

SEQ ID NO: 97         moltype = DNA  length = 580
FEATURE               Location/Qualifiers
source                1..580
                      mol_type = other DNA
                      organism = synthetic construct
SEQUENCE: 97
ggcctaactg gccggtacca ctagtgacgt ctgtagctga gcgacagtat agtgcacagt    60
gactgcagca gtcattgtcg taaattgagt atcgtcgtaa attgacgaac gtcgtaaatt   120
agcgacagtc gtaaattagt acctgtcgta aattactctg cgtcgtaaat tgacgtctac   180
gtaacatcgg ctatgctgct gctaatgcca cgtcaccaca tcgacatgcc acgtcaccat   240
catgccatgc cacgtcacca ctgcaagatg ccacgtcacc acagtataat gccacgtcac   300
caagttacta tgccacgtca ccaggtacct acgtacggga aaagttcagc tgagagatat   360
aaaagagcag tctttccagc acctgcaaat ccagagcggc gggcactgac gggcacttgc   420
accgtggtga cagactctcc ggttctgtga gtggtttttc ttttcccggg tcggacctgg   480
agttcttagg gggatggctg aaccggtgct agcctcgagg atatcaagat ctggcctcgg   540
cggccaagct tggcaatccg gtactgttgg taaagccacc                       580

SEQ ID NO: 98         moltype = DNA  length = 459
FEATURE               Location/Qualifiers
source                1..459
                      mol_type = other DNA
                      organism = synthetic construct
SEQUENCE: 98
ggcctaactg gccggtacca ctagtgacgt ctacgtaaca tcggctatgc tgctgctaat    60
gccacgtcac cacatcgaca tgccacgtca ccatcatgcc atgccacgtc accactgcaa   120
gatgccacgt caccacagta taatgccacg tcaccaagtt actatgccac gtcaccaggt   180
acctacgtaa gtggtggggg agtgaaaaga gagatggaga aagaggggat gggcagaaag   240
aggaggagga gtcaggggca gggcatggag gtgggtgggg ctgggctgcc aaagcaggat   300
aaatgcacac ctgcctgctg gtctgggctc cctgcctcgg gctctcaccc tcctctcctg   360
```

-continued

```
cagctccagc tttgtgctct accggtgcta gcctcgagga tatcaagatc tggcctcggc   420
ggccaagctt ggcaatccgg tactgttggt aaagccacc                          459

SEQ ID NO: 99          moltype = DNA   length = 570
FEATURE                Location/Qualifiers
source                 1..570
                       mol_type = other DNA
                       organism = synthetic construct
SEQUENCE: 99
ggcctaactg gccggtacaa ctagtgacgt ctacgtaaca tcggctatgc tgctgctaat   60
gccacgtcac cacatcgaca tgccacgtca ccatcatgcc atgccacgtc accactgcaa   120
gatgccacgt caccacagta taatgccacg tcaccaagtt actatgccac gtcaccaggt   180
acctacgtac atactgaaaa gcatactttt gcaatgttat ttttaaaaac aaggaactct   240
ttaacccagg gaagataatc acttgggaa aggaaggttc gtttctgagt tagcaacaag    300
taaatgcagc actagtgggt gggattgagg tgtgccctgg tgcataaata gagactcagc   360
tgtgctggca cactcagaag cttggaccgc atcctagccg ccgactcaca caaggcaggt   420
gggtgaggaa atccaggtaa ggctcctgac agcagcttta gaagggtact tgctggagtg   480
aattcgggcc tctgattact agcctcgagg atatcaagat ctggcctcgg cggccaagct   540
tggcaatccg gtactgttgg taaagccacc                                    570

SEQ ID NO: 100         moltype = DNA   length = 518
FEATURE                Location/Qualifiers
source                 1..518
                       mol_type = other DNA
                       organism = synthetic construct
SEQUENCE: 100
ggcctaactg gccggtacca ctagtgacgt ctacgtaaca tcggctatgc tgctgctaat   60
gccacgtcac cacatcgaca tgccacgtca ccatcatgcc atgccacgtc accactgcaa   120
gatgccacgt caccacagta taatgccacg tcaccaagtt actatgccac gtcaccaggt   180
acctacgtag gcccgccccc tttccttacg cggattggta gctgcaggct tccctatctg   240
attggccgaa cgaacgcagc gcgtaattta aaatattgta tctgtaacaa agctgcacct   300
cgtgggcgga gttgtgctct gcggctgcga aagtccagct tcggcgacta ggtgtgagta   360
agccagtatc ccaggaggag caagtggcac gtcttcgggt gagtgtgcgg ctgtgctgga   420
gcccgggtta ccagctcttt accggtctag cctcgaggat atcaagatct ggcctcggcg   480
gccaagcttg gcaatccggt actgttggta aagccacc                          518

SEQ ID NO: 101         moltype = DNA   length = 379
FEATURE                Location/Qualifiers
source                 1..379
                       mol_type = other DNA
                       organism = synthetic construct
SEQUENCE: 101
ggcctaactg gccggtacca ctagtgacgt ctacgtaaca tcggctatgc tgctgctaat   60
gccacgtcac cacatcgaca tgccacgtca ccatcatgcc atgccacgtc accactgcaa   120
gatgccacgt caccacagta taatgccacg tcaccaagtt actatgccac gtcaccaggt   180
acctacgtaa cccacgtgat gctgagaagt actcctgccc taggaagaga ctcagggcag   240
agggaggaag gacagcagac cagacagtca cagcagcctt gacaaaacgt tcctggaact   300
accggtgcta gcctcgagga tatcaagatc tggcctcggc ggccaagctt ggcaatccgg   360
tactgttggt aaagccacc                                               379

SEQ ID NO: 102         moltype = DNA   length = 434
FEATURE                Location/Qualifiers
source                 1..434
                       mol_type = other DNA
                       organism = synthetic construct
SEQUENCE: 102
ggcctaactg gccggtacca ctagtgacgt ctacgtaaca tcggctatgc tgctgctaat   60
gccacgtcac cacatcgaca tgccacgtca ccatcatgcc atgccacgtc accactgcaa   120
gatgccacgt caccacagta taatgccacg tcaccaagtt actatgccac gtcaccaggt   180
acctacgtac gggaaaagtt cagctgagag atataaaaga gcagtctttc cagcacctgc   240
aaatccagag cggcgggcac tgacgggcac ttgcaccgtg tggacagact ctccggttct   300
gtgagtggtt tttctttttcc cgggtcggac ctggagttct taggggggatg gctgaaccgg   360
tgctagcctc gaggatatca agatctggcc tcggcggcca gcttggcaa tccggtactg   420
ttggtaaagc cacc                                                    434

SEQ ID NO: 103         moltype = DNA   length = 317
FEATURE                Location/Qualifiers
source                 1..317
                       mol_type = other DNA
                       organism = synthetic construct
SEQUENCE: 103
gaattcaaga ctgcaagcga gcgacagtat agtgcacagt gactgcagca gtcattatac   60
gtcgcctaaa tcgagatgct gtaggcacgt gtatctggca cgtgtactcg gcacgtgtac   120
taggcacgtg taagaggcac gtgtacgcgt gcacgtgtagg tacctgcgct cccgacatgc   180
cccgcgcgc gccattaacc gccagatttg agtcgcggga cccgttggca gaggtgggct   240
agcctcgagg atatcaagat ctggcctcgg cggccaagct tggcaatccg gtactgttgg   300
taaagccacc atggaag                                                 317

SEQ ID NO: 104         moltype = DNA   length = 274
```

-continued

```
FEATURE            Location/Qualifiers
source             1..274
                   mol_type = other DNA
                   organism = synthetic construct
SEQUENCE: 104
gaattcaaga ctgcaagcga gcgacagtat agtgcacagt gactgcagca gtcattatac    60
gtcgcctaaa tcgagatgct gtaggcacgt gtatctggca cgtgtactcg gcacgtgtac   120
taggcacgtg taagaggcac gtgtacgcgg cacgtgtagg tacctataaa aggccagcag   180
cagcctgacc acatctcatc cgctagcctc gaggatatca agatctggcc tcggcggcca   240
agcttggcaa tccggtactg ttggtaaagc cacc                               274

SEQ ID NO: 105          moltype = DNA   length = 310
FEATURE            Location/Qualifiers
source             1..310
                   mol_type = other DNA
                   organism = synthetic construct
SEQUENCE: 105
gaattcaaga ctgcaagcct gagcgacagt atagtgcaca gtgactgcag cagtcattat    60
acgtcgccta atcgagatg ctggacacgt gtccgagaca cgtgtctgtg acacgtgtcc   120
gggacacgtg tcgcagacac gtgtcgtgga cacgtgtcgg tacctgcgct cccgacatgc   180
cccgcggcgc gccattaacc gccagatttg agtcgcggga cccgttggca gaggtgggct   240
agcctcgagg atatcaagat ctggcctcgg cggccaagct tggcaatccg gtactgttgg   300
taaagccacc                                                          310

SEQ ID NO: 106          moltype = DNA   length = 274
FEATURE            Location/Qualifiers
source             1..274
                   mol_type = other DNA
                   organism = synthetic construct
SEQUENCE: 106
gaattcaaga ctgcaagcct gagcgacagt atagtgcaca gtgactgcag cagtcattat    60
acgtcgccta atcgagatg ctggacacgt gtccgagaca cgtgtctgtg acacgtgtcc   120
gggacacgtg tcgcagacac gtgtcgtgga cacgtgtcgg tacctataaa aggccagcag   180
cagcctgacc acatctcatc cgctagcctc gaggatatca agatctggcc tcggcggcca   240
agcttggcaa tccggtactg ttggtaaagc cacc                               274

SEQ ID NO: 107          moltype = DNA   length = 764
FEATURE            Location/Qualifiers
source             1..764
                   mol_type = other DNA
                   organism = synthetic construct
SEQUENCE: 107
ggcctaactg gccggtacca ctagtatcga tccttcatag ggcagggagg ggtgggcact    60
tgggtgtgac caaggagagg aggcgcgcct ggtcaacagc tctccctggc ccgtgtccag   120
ctccctcctc acacagagag gggggcgcat ctcaggatg gcatctttcc cccccacagg   180
gaaattctta tctttgaaac agcatgggaa tcgaggcacc caggaggga gcagaggcag   240
gcaggcctcc ttcaggccca tcctccagct gggctggtg tgccagggag gctccctgct   300
tggtaacaaa ggcctgaggg agagttgcga aacccagcag gaaagccggc tcaccttcgc   360
ctcccctgc ggctgggagg agaggaaata tcccatggct gactgtgcca aggaggtgtc   420
tgagccagcc ctcccggccc gagggcaggg caggtggccc tgagagataa gccaatcccg   480
cagctgcaga tgaggagttc tgagaagcat tgctcaggac agcggtaaat cacttcttcg   540
aggtgccctg cacgccggtc ctgggagcag gcggcctccc gggggtgcgg gagccccact   600
cctccgtggt gtgttccatt tgcttcccac atctggagga gctgacgtgc cagcctcccc   660
cagcaccacc cagggacggg aggcaaccgg tgctagcctc gaggatatca agatctggcc   720
tcggcggcca agcttggcaa tccggtactg ttggtaaagc cacc                    764

SEQ ID NO: 108          moltype = DNA   length = 283
FEATURE            Location/Qualifiers
source             1..283
                   mol_type = other DNA
                   organism = synthetic construct
SEQUENCE: 108
ggcctaactg gccggtaccg acgtctacct gatcaaacat gcccggacat gtcgtaagac    60
ataaacatgc ccggacatgt cctcgcaatc taacatgccc ggacatgtcc tcgcaatcta   120
acatgcccgg acatgtctgc aagctacaac atgcccggac atgtctacgt agctagctat   180
aaaaggccag cagcagcctg accacatctc atcctcctcg aggatatcaa gatctggcct   240
cggcggccaa gcttggcaat ccggtactgt tggtaaagcc acc                     283

SEQ ID NO: 109          moltype = DNA   length = 283
FEATURE            Location/Qualifiers
source             1..283
                   mol_type = other DNA
                   organism = synthetic construct
SEQUENCE: 109
ggcctaactg gccggtaccg acgtccctga tcggtacaac ttctcacaac atgcctgggc    60
atgtcgctat gcaacatgcc tgggcatgtc agatgcaaac atgcctgggc atgtcctgct   120
ataacatgcc tgggcatgtc ctgctataac atgcctgggc atgtctacgt agctagctat   180
aaaaggccag cagcagcctg accacatctc atcctcctcg aggatatcaa gatctggcct   240
cggcggccaa gcttggcaat ccggtactgt tggtaaagcc acc                     283
```

-continued

```
SEQ ID NO: 110              moltype = DNA   length = 283
FEATURE                     Location/Qualifiers
source                      1..283
                            mol_type = other DNA
                            organism = synthetic construct
SEQUENCE: 110
ggcctaactg gccggtaccg acgtctcggg caagcgctcc cgacatgccc gggcaagcgc      60
tcccgacatg cccgggcaag cgctcccgac atgcccgggc aagcgctccc gacatgcccg     120
ggcaagcgct cccgacatgc ccgggcaagc gctcccgaca tgccctacgt agctagctat     180
aaaaggccag cagcagcctg accacatctc atcctcctcg aggatatcaa gatctggcct     240
cggcggccaa gcttggcaat ccggtactgt tggtaaagcc acc                       283

SEQ ID NO: 111              moltype = DNA   length = 435
FEATURE                     Location/Qualifiers
source                      1..435
                            mol_type = other DNA
                            organism = synthetic construct
SEQUENCE: 111
ggcctaactg gccggtacct tttgataaaa atcattaggt acggccgcgg tgccagggcg      60
tgcccttggg ctccccgggc gcgaaactag tgacgtcctg agcgacagta tagtgcacag     120
tgactgcagc agtcattcct ttgatgtacg caactccttg atgtctatg cgtcctttga      180
tgttaaggat tcctttgatg taggtacatc ctttgatgtc cgtaaatcct ttgatgtgac     240
gtctacgtag gtgactcatg ggtgactcat gtacgtaacg cgtcccgaca tgccccgcgg     300
cgcgccatta accgccagat ttgagtcgcg ggacccgttg gcagaggtgg gaattcaccg     360
gtgctagcct cgaggatatc aagatctggc ctcggcggcc aagcttggca atccggtact     420
gttggtaaag ccacc                                                      435

SEQ ID NO: 112              moltype = DNA   length = 434
FEATURE                     Location/Qualifiers
source                      1..434
                            mol_type = other DNA
                            organism = synthetic construct
SEQUENCE: 112
ggcctaactg gccggtacct tttgataaaa atcattaggt acggccgcgg tgccagggcg      60
tgcccttggg ctccccgggc gcgaaactag tgacgtcggt gactcatggg tgactcatga     120
cgtctacgta ctgagcgaca gtatagtgca cagtgactgc agcagtcatt cctttgatgt     180
acgcaactcc tttgatgtct atgcgtcctt tgatgttaag gattcctttg atgtaggtac     240
atcctttgat gtccgtaaat cctttgatgt tacgtaacgc gtcccgacat gccccgcggc     300
gcgccattaa ccgccagatt tgagtcgcgc gacccgttgg cagaggtggg aattcaccg      360
tgctagcctc gaggatatca agatctggcc tcggcggcca agcttggcaa tccggtactg     420
ttggtaaagc cacc                                                       434

SEQ ID NO: 113              moltype = DNA   length = 594
FEATURE                     Location/Qualifiers
source                      1..594
                            mol_type = other DNA
                            organism = synthetic construct
SEQUENCE: 113
ggcctaactg gccggtacca actagtgacg tcctgagcga cagtatagtg cacagtgact      60
gcagcagtca ttcctttgat gtacgcaact cctttgatgt ctatgcgtcc tttgatgtta     120
aggattcctt tgatgtaggt acatcctttg atgtccgtaa atcctttgat gtgacgtcta     180
cgtaggtgac tcatgggtga ctcatgtacg tacatactga aaagcatact tttgcaatgt     240
tatttttaaa aacaaggaac tctttaaccc agggaagata atcacttggg gaaaggaagg     300
ttcgtttctg agttagcaac aagtaaatgc agcactagtg ggtgggattg aggtgtgccc     360
tggtgcataa atagagactc agctgtgctg gcacactcag aagcttggac cgcatcctag     420
ccgccgactc acacaaggca ggtgggtgag gaaatccagg taaggctcct gacagcagct     480
ttagaagggt acttgctgga gtgaattcgg gcctctgatt agctagcctc gaggatatca     540
agatctggcc tcggcggcca agcttggcaa tccggtactg ttggtaaagc cacc           594

SEQ ID NO: 114              moltype = DNA   length = 594
FEATURE                     Location/Qualifiers
source                      1..594
                            mol_type = other DNA
                            organism = synthetic construct
SEQUENCE: 114
ggcctaactg gccggtacca actagtgacg tcggtgactc atgggtgact catggacgtc      60
tacgtactga gcgacagtat agtgcacagt gactgcagca gtcattcctt tgatgtacgc     120
aactcctttg atgtctatgc gtcctttgat gttaaggatt cctttgatgt aggtacatcc     180
tttgatgtcc gtaaatcctt tgatgttacg tacatactga aaagcatact tttgcaatgt     240
tatttttaaa aacaaggaac tctttaaccc agggaagata atcacttggg gaaaggaagg     300
ttcgtttctg agttagcaac aagtaaatgc agcactagtg ggtgggattg aggtgtgccc     360
tggtgcataa atagagactc agctgtgctg gcacactcag aagcttggac cgcatcctag     420
ccgccgactc acacaaggca ggtgggtgag gaaatccagg taaggctcct gacagcagct     480
ttagaagggt acttgctgga gtgaattcgg gcctctgatt agctagcctc gaggatatca     540
agatctggcc tcggcggcca agcttggcaa tccggtactg ttggtaaagc cacc           594

SEQ ID NO: 115              moltype = DNA   length = 566
FEATURE                     Location/Qualifiers
```

```
source                    1..566
                          mol_type = other DNA
                          organism = synthetic construct
SEQUENCE: 115
ggcctaactg gccggtacca actagtgacg tcctgagcga cagtatagtg cacagtgact   60
gcagcagtca ttcctttgat gtacgcaact cctttgatgt ctatgcgtcc tttgatgtta  120
aggattcctt tgatgtaggt acatcctttg atgtccgtaa atcctttgat gtgacgtcta  180
cgtacatact gaaaagcata cttttgcaat gttattttta aaaacaagga actctttaac  240
ccagggaaga taatcacttg gggaaaggaa ggttcgtttc tgagttagca acaagtaaat  300
gcagcactag tgggtgggat tgaggtgtgc cctggtgcat aaatagagac tcagctgtgc  360
tggcacactc agaagcttgg accgcatcct agccgccgac tcacacaagg caggtgggtg  420
aggaaatcca ggtaaggctc ctgacagcag ctttagaagg gtacttgctg gagtgaattc  480
gggcctctga ttagctagcc tcgaggatat caagatctgg cctcggcggc caagcttggc  540
aatccggtac tgttggtaaa gccacc                                       566

SEQ ID NO: 116          moltype = DNA   length = 311
FEATURE                 Location/Qualifiers
source                  1..311
                        mol_type = other DNA
                        organism = synthetic construct
SEQUENCE: 116
caactagtga cgtcctgagc gacagtatag tgcacagtga ctgcagcagt cattcctttg   60
atgtacgcaa ctcctttgat gtctatgcgt cctttgatgt taaggattcc tttgatgtag  120
gtacatcctt tgatgtccgt aaatcctttg atgtgacgtc tacgtaggtg actcatgggt  180
gactcatgta cgtaacccac gtgatgctga gaagtactcc tgccctagga agagactcag  240
ggcagaggga ggaaggacag cagaccagac agtcacagca gccttgacaa aacgttcctg  300
gaactaccgg t                                                       311

SEQ ID NO: 117          moltype = DNA   length = 374
FEATURE                 Location/Qualifiers
source                  1..374
                        mol_type = other DNA
                        organism = synthetic construct
SEQUENCE: 117
ggcctaactg gccggtacca actagtgacg tcctgagcga cagtatagtg cacagtgact   60
gcagcagtca ttcctttgat gtacgcaact cctttgatgt ctatgcgtcc tttgatgtta  120
aggattcctt tgatgtaggt acatcctttg atgtccgtaa atcctttgat gtgacgtcta  180
cgtaacccac gtgatgctga gaagtactcc tgccctagga agagactcag ggcagaggga  240
ggaaggacag cagaccagac agtcacagca gccttgacaa aacgttcctg gaactaccgg  300
tgctagcctc gaggatatca agatctggcc tcggcggcca agcttggcaa tccggtactg  360
ttggtaaagc cacc                                                    374

SEQ ID NO: 118          moltype = DNA   length = 343
FEATURE                 Location/Qualifiers
source                  1..343
                        mol_type = other DNA
                        organism = synthetic construct
SEQUENCE: 118
aactagtgac gtcctgagcg acagtatagt gcacagtgac tgcagcagtc attcctttga   60
tgtacgcaac tcctttgatg tctatgcgtc ctttgatgtt aaggattcct ttgatgtagg  120
tacatccttt gatgtccgta aatcctttga tgtgacgtct acgtatacgt acgggaaaag  180
ttcagctgag agatataaaa gagcagtctt tccagcacct gcaaatccag agcggcgggc  240
actgacgggc acttgcaccg tgtggacaga ctctccggtt ctgtgagtgg ttttttctttt  300
cccgggtcgg acctggagtt cttagggga tggctgaacc ggt                    343

SEQ ID NO: 119          moltype = DNA   length = 361
FEATURE                 Location/Qualifiers
source                  1..361
                        mol_type = other DNA
                        organism = synthetic construct
SEQUENCE: 119
ctagtgacgt cctgagcgac agtatagtgc acagtgactg cagcagtcat tcctttgatg   60
tacgcaactc ctttgatgtc tatgcgtcct ttgatgttaa ggattccttt gatgtaggta  120
catcctttga tgtccgtaaa tcctttgatg tgacgtctac gtatacgtag gccgcccccc  180
agtgaaaaga gagatggaga aagagggggat gggcagaaag aggaggagga gtcagggca  240
gggcatggag gtgggtgggg ctgggctgcc aaagcaggat aaatgcacac ctgcctgctg  300
gtctgggctc cctgcctcgg gctctcaccc tcctctcctg cagctccagc tttgtgctct  360
a                                                                  361

SEQ ID NO: 120          moltype = DNA   length = 421
FEATURE                 Location/Qualifiers
source                  1..421
                        mol_type = other DNA
                        organism = synthetic construct
SEQUENCE: 120
ctagtgacgt cctgagcgac agtatagtgc acagtgactg cagcagtcat tcctttgatg   60
tacgcaactc ctttgatgtc tatgcgtcct ttgatgttaa ggattccttt gatgtaggta  120
catcctttga tgtccgtaaa tcctttgatg tgacgtctac gtatacgtag gccgccccc  180
tttccttacg cggattggta gctgcaggct tccctatctg attggccgaa cgaacgcagc  240
```

-continued

```
gcgtaattta aaatattgta tctgtaacaa agctgcacct cgtgggcgga gttgtgctct    300
gcggctgcga aagtccagct tcggcgacta ggtgtgagta agccagtatc ccaggaggag    360
caagtggcac gtcttcgggt gagtgtgcgg ctgtgctgga gcccgggtta ccagctcttt    420
a                                                                    421

SEQ ID NO: 121          moltype = DNA   length = 895
FEATURE                 Location/Qualifiers
source                  1..895
                        mol_type = other DNA
                        organism = synthetic construct
SEQUENCE: 121
ggcctaactg gccggtacca ccatgggga  ggtggggtga tcacaggaca gtcagcctcg    60
cagaggacag agaccaccca ggactgtcag ggagaacatg gacaggccct gagccgcagc    120
tcagccaaca gacacggaga gggagggtcc ccctggagcc ttccccaagg acagcagagc    180
ccagagtcac ccacctccct ccaccacagt cctctctttc caggacacac aagacacctc    240
cccctccaca tgcaggatct ggggactcct gagacctctg ggcctgggtc tccatccctg    300
ggtcagtggc ggggttggtg gtactggaga cagagggctg gtccctcccc agccaccacc    360
cagtgagcct ttttctagcc cccagagcca cctctgtcac cttcctgttg ggcatcatcc    420
caccttccca gagccctgga gagcatgggg agacccggga ccctgctggg tttctctgtc    480
acaaaggaaa ataatccccc tggtgtgaca gacccaagga cagaacacag cagaggtcag    540
cactgggaa gacaggttgt cctcccaggg gatgggggtc catccacctt gccgaaaaga    600
tttgtctgag gaactgaaaa tagaagggaa aaaagaggag ggacaaaaga cagaaaatg    660
agaggggagg ggacagagga cacctgaata aagaccacac ccatgaccca cgtgatgctg    720
agaagtactc ctgccctagg aagagactca gggcagaggg aggaaggaca gcagaccaga    780
cagtcacagc agccttgaca aaacgttcct ggaactaccg gtgctagcct cgaggatatc    840
aagatctggc ctcggcggcc aagcttggca atccggtact gttggtaaag ccacc         895

SEQ ID NO: 122          moltype = DNA   length = 401
FEATURE                 Location/Qualifiers
source                  1..401
                        mol_type = other DNA
                        organism = synthetic construct
SEQUENCE: 122
ggcctaactg gccggtacct tttgataaaa atcattaggt acggccgcgg tgccagggcg    60
tgcccttggg ctccccgggc gcgaaaactag tgacgtctac ctgatcaaac atgcccggac    120
atgtcgtaag acataaacat gcccggacat gtcctcgcaa tctaacatgc ccggacatgt    180
cctcgcaatc taacatgccc ggacatgtct gcaagctaca acatgcccgg acatgtctac    240
gtaacgcgtc ccgacatgcc ccgcggcgcg ccattaaccg ccagatttga gtcgcgggac    300
ccgttggcag aggtgggaat tcaccggtgc tagcctcgag gatatcaaga tctggcctcg    360
gcggccaagc ttggcaatcc ggtactgttg gtaaagccac c                        401

SEQ ID NO: 123          moltype = DNA   length = 560
FEATURE                 Location/Qualifiers
source                  1..560
                        mol_type = other DNA
                        organism = synthetic construct
SEQUENCE: 123
ggcctaactg gccggtacca actagtgacg tctacctgat caaacatgcc cggacatgtc    60
gtaagacata aacatgcccg gacatgtcct cgcaatctaa catgcccgga catgtcctcg    120
caatctaaca tgcccggaca tgtctgcaag ctacaacatg cccggacatg tctacgtaca    180
tactgaaaag catactttg caatgttatt tttaaaaaca aggaactctt taacccaggg    240
aagataatca cttggggaaa ggaaggttcg tttctgagtt agcaacaagt aaatgcagca    300
ctagtgggtg ggattgaggt gtgcctggt gcataaatag agactcagct gtgctggcac    360
actcagaagc ttggaccgca tcctagccgc cgactcacac aaggcaggtg ggtgaggaaa    420
tccaggtaag gctcctgaca gcagctttag aagggtactt gctggagtga attcgggcct    480
ctgattagct agcctcgagg atatcaagat ctggcctcgg cggccaagct ggcaatccg     540
gtactgttgg taaagccacc                                                560

SEQ ID NO: 124          moltype = DNA   length = 423
FEATURE                 Location/Qualifiers
source                  1..423
                        mol_type = other DNA
                        organism = synthetic construct
SEQUENCE: 124
ggcctaactg gccggtacca actagtgacg tctacctgat caaacatgcc cggacatgtc    60
gtaagacata aacatgcccg gacatgtcct cgcaatctaa catgcccgga catgtcctcg    120
caatctaaca tgcccggaca tgtctgcaag ctacaacatg cccggacatg tctacgtacg    180
ggaaaagttc agctgagaga tataaaagag cagtctttcc agcacctgca aatccagagc    240
ggcggcact gacgggcact tgcaccgtgt ggacagactc tccggttctg tgagtggttt    300
ttcttttccc gggtcggacc tggagttctt aggggatgg ctgaaccggt gctagcctcg    360
aggatatcaa gatctggcct cggcggccaa gcttggcaat ccggtactgt tggtaaagcc    420
acc                                                                  423

SEQ ID NO: 125          moltype = DNA   length = 586
FEATURE                 Location/Qualifiers
source                  1..586
                        mol_type = other DNA
                        organism = synthetic construct
SEQUENCE: 125
```

-continued

```
ggcctaactg gccggtacca actagtgacg tctacctgat caaacatgcc cggacatgtc    60
gtaagacata aacatgcccg gacatgtcct cgcaatctaa catgcccgga catgtcctcg   120
caatctaaca tgcccggaca tgtctgcaag ctacaacatg cccggacatg tctacccgtt   180
cgacaagccc ggacatgcta agacataaac atgcccggac atgtcctcgc aatctaacca   240
tgcccggaca tgtcctcgca atctaacatg cccggacatg tctgcaagct acaacatgcc   300
cggacatgtc tacgtaagtg gtgggggagt gaaaagagag atggagaaag aggggatggg   360
cagaaagagg aggaggagtc aggggcaggg catggaggtg ggtggggctg ggctgccaaa   420
gcaggataaa tgcacacctg cctgctggtc tgggctccct gcctcgggct ctcaccctcc   480
tctcctgcag ctccagcttt gtgctctacc ggtgctagcc tcgaggatat caagatctgg   540
cctcggcggc caagcttggc aatccggtac tgttggtaaa gccacc                  586
```

SEQ ID NO: 126          moltype = DNA  length = 555
FEATURE                  Location/Qualifiers
source                  1..555
                        mol_type = other DNA
                        organism = synthetic construct
SEQUENCE: 126

```
ggcctaactg gccggtacct tttgataaaa atcattaggt acggccgcgg tgccagggcg    60
tgcccttggg ctccccgggc gcgaaactag tgacgtcctg agcgacagta tagtgcacag   120
tgactgcagc agtcattcct ttgatgtacg caactccttt gatgtctatg cgtcctttga   180
tgttaaggat tcctttgatg taggtacatc ctttgatgtc cgtaaatcct ttgatgtgac   240
gtctacgtat ctacctgatc aaacatgccc ggacatgtcg taagacataa acatgcccgg   300
acatgtcctc gcaatctaac atgcccggac atgtcctcgc aatctaacat gcccggacat   360
gtctgcaagc tacaacatgc ccggacatgt ctacgtaacg cgtcccgaca tgccccgcgg   420
cgcgccatta accgccagat ttgagtcgcg ggacccgttg gcagaggtgg gaattcaccg   480
gtgctagcct cgaggatatc aagatctggc tcggcggc aagcttggca atccggtact   540
gttggtaaag ccacc                                                    555
```

SEQ ID NO: 127          moltype = DNA  length = 869
FEATURE                  Location/Qualifiers
source                  1..869
                        mol_type = other DNA
                        organism = synthetic construct
SEQUENCE: 127

```
ggcctaactg gccggtacca actagtgacg tcctgagcga cagtatagtg cacagtgact    60
gcagcagtca ttcctttgat gtacgcaact cctttgatgt ctatgcgtcc tttgatgtta   120
aggattcctt tgatgtaggt acatcctttg atgtccgtaa atcctttgat gtgacgtcta   180
cgtatctacc tgatcaaaca tgcccggaca tgtcgtaaga cataaacatg cccggacatg   240
tcctgcaat ctaacatgcc cggacatgtc ctcgcaatct aacatgcccg gacatgtctg   300
caagctacaa catgcccgga catgtctaca atatacgtat ctacctgatc aaacatgccc   360
ggacatgtcg taagacataa acatgcccgg acatgtcctc gcaatctaac atgcccggac   420
atgtcctcgc aatctaacat gcccggacat gtctgcaagc tacaacatgc ccggacatgt   480
ctacgtacat actgaaaagc atactttgc aatgttattt ttaaaaacaa ggaactcttt   540
aacccaggga agataatcac ttggggaaag gaaggttcgt ttctgagtta gcaacaagta   600
aatgcagcac tagtgggtgg gattgaggtg tgcctggtg cataaataga gactcagctg   660
tgctggcaca ctcagaagct tggaccgcat cctagccgcc gactcacaca aggcaggtgg   720
gtgaggaaat ccaggtaagg ctcctgacag cagctttaga agggtacttg ctggagtgaa   780
ttcgggcctc tgattagcta gcctcgagga tatcaagatc tggcctcggc ggccaagctt   840
ggcaatccgg tactgttggt aaagccacc                                     869
```

SEQ ID NO: 128          moltype = DNA  length = 13
FEATURE                  Location/Qualifiers
source                  1..13
                        mol_type = other DNA
                        organism = synthetic construct
SEQUENCE: 128

```
gttaattatt aac                                                       13
```

SEQ ID NO: 129          moltype = DNA  length = 12
FEATURE                  Location/Qualifiers
source                  1..12
                        mol_type = other DNA
                        organism = synthetic construct
SEQUENCE: 129

```
tattttatct tt                                                        12
```

SEQ ID NO: 130          moltype = DNA  length = 526
FEATURE                  Location/Qualifiers
source                  1..526
                        mol_type = other DNA
                        organism = synthetic construct
SEQUENCE: 130

```
ggcctaactg gccggtacca ctagtaagcc tcaagatttc ctttaggctc ttaggtaaga    60
aatgtctaag gttcaaggaa aaaggttaag ttggaagaat cccaggcaaa ataagtgcag   120
atccacgaca gttggtaacc cggacccaca ttagaactca gaggtcaagc agaagcgaac   180
gactggaatt ccagtcaggc ccgcccctt tccttacgcg gattggtagc tgcaggcttc   240
cctatctgat tggccgaacg aacgcagcgc gtaatttaaa atattgtatc tgtaacaaag   300
ctgcacctcg tgggcggagt tgtgctctgc ggctgcgaaa gtccagcttc ggcgactagg   360
tgtgagtaag ccagtatccc aggaggagca agtggcacgt cttcgggtga gtgtgcggct   420
```

```
gtgctggagc ccgggttacc agctcttacc ggtgctagcc tcgaggatat caagatctgg   480
cctcggcggc caagcttggc aatccggtac tgttggtaaa gccacc               526

SEQ ID NO: 131          moltype = DNA   length = 13
FEATURE                 Location/Qualifiers
source                  1..13
                        mol_type = other DNA
                        organism = synthetic construct
SEQUENCE: 131
attccagatg ttt                                                    13

SEQ ID NO: 132          moltype = DNA   length = 10
FEATURE                 Location/Qualifiers
source                  1..10
                        mol_type = other DNA
                        organism = synthetic construct
SEQUENCE: 132
accggaagtg                                                        10

SEQ ID NO: 133          moltype = DNA   length = 11
FEATURE                 Location/Qualifiers
source                  1..11
                        mol_type = other DNA
                        organism = synthetic construct
SEQUENCE: 133
ttctaatcta t                                                      11

SEQ ID NO: 134          moltype = DNA   length = 10
FEATURE                 Location/Qualifiers
source                  1..10
                        mol_type = other DNA
                        organism = synthetic construct
SEQUENCE: 134
accggaaatg                                                        10

SEQ ID NO: 135          moltype = DNA   length = 11
FEATURE                 Location/Qualifiers
source                  1..11
                        mol_type = other DNA
                        organism = synthetic construct
SEQUENCE: 135
ggatgactca t                                                      11

SEQ ID NO: 136          moltype = DNA   length = 11
FEATURE                 Location/Qualifiers
source                  1..11
                        mol_type = other DNA
                        organism = synthetic construct
SEQUENCE: 136
ttcttggcag a                                                      11

SEQ ID NO: 137          moltype = DNA   length = 10
FEATURE                 Location/Qualifiers
source                  1..10
                        mol_type = other DNA
                        organism = synthetic construct
SEQUENCE: 137
accggaagcg                                                        10

SEQ ID NO: 138          moltype = DNA   length = 12
FEATURE                 Location/Qualifiers
source                  1..12
                        mol_type = other DNA
                        organism = synthetic construct
SEQUENCE: 138
gagaacaaag ga                                                     12

SEQ ID NO: 139          moltype = DNA   length = 12
FEATURE                 Location/Qualifiers
source                  1..12
                        mol_type = other DNA
                        organism = synthetic construct
SEQUENCE: 139
taacttatct tt                                                     12

SEQ ID NO: 140          moltype = DNA   length = 11
FEATURE                 Location/Qualifiers
source                  1..11
                        mol_type = other DNA
```

```
                             organism = synthetic construct
SEQUENCE: 140
gggcgggaac g                                                              11

SEQ ID NO: 141          moltype = DNA   length = 11
FEATURE                 Location/Qualifiers
source                  1..11
                        mol_type = other DNA
                        organism = synthetic construct
SEQUENCE: 141
tcctttgata t                                                              11

SEQ ID NO: 142          moltype = DNA   length = 12
FEATURE                 Location/Qualifiers
source                  1..12
                        mol_type = other DNA
                        organism = synthetic construct
SEQUENCE: 142
tagcttatct tt                                                             12

SEQ ID NO: 143          moltype = DNA   length = 12
FEATURE                 Location/Qualifiers
source                  1..12
                        mol_type = other DNA
                        organism = synthetic construct
SEQUENCE: 143
aaacatcaaa gg                                                             12

SEQ ID NO: 144          moltype = DNA   length = 14
FEATURE                 Location/Qualifiers
source                  1..14
                        mol_type = other DNA
                        organism = synthetic construct
SEQUENCE: 144
atgccacgtc acca                                                           14

SEQ ID NO: 145          moltype = DNA   length = 395
FEATURE                 Location/Qualifiers
source                  1..395
                        mol_type = other DNA
                        organism = synthetic construct
SEQUENCE: 145
ggcctaactg gccggtacca ctagtggggc ggggtgatga cacagcaatt cgggactttc  60
cacgcttgcg tgagaagaga ccggaagtga atgacacagc aattcgcttg cgtgagaagc  120
tgggactttc ctaggggcgg ggttgggact ttccacatga cacagcaata cactagtaac  180
atttctctgg cctaactggc cggtaccggg aaaagttcag ctgagagata taaaagagca  240
gtctttccag cacctgcaaa tccagagcgg cgggcactga cgggcacttg caccgtgtgg  300
acagactctc cggttctgtg agtggttttt cttttcccgg gtcggacctg gagttcttag  360
ggggatggct gaagaattca ccggtcgacg ctagc                             395

SEQ ID NO: 146          moltype = DNA   length = 12
FEATURE                 Location/Qualifiers
source                  1..12
                        mol_type = other DNA
                        organism = synthetic construct
SEQUENCE: 146
ttcgcgctaa aa                                                            12

SEQ ID NO: 147          moltype = DNA   length = 348
FEATURE                 Location/Qualifiers
source                  1..348
                        mol_type = other DNA
                        organism = synthetic construct
SEQUENCE: 147
ggcctaactg gccggtacca ctagtgtcat ctctttgaat attctgtagt ttgaggagaa  60
tatttgttat attgcacaat aaaataagtt tgcaagtttt ttttttctgc cccaaagagc  120
tctgtgtcct tgaacataaa atacaaataa ccgctatgct gttaattatt aacaaatgtc  180
ccattttcaa cctaaggaaa taccataaag taacagatat accaacaaaa ggttaataat  240
taacaggcat tgcctgaaaa gagtataaaa ggctttcagc atgattttcc atattgtgct  300
tccaccactg ccaataacaa accggtgaat tcaccggtcg acgctagc                348

SEQ ID NO: 148          moltype = DNA   length = 196
FEATURE                 Location/Qualifiers
source                  1..196
                        mol_type = other DNA
                        organism = synthetic construct
SEQUENCE: 148
gaattcacta gtgacagtat agtgcacagt gactgcagca gggtgactca tgatgccacg  60
tcaccaggtg actcatgatg ccacgtcacc aggtgactca tgatgccacg tcaccaggtg  120
```

-continued

```
actcatgatg ccacgtcacc aggtgactca tgggtaccta taaaaggcca gcagcagcct   180
gaccacatct catcca                                                    196

SEQ ID NO: 149         moltype = DNA   length = 196
FEATURE                Location/Qualifiers
source                 1..196
                       mol_type = other DNA
                       organism = synthetic construct
SEQUENCE: 149
gaattcacta gtagtatagt gcacagtgac tgcagcaggg tgactcatga tgatgccacg   60
tcaccaatgc cacgtcacca ggtgactcat gggtgactca tgatgccacg tcaccaatgc   120
cacgtcacca ggtgactcat gggtgactca tgggtaccta taaaaggcca gcagcagcct   180
gaccacatct catcca                                                    196

SEQ ID NO: 150         moltype = DNA   length = 196
FEATURE                Location/Qualifiers
source                 1..196
                       mol_type = other DNA
                       organism = synthetic construct
SEQUENCE: 150
gaattcacta gtctcaagta taaggtaaga catagttact gcgacatcgg ctagtaaacc   60
ggaagtgtct gtaaaccgga agtgatcgta aaccggaagt gagcgtaaac cggaagtgct   120
agtaaaccgg aagtggaagt aaaccggaag tgggtaccta taaaaggcca gcagcagcct   180
gaccacatct catcca                                                    196

SEQ ID NO: 151         moltype = DNA   length = 202
FEATURE                Location/Qualifiers
source                 1..202
                       mol_type = other DNA
                       organism = synthetic construct
SEQUENCE: 151
gaattcacta gtgtactcaa gtataaggta agatttgcac acggtacgta ctcatttgca   60
cacggtacgt gcgagtttgc acacggtaca gctcagtttg cacacggtac gtcagctttt   120
gcacacggta catcagaatt tgcacacggt acggtaccta taaaaggcca gcagcagcct   180
gaccacatct catccaccgg tg                                             202

SEQ ID NO: 152         moltype = DNA   length = 196
FEATURE                Location/Qualifiers
source                 1..196
                       mol_type = other DNA
                       organism = synthetic construct
SEQUENCE: 152
gaattcacta gttaattgct gagtcattgc tgctatgtaa ttgctgagtc atatgcctat   60
cctaattgct gagtcataat cgagatgtaa ttgctgagtc atgtccgacg cataattgct   120
gagtcattct aactcgctaa ttgctgagtc atggtaccta taaaaggcca gcagcagcct   180
gaccacatct catcca                                                    196

SEQ ID NO: 153         moltype = DNA   length = 196
FEATURE                Location/Qualifiers
source                 1..196
                       mol_type = other DNA
                       organism = synthetic construct
SEQUENCE: 153
gaattcacta gtgctgagcg acagtatagt gcacagtgac tgcagcagtc attatacgta   60
ggggaatccc ctcgaagggg aatccccttt aaggggaatc ccctcgcagg ggaatcccct   120
ctcagggaa  tccctaaca ggggaatccc ctggtaccta taaaaggcca gcagcagcct   180
gaccacatct catcca                                                    196

SEQ ID NO: 154         moltype = DNA   length = 196
FEATURE                Location/Qualifiers
source                 1..196
                       mol_type = other DNA
                       organism = synthetic construct
SEQUENCE: 154
gaattcacta gtgcatcctt tgatgttacc tgatcaaaca tgcccggaca tgtcgtaaga   60
catatccttt gatgtctcgc aatctaacat gcccggacat gtcctcgcaa tcttcctttg   120
atgttgcaag ctacaacatg cccggacatg tcggtaccta taaaaggcca gcagcagcct   180
gaccacatct catcca                                                    196

SEQ ID NO: 155         moltype = DNA   length = 196
FEATURE                Location/Qualifiers
source                 1..196
                       mol_type = other DNA
                       organism = synthetic construct
SEQUENCE: 155
gaattcacta gtgcaccatt agtacttgat cagtatgcca cgtcatcact actctatgcc   60
acgtcatctc ctagatatgc cacgtcatcg taagactatg ccacgtcatc tacagcttat   120
gccacgtcat cacgtactta tgccacgtca tcggtaccta taaaaggcca gcagcagcct   180
gaccacatct catcca                                                    196
```

-continued

```
SEQ ID NO: 156              moltype = DNA   length = 292
FEATURE                     Location/Qualifiers
source                      1..292
                            mol_type = other DNA
                            organism = synthetic construct
SEQUENCE: 156
ggcctaactg gccggtacca ctagtgtccc cacccacaca ttcctgtccc cacccacaca   60
ttcctgtccc cacccacaca ttcctgtccc cacccacaca ttcctgtccc cacccacaca  120
ttcctgtccc cacccacaca ttcctgtgcg ctcccgacat gccccgcggc gcgccattaa  180
ccgccagatt tgagtcgcgg gacccgttgg cagaggtggg ctagcctcga ggatatcaag  240
atctggcctc ggcggccaag cttggcaatc cggtactgtt ggtaaagcca cc          292

SEQ ID NO: 157              moltype = DNA   length = 282
FEATURE                     Location/Qualifiers
source                      1..282
                            mol_type = other DNA
                            organism = synthetic construct
SEQUENCE: 157
ggcctaactg gccggtacca gcttgcatgc ctgcaggtcg gagtactgtc ctccgagcgg   60
agtactgtcc tccgagcgga gtactgtcct ccgagcggag tactgtcctc cgagcggagt  120
actgtcctcc gagcggtgcg ctcccgacat gccccgcggc gcgccattaa ccgccagatt  180
tgagtcgcgg gacccgttgg cagaggtggg ctagcctcga ggatatcaag atctggcctc  240
ggcggccaag cttggcaatc cggtactgtt ggtaaagcca cc                     282

SEQ ID NO: 158              moltype = DNA   length = 271
FEATURE                     Location/Qualifiers
source                      1..271
                            mol_type = other DNA
                            organism = synthetic construct
SEQUENCE: 158
ggcctaactg gccggtacca ctagtggttt tgtggggttt tgtggggttt tgtggggttt   60
tgtggggttt tgtggggttt tgtggggttt tgtggggttt tgtggggttt tgtggggttt  120
tgtggtgcgc tcccgacatg ccccgcggcg cgccattaac cgccagattt gagtcgcggg  180
acccgttggc agaggtgggc tagcctcgag gatatcaaga tctggcctcg gcggccaagc  240
ttggcaatcc ggtactgttg gtaaagccac c                                 271

SEQ ID NO: 159              moltype = DNA   length = 269
FEATURE                     Location/Qualifiers
source                      1..269
                            mol_type = other DNA
                            organism = synthetic construct
SEQUENCE: 159
ggcctaactg gccggtacca ctagtagcca cttgaaatta gccacttgaa attagccact   60
tgaaattagc cacttgaaat tagccacttg aaattagcca cttgaaatta gccacttgaa  120
atttgcgctc ccgacatgcc ccgcggcgcg ccattaaccg ccagatttga gtcgcgggac  180
ccgttggcag aggtgggcta gcctcgagga tatcaagatc tggcctcggc ggccaagctt  240
ggcaatccgg tactgttggt aaagccacc                                    269

SEQ ID NO: 160              moltype = DNA   length = 275
FEATURE                     Location/Qualifiers
source                      1..275
                            mol_type = other DNA
                            organism = synthetic construct
SEQUENCE: 160
ggcctaactg gccggtacca ctagtctggg aacaagtgct gggaacaagt gctgggaaca   60
agtgctggga acaagtgctg ggaacaagtg ctgggaacaa gtgctgggaa caagtgctgg  120
gaacaagtgt gcgctcccga catgccccgc ggcgcgccat taaccgccag atttgagtcg  180
cgggacccgt tggcagaggt gggctagcct cgaggatatc aagatctggc ctcggcggcc  240
aagcttggca atccggtact gttggtaaag ccacc                             275

SEQ ID NO: 161              moltype = DNA   length = 275
FEATURE                     Location/Qualifiers
source                      1..275
                            mol_type = other DNA
                            organism = synthetic construct
SEQUENCE: 161
ggcctaactg gccggtacca ctagtgactc ctcaagggga ctcctcaagg ggactcctca   60
aggggactcc tcaaggggac tcctcaaggg gactcctcaa ggggactcct caaggggact  120
cctcaagggt gcgctcccga catgccccgc ggcgcgccat taaccgccag atttgagtcg  180
cgggacccgt tggcagaggt gggctagcct cgaggatatc aagatctggc ctcggcggcc  240
aagcttggca atccggtact gttggtaaag ccacc                             275

SEQ ID NO: 162              moltype = DNA   length = 276
FEATURE                     Location/Qualifiers
source                      1..276
                            mol_type = other DNA
                            organism = synthetic construct
SEQUENCE: 162
```

```
ggcctaactg gccggtacca ctagtcgggc tttgatcttt cgggctttga tctttcgggc    60
tttgatcttt cgggctttga tctttcgggc tttgatcttt cgggctttga tctttcgggc   120
tttgatcttt tgcgctcccg acatgccccg cggcgcgcca ttaaccgcca gatttgagtc   180
gcgggaccg ttggcagagg tgggctagcc tcgaggatat caagatctgg cctcggcggc   240
caagcttggc aatccggtac tgttggtaaa gccacc                              276

SEQ ID NO: 163              moltype = DNA   length = 273
FEATURE                    Location/Qualifiers
source                     1..273
                           mol_type = other DNA
                           organism = synthetic construct
SEQUENCE: 163
ggcctaactg gccggtacca ctagtgcgct ttgatgtgcg gggcggccct ttgaagttgg    60
cgctttgatg tgcggggcgg ccctttgaag ttggcgcttt gatgtgcggg gcggcccttt   120
gaagttgtgc gctcccgaca tgccccgcgg cgcgccatta accgccagat ttgagtcgcg   180
ggacccgttg gcagaggtgg gctagcctcg aggatatcaa gatctggcct cggcggccaa   240
gcttggcaat ccggtactgt tggtaaagcc acc                                273

SEQ ID NO: 164              moltype = DNA   length = 261
FEATURE                    Location/Qualifiers
source                     1..261
                           mol_type = other DNA
                           organism = synthetic construct
SEQUENCE: 164
ggcctaactg gccggtacca ctagtaacag ctgttaacag ctgttaacag ctgttaacag    60
ctgttaacag ctgttaacag ctgttaacag ctgttaacag ctgtttgcgc                120
tcccgacatg ccccgcggcg cgccattaac cgccagattt gagtcgcggg acccgttggc   180
agaggtgggc tagcctcgag gatatcaaga tctggcctcg cggccaagc ttggcaatcc   240
ggtactgttg gtaaagccac c                                             261

SEQ ID NO: 165              moltype = DNA   length = 243
FEATURE                    Location/Qualifiers
source                     1..243
                           mol_type = other DNA
                           organism = synthetic construct
SEQUENCE: 165
ggcctaactg gccggtacca ctagtcacct gcacctgcac ctgcacctgc acctgcacct    60
gcacctgcac ctgcacctgc acctgcacct gcacctgtgc gctcccgaca tgccccgcgg   120
cgcgccatta accgccagat ttgagtcgcg ggacccgttg gcagaggtgg gctagcctcg   180
aggatatcaa gatctggcct cggcggccaa gcttggcaat ccggtactgt tggtaaagcc   240
acc                                                                 243

SEQ ID NO: 166              moltype = DNA   length = 271
FEATURE                    Location/Qualifiers
source                     1..271
                           mol_type = other DNA
                           organism = synthetic construct
SEQUENCE: 166
ggcctaactg gccggtacca ctagtagttc aacacgtggt ctgggagttc aacacgtggt    60
ctgggagttc aacacgtggt ctgggagttc aacacgtggt ctgggagttc aacacgtggt   120
ctgggtgcgc tcccgacatg ccccgcggcg cgccattaac cgccagattt gagtcgcggg   180
acccgttggc agaggtgggc tagcctcgag gatatcaaga tctggcctcg cggccaagc   240
ttggcaatcc ggtactgttg gtaaagccac c                                 271

SEQ ID NO: 167              moltype = DNA   length = 275
FEATURE                    Location/Qualifiers
source                     1..275
                           mol_type = other DNA
                           organism = synthetic construct
SEQUENCE: 167
ggcctaactg gccggtacca ctagtgacag ataagaaaga cagataagaa agacagataa    60
gaaagacaga taagaaagac agataagaaa gacagataag aaagacagat aagaaagaca   120
gataagaaat gcgctcccga catgccccgc ggcgcgccat taaccgccag atttgagtcg   180
cgggacccgt tggcagaggt gggctagcct cgaggatatc aagatctggc ctcggcggcc   240
aagcttggca atccggtact gttggtaaag ccacc                              275

SEQ ID NO: 168              moltype = DNA   length = 270
FEATURE                    Location/Qualifiers
source                     1..270
                           mol_type = other DNA
                           organism = synthetic construct
SEQUENCE: 168
ggcctaactg gccggtacca ctagtttcta atctatttct aatctatttc taatctattt    60
ctaatctatt tctaatctat ttctaatct atttctaatc tatttctaat                120
ctattgcgct cccgacatgc cccgcggcgc gccattaacc gccagatttg agtcgcggga   180
cccgttggca gaggtgggct agcctcgagg atatcaagat ctggcctcgg cggccaagct   240
tggcaatccg gtactgttgg taaagccacc                                    270

SEQ ID NO: 169              moltype = DNA   length = 270
```

-continued

```
FEATURE                    Location/Qualifiers
source                     1..270
                           mol_type = other DNA
                           organism = synthetic construct
SEQUENCE: 169
ggcctaactg gccggtacca ctagtggtga ctcatgggtg actcatgggt gactcatggg   60
tgactcatgg gtgactcatg ggtgactcat gggtgactca tgggtgactc atgggtgact  120
catgtgcgct cccgacatgc cccgcggcgc gccattaacc gccagatttg agtcgcggga  180
cccgttggca gaggtgggct agcctcgagg atatcaagat ctggcctcgg cggccaagct  240
tggcaatccg gtactgttgg taaagccacc                                    270

SEQ ID NO: 170          moltype = DNA   length = 270
FEATURE                    Location/Qualifiers
source                     1..270
                           mol_type = other DNA
                           organism = synthetic construct
SEQUENCE: 170
ggcctaactg gccggtacca ctagtcttct gggaaacttc tgggaaactt ctgggaaact   60
tctgggaaac ttctgggaaa cttctgggaa acttctggga aacttctggg aaacttctgg  120
gaaatgcgct cccgacatgc cccgcggcgc gccattaacc gccagatttg agtcgcggga  180
cccgttggca gaggtgggct agcctcgagg atatcaagat ctggcctcgg cggccaagct  240
tggcaatccg gtactgttgg taaagccacc                                    270

SEQ ID NO: 171          moltype = DNA   length = 269
FEATURE                    Location/Qualifiers
source                     1..269
                           mol_type = other DNA
                           organism = synthetic construct
SEQUENCE: 171
ggcctaactg gccggtacca ctagtaattc ttagaaataa attcttagaa ataaattctt   60
agaaataaat tcttagaaat aaattcttag aaataaattc ttagaaataa attcttagaa  120
atatgcgctc ccgacatgcc ccgcggcgcg ccattaaccg ccagatttga gtcgcgggac  180
ccgttggcag aggtgggcta gcctcgagga tatcaagatc tggcctcggc ggccaagctt  240
ggcaatccgg tactgttggt aaagccacc                                     269

SEQ ID NO: 172          moltype = DNA   length = 282
FEATURE                    Location/Qualifiers
source                     1..282
                           mol_type = other DNA
                           organism = synthetic construct
SEQUENCE: 172
ggcctaactg gccggtacca ctagtaaaac aaaggatcct ttgttttaaa acaaaggatc   60
ctttgtttta aaacaaagga tcctttgttt taaaacaaag gatcctttgt tttaaaacaa  120
aggatccttt gttttctgcg ctcccgacat gccccgcggc gcgccattaa ccgccagatt  180
tgagtcgcgg gacccgttgg cagaggtggg ctagcctcga ggatatcaag atctggcctc  240
ggcggccaag cttggcaatc cggtactgtt ggtaaagcca cc                      282

SEQ ID NO: 173          moltype = DNA   length = 269
FEATURE                    Location/Qualifiers
source                     1..269
                           mol_type = other DNA
                           organism = synthetic construct
SEQUENCE: 173
ggcctaactg gccggtacca ctagtaaagt ccaagtccaa aagtccaagt ccaaaagtcc   60
aagtccaaaa gtccaagtcc aaaagtccaa gtccaaaagt ccaagtccaa gtccaaagt   120
ccatgcgctc ccgacatgcc ccgcggcgcg ccattaaccg ccagatttga gtcgcgggac  180
ccgttggcag aggtgggcta gcctcgagga tatcaagatc tggcctcggc ggccaagctt  240
ggcaatccgg tactgttggt aaagccacc                                     269

SEQ ID NO: 174          moltype = DNA   length = 272
FEATURE                    Location/Qualifiers
source                     1..272
                           mol_type = other DNA
                           organism = synthetic construct
SEQUENCE: 174
ggcctaactg gccggtacca ctagtggttt tgtggagagg ttttgtggtc gggttttgtg   60
ggacggtttt gtggctaggt tttgtggact ggttttgtgg tgcggttttg tgggtaggtt  120
ttgtggtgcg ctcccgacat gccccgcggc gcgccattaa ccgccagatt tgagtcgcgg  180
gacccgttgg cagaggtggg ctagcctcga ggatatcaag atctggcctc ggcggccaag  240
cttggcaatc cggtactgtt ggtaaagcca cc                                 272

SEQ ID NO: 175          moltype = DNA   length = 270
FEATURE                    Location/Qualifiers
source                     1..270
                           mol_type = other DNA
                           organism = synthetic construct
SEQUENCE: 175
ggcctaactg gccggtacca ctagtagcca cttgaaatta gaagccactt gaaatttcga   60
gccacttgaa attgacagcc acttgaaatt ctaagccact gaaattact agccacttga  120
```

```
aatttgcgct cccgacatgc cccgcggcgc gccattaacc gccagatttg agtcgcggga  180
cccgttggca gaggtgggct agcctcgagg atatcaagat ctggcctcgg cggccaagct  240
tggcaatccg gtactgttgg taaagccacc                                    270

SEQ ID NO: 176           moltype = DNA   length = 280
FEATURE                  Location/Qualifiers
source                   1..280
                         mol_type = other DNA
                         organism = synthetic construct
SEQUENCE: 176
ggcctaactg gccggtacca ctagtctggg aacaagtgag actgggaaca agtgtcgctg   60
ggaacaagtg gacctgggaa caagtgctac tgggaacaag tgactctggg aacaagtgtg  120
cctgggaaca agtgtcgctg cccgacatgc cccgcggcgc gccattaacc gccagatttg  180
agtcgcggga cccgttggca gaggtgggct agcctcgagg atatcaagat ctggcctcgg  240
cggccaagct tggcaatccg gtactgttgg taaagccacc                        280

SEQ ID NO: 177           moltype = DNA   length = 280
FEATURE                  Location/Qualifiers
source                   1..280
                         mol_type = other DNA
                         organism = synthetic construct
SEQUENCE: 177
ggcctaactg gccggtacca ctagtgactc ctcaagggag agactcctca agggtcggac   60
tcctcaaggg gacgactcct caagggctag actcctcaag ggactgactc ctcaagggtg  120
cgactcctca agggtcgctg cccgacatgc cccgcggcgc gccattaacc gccagatttg  180
agtcgcggga cccgttggca gaggtgggct agcctcgagg atatcaagat ctggcctcgg  240
cggccaagct tggcaatccg gtactgttgg taaagccacc                        280

SEQ ID NO: 178           moltype = DNA   length = 276
FEATURE                  Location/Qualifiers
source                   1..276
                         mol_type = other DNA
                         organism = synthetic construct
SEQUENCE: 178
ggcctaactg gccggtacca ctagtccggc tttgatcttt agacgggctt tgatcttttc   60
gcgggctttg atctttgacc gggctttgat ctttctacgg gctttgatct ttactcgggc  120
tttgatcttt tgcgctcccg acatgccccg cggcgcgcca ttaaccgcca gatttgagtc  180
gcgggacccg ttggcagagg tgggctagcc tcgaggatat caagatctgg cctcggcggc  240
caagcttggc aatccggtac tgttggtaaa gccacc                            276

SEQ ID NO: 179           moltype = DNA   length = 279
FEATURE                  Location/Qualifiers
source                   1..279
                         mol_type = other DNA
                         organism = synthetic construct
SEQUENCE: 179
ggcctaactg gccggtacca ctagtgcgct ttgatgtgcg gggcggccct ttgaagttga   60
gagcgctttg atgtgcgggg cggccctttg aagttgtcgg cgctttgatg tgcggggcgg  120
ccctttgaag ttgtgcgctc ccgacatgcc ccgcggcgcg ccattaaccg ccagatttga  180
gtcgcgggac ccgttggcag aggtgggcta gcctcgagga tatcaagatc tggcctcggc  240
ggccaagctt ggcaatccgg tactgttggt aaagccacc                         279

SEQ ID NO: 180           moltype = DNA   length = 272
FEATURE                  Location/Qualifiers
source                   1..272
                         mol_type = other DNA
                         organism = synthetic construct
SEQUENCE: 180
ggcctaactg gccggtacca ctagtaacag ctgttagaaa cagctgtttc gaacagctgt   60
tgacaacagc tgttctaaac agctgttact aacagctgtt tgcaacagct gttgtaaaca  120
gctgtttgcg ctcccgacat gccccgcggc gcgccattaa ccgccagatt tgagtcgcgg  180
gacccgttgg cagaggtggg ctagcctcga ggatatcaag atctggcctc ggcggccaag  240
cttggcaatc cggtactgtt ggtaaagcca cc                                272

SEQ ID NO: 181           moltype = DNA   length = 258
FEATURE                  Location/Qualifiers
source                   1..258
                         mol_type = other DNA
                         organism = synthetic construct
SEQUENCE: 181
ggcctaactg gccggtacca ctagtcacct gagacacctg tcgcacctgg accacctgct   60
acacctgact cacctgtgcc acctgagaca cctgtcgcac ctggaccacc tgtgcgctcc  120
cgacatgccc cgcggcgcgc cattaaccgc cagatttgag tcgcgggacc cgttggcaga  180
ggtgggctag cctcgaggat atcaagatct ggcctcggcg gccaagcttg gcaatccggt  240
actgttggta aagccacc                                                258

SEQ ID NO: 182           moltype = DNA   length = 283
FEATURE                  Location/Qualifiers
source                   1..283
```

```
                          mol_type = other DNA
                          organism = synthetic construct
SEQUENCE: 182
ggcctaactg gccggtacca ctagtagttc aacacgtggt ctgggagaag ttcaacacgt   60
ggtctgggtc gagttcaaca cgtggtctgg ggacagttca acacgtggtc tgggctaagt  120
tcaacacgtg gtctgggtgc gctcccgaca tgccccgcgg cgcgccatta accgccagat  180
ttgagtcgcg ggacccgttg gcagaggtgg gctagcctcg aggatatcaa gatctggcct  240
cggcggccaa gcttggcaat ccggtactgt tggtaaagcc acc                     283

SEQ ID NO: 183          moltype = DNA   length = 280
FEATURE                 Location/Qualifiers
source                  1..280
                        mol_type = other DNA
                        organism = synthetic construct
SEQUENCE: 183
ggcctaactg gccggtacca ctagtgacag ataagaaaag agacagataa gaaatcggac   60
agataagaaa gacgacagat aagaaactag acagataaga aaactgacag ataagaaatg  120
cgacagataa gaaatgcgct cccgacatgc cccgcggcgc gccattaacc gccagatttg  180
agtcgcggga cccgttggca gaggtgggct agcctcgagg atatcaagat ctggcctcgg  240
cggccaagct tggcaatccg gtactgttgg taaagccacc                         280

SEQ ID NO: 184          moltype = DNA   length = 266
FEATURE                 Location/Qualifiers
source                  1..266
                        mol_type = other DNA
                        organism = synthetic construct
SEQUENCE: 184
ggcctaactg gccggtacca ctagtttcta atctatagat tctaatctat tcgttctaat   60
ctatgacttc taatctatct attctaatct atactttcta atctattgct tctaatctat  120
tgcgctcccg acatgccccg cggcgcgcca ttaaccgcca gatttgagtc gcgggacccg  180
ttggcagagg tgggctagcc tcgaggatat caagatctgg cctcggcggc caagcttggc  240
aatccggtac tgttggtaaa gccacc                                        266

SEQ ID NO: 185          moltype = DNA   length = 267
FEATURE                 Location/Qualifiers
source                  1..267
                        mol_type = other DNA
                        organism = synthetic construct
SEQUENCE: 185
ggcctaactg gccggtacca ctagtggtga ctcatgagag gtgactcatg tcgggtgact   60
catggacggt gactcatgct aggtgactca tgactggtga ctcatgtgcg gtgactcatg  120
ctgcgctccc gacatgcccc gcggcgcgcc attaaccgcc agatttgagt cgcgggaccc  180
gttggcagag gtgggctagc ctcgaggata tcaagatctg gcctcggcgg ccaagcttgg  240
caatccggta ctgttggtaa agccacc                                       267

SEQ ID NO: 186          moltype = DNA   length = 266
FEATURE                 Location/Qualifiers
source                  1..266
                        mol_type = other DNA
                        organism = synthetic construct
SEQUENCE: 186
ggcctaactg gccggtacca ctagtcttct gggaaaagac ttctgggaaa tcgcttctgg   60
gaaagacctt ctgggaaact acttctggga aaactcttct gggaaatgcc ttctgggaaa  120
tgcgctcccg acatgccccg cggcgcgcca ttaaccgcca gatttgagtc gcgggacccg  180
ttggcagagg tgggctagcc tcgaggatat caagatctgg cctcggcggc caagcttggc  240
aatccggtac tgttggtaaa gccacc                                        266

SEQ ID NO: 187          moltype = DNA   length = 270
FEATURE                 Location/Qualifiers
source                  1..270
                        mol_type = other DNA
                        organism = synthetic construct
SEQUENCE: 187
ggcctaactg gccggtacca ctagtaattc ttagaaataa gaaattctta gaaatatcga   60
attcttagaa atagacaatt cttagaaata ctaaattctt agaaataact aattcttaga  120
aatatgcgct cccgacatgc cccgcggcgc gccattaacc gccagatttg agtcgcggga  180
cccgttggca gaggtgggct agcctcgagg atatcaagat ctggcctcgg cggccaagct  240
tggcaatccg gtactgttgg taaagccacc                                    270

SEQ ID NO: 188          moltype = DNA   length = 268
FEATURE                 Location/Qualifiers
source                  1..268
                        mol_type = other DNA
                        organism = synthetic construct
SEQUENCE: 188
ggcctaactg gccggtacca ctagtaaaac aaaggatcct ttgttttaga aaaacaaagg   60
atcctttgtt tttcgaaaac aaaggatcct ttgttttgac aaaacaaagg atcctttgtt  120
tttgcgctcc cgacatgccc cgcggcgcgc cattaaccgc cagatttgag tcgcgggacc  180
cgttggcaga ggtgggctag cctcgaggat atcaagatct ggcctcggcg ccaagcttg   240
```

```
gcaatccggt actgttggta aagccacc                                        268

SEQ ID NO: 189           moltype = DNA   length = 270
FEATURE                  Location/Qualifiers
source                   1..270
                         mol_type = other DNA
                         organism = synthetic construct
SEQUENCE: 189
ggcctaactg gccggtacca ctagtaaagt ccaagtccaa gaaaagtcca agtccatcga     60
aagtccaagt ccagacaaag tccaagtcca ctaaaagtcc aagtccaact aaagtccaag    120
tccatgcgct cccgacatgc cccgcggcgc gccattaacc gccagatttg agtcgcggga    180
cccgttggca gaggtgggct agcctcgagg atatcaagat ctggcctcgg cggccaagct    240
tggcaatccg gtactgttgg taaagccacc                                     270

SEQ ID NO: 190           moltype = DNA   length = 339
FEATURE                  Location/Qualifiers
source                   1..339
                         mol_type = other DNA
                         organism = synthetic construct
SEQUENCE: 190
ggcctaactg gccggtacca ctagtaattc ttagaaataa attcttagaa ataaattctt     60
agaataaat tcttagaaat aaattcttag aaataaattc ttagaaataa attcttagaa    120
atatgcgctc ccgacatgtc ccgcggcgcg ccattaaccg ccagatttga gtcgcgggac    180
ccgttggcag aggtgggcta gcctcgagga tatcaagatc tggcctcggc ggccaagctt    240
ggcaatccgt actgttggt aaagccacca tcctcgagga tatcaagatc tggcctcggc    300
ggccaagctt ggcaatccgg tactgttggt aaagccacc                          339

SEQ ID NO: 191           moltype = DNA   length = 261
FEATURE                  Location/Qualifiers
source                   1..261
                         mol_type = other DNA
                         organism = synthetic construct
SEQUENCE: 191
ggcctaactg gccggtacca ctagtccaat aaaaaccaat aaaaaccaat aaaaaccaat     60
aaaaaccaat aaaaaccaat aaaaaccaat aaaaaccaat aaaaaccaat aaaaatgcgc    120
tcccgacatg ccccgcggcg cgccattaac cgccagattt gagtcgcggg acccgttggc    180
agaggtgggc tagcctcgag gatatcaaga tctggcctcg gcggccaagc ttggcaatcc    240
ggtactgttg gtaaagccac c                                             261

SEQ ID NO: 192           moltype = DNA   length = 12
FEATURE                  Location/Qualifiers
source                   1..12
                         mol_type = other DNA
                         organism = synthetic construct
SEQUENCE: 192
gcgaccacca aa                                                        12

SEQ ID NO: 193           moltype = DNA   length = 261
FEATURE                  Location/Qualifiers
source                   1..261
                         mol_type = other DNA
                         organism = synthetic construct
SEQUENCE: 193
ggcctaactg gccggtacca ctagttgttt acttatgttt acttatgttt acttatgttt     60
acttatgttt acttatgttt acttatgttt acttatgttt acttatgttt acttatgcgc    120
tcccgacatg ccccgcgcg cgccattaac cgccagattt gagtcgcggg acccgttggc     180
agaggtgggc tagcctcgag gatatcaaga tctggcctcg gcggccaagc ttggcaatcc    240
ggtactgttg gtaaagccac c                                             261

SEQ ID NO: 194           moltype = DNA   length = 267
FEATURE                  Location/Qualifiers
source                   1..267
                         mol_type = other DNA
                         organism = synthetic construct
SEQUENCE: 194
ggcctaactg gccggtacca ctagtaaaat ggcgccattt aaaatggcg ccattttaaa     60
atggcgccat tttaaaatgg cgccatttta aaatggcgcc attttaaaat ggcgccattt    120
ttgcgctccc gacatgcccc gcggcgcgcc attaaccgcc agatttgagt cgcgggaccc    180
gttggcagag gtgggctagc ctcgaggata tcaagatctg gcctcggcgg ccaagcttgg    240
caatccgta ctgttggtaa agccacc                                        267

SEQ ID NO: 195           moltype = DNA   length = 259
FEATURE                  Location/Qualifiers
source                   1..259
                         mol_type = other DNA
                         organism = synthetic construct
SEQUENCE: 195
ggcctaactg gccggtacca ctagttattg tggttatatt gtggttatat gtgttttata     60
ttgtggttat attgtggtta tattgtggtt atattgtggt tatattgtgg ttatgcgctc    120
```

```
ccgacatgcc ccgcggcgcg ccattaaccg ccagatttga gtcgcgggac ccgttggcag   180
aggtgggcta gcctcgagga tatcaagatc tggcctcggc ggccaagctt ggcaatccgg   240
tactgttggt aaagccacc                                                259

SEQ ID NO: 196          moltype = DNA   length = 283
FEATURE                 Location/Qualifiers
source                  1..283
                        mol_type = other DNA
                        organism = synthetic construct
SEQUENCE: 196
ggcctaactg gccggtacca ctagtgaaca attgcagtgt tgaacaattg cagtgttgaa   60
caattgcagt gttgaacaat tgcagtgttg aacaattgca gtgttgaaca attgcagtgt   120
tgaacaattg cagtgtttgc gctcccgaca tgccccgcgg cgcgccatta accgccagat   180
ttgagtcgcg ggacccgttg gcagaggtgg gctagcctcg aggatatcaa gatctggcct   240
cggcggccaa gcttggcaat ccggtactgt tggtaaagcc acc                     283

SEQ ID NO: 197          moltype = DNA   length = 271
FEATURE                 Location/Qualifiers
source                  1..271
                        mol_type = other DNA
                        organism = synthetic construct
SEQUENCE: 197
ggcctaactg gccggtacca ctagtcccca aaccaccccc cccccccca aaccacccc     60
ccccccccca aaccacccc cccccccca aaccacccc cccccccca aaccacccc       120
ccccctgcgc tcccgacatg ccccgcggcg cgccattaac cgccagattt gagtcgcggg   180
acccgttggc agaggtgggc tagcctcgag gatatcaaga tctggcctcg gcggccaagc   240
ttggcaatcc ggtactgttg gtaaagccac c                                  271

SEQ ID NO: 198          moltype = DNA   length = 243
FEATURE                 Location/Qualifiers
source                  1..243
                        mol_type = other DNA
                        organism = synthetic construct
SEQUENCE: 198
cactagtacc ggaagtaacc ggaagtaacc ggaagtaacc ggaagtaacc ggaagtaacc   60
ggaagtaacc ggaagtaacc ggaagtaacc ggaagtatgc gctcccgaca tgccccgcgg   120
cgcgccatta accgccagat ttgagtcgcg ggacccgttg gcagaggtgg gctagcctcg   180
aggatatcaa gatctggcct cggcggccaa gcttggcaat ccggtactgt tggtaaagcc   240
acc                                                                 243

SEQ ID NO: 199          moltype = DNA   length = 261
FEATURE                 Location/Qualifiers
source                  1..261
                        mol_type = other DNA
                        organism = synthetic construct
SEQUENCE: 199
ggcctaactg gccggtacca ctagtggcac gtgttggcac gtgttggcac gtgttggcac   60
gtgttggcac gtgttggcac gtgttggcac gtgttggcac gtgttggcac gtgtttgcgc   120
tcccgacatg ccccgcggcg cgccattaac cgccagattt gagtcgcggg acccgttggc   180
agaggtgggc tagcctcgag gatatcaaga tctggcctcg gcggccaagc ttggcaatcc   240
ggtactgttg gtaaagccac c                                             261

SEQ ID NO: 200          moltype = DNA   length = 262
FEATURE                 Location/Qualifiers
source                  1..262
                        mol_type = other DNA
                        organism = synthetic construct
SEQUENCE: 200
ggcctaactg gccggtacca ctagtcgagc agctggtgcg agcagctggt gcgagcagct   60
ggtgcgagca gctggtgcga gcagctggtg cgagcagctg gtgcgagcag ctggtgtgcg   120
ctcccgacat gccccgcggc gcgccattaa ccgccagatt tgagtcgcgg gacccgttgg   180
cagaggtggg ctagcctcga ggatatcaag atctggcctc ggcggccaag cttggcaatc   240
cggtactgtt ggtaaagcca cc                                            262

SEQ ID NO: 201          moltype = DNA   length = 251
FEATURE                 Location/Qualifiers
source                  1..251
                        mol_type = other DNA
                        organism = synthetic construct
SEQUENCE: 201
ggcctaactg gccggtacca ctagttccag atgtttccag atgtttccag atgtttccag   60
atgtttccag atgtttccag atgtttccag atgtttccag atgtttgcgc tcccgacatg   120
ccccgcggcg cgccattaac cgccagattt gagtcgcggg acccgttggc agaggtgggc   180
tagcctcgag gatatcaaga tctggcctcg gcggccaagc ttggcaatcc ggtactgttg   240
gtaaagccac c                                                        251

SEQ ID NO: 202          moltype = DNA   length = 251
FEATURE                 Location/Qualifiers
source                  1..251
```

-continued

```
                          mol_type = other DNA
                          organism = synthetic construct
SEQUENCE: 202
ggcctaactg gccggtacca ctagtatagt aaacaatagt aaacaatagt aaacaatagt   60
aaacaatagt aaacaatagt aaacaatagt aaacatgcgc tcccgacatg               120
ccccgcggcg cgccattaac cgccagattt gagtcgcggg acccgttggc agaggtgggc   180
tagcctcgag gatatcaaga tctggcctcg gcggccaagc ttggcaatcc ggtactgttg   240
gtaaagccac c                                                        251

SEQ ID NO: 203         moltype = DNA   length = 248
FEATURE                Location/Qualifiers
source                 1..248
                       mol_type = other DNA
                       organism = synthetic construct
SEQUENCE: 203
ggcctaactg gccggtacca ctagttaatc cctaatccct aatccctaat ccctaatccc   60
taatcccta a tccctaatcc ctaatcccta atccctaatc cctgcgctcc cgacatgccc   120
cgcggcggc cattaaccgc cagatttgag tcgcgggacc cgttggcaga ggtgggctag    180
cctcgaggat atcaagatct ggcctcggcg gccaagcttg gcaatccggt actgttggta   240
aagccacc                                                            248

SEQ ID NO: 204         moltype = DNA   length = 251
FEATURE                Location/Qualifiers
source                 1..251
                       mol_type = other DNA
                       organism = synthetic construct
SEQUENCE: 204
ggcctaactg gccggtacca ctagtctaat taactaatta actaattaac taattaacta   60
attaactaat taactaatta actaattaac taattaacta attaatgcgc tcccgacatg   120
ccccgcggcg cgccattaac cgccagattt gagtcgcggg acccgttggc agaggtgggc   180
tagcctcgag gatatcaaga tctggcctcg gcggccaagc ttggcaatcc ggtactgttg   240
gtaaagccac c                                                        251

SEQ ID NO: 205         moltype = DNA   length = 251
FEATURE                Location/Qualifiers
source                 1..251
                       mol_type = other DNA
                       organism = synthetic construct
SEQUENCE: 205
ggcctaactg gccggtacca ctagtcccaa ttagccccaa ttagccccaa ttagccccaa   60
ttagccccaa ttagccccaa ttagccccaa ttagccccaa ttagctgcgc tcccgacatg   120
ccccgcggcg cgccattaac cgccagattt gagtcgcggg acccgttggc agaggtgggc   180
tagcctcgag gatatcaaga tctggcctcg gcggccaagc ttggcaatcc ggtactgttg   240
gtaaagccac c                                                        251

SEQ ID NO: 206         moltype = DNA   length = 243
FEATURE                Location/Qualifiers
source                 1..243
                       mol_type = other DNA
                       organism = synthetic construct
SEQUENCE: 206
ggcctaactg gccggtacca ctagtcaatt acaattacaa ttacaattac aattacaatt   60
acaattacaa ttacaattac aattacaatt acaattatgc gctcccgaca tgccccgcgg   120
cgcgccatta accgccagat ttgagtcgcg ggacccgttg gcagaggtgg gctagcctcg   180
aggatatcaa gatctggcct cggcggccaa gcttggcaat ccggtactgt tggtaaagcc   240
acc                                                                 243

SEQ ID NO: 207         moltype = DNA   length = 267
FEATURE                Location/Qualifiers
source                 1..267
                       mol_type = other DNA
                       organism = synthetic construct
SEQUENCE: 207
ggcctaactg gccggtacca ctagtaaaac cggtttttaaa accgtttttaa aaaccggttt   60
taaaaccggt tttaaaaccg gtttttaaaac cggtttttaaa accggtttttaa aaacccggttt   120
ttgcgctccc gacatgcccc gcggcgcgcc attaaccgcc agatttgagt cgcgggaccc   180
gttggcagag gtgggctagc ctcgaggata tcaagatctg gcctcggcgg ccaagcttgg   240
caatccggta ctgttggtaa agccacc                                       267

SEQ ID NO: 208         moltype = DNA   length = 259
FEATURE                Location/Qualifiers
source                 1..259
                       mol_type = other DNA
                       organism = synthetic construct
SEQUENCE: 208
ggcctaactg gccggtacca ctagttgttt acttaagatg tttacttatc gtgtttactt   60
agactgttta cttactatgt ttacttaact tgtttactta tgctgtttac ttatgcgctc   120
ccgacatgcc ccgcggcgcg ccattaaccg ccagatttga gtcgcgggac cgttggcag    180
aggtgggcta gcctcgagga tatcaagatc tggcctcggc ggccaagctt ggcaatccgg   240
```

-continued

```
tactgttggt aaagccacc                                              259

SEQ ID NO: 209          moltype = DNA   length = 282
FEATURE                 Location/Qualifiers
source                  1..282
                        mol_type = other DNA
                        organism = synthetic construct
SEQUENCE: 209
ggcctaactg gccggtacca ctagtaaaat ggcgccattt ttcgaaaatg gcgccatttt   60
gacaaaatgg cgccattttc taaaaatggc gccattttac taaaaatggcg ccattttgc  120
aaaatggcgc catttttgcg ctcccgacat gccccgcggc gcgccattaa ccgcagatt  180
tgagtcgcgg gacccgttgg cagaggtggg ctagcctcga ggatatcaag atctggcctc  240
ggcggccaag cttggcaatc cggtactgtt ggtaaagcca cc                     282

SEQ ID NO: 210          moltype = DNA   length = 252
FEATURE                 Location/Qualifiers
source                  1..252
                        mol_type = other DNA
                        organism = synthetic construct
SEQUENCE: 210
ggcctaactg gccggtacca ctagttattg tggttatcgt attgtggtta gactattgtg   60
gttactatat tgtggttaac ttattgtggt tatgctattg tggttatgcg ctcccgacat  120
gccccgcggc gcgccattaa ccgcagatt tgagtcgcgg gacccgttgg cagaggtggg  180
ctagcctcga ggatatcaag atctggcctc ggcggccaag cttggcaatc cggtactgtt  240
ggtaaagcca cc                                                      252

SEQ ID NO: 211          moltype = DNA   length = 263
FEATURE                 Location/Qualifiers
source                  1..263
                        mol_type = other DNA
                        organism = synthetic construct
SEQUENCE: 211
ggcctaactg gccggtacca ctagtgaaca attgcagtgt tgacgaacaa ttgcagtgtt   60
ctagaacaat tgcagtgtta ctgaacaatt gcagtgtttg cgaacaattg cagtgtttgc  120
gctcccgaca tgccccgcgg cgcgccatta accgccagat ttgagtcgcg ggacccgttg  180
gcagaggtgg gctagcctcg aggatatcaa gatctggcct cggcggccaa gcttggcaat  240
ccggtactgt tggtaaagcc acc                                          263

SEQ ID NO: 212          moltype = DNA   length = 260
FEATURE                 Location/Qualifiers
source                  1..260
                        mol_type = other DNA
                        organism = synthetic construct
SEQUENCE: 212
ggcctaactg gccggtacca ctagtcccca aaccacccc ccccgaccc ccaaaccacc   60
cccccccct accccaaacc accccccccc cactccccaa accacccccc ccctgcgct  120
cccgacatgc cccgcggcgc gccattaacc gccagatttg agtcgcggga cccgttggca  180
gaggtgggct agcctcgagg atatcaagat ctggcctcgg cggccaagct tggcaatccg  240
gtactgttgg taaagccacc                                              260

SEQ ID NO: 213          moltype = DNA   length = 259
FEATURE                 Location/Qualifiers
source                  1..259
                        mol_type = other DNA
                        organism = synthetic construct
SEQUENCE: 213
ggcctaactg gccggtacca ctagtaccgg aagtaagaac cggaagtatc gaccggaagt   60
agacaccgga agtactaacc ggaagtaact accggaagta tgcaccggaa gtatgcgctc  120
ccgacatgcc ccgcggcgcg ccattaaccg ccagatttga gtcgcgggac ccgttggcag  180
aggtgggcta gcctcgagga tatcaagatc tggcctcggc ggccaagctt ggcaatccgg  240
tactgttggt aaagccacc                                               259

SEQ ID NO: 214          moltype = DNA   length = 259
FEATURE                 Location/Qualifiers
source                  1..259
                        mol_type = other DNA
                        organism = synthetic construct
SEQUENCE: 214
ggcctaactg gccggtacca ctagtggcac gtgttagagg cacgtgtttc gggcacgtgt   60
tgacggcacg tgttctaggc acgtgttact ggcacgtgtt tgcggcacgt gtttgcgctc  120
ccgacatgcc ccgcggcgcg ccattaaccg ccagatttga gtcgcgggac ccgttggcag  180
aggtgggcta gcctcgagga tatcaagatc tggcctcggc ggccaagctt ggcaatccgg  240
tactgttggt aaagccacc                                               259

SEQ ID NO: 215          moltype = DNA   length = 264
FEATURE                 Location/Qualifiers
source                  1..264
                        mol_type = other DNA
                        organism = synthetic construct
```

-continued

```
SEQUENCE: 215
ggcctaactg gccggtacca ctagtcgagc agctggtgag acgagcagct ggtgtcgcga    60
gcagctggtg gaccgagcag ctggtgctac gagcagctgg tgactcgagc agctggtgtg   120
cgctcccgac atgccccgcg gcgcgccatt aaccgccaga tttgagtcgc gggacccgtt   180
ggcagaggtg ggctagcctc gaggatatca agatctggcc tcggcggcca agcttggcaa   240
tccggtactg ttggtaaagc cacc                                          264

SEQ ID NO: 216         moltype = DNA   length = 259
FEATURE                Location/Qualifiers
source                 1..259
                       mol_type = other DNA
                       organism = synthetic construct
SEQUENCE: 216
ggcctaactg gccggtacca ctagttccag atgttagatc cagatgtttc gtccagatgt    60
tgactccaga tgttctatcc agatgttact tccagatgtt tgctccagat gtttgcgctc   120
ccgacatgcc ccgcggcgcg ccattaaccg ccagatttga gtcgcgggac ccgttggcag   180
aggtgggcta gcctcgagga tatcaagatc tggcctcggc ggccaagctt ggcaatccgg   240
tactgttggt aaagccacc                                                259

SEQ ID NO: 217         moltype = DNA   length = 259
FEATURE                Location/Qualifiers
source                 1..259
                       mol_type = other DNA
                       organism = synthetic construct
SEQUENCE: 217
ggcctaactg gccggtacca ctagtatagt aaacaagaat agtaaacatc gatagtaaac    60
agacatagta aacactaata gtaaacaact atagtaaaca tgcatagtaa acatgcgctc   120
ccgacatgcc ccgcggcgcg ccattaaccg ccagatttga gtcgcgggac ccgttggcag   180
aggtgggcta gcctcgagga tatcaagatc tggcctcggc ggccaagctt ggcaatccgg   240
tactgttggt aaagccacc                                                259

SEQ ID NO: 218         moltype = DNA   length = 258
FEATURE                Location/Qualifiers
source                 1..258
                       mol_type = other DNA
                       organism = synthetic construct
SEQUENCE: 218
ggcctaactg gccggtacca ctagttaatc ccagataatc cctcgtaatc ccgactaatc    60
ccctataatc ccacttaatc cctgctaatc ccacttaatc cctgctaatc cctgcgctcc   120
cgacatgccc cgcggcgcgt cattaaccgc cagatttgag tcgcgggacc cgttggcaga   180
ggtgggctag cctcgaggat atcaagatct ggcctcggcg gccaagcttg gcaatccggt   240
actgttggta aagccacc                                                 258

SEQ ID NO: 219         moltype = DNA   length = 256
FEATURE                Location/Qualifiers
source                 1..256
                       mol_type = other DNA
                       organism = synthetic construct
SEQUENCE: 219
ggcctaactg gccggtacca ctagtctaat taaagactaa ttaatcgcta attaagacct    60
aattaactac taattaaact ctaattaatg cctaattaaa ctctaattaa tgcgctcccg   120
acatgccccg cggcgcgcca ttaaccgcca gatttgagtc gcgggacccg ttggcagagg   180
tgggctagcc tcgaggatat caagatctgg cctcggcggc caagcttggc aatccggtac   240
tgttggtaaa gccacc                                                   256

SEQ ID NO: 220         moltype = DNA   length = 259
FEATURE                Location/Qualifiers
source                 1..259
                       mol_type = other DNA
                       organism = synthetic construct
SEQUENCE: 220
ggcctaactg gccggtacca ctagtcccaa ttagcagacc caattagctc gcccaattag    60
cgaccccaat tagcctaccc aattagcact cccaattagc tgcccaatt agctgcgctc   120
ccgacatgcc ctgcggcgcg ccattaaccg ccagatttga gtcgcgggac ccgttggcag   180
aggtgggcta gcctcgagga tatcaagatc tggcctcggc ggccaagctt ggcaatccgg   240
tactgttggt aaagccacc                                                259

SEQ ID NO: 221         moltype = DNA   length = 258
FEATURE                Location/Qualifiers
source                 1..258
                       mol_type = other DNA
                       organism = synthetic construct
SEQUENCE: 221
ggcctaactg gccggtacca ctagtcaatt aagacaatta tcgcaattag accaattact    60
acaattaact caattatgcc aattaactca attatgccaa ttaagacaat tatgcgctcc   120
cgacatgccc cgcggcgtgc cattaaccgc cagatttgag tcgcgggacc cgttggcaga   180
ggtgggctag cctcgaggat atcaagatct ggcctcggcg gccaagcttg gcaatccggt   240
actgttggta aagccacc                                                 258
```

-continued

```
SEQ ID NO: 222          moltype = DNA   length = 273
FEATURE                 Location/Qualifiers
source                  1..273
                        mol_type = other DNA
                        organism = synthetic construct
SEQUENCE: 222
ggcctaactg gccggtacca ctagtaaaac cggtttttaga aaaaccggtt tttcgaaaac    60
cggttttgac aaaaccggtt ttctaaaaac cggtttttact aaaaccggtt tttgcaaaac   120
cggtttttgc gctcccgaca tgccccgcgg cgcgccatta accgccagat ttgagtcgcg   180
ggacccgttg gcagaggtgg gctagcctcg aggatatcaa gatctggcct cggcggccaa   240
gcttggcaat ccggtactgt tggtaaagcc acc                                273

SEQ ID NO: 223          moltype = DNA   length = 226
FEATURE                 Location/Qualifiers
source                  1..226
                        mol_type = other DNA
                        organism = synthetic construct
SEQUENCE: 223
ggcctaactg gccggtacca ctagtggtga ctcatgggtg actcatgggt gactcatggg    60
tgactcatgg gtgactcatg tgcgctcccg acatgccccg cggcgcgcca ttaaccgcca   120
gatttgagtc gcgggacccg ttggcagagg tgggctagcc tcgaggatat caagatctgg   180
cctcggcggc caagcttggc aatccggtac tgttggtaaa gccacc                  226

SEQ ID NO: 224          moltype = DNA   length = 292
FEATURE                 Location/Qualifiers
source                  1..292
                        mol_type = other DNA
                        organism = synthetic construct
SEQUENCE: 224
ggcctaactg gccggtacca ctagtggtga ctcatgggtg actcatgggt gactcatggg    60
tgactcatgg gtgactcatg ggtgactcat gggtgactca tgggtgactc atgggtgact   120
catgggtgac tcatgggtga ctcatgtgcg ctcccgacat gccccgcggc gcgccattaa   180
ccgccagatt tgagtcgcgg gacccgttgg cagaggtggg ctagcctcga ggatatcaag   240
atctggcctc ggcggccaag cttggcaatc cggtactgtt ggtaaagcca cc           292

SEQ ID NO: 225          moltype = DNA   length = 248
FEATURE                 Location/Qualifiers
source                  1..248
                        mol_type = other DNA
                        organism = synthetic construct
SEQUENCE: 225
ggcctaactg gccggtacca ctagtggtga ctcatgggtg actcatgggt gactcatggg    60
tgactcatgg gtgactcatg ggtgactcat gggtgactca tgtgcgctcc cgacatgccc   120
cgcggcgcgc cattaaccgc cagatttgag tcgcgggacc cgttggcaga ggtgggctag   180
cctcgaggat atcaagatct ggcctcggcg gccaagcttg gcaatccggt actgttggta   240
aagccacc                                                            248

SEQ ID NO: 226          moltype = DNA   length = 250
FEATURE                 Location/Qualifiers
source                  1..250
                        mol_type = other DNA
                        organism = synthetic construct
SEQUENCE: 226
ggcctaactg gccggtacca ctagtggtga ctcatgggtg actcatgggt gactcatggg    60
tgactcatgg gtgactcatg ggtgactcat gggtgactca tgggtgactc atgggtgact   120
catgcggcgc gccattaacc gccagatttg agtcgcggga cccgttggca gaggtgggct   180
agcctcgagg atatcaagat ctggcctcgg cggccaagct tggcaatccg gtactgttgg   240
taaagccacc                                                          250

SEQ ID NO: 227          moltype = DNA   length = 240
FEATURE                 Location/Qualifiers
source                  1..240
                        mol_type = other DNA
                        organism = synthetic construct
SEQUENCE: 227
ggcctaactg gccggtacca ctagtggtga ctcatgggtg actcatgggt gactcatggg    60
tgactcatgg gtgactcatg ggtgactcat gggtgactca tgggtgactc atgggtgact   120
catgcggtgc tagctataaa aggccagcag cagcctgacc acatctcatc ctcctcgagg   180
atatcaagat ctggcctcgg cggccaagct tggcaatccg gtactgttgg taaagccacc   240

SEQ ID NO: 228          moltype = DNA   length = 230
FEATURE                 Location/Qualifiers
source                  1..230
                        mol_type = other DNA
                        organism = synthetic construct
SEQUENCE: 228
ggcctaactg gccggtacca ctagtggtga ctcatgggtg actcatgggt gactcatggg    60
tgactcatgg gtgactcatg ggtgactcat gggtgactca tgggtgactc atgggtgact   120
catgtataaa aggccagcag cagcctgacc acatctcatc ctcctcgagg atatcaagat   180
```

```
ctggcctcgg cggccaagct tggcaatccg gtactgttgg taaagccacc              230

SEQ ID NO: 229          moltype = DNA   length = 255
FEATURE                 Location/Qualifiers
source                  1..255
                        mol_type = other DNA
                        organism = synthetic construct
SEQUENCE: 229
ggcctaactg gccggtacca ctagtggtga ctcatgggtg actcatgggt gactcatggg    60
tgactcatgg gtgactcatg ggtgactcat gggtgactca tgggtgactc atgggtgact   120
catgacatct ttcagggacc ggtgctagct ataaaaggcc agcagcagcc tgaccacatc   180
tcatcctcct cgaggatatc aagatctggc ctcggcggcc aagcttggca atccggtact   240
gttggtaaag ccacc                                                    255

SEQ ID NO: 230          moltype = DNA   length = 280
FEATURE                 Location/Qualifiers
source                  1..280
                        mol_type = other DNA
                        organism = synthetic construct
SEQUENCE: 230
ggcctaactg gccggtacca ctagtggtga ctcatgggtg actcatgggt gactcatggg    60
tgactcatgg gtgactcatg ggtgactcat gggtgactca tgggtgactc atgggtgact   120
catgtggcta ttagcagtac cgcttagaca catctttcag ggaccggtgc tagctataaa   180
aggccagcag cagcctgacc acatctcatc ctcctcgagg atatcaagat ctggcctcgg   240
cggccaagct tggcaatccg gtactgttgg taaagccacc                         280

SEQ ID NO: 231          moltype = DNA   length = 310
FEATURE                 Location/Qualifiers
source                  1..310
                        mol_type = other DNA
                        organism = synthetic construct
SEQUENCE: 231
ggcctaactg gccggtacca ctagtctgtt tacctgttta cctgtttacc tgtttacctg    60
tttacggtga ctcatgggtg actcatgggt gactcatggg tgactcatgg gtgactcatg   120
ggtgactcat gggtgactca tgggtgactc atgggtgact catgtgcgct cccgacatgc   180
cccgcggcgc gccattaacc gccagatttg agtcgcggga cccgttggca gaggtgggct   240
agcctcgagg atatcaagat ctggcctcgg cggccaagct tggcaatccg gtactgttgg   300
taaagccacc                                                          310

SEQ ID NO: 232          moltype = DNA   length = 322
FEATURE                 Location/Qualifiers
source                  1..322
                        mol_type = other DNA
                        organism = synthetic construct
SEQUENCE: 232
ggcctaactg gccggtacca ctagtctgtt tacagactgt ttactcgctg tttacgacct    60
gtttacctac tgtttacggt gactcatggg tgactcatgg gtgactcatg ggtgactcat   120
gggtgactca tgggtgactc atgggtgact catgggtgac tcatgggtga ctcatgtgcg   180
ctcccgacat gccccgcggc gcgccattaa ccgccagatt tgagtcgcgg acccgttgg   240
cagaggtggg ctagcctcga ggatatcaag atctggcctc ggcggccaag cttggcaatc   300
cggtactgtt ggtaaagcca cc                                            322

SEQ ID NO: 233          moltype = DNA   length = 286
FEATURE                 Location/Qualifiers
source                  1..286
                        mol_type = other DNA
                        organism = synthetic construct
SEQUENCE: 233
ggcctaactg gccggtacca ctagtggtga ctcatgggtg actcatgggt gactcatggg    60
tgactcatgg gtgactcatg ggtgactcat gggtgactca tgggtgactc atgggtgact   120
catgcatagg cctctgaaca acgcgtcccg acatgccccg cggcgcgcca ttaaccgcca   180
gatttgagtc gcgggacccg ttggcagagg tgggctagcc tcgaggatat caagatctgg   240
cctcggcggc caagcttggc aatccggtac tgttggtaaa gccacc                  286

SEQ ID NO: 234          moltype = DNA   length = 306
FEATURE                 Location/Qualifiers
source                  1..306
                        mol_type = other DNA
                        organism = synthetic construct
SEQUENCE: 234
ggcctaactg gccggtacca ctagtggtga ctcatgggtg actcatgggt gactcatggg    60
tgactcatgg gtgactcatg ggtgactcat gggtgactca tgggtgactc atgggtgact   120
catgcatagg cctctgatag agctgcgata gaccaagaca acgcgtcccg acatgccccg   180
cggcgcgcca ttaaccgcca gatttgagtc gcgggacccg ttggcagagg tgggctagcc   240
tcgaggatat caagatctgg cctcggcggc caagcttggc aatccggtac tgttggtaaa   300
gccacc                                                              306

SEQ ID NO: 235          moltype = DNA   length = 364
FEATURE                 Location/Qualifiers
```

```
source                  1..364
                        mol_type = other DNA
                        organism = synthetic construct
SEQUENCE: 235
ggcctaactg gccggtacca ctagtggtga ctcatgggtg actcatgggt gactcatggg     60
tgactcatgg gtgactcatg ggtgactcat gggtgactca tgggtgactc atgggtgact    120
catgcataga aacgacgcaa tatctccata gggttaacgg cggaacttga cggcgtccat    180
tagccacttg gtcatgggac aggggggga aacggacaac gcgtcccgac atgccccgcg     240
gcgcgcgcatt aaccgccaga tttgagtcgc gggacccgtt ggcagaggtg ggctagcctc    300
gaggatatca agatctggcc tcggcggcca agcttggcaa tccggtactg ttggtaaagc    360
cacc                                                                  364

SEQ ID NO: 236          moltype = DNA  length = 306
FEATURE                 Location/Qualifiers
source                  1..306
                        mol_type = other DNA
                        organism = synthetic construct
SEQUENCE: 236
ggcctaactg gccggtacca ctagtggtga ctcatgggtg actcatgggt gactcatggg     60
tgactcatgg gtgactcatg ggtgactcat gggtgactca tgggtgactc atgggtgact    120
catgcatacc ggaagtactt gcgcaatgac cggaagtaca acgcgtcccg acatgccccg    180
cggcgcgcgacca ttaaccgcca gatttgagtc gcgggacccg ttggcagagg tgggctagcc    240
tcgaggatat caagatctgg cctcggcggc caagcttggc aatccggtac tgttggtaaa    300
gccacc                                                                306

SEQ ID NO: 237          moltype = DNA  length = 364
FEATURE                 Location/Qualifiers
source                  1..364
                        mol_type = other DNA
                        organism = synthetic construct
SEQUENCE: 237
ggcctaactg gccggtacca ctagtggtga ctcatgggtg actcatgggt gactcatggg     60
tgactcatgg gtgactcatg ggtgactcat gggtgactca tgggtgactc atgggtgact    120
catgcatttg cgcaacaggg gcggggtgat gacacagcaa ttcgcttgcg tgagaagaga    180
ccggaagtga gggactttcc acatgacaca gcaatacaac gcgtcccgac atgccccgcg    240
gcgcgcgcatt aaccgccaga tttgagtcgc gggacccgtt ggcagaggtg ggctagcctc    300
gaggatatca agatctggcc tcggcggcca agcttggcaa tccggtactg ttggtaaagc    360
cacc                                                                  364

SEQ ID NO: 238          moltype = DNA  length = 420
FEATURE                 Location/Qualifiers
source                  1..420
                        mol_type = other DNA
                        organism = synthetic construct
SEQUENCE: 238
ggcctaactg gccggtacca ctagtggtga ctcatgggtg actcatgggt gactcatggg     60
tgactcatgg gtgactcatg ggtgactcat gggtgactca tgggtgactc atgggtgact    120
catgcatggg gcggggtgat gacacagcaa ttcgggactt ccacgcttg cgtgagaaga     180
gaccggaagt gaatgacaca gcaattcgct tgcgtgagaa gctgggactt cctaggggc     240
ggggttggga ctttccacat gacacagcaa tacaacgcgt cccgacatgc cccgcggcgc    300
gccattaacc gccagatttg agtcgcggga cccgttggca gaggtgggct agcctcgagg    360
atatcaagat ctggcctcgg cggccaagct tggcaatccg gtactgttgg taaagccacc    420

SEQ ID NO: 239          moltype = DNA  length = 204
FEATURE                 Location/Qualifiers
source                  1..204
                        mol_type = other DNA
                        organism = synthetic construct
SEQUENCE: 239
ggcctaactg gccggtacca ctagtaccgg aagtacttgc gcaatgaccg gaagtacaac     60
gcgtcccgac atgccccgcg gcgcgccatt aaccgccaga tttgagtcgc gggacccgtt    120
ggcagaggtg ggctagcctc gaggatatca agatctggcc tcggcggcca agcttggcaa    180
tccggtactg ttggtaaagc cacc                                            204

SEQ ID NO: 240          moltype = DNA  length = 262
FEATURE                 Location/Qualifiers
source                  1..262
                        mol_type = other DNA
                        organism = synthetic construct
SEQUENCE: 240
ggcctaactg gccggtacca ctagtttgcg caacaggggc ggggtgatga cacagcaatt     60
cgcttgcgtg agaagagacc ggaagtgagg gactttccac atgacacagc aatacaacgc    120
gtcccgacat gccccgcggc gcgccattaa ccgccagatt tgagtcgcgg gacccgttgg    180
cagaggtggg ctagcctcga ggatatcaag atctggcctc ggcggccaag cttggcaatc    240
cggtactgtt ggtaaagcca cc                                              262

SEQ ID NO: 241          moltype = DNA  length = 318
FEATURE                 Location/Qualifiers
source                  1..318
```

```
                          mol_type = other DNA
                          organism = synthetic construct
SEQUENCE: 241
ggcctaactg gccggtacca ctagtggggc ggggtgatga cacagcaatt cgggactttc      60
cacgcttgcg tgagaagaga ccggaagtga atgacacagc aattcgcttg cgtgagaagc     120
tgggactttc ctaggggcgg ggttgggact ttccacatga cacagcaata caacgcgtcc     180
cgacatgccc cgcggcgcgc cattaaccgc cagatttgag tcgcgggacc cgttggcaga     240
ggtgggctag cctcgaggat atcaagatct ggcctcggcg gccaagcttg gcaatccggt     300
actgttggta aagccacc                                                    318

SEQ ID NO: 242         moltype = DNA   length = 307
FEATURE                Location/Qualifiers
source                 1..307
                       mol_type = other DNA
                       organism = synthetic construct
SEQUENCE: 242
ggcctaactg gccggtacca ctagtggtga ctcatgggtg actcatgggt gactcatggg      60
tgactcatgg gtgactcatg ggtgactcat gggtgactca tgggtgactc atgggtgact     120
catgcataca acgcgtcccg acatgccccg acatgcccat cgacatgccc cgacatgccc     180
gcggcgcgcc attaaccgcc agatttgagt cgcgggaccc gttggcagag gtgggctagc     240
ctcgaggata tcaagatctg gcctcggcgg ccaagcttgg caatccggta ctgttggtaa     300
agccacc                                                                307

SEQ ID NO: 243         moltype = DNA   length = 431
FEATURE                Location/Qualifiers
source                 1..431
                       mol_type = other DNA
                       organism = synthetic construct
SEQUENCE: 243
ggcctaactg gccggtacca ctagtggtga ctcatgggtg actcatgggt gactcatggg      60
tgactcatgg gtgactcatg ggtgactcat gggtgactca tgggtgactc atgggtgact     120
catgcatgaa ttcggacatg cccgggcatg tccccaggga catgcccggg catgtcccca     180
gagacatgtc cagacatgtc cccaggaaca tgtcccaaca tgttgtccag gagacatgtc     240
cagacatgtc cccaggaaca tgtcccaaca tgttgtacta gtacaacgcg tcccgacatg     300
ccccgcggcg cgccattaac cgccagattt gagtcgcggg acccgttggc agaggtgggc     360
tagcctcgag gatatcaaga tctggcctcg gcggccaagc ttggcaatcc ggtactgttg     420
gtaaagccac c                                                          431

SEQ ID NO: 244         moltype = DNA   length = 338
FEATURE                Location/Qualifiers
source                 1..338
                       mol_type = other DNA
                       organism = synthetic construct
SEQUENCE: 244
ggcctaactg gccggtacct gccactcaaa gtggcacact ccctgctcag gaggccggga      60
gggaggacac agccctggca actcctctgc cccgggggg  caggaagggg tcaccccaca     120
ctccagaacc ctacagaatg tggccttggc ttttcccatc aagagctggg gaaagccagg     180
ccccgacttc attaccccct gccccgtcc  catgctcagt gggcccatc  gtgggtccat     240
gccacactcc caactgagca gccccgcagc cccgcgtgtc acagacatgg ggcctcctaa     300
ttgctgctga ggtcccaatc cctggctgga cgtgcctg                             338

SEQ ID NO: 245         moltype = DNA   length = 386
FEATURE                Location/Qualifiers
source                 1..386
                       mol_type = other DNA
                       organism = synthetic construct
SEQUENCE: 245
ggcctaactg gccggtacca ctagtggtga ctcatgggtg actcatgggt gactcatggg      60
tgactcatgg gtgactcatg ggtgactcat gggtgactca tgggtgactc atgactagtg     120
tccccaccca cacattcctg tccccaccca cacattcctg tccccaccca cacattcctg     180
tccccaccca cacattcctg tccccaccca cacattcctg tccccaccca cacattcctg     240
tgcgctcccg acatgccccg cggcgcgcca ttaaccgcca gatttgagtc gcgggacccg     300
ttggcagagg tgggctagcc tcgaggatat caagatctgg cctcggcggc caagcttggc     360
aatccggtac tgttggtaaa gccacc                                          386

SEQ ID NO: 246         moltype = DNA   length = 366
FEATURE                Location/Qualifiers
source                 1..366
                       mol_type = other DNA
                       organism = synthetic construct
SEQUENCE: 246
ggcctaactg gccggtacca agacaggttg tcctcccagg ggatgggggt ccatccacct      60
tgccgaaaag atttgtctga ggaactgaaa atagaaggga aaaagaggga gggacaaaag     120
aggcagaaat gagaggggag gggacagagg acacctgaat aaagaccaca cccatgaccc     180
acgtgatgct gagaagtact cctgccctag gaagagactc agggcagagg gaggaaggac     240
agcagaccag acagtcacag cagccttgac aaaacgttcc tggaactacc ggtgctagcc     300
tcgaggatat caagatctgg cctcggcggc caagcttggc aatccggtac tgttggtaaa     360
gccacc                                                                366
```

-continued

```
SEQ ID NO: 247          moltype = DNA   length = 212
FEATURE                 Location/Qualifiers
source                  1..212
                        mol_type = other DNA
                        organism = synthetic construct
SEQUENCE: 247
ggcctaactg gccggtacca tgacccacgt gatgctgaga agtactcctg ccctaggaag   60
agactcaggg cagagggagg aaggacagca gaccagacag tcacagcagc cttgacaaaa  120
cgttcctgga actaccggtg ctagcctcga ggatatcaag atctggcctc ggcggccaag  180
cttggcaatc cggtactgtt ggtaaagcca cc                                212

SEQ ID NO: 248          moltype = DNA   length = 868
FEATURE                 Location/Qualifiers
source                  1..868
                        mol_type = other DNA
                        organism = synthetic construct
SEQUENCE: 248
ggcctaactg gccggtaccc tggatgctca tcccgccacc gtcgcccacc ccgccgctgc   60
agaaaggcag caactgccac acacctaagc aacttggcgg gctattcgcc ctgcagctgc  120
cgccagcgcg cggctcccgc cagcgcgctg gcaatcaaaa gtcggagaaa gcgcgaaacc  180
tccaggcacc tcccactccg cccagctacc gcgcagctcc tccctagcct ccactgggag  240
acagggacg cccatgagcg ggaaagagca gggcggtgat tgcttagttt atcctgggac  300
acgggaactg gccgtggact gagtggtgcc ggggaggga tcactgagac cgggaagggt  360
catccagaca aataggggagg gtgggcgggt tggcgcgcag taccctcggc ccggccttca  420
gacccacctg cgcgcgctgc gcgctcatcc ggtccttccc ttcaatcact gtctggagtg  480
atgataattg gcttccacag tggatgagag atgagtcatt aatccaat gagagaaaaa  540
cagcctccag agactcttcg tccattggcc agcgagagtg tcagttccca ggctcctgcc  600
gcgcacgggc gagcccttct aggcgggaaa agttcagctg agagatataa aagagcagtc  660
tttccagcac ctgcaaatcc agagcggcgg gcactgacgg gcacttgcac cgtgtggaca  720
gactctccgg ttctgtgagt ggtttttctt ttcccgggtc ggacctggag ttcttagggg  780
gatggctgaa ccggtgctag cctcgaggat atcaagatct ggcctcggcg gccaagcttg  840
gcaatccggt actgttggta aagccacc                                     868

SEQ ID NO: 249          moltype = DNA   length = 543
FEATURE                 Location/Qualifiers
source                  1..543
                        mol_type = other DNA
                        organism = synthetic construct
SEQUENCE: 249
ggcctaactg gccggtacct gagaccggga agggtcatcc agacaaatag ggagggtggg   60
cgggttggcg cgcagtaccc tcggcccggc cttcagaccc acctgcgcgc gctgcgcgct  120
catccggtcc ttcccttcaa tcactgtctg gagtgatgat aattggcttc cacagtggat  180
gagagatgag tcatttacat ccaatgagag aaaaacagcc tccagagact cttcgtccat  240
tggccagcga gagtgtcagt tcccaggctc ctgccgcgca cgggcgagcc cttctaggcg  300
ggaaaagttc agctgagaga tataaaagag cagtctttcc agcacctgca aatccagagc  360
ggcgggcact gacgggcact tgcaccgtgt ggacagactc tccggttctg tgagtggttt  420
ttctttccc gggtcggacc tggagttctt aggggatgg ctgaaccggt gctagcctcg  480
aggatatcaa gatctggcct cggcggccaa gcttggcaat ccggtactgt tggtaaagcc  540
acc                                                                543

SEQ ID NO: 250          moltype = DNA   length = 263
FEATURE                 Location/Qualifiers
source                  1..263
                        mol_type = other DNA
                        organism = synthetic construct
SEQUENCE: 250
ggcctaactg gccggtaccg ggaaaagttc agctgagaga tataaaagag cagtctttcc   60
agcacctgca aatccagagc ggcgggcact gacgggcact tgcaccgtgt ggacagactc  120
tccggttctg tgagtggttt ttctttccc gggtcggacc tggagttctt aggggatgg  180
ctgaaccggt gctagcctcg aggatatcaa gatctggcct cggcggccaa gcttggcaat  240
ccggtactgt tggtaaagcc acc                                          263

SEQ ID NO: 251          moltype = DNA   length = 242
FEATURE                 Location/Qualifiers
source                  1..242
                        mol_type = other DNA
                        organism = synthetic construct
SEQUENCE: 251
ggcctaactg gccggtaccc tgctcctcct tcttgcgggc cgcgccctgc cggcagtgac   60
gtgccccgcc ctgcagccgc gggattcaaa ctcccggaag cggcatccac acctgatggt  120
gtgactcggc cgacgcgagc gccgcgcttc gcttcagctg ctaaccggtg ctagcctcga  180
ggatatcaag atctggcctc ggcggccaag cttggcaatc cggtactgtt ggtaaagcca  240
cc                                                                 242

SEQ ID NO: 252          moltype = DNA   length = 348
FEATURE                 Location/Qualifiers
source                  1..348
                        mol_type = other DNA
                        organism = synthetic construct
```

```
SEQUENCE: 252
ggcctaactg gccggtaccg gcccgccccc tttccttacg cggattggta gctgcaggct   60
tccctatctg attggccgaa cgaacgcagc gcgtaattta aaatattgta tctgtaacaa  120
agctgcacct cgtgggcgga gttgtgctct gcggctgcga aagtccagct tcggcgacta  180
ggtgtgagta agccagtatc ccaggaggag caagtggcac gtcttcggct gagtgtgcgg  240
ctgtgctgga gcccgggtta ccagctctta ccggtgctag cctcgaggat atcaagatct  300
ggcctcggcg gccaagcttg gcaatccggt actgttggta aagccacc                348

SEQ ID NO: 253          moltype = DNA   length = 710
FEATURE                 Location/Qualifiers
source                  1..710
                        mol_type = other DNA
                        organism = synthetic construct
SEQUENCE: 253
ggcctaactg gccggtacct tgttttgaca ggagcaggga agtattgtag aaaataattt   60
ttatcataat ggagtatggc aggttatatg actgcgagga tcagaattgt gaatcatctc  120
ttgtgtgtct tcaagtaaat aaaggcaatc tgcccacggg gcagaaaaaa aatctacaaa  180
ctacaaactc tgtccaatca tgtaaagaca aatcagcctt caggcaaatc aaatgtcttc  240
attcaaagtc tacctggatt tggcactctg cccatcgttt caaaacctct taacaatacg  300
tttcacaaat agttaaaaac atgcatactg aaaagcatac ttttgcaatg ttatttttaa  360
aaacaaggaa ctctttaacc cagggaagat aatcacttgg ggaaaggaag gttcgtttct  420
gagttagcaa caagtaaatg cagcactagt gggtgggatt gggtgtgcc ctggtgcata  480
aatagagact cagctgtgct ggcacactca gaagcttgga ccgcatccta gccgccgact  540
cacacaaggc aggtgggtga ggaaatccag gtaaggctcc tgacagcagc tttagaaggg  600
tacttgctgg agtgaattcg ggcctctgat taccggtgct agcctcgagg atatcaagat  660
ctggcctcgg cggccaagct tggcaatccg gtactgttgg taaagccacc                710

SEQ ID NO: 254          moltype = DNA   length = 445
FEATURE                 Location/Qualifiers
source                  1..445
                        mol_type = other DNA
                        organism = synthetic construct
SEQUENCE: 254
ggcctaactg gccggtacca cctcttaaca atacgtttca caaatagtta aaaacatgca   60
tactgaaaag catacttttg caatgttatt tttaaaaaca aggaactctt taacccaggg  120
aagataatca cttggggaaa ggaaggttcg tttctgagtt agcaacaagt aaatgcagca  180
ctagtgggtg ggattgaggt gtgccctggt gcataaatag agactcagct gtgctggcac  240
actcagaagc ttggaccgca tcctagccgc cgactcacac aaggcaggtg ggtgaggaaa  300
tccaggtaag gctcctgaca gcagctttag aagggtactt gctggagtga attcgggcct  360
ctgattaccg gtgctagcct cgaggatatc aagatctggc ctcggcggcc aagcttggca  420
atccggtact gttggtaaag ccacc                                          445

SEQ ID NO: 255          moltype = DNA   length = 275
FEATURE                 Location/Qualifiers
source                  1..275
                        mol_type = other DNA
                        organism = synthetic construct
SEQUENCE: 255
ggcctaactg gccggtaccc agtgggtagg tctagcagtg gcgcagcaat agagcgctcc   60
ggagcgtctc attggctgga tcaaacccaa gcgagccatt gattggtcga cgcccccaga  120
gggttacaat tcaaacgcgg gcgggcgggc ccgcagtcgt gcagttgcag tcgtgttctc  180
cgagttcctg tctctctgcc gagctagcct cgaggatatc aagatctggc ctcggcggcc  240
aagcttggca atccggtact gttggtaaag ccacc                               275

SEQ ID NO: 256          moltype = DNA   length = 289
FEATURE                 Location/Qualifiers
source                  1..289
                        mol_type = other DNA
                        organism = synthetic construct
SEQUENCE: 256
ggcctaactg gccggtacca gtggtggggg agtgaaaaga gagatggaga aagaggggat   60
gggcagaaag aggaggagga gtcaggggca gggcatggag gtgggtgggg ctgggctgcc  120
aaagcaggat aaatgcacac ctgcctgctg gtctgggctc cctgcctcgg gctctcaccc  180
tcctctcctg cagctccagc tttgtgctct accggtgcta gcctcgagga tatcaagatc  240
tggcctcggc ggccaagctt ggcaatccgg tactgttggt aaagccacc                289

SEQ ID NO: 257          moltype = DNA   length = 557
FEATURE                 Location/Qualifiers
source                  1..557
                        mol_type = other DNA
                        organism = synthetic construct
SEQUENCE: 257
ggcctaactg gccggtacca ctagtcgggt taccccacag cctaggccga ttcgacctct   60
ctccgctggg gccctcgctg gcgtccctgc acctgggag cgcgagcggc gcgcgggcgg  120
ggaagcgcgg cccagacccc cgggtccgcc cggagcagct gcgctgtcgg ggccaggccg  180
ggctcccagt ggattcgcgg gcacagacgc ccaggaccgc gcttcccacg tggcggaggg  240
actgggacc cggcacccg tcctgcccct tcaccttcca gctccgcctc ctccgcgcgg  300
accccgcccc gtcccgaccc ctccggggtc ccggcccag ccccctccgg gccctcccag  360
cccctcccct tcctttccgc ggccccgccc tctcctcgcg gcgcgagttt caggcagcgc  420
```

-continued

```
tgcgtcctgc tgcgcacgtg ggaagccctg gcccccggcca cccccgcgat gccgcgcgct    480
cctagctatc ctcgaggata tcaagatctg gcctcggcgg ccaagcttgg caatccggta    540
ctgttggtaa agccacc                                                    557

SEQ ID NO: 258            moltype = DNA   length = 971
FEATURE                   Location/Qualifiers
source                    1..971
                          mol_type = other DNA
                          organism = synthetic construct
SEQUENCE: 258
ggcctaactg gccggtaccc tggcaggaag cctactgaga tttattgaaa aggaaaccga     60
attatcaggg cactcgtttg caacgccaac ctgggctgtg ttcggggcat gcccagcctg    120
ctgtctgcag tgtgaagctc tttagaagcc actgcaacca caggccgccc gacaggaaca    180
gagacactga aaacgggccc gcagcaaggc aggctcagca gccaacagtc acacccagga    240
agcagtattt ttcttctgct cctggactct cttgcggtgt atggctgctt ccctttggtc    300
tgagccaggc cgatggtctc agaaatagac acccattgac tttcttttcc agcgctggga    360
catacagacc ccgcctccat cccagggtgt ctataggaag gatggcggct gctgcaggga    420
ggagggtctc ctgtcttcct aagggcgccc ctccaccagc ctgtgggtgg gtccgaggca    480
cttccattcc gatatctagc tggccaaatc ctgcaaacct tgaggcagga agaacctgca    540
gagcacatgg gacttgcagc ggacatgctt aaagaggtg ccccaggccc gtccaccgcc     600
ctcggccacc ctccgtgtcc tctggggagc agctgcggaa gattcgagtc agaatagcaa    660
gaaggaaccg cagcagaagg tacaactccc agcatgccgt cgcccgcca cgcccacaag     720
gccaggcgca gatgggcgtg gggcgggact ttcccggctc gcctcgcgcc gtccactccc    780
agaaggcagc gggcgagggc gtggggccgg ggctctcccg gcatgctctg cggcgcgcct    840
ccgcccgcgc gatttgaatc ctgcgtttga gtcgtcttgg cggaggttgt ggtgacgcgc    900
tagcctcgag gatatcaaga tctggcctcg gcggccaagc ttggcaatcc ggtactgttg    960
gtaaagccac c                                                          971

SEQ ID NO: 259            moltype = DNA   length = 225
FEATURE                   Location/Qualifiers
source                    1..225
                          mol_type = other DNA
                          organism = synthetic construct
SEQUENCE: 259
ggcctaactg gccggtacca ctcccagaag gcagcgggcg agggcgtggg gccggggctc     60
tcccggcatg ctctgcggcg cgcctccgcc cgcgcgattt gaatcctgcg tttgagtcgt    120
cttggcggag gttgtggtga cgcgctagct attctagcct cgaggatatc aagatctggc    180
ctcggcggcc aagcttggca atccggtact gttggtaaag ccacc                     225

SEQ ID NO: 260            moltype = DNA   length = 355
FEATURE                   Location/Qualifiers
source                    1..355
                          mol_type = other DNA
                          organism = synthetic construct
SEQUENCE: 260
ggcctaactg gccggtacca ctagtggtga ctcatgggtg actcatgggt gactcatggg     60
tgactcatgg gtgactcatg ggtgactcat gggtgactca tgggtgactc atgggtgact    120
catggtgatc atgctagcct cgaggatatc aagatcggta ccatgaccca cgtgatgctg    180
agaagtactc ctgccctagg aagagactca gggcagaggg aggaaggaca gcagaccaga    240
cagtcacagc agccttgaca aaacgttcct ggaactaccg gtgctagcct cgaggatatc    300
aagatctggc ctcggcggcc aagcttggca atccggtact gttggtaaag ccacc          355

SEQ ID NO: 261            moltype = DNA   length = 377
FEATURE                   Location/Qualifiers
source                    1..377
                          mol_type = other DNA
                          organism = synthetic construct
SEQUENCE: 261
ggcctaactg gccggtacca ctagtggtga ctcatgggtg actcatgggt gactcatggg     60
tgactcatgg gtgactcatg ggtgactcat gggtgactca tgggtgactc atgggtgact    120
catggtgatc atcgggaaaa gttcagctga gagatataaa agagcagtct ttccagcacc    180
tgcaaatcca gagcggcggg cactgacggg cacttgcacc gtgtggacag actctccggt    240
tctgtgagtg gttttctttt tcccgggtcg gacctggagt tcttaggggg atggctgaac    300
cggtgctagc ctcgaggata tcaagatctg gcctcggcgg ccaagcttgg caatccggta    360
ctgttggtaa agccacc                                                    377

SEQ ID NO: 262            moltype = DNA   length = 491
FEATURE                   Location/Qualifiers
source                    1..491
                          mol_type = other DNA
                          organism = synthetic construct
SEQUENCE: 262
ggcctaactg gccggtacca ctagtggtga ctcatgggtg actcatgggt gactcatggg     60
tgactcatgg gtgactcatg ggtgactcat gggtgactca tgggtgactc atgggtgact    120
catggtgatc atgctagcct cgaggatatc aagatcggta ccggcccgcc ccctttcctt    180
acgcggattg gtagctgcag gcttccctat ctgattggcc gaacgaacgc agcgcgtaat    240
ttaaaatatt gtatctgtaa caaagctgca cctcgtgggc ggagttgtgc tctgcggctg    300
cgaaagtcca gcttcggcga ctaggtgtga gtaagccagt atcccaggag gagcaagtgg    360
cacgtcttcg ggtgagtgtg cggctgtgct ggagcccggg ttaccagctc ttaccggtgc    420
```

-continued

```
tagcctcgag gatatcaaga tctggcctcg gcggccaagc ttggcaatcc ggtactgttg   480
gtaaagccac c                                                        491

SEQ ID NO: 263          moltype = DNA   length = 432
FEATURE                 Location/Qualifiers
source                  1..432
                        mol_type = other DNA
                        organism = synthetic construct
SEQUENCE: 263
ggcctaactg gccggtacca ctagtggtga ctcatgggtg actcatgggt gactcatggg   60
tgactcatgg gtgactcatg ggtgactcat gggtgactca tgggtgactc atgggtgact   120
catggtgatc atgctagcct cgaggatatc aagatcggta ccagtggtgg gggagtgaaa   180
agagagatgg agaaagaggg gatgggcaga aagaggagga ggagtcaggg gcagggcatg   240
gaggtgggtg gggctgggct gccaaagcag gataaatgca cacctgcctg ctggtctggg   300
ctccctgcct cgggctctca ccctcctctc ctgcagctcc agctttgtgc tctaccggtg   360
ctagcctcga ggatatcaag atctggcctc ggcggccaag cttggcaatc cggtactgtt   420
ggtaaagcca cc                                                       432

SEQ ID NO: 264          moltype = DNA   length = 375
FEATURE                 Location/Qualifiers
source                  1..375
                        mol_type = other DNA
                        organism = synthetic construct
SEQUENCE: 264
ggcctaactg gccggtacca ctagtgtccc cacccacaca ttcctgtccc cacccacaca   60
ttcctgtccc cacccacaca ttcctgtccc cacccacaca ttcctgtccc cacccacaca   120
ttcctgtccc cacccacaca ttcctgaccg gtgctagcct cgaggatatc aagatcggta   180
ccatgaccca cgtgatgctg agaagtactc ctgccctagg aagagactca gggcagaggg   240
aggaaggaca gcagaccaga cagtcacagc agccttgaca aaacgttcct ggaactaccg   300
gtgctagcct cgaggatatc aagatctggc ctcggcggcc aagcttggca atccggtact   360
gttggtaaag ccacc                                                    375

SEQ ID NO: 265          moltype = DNA   length = 391
FEATURE                 Location/Qualifiers
source                  1..391
                        mol_type = other DNA
                        organism = synthetic construct
SEQUENCE: 265
ggcctaactg gccggtacca ctagtgtccc cacccacaca ttcctgtccc cacccacaca   60
ttcctgtccc cacccacaca ttcctgtccc cacccacaca ttcctgtccc cacccacaca   120
ttcctgtccc cacccacaca ttcctgcggg aaaagttcag ctgagagata taaaagagca   180
gtctttccag cacctgcaaa tccagagcgg cgggcactga cgggcacttg caccgtgtgg   240
acagactctc cggttctgtg agtggttttt cttttcccgg gtcggacctg gagttcttag   300
ggggatggct gaaccggtgc tagcctcgag gatatcaaga tctggcctcg gcggccaagc   360
ttggcaatcc ggtactgttg gtaaagccac c                                  391

SEQ ID NO: 266          moltype = DNA   length = 476
FEATURE                 Location/Qualifiers
source                  1..476
                        mol_type = other DNA
                        organism = synthetic construct
SEQUENCE: 266
ggcctaactg gccggtacca ctagtgtccc cacccacaca ttcctgtccc cacccacaca   60
ttcctgtccc cacccacaca ttcctgtccc cacccacaca ttcctgtccc cacccacaca   120
ttcctgtccc cacccacaca ttcctgcggc ccgcccccctt tccttacgcg gattggtagc   180
tgcaggcttc cctatctgat tggccgaacg aacgcagcgc gtaatttaaa atattgtatc   240
tgtaacaaag ctgcacctcg tgggcggagt tgtgctctgc ggctgcgaaa gtccagcttc   300
ggcgactagg tgtgagtaag ccagtatccc aggaggagca agtggcacgt cttcgggtga   360
gtgtgcggct gtgctggagc ccgggttacc agctcttacc ggtgctagcc tcgaggatat   420
caagatctgg cctcggcggc caagcttggc aatccggtac tgttggtaaa gccacc       476

SEQ ID NO: 267          moltype = DNA   length = 608
FEATURE                 Location/Qualifiers
source                  1..608
                        mol_type = other DNA
                        organism = synthetic construct
SEQUENCE: 267
ggcctaactg gccggtacca ctagtgtccc cacccacaca ttcctgtccc cacccacaca   60
ttcctgtccc cacccacaca ttcctgtccc cacccacaca ttcctgtccc cacccacaca   120
ttcctgtccc cacccacaca ttcctgaccg gtgctagcct cgaggatatc aagatcggta   180
ccacctctta acaatacgtt tcacaaatag ttaaaaacat gcatactgaa aagcatactt   240
ttgcaatgtt atttttaaaa acaaggaact ctttaaccca gggaagataa tcacttgggg   300
aaaggaaggt tcgtttctga gttagcaaca agtaaatgca gcactagtgg gtgggattga   360
ggtgtgccct ggtgcataaa tagagactca gctgtgctgg cacactcaga agcttggacc   420
gcatcctagc cgccgactca cacaaggcag gtgggtgagg aaatccaggt aaggctcctg   480
acagcagctt tagaagggta cttgctggag tgaattcggg cctctgatta ccggtgctag   540
cctcgaggat atcaagatct ggcctcggcg gccaagcttg gcaatccggt actgttggta   600
aagccacc                                                            608
```

-continued

```
SEQ ID NO: 268          moltype = DNA  length = 452
FEATURE                 Location/Qualifiers
source                  1..452
                        mol_type = other DNA
                        organism = synthetic construct
SEQUENCE: 268
ggcctaactg gccggtacca ctagtgtccc cacccacaca ttcctgtccc cacccacaca    60
ttcctgtccc cacccacaca ttcctgtccc cacccacaca ttcctgtccc cacccacaca   120
ttcctgtccc cacccacaca ttcctgaccg gtgctagcct cgaggatatc aagatcggta   180
ccagtggtgg gggagtgaaa agagagatgg agaaagaggg gatgggcaga aagaggagga   240
ggagtcaggg gcagggcatg gaggtggggt gggctgggct gccaaagcag gataaatgca   300
cacctgcctg ctggtctggg ctccctgcct cgggctctca ccctcctctc ctgcagctcc   360
agctttgtgc tctaccggtg ctagcctcga ggatatcaag atctggcctc ggcggccaag   420
cttggcaatc cggtactgtt ggtaaagcca cc                                 452

SEQ ID NO: 269          moltype = DNA  length = 588
FEATURE                 Location/Qualifiers
source                  1..588
                        mol_type = other DNA
                        organism = synthetic construct
SEQUENCE: 269
ggcctaactg gccggtacca ctagtggtga ctcatgggtg actcatgggt gactcatggg    60
tgactcatgg gtgactcatg ggtgactcat gggtgactca tgggtgactc atgggtgact   120
catggtgatc atgctagcct cgaggatatc aagatcggta ccacctctta acaatacgtt   180
tcacaaatag ttaaaaacat gcatactgaa aagcatactt ttgcaatgtt attttttaaa   240
acaaggaact ctttaaccca gggaagataa tcacttgggg aaaggaaggt tcgtttctga   300
gttagcaaca agtaaatgca gcactagtgg tgtgggattga ggtgtgccct ggtgcataaa   360
tagagactca gctgtgctgg cacactcaga agcttggacc gcatcctagc cgccgactca   420
cacaaggcag gtgggtgagg aaatccaggt aaggctcctg acagcagctt tagaagggta   480
cttgctggag tgaattcggg cctctgatta ccggtgctag cctcgaggat atcaagatct   540
ggcctcggcg gccaagcttg gcaatccggt actgttggta aagccacc               588

SEQ ID NO: 270          moltype = DNA  length = 12
FEATURE                 Location/Qualifiers
source                  1..12
                        mol_type = other DNA
                        organism = synthetic construct
SEQUENCE: 270
gcaaccaccg aa                                                        12

SEQ ID NO: 271          moltype = DNA  length = 520
FEATURE                 Location/Qualifiers
source                  1..520
                        mol_type = other DNA
                        organism = synthetic construct
SEQUENCE: 271
aattttattg ttcaaacatg agagcttagt acgtgaaaca tgagagctta gtacgttagc    60
catgagagct tagtacgtta gccatgaggg tttagttcgt taaacatgag agcttagtac   120
gttaaacatg agagcttagt acgtactatc aacaggttga actgctgatc cacgttgtgg   180
tagaattggt aaagagagtc gtgtaaaata tcgagttcgc acatcttgtt gtctgattat   240
tgatttttgg cgaaaccatt tgatcatatg acaagatgtg tatctacctt aacttaatga   300
ttttgataaa aatcattagg tacggccgcg gtgccagggc gtgcccttgg gctccccggg   360
cgcgactagt ggtgactcat gggtgactca tgggtgactc atgggtgact catgggtgac   420
tcatgtgcgc tcccgacatg ccccgcggcg cgccattaac cgccagattt gagtcgcggg   480
acccgttggc agaggtggga attcaccggt cgacgctagc                        520

SEQ ID NO: 272          moltype = DNA  length = 11
FEATURE                 Location/Qualifiers
source                  1..11
                        mol_type = other DNA
                        organism = synthetic construct
SEQUENCE: 272
tcctttgaac t                                                        11

SEQ ID NO: 273          moltype = DNA  length = 542
FEATURE                 Location/Qualifiers
source                  1..542
                        mol_type = other DNA
                        organism = synthetic construct
SEQUENCE: 273
aattttattg ttcaaacatg agagcttagt acgtgaaaca tgagagctta gtacgttagc    60
catgagagct tagtacgtta gccatgaggg tttagttcgt taaacatgag agcttagtac   120
gttaaacatg agagcttagt acgtactatc aacaggttga actgctgatc cacgttgtgg   180
tagaattggt aaagagagtc gtgtaaaata tcgagttcgc acatcttgtt gtctgattat   240
tgatttttgg cgaaaccatt tgatcatatg acaagatgtg tatctacctt aacttaatga   300
ttttgataaa aatcattagg tacggccgcg gtgccagggc gtgcccttgg gctccccggg   360
cgcgactagt ggtgactcat gggtgactca tgggtgactc atgggtgact catgggtgac   420
tcatgggtga ctcatgggtg actcatgtgc gctcccgaca tgccccgcgg cgcgccatta   480
accgccagat ttgagtcgcg ggacccgttg gcagaggtgg gaattcaccg gtcgacgcta   540
```

-continued

```
gc                                                                            542

SEQ ID NO: 274              moltype = DNA   length = 294
FEATURE                     Location/Qualifiers
source                      1..294
                            mol_type = other DNA
                            organism = synthetic construct
SEQUENCE: 274
tctgtagttt gaggagaata tttgttatat tgcacaataa aataagtttg caagtttttt   60
ttttctgccc caaagagctc tgtgtccttg aacataaaat acaaataacc gctatgctgt   120
taattattaa caaatgtccc attttcaacc taaggaaata ccataaagta acagatatac   180
caacaaaagg ttaataatta acaggcattg cctgaaaaga gtataaaagg ctttcagcat   240
gattttccat attgtgcttc caccactgcc aataacaaac cggtcgacgc tagc          294

SEQ ID NO: 275              moltype = DNA   length = 10
FEATURE                     Location/Qualifiers
source                      1..10
                            mol_type = other DNA
                            organism = synthetic construct
SEQUENCE: 275
gtcgttaaat                                                                    10

SEQ ID NO: 276              moltype = DNA   length = 10
FEATURE                     Location/Qualifiers
source                      1..10
                            mol_type = other DNA
                            organism = synthetic construct
SEQUENCE: 276
agaggaagtg                                                                    10

SEQ ID NO: 277              moltype = DNA   length = 11
FEATURE                     Location/Qualifiers
source                      1..11
                            mol_type = other DNA
                            organism = synthetic construct
SEQUENCE: 277
tacttggcag a                                                                  11

SEQ ID NO: 278              moltype = DNA   length = 1196
FEATURE                     Location/Qualifiers
source                      1..1196
                            mol_type = other DNA
                            organism = synthetic construct
SEQUENCE: 278
gcccctcccc cgtgccttcc ttgaccctgg aaggtgccac tcccactgtc ctttcctaat   60
aaaatgagga aattgcatcg cattgtctga gtaggtgtca ttctattctg gggggtgggg   120
tggggcagga cagcaagggg gaggattggg aagacaatag caggcatgct ggggatgcgg   180
tgggctctat ggcccgggac ggccgctagc ccgcctaatg agcgggcttt ttttttggctt   240
gttgtccaca accgttaaac cttaaaagct ttaaaagcct tatatattct tttttttcatt   300
ataaaactta aaaccttaga ggctatttaa gttgctgatt tatattaatt ttattgttca   360
aacatgagag cttagtacgt gaaacatgag agcttagtac gttagccatg agagcttagt   420
acgttagcca tgagggttta gttcgttaaa catgagagct tagtacgtta aacatgagag   480
cttagtacgt actatcaaca ggttgaactg ctgatccacg ttgtggtaga attggtaaag   540
agagtcgtgt aaaatatcga gttcgcacat cttgttgtct gattattgat ttttggcgaa   600
accatttgat catatgacaa gatgtgtatc taccttaact taatgatttt gataaaaatc   660
attaggtacg gccgcggtgc cagggcgtgc ccttgggctc cccgggcgcg actagtctcg   720
agtcttgtgt gcctggcata tgataggcat ttaaatagttt taaagaatta atgtatttag   780
atgaattgca taccaaatct gctgtctttt ctttatggct tcattaactt aatttgagag   840
aaattaatta ttctgcaact tagggacaag tcatctcttt gaatattctg tagtttgagg   900
agaatatttg ttatatttgc aaaataaaat aagtttgcaa gttttttttt tctgccccaa   960
agagctctgt gtccttgaac ataaaataca aataaccgct atgctgttaa ttattggcaa   1020
atgtcccatt tcaacctaa ggaaatacca taaagtaaca gatataccaa caaaaggtta   1080
ctagttaaca ggcattgcct gaaaagagta aaaagaatt tcagcatgat tttccatatt   1140
gtgcttccac cactgccaat aacaaataa ctagcagagc tagcctcgag gctagc         1196

SEQ ID NO: 279              moltype = DNA   length = 770
FEATURE                     Location/Qualifiers
source                      1..770
                            mol_type = other DNA
                            organism = synthetic construct
SEQUENCE: 279
aattttattg ttcaaacatg agagcttagt acgtgaaaca tgagagctta gtacgttagc   60
catgagagct tagtacgtta gccatgaggg tttagttcgt aaacatgag agcttagtac   120
gttaaacatg agagcttagt acgtactatc aacaggttga actgctgatc cacgttgtgg   180
tagaattggt aaagagagtc gtgtaaaata tcgagttcgc acatcttgtt gtctgattat   240
tgatttttgg cgaaaccatt tgatcatatg acaagatgtg tatctacctt aacttaatga   300
ttttgataaa aatcattagg tacggccgcg gtgccagggc gtgcccttgg ctccccgggg   360
cgcgaatgca tactagtaac atttctctgg cctaactggc cggtaccacc tcttaacaat   420
acgtttcaca aatagttaaa aacatgcata ctgaaaagca tacttttgca atgttatttt   480
```

-continued

```
taaaaacaag gaactcttta acccagggaa gataatcact tggggaaagg aaggttcgtt   540
tctgagttag caacaagtaa atgcagcact agtgggtggg attgaggtgt gccctggtgc   600
ataaatagag actcagctgt gctggcacac tcagaagctt ggaccgcatc ctagccgccg   660
actcacacaa ggcaggtggg tgaggaaatc caggtaaggc tcctgacagc agctttagaa   720
gggtacttgc tggagtgaat tcgggcctct gattaccggg cgacgctagc              770

SEQ ID NO: 280         moltype = DNA  length = 11
FEATURE                Location/Qualifiers
source                 1..11
                       mol_type = other DNA
                       organism = synthetic construct
SEQUENCE: 280
tacttggcaa a                                                          11

SEQ ID NO: 281         moltype = DNA  length = 537
FEATURE                Location/Qualifiers
source                 1..537
                       mol_type = other DNA
                       organism = synthetic construct
SEQUENCE: 281
aattttattg ttcaaacatg agagcttagt acgtgaaaca tgagagctta gtacgttagc    60
catgagagct tagtacgtta gccatgaggg tttagttcgt taaacatgag agcttagtac   120
gttaaacatg agagcttagt acgtactatc aacaggttga actgctgatc cacgttgtgg   180
tagaattggt aaagagagtc gtgtaaaata tcgagttcgc acatcttgtt gtctgattat   240
tgattttggg cgaaaccatt tgatcatatg acaagatgtg tatctacctt aacttaatga   300
ttttgataaa aatcattagg tacggccgcg gtgccagggc gtgcccttgg gctccccggg   360
cgcgaatgca tactagtaac atttctctgg cctaactggc cggtaccatg acccacgtga   420
tgctgagaag tactcctgcc ctaggaagag actcagggca gagggaggaa ggacagcaga   480
ccagacagtc acagcagcct tgacaaaacg ttcctggaac taccggtcga cgctagc      537

SEQ ID NO: 282         moltype = DNA  length = 613
FEATURE                Location/Qualifiers
source                 1..613
                       mol_type = other DNA
                       organism = synthetic construct
SEQUENCE: 282
aattttattg ttcaaacatg agagcttagt acgtgaaaca tgagagctta gtacgttagc    60
catgagagct tagtacgtta gccatgaggg tttagttcgt taaacatgag agcttagtac   120
gttaaacatg agagcttagt acgtactatc aacaggttga actgctgatc cacgttgtgg   180
tagaattggt aaagagagtc gtgtaaaata tcgagttcgc acatcttgtt gtctgattat   240
tgattttggg cgaaaccatt tgatcatatg acaagatgtg tatctacctt aacttaatga   300
ttttgataaa aatcattagg tacggccgcg gtgccagggc gtgcccttgg gctccccggg   360
cgcgaatgca tactagtaac atttctctgg cctaactggc cggtaccagt ggtggggag    420
tgaaaagaga gatggagaaa gaggggatgg gcagaaagag gaggaggagt caggggcagg   480
gcatggaggt gggtggggct gggctgccaa agcaggataa atgcacacct gcctgctggt   540
ctgggctccc tgcctcgggc tctcaccctc ctctcctgca gctccagctt tgtgctctcc   600
ggtcgacgct agc                                                       613

SEQ ID NO: 283         moltype = DNA  length = 588
FEATURE                Location/Qualifiers
source                 1..588
                       mol_type = other DNA
                       organism = synthetic construct
SEQUENCE: 283
aattttattg ttcaaacatg agagcttagt acgtgaaaca tgagagctta gtacgttagc    60
catgagagct tagtacgtta gccatgaggg tttagttcgt taaacatgag agcttagtac   120
gttaaacatg agagcttagt acgtactatc aacaggttga actgctgatc cacgttgtgg   180
tagaattggt aaagagagtc gtgtaaaata tcgagttcgc acatcttgtt gtctgattat   240
tgattttggg cgaaaccatt tgatcatatg acaagatgtg tatctacctt aacttaatga   300
ttttgataaa aatcattagg tacggccgcg gtgccagggc gtgcccttgg gctccccggg   360
cgcgaatgca tactagtaac atttctctgg cctaactggc cggtaccggg aaaagttcag   420
ctgagagata taaaagagca gtctttccag cacctgcaaa tccagagcgg cgggcactga   480
cgggcacttg caccgtgtgg acagactctc cggttctgtg agtggttttt ctttccccgg   540
gtcggacctg gagttcttag ggggatggct gaaccggtcg acgctagc                588

SEQ ID NO: 284         moltype = DNA  length = 673
FEATURE                Location/Qualifiers
source                 1..673
                       mol_type = other DNA
                       organism = synthetic construct
SEQUENCE: 284
aattttattg ttcaaacatg agagcttagt acgtgaaaca tgagagctta gtacgttagc    60
catgagagct tagtacgtta gccatgaggg tttagttcgt taaacatgag agcttagtac   120
gttaaacatg agagcttagt acgtactatc aacaggttga actgctgatc cacgttgtgg   180
tagaattggt aaagagagtc gtgtaaaata tcgagttcgc acatcttgtt gtctgattat   240
tgattttggg cgaaaccatt tgatcatatg acaagatgtg tatctacctt aacttaatga   300
ttttgataaa aatcattagg tacggccgcg gtgccagggc gtgcccttgg gctccccggg   360
cgcaatgcat actagtaaca tttctctggc ctaactggcg gtaccggcc cgccccttt     420
ccttacgcgg attggtagct gcaggcttcc ctatctgatt ggccgaacga acgcagcgcg   480
```

-continued

```
taatttaaaa tattgtatct gtaacaaagc tgcacctcgt gggcggagtt gtgctctgcg    540
gctgcgaaag tccagcttcg gcgactaggt gtgagtaagc cagtatccca ggaggagcaa    600
gtggcacgtc ttcgggtgag tgtgcggctg tgctggagcc cgggttacca gctcttaacc    660
ggtcgacgct agc                                                       673

SEQ ID NO: 285              moltype = DNA   length = 2615
FEATURE                     Location/Qualifiers
source                      1..2615
                            mol_type = other DNA
                            organism = synthetic construct
SEQUENCE: 285
gagagcaact gcataaggct atgaagagat acgccctggt tcctggaaca attgctttta    60
cagatgcaca tatcgaggtg gacatcactt acgctgagta cttcgaaatg tccgttcggt    120
tggcagaagc tatgaaacga tatgggctga atacaaatca cagaatcgtc gtatgcagtg    180
aaaactctct tcaattcttt atgccggtgt gggcgcgtt atttatcgga gttgcagttg     240
cgcccgcgaa cgacatttat aatgaacgtg aattgctcaa cagtatgggc atttcgcagc    300
ctaccgtggt gttcgtttcc aaaaagggg tgcaaaaaat tttgaacgtg caaaaaaagc     360
tcccaatcat ccaaaaaatt attatcatgg attctaaaac ggattaccag ggatttcaat    420
cgatgtacac gttcgtcaca tctcatctac ctccccggttt taatgaatac gattttgtgc    480
cagagtcctt cgatagggac aagacaattg cactgatcat gaactcctct ggatctactg    540
gtctgcctaa aggtgtcgct ctgcctcata gaactgcctg cgtgagattc tcgcatgcca    600
gagatcctat ttttggcaat caaatcattc cggatactgc gattttaagt gttgttccat    660
tccatcacgg ttttggaatg tttactacac tcggatattt gatatgtgga tttcgagtcg    720
tcttaatgta tagatttgaa gaagagctgt ttctgaggag ccttcaggat tacaagattc    780
aaagtgcgct gctggtgcca accctattct ccttcttcgc caaaagcact ctgattgaca    840
aatacgattt atctaattta cacgaaattg cttctggtgg cgttccccctc tctaaggaag    900
tcggggaagc ggttgccaag aggttccatc tgccaggtat caggcaagga tatgggctca    960
ctgagactac atcagctatt ctgattacac ccgaggggga tgataaaccg ggcgcggtcg   1020
gtaaagttgt tccattttt gaagcgaagg ttgtggatct ggataccggg aaaacgctgg    1080
gcgttaatca aagaggcgaa ctgtgtgtga gaggtcctat gattatgtcc ggttatgtaa   1140
acaatccgga agcgaccaac gccttgattg acaaggatgg atggctacat tctggagaca   1200
tagcttactg ggacgaagac gaacacttct tcatcgttga ccgcctgaag tctctgatta   1260
agtacaaagg ctatcaggtg gctcccgctg aattggaatc catcttgctc caacacccca   1320
acatcttcga cgcaggtgtc gcaggtcttc ccgacgatga cgccggtgaa cttcccgccg   1380
ccgttgttgt tttggagcac ggaaagacga tgacggaaaa agagatcgtg gattacgtcg   1440
ccagtcaagt aacaaccgcg aaaaagttgc gcggaggagt tgtgtttgtg gacgaagtac   1500
cgaaaggtct taccggaaaa ctcgacgcaa gaaaaatcag agagatcctc ataaaggcca   1560
agaagggcgg aaagatcgcc gtgtaatgaa tgcatgaatt cctgtgcctt ctagttgcca   1620
gccatctgtt gtttgcccct ccccgtgcc ttccttgacc ctggaaggtg ccactcccac    1680
tgtcctttcc taataaaatg aggaaattgc atcgcattgt ctgagtaggt gtcattctat    1740
tctgggggt ggggtggggc aggacagcaa ggggggaggat tgggaagaca atagcaggca    1800
tgctggggat gcggtgggct ctatggcccg ggacggccgc tagcccgcct aatgagcggg    1860
cttttttttg gcttgttgtc cacaaccgtt aaaccttaaa agctttaaaa gccttatata   1920
ttcttttttt tcttataaaa cttaaaacct tagaggctat ttaagttgct gatttatatt   1980
aatttttattg ttcaaacatg agagcttagt acgtgaaaca tgagagctta gtacgttagc   2040
catgagagct tagtacgtta gccatgaggg tttagttcgt taaacatgag agcttagtac    2100
gttaaacatg agagcttagt acgtactatc aacaggttga acatgctgatc cacgttgtgg   2160
tagaattggt aaagagagtc gtgtaaaata tcgagttcgc acatcttgtt gtctgattat    2220
tgatttttgg cgaaaccatt tgatcatatg acaagatgtg tatctacctt aacttaatga    2280
ttttgataaa aatcattagg tacggccgcg gtgccagggc gtgcccttgg gctccccggg    2340
cgcgactagt aacatttctc tggcctaact ggccggtacc acatcggcta tgctgctgct    2400
aatgccacgt caccacatcg acatgccacg tcaccatcat gccatgccac gtcaccactg    2460
caagatgcca cgtcaccaca gtataatgcc acgtcaccaa gttactatgc cacgtcacca    2520
ggtacctgcg ctcccgacat gccccgcggc gcgccattaa ccgccagatt tgagtcgcgg   2580
gacccgttcg cagaggtgga ccggtcgacg ctagc                              2615

SEQ ID NO: 286              moltype = DNA   length = 14
FEATURE                     Location/Qualifiers
source                      1..14
                            mol_type = other DNA
                            organism = synthetic construct
SEQUENCE: 286
ttttggcgcc cttt                                                       14

SEQ ID NO: 287              moltype = DNA   length = 11
FEATURE                     Location/Qualifiers
source                      1..11
                            mol_type = other DNA
                            organism = synthetic construct
SEQUENCE: 287
tcctttgatt t                                                          11

SEQ ID NO: 288              moltype = DNA   length = 17
FEATURE                     Location/Qualifiers
source                      1..17
                            mol_type = other DNA
                            organism = synthetic construct
SEQUENCE: 288
tgaacaggat taatgta                                                    17
```

```
SEQ ID NO: 289          moltype = DNA  length = 1809
FEATURE                 Location/Qualifiers
source                  1..1809
                        mol_type = other DNA
                        organism = synthetic construct
SEQUENCE: 289
cgttgtggta gaattggtaa agagagtcgt gtaaaatatc gagttcgcac atcttgttgt   60
ctgattattg attttggcg aaaccatttg atcatatgac aagatgtgta tctaccttaa   120
cttaatgatt ttgataaaaa tcattaggta ccactagtta ttaatagtaa tcaattacgg   180
ggtcattagt tcatagccca tatatggagt tccgcgttac ataacttacg gtaaatggcc   240
cgccttgacc gcccaacgac ccccgcccat tgacgtcaat aatgacgtat gttcccatag   300
taacgccaat agggactttc cattgacgtc aatgggtgga gtatttacgg taaactgccc   360
acttggcagt acatcaagtg tatcatatgc caagtacgcc ccctattgac gtcaatgacg   420
gtaaatggcc cgcctggcat tatgcccagt acatgacctt atgggacttt cctacttggc   480
agtacatcta cgtattagtc atcgctatta ccatggtgat gcggttttgg cagtacatca   540
atgggcgtgg atagcggttt gactcacggg gatttccaag tctccacccc attgacgtca   600
atgggagttt gttttggcac caaaatcaac gggactttcc aaaatgtcgt aacaactccg   660
ccccatggat ctcagattga attatttgcc tgtcatacag ctaataattg accataagac   720
aattagattt aaaattagtt tgaatctttc taataccaaa gttcagttta ctgttccatg   780
ttgcttctga gtggcttcac agacttatga aaaagtaaac ggaatcagaa ttacatcaat   840
gcaaaagcat tgctgtgaac tctgtactta ggactaaact ttgagcaata acacatatag   900
attgaggatt gtttgctgtt agtatacaaa ctctggttca aagctcctct ttattgcttg   960
tcttggaaaa tttgctgttc ttcatggttt ctcttttcac tgctatctat ttttctcaac  1020
cactcacatg gctacaataa ctgtctgcaa gcttatgatt cccaaatatc tatctctagc  1080
ctcaatcttg ttccagaaga taaaaagtag tattcaaatg cacatcaacg tctccacttg  1140
gagggcttaa agacgtttca acatacaaac cggggagttt tgcctggaat gtttcctaaa  1200
atgtgtcctg tagcacatag ggtcctcttg ttccttaaaa tctaattact tttagcccag  1260
tgctcatccc acctatgggg agatgagagt gaaaagggag cctgattaat aattacacta  1320
agtcaatagg catagagcca ggactgtttg ggtaaactgg tcactttatc ttaaactaaa  1380
tatatccaaa actgaacatg tacttagtta ctaagtcttt gacttatct cattcatacc  1440
actcagcttt atccaggcca cttatttgac agtattattg cgaaaacttc ctactagtgt  1500
catctctttg aatattctgt agtttgagga gaatatttgt tatattgcac aataaaataa  1560
gtttgcaagt ttttttttc tgccccaaag agctctgtgt ccttgaacat aaaatacaaa  1620
taaccgctat gctgttaatt attaacaaat gtcccatttt caacctaagg aaataccata  1680
aagtaacaga tataccaaca aaaggttaat aattaacagg cattgcctga aaagagtata  1740
aaaggctttc agcatgattt tccatattgt gcttccacca ctgccaataa caaaccggtc  1800
gacgctagc                                                          1809

SEQ ID NO: 290          moltype = DNA  length = 3243
FEATURE                 Location/Qualifiers
source                  1..3243
                        mol_type = other DNA
                        organism = synthetic construct
SEQUENCE: 290
actggtctgc ctaaaggtgt cgctctgcct catagaactg cctgcgtgag attctcgcat   60
gccagagatc ctatttttgg caatcaaatc attccggata ctgcgatttt aagtgttgtt   120
ccattccatc acggttttgg aatgtttact acactcggat atttgatatg tggatttcga   180
gtcgtcttaa tgtatagatt tgaagaagag ctgtttctga ggagccttca ggattacaag   240
attcaaagtc cgctgctggt gccaacccta ttctccttct tcgccaaaag cactctgatt   300
gacaaatacg atttatctaa tttacacgaa attgcttctg gtggcgctcc cctctctaag   360
gaagtcgggg aagcggttgc caagaggttc catctgccag gtatcaggca aggatatggg   420
ctcactgaga ctacatcagc tattctgatt acacccgagg gggatgataa accgggcgcg   480
gtcggtaaag ttgttccatt ttttgaagcg aaggttgtgg atctggatac cgggaaaacg   540
ctgggcgtta atcaaagagg cgaactgtgt gtgagaggtc ctatgattat gtccggttat   600
gtaaacaatc cggaagcgac caacgccttg attgacaagg atggatggct acattctgga   660
gacatagctt actgggacga agacgaacac ttcttcatcg ttgaccgcct gaagtctctg   720
attaagtaca aaggctatca ggtggctccc gctgaattgg aatccatctt gctccaacac   780
cccaacatct tcgacgcagg tgtcgcaggt cttcccgacg atgacgccgg tgaacttccc   840
gccgccgttg ttgttttgga gcacggaaag acgatgacgg aaaaagagat cgtggattac   900
gtcgccagtc aagtaacaac cgcgaaaaag ttgcgcggag gagttgtgtt gtgtgacgaa   960
gtaccgaaag gtcttaccgg aaaactcgac gcaagaaaaa tcagagagat cctcataaag  1020
gccaagaagg gcggaaagat cgccgtgtaa tgaatgcatg aattcctgtg ccttctagtt  1080
gccagccatc tgttgtttgc ccctcccccg tgccttcctt gaccctggaa ggtgccactc  1140
ccactgtcct ttcctaataa aatgaggaaa ttgcatcgca ttgtctgagt aggtgtcatt  1200
ctattctggg gggtggggtg gggcaggaca gcaaggggga ggattgggaa gacaatagca  1260
ggcatgctgg ggatgcggtg ggctctatgg cccgggacgg ccgctagccc gcctaatgag  1320
cgggcttttt tttggcttgt tgtccacaac cgttaaacct taaaagcttt aaaagcctta  1380
tatattcttt tttttcttat aaaacttaaa accttagagg ctatttaagt tgctgattta  1440
tattaatttt attgttcaaa catgagagct tagtacgtga aacatgagag cttagtacgt  1500
tagccatgag agcttagtac gttagccatg agggtttagt tcgtaaaaca tgagagctta  1560
gtacgttaaa catgagagct tagtacgtac tatcaacagg ttgaactgct gatccacgtt  1620
gtggtagaat tggtaaagag agtcgtgtaa aatatcgagt tcgcacatct tgttgtctga  1680
ttattggcaaac catttgatca tatgacaaga tgtgtatcta ccttaactaa  1740
atgatttgga taaaaatcat taggtacggc cgcggtgcca gggcgtgccc ttgggctccc  1800
cgggcgcgac tagtaacatt tctctggcct aactggccgg tacctgccac tcaaagtggc  1860
acactccctg ctcaggaggc cgggaggag gacacagccc tggcaactcc tctgccccgg  1920
ggggtcagga agggggtcacc ccacactcca gaaccctaca gaatgtggcc ttggctttttc  1980
ccatcaagag ctggggaaag ccaggccccg acttcattac cccctgcccc cgtcccatgc  2040
```

```
tcagtgggcc ccatcgtggg tccatgccac actcccaact gagcagcccc gcagcccgc     2100
gtgtcacaga catggggcct cctaattgct gctgaggtcc caatccctgg ctggacgtgc    2160
ctgatggaag agccagctct ggtctcaggg ggctggtttg caggagtctc cacagacctg    2220
gctccagctt tgtgtcttca aatgaatacc cggccaagat tgcaactaaa ttaccagaaa    2280
cacttaggtt tcctcacaga ctccacaaca gggatggaga aggaagtcag ctgacgaggt    2340
tacgacgctg ttcgagggag tctttcttgg gtcacaagtg gtaaactgtg ttccctgaac    2400
aaaaccagga agctttcagt gtttattgta tgtactaagt ggagggaggg gcttcagatt    2460
ctgataaaaa tatctcccca ttcccagtgc ccaatgtgac atgaatagga gggcccctcc    2520
ctgaattccc aagcagatct ccagagacag cttcagagag cagggagccc acggtggctg    2580
gggctttagg gactttctgg gttgtgggga ggctagaggc tgggcagtcc cagcaggatt    2640
tggcctctag ggaccgggca ctgtagggct caggagagca gctgccgtcc cagtatataa    2700
gcataggtgg aattatctgg aaacatattt ctgcgtttca caggcagaga aatcagtcta    2760
tccctaaaga atggaagagc tacagtagca gacctaccac cctccaccct cccacaggca    2820
aaagcccctg agattcaggt ttgggaagaa aaagaaaata tcccaaatat gtcatttgag    2880
aaagcagctg ctaaccacag gcggccccag cttttctcaa gatccaggat gtgggttcag    2940
tgcccttact agggcagtgg gggaggacgg tcagtaccag gaccccaggc acaggcctgg    3000
aggacttgct cccccaagca actcagatcc acgcagaacc catggtacca ctagtggtga    3060
ctcatgggtg actcatgggt gactcatggg tgactcatgg gtgactcatg ggtgactcat    3120
gggtgactca tgggtgactc atgggtgact catgtgcgct cccgacatgc ccgcggcgc     3180
gccattaacc gccagatttg agtcgcggga cccgttggca gaggtggacc ggtcgacgct    3240
agc                                                                  3243

SEQ ID NO: 291         moltype = DNA  length = 2602
FEATURE                Location/Qualifiers
source                 1..2602
                       mol_type = other DNA
                       organism = synthetic construct
SEQUENCE: 291
cgattttgtg ccagagtcct tcgataggga caagacaatt gcactgatca tgaactcctc     60
tggatctact ggtctgccta aaggtgtcgc tctgcctcat agaactgcct gcgtgagatt    120
ctcgcatgcc agagatccta ttttttggcaa tcaaatcatt ccggatactg cgattttaag   180
tgttgttcca ttccatcacg gttttggaat gtttactaca ctcggatatt tgatatgtgg    240
atttcgagtc gtcttaatgt atagatttga agaagagctg tttctgagga gccttcagga    300
ttacaagatt caaagtgcgc tgctggtgcc aaccctattc tccttcttcg ccaaaagcac    360
tctgattgac aaatacgatt tatctaattt acacgaaatt gcttctggtg gcgctcccct    420
ctctaaggaa gtcgggggaag cggttgccaa gaggttccat ctgccaggta tcaggcaagg   480
atatgggctc actgagacta catcagctat tctgattaca cccgaggggg atgataaacc    540
gggcgcggtc ggtaaagttg ttccattttt tgaagcgaag gttgtggatc tggataccgg    600
gaaaacgctg ggcgttaatc aaagagcga actgtgtggt agaggtccta tgattatgtc     660
cggttatgta aacaatccgg aagcgaccaa cgccttgatt gacaaggatg gatggctaca    720
ttctggagac atagcttact gggacgaaga cgaacacttc ttcatcgttg accgcctgaa    780
gtctctgatt aagtacaaag gctatcaggt ggctcccgct gaattggaat ccatcttgct    840
ccaacacccc aacatcttcg acgcaggtgt cgcaggtcat cccacgacatg acgccggtca   900
acttcccgcc gccgttgttg ttttggagca cggaaagacg atgacggaaa aagagatcgt    960
ggattacgtc gccagtcaag taacaaccgc gaaaaagttg cgcggaggag ttgtgtttgt   1020
ggacgaagta ccgaaaggtc ttaccggaaa actcgacgca agaaaaatca gagagatcct   1080
cataaaggcc aagaagggcg gaaagatcgc cgtgtaatga atgcatgaat tcctgtgcct   1140
tctagttgcc agccatctgt tgtttgcccc tccccgtgc cttccttgac cctggaaggt    1200
gccactccca ctgtcctttc ctaataaaat gaggaaattg catcgcattg tctgagtagg   1260
tgtcattcta ttctgggggg tggggtgggg caggacagca aggggagga ttgggaagac    1320
aatagcaggc atgctgggga tgcggtgggc tctatggccc gggacggccg ctagcccgcc   1380
taatgagcgg gcttttttt ggcttgttgt ccacaaccgt taaaccttaa aagctttaaa    1440
agccttatat attcttttt ttcttataaa acttaaaacc ttagaggcta tttaagttgc    1500
tgatttatat taatttttatt gttcaaacat gagagcttag tacgtgaaac atgagagctt   1560
agtacgttag ccatgagagc ttagtacgtt agccatgaggc gtttagttcg ttaaacatga   1620
gagcttagta cgttaaacat gagagcttag tacgtactat caacaggttg aactgctgat   1680
ccacgttgtg gtagaattgg taaagagagt cgtgtaaaat atcgagttcg cacatcttgt   1740
tgtctgatta ttgatttttg gcgaaaccat ttgatcatat gacaagatgt gtatctacct   1800
taacttaatg attttgataa aaatcattag gtacggccgc ggtgccaggg cgtgcccttg   1860
ggctccccgg gcgcgactag tcttctgccc tgagaaagac ctatgattgc atgacacaaa   1920
agagactgtt caaagggaca ccatcattca gcagggcaag cctccttgct ggggggcaacc  1980
tggtagctcc tgagcctccc tcatcttcac tgagcccctc caactctctg agttccatg    2040
cccctcactg aacctccctt cccccatggc gagcctccgc cagcaccttt gcacacactc   2100
agcccccttcc ccctactgag cccagcaca gtcactgaac agctcttctt ccctctgac    2160
tgagtcatcc tcccaagccc tcccccttccc ctcactgagt ctccaccacc cctggtcact  2220
gggcaccctg cttctgacct cctccctccc ccaacccctc caccttcct cttcactgag    2280
cctggcgcct ctcacccacc cgccttcctc tcccagccgc ttctgagctg cctcttttgga  2340
gcccaactgt ctcgcccacg agtccccatc actcagtcct actcactcta agacacctga   2400
aagcagttag agaacatgtg ttcatggggg gaggatgagg tctatcatc atcctgcaaa    2460
ctagtgtccc cacccacaca ttcctgtccc cacccacaca ttcctgtccc cacccacaca   2520
ttcctgtccc cacccacaca ttcctgtccc cacccacaca ttcctgtccc cacccacaca   2580
ttcctgaccg gtcgacgcta gc                                            2602

SEQ ID NO: 292         moltype = DNA  length = 2543
FEATURE                Location/Qualifiers
source                 1..2543
                       mol_type = other DNA
                       organism = synthetic construct
SEQUENCE: 292
```

```
cgattttgtg ccagagtcct tcgatatggga caagacaatt gcactgatca tgaactcctc  60
tggatctact ggtctgccta aaggtgtcgc tctgcctcat agaactgcct gcgtgagatt  120
ctcgcatgcc agagatccta tttttggcaa tcaaatcatt ccggatactg cgattttaag  180
tgttgttcca ttccatcacg gttttggaat gtttactaca ctcggatatt tgatatgtgg  240
atttcgagtc gtcttaatgt atagatttga agaagagctg tttctgagga gccttcagga  300
ttacaagatt caaagtgcgc tgctggtgcc aaccctattc tccttcttcg ccaaaagcac  360
tctgattgac aaatacgatt tatctaattt acacgaaatt gcttctggtg gcgctcccct  420
ctctaaggaa gtcgggggaag cggttgccaa gaggttccat ctgccaggta tcaggcaagg  480
atatgggctc actgagacta catcagctat tctgattaca cccgagggggg atgataaacc  540
gggcgcggtc ggtaaagttg ttccatttt tgaagcgaag gttgtggatc tggataccgg  600
gaaaacgctg ggcgttaatc aaagaggcga actgtgtgtg agaggtccta tgattatgtc  660
cggttatgta aacaatccgg aagcgaccaa cgccttgatt gacaaggatg gatggctaca  720
ttctggagac atagcttact gggacgaaga cgaacacttc ttcatcgttg accgcctgaa  780
gtctctgatt aagtacaaag gctatcaggt ggctcccgct gaattggaat ccatcttgct  840
ccaacacccc aacatcttcg acgcaggtgt cgcaggtctt cccgacgatg acgccggtga  900
acttcccgcc gccgttgttg tttttggagca cggaaagacg atgacggaaa aagagatcgt  960
ggattacgtc gccagtcaag taacaaccgc gaaaaagttg cgcggaggag ttgtgtttgt  1020
ggacgaagtc ccgaaaggtc ttaccggaaa actcgacgca agaaaaatca gagagatcct  1080
cataaaggcc aagaagggcg gaaagatcgc cgtgtaatga atgcatgaat cctgtgtcct  1140
tctagttgcc agccatctgt tgtttgcccc tccccccgtgc cttccttgac cctgaaggt  1200
gccactccca ctgtcctttc ctaataaaat gaggaaattg catcgcattg tctgagtagg  1260
tgtcattcta ttctgggggg tggggtgggg caggacagca aggggggagga ttgggaagac  1320
aatagcaggc atgctgggga tgcggtgggc tctatggccc gggacggccg ctagcccgcc  1380
taatgagcgg gctttttttt ggcttgttgt ccacaaccgt taaaccttaa aagctttaaa  1440
agccttatat attctttttt ttcttataaa acttaaaacc ttagaggcta tttaagttgc  1500
tgatttatat taattttatt gttcaaacat gagagcttag tacgtgaaac atgagagctt  1560
agtacgttag ccatgagagc ttagtacgtt agccatgagg gtttagttcg ttaaacatga  1620
gagcttagta cgttaaacat gagagcttag tacgtactat caacaggttg aactgctgat  1680
ccacgttgtg gtagaattgg taaagagagt cgtgtaaaat atcgagttcg cacatcttgt  1740
tgtctgatta ttgatttttg gcgaaaccat ttgatcatat gacaagatgt gtatctacct  1800
taacttaatg attttgataa aaatcattag gtacggccgc ggtgccaggg cgtgcccttg  1860
ggctccccgg gcgcgactag tgaacataca cacctgtggg ggtgtctaag gggctcccag  1920
ggagttctgg ggggtcctgg ggagcaggac cctcttcact ccctcctcca ggggaagtgg  1980
ccctgggggca ccccaggctg ttcccccagc tctgtggggc cgaagccatc cacaggggggc  2040
tttccccacc ggatgtggtg cgggccgtgg ttaatctcac ttgagttagt caccaggac  2100
aaacagctaa ccgacacaat tcctcccaag tccaggggggc cggaggcggg gtcagcacct  2160
ggcggcagga gacagtgctg ccctgggatg tggccgggcc tccctccatt cccaatcctg  2220
ttgtctctgt ggcaatacct ggctgggagc tcctatcagg cccgtgaccc ccgcccttc  2280
tccagtgccc tcctgtctgc attcacctgt cagatcccgg ggagagaggg gcactggcgg  2340
ccgcccagga ccagagctgt ggggcctccc gcaccagagt gcagtgaagg tttgtgggct  2400
gctagtgtcc ccacccacac attcctgtcc ccacccacac attcctgtcc ccacccacac  2460
attcctgtcc ccacccacac attcctgtcc ccacccacac attcctgtcc ccacccacac  2520
attcctgacc ggtcgacgct agc                                          2543
```

```
SEQ ID NO: 293          moltype = DNA  length = 2585
FEATURE                 Location/Qualifiers
source                  1..2585
                        mol_type = other DNA
                        organism = synthetic construct
SEQUENCE: 293
gagagcaact gcataaggct atgaagagat acgccctggt tcctggaaca attgctttta  60
cagatgcaca tatcgaggtg gacatcactt acgctgagta cttcgaaatg tccgttcggt  120
tggcagaagc tatgaaacga tatgggctga atacaaatca cagaatcgtc gtatgcagtg  180
aaaactctct tcaattcttt atgccggtgt tgggcgcgtt atttatcgga gttgcagttg  240
cgcccgcgaa cgacatttat aatgaacgtg aattgctcaa cagtatgggc atttcgcagc  300
ctaccgtggt gttcgtttcc aaaaagggggg tgcaaaaaat tttgaacgtg caaaaaaagc  360
tcccaatcat ccaaaaaatt attatcatgg attctaaaac ggattaccag ggatttcagt  420
cgatgtacac gttcgtcaca tctcatctac ctcccggttt taatgaatac gattttgtgc  480
cagagtcctt cgatagggac aagacaattg cactgatcat gaactcctct ggatctactg  540
gtctgcctaa aggtgtcgct ctgcctcata gaactgcctg cgtgagattc tcgcatgcca  600
gagatcctat ttttggcaat caaatcattc ggatactgc gattttaagt gttgttccat  660
tccatcacgg ttttggaatg tttactacac tcggatattt gatatgtgga tttcgagtcg  720
tcttaatgta tagatttgaa gaagagctgt ttctgaggag ccttcaggat tacaagattc  780
aaagtgcgct gctggtgcca acccctattct ccttcttcgc caaaagcact ctgattgaca  840
aatacgattt atctaattta cacgaaattg cttctggtgg cgctcccctc tctaaggaag  900
tcgggggaagc ggttgccaag aggttccatc tgccaggtat caggcaagga tatgggctca  960
ctgagactac atcagctatt ctgattacac ccgaggggga tgataaaccg gcgcggtcg  1020
gtaaagttgt tccatttttt gaagcgaagg ttgtggatct ggataccggg aaaacgctgg  1080
gcgttaatca aagaggcgaa ctgtgtgtga gaggtcctat gattatgtcc ggttatgtaa  1140
acaatccgga agcgaccaac gccttgattg acaaggatgg atggctacat ctggagacaa  1200
tagcttactg ggacgaagac gaacacttct tcatcgttga ccgcctgaag tctctgatta  1260
agtacaaagg ctatcaggtg gctcccgctg aattggaatc catcttgctc caacacccca  1320
acatcttcga cgcaggtgtc gcaggtcttc ccgacgatga cgccggtgaa cttcccgccg  1380
ccgttgttgt ttttggagca cggaaagacg atgacggaaa aagagatcgt gattacgtcg  1440
ccagtcaagt aacaaccgcg aaaaagttgc gcggaggagt tgtgtttgtg acgaagtac  1500
cgaaaggtct taccggaaaa ctcgacgcaa gaaaaatcag agagatcctc ataaaggcca  1560
agaagggcgg aaagatcgcc gtgtaatgaa tgcatgaatc ctgtgtcctt ctagttgcca  1620
gccatctgtt gtttgcccct ccccccgtgcc ttccttgacc ctgaaggtg ccactcccac  1680
tgtcctttcc taataaaatg aggaaattgc atcgcattgt ctgagtaggt gtcattctat  1740
```

-continued

```
tctgggggt ggggtggggc aggacagcaa gggggaggat tgggaagaca atagcaggca   1800
tgctgggggat gcggtgggct ctatggcccg ggacggccgc tagcccgcct aatgagcggg   1860
cttttttttg gcttgttgtc cacaaccgtt aaaccttaaa agctttaaaa gccttatata   1920
ttctttttttt tcttataaaa cttaaaacct tagaggctat ttaagttgct gatttatatt   1980
aattttattg ttcaaacatg agagcttagt acgtgaaaca tgagagctta gtacgtgaaa   2040
catgagagct tagtacgtta gccatgagag cttagtacgt tagccatgag ggtttagttc   2100
gttaaacatg agagcttagt acgttaaaca tgagagctta gtacgtacta tcaacaggtt   2160
gaactgctga tccacgttgt ggtagaattg gtaaagagag tcgtgtaaaa tatcgagttc   2220
gcacatcttg ttgtctgatt attgattttt ggcgaaacca tttgatcata tgacaagatg   2280
tgtatctacc ttaacttaat gattttgata aaaatcatta ggtacggccg cggtgccagg   2340
gcgtgcccctt gggctccccg ggcgcgacta gtaacatttc tctggcctaa ctggccggta   2400
ccactagtac cggaagtaag aaccggaagt atcgaccgga agtagacacc ggaagtacta   2460
accggaagta actaccggaa gtatgcaccg gaagtatgcg ctcccgacat gccccgcggc   2520
gcgccattaa ccgccagatt tgagtcgcgg gaccgttgg cagaggtgga ccggtcgacg   2580
ctagc                                                                2585
```

```
SEQ ID NO: 294          moltype = DNA   length = 14
FEATURE                 Location/Qualifiers
source                  1..14
                        mol_type = other DNA
                        organism = synthetic construct
SEQUENCE: 294
atgccacgta atca                                                      14
```

```
SEQ ID NO: 295          moltype = DNA   length = 12
FEATURE                 Location/Qualifiers
source                  1..12
                        mol_type = other DNA
                        organism = synthetic construct
SEQUENCE: 295
gagaacaaag aa                                                        12
```

```
SEQ ID NO: 296          moltype = DNA   length = 10
FEATURE                 Location/Qualifiers
source                  1..10
                        mol_type = other DNA
                        organism = synthetic construct
SEQUENCE: 296
atcggaagtg                                                           10
```

```
SEQ ID NO: 297          moltype = DNA   length = 11
FEATURE                 Location/Qualifiers
source                  1..11
                        mol_type = other DNA
                        organism = synthetic construct
SEQUENCE: 297
gggtgactca t                                                         11
```

```
SEQ ID NO: 298          moltype = DNA   length = 12
FEATURE                 Location/Qualifiers
source                  1..12
                        mol_type = other DNA
                        organism = synthetic construct
SEQUENCE: 298
gcgaccaccg aa                                                        12
```

```
SEQ ID NO: 299          moltype = DNA   length = 11
FEATURE                 Location/Qualifiers
source                  1..11
                        mol_type = other DNA
                        organism = synthetic construct
SEQUENCE: 299
gaaatctgag c                                                         11
```

```
SEQ ID NO: 300          moltype = DNA   length = 11
FEATURE                 Location/Qualifiers
source                  1..11
                        mol_type = other DNA
                        organism = synthetic construct
SEQUENCE: 300
tcctttgatg t                                                         11
```

```
SEQ ID NO: 301          moltype = DNA   length = 924
FEATURE                 Location/Qualifiers
source                  1..924
                        mol_type = other DNA
                        organism = synthetic construct
SEQUENCE: 301
tcaaacatga gagcttagta cgtgaaacat gagagcttag tacgttagcc atgagagctt   60
```

-continued

```
agtacgttag ccatgagagc ttagtacgtt agccatgagg gtttagttcg ttaaacatga   120
gagcttagta cgttaaacat gagagcttag tacgtactat caacaggttg aactgctgat   180
ccacgttgtg gtagaattgg taaagagagt cgtgtaaaat atcgagttcg cacatcttgt   240
tgtctgatta ttgatttttg gcgaaaccat ttgatcatat gacaagatgt gtatctacct   300
taacttaatg attttgataa aaatcattag gtacggccgc ggtgccaggg cgtgcccttg   360
ggctccccgg gcgcgaatgc atactagtaa catttctctg gcctaactgg ccggtaccga   420
tcttgatatc ctcgaggcta gcatgatcac catgagtcac ccatgagtca cccatgagtc   480
acccatgagt cacccatgag tcacccatga gtcacccatg agtcacccat gagtcaccca   540
tgagtcacca ctagtggtac cacctcttaa caatacgttt cacaaatagt taaaaacatg   600
catactgaaa agcatacttt tgcaatgtta tttttaaaaa caaggaactc tttaacccag   660
ggaagataat cacttgggga aaggaaggtt cgtttctgag ttagcaacaa gtaaatgcag   720
cactagtggg tgggattgag gtgtgccctg gtgcataaat agagactcag ctgtgctggc   780
acactcagaa gcttggaccg catcctagcc gccgactcac acaaggcagg tgggtgagga   840
aatccaggta aggctcctga cagcagcttt agaagggtac ttgctggagt gaattcgggc   900
ctctgattac cggtcgacgc tagc                                          924
```

SEQ ID NO: 302        moltype = DNA  length = 644
FEATURE               Location/Qualifiers
source                1..644
                      mol_type = other DNA
                      organism = synthetic construct
SEQUENCE: 302
```
aattttattg ttcaaacatg agagcttagt acgtgaaaca tgagagctta gtacgttagc   60
catgagagct tagtacgtta gccatgaggg tttagttcgt taaacatgag agcttagtac   120
gttaaacatg agagcttagt acgtactatc aacaggttga actgctgatc cacgttgtgg   180
tagaattggt aaagagagtc gtgtaaaata tcgagttcgc acatcttgtt gtctgattat   240
tgattttggg cgaaaccatt tgatcatatg acaagatgtg tatctacctt aacttaatga   300
ttttgataaa aatcattagg tacggccgcg gtgccagggc gtgcccttgg gctccccggg   360
cgcgaatgca tactagtggt gactcatggg tgactcatgg gtgactcatg ggtgactcat   420
gggtgactca tgggtgactc atgggtgact catgggtgac tcatggtga ctcatggtac   480
tcatgctagc ctcgaggata tcaagatcgg taccatgacc cacgtgatgc tgagaagtac   540
tcctgcccta ggaagagact cagggcagag ggaggaagga cagcagacca gacagtcaca   600
gcagccttga caaacgttc ctggaactac cggtcgacgc tagc                     644
```

SEQ ID NO: 303        moltype = DNA  length = 779
FEATURE               Location/Qualifiers
source                1..779
                      mol_type = other DNA
                      organism = synthetic construct
SEQUENCE: 303
```
aattttattg ttcaaacatg agagcttagt acgtgaaaca tgagagctta gtacgttagc   60
catgagagct tagtacgtta gccatgagag cttagtacgt tagccatgag ggtttagttc   120
gttaaacatg agagcttagt acgttaaaca tgagagctta gtacgtacta tcaacaggtt   180
gaactgctga tccacgttgt ggtagaattg gtaaagagag tcgtgtaaaa tatcgagttc   240
gcacatcttg ttgtctgatt attgattttt ggcgaaacca tttgatcata tgacaagatg   300
tgtatctacc ttaacttaat gattttgata aaaatcatta ggtacggccg cggtgccagg   360
gcgtgccctt gggctccccg ggcgcgaatg catactagtc acatttctct ggcctaactg   420
gccggtaccg atcttgatat cctcgaggct agcatgatca ccatgagtca cccatgagtc   480
acccatgagt cacccatgag tcacccatga gtcacccatg agtcacccat gagtcaccca   540
tgagtcaccc atgagtcacc actagtggta ccagtggtgg gggagtgaaa agagagatgg   600
agaaagaggg gatgggcaga aagaggagga ggagtcaggg gcaggacatg gaggtgggtg   660
gggctgggct gccaaagcag gataaatgca cacctgcctg ctggtctggg ctccctgcct   720
cgggctctca ccctcctctc ctgcagctcc agctttgtgc tctaccggtc gacgctagc    779
```

SEQ ID NO: 304        moltype = DNA  length = 724
FEATURE               Location/Qualifiers
source                1..724
                      mol_type = other DNA
                      organism = synthetic construct
SEQUENCE: 304
```
aattttattg ttcaaacatg agagcttagt acgtgaaaca tgagagctta gtacgttagc   60
catgagagct tagtacgtta gccatgaggg tttagttcgt taaacatgag agcttagtac   120
gttaaacatg agagcttagt acgtactatc aacaggttga actgctgatc cacgttgtgg   180
tagaattggt aaagagagtc gtgtaaaata tcgagttcgc acatcttgtt gtctgattat   240
tgattttggg cgaaaccatt tgatcatatg acaagatgtg tatctacctt aacttaatga   300
ttttgataaa aatcattagg tacggccgcg gtgccagggc gtgcccttgg gctccccggg   360
cgcgactagt aacatttctc tggcctaact ggccggtacc actagtggtg actcatgggt   420
gactcatggg tgactcatgg gtgactcatg ggtgactcat gggtgactca tgggtgactc   480
atgggtgact catggtgat catgctagcc tcgaggatat caagatcggt accgggaaaa   540
accgggaaaa gttcagctga gagatataaa agagcagtct ttccagcacc tgcaaatcca   600
gagcggcggg cactgacggg cacttgcacc gtgtggacag actctccggt tctgtgagtg   660
gttttttcttt tcccgggtcg gacctggagt tcttaggggg atggctgaac cggtcgacgc   720
tagc                                                                724
```

SEQ ID NO: 305        moltype = DNA  length = 1697
FEATURE               Location/Qualifiers
source                1..1697
                      mol_type = other DNA
                      organism = synthetic construct

```
SEQUENCE: 305
ataccgggaa aacgctgggc gttaatcaaa gaggcgaact gtgtgtgaga ggtcctatga  60
ttatgtccgg ttatgtaaac aatccggaag cgaccaacgc cttgattgac aaggatggat  120
ggctacattc tggagacata gcttactggg acgaagacga acacttcttc atcgttgacc  180
gcctgaagtc tctgattaag tacaaaggct atcaggtgtc tcccgctgaa ttggaatcca  240
tcttgctcca acaccccaac atcttcgacg caggtgtcgc aggtcttccc gacgatgacg  300
ccggtgaact tcccgccgcc gttgttgttt tggagcacgg aaagacgatg acggaaaaag  360
agatcgtgga ttacgtcgcc agtcaagtaa caaccgcgaa aaagttgcgc ggaggagttg  420
tgtttgtgga cgaagtaccg aaaggtctta ccggaaaact cgacgcaaga aaaatcagag  480
agatcctcat aaaggccaag aagg9cggaa agatcgccgt gtaatgaatg catgaattcc  540
tgtgccttct agttgccagc catctgttgt ttgcccctcc cccgtgcctt ccttgaccct  600
ggaaggtgcc actcccactg tcctttccta ataaaatgag gaaattgcat cgcattgtct  660
gagtaggtgt cattctattc tggggggtgg ggtggggcag gacagcaagg gggaggattg  720
ggaagacaat agcaggcatg ctggggatgc ggtgggctc atggcccggc acggccgcta  780
gcccgcctaa tgagcgggct ttttttttggc ttgttgtcca caaccgttaa accttaaaag  840
ctttaaaagc cttatatatt cttttttttc ttataaaact taaaaccttag gaggctattt  900
aagttgctga tttatattaa ttttattgtt caaacatgag agcttagtac gtgaaacatg  960
agagcttagt acgttagcca tgagagctta gtacgttagc catgagggtt tagttcgtta  1020
aacatgagag cttagtacgt taaacatgag agcttagtac gtactatcaa caggttgaac  1080
tgctgatcca cgttgtggta gaattggtaa agagagtcgt gtaaaatatc gagttcgcac  1140
atcttgttgt ctgattattg attttttggcg aaaccatttg atcatatgac aagatgtgta  1200
tctaccttaa cttaatgatt ttgataaaaa tcattaggta ggccgcgcgt gccagggcgt  1260
gcccttgggc tccccgggcg cgaatgcata ctagtggtga ctcatgggtg actcatgggt  1320
gactcatggg tgactcatgg gtgactcatg ggtgactcat gggtgactca tgggtgactc  1380
atgggtgact catggtgatc atgctagcct cgaggatatc aagatcggta ccggcccgcc  1440
cccttttccctt acgcggattg gtagctgcag gcttccctat ctgattggcc gaacgaacgc  1500
agcgcgtaat ttaaaatatt gtatctgtaa caaagctgca cctcgtgggc ggagttgtgc  1560
tctgcggctg cgaaagtcca gcttcggcga ctaggtgtga gtaagccagt atcccaggag  1620
gagcaagtgg cacgtcttcg ggtgagtgtg cggctgtgct ggagcccggg ttaccagctc  1680
ttccggtcga cgctagc  1697

SEQ ID NO: 306       moltype = DNA   length = 11
FEATURE              Location/Qualifiers
source               1..11
                     mol_type = other DNA
                     organism = synthetic construct
SEQUENCE: 306
tacttggcat a  11

SEQ ID NO: 307       moltype = DNA   length = 11
FEATURE              Location/Qualifiers
source               1..11
                     mol_type = other DNA
                     organism = synthetic construct
SEQUENCE: 307
ggatgactca c  11

SEQ ID NO: 308       moltype = DNA   length = 11
FEATURE              Location/Qualifiers
source               1..11
                     mol_type = other DNA
                     organism = synthetic construct
SEQUENCE: 308
ttctaatctc t  11

SEQ ID NO: 309       moltype = DNA   length = 11
FEATURE              Location/Qualifiers
source               1..11
                     mol_type = other DNA
                     organism = synthetic construct
SEQUENCE: 309
gggtgactca c  11

SEQ ID NO: 310       moltype = DNA   length = 1128
FEATURE              Location/Qualifiers
source               1..1128
                     mol_type = other DNA
                     organism = synthetic construct
SEQUENCE: 310
cttataaaac ttaaaacctt agaggctatt taagttgctg atttatatta attttattgt  60
tcaaacatga gagcttagta cgtgaaacat gagagcttag tacgttagcc atgagagctt  120
agtacgttag ccatgagagc ttagtacgtt agccatgagg gtttagttcg ttaaacatga  180
gagcttagta cgtaaacat gagagcttag tacgtactat caacaggttg aactgctgat  240
ccacgttgtg gtagaattgg taaagagagt cgtgtaaaat atcgagttcg cacatcttgt  300
tgtctgatta ttgatttttg gcgaaaccat ttgatcatat gacaagatgt gtatctacct  360
taacttaatg attttgataa aaatcattag gtacggccgc ggtgccaggg cgtgcccttg  420
ggctccccgg gcgcgaatgc atactagtaa catttctctg cctaactgg ccggtaccga  480
tcttgatatc ctcgaggcta gcatgatcac catgagtcac catgagtca cccatgagtc  540
acccatgagt cacccatgag tcacccatga gtcacccatg agtcacccat gagtcaccca  600
```

```
tgagtcacca ctagtggtac cgattcttga tatcctcgag gctagcatga tcaccatgag  660
tcacccatga gtcacccatg agtcacccat gagtcaccca tgagtcaccc atgagtcacc  720
catgagtcac ccatgagtca cccatgagtc accactagtg gtaccacctc ttaacaatac  780
gtttcacaaa tagttaaaaa catgcatact gaaaagcata cttttgcaat gttattttta  840
aaaacaagga actctttaac ccagggaaga taatcacttg gggaaaggaa ggttcgtttc  900
tgagttagca acaagtaaat gcagcactag tgggtgggat tgaggtgtgc cctggtgcat  960
aaatagagac tcagctgtgc tggcacactc agaagcttgg accgcatcct agccgccgac  1020
tcacacaagg caggtgggtg aggaaatcca ggtaaggctc ctgacagcag ctttagaagg  1080
gtacttgctg gagtgaattc gggcctctga ttaccggtcg acgctagc  1128
```

```
SEQ ID NO: 311           moltype = DNA   length = 823
FEATURE                  Location/Qualifiers
source                   1..823
                         mol_type = other DNA
                         organism = synthetic construct
SEQUENCE: 311
aattttattg ttcaaacatg agagcttagt acgtgaaaca tgagagctta gtacgttagc  60
catgagagct tagtacgtta gccatgaggg tttagttcgt taaacatgag agcttagtac  120
gttaaacatg agagcttagt acgtactatc aacaggttga actgctgatc cacgttgtgg  180
tagaattggt aaagagagtc gtgtaaaata tcgagttcgc acatcttgtt gtctgattat  240
tgatttttgg cgaaaccatt tgatcatatg acaagatgtg tatctacctt aacttaatga  300
ttttgataaa aatcattagg tacggccgcg gtgccagggc gtgcccttgg gctccccggg  360
cgcgaatgca tactagtaac atttctctgg cctaactggc cggtaccact agtggtgact  420
catgggtgac tcatgggtga ctcatgggtg actcatgggt gactcatggg tgactcatgg  480
gtgactcatg ggtgactcat gggtgactca tggtgatcat gctagcctcg aggatatcaa  540
gatcggtacc actagtggtg actcatgggt gactcatggg tgactcatgg tgtgactcatg  600
ggtgactcat gggtgactca tgggtgactc atgggtgact catgggtgac tcatggtgat  660
catgctagcc tcgaggatat caagatcggt accatgaccc acgtgatgct gagaagtact  720
cctgccctag gaagagactc agggcagagg gaggaaggac agcagaccag acagtcacag  780
cagccttgac aaaacgttcc tggaactacc ggtcgacgct agc  823
```

```
SEQ ID NO: 312           moltype = DNA   length = 1216
FEATURE                  Location/Qualifiers
source                   1..1216
                         mol_type = other DNA
                         organism = synthetic construct
SEQUENCE: 312
cttataaaac ttaaaacctt agaggctatt taagttgctg atttatatta attttattgt  60
tcaaacatga gagcttagta cgtgaaacat gagagcttag tacgttagcc atgagagctt  120
agtacgttag ccatgagagc ttagtacgtt agccatgagg gtttagttcg ttaaacatga  180
gagcttagta cgttaaacat gagagcttag tacgtactat caacaggttg aactgctgat  240
ccacgttgtg gtagaattgg taaagagagt cgtgtaaaat atcgagttcg cacatcttgt  300
tgtctgatta ttgatttttg gcgaaaccat ttgatcatat gacaagatgt gtatctacct  360
taacttaatg attttgataa aaatcattag gtacggccgc ggtgccaggg cgtgcccttg  420
ggctccccgg gcgcgaatgc atactagtaa catttctctg gcctaactgg ccggtaccga  480
tcttgatatc ctcgaggcta gcatgatcac catgagtcac ccatgagtca cccatgagtc  540
acccatgagt caccactagt ggtaccgatc ttgatatcct gaggctagc atgatcacca  600
tgagtcaccc atgagtcacc catgagtcac ccatgagtca cccatgagtc acccatgagt  660
cacccatgag tcacccatga gtcacccatg agtcaccact agtggtaccg attcttgata  720
tcctcgaggc tagcatgatc accatgagtc acccatgagt cacccatgag tcacccatga  780
gtcacccatg agtcacccat gagtcaccca tgagtcaccc atgagtcac catgagtcac  840
cactagtggt accacctctt aacaatacg ttcacaaata gttaaaaaca tgcatactga  900
aaagcatact tttgcaatgt tattttttaa aacaaggaac tctttaaccc agggaagata  960
atcacttggg gaaaggaagg ttcgtttctg agttagcaac aagtaaatgc agcactagtg  1020
ggtgggattg aggtgtgccc tggtgcataa atagagactc agctgtgctg gcacactcag  1080
aagcttggac cgcatcctag ccgccgactc acacaaggca ggtgggtgag gaaatccagg  1140
taaggctcct gacagcagct ttagaagggt acttgctgga gtgaattcgg gcctctgatt  1200
accggtcgac gctagc  1216
```

```
SEQ ID NO: 313           moltype = DNA   length = 11
FEATURE                  Location/Qualifiers
source                   1..11
                         mol_type = other DNA
                         organism = synthetic construct
SEQUENCE: 313
ggatgactca g  11
```

```
SEQ ID NO: 314           moltype = DNA   length = 10
FEATURE                  Location/Qualifiers
source                   1..10
                         mol_type = other DNA
                         organism = synthetic construct
SEQUENCE: 314
gacacgtgtc  10
```

```
SEQ ID NO: 315           moltype = DNA   length = 1395
FEATURE                  Location/Qualifiers
source                   1..1395
                         mol_type = other DNA
```

-continued

```
                                             organism = synthetic construct
SEQUENCE: 315
ctgggacgaa gacgaacact tcttcatcgt tgaccgcctg aagtctctga ttaagtacaa    60
aggctatcag gtggctcccg ctgaattgga atccatcttg ctccaacacc ccaacatctt   120
cgacgcaggt gtcgcaggtc ttcccgacga tgacgccggt gaacttcccg ccgccgttgt   180
tgttttggag cacggaaaga cgatgacgga aaaagagatc gtggattacg tcgccagtca   240
agtaacaacc gcgaaaaagt tgcgcggagg agttgtgttt gtggacgaag taccgaaagg   300
tcttaccgga aaactcgacg caagaaaaat cagagagatc ctcataaagg ccaagaaggg   360
cggaaagatc gccgtgtaat gaattgggat cttcacacag caggtaaggt tgcgggccgg   420
gcctgggccg ggtccgggcc ggggcccgcc taatgagcgg gctttttttt ggcttgttgt   480
ccacaaccgt taaaccttaa aagctttaaa agcctatat attctttttt ttcttataaa    540
acttaaaacc ttagaggcta tttaagttgc tgatttatat taattttatt gttcaaacat   600
gagagcttag tacgtgaaac atgagagctt agtacgttag ccatgagagc ttagtacgtt   660
agccatgagg gtttagttcg ttaaacatga gagcttagta cgttaaacat gagagcttag   720
tacgtactat caacaggttg aactgctgat ccacgttgtg gtagaattgg taaagagagt   780
cgtgtaaaat atcgagttcg cacatcttgt tgtctgatta ttgatttttg gcgaaaccat   840
ttgatcatat gacaagatgt gtatctacct taacttaatg attttgataa aaatcattac   900
cgcactgacc cctggtgttg cttttttttt ttaggccgca agctgaagcg tgtccctgga   960
ccttctagtt gccagccatc tgttgtttgc ccctcccccg tgccttcctt gaccctggaa  1020
ggtgccactc ccactgtcct ttcctaataa aatgaggaaa ttgcatcgca ttgtctgagt  1080
aggtgtcatt ctattctggg gggtggggtg gggcaggaca gcaaggggga ggattgggaa  1140
gacaatagca ggcatgctgg ggatgcggtg ggctcatgg ggtaccatgc atactagtgg  1200
tgactcatgg gtgactcatg ggtgactcat gggtgactca tgggtgactc atgggtgact  1260
catgggtgac tcatgggtga ctcatgggtg actcatgcgg tgctagctat aaaaggccaa  1320
cagcagcctg accacatctc atcctcctcg aggatatcaa gatctggcct cggcggccag  1380
aattcaccgg tcacc                                                    1395

SEQ ID NO: 316               moltype = DNA   length = 10
FEATURE                      Location/Qualifiers
source                       1..10
                             mol_type = other DNA
                             organism = synthetic construct
SEQUENCE: 316
ggcacgtgta                                                            10

SEQ ID NO: 317               moltype = DNA   length = 10
FEATURE                      Location/Qualifiers
source                       1..10
                             mol_type = other DNA
                             organism = synthetic construct
SEQUENCE: 317
ggcacgtgtc                                                            10

SEQ ID NO: 318               moltype = DNA   length = 814
FEATURE                      Location/Qualifiers
source                       1..814
                             mol_type = other DNA
                             organism = synthetic construct
SEQUENCE: 318
ggccgctagc ccgcctaatg agcgggcttt tttttggctt gttgtccaca accgttaaac    60
cttaaaagcct tatatattct tttttttctt ataaaactta aaaccttaga            120
ggctatttaa gttgctgatt tatattaatt ttattgttca aacatgagag cttagtacgt   180
gaaacatgag agcttagtac gttagccatg agagcttagt acgttagcca tgagggttta   240
gttcgttaaa catgagagct tagtacgtta aacatgagag cttagtacgt actatcaaca   300
ggttgaactg ctgatccacg ttgtggtaga attggtaaag agagtcgtgt aaaatatcga   360
gttcgcacat cttgttgtct gattattgat ttttggcgaa accatttgat catatgacaa   420
gatgtgtatc taccttaact taatgatttt gataaaaatc attaggtacc actagtggtg   480
actcatgggt gactcatggg tgactcatgg gtgactcatg ggtgactcat gggtgactca   540
tgggtgactc atgggtgact catgactagt gtccccaccc acacattccg gtccccaccc   600
acacattcct gtccccaccc acacattcct gtccccaccc acacattcct gtccccaccc   660
acacattcct gtccccaccc acacattcct gtgcgctccc gacatgcccc gcggcgcgcc   720
attaaccgcc agatttgagt cgcgggaccc gttggcagag gtgggctagc ctcgaggata   780
tcaagatctg gcctcggcgg ccaagcttgc tagc                              814

SEQ ID NO: 319               moltype = DNA   length = 558
FEATURE                      Location/Qualifiers
source                       1..558
                             mol_type = other DNA
                             organism = synthetic construct
SEQUENCE: 319
aattttattg ttcaaacatg agagcttagt acgtgaaaca tgagagctta gtacgttagc    60
catgagagct tagtacgtta gccatgaggg tttagttcgt taaacatgag agcttagtac   120
gttaaacatg agagcttagt acgtactatc aacaggttga actgctgatc cacgttgtgg   180
tagaattggt aaagagagtc gtgtaaaata tcgagttcg acatcttgtt gtctgattat   240
tgatttttgg cgaaaccatt tgatcatatg acaagatgtg tatctacctt aacttaatga   300
ttttgataaa aatcattagg tacggccgcg gtgccaggc gtgcccttgg gctccccggg   360
cgcgactagt ggtgactcat gggtgactca tgggtgactc atgggtgact catgggtgac   420
tcatgggtga ctcatgggtg actcatgggt gactcatggg tgactcatgt gcgctcccga   480
catgccccgg ggcgcgccat taaccgccag atttgagtcg cggacccgt tggcagaggt   540
```

```
ggaccggtcg acgctagc                                                       558

SEQ ID NO: 320          moltype = DNA   length = 14
FEATURE                 Location/Qualifiers
source                  1..14
                        mol_type = other DNA
                        organism = synthetic construct
SEQUENCE: 320
atgccacgtc aaca                                                           14

SEQ ID NO: 321          moltype = DNA   length = 10
FEATURE                 Location/Qualifiers
source                  1..10
                        mol_type = other DNA
                        organism = synthetic construct
SEQUENCE: 321
ggcacgtgtt                                                                10

SEQ ID NO: 322          moltype = DNA   length = 10
FEATURE                 Location/Qualifiers
source                  1..10
                        mol_type = other DNA
                        organism = synthetic construct
SEQUENCE: 322
ggcacgtgcc                                                                10

SEQ ID NO: 323          moltype = DNA   length = 12
FEATURE                 Location/Qualifiers
source                  1..12
                        mol_type = other DNA
                        organism = synthetic construct
SEQUENCE: 323
aaaaccggtt ct                                                             12

SEQ ID NO: 324          moltype = DNA   length = 885
FEATURE                 Location/Qualifiers
source                  1..885
                        mol_type = other DNA
                        organism = synthetic construct
SEQUENCE: 324
gacggccgct agcccgccta atgagcgggc ttttttttgg cttgttgtcc acaaccgtta        60
aaccttaaaa gctttaaaag ccttatatat tctttttttt cttataaaac ttaaaacctt        120
agaggctatt taagttgctg atttatatta attttattgt tcaaacatga gagcttagta        180
cgtgaaacat gagagcttag tacgtgaaac atgagagctt agtacgttag ccatgagagc        240
ttagtacgtt agccatgagg gtttagttcg ttaaacatga gagcttagta cgttaaacat        300
gagagcttag tacgtactat caacaggttg aactgctgat ccacgttgtg gtagaattgg        360
taaagagagt cgtgtaaaat atcgagttcg cacatcttgt tgtctgatta ttgatttttg        420
gcgaaaccat ttgatcatat gacaagatgt gtatctacct taacttaatg attttgataa        480
aaatcattag gtacggccgc ggtgccaggg cgtgcccttg ggctccccgg gcgcgactag        540
tggtgactca tgggtgactc atgggtgact catgggtgac tcatgggtga ctcatgggtg        600
actcatgggt gactcatggg tgactcatgg gtgactcatg catggggcgg ggtgatgaca        660
cagcaattcg ggactttcca cgcttgcgtg agaagagacc ggaagtgaat gacacagcaa        720
ttcgcttgcg tgagaagctg ggactttcct aggggcgggg ttgggacttt ccacatgaca        780
cagcaataca acgcgtcccg acatgccccg cggcgcgcca ttaaccgcca gatttgagtc        840
gcgggacccg ttggcagagg tgggaattca ccggtcgacg ctagc                        885

SEQ ID NO: 325          moltype = DNA   length = 597
FEATURE                 Location/Qualifiers
source                  1..597
                        mol_type = other DNA
                        organism = synthetic construct
SEQUENCE: 325
tttattgttc aaacatgaga gcttagtacg tgaaacatga gagcttagta cgttagccat        60
gagagcttag tacgttagcc atgagggttt agttcgttaa acatgagagc ttagtacgtt        120
aaacatgaga gcttagtacg tactatcaac aggttgaact gctgatccac gttgtggtag        180
aattggtaaa gagagtcgtg taaaatatcg agttcgcaca tcttgttgtc tgattattga        240
tttttggcga aaccatttga tcatatgaca agatgtgtat ctaccttaac ttaatgattt        300
tgataaaaat cattaggtac ggccgcggtg ccagggcgtg cccttgggct ccccgggcgc        360
gactagtggt gactcatggg tgactcatgg gtgactcatg gggtgactca tgggtgactc        420
tgggtgactc atgggtgact catgggtgac tcatgggtga ctcatgcata ccggaagtac        480
ttgcgcaatg accggaagta caacgcgtcc cgacatgccc cgcggcgcgc cattaaccgc        540
cagatttgag tcgcgggacc cgttggcaga ggtgggaatt caccggtcga cgctagc          597

SEQ ID NO: 326          moltype = DNA   length = 659
FEATURE                 Location/Qualifiers
source                  1..659
                        mol_type = other DNA
                        organism = synthetic construct
SEQUENCE: 326
```

```
taattttatt gttcaaacat gagagcttag tacgtgaaac atgagagctt agtacgttag  60
ccatgagagc ttagtacgtt agccatgagg gtttagttcg ttaaacatga gagcttagta 120
cgttaaacat gagagcttag tacgtactat caacaggttg aactgctgat ccacgttgtg 180
gtagaattgg taaagagagt cgtgtaaaat atcgagttcg cacatcttgt tgtctgatta 240
ttgatttttg gcgaaaccat ttgatcatat gacaagatgt gtatctacct taacttaatg 300
attttgataa aaatcattag gtacggccgc ggtgccaggg cgtgcccttg ggctccccgg 360
gcgcgactag tggtgactca tgggtgactc atgggtgact catgggtgac tcatgggtga 420
ctcatgggtg actcatgggt gactcatggg tgactcatgg gtgactcatg catttgcgca 480
acaggggcgg ggtgatgaca cagcaattcg cttgcgtgag aagagaccgg aagtgaggga 540
ctttccacat gacacagcaa tacaacgcgt cccgacatgc cccgcggcgc gccattaacc 600
gccagatttg agtcgcggga cccgttggca gaggtgggaa ttcaccggtc gacgctagc  659
```

SEQ ID NO: 327          moltype = DNA   length = 21
FEATURE                 Location/Qualifiers
source                  1..21
                        mol_type = other DNA
                        organism = synthetic construct
SEQUENCE: 327
```
ataaataaaa atggactaat t                                             21
```

SEQ ID NO: 328          moltype = DNA   length = 660
FEATURE                 Location/Qualifiers
source                  1..660
                        mol_type = other DNA
                        organism = synthetic construct
SEQUENCE: 328
```
gcccgcctaa tgagcgggct tttttttggc ttgttgtcca caaccgttaa accttaaaag  60
ctttaaaagc cttatatatt cttttttttc ttataaaact taaaacctta gaggctattt 120
aagttgctga tttatattaa ttttattgtt caaacatgag agcttagtac gtgaaacatg 180
agagcttagt acgttagcca tgagagctta gtacgttagc catgagggtt tagttcgtta 240
aacatgagag cttagtacgt taaacatgag agcttagtac gtactatcaa caggttgaac 300
tgctgatcca cgttgtggta gaattggtaa agagagtcgt gtaaaatatc gagttcgcac 360
atcttgttgt ctgattattg attttggcg aaaccatttg atcatatgac aagatgtgta 420
tctacctaa cttaatgatt ttgataaaaa tcattaggta cggccgc tgactcatgg 480
gtgactcatg ggtgactcat gggtgactca tgggtgactc atgggtgact catgggtgac 540
tcatgggtga ctcatgggtg actcatgcgg tgctagctat aaaaggccag cagcagcctg 600
accacatctc atcctcctcg aggatatcaa gatctggcct cggcggccaa gcttgctagc 660
```

SEQ ID NO: 329          moltype = DNA   length = 885
FEATURE                 Location/Qualifiers
source                  1..885
                        mol_type = other DNA
                        organism = synthetic construct
SEQUENCE: 329
```
aattttattg ttcaaacatg agagcttagt acgtgaaaca tgagagctta gtacgttagc  60
catgagagct tagtacgtta gccatgaggg tttagttcgt taaacatgag agcttagtac 120
gttaaacatg agagcttagt acgtactatc aacaggttga actgctgatc cacgttgtgg 180
tagaattggt aaagagagtc gtgtaaaata tcgagttcgc acatcttgtt gtctgattat 240
tgattttgg cgaaaccatt tgatcatatg acaagatgtg tatctacctt aacttaatga 300
ttttgataaa aatcattagg tacggccgcg gtgccagggc gtgcccttgg gctccccggg 360
cgcgactagt gggcggggt gatgacacag caattcggga ctttccacgc ttgcgtgaga 420
agagaccgga agtgaatgac acagcaattc gcttgcgtga gaagctggga ctttcctagg 480
ggcggggttg ggactttcca catgacacag caatacagta ccacctctta acaatacgtt 540
tcacaaatag ttaaaaacat gcatactgaa aagcatactt ttgcaatgtt attttaaaa 600
acaaggaact ctttaaccca gggaagataa tcacttgggg aaaggaaggt tcgtttctga 660
gttagcaaca agtaaatgca gcactagtgg gtgggattga ggtgtgccct ggtgcataaa 720
tagagactca gctgtgctgg cacactcaga agcttggacc gcatcctagc cgccgactca 780
cacaaggcag gtgggtgagg aaatccaggt aaggctcctg acagcagctt tagaagggta 840
cttgctggag tgaattcggg cctctgatta ccggtcgacg ctagc            885
```

SEQ ID NO: 330          moltype = DNA   length = 242
FEATURE                 Location/Qualifiers
source                  1..242
                        mol_type = other DNA
                        organism = synthetic construct
SEQUENCE: 330
```
ggggcggggt gatgacacag caattcggga ctttccacgc ttgcgtgaga agagaccgga  60
agtgaatgac acagcaattc gcttgcgtga gaagctggga ctttcctagg ggcggggttg 120
ggactttcca catgacacag caatacaacg cgtcccgaca tgccccgcgg cgcgccatta 180
accgccagat ttgagtcgcg ggacccgttg gcagaggtgg gaattcaccg gtcgacgcta 240
gc                                                                 242
```

SEQ ID NO: 331          moltype = DNA   length = 682
FEATURE                 Location/Qualifiers
source                  1..682
                        mol_type = other DNA
                        organism = synthetic construct
SEQUENCE: 331
```
aattttattg ttcaaacatg agagcttagt acgtgaaaca tgagagctta gtacgttagc  60
```

-continued

```
catgagagct tagtacgtta gccatgaggg tttagttcgt taaacatgag agcttagtac  120
gttaaacatg agagcttagt acgtactatc aacaggttga actgctgatc cacgttgtgg  180
tagaattggt aaagagagtc gtgtaaaata tcgagttcgc acatcttgtt gtctgattat  240
tgatttttgg cgaaaccatt tgatcatatg acaagatgtg tatctacctt aacttaatga  300
ttttgataaa aatcattagg tacggccgcg gtgccagggc gtgcccttgg gctccccggg  360
cgcgactagt ggggcggggt gatgacacag caattcggga ctttccacgc ttgcgtgaga  420
agagaccgga agtgaatgac acagcaattc gcttgcgtga gaagctggga ctttcctagg  480
ggcggggttg ggactttcca catgacacag caatacacta gtaacatttc tctggcctaa  540
ctggccggta ccatgaccca cgtgatgctg agaagtactc ctgccctagg aagagactca  600
gggcagaggg aggaaggaca gcagaccaga cagtcacagc agccttgaca aaacgttcct  660
ggaactaccg gtcgacgcta gc                                            682
```

```
SEQ ID NO: 332          moltype = DNA  length = 759
FEATURE                 Location/Qualifiers
source                  1..759
                        mol_type = other DNA
                        organism = synthetic construct
SEQUENCE: 332
aattttattg ttcaaacatg agagcttagt acgtgaaaca tgagagctta gtacgttagc  60
catgagagct tagtacgtta gccatgaggg tttagttcgt taaacatgag agcttagtac  120
gttaaacatg agagcttagt acgtactatc aacaggttga actgctgatc cacgttgtgg  180
tagaattggt aaagagagtc gtgtaaaata tcgagttcgc acatcttgtt gtctgattat  240
tgatttttgg cgaaaccatt tgatcatatg acaagatgtg tatctacctt aacttaatga  300
ttttgataaa aatcattagg tacggccgcg gtgccaggac gtgcccttgg gctccccggg  360
cgcgactagt ggggcggggt gatgacacag caattcggga ctttccacgc ttgcgtgaga  420
agagaccgga agtgaatgac acagcaattc gcttgcgtga gaagctggga ctttcctagg  480
ggcggggttg ggactttcca catgacacag caatacacta gtaacatttc tctggcctaa  540
ctggccggta ccagtggtgg gggagtgaaa agagagatgg agaaagaggg gatgggcaga  600
aagaggagga ggagtcaggg gcagggcatg gaggtgggtg gggctgggct gccaaagcag  660
gataaatgca cacctgcctg ctggtctggg ctccctgcct cgggtctctca ccctcctctc  720
ctgcagctcc agctttgtgc tctaccggtc gacgctagc                          759
```

```
SEQ ID NO: 333          moltype = DNA  length = 733
FEATURE                 Location/Qualifiers
source                  1..733
                        mol_type = other DNA
                        organism = synthetic construct
SEQUENCE: 333
aattttattg ttcaaacatg agagcttagt acgtgaaaca tgagagctta gtacgttagc  60
catgagagct tagtacgtta gccatgaggg tttagttcgt taaacatgag agcttagtac  120
gttaaacatg agagcttagt acgtactatc aacaggttga actgctgatc cacgttgtgg  180
tagaattggt aaagagagtc gtgtaaaata tcgagttcgc acatcttgtt gtctgattat  240
tgatttttgg cgaaaccatt tgatcatatg acaagatgtg tatctacctt aacttaatga  300
ttttgataaa aatcattagg tacggccgcg gtgccagggc gtgcccttgg gctccccggg  360
cgcgactagt ggggcggggt gatgacacag caattcggga ctttccacgc ttgcgtgaga  420
agagaccgga agtgaatgac acagcaattc gcttgcgtga gaagctggga ctttcctagg  480
ggcggggttg ggactttcca catgacacag caatacacta gtaacatttc tctggcctaa  540
ctggccggta ccgggaaaag ttcagctgag agatatataaaa gagcagtctt tccagcacct  600
gcaaatccag agcggcgggc actgacgggc acttgcaccg tgtggacaga ctctccggtt  660
ctgtgagtgg tttttctttt cccgggtcgg acctggagtt cttaggggga tggctgaacc  720
ggtcgacgct agc                                                     733
```

```
SEQ ID NO: 334          moltype = DNA  length = 630
FEATURE                 Location/Qualifiers
source                  1..630
                        mol_type = other DNA
                        organism = synthetic construct
SEQUENCE: 334
aggccgcaag ctgaagcgtg tccctgtgcc ttctagttgc cagccatctg ttgtttgccc  60
ctccccgtg ccttccttga ccctggaagg tgccactccc actgtccttt cctaataaaa  120
tgaggaaatt gcatcgcatt gtctgagtag gtgtcattct attctggggg gtggggtggg  180
gcaggacagc aaggggagg attgggaaga caatagcagg catgctgggg atgcggtggg  240
ctctatgggg taccatgcat actagtgggg cggggtgatg acacagcaat tcgggacttt  300
ccacgcttgc gtgagaagag accgaagtg aatgacacag caattcgctt gcgtgagagg  360
ctgggacttt cctaggggcg gggttgggac tttccacatg acacagcaat acactagtaa  420
catttctctg gctaactgg ccggtaccgg gaaaagttca gctgagagat ataaagagc  480
agtctttcca gcacctgcaa atccagagcg gcgggcactg acgggcactt gcaccgtgtg  540
gacagactct ccggttctgt gagtggtttt tcttttcccg gtcggacct ggagttctta  600
gggggatggc tgaagaattc accggtcacc                                    630
```

```
SEQ ID NO: 335          moltype = DNA  length = 819
FEATURE                 Location/Qualifiers
source                  1..819
                        mol_type = other DNA
                        organism = synthetic construct
SEQUENCE: 335
aattttattg ttcaaacatg agagcttagt acgtgaaaca tgagagctta gtacgttagc  60
catgagagct tagtacgtta gccatgaggg tttagttcgt taaacatgag agcttagtac  120
gttaaacatg agagcttagt acgtactatc aacaggttga actgctgatc cacgttgtgg  180
```

```
tagaattggt aaagagagtc gtgtaaaata tcgagttcgc acatcttgtt gtctgattat   240
tgatttttgg cgaaaccatt tgatcatatg acaagatgtg tatctacctt aacttaatga   300
ttttgataaa aatcattagg tacgccgcg gtgccaggc gtgcccttgg gctccccggg     360
cgcgactagt ggggcggggt gatgacacag caattcggga ctttccacgc ttgcgtgaga   420
agagaccgga agtgaatgac acagcaattc gcttgcgtga gaagctggga ctttcctagg   480
ggcggggttg ggactttcca catgacacag caatacacta gtaacatttc tctggcctaa   540
ctggccggta ccgcccgcc cccttttcctt acgcggattg gtagctgcag gcttccctat   600
ctgattggcc gaacgaacgc agcgcgtaat ttaaaatatt gtatctgtaa caaagctgca   660
cctcgtgggc ggagttgtgc tctgcggctg cgaaagtcca gcttcggcga ctaggtgtga   720
gtaagccagt atcccaggag gagcaagtgg cacgtcttcg ggtgagtgtg cggctgtgct   780
ggagcccggg ttaccagctc ttaaccggtc gacgctagc                          819

SEQ ID NO: 336        moltype = DNA   length = 10
FEATURE               Location/Qualifiers
source                1..10
                      mol_type = other DNA
                      organism = synthetic construct
SEQUENCE: 336
accggatgtg                                                          10

SEQ ID NO: 337        moltype = DNA   length = 11
FEATURE               Location/Qualifiers
source                1..11
                      mol_type = other DNA
                      organism = synthetic construct
SEQUENCE: 337
gggcgggacc g                                                        11

SEQ ID NO: 338        moltype = DNA   length = 11
FEATURE               Location/Qualifiers
source                1..11
                      mol_type = other DNA
                      organism = synthetic construct
SEQUENCE: 338
gggtgactca g                                                        11

SEQ ID NO: 339        moltype = DNA   length = 16
FEATURE               Location/Qualifiers
source                1..16
                      mol_type = other DNA
                      organism = synthetic construct
SEQUENCE: 339
aactgaaact tgatac                                                   16

SEQ ID NO: 340        moltype = DNA   length = 13
FEATURE               Location/Qualifiers
source                1..13
                      mol_type = other DNA
                      organism = synthetic construct
SEQUENCE: 340
attgcagatg ttt                                                      13

SEQ ID NO: 341        moltype = DNA   length = 16
FEATURE               Location/Qualifiers
source                1..16
                      mol_type = other DNA
                      organism = synthetic construct
SEQUENCE: 341
aactgtaacc tgatac                                                   16

SEQ ID NO: 342        moltype = DNA   length = 2637
FEATURE               Location/Qualifiers
source                1..2637
                      mol_type = other DNA
                      organism = synthetic construct
SEQUENCE: 342
gagagcaact gcataaggct atgaagagat acgccctggt tcctggaaca attgctttta   60
cagatgcaca tatcgaggtg gacatcactt acgctgagta cttcgaaatg tccgttcggt   120
tggcagaagc tatgaaacga tatgggctga atacaaatca cagaatcgtc gtatgcagtg   180
aaaactctct tcaattcttt atgccggtgt gtgggcgcgtt atttatcgga gttgcagttg   240
cgcccgcgaa cgacatttat aatgaacgtg aattgctcaa cagtatgggc atttcgcagc   300
ctaccgtggt gttcgtttcc aaaaaggggt tgcaaaaaat tttgaacgtg caaaaaaagc   360
tcccaatcat ccaaaaaatt attatcatgg attctaaaac ggattaccag ggatttcagt   420
cgatgtacac gttcgtcaca tctcatctac ctcccggttt taatgaatac gattttgtgc   480
cagagtcctt cgatagggac aagacaattg cactgatcat gaactcctct ggatctactg   540
gtctgcctaa aggtgtcgct ctgcctcata gaactgcctg cgtgagattc tcgcatgcca   600
gagatcctat ttttggcaat caaatcattc cggatactgc gatttaagt gttgttccat    660
tccatcacgt ttttggaatg tttactcac tcggatattt gatatgtgga tttcgagtcg    720
tcttaatgta tagatttgaa gaagagctgt ttctgaggag ccttcaggat tacaagattc   780
```

```
aaagtgcgct gctggtgcca acccctattct ccttcttcgc caaaagcact ctgattgaca   840
aatacgattt atctaattta cacgaaattg cttctggtgg cgctcccctc tctaaggaag   900
tcggggaagc ggttgccaag aggttccatc tgccaggtat caggcaagga tatgggctca   960
ctgagactac atcagctatt ctgattacac ccgaggggga tgataaaccg ggcgcggtcg  1020
gtaaagttgt tccatttttt gaagcgaagg ttgtggatca ggataccggg aaaacgctgg  1080
gcgttaatca aagaggcgaa ctgtgtgtga gaggtcctat gattatgtcc ggttatgtaa  1140
acaatccgga agcgaccaac gccttgattg acaaggatgg atggctacat tctggagaca  1200
tagcttactg ggacgaagac gaacacttct tcatcgttga ccgcctgaag tctctgatta  1260
agtacaaagg ctatcaggtg gctcccgctg aattggaatc catcttgctc caacacccca  1320
acatcttcga cgcaggtgtc gcaggtcttc ccgacgatga cgccggtgaa cttcccgccg  1380
ccgttgttgt tttggagcac ggaaagacga tgacggaaaa agagatcgtg gattacgtcg  1440
ccagtcaagt aacaaccgcg aaaaagttgc gcggaggagt tgtgtttgtg gacgaagtac  1500
cgaaaggtct taccggaaaa ctcgacgcaa gaaaaatcag agagatcctc ataaaggcca  1560
agaagggcgg aaagatcgcc gtgtaatgaa tgcatgaatt cctgtgcctt ctagttgcca  1620
gccatctgtt gtttgcccct cccccgtgcc ttccttgacc ctggaaggtg ccactcccac  1680
tgtcctttcc taataaaatg aggaaattgc atcgcattgt ctgagtaggt gtcattctat  1740
tctggggggt ggggtggggc aggacagcaa ggggggaggat tgggaagaca atagcaggca  1800
tgctgggat gcggtgggct ctatggcccg ggacggccgc tagcccgcct aatgagcggg  1860
ctttttttg gcttgttgtc cacaaccgtt aaaccttaaa agctttaaaa gccttatata  1920
ttcttttttt tcttataaaa cttaaaacct tagaggctat ttaagttgct gatttatatt  1980
aattttattg ttcaaacatg agagcttagt acgtgaaaca tgagagctta gtacgtgaaa  2040
catgagagct tagtacgtta gccatgagag cttagtacga tgttagttc  2100
gttaaacatg agagcttagt acgttaaaca tgagagctta gtacgtacta tcaacaggtt  2160
gaactgctga tccacgttgt ggtagaattg gtaaagagag tcgtgtaaaa tatcgagttc  2220
gcacatcttg ttgtctgatt attgattttt ggcgaaacca tttgatcata tgacaagatg  2280
tgtatctacc ttaacttaat gattttgata aaaatcatta ggtacggccg cggtgccagg  2340
gcgtgccctt gggctcccg ggcgcgacta gtaacatttc tctggcctaa ctggccggta  2400
cccgatgtag ctgagcgaca gtatagtgca cagtgactgc agcagtcatt atacgtcgcc  2460
taaatcgaga tgctgtactg atctataagg atcggtaatg acgtaatgac gtaatgacgt  2520
aatgacgtaa tgacgtaatg acggtacctg cgctcccgac atgccccgcg gcgcgccatt  2580
aaccgccaga tttgagtcgc gggacccgtt ggcagaggtg gaccggtcga cgctagc     2637
```

SEQ ID NO: 343          moltype = DNA   length = 2631
FEATURE                  Location/Qualifiers
source                   1..2631
                           mol_type = other DNA
                           organism = synthetic construct
SEQUENCE: 343

```
aactgcataa ggctatgaag agatacgccc tggttcctgg aacaattgct tttacagatg    60
cacatatcga ggtggacatc acttacgctg agtacttcga aatgtccgtt cggttggcag   120
aagctatgaa acgatatggg ctgaatacaa atcacagaat cgtcgtatgc agtgaaaact   180
ctcttcaatt ctttatgccg gtgttgggcg cgttatttat cggagttgca gttgcgcccg   240
cgaacgacat ttataatgaa cgtgaattgc tcaacagtat gggcatttcg cagcctaccg   300
tggtgttcgt ttccaaaaag gggttgcaaa aaattttgaa cgtgcaaaaa aagctcccaa   360
tcatccaaaa aattattatc atggattcta aaacggatta ccagggattt cagtcgatgt   420
acacgttcgt cacatctcat ctacctcccg gttttaatga atacgatttt gtgccagagt   480
ccttcgatag ggacaagaca attgcactga tcatgaatcc ctctggatct actggtctgc   540
ctaaaggtgt cgctctgcct catagaactg cctgcgtgag attctcgcat gccagagatc   600
ctattttggg caatcaaatc attccggata ctgcgatttt aagtgttgtt ccattccatc   660
acggttttgg aatgtttact acactcggat atttgatatg tggatttcga gtcgtcttaa   720
tgtatagatt tgaagaagag ctgtttctga ggagccttca ggattacaag attcaaagtg   780
cgctgctggt gccaacccta ttctccttct tcgccaaaag cactctgatt gacaaatacg   840
atttatctaa tttacacgaa attgcttctg tggcgctcc cctctctaag gaagtcgggg   900
aagcggttgc caagaggttc catctgccag gtatcaggca aggatatggg ctcactgaga   960
ctacatcagc tattctgatt acacccgagg gggatgataa accgggcgcg gtcggtaaag  1020
ttgttccatt ttttgaagcg aaggttgtgg atctggatac cgggaaaacg ctgggcgtta  1080
atcaaagagg cgaactgtgt gtgagaggtc ctatgattat gtccggttat gtaaacaatc  1140
cggaagcgac caacgccttg attgacaagg atggatggct acattctgga gacatagctt  1200
actgggacga agacgaacac ttcttcatcg ttgaccgcct gaagtctctg attaagtaca  1260
aaggctatca ggtggctccc gctgaattgg aatccatctt gctccaacac cccaacatct  1320
tcgacgcagg tgtcgcaggt cttcccgacg atgacgccgg tgaacttccc gccgccgttg  1380
ttgttttgga gcacggaaag acgatgacgg aaaaagagat cgtggattac gtcgccagtc  1440
aagtaacaac cgcgaaaaag ttgcgcggag gagttgtgtt tgtggacgaa gtaccgaaag  1500
gtcttaccgg aaaactcgac gcaagaaaaa tcagagagat cctcataaag gccaagaag   1560
gcggaaagat cgccgtgtaa tgaatgcatg aattcctgtg ccttctagtt gccagccatc  1620
tgttgtttgc cctcccccg tgccttcctt gaccctggaa ggtgccactc ccactgtcct  1680
ttcctaataa aatgaggaaa ttgcatcgca ttgtctgagt aggtgtcatt ctattctggg  1740
gggtggggtg gggcaggaca gcaagggga ggattgggaa gacaatagca ggcatgctgg  1800
ggatgcggtg ggctctatgg cccgggacgg ccgctagcc gcctaatgag cgggcttttt  1860
tttggcttgt gtccacaac cgttaaacct taaaagcttt aaaagcctta tatattcttt  1920
tttttcttat aaaacttaaa acctagagg ctatttaagt tgctgattta tattaatttt  1980
attgttcaaa catgagagct tagtacgtga aacatgagag cttagtacgt tagccatgag  2040
agcttagtac gttagccatg agagcttagt acgttagcca tgagggttta gttcgttaaa  2100
catgagagct tagtacgtta aacatgagag cttagtacgt actatcaaca ggttgaactg  2160
ctgatccacg ttgtggtaga attggtaaag agagtcgtg aaaatatcga gttcgcacat  2220
cttgttgtct gattattgat ttttggcgaa accatttgat catatgacaa gatgtgtatc  2280
taccttaact taatgatttt gataaaaatc attaggtacg gccgcggtgc cagggcgtgc  2340
ccttgggctc cccgggcgcg actagtaaca tttctctggc ctaactggcc ggtaccagct  2400
gagcgacagt atagtgcaca gtgactgcag cagtcattat acgtcgccta aatcgagatg  2460
```

```
ctgtactgat ctataagtcg taaactgtcg taaactgtcg taaactgtcg taaactgtcg   2520
taaactgtcg taaactggta cctgcgctcc cgacatgccc cgcggcgcgc cattaaccgc   2580
cagatttgag tcgcgggacc cgttggcaga ggtggaccgg tcgacgctag c            2631

SEQ ID NO: 344         moltype = DNA   length = 137
FEATURE                Location/Qualifiers
source                 1..137
                       mol_type = other DNA
                       organism = synthetic construct
SEQUENCE: 344
aataggtacc actagtggtt ttgtgggggtt ttgtgggggtt ttgtgggggtt ttgtgggggtt   60
ttgtgggggtt ttgtgggggtt ttgtgggggtt ttgtgggggtt ttgtgggggtt ttgtggtgcg   120
ctcccgacat gccccgc                                                    137

SEQ ID NO: 345         moltype = DNA   length = 137
FEATURE                Location/Qualifiers
source                 1..137
                       mol_type = other DNA
                       organism = synthetic construct
SEQUENCE: 345
aataggtacc actagtagtt caacacgtgg tctgggagtt caacacgtgg tctgggagtt   60
caacacgtgg tctgggagtt caacacgtgg tctgggagtt caacacgtgg tctgggtgcg   120
ctcccgacat gccccgc                                                    137

SEQ ID NO: 346         moltype = DNA   length = 138
FEATURE                Location/Qualifiers
source                 1..138
                       mol_type = other DNA
                       organism = synthetic construct
SEQUENCE: 346
aataggtacc actagtggtt ttgtggagag gttttgtggt cgggtttttgt gggacggttt   60
tgtggctagg ttttgtggac tggttttgtg gtgcggtttt gtgggtaggt tttgtggtgc   120
gctcccgaca tgccccgc                                                   138

SEQ ID NO: 347         moltype = DNA   length = 149
FEATURE                Location/Qualifiers
source                 1..149
                       mol_type = other DNA
                       organism = synthetic construct
SEQUENCE: 347
aataggtacc actagtagtt caacacgtgg tctgggagaa gttcaacacg tggtctgggt   60
cgagttcaac acgtggtctg gggacagttc aacacgtggt ctgggctaag ttcaacacgt   120
ggtctgggtg cgctcccgac atgccccgc                                       149

SEQ ID NO: 348         moltype = DNA   length = 135
FEATURE                Location/Qualifiers
source                 1..135
                       mol_type = other DNA
                       organism = synthetic construct
SEQUENCE: 348
aataggtacc actagtagcc acttgaaatt agccacttga aattagccac ttgaaattag   60
ccacttgaaa ttagccactt gaaattagcc acttgaaatt agccacttga aatttgcgct   120
cccgacatgc cccgc                                                      135

SEQ ID NO: 349         moltype = DNA   length = 141
FEATURE                Location/Qualifiers
source                 1..141
                       mol_type = other DNA
                       organism = synthetic construct
SEQUENCE: 349
aataggtacc actagtgaca gataagaaag acagataaga aagacagata agaaagacag   60
ataagaaaga cagataagaa agacagataa gaaagacaga taagaaagac agataagaaa   120
tgcgctcccg acatgccccg c                                               141

SEQ ID NO: 350         moltype = DNA   length = 136
FEATURE                Location/Qualifiers
source                 1..136
                       mol_type = other DNA
                       organism = synthetic construct
SEQUENCE: 350
aataggtacc actagtagcc acttgaaatt agaagccact tgaaatttcg agccacttga   60
aattgacagc cacttgaaat tctaagccac ttgaaattac tagccacttg aaatttgcgc   120
tcccgacatg cccgc                                                     136

SEQ ID NO: 351         moltype = DNA   length = 146
FEATURE                Location/Qualifiers
source                 1..146
                       mol_type = other DNA
                       organism = synthetic construct
```

```
SEQUENCE: 351
aataggtacc actagtgaca gataagaaaa gagacagata agaaatcgga cagataagaa    60
agacgacaga taagaaacta gacagataag aaaactgaca gataagaaat gcgacagata   120
agaaatgcgc tcccgacatg ccccgc                                        146

SEQ ID NO: 352            moltype = DNA   length = 141
FEATURE                   Location/Qualifiers
source                    1..141
                          mol_type = other DNA
                          organism = synthetic construct
SEQUENCE: 352
aataggtacc actagtctgg gaacaagtgc tgggaacaag tgctgggaac aagtgctggg    60
aacaagtgct gggaacaagt gctgggaaca agtgctggga caagtgctg ggaacaagtg    120
tgcgctcccg acatgccccg c                                             141

SEQ ID NO: 353            moltype = DNA   length = 136
FEATURE                   Location/Qualifiers
source                    1..136
                          mol_type = other DNA
                          organism = synthetic construct
SEQUENCE: 353
aataggtacc actagtttct aatctatttc taatctattt ctaatctatt tctaatctat    60
ttctaatcta tttctaatct atttctaatc tatttctaat ctatttctaa tctattgcgc   120
tcccgacatg ccccgc                                                   136

SEQ ID NO: 354            moltype = DNA   length = 146
FEATURE                   Location/Qualifiers
source                    1..146
                          mol_type = other DNA
                          organism = synthetic construct
SEQUENCE: 354
aataggtacc actagtctgg gaacaagtga gactgggaac aagtgtcgct gggaacaagt    60
ggacctggga acaagtgcta ctgggaacaa gtgactctgg gaacaagtgt gcctgggaac   120
aagtgtgcgc tcccgacatg ccccgc                                        146

SEQ ID NO: 355            moltype = DNA   length = 132
FEATURE                   Location/Qualifiers
source                    1..132
                          mol_type = other DNA
                          organism = synthetic construct
SEQUENCE: 355
aataggtacc actagtttct aatctataga ttctaatcta ttcgttctaa tctatgactt    60
ctaatctatc tattctaatc tatactttct aatctattgc ttctaatcta ttgcgctccc   120
gacatgcccc gc                                                       132

SEQ ID NO: 356            moltype = DNA   length = 141
FEATURE                   Location/Qualifiers
source                    1..141
                          mol_type = other DNA
                          organism = synthetic construct
SEQUENCE: 356
aataggtacc actagtgact cctcaagggg actcctcaag gggactcctc aaggggactc    60
ctcaagggga ctcctcaagg ggactcctca aggggactcc tcaaggggac tcctcaaggg   120
tgcgctcccg acatgccccg c                                             141

SEQ ID NO: 357            moltype = DNA   length = 136
FEATURE                   Location/Qualifiers
source                    1..136
                          mol_type = other DNA
                          organism = synthetic construct
SEQUENCE: 357
aataggtacc actagtggtg actcatgggt gactcatggg tgactcatgg gtgactcatg    60
ggtgactcat gggtgactca tgggtgactc atgggtgact catgggtgac tcatgtgcgc   120
tcccgacatg ccccgc                                                   136

SEQ ID NO: 358            moltype = DNA   length = 146
FEATURE                   Location/Qualifiers
source                    1..146
                          mol_type = other DNA
                          organism = synthetic construct
SEQUENCE: 358
aataggtacc actagtgact cctcaaggga gagactcctc aagggtcgga ctcctcaagg    60
ggacgactcc tcaagggcta gactcctcaa gggactgact cctcaagggt gcgactcctc   120
aagggtgcgc tcccgacatg ccccgc                                        146

SEQ ID NO: 359            moltype = DNA   length = 132
FEATURE                   Location/Qualifiers
source                    1..132
                          mol_type = other DNA
```

-continued

```
                                organism = synthetic construct
SEQUENCE: 359
aataggtacc actagtggtg actcatgaga ggtgactcat gtcgggtgac tcatggacgg   60
tgactcatgc taggtgactc atgactggtg actcatgtgc ggtgactcat gtgcgctccc  120
gacatgcccc gc                                                       132

SEQ ID NO: 360         moltype = DNA   length = 142
FEATURE                Location/Qualifiers
source                 1..142
                       mol_type = other DNA
                       organism = synthetic construct
SEQUENCE: 360
aataggtacc actagtcggg ctttgatctt tcgggctttg atctttcggg ctttgatctt   60
tcgggctttg atctttcggg ctttgatctt tcgggctttg atctttcggg ctttgatctt  120
ttgcgctccc gacatgcccc gc                                            142

SEQ ID NO: 361         moltype = DNA   length = 136
FEATURE                Location/Qualifiers
source                 1..136
                       mol_type = other DNA
                       organism = synthetic construct
SEQUENCE: 361
aataggtacc actagtcttc tgggaaactt ctgggaaact tctgggaaac ttctgggaaa   60
cttctgggaa acttctggga aacttctggg aaacttctgg gaaacttctg ggaaatgcgc  120
tcccgacatg ccccgc                                                   136

SEQ ID NO: 362         moltype = DNA   length = 142
FEATURE                Location/Qualifiers
source                 1..142
                       mol_type = other DNA
                       organism = synthetic construct
SEQUENCE: 362
aataggtacc actagtcggg ctttgatctt tagacgggct ttgatctttt cgcgggcttt   60
gatctttgac cgggctttga tctttctacg ggctttgatc tttactcggg ctttgatctt  120
ttgcgctccc gacatgcccc gc                                            142

SEQ ID NO: 363         moltype = DNA   length = 132
FEATURE                Location/Qualifiers
source                 1..132
                       mol_type = other DNA
                       organism = synthetic construct
SEQUENCE: 363
aataggtacc actagtcttc tgggaaaaga cttctgggaa atcgcttctg ggaaagacct   60
tctgggaaac tacttctggg aaaactcttc tgggaaatgc cttctgggaa atgcgctccc  120
gacatgcccc gc                                                       132

SEQ ID NO: 364         moltype = DNA   length = 139
FEATURE                Location/Qualifiers
source                 1..139
                       mol_type = other DNA
                       organism = synthetic construct
SEQUENCE: 364
aataggtacc actagtgcgc tttgatgtgc ggggcggccc tttgaagttg gcgctttgat   60
gtgcggggcg gccctttgaa gttggcgctt tgatgtgcgg ggcggccctt tgaagttgtg  120
cgctcccgac atgccccgc                                                139

SEQ ID NO: 365         moltype = DNA   length = 135
FEATURE                Location/Qualifiers
source                 1..135
                       mol_type = other DNA
                       organism = synthetic construct
SEQUENCE: 365
aataggtacc actagtaatt cttagaaata aattcttaga aataaattct tagaaataaa   60
ttcttagaaa taaattctta gaaataaatt cttagaaata aattcttaga aatatgcgct  120
cccgacatgc cccgc                                                    135

SEQ ID NO: 366         moltype = DNA   length = 145
FEATURE                Location/Qualifiers
source                 1..145
                       mol_type = other DNA
                       organism = synthetic construct
SEQUENCE: 366
aataggtacc actagtgcgc tttgatgtgc ggggcggccc tttgaagttg agagcgcttt   60
gatgtgcggg gcggcccttt gaagttgtcg gcgctttgat gtgcggggcg gccctttgaa  120
gttgtgcgct cccgacatgc cccgc                                         145

SEQ ID NO: 367         moltype = DNA   length = 136
FEATURE                Location/Qualifiers
source                 1..136
```

```
                        mol_type = other DNA
                        organism = synthetic construct
SEQUENCE: 367
aataggtacc actagtaatt cttagaaata agaaattctt agaaatatcg aattcttaga    60
aatagacaat tcttagaaat actaaattct tagaaataac taattcttag aaatatgcgc   120
tcccgacatg ccccgc                                                    136

SEQ ID NO: 368        moltype = DNA   length = 127
FEATURE               Location/Qualifiers
source                1..127
                      mol_type = other DNA
                      organism = synthetic construct
SEQUENCE: 368
aataggtacc actagtaaca gctgttaaca gctgttaaca gctgttaaca gctgttaaca    60
gctgttaaca gctgttaaca gctgttaaca gctgttaaca gctgtttgcg ctcccgacat   120
gccccgc                                                              127

SEQ ID NO: 369        moltype = DNA   length = 147
FEATURE               Location/Qualifiers
source                1..147
                      mol_type = other DNA
                      organism = synthetic construct
SEQUENCE: 369
aataggtacc actagtaaaa caaaggatcc tttgttttaa aacaaaggat cctttgtttt    60
aaaacaaagg atcctttgtt ttaaaacaaa ggatcctttg ttttaaaaca aaggatcctt   120
tgtttttgcg ctcccgacat gccccgc                                       147

SEQ ID NO: 370        moltype = DNA   length = 138
FEATURE               Location/Qualifiers
source                1..138
                      mol_type = other DNA
                      organism = synthetic construct
SEQUENCE: 370
aataggtacc actagtaaca gctgttagaa acagctgttt cgaacagctg ttgacaacag    60
ctgttctaaa cagctgttac taacagctgt ttgcaacagc tgttgtaaac agctgtttgc   120
gctcccgaca tgccccgc                                                 138

SEQ ID NO: 371        moltype = DNA   length = 134
FEATURE               Location/Qualifiers
source                1..134
                      mol_type = other DNA
                      organism = synthetic construct
SEQUENCE: 371
aataggtacc actagtaaaa caaaggatcc tttgttttag aaaaacaaag gatcctttgt    60
ttttcgaaaa caaaggatcc tttgttttga caaaacaaag gatcctttgt ttttgcgctc   120
ccgacatgcc ccgc                                                     134

SEQ ID NO: 372        moltype = DNA   length = 109
FEATURE               Location/Qualifiers
source                1..109
                      mol_type = other DNA
                      organism = synthetic construct
SEQUENCE: 372
aataggtacc actagtcacc tgcacctgca cctgcacctg cacctgcacc tgcacctgca    60
cctgcacctg cacctgcacc tgcacctgtg cgctcccgac atgccccgc               109

SEQ ID NO: 373        moltype = DNA   length = 135
FEATURE               Location/Qualifiers
source                1..135
                      mol_type = other DNA
                      organism = synthetic construct
SEQUENCE: 373
aataggtacc actagtaaag tccaagtcca aaagtccaag tccaaaagtc caagtccaaa    60
agtccaagtc caaaagtcca agtccaaaag tccaagtcca aaagtccaag tccatgcgct   120
cccgacatgc cccgc                                                    135

SEQ ID NO: 374        moltype = DNA   length = 124
FEATURE               Location/Qualifiers
source                1..124
                      mol_type = other DNA
                      organism = synthetic construct
SEQUENCE: 374
aataggtacc actagtcacc tgagacacct gtcgcacctg gaccacctgc tacacctgac    60
tcacctgtgc cacctgagac acctgtcgca cctggaccac ctgtgcgctc cgacatgcc   120
ccgc                                                                124

SEQ ID NO: 375        moltype = DNA   length = 136
FEATURE               Location/Qualifiers
source                1..136
```

```
                              mol_type = other DNA
                              organism = synthetic construct
SEQUENCE: 375
aataggtacc actagtaaag tccaagtcca agaaaagtcc aagtccatcg aaagtccaag    60
tccagacaaa gtccaagtcc actaaaagtc caagtccaac taaagtccaa gtccatgcgc   120
tcccgacatg ccccgc                                                    136

SEQ ID NO: 376        moltype = DNA   length = 157
FEATURE               Location/Qualifiers
source                1..157
                      mol_type = other DNA
                      organism = synthetic construct
SEQUENCE: 376
ccatggtggc tttaccaaca gtaccggatt gccaagcttg gccgccgagg ccagatcttg    60
atatcctcga ggctagccca cctctgccaa cgggtcccgc gactcaaatc tggcggttaa   120
tggcgcgccg cggggcatgt cgggagcgca ggtaccg                            157

SEQ ID NO: 377        moltype = DNA   length = 95
FEATURE               Location/Qualifiers
source                1..95
                      mol_type = other DNA
                      organism = synthetic construct
SEQUENCE: 377
cggagtactg tcctccgagc ggagtactgt cctccgagcg gagtactgtc ctccgagcgg    60
agtactgtcc tccgagcgga gtactgtcct ccgag                               95

SEQ ID NO: 378        moltype = DNA   length = 99
FEATURE               Location/Qualifiers
source                1..99
                      mol_type = other DNA
                      organism = synthetic construct
SEQUENCE: 378
ggtgactcat gggtgactca tgggtgactc atgggtgact catgggtgac tcatgggtga    60
ctcatgggtg actcatgggt gactcatggg tgactcatg                           99

SEQ ID NO: 379        moltype = DNA   length = 146
FEATURE               Location/Qualifiers
source                1..146
                      mol_type = other DNA
                      organism = synthetic construct
SEQUENCE: 379
ggggcggggt gatgacacag caattcggga ctttccacgc ttgcgtgaga agagaccgga    60
agtgaatgac acagcaattc gcttgcgtga gaagctggga ctttcctagg ggcggggttg   120
ggactttcca catgacacag caatac                                        146

SEQ ID NO: 380        moltype = DNA   length = 155
FEATURE               Location/Qualifiers
source                1..155
                      mol_type = other DNA
                      organism = synthetic construct
SEQUENCE: 380
aataggtacc actagtgtcc ccacccacac attcctgtcc ccacccacac attcctgtcc    60
ccacccacac attcctgtcc ccacccacac attcctgtcc ccacccacac attcctgtcc   120
ccacccacac attcctgacc ggtgctagcc tcgag                              155

SEQ ID NO: 381        moltype = DNA   length = 155
FEATURE               Location/Qualifiers
source                1..155
                      mol_type = other DNA
                      organism = synthetic construct
SEQUENCE: 381
ctgagcgaca gtatagtgca cagtgactgc agcagtcatt cctttgatgt acgcaactcc    60
tttgatgtct atgcgtcctt tgatgttaag gattcctttg atgtaggtac atcctttgat   120
gtccgtaaat cctttgatgt gacgatcttg atatc                              155

SEQ ID NO: 382        moltype = DNA   length = 140
FEATURE               Location/Qualifiers
source                1..140
                      mol_type = other DNA
                      organism = synthetic construct
SEQUENCE: 382
tacctgatca aacatgcccg gacatgtcgt aagacataaa catgcccgga catgcctcg     60
caatctaaca tgcccggaca tgtcctcgca atctaacatg cccggacatg tctgcaagct   120
acaacatgcc cggacatgtc                                               140

SEQ ID NO: 383        moltype = DNA   length = 78
FEATURE               Location/Qualifiers
source                1..78
                      mol_type = other DNA
```

```
                          organism = synthetic construct
SEQUENCE: 383
ggggcggggt gatgacacag caattcggga ctttccacgc ttgcgtgaga agagaccgga    60
agtgaatgac acagcaat                                                  78

SEQ ID NO: 384          moltype = DNA   length = 66
FEATURE                 Location/Qualifiers
source                  1..66
                        mol_type = other DNA
                        organism = synthetic construct
SEQUENCE: 384
gcttgcgtga gaagctggga ctttcctagg ggcggggttg ggactttcca catgacacag    60
caatac                                                               66

SEQ ID NO: 385          moltype = DNA   length = 122
FEATURE                 Location/Qualifiers
source                  1..122
                        mol_type = other DNA
                        organism = synthetic construct
SEQUENCE: 385
ggtgactcat gggtgactca tgggtgactc atgctacgtg tgacggtgac tcatgggtga    60
ctcatgggtg actcatgaag tcgcagattg gtgactcatg ggtgactcat gggtgactca   120
tg                                                                  122

SEQ ID NO: 386          moltype = DNA   length = 123
FEATURE                 Location/Qualifiers
source                  1..123
                        mol_type = other DNA
                        organism = synthetic construct
SEQUENCE: 386
ggtgactcat gatgatgcca cgtcaccaat gccacgtcac caggtgactc atgggtgact    60
catgacgtgt gacatgccac gtcaccaatg ccacgtcacc aggtgactca tgggtgactc   120
atg                                                                 123

SEQ ID NO: 387          moltype = DNA   length = 117
FEATURE                 Location/Qualifiers
source                  1..117
                        mol_type = other DNA
                        organism = synthetic construct
SEQUENCE: 387
gggaggaagt cgtaaaactt gggaggaagt cgtaaaaaat gggaggaagt cgtaaaatgc    60
gggaggaagt cgtaaaagaa gggaggaagt cgtaaaaatc gggaggaagt cgtaaaa      117

SEQ ID NO: 388          moltype = DNA   length = 140
FEATURE                 Location/Qualifiers
source                  1..140
                        mol_type = other DNA
                        organism = synthetic construct
SEQUENCE: 388
atgactcagc aattagcgag ttagaatgac tcagcaatta tgcgtcggac atgactcagc    60
aattacatct cgattatgac tcagcaatta ggataggcat atgactcagc aattacatag   120
cagcaatgac tcagcaatta                                               140

SEQ ID NO: 389          moltype = DNA   length = 101
FEATURE                 Location/Qualifiers
source                  1..101
                        mol_type = other DNA
                        organism = synthetic construct
SEQUENCE: 389
acatcaaagg atttacggac atcaaaggat gtacctacat caaaggaatc cttaacatca    60
aaggacgcat agacatcaaa ggagttgcgt acatcaaagg a                       101

SEQ ID NO: 390          moltype = DNA   length = 99
FEATURE                 Location/Qualifiers
source                  1..99
                        mol_type = other DNA
                        organism = synthetic construct
SEQUENCE: 390
cacttccggt ttacttccac ttccggttta ctagcacttc cggtttacgc tcacttccgg    60
tttacgatca cttccggttt acagacactt ccggtttac                          99

SEQ ID NO: 391          moltype = DNA   length = 124
FEATURE                 Location/Qualifiers
source                  1..124
                        mol_type = other DNA
                        organism = synthetic construct
SEQUENCE: 391
gcgtccgccc gagtccccgc ctcgccgcca acgccaatgc tcatgcgtcc gcccgagtcc    60
ccgcctcgcc gccaacgcca tcatgcctgc gtccgcccga gtccccgcct cgccgccaac   120
```

```
gcca                                                                       124

SEQ ID NO: 392          moltype = DNA   length = 87
FEATURE                 Location/Qualifiers
source                  1..87
                        mol_type = other DNA
                        organism = synthetic construct
SEQUENCE: 392
caacatggcg gcgcccaaca tggcggctac caacatggcg gcctccaaca tggcggcagg   60
caacatggcg gctgccaaca tggcggc                                        87

SEQ ID NO: 393          moltype = DNA   length = 71
FEATURE                 Location/Qualifiers
source                  1..71
                        mol_type = other DNA
                        organism = synthetic construct
SEQUENCE: 393
tggttgctga ctaattgaga tgcatgcttt gcatacttct gcctgctggg gagcctgggg   60
actttccaca c                                                        71

SEQ ID NO: 394          moltype = DNA   length = 128
FEATURE                 Location/Qualifiers
source                  1..128
                        mol_type = other DNA
                        organism = synthetic construct
SEQUENCE: 394
gctcactcac tcactcactg aggcctgcag agcaaagctc tgcagtctgg ggacctttgg   60
tccccaggcc tcagtgagtg agtgagtgag cagagaggga gtggccaact ccatcactag  120
gggttcct                                                            128

SEQ ID NO: 395          moltype = DNA   length = 105
FEATURE                 Location/Qualifiers
source                  1..105
                        mol_type = other DNA
                        organism = synthetic construct
SEQUENCE: 395
ggtgactcat gggtgactca tgggtgactc atgggtgact catgctacgt ggtgactcat   60
gggtgactca tgggtgactc atgggtgact catgggtgac tcatg                  105

SEQ ID NO: 396          moltype = DNA   length = 140
FEATURE                 Location/Qualifiers
source                  1..140
                        mol_type = other DNA
                        organism = synthetic construct
SEQUENCE: 396
agtatagtgc acagtgactg cagcagggtg actcatgatg atgccacgtc accaatgcca   60
cgtcaccagg tgactcatgg gtgactcatg atgccacgtc accaatgcca cgtcaccagg  120
tgactcatgg gtgactcatg                                               140

SEQ ID NO: 397          moltype = DNA   length = 251
FEATURE                 Location/Qualifiers
source                  1..251
                        mol_type = other DNA
                        organism = synthetic construct
SEQUENCE: 397
taattgctga gtcattgctg ctatgtaatt gctgagtcat atgcctatcc tcctttgatg   60
tacgcaactc ctttgatgtc tatgcgtaat tgctgagtca taatcgagat gtaattgctg  120
agtcatgtcc gacgcatcct ttgatgttaa ggattccttt gatgtaggta cataattgct  180
gagtcatttc aactcgctaa ttgctgagtc atcatctcga cctcctttga tgtccgtaaa  240
tcctttgatg t                                                        251

SEQ ID NO: 398          moltype = DNA   length = 178
FEATURE                 Location/Qualifiers
source                  1..178
                        mol_type = other DNA
                        organism = synthetic construct
SEQUENCE: 398
actagtggtg actcatgggt gactcatggg tgactcatgg gtgactcatg ggtgactcat   60
gggtgactca tgggtgactc atgggtgact catgtgcgcg tcccgacatg             120
ccccgcggcg cgccattaac cgccagattt gagtcgcggg acccgttggc agaggtgg     178

SEQ ID NO: 399          moltype = DNA   length = 191
FEATURE                 Location/Qualifiers
source                  1..191
                        mol_type = other DNA
                        organism = synthetic construct
SEQUENCE: 399
agcttgcatg cctgcaggtc ggagtactgt cctccgagcg gagtactgtc ctccgagcgg   60
agtactgtcc tccgagcgga gtactgtcct ccgagcggag tactgtcctc cgagcggtgc  120
```

-continued

```
gctcccgaca tgccccgcgg cgcgccatta accgccagat ttgagtcgcg ggacccgttg    180
gcagaggtgg g                                                          191

SEQ ID NO: 400            moltype = DNA   length = 479
FEATURE                   Location/Qualifiers
source                    1..479
                          mol_type = other DNA
                          organism = synthetic construct
SEQUENCE: 400
ctcgaggcta gcatgatcac catgagtcac ccatgagtca cccatgagtc acccatgagt    60
cacccatgag tcacccatga gtcacccatg agtcacccat gagtcaccca tgagtcacca    120
ctagtggtac cacctcttaa caatacgttt cacaaatagt taaaaacatg catactgaaa    180
agcatacttt tgcaatgtta tttttaaaaa caaggaactc tttaacccag ggaagataat    240
cacttgggga aaggaaggtt cgtttctgag ttagcaacaa gtaaatgcag cactagtggg    300
tgggattgag gtgtgccctg gtgcataaat agagactcag ctgtgctggc acactcagaa    360
gcttggaccg catcctagcc gccgactcac acaaggcagg tgggtgagga aatccaggta    420
aggctcctga cagcagcttt agaagggtac ttgctggagt gaattcgggc ctctgatta     479

SEQ ID NO: 401            moltype = DNA   length = 302
FEATURE                   Location/Qualifiers
source                    1..302
                          mol_type = other DNA
                          organism = synthetic construct
SEQUENCE: 401
ggtgactcat gggtgactca tgggtgactc atgggtgact catgggtgac tcatgggtga    60
ctcatgggtg actcatgggt gactcatggg tgactcatgg tgatcatgct agcctcgagg    120
atatcaagat cggtaccggg aaaagttcag ctgagagata taaaagagca gtctttccag    180
cacctgcaaa tccagagcgg cgggcactga cgggcacttg caccgtgtgg acagactctc    240
cggttctgtg agtggttttt cttttcccgg gtcggacctg gagttcttag ggggatggct    300
ga                                                                    302

SEQ ID NO: 402            moltype = DNA   length = 251
FEATURE                   Location/Qualifiers
source                    1..251
                          mol_type = other DNA
                          organism = synthetic construct
SEQUENCE: 402
ggtgactcat gggtgactca tgggtgactc atgggtgact catgggtgac tcatgggtga    60
ctcatgggtg actcatgggt gactcatggg tgactcatgg tgatcatgct agcctcgagg    120
atatcaagat cggtaccatg acccacgtga tgctgagaag tactcctgcc ctaggaagag    180
actcagggca gagggaggaa ggacagcaga ccagacagtc acagcagcct tgacaaaacg    240
ttcctggaac t                                                          251

SEQ ID NO: 403            moltype = DNA   length = 387
FEATURE                   Location/Qualifiers
source                    1..387
                          mol_type = other DNA
                          organism = synthetic construct
SEQUENCE: 403
ggtgactcat gggtgactca tgggtgactc atgggtgact catgggtgac tcatgggtga    60
ctcatgggtg actcatgggt gactcatggg tgactcatgg tgatcatgct agcctcgagg    120
atatcaagat cggtaccggc ccgcccctt tccttacgcg gattggtagc tgcaggcttc    180
cctatctgat tggccgaacg aacgcagcgc gtaatttaaa atattgtatc tgtaacaaag    240
ctgcacctcg tgggcggagt tgtgctctgc ggctgcgaaa gtccagcttc ggcgactagg    300
tgtgagtaag ccagtatccc aggaggagca agtggcacgt cttcgggtga gtgtgcggct    360
gtgctggagc ccgggttacc agctctt                                        387

SEQ ID NO: 404            moltype = DNA   length = 187
FEATURE                   Location/Qualifiers
source                    1..187
                          mol_type = other DNA
                          organism = synthetic construct
SEQUENCE: 404
ggtgactcat gggtgactca tgggtgactc atgggtgact catgggtgac tcatgggtga    60
ctcatgggtg actcatgggt gactcatggg tgactcatgc ggtgctagct ataaaaggcc    120
agcagcagcc tgaccacatc tcatcctcct cgaggatatc aagatctggc ctcggcggcc    180
aaattca                                                               187

SEQ ID NO: 405            moltype = DNA   length = 220
FEATURE                   Location/Qualifiers
source                    1..220
                          mol_type = other DNA
                          organism = synthetic construct
SEQUENCE: 405
ggggcgggt gatgacacag caattcggga ctttccacgc ttgcgtgaga agagaccgga     60
agtgaatgac acagcaattc gcttgcgtga gaagctggga ctttcctagg ggcgggggttg   120
ggactttcca catgacacag caatacaacg cgtcccgaca tgccccgcgg cgcgccatta    180
accgccagat ttgagtcgcg ggacccgttg gcagaggtgg                          220
```

-continued

```
SEQ ID NO: 406            moltype = DNA   length = 499
FEATURE                   Location/Qualifiers
source                    1..499
                          mol_type = other DNA
                          organism = synthetic construct
SEQUENCE: 406
ggggcggggt gatgacacag caattcggga ctttccacgc ttgcgtgaga agagaccgga   60
agtgaatgac acagcaattc gcttgcgtga gaagctggga ctttcctagg ggcggggttg  120
ggactttcca catgacacag caatacagta ccacctctta acaatacgtt tcacaaatag  180
ttaaaaacat gcatactgaa aagcatactt ttgcaatgtt atttttaaaa acaaggaact  240
ctttaaccca gggaagataa tcacttgggg aaaggaaggt tcgtttctga gttagcaaca  300
agtaaatgca gcactagtgg gtgggattga ggtgtgccct ggtgcataaa tagagactca  360
gctgtgctgg cacactcaga agcttggacc gcatcctagc cgccgactca cacaaggcag  420
gtgggtgagg aaatccaggt aaggctcctg acagcagctt tagaagggta cttgctggag  480
tgaattcggg cctctgatt                                              499

SEQ ID NO: 407            moltype = DNA   length = 347
FEATURE                   Location/Qualifiers
source                    1..347
                          mol_type = other DNA
                          organism = synthetic construct
SEQUENCE: 407
ggggcggggt gatgacacag caattcggga ctttccacgc ttgcgtgaga agagaccgga   60
agtgaatgac acagcaattc gcttgcgtga gaagctggga ctttcctagg ggcggggttg  120
ggactttcca catgacacag caatacacta gtaacatttc tctggcctaa ctggccggta  180
ccgggaaaag ttcagctgag agatataaaa gagcagtctt tccagcacct gcaaatccag  240
agcggcgggc actgacgggc acttgcaccg tgtggacaga ctctccggtt ctgtgagtgg  300
tttttctttt cccgggtcgg acctggagtt cttaggggga tggctga             347

SEQ ID NO: 408            moltype = DNA   length = 296
FEATURE                   Location/Qualifiers
source                    1..296
                          mol_type = other DNA
                          organism = synthetic construct
SEQUENCE: 408
ggggcggggt gatgacacag caattcggga ctttccacgc ttgcgtgaga agagaccgga   60
agtgaatgac acagcaattc gcttgcgtga gaagctggga ctttcctagg ggcggggttg  120
ggactttcca catgacacag caatacacta gtaacatttc tctggcctaa ctggccggta  180
ccatgaccca cgtgatgctg agaagtactc ctgccctagg aagagactca gggcagaggg  240
aggaaggaca gcagaccaga cagtcacagc agccttgaca aaacgttcct ggaact      296

SEQ ID NO: 409            moltype = DNA   length = 433
FEATURE                   Location/Qualifiers
source                    1..433
                          mol_type = other DNA
                          organism = synthetic construct
SEQUENCE: 409
ggggcggggt gatgacacag caattcggga ctttccacgc ttgcgtgaga agagaccgga   60
agtgaatgac acagcaattc gcttgcgtga gaagctggga ctttcctagg ggcggggttg  120
ggactttcca catgacacag caatacacta gtaacatttc tctggcctaa ctggccggta  180
ccggcccgcc cccttttcctt acgcggattg gtagctgcag gcttccctat ctgattggcc  240
gaacgaacgc agcgcgtaat ttaaaatatt gtatctgtaa caaagctgca cctcgtgggc  300
ggagttgtgc tctgcggctg cgaaagtcca gcttcggcga ctaggtgtga gtaagccagt  360
atcccaggag gagcaagtgg cacgtcttcg ggtgagtgtg cggctgtgct ggagcccggg  420
ttaccagctc tta                                                    433

SEQ ID NO: 410            moltype = DNA   length = 193
FEATURE                   Location/Qualifiers
source                    1..193
                          mol_type = other DNA
                          organism = synthetic construct
SEQUENCE: 410
tccccaccca cacattcctg tccccaccca cacattcctg tccccaccca cacattcctg   60
tccccaccca cacattcctg tccccaccca cacattcctg tccccaccca cacattcctg  120
tgcgctcccg acatgccccg cggcgcgcca ttaaccgcca gatttgagtc gcgggacccg  180
ttggcagagg tgg                                                    193

SEQ ID NO: 411            moltype = DNA   length = 288
FEATURE                   Location/Qualifiers
source                    1..288
                          mol_type = other DNA
                          organism = synthetic construct
SEQUENCE: 411
ggtgactcat gggtgactca tgggtgactc atgggtgact catgggtgac tcatgggtga   60
ctcatgggtg actcatgggt gactcatgac tagtgtcccc acccacacat tcctgtcccc  120
acccacacat tcctgtcccc acccacacat tcctgtcccc acccacacat tcctgtcccc  180
acccacacat tcctgtcccc acccacacat tcctgtcgc tcccgacatg ccccgcggcg  240
cgccattaac cgccagattt gagtcgcggg acccgttggc agaggtgg             288
```

```
SEQ ID NO: 412          moltype = DNA   length = 461
FEATURE                 Location/Qualifiers
source                  1..461
                        mol_type = other DNA
                        organism = synthetic construct
SEQUENCE: 412
ctgagcgaca gtatagtgca cagtgactgc agcagtcatt cctttgatgt acgcaactcc   60
tttgatgtct atgcgtcctt tgatgttaag gattcctttg atgtaggtac atcctttgat   120
gtccgtaaat cctttgatgt gacgtctacg tacatactga aaagcatact tttgcaatgt   180
tatttttaaa aacaaggaac tctttaaccc agggaagata atcacttggg gaaaggaagg   240
ttcgtttctg agttagcaac aagtaaatgc agcactagtg ggtgggattg aggtgtgccc   300
tggtgcataa atagagactc agctgtgctg gcacactcag aagcttggac cgcatcctag   360
ccgccgactc acacaaggca ggtgggtgag gaaatccagg taaggctcct gacagcagct   420
ttagaagggt acttgctgga gtgaattcgg gcctctgatt a                       461

SEQ ID NO: 413          moltype = DNA   length = 634
FEATURE                 Location/Qualifiers
source                  1..634
                        mol_type = other DNA
                        organism = synthetic construct
SEQUENCE: 413
ctgagcgaca gtatagtgca cagtgactgc agcagtcatt cctttgatgt acgcaactcc   60
tttgatgtct atgcgtcctt tgatgttaag gattcctttg atgtaggtac atcctttgat   120
gtccgtaaat cctttgatgt gacgatcttg atatcctcga ggctagcatg atcaccatga   180
gtcacccatg agtcacccat gagtcaccca tgagtcaccc atgagtcacc catgagtcac   240
ccatgagtca cccatgagtc acccactagt ggtaccacct cttaacaata   300
cgtttcacaa atagttaaaa acatgcatac tgaaaagcat acttttgcaa tgttattttt   360
aaaaacaagg aactctttaa cccagggaag ataatcactt ggggaaagga aggttcgttt   420
ctgagttagc aacaagtaaa tgcagcacta gtgggtggga ttgaggtgtg ccctggtgca   480
taaatagaga ctcagctgtg ctggcacact cagaagcttg gaccgcatcc tagccgccga   540
ctcacacaag gcaggtgggt gaggaaatcc aggtaaggct cctgacagca gctttagaag   600
ggtacttgct ggagtgaatt cgggcctctg atta                              634

SEQ ID NO: 414          moltype = DNA   length = 764
FEATURE                 Location/Qualifiers
source                  1..764
                        mol_type = other DNA
                        organism = synthetic construct
SEQUENCE: 414
ctgagcgaca gtatagtgca cagtgactgc agcagtcatt cctttgatgt acgcaactcc   60
tttgatgtct atgcgtcctt tgatgttaag gattcctttg atgtaggtac atcctttgat   120
gtccgtaaat cctttgatgt gacgtctacg tatctacctg atcaaacatg cccggacatg   180
tcgtaagaca taaacatgcc cggacatgtc ctcgcaacct aacatgcccg gacatgtcct   240
cgcaatctaa catgcccgga catgtctgca agctacaaca tgcccggaca tgtctacaat   300
atacgtatct acctgatcaa acatgcccgg acatgtcgta agacataaac atgcccggac   360
atgtcctcgc aatctaacat gcccggacat gtcctcgcaa tctaacatgc cggacatgt   420
ctgcaagcta caacatgccc ggacatgtct acgtacatac tgaaaagcat acttttgcaa   480
tgttattttt aaaaacaagg aactctttaa cccagggaag ataatcactt ggggaaagga   540
aggttcgttt ctgagttagc aacaagtaaa tgcagcacta gtgggtggga ttgaggtgtg   600
ccctggtgca taaatagaga ctcagctgtg ctggcacact cagaagcttg gaccgcatcc   660
tagccgccga ctcacacaag gcaggtgggt gaggaaatcc aggtaaggct cctgacagca   720
gctttagaag ggtacttgct ggagtgaatt cgggcctctg atta                    764

SEQ ID NO: 415          moltype = DNA   length = 412
FEATURE                 Location/Qualifiers
source                  1..412
                        mol_type = other DNA
                        organism = synthetic construct
SEQUENCE: 415
ggggcggggt gatgacacag caattcggga ctttccacgc ttgcgtgaga agagaccgga   60
agtgaatgac acagcaatgg atccgcttgc gtgagaagct gggactttcc taggggcggg   120
gttgggactt ccacatgac acagcaatac ctcgagggta ccggcccgcc ccctttcctt   180
acgcggattg gtagctgcag gcttccctat ctgattggcc gaacgaacgc agcgcgtaat   240
ttaaaatatt gtatctgtaa caaagctgca cctcgtcggac ggagttgtgc tctgcggctg   300
cgaaagtcca gcttcggcga ctaggtgtga gtaagccagt atcccaggag gagcaagtgg   360
cacgtcttcg ggtgagtgtg cggctgtgct ggagcccggg ttaccagctc tt           412

SEQ ID NO: 416          moltype = DNA   length = 326
FEATURE                 Location/Qualifiers
source                  1..326
                        mol_type = other DNA
                        organism = synthetic construct
SEQUENCE: 416
ggggcggggt gatgacacag caattcggga ctttccacgc ttgcgtgaga agagaccgga   60
agtgaatgac acagcaatgg atccgcttgc gtgagaagct gggactttcc taggggcggg   120
gttgggactt ccacatgac acagcaatac ctcgagggta ccgggaaaag ttcagctgag   180
agatataaaa gagcagtctt tccagcacct gcaaatccag agcggcgggc actgacgggc   240
acttgcaccg tgtggacaga ctctccggtt ctgtgagtgg tttttctttt cccgggtcgg   300
acctggagtt cttaggggga tggctg                                        326
```

```
SEQ ID NO: 417            moltype = DNA  length = 534
FEATURE                   Location/Qualifiers
source                    1..534
                          mol_type = other DNA
                          organism = synthetic construct
SEQUENCE: 417
ggggcggggt gatgacacag caattcggga ctttccacgc ttgcgtgaga agagaccgga    60
agtgaatgac acagcaatgg atccgcttgc gtgagaagct gggactttcc taggggcggg   120
gttgggactt tccacatgac acagcaatac ctcgagggtg actcatgggt gactcatggg   180
tgactcatgc tacgtgtgac ggtgactcat gggtgactca tgggtgactc atgaagtcgc   240
agattggtga ctcatgggtg actcatgggt gactcatggg taccggcccg cccccttttcc   300
ttacgcggat tggtagctgc aggcttccct atctgattgg ccgaacgaac gcagcgcgta   360
atttaaaata ttgtatctgt aacaaagctg cacctcgtg gcggagttgt gctctgcggc   420
tgcgaaagtc cagcttcggc gactaggtgt gagtaagcca gtatcccagg aggagcaagt   480
ggcacgtctt cgggtgagtg tgcggctgtg ctggagcccg ggttaccagc tctt          534

SEQ ID NO: 418            moltype = DNA  length = 535
FEATURE                   Location/Qualifiers
source                    1..535
                          mol_type = other DNA
                          organism = synthetic construct
SEQUENCE: 418
ggggcggggt gatgacacag caattcggga ctttccacgc ttgcgtgaga agagaccgga    60
agtgaatgac acagcaatgg atccgcttgc gtgagaagct gggactttcc taggggcggg   120
gttgggactt tccacatgac acagcaatac ctcgagggtg actcatgatg atgccacgtc   180
accaatgcca cgtcaccagg tgactcatg gtgactcatg acgtgtgaca tgccacgtca   240
ccaatgccac gtcaccaggt gactcatggg tgactcatgg gtaccggccc gccccctttc   300
cttacgcgga ttggtagctg caggcttccc tatctgattg gccgaacgaa cgcagcgcgt   360
aatttaaaat attgtatctg taacaaagct gcacctcgtg ggcggagttg tgctctgcgg   420
ctgcgaaagt ccagcttcgg cgactaggtg tgagtaagcc agtatcccag gaggagcaag   480
tggcacgtct tcgggtgagt gtgcggctgt gctggagccc gggttaccag ctctt          535

SEQ ID NO: 419            moltype = DNA  length = 529
FEATURE                   Location/Qualifiers
source                    1..529
                          mol_type = other DNA
                          organism = synthetic construct
SEQUENCE: 419
ggggcggggt gatgacacag caattcggga ctttccacgc ttgcgtgaga agagaccgga    60
agtgaatgac acagcaatgg atccgcttgc gtgagaagct gggactttcc taggggcggg   120
gttgggactt tccacatgac acagcaatac ctcgaggga ggaagtcgta aaacttggga   180
ggaagtcgta aaaatggga ggaagtcgta aaatgcggta aaagaaggga   240
ggaagtcgta aaaatcggga ggaagtcgta aaaggtaccg gccgcccccc tttccttacg   300
cggattggta gctgcaggct tccctatctg attggccgaa cgaacgcagc gcgtaattta   360
aaatattgta tctgtaacaa agctgcacct cgtgggcgga gttgtgctct gcggctgcga   420
aagtccagct tcggcgacta ggtgtgagta agccagtatc ccaggaggag caagtggcac   480
gtcttcgggt gagtgtgcgg ctgtgctgga gcccgggtta ccagctctt              529

SEQ ID NO: 420            moltype = DNA  length = 448
FEATURE                   Location/Qualifiers
source                    1..448
                          mol_type = other DNA
                          organism = synthetic construct
SEQUENCE: 420
ggggcggggt gatgacacag caattcggga ctttccacgc ttgcgtgaga agagaccgga    60
agtgaatgac acagcaatgg atccgcttgc gtgagaagct gggactttcc taggggcggg   120
gttgggactt tccacatgac acagcaatac ctcgagggtg actcatgggt gactcatggg   180
tgactcatgc tacgtgtgac ggtgactcat gggtgactca tgggtgactc atgaagtcgc   240
agattggtga ctcatgggtg actcatgggt gactcatggg taccgggaaa agttcagctg   300
agagatataa aagagcagtc tttccagcac ctgcaaatcc agagcggcgg gcactgacgg   360
gcacttgcac cgtgtggaca gactctccgg ttctgtgagt ggtttttctt ttcccgggtc   420
ggacctggag ttcttagggg gatggctg                                        448

SEQ ID NO: 421            moltype = DNA  length = 449
FEATURE                   Location/Qualifiers
source                    1..449
                          mol_type = other DNA
                          organism = synthetic construct
SEQUENCE: 421
ggggcggggt gatgacacag caattcggga ctttccacgc ttgcgtgaga agagaccgga    60
agtgaatgac acagcaatgg atccgcttgc gtgagaagct gggactttcc taggggcggg   120
gttgggactt tccacatgac acagcaatac ctcgagggtg actcatgatg atgccacgtc   180
accaatgcca cgtcaccagg tgactcatg gtgactcatg acgtgtgaca tgccacgtca   240
ccaatgccac gtcaccaggt gactcatggg tgactcatgg gtaccgggaa aagttcagct   300
gagagatata aaagagcagt ctttccagca cctgcaaatc cagagcggcg ggcactgacg   360
ggcacttgca ccgtgtggac agactctccg gttctgtgag tggtttttct tttcccgggt   420
cggacctgga gttcttaggg ggatggctg                                       449
```

```
SEQ ID NO: 422           moltype = DNA   length = 564
FEATURE                  Location/Qualifiers
source                   1..564
                         mol_type = other DNA
                         organism = synthetic construct
SEQUENCE: 422
atgactcagc aattagcgag ttagaatgac tcagcaatta tgcgtcggac atgactcagc      60
aattacatct cgattatgac tcagcaatta ggataggcat atgactcagc aattacatag     120
cagcaatgac tcagcaatta gctagtaagc ttggggcggg gtgatgacac agcaattcgg     180
gactttccac gcttgcgtga aagagaccg gaagtgaatg acacagcaat ggatccgctt      240
gcgtgagaag ctgggacttt cctaggggcg gggttgggac tttccacatg acacagcaat     300
acctcgaggt taccggcccg cccccttccc ttacgcggat tggtagctgc aggcttccct     360
atctgattgg ccgaacgaac gcagcgcgta atttaaaata ttgtatctgt aacaaagctg     420
cacctcgtgg gcggagttgt gctctgcggc tgcgaaagtc cagcttcggc gactaggtgt     480
gagtaagcca gtatcccagg aggagcaagt ggcacgtctt cgggtgagtg tgcggctgtg     540
ctggagcccg ggttaccagc tctt                                            564

SEQ ID NO: 423           moltype = DNA   length = 471
FEATURE                  Location/Qualifiers
source                   1..471
                         mol_type = other DNA
                         organism = synthetic construct
SEQUENCE: 423
ggggcggggt gatgacacag caattcggga ctttccacgc ttgcgtgaga agagaccgga      60
agtgaatgac acagcaatgg atccgcttgc gtgagaagct gggactttcc taggggcggg     120
gttgggactt tccacatgac acagcaatac ctcgaggta cccatactga aaagcatact      180
tttgcaatgt tattttttaaa aacaaggaac tctttaaccc agggaagata atcacttggg     240
gaaaggaagg ttcgtttctg agttagcaac aagtaaatgc agcactagtg ggtgggattg     300
aggtatgccc tggtgcataa atagagactc agctgtgctg gcacactcag aagcttggac     360
cgcatcctag ccgccgactc acacaaggca ggtgggtgag gaaatccagg taaggctcct     420
gacagcagct ttagaagggt acttgctgga gtgaattcgg gcctctgatt a             471

SEQ ID NO: 424           moltype = DNA   length = 525
FEATURE                  Location/Qualifiers
source                   1..525
                         mol_type = other DNA
                         organism = synthetic construct
SEQUENCE: 424
acatcaaagg atttacggac atcaaaggat gtacctacat caaaggaatc cttaacatca      60
aaggacgcat agacatcaaa ggagttgcgt acatcaaagg agctagtaag cttggggcgg     120
ggtgatgaca cagcaattcg ggactttcca cgcttgcgtg agaagagacc ggaagtgaat     180
gacacagcaa tggatccgct tgcgtgagaa gctgggactt tcctaggggc ggggttggga     240
ctttccacat gacacagcaa tacctcgagg gtaccggccc gccccctttc cttacgcgga     300
ttggtagctg caggcttccc tatctgattg gccgaacgaa cgcagcgcgt aatttaaaat     360
attgtatctg taacaaagct gcacctcgtg ggcggagttg tgctctgcgg ctgcgaaagt     420
ccagcttcgg cgactaggtg tgagtaagcc agtatcccag gaggagcaag tggcacgtct     480
tcgggtgagt gtgcggctgt gctggagccc gggttaccag ctctt                     525

SEQ ID NO: 425           moltype = DNA   length = 546
FEATURE                  Location/Qualifiers
source                   1..546
                         mol_type = other DNA
                         organism = synthetic construct
SEQUENCE: 425
ggtgactcat gggtgactca tgggtgactc atgctacgtg tgacggtgac tcatgggtga      60
ctcatgggtg actcatgaag tcgcagattg gtgactcatg ggtgactcat gggtgactca     120
tgactagtaa gcttggggcg gggtgatgac acagcaattc gggactttcc acgcttgcgt     180
gagaagagac cggaagtgaa tgacacagca atggatccgc ttgcgtgaga gctgggact      240
ttcctagggg cggggttggg actttccaca tgacacagca atacctcgag ggtaccggcc     300
cgccccctttt ccttacgcgg attggtagct gcaggcttcc ctatctgatt ggccgaacga     360
acgcagcgcg taatttaaaa tattgtatct gtaacaaagc tgcacctcgt gggcggagtt     420
gtgctctgcg gctgcgaaag tccagcttcg gcgactaggt gtgagtaagc cagtatccca     480
ggaggagcaa gtggcacgtc ttcgggtgag tgtgcggctg tgctggagcc cgggttacca     540
gctctt                                                                546

SEQ ID NO: 426           moltype = DNA   length = 547
FEATURE                  Location/Qualifiers
source                   1..547
                         mol_type = other DNA
                         organism = synthetic construct
SEQUENCE: 426
ggtgactcat gatgatgcca cgtcaccaat gccacgtcac caggtgactc atgggtgact      60
catgacgtgt gacatgccac gtcaccaatg ccacgtcacc aggtgactca tgggtgactc     120
atgactagta agcttggggc ggggtgatga cacagcaatt cgggactttc cacgcttgcg     180
tgagaagaga ccggaagtga atgacacagc aatggatccg cttgcgtgag aagctgggac     240
tttcctaggg gcgggggttgg actttccac atgacacagc aatacctcga gggtaccggc     300
cgccccctt tccttacgcg gattggtagc tgcaggcttc cctatctgat tggccgaacg     360
aacgcagcgc gtaatttaaa atattgtatc tgtaacaaag ctgcacctcg tgggcggagt     420
tgtgctctgc ggctgcgaaa gtccagcttc ggcgactagg tgtgagtaag ccagtatccc     480
```

-continued

```
aggaggagca agtggcacgt cttcgggtga gtgtgcggct gtgctggagc ccgggttacc   540
agctctt                                                             547

SEQ ID NO: 427          moltype = DNA   length = 523
FEATURE                 Location/Qualifiers
source                  1..523
                        mol_type = other DNA
                        organism = synthetic construct
SEQUENCE: 427
cacttccggt ttacttccac ttccggttta ctagcacttc cggtttacgc tcacttccgg   60
tttacgatca cttccggttt acagacactt ccggtttacg ctagtaagct tggggcgggg   120
tgatgacaca gcaattcggg actttccacg cttgcgtgag aagagaccgg aagtgaatga   180
cacagcaatg gatccgcttg cgtgagaagc tgggactttc ctaggggcgg ggttgggact   240
ttccacatga cacagcaata cctcgagggt accggcccgc ccctttcct tacgcggatt    300
ggtagctgca ggcttcccta tctgattggc cgaacgaacg cagcgcgtaa tttaaaatat   360
tgtatctgta acaaagctgc acctcgtggg cggagttgtg ctctgcggct gcgaaagtcc   420
agcttcggcg actaggtgtg agtaagccag tatcccagga ggagcaagtg gcacgtcttc   480
gggtgagtgt gcggctgtgc tggagcccgg gttaccagct ctt                     523

SEQ ID NO: 428          moltype = DNA   length = 478
FEATURE                 Location/Qualifiers
source                  1..478
                        mol_type = other DNA
                        organism = synthetic construct
SEQUENCE: 428
atgactcagc aattagcgag ttagaatgac tcagcaatta tgcgtcggac atgactcagc   60
aattacatct cgattatgac tcagcaatta ggataggcat atgactcagc aattacatag   120
cagcaatgac tcagcaatta gctagtaagc ttggggcggg gtgatgacac agcaattcgg   180
gactttccac gcttgcgtga gaagagaccg gaagtgaatg acacagcaat ggatccgctt   240
gcgtgagaag ctgggacttt cctaggggcg gggttgggac tttccacatg acacagcaat   300
acctcgaggg taccgggaaa agttcagctg agagatataa aagagcagtc tttccacac    360
ctgcaaatcc agagcggcgg gcactgacgg gcacttgcac cgtgtggaca gactctccgg   420
ttctgtgagt ggtttttctt ttcccgggtc ggacctggag ttcttagggg gatggctg     478

SEQ ID NO: 429          moltype = DNA   length = 439
FEATURE                 Location/Qualifiers
source                  1..439
                        mol_type = other DNA
                        organism = synthetic construct
SEQUENCE: 429
acatcaaagg atttacggac atcaaaggat gtacctacat caaaggaatc cttaacatca   60
aaggacgcat agacatcaaa ggagttgcgt acatcaaagg agctagtaag cttggggcgg   120
ggtgatgaca gcaattcgg gactttcca cgcttgcgta agagagacc ggaagtgaat     180
gacacagcaa tggatccgct tgcgtgagaa gctgggactt tcctaggggc ggggttggga   240
ctttccacat gacacagcaa tacctcgagg gtaccgggaa aagttcagct gagagatata   300
aaagagcagt ctttccagca cctgcaaatc cagagcggcg ggcactgacg ggcacttgca   360
ccgtgtggac agactctccg gttctgtgag tggtttttct tttcccgggt cggacctgga   420
gttcttaggg ggatggctg                                                439

SEQ ID NO: 430          moltype = DNA   length = 460
FEATURE                 Location/Qualifiers
source                  1..460
                        mol_type = other DNA
                        organism = synthetic construct
SEQUENCE: 430
ggtgactcat gggtgactca tgggtgactc atgctacgtg tgacggtgac tcatgggtga   60
ctcatgggtg actcatgaag tcgcagattg gtgactcatg ggtgactcat gggtgactca   120
tgactagtaa gcttggggcg gggtgatgac acagcaattc gggactttcc acgcttgcgt   180
gagaagagac cggaagtgaa tgacacagca atggatccgc ttgcgtgaga agctgggact   240
ttcctagggg cggggttggg actttccaca tgacacagca atacctcgag ggtaccggga   300
aaagttcagc tgagagatat aaaagagcag tctttccagc acctgcaaat ccagagcggc   360
gggcactgac gggcacttgc accgtgtgga cagactctcc ggttctgtga gtggtttttc   420
ttttcccggg tcggacctgg agttcttagg gggatggctg                         460

SEQ ID NO: 431          moltype = DNA   length = 461
FEATURE                 Location/Qualifiers
source                  1..461
                        mol_type = other DNA
                        organism = synthetic construct
SEQUENCE: 431
ggtgactcat gatgatgcca cgtcaccaat gccacgtcac caggtgactc atgggtgact   60
catgacgtgt gacatgccac gtcaccaatg ccacgtcacc aggtgactca tgggtgactc   120
atgactagta agcttggggc ggggtgatga cacagcaatt cgggactttc cacgcttgcg   180
tgagaagaga ccggaagtga atgacacagc aatggatccg cttgcgtgag aagctgggac   240
tttcctaggg gcgggggttgg gactttccac atgacacagc aatacctcga gggtaccggg   300
aaaagttcag ctgagagata taaaagagca gtctttccag cacctgcaaa tccagagcgg   360
cgggcactga cgggcacttg caccgtgtgg acagactctc cggttctgtg agtggttttt   420
cttttcccgg tcggacctg gagttcttag gggatggct g                         461
```

-continued

```
SEQ ID NO: 432        moltype = DNA   length = 437
FEATURE               Location/Qualifiers
source                1..437
                      mol_type = other DNA
                      organism = synthetic construct
SEQUENCE: 432
gtaaaccgga agtgtctgta aaccggaagt gatcgtaaac cggaagtgag cgtaaaccgg   60
aagtgctagt aaaccggaag tggaagtaaa ccggaagtga ctagtaagct tggggcgggg  120
tgatgacaca gcaattcggg actttccacg cttgcgtgag aagagaccgg aagtgaatga  180
cacagcaatg gatccgcttg cgtgagaagc tgggactttc ctaggggcgg ggttgggact  240
ttccacatga cacagcaata cctcgagggt accgggaaaa gttcagctga gagatataaa  300
agagcagtct ttccagcacc tgcaaatcca gagcggcggg cactgacggg cacttgcacc  360
gtgtggacag actctccggt tctgtgagtg gtttttcttt tcccgggtcg gacctggagt  420
tcttagggggg atggctg                                              437

SEQ ID NO: 433        moltype = DNA   length = 665
FEATURE               Location/Qualifiers
source                1..665
                      mol_type = other DNA
                      organism = synthetic construct
SEQUENCE: 433
ggggcggggt gatgacacag caattcggga ctttccacgc ttgcgtgaga agagaccgga   60
agtgaatgac acagcaatgg atccgcgtcc gcccgagtcc ccgcctcgcc gccaacgcca  120
atgctcatgc gtccgcccga gtccccgcct cgccgccaac gccatcatgc ctgcgtccgc  180
ccgagtcccc gcctcgccgc caacgccagg atccgcttgc gtgagaagct gggactttcc  240
taggggcggg gttgggactt tccacatgac acagcaataa ctcgagggtg actcatgatg  300
atgccacgtc accaatgcca cgtcaccagg tgactcatgg tgactcatg acgtgtgaca  360
tgccacgtca ccaatgccac gtcaccaggt gactcatggg tgactcatgg gtaccggccc  420
gcccccttttc cttacgcgga ttggtagctg caggcttccc tatctgattg ccgaacgaa  480
cgcagcgcgt aatttaaaat attgtatctg taacaaagct gcacctcgtg ggcggagttg  540
tgctctgcgg ctgcgaaagt ccagcttcgg cgactaggtg tgagtaagcc agtatcccag  600
gaggagcaag tggcacgtct tcgggtgagt gtgcggctgt gctggagccc gggttaccag  660
ctctt                                                            665

SEQ ID NO: 434        moltype = DNA   length = 687
FEATURE               Location/Qualifiers
source                1..687
                      mol_type = other DNA
                      organism = synthetic construct
SEQUENCE: 434
atgactcagc aattagcgag ttagaatgac tcagcaatta tgcgtcggac atgactcagc   60
aattacatct cgattatgac tcagcaatta ggataggcat atgactcagc aattacatag  120
cagcaatgac tcagcaatta gctagtaagc ttggggcggg gtgatgacac agcaattcgg  180
gactttccac gcttgcgtga aagagaccg gaagtgaatg acacagcaat ggatccgctt  240
gcgtgagaag ctgggacttt cctaggggcg gggttgggac tttccacatg acacagcaat  300
acctcgaggg tgactcatga tgatgccacg tcaccaatgc cacgtcacca ggtgactcat  360
gggtgactca tgacgtgtga catgccacgt caccaatgcc acgtcaccag gtgactcatg  420
ggtgactcat gggtaccggc ccgccccctt tccttacgcg gattggtagc tgcaggcttc  480
cctatctgat tggccgaacg aacgcagcgc gtaatttaaa atattgtatc tgtaacaaag  540
ctgcacctcg tgggcggagt tgtgctctgc ggctgcgaaa gtccagcttc ggcgactagg  600
tgtgagtaag ccagtatccc aggaggagca agtggcacgt cttcgggtga gtgtgcggct  660
gtgctggagc ccgggttacc agctctt                                     687

SEQ ID NO: 435        moltype = DNA   length = 648
FEATURE               Location/Qualifiers
source                1..648
                      mol_type = other DNA
                      organism = synthetic construct
SEQUENCE: 435
acatcaaagg atttacggac atcaaaggat gtacctacat caaaggaatc cttaacatca   60
aaggacgcat agacatcaaa ggagttgcgt acatcaaagg agctagtaag cttggggcgg  120
ggtgatgaca cagcaattcg ggactttcca cgcttgcgtg agaagagacc ggaagtgaat  180
gacacagcaa tggatccgct tgcgtgagaa gctgggactt cctaggggc ggggttggga  240
ctttccacat gacacagcaa tacctcgagg tgactcatga tgatgccac gtcaccaatg  300
ccacgtcacc aggtgactca tgggtgactc atgacgtgtg acatgccacg tcaccaatgc  360
cacgtcacca ggtgactcat gggtgactca tgggtaccgg cccgccccct tccttacgc  420
ggattggtag ctgcaggctt ccctatctga ttggccgaac gaacgcagcg cgtaatttaa  480
aatattgtat ctgtaacaaa gctgcacctc gtgggcggag ttgtgctctg cggctgcgaa  540
agtccagctt cggcgactag gtgtgagtaa gccagtatcc caggaggagc aagtggcacg  600
tcttcgggtg agtgtgcggc tgtgctggag cccgggttac cagctctt              648

SEQ ID NO: 436        moltype = DNA   length = 646
FEATURE               Location/Qualifiers
source                1..646
                      mol_type = other DNA
                      organism = synthetic construct
SEQUENCE: 436
cacttccggt ttacttccac ttccggttta ctagcacttc cggtttacgc tcacttccgg   60
tttacgatca cttccggttt acagacactt ccggtttacg ctagtaagct tggggcgggg  120
```

```
tgatgacaca gcaattcggg actttccacg cttgcgtgag aagagaccgg aagtgaatga  180
cacagcaatg gatccgcttg cgtgagaagc tgggactttc ctaggggcgg ggttgggact  240
ttccacatga cacagcaata cctcgagggt gactcatgat gatgccacgt caccaatgcc  300
acgtcaccag gtgactcatg ggtgactcat gacgtgtgac atgccacgtc accaatgcca  360
cgtcaccagg tgactcatgg gtgactcatg ggtaccggcc cgcccccttt ccttacgcgg  420
attggtagct gcaggcttcc ctatctgatt ggccgaacga acgcagcgcg taatttaaaa  480
tattgtatct gtaacaaagc tgcacctcgt gggcggagtt gtgctctgcg gctgcgaaag  540
tccagcttcg gcgactaggt gtgagtaagc cagtatccca ggaggagcaa gtggcacgtc  600
ttcgggtgag tgtgcggctg tgctggagcc cgggttacca gctctt        646
```

SEQ ID NO: 437          moltype = DNA   length = 628
FEATURE                 Location/Qualifiers
source                  1..628
                        mol_type = other DNA
                        organism = synthetic construct SEQUENCE: 437
```
ggggcggggt gatgacacag caattcggga ctttccacgc ttgcgtgaga agagaccgga  60
agtgaatgac acagcaatgg atcccaacat ggcggcgccc aacatggcgg ctaccaacat  120
ggcggcctcc aacatggcgg caggcaacat ggcggctgcc aacatggcgg cggatccgct  180
tgcgtgagaa gctgggactt tcctaggggc ggggttggga ctttccacat gacacagcaa  240
tacctcgagg gtgactcatg atgatgccac gtcaccaatg ccacgtcacc aggtgactca  300
tgggtgactc atgacgtgtg acatgccacg tcaccaatgc cacgtcacca ggtgactcat  360
gggtgactca tgggtaccgg cccgcccct ttccttacgc ggattggtag ctgcaggctt  420
ccctatctga ttggccgaac gaacgcagcg cgtaatttaa aatattgtat ctgtaacaaa  480
gctgcacctc gtgggcggag ttgtgctctg cggctgcgaa agtccagctt cggcgactag  540
gtgtgagtaa gccagtatcc caggaggagc aagtggcacg tcttcgggtg agtgtgcggc  600
tgtgctggag cccgggttac cagctctt        628
```

SEQ ID NO: 438          moltype = DNA   length = 642
FEATURE                 Location/Qualifiers
source                  1..642
                        mol_type = other DNA
                        organism = synthetic construct SEQUENCE: 438
```
ggggcggggt gatgacacag caattcggga ctttccacgc ttgcgtgaga agagaccgga  60
agtgaatgac acagcaatgg atcctccttt gatgtacgca actcctttga tgtctatgcg  120
tcctttgatg ttaaggattc ctttgatgta ggtacatcct ttgatgtccg taaatccttt  180
gatgtggatc cgcttgcgtg agaagctggg actttcctag gggcggggtt gggactttcc  240
acatgacaca gcaataacct cgagggtgac catgatgatg ccacgtcacc aatgccacgt  300
caccaggtga ctcatgggtg actcatgacg tgtgacatgc cacgtcacca atgccacgtc  360
accaggtgac tcatgggtga ctcatgggta ccggcccgcc ccctttcctt acgcggattg  420
gtagctgcag gcttccctat ctgattggcc gaacgaacgc agcgcgtaat ttaaaatatt  480
gtatctggca caaagctgca cctcgtgggc ggagttgtgc tctgcggctg cgaaagtcca  540
gcttcggcga ctaggtgtga gtaagccagt atcccaggag gagcaagtgg cacgtcttcg  600
ggtgagtgtg cggctgtgct ggagcccggg ttaccagctc tt        642
```

SEQ ID NO: 439          moltype = DNA   length = 699
FEATURE                 Location/Qualifiers
source                  1..699
                        mol_type = other DNA
                        organism = synthetic construct SEQUENCE: 439
```
taattgctga gtcattgctg ctatgtaatt gctgagtcat atgcctatcc taattgctga  60
gtcataatcg agatgtaatt gctgagtcat gtccgacgca taattgctga gtcattctaa  120
ctcgctaatt gctgagtcat gtcgacgcta gcggtgactc atgatgatgc cacgtcacca  180
atgccacgtc accaggtgac tcatgggtga ctcatgacgt gtgacatgcc acgtcaccaa  240
tgccacgtca ccaggtgact catgggtgac tcatgactag taagcttggg cggggtgat  300
gacacagcaa ttcgggactt ccacgcttg cgtgagaaga ccggaagt gaatgacaca  360
gcaatggatc cgcttgcgtg agaagctggg actttcctag gggcggggtt gggactttcc  420
acatgacaca gcaataacct cgagggtaccg gcccgccccc tttccttacg cggattggta  480
gctgcaggct tccctatctg attggccgaa cgaacgcagc gcgtaattta aaatattgta  540
tctgtaacaa agctgcacct cgtgggcgga gttgtgctct cggctgcga aagtccagct  600
tcggcgacta ggtgtgagta agccagtatc ccaggaggag caagtggcac gtcttcgggt  660
gagtgtgcgg ctgtgctgga gcccgggtta ccagctctt        699
```

SEQ ID NO: 440          moltype = DNA   length = 810
FEATURE                 Location/Qualifiers
source                  1..810
                        mol_type = other DNA
                        organism = synthetic construct SEQUENCE: 440
```
taattgctga gtcattgctg ctatgtaatt gctgagtcat atgcctatcc tcctttgatg  60
tacgcaactc ctttgatgtc tatgcgtaat tgctgagtca taatcgagat gtaattgctg  120
agtcatgtcc gacgcatcct ttgatgttaa ggattccttt gatgtaggta cataattgct  180
gagtcattct aactcgctaa ttgctgagtc atcatctcga cctcctttga tgtccgtaaa  240
tcctttgatg tgtcgacgct agcggtgact catgatgatg ccacgtcacc aatgccacgt  300
caccaggtga ctcatgggtg actcatgacg tgtgacatgc cacgtcacca atgccacgt  360
accaggtgac tcatgggtga ctcatgacta gtaagcttgg ggcggggtga tgacacagca  420
attcgggact ttccacgctt gcgtgagaag agaccggaag tgaatgacac agcaatggat  480
```

-continued

```
ccgcttgcgt gagaagctgg gactttccta ggggcggggt tgggactttc cacatgacac   540
agcaatacct cgagggtacc ggcccgcccc ctttccttac gcggattggt agctgcaggc   600
ttccctatct gattggccga acgaacgcag cgcgtaattt aaaatattgt atctgtaaca   660
aagctgcacc tcgtgggcgg agttgtgctc tgcggctgcg aaagtccagc ttcggcgact   720
aggtgtgagt aagccagtat cccaggagga gcaagtggca cgtcttcggg tgagtgtgcg   780
gctgtgctgg agcccgggtt accagctctt                                    810
```

SEQ ID NO: 441          moltype = DNA   length = 570
FEATURE                 Location/Qualifiers
source                  1..570
                        mol_type = other DNA
                        organism = synthetic construct
SEQUENCE: 441
```
taattgctga gtcattgctg ctatgtaatt gctgagtcat atgcctatcc taattgctga   60
gtcataatcg agatgtaatt gctgagtcat gtccgacgca taattgctga gtcattctaa   120
ctcgctaatt gctgagtcat gtcgacacta gtaagcttgg ggcgggggtga tgacacagca   180
attcgggact ttccacgctt gcgtgagaag agaccggaag tgaatgacac agcaatggat   240
ccgcttgcgt gagaagctgg gactttccta ggggcggggt tgggactttc cacatgacac   300
agcaatacct cgagggtacc ggcccgcccc ctttccttac gcggattggt agctgcaggc   360
ttccctatct gattggccga acgaacgcag cgcgtaattt aaaatattgt atctgtaaca   420
aagctgcacc tcgtgggcgg agttgtgctc tgcggctgcg aaagtccagc ttcggcgact   480
aggtgtgagt aagccagtat cccaggagga gcaagtggca cgtcttcggg tgagtgtgcg   540
gctgtgctgg agcccgggtt accagctctt                                    570
```

SEQ ID NO: 442          moltype = DNA   length = 816
FEATURE                 Location/Qualifiers
source                  1..816
                        mol_type = other DNA
                        organism = synthetic construct
SEQUENCE: 442
```
ggtgactcat gatgatgcca cgtcaccaat gccacgtcac caggtgactc atgggtgact   60
catgacgtgt gacatgccac gtcaccaatg ccacgtcacc aggtgactca tgggtgactc   120
atgactagta aattctaatt gctgagtcat tgctgctatg taattgctga gtcatatgcc   180
tatcctcctt tgatgtacgc aactcctttg atgtctagtc gtaattgctg agtcataatc   240
gagatgtaat tgctgagtca tgtccgacgc atcctttgat gttaaggatt cctttgatgt   300
aggtacataa ttgctgagtc attctaactc gctaattgct gagtcatcat ctcgacctcc   360
tttgatgtcc gtaaatcctt tgatgtgtcg cacactagta agcttggggcg gggtgatgac   420
acagcaattc gggactttcc acgcttgcgt gagaagagac cggaagtgaa tgacacagca   480
atggatccgc ttgcgtgaga agctgggact tcctaggga cgggttggtt actttccaca   540
tgacacagca atacctcgag ggtaccggcc cgcccctttt ccttacgcgg attggtagct   600
gcaggcttcc ctatctgatt ggccgaacga acgcagcgcg taatttaaaa tattgtatct   660
gtaacaaagc tgcacctcgt gggcggagtt gtgctctgcg gctgcgaaag tccagcttcg   720
gcgactaggt gtgagtaagc cagtatccca ggaggagcaa gtggcacgtc ttcgggtgag   780
tgtgcggctg tgctggagcc cgggttacca gctctt                              816
```

SEQ ID NO: 443          moltype = DNA   length = 660
FEATURE                 Location/Qualifiers
source                  1..660
                        mol_type = other DNA
                        organism = synthetic construct
SEQUENCE: 443
```
tcctttgatg tacgcaactc ctttgatgtc tatgcgtcct ttgatgttaa ggattccttt   60
gatgtaggta catcctttga tgtccgtaaa tcctttgatg tgtcgacgct agcggtgact   120
catgatgatg ccacgtcacc aatgccacgt caccaggtga ctcatgggtg actcatgacg   180
tgtgacatgc cacgtcacca atgccacgtc accaggtgac tcatgggtga ctcatgacta   240
gtaagcttgg ggcggggtga tgacacagca attcgggact ttccacgctt gcgtgagaag   300
agaccggaag tgaatgacac agcaatggat ccgcttgcgt gagaagctgg gactttccta   360
ggggcggggt tgggactttc cacatgacac agcaatacct cgagggtacc ggcccgcccc   420
ctttccttac gcggattggt agctgcaggc ttccctatct gattggccga acgaacgcag   480
cgcgtaattt aaaatattgt atctgtaaca aagctgcacc tcgtgggcgg agttgtgctc   540
tgcggctgcg aaagtccagc ttcggcgact aggtgtgagt aagccagtat cccaggagga   600
gcaagtggca cgtcttcggg tgagtgtgcg gctgtgctgg agcccgggtt accagctctt   660
```

SEQ ID NO: 444          moltype = DNA   length = 669
FEATURE                 Location/Qualifiers
source                  1..669
                        mol_type = other DNA
                        organism = synthetic construct
SEQUENCE: 444
```
ggtgactcat gatgatgcca cgtcaccaat gccacgtcac caggtgactc atgggtgact   60
catgacgtgt gacatgccac gtcaccaatg ccacgtcacc aggtgactca tgggtgactc   120
atgactagta aattcgactc ctttgatgta cgcaactcct tgatgtctc tgcgtccttt   180
gatgttaagg attcctttga tgtaggtaca tcctttgatg tccgtaaatc ctttgatgtg   240
tcgacactag taagcttggg gcggggtgat gacacagca attcgggactt tccacgcttg   300
cgtgagaaga gaccggaagt gaatgacaca gcaatggatc cgcttgcgtg agaagctggg   360
actttcctag gggcggggtt gggacttcc acatgacaca gcaatacctc gagggtaccg   420
gcccgccccc tttccttacg cggattggta gctgcaggct ccctatctg attggccgaa   480
cgaacgcagc gcgtaattta aaatattgta tctgtaacaa agctgcacct cgtgggcgga   540
gttgtgctct gcggctgcga aagtccagct tcggcgacta ggtgtgagta agccagtatc   600
```

-continued

```
ccaggaggag caagtggcac gtcttcgggt gagtgtgcgg ctgtgctgga gcccgggtta   660
ccagctctt                                                            669

SEQ ID NO: 445          moltype = DNA   length = 439
FEATURE                 Location/Qualifiers
source                  1..439
                        mol_type = other DNA
                        organism = synthetic construct
SEQUENCE: 445
atgactcagc aattagcgag ttagaatgac tcagcaatta tgcgtcggac atgactcagc    60
aattacatct cgattatgac tcagcaatta ggataggcat atgactcagc aattacatag   120
cagcaatgac tcagcaatta gctagtaagc ttggggcggg gtgatgacac agcaattcgg   180
gactttccac gcttgcgtga gaagagaccg gaagtgaatg acacagcaat ggatccgctt   240
gcgtgagaag ctgggacttt cctaggggcg gggttgggac tttccacatg acacagcaat   300
acctcgaggg taccgggaaa agttcagctg agagatataa aagagcagtc tttccagcac   360
ctgcgtatcc caggaggagc aagtggcacg tcttcgggtg agtgtgcggc tgtgctggag   420
cccgggttac cagctctta                                                439

SEQ ID NO: 446          moltype = DNA   length = 387
FEATURE                 Location/Qualifiers
source                  1..387
                        mol_type = other DNA
                        organism = synthetic construct
SEQUENCE: 446
atgactcagc aattagcgag ttagaatgac tcagcaatta tgcgtcggac atgactcagc    60
aattacatct cgattatgac tcagcaatta ggataggcat atgactcagc aattacatag   120
cagcaatgac tcagcaatta gctagtaagc ttggggcggg gtgatgacac agcaattcgg   180
gactttccac gcttgcgtga gaagagaccg gaagtgaatg acacagcaat ggatccgctt   240
gcgtgagaag ctgggacttt cctaggggcg gggttgggac tttccacatg acacagcaat   300
acctcgaggg tacctgcgct cccgacatgc ccgcggcgc gccattaacc gccagatttg    360
agtcgcggga cccgttggca gaggtgg                                       387

SEQ ID NO: 447          moltype = DNA   length = 422
FEATURE                 Location/Qualifiers
source                  1..422
                        mol_type = other DNA
                        organism = synthetic construct
SEQUENCE: 447
ggtgactcat gatgatgcca cgtcaccaat gccacgtcac caggtgactc atgggtgact    60
catgacgtgt gacatgccac gtcaccaatg ccacgtcacc aggtgactca tgggtgactc   120
atgactagta agcttggggc ggggtgatga cacagcaatt cgggactttc cacgcttgcg   180
tgagaagaga ccggaagtga atgacacagc aatggatccg cttgcgtgag aagctgggac   240
tttcctaggg gcggggttgg gactttccac atgacacagc aataccctcga gggtaccggg   300
aaaagttcag ctgagagata taaaagagca gtctttccag cacctgcgta tcccaggagg   360
agcaagtggc acgtcttcgg gtgagtgtgc ggctgtgctg gagcccgggt taccagctct   420
ta                                                                  422

SEQ ID NO: 448          moltype = DNA   length = 370
FEATURE                 Location/Qualifiers
source                  1..370
                        mol_type = other DNA
                        organism = synthetic construct
SEQUENCE: 448
ggtgactcat gatgatgcca cgtcaccaat gccacgtcac caggtgactc atgggtgact    60
catgacgtgt gacatgccac gtcaccaatg ccacgtcacc aggtgactca tgggtgactc   120
atgactagta agcttggggc ggggtgatga cacagcaatt cgggactttc cacgcttgcg   180
tgagaagaga ccggaagtga atgacacagc aatggatccg cttgcgtgag aagctgggac   240
tttcctaggg gcggggttgg gactttccac atgacacagc aataccctcga gggtacctgc   300
gctcccgaca tgccccgcgg cgcgccatta accgccagat ttgagtcgcg ggaccctgttg   360
gcagaggtgg                                                          370

SEQ ID NO: 449          moltype = DNA   length = 687
FEATURE                 Location/Qualifiers
source                  1..687
                        mol_type = other DNA
                        organism = synthetic construct
SEQUENCE: 449
atgactcagc aattagcgag ttagaatgac tcagcaatta tgcgtcggac atgactcagc    60
aattacatct cgattatgac tcagcaatta ggataggcat atgactcagc aattacatag   120
cagcaatgac tcagcaatta gctagtaagc ttggggcggg gtgatgacac agcaattcgg   180
gactttccac gcttgcgtga gaagagaccg gaagtgaatg acacagcaat ggatccggga   240
ggaagtcgta aaacttggga ggaagtcgta aaaaatggga ggaagtcgta aaatgcggga   300
ggaagtcgta aaagaaggga ggaagtcgta aaaatcggga ggaagtcgta aaggatccg    360
cttgcgtgag aagctgggac tttcctaggg gcggggttgg gactttccac atgacacagc   420
aataccctcga gggtaccggc ccgccccctt tccttacgcg gattggtagc tgcaggcttc   480
cctatctgat tggccgaacg aacgcagcgc gtaatttaaa atattgtatc tgtaacaaag   540
ctgcacctcg tgggcggagt tgtgctctgc ggctgcgaaa gtccagcttc ggcgactagg   600
tgtgagtaag ccagtatccc aggaggagca agtggcacgt cttcgggtga gtgtgcggct   660
gtgctggagc ccgggttacc agctctt                                       687
```

```
SEQ ID NO: 450          moltype = DNA   length = 671
FEATURE                 Location/Qualifiers
source                  1..671
                        mol_type = other DNA
                        organism = synthetic construct
SEQUENCE: 450
atgactcagc aattagcgag ttagaatgac tcagcaatta tgcgtcggac atgactcagc      60
aattacatct cgattatgac tcagcaatta ggataggcat atgactcagc aattacatag     120
cagcaatgac tcagcaatta gctagtaagc ttggggcggg gtgatgacac agcaattcgg     180
gactttccac gcttgcgtga aagagaccg gaagtgaatg acacagcaat ggatcctcct     240
ttgatgtacg caactccttt gatgtctatg cgtcctttga tgttaaggat tcctttgatg     300
taggtacatc ctttgatgtc cgtaaatcct ttgatgtgga tccgcttgcg tgagaagctg     360
ggactttcct aggggcgggg ttgggacttt ccacatgaca cagcaatacc tcgagggtac     420
cggcccgccc cctttcctta cgcggattgg tagctgcagg cttccctatc tgattggccg     480
aacgaacgca gcgcgtaatt taaaatattg tatctgtaac aaagctgcac ctcgtgggcg     540
gagttgtgct ctgcggctgc gaaagtccag cttcggcgac taggtgtgag taagccagta     600
tcccaggagg agcaagtggc acgtcttcgg gtgagtgtg gctgtgctg gagcccgggt      660
taccagctct t                                                          671

SEQ ID NO: 451          moltype = DNA   length = 670
FEATURE                 Location/Qualifiers
source                  1..670
                        mol_type = other DNA
                        organism = synthetic construct
SEQUENCE: 451
ggtgactcat gatgatgcca cgtcaccaat gccacgtcac caggtgactc atgggtgact      60
catgacgtgt gacatgccac gtcaccaatg ccacgtcacc aggtgactca tgggtgactc     120
atgactagta agcttggggc ggggtgatga cacagcaatt cgggactttc cacgcttgcg     180
tgagaagaga ccggaagtga atgacacagc aatggatcct tttacgactt cctcccgatt     240
tttacgactt cctcccttct tttacgactt cctcccgcat tttacgactt cctcccattt     300
tttacgactt cctcccaagt tttacgactt cctcccggat ccgcttgcgt gagaagctgg     360
gactttccta ggggcggggt tgggactttc cacatgacac agcaatacct cgagggtacc     420
ggcccgccc ctttccttac gcggattggt agctgcaggc ttccctatc gattggccga      480
acgaacgcag cgcgtaattt aaaatattgt atctgtaac aagctgcacc tcgtgggcg      540
agttgtgctc tgcggctgcg aaagtccagc ttcggcgact aggtgtgagt aagccagtat     600
cccaggagga gcaagtggca cgtcttcggg tgagtgtgcg ctgtgctgg agcccgggtt      660
accagctctt                                                            670

SEQ ID NO: 452          moltype = DNA   length = 654
FEATURE                 Location/Qualifiers
source                  1..654
                        mol_type = other DNA
                        organism = synthetic construct
SEQUENCE: 452
ggtgactcat gatgatgcca cgtcaccaat gccacgtcac caggtgactc atgggtgact      60
catgacgtgt gacatgccac gtcaccaatg ccacgtcacc aggtgactca tgggtgactc     120
atgactagta agcttggggc ggggtgatga cacagcaatt cgggactttc cacgcttgcg     180
tgagaagaga ccggaagtga atgacacagc aatggatcct cctttgatgt acgcaactcc     240
tttgatgtct atgcgtcctt tgatgttaag gattcctttg atgtaggtac atcctttgat     300
gtccgtaaat cctttgatgt ggatccgctt gcgtgagaag ctgggacttt cctaggggcg     360
gggttgggac tttccacatg acacagcaat acctcgaggg taccggcccg ccccctttcc     420
ttacgcggat tggtagctgc aggcttccct atctgattgg ccgaacgaac gcagcgcgta     480
atttaaaata ttgtatctgt aacaaagctg cacctcgtgg gcggagttgt gctctgcggc     540
tgcgaaagtc cagcttcggc gactaggtgt gagtaagcca gtatcccagg aggagcaagt     600
ggcacgtctt cgggtgagtg tgcggctgtg ctggagcccg ggttaccagc tctt          654

SEQ ID NO: 453          moltype = DNA   length = 351
FEATURE                 Location/Qualifiers
source                  1..351
                        mol_type = other DNA
                        organism = synthetic construct
SEQUENCE: 453
atgactcagc aattagcgag ttagaatgac tcagcaatta tgcgtcggac atgactcagc      60
aattacatct cgattatgac tcagcaatta ggataggcat atgactcagc aattacatag     120
cagcaatgac tcagcaatta gctagtaagc ttggggcggg gtgatgacac agcaattcgg     180
gactttccac gcttgcgtga aagagaccg gaagtgaatg acacagcaat ggatccgctt     240
gcgtgagaag ctgggacttt cctaggggcg gggttgggac tttccacatg acacagcaat     300
acctcgaggg tacctataaa aggccagcag cagcctgacc acatctcatc c              351

SEQ ID NO: 454          moltype = DNA   length = 334
FEATURE                 Location/Qualifiers
source                  1..334
                        mol_type = other DNA
                        organism = synthetic construct
SEQUENCE: 454
ggtgactcat gatgatgcca cgtcaccaat gccacgtcac caggtgactc atgggtgact      60
catgacgtgt gacatgccac gtcaccaatg ccacgtcacc aggtgactca tgggtgactc     120
atgactagta agcttggggc ggggtgatga cacagcaatt cgggactttc cacgcttgcg     180
```

-continued

```
tgagaagaga ccggaagtga atgacacagc aatggatccg cttgcgtgag aagctgggac  240
tttcctaggg gcggggttgg gactttccac atgacacagc aatacctcga gggtacctat  300
aaaaggccag cagcagcctg accacatctc atcc                              334

SEQ ID NO: 455        moltype = DNA  length = 662
FEATURE               Location/Qualifiers
source                1..662
                      mol_type = other DNA
                      organism = synthetic construct
SEQUENCE: 455
atgactcagc aattagcgag ttagaatgac tcagcaatta tgcgtcggac atgactcagc   60
aattacatct cgattatgac tcagcaatta ggataggcat atgactcagc aattacatag  120
cagcaatgac tcagcaatta gctagtaagc ttggggcggg gtgatgacac agcaattcgg  180
gactttccac gcttgcgtga gaagagaccg gaagtgaatg acacagcaat ggatccgctt  240
gcgtgagaag ctgggacttt cctaggggcg gggttgggac tttccacatg acacagcaat  300
acctcgaggg taccacctct taacaatacg tttcacaaat agttaaaaac atgcatactg  360
aaaagcatac ttttgcaatg ttatttttaa aaacaaggaa ctctttaacc cagggaagat  420
aatcacttgg ggaaaggaag gttcgtttct gagttagcaa caagtaaatg cagcactagt  480
gggtgggatt gaggtgtgcc ctggtgcata aatagagact cagctgtgct ggcacactca  540
agaagcttgg accgcatcct agccgccgac tcacacaagg caggtgggtg aggaaatcca  600
ggtaaggctc ctgacagcag ctttagaagg gtacttgctg gagtgaattc gggcctctga  660
tt                                                                 662

SEQ ID NO: 456        moltype = DNA  length = 645
FEATURE               Location/Qualifiers
source                1..645
                      mol_type = other DNA
                      organism = synthetic construct
SEQUENCE: 456
ggtgactcat gatgatgcca cgtcaccaat gccacgtcac caggtgactc atgggtgact   60
catgacgtgt gacatgccac gtcaccaatg ccacgtcacc aggtgactca tgggtgactc  120
atgactagta agcttggggc ggggtgatga cacagcaatt cgggactttc cacgcttgcg  180
tgagaagaga ccggaagtga atgacacagc aatggatccg cttgcgtgag aagctgggac  240
tttcctaggg gcggggttgg gactttccac atgacacagc aatacctcga gggtaccacc  300
tcttaacaat acgtttcaca aatagttaaa aacatgcata ctgaaaagca cttttttgca  360
atgttatttt taaaaacaag gaactcttta acccagggaa gataatcact ggggaaaagg  420
aaggttcgtt tctgagttag caacaagtaa atgcagcact agtgggtggg attgaggtgt  480
gccctggtgc ataaatagag actcagctgt gctggcacac tcaagaagct tggaccgcat  540
cctagccgcc gactcacaca aggcaggtgg gtgaggaaat ccaggtaagg ctcctgacag  600
cagctttaga agggtacttg ctggagtgaa ttcgggcctc tgatt                  645

SEQ ID NO: 457        moltype = DNA  length = 644
FEATURE               Location/Qualifiers
source                1..644
                      mol_type = other DNA
                      organism = synthetic construct
SEQUENCE: 457
taattgctga gtcattgctg ctatgtaatt gctgagtcat atgcctatcc taattgctga   60
gtcataatcg agatgtaatt gctgagtcat gtccgacgca taattgctga gtcattctaa  120
ctcgctaatt gctgagtcat gtcgacgcta gcggtgactc atgatgatgc cacgtcacca  180
atgccacgtc accaggtgac tcatgggtga ctcatgactg atgacatgcc acgtcaccaa  240
tgccacgtca ccaggtgact catgggtgac tcatgactag ttcctttgat gtacgcaact  300
cctttgatgt ctatgcgtcc tttgatgtta aggattcctt tgatgtaggt acatcctttg  360
atgtccgtaa atcctttgat gtctcgaggg taccggcccg cccccttttcc ttacgcggat  420
tggtagctgc aggcttccct atctgattgg ccgaacgaac gcagcgcgta atttaaaata  480
ttgtatctgt aacaaagctg cacctcgtgg gcggagttgt gctctgcggc tgcgaaagtc  540
cagcttcggc gactaggtgt gagtaagcca gtatcccagg aggagcaagt ggcacgtctt  600
cgggtgagtg tgcggctgtg ctggagcccg ggttaccagc tctt                   644

SEQ ID NO: 458        moltype = DNA  length = 630
FEATURE               Location/Qualifiers
source                1..630
                      mol_type = other DNA
                      organism = synthetic construct
SEQUENCE: 458
taattgctga gtcattgctg ctatgtaatt gctgagtcat atgcctatcc taattgctga   60
gtcataatcg agatgtaatt gctgagtcat gtccgacgca taattgctga gtcattctaa  120
ctcgctaatt gctgagtcat gtcgacgcta gcggtgactc atgatgatgc cacgtcacca  180
atgccacgtc accaggtgac tcatgggtga ctcatgactag tcaacatggc ggcgcccaac  240
atggcggcta ccaacatggc ggcctccaac atggcggcag gcaacatggc ggctgccaac  300
atggcggcct cgagggtacc ggcccgcccc ctttccttac gcggattggt agctgcaggc  360
ttccctatct gattggccga cgaacgcag cgcgtaattt aaaatattgt atctgtaaca  420
aagctgcacc tcgtgggcgg agttgtgctc tgcggctgcg aaagtccagc ttcggcgact  480
aggtgtgagt aagccagtat cccaggagga gcaagtggca cgtcttcggg tgagtgtgcg  540
gctgtgctgg agcccgggtt accagctctt                                   630

SEQ ID NO: 459        moltype = DNA  length = 644
FEATURE               Location/Qualifiers
```

-continued

```
source                    1..644
                          mol_type = other DNA
                          organism = synthetic construct
SEQUENCE: 459
tcctttgatg tacgcaactc ctttgatgtc tatgcgtcct ttgatgttaa ggattccttt      60
gatgtaggta catcctttga tgtccgtaaa tcctttgatg tgtcgacgct agcggtgact     120
catgatgatg ccacgtcacc aatgccacgt caccaggtga ctcatgggtg actcatgacg     180
tgtgacatgc cacgtcacca atgccacgtc accaggtgac tcatgggtga ctcatgacta     240
gttaattgct gagtcattgc tgctatgtaa ttgctgagtc atatgcctat cctaattgct     300
gagtcataat cgagatgtaa ttgctgagtc atgtccgacg cataattgct gagtcattct     360
aactcgctaa ttgctgagtc atctcgaggg taccggcccg cccccttttcc ttacgcggat     420
tggtagctgc aggcttccct atctgattgg ccgaacgaac gcagcgcgta atttaaaata     480
ttgtatctgt aacaaagctg cacctcgtgg gcggagttgt gctctgcggc tgcgaaagtc     540
cagcttcggc gactaggtgt gagtaagcca gtatcccagg aggagcaagt ggcacgtctt     600
cgggtgagtg tgcggctgtg ctggagcccg ggttaccagc tctt                      644

SEQ ID NO: 460           moltype = DNA   length = 73
FEATURE                  Location/Qualifiers
source                   1..73
                         mol_type = other DNA
                         organism = synthetic construct
SEQUENCE: 460
acgcgtcccg acatgccccg cggcgcgcca ttaaccgcca gatttgagtc gcgggacccg      60
ttggcagagg tgg                                                         73

SEQ ID NO: 461           moltype = DNA   length = 635
FEATURE                  Location/Qualifiers
source                   1..635
                         mol_type = other DNA
                         organism = synthetic construct
SEQUENCE: 461
ggggcggggt gatgacacag caattcggga ctttccacgc ttgcgtgaga agagaccgga      60
agtgaatgac acagcaatgg atccgcttgc gtgagaagct gggactttcc taggggcggg     120
gttgggactt tccacatgac acagcaatac ctcgagggtg actcatgatg atgccacgtc     180
accaatgcca cgtcaccagg tgactcatgg gtgactcatg acgtgtgaca tgccacgtca     240
ccaatgccac gtcaccaggt gactcatggg tgactcatgg gtaccacctc ttaacaatac     300
gtttcacaaa tagttaaaaa catgcatact gaaaagcata cttttgcaat gttatttta      360
aaaacaagga actctttaac ccagggaaga taatcacttg gggaaaggaa ggttcgtttc     420
tgagttagca acaagtaaat gcagcactag tgggtgtgtgc cctggtgcat                480
aaatagagac tcagctgtgc tggcacactc aaaaatccag agcggcgggc actgacgggc     540
acttgcaccg tgtggacaga ctctccggtt ctgtgagtgg tttttctttt cccgggtcgg     600
acctggagtt cttaggggga tggctgaaga attca                                635

SEQ ID NO: 462           moltype = DNA   length = 634
FEATURE                  Location/Qualifiers
source                   1..634
                         mol_type = other DNA
                         organism = synthetic construct
SEQUENCE: 462
ggggcggggt gatgacacag caattcggga ctttccacgc ttgcgtgaga agagaccgga      60
agtgaatgac acagcaatgg atccgcttgc gtgagaagct gggactttcc taggggcggg     120
gttgggactt tccacatgac acagcaatac ctcgagggtg actcatgatg atgccacgtc     180
accaatgcca cgtcaccagg tgactcatgg gtgactcatg acgtgtgaca tgccacgtca     240
ccaatgccac gtcaccaggt gactcatggg tgactcatgg gtaccacctc ttaacaatac     300
gtttcacaaa tagttaaaaa catgcatact gaaaagcata cttttgcaat gttatttta      360
aaaacaagga actctttaac ccagggaaga taatcacttg gggaaaggaa ggttcgtttc     420
tgagttagca acaagtaaat gcagcactag tgggtgggat tgaggtgtgc cctggtgcat     480
aaatagagac tcagctgtgc tggcacactc aagaagcttg accgcatcc  tagccgccga     540
ctcacacaag gcaggtgggt gaggaaatcc aggtaaggct cctgacagca gctttagaag     600
ggtacttgct ggagtgaatt cgggcctctg atta                                 634

SEQ ID NO: 463           moltype = DNA   length = 588
FEATURE                  Location/Qualifiers
source                   1..588
                         mol_type = other DNA
                         organism = synthetic construct
SEQUENCE: 463
ggggcggggt gatgacacag caattcggga ctttccacgc ttgcgtgaga agagaccgga      60
agtgaatgac acagcaatgg atccgcttgc gtgagaagct gggactttcc taggggcggg     120
gttgggactt tccacatgac acagcaatac ctcgagggtg actcatgatg atgccacgtc     180
accaatgcca cgtcaccagg tgactcatgg gtgactcatg acgtgtgaca tgccacgtca     240
ccaatgccac gtcaccaggt gactcatggg tgactcatgg gtaccacctc ttaacaatac     300
gtttcacaaa tagttaaaaa catgcatact gaaaagcata cttttgcaat gttatttta      360
aaaacaagga actctttaac ccagggaaga taatcacttg gggaaaggaa ggttcgtttc     420
tgagttagca acaagtaaat gcagcactag tgggtgggat tgaggtgtgc cctggtgcat     480
aaatagagac tcagctgtgc tggcacactc aagtatccca ggaggagcaa gtggcacgtc     540
ttcgggtgag tgtgcggctg tgctggagcc cgggttacca gctcttaa                  588

SEQ ID NO: 464           moltype = DNA   length = 609
```

-continued

```
FEATURE            Location/Qualifiers
source             1..609
                   mol_type = other DNA
                   organism = synthetic construct
SEQUENCE: 464
ggggcggggt gatgacacag caattcggga ctttccacgc ttgcgtgaga agagaccgga    60
agtgaatgac acagcaatgg atccgcttgc gtgagaagct gggactttcc taggggcggg   120
gttgggactt tccacatgac acagcaatac ctcgagggtg actcatgatg atgccacgtc   180
accaatgcca cgtcaccagg tgactcatgg gtgactcatg acgtgtgaca tgccacgtca   240
ccaatgccac gtcaccaggt gactcatggg tgactcatgg gtaccacctc ttaacaatac   300
gtttcacaaa tagttaaaaa catgcatact gaaaagcata cttttgcaat gttattttta   360
aaaacaagga actctttaac ccagggaaga taatcacttg gggaaaggaa ggttcgtttc   420
tgagttagca acaagtaaat gcagcactag tgggtgggat tgaggtgtgc cctggtgcat   480
aaatagagac tcagctgtgc tggcacactc aacactcgcg ctgccatcac tcttccgccg   540
tcttcgccgc catcctcggc gcgactcgct cttttcggtt ctaccaggta gagtccgccg   600
ccatcctca                                                          609

SEQ ID NO: 465        moltype = DNA  length = 563
FEATURE            Location/Qualifiers
source             1..563
                   mol_type = other DNA
                   organism = synthetic construct
SEQUENCE: 465
ggggcggggt gatgacacag caattcggga ctttccacgc ttgcgtgaga agagaccgga    60
agtgaatgac acagcaatgg atccgcttgc gtgagaagct gggactttcc taggggcggg   120
gttgggactt tccacatgac acagcaatac ctcgagggtg actcatgatg atgccacgtc   180
accaatgcca cgtcaccagg tgactcatgg gtgactcatg acgtgtgaca tgccacgtca   240
ccaatgccac gtcaccaggt gactcatggg tgactcatgg gtaccacctc ttaacaatac   300
gtttcacaaa tagttaaaaa catgcatact gaaaagcata cttttgcaat gttattttta   360
aaaacaagga actctttaac ccagggaaga taatcacttg gggaaaggaa ggttcgtttc   420
tgagttagca acaagtaaat gcagcactag tgggtgggat tgaggtgtgc cctggtgcat   480
aaatagagac tcagctgtgc tggcacactc aactttttcc gtgctacctg cagaggggtc   540
catacggcgt tgttctggat tca                                           563

SEQ ID NO: 466        moltype = DNA  length = 716
FEATURE            Location/Qualifiers
source             1..716
                   mol_type = other DNA
                   organism = synthetic construct
SEQUENCE: 466
ggggcggggt gatgacacag caattcggga ctttccacgc ttgcgtgaga agagaccgga    60
agtgaatgac acagcaatgg atccgcttgc gtgagaagct gggactttcc taggggcggg   120
gttgggactt tccacatgac acagcaatac ctcgagggtg actcatgatg atgccacgtc   180
accaatgcca cgtcaccagg tgactcatgg gtgactcatg acgtgtgaca tgccacgtca   240
ccaatgccac gtcaccaggt gactcatggg tgactcatgg gtaccacctc ttaacaatac   300
gtttcacaaa tagttaaaaa catgcatact gaaaagcata cttttgcaat gttattttta   360
aaaacaagga actctttaac ccagggaaga taatcacttg gggaaaggaa ggttcgtttc   420
tgagttagca acaagtaaat gcagcactag tgggtgggat tgaggtgtgc cctggtgcat   480
aaatagagac tcagctgtgc tggcacactc aacggcggcg cagatcgccc ggcgcggctc   540
cgccccctgc gccggtcacg tggggcgcc ggctgcgcct gcggagaagc ggtggccgcc    600
gagcgggatc tgtgcgggga gccggaaatg gttgtgact acgtctgtgc ggctgcgtgg    660
ggctcggccg cgcggactga aggagactga aggtgctggg gggaccctga tgtgga        716

SEQ ID NO: 467        moltype = DNA  length = 457
FEATURE            Location/Qualifiers
source             1..457
                   mol_type = other DNA
                   organism = synthetic construct
SEQUENCE: 467
ggggcggggt gatgacacag caattcggga ctttccacgc ttgcgtgaga agagaccgga    60
agtgaatgac acagcaatgg atccgcttgc gtgagaagct gggactttcc taggggcggg   120
gttgggactt tccacatgac acagcaatac ctcgagggtg actcatgatg atgccacgtc   180
accaatgcca cgtcaccagg tgactcatgg gtgactcatg acgtgtgaca tgccacgtca   240
ccaatgccac gtcaccaggt gactcatggg tgactcatgg gtaccgggaa aagttcagct   300
gagagatata aaagagcagt ctttccagca cctgcgaagc ttggaccgca tcctagccgc   360
cgactcacac aaggcaggtg ggtgaggaaa tccaggtaag gctcctgaca gcagctttag   420
aagggtactt gctggagtga attcgggcct ctgatta                            457

SEQ ID NO: 468        moltype = DNA  length = 411
FEATURE            Location/Qualifiers
source             1..411
                   mol_type = other DNA
                   organism = synthetic construct
SEQUENCE: 468
ggggcggggt gatgacacag caattcggga ctttccacgc ttgcgtgaga agagaccgga    60
agtgaatgac acagcaatgg atccgcttgc gtgagaagct gggactttcc taggggcggg   120
gttgggactt tccacatgac acagcaatac ctcgagggtg actcatgatg atgccacgtc   180
accaatgcca cgtcaccagg tgactcatgg gtgactcatg acgtgtgaca tgccacgtca   240
ccaatgccac gtcaccaggt gactcatggg tgactcatgg gtaccgggaa aagttcagct   300
```

```
gagagatata aaaagagcagt ctttccagca cctgcgtatc ccaggaggag caagtggcac    360
gtcttcgggt gagtgtgcgg ctgtgctgga gcccgggtta ccagctctta a             411

SEQ ID NO: 469          moltype = DNA   length = 432
FEATURE                 Location/Qualifiers
source                  1..432
                        mol_type = other DNA
                        organism = synthetic construct
SEQUENCE: 469
ggggcggggt gatgacacag caattcggga ctttccacgc ttgcgtgaga agagaccgga    60
agtgaatgac acagcaatgg atccgcttgc gtgagaagct gggactttcc taggggcggg    120
gttgggactt tccacatgac acagcaatac ctcgagggtg actcatgatg atgccacgtc    180
accaatgcca cgtcaccagg tgactcatgg gtgactcatg acgtgtgaca tgccacgtca    240
ccaatgccac gtcaccaggt gactcatggg tgactcatgg gtaccgggaa aagttcagct    300
gagagatata aaaagagcagt ctttccagca cctgccactc gcgctgccat cactcttccg    360
ccgtcttcgc cgccatcctc ggcgcgactc gcttctttcg gttctaccag gtagagtccg    420
ccgccatcct ca                                                        432

SEQ ID NO: 470          moltype = DNA   length = 385
FEATURE                 Location/Qualifiers
source                  1..385
                        mol_type = other DNA
                        organism = synthetic construct
SEQUENCE: 470
ggggcggggt gatgacacag caattcggga ctttccacgc ttgcgtgaga agagaccgga    60
agtgaatgac acagcaatgg atccgcttgc gtgagaagct gggactttcc taggggcggg    120
gttgggactt tccacatgac acagcaatac ctcgagggtg actcatgatg atgccacgtc    180
accaatgcca cgtcaccagg tgactcatgg gtgactcatg acgtgtgaca tgccacgtca    240
ccaatgccac gtcaccaggt gactcatggg tgactcatgg gtaccgggaa aagttcagct    300
gagagatata aaaagagcagt ctttccagca cctgcctttt tccgtgctac ctgcagaggg    360
gtccatacgg cgttgttctg gattc                                          385

SEQ ID NO: 471          moltype = DNA   length = 538
FEATURE                 Location/Qualifiers
source                  1..538
                        mol_type = other DNA
                        organism = synthetic construct
SEQUENCE: 471
ggggcggggt gatgacacag caattcggga ctttccacgc ttgcgtgaga agagaccgga    60
agtgaatgac acagcaatgg atccgcttgc gtgagaagct gggactttcc taggggcggg    120
gttgggactt tccacatgac acagcaatac ctcgagggtg actcatgatg atgccacgtc    180
accaatgcca cgtcaccagg tgactcatgg gtgactcatg acgtgtgaca tgccacgtca    240
ccaatgccac gtcaccaggt gactcatggg tgactcatgg gtaccgggaa aagttcagct    300
gagagatata aaaagagcagt ctttccagca cctgccggcg gcgcagatcg cccggcgcgg    360
ctccgccccc tgcgccggtc acgtgggggc gccggctgcg cctgcggaga agcggtggcc    420
gccgagcggg atctgtgcgg ggagccggaa atggttgtgg actacgtctg tgcggctgcg    480
tggggctcgg ccgcgcggac tgaaggagac tgaaggtgct gggggggaccc tgatgtgg     538

SEQ ID NO: 472          moltype = DNA   length = 584
FEATURE                 Location/Qualifiers
source                  1..584
                        mol_type = other DNA
                        organism = synthetic construct
SEQUENCE: 472
ggggcggggt gatgacacag caattcggga ctttccacgc ttgcgtgaga agagaccgga    60
agtgaatgac acagcaatgg atccgcttgc gtgagaagct gggactttcc taggggcggg    120
gttgggactt tccacatgac acagcaatac ctcgagggtg actcatgatg atgccacgtc    180
accaatgcca cgtcaccagg tgactcatgg gtgactcatg acgtgtgaca tgccacgtca    240
ccaatgccac gtcaccaggt gactcatggg tgactcatgg gtacccggcc cgccccttt     300
ccttacgcgg attggtagct gcaggcttcc ctatctgatt ggccgaacga acgcagcgcg    360
taatttaaaa tattgtatct gtaacaaagc tgcacctcgt gggcggagtt gtgctctgcg    420
gctgcgaaag tccagcttcg gcgactaggt gtgagtaagc caaaatccag agcggcgggc    480
actgacgggc acttgcaccg tgtggacaga ctctccggtt ctgtgagtgg ttttttctttt    540
cccgggtcgg acctggagtt cttaggggga tggctgaaga attc                     584

SEQ ID NO: 473          moltype = DNA   length = 583
FEATURE                 Location/Qualifiers
source                  1..583
                        mol_type = other DNA
                        organism = synthetic construct
SEQUENCE: 473
ggggcggggt gatgacacag caattcggga ctttccacgc ttgcgtgaga agagaccgga    60
agtgaatgac acagcaatgg atccgcttgc gtgagaagct gggactttcc taggggcggg    120
gttgggactt tccacatgac acagcaatac ctcgagggtg actcatgatg atgccacgtc    180
accaatgcca cgtcaccagg tgactcatgg gtgactcatg acgtgtgaca tgccacgtca    240
ccaatgccac gtcaccaggt gactcatggg tgactcatgg gtacccggcc cgccccttt     300
ccttacgcgg attggtagct gcaggcttcc ctatctgatt ggccgaacga acgcagcgcg    360
taatttaaaa tattgtatct gtaacaaagc tgcacctcgt gggcggagtt gtgctctgcg    420
gctgcgaaag tccagcttcg gcgactaggt gtgagtaagc cagaagcttg gaccgcatcc    480
```

```
tagccgccga ctcacacaag gcaggtgggt gaggaaatcc aggtaaggct cctgacagca    540
gctttagaag ggtacttgct ggagtgaatt cgggcctctg att                       583

SEQ ID NO: 474            moltype = DNA   length = 558
FEATURE                   Location/Qualifiers
source                    1..558
                          mol_type = other DNA
                          organism = synthetic construct
SEQUENCE: 474
ggggcggggt gatgacacag caattcggga ctttccacgc ttgcgtgaga agagaccgga    60
agtgaatgac acagcaatgg atccgcttgc gtgagaagct gggactttcc taggggcggg    120
gttgggactt tccacatgac acagcaatac ctcgagggtg actcatgatg atgccacgtc    180
accaatgcca cgtcaccagg tgactcatgg gtgactcatg acgtgtgaca tgccacgtca    240
ccaatgccac gtcaccaggt gactcatggg tgactcatgg gtacccggcc cgccccctttt   300
ccttacgcgg attggtagct gcaggcttcc ctatctgatt ggccgaacga acgcagcgcg    360
taatttaaaa tattgtatct gtaacaaagc tgcacctcgt gggcggagtt gtgctctgcg    420
gctgcgaaag tccagcttcg gcgactaggt gtgagtaagc cacactcgcg ctgccatcac    480
tcttccgccg tcttcgccgc catcctcggc gcgactcgct tctttcggtt ctaccaggta    540
gagtccgccg ccatcctc                                                   558

SEQ ID NO: 475            moltype = DNA   length = 512
FEATURE                   Location/Qualifiers
source                    1..512
                          mol_type = other DNA
                          organism = synthetic construct
SEQUENCE: 475
ggggcggggt gatgacacag caattcggga ctttccacgc ttgcgtgaga agagaccgga    60
agtgaatgac acagcaatgg atccgcttgc gtgagaagct gggactttcc taggggcggg    120
gttgggactt tccacatgac acagcaatac ctcgagggtg actcatgatg atgccacgtc    180
accaatgcca cgtcaccagg tgactcatgg gtgactcatg acgtgtgaca tgccacgtca    240
ccaatgccac gtcaccaggt gactcatggg tgactcatgg gtacccggcc cgccccctttt   300
ccttacgcgg attggtagct gcaggcttcc ctatctgatt ggccgaacga acgcagcgcg    360
taatttaaaa tattgtatct gtaacaaagc tgcacctcgt gggcggagtt gtgctctgcg    420
gctgcgaaag tccagcttcg gcgactaggt gtgagtaagc cacttttttcc gtgctacctg    480
cagagggtc catacggcgt tgttctggat tc                                    512

SEQ ID NO: 476            moltype = DNA   length = 665
FEATURE                   Location/Qualifiers
source                    1..665
                          mol_type = other DNA
                          organism = synthetic construct
SEQUENCE: 476
ggggcggggt gatgacacag caattcggga ctttccacgc ttgcgtgaga agagaccgga    60
agtgaatgac acagcaatgg atccgcttgc gtgagaagct gggactttcc taggggcggg    120
gttgggactt tccacatgac acagcaatac ctcgagggtg actcatgatg atgccacgtc    180
accaatgcca cgtcaccagg tgactcatgg gtgactcatg acgtgtgaca tgccacgtca    240
ccaatgccac gtcaccaggt gactcatggg tgactcatgg gtacccggcc cgcccccttt    300
ccttacgcgg attggtagct gcaggcttcc ctatctgatt ggccgaacga acgcagcgcg    360
taatttaaaa tattgtatct gtaacaaagc tgcacctcgt gggcggagtt gtgctctgcg    420
gctgcgaaag tccagcttcg gcgactaggt gtgagtaagc cacggcggcg cagatcgccc    480
ggcgggctc cgcccctgc gccggtcacg tgggggcgcc ggctgcgcct gcggagagc      540
ggtggccgcc gagcgggatc tgtgcgggga gccggaaatg gttgtggact acgtctgtgc    600
ggctgcgtgg ggctcggccg cgcggactga aggagactga aggtgctggg gggaccctga    660
tgtgg                                                                 665

SEQ ID NO: 477            moltype = DNA   length = 183
FEATURE                   Location/Qualifiers
source                    1..183
                          mol_type = other DNA
                          organism = synthetic construct
SEQUENCE: 477
agtatagtgc acagtgactg cagcagggtg actcatgatg atgccacgtc accaatgcca    60
cgtcaccagg tgactcatgg gtgactcatg atgccacgtc accaatgcca cgtcaccagg    120
tgactcatgg gtgactcatg ggtacctata aaaggccagc agcagcctga ccacatctca    180
tcc                                                                   183

SEQ ID NO: 478            moltype = DNA   length = 439
FEATURE                   Location/Qualifiers
source                    1..439
                          mol_type = other DNA
                          organism = synthetic construct
SEQUENCE: 478
tcctttgatg tacgcaactc ctttgatgtc tatgcgtcct ttgatgttaa ggattccttt    60
gatgtaggta catcctttga tgtccgtaaa tcctttgatg taagcttaac tcgcaatcta    120
gcatcgtccg acgcaacgcc ttacaccatc agaatctgct agcggtgact catgggtgac    180
tcatgggtga ctcatgggtg actcatgcta cgtggtgact catgggtgac tcatgggtga    240
ctcatgggtg actcatgggt gactcatggg taccgggaaa agttcagctg agagatataa    300
aagagcagtc tttccagcac ctgcaaatcc agagcggcgg gcactgacgg gcacttcac     360
cgtgtggaca gactctccgg ttctgtgagt ggtttttctt ttcccgggtc ggacctggag    420
```

-continued

```
ttcttagggg gatggctga                                              439

SEQ ID NO: 479          moltype = DNA   length = 464
FEATURE                 Location/Qualifiers
source                  1..464
                        mol_type = other DNA
                        organism = synthetic construct
SEQUENCE: 479
tcctttgatg tacgcaactc ctttgatgtc tatgcgtcct ttgatgttaa ggattccttt   60
gatgtaggta catcctttga tgtccgtaaa tcctttgatg taagcttggt acaacttctc  120
acggaggctt ctaactcgca atctagcatc gtccgacgca acgccttaca ccatcagaat  180
ctgctagcgg tgactcatgg gtgactcatg ggtgactcat gggtgactca tgctacgtgg  240
tgactcatgg gtgactcatg ggtgactcat gggtgactca tgggtgactc atgggtaccg  300
ggaaaagttc agctgagaga tataaaagag cagtcttttcc agcacctgca aatccagagc  360
ggcgggcact gacgggcact tgcaccgtgt ggacagactc tccggttctg tgagtggttt  420
ttcttttccc gggtcggacc tggagttctt aggggggatgg ctga                  464

SEQ ID NO: 480          moltype = DNA   length = 596
FEATURE                 Location/Qualifiers
source                  1..596
                        mol_type = other DNA
                        organism = synthetic construct
SEQUENCE: 480
tcctttgatg tacgcaactc ctttgatgtc tatgcgtcct ttgatgttaa ggattccttt   60
gatgtaggta catcctttga tgtccgtaaa tcctttgatg tgacgattct tgatatcctc  120
gaggctagca tgatcaccat gagtcaccca tgagtcaccc atgagtcac                180
ccatgagtca cccatgagtc acccatgagt cacccatgag tcacccatga gtcaccacta  240
gtggtaccac ctcttaacaa tacgtttcac aaatagttaa aaacatgcat actgaaaagc  300
atactttgtc aatgttattt ttaaaaacaa ggaactcttt aacccaggga agataatcac  360
ttggggaaag gaaggttcgt ttctgagtta gcaacaagta aatgcagcac tagtgggtgg  420
gattgaggtg tgccctggtg cataaataga gactcagctg tgctggcaca ctcagaagct  480
tggaccgcat cctagccgcc gactcacaca aggcaggtgg gtgaggaaat ccaggtaagg  540
ctcctgacag cagctttaga aggggtacttg ctggagtgaa ttcgggcctc tgatta       596

SEQ ID NO: 481          moltype = DNA   length = 641
FEATURE                 Location/Qualifiers
source                  1..641
                        mol_type = other DNA
                        organism = synthetic construct
SEQUENCE: 481
tcctttgatg tacgcaactc ctttgatgtc tatgcgtcct ttgatgttaa ggattccttt   60
gatgtaggta catcctttga tgtccgtaaa tcctttgatg tgacgatctt gatatcctcg  120
aggctagcat gatcaccatg agtcacccat gagtcaccc                          180
catgagtcac ccatgagtca cccatgagtc acccatgagt cacccatgag tcaccactag  240
tggtaccacc tcttaacaat acgtttcaca aatagttaaa aacatgcata ctagtggggc  300
ggggtgatga cacagcaatt cgggactttc cacgcttgcg tgagaagaga ccggaagtga  360
atgacacagc aattcgcttg cgtgagaagc tgggactttc ctaggggcgg ggttgggact  420
ttccacatga cacagcaata cactagtaac atttctctgg cctaactggc cggtaccggg  480
aaaagttcag ctgagagata taaaagagca gtctttccag cacctgcaaa tccagagcgg  540
cgggcactga cgggcacttg caccgtgtgg acagactctc cggttctgtg agtggttttt  600
cttttcccgg gtcggacctg gagttcttag ggggatggct g                       641

SEQ ID NO: 482          moltype = DNA   length = 643
FEATURE                 Location/Qualifiers
source                  1..643
                        mol_type = other DNA
                        organism = synthetic construct
SEQUENCE: 482
tcctttgatg tacgcaactc ctttgatgtc tatgcgtcct ttgatgttaa ggattccttt   60
gatgtaggta catcctttga tgtccgtaaa tcctttgatg tgacgatctt gatatcctcg  120
aggctagcat gatcaccatg agtcacccat gagtcaccc atgagtcacc atgagtcacc  180
catgagtcac ccatgagtca cccatgagtc acccatgagt cacccatgag tcaccactag  240
tggtaccacc tcttaacaat acgtttcaca aatagttaaa aacatgcata ctagtggggc  300
ggggtgatga cacagcaatt cgggactttc cacgcttgcg tgagaagaga ccggaagtga  360
atgacacagc aattcgcttg cgtgagaagc tgggactttc ctaggggcgg ggttgggact  420
ttccacatga cacagcaata cactagtaac atttctctgg cctaactggc cggtaccggg  480
aaaagttcag ctgagagata taaaagagca gtctttccag cacctgcaaa tccagagcgg  540
cgggcactga cgggcacttg caccgtgtgg acagactctc cggttctgtg agtggttttt  600
cttttcccgg gtcggacctg gagttcttag ggggatggct gaa                     643

SEQ ID NO: 483          moltype = DNA   length = 1090
FEATURE                 Location/Qualifiers
source                  1..1090
                        mol_type = other DNA
                        organism = synthetic construct
SEQUENCE: 483
atgactcagc aattagcgag ttagaatgac tcagcaatta tgcgtcggac atgactcagc   60
aattacatct cgattatgac tcagcaatta ggataggcat atgactcagc aattacatag  120
cagcaatgac tcagcaatta gctagtaagc ttggggcggg gtgatgacac agcaattcgg  180
```

```
gactttccac gcttgcgtga gaagagaccg gaagtgaatg acacagcaat ggatccgctt   240
gcgtgagaag ctgggacttt cctaggggcg gggttgggac tttccacatg acacagcaat   300
acctcgaggg taccatgcat actagtctga gcgacagtat agtgcacagt gactgcagca   360
gtcattcctt tgatgtacgc aactcctttg atgtctatgc gtcctttgat gttaaggatt   420
cctttgatgt aggtacatcc tttgatgtcc gtaaatcctt tgatgtgacg tctacgtatc   480
tacctgatca aacatgcccg gacatgtcgt aagacataaa catgcccgga catgtcctcg   540
caatctaaca tgcccggaca tgtcctcgca atctaacatg cccggacatg tctgcaagct   600
acaacatgcc cggacatgtc tacaatatac gtatctacct gatcaaacat gcccggacat   660
gtcgtaagac ataaacatgc ccggacatgt cctcgcaatc taacatgccc ggacatgtcc   720
tcgcaatcta acatgcccgg acatgtctgc aagctacaac atgcccggac atgtctacgt   780
acatactgaa aagcatactt ttgcaatgtt atttttaaaa acaaggaact ctttaaccca   840
gggaagataa tcacttgggg aaaggaaggt tcgtttctga gttagcaaca agtaaatgca   900
gcactagtgg gtgggattga ggtgtgccct ggtgcataaa tagagactca gctgtgctgg   960
cacactcaga agcttggacc gcatcctagc cgccgactca cacaaggcag gtgggtgagg  1020
aaatccaggt aaggctcctg acagcagctt tagaagggta cttgctggag tgaattcggg  1080
cctctgatta                                                          1090
```

```
SEQ ID NO: 484              moltype = DNA   length = 616
FEATURE                     Location/Qualifiers
source                      1..616
                            mol_type = other DNA
                            organism = synthetic construct
SEQUENCE: 484
atgactcagc aattagcgag ttagaatgac tcagcaatta tgcgtcggac atgactcagc    60
aattacatct cgattatgac tcagcaatta ggataggcat atgactcagc aattacatag   120
cagcaatgac tcagcaatta gctagtaagc ttggggcggg gtgatgacac agcaattcgg   180
gactttccac gcttgcgtga gaagagaccg gaagtgaatg acacagcaat ggatccgctt   240
gcgtgagaag ctgggacttt cctaggggcg gggttgggac tttccacatg acacagcaat   300
acctcgaggg taccactagt gtcatctctt tgaatattct gtagtttgag gagaatattt   360
gttatattgc acaataaaat aagtttgcaa gttttttttt tctgcccaa agagctctgt   420
gtccttgaac ataaaataca aataaccgct atgctgttaa ttattaacaa atgtcccatt   480
ttcaacctaa ggaaatacca taaagtaaca gatataccaa caaaaggtta ataattaaca   540
ggcattgcct gaaaagagta taaaaggctt tcagcatgat tttccatatt gtgcttccac   600
cactgccaat aacaaa                                                    616
```

```
SEQ ID NO: 485              moltype = DNA   length = 458
FEATURE                     Location/Qualifiers
source                      1..458
                            mol_type = other DNA
                            organism = synthetic construct
SEQUENCE: 485
atgactcagc aattagcgag ttagaatgac tcagcaatta tgcgtcggac atgactcagc    60
aattacatct cgattatgac tcagcaatta ggataggcat atgactcagc aattacatag   120
cagcaatgac tcagcaatta gctagtaagc ttggggcggg gtgatgacac agcaattcgg   180
gactttccac gcttgcgtga gaagagaccg gaagtgaatg acacagcaat ggatccgctt   240
gcgtgagaag ctgggacttt cctaggggcg gggttgggac tttccacatg acacagcaat   300
acctcgaggg taccagcttg catgcctgca ggtcggaacta ctgtcctccg agcggagtac   360
tgtcctccga gcggagtact gtcctccgag cggagtactg tcctccgagc ggagtactgt   420
cctccgagcg gagactctag agggtatata atggatcc                           458
```

```
SEQ ID NO: 486              moltype = DNA   length = 279
FEATURE                     Location/Qualifiers
source                      1..279
                            mol_type = other DNA
                            organism = synthetic construct
SEQUENCE: 486
tctgtagttt gaggagaata tttgttatat tgcacaataa aataagtttg caagtttttt    60
ttttctgccc caaagagctc tgtgtccttg aacataaaat acaaataacc gctatgctgt   120
taattattaa caaatgtccc atttttcaacc taaggaataa ccataaagta acagatatac   180
caacaaaagg ttaataatta acaggcattg cctgaaaaga gtataaaagg ctttcagcat   240
gattttccat attgtgcttc caccactgcc aataacaaa                          279
```

```
SEQ ID NO: 487              moltype = DNA   length = 14
FEATURE                     Location/Qualifiers
source                      1..14
                            mol_type = other DNA
                            organism = synthetic construct
SEQUENCE: 487
ttttcccgcc aaaa                                                       14
```

```
SEQ ID NO: 488              moltype = DNA   length = 10
FEATURE                     Location/Qualifiers
source                      1..10
                            mol_type = other DNA
                            organism = synthetic construct
SEQUENCE: 488
tgatcaataa                                                           10
```

```
SEQ ID NO: 489              moltype = DNA   length = 11
```

-continued

```
FEATURE                 Location/Qualifiers
source                  1..11
                        mol_type = other DNA
                        organism = synthetic construct
SEQUENCE: 489
gaaacatgag c                                                        11

SEQ ID NO: 490          moltype = DNA   length = 12
FEATURE                 Location/Qualifiers
source                  1..12
                        mol_type = other DNA
                        organism = synthetic construct
SEQUENCE: 490
agacatcaaa gg                                                       12

SEQ ID NO: 491          moltype = DNA   length = 12
FEATURE                 Location/Qualifiers
source                  1..12
                        mol_type = other DNA
                        organism = synthetic construct
SEQUENCE: 491
aaacttcaaa gg                                                       12

SEQ ID NO: 492          moltype = DNA   length = 11
FEATURE                 Location/Qualifiers
source                  1..11
                        mol_type = other DNA
                        organism = synthetic construct
SEQUENCE: 492
tcctttgatc t                                                        11

SEQ ID NO: 493          moltype = DNA   length = 10
FEATURE                 Location/Qualifiers
source                  1..10
                        mol_type = other DNA
                        organism = synthetic construct
SEQUENCE: 493
gtcgtaaact                                                          10

SEQ ID NO: 494          moltype = DNA   length = 10
FEATURE                 Location/Qualifiers
source                  1..10
                        mol_type = other DNA
                        organism = synthetic construct
SEQUENCE: 494
gtcgtaaagt                                                          10

SEQ ID NO: 495          moltype = DNA   length = 10
FEATURE                 Location/Qualifiers
source                  1..10
                        mol_type = other DNA
                        organism = synthetic construct
SEQUENCE: 495
gtcgtaaatt                                                          10

SEQ ID NO: 496          moltype = DNA   length = 12
FEATURE                 Location/Qualifiers
source                  1..12
                        mol_type = other DNA
                        organism = synthetic construct
SEQUENCE: 496
gtccacgtgg cc                                                       12

SEQ ID NO: 497          moltype = DNA   length = 13
FEATURE                 Location/Qualifiers
source                  1..13
                        mol_type = other DNA
                        organism = synthetic construct
SEQUENCE: 497
ggccccgccc acc                                                      13

SEQ ID NO: 498          moltype = DNA   length = 11
FEATURE                 Location/Qualifiers
source                  1..11
                        mol_type = other DNA
                        organism = synthetic construct
SEQUENCE: 498
tcctttgaag t                                                        11
```

-continued

```
SEQ ID NO: 499        moltype = DNA   length = 10
FEATURE               Location/Qualifiers
source                1..10
                      mol_type = other DNA
                      organism = synthetic construct SEQUENCE: 499
agcggaagtg                                                        10

SEQ ID NO: 500        moltype = DNA   length = 12
FEATURE               Location/Qualifiers
source                1..12
                      mol_type = other DNA
                      organism = synthetic construct SEQUENCE: 500
ggggggaaggg ag                                                    12

SEQ ID NO: 501        moltype = DNA   length = 10
FEATURE               Location/Qualifiers
source                1..10
                      mol_type = other DNA
                      organism = synthetic construct SEQUENCE: 501
gtcgtaaaat                                                        10

SEQ ID NO: 502        moltype = DNA   length = 15
FEATURE               Location/Qualifiers
source                1..15
                      mol_type = other DNA
                      organism = synthetic construct SEQUENCE: 502
gtcatgcatg actgc                                                  15

SEQ ID NO: 503        moltype = DNA   length = 16
FEATURE               Location/Qualifiers
source                1..16
                      mol_type = other DNA
                      organism = synthetic construct SEQUENCE: 503
gtttgggcgc catttc                                                 16

SEQ ID NO: 504        moltype = DNA   length = 13
FEATURE               Location/Qualifiers
source                1..13
                      mol_type = other DNA
                      organism = synthetic construct SEQUENCE: 504
ggacccgccc acc                                                    13

SEQ ID NO: 505        moltype = DNA   length = 11
FEATURE               Location/Qualifiers
source                1..11
                      mol_type = other DNA
                      organism = synthetic construct SEQUENCE: 505
gaaacctgag c                                                      11

SEQ ID NO: 506        moltype = DNA   length = 11
FEATURE               Location/Qualifiers
source                1..11
                      mol_type = other DNA
                      organism = synthetic construct SEQUENCE: 506
gaaacttgag c                                                      11

SEQ ID NO: 507        moltype = DNA   length = 15
FEATURE               Location/Qualifiers
source                1..15
                      mol_type = other DNA
                      organism = synthetic construct SEQUENCE: 507
attaatcgat tattt                                                  15

SEQ ID NO: 508        moltype = DNA   length = 11
FEATURE               Location/Qualifiers
source                1..11
                      mol_type = other DNA
                      organism = synthetic construct SEQUENCE: 508
gtctgtggct t                                                      11
```

-continued

```
SEQ ID NO: 509          moltype = DNA   length = 20
FEATURE                 Location/Qualifiers
source                  1..20
                        mol_type = other DNA
                        organism = synthetic construct
SEQUENCE: 509
ccccaaacca ccaccccccc                                        20

SEQ ID NO: 510          moltype = DNA   length = 12
FEATURE                 Location/Qualifiers
source                  1..12
                        mol_type = other DNA
                        organism = synthetic construct
SEQUENCE: 510
aaagatcaaa gg                                                12

SEQ ID NO: 511          moltype = DNA   length = 21
FEATURE                 Location/Qualifiers
source                  1..21
                        mol_type = other DNA
                        organism = synthetic construct
SEQUENCE: 511
ataaatataa aaggactaat t                                      21

SEQ ID NO: 512          moltype = DNA   length = 12
FEATURE                 Location/Qualifiers
source                  1..12
                        mol_type = other DNA
                        organism = synthetic construct
SEQUENCE: 512
agagatcaaa gg                                                12

SEQ ID NO: 513          moltype = DNA   length = 12
FEATURE                 Location/Qualifiers
source                  1..12
                        mol_type = other DNA
                        organism = synthetic construct
SEQUENCE: 513
ttgaaaaaaa aa                                                12

SEQ ID NO: 514          moltype = DNA   length = 15
FEATURE                 Location/Qualifiers
source                  1..15
                        mol_type = other DNA
                        organism = synthetic construct
SEQUENCE: 514
agttaattat taact                                             15

SEQ ID NO: 515          moltype = DNA   length = 15
FEATURE                 Location/Qualifiers
source                  1..15
                        mol_type = other DNA
                        organism = synthetic construct
SEQUENCE: 515
attaatcaat tattt                                             15

SEQ ID NO: 516          moltype = DNA   length = 13
FEATURE                 Location/Qualifiers
source                  1..13
                        mol_type = other DNA
                        organism = synthetic construct
SEQUENCE: 516
ggccccgcct acc                                               13

SEQ ID NO: 517          moltype = DNA   length = 16
FEATURE                 Location/Qualifiers
source                  1..16
                        mol_type = other DNA
                        organism = synthetic construct
SEQUENCE: 517
attttggcgc gaaaat                                            16

SEQ ID NO: 518          moltype = DNA   length = 11
FEATURE                 Location/Qualifiers
source                  1..11
                        mol_type = other DNA
                        organism = synthetic construct
SEQUENCE: 518
```

-continued

```
aattaggtca c                                                       11

SEQ ID NO: 519         moltype = DNA   length = 15
FEATURE                Location/Qualifiers
source                 1..15
                       mol_type = other DNA
                       organism = synthetic construct SEQUENCE: 519
attaatcaat ttttt                                                   15

SEQ ID NO: 520         moltype = DNA   length = 13
FEATURE                Location/Qualifiers
source                 1..13
                       mol_type = other DNA
                       organism = synthetic construct SEQUENCE: 520
ggacacgccc acc                                                     13

SEQ ID NO: 521         moltype = DNA   length = 10
FEATURE                Location/Qualifiers
source                 1..10
                       mol_type = other DNA
                       organism = synthetic construct SEQUENCE: 521
accggaaggg                                                         10

SEQ ID NO: 522         moltype = DNA   length = 18
FEATURE                Location/Qualifiers
source                 1..18
                       mol_type = other DNA
                       organism = synthetic construct SEQUENCE: 522
aacatgcctg ggcatgtc                                                18

SEQ ID NO: 523         moltype = DNA   length = 18
FEATURE                Location/Qualifiers
source                 1..18
                       mol_type = other DNA
                       organism = synthetic construct SEQUENCE: 523
aacatgcccg gacatgtc                                                18

SEQ ID NO: 524         moltype = DNA   length = 12
FEATURE                Location/Qualifiers
source                 1..12
                       mol_type = other DNA
                       organism = synthetic construct SEQUENCE: 524
gcccacgtgg cc                                                      12

SEQ ID NO: 525         moltype = DNA   length = 18
FEATURE                Location/Qualifiers
source                 1..18
                       mol_type = other DNA
                       organism = synthetic construct SEQUENCE: 525
aacatgcccg ggcatgtc                                                18

SEQ ID NO: 526         moltype = DNA   length = 18
FEATURE                Location/Qualifiers
source                 1..18
                       mol_type = other DNA
                       organism = synthetic construct SEQUENCE: 526
aacatgtccg ggcatgtc                                                18

SEQ ID NO: 527         moltype = DNA   length = 18
FEATURE                Location/Qualifiers
source                 1..18
                       mol_type = other DNA
                       organism = synthetic construct SEQUENCE: 527
aacatgttgg gacatgtc                                                18

SEQ ID NO: 528         moltype = DNA   length = 12
FEATURE                Location/Qualifiers
source                 1..12
                       mol_type = other DNA
                       organism = synthetic construct
```

-continued

```
SEQUENCE: 528
gagaacaaag ca                                                   12

SEQ ID NO: 529        moltype = DNA   length = 14
FEATURE               Location/Qualifiers
source                1..14
                      mol_type = other DNA
                      organism = synthetic construct
SEQUENCE: 529
atgccacgtc atca                                                 14

SEQ ID NO: 530        moltype = DNA   length = 23
FEATURE               Location/Qualifiers
source                1..23
                      mol_type = other DNA
                      organism = synthetic construct
SEQUENCE: 530
gggcgtgcgc tcccgacaag ccc                                       23

SEQ ID NO: 531        moltype = DNA   length = 18
FEATURE               Location/Qualifiers
source                1..18
                      mol_type = other DNA
                      organism = synthetic construct
SEQUENCE: 531
aacatgccca ggcatgtc                                             18

SEQ ID NO: 532        moltype = DNA   length = 14
FEATURE               Location/Qualifiers
source                1..14
                      mol_type = other DNA
                      organism = synthetic construct
SEQUENCE: 532
cctaaataaa caaa                                                 14

SEQ ID NO: 533        moltype = DNA   length = 15
FEATURE               Location/Qualifiers
source                1..15
                      mol_type = other DNA
                      organism = synthetic construct
SEQUENCE: 533
aaccgttaaa cggtc                                                15

SEQ ID NO: 534        moltype = DNA   length = 18
FEATURE               Location/Qualifiers
source                1..18
                      mol_type = other DNA
                      organism = synthetic construct
SEQUENCE: 534
aacatgtccg gacatgtc                                             18

SEQ ID NO: 535        moltype = DNA   length = 10
FEATURE               Location/Qualifiers
source                1..10
                      mol_type = other DNA
                      organism = synthetic construct
SEQUENCE: 535
ggtaattgac                                                      10

SEQ ID NO: 536        moltype = DNA   length = 14
FEATURE               Location/Qualifiers
source                1..14
                      mol_type = other DNA
                      organism = synthetic construct
SEQUENCE: 536
ttttggcgcc tttt                                                 14

SEQ ID NO: 537        moltype = DNA   length = 16
FEATURE               Location/Qualifiers
source                1..16
                      mol_type = other DNA
                      organism = synthetic construct
SEQUENCE: 537
gttttggcgc cttttc                                               16

SEQ ID NO: 538        moltype = DNA   length = 11
FEATURE               Location/Qualifiers
source                1..11
                      mol_type = other DNA
```

-continued

```
                              organism = synthetic construct
SEQUENCE: 538
gaaatttgag c                                                              11

SEQ ID NO: 539       moltype = DNA  length = 23
FEATURE              Location/Qualifiers
source               1..23
                     mol_type = other DNA
                     organism = synthetic construct
SEQUENCE: 539
gggcaagcgc tcccgacatg ccc                                                 23

SEQ ID NO: 540       moltype = DNA  length = 14
FEATURE              Location/Qualifiers
source               1..14
                     mol_type = other DNA
                     organism = synthetic construct
SEQUENCE: 540
gaggtcaaag gtca                                                           14

SEQ ID NO: 541       moltype = DNA  length = 23
FEATURE              Location/Qualifiers
source               1..23
                     mol_type = other DNA
                     organism = synthetic construct
SEQUENCE: 541
gggctagcgc tcccgacatg ccc                                                 23

SEQ ID NO: 542       moltype = DNA  length = 11
FEATURE              Location/Qualifiers
source               1..11
                     mol_type = other DNA
                     organism = synthetic construct
SEQUENCE: 542
gggcgggaag g                                                              11

SEQ ID NO: 543       moltype = DNA  length = 11
FEATURE              Location/Qualifiers
source               1..11
                     mol_type = other DNA
                     organism = synthetic construct
SEQUENCE: 543
gggcgggacg g                                                              11

SEQ ID NO: 544       moltype = DNA  length = 12
FEATURE              Location/Qualifiers
source               1..12
                     mol_type = other DNA
                     organism = synthetic construct
SEQUENCE: 544
ggacacgtgc cc                                                             12

SEQ ID NO: 545       moltype = DNA  length = 12
FEATURE              Location/Qualifiers
source               1..12
                     mol_type = other DNA
                     organism = synthetic construct
SEQUENCE: 545
gggaacaaag aa                                                             12

SEQ ID NO: 546       moltype = DNA  length = 23
FEATURE              Location/Qualifiers
source               1..23
                     mol_type = other DNA
                     organism = synthetic construct
SEQUENCE: 546
gggcatgcgc tcccgacatg ccc                                                 23

SEQ ID NO: 547       moltype = DNA  length = 14
FEATURE              Location/Qualifiers
source               1..14
                     mol_type = other DNA
                     organism = synthetic construct
SEQUENCE: 547
atgccacgtc agca                                                           14

SEQ ID NO: 548       moltype = DNA  length = 13
FEATURE              Location/Qualifiers
source               1..13
```

-continued

```
                              mol_type = other DNA
                              organism = synthetic construct
SEQUENCE: 548
ggccacgccc acc                                                    13

SEQ ID NO: 549          moltype = DNA   length = 20
FEATURE                 Location/Qualifiers
source                  1..20
                        mol_type = other DNA
                        organism = synthetic construct
SEQUENCE: 549
ccccaaaaca acccccccc                                              20

SEQ ID NO: 550          moltype = DNA   length = 12
FEATURE                 Location/Qualifiers
source                  1..12
                        mol_type = other DNA
                        organism = synthetic construct
SEQUENCE: 550
ggccacgtgg cc                                                     12

SEQ ID NO: 551          moltype = DNA   length = 116
FEATURE                 Location/Qualifiers
source                  1..116
                        mol_type = other DNA
                        organism = synthetic construct
SEQUENCE: 551
ccttgccgaa aagatttgtc tgaggaactg aaaatagaag ggaaaaaaga ggagggacaa   60
aagaggcaga aatgagaggg gaggggacag aggacacctg aataaagacc acaccc       116

SEQ ID NO: 552          moltype = DNA   length = 66
FEATURE                 Location/Qualifiers
source                  1..66
                        mol_type = other DNA
                        organism = synthetic construct
SEQUENCE: 552
gacccacgtg atgctgagaa gtactcctgc cctaggaaga gactcagggc agagggagga   60
aggaca                                                            66

SEQ ID NO: 553          moltype = DNA   length = 69
FEATURE                 Location/Qualifiers
source                  1..69
                        mol_type = genomic DNA
                        organism = Homo sapiens
SEQUENCE: 553
gctgttaatt attggcaaat nnnnnnnnnn nnnnnnnnnn nnnnnnnnnn nnnnaggtta   60
ctagttaac                                                         69

SEQ ID NO: 554          moltype = DNA   length = 69
FEATURE                 Location/Qualifiers
source                  1..69
                        mol_type = other DNA
                        organism = synthetic construct
SEQUENCE: 554
gctgttaatt attaacaaat nnnnnnnnnn nnnnnnnnnn nnnnnnnnnn nnnnaggtta   60
ataattaac                                                         69

SEQ ID NO: 555          moltype = DNA   length = 74
FEATURE                 Location/Qualifiers
source                  1..74
                        mol_type = other DNA
                        organism = synthetic construct
SEQUENCE: 555
ctgcgctccc gacatgcccc gcggcgcgcc attaaccgcc agatttgagt cgcgggaccc   60
gttggcagag gtgg                                                   74

SEQ ID NO: 556          moltype = DNA   length = 581
FEATURE                 Location/Qualifiers
source                  1..581
                        mol_type = other DNA
                        organism = synthetic construct
SEQUENCE: 556
ggtgactcat gatgatgcca cgtcaccaat gccacgtcac caggtgactc atgggtgact   60
catgacgtgt gacatgccac gtcaccaatg ccacgtcacc aggtgactca tgggtgactc   120
atgactagtg aattctaatt gctgagtcat tgctgctatg taattgctga gtcatatgcc   180
tatcctaatt gctgagtcat aatcgagatg taattgctga gtcatgtccg acgcataatt   240
gctgagtcat tctaactcgc taattgctga gtcatgtcga cactagtaag cttgggcgg    300
ggtgatgaca cagcaattcg ggactttcca cgcttgcgtg agaagagacc ggaagtgaat   360
gacacagcaa tggatccgct tgcgtgagaa gctgggactt tcctaggggc ggggttggga   420
```

-continued

```
ctttccacat gacacagcaa tacctcgagg gtaccgggaa aagttcagct gagagatata    480
aaagagcagt ctttccagca cctgcgtatc ccaggaggag caagtggcac gtcttcgggt    540
gagtgtgcgg ctgtgctgga gcccgggtta ccagctctta a                        581

SEQ ID NO: 557            moltype = DNA   length = 705
FEATURE                   Location/Qualifiers
source                    1..705
                          mol_type = other DNA
                          organism = synthetic construct
SEQUENCE: 557
ggtgactcat gatgatgcca cgtcaccaat gccacgtcac caggtgactc atgggtgact    60
catgacgtgt gacatgccac gtcaccaatg ccacgtcacc aggtgactca tgggtgactc    120
atgactagtg aattctaatt gctgagtcat tgctgctatg taattgctga gtcatatgcc    180
tatcctaatt gctgagtcat aatcgagatg taattgctga gtcatgtccg acgcataatt    240
gctgagtcat tctaactcgc taattgctga gtcatgtcga cactagtaag cttggggcgg    300
ggtgatgaca cagcaattcg ggactttcca cgcttgcgtg agaagagacc ggaagtgaat    360
gacacagcaa tggatccgct tgcgtgagaa gctgggactt tcctagggggc ggggttggga    420
ctttccacat gacacagcaa tacctcgagg gtacggcccg ccccctttcc ttacgcggat    480
tggtagctgc aggcttccct atctgattgg ccgaacgaac gcagcgcgta atttaaaata    540
ttgtatctgt aacaaagctg cacctcgtgg gcggagttgt gctctgcggc tgcgaaagtc    600
cagcttcggc gactaggtgt gagtaagcca gtatcccagg aggagcaagt ggcacgtctt    660
cgggtgcagt gtgcggctgt gctggagccc gggttaccag ctctt                    705

SEQ ID NO: 558            moltype = DNA   length = 309
FEATURE                   Location/Qualifiers
source                    1..309
                          mol_type = other DNA
                          organism = synthetic construct
SEQUENCE: 558
catactgaaa agcatacttt tgcaatgtta tttttaaaaa caaggaactc tttaacccag    60
ggaagataat cacttgggga aaggaaggtt cgtttctgag ttagcaacaa gtaaatgcag    120
cactagtggg tgggattgag gtatgccctg gtgcataaat agagactcag ctgtgctggc    180
acactcagaa gcttggaccg catcctagcc gccgactcac acaaggcagg tgggtgagga    240
aatccaggta aggctcctga cagcagcttt agaagggtac ttgctggagt gaattcgggc    300
ctctgatta                                                            309

SEQ ID NO: 559            moltype = DNA   length = 348
FEATURE                   Location/Qualifiers
source                    1..348
                          mol_type = other DNA
                          organism = synthetic construct
SEQUENCE: 559
acctcttaac aatacgtttc acaaatagtt aaaaacatgc atactgaaaa gcatactttt    60
gcaatgttat ttttaaaaac aaggaactct ttaacccagg gaagataatc acttggggaa    120
aggaaggttc gtttctgagt tagcaacaag taaatgcagc actagtgggt gggattgagg    180
tgtgccctg tgcataaata gagactcagc tgtgctggca cactcaagaa gcttggaccg    240
catcctagcc gccgactcac acaaggcagg tgggtgagga aatccaggta aggctcctga    300
cagcagcttt agaagggtac ttgctggagt gaattcgggc ctctgatt                 348

SEQ ID NO: 560            moltype = DNA   length = 382
FEATURE                   Location/Qualifiers
source                    1..382
                          mol_type = other DNA
                          organism = synthetic construct
SEQUENCE: 560
ccggcccgcc ccctttcctt acgcggattg gtagctgcag gcttccctat ctgattggcc    60
gaacgaacgc agcgcgtaat ttaaaatatt gtatctgtaa caaagctgca cctcgtgggc    120
ggagttgtgc tctgcggctg cgaaagtcca gcttcggcga ctaggtgtga gtaagccacg    180
gcggcgcaga tcgcccggcg cggctccgcc ccctgcgccg gtcacgtggg ggcgccggct    240
gcgcctgcgg agaagcggtg gccgccgagc gggatctgtg cggggagccg gaaatggttg    300
tggactacgt ctgtgcggct gcgtggggct cggccgcgcg gactgaagga gactgaaggt    360
gctggggga ccctgatgtg ga                                              382

SEQ ID NO: 561            moltype = DNA   length = 235
FEATURE                   Location/Qualifiers
source                    1..235
                          mol_type = other DNA
                          organism = synthetic construct
SEQUENCE: 561
ccggcccgcc ccctttcctt acgcggattg gtagctgcag gcttccctat ctgattggcc    60
gaacgaacgc agcgcgtaat ttaaaatatt gtatctgtaa caaagctgca cctcgtgggc    120
ggagttgtgc tctgcggctg cgaaagtcca gcttcggcga ctaggtgtga gtaagccact    180
ttttccgtgc tacctgcaga ggggtccata cggcgttgtt ctggattcac cggta         235

SEQ ID NO: 562            moltype = DNA   length = 275
FEATURE                   Location/Qualifiers
source                    1..275
                          mol_type = other DNA
                          organism = synthetic construct
```

```
SEQUENCE: 562
ccggcccgcc ccctttcctt acgcggattg gtagctgcag gcttccctat ctgattggcc    60
gaacgaacgc agcgcgtaat ttaaaatatt gtatctgtaa caaagctgca cctcgtgggc   120
ggagttgtgc tctgcggctg cgaaagtcca gcttcggcga ctaggtgtga gtaagccaca   180
ctcgcgctgc catcactctt ccgccgtctt cgccgccatc ctcggcgcga ctcgcttctt   240
tcggttctac caggtagagt ccgccgccat cctca                              275

SEQ ID NO: 563          moltype = DNA   length = 300
FEATURE                 Location/Qualifiers
source                  1..300
                        mol_type = other DNA
                        organism = synthetic construct
SEQUENCE: 563
ccggcccgcc ccctttcctt acgcggattg gtagctgcag gcttccctat ctgattggcc    60
gaacgaacgc agcgcgtaat ttaaaatatt gtatctgtaa caaagctgca cctcgtgggc   120
ggagttgtgc tctgcggctg cgaaagtcca gcttcggcga ctaggtgtga gtaagccaga   180
agcttggacc gcatcctagc cgccgactca cacaaggcag gtgggtgagg aaatccaggt   240
aaggctcctg acagcagctt tagaagggta cttgctggag tgaattcggg cctctgatta   300

SEQ ID NO: 564          moltype = DNA   length = 301
FEATURE                 Location/Qualifiers
source                  1..301
                        mol_type = other DNA
                        organism = synthetic construct
SEQUENCE: 564
ccggcccgcc ccctttcctt acgcggattg gtagctgcag gcttccctat ctgattggcc    60
gaacgaacgc agcgcgtaat ttaaaatatt gtatctgtaa caaagctgca cctcgtgggc   120
ggagttgtgc tctgcggctg cgaaagtcca gcttcggcga ctaggtgtga gtaagccaaa   180
atccagagcg gcgggcactg acgggcactt gcaccgtgtg gacagactct ccggttctgt   240
gagtggtttt tcttttcccg ggtcggacct ggagttctta gggggatggc tgaagaattc   300
a                                                                    301

SEQ ID NO: 565          moltype = DNA   length = 432
FEATURE                 Location/Qualifiers
source                  1..432
                        mol_type = other DNA
                        organism = synthetic construct
SEQUENCE: 565
cacctcttaa caatacgttt cacaaatagt taaaaacatg catactgaaa agcatacttt    60
tgcaatgtta tttttaaaaa caaggaactc tttaacccag ggaagataat cacttgggga   120
aaggaaggtt cgtttctgag ttagcaacaa gtaaatgcag cactagtggg tgggattgag   180
gtgtgccctg gtgcataaat agagactcag ctgtgctggc acactcaacg gcggcgcaga   240
tcgcccggcg cggctccgcc ccctgcgccg gtcacgtggg ggcgccggct cgcctgcgg   300
agaagcggtg gccgccgagc gggatctgtg cggggagccg gaaatggttg tggactacgt   360
ctgtgcggct gcgtgggggct cggccgcgcg gactgaagga gactgaaggt gctgggggga   420
ccctgatgtg ga                                                        432

SEQ ID NO: 566          moltype = DNA   length = 279
FEATURE                 Location/Qualifiers
source                  1..279
                        mol_type = other DNA
                        organism = synthetic construct
SEQUENCE: 566
cacctcttaa caatacgttt cacaaatagt taaaaacatg catactgaaa agcatacttt    60
tgcaatgtta tttttaaaaa caaggaactc tttaacccag ggaagataat cacttgggga   120
aaggaaggtt cgtttctgag ttagcaacaa gtaaatgcag cactagtggg tgggattgag   180
gtgtgccctg gtgcataaat agagactcag ctgtgctggc acactcaact ttttccgtgc   240
tacctgcaga ggggtccata cggcgttgtt ctggattca                          279

SEQ ID NO: 567          moltype = DNA   length = 325
FEATURE                 Location/Qualifiers
source                  1..325
                        mol_type = other DNA
                        organism = synthetic construct
SEQUENCE: 567
cacctcttaa caatacgttt cacaaatagt taaaaacatg catactgaaa agcatacttt    60
tgcaatgtta tttttaaaaa caaggaactc tttaacccag ggaagataat cacttgggga   120
aaggaaggtt cgtttctgag ttagcaacaa gtaaatgcag cactagtggg tgggattgag   180
gtgtgccctg gtgcataaat agagactcag ctgtgctggc acactcaaca ctcgcgctct   240
catcactctt ccgccgtctt cgccgccatc ctcggcgcga ctcgcttctt tcggttctac   300
caggtagagt ccgccgccat cctca                                          325

SEQ ID NO: 568          moltype = DNA   length = 304
FEATURE                 Location/Qualifiers
source                  1..304
                        mol_type = other DNA
                        organism = synthetic construct
SEQUENCE: 568
cacctcttaa caatacgttt cacaaatagt taaaaacatg catactgaaa agcatacttt    60
```

-continued

```
tgcaatgtta tttttaaaaa caaggaactc tttaacccag ggaagataat cacttgggga   120
aaggaaggtt cgtttctgag ttagcaacaa gtaaatgcag cactagtggg tgggattgag   180
gtgtgccctg gtgcataaat agagactcag ctgtgctggc acactcaagt atcccaggag   240
gagcaagtgg cacgtcttcg ggtgagtgtg cggctgtgct ggagcccggg ttaccagctc   300
ttaa                                                                304
```

```
SEQ ID NO: 569           moltype = DNA  length = 351
FEATURE                  Location/Qualifiers
source                   1..351
                         mol_type = other DNA
                         organism = synthetic construct
SEQUENCE: 569
cacctcttaa caatacgttt cacaaatagt taaaaacatg catactgaaa agcatacttt   60
tgcaatgtta tttttaaaaa caaggaactc tttaacccag ggaagataat cacttgggga   120
aaggaaggtt cgtttctgag ttagcaacaa gtaaatgcag cactagtggg tgggattgag   180
gtgtgccctg gtgcataaat agagactcag ctgtgctggc acactcaaaa atccagagcg   240
gcgggcactg acgggcactt gcaccgtgtg dacagactct ccggttctgt gagtggtttt   300
tcttttcccg ggtcggacct ggagttctta gggggatggc tgaagaattc a            351
```

```
SEQ ID NO: 570           moltype = DNA  length = 255
FEATURE                  Location/Qualifiers
source                   1..255
                         mol_type = other DNA
                         organism = synthetic construct
SEQUENCE: 570
cgggaaaagt tcagctgaga gatataaaag agcagtcttt ccagcacctg ccggcggcgc   60
agatcgcccg gcgcgggctcc gcccctgcg ccggtcacgt gggggcgccg gctgcgcctg   120
cggagaagcg gtgccgccg agcgggatct gtgcggggag ccggaaatgg ttgtggacta   180
cgtctgtgcg gctgcgtggg gctcggccgc gcggactgaa ggagactgaa ggtgctgggg   240
ggaccctgat gtgga                                                    255
```

```
SEQ ID NO: 571           moltype = DNA  length = 102
FEATURE                  Location/Qualifiers
source                   1..102
                         mol_type = other DNA
                         organism = synthetic construct
SEQUENCE: 571
cgggaaaagt tcagctgaga gatataaaag agcagtcttt ccagcacctg cctttttccg   60
tgctacctgc agagggtcc atacggcgtt gttctggatt ca                       102
```

```
SEQ ID NO: 572           moltype = DNA  length = 148
FEATURE                  Location/Qualifiers
source                   1..148
                         mol_type = other DNA
                         organism = synthetic construct
SEQUENCE: 572
cgggaaaagt tcagctgaga gatataaaag agcagtcttt ccagcacctg ccactcgcgc   60
tgccatcact cttccgccgt cttcgccgcc atcctcggcg cgactcgctt ctttcggttc   120
taccaggtag agtccgccgc catcctca                                      148
```

```
SEQ ID NO: 573           moltype = DNA  length = 127
FEATURE                  Location/Qualifiers
source                   1..127
                         mol_type = other DNA
                         organism = synthetic construct
SEQUENCE: 573
cgggaaaagt tcagctgaga gatataaaag agcagtcttt ccagcacctg cgtatcccag   60
gaggagcaag tggcacgtct tcgggtgagt gtgcggctgt gctggagccc gggttaccag   120
ctcttaa                                                             127
```

```
SEQ ID NO: 574           moltype = DNA  length = 173
FEATURE                  Location/Qualifiers
source                   1..173
                         mol_type = other DNA
                         organism = synthetic construct
SEQUENCE: 574
cgggaaaagt tcagctgaga gatataaaag agcagtcttt ccagcacctg cgaagcttgg   60
accgcatcct agccgccgac tcacacaagg caggtgggtg aggaaatcca ggtaaggctc   120
ctgacagcag cttttagaagg gtacttgctg gagtgaattc gggcctctga tta         173
```

```
SEQ ID NO: 575           moltype = DNA  length = 191
FEATURE                  Location/Qualifiers
source                   1..191
                         mol_type = other DNA
                         organism = synthetic construct
SEQUENCE: 575
agcttgcatg cctgcaggtc ggagtactgt cctccgagcg gagtactgtc ctccgagcgg   60
agtactgtcc tccgagcgga gtactgtcct ccgagcggag tactgtcctc cgagcggtgc   120
gctcccgaca tgccccgcgg cgcgccatta accgccagat ttgagtcgcg ggaccggttg   180
```

-continued

```
gcagaggtgg g                                                        191

SEQ ID NO: 576          moltype = DNA   length = 191
FEATURE                 Location/Qualifiers
source                  1..191
                        mol_type = other DNA
                        organism = synthetic construct
SEQUENCE: 576
agtggtgggg gagtgaaaag agagatggag aaagagggga tgggcagaaa gaggaggagg   60
agtcaggggc agggcatgga ggtgggtggg gctgggctgc caaagcagga taaatgcaca  120
cctgcctgct ggtctgggct ccctgcctcg ggctctcacc ctcctctcct gcagctccag  180
ctttgtgctc t                                                       191

SEQ ID NO: 577          moltype = DNA   length = 291
FEATURE                 Location/Qualifiers
source                  1..291
                        mol_type = other DNA
                        organism = synthetic construct
SEQUENCE: 577
catactgaaa agcatacttt tgcaatgtta tttttaaaaa caaggaactc tttaacccag   60
ggaagataat cacttgggga aaggaaggtt cgtttctgag ttagcaacaa gtaaatgcag  120
cactagtggg tgggattgag gtgtgccctg gtgcataaat agagactcag ctgtgctggc  180
acactcagaa gcttggaccg catcctagcc gccgactcac acaaggcagg tgggtgagga  240
aatccaggta aggctcctga cagcagcttt agaagggtac ttgctggagt g           291

SEQ ID NO: 578          moltype = DNA   length = 250
FEATURE                 Location/Qualifiers
source                  1..250
                        mol_type = other DNA
                        organism = synthetic construct
SEQUENCE: 578
ggcccgcccc ctttccttac gcggattggt agctgcaggc ttccctatct gattggccga   60
acgaacgcag cgcgtaattt aaaatattgt atctgtaaca aagctgcacc tcgtgggcgg  120
agttgtgctc tgcggctgcg aaagtccagc ttcggcgact aggtgtgagt aagccagtat  180
cccaggagga gcaagtggca cgtcttcggg tgagtgtgcg gctgtgctgg agcccgggtt  240
accagctctt                                                         250

SEQ ID NO: 579          moltype = DNA   length = 165
FEATURE                 Location/Qualifiers
source                  1..165
                        mol_type = other DNA
                        organism = synthetic construct
SEQUENCE: 579
gggaaaagtt cagctgagag atataaaaga gcagtctttc cagcacctgc aaatccagag   60
cggcgggcac tgacgggcac ttgcaccgtg tggacagact ctccggttct gtgagtggtt  120
tttcttttcc cgggtcggac ctggagttct taggggatg gctga                   165

SEQ ID NO: 580          moltype = DNA   length = 110
FEATURE                 Location/Qualifiers
source                  1..110
                        mol_type = other DNA
                        organism = synthetic construct
SEQUENCE: 580
acccacgtga tgctgagaag tactcctgcc ctaggaagag actcagggca gagggaggaa   60
ggacagcaga ccagacagtc acagcagcct tgacaaaacg ttcctggaac              110

SEQ ID NO: 581          moltype = DNA   length = 37
FEATURE                 Location/Qualifiers
source                  1..37
                        mol_type = other DNA
                        organism = synthetic construct
SEQUENCE: 581
tataaaaggc cagcagcagc ctgaccacat ctcatcc                            37

SEQ ID NO: 582          moltype = DNA   length = 125
FEATURE                 Location/Qualifiers
source                  1..125
                        mol_type = other DNA
                        organism = synthetic construct
SEQUENCE: 582
cactcccaga aggcagcggg cgagggcgtg gggccggggc tctcccggca tgctctgcgg   60
cgcgcctccg cccgcgcgat ttgaatcctg cgtttgagtc gtcttggcgg aggttgtggt  120
gacgc                                                              125

SEQ ID NO: 583          moltype = DNA   length = 67
FEATURE                 Location/Qualifiers
source                  1..67
                        mol_type = other DNA
                        organism = synthetic construct
```

```
SEQUENCE: 583
tcccgacatg ccccgcggcg cgccattaac cgccagattt gagtcgcggg acccgttggc  60
agaggtg                                                              67

SEQ ID NO: 584        moltype = DNA  length = 35
FEATURE               Location/Qualifiers
source                1..35
                      mol_type = other DNA
                      organism = synthetic construct
SEQUENCE: 584
gtatcccagg aggagcaagt ggcacgtctt cgggt                                        35

SEQ ID NO: 585        moltype = DNA  length = 51
FEATURE               Location/Qualifiers
source                1..51
                      mol_type = other DNA
                      organism = synthetic construct
SEQUENCE: 585
cgggaaaagt tcagctgaga gatataaaag agcagtcttt ccagcacctg c                     51

SEQ ID NO: 586        moltype = DNA  length = 76
FEATURE               Location/Qualifiers
source                1..76
                      mol_type = other DNA
                      organism = synthetic construct
SEQUENCE: 586
gtatcccagg aggagcaagt ggcacgtctt cgggtgagtg tgcggctgtg ctggagcccg  60
ggttaccagc tcttaa                                                    76

SEQ ID NO: 587        moltype = DNA  length = 39
FEATURE               Location/Qualifiers
source                1..39
                      mol_type = other DNA
                      organism = synthetic construct
SEQUENCE: 587
cagtgtgcgg ctgtgctgga gcccgggtta ccagctctt                                   39
```

SYNTHETIC CANCER-SPECIFIC PROMOTERS

CROSS REFERENCE

This application claims the benefit of U.S. Provisional Application No. 63/834,389, filed on Jan. 22, 2025, and is a Continuation in-part of U.S. Nonprovisional Application No. 18/455,209, filed on Aug. 24, 2023, which is a Continuation of U.S. Nonprovisional Application No. 17/219, 666, filed Mar. 31, 2021, now U.S. Pat. No. 12,060,613, issued Aug. 13, 2024, which is a Continuation in-part of International Application No. PCT/US2020/026758, filed Apr. 4, 2020, which claims benefit of U.S. patent application No. 62/955,925, filed Dec. 31, 2019, and U.S. Provisional Application No. 62/830,279, filed Apr. 5, 2019, each of which are incorporated by reference herein in their entirety.

SEQUENCE LISTING

The instant application contains a Sequence Listing which has been submitted electronically in XML format and is hereby incorporated by reference in its entirety. Said XML format sequence listing, created on May 22, 2025, is named 53531-724_201_SL.xml, and is 704,717 bytes in size.

BACKGROUND

Endogenous cancer-activated promoters are controlled by a wide network of transcription factors (TFs), which can lead to non-ideal basal activity in non-target cells. It is also difficult to reliably predict the activity in a wide variety of cancer models.

SUMMARY

There is a need to develop synthetic cancer-specific promoters with high specificity and sensitivity, for use in delivering polypeptides to cancer cells.

In some aspects, provided herein is a recombinant poly-nucleotide comprising: (a) a core promoter comprising a transcription start site (TSS), wherein the core promoter is derived from one or cancer-responsive genes that are either expressed at a higher level or are more active in cancer cells compared to non-cancer cells and operably linked to an open reading frame (ORF) and (b) a plurality of binding sites for one or more transcription factors (TFs), wherein said one or more TFs are expressed at higher levels or more active in cancer cells compared to non-cancer cells. In some embodiments, the recombinant polynucleotide further comprises a plurality of enhancers. In some embodiments, said plurality of enhancers are derived from one or more cancer-responsive genes that are either expressed at a higher level or are more active in cancer cells compared to non-cancer cells. In some embodiments, said plurality of enhancers are derived from two or more cancer-responsive genes that are either expressed at a higher level or are more active in cancer cells compared to non-cancer cells, wherein one of said plurality of enhancers comprises: (i) a transcription regulatory element with at least 90% sequence homology to an enhancer consensus sequence of two or more homologous cancer-responsive genes, and/or (ii) a sequence capable of binding a transcription associated protein as determined by chromatin immunoprecipitation (ChIP) or an in vitro transfection reporter assay.

In some aspects, provided herein is a recombinant poly-nucleotide comprising: (a) a core promoter comprising a transcription start site (TSS) and two or more promoter elements derived from two or more cancer-responsive genes that are either expressed at a higher level or are more active in cancer cells compared to non-cancer cells and operably linked to an open reading frame (ORF) and (b) a plurality of binding sites for one or more transcription factors (TFs), wherein said one or more TFs are expressed at higher levels or more active in cancer cells compared to non-cancer cells. In some embodiments, the recombinant polynucleotide further comprises a plurality of enhancers. In some embodiments, said plurality of enhancers are derived from one or more cancer-responsive genes that are either expressed at a higher level or are more active in cancer cells compared to non-cancer cells. In some embodiments, said plurality of enhancers are derived from two or more cancer-responsive genes that are either expressed at a higher level or are more active in cancer cells compared to non-cancer cells, wherein one of said plurality of enhancers comprises: (i) a transcription regulatory element with at least 90% sequence homology to an enhancer consensus sequence of two or more homologous cancer-responsive genes, and/or (ii) a sequence capable of binding a transcription associated protein as determined by chromatin immunoprecipitation (ChIP) or an in vitro transfection reporter assay.

In some aspects, provided herein is a recombinant poly-nucleotide comprising: (a) a core promoter comprising a transcription start site (TSS), wherein the core promoter is derived from one or more cancer-responsive genes that are either expressed at a higher level or are more active in cancer cells compared to non-cancer cells and operably linked to an open reading frame (ORF) and (b) a plurality of enhancers. In some embodiments, said plurality of enhancers are derived from one or more cancer-responsive genes that are either expressed at a higher level or are more active in cancer cells compared to non-cancer cells. In some embodiments, said plurality of enhancers are derived from two or more cancer-responsive genes that are either expressed at a higher level or are more active in cancer cells compared to non-cancer cells, wherein one of said plurality of enhancers comprises: (i) a transcription regulatory element with at least 90% sequence homology to an enhancer consensus sequence of two or more homologous cancer-responsive genes, and/or (ii) a sequence capable of binding a transcription associated protein as determined by chromatin immunoprecipitation (ChIP) or an in vitro transfection reporter assay.

In some aspects, provided herein, is a recombinant poly-nucleotide comprising: (a) a core promoter comprising a transcription start site (TSS), wherein the core promoter is derived from one or more cancer-responsive genes that are either expressed at a higher level or are more active in cancer cells compared to non-cancer cells and operably linked to an open reading frame (ORF), (b) a plurality of binding sites for one or more transcription factors (TFs), wherein said one or more TFs are expressed at higher levels or more active in cancer cells compared to non-cancer cells, and (c) a plurality of enhancers. In some embodiments, said plurality of enhancers are derived from one or more cancer-responsive genes that are either expressed at a higher level or are more active in cancer cells compared to non-cancer cells. In some embodiments, said plurality of enhancers are derived from two or more cancer-responsive genes that are either expressed at a higher level or are more active in cancer cells compared to non-cancer cells, wherein one of said plurality of enhancers comprises: (i) a transcription regulatory element with at least 90% sequence homology to an enhancer consensus sequence of two or more homologous cancer-responsive genes, and/or (ii) a sequence capable of binding a transcription associated protein as determined by chromatin immunoprecipitation (ChIP) or an in vitro transfection reporter assay.

In some aspects, provided herein is a recombinant polynucleotide comprising any of the sequences from Table 1A, Table 1B, or Table 1C. In some aspects, provided herein is a recombinant polynucleotide comprising a human alpha-fetoprotein (AFP) promoter sequence comprising a plurality of HNF-1A TF binding sites, wherein each HNF-1A binding site comprises the sequence 5'-GTTAATTATTAAC-3.'

In some aspects, provided herein is a vector comprising any of the recombinant polynucleotide described herein. In some aspects, provided herein is a pharmaceutical composition comprising any of the recombinant polynucleotide described herein or any the vector described herein and a pharmaceutically acceptable excipient, carrier, or diluents. In some aspects, provided herein is a lipid nanoparticle (LNP) comprising any of the recombinant polynucleotide described herein, any of the vector described herein, or any of the pharmaceutical composition described herein. In some aspects, provided herein is a cell comprising any the recombinant polynucleotide described herein, any of the vector described herein, any of the pharmaceutical composition described herein, or any of the LNP described herein.

In some aspects, provided herein is a method of selectively expressing a reporter protein in a cancer or tumor cell, comprising contacting said tumor cell with any of the recombinant polynucleotide described herein, any of the vector described herein, any of the pharmaceutical composition described herein, or any of the LNP described herein, wherein the recombinant polynucleotide further comprises an open reading frame (ORF) encoding said reporter protein, wherein said ORF is operatively linked to said synthetic promoter.

In some aspects, provided herein is a method comprising: (a) administering to a subject any of the pharmaceutical composition described herein; or a composition any of the recombinant polynucleotide described herein, any of the vector described herein, or any of the LNP described herein; wherein the recombinant polynucleotide further comprises an open reading frame (ORF) encoding a reporter protein, wherein said ORF is operatively linked to a synthetic promoter in said recombinant polynucleotide, and (b) detecting said reporter protein, wherein said pharmaceutical composition or said composition induces expression of said reporter protein preferentially in diseased cells in said subject compared to in non-disease cells, and wherein a relative ratio of said reporter protein expressed in said diseased cells over said non-diseased cells is greater than 1.0.

In some aspects, provided herein is a method for treating a subject having or suspected of having a disease, comprising administering to said subject any of the pharmaceutical composition described herein; or a composition any of the recombinant polynucleotide described herein, any of the vector described herein, or any of the LNP described herein; wherein the recombinant polynucleotide further comprises an open reading frame (ORF) encoding a therapeutic protein, wherein said ORF is operatively linked to a synthetic promoter in said recombinant polynucleotide, wherein said pharmaceutical composition or said composition induces expression of said therapeutic protein preferentially in diseased cells in said subject compared to in non-disease cells, and wherein a relative ratio of said therapeutic protein expressed in said diseased cells over said non-diseased cells is greater than 1.0.

In some aspects, provided herein is a method comprising: (a) administering to a subject any of the pharmaceutical composition described herein; or a composition any of the recombinant polynucleotide described herein, any of the vector described herein, or any of the LNP described herein; wherein the recombinant polynucleotide further comprises an open reading frame (ORF) encoding a reporter protein, wherein said ORF is operatively linked to a synthetic promoter in said recombinant polynucleotide, and (b) localizing a tumor or an absence thereof in a body of said subject via expression of said reporter protein using an imaging technique performed on said body of said subject.

In some aspects, provided herein is a method comprising: (a) introducing to a subject suspected of having a cancer via intravenous administration any of the pharmaceutical composition described herein; or a composition any of the recombinant polynucleotide described herein, any of the vector described herein, or any of the LNP described herein; wherein said recombinant polynucleotide further comprises an open reading frame (ORF) encoding a reporter protein, wherein said ORF is operatively linked to a synthetic promoter in said recombinant polynucleotide, and (b) detecting said reporter protein from said subject.

In some aspects, provided herein is a method comprising: (a) introducing to a subject suspected of having a cancer via intravenous administration a plurality of recombinant polynucleotides, wherein: said plurality of recombinant polynucleotides comprises a plurality of different promoters of genes overexpressed in a tumor cell versus a normal tissue or functional fragments thereof operably linked to genes encoding reporter proteins, wherein said plurality of different promoters of genes overexpressed in said tumor cell versus said normal tissue drive expression of said corresponding reporter proteins in a cell affected by said cancer, wherein said DNA molecules are selected from the group consisting of nanoplasmids and linear double-stranded DNA molecules; and (b) detecting said reporter proteins from said subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

FIG. 1 shows a schematic of synthetic promoter architecture and design including, for example, a fragment of SEQ ID NO: 378.

FIG. 3 describes coreCEP55 design.

FIG. 4 describes coreFAM111B design.

FIG. 10 describes the workflow of synthetic promoter design and construction.

Figure 11:
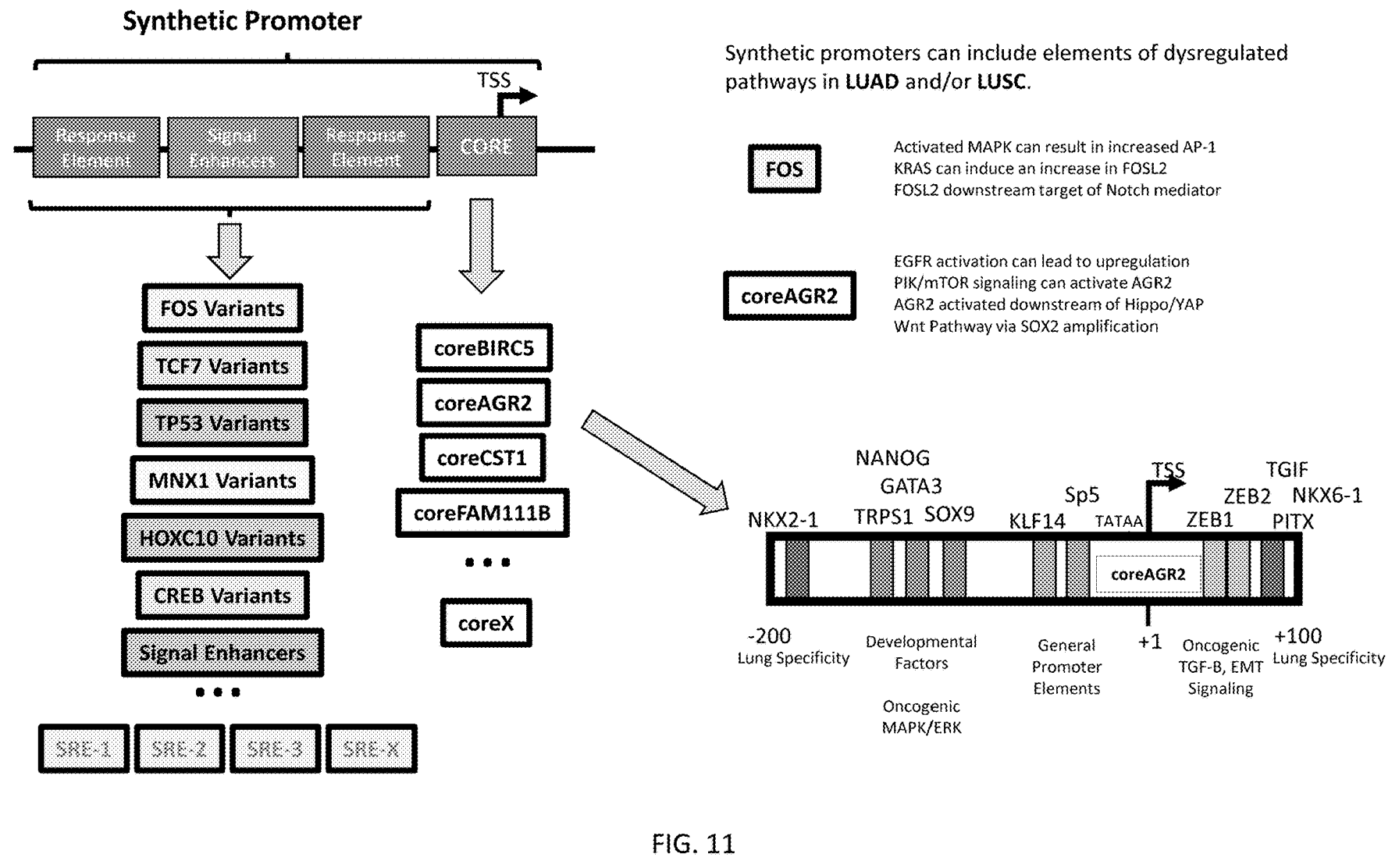

FIG. 11 describes the workflow of synthetic promoter design and construction with coreAGR2.

FIG. 12 describes the synthetic promoter architecture, design, discovery and validation pipeline.

FIG. 13 describes Transcription Factor Tile Design (top) and how to measure synthetic element expression (bottom). Each synthetic DNA sequence was designed as a series of repeated transcription factor (TF) binding sites derived from the consensus binding motif for the TF of interest (blue). To test the impact of the different relative positioning of these sites around the helical nature of the double stranded DNA (one helical turn is equivalent to ~10.5 base pairs), the repeated binding sites are separated by a variable length of nucleic acid spacer sequences (yellow). Lastly, the synthetic DNA sequence contains a short filler sequence (grey) to maintain consistent total length of the candidate enhancer sequence block.

FIG. 15 shows the reporter gene expression by HOXC10 tiles. Using a luciferase reporter assay lead candidates representing the MNX1, HOXC10 and CREB3L1 transcription factors were tested across seven lung cancer cell line models (H1299, PDX430, PDX1121, PDX629, PDX529, PDX586, and PDX2184) and one lung normal cell line (IMR90). Higher expression compared to FOSL-coreBIRC5 lead synthetic promoter with up to 50-80 fold improvement was observed.

Figure 16:
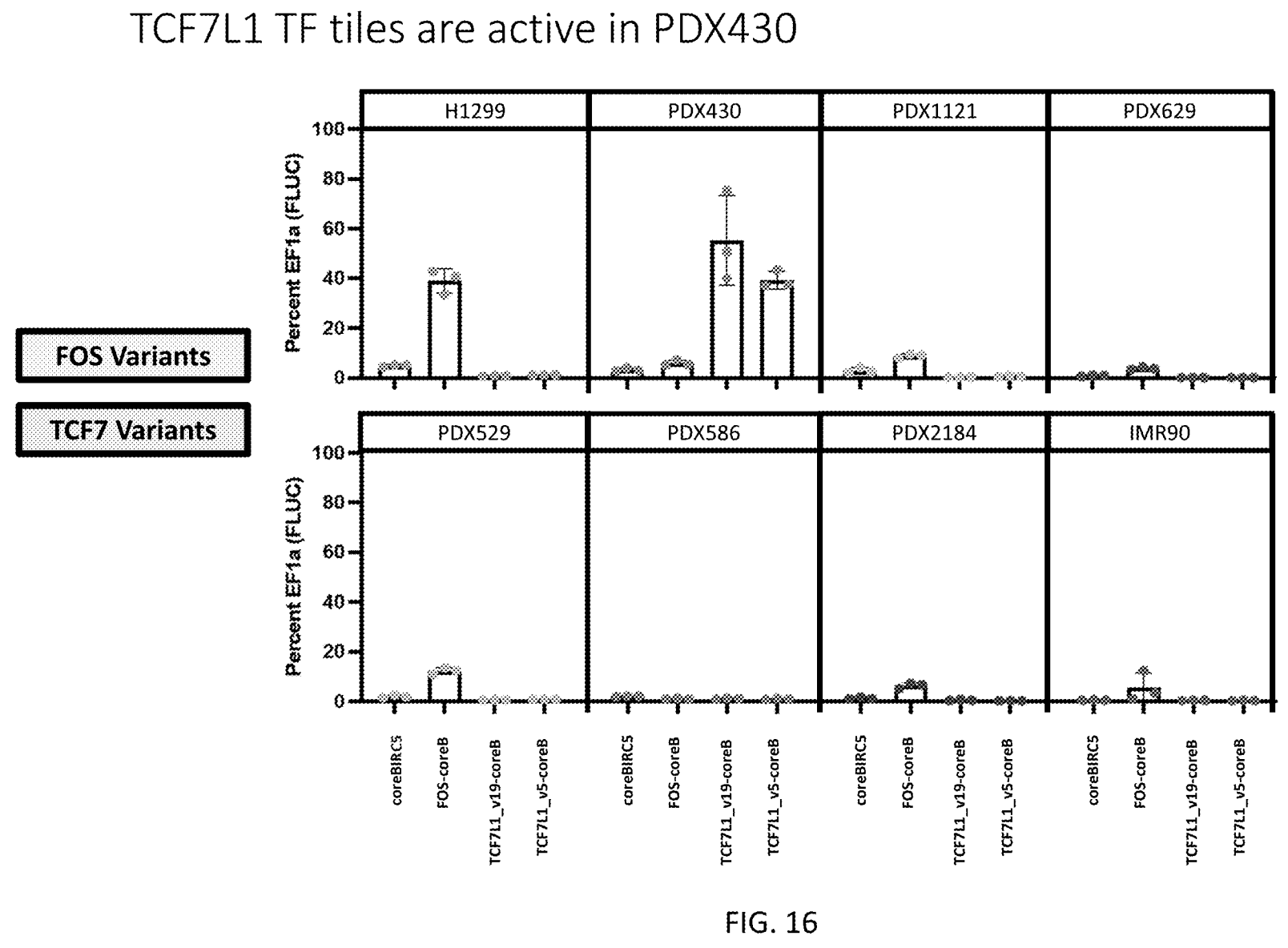

FIG. 16 shows the reporter gene expression by TCF7L1 TF tiles in PDX430 cell line.

FIG. 23 shows a table comparing TP53 status and reporter gene expression in different cell lines.

FIG. 30B shows that the synthetic promoter also demonstrates lack of expression in normal human fibroblast cell line (IMR-90), small airway epithelial cells (SAEC) and normal human bronchial epithelial cells (NHBE).

FIG. 33 shows the binding of FOSL2 and C-Jun TFs to the FOS element in the FOS-coreBIRC5 promoter. Chromatin immunoprecipitation (ChIP) was performed on two different cell lines transfected with the FOS-coreBIRC5 promoter construct (e.g., SEQ ID NO: 169). Pulldowns for FOSL2 and c-Jun showed significant enrichment of the coreBIRC5 element compared to nonspecific pulldown, by 14× for FOSL2 in H1299 and 5× for FOSL2 in A549. With the comparison to the control construct of solely coreBIRC5, this makes it clear that the FOS response element is responsible for the association of FOSL2 and C-Jun with the synthetic promoter.

In FIG. 38A, the primary changes to the AFP promoter sequence are shown, changing the HNF-1A sites to the consensus sequence for the transcription factor binding site. FIG. 38A discloses SEQ ID NOs: 553-554 and 128, respectively, in order of appearance. FIG. 38B shows that engineered AFP-3 (SEQ ID NO: 554) drives up to 200-fold higher expression in liver cancer cell lines than the wildtype AFP promoter (SEQ ID NOs: 553), while still maintaining high specificity against lung normal (IMR-90, MRC-9), lung cancer (H1299) and melanoma (MeWo) cell lines, as compared to the Survivin (BIRC5) promoter which shows some cancer-activated activity in both liver and non-liver cancer cell lines.

FIGS. 40A, 40B, and 40C show immunohistochemistry (IHC) results for AFP-3-sr39tk, using HA epitope. FIGS. 40A and 40B show representative serial sections from the tumor-bearing left lobe of a mouse in Group 6 (AFP-3-sr39tk) dosed at 2.8mpk of EM-40 stained by H&E and by HA antibody for the reporter expression. The tumor boundary has been outlined in the H&E slide. Reporter expression is confined to the tumor cells only. In FIG. 40C, the same mouse's right liver lobe, devoid of tumor is shown to have no positive cells.

FIG. 47 shows an exemplary workflow of diagnostic medical sonography (DMS) study.

FIG. 56 shows a table of top 10 enhancer candidates.

FIG. 58 shows comparison of the reporter gene expression performance by different synthetic promoters comprising enhancer elements in various cancer cell lines.

FIG. 63 shows exemplary core promoters with annotations. FIG. 63 discloses SEQ ID NO: 555.

FIG. 64A shows a diagram of an annotated core FAM111B promoter with predicted TF binding sites.

FIG. 64B shows activating and repressing elements within coreFAM111B identified from core promoter element deletion studies.

FIG. 67, left, e.g., a fragment of SEQ ID NO: 202), ELK3 (FIG. 67, middle, e.g., a fragment of SEQ ID NO: 150), FOXO::ELK (FIG. 67, right, e.g., a fragment of SEQ ID NO: 150), XBP1 (FIG. 68, top left, e.g., a fragment of SEQ ID NO: 155), NFE2L2 (FIG. 68, top right, e.g., a fragment of SEQ ID NO: 152), and MTF1 (FIG. 68, bottom, e.g., a fragment of SEQ ID NO: 151).

(FIG. 74K).

FIGS. 74B, 74D, 74F, 74H, 74J, and 74L show graphs of gene expression activated by an SRS designed to drive gene expression in lung cancers (SRS-A, SRS-B, SRS-C, SRS-D, SRS-E, and SRS-F). A luciferase reporter expression system was used to evaluate the strength of activation in cell lines that represent the NSCLC subtypes as well as normal primary lung cells. Expression values are shown as the fold change over a strong constitutive promoter on the left. Same data plotted as an ROC curve is presented on the right.

FIG. 75 shows graphs of expression pattern of a reporter gene activated by a constitutive or non-cancer specific promoter, Cytomegalovirus (CMV). A luciferase reporter expression system was used to evaluate the strength of activation in cell lines that represent the NSCLC subtypes as well as normal primary lung cells. Expression values are shown as the fold change over a strong constitutive promoter on the left. Same data plotted as an ROC curve is presented on the right.

DETAILED DESCRIPTION

Figure 2:
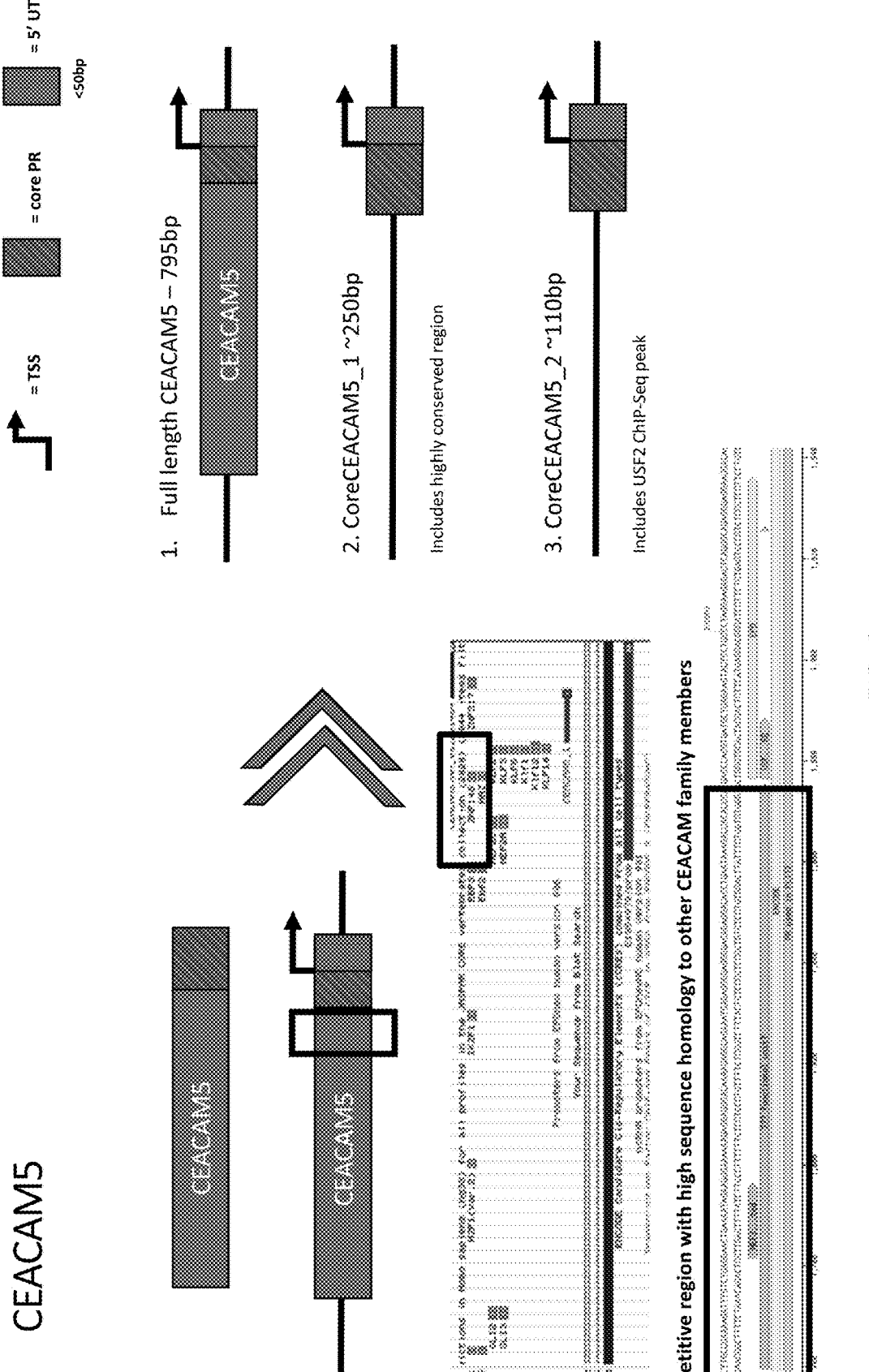
FIG. 2 describes coreCEACAM5 design, including, for example, a fragment of SEQ ID NO: 121.
Figure 5:
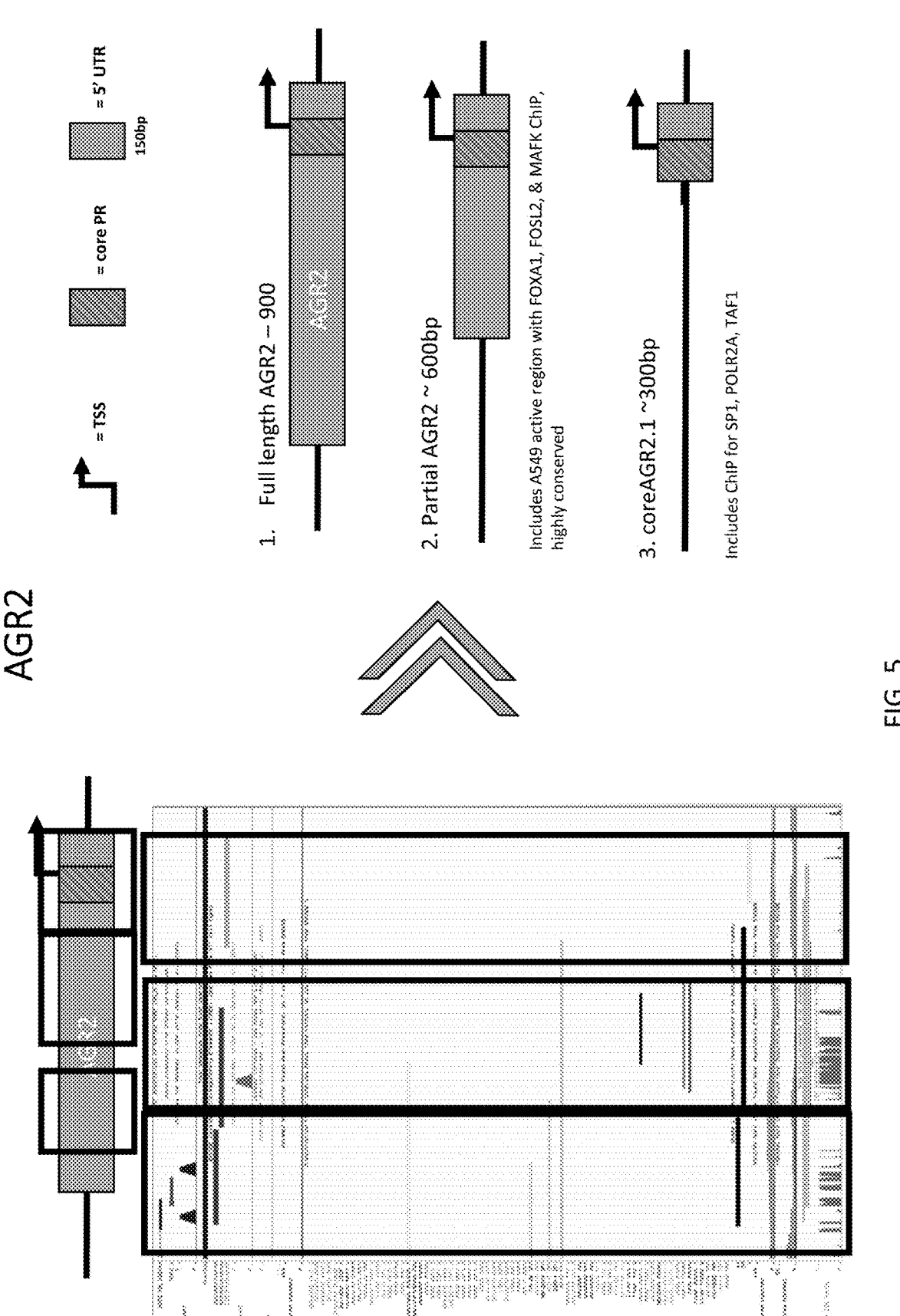
FIG. 5 describes coreAGR2 design.
Figure 6:
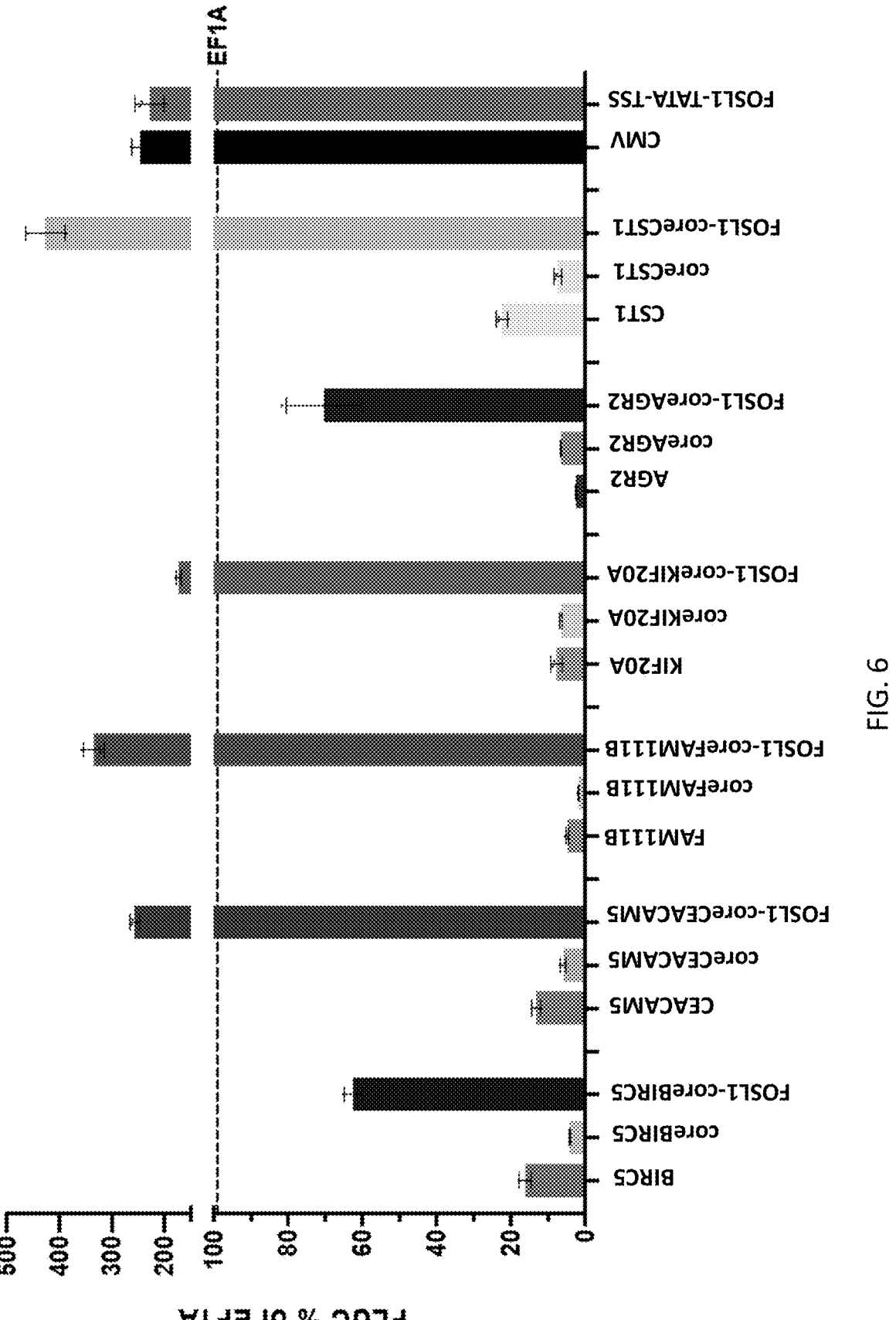
FIG. 6 shows the comparison of the reporter gene expression by endogenous promoter and synthetic promoter in H1299 cells.
Figure 7:
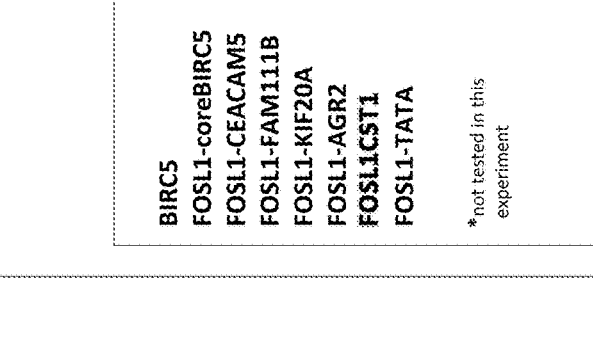
FIG. 7 shows the reporter gene expression performance by synthetic promoters in human PDX models. Bar graphs from left to right: BIRC5, FOSL1-coreBIRC5, FOSL1-CEACAM5, FOSL1-FAM111B, FOSL1-KIF20A, FOSL1-AGR2, and FOSL1-TATA, respectively.
Figure 8:
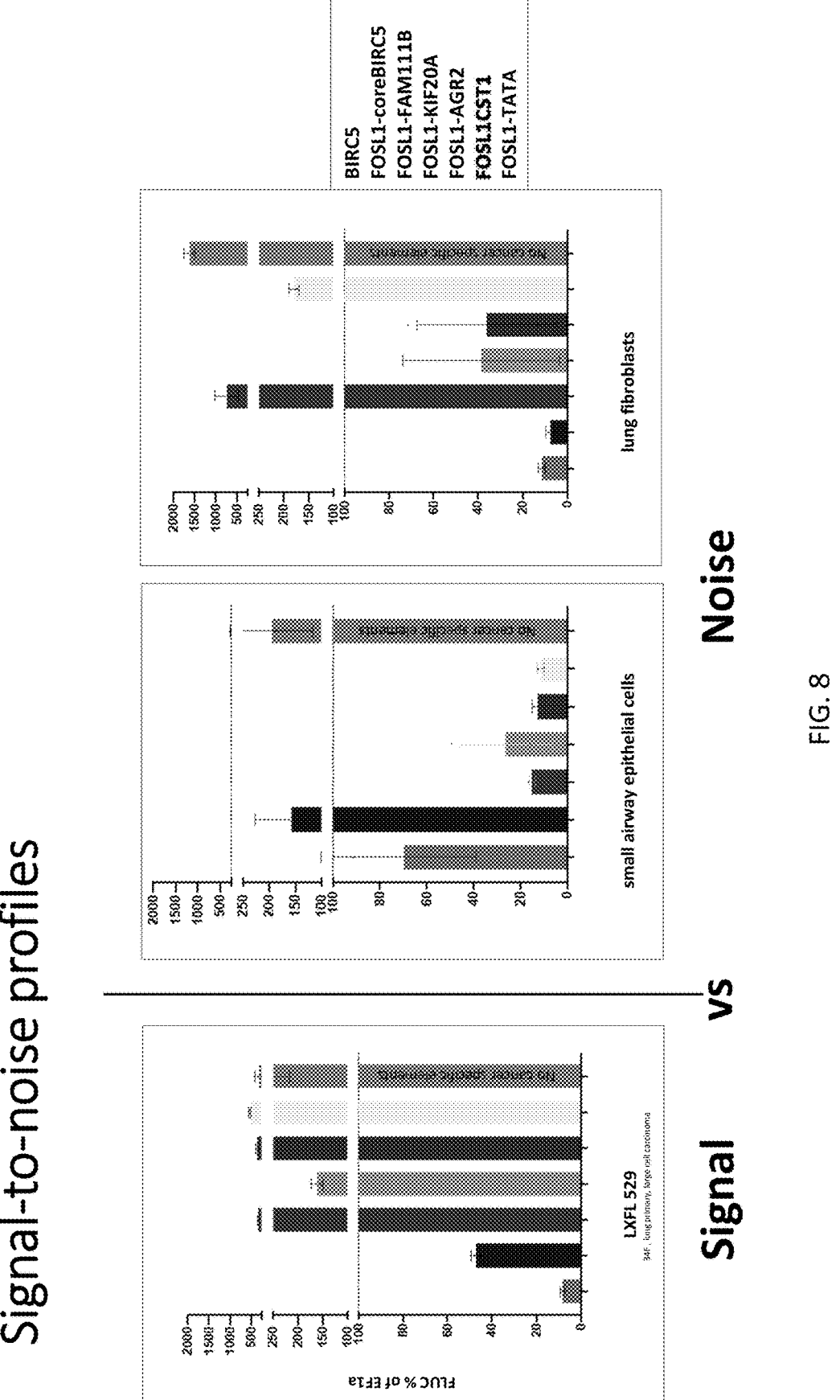
FIG. 8 shows signal-to-noise profiles of the reporter gene expression by synthetic promoters. Bar graphs from left to right: BIRC5, FOSL1-coreBIRC5, FOSL1-FAM111B, FOSL1-KIF20A, FOSL1-AGR2, FOSL1-CST1, and FOSL1-TATA, respectively.
Figure 9:
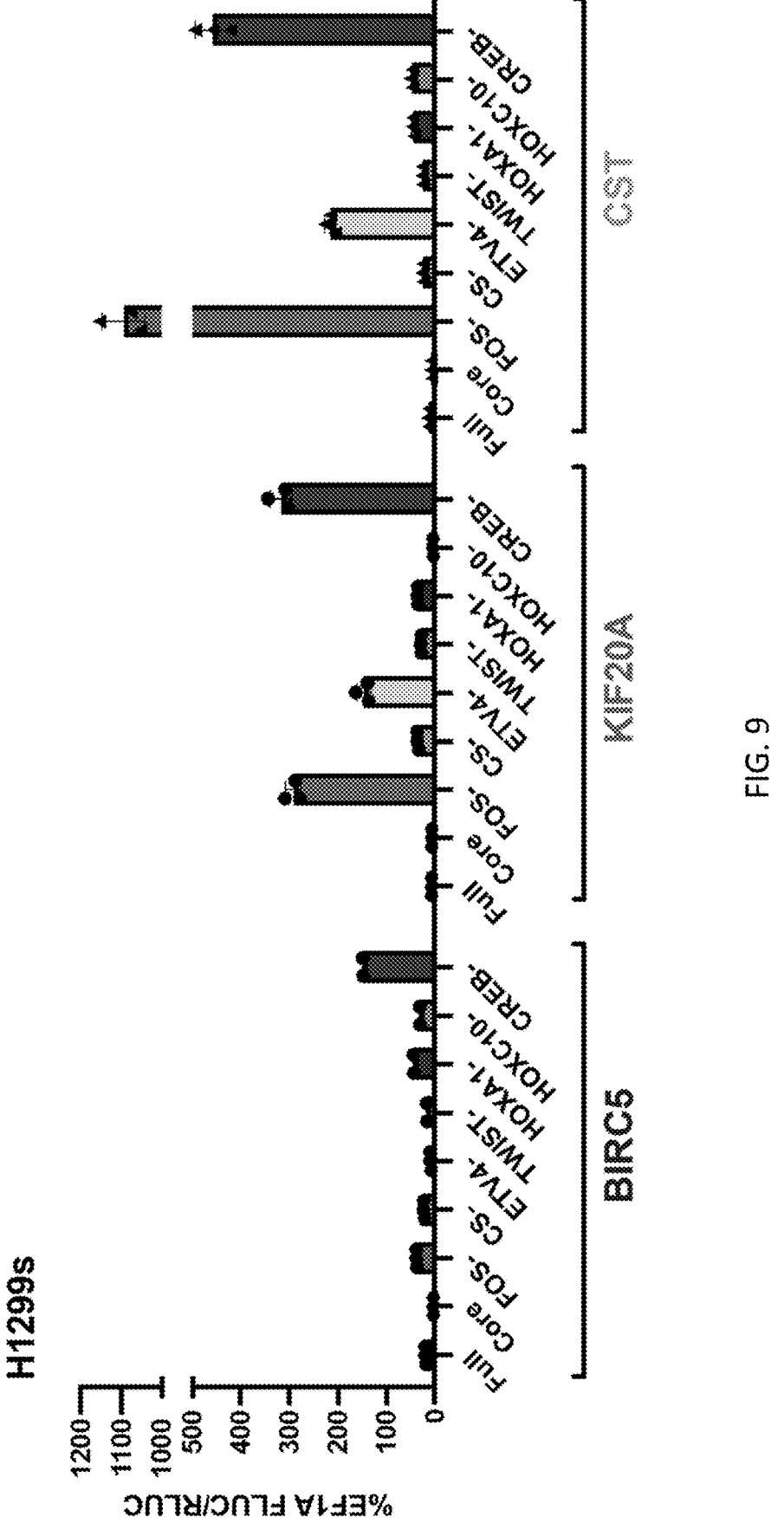
FIG. 9 shows the reporter gene expression by synthetic promoters in H1299 cells.

The compositions and methods described herein contem-plates a general strategy of identifying important elements of cancer-specific (or cancer-activated) promoters and design-ing and/or engineering cancer-specific promoters using ele-ments of cancer-specific promoters identified. Cancer-spe-cific promoters or cancer-activated promoters described herein can comprise promoters of genes that are preferentially expressed in cancer cells compared to non-cancer cells or expressed in higher level in cancer cells compared to non-cancer cells. Methods described herein can comprise identifying endogenous cancer-activated promoters by evaluating candidate promoter and/or enhancer sequences using bioinformatic analysis and designing/engineering a minimal cancer-activated promoter sequence (core pro-moter). For example, a candidate sequence (e.g., low-throughput or high-throughput screening) can be examined using a genome browser. The assessment range (e.g., sequence boundary) can be set based on the predicted transcriptional start site (TSS) of an endogenous promoter. For example, the assessment range can be from about −1000 bp to about +1000 bp relative to the predicted TSS. The assessment range can be adjusted based on chromatin immu-noprecipitation (ChIP) data including, but not limited to, ChIP peaks of general transcription factors (TFs), indicators of active promoter regions, and TFs that may indicate cancer specificity by presence in cancer cells and absence in non-cancer cells; and abundance of predicted TF binding sequence (TFBS); and regions of high species conservation. In some embodiments, indicators of active promoter regions can include, but not limited to, RNA Polymerase II, DNAse I, H3K4me1, and H3K4me3. In some embodiments, TFBS abundance can be predicted using methods including, but not limited, to JASPAR or HOMER motif analysis. Methods described herein can also comprise testing highlight regu-lated TFs using Massively Parallel Reporter Assay (MPRA) to identify optimal sequences, optimal spacing between each sequence, and/or optimal combinations of different enhancer sequences to design synthetic tiled enhancers. Methods described herein can comprise a rationally designed (e.g., low-throughput) screening or a high-throughput screening to identify enhancer elements to increase transcription signal. In some embodiments, a synthetic tiled enhancer can com-prise one or more copies of TFBS, or other highly conserved regulatory element repeats with spacing between repeats. One or more synthetic elements described herein can be placed upstream of core promoters. Synthetic elements described herein can also function as a promoter without a promoter or a core promoter.

A cancer-specific promoter described herein can comprise a recombinant polynucleotide comprising a core promoter sequence comprising a transcription start site (TSS). In some embodiments, a core promoter can be derived from a cancer-responsive gene and can be operably linked to an open reading frame (ORF). In some embodiments, a cancer-responsive gene can comprise a human cancer-responsive gene. In some embodiments, a core promoter can comprise a plurality of binding sites for a plurality of transcription factors (TFs) that are expressed in higher levels in cancer cells compared to non-cancer cells. In some embodiments, a core promoter can comprise a plurality of binding sites for a plurality of transcription factors (TFs) that are more active in cancer cells compared to non-cancer cells. In some embodiments, a core promoter can comprise a plurality of enhancers derived from two or more human cancer-response genes. In one embodiment, each of the plurality of enhancers can comprise a transcription regulatory element with at least 80% sequence homology to the enhancer consensus sequence of the two or more human cancer-response genes. In another embodiment, each of the plurality of enhancers can comprise a sequence capable of binding a transcription associated protein as assessed by ChIP.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below.

Definitions

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. The terms "and/or," "a combination thereof," and "any combination thereof" and their grammatical equivalents as used herein, can be used interchangeably. These terms can convey that any combination is specifically contemplated. Solely for illustrative purposes, the following phrases "A, B, and/or C," "A, B, C, or a combination thereof," or "A, B, C, or any combination thereof" can mean "A individually; B individually; C individually; A and B; B and C; A and C; and A, B, and C." The term "or" can be used conjunctively or disjunctively, unless the context specifically refers to a disjunctive use. The term "about" or "approximately" can mean within an acceptable error range for the particular value, which may depend in part on how the value is measured or determined, e.g., the limitations of the measurement system. For example, "about" can mean within 1 or more than 1 standard deviation. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed.

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the present disclosure, subject to any specifically excluded limit in the stated range. Where the stated range includes one or both of the limits, ranges excluding either or both of those included limits are also included in the present disclosure, unless the context clearly dictates otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "embodiments," "certain embodiments," "preferred embodiments," "specific embodiments," "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

Certain specific details of this description are set forth in order to provide a thorough understanding of various embodiments. However, one skilled in the art will understand that the present disclosure may be practiced without these details. In other instances, well-known techniques or methods have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

The terms "nucleic acid sequence," "polynucleic acid sequence," and/or "nucleotide sequence" are used herein interchangeably and have the identical meaning herein and refer to DNA or RNA. In some embodiments, a nucleic acid sequence is a polymer comprising or consisting of nucleotide monomers, which are covalently linked to each other by phosphodiester-bonds of a sugar/phosphate-backbone. The terms "nucleic acid sequence," "polynucleic acid sequence," and "nucleotide sequence" may encompass unmodified nucleic acid sequences, i.e., comprise unmodified nucleotides, or natural nucleotides. In some embodiments, "natural nucleotide," "unmodified nucleotide," and/or "canonical nucleotide" are used herein interchangeably and have the identical meaning herein and refer to the naturally occurring nucleotide bases adenine (A), guanine (G), cytosine (C), uracil (U), and/or thymine (T). The terms "nucleic acid sequence," "polynucleic acid sequence," and "nucleotide sequence" may also encompass modified nucleic acid sequences, such as base-modified, sugar-modified or backbone-modified etc., DNA or RNA. The term "nucleic acid sequence" generally is understood to include, as applicable to the embodiment being described, single-stranded (such as sense or antisense) and double-stranded polynucleotides. The term "nucleic acid" generally is understood to include, as applicable to the embodiment being described, polymers containing a non-natural linkage or a non-natural nucleotide.

In some embodiments, a nucleic sequence acid as described herein comprises one or more non-natural linkages or one or more non-natural nucleotides. Non-natural nucleotides can include, but are not limited to, 2'-fluoro, 2'-O-methyl, 2'-O-methyl, 2'-O-methoxy-ethyl, 2'-O-methoxy-ethoxy, 5'-methyl, SNA, hGNA, hhGNA, mGNA, TNA, h'GNA, locked nucleic acids (LNAs), GNA-isoC, GNA-isoG, 5'-mUNA, 4'-mUNA, 3'-mUNA, 2'-mUNA, or an abasic nucleotide (e.g. DNA or RNA). Non-natural linkages can include, but are not limited to, phosphorothioate and methylphosphonate. In some embodiments, an oligonucleotide as described herein comprises a modified uracil. Example nucleobases and nucleosides having a modified uracil include pseudouridine (Ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridine or 5-bromo-uridine), 3-methyl-uridine (m3U), 5-methoxy-uridine (mo5U), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine (τm5s2U), 1-taurinomethyl-4-thio-pseudouridine, 5-methyl-uridine (m5U, i.e., having the nucleobase deoxythymine), 1-methylpseudouridine (m1ψ), 5-methyl-2-thio-uridine (m5s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine (aka 1-methylpseudouridine (m1ψ)), 3-(3-amino-3-carboxypropyl)uridine (acp3U), 1-methyl-3-(3-amino-3-carboxypropyl)pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψ m), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine. In some embodiments, an oligonucleotide as described herein comprises a modified cytosine. Example nucleobases and nucleosides having a modified cytosine include 5-aza-cytidine, 6-aza-cytidine, pseudoisocytidine, 3-methyl-cytidine (m3C), N4-acetyl-cytidine (ac4C), 5-formyl-cytidine (f5C), N4-methyl-cytidine (m4C), 5-methyl-cytidine (m5C), 5-halo-cytidine (e.g., 5-iodo-cytidine), 5-hydroxymethyl-cytidine (hm5C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k2C), α-thio-cytidine, 2'-O-methyl-cytidine (Cm), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m4 2Cm), 1-thio-cytidine, 2'-F-aracytidine, 2'-F-cytidine, and 2'-OH-aracytidine The term "subject" can generally include human or non-human animals. Thus, the methods and compositions described herein are applicable to both human and veterinary disease and animal models. Preferred subjects are "patients," i.e., living humans that are receiving medical care for a disease or condition (e.g., cancer). This includes persons with no defined illness who are being investigated for signs of pathology. Also included are persons suspected of possessing or being at-risk for a defined illness. In some embodiments, the subject has at least one risk factor for cancer.

A "vector" as used herein generally refers to a nucleic acid sequence capable of transferring other operably-linked heterologous or recombinant nucleic acid sequences to target cells. In some examples, a vector is a minicircle, plasmid, nanoplasmid, yeast artificial chromosome (YAC), bacterial artificial chromosome (BAC), cosmid, phagemid, bacteriophage genome, or baculovirus genome. Suitable vectors also include vectors derived from bacteriophages or plant, invertebrate, or animal (including human) viruses such as CELiD vectors, doggybone DNA (dbDNA) vectors, closed-end linear duplex DNA vectors (e.g., wherein each end is covalently closed by chemical modification), adeno-associated viral vectors (e.g., AAV1, AAV2, AAV4, AAV5, AAV6, AAV7, AAV8, AAV9, or pseudotyped combinations thereof such as AAV2/5, AAV2/2, AAV-DJ, or AAV-DJ8), retroviral vectors (e.g. MLV or self-inactivating or SIN versions thereof, or pseudotyped versions thereof), herpesviral (e.g. HSV- or EBV-based), lentiviral vectors (e.g., HIV-, FIV-, or EIAV-based, or pseudotyped versions thereof), or adenoviral vectors (e.g., AdS-based, including replication-deficient, replication-competent, or helper-dependent versions thereof). In some embodiments, a vector is a replication competent viral-derived vector. In some embodiments, a vector is a replication-incompetent viral-derived vector. In some cases, the vector may comprise an episomal maintenance element to facilitate replication in one or more target cell type, such as a Scaffold/Matrix Attachment Region (S/MAR). S/MAR elements are particularly useful to facilitate replication in the context of "naked" nucleic acid vectors such as minicircles.

Exemplary suitable S/MAR elements include, but are not limited to, EµMAR from the immunoglobulin heavy chain locus, the apoB MAR from the human apolipoprotein B locus, the Ch-LysMAR from the chicken lysozyme locus, and the huIFNβ MAR from the human IFNβ-locus. A vector may comprise a coding sequence capable of being expressed in a target cell. Accordingly, as used herein, the terms "vector construct," "expression vector," and "gene transfer vector," may refer to any nucleic acid construct capable of directing the expression of a gene of interest and which is useful in transferring the gene of interest into target cells. Vectors as described herein may additionally comprise one or more cis-acting elements to stabilize or improve expression of mRNAs therefrom. Such cis-acting elements include, but are not limited to, any of the elements described e.g., in Johansen et al. The Journal of Gene Medicine. (5)12:1080-1089 (doi: 10.1002/jgm.444) or Vlasova-St. Louis and Sagarsky. Mammalian Cis-Acting RNA Sequence Elements (doi: 10.5772/intechopen.72124).

The term "promoter" generally can refer to a DNA sequence that directs the transcription of a polynucleotide. Typically, a promoter can be located in the 5' region of a polynucleotide to be transcribed, proximal to the transcriptional start site of such polynucleotide. More typically, promoters can be defined as the region upstream of the first exon; more typically, as a region upstream of the first of multiple transcription start sites. Frequently promoters are capable of directing transcription of genes located on each of the complementary DNA strands that are 3' to the promoter. Stated differently, many promoters can exhibit bidirectionality and can direct transcription of a downstream gene when present in either orientation (i.e., 5' to 3' or 3' to 5' relative to the coding region of the gene). Additionally, the promoter may also include at least one control element such as an upstream element. Such elements include upstream activator regions (UARs) and optionally, other DNA sequences that affect transcription of a polynucleotide such as a synthetic upstream element. Some promoters may be assembled from fragments of endogenous promoters (e.g., derived from the human genome).

The term "coding sequence," and "encodes" when used in reference to a polypeptide herein generally refer to a nucleic acid molecule that is transcribed (in the case of DNA) and translated (in the case of mRNA) into a polypeptide, for example, when the nucleic acid is present in a living cell (in vivo) and placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral, eukaryotic, or prokaryotic DNA, and synthetic DNA sequences. A transcription termination sequence may be located 3' to the coding sequence, and a promoter may be located 5' to the coding sequence; along with additional control sequences if desired, such as enhancers, introns, poly adenylation site, etc. A DNA sequence encoding a polypeptide may be optimized for expression in a selected cell by using the codons preferred by the selected cell to represent the DNA copy of the desired polypeptide coding sequence.

The term "operably linked" as used herein generally can refer to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "sequence identity" or "percent identity" in the context of two or more nucleic acids or polypeptide sequences, generally refers to two (e.g., in a pairwise alignment) or more (e.g., in a multiple sequence alignment) sequences that are the same or have a specified percentage of amino acid residues or nucleotides that are the same, when compared and aligned for maximum correspondence over a local or global comparison window, as measured using a sequence comparison algorithm. Suitable sequence comparison algorithms for polypeptide sequences include, e.g., BLASTP using parameters of a wordlength (W) of 3, an expectation (E) of 10, and the BLOSUM62 scoring matrix setting gap costs at existence of 11, extension of 1, and using a conditional compositional score matrix adjustment for polypeptide sequences longer than 30 residues; BLASTP using parameters of a wordlength (W) of 2, an expectation (E) of 1000000, and the PAM30 scoring matrix setting gap costs at 9 to open gaps and 1 to extend gaps for sequences of less than 30 residues (these are the default parameters for BLASTP in the BLAST suite available at blast.ncbi.nlm-.nih.gov); CLUSTALW with parameters of; the Smith-Waterman homology search algorithm with parameters of a match of 2, a mismatch of −1, and a gap of −1; MUSCLE with default parameters; MAFFT with parameters retree of 2 and maxiterations of 1000; Novafold with default parameters; HMMER hmmalign with default parameters.

The term "lipid particle" generally includes a lipid formulation that can be used to deliver an active agent or therapeutic agent, such as a nucleic acid to a target site of interest (e.g., cell, tissue, organ, and the like). In preferred embodiments, the lipid particle of the invention is a nucleic acid-lipid particle (e.g. a particle that has only nucleic acids and lipids), which is typically formed from a cationic lipid, a non-cationic lipid, and optionally a conjugated lipid that prevents aggregation of the particle. In other preferred embodiments, the active agent or therapeutic agent, such as a nucleic acid, may be encapsulated in the lipid portion of the particle, thereby protecting it from enzymatic degradation. In some cases, a "lipid particle" is a lipid nanoparticle (LNP). The lipid particles can be prepared by any suitable method, including but not limited to microfluidic assembly or extrusion. In some embodiments, for a lipid particle (e.g. LNP composition), a particle has a particular composition. In some embodiments, for a lipid particle (e.g. LNP composition), each particle has a particular composition. In some embodiments, for a lipid particle (e.g. LNP composition), at least 1%, 5%, 10%, 15%, 20%, 25%, 30%, 35%, 40%, 45%, 50%, 55%, 60%, 65%, 70%, 75%, 80%, 85%, 90%, 95%, 98%, 99%, 99.5%, 99.9% of the particles have a particular composition.

When nucleic acid sequences are referred to herein, the current disclosure is generally understood to include nucleic acid sequences with at least about 80-100% identity to the sequences described herein, or to reverse complements of the sequences described herein.

In some embodiments, the disclosure provides for a nucleic acid comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any of the sequences listed in Table 1A, or to reverse complements of any of the sequences listed in Table 1A. In some embodiments, the disclosure provides for a nucleic acid comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any of SEQ ID NOs: 1-343, or to reverse complements of any of SEQ ID NOs: 1-343. In some embodiments, the disclosure provides for a promoter comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any of SEQ ID NOs: 1-343, or to reverse complements of any of SEQ ID NOs: 1-343. In some embodiments, the nucleic acid can be a double-stranded nucleic acid.

In some embodiments, the disclosure provides for a nucleic acid comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any of the sequences listed in Table 1B, or to reverse complements of any of the sequences listed in Table 1B. In some embodiments, the disclosure provides for a nucleic acid comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any of SEQ ID NOs: 377-397, or to reverse complements of any of SEQ ID NOs: 377-397. In some embodiments, the disclosure provides for a promoter comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any of SEQ ID NOs: 377-397, or to reverse complements of any of SEQ ID NOs: 377-397. In some embodiments, the disclosure provides for an enhancer comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any of SEQ ID NOs: 377-397, or to reverse complements of any of SEQ ID NOs: 377-397. In some embodiments, the nucleic acid can be a double-stranded nucleic acid.

In some embodiments, the disclosure provides for a nucleic acid comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any of the sequences listed in Table 1C, or to reverse complements of any of the sequences listed in Table 1C. In some embodiments, the disclosure provides for a nucleic acid comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any of SEQ ID NOs: 398-488, or to reverse complements to any of SEQ ID NOs: 398-488. In some embodiments, the disclosure provides for a promoter having a sequence having at least 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any of the sequences listed in Table 1C, or to reverse complements of any of the sequences listed in Table 1C. In some embodiments, the disclosure provides for a promoter comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any of SEQ ID NOs: 398-486 and SEQ ID NOs: 556-557, or to reverse complements to any of SEQ ID NOs: 398-486 and SEQ ID NOs: 556-557. In some embodiments, the nucleic acid can be a double-stranded nucleic acid.

In some embodiments, the disclosure provides for a nucleic acid comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any one of the of the sequences listed in Table 1J, or to reverse complements of any one of the sequences listed in Table 1J. In some embodiments, the disclosure provides for a nucleic acid comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any SEQ ID NOs: 558-587, or to any reverse complements of any SEQ ID NOs: 558-587. In some embodiments, the disclosure provides for a core promoter comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any one of the of the sequences listed in Table 1J, or to reverse complements of any one of the sequences listed in Table 1J. In some embodiments, the disclosure provides for the core promoter comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to any SEQ ID NOs: 558-587, or to any reverse complements of any SEQ ID NOs: 558-587. In some embodiments, the nucleic acid can be a double-stranded nucleic acid.

In some embodiments, the disclosure provides for a nucleic acid comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to SEQ ID NO: 556, listed in Table 1C, or to a reverse complement thereof. In some embodiments, the nucleic acid can be a double-stranded nucleic acid.

In some embodiments, the disclosure provides for a nucleic acid comprising a sequence having at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% sequence identity to SEQ ID NO: 557, listed in Table 1C, or to a reverse complement thereof. In some embodiments, the nucleic acid can be a double-stranded nucleic acid.

In some embodiments, any of the nucleic acids disclosed herein can have at least about 20, at least about 40, at least about 60, at least about 80, at least about 100, at least about 120, at least about 140, at least about 160, at least about 180, at least about 200, at least about 220, at least about 240, at least about 260, at least about 280, at least about 300, at least about 320, at least about 340, at least about 360, at least about 380, at least about 400, at least about 420, at least about 440, at least about 460, at least about 480, at least about 500, at least about 520, at least about 540, at least about 560, at least about 580, at least about 600, at least about 620, at least about 640, at least about 680, at least about 700, at least about 720, at least about 740, at least about 760, at least about 780, at least about 800, at least about 820, at least about 840, at least about 860, at least about 880, at least about 900, at least about 920, at least about 940, at least about 960, at least about 980, at least about 1000, at least about 1020, at least about 1040, at least about 1060, at least about 1080, at least about 1100, at least about 1120, at least about 1140, at least about 1160, at least about 1180, at least about 1200, at least about 1220, at least about 1240, at least about 1260, at least about 1280, at least about 1300, at least about 1320, at least about 1340, at least about 1360, at least about 1380, at least about 1400, at least about 1420, at least about 1440, at least about 1460, at least about 1480, at least about 1500, at least about 1520, at least about 1540, at least about 1560, at least about 1580, at least about 1600, at least about 1620, at least about 1640, at least about 1660, at least about 1680, at least about 1700, at least about 1720, at least about 1740, at least about 1760, at least about 1780, at least about 1800, at least about 1820, at least about 1840, at least about 1860, at least about 1880, at least about 2000, at least about 2020, at least about 2040, at least about 2060, at least about 2080, at least about 2100, at least about 2120, at least about 2140, at least about 2160, at least about 2180, at least about 2200, at least about 2220, at least about 2240, at least about 2260, at least about 2280, at least about 2300, at least about 2320, at least about 2340, at least about 2360, at least about 2380, at least about 2400, at least about 2420, at least about 2440, at least about 2460, at least about 2480, at least about 2500, at least about 2520, at least about 2540, at least about 2560, at least about 2580, at least about 2600, at least about 2620, at least about 2640, at least about 2660, at least about 2680, at least about 2700, at least about 2720, at least about 2740, at least about 2760, at least about 2780, at least about 2800, at least about 2820, at least about 2840, at least about 2860, at least about 2880, at least about 2900, at least about 2920, at least about 2940, at least about 2960, at least about 2980, at least about 3000, at least about 3020, at least about 3040, at least about 3060, at least about 3080, at least about 3100, at least about 3120, at least about 3140, at least about 3160, at least about 3180, at least about 3200, at least about 3220, or at least about 3240 consecutive nucleotides of any of the nucleic acid sequences disclosed herein, or of any reverse complements of any of the nucleic acid sequences disclosed herein.

Although methods and materials similar or equivalent to those described herein can be used in the practice or testing of the present disclosure, suitable methods, and materials are described below.

Synthetic Promoter Strategy and Design

Provided herein are synthetic promoters that can be activated in target cells with high sensitivity and specificity. These promoters can be modular and engineerable. In some embodiments, synthetic promoters described herein can be designed to drive specificity and sensitivity. For example, synthetic promoters can be designed to specifically respond to dysregulated pathways in cancer. In one embodiment, synthetic promoters described herein can comprise an endogenous promoter of a gene that is expressed specifically or preferentially in cancer cells compared to non-cancer cells. In another embodiment, synthetic promoters described herein can comprise a core promoter. A core promoter described herein can comprise a minimal promoter sequence of an endogenous promoter of a gene expressed specifically or preferentially in cancer cells compared to non-cancer cells. A minimal promoter can refer to a short DNA sequence that can allow for the formation of a transcription initiation complex or a DNA sequence comprising a minimal number of nucleotides sufficient to allow for the formation of a transcription initiation complex. In some embodiments, synthetic promoters described herein can comprise a structure comprising three major components (1) a cancer-specific promoter or core promoter, (2) cancer-activated response elements (e.g., binding sites of one or more transcription factors specific for cancer cells), and optionally (3) an enhancer to boost signal strength (e.g., see FIG. 1 or FIG. 72). In some embodiments, synthetic promoters described herein can comprise only (1) a cancer-specific promoter or core promoter. In some embodiments, synthetic promoters described herein can comprise only (1) a cancer-specific promoter or core promoter and (3) an enhancer to boost signal strength. In some embodiments, an enhancer or a transcription binding site can be referred to as a Synthetic Response Element (SRE). In some embodiments, a synthetic promoter comprising a promoter or core promoter and one or more SREs can be referred to as a Synthetic Response Sensor (SRS). In some embodiments, cancer-activated response elements can be designed and constructed to respond to specific dysregulated transcription factors. In some embodiments, cancer-activated response elements described herein can demonstrate predictable activity based on transcriptomic and proteomic data when applied in new cancer models.

In some embodiments, bioinformatics can be used to identify endogenous cancer-activated core promoter sequences. In some embodiments, multi-omic approaches can be used to identify transcription factors (TFs) and their binding sites that are master-regulated. In some embodiments, such TF binding sites can be tiled and tested using high-throughput sequencing (HTS) to optimize promoter sequences, spacing, and combinations thereof. In some embodiments, one or more rationally designed enhancer elements that increase transcription and boost reporter signal can be used. An exemplary workflow and synthetic promoter are described in FIGS. 10-13.

In some embodiments, candidate TF binding site sequences can be identified using Multi-Omics Factor Analysis (MOFA). In some embodiments, candidate TF binding site sequences can be highly dysregulated. In some embodiments, Multi-Omics Factor Analysis (MOFA) can be used to identify TFs specific for a cancer. In some embodiments, a cancer can comprise lung cancer, breast cancer, liver cancer, and/or colorectal cancer. In some embodiments, a lung cancer can comprise non-small cell lung cancer (NSCLC).

In some embodiments, a synthetic promoter can comprise a core promoter sequence. In some embodiments, a core promoter can be identified by analyzing one or more endogenous promoters that can drive cancer specific expression in vitro and/or in vivo, that is the one or more endogenous promoters can preferentially activate gene expression of a gene that is functionally or operatively linked to said one or more promotors in cancer cells (e.g., either in a subject or cancer cell lines) compared to corresponding healthy or normal cells. In some embodiments, one or more endogenous promoters can be analyzed and annotated using UCSC genome browser to build and test core promoters. In some embodiments, core promoters identified can be combined with other elements described herein. In some embodiments, a core promoter sequence can comprise a minimal cancer-activated core promoters. For example, a core promoter sequence can comprise a promoter sequence comprising a minimal number of nucleotides sufficient to drive expression (e.g., recruit transcription initiation complex) of a gene that is functionally or operatively linked to the core promoter in cancer cells. Examples of a minimal cancer-activated cores can include, but are not limited to, coreBIRC5, coreCST1, coreAGR2, coreFAM111B, CEACAM5, CEP55, UBE2C, FAM111B, KIF20A, FOXA1, MYC, or TP53 (e.g., FIGS. 2-5 and FIG. 11). In some embodiments, a core promoter sequence can provide specificity. In some embodiments, a synthetic promoter can comprise a response element. In some embodiments, a response element can comprise a binding site for a master regulated transcription factor (TF). Examples of a master regulated TF can include, but are not limited to, tiled TFBS for FOS, CREB, MYC, HOXC10, TCF7, or combinations thereof. In some embodiments, a response element can provide specificity and/or sensitivity. In some embodiments, a synthetic promoter can comprise a signal strength enhancer. In some embodiments, a signal strength enhancer can comprise a synthetic enhancer (also referred herein as a Synthetic Response Element or SRE). Examples of a synthetic enhancer can include, but are not limited to enhancers of SP1, ETS, CEBP, NF-KB, or combinations thereof. In some embodiments, a synthetic enhancer can provide signal strength. Table A shows a table comparing different synthetic promoters. In some embodiments, synthetic promoters (FOS-AGR2, FOS-CST1, and HIGH-FAM111B) can drive high expression of the reporter gene and have improved signal-to-noise ratio (SNR) compared to BIRC5 variant promoters.

TABLE A

| | | | | H1299 SubQ Tumor SNR Lung | H1299 SubQ Tumor SNR Liver |
|---|---|---|---|---|---|
| Promoter | In Vitro Signal | In Vitro Noise | H1299 SubQ Tumor Signal | | |
| CAG | +++ | --- | 38/11 | 10/3 | <<1 |
| FOS-TATA | +++ | --- | 9 | 3.6 | <<1 |
| BIRC5 | + | -- | | n/a at 1.4 mpk | |
| FOSL-coreBIRC5 | ++ | -- | | n/a at 1.4 mpk | |
| HIGH-coreBIRC5 | +++ | -- | 3.6 | 3.2 | 1.8 |
| FOS-coreAGR2 | +++ | -- | 9.3/3 3.8 | 10/3.3 5 | 3.2 2.5 |
| FOS-coreCST1 | +++ | -- | 3.7 | 4.1 | 1 |
| HIGH-coreFAM111B | +++ | -- | 7.5 | 3.4 | 1.33 |

Exemplary Synthetic Promoters

In some embodiments, synthetic promoters described herein that can drive expression in a broad range of cancer cells or cancer tissues including, but not limited to, lung cancer cells, can be identified using methods described herein. In one example, promoters identified using methods described herein can include promoters or binding sites/motifs of TCF7, one of TCFs that can be activated by Wnt/B-cat pathway, known for functioning in development pathways. In some embodiments, cancer cell lines based on Wnt/B-cat pathway can be used for further analysis. For example, a principal component analysis (PCA) of PDX database and CCLE focused on the B-cat/Wnt pathway can be used to choose cell lines for further analysis (e.g., 163 genes involved in Wnt/B-cat pathway, 50 CCLE lung cell lines, and 91 PDX lung cell lines). In some embodiments, a PCA including all lung-related PDXs from CRL as well as the CCLE transcriptome database can be used. Examples of cell lines include, but are not limited to, PC2, H520, LK2, or PDX430. In some embodiments, these cell lines can have similar level of expressions of Wnt7B, CCND1, FZD3, AXIN2 or NKD1. In another example, promoters identified using methods described herein can include promoters of TP53, a tumor suppressor that can activate or repress expression depending on location of the binding site. In some embodiments, TP53 binding sequence or motifs can be included in a promoter or a core promoter.

In some embodiments, synthetic promoters that can integrate multiple signaling can be engineered using methods described herein. For example, binding sequences or motifs of TCF, TP53, FOS, MNX1, HOXC10, of CREB can be combined with core promoters described herein to engineer synthetic promoters. In some embodiments, synthetic promoters can comprise promoters or binding sequences/motifs/sites TFs of genes in multiple regulatory pathways. In some embodiments, synthetic promoters comprising two or more endogenous or core promoters can result in gene expression with greater signal and coverage. Details of synthetic promoter design and construction are described in Example 1 and Example 2.

Synthetic Response Sensor (SRSs or synthetic promoter) and Synthetic Response Elements (SREs)

In some aspects, provided herein is a recombinant polynucleotide comprising a Synthetic Response Sensor (SRS) that can drive expression of a gene or an ORF operatively linked to the SRS in tissue- or cell-specific manner. In some embodiments, an SRS described herein can drive cancer specific or cancer-activated expression of a gene or an ORF operatively linked to the SRS. For example, an SRS described herein can drive expression of a gene or an ORF operatively linked to the SRS preferentially or specifically in cancer cells or cancer tissues compared to non-cancer cells or non-cancer tissues. In some embodiments, the expression level of a gene or an ORF operatively linked to an SRS is higher in cancer cells or cancer tissues compared to non-cancer cells or non-cancer tissues. In some embodiments, an SRS can comprise a promoter or a core promoter and one or more Synthetic Response Elements (SREs). In some embodiments, the promoter or the core promoter can provide tissue- or cell-specificity for gene expression. In some embodiments, an SRE can provide tissue- or cell-specificity for gene expression and/or enhance the tissue- or cell-specificity of gene expression. In some embodiments, an SRE can comprise a plurality of binding sites for one or more transcription factors or a plurality of enhancers. For example, an SRE can comprise a plurality of binding sites for one or more transcription factors that are activated in cancer cells or cancer pathways or are dysregulated (e.g., expressed in aberrantly higher levels, etc.) in cancer cells or cancer pathways. In some embodiments, an SRS can drive expression of an ORF operatively linked to the SRS in cancer cells or cancer tissues but not in normal cells or tissues (including normal tissues or cells adjacent to cancer cells or cancer tissues) and/or benign lesions.

Figure 72:
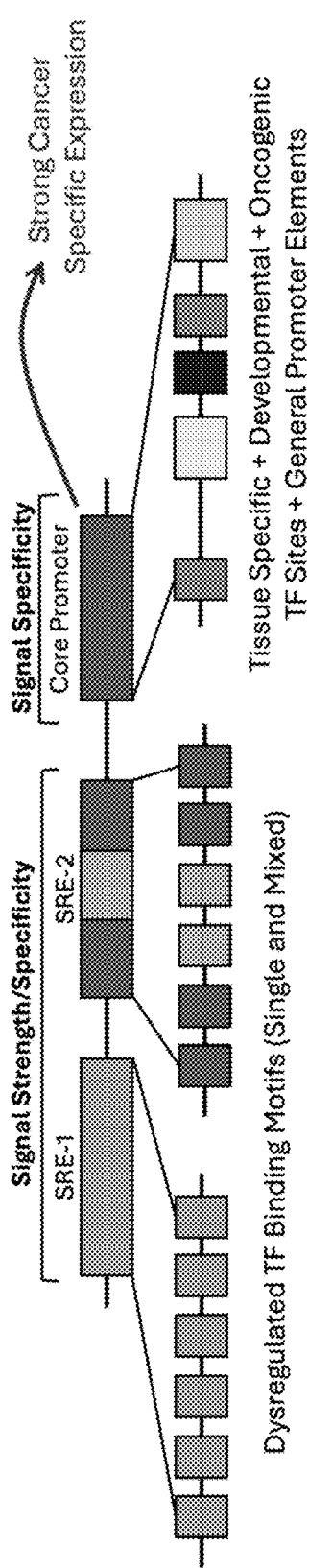
FIG. 72 shows Synthetic Response Sensors (SRS) that drive cancer specific expression where the SRS comprises a series of Synthetic Response Elements (SREs), or enhancers, and a cancer activated core promoter. TF: Transcription Factor.
Figure 73:
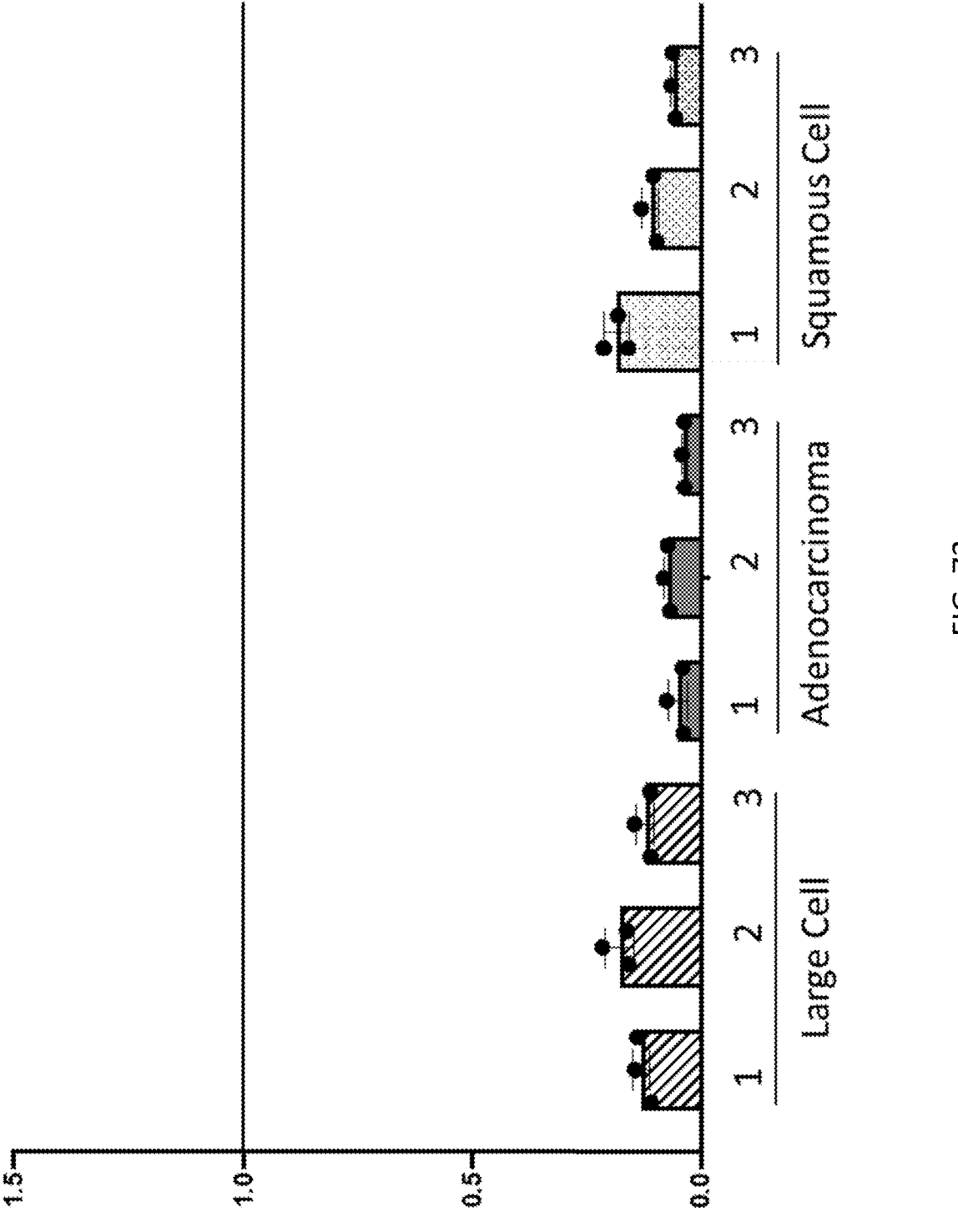
FIG. 73 shows a graph of gene expression activated by SRS-G comprising the core promoter specific for lung cancer and a single SRE. A luciferase reporter expression system was used to evaluate the strength of activation in cell lines that represent the three main Non-Small Cell Lung Cancer (NSCLC) subtypes. The expression values are shown as the fold change over a strong constitutive promoter. SRS-G was able to achieve expression that is 10-20% on the expression of the constitutive promoter.
Figure 74A:
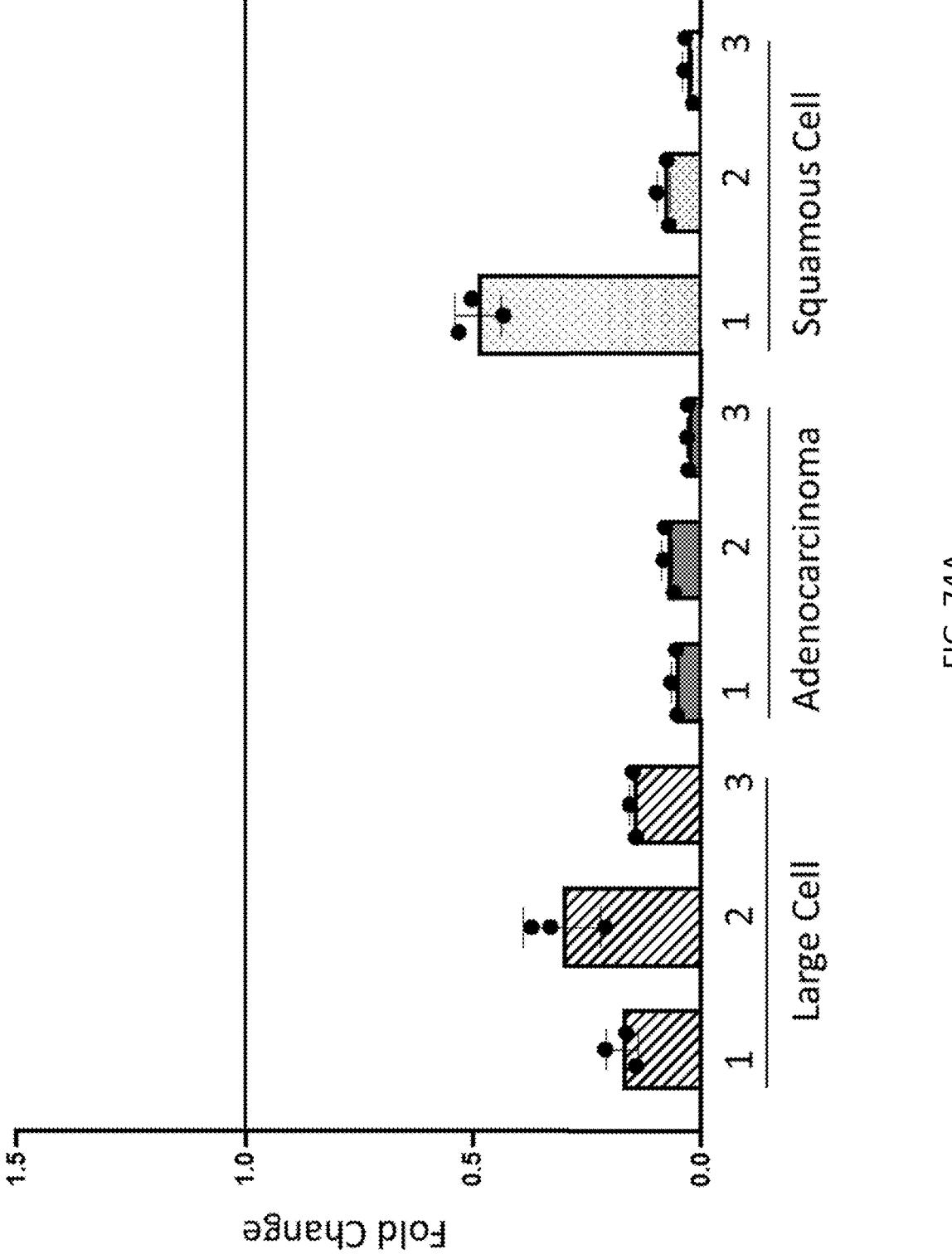
FIGS. 74A, 74C, 74E, 74G, 74I, and 74K show graphs of gene expression activated by different SRSs (SRS-A, SRS-B, SRS-C, SRS-D, SRS-E, and SRS-F) designed to drive gene expression in lung cancers. A luciferase reporter expression system was used to evaluate the strength of activation in cell lines that represent the three main NSCLC subtypes. The expression values are shown as the fold change over a strong constitutive promoter. SRS-A was able to achieve expression that is 5-50% on the expression of the constitutive promoter (FIG. 74A). SRS-B was able to achieve expression that is 20-50% on the expression of the constitutive promoter (FIG. 74C). SRS-C was able to achieve expression similar to or 3-fold above the constitutive promoter (FIG. 74E). SRS-D was able to achieve expression similar to or 2-10-fold above the constitutive promoter (FIG. 74G). SRS-E was able to achieve expression similar to or 2-8-fold above the constitutive promoter (FIG. 74I). SRS-F was able to achieve expression similar to or 3-5-fold above the constitutive promoter.
Figure 74C:
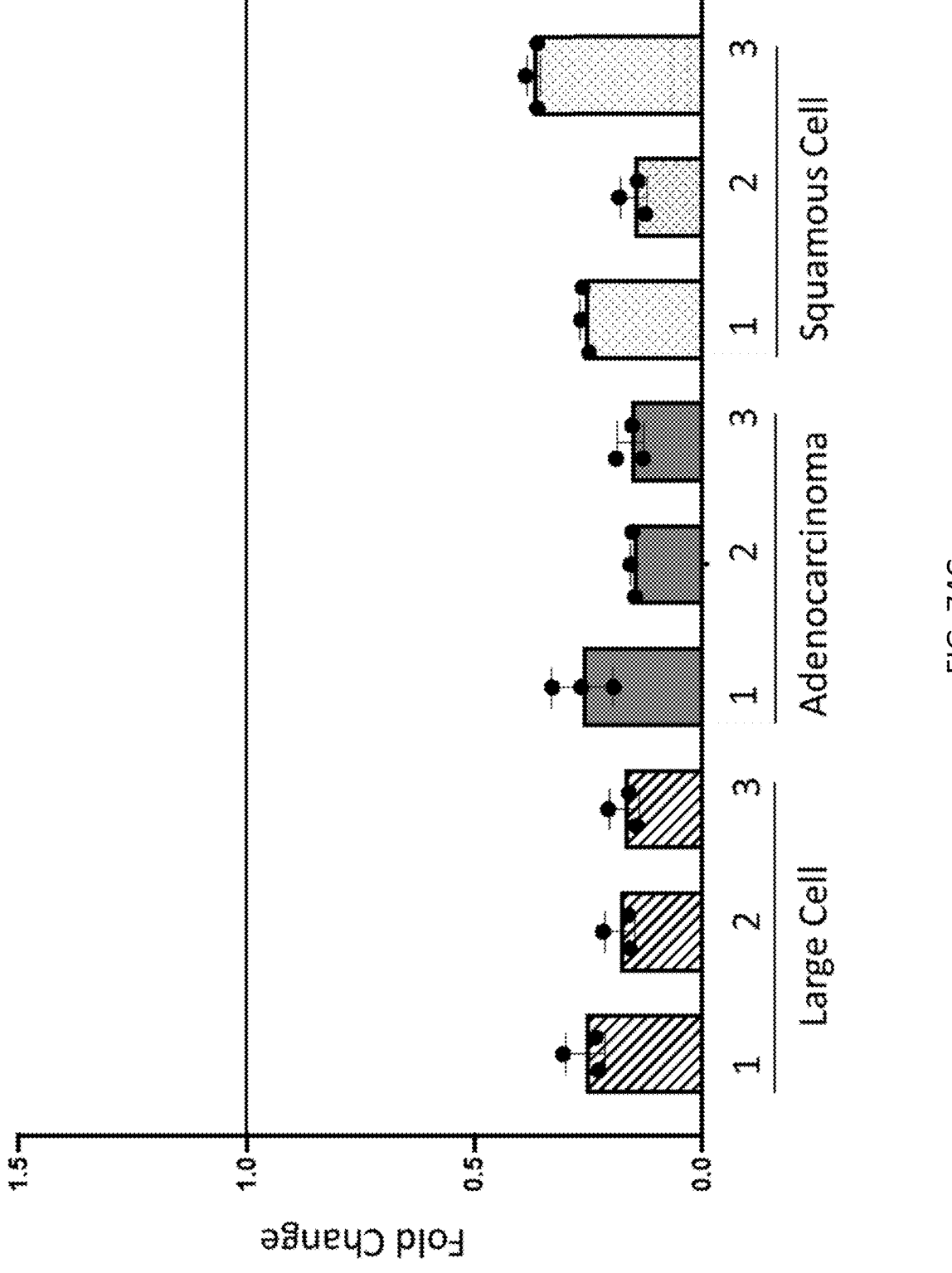
Figure 74E:
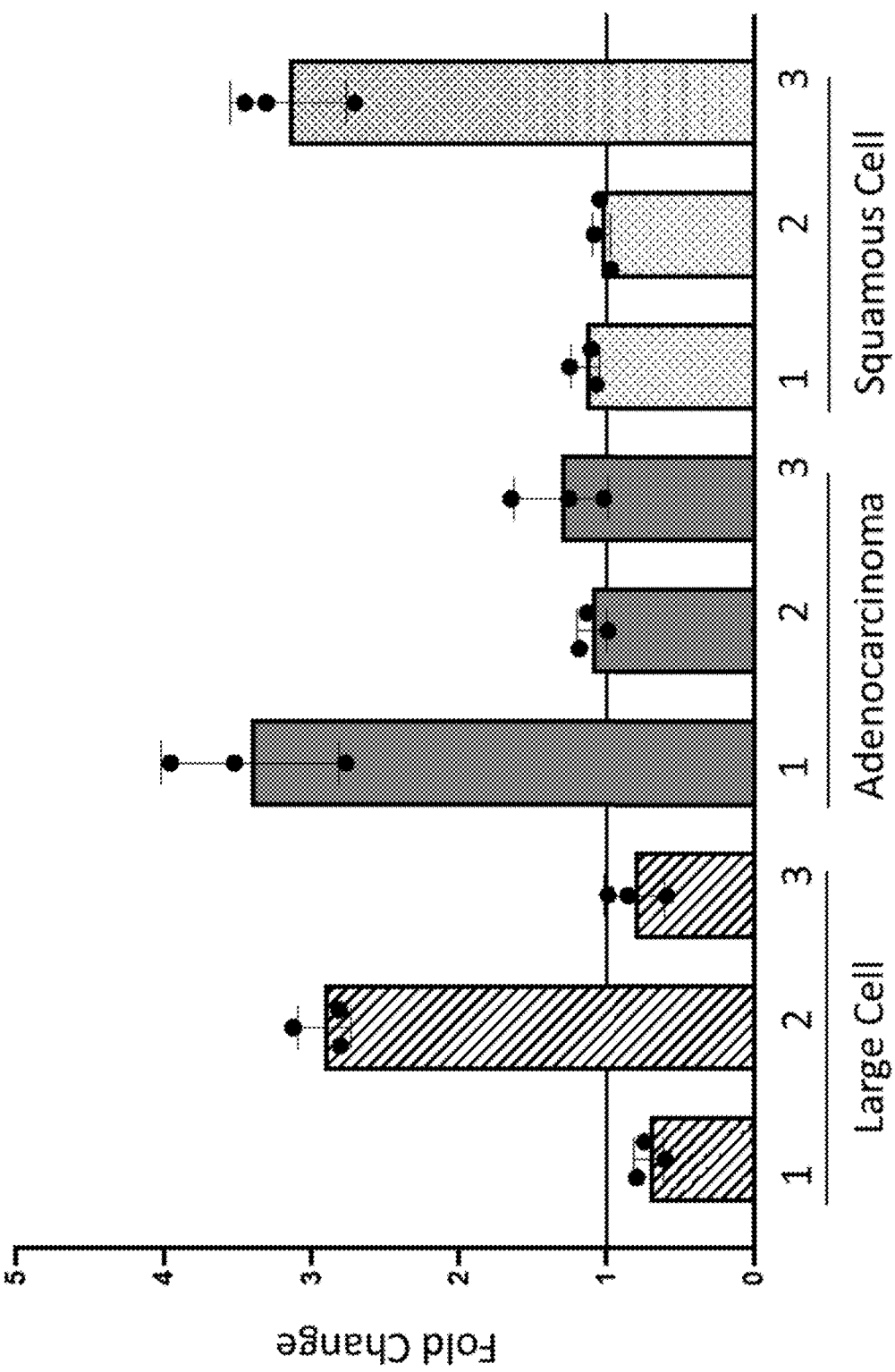
Figure 74G:
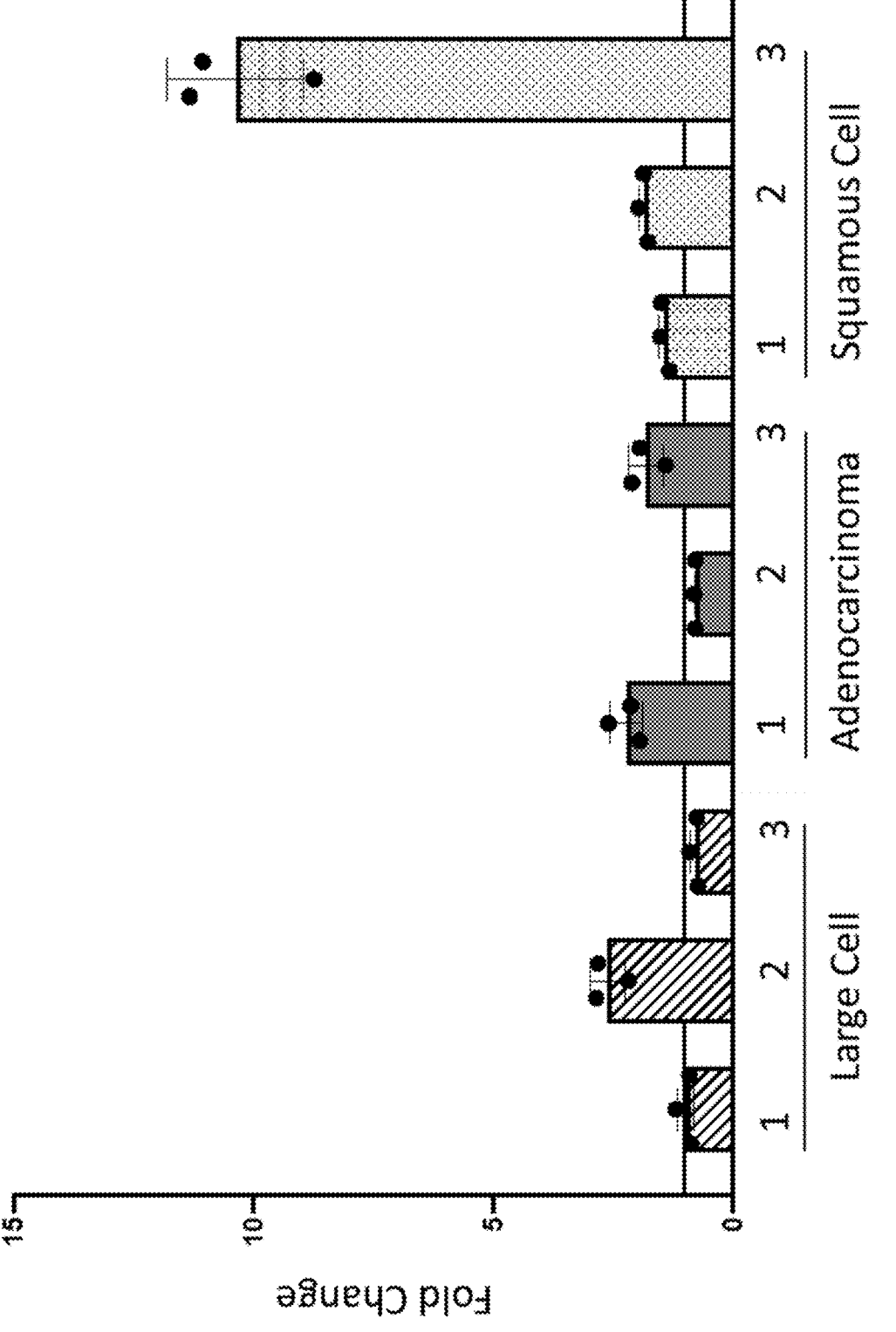
Figure 74I:
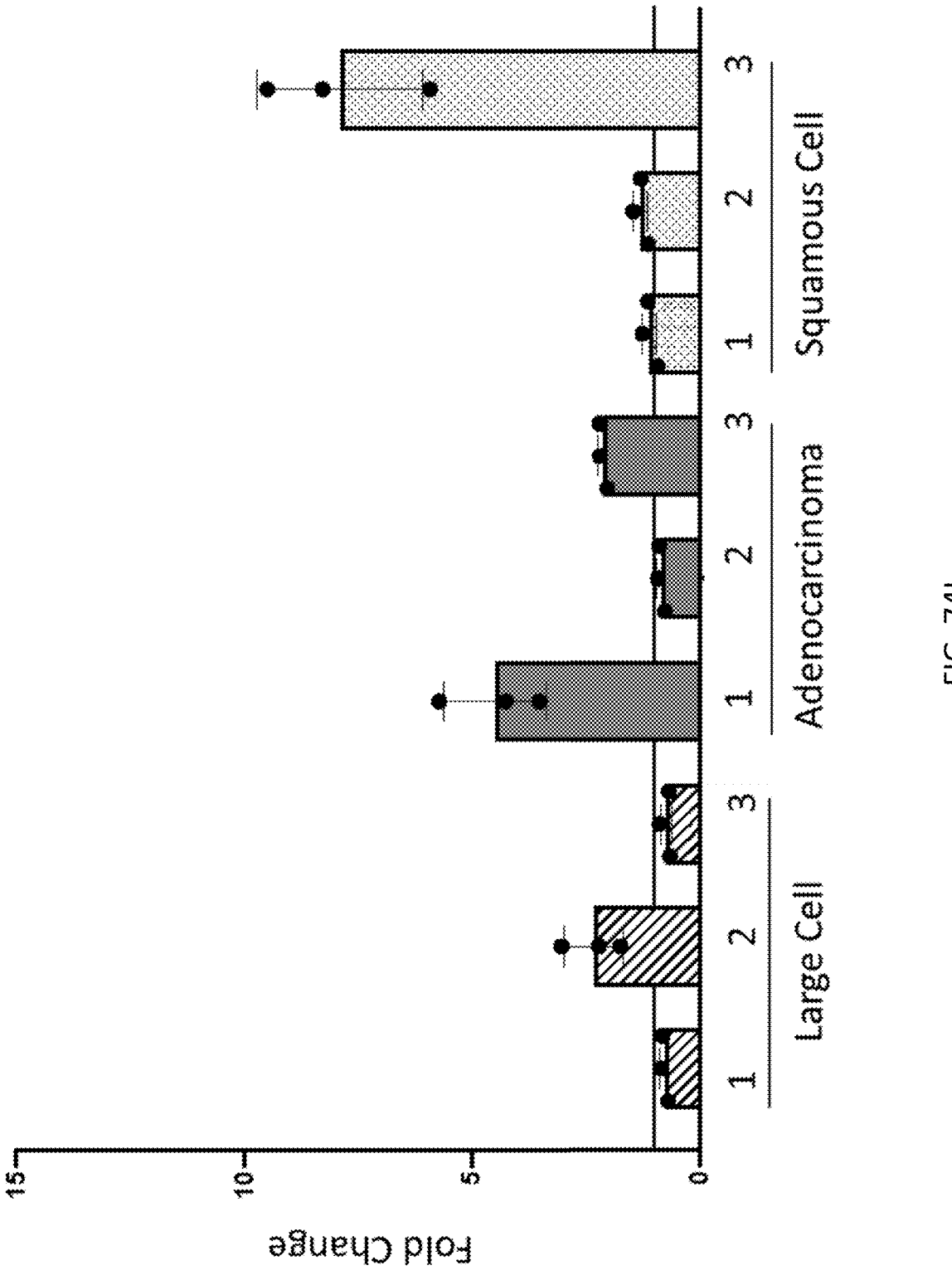
Figure 74K:
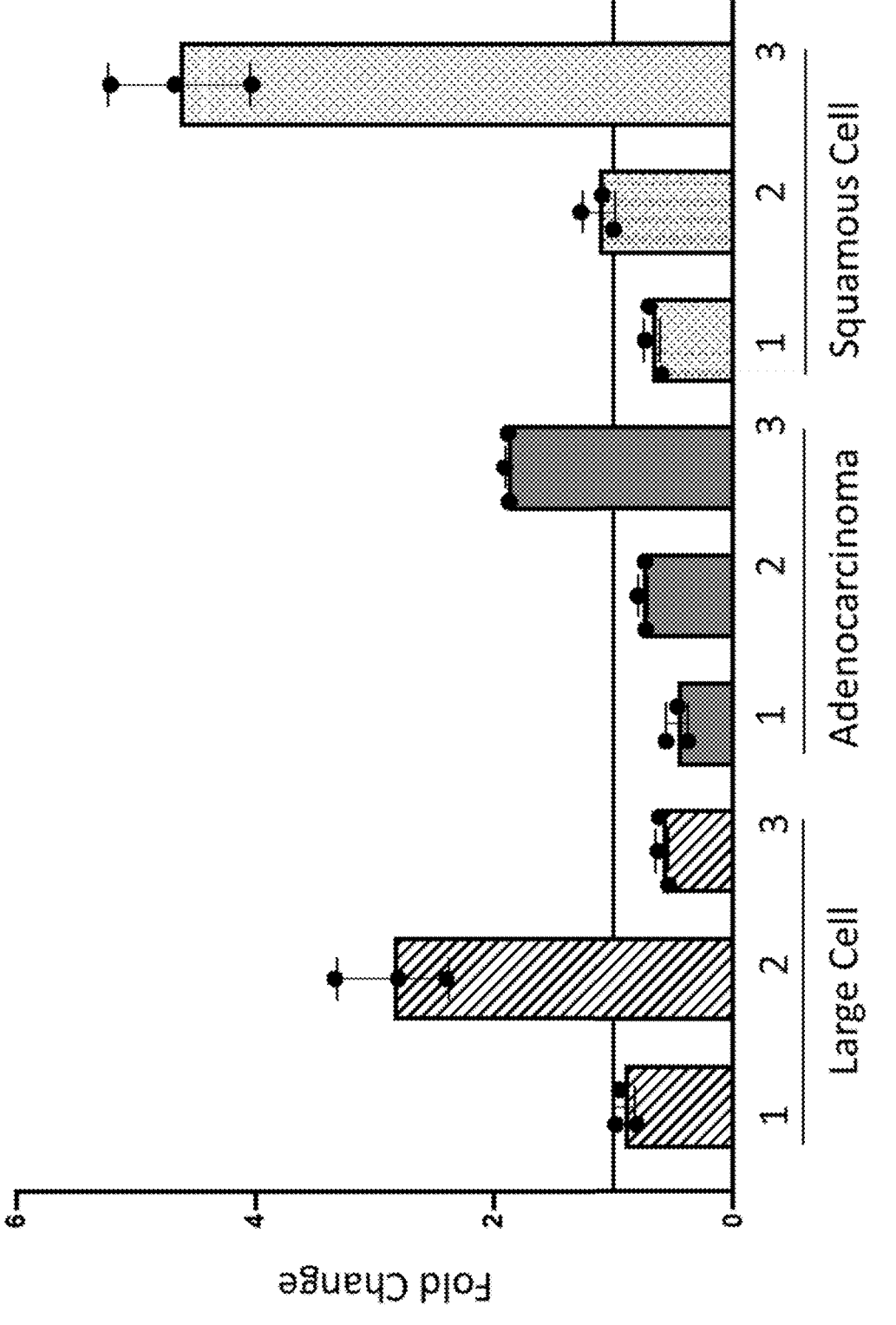
Figure 76:
FIG. 76 shows graphs of gene expression activated by SRSs, demonstrating that SRSs can be active in both lung and liver cancer models, or selectively active in a target model. H358 lung cancer cells, HepG2 liver cancer cells, and Hep3B liver cancer cells were seeded in 96-well plates at a density of 10,000 cells per well, with each plasmid containing luciferase reporter expression system tested in triplicate. Transfection was performed using Lipo-fectamine™ 3000, a transfection agent comprising DOSPA (2,3-dioleoyloxy-N-[2(sperminecarboxamido)ethyl]-N,N-dimethyl-1-propaniminium trifluoroacetate) and DOPE (dioleoyl phosphatidylethanolamine), following the manu-facturers protocol. After 24 hours of incubation, expression levels were measured using the Promega Luciferase Assay System (E1501). The expression values are shown as the fold change over a strong constitutive promoter, where greater than 10% expression is set as a threshold for positive signal. The results demonstrate that SRS-G and SRS-B are active in both lung and liver cancer cell lines, whereas SRS-H, a liver-specific promoter, is active only in liver cancer cell lines.
Figure 77:
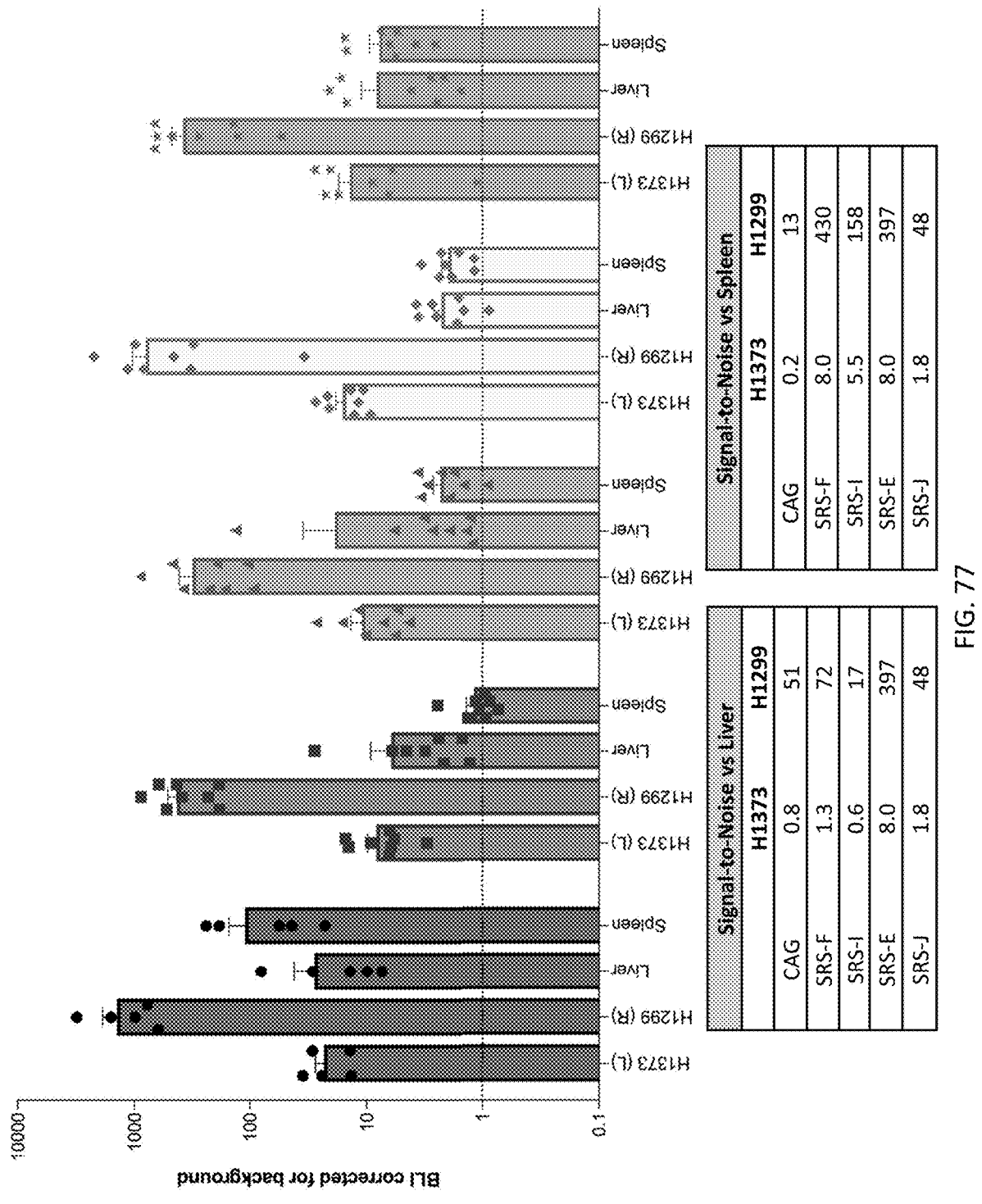
FIG. 77 shows a graph of gene expression activated by SRSs in different tissues, illustrating the in vivo performance of several SRSs when administered via intravenous (i.v.) bolus to tumor-bearing mice. Quantification of firefly bio-luminescence of tissues ex vivo was taken 24 hours after compound dosing normalized to the average biolumines-cence imaging (BLI) of PBS dosed animals (n=3, dotted line set at 1). Plotted by dosing group with each tissue in column. Each point represents a tissue from a unique animal. Circles: CAG constitutive promoter; squares: SRS-F; triangles: SRS-I; diamonds: SRS-E; stars: SRS-J. Error bars represent standard error of the mean (SEM). Tables on the bottom show calculated signal to noise ratios (SNR) for a given promoter over potential background noise tissues (liver, spleen) demonstrating improved SNR and selectivity for synthetic promoters relative to constitutively active CAG promoter.
Figure 78:
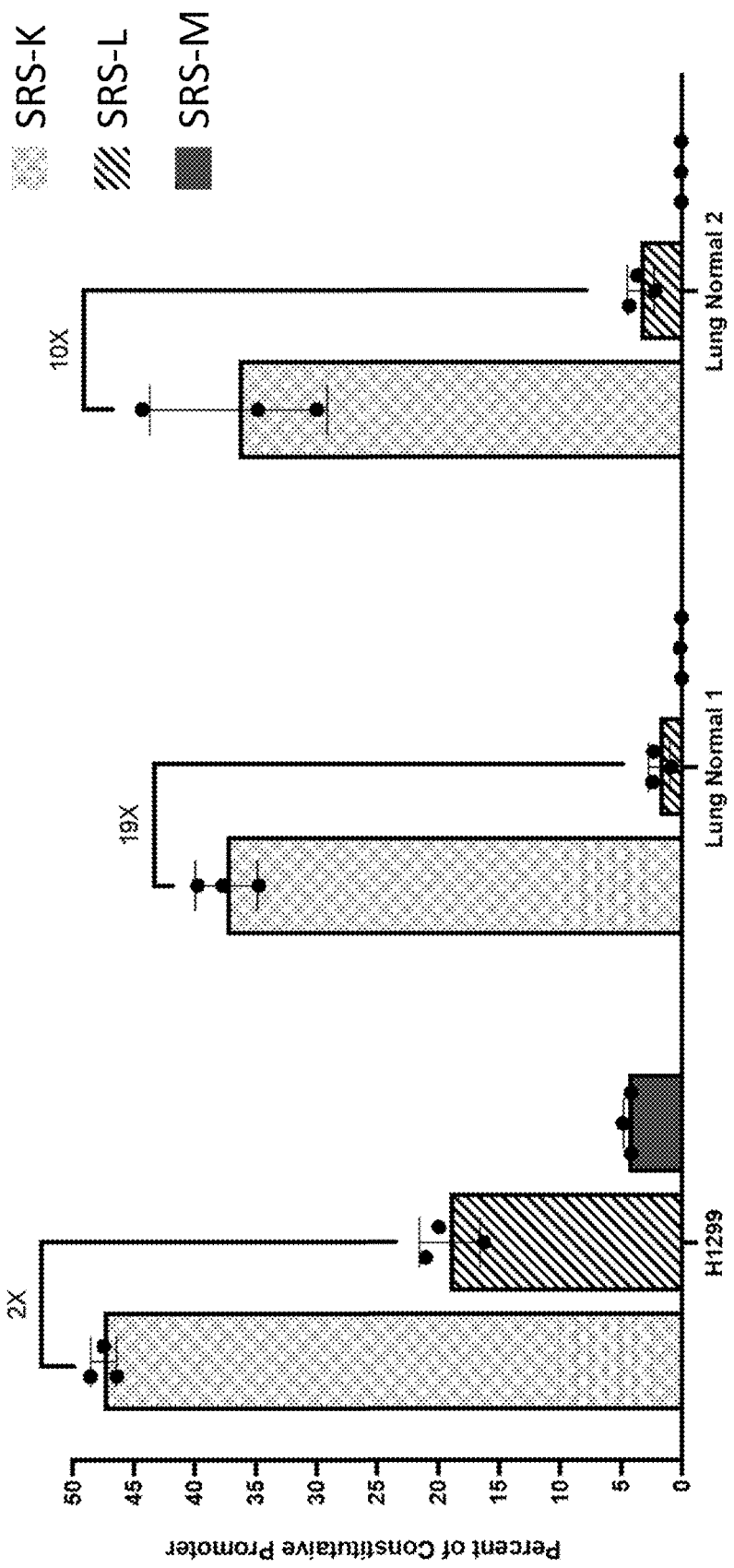
FIG. 78 shows a graph of reporter gene expression under different SRSs compared to a constitutive promoter. A FLUC reporter readout was used to assess specificity of SRSs comprising combinations of different promoters and SREs in lung cancer (H1299) and two different normal lung cell lines (Lung Normal 1 and Lung Normal 2). Reporter expression under SRS-K (using the non-specific promoter TATA-TSS) was high in both lung cancer and normal cell lines. Reporter expression under SRS-L and SRS-M was lower in all cell lines compared to that under SRS-K, especially in normal cell lines. Specifically, reporter gene expression under SRS-L was reduced 2× in cancer cell line and 10-20× in normal cell lines compared to reporter gene expression under SRS-K, which comprises non-specific promoter TATA-TSS, indicating that core promoters provide selectiv-ity and specificity for cancer cells compared to normal cells.

In some embodiments, an SRS can comprise a promoter and one or more SREs comprising a plurality of binding sites for one or more transcription factors and a plurality of enhancers. In some embodiments, an SRS can comprise a promoter and one or more SREs comprising a plurality of binding sites for one or more transcription factors. In some embodiments, an SRS can comprise a core promoter and one or more SREs comprising a plurality of binding sites for one or more transcription factors. In some embodiments, an SRS can comprise a promoter and one or more SREs comprising a plurality of enhancers. In some embodiments, an SRS can comprise a core promoter and one or more SREs comprising a plurality of enhancers. In some embodiments, an SRS can comprise a core promoter and one or more SREs comprising a plurality of binding sites for one or more transcription factors and a plurality of enhancers. An exemplary SRS is shown in FIG. 72. In one embodiment, an SRE can comprise a plurality of binding sites for one or more transcription factors, wherein each of the plurality of transcription binding sites can comprise the same binding site sequences or motifs (FIG. 72, left). In another embodiment, an SRE can comprise a plurality of binding sites for one or more transcription factors, wherein each of the plurality of transcription binding sites can comprise different binding site sequences or motifs. In yet another embodiment, an SRE can comprise a plurality of binding sites for one or more transcription factors, wherein the plurality of transcription binding sites can comprise a mixture of the same binding site sequences and different binding site sequences (FIG. 72, middle). In some embodiments, an SRS comprising an SRE that comprises a mixture of different transcription factor binding sequences or motifs can drive stronger or higher expression of an ORF operatively linked to the SRS in cancer cells or cancer tissues compared to a corresponding SRS comprising an SRE that that comprises a plurality of the same transcription binding sequences or motifs.

In some embodiments, an SRS can comprise one or more SREs comprising a plurality of binding sites for one or more transcription factors at the 5' or upstream of a promoter or a core promoter. In some embodiments, an SRS can comprise one or more SREs comprising a plurality of enhancers at the 5' or upstream of a promoter or a core promoter. In some embodiments, an SRS can comprise a plurality of enhancers at the 5' or upstream of a plurality of binding sites for one or more transcription factors, wherein the plurality of binding sites for one or more transcription factors are at the 5' or upstream of a promoter or a core promoter. For example, an SRS can comprise (i) a plurality of enhancers, (ii) a plurality of binding sites for one or more transcription factors, and (iii) a promoter or a core promotor in 5' to 3' direction. In some embodiments, an SRS can comprise a plurality of enhancers at the 5' or upstream of a promoter or a core promoter and at the 3' or downstream of a plurality of binding sites for one or more transcription factors. For example, an SRS can comprise (i) a plurality of binding sites for one or more transcription factors, (ii) a plurality of enhancers, and (ii) a promoter or a core promoter in 5' to 3' direction.

In some embodiments, an SRS described herein can drive the expression of an ORF operably linked to the SRS in one specific type of cancer cells. In some embodiments, an SRS described herein can drive the expression of an ORF operably linked to the SRS in two or more types of cancer cells.

In some embodiments, a recombinant polynucleotide comprising an SRS describe herein can drive the expression of an ORF operably linked to the SRS at a higher level compared to a corresponding recombinant polynucleotide comprising a constitutive promoter and an ORF operatively linked to the constitutive promoter. For example, a recombinant polynucleotide comprising an SRS describe herein can drive the expression of an ORF operably linked to the SRS at a level that is at least 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 110%, 920%, 930%, 940%, 950%, 960%, 970%, 980%, 990%, or at least 1000% higher compared to a corresponding recombinant polynucleotide comprising a constitutive promoter and an ORF operatively linked to the constitutive promoter. In some embodiments, an ORF can comprise an ORF of a natural gene or a synthetic gene. In some embodiments, a natural gene or a synthetic can comprise a gene encoding a reporter protein, a biomarker protein, or a therapeutic protein.

In some embodiments, a recombinant polynucleotide comprising an SRS describe herein can drive the expression of an ORF operably linked to the SRS at a higher level in cancer cells compared to a corresponding recombinant polynucleotide comprising a constitutive promoter and an ORF operatively linked to the constitutive promoter. For example, a recombinant polynucleotide comprising an SRS describe herein can drive the expression of an ORF operably linked to the SRS in cancer cells at a level that is at least 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 110%, 920%, 930%, 940%, 950%, 960%, 970%, 980%, 990%, or at least 1000% higher compared to a corresponding recombinant polynucleotide comprising a constitutive promoter and an ORF operatively linked to the constitutive promoter.

Promoter/Core Promoter

A core promoter described herein can comprise a minimal promoter that can comprise a transcription start site or a transcription start site sequence that is derived from a promoter of one or more genes expressed in cancer cells or cancer tissues (also referred to as a cancer-responsive gene herein). In some embodiments, a core promoter described herein can comprise a minimal promoter that can comprise a transcription start site or a transcription start site sequence that is derived from a promoter of one or more genes expressed at a higher level in cancer cells or cancer tissues compared to non-cancer cells or non-cancer tissues. For example, a core promoter described herein can comprise a minimal promoter that can comprise a transcription start site or a transcription start site sequence that is derived from a promoter of one or more genes expressed at a level that is at least 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 110%, 920%, 930%, 940%, 950%, 960%, 970%, 980%, 990%, or at least 1000% higher in cancer cells or cancer tissues compared to non-cancer cells or non-cancer tissues.

In some embodiments, a core promoter can further comprise one or more promoter elements that are derived from a promoter of one or more genes expressed in cancer cells or cancer tissues. In some embodiments, a core promoter can further comprise one or more promoter elements that are derived from a promoter of one or more genes expressed at a level that is at least 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 110%, 920%, 930%, 940%, 950%, 960%, 970%, 980%, 990%, or at least 1000% higher in cancer cells or cancer tissues compared to non-cancer cells or non-cancer tissues. In some embodiments, promoter elements can include, but are not limited to, elements specific for tissue, elements specific for development or development stage, elements specific for cancer (e.g., transcription factor binding sites specific for cancer or oncogenic transcription factor binding sites), elements important for transcription (e.g., general promoter elements). In some embodiments, a core promoter can comprise two or more promoter elements that are derived from a promoter of two or more genes expressed in cancer cells or cancer tissues. For example, a core promoter can comprise two or more promoter elements that are derived from a promoter of at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20 genes expressed in cancer cells or cancer tissues. Non-limiting examples of cancer-responsive genes can include TCF7, MNX1, HOXC10, TPS3, CEACAM5, CEP55, FAM111B, CST1, BIRC5, AGR2, FOXA1, cMYC, FOS, TWIST1, E2F2, UBE2C, KIF20A, or ETV4.

In some embodiments, a core promoter can comprise a minimal promoter derived from one or more genes expressed in cancer cells or cancer tissues. In one example, a core promoter can comprise a minimal promoter derived from one or more cancer-responsive genes comprising TCF7, MNX1, HOXC10, TPS3, CEACAM5, CEP55, FAM111B, CST1, BIRC5, AGR2, FOXA1, cMYC, FOS, TWIST1, E2F2, UBE2C, KIF20A, or ETV4. In another example, a core promoter can comprise a hybrid minimal promoter derived from two or more cancer-responsive genes comprising TCF7, MNX1, HOXC10, TPS3, CEACAM5, CEP55, FAM111B, CST1, BIRC5, AGR2, FOXA1, cMYC, FOS, TWIST1, E2F2, UBE2C, KIF20A, or ETV4. In some embodiments, a core promoter can comprise a minimal promoter and one or more promoter elements described herein derived from two or more cancer-responsive genes comprising TCF7, MNX1, HOXC10, TPS3, CEACAM5, CEP55, FAM111B, CST1, BIRC5, AGR2, FOXA1, cMYC, FOS, TWIST1, E2F2, UBE2C, KIF20A, or ETV4. In some embodiments, a core promoter can comprise a minimal promoter and two or more promoter elements described herein derived from TCF7 and HOXC10. In some embodiments, a core promoter can comprise a minimal promoter and two or more promoter elements described herein derived from TP53 and CEP55.

In some embodiments, a core promoter can comprise a minimal promoter and two or more promoter elements described herein derived from FAM111B and KIF20A. In some embodiments, a core promoter can comprise a minimal promoter and two or more promoter elements described herein derived from BIRC5 and E2F2. In some embodiments, a core promoter can comprise a minimal promoter and two or more promoter elements described herein derived from CEACAM5 and TWIST1. In some embodiments, a core promoter can comprise a hybrid promoter comprising two or more promoter elements described herein derived from two or more cancer-responsive genes comprising TCF7, MNX1, HOXC10, TP53, CEACAM5, CEP55, FAM111B, CST1, BIRC5, AGR2, FOXA1, cMYC, FOS, TWIST1, E2F2, UBE2C, KIF20A, or ETV4. In some embodiments, a core promoter can comprise a hybrid promoter comprising two or more promoter elements described herein derived from TCF7 and HOXC10. In some embodiments, a core promoter can comprise a hybrid promoter comprising two or more promoter elements described herein derived from TP53 and CEP55. In some embodiments, a core promoter can comprise a hybrid promoter comprising two or more promoter elements described herein derived from FAM111B and KIF20A. In some embodiments, a core promoter can comprise a hybrid promoter comprising two or more promoter elements described herein derived from BIRC5 and E2F2. In some embodiments, a core promoter can comprise a hybrid promoter comprising two or more promoter elements described herein derived from CEACAM5 and TWIST1. In some embodiments, a core promoter can comprise a hybrid promoter comprising a minimal promoter and two or more promoter elements described herein derived from two or more cancer-responsive genes comprising TCF7, MNX1, HOXC10, TP53, CEACAM5, CEP55, FAM111B, CST1, BIRC5, AGR2, FOXA1, cMYC, FOS, TWIST1, E2F2, UBE2C, KIF20A, or ETV4. In some embodiments, a core promoter can comprise a hybrid promoter comprising a minimal promoter and two or more promoter elements described herein derived from TCF7 and HOXC10. In some embodiments, a core promoter can comprise a hybrid promoter comprising a minimal promoter and two or more promoter elements described herein derived from TP53 and CEP55.

In some embodiments, a core promoter can comprise a hybrid promoter comprising a minimal promoter and two or more promoter elements described herein derived from FAM111B and KIF20A. In some embodiments, a core promoter can comprise a hybrid promoter comprising a minimal promoter and two or more promoter elements described herein derived from BIRC5 and E2F2. In some embodiments, a core promoter can comprise a hybrid promoter comprising a minimal promoter and two or more promoter elements described herein derived from CEACAM5 and TWIST1.

In some embodiments, a core promoter can comprise a hybrid promoter comprising a chimeric sequence of two or more promoter elements from two or more cancer-responsive genes comprising TCF7, MNX1, HOXC10, TP53, CEACAM5, CEP55, FAM111B, CST1, BIRC5, AGR2, FOXA1, cMYC, FOS, TWIST1, E2F2, UBE2C, KIF20A, or ETV4. In some embodiments, a core promoter can comprise a hybrid promoter comprising a chimeric sequence of two or more promoter elements derived from TCF7 and HOXC10. In some embodiments, a core promoter can comprise a hybrid promoter comprising a chimeric sequence of two or more promoter elements derived from TPS3 and CEP55. In some embodiments, a core promoter can comprise a hybrid promoter comprising a chimeric sequence of two or more promoter elements derived from FAM111B and KIF20A. In some embodiments, a core promoter can comprise a hybrid promoter comprising a chimeric sequence of two or more promoter elements derived from BIRC5 and E2F2. In some embodiments, a core promoter can comprise a hybrid promoter comprising a chimeric sequence of two or more promoter elements derived from CEACAM5 and TWIST1.

In some embodiments, a core promoter can comprise a TATA box or a TATA box sequence. In some embodiments, a core promoter can comprise a sequence of a region from about −300 bp to about +100 bp, from about −250 bp to about +100 bp, from about −200 bp to about +100 bp, from about −150 bp to about +100 bp, from about −100 bp to about +100 bp, from about −90 bp to about +100 bp, from about −80 bp to about +100 bp, from about −70 bp to about +100 bp, from about −60 bp to about +100 bp, from about −50 bp to about +100 bp, from about −40 bp to about +100 bp, or from about −30 bp to about +100 bp relative to a transcription start site (TSS) of a cancer-responsive gene. In some embodiments, a core promoter can comprise a sequence of a region from about 300 bp upstream of a TSS to about 100 bp downstream of a TSS, from about 250 bp upstream of a TSS to about 100 bp downstream of a TSS, from about 200 bp upstream of a TSS to about 100 bp downstream of a TSS, from about 150 bp upstream of a TSS to about 100 bp downstream of a TSS, from about 100 bp upstream of a TSS to about 100 bp downstream of a TSS, from about 90 bp upstream of a TSS to about 100 bp downstream of a TSS, from about 80 bp upstream of a TSS to about 100 bp downstream of a TSS, from about 70 bp upstream of a TSS to about 100 bp downstream of a TSS, from about 60 bp upstream of a TSS to about 100 bp downstream of a TSS, from about 50 bp upstream of a TSS to about 100 bp downstream of a TSS, from about 40 bp upstream of a TSS to about 100 bp downstream of a TSS, or from about 30 bp upstream of a TSS to about 100 bp downstream of a TSS of a cancer-responsive gene. In some embodiments, a cancer-responsive gene can comprise a human cancer-responsive gene.

In some embodiments, the sequence of a region from about −300 bp to about +100 bp relative to a TSS (or from about 300 bp upstream of a TSS to about 100 bp downstream of a TSS) can comprise elements that are important for transcription, elements that are tissue specific, elements that are specific for certain development stage, and/or one or more binding sites for transcription factors specific for cancer (e.g., oncogenic transcription factors). In some embodiments, a promoter or a core promoter can comprise one or more elements or sequences binding to NKX2-1, NANOG, GATA3, TRPS1, SOX9, KSLF14, Sp5, ZEB1, ZEB2, TGIF, PITX, NKX6-1, THRb, ERRa, COUP-TFII, PR, Asc12, Slug, E2A, PITX1, or NKX3.2.

In some embodiments, a promoter or a core promoter can be operably linked to an open reading frame (ORF) of a gene of interest. A gene of interest can be any gene for which expression is desired specifically in cancer cells. Non-limiting examples of a gene of interest can include a gene encoding a therapeutic protein, a gene encoding a synthetic protein, a gene encoding a marker protein (e.g., biomarker for diagnostics, etc.), or a gene encoding a reporter protein.

In some embodiments, the core promoter can be derived from a promoter of one or more genes that are expressed at a higher level in cancer cells compared to non-cancer cells. For example, the core promoter can be derived from a promoter of one or more genes that are expressed at a level that is at least 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 110%, 920%, 930%, 940%, 950%, 960%, 970%, 980%, 990%, or at least 1000% higher in cancer cells compared to non-cancer cells. In some embodiments, the core promoter can be derived from a promoter of one or more genes that are more active in cancer cells compared to non-cancer cells. For example, the core promoter can be derived from a promoter of one or more genes that are at least 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 110%, 920%, 930%, 940%, 950%, 960%, 970%, 980%, 990%, or at least 1000% more active in cancer cells compared to non-cancer cells.

In some embodiments, a phosphorylation assay can be used to measure activation or activity levels of cancer-responsive genes described herein.

In some embodiments, the core promoter can be derived from one or more cancer-responsive genes that are expressed at a higher level in cancer cells compared to non-cancer cells. For example, the core promoter can be derived from one or more cancer-responsive genes that are either expressed at a level that is at least 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 110%, 920%, 930%, 940%, 950%, 960%, 970%, 980%, 990%, or at least 1000% higher in cancer cells compared to non-cancer cells. In some embodiments, the core promoter can be derived from one or more cancer-responsive genes that are more active in cancer cells compared to non-cancer cells. For example, the core promoter can be derived from one or more cancer-responsive genes that are at least 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 110%, 920%, 930%, 940%, 950%, 960%, 970%, 980%, 990%, or at least 1000% more active in cancer cells compared to non-cancer cells. In some embodiments, a phosphorylation assay can be used to measure activation or activity levels of cancer-responsive genes described herein.

Synthetic Response Elements—Transcription Factors (TFs)

In some embodiments, an SRS can comprise one or more SREs, wherein the one or more SREs can comprise a plurality of binding sites for one or more transcription factors. In some embodiments, a plurality of binding sites (e.g., binding site DNA sequence) for one or more transcription factors can be identified from a multi-omics approach, including but not limited to, transcriptomics, proteomics, and/or phospho-proteomics to be upregulated in cancer cells or tissues compared to normal (e.g., non-cancer) cells or tissues. In some embodiments, the one or more SREs can comprise a plurality of binding sites for one or more transcription factors that are expressed in higher levels in cancer cells compared to non-cancer cells. In some embodiments, ChIP assay can be used to measure expression levels of transcription factors described herein. In some embodiments, the one or more SREs can comprise a plurality of binding sites for one or more transcription factors that are more active in cancer cells compared to non-cancer cells. For example, the one or more SREs can comprise a plurality of binding sites for one or more transcription factors that have higher level of phosphorylation in cancer cells compared to non-cancer cells. In some embodiments, a phosphorylation assay can be used to measure activation or activity levels of transcription factors described herein.

In some embodiments, an SRS comprising a promoter (or a core promoter) and a plurality of binding sites for one or more transcription factors can drive the expression of an ORF operably linked to the promoter (or the core promoter) at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 3.1-fold, at least 3.2-fold, at least 3.3-fold, at least 3.4-fold, at least 3.5-fold, at least 3.6-fold, at least 3.7-fold, at least 3.8-fold, at least 3.9-fold, at least 4-fold, at least 4.1-fold, at least 4.2-fold, at least 4.3-fold, at least 4.4-fold, at least 4.5-fold, at least 4.6-fold, at least 4.7-fold, at least 4.8-fold, at least 4.9-fold, at least 5-fold, at least 10-fold, at least 20-fold, at least 30-fold, at least 40-fold, at least 50-fold, at least 60-fold, at least 70-fold, at least 80-fold, at least 90-fold, or at least 100-fold higher than the expression of a corresponding ORF driven by a promoter (or a core promoter) without the plurality of binding sites for one or more transcription factors.

In some embodiments, an SRS comprising a promoter described herein (or a core promoter described herein, e.g., a cancer-specific core promoter comprising a TATA-TSS and other elements in−300 bp to about +100 bp relative to a TSS) and a plurality of binding sites for one or more transcription factors can drive the expression of an ORF operably linked to the promoter (or the core promoter) at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3-fold, at least 3.1-fold, at least 3.2-fold, at least 3.3-fold, at least 3.4-fold, at least 3.5-fold, at least 3.6-fold, at least 3.7-fold, at least 3.8-fold, at least 3.9-fold, at least 4-fold, at least 4.1-fold, at least 4.2-fold, at least 4.3-fold, at least 4.4-fold, at least 4.5-fold, at least 4.6-fold, at least 4.7-fold, at least 4.8-fold, at least 4.9-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 21-fold, at least 22-fold, at least 23-fold, at least 24-fold, at least 25-fold, at least 26-fold, at least 27-fold, at least 28-fold, at least 29-fold, at least 30-fold, at least 31-fold, at least 32-fold, at least 33-fold, at least 34-fold, at least 35-fold, at least 36-fold, at least 37-fold, at least 38-fold, at least 39-fold, at least 40-fold, at least 41-fold, at least 42-fold, at least 43-fold, at least 44-fold, at least 45-fold, at least 46-fold, at least 47-fold, at least 48-fold, at least 49-fold, at least 50-fold, at least 55-fold, at least 60-fold, at least 65-fold, at least 70-fold, at least 75-fold, at least 80-fold, at least 85-fold, at least 90-fold, at least 95-fold, or at least 100-fold higher than the expression of a corresponding ORF driven by a non-cancer specific promoter (e.g., TATA-TSS promoter only) and the plurality of binding sites for one or more transcription factors.

Non-limiting examples of transcription factors can include TRPS1, MNX1, TWIST1, ETV4, FOSL2, NFIC, EN2, TFDP1, PITX2, TCF7L1, VENTX, HOXB9, DLX1, MYCN, SIX4, TP63, SOX11, E2F8, TFDP1, SURV, TOXE, EN1, ZBTB7B, SP3, SIX2, XBP1, HIF-1A, CREB3L1, HSF-1, MTF1, NFE2L2, USF2, TP73, POU2F2, HOXA1, FOXO1, TFAP4, BACH1, E2F4, HOXC10, KLF11, FOXM1, E2F2, E2F3, E2F1, GLIS3, GATA1, DLX3, LHX2, BARX1, HOXC9, FOXK1, RUNX2, RUNX1, SOX4, RREB1, HES6, ASCL1, FOXA3, HOXB2, DLX4, GRHL1, FOXA, HIF, E2F6, FOSL1, JUN, JUNB, FOSB, AP-1, NF-1, RFX6, EL4, TCF3, TCF12, SNAI2, REST, DMRTA2, RFX7, NRF1, ZNF148, ZNF652, PRDM1, HIF1A, TGIF1, STAT2, ESRRA, RELB, HSF1, MAFB, TFAP2C, YBX1, YY1, PITX1, SATB1, ARID3A, POU3F1, SP4, MGA, SALL4, AHR, MLXIP, PRDM4, NFIL3, TFAP2A, ZBTB17, ZFP91, ARID5A, IRF6, ZFX, POU2F1, NKX2-1, NKX2-8, FOXA1, NFKB1, HNF4G, ARID1A, NFATC2, SMAD2, ARID3B, TPS3, FOS, FOS-CREB, ELK3, FOXO1::ELK3, TCF7, E2F2, CREB3L1, SHOX2, TCF7L1, HOXA1, MYBL2, NR2C2, MYCN, FOXN1, PITX2, EN2, NFIC, MYC, DLX4, SP3, FOXE1, VENTX, TPS3, GLIS3, CUX1, MGA, DLX1, DLX6, GATA1, RUNX2, E2F7, GRHL1, ZBTB7B, HNF1A, FOXA3, NPAS2, TP63, RREB1, SOX4, ZIC2, TCF7, EN1, DMBX1, E2F8, FOSL2, PBX3, NKX3-2, DLX3, HOXB7, TRPS1, SOX11, PAX8, HES6, HOXC10, MNX1, SIX2, ZNF281, ETV4, ZNF384, ASCL1, BARX1, PAX7, LHX2, OTX1, RUNX1, ETV6, FOXK1, HOXB9, E2F4, NR2F6, TWIST1 HOXC9, IRF6, NR2E1, RORB, E2F1, E2F3, TFDP1, FOXJ3, SIX4, MAX::MYC, ONECUT1, or NFκB.

In some embodiments, transcription factors enriched in lung adenocarcinoma (LUAD) can comprise E2F2, CREB3L1, SHOX2, TCF7L1, HOXA1, MYBL2, NR2C2, MYCN, FOXN1, PITX2, EN2, NFIC, MYC, DLX4, SP3, FOXE1, VENTX, TP53, GLIS3, CUX1, MGA, DLX1, DLX6, GATA1, RUNX2, E2F7, GRHL1, ZBTB7B, HNF1A, FOXA3, NPAS2, TP63, RREB1, SOX4, ZIC2, TCF7, EN1, DMBX1, E2F8, FOSL2, PBX3, NKX3-2, DLX3, HOXB7, TRPS1, SOX11, PAX8, HES6, HOXC10, MNX1, SIX2, ZNF281, ETV4, ZNF384, ASCL1, BARX1, PAX7, LHX2, OTX1, RUNX1, ETV6, FOXK1, HOXB9, E2F4, NR2F6, TWIST1, HOXC9, IRF6, NR2E1, RORB, E2F1, E2F3, TFDP1, FOXJ3, SIX4, MAX::MYC, or ONE-CUT1.

In some embodiments, transcription factors can comprise E2F4, E2F3, E2F1, GLIS3, GATA1, DLX1, DLX3, LHX2, BARX1, PBX3, HOXC9, FOXK1, FOXA3, TRPS1, RUNX2, HOXA1, NFE2L2, TCF3, TCF12, SNAI2, REST, DMRTA2, RFX7, NRF1, ZNF148, ZNF652, PRDM1, HIF1A, TGIF1, STAT2, ESRRA, RELB, HSF1, MAFB, TFAP2C, YBX1, YY1, PITX1, SATB1, ARID3A, USF2, POU3F1, SP4, MGA, SALL4, AHR, MLXIP, MTF1, PRDM4, ZBTB7B, NFIL3, TFAP2A, ZBTB17, ZFP91, BACH1, MLXIP, ARID5A, IRF6, ZFX, POU2F1, NKX2-1, NKX2-8, FOXA1, NFKB1, MGA, HNF4G, ARID1A, NFATC2, POU2F2, SMAD2, PRDM4, MLXIP, or ARID3B. In some embodiments, control TF tiles can comprise TCF7_v2, TCF7L1_v19, TP53_v5, TP53_v22, Control-1-FOSL1_v1, HOXC10_v24, HOXC10_v14, CREB3L1_v6, CREB3L1_v14, Control-Filler_v1, Control-Filler_v2, Control-Filler_v3, Control-Filler_v4, or Control-Filler_v5. In some embodiments, TF tiles can comprise homotypic TF-tiles or heterotypic TF tiles. For examples, TF-tiles comprising mixed binding sequences/sites/motifs from the same TF can be referred to as homotypic TF-tiles. For example, TF-tiles comprising mixed binding sequences/sites/motifs from different TF can be referred to as heterotypic TF-tiles. In some embodiments, SREs can comprise binding sequences, sites, or motifs of TFs of dysregulated genes that are involved in the EGFR, KRAS or p53 pathways in NSCLC.

In some embodiments, a binding site for a transcription factor can comprise a known transcription factor binding site (TFBS) sequence element or DNA binding site sequence element. In some embodiments, a transcription factor can bind to TFBS sequence element or DNA binding site sequence element and can recruit additional transcriptional machinery and co-factors (e.g., RNA polymerase, etc.) to the promoter or the core promoter. In some embodiments, a transcription factor can comprise a transcription co-factor.

In one embodiment, transcription factors that bind to the plurality of transcription binding sites can drive the expression of an ORF operably linked to the promoter in one specific type of cancer cells. In another embodiment, transcription factors that bind to the plurality of transcription binding sites can drive the expression of an ORF operably linked to the promoter in two or more types of cancer cells.

In some embodiments, an SRE can comprise at least about one, at least about two, at least about three, at least about four, at least about five, at least about six, at least about seven, at least about eight, at least about nine, or at least about ten binding sites for one or more transcription factors. In some embodiments, an SRE can comprise at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 binding sites for one or more transcription factors. In some embodiments, an SRE can comprise at most about 50, at most about 45, at most about 40, at most about 35, at most about 30, at most about 25, at most about 24, at most about 23, at most about 22, at most about 21, at most about 20, at most about 19, at most about 18, at most about 17, at most about 16, at most about 15, at most about 14, at most about 13, at most about 12, at most about 11, at most about 10, at most about 9, at most about 8, at most about 7, at most about 6, or at most about 5 binding sites for one or more transcription factors.

In some embodiments, an SRE can comprise a plurality of binding sites for at least about one, at least about two, at least about three, at least about four, at least about five, at least about six, at least about seven, at least about eight, at least about nine, or at least about ten transcription factors. In some embodiments, an SRE can comprise a plurality of binding sites for at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 transcription factors. In some embodiments, an SRE can comprise a plurality of binding sites for at most about 50, at most about 45, at most about 40, at most about 35, at most about 30, at most about 25, at most about 24, at most about 23, at most about 22, at most about 21, at most about 20, at most about 19, at most about 18, at most about 17, at most about 16, at most about 15, at most about 14, at most about 13, at most about 12, at most about 11, at most about 10, at most about 9, at most about 8, at most about 7, at most about 6, or at most about 5 transcription factors.

In some embodiments, an SRE can comprise two or more transcription factor binding sites for one transcription factor, wherein each of the two or more transcription factor binding sites can be sequentially arranged or tiled in a sequential manner. For example, an SRE can comprise two or more transcription factor binding site sequences for one transcription factor and each of the two or more transcription factor binding sites can be sequentially arranged or tiled in a sequential manner (e.g., arranged side by side). In some embodiments, an SRE can comprise two or more transcription factor binding sites for one transcription factor, wherein each of two or more transcription factor binding sites can be sequentially arranged or tiled in a sequential manner at 5' to a core promoter in the recombinant polynucleotide comprising the SRE and the core promoter.

In some embodiments, an SRE can comprise two or more transcription factor binding sites for two or more transcription factors, wherein each of two or more transcription factor binding sites can be non-sequentially arranged or tiled in a non-sequential manner. For example, an SRE can comprise two or more transcription factor binding site sequences for two or more transcription factors and the two or more transcription factor binding site sequences may be (i) the same, (ii) different, or (iii) a combination of (i) and (ii). In this example, the two or more transcription binding sites can comprise (ii) different transcription factor binding site sequences that are non-sequentially arranged or tiled in a non-sequential manner (e.g., shuffled) in the recombinant polynucleotide. In another example, the two or more transcription factor binding sites can comprise (iii) a combination of the same and different transcription factor binding site sequences, wherein all of the two or more transcription factor binding sites are non-sequentially arranged or tiled in a non-sequential manner in the recombinant polynucleotide. In yet another example, the two or more transcription factor binding sites can comprise (iii) a combination of the same and different transcription factor binding site sequences, wherein some of the two or more transcription factor binding sites are sequentially arranged or tiled in a sequential manner and the some of the two or more transcription factor binding sites are non-sequentially arranged or tiled in a non-sequential manner in the recombinant polynucleotide. In some embodiments, an SRE can comprise two or more transcription factor binding sites for two or more transcription factors, wherein each of two or more transcription factor binding sites can be non-sequentially arranged or tiled in a non-sequential manner at 5' to a core promoter in the recombinant polynucleotide comprising the SRE and the core promoter.

In some embodiments, an SRE comprising a plurality of binding sites for one or more transcription factors can further comprise a spacer element between each of the plurality of binding sites for one or more transcription factors. In some embodiments, a spacer element can comprise a nucleotide sequence of from about 1 to about 10 nucleotides or base pairs. For example, a spacer element can comprise a nucleotide sequence of from about 1 to about 10 nucleotides, from about 2 to about 15 nucleotides, from about 3 to about 20 nucleotides, from about 4 to about 25 nucleotides, from about 4 to about 30 nucleotides, from about 5 to about 35 nucleotides, from about 6 to about 40 nucleotides, from about 7 to about 50 nucleotides, from about 8 to about 55 nucleotides, from about 9 to about 60 nucleotides, from about 10 to about 65 nucleotides, from about 15 to about 70 nucleotides, from about 20 to about 75 nucleotides, from about 25 to about 80 nucleotides, from about 30 to about 85 nucleotides, from about 35 to about 90 nucleotides, from about 40 to about 95 nucleotides, or from about 45 to about 100 nucleotides. In some embodiments, a spacer element can comprise a nucleotide sequence of at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleotides. In some embodiments, a spacer element can comprise a nucleotide sequence of at most about 100, at most about 95, at most about 90, at most about 85, at most about 80, at most about 75, at most about 70, at most about 65, at most about 60, at most about 55, at most about 50, at most about 45, at most about 40, at most about 35, at most about 30, at most about 25, at most about 24, at most about 23, at most about 22, at most about 21, at most about 20, at most about 19, at most about 18, at most about 17, at most about 16, at most about 15, at most about 14, at most about 13, at most about 12, at most about 11, or at most about 10 nucleotides. In some embodiments, a spacer element can comprise a nucleotide sequence of 0, 3, 7, or 10 nucleotides or base pairs.

In some embodiments, an SRS can comprise a plurality of binding sites for one or more transcription factors (TFs), wherein said one or more TFs are expressed at higher levels in cancer cells compared to non-cancer cells. For example, the one or more TFs core promoter may be expressed at a level that is at least 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 110%, 920%, 930%, 940%, 950%, 960%, 970%, 980%, 990%, or at least 1000% higher in cancer cells compared to non-cancer cells.

In some embodiments, an SRS can comprise a plurality of binding sites for one or more transcription factors (TFs), wherein said one or more TFs are more active in cancer cells compared to non-cancer cells. For example, the one or more TFs may be at least 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 510%, 520%, 530%, 540%, 550%, 560%, 570%, 580%, 590%, 600%, 610%, 620%, 630%, 640%, 650%, 660%, 670%, 680%, 690%, 700%, 710%, 720%, 730%, 740%, 750%, 760%, 770%, 780%, 790%, 800%, 810%, 820%, 830%, 840%, 850%, 860%, 870%, 880%, 890%, 900%, 110%, 920%, 930%, 940%, 950%, 960%, 970%, 980%, 990%, or at least 1000% more active in cancer cells compared to non-cancer cells. In some embodiments, a phosphorylation assay can be used to measure activation or activity levels of TFs described herein.

Synthetic Response Elements—Enhancers

In some embodiments, an SRE can comprise a plurality of enhancers. For example, an SRE can comprise a plurality of any known enhancers that can increase the level of transcription of a gene. In some embodiments, an SRE can comprise a plurality of endogenous enhancer sequences. In some embodiments, an SRE can comprise a plurality of enhancers derived from a cancer-responsive gene described herein. In some embodiments, a cancer-responsive gene can comprise a human cancer-responsive gene. In some embodiments, an SRE can comprise at least about one, at least about two, at least about three, at least about four, at least about five, at least about six, at least about seven, at least about eight, at least about nine, or at least about ten enhancers derived from a cancer-responsive gene. In some embodiments, an SRE can comprise at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 enhancers derived from a cancer-responsive gene. In some embodiments, an SRE can comprise at most about 50, at most about 45, at most about 40, at most about 35, at most about 30, at most about 25, at most about 24, at most about 23, at most about 22, at most about 21, at most about 20, at most about 19, at most about 18, at most about 17, at most about 16, at most about 15, at most about 14, at most about 13, at most about 12, at most about 11, at most about 10, at most about 9, at most about 8, at most about 7, at most about 6, or at most about 5 enhancers derived from a cancer-responsive gene.

In some embodiments, an SRE can comprise a plurality of enhancers derived from two or more cancer-responsive genes described herein. In some embodiments, a cancer-responsive gene can refer to a gene specifically or preferentially expressed in cancer cells or cancer tissues compared to non-cancer cells or non-cancer tissues. In some embodiments, a cancer-responsive gene can comprise a human cancer-responsive gene. In some embodiments, an SRE can comprise a plurality of enhancers derived from at least about two, at least about three, at least about four, at least about five, at least about six, at least about seven, at least about eight, at least about nine, or at least about ten cancer-responsive genes. In some embodiments, an SRE can comprise a plurality of enhancers derived from at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 cancer-responsive genes. In some embodiments, an SRE can comprise a plurality of enhancers derived from at most about 100, at most about 95, at most about 90, at most about 85, at most about 80, at most about 75, at most about 70, at most about 65, at most about 60, at most about 55, at most about 50, at most about 45, at most about 40, at most about 35, at most about 30, at most about 25, at most about 24, at most about 23, at most about 22, at most about 21, at most about 20, at most about 19, at most about 18, at most about 17, at most about 16, at most about 15, at most about 14, at most about 13, at most about 12, at most about 11, at most about 10, at most about 9, at most about 8, at most about 7, at most about 6, or at most about 5 cancer-responsive genes.

In some embodiments, a plurality of enhancers described herein can comprise a transcription regulatory element (TRE). A TRE can refer to a region of DNA that can regulate transcription of a gene.

In some embodiments, a TRE can increase the transcription of a gene. In some embodiments, a TRE can decrease the transcription of a gene. In some embodiments, a TRE can comprise a transcription binding site. In some embodiments, a plurality of enhancers can comprise a transcription regulatory element that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence homology to an enhancer consensus sequence of two or more homologous cancer-responsive genes. In some embodiments, a plurality of enhancers can comprise a transcription regulatory element that has 90% sequence homology to an enhancer consensus sequence of two or more homologous cancer-responsive genes.

In some embodiments, a plurality of enhancers can comprise an enhancer consensus sequence of two or more homologous cancer-responsive genes. In some embodiments, an enhancer consensus sequence of two or more homologous cancer-responsive genes can comprise a consensus sequence of an enhancer sequence derived from two or more cancer-responsive genes that has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity between the two or more cancer-responsive genes. In some embodiments, an enhancer consensus sequence of two or more homologous cancer-responsive genes can comprise a consensus sequence of an enhancer sequence derived from two or more cancer-responsive genes that has at least 90% sequence identity between the two or more cancer-responsive genes.

In some embodiments, an SRE can comprise a plurality of enhancers comprising at least two enhancer sequences, wherein each of the at least two enhancer sequences can comprise (i) the same enhancer sequences, (ii) different enhancer sequences, or (iii) a combination of (i) and (ii). In some embodiments, each of the at least two enhancer sequences can be sequentially arranged or tiled in a sequential manner in a recombinant polynucleotide. In some embodiments, each of the at least two enhancer sequences can be sequentially arranged or tiled in a sequential manner at 5' to a core promoter in the recombinant polynucleotide comprising the core promoter and an SRE comprising the plurality of enhancers. In some embodiments, each of said at least two enhancer sequences can be sequentially arranged or tiled in a sequential manner at 5' to a core promoter and/or at 3' to a plurality of binding sites for one or more TFs, if present, in the recombinant polynucleotide comprising the core promoter, an SRE comprising the plurality of enhancers, and/or the plurality of transcription factor binding sites.

In some embodiments, an SRE can comprise a plurality of enhancers comprising at least two enhancer sequences, wherein each of the at least two enhancer sequences can comprise (ii) different enhancer sequences. In this embodiment, each of said plurality of enhancers comprising different enhancer sequences can be non-sequentially arranged or tiled in a non-sequential manner. In some embodiments, each of said plurality of enhancers comprising different enhancer sequences can be non-sequentially arranged or tiled in a non-sequential manner at 5' to a core promoter in the recombinant polynucleotide comprising the core promoter and an SRE comprising the plurality of enhancers. In some embodiments, each of said plurality of enhancers comprising different enhancer sequences can be non-sequentially arranged or tiled in a non-sequential manner at 5' to a core promoter and/or at 3' to a plurality of binding sites for one or more TFs, if present, in the recombinant polynucleotide comprising the core promoter, an SRE comprising the plurality of enhancers, and/or the plurality of transcription factor binding sites.

In some embodiments, an SRE can comprise a plurality of enhancers comprising at least two enhancer sequences, wherein each of the at least two enhancer sequences can comprise (iii) a combination of the same and different enhancer sequences. In this embodiment, each of said plurality of enhancers comprising a combination of the same and different enhancer sequences can be non-sequentially arranged or tiled in a non-sequential manner. In some embodiments, each of said plurality of enhancers comprising a combination of the same and different enhancer sequences can be non-sequentially arranged or tiled in a non-sequential manner at 5' to a core promoter in the recombinant polynucleotide comprising the core promoter and an SRE comprising the plurality of enhancers. In some embodiments, each of said plurality of enhancers comprising a combination of the same and different enhancer sequences can be non-sequentially arranged or tiled in a non-sequential manner at 5' to a core promoter and/or at 3' to a plurality of binding sites for one or more TFs, if present, in the recombinant polynucleotide comprising the core promoter, an SRE comprising the plurality of enhancers, and/or the plurality of transcription factor binding sites.

In some embodiments, a plurality of enhancers described herein can comprise a sequence capable of binding to a transcription associated protein. A transcription associated protein as described herein can comprise any protein that is involved in transcription of a DNA sequence to an RNA sequence. In some embodiments, a transcription associated protein can bind to an enhancer sequence. In some embodiments, an assay can be used to determine if a transcription associated protein can bind to a sequence comprised in a plurality of enhancers. For example, chromatin immunoprecipitation (ChIP) assay, an in vitro transfection reporter assay, or any other suitable assays or methods can be used to determine if a transcription associated protein can bind to a sequence comprised in a plurality of enhancers. In some embodiments, a plurality of enhancers described herein can comprise a sequence capable of binding to a transcription associated protein determined by chromatin immunoprecipitation (ChIP) or an in vitro transfection reporter assay.

In some embodiments, a plurality of enhancers can comprise a CpG island. For example, at least one enhancer of the plurality of enhancers can comprise a CpG island. In some embodiments, a plurality of enhancers may not comprise a CpG island. For example, at least one enhancer of the plurality of enhancers may not comprise a CpG island.

In some embodiments, an SRS can comprise a core promoter and a plurality of binding sites for one or more transcription factors derived from two or more cancer-responsive genes, wherein the core promoter and the plurality of binding sites for one or more transcription factors are not derived from the same cancer-responsive gene. In some embodiments, an SRS can comprise a core promoter and a plurality of enhancers derived from two or more cancer-responsive genes, wherein the core promoter and the plurality of enhancers are not derived from the same cancer-responsive gene. In some embodiments, an SRS can comprise a core promoter, a plurality of binding sites for one or more transcription factors, and a plurality of enhancer derived from two or more cancer-responsive genes, wherein the core promoter, the plurality of binding sites for one or more transcription factors, and the plurality of enhancer are not derived from the same cancer-responsive gene. In some embodiments, a cancer-responsive gene can comprise a human cancer-responsive gene.

In some embodiments, a plurality of enhancers can comprise an enhancer sequence that can bind to SP1, ETS, CEBP, NF-KB, EBS, C/EBP, ARE, DRE, NFκB, GC-box, UN5CL, BOP1, RTN4RL2, ARNTL2, AGR2, LHX2, TRNP1, MU5AC, or DOK4. In some embodiments, a plurality of enhancers can comprise at least two, at least about three, at least about four, at least about five, at least about six, at least about seven, at least about eight, at least about nine, or at least about ten enhancer sequences. In some embodiments, a plurality of enhancers can comprise at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 enhancer sequences. In some embodiments, a plurality of enhancers can comprise at least two SP1, ETS, CEBP, NF-KB, EBS, C/EBP, ARE, DRE, NFκB, GC-box, UN5CL, BOP1, RTN4RL2, ARNTL2, AGR2, LHX2, TRNP1, MU5AC, or DOK4 enhancer sequences.

In some embodiments, core promoter, plurality of binding sites for one or more transcription factors, or plurality of enhancers derived from two or more cancer-responsive genes can comprise a sequence listed in Table 1A, Table 1B, or Table 1C. In some embodiments, an SRS described herein can comprise a sequence listed in Table 1A, Table 1B, or Table 1C.

In some embodiments, an SRS can comprise a sequence comprising a human alpha-fetoprotein (AFP) promoter sequence comprising a plurality of HNF-1A transcription binding sites. AFP level is elevated in liver cancer including, but not limited to, hepatic carcinomas. In some embodiments, an HNF-1A transcription binding site can comprise a sequence of 5'-GTTAATTATTAAC-3' (SEQ ID NO: 128).

Cancer Cells or Cell Lines

Described herein is a method of selectively expressing a protein in cancer or tumor cells. In some embodiments, the method can comprise contacting cancer or tumor cells with a recombinant polynucleotide comprising any SRS described herein that comprises a promoter or a core promoter, one or more SREs, and an open reading frame (ORF) encoding a protein. In some embodiments, the ORF can be operatively linked to the SRS or the promoter (or the core promoter) in the SRS. In some embodiments, cancer or tumor cells described herein can comprise malignant cancer cells. Examples of cancer or tumor cells include, but are not limited to, colorectal cancer (CRC) cells, hepatocellular carcinoma cells, breast cancer cells, or lung cancer cells. In some embodiments, cancer or tumor cells can comprise cancer or tumor cells associated with colorectal cancer (CRC), hepatocellular carcinoma, lung cancer, liver cancer, breast cancer, prostate cancer, cervix cancer, uterus cancer, pancreas cancer, kidney cancer, stomach cancer, bladder cancer, ovary cancer, brain cancer, head and neck cancer, eye cancer, mouth cancer, throat cancer, esophagus cancer, chest cancer, bone cancer, rectum or other gastrointestinal tract organ cancer, spleen cancer, skeletal muscle cancer, subcutaneous tissue cancer, testicles or other reproductive organ cancer, skin cancer, thyroid cancer, blood cancer, or lymph nodes cancer. In some embodiments, adenocarcinoma (LUAD) cells can comprise LXFA586, LXFA629, LXFA2184, or A549.

In some embodiments, large cell carcinoma cells can comprise H1299, LXFL430, LXFL1121, or LXFL529. In some embodiments, squamous cell carcinoma (LUSC) cells can comprise LK2, H520, H1703, SK-MES-1, or Calu-1. In some embodiments, hepatocellular carcinoma (HCC) cells can comprise HUH7.

In some embodiments, promoters active in LXFA586 cell lines can comprise promoters of TP53, HES6, FOS, FOS-CREB, FOXO1::ELK3, or MTF1. In some embodiments, promoters active in LXFA629 cell lines can comprise promoters of FOS, CREB3L1, or HES6. In some embodiments, promoters active in LXFA2184 cell lines can comprise promoters of FOS or MNX. In some embodiments, promoters active in H1299 cell lines can comprise promoters of FOS, CREB3L1, HES6, FOS-CREB, NFE2L2, FOXO1::ELK3, or XBP1. In some embodiments, promoters active in LXFL430 cell lines can comprise promoters of TCF7, ETV4, HOXC10, FOS-CREB, FOXO1::ELK3, or XBP1. In some embodiments, promoters active in LXFL1121 cell lines can comprise promoters of FOS, CREB3L1, or ETV4. In some embodiments, promoters active in LXFL529 cell lines can comprise promoters of FOS.

In some embodiments, expression of the protein encoded by the ORF may be increased in cancer cells compared to non-cancer cells. In some embodiments, expression of the protein encoded by the ORF may be increased when the recombinant polynucleotide comprising the SRS and the ORF is introduced to cancer cells compared to non-cancer cells. For example, expression of the protein encoded by the ORF may be increased at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 100%, at least about 110%, at least about 120%, at least about 130%, at least about 140%, at least about 150%, at least about 160%, at least about 170%, at least about 180%, at least about 190%, at least about 200%, or at least about 250% in cancer cells compared to non-cancer cells. In some embodiments, the ORF can comprise a sequence encoding a therapeutic protein, marker protein (e.g., for diagnostic imaging, etc.), or a reporter protein (e.g., luciferase). In some embodiments, the ORF can comprise a sequence encoding a recombinant, synthetic, or engineered protein.

In some embodiments, expression of the protein encoded by the ORF may be increased in a first plurality of cancer cells when said recombinant polynucleotide is introduced to the first plurality of cancer cells compared to a second plurality of cancer cells, wherein the first plurality of cancer cells and the second plurality of cancer cells are different types of cancer cells. In some embodiments, expression of the protein encoded by the ORF may be increased in a first plurality of cancer cells when the recombinant polynucleotide comprising the SRS and the ORF is introduced to the first plurality of cancer cells compared to a second plurality of cancer cells, wherein the first plurality of cancer cells and the second plurality of cancer cells are different types of cancer cells. For example, expression of the protein encoded by the ORF operatively linked to a first type of SRS in the recombinant polynucleotide may be increased in cells of one type of cancer in which the first type of SRS can drive expression of the ORF compared to in cells of another type of cancer in which the first type of SRS cannot drive expression of the ORF. For example, expression of the protein encoded by the ORF operatively linked to an SRS that is specific for lung cancer may be increased in lung cancer cells compared to in liver cancer cells.

In some embodiments, expression of the protein encoded by the ORF may be increased in a first plurality of cancer cells comprising two or more types of cancer cells when the recombinant polynucleotide comprising the SRS and the ORF is introduced to the first plurality of cancer cells compared to a second plurality of cancer cells. For example, expression of the protein encoded by the ORF operatively linked to a first type of SRS in the recombinant polynucleotide may be increased in cells of two or more types of cancer in which the first type of SRS can drive expression of the ORF compared to in cells of another type of cancer in which the first type of SRS cannot drive expression of the ORF. For example, expression of the protein encoded by the ORF operatively linked to an SRS that is specific for lung and liver cancer may be increased in lung cancer cells and liver cancer cells compared to in non-lung cancer cells and non-liver cancer cells (e.g., breast cancer cells, etc.). In some embodiments, the first plurality of cancer cells comprising two or more types of cancer cells can comprise cells associated with two or more cancers comprising colorectal cancer, hepatocellular carcinoma, lung cancer, liver cancer, breast cancer, prostate cancer, cervix cancer, uterus cancer, pancreas cancer, kidney cancer, stomach cancer, bladder cancer, ovary cancer, brain cancer, head and neck cancer, eye cancer, mouth cancer, throat cancer, esophagus cancer, chest cancer, bone cancer, rectum or other gastrointestinal tract organ cancer, spleen cancer, skeletal muscle cancer, subcutaneous tissue cancer, testicles or other reproductive organ cancer, skin cancer, thyroid cancer, blood cancer, or lymph nodes cancer.

Therapeutic or Diagnostic Applications

Provided herein are recombinant polynucleotides (or any vector, pharmaceutical composition, or lipid nanoparticle comprising any recombinant polynucleotides described herein) useful for the diagnosis or the treatment of a disease or condition. In some aspects, recombinant polynucleotides described herein (or any vector, pharmaceutical composition, or lipid nanoparticle comprising any recombinant polynucleotides described herein) are present or administered in an amount for sufficient expression of a protein (e.g., a reporter protein or a biomarker) useful for a diagnosis of a disease or condition. In some embodiments, the disease or condition comprise a cancer. In some aspects, provided herein is a method of selectively expressing a reporter protein or a biomarker in a cancer or tumor cell. In some aspects, the method comprises contacting a tumor cell with any of recombinant polynucleotides described herein, any of vectors comprising recombinant polynucleotide described herein, any of pharmaceutical composition comprising recombinant polynucleotide described herein, or any of lipid nanoparticle (LNP) comprising the recombinant polynucleotide, the vector, or the pharmaceutical composition described herein, wherein recombinant polynucleotides can comprise an open reading frame (ORF) encoding the reporter protein or the biomarker operatively linked to a synthetic promoter described herein (e.g., a synthetic promoter that can drive expression of the ORF preferentially or specifically in cancer cells).

In some aspects, provided herein is a method for diagnosing a disease or a condition. In some embodiments, the method can comprise administering to any of recombinant polynucleotide described herein, a vector comprising the recombinant polynucleotide described herein, the pharmaceutical composition comprising the recombinant polynucleotide described herein, or a lipid nanoparticle (LNP) comprising the recombinant polynucleotide, the vector, or the pharmaceutical composition described herein to a subject. In some embodiments, the recombinant polynucleotide can further comprise an open reading frame (ORF) encoding a reporter protein or a biomarker, wherein the ORF is operatively linked to a synthetic promoter in the recombinant polynucleotide that can drive expression of the ORF selectively, preferentially, or specifically in diseased cells compared to non-disease cells. In some embodiments, the method can further comprise detecting the reporter protein or a biomarker of which expression can be induced by a synthetic promoter in the recombinant polynucleotide described herein selectively, preferentially, or specifically in diseased cells compared to non-disease cells. In some embodiments, a relative ratio of the reporter protein or the biomarker expressed in the diseased cells over the non-diseased cells can be greater than 1.0. For example, a relative ratio of the reporter protein or the biomarker expressed in the diseased cells over the non-diseased cells can be greater than about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 20.0, 25.0, 30.0, 35.0, 40.0, 45.0, 50.0, 55.0, 60.0, 65.0, 70.0, 75.0, 80.0, 85.0, 90.0, 95.0, or about 100.0. In some embodiments, the disease or condition can comprise a cancer.

In some aspects, recombinant polynucleotides (or any vector, pharmaceutical composition, or lipid nanoparticle comprising any recombinant polynucleotides described herein) are present or administered in an amount sufficient to treat or prevent a disease or condition. In some aspects, provided herein, is a method of treating a disease or condition comprising administering to a subject in need thereof the recombinant polynucleotide described herein, a vector comprising the recombinant polynucleotide described herein, a pharmaceutical composition comprising the recombinant polynucleotide described herein, or a lipid nanoparticle (LNP) comprising the vector, the pharmaceutical composition or the recombinant polynucleotide described herein. In some aspects, provided herein, is recombinant polynucleotide described herein, a vector comprising the recombinant polynucleotide described herein, the pharmaceutical composition comprising the recombinant polynucleotide described herein, or a lipid nanoparticle (LNP) comprising the recombinant polynucleotide, the vector, or the pharmaceutical composition described herein for use in a method of treating a disease or a condition in a subject in need thereof. In some aspects, provided herein, is the use of recombinant polynucleotide described herein, a vector comprising the recombinant polynucleotide described herein, the pharmaceutical composition comprising the recombinant polynucleotide described herein, or a lipid nanoparticle (LNP) comprising the recombinant polynucleotide, the vector, or the pharmaceutical composition described herein for the manufacture of a medicament for treating a disease or a condition in a subject in need thereof.

In some aspects, provided herein is a method for treating a subject having or suspected of having a disease or a condition. In some embodiments, the method can comprise administering any of recombinant polynucleotide described herein, a vector comprising the recombinant polynucleotide described herein, the pharmaceutical composition comprising the recombinant polynucleotide described herein, or a lipid nanoparticle (LNP) comprising the recombinant polynucleotide, the vector, or the pharmaceutical composition described herein to a subject. In some embodiments, the recombinant polynucleotide can further comprise an open reading frame (ORF) encoding a therapeutic protein, wherein the ORF is operatively linked to a synthetic promoter in the recombinant polynucleotide that can drive expression of the ORF selectively, preferentially, or specifically in diseased cells compared to non-disease cells. In some embodiments, a relative ratio of the therapeutic protein expressed in the diseased cells over the non-diseased cells can be greater than 1.0. For example, a relative ratio of the therapeutic protein expressed in the diseased cells over the non-diseased cells can be greater than about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, or about 15.0.

In some embodiments, the disease or disorder can comprise a cancer. Examples of cancer can include, but are not limited to, colorectal cancer (CRC), hepatocellular carcinoma, breast cancer, lung cancer, liver cancer, prostate cancer, cervix cancer, uterus cancer, pancreas cancer, kidney cancer, stomach cancer, bladder cancer, ovary cancer, brain cancer, head and neck cancer, eye cancer, mouth cancer, throat cancer, esophagus cancer, chest cancer, bone cancer, rectum or other gastrointestinal tract organ cancer, spleen cancer, skeletal muscle cancer, subcutaneous tissue cancer, testicles or other reproductive organ cancer, skin cancer, thyroid cancer, blood cancer, or lymph nodes cancer.

Also provided herein are pharmaceutical compositions comprising any recombinant polynucleotide described herein or any vector comprising the recombinant polynucleotide described herein and a pharmaceutically acceptable excipient, carrier, or diluent. A pharmaceutical composition can denote a mixture or solution comprising a therapeutically effective amount of an active pharmaceutical ingredient together with one or more pharmaceutically acceptable excipients to be administered to a subject in need thereof. The term "pharmaceutically acceptable" can denote an attribute of a material which is useful in preparing a pharmaceutical composition that is generally safe, non-toxic, and neither biologically nor otherwise undesirable and is acceptable for veterinary as well as human pharmaceutical use. The term "Pharmaceutically acceptable" can refer to a material, such as a excipient, carrier, or diluent, which does not abrogate the biological activity or properties of the recombinant polynucleotide or the compound, and is relatively nontoxic, i.e., the material may be administered to an individual without causing undesirable biological effects or interacting in a deleterious manner with any of the components of the composition in which it is contained. A pharmaceutically acceptable excipient can denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents, excipients, preservatives, or lubricants used in formulating pharmaceutical products. Pharmaceutical compositions can facilitate administration of a recombinant polynucleotide, a vector comprising recombinant polynucleotide, or a compound to an organism and can be formulated in a conventional manner using one or more pharmaceutically acceptable inactive ingredients that facilitate processing of the active compounds into preparations that can be used pharmaceutically. A proper formulation is dependent upon the route of administration chosen and a summary of pharmaceutical compositions can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference. In some embodiments, pharmaceutical compositions can be formulated by dissolving active substances (e.g., recombinant polynucleotides or vectors comprising the recombinant polynucleotides described herein) in aqueous solution for administration into a cell, a tissue or a subject (e.g., a disease cell, disease tissue, or a subject in need thereof). In some embodiments, pharmaceutical compositions can be formulated by dissolving active substances (e.g., recombinant polynucleotides or vectors comprising the recombinant polynucleotides described herein) in aqueous solution for administration into a cell, a tissue or a subject (e.g., a disease cell, disease tissue, or a subject in need thereof).

Also provided herein are methods of treating a disease or condition in a subject in need thereof, comprising administering to the subject a therapeutically effective amount of any recombinant polynucleotide described herein, any vector comprising recombinant polynucleotide described herein, or pharmaceutical compositions described herein. The terms "effective amount" or "therapeutically effective amount," as used herein, can refer to a sufficient amount of an agent, a compound, any recombinant polynucleotide described herein, any vector comprising recombinant polynucleotide described herein, or pharmaceutical compositions described herein being administered which will relieve to some extent one or more of the symptoms of the disease or the condition being treated; for example a reduction and/or alleviation of one or more signs, symptoms, or causes of a disease, or any other desired alteration of a biological system. For example, an "effective amount" for therapeutic uses can be an amount of an agent that provides a clinically significant decrease in one or more disease symptoms. An appropriate "effective" amount may be determined using techniques, such as a dose escalation study, in individual cases. In some embodiments, an "effective amount" can comprise an amount for sufficient expression of a protein (e.g., a reporter protein or a biomarker) useful for diagnosing a disease or condition in a subject.

The terms "treat," "treating" or "treatment," as used herein, can include alleviating, abating or ameliorating at least one symptom of a disease or a condition, preventing additional symptoms, inhibiting the disease or the condition, e.g., arresting the development of the disease or the condition, relieving the disease or the condition, causing regression of the disease or the condition, relieving a condition caused by the disease or the condition, or stopping the symptoms of the disease or the condition either prophylactically and/or therapeutically. In some embodiments, treating a disease or condition comprises reducing the size of disease tissues or diseased cells. In some embodiments, treating a disease or a condition in a subject comprises increasing the survival of a subject. In some embodiments, treating a disease or condition comprises reducing or ameliorating the severity of a disease, delaying onset of a disease, inhibiting the progression of a disease, reducing hospitalization of or hospitalization length for a subject, improving the quality of life of a subject, reducing the number of symptoms associated with a disease, reducing or ameliorating the severity of a symptom associated with a disease, reducing the duration of a symptom associated with a disease, preventing the recurrence of a symptom associated with a disease, inhibiting the development or onset of a symptom of a disease, or inhibiting of the progression of a symptom associated with a disease. In some embodiments, treating a cancer comprises reducing the size of tumor or increasing survival of a patient with a cancer.

In some cases, a subject can encompass mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In some cases, the mammal is a human. In some cases, the subject may be an animal. In some cases, an animal may comprise human beings and non-human animals. In one embodiment, a non-human animal may be a mammal, for example a rodent such as rat or a mouse. In another embodiment, a non-human animal may be a mouse. In some instances, the subject is a mammal. In some instances, the subject is a human. In some instances, the subject is an adult, a child, or an infant. In some instances, the subject is a companion animal. In some instances, the subject is a feline, a canine, or a rodent. In some instances, the subject is a dog or a cat.

Recombinant polynucleotides, vectors, or pharmaceutical compositions described herein can be administered to a subject using any suitable methods known in the art. Suitable formulations for use in the present invention and methods of delivery are generally well known in the art. For example, compositions described herein can be administered to the subject in a variety of ways, including parenterally, intravenously, intradermally, intramuscularly, colonically, rectally, or intraperitoneally. In some embodiments, compositions described herein is administered by intraperitoneal injection, intramuscular injection, subcutaneous injection, or intravenous injection of the subject. In some embodiments, compositions described herein can be administered parenterally, intravenously, intramuscularly or orally. In some embodiments, compositions described herein can be administered via injection into disease tissues or cells.

In some embodiments, compositions or pharmaceutical compositions comprising any recombinant polynucleotide described herein can be delivered to a cell via direct DNA transfer (Wolff et al. (1990) Science 247, 1465-1468). In some embodiments, recombinant polynucleotides can be delivered to cells following mild mechanical disruption of the cell membrane, temporarily permeabilizing the cells. Such a mild mechanical disruption of the membrane can be accomplished by gently forcing cells through a small aperture (Sharei et al. PLOS ONE (2015) 10(4), e0118803). In another embodiment, compositions or pharmaceutical compositions comprising any recombinant polynucleotide described herein can be delivered to via liposome or lipid nanoparticle (LNP) (e.g., Gao & Huang (1991) Biochem. Ciophys. Res. Comm. 179, 280-285, Crystal (1995) Nature Med. 1, 15-17, Caplen et al. (1995) Nature Med. 3, 39-46). A liposome or LNP can encompass a variety of single and multilamellar lipid vehicles formed by the generation of enclosed lipid bilayers or aggregates. Recombinant polynucleotides can be encapsulated in the aqueous interior of a liposome or LNP, interspersed within the lipid bilayer of a liposome, attached to a liposome via a linking molecule that is associated with both the liposome and the oligonucleotide, entrapped in a liposome, or complexed with a liposome.

In some aspects, provided herein is a method comprising: (a) administering to a subject any of the pharmaceutical composition described herein; or a composition any of the recombinant polynucleotide described herein, any of the vector described herein, or any of the LNP described herein; wherein the recombinant polynucleotide further comprises an open reading frame (ORF) encoding a reporter protein, wherein said ORF is operatively linked to a synthetic promoter in said recombinant polynucleotide, and (b) localizing a tumor or an absence thereof in a body of said subject via expression of said reporter protein using an imaging technique performed on said body of said subject. In some embodiments, the imaging technique comprises photoacoustic imaging, Magnetic resonance imaging (MRI) imaging, positron emission tomography (PET) imaging, or single-photon emission computed tomography (SPECT) imaging.

Embodiments

In some aspects, provided herein is a recombinant polynucleotide comprising: (a) a core promoter comprising a transcription start site (TSS), wherein the core promoter is derived from one or more cancer-responsive genes that are either expressed at a higher level or are more active in cancer cells compared to non-cancer cells and operably linked to an open reading frame (ORF) and (b) a plurality of binding sites for one or more transcription factors (TFs), wherein said one or more TFs are expressed at higher levels or more active in cancer cells compared to non-cancer cells. In some embodiments, the recombinant polynucleotide further comprises a plurality of enhancers.

In some aspects, provided herein is a recombinant polynucleotide comprising: (a) a core promoter comprising a transcription start site (TSS) and two or more promoter elements derived from two or more cancer-responsive genes that are either expressed at a higher level or are more active in cancer cells compared to non-cancer cells and operably linked to an open reading frame (ORF) and (b) a plurality of binding sites for one or more transcription factors (TFs), wherein said one or more TFs are expressed at higher levels or more active in cancer cells compared to non-cancer cells. In some embodiments, the recombinant polynucleotide further comprises a plurality of enhancers.

In some embodiments, said plurality of enhancers are derived from one or more cancer-responsive genes that are either expressed at a higher level or are more active in cancer cells compared to non-cancer cells. In some embodiments, said plurality of enhancers are derived from two or more cancer-responsive genes that are either expressed at a higher level or are more active in cancer cells compared to non-cancer cells, wherein one of said plurality of enhancers comprises: (i) a transcription regulatory element with at least 90% sequence homology to an enhancer consensus sequence of two or more homologous cancer-responsive genes, and/or (ii) a sequence capable of binding a transcription associated protein as determined by chromatin immunoprecipitation (ChIP) or an in vitro transfection reporter assay.

In some aspects, provided herein is a recombinant polynucleotide comprising: (a) a core promoter comprising a transcription start site (TSS), wherein the core promoter is derived from one or more cancer-responsive genes that are either expressed at a higher level or are more active in cancer cells compared to non-cancer cells and operably linked to an open reading frame (ORF) and (b) a plurality of enhancers. In some embodiments, said plurality of enhancers are derived from one or more cancer-responsive genes that are either expressed at a higher level or are more active in cancer cells compared to non-cancer cells. In some embodiments, said plurality of enhancers are derived from two or more cancer-responsive genes that are either expressed at a higher level or are more active in cancer cells compared to non-cancer cells, wherein one of said plurality of enhancers comprises: (i) a transcription regulatory element with at least 90% sequence homology to an enhancer consensus sequence of two or more homologous cancer-responsive genes, and/or (ii) a sequence capable of binding a transcription associated protein as determined by chromatin immunoprecipitation (ChIP) or an in vitro transfection reporter assay.

In some aspects, provided herein, is a recombinant polynucleotide comprising: (a) a core promoter comprising a transcription start site (TSS), wherein the core promoter is derived from one or more cancer-responsive genes that are either expressed at a higher level or are more active in cancer cells compared to non-cancer cells and operably linked to an open reading frame (ORF), (b) a plurality of binding sites for one or more transcription factors (TFs), wherein said one or more TFs are expressed at higher levels or more active in cancer cells compared to non-cancer cells, and (c) a plurality of enhancers. In some embodiments, said plurality of enhancers are derived from one or more cancer-responsive genes that are either expressed at a higher level or are more active in cancer cells compared to non-cancer cells. In some embodiments, said plurality of enhancers are derived from two or more cancer-responsive genes that are either expressed at a higher level or are more active in cancer cells compared to non-cancer cells, wherein one of said plurality of enhancers comprises: (i) a transcription regulatory element with at least 90% sequence homology to an enhancer consensus sequence of two or more homologous cancer-responsive genes, and/or (ii) a sequence capable of binding a transcription associated protein as determined by chromatin immunoprecipitation (ChIP) or an in vitro transfection reporter assay.

In some embodiments, said core promoter further comprises two or more promoter elements derived from two or more cancer-responsive genes that are either expressed at a higher level or are more active in cancer cells compared to non-cancer cells and operably linked to an open reading frame (ORF). In some embodiments, said one or more cancer-responsive genes are derived from a human subject. In some embodiments, (a) said core promoter, and (b) said plurality of binding sites for one or more TFs or said plurality of enhancers derived from one or more cancer-responsive genes are not derived from a same cancer-responsive gene. In some embodiments, said enhancer consensus sequence of two or more homologous cancer-responsive genes is a consensus sequence of an enhancer sequence derived from two or more cancer-responsive genes that has at least 90% sequence identity between two or more human cancer-responsive genes.

In some embodiments, the recombinant polynucleotide comprises (a) a plurality of binding sites for one or more transcription factors (TFs), wherein one or more TFs are expressed in higher levels or more active in cancer cells compared to non-cancer cells and (b) a plurality of enhancers derived from two or more cancer-responsive genes, wherein each of said plurality of enhancers comprising: (i) a transcription regulatory element with at least 90% sequence homology to an enhancer consensus sequence of two or more homologous cancer-responsive genes, and/or (ii) a sequence capable of binding a transcription associated protein as determined by chromatin immunoprecipitation (ChIP) or an in vitro transfection reporter assay.

In some embodiments, at least one of the plurality of enhancers comprises a CpG island. In some embodiments, at least one of the plurality of enhancers does not comprise a CpG island. In some embodiments, said higher levels of TF expression in cancer cells compared to non-cancer cells is determined by chromatin immunoprecipitation (ChIP).

In some embodiments, the recombinant polynucleotide further comprises an open reading frame (ORF), wherein said core promoter is operably linked to said ORF. In some embodiments, said plurality of binding sites for one or more TFs are 5' to said core promoter. In some embodiments, said plurality of enhancers are 5' to said core promoter and 3' to said plurality of binding sites for one or more TFs, if present. In some embodiments, said plurality of binding sites for one or more TFs comprises two or more binding sites for one TF, wherein each of the plurality of binding sites for one or more TFs is sequentially arranged at 5' to said core promoter in the recombinant polynucleotide. In some embodiments, said plurality of binding sites for one or more TFs comprises two or more binding sites for two or more TFs, wherein each of the plurality of binding sites for one or more TFs is non-sequentially arranged at 5' to said core promoter in the recombinant polynucleotide.

In some embodiments, said plurality of binding sites for one or more TFs comprise a plurality of TRPS1, MNX1, TWIST1, ETV4, FOSL2, NFIC, EN2, TFDP1, PITX2, TCF7L1, VENTX, HOXB9, DLX1, MYCN, SIX4, TP63, SOX11, E2F8, TFDP1, SURV, TOXE1, EN1, ZBTB7B, SP3, SIX2, XBP1, HIF-1A, CREB3L1, HSF-1, MTF1, NFE2L2, USF2, TP73, USF2, POU2F2, HOXA1, FOXO1, TFAP4, BACH1, E2F4, HOXC10, KLF11, FOXM1, E2F2, RUNX1, SOX4, RREB1, ETV4, HES6, ASCL1, TWIST1, FOXA3, PITX2, HOXB2, EN2, DLX4, GRHL1, FOXA, HIF, E2F6, FOSL1, NF-1, RFX6, EL4, or NFκB TF binding sites.

In some embodiments, the recombinant polynucleotide further comprises a spacer element comprising 1-10 nucleotides between each of plurality of binding sites for one or more TFs. In some embodiments, said one or more cancer-responsive genes from which said core promoter is derived comprises TCF7, MNX1, HOXC10, TP53, CEACAM5, CEP55, FAM111B, CST1, BIRC5, FOS, TWIST1, E2F2, KIF20A, or ETV4. In some embodiments, said one or more cancer-responsive genes from which said core promoter is derived comprise two or more of TCF7, MNX1, HOXC10, TP53, CEACAM5, CEP55, FAM111B, CST1, BIRC5, FOS, TWIST1, E2F2, KIF20A, or ETV4. In some embodiments, said one or more cancer-responsive genes from which said core promoter is derived comprise TCF7 and HOXC10. In some embodiments, said one or more cancer-responsive genes from which said core promoter is derived comprise TP53 and CEP55. In some embodiments, said one or more cancer-responsive genes from which said core promoter is derived comprise FAM111B and KIF20A. In some embodiments, said one or more cancer-responsive genes from which said core promoter is derived comprise BIRC5 and E2F2. In some embodiments, said one or more cancer-responsive genes from which said core promoter is derived comprise CEACAM5 and TWIST1. In some embodiments, said core promoter comprises a region from about −300 bp to +100 bp relative to said TSS.

In some embodiments, said plurality of enhancers comprises at least two enhancer sequences, wherein each of said at least two enhancer sequences comprises (i) the same enhancer sequences, (ii) different enhancer sequences, or (iii) a combination thereof. In some embodiments, each of said at least two enhancer sequences is sequentially arranged at 5' to said core promoter in the recombinant polynucleotide. In some embodiments, each of said at least two enhancer sequences is sequentially arranged at 5' to said core promoter and at 3' to said plurality of binding sites for one or more TFs, if present, in the recombinant polynucleotide. In some embodiments, each of said at least two enhancer sequences comprises (ii), wherein each of said plurality of enhancers comprising different enhancer sequences is non-sequentially arranged at 5' to said core promoter in the recombinant polynucleotide. In some embodiments, each of said at least two enhancer sequences comprises (ii), wherein each of said plurality of enhancers is non-sequentially arranged at 5' to said core promoter and at 3' to said plurality of binding sites of one or more TF binding sites, if present, in the recombinant polynucleotide. In some embodiments, each of said at least two enhancer sequences comprises (iii), wherein each of said plurality of enhancers comprising a combination of the same and different enhancer sequences is non-sequentially arranged at 5' to said core promoter in the recombinant polynucleotide. In some embodiments, each of said at least two enhancer sequences comprises (iii), wherein each of said plurality of enhancers comprising a combination of the same and different enhancer sequences is non-sequentially arranged at 5' to said core promoter and at 3' to said plurality of binding sites for one or more TFs, if present, in the recombinant polynucleotide. In some embodiments, said plurality of enhancers comprises at least two EBS, C/EBP, ARE, DRE, NFκB, GC-box, UN5CL, BOP1, RTN4RL2, ARNTL2, AGR2, LHX2, TRNP1, MU5AC, or DOK4 enhancer sequences.

In some embodiments, expression of said ORF is increased when said recombinant polynucleotide is introduced to cancer cells compared to non-cancer cells. In some embodiments, expression of said ORF is increased in a first plurality of cancer cells when said recombinant polynucleotide is introduced to said first plurality of cancer cells compared to a second plurality of cancer cells, wherein said first plurality of cancer cells and said second plurality of cancer cells are different types of cancer cells. In some embodiments, said cancer cells comprise malignant cancer cells. In some embodiments, said cancer cells comprise lung cancer cells, colorectal cancer cells, breast cancer cells, or hepatocellular carcinoma cells. In some embodiments, said cancer cells comprise cells associated with colorectal cancer, hepatocellular carcinoma, lung cancer, liver cancer, breast cancer, prostate cancer, cervix cancer, uterus cancer, pancreas cancer, kidney cancer, stomach cancer, bladder cancer, ovary cancer, brain cancer, head and neck cancer, eye cancer, mouth cancer, throat cancer, esophagus cancer, chest cancer, bone cancer, rectum or other gastrointestinal tract organ cancer, spleen cancer, skeletal muscle cancer, subcutaneous tissue cancer, testicles or other reproductive organ cancer, skin cancer, thyroid cancer, blood cancer, or lymph nodes cancer. In some embodiments, said cancer cells comprise cells associated with two or more cancers comprising colorectal cancer, hepatocellular carcinoma, lung cancer, liver cancer, breast cancer, prostate cancer, cervix cancer, uterus cancer, pancreas cancer, kidney cancer, stomach cancer, bladder cancer, ovary cancer, brain cancer, head and neck cancer, eye cancer, mouth cancer, throat cancer, esophagus cancer, chest cancer, bone cancer, rectum or other gastrointestinal tract organ cancer, spleen cancer, skeletal muscle cancer, subcutaneous tissue cancer, testicles or other reproductive organ cancer, skin cancer, thyroid cancer, blood cancer, or lymph nodes cancer.

In some embodiments, said core promoter, said plurality of binding sites for one or more transcription factors (TFs), said plurality of enhancers, or said recombinant polynucleotide comprises a sequence from Table 1A, Table 1B, or Table 1C.

In some aspects, provided herein is a recombinant polynucleotide comprising any of the sequences from Table 1A, Table 1B, or Table 1C.

In some aspects, provided herein is a recombinant polynucleotide comprising a human alpha-fetoprotein (AFP) promoter sequence comprising a plurality of HNF-1A TF binding sites, wherein each HNF-1A binding site comprises the sequence 5'-GTTAATTATTAAC-3' (SEQ ID NO: 128).

In some aspects, provided herein is a vector comprising any of the recombinant polynucleotide described herein. In some aspects, provided herein is a pharmaceutical composition comprising any of the recombinant polynucleotide described herein or any the vector described herein and a pharmaceutically acceptable excipient, carrier, or diluents. In some aspects, provided herein is a lipid nanoparticle (LNP) comprising any of the recombinant polynucleotide described herein, any of the vector described herein, or any of the pharmaceutical composition described herein. In some aspects, provided herein is a cell comprising any the recombinant polynucleotide described herein, any of the vector described herein, any of the pharmaceutical composition described herein, or any of the LNP described herein.

In some aspects, provided herein is a method of selectively expressing a reporter protein in a cancer or tumor cell, comprising contacting said tumor cell with any of the recombinant polynucleotide described herein, any of the vector described herein, any of the pharmaceutical composition described herein, or any of the LNP described herein, wherein the recombinant polynucleotide further comprises an open reading frame (ORF) encoding said reporter protein, wherein said ORF is operatively linked to said synthetic promoter.

In some aspects, provided herein is a method comprising: (a) administering to a subject any of the pharmaceutical composition described herein; or a composition any of the recombinant polynucleotide described herein, any of the vector described herein, or any of the LNP described herein; wherein the recombinant polynucleotide further comprises an open reading frame (ORF) encoding a reporter protein, wherein said ORF is operatively linked to a synthetic promoter in said recombinant polynucleotide, and (b) detecting said reporter protein, wherein said pharmaceutical composition or said composition induces expression of said reporter protein preferentially in diseased cells in said subject compared to in non-disease cells, and wherein a relative ratio of said reporter protein expressed in said diseased cells over said non-diseased cells is greater than 1.0. In some embodiments, said relative ratio of said reporter protein expressed in said diseased cells over said non-diseased cells is greater than 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, or about 15.0, 20.0, 25.0, 30.0, 35.0, 40.0, 45.0, 50.0, 55.0, 60.0, 65.0, 70.0, 75.0, 80.0, 85.0, 90.0, 95.0, or about 100.0.

In some aspects, provided herein is a method for treating a subject having or suspected of having a disease, comprising administering to said subject any of the pharmaceutical composition described herein; or a composition any of the recombinant polynucleotide described herein, any of the vector described herein, or any of the LNP described herein; wherein the recombinant polynucleotide further comprises an open reading frame (ORF) encoding a therapeutic protein, wherein said ORF is operatively linked to a synthetic promoter in said recombinant polynucleotide, wherein said pharmaceutical composition or said composition induces expression of said therapeutic protein preferentially in diseased cells in said subject compared to in non-disease cells, and wherein a relative ratio of said therapeutic protein expressed in said diseased cells over said non-diseased cells is greater than 1.0.

In some embodiments, said diseased cells comprise a cancer or tumor cell. In some embodiments, said cancer or tumor cell is associated with colorectal cancer (CRC), hepatocellular carcinoma, lung cancer, liver cancer, breast cancer, prostate cancer, cervix cancer, uterus cancer, pancreas cancer, kidney cancer, stomach cancer, bladder cancer, ovary cancer, brain cancer, head and neck cancer, eye cancer, mouth cancer, throat cancer, esophagus cancer, chest cancer, bone cancer, rectum or other gastrointestinal tract organ cancer, spleen cancer, skeletal muscle cancer, subcutaneous tissue cancer, testicles or other reproductive organ cancer, skin cancer, thyroid cancer, blood cancer, or lymph nodes cancer.

In some aspects, provided herein is a method comprising: (a) administering to a subject any of the pharmaceutical composition described herein; or a composition any of the recombinant polynucleotide described herein, any of the vector described herein, or any of the LNP described herein; wherein the recombinant polynucleotide further comprises an open reading frame (ORF) encoding a reporter protein, wherein said ORF is operatively linked to a synthetic promoter in said recombinant polynucleotide, and (b) localizing a tumor or an absence thereof in a body of said subject via expression of said reporter protein using an imaging technique performed on said body of said subject.

In some aspects, provided herein is a method comprising: (a) introducing to a subject suspected of having a cancer via intravenous administration any of the pharmaceutical composition described herein; or a composition any of the recombinant polynucleotide described herein, any of the vector described herein, or any of the LNP described herein; wherein said recombinant polynucleotide further comprises an open reading frame (ORF) encoding a reporter protein, wherein said ORF is operatively linked to a synthetic promoter in said recombinant polynucleotide, and (b) detecting said reporter protein from said subject.

In some aspects, provided herein is a method comprising: (a) introducing to a subject suspected of having a cancer via intravenous administration a plurality of recombinant polynucleotides, wherein: said plurality of recombinant polynucleotides comprises a plurality of different promoters of genes overexpressed in a tumor cell versus a normal tissue or functional fragments thereof operably linked to genes encoding reporter proteins, wherein said plurality of different promoters of genes overexpressed in said tumor cell versus said normal tissue drive expression of said corresponding reporter proteins in a cell affected by said cancer, wherein said DNA molecules are selected from the group consisting of nanoplasmids and linear double-stranded DNA molecules; and (b) detecting said reporter proteins from said subject.

TABLE 1A

| SEQ ID NO: | EA RLI. ID | Name | Regulatory element sequence (nucleotide) |
|---|---|---|---|
| 1 | PL1 009 | 1-TRPS1_ v22-coreBIR C5-FLUC | ggcctaactggccggtaccacatcggctatgctgctgctatgcgagcgtcagtattt tatctttgatcagctattttatctttagtatcgtattttatctttctcatcgtattt tatctttatccgattattttatctttcagcagttattttatctttggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 2 | PL1 010 | 2-TRPS1_ v9-coreBIR C5-FLUC | ggcctaactggccggtaccagctcatgcctatccgattagcttatcttttgaccaga gctagcttatctttctaactcgcatagcttatcttttgcaagctactagcttatctt tcgatgctcattagcttatctttagacgtactctagcttatctttggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 3 | PL1 011 | 3-MNX1_v 18-coreBIR C5-FLUC | ggcctaactggccggtaccatcactgctgaggtacagatgcacgatgtagctgagcg acagtatagtgcacagtgagtcattatgatacgtgtcattatcaccattgtcattat tagacgtgtcattatctgctatgtcattatgctacaggtcattatggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 4 | PL1 012 | 4-TWIST1_ v3-coreBIR C5-FLUC | ggcctaactggccggtacccagcagtcattatacgtcgcctaaatcgagatgctgta ctgatctatattccagatgtttcaattccagatgtttacattccagatgttttac attccagatgtttctcattccagatgttttgaattccagatgtttggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 5 | PL1 013 | 5-TWIST1_ v18-coreBIR C5-FLUC | ggcctaactggccggtaccctgagcgacagtatagtgcacagtgacattacagatgt ttacgacgaattacagatgtttctcatcgattacagatgtttcagctcaattacaga tgtttgctgctgattacagatgtttaccagagattacagatgtttggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 6 | PL1 014 | 6-HOXA1_ v8-coreBIR C5-FLUC | ggcctaactggccggtacccgatgtagctgagcgacagtatagtgcacagtgactgc agcagtcattatacgtcgcctaaatcgagatgctgtactgatctataaggatcggta atgacgtaatgacgtaatgacgtaatgacgtaatgacggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 7 | PL1 015 | 7-HOXC10_ v24-coreBIR C5-FLUC | ggcctaactggccggtaccagctgagcgacagtatagtgcacagtgactgcagcagt cattatacgtcgcctaaatcgagatgctgtactgatctataagtcgtaaactgtcgt aaactgtcgtaaactgtcgtaaactgtcgtaaactggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 8 | PL1 016 | 8-HOXC10_ v14-coreBIR C5-FLUC | ggcctaactggccggtacctgtagctgagcgacagtatagtgcacagtgactgcagc agtcattgtcgtaaattgagtatcgtcgtaaattgacgaacgtcgtaaattagcgac agtcgtaaattagtacctgtcgtaaattactctgcgtcgtaaattggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 9 | PL1 017 | 9-GATA1_ v1-coreBIR C5-FLUC | ggcctaactggccggtaccatccgatgtgcctgacgaactcatttctaatctatcga tgtagctttctaatctatgcagtcattattctaatctattcgcaatctattctaatc tatcttctaactcttctaatctattgctacagctttctaatctatggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 10 | PL1 018 | 10-NFIC_v1 5-coreBIR C5-FLUC | ggcctaactggccggtaccgcacagtgactgcagcagtcattatacgtcgcctaaat cgagatgctgtactgatctatttcttggcagatgattcttggcagatcgttcttggc agagcattcttggcagaggtttcttggcagactcttcttggcagaggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |

TABLE 1A-continued

Sequences of engineered promoters according to the disclosure

| SEQ ID NO: | EA RLI. ID | Name | Regulatory element sequence (nucleotide) |
|---|---|---|---|
| 11 | PL1 019 | 11-EN2_v7-coreBIR C5-FLUC | ggcctaactggccggtaccgtgcaccattagtacctgatcagcgatgctcatctcga cctgatcggtacaacttctcacggaggcttctaactcgccgcaattataacgcaatt attccgcaattactacgcaattacctcgcaattaactcgcaattaggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 12 | PL1 020 | 12-CREB3L 1_v6-coreBIR C5-FLUC | ggcctaactggccggtaccacatcggctatgctgctgctaatgccacgtcaccacat cgacatgccacgtcaccatcatgccatgccacgtcaccactgcaagatgccacgtca ccacagtataatgccacgtcaccaagttactatgccacgtcaccaggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 13 | PL1 021 | 13-RREB1_ v17-coreBIR C5-FLUC | ggcctaactggccggtaccccccaaatcacccccccccaccgtaaagtccccaaat caccccccccccaaggtaagaccccaaatcacccccccccccgtcgcctaacccca aatcaccccccccccctactctgctcccccaaatcaccccccccccggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 14 | PL1 022 | 14-SIX4_v9 coreBIR C5-FLUC | ggcctaactggccggtaccgaccgtaaagtggtgtgcaccattgaaacttgagctta caccatcgaaacttgagcgtatcgcatcgaaacttgagcggtacagatggaaacttg agcaccattagtagaaacttgagcagcgacagtagaaacttgagcggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 15 | PL1 023 | 15-SURV_v 11-coreBIR C5-FLUC | ggcctaactggccggtacctgcacagtgactgcagcagtcgggcgtgcgctcccgac tagcccagggcgtgcgctcccgactagccccgggcgtgcgctcccgactagccctgg gcgtgcgctcccgactagccccgggcgtgcgctcccgactagccggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 16 | PL1 024 | 16-TCF7_v3 coreBIR C5-FLUC | ggcctaactggccggtaccaggatcgactagaagtcgcgagattagacgacgatacgt actactctgctcctagacgtatcctttgatgtaaatcctttgatgtcaatcctttga tgttaatcctttgatgttagtcctttgatgtctgtcctttgatgtggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 17 | PL1 025 | 17-TCF7L1_ v19-coreBIR C5-FLUC | ggcctaactggccggtacctgagcgacagtatagtgcacagtgactgcagcagtcat tatacgtcgcctaaaagacatcaaaggtccagacatcaaaggtacagacatcaaagg ggaagacatcaaagggacagacatcaaaggtgcagacatcaaaggggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 18 | PL1 026 | 18-TCF7L1_ v5-coreBIR C5-FLUC | ggcctaactggccggtaccatgcacgatgtagctgagaaacatcaaaggacgcaacg ccaaacatcaaaggagcctacacgaaacatcaaagggacgctgctaaaacatcaaag gctacacgaccaaacatcaaagggcctacaccaaacatcaaagggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 19 | PL1 030 | CREB3L 1_v14 | GAATTCTAGTGCACAGTGACTGCAGCAATGCCACGTCAACATCATGCCATGCCACGT CAACACCTACACATGCCACGTCAACAACCAGAGATGCCACGTCAACACTAGCATATG CCACGTCAACATAAGGATATGCCACGTCAACAGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 20 | PL1 031 | EN2_v7 | GAATTCGTGCACCATTAGTACCTGATCAGCGATGCTCATCTCGACCTGATCGGTACA ACTTCTCACGGAGGCTTCTAACTCGCCGCAATTATAACGCAATTATTCCGCAATTAC TACGCAATTACCTCGCAATTAACTCGCAATTAGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 21 | PL1 032 | ETV4_v 14 | ggcctaacgaattcgacgctgctacagctcagcctacacgaccgtaaagtggtgtgc acaccggaaatgagtatagaccggaaatggccttacaccggaaatgcagctcaaccg gaaatgactgcagaccggaaatgcgctgctaccggaaatgggtacctgcgctcccga |

TABLE 1A-continued

Sequences of engineered promoters according to the disclosure

| SEQ ID NO: | EA RLI. ID | Name | Regulatory element sequence (nucleotide) |
|---|---|---|---|
| 22 | PL1 033 | ETV4_v 2 | catgccccgcggcgcgccattaaccgccagatttgagtcgcgggacccgttggcaga ggtgggctagcctcgaggatatcaagatctggcctcggcggccaagcttggcaatcc ggtactgttggtaaagccaccatggtggcc ggcctaactggccgaattctgagcgacagtatagtgcacagtgactgcagcagtcat tatacgtaccggaagtgtgtgcctaccggaagtgctatgcgaccggaagtgtagacg aaccggaagtgcagattaaccggaagtggctgctaaccggaagtgggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 23 | PL1 034 | MYCN v22 | GAATTCGTGCACCATTAGTACCTGATCAGCGATGCTCATCTCGACCTGATCGGTACA ACTTCTCACGGAGGCTTCTAACTCGCCGCAATTATAACGCAATTATTCCGCAATTAC TACGCAATTACCTCGCAATTAACTCGCAATTAGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 24 | PL1 035 | PAX8_v 18 | GAATTCGTCATTATACGTCGCGTCATGCATGACTGCCTGAGCGGTCATGCATGACTG CTACTCAAGTCATGCATGACTGCGACCAGAGTCATGCATGACTGCCGCCTAAGTCAT GCATGACTGCCTCTGCTGTCATGCATGACTGCGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 25 | PL1 036 | PITX2_v 22 | GAATTCAAGTCGCAGATTAGACGACGATACGTACTACTCTGCTCCTAGACGTACTCA AGTATATTAATCCAGTGACCATTAATCCACTCAGTGCTTAATCCAATAACTGTTAATC CAGTATCGCTTAATCCACTACAGCTTAATCCAGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 26 | PL1 037 | SIX2_v7 | ggcctaactggccgaattccagatgcacgatgtagctgagcgacagtaaactgtaac ctgatacagcaactgtaacctgataccctaactgtaacctgatacgataactgtaac ctgatacaaaaactgtaacctgatacggcaactgtaacctgatacggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 27 | PL1 038 | SOX11_ v2 | ggcctaactggccgaattcgactgcagcagtcattatacgtcgcctaaatcggagaa caaaggatggtgtggagaacaaaggataaactgagagaacaaaggaaggatcggagaa caaaggaactgctggagaacaaaggatatagtggagaacaaaggaggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 28 | PL1 039 | TCF7_v2 | ggcctaactggccgaattcctgagcgacagtatagtgcacagtgactgcagcagtca ttcctttgatgtacgcaactcctttgatgtctatgcgtcctttgatgttaaggattc ctttgatgtaggtacatcctttgatgtccgtaaatcctttgatgtgtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 29 | PL1 040 | TCF7_v3 | GAATTCAGGATCGACTAGAAGTCGCAGATTAGACGACGATACGTACTACTCTGCTCC TAGACGTATCCTTTGATGTAAATCCTTTGATGTCAATCCTTTGATGTTAATCCTTTG ATGTTAGTCCTTTGATGTCTGTCCTTTGATGTGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 30 | PL1 041 | TFDP1_ v6 | ggcctaactggccgaattccaagactgcaagctacgtgtgaccagagccgataactg agggcgggaacgcgcaacggggcgggaacgatgctgtgggggggaacgacagctcgg gcgggaacgctctgctgggggggaacggctcctagggcgggaacgggtacctgcgct cccgacatgccccgcggcgcgccattaaccgccagatttgagtcgcgggacccgttg gcagaggtgggctagcctcgaggatatcaagatctggcctcggcggccaagcttggc aatccggtactgttggtaaagccacc |
| 31 | PL1 042 | E2F7_v1 1 | GAATTCAGGATCGACTAGAAGTCGCAGATTAGACGACGATACGTACTACTCTGCTCC TAGACGTATCCTTTGATGTAAATCCTTTGATGTCAATCCTTTGATGTTAATCCTTTG ATGTTAGTCCTTTGATGTCTGTCCTTTGATGTGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |

TABLE 1A-continued

Sequences of engineered promoters according to the disclosure

| SEQ ID NO: | EARLI. ID | Name | Regulatory element sequence (nucleotide) |
|---|---|---|---|
| 32 | PL1 043 | E2F7_v1 3 | GAATTCAGGTAAGTTTCCCGCCAAAATGTGACCAGAGTTTCCCGCCAAAATGACGAA CTCGTTTCCCGCCAAAATGTAGCTGAGTTTCCCGCCAAAACATAGTTACTGTTTCC CGCCAAAACCTAAATCGAGTTTCCCGCCAAAAGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 33 | PL1 044 | FOXA3_ v2 | GAATTCTGCTATGCGAGCGTCAGCTCATGCCTATCCGATGTGCCTATGTAAACATAA GAGCCGATGTAAACATATAAGGATATGTAAACATATAGACGAATGTAAACATAGAGG TACATGTAAACATAACACGACATGTAAACATAGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 34 | PL1 045 | GLIS3_v 7 | GAATTCTACAGCTCAGCCTACACGACCGTAAAGTGGTGTGCACCATTGACCCCCCAC AAAGCAGGACCCCCCACAAAGCGAGACCCCCCACAAAGGACGACCCCCCACAAAGCC TGACCCCCCACAAAGAGTGACCCCCCACAAAGGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 35 | PL1 046 | GLIS3_v 9 | GAATTCAAGGTAGACCCCCCACTAAGCTCAAGTATAGACCCCCCACTAAGATAGTGC ACAGACCCCCCACTAAGTATCCGATGTGACCCCCCACTAAGCGACAACGCCTGACCCC CCACTAAGTCCTAGACGTGACCCCCCACTAAGGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 36 | PL1 047 | HOXC9_ v21 | GAATTCAACTGAGTATCGCATCGCTCAAGATCAGTGGTCATAAATTAGCAGTCATTG TCATAAATTCCTGATCGGTGTCATAAATTGCCTAAATCGGTCATAAATTCAGCTCAT GCGTCATAAATTACGCTGCTACGTCATAAATTGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 37 | PL1 048 | NR2F6_ v11 | GAATTCAGTATAGTGCACAGTGACTGCAGCAGTCATTATACGTCGCCGGGGTCAAAG GTCACCAGGGGTCAAAGGTCATCTGGGGTCAAAGGTCATTAGGGGTCAAAGGTCATA GGGGGTCAAAGGTCACGAGGGGTCAAAGGTCAGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 38 | PL1 049 | NR2F6_ v18 | AATTCACATCGGCTATGCTGCTGCTACAGGTCAAAGGTCATTAGACGCAGGTCAAAG GTCACACAGTGCAGGTCAAAGGTCAAGGTACACAGGTCAAAGGTCACTGACGACAGG TCAAAGGTCACTCATCTCAGGTCAAAGGTCAGGTACCTGCGCTCCCGACATGCCCCG CGGCGCGCCATTAACCGCCAGATTTGAGTCGCGGGACCCGTTGGCAGAGGTGGGCTA GCCTCGAGGATATCAAGATCTGGCCTCGGCGGCCAAGCTTGGCAATCCGGTACTGTT GGTAAAGCCACC |
| 39 | PL1 050 | E2F3_v1 1 | GAATTCTGCACCATTAGTACCTGATCAGCGATGCTATTTTGGCGCCCAAATCATATT TTGGCGCCCAAATGACATTTTGGCGCCCAAATACAATTTTGGCGCCCAAATACGATT TTGGCGCCCAAATAGCATTTTGGCGCCCAAATGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 40 | PL1 051 | E2F4_v2 | GAATTCGGTACAACTTCTCACGGAGGCTTTTGGCGCCATTTCGACGATTTTTGGCGC CATTTACTCAAGTTTTGGCGCCATTTTAGTGCATTTTGGCGCCATTTCGCAATCTTT TGGCGCCATTTGGAGGCTTTTTGGCGCCATTTGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 41 | PL1 052 | EN2_v6 | GAATTCACGATACGTACTACTCTGCTCCTAGACGTACTCAAGTATAAGGTAAGACAT AGTTACCGCAATTATAAGACACGCAATTACTAGAAGCGCAATTAACGTCGCCGCAAT TAGACTGCACGCAATTAGAATCTCCGCAATTAGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 42 | PL1 053 | FOXK1_ v9 | GAATTCAAGTATAATGTAAACACGGCAGCATCGTCCAATGTAAACACGGCAAGACAT AGTAATGTAAACACGGCTCTCACGGAGAATGTAAACACGGCCTAGCATCGTAATGTA AACACGGCGATGCTCATCAATGTAAACACGGCGGTACCTGCGCTCCCGACATGCCCC GCGGCGCGCCATTAACCGCCAGATTTGAGTCGCGGGACCCGTTGGCAGAGGTGGGCT |

TABLE 1A-continued

Sequences of engineered promoters according to the disclosure

| SEQ ID NO: | EA RLI. ID | Name | Regulatory element sequence (nucleotide) |
|---|---|---|---|
| | | | AGCCTCGAGGATATCAAGATCTGGCCTCGGCGGCCAAGCTTGGCAATCCGGTACTGT TGGTAAAGCCACC |
| 43 | PL1 054 | GRHL1_ v5 | GAATTCAAGTCGCAGATTAGACGAAAAACCGGTTATGACGTACTCAAAAACCGGTTA TGAGATGCTGTAAAACCGGTTATTCCGACGCAAAAAACCGGTTATACGAACTCATAA AACCGGTTATAGCTCAGCCTAAAACCGGTTATGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 44 | PL1 055 | HOXB9_ v6 | GAATTCTGACTGCAGCAGTCATTATACGTCGCCTAAATCGAGATGCTGTACGTCGTA AATTCACGACCGTCGTAAATTCGATAACGTCGTAAATTCTAGCATGTCGTAAATTTG CAGCAGTCGTAAATTAGATTAGGTCGTAAATTGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 45 | PL1 056 | MNX1_v 10 | GAATTCATTAGACGACGATACGTACTACTCTGCTCCTAGACGTACTCAAGTATAAGG TAAGACGCAATTATTGCACAGGCAATTATTCAGCCTGCAATTATCTACAGCGCAATT ATCTGATCAGCAATTATGATACGTGCAATTATGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 46 | PL1 057 | MYC_v2 2 | GAATTCACTCTGCTCCTAGACGTACTCAAGTATAAGGTAGGACACGTGCCCGATGCA CGGACACGTGCCCCCGTAAAGGACACGTGCCCTAAATCGGGACACGTGCCCTAGACG TGGACACGTGCCCGACTAGAGGACACGTGCCCGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 47 | PL1 058 | OTX1_v 14 | GAATTCCACAGTGACTGCAGCAGTCATTATACGTCGCCTAAATCGAGATGCTGTACT GATCTATTAAGCCGCGTACTCTTAAGCCGGTCATTATTAAGCCGCTATAAGTTAAGC CGCAACGCCTTAAGCCGACGACCGTTAAGCCGGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 48 | PL1 059 | PITX2_v 19 | GAATTCTCGGCTATGCTGCTGCTATGCGAGCGTCAGCTCATGCCTATCCGATGTGCC TGACGAACTCATCGACGCTGCTACAGCTAATCCTATGCTAATCCTAACCTAATCCTA CCCTAATCCTAGCCTAATCCTTGCCTAATCCTGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 49 | PL1 060 | RUNX1_ v22 | GAATTCTGTACTGATCTATAAGGATCGACTAGAAGTCGCAGATTAGTATGTGGTTTA GTACCTGTATGTGGTTTTCGCAATGTATGTGGTTTATGCTGCGTATGTGGTTTAGCA GTCGTATGTGGTTTGAGCGTCGTATGTGGTTTGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 50 | PL1 061 | RUNX1_ v23 | GAATTCCTGCAGCAGTCATTATACGTCGCCTAAATCGAGATGCTGTACTGATCTATA AGGATCGAGTATGTGGTTTATCGTATGTGGTTTGTAGTATGTGGTTTCTGGTATGTG GTTTTGTGTATGTGGTTTCCAGTATGTGGTTTGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 51 | PL1 062 | SHOX2_ v5 | GAATTCCACGATGTAGCTGAGCGACAGTATAGTGCACAGTGACTGCAGCCAATTAAC TGACGAACTCCAATTAAATCAGTGATCCCAATTAATGCAAGCTACCCAATTAATATG CTGCTGCCAATTAACATCGGCTATCCAATTAAGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 52 | PL1 063 | SHOX2_ v21 | GAATTCTTAGTACCTGATCAGCGATGCTCATCTCGACCTGATCGGTACTCAATTAAT GTACTGATCTCAATTAAGTCGCCTAAATCAATTAACGTACTACTCTCAATTAAGATC GGTACATCAATTAAAAGTCGCAGATCAATTAAGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |

TABLE 1A-continued

Sequences of engineered promoters according to the disclosure

| SEQ ID NO: | EARLI. ID | Name | Regulatory element sequence (nucleotide) |
|---|---|---|---|
| 53 | PL1 064 | SIX4_v2 3 | GAATTCCTACGTGTGACCAGAGCCGATAACTGAGTATCGCATCGCTCAAGATCAGTG ATCACTGCGAAATTTGAGCCCTGAAATTTGAGCCGAGAAATTTGAGCGCTGAAATTT GAGCCACGAAATTTGAGCTTAGAAATTTGAGCGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 54 | PL1 065 | TCF7_v1 0 | GAATTCGACCTGATCGGTACAACTTCTCACGGAGGCTTCTAACTCTCCTTTGATATA ACTCGCTCCTTTGATATAGCAGTCTCCTTTGATATCTCATCTTCCTTTGATATCTGT ACTTCCTTTGATATTGCTATGTCCTTTGATATGGTACCTGCGCTCCCGACATGCCCC GCGGCGCGCCATTAACCGCCAGATTTGAGTCGCGGGACCCGTTGGCAGAGGTGGGCT AGCCTCGAGGATATCAAGATCTGGCCTCGGCGGCCAAGCTTGGCAATCCGGTACTGT TGGTAAAGCCACC |
| 55 | PL1 068 | PL-3XFOSL 1-coreAGR 2_2 | ggcctaactggccggtaccactagtggtgactcatgggtgactcatgggtgactcat ggtgatcatgctagcctcgaggatatcaagatcggtaccacctcttaacaatacgtt tcacaaatagttaaaaacatgcatactgaaaagcatactttttgcaatgttattttta aaaacaaggaactctttaacccagggaagataatcacttggggaaaggaaggttcgt ttctgagttagcaacaagtaaatgcagcactagtgggtgggattgaggtgtgccctg gtgcataaatagagactcagctgtgctggcacactcagaagcttggaccgcatccta gccgccgactcacacaaggcaggtgggtgaggaaatccaggtaaggctcctgacagc agctttagaagggtacttgctggagtgaattcgggcctctgattaccggtgctagcc tcgaggatatcaagatctggcctcggcggccaagcttggcaatccggtactgttggt aaagccacc |
| 56 | PL1 069 | PL-revFOSL 1-coreAGR 2_2 | ggcctaactggccggtaccgatcttgatatcctcgaggctagcatgatcaccatgag tcacccatgagtcacccatgagtcacccatgagtcacccatgagtcacccatgagtc acccatgagtcacccatgagtcacccatgagtcaccactagtggtgactcatccttaa caatacgtttcacaaatagttaaaaacatgcatactgaaaagcatacttttgcaatg ttattttaaaaacaaggaactctttaacccagggaagataatcacttggggaaagg aaggttcgtttctgagttagcaacaagtaaatgcagcactagtgggtgggattgagg tgtgccctggtgcataaatagagactcagctgtgctggcacactcagaagcttggac cgcatcctagccgccgactcacacaaggcaggtgggtgaggaaatccaggtaaggct cctgacagcagctttagaagggtacttgctggagtgaattcgggcctctgattaccg gtgctagcctcgaggatatcaagatctggcctcggcggccaagcttggcaatccggt actgttggtaaagccacc |
| 57 | PL1 070 | PL-revFOSL 1-coreCST 1 | ggcctaactggccggtaccgattcttgatatcctcgaggctagcatgatcaccatga gtcacccatgagtcacccatgagtcacccatgagtcacccatgagtcacccatgagt cacccatgagtcacccatgagtcacccatgagtcaccactagtggtaccagtggtga tatcctcgaggctagcatgatcaccatgagtcacccatgagtcacccatgagtcacc catgagtcacccatgagtcacccatgagtcacccatgagtcacccatgagtcaccca tgagtcaccactagtggtaccagtggtgggggagtgaaaagagagatggagaaagag gggatgggcagaaagaggaggaggagtcaggggcagggcatggaggtgggtgggggct gggctgccaaagcaggatataatgcacacctgcctgctggtctgggctccctgcctcg ggctctcaccctcctctcctgcagctccagctttgtgcttctaccggtgctagcctc gaggatatcaagatctggcctcggcggccaagcttggcaatccggtactgttggtaa agccacc |
| 58 | PL1 071 | PL-ETV4-coreCST | ggcctaactggccggtaccactagtgacgtcaccggaagtaagaaccggaagtatcg accggaagtagacaccggaagtactaaccggaagtaactaccggaagtatgcaccgg aagtagacgtctacgtaagtggtgggggagtgaaaagagagatggagaaagagggga tgggcagaaagaggaggaggagtcaggggcagggcatggaggtgggtgggggctgggc tgccaaagcaggatataatgcacacctgcctgctggtctgggctccctgcctcgggct ctcaccctcctctcctgcagctccagctttgtgctctaccggtgctagcctcgagga tatcaagatctggcctcggcggccaagcttggcaatccggtactgttggtaaagcca cc |
| 59 | PL1 072 | PL-ETV4-coreKIF | ggcctaactggccggtaccactagtgacgtcaccggaagtaagaaccggaagtatcg accggaagtagacaccggaagtactaaccggaagtaactaccggaagtatgcaccgg aagtagacgtctacgtaggcccgcccccctttccttacgcggattggtagctgcaggc ttccctatctgattggccgaacgaacgcagcgcgtaatttaaaatattgtatctgta acaaagctgcacctcgtgggcggagttgtgctctgcggctgcgaaagtccagcttcg gcgactaggtgtgagtaagccagtatcccaggaggagcaagtggcacgtcttcgggt gagtgtgcggctgtgctggagcccgggttaccagctctttaccggtgctagcctcga ggatatcaagatctggcctcggcggccaagcttggcaatccggtactgttggtaaag ccacc |
| 60 | PL1 073 | PL-ETV4-coreAGR 2 | ggcctaactggccggtacactagtgacgtcaccggaagtaagaaccggaagtatcga ccggaagtagacaccggaagtactaaccggaagtaactaccggaagtatgcaccgga agtagacgtctacgtacatactgaaaagcatactttttgcaatgttattttttaaaaac aaggaactctttaacccagggaagataatcacttggggaaaggaaggttcgtttctg agttagcaacaagtaaatgcagcactagtgggtgggattgaggtgtgccctggtgca taaatagagactcagctgtgctggcacactcagaagcttggaccgcatcctagccgc |

TABLE 1A-continued

Sequences of engineered promoters according to the disclosure

| SEQ ID NO: | EARLI. ID | Name | Regulatory element sequence (nucleotide) |
|---|---|---|---|
| | | | cgactcacacaaggcaggtgggtgaggaaatccaggtaaggctcctgacagcagctt tagaagggtacttgctggagtgaattcgggcctctgattactagcctcgaggatatc aagatctggcctcggcggccaagcttggcaatccggtactgttggtaaagccacc |
| 61 | PL1 074 | PL-ETV4-coreCEACAM | ggcctaactggccggtaccactagtgacgtcaccggaagtaagaaccggaagtatcg accggaagtagacaccggaagtactaaccggaagtaactaccggaagtatgcaccgg aagtagacgtctacgtaacccacgtgatgctgagaagtactcctgccctaggaagag actcagggcagagggaggaaggacagcagaccagacagtcacagcagccttgacaaa acgttcctggaactaccggtgctagcctcgaggatatcaagatctggcctcggcggc caagcttggcaatccggtactgttggtaaagccacc |
| 62 | PL1 075 | PL-ETV4-coreFAM111B | GGCCTAACTGGCCGGTACCACTAGTGACGTCACCGGAAGTAAGAACCGGAAGTATCG ACCGGAAGTAGACACCGGAAGTACTAACCGGAAGTAACTACCGGAAGTATGCACCGG AAGTAGACGTCTACGTACGGGAAAAGTTCAGCTGAGAGATATAAAAGAGCAGTCTTT CCAGCACCTGCAAATCCAGAGCGGCGGGCACTGACGGGCACTTGCACCGTGTGGACA GACTCTCCGGTTCTGTGAGTGGTTTTTCTTTTCCCGGGTCGGACCTGGAGTTCTTAG GGGGATGGCTGAACCGGTGCTAGCCTCGAGGATATCAAGATCTGGCCTCGGCGGCCA AGCTTGGCAATCCGGTACTGTTGGTAAAGCCACC |
| 63 | PL1 076 | PL-ETV4-Twist_v18-coreCST | ggcctaactggccggtaccactagtgacgtcaccggaagtaagaaccggaagtatcg accggaagtagacaccggaagtactaaccggaagtaactaccggaagtatgcaccgg aagtagacgtctacgtactgagcgacagtatagtgcacagtgacattacagatgttt acgacgaattacagatgtttctcatcgattacagatgtttcagctcaattacagatg tttgctgctgattacagatgtttaccagagattacagatgtttttacgtaagtggtgg gggagtgaaaagagagatggagaaagaggggatgggcagaaagaggaggaggagtca ggggcagggcatggaggtgggtggggctgggctgccaaagcaggataaatgcacacc tgcctgctggtctgggctccctgcctcgggctctcaccctcctctcctgcagctcca gctttgtgctctaccggtgctagcctcgaggatatcaagatctggcctcggcggcca agcttggcaatccggtactgttggtaaagccacc |
| 64 | PL1 077 | PL-ETV4-Twist_v18-coreKIF | ACTAGTGACGTCACCGGAAGTAAGAACCGGAAGTATCGACCGGAAGTAGACACCGGA AGTACTAACCGGAAGTAACTACCGGAAGTATGCACCGGAAGTAGACGTCTACGTACT GAGCGACAGTATAGTGCACAGTGACATTACAGATGTTTACGACGAATTACAGATGTT TCTCATCGATTACAGATGTTTCAGCTCAATTACAGATGTTTGCTGCTGATTACAGAT GTTTACCAGAGATTACAGATGTTTTACGTAGGCCCGCCCCCTTTCCTTACGCGGATT GGTAGCTGCAGGCTTCCCTATCTGATTGGCCGAACGAACGCAGCGCGTAATTTAAAA TATTGTATCTGTAACAAAGCTGCACCTCGTGGGCGGAGTTGTGCTCTGCGGCTGCGA AAGTCCAGCTTCGGCGACTAGGTGTGAGTAAGCCAGTATCCCAGGAGGAGCAAGTGG CACGTCTTCGGGTGAGTGTGCGGCTGTGCTGGAGCCCGGGTTACCAGCTCTTtaccg gtgctagcctcgaggatatcaagatctggcctcggcggccaagcttggcaatccggt actgttggtaaagccacc |
| 65 | PL1 078 | PL-ETV4-Twist_v18-coreAGR2 | ggcctaactggccggtacactagtgacgtcaccggaagtaagaaccggaagtatcga ccggaagtagacaccggaagtactaaccggaagtaactaccggaagtatgcaccgga agtagacgtctacgtactgagcgacagtatagtgcacagtgacattacagatgttta cgacgaattacagatgtttctcatcgattacagatgtttcagctcaattacagatgt ttgctgctgattacagatgtttaccagagattacagatgtttttacgtacatactgaa aagcatacttttgcaatgttatttttaaaaacaaggaactctttaacccagggaaga taatcacttggggaaaggaaggttcgtttctgagttagcaacaagtaaatgcagcac tagtgggtgggattgaggtgtgccctggtgcataaatagagactcagctgtgctggc acactcagaagcttggaccgcatcctagccgccgactcacacaaggcaggtgggtga ggaaatccaggtaaggctcctgacagcagctttagaagggtacttgctggagtgaat tcgggcctctgattactagcctcgaggatatcaagatctggcctcggcggccaagct tggcaatccggtactgttggtaaagccacc |
| 66 | PL1 079 | PL-ETV4-Twist_v18-coreFAM111B | ggcctaactggccggtaccactagtgacgtcaccggaagtaagaaccggaagtatcg accggaagtagacaccggaagtactaaccggaagtaactaccggaagtatgcaccgg aagtagacgtctacgtactgagcgacagtatagtgcacagtgacattacagatgttt acgacgaattacagatgtttctcatcgattacagatgtttcagctcaattacagatg tttgctgctgattacagatgtttaccagagattacagatgtttttacgtacgggaaa gttcagctgagagatataaaagagcagtctttccagcacctgcaaatccagagcggc gggcactgacgggcacttgcaccgtgtggacagactctccggttctgtgagtggttt ttcttttcccgggtcggacctggagttcttaggggggatggctgaaccggtgctagcc tcgaggatatcaagatctggcctcggcggccaagcttggcaatccggtactgttggt aaagccacc |
| 67 | PL1 080 | PL-ETV4-Twist_v18-coreCEACAM | ggcctaactggccggtaccactagtgacgtcaccggaagtaagaaccggaagtatcg accggaagtagacaccggaagtactaaccggaagtaactaccggaagtatgcaccgg aagtagacgtctacgtactgagcgacagtatagtgcacagtgacattacagatgttt acgacgaattacagatgtttctcatcgattacagatgtttcagctcaattacagatg tttgctgctgattacagatgtttaccagagattacagatgtttttacgtaacccacgt gatgctgagaagtactcctgccctaggaagagactcagggcagagggaggaaggaca |

TABLE 1A-continued

Sequences of engineered promoters according to the disclosure

| SEQ ID NO: | EA RLI. ID | Name | Regulatory element sequence (nucleotide) |
|---|---|---|---|
| | | | gcagaccagacagtcacagcagccttgacaaaacgttcctggaactaccggtgctag cctcgaggatatcaagatctggcctcggcggccaagcttggcaatccggtactgttg gtaaagccacc |
| 68 | PL1 081 | PL-Twist_v1 8-coreCST | ggcctaactggccggtaccactagtgacgtctacgtactgagcgacagtatagtgca cagtgacattacagatgtttacgacgaattacagatgtttctcatcgattacagatg tttcagctcaattacagatgtttgctgctgattacagatgtttaccagagattacag atgttttacgtaagtggtgggggagtgaaaagagagatggagaaagagggatgggc agaaagaggaggaggagtcaggggcagggcatggaggtgggtggggctgggctgcca aagcaggatataatgcacacctgcctgctggtctgggctccctgcctcgggctctcac cctcctctcctgcagctccagctttgtgctctaccggtgctagcctcgaggatatca agatctggcctcggcggccaagcttggcaatccggtactgttggtaaagccacc |
| 69 | PL1 082 | PL-Twist_v1 8-coreKIF | ggcctaactggccggtaccactagtgacgtctacgtactgagcgacagtatagtgca cagtgacattacagatgtttacgacgaattacagatgtttctcatcgattacagatg tttcagctcaattacagatgtttgctgctgattacagatgtttaccagagattacag atgtttttacgtaggcccgcccccttttccttacgcggattggtagctgcaggcttccc tatctgattggccgaacgaacgcagcgcgtaatttaaaatattgtatctgtaacaaa gctgcacctcgtgggcggagttgtgctctgcggctgcgaaagtccagcttcggcgac taggtgtgagtaagccagtatcccaggaggagcaagtggcacgtcttcgggtgagtg tgcggctgtgctggagcccgggttaccagctctttaccggtgctagcctcgaggata tcaagatctggcctcggcggccaagcttggcaatccggtactgttggtaaagccacc |
| 70 | PL1 083 | PL-Twist_v1 8-coreAGR 2 | ggcctaactggccggtaccactagtgacgtctacgtactgagcgacagtatagtgca cagtgacattacagatgtttacgacgaattacagatgtttctcatcgattacagatg tttcagctcaattacagatgtttgctgctgattacagatgtttaccagagattacag atgtttttacgtacatactgaaaagcatactttttgcaatgttatttttaaaaacaagg aactctttaacccagggaagataatcacttggggaaaggaaggttcgtttctgagtt agcaacaagtaaatgcagcactagtgggtgggattgaggtgtgccctggtgcataaa tagagactcagctgtgctggcacactcagaagcttggaccgcatcctagccgccgac tcacacaaggcaggtgggtgaggaaatccaggtaaggctcctgacagcagctttaga agggtacttgctggagtgaattcgggcctctgattagctagcctcgaggatatcaag atctggcctcggcggccaagcttggcaatccggtactgttggtaaagccacc |
| 71 | PL1 084 | PL-Twist_v1 8.2-coreKIF | ggcctaactggccggtaccactagtgacgtcctgagcgacagtatagtgcacagtga cattacagatgtttacgacgaattacagatgtttctcatcgattacagatgtttcag ctcaattacagatgtttgctgctgattacagatgtttaccagagattacagatgttt gacgtctacgtaggcccgcccccttttccttacgcggattggtagctgcaggcttccc tatctgattggccgaacgaacgcagcgcgtaatttaaaatattgtatctgtaacaaa gctgcacctcgtgggcggagttgtgctctgcggctgcgaaagtccagcttcggcgac taggtgtgagtaagccagtatcccaggaggagcaagtggcacgtcttcgggtgagtg tgcggctgtgctggagcccgggttaccagctctttaccggtgctagcctcgaggata tcaagatctggcctcggcggccaagcttggcaatccggtactgttggtaaagccacc |
| 72 | PL1 085 | PL-Twist_v1 8.2-coreCST | ggcctaactggccggtaccactagtgacgtcctgagcgacagtatagtgcacagtga cattacagatgtttacgacgaattacagatgtttctcatcgattacagatgtttcag ctcaattacagatgtttgctgctgattacagatgtttaccagagattacagatgttt gacgtctacgtactgatcagcgatgctcatctcgacctgatcggtacaacttctcac ggaggcttctaagtcattacatacgtagtcattactatacgtgtcattacagatgct gtcattacacgaactgtcattacgtactcagtcattactacgtaagtggtgggggag tgaaaagagagatggagaaagagggatgggcagaaagaggaggaggagtcaggggc agggcatggaggtgggtggggctgggctgccaaagcaggatataatgcacacctgcct gctggtctgggctccctgcctcgggctctcaccctcctctcctgcagctccagcttt gtgctctaccggtgctagcctcgaggatatcaagatctggcctcggcggccaagctt ggcaatccggtactgttggtaaagccacc |
| 73 | PL1 086 | PL-Twist_v1 8-coreFA M111B | ggcctaactggccggtaccactagtgacgtctacgtactgagcgacagtatagtgca cagtgacattacagatgtttacgacgaattacagatgtttctcatcgattacagatg tttcagctcaattacagatgtttgctgctgattacagatgtttaccagagattacag atgtttttacgtacgggaaaagttcagctgagagatataaaagagcagtctttccagc acctgcaaatccagagcggcgggcactgacgggcacttgcaccgtgtggacagactc tccggttctgtgagtggttttttcttttcccgggtcggacctggagttcttagggggga tggctgaaccggtgctagcctcgaggatatcaagatctggcctcggcggccaagctt ggcaatccggtactgttggtaaagccacc |
| 74 | PL1 087 | PL-Twist_v1 8-coreCEA CAM | ggcctaactggccggtaccactagtgacgtctacgtactgagcgacagtatagtgca cagtgacattacagatgtttacgacgaattacagatgtttctcatcgattacagatg tttcagctcaattacagatgtttgctgctgattacagatgtttaccagagattacag atgtttttacgtaacccacgtgatgctgagaagtactcctgccctaggaagagactca gggcagagggaggaaggacagcagaccagacagtcacagcagccttgacaaaacgtt cctggaactaccggtgctagcctcgaggatatcaagatctggcctcggcggccaagc ttggcaatccggtactgttggtaaagccacc |

TABLE 1A-continued

Sequences of engineered promoters according to the disclosure

| SEQ ID NO: | EA RLI. ID | Name | Regulatory element sequence (nucleotide) |
|---|---|---|---|
| 75 | PL1 088 | PL-Twist_v1 8.2-coreAGR 2 | ggcctaactggccggtaccactagtgacgtcctgagcgacagtatagtgcacagtga cattacagatgtttacgacgaattacagatgtttctcatcgattacagatgtttcag ctcaattacagatgtttgctgctgattacagatgtttaccagagattacagatgttt gacgtctacgtacatactgaaaagcatactttttgcaatgttattttttaaaaacaagg aactctttaacccagggaagataatcacttggggaaaggaaggttcgtttctgagtt agcaacaagtaaatgcagcactagtgggtgggattgaggtgtgccctggtgcataaa tagagactcagctgtgctggcacactcagaagcttggaccgcatcctagccgccgac tcacacaaggcaggtgggtgaggaaatccaggtaaggctcctgacagcagctttaga agggtacttgctggagtgaattcgggcctctgattagctagcctcgaggatatcaag atctggcctcggcggccaagcttggcaatccggtactgttggtaaagccacc |
| 76 | PL1 089 | PL-Twist_v1 8.2-coreCEA CAM | ggcctaactggccggtaccactagtgacgtcctgagcgacagtatagtgcacagtga cattacagatgtttacgacgaattacagatgtttctcatcgattacagatgtttcag ctcaattacagatgtttgctgctgattacagatgtttaccagagattacagatgttt gacgtctacgtaacccacgtgatgctgagaagtactcctgccctaggaaggagactca gggcagagggaggaaggacagcagaccagacagtcacagcagccttgacaaaacgtt cctggaactaccggtgctagcctcgaggatatcaagatctggcctcggggccaagc ttggcaatccggtactgttggtaaagccacc |
| 77 | PL1 090 | PL-Twist_v1 8.2-coreFA M111B | ggcctaactggccggtaccactagtgacgtcctgagcgacagtatagtgcacagtga cattacagatgtttacgacgaattacagatgtttctcatcgattacagatgtttcag ctcaattacagatgtttgctgctgattacagatgtttaccagagattacagatgttt gacgtctacgtacgggaaaagttcagctgagagatataaaagagcagtcttttccagc acctgcaaatccagagcggcgggcactgacgggcacttgcaccgtgtggacagactc tccggttctgtgagtggtttttcttttcccgggtcggacctggagttcttaggggga tggctgaaccggtgctagcctcgaggatatcaagatctggcctcggcggccaagctt ggcaatccggtactgttggtaaagccacc |
| 78 | PL1 091 | PL-Twist_v1 8-HOXA1_v10-coreKIF | ggcctaactggccggtaccactagtgacgtcctgagcgacagtatagtgcacagtga cattacagatgtttacgacgaattacagatgtttctcatcgattacagatgtttcag ctcaattacagatgtttgctgctgattacagatgtttaccagagattacagatgttt gacgtctacgtactgatcagcgatgctcatctcgacctgatcggtacaacttctcac ggaggcttctaagtcattacatacgtagtcattactatacgtgtcattacagatgct gtcattacacgaactgtcattacgtactcagtcattactacgtaggcccgcccctt tccttacgcggattggtagctgcaggcttccctatctgattggccgaacgaacgcag cgcgtaatttaaaatattgtatctgtaacaaagctgcacctcgtgggcggagttgtg ctctgcggctgcgaaagtccagcttcggcgactaggtgtgagtaagccagtatccca ggaggagcaagtggcacgtcttcgggtgagtgtgcggctgtgctggagcccgggtta ccagctctttaccggtgctagcctcgaggatatcaagatctggcctcggcggccaag cttggcaatccggtactgttggtaaagccacc |
| 79 | PL1 092 | PL-Twist_v1 8-HOXA1_v10-coreCST | ggcctaactggccggtaccacactagtgacgtcctgagcgacagtatagtgcacagt gacattacagatgtttacgacgaattacagatgtttctcatcgattacagatgtttc agctcaattacagatgtttgctgctgattacagatgtttaccagagattacagatgt ttgacgtctacgtactgatcagcgatgctcatctcgacctgatcggtacaacttctc acggaggcttctaagtcattacatacgtagtcattactatacgtgtcattacagatg ctgtcattacacgaactgtcattacgtactcagtcattactacgtacatactgaaaa gcatactttttgcaatgttattttaaaaacaaggaactctttaacccagggaagata atcacttggggaaaggaaggttcgtttctgagttagcaacaagtaaatgcagcacta gtgggtgggattgaggtgtgccctggttaagtggtgggggagtgaaaagagagatgg agaaagaggggatgggcagaaagaggaggaggagtcaggggcagggcatggaggtgg gtggggctgggctgccaaagcaggatiaaatgcacacctgcctgctggtctgggctcc ctgcctcgggctctcaccctcctctcctgcagctccagctttgtgctctaccggtgc tagcctcgaggatatcaagatctggcctcggcggccaagcttggcaatccggtactg ttggtaaagccacc |
| 80 | PL1 093 | PL-Twist_v1 8-HOXA1_v10-coreAGR 2 | ggcctaactggccggtacaactagtgactcctttgatgtacgcaactcctttgatgt ctatgcgtcctttgatgttaaggattcctttgatgtaggtacatcctttgatgtccg taaatcctttgatgtggtaccgtctactacctgatcaaacatgcccggacatgtcgt aagacataaacatgcccggacatgtcctcgcaatctaacatgcccggacatgtcctc gcaatctaacatgcccggacatgtctgcaagctacaacatgcccggacatgtctac tcagtcattactacgtacatactgaaaagcatactttttgcaatgttattttttaaaaa caaggaactctttaacccagggaagataatcacttggggaaaggaaggttcgtttct gagttagcaacaagtaaatgcagcactagtgggtgggattgaggtgtgccctggtgc ataaatagagactcagctgtgctggcacactcagaagcttggaccgcatcctagccg ccgactcacacaaggcaggtgggtgaggaaatccaggtaaggctcctgacagcagct ttagaagggtacttgctggagtgaattcgggcctctgattactagcctcgaggatat caagatctggcctcggcggccaagcttggcaatccggtactgttggtaaagccacc |
| 81 | PL1 094 | PL-Twist_v1 8-HOXA1_v10- | ggcctaactggccggtaccactagtgacgtcctgagcgacagtatagtgcacagtga cattacagatgtttacgacgaattacagatgtttctcatcgattacagatgtttcag ctcaattacagatgtttgctgctgattacagatgtttaccagagattacagatgttt gacgtctacgtactgatcagcgatgctcatctcgacctgatcggtacaacttctcac ggaggcttctaagtcattacatacgtagtcattactatacgtgtcattacagatgct |

TABLE 1A-continued

Sequences of engineered promoters according to the disclosure

| SEQ ID NO: | EA RLI. ID | Name | Regulatory element sequence (nucleotide) |
|---|---|---|---|
| | | coreCEA CAM | gtcattacacgaactgtcattacgtactcagtcattactacgtaacccacgtgatgc tgagaagtactcctgccctaggaagagactcagggcagagggaggaaggacagcaga ccagacagtcacagcagccttgacaaaacgttcctggaactaccggtgctagcctcg aggatatcaagatctggcctcggcggccaagcttggcaatccggtactgttggtaaa gccacc |
| 82 | PL1 095 | PL-Twist_v1 8-HOXA1_ v10-coreFA M111B | ggcctaactggccggtaccactagtgacgtcctgagcgacagtatagtgcacagtga cattacagatgtttacgacgaattacagatgtttctcatcgattacagatgtttcag ctcaattacagatgtttgctgctgattacagatgtttaccagagattacagatgttt gacgtctacgtactgatcagcgatgctcatctcgacctgatcggtacaacttctcac ggaggcttctaagtcattacatacgtagtcattactatacgtgtcattacagatgct gtcattacacgaactgtcattacgtactcagtcattactacgtacgggaaaagttca gctgagagatataaaagagcagtctttccagcacctgcaaatccagagcggcgggca ctgacgggcacttgcaccgtgtggacagactctccggttctgtgagtggttttttctt ttcccgggtcggacctggagttcttaggggggatggctgaaccggtgctagcctcgag gatatcaagatctggcctcggcggccaagcttggcaatccggtactgttggtaaagc cacc |
| 83 | PL1 096 | PL-HOXC10_ v14-coreKIF | ggcctaactggccggtaccactagtgacgtctgtagctgagcgacagtatagtgcac agtgactgcagcagtcattgtcgtaaattgagtatcgtcgtaaattgacgaacgtcg taaattagcgacagtcgtaaattagtacctgtcgtaaattactctgcgtcgtaaatt gacgtctacgtaggcccgcccccttttccttacgcggattggtagctgcaggcttccc tatctgattggccgaacgaacgcagcgcgtaatttaaaatattgtatctgtaacaaa gctgcacctcgtgggcggagttgtgctctgcggctgcgaaagtccagcttcggcgac taggtgtgagtaagccagtatcccaggaggagcaagtggcacgtcttcgggtgagtg tgcggctgtgctggagcccgggttaccagctctttaccggtctagcctcgaggatat caagatctggcctcggcggccaagcttggcaatccggtactgttggtaaagccacc |
| 84 | PL1 097 | PL-HOXA1_ v10-coreCST | ggcctaactggccggtaccactagtgacgtctacgtactgatcagcgatgctcatct cgacctgatcggtacaacttctcacggaggcttctaagtcattacatacgtagtcat tactatacgtgtcattacagatgctgtcattacacgaactgtcattacgtactcagt cattactacgtaagtggtgggggagtgaaaagagagatggagaaagagggggatgggc agaaagaggaggaggagtcaggggcagggcatggaggtgggtggggctgggctgcca aagcaggatataaatgcacacctgcctgctggtctgggctccctgcctcgggctctcac cctcctctcctgcagctccagctttgtgctctaccggtgctagcctcgaggatatca agatctggcctcggcggccaagcttggcaatccggtactgttggtaaagccacc |
| 85 | PL1 098 | PL-HOXA1_ v10-coreKIF | ggcctaactggccggtaccactagtgacgtctacgtactgatcagcgatgctcatct cgacctgatcggtacaacttctcacggaggcttctaagtcattacatacgtagtcat tactatacgtgtcattacagatgctgtcattacacgaactgtcattacgtactcagt cattactacgtaggcccgcccccttttccttacgcggattggtagctgcaggcttccc tatctgattggccgaacgaacgcagcgcgtaatttaaaatattgtatctgtaacaaa gctgcacctcgtgggcggagttgtgctctgcggctgcgaaagtccagcttcggcgac taggtgtgagtaagccagtatcccaggaggagcaagtggcacgtcttcgggtgagtg tgcggctgtgctggagcccgggttaccagctctttaccggtgctagcctcgaggata tcaagatctggcctcggcggccaagcttggcaatccggtactgttggtaaagccacc |
| 86 | PL1 099 | PL-HOXA1_ v10-coreCEA CAM | ggcctaactggccggtaccactagtgacgtctacgtactgatcagcgatgctcatct cgacctgatcggtacaacttctcacggaggcttctaagtcattacatacgtagtcat tactatacgtgtcattacagatgctgtcattacacgaactgtcattacgtactcagt cattactacgtaacccacgtgatgctgagaagtactcctgccctaggaagagactca gggcagagggaggaaggacagcagaccagacagtcacagcagccttgacaaaacgtt cctggaactaccggtgctagcctcgaggatatcaagatctggcctcggcggccaagc ttggcaatccggtactgttggtaaagccacc |
| 87 | PL1 100 | PL-HOXA1_ v10-coreAGR 2 | ggcctaactggccggtaccactagtgacgtctacgtactgatcagcgatgctcatct cgacctgatcggtacaacttctcacggaggcttctaagtcattacatacgtagtcat tactatacgtgtcattacagatgctgtcattacacgaactgtcattacgtactcagt cattactacgtacatactgaaaagcatactttttgcaatgttattttttaaaaacaagg aactctttaacccagggaagataatcacttggggaaaggaaggttcgtttctgagtt agcaacaagtaaatgcagcactagtgggtgggattgaggtgtgccctggtgcataaa tagagactcagctgtgctggcacactcagaagcttggaccgcatcctagccgccgac tcacacaaggcaggtgggtgaggaaatccaggtaaggctcctgacagcagctttaga agggtacttgctggagtgaattcgggcctctgattagctagcctcgaggatatcaag atctggcctcggcggccaagcttggcaatccggtactgttggtaaagccacc |
| 88 | PL1 101 | PL-HOXC10_ v14-coreCST | ggcctaactggccggtaccactagtgacgtctgtagctgagcgacagtatagtgcac agtgactgcagcagtcattgtcgtaaattgagtatcgtcgtaaattgacgaacgtcg taaattagcgacagtcgtaaattagtacctgtcgtaaattactctgcgtcgtaaatt gacgtctacgtaagtggtgggggagtgaaaagagagatggagaaagagggggatgggc agaaagaggaggaggagtcaggggcagggcatggaggtgggtggggctgggctgcca aagcaggatataaatgcacacctgcctgctggtctgggctccctgcctcgggctctcac cctcctctcctgcagctccagctttgtgctctaccggtgctagcctcgaggatatca agatctggcctcggcggccaagcttggcaatccggtactgttggtaaagccacc |

TABLE 1A-continued

Sequences of engineered promoters according to the disclosure

| SEQ ID NO: | EA RLI. ID | Name | Regulatory element sequence (nucleotide) |
|---|---|---|---|
| 89 | PL1 102 | PL-HOXC10_v14-coreFAM111B | ggcctaactggccggtaccactagtgacgtctgtagctgagcgacagtatagtgcac agtgactgcagcagtcattgtcgtaaattgagtatcgtcgtaaattgacgaacgtcg taaattagcgacagtcgtaaattagtacctgtcgtaaattactctgcgtcgtaaatt gacgtctacgtacgggaaaagttcagctgagagatataaaagagcagtctttccagc acctgcaaatccagagcggcgggcactgacgggcacttgcaccgtgtggacagactc tccggttctgtgagtggttttttcttttcccgggtcggacctggagttcttaggggga tggctgaaccggtgctagcctcgaggatatcaagatctggcctcggcggccaagctt ggcaatccggtactgttggtaaagccacc |
| 90 | PL1 103 | PL-HOXC10_v14-coreAGR2 | ggcctaactggccggtacaactagtgacgtctgtagctgagcgacagtatagtgcac agtgactgcagcagtcattgtcgtaaattgagtatcgtcgtaaattgacgaacgtcg taaattagcgacagtcgtaaattagtacctgtcgtaaattactctgcgtcgtaaatt gacgtctacgtacatactgaaaagcatactttttgcaatgttattttttaaaaacaagg aactctttaacccagggaagataatcacttggggaaaggaaggttcgtttctgagtt agcaacaagtaaatgcagcactagtgggtgggattgaggtgtgccctggtgcataaa tagagactcagctgtgctggcacactcagaagcttggaccgcatcctagccgccgac tcacacaaggcaggtgggtgaggaaatccaggtaaggctcctgacagcagctttaga agggtacttgctggagtgaattcgggcctctgattactagcctcgaggatatcaaga tctggcctcggcggccaagcttggcaatccggtactgttggtaaagccacc |
| 91 | PL1 104 | PL-HOXC10_v14-coreCEACAM | ggcctaactggccggtaccactagtgacgtctgtagctgagcgacagtatagtgcac agtgactgcagcagtcattgtcgtaaattgagtatcgtcgtaaattgacgaacgtcg taaattagcgacagtcgtaaattagtacctgtcgtaaattactctgcgtcgtaaatt gacgtctacgtaacccacgtgatgctgagaagtactcctgccctaggaagagactca gggcagagggaggaaggacagcagaccagacagtcacagcagccttgacaaaacgtt cctggaactaccggtgctagcctcgaggatatcaagatctggcctcggcggccaagc ttggcaatccggtactgttggtaaagccacc |
| 92 | PL1 105 | PL-HOXA1_v10-coreFAM111B | ggcctaactggccggtaccactagtgacgtctacgtactgatcagcgatgctcatct cgacctgatcggtacaaacttctcacggaggcttctaagtcattacatacgtagtcat tactatacgtgtcattacagatgctgtcattacacgaactgtcattacgtactcagt cattactacgtacgggaaaagttcagctgagagatataaaagagcagtctttccagc acctgcaaatccagagcggcgggcactgacgggcacttgcaccgtgtggacagactc tccggttctgtgagtggttttttcttttcccgggtcggacctggagttcttaggggga tggctgaaccggtgctagcctcgaggatatcaagatctggcctcggcggccaagctt ggcaatccggtactgttggtaaagccacc |
| 93 | PL1 106 | PL-HOXC10_v14-CREB V 6-coreCST | ggcctaactggccggtaccactagtgacgtctgtagctgagcgacagtatagtgcac agtgactgcagcagtcattgtcgtaaattgagtatcgtcgtaaattgacgaacgtcg taaattagcgacagtcgtaaattagtacctgtcgtaaattactctgcgtcgtaaatt gacgtctacgtaacatcggctatgctgctgctaatgccacgtcaccacatcgacatg ccacgtcaccatcatgccatgccacgtcaccactgcaagatgccacgtcaccacagt ataatgccacgtcaccaagttactatgccacgtcaccaggtacctacgtaagtaagtg ggggagtgaaaagagagatggagaaagagggggatgggcagaaagaggaggaggagtc aggggcagggcatggaggtgggtggggctgggctgccaaagcaggataaatgcacac ctgcctgctggtctgggctccctgcctcgggctctcaccctcctctcctgcagctcc agctttgtgctctaccggtgctagcctcgaggatatcaagatctggcctcggcggcc aagcttggcaatccggtactgttggtaaagccacc |
| 94 | PL1 107 | PL-HOXC10_v14-CREB_v 6-coreKIF | ggcctaactggccggtacactagtgacgtctgtagctgagcgacagtatagtgcaca gtgactgcagcagtcattgtcgtaaattgagtatcgtcgtaaattgacgaacgtcgt aaattagcgacagtcgtaaattagtacctgtcgtaaattactctgcgtcgtaaattg acgtctacgtaacatcggctatgctgctgctaatgccacgtcaccacatcgacatgc cacgtcaccatcatgccatgccacgtcaccactgcaagatgccacgtcaccacagta taatgccacgtcaccaagttactatgccacgtcaccaggtacctacgtaggcccgcc cccttttccttacgcggattggtagctgcaggcttccctatctgattggcgaacgaa cgcagcgcgtaatttaaaatattgtatctgtaacaaagctgcacctcgtgggcggag ttgtgctctgcggctgcgaaagtccagcttcggcgactaggtgtgagtaagccagta tcccaggaggagcaagtggcacgtcttcgggtgagtgtgcggctgtgctggagcccg ggttaccagctctttaccggtctagcctcgaggatatcaagatctggcctcggcggc caagcttggcaatccggtactgttggtaaagccacc |
| 95 | PL1 108 | PL-HOXC10_v14-CREB_ 6-coreAGR2 | ggcctaactggccggtacaactagtgacgtctgtagctgagcgacagtatagtgcac agtgactgcagcagtcattgtcgtaaattgagtatcgtcgtaaattgacgaacgtcg taaattagcgacagtcgtaaattagtacctgtcgtaaattactctgcgtcgtaaatt gacgtctacgtaacatcggctatgctgctgctaatgccacgtcaccacatcgacatg ccacgtcaccatcatgccatgccacgtcaccactgcaagatgccacgtcaccacagt ataatgccacgtcaccaagttactatgccacgtcaccaggtacctacgtacatactg aaaagcatactttttgcaatgttattttttaaaaacaaggaactctttaacccaggaa gataatcacttggggaaaggaaggttcgtttctgagttagcaacaagtaaatgcagc actagtgggggggattgaggtgtgccctggtgcataaatagagactcagctgtgctg gcacactcagaagcttggaccgcatcctagccgccgactcacacaaggcaggtgggt gaggaaatccaggtaaggctcctgacagcagctttagaagggtacttgctggagtga |

TABLE 1A-continued

Sequences of engineered promoters according to the disclosure

| SEQ ID NO: | EA RLI. ID | Name | Regulatory element sequence (nucleotide) |
|---|---|---|---|
| | | | attcgggcctctgattactagcctcgaggatatcaagatctggcctcggcggccaag cttggcaatccggtactgttggtaaagccacc |
| 96 | PL1 109 | PL-HOXC10_v14-CREB_v6-coreCEACAM | ggcctaactggccggtaccactagtgacgtctgtagctgagcgacagtatagtgcac agtgactgcagcagtcattgtcgtaaattgagtatcgtcgtaaattgacgaacgtcg taaattagcgacagtcgtaaattagtacctgtcgtaaattactctgcgtcgtaaatt gacgtctacgtaacatcggctatgctgctgctaatgccacgtcaccacatcgacatg ccacgtcaccatcatgccatgccacgtcaccactgcaagatgccacgtcaccacagt ataatgccacgtcaccaagttactatgccacgtcaccaggtacctacgtaacccacg tgatgctgagaagtactcctgccctaggaagagactcagggcagagggaggaaggac agcagaccagacagtcacagcagccttgacaaaacgttcctggaactaccggtgcta gcctcgaggatatcaagatctggcctcggcggccaagcttggcaatccggtactgtt ggtaaagccacc |
| 97 | PL1 110 | PL-HOXC10_v14-CREB_v6-coreFAM111B | ggcctaactggccggtaccactagtgacgtctgtagctgagcgacagtatagtgcac agtgactgcagcagtcattgtcgtaaattgagtatcgtcgtaaattgacgaacgtcg taaattagcgacagtcgtaaattagtacctgtcgtaaattactctgcgtcgtaaatt gacgtctacgtaacatcggctatgctgctgctaatgccacgtcaccacatcgacatg ccacgtcaccatcatgccatgccacgtcaccactgcaagatgccacgtcaccacagt ataatgccacgtcaccaagttactatgccacgtcaccaggtacctacgtacgggaaa agttcagctgagagatataaaagagcagtctttccagcacctgcaaatccagagcgg cgggcactgacgggcacttgcaccgtgtggacagactctccggttctgtgagtggtt tttcttttcccgggtcggacctggagttcttaggggatggctgaaccggtgctagc ctcgaggatatcaagatctggcctcggcggccaagcttggcaatccggtactgttgg taaagccacc |
| 98 | PL1 111 | PL-CREB_v6-coreCST | ggcctaactggccggtaccactagtgacgtctacgtaacatcggctatgctgctgct aatgccacgtcaccacatcgacatgccacgtcaccatcatgccatgccacgtcacca ctgcaagatgccacgtcaccacagtataatgccacgtcaccaagttactatgccacg tcaccaggtacctacgtaagtggtgggggagtgaaaagagagatggagaaagagggg atgggcagaaagaggaggaggagtcaggggcagggcatggaggtgggtggggctggg ctgccaaagcaggataaaatgcacacctgcctgctggtctgggctgcgaaagtccggg tctcaccctcctctcctgcagctccagctttgtgctctaccggtgctagcctcgagg atatcaagatctggcctcggcggccaagcttggcaatccggtactgttggtaaagcc acc |
| 99 | PL1 112 | PL-CREB_v6-coreAGR2 | ggcctaactggccggtacaactagtgacgtctacgtaacatcggctatgctgctgct aatgccacgtcaccacatcgacatgccacgtcaccatcatgccatgccacgtcacca ctgcaagatgccacgtcaccacagtataatgccacgtcaccaagttactatgccacg tcaccaggtacctacgtacatactgaaaagcactttttgtcaatgttattttaaaa acaaggaactctttaacccagggaagataatcacttggggaaaggaaggttcgtttc tgagttagcaacaagtaaatgcagcactagtgggggggattgaggtgtgccctggtg cataaatagagactcagctgtgctggcacactcagaagcttggaccgcatcctagcc gccgactcacacaaggcaggtgggtgaggaaatccaggtaaggctcctgacagcagc tttagaagggtacttgctggagtgaattcgggcctctgattactagcctcgaggata tcaagatctggcctcggcggccaagcttggcaatccggtactgttggtaaagccacc |
| 100 | PL1 113 | PL-CREB_v6-coreKIF | ggcctaactggccggtaccactagtgacgtctacgtaacatcggctatgctgctgct aatgccacgtcaccacatcgacatgccacgtcaccatcatgccatgccacgtcacca ctgcaagatgccacgtcaccacagtataatgccacgtcaccaagttactatgccacg tcaccaggtacctacgtaggcccgcccccctttccttacgcggattggtagctgcagg cttccctatctgattggccgaacgaacgcagcgcgtaatttaaaatattgtatctgt aacaaagctgcacctcgtgggcggagttgtgctctgcggctgcgaaagtccagcttc ggcgactaggtgtgagtaagccagtatcccaggaggagcaagtggcacgtcttcggg tgagtgtgcggctgtgctggagcccgggttaccagctctttaccggtctagcctcga ggatatcaagatctggcctcggcggccaagcttggcaatccggtactgttggtaaag ccacc |
| 101 | PL1 114 | PL-CREB_v6-coreCEACAM | ggcctaactggccggtaccactagtgacgtctacgtaacatcggctatgctgctgct aatgccacgtcaccacatcgacatgccacgtcaccatcatgccatgccacgtcacca ctgcaagatgccacgtcaccacagtataatgccacgtcaccaagttactatgccacg tcaccaggtacctacgtaacccacgtgatgctgagaagtactcctgccctaggaaga gactcagggcagagggaggaaggacagcagaccagacagtcacagcagccttgacaa aacgttcctggaactaccggtgctagcctcgaggatatcaagatctggcctcggcgg ccaagcttggcaatccggtactgttggtaaagccacc |
| 102 | PL1 115 | PL-CREB_v6-coreFAM111B | ggcctaactggccggtaccactagtgacgtctacgtaacatcggctatgctgctgct aatgccacgtcaccacatcgacatgccacgtcaccatcatgccatgccacgtcacca ctgcaagatgccacgtcaccacagtataatgccacgtcaccaagttactatgccacg tcaccaggtacctacgtacgggaaaagttcagctgagagatataaaagagcagtctt tccagcacctgcaaatccagagcggcgggcactgacgggcacttgcaccgtgtggac agactctccggttctgtgagtggtttttcttttcccgggtcggacctggagttctta ggggatggctgaaccggtgctagcctcgaggatatcaagatctggcctcggcggcc aagcttggcaatccggtactgttggtaaagccacc |

TABLE 1A-continued

| SEQ ID NO: | EARLI. ID | Name | Regulatory element sequence (nucleotide) |
|---|---|---|---|
| 103 | PL1 144 | HES6_v 11- coreBIR C5 | GAATTCaagaCtgcaagCGAGCGACAGTATAGTGCACAGTGACTGCAGCAGTCATTA TACGTCGCCTAAATCGAGATGCTGTAGGCACGTGTATCTGGCACGTGTACTCGGCAC GTGTACTAGGCACGTGTAAGAGGCACGTGTACGCGGCACGTGTAGGTACCTGCGCTC CCGACATGCCCCGCGGCGCGCCATTAACCGCCAGATTTGAGTCGCGGGACCCGTTGG CAGAGGTGGGCTAGCCTCGAGGATATCAAGATCTGGCCTCGGCGGCCAAGCTTGGCA ATCCGGTACTGTTGGTAAAGCCACCATGGAAG |
| 104 | PL1 145 | HES6_v 11- TATA- TSS | GAATTCaagaCtgcaagCGAGCGACAGTATAGTGCACAGTGACTGCAGCAGTCATTA TACGTCGCCTAAATCGAGATGCTGTAGGCACGTGTATCTGGCACGTGTACTCGGCAC GTGTACTAGGCACGTGTAAGAGGCACGTGTACGCGGCACGTGTAGGTACCTATAAAA GGCCAGCAGCAGCCTGACCACATCTCATCCGCTAGCCTCGAGGATATCAAGATCTGG CCTCGGCGGCCAAGCTTGGCAATCCGGTACTGTTGGTAAAGCCACC |
| 105 | PL1 146 | NPAS2_ v11- coreBIR C5 | GAATTCaagaCtgcaagCCTGAGCGACAGTATAGTGCACAGTGACTGCAGCAGTCAT TATACGTCGCCTAAATCGAGATGCTGGACACGTGTCCGAGACACGTGTCTGTGACAC GTGTCCGGGACACGTGTCGCAGACACGTGTCGTGGACACGTGTCGGTACCTGCGCTC CCGACATGCCCCGCGGCGCGCCATTAACCGCCAGATTTGAGTCGCGGGACCCGTTGG CAGAGGTGGGCTAGCCTCGAGGATATCAAGATCTGGCCTCGGCGGCCAAGCTTGGCA ATCCGGTACTGTTGGTAAAGCCACC |
| 106 | PL1 147 | NPAS2_ v11- TATA- TSS | GAATTCaagaCtgcaagCCTGAGCGACAGTATAGTGCACAGTGACTGCAGCAGTCAT TATACGTCGCCTAAATCGAGATGCTGGACACGTGTCCGAGACACGTGTCTGTGACAC GTGTCCGGGACACGTGTCGCAGACACGTGTCGTGGACACGTGTCGGTACCTATAAAA GGCCAGCAGCAGCCTGACCACATCTCATCCGCTAGCCTCGAGGATATCAAGATCTGG CCTCGGCGGCCAAGCTTGGCAATCCGGTACTGTTGGTAAAGCCACC |
| 107 | PL1 15 | pGL4.10- FAM83 A-43 | ggcctaactggccggtaccactagtatcgatccttcatagggcagggaggggtgggc acttgggtgtgaccaaggagaggaggcgcgcctggtcaacagctctccctggcccgt gtccagctccctcctcacacagagagggggcgcatctcagggatggcatctttccc ccccacagggaaattcttatctttgaaacagcatgggaatcgaggcacccaggaggg gagcagaggcaggcaggcctccttcaggcccatcctccagctgggctggtggtgcca gggaggctccctgcttggtaacaaaggcctgagggagagttgcgaaacccagcagga aagccggctcaccttcgcctcccctgcggctgggaggagaggaaatatcccatggc tgactgtgccaaggaggtgtctgagccagccctcccggcccgagggcagggcaggtg gccctgagagataagccaatcccgcagctgcagatgaggagttctgagaagcattgc tcaggacagcggtaaatcacttcttggaggtgccctgcacgccggtcctgggagcag gcggcctcccgggggtgcgggagccccactcctccgtggtgtgttccatttgcttcc cacatctggaggagctgacgtgccagcctcccccagcaccacccagggacgggaggc aaccggtgctagcctcgaggatatcaagatctggcctcggcggccaagcttggcaat ccggtactgttggtaaagccacc |
| 108 | PL1 156 | PL- TP53_v5- TATA- TSS FLUC | ggcctaactggccggtaccgacgtctacctgatcaaacatgcccggacatgtcgtaa gacataaacatgcccggacatgtcctcgcaatctaacatgcccggacatgtcctcgc aatctaacatgcccggacatgtctgcaagctacaacatgcccggacatgtctacgta gctagctataaaaggccagcagcagcctgaccacatctcatcctcctcgaggatatc aagatctggcctcggcggccaagcttggcaatccggtactgttggtaaagccacc |
| 109 | PL1 157 | PL- TP53_v2 2-TATA- TSS FLUC | ggcctaactggccggtaccgacgtccctgatcggtacaacttctcacaacatgcctg ggcatgtcgctatgcaacatgcctgggcatgtcgagatgcaaacatgcctgggcatgt cctgctataacatgcctgggcatgtcctgctataacatgcctgggcatgtctacgta gctagctataaaaggccagcagcagcctgaccacatctcatcctcctcgaggatatc aagatctggcctcggcggccaagcttggcaatccggtactgttggtaaagccacc |
| 110 | PL1 158 | PL-TP53 SURV_v 3-TATA- TSS FLUC | ggcctaactggccggtaccgacgtctcgggcaagcgctcccgacatgcccgggcaag cgctcccgacatgcccgggcaagcgctcccgacatgcccgggcaagcgctcccgaca tgcccgggcaagcgctcccgacatgcccgggcaagcgctcccgacatgccctacgta gctagctataaaaggccagcagcagcctgaccacatctcatcctcctcgaggatatc aagatctggcctcggcggccaagcttggcaatccggtactgttggtaaagccacc |
| 111 | PL1 159 | PL- TCF7_v2- FOS- coreBIR C5 | ggcctaactggccggtacctttttgataaaaatcattaggtacggccgcggtgccagg gcgtgcccttgggctccccgggcgcgaaactagtgacgtcctgagcgacagtatagt gcacagtgactgcagcagtcattcctttgatgtacgcaactcctttgatgtctatgc gtcctttgatgttaaggattcctttgatgtaggtacatcctttgatgtccgtaaatc ctttgatgtgacgtctacgtaggtgactcatgggtgactcatgtacgtaacgcgtcc cgacatgccccgcggcgcgccattaaccgccagatttgagtcgcgggacccgttggc agaggtgggaattcaccggtgctagcctcgaggatatcaagatctggcctcggcggc caagcttggcaatccggtactgttggtaaagccacc |
| 112 | PL1 160 | PL-FOS- TCF_v2- coreBIR C5 | ggcctaactggccggtacctttttgataaaaatcattaggtacggccgcggtgccagg gcgtgcccttgggctcccgggcgcgaaactagtgacgtcggtgactcatgggtgac tcatgacgtctacgtactgagcgacagtatagtgcacagtgactgcagcagtcattc ctttgatgtacgcaactcctttgatgtctatgcgtcctttgatgttaaggattcctt tgatgtaggtacatcctttgatgtccgtaaatcctttgatgttacgtaacgcgtccc |

TABLE 1A-continued

Sequences of engineered promoters according to the disclosure

| SEQ ID NO: | EARLI. ID | Name | Regulatory element sequence (nucleotide) |
|---|---|---|---|
| | | | gacatgccccgcggcgcgccattaaccgccagatttgagtcgcgggacccgttggca gaggtgggaattcaccggtgctagcctcgaggatatcaagatctggcctcggcggcc aagcttggcaatccggtactgttggtaaagccacc |
| 113 | PL1 161 | PL-TCF7_v2-FOS-coreAGR2 | ggcctaactggccggtaccaactagtgacgtcctgagcgacagtatagtgcacagtg actgcagcagtcattcctttgatgtacgcaactcctttgatgtctatgcgtcctttg atgttaaggattcctttgatgtaggtacatcctttgatgtccgtaaatcctttgatg tgacgtctacgtaggtgactcatgggtgactcatgtacgtacatactgaaaagcata cttttgcaatgttatttttaaaaacaaggaactctttaacccagggaagataatcac ttggggaaaggaaggttcgtttctgagttagcaacaagtaaatgcagcactagtggg tgggattgaggtgtgccctggtgcatgaatagagactcagctgtgctggcacactca gaagcttggaccgcatcctagccgccgactcacacaaggcaggtgggtgaggaaatc caggtaaggctcctgacagcagctttagaagggtacttgctggagtgaattcgggcc tctgattagctagcctcgaggatatcaagatctggcctcggcggccaagcttggcaa tccggtactgttggtaaagccacc |
| 114 | PL1 162 | PL-FOS-TCF7_v2-coreAGR2 | ggcctaactggccggtaccaactagtgacgtcggtgactcatgggtgactcatggac gtctacgtactgagcgacagtatagtgcacagtgactgcagcagtcattcctttgat gtacgcaactcctttgatgtctatgcgtcctttgatgttaaggattcctttgatgta ggtacatcctttgatgtccgtaaatcctttgatgttacgtacatactgaaaagcata cttttgcaatgttattttaaaaacaaggaactctttaacccagggaagataatcac ttggggaaaggaaggttcgtttctgagttagcaacaagtaaatgcagcactagtggg tgggattgaggtgtgccctggtgcatgaatagagactcagctgtgctggcacactca gaagcttggaccgcatcctagccgccgactcacacaaggcaggtgggtgaggaaatc caggtaaggctcctgacagcagctttagaagggtacttgctggagtgaattcgggcc tctgattagctagcctcgaggatatcaagatctggcctcggcggccaagcttggcaa tccggtactgttggtaaagccacc |
| 115 | PL1 163 | PL-TCF7_v2 coreAGR2 | ggcctaactggccggtaccaactagtgacgtcctgagcgacagtatagtgcacagtg actgcagcagtcattcctttgatgtacgcaactcctttgatgtctatgcgtcctttg atgttaaggattcctttgatgtaggtacatcctttgatgtccgtaaatcctttgatg tgacgtctacgtacatactgaaaagcatactttttgcaatgttattttaaaaacaag gaactctttaacccagggaagataatcacttggggaaaggaaggttcgtttctgagt tagcaacaagtaaatgcagcactagtgggtgggattgaggtgtgccctggtgcataa atagagactcagctgtgctggcacactcagaagcttggaccgcatcctagccgccga ctcacacaaggcaggtgggtgaggaaatccaggtaaggctcctgacagcagctttag aagggtacttgctggagtgaattcgggcctctgattagctagcctcgaggatatcaa gatctggcctcggcggccaagcttggcaatccggtactgttggtaaagccacc |
| 116 | PL1 164 | PL-TCF7_v2-FOS-coreCEACAM5 | CAACTAGTGACGTCCTGAGCGACAGTATAGTGCACAGTGACTGCAGCAGTCATTCCT TTGATGTACGCAACTCCTTTGATGTCTATGCGTCCTTTGATGTTAAGGATTCCTTTG ATGTAGGTACATCCTTTGATGTCCGTAAATCCTTTGATGTGACGTCTACGTAGGTGA CTCATGGGTGACTCATGTACGTAACCCACGTGATGCTGAGAAGTACTCCTGCCCTAG GAAGAGACTCAGGGCAGAGGGAGGAAGGACAGCAGACCAGACAGTCACAGCAGCCTT GACAAAACGTTCCTGGAACTACCGGT |
| 117 | PL1 165 | PL-TCF7_v2 coreCEACAM5 | ggcctaactggccggtaccaactagtgacgtcctgagcgacagtatagtgcacagtg actgcagcagtcattcctttgatgtacgcaactcctttgatgtctatgcgtcctttg atgttaaggattcctttgatgtaggtacatcctttgatgtccgtaaatcctttgatg tgacgtctacgtaacccacgtgatgctgagaagtactcctgccctaggaagagactc agggcagagggaggaaggacagcagaccagacagtcacagcagccttgacaaaacgt tcctggaactaccggtgctagcctcgaggatatcaagatctggcctcggcggccaag cttggcaatccggtactgttggtaaagccacc |
| 118 | PL1 166 | PL-TCF7_v2-coreFAM111B | AACTAGTGACGTCCTGAGCGACAGTATAGTGCACAGTGACTGCAGCAGTCATTCCTT TGATGTACGCAACTCCTTTGATGTCTATGCGTCCTTTGATGTTAAGGATTCCTTTGA TGTAGGTACATCCTTTGATGTCCGTAAATCCTTTGATGTGACGTCTACGTATACGTA CGGGAAAAGTTCAGCTGAGAGATATAAAAGAGCAGTCTTTCCAGCACCTGCAAATCC AGAGCGGCGGGCACTGACGGGCACTTGCACCGTGTGGACAGACTCTCCGGTTCTGTG AGTGGTTTTTCTTTTCCCGGGTCGGACCTGGAGTTCTTAGGGGGATGGCTGaaccgg t |
| 119 | PL1 167 | PL-TCF7_v2 coreCST | CTAGTGACGTCCTGAGCGACAGTATAGTGCACAGTGACTGCAGCAGTCATTCCTTTG ATGTACGCAACTCCTTTGATGTCTATGCGTCCTTTGATGTTAAGGATTCCTTTGATG TAGGTACATCCTTTGATGTCCGTAAATCCTTTGATGTGACGTCTACGTATACGTAAG TGGTGGGGGAGTGAAAAGAGAGATGGAGAAAGAGGGGATGGGCAGAAAGAGGAGGAG GAGTCAGGGGCAGGGCATGGAGGTGGGTGGGGCTGGGCTGCCAAAGCAGGATAAATG CACACCTGCCTGCTGGTCTGGGCTCCCTGCCTCGGGCTCTCACCCTCCTCTCCTGCA GCTCCAGCTTTGTGCTCTa |
| 120 | PL1 168 | PL-TCF7_v2 coreKIF20A | CTAGTGACGTCCTGAGCGACAGTATAGTGCACAGTGACTGCAGCAGTCATTCCTTTG ATGTACGCAACTCCTTTGATGTCTATGCGTCCTTTGATGTTAAGGATTCCTTTGATG TAGGTACATCCTTTGATGTCCGTAAATCCTTTGATGTGACGTCTACGTATACGTAGG CCCGCCCCCTTTCCTTACGCGGATTGGTAGCTGCAGGCTTCCCTATCTGATTGGCCG |

TABLE 1A-continued

Sequences of engineered promoters according to the disclosure

| SEQ ID NO: | EA RLI. ID | Name | Regulatory element sequence (nucleotide) |
|---|---|---|---|
| | | | AACGAACGCAGCGCGTAATTTAAAATATTGTATCTGTAACAAAGCTGCACCTCGTGG GCGGAGTTGTGCTCTGCGGCTGCGAAAGTCCAGCTTCGGCGACTAGGTGTGAGTAAG CCAGTATCCCAGGAGGAGCAAGTGGCACGTCTTCGGGTGAGTGTGCGGCTGTGCTGG AGCCCGGGTTACCAGCTCTTTA |
| 121 | PL1 17 | pGL4.10-CEACAM5 | ggcctaactggccggtaccaccatggggaaggtggggtgatcacaggacagtcagcc tcgcagaggacagagaccacccaggactgtcagggagaacatggacaggccctgagc cgcagctcagccaacagacacggagagggagggtcccctggagccttccccaagga cagcagagcccagagtcacccacctccctccaccacagtcctctctttccaggacac acaagacacctcccctccacatgcaggatctggggactcctgagacctctgggcct gggtctccatccctgggtcagtgggggttggtggtactggagacagagggctggt ccctccccagccaccacccagtgagccttttctagcccccagagccacctctgtca ccttcctgttgggcatcatcccaccttccagagccctggagagcatggggagaccc gggaccctgctgggtttctctgtcacaaaggaaaataatcccctggtgtgacagac ccaaggacagaacacagcagaggtcagcactgggaagacaggttgtcctcccaggg gatggggtccatccaccttgccgaaaagatttgtctgaggaactgaaaatagaagg gaaaaaagaggagggacaaaagaggcagaaatgagaggggagggacagaggacacc tgaataaagaccacacccatgacccacgtgatgctgagaagtactcctgccctagga agagactcagggcagagggaggaaggacagcagaccagacagtcacagcagccttga caaaacgttcctggaactaccggtgctagcctcgaggatatcaagatctggcctcgg cggccaagcttggcaatccggtactgttggtaaagccacc |
| 122 | PL1 183 | PL-TP53_v5-coreBIRC5 | ggcctaactggccggtacctttttgataaaaatcattaggtacggccgcggtgccagg gcgtgcccttgggctcccgggcgcgaaactagtgacgtctacctgatcaaacatgc ccggacatgtcgtaagacataaacatgcccggacatgtcctcgcaatctaacatgcc cggacatgtcctcgcaatctaacatgcccggacatgtctgcaagctacaacatgccc ggacatgtctacgtaacgcgtcccgacatgcccgcggcgcgccattaaccgccaga tttgagtcgcgggacccgttggcagaggtgggaattcaccggtgctagcctcgagga tatcaagatctggcctcggcggccaagcttggcaatccggtactgttggtaaagcca cc |
| 123 | PL1 184 | PL-TP53_v5-coreAGR2 | ggcctaactggccggtaccaactagtgacgtctacctgatcaaacatgcccggacat gtcgtaagacataaacatgcccggacatgtcctcgcaatctaacatgcccggacatg tcctcgcaatctaacatgcccggacatgtctgcaagctacaacatgcccggacatgt ctacgtacatactgaaaagcatacttttgcaatgttattttaaaaacaaggaactc tttaacccagggaagataatcacttgggaaggaaggttcgtttctgagttagcaa caagtaaatgcagcactagtgggtgggattgaggtgtgccctggtgcataaatagag actcagctgtgctggcacactcagaagcttggaccgcatcctagccgccgactcaca caaggcaggtgggtgaggaaatccaggtaaggctcctgacagcagctttagaagggt acttgctggagtgaattcgggcctctgattagctagcctcgaggatatcaagatctg gcctcggcggccaagcttggcaatccggtactgttggtaaagccacc |
| 124 | PL1 185 | PL-TP53_v5-coreFAM111B | ggcctaactggccggtaccaactagtgacgtctacctgatcaaacatgcccggacat gtcgtaagacataaacatgcccggacatgtcctcgcaatctaacatgcccggacatgt tcctcgcaatctaacatgcccggacatgtctgcaagctacaacatgcccggacatgt ctacgtacgggaaaagttcagctgagagatataaaagagcagtctttccagcacctg caaatccagagcggcgggcactgacgggcacttgcaccgtgtggacagactctccgg ttctgtgagtggttttttcttttcccgggtcggacctggagttcttaggggggatggct gaaccggtgctagcctcgaggatatcaagatctggcctcggcggccaagcttggcaa tccggtactgttggtaaagccacc |
| 125 | PL1 186 | PL-TP53_v5-coreCST | ggcctaactggccggtaccaactagtgacgtctacctgatcaaacatgcccggacat gtcgtaagacataaacatgcccggacatgtcctcgcaatctaacatgcccggacatgt tcctcgcaatctaacatgcccggacatgtctgcaagctacaacatgcccggacatgt ctacccgttcgacaagcccggacatgctaagacataaacatgcccggacatgtcctc gcaatctaaccatgcccggacatgtcctcgcaatctaacatgcccggacatgtctgc aagctacaacatgcccggacatgtctacgtaagtggtgggggagtgaaaagagagat ggagaaagaggggatgggcagaaagaggaggaggagtcaggggcagggcatggaggt gggtggggctgggctgccaaagcaggatataatgcacacctgcctgctggtctgggct ccctgcctcgggctctcaccctcctctcctgcagctccagctttgtgctctaccggt gctagcctcgaggatatcaagatctggcctcggcggccaagcttggcaatccggtac tgttggtaaagccacc |
| 126 | PL1 187 | PL-TCF7_v2 TP53_v5 coreBIRC5 | ggcctaactggccggtacctttttgataaaaatcattaggtacggccgcggtgccagg gcgtgcccttgggctcccgggcgcgaaactagtgacgtctcctgagcgacagtatagt gcacagtgactgcagcagtcattcctttgatgtacgcaactcctttgatgtctatgc gtcctttgatgttaaggattcctttgatgtaggtacatcctttgatgtccgtaaatc ctttgatgtgacgtctacgtatctacctgatcaaacatgcccggacatgtcgtaaga cataaacatgcccggacatgtcctcgcaatctaacatgcccggacatgtctgcaa tctaacatgcccggacatgtctgcaagctacaacatgcccggacatgtctacgtaac gcgtcccgacatgccccgcggcgcgccattaaccgccagatttgagtcgcgggaccc gttggcagaggtgggaattcaccggtgctagcctcgaggatatcaagatctggcctc ggcggccaagcttggcaatccggtactgttggtaaagccacc |

TABLE 1A-continued

Sequences of engineered promoters according to the disclosure

| SEQ ID NO: | EA RLI. ID | Name | Regulatory element sequence (nucleotide) |
|---|---|---|---|
| 127 | PL1 188 | PL-TCF7_v2-TP53_v5-coreAGR 2 | ggcctaactggccggtaccaactagtgacgtcctgagcgacagtatagtgcacagtg actgcagcagtcattcctttgatgtacgcaactcctttgatgtctatgcgtcctttg atgttaaggattcctttgatgtaggtacatcctttgatgtccgtaaatcctttgatg tgacgtctacgtatctacctgatcaaacatgcccggacatgtcgtaagacataaaca tgcccggacatgtcctcgcaatctaacatgcccggacatgtcctcgcaatctaacat gcccggacatgtctgcaagctacaacatgcccggacatgtctacaatatacgtatct acctgatcaaacatgcccggacatgtcgtaagacataaacatgcccggacatgtcct cgcaatctaacatgcccggacatgtcctcgcaatctaacatgcccggacatgtctgc aagctacaacatgcccggacatgtctacgtacatactgaaaagcatacttttgcaat gttatttttaaaaacaaggaactctttaacccagggaagataatcacttgggaaag gaaggttcgtttctgagttagcaacaagtaaatgcagcactagtgggtgggattgag gtgtgccctggtgcataaatagagactcagctgtgctggcacactcagaagcttgga ccgcatcctagccgccgactcacacaaggcaggtgggtgaggaaatccaggtaaggc tcctgacagcagctttagaagggtacttgctggagtgaattcgggcctctgattagc tagcctcgaggatatcaagatctggcctcggcggccaagcttggcaatccggtactg ttggtaaagccacc |
| 130 | PL1 21 | pGL4.10-KIF20A | ggcctaactggccggtaccactagtaagcctcaagatttcctttaggctcttaggta agaaatgtctaaggttcaaggaaaaaggttaagttggaagaatcccaggcaaaataa gtgcgaatccacgacagttggtaacccggacccacattagaactcagaggtcaagca gaagcgaacgactggaattccagtcaggcccgccccctttccttacgcggattggta gctgcaggcttccctatctgattggccgaacgaacgcagcgcgtaatttaaaatatt gtatctgtaacaaagctgcacctcgtgggcgggagttgtgctctgcggctgcgaaagt ccagcttcggcgactaggtgtgagtaagccagtatcccaggaggagcaagtggcacg tcttcgggtgagtgtgcggctgtgctggagcccgggttaccagctcttaccggtgct agcctcgaggatatcaagatctggcctcggcggccaagcttggcaatccggtactgt tggtaaagccacc |
| 145 | PL1 236 | PL-HIGH-coreFAM111B-FLUC-HA | ggcctaactggccggtaccactagtggggcggggtgatgacacagcaattcgggact ttccacgcttgcgtgagaagagaccggaagtgaatgacacagcaattcgcttgcgtg agaagctgggactttcctaggggcggggttgggactttccacatgacacagcaatac actagtaacatttctctggcctaactggccggtaccgggaaaagttcagctgagaga tataaaagagcagtctttccagcacctgcaaatccagagcggggggcactgacgggc acttgcaccgtgtggacagactctccggttctgtgagtggttttttcttttcccgggt cggacctggagttcttaggggatggctgaagaattcaccggtcgacgctagc |
| 147 | PL1 238 | PL-AFP3-FLUC-HA | ggcctaactggccggtaccactagtgtcatctctttgaatattctgtagtttgagga gaatatttgttatattgcacaataaaataagtttgcaagtttttttttttctgcccca aagagctctgtgtccttgaacataaaatacaaataaccgctatgctgttaattatta acaaatgtcccattttcaacctaaggaaataccataaagtaacagatataccaacaa aaggttaataattaacaggcattgcctgaaaagagtataaaaaggctttcagcatgat tttccatattgtgcttccaccactgccaataacaaaccggtgaattcaccggtcgac gctagc |
| 148 | PL1 239 | FOSL1-v1-CREB3L1-v6-1x1_v1 | GAATTCACTAGTGACAGTATAGTGCACAGTGACTGCAGCAGGGTGACTCATGATGCC ACGTCACCAGGTGACTCATGATGCCACGTCACCAGGTGACTCATGATGCCACGTCAC CAGGTGACTCATGATGCCACGTCACCAGGTGACTCATGGGTACCTATAAAAGGCCAG CAGCAGCCTGACCACATCTCATCCA |
| 149 | PL1 240 | FOSL1-v1-CREB3L1-v6-2x2_v1 | GAATTCACTAGTAGTATAGTGCACAGTGACTGCAGCAGGGTGACTCATGATGATGCC ACGTCACCAATGCCACGTCACCAGGTGACTCATGGGTGACTCATGATGCCACGTCAC CAATGCCACGTCACCAGGTGACTCATGGGTGACTCATGGGTACCTATAAAAGGCCAG CAGCAGCCTGACCACATCTCATCCA |
| 150 | PL1 241 | FOXO1 :: ELK3_v 6 | GAATTCACTAGTCTCAAGTATAAGGTAAGACATAGTTACTGCGACATCGGCTAGTAA ACCGGAAGTGTCTGTAAACCGGAAGTGATCGTAAACCGGAAGTGAGCGTAAACCGGA AGTGCTAGTAAACCGGAAGTGGAAGTAAACCGGAAGTGGGTACCTATAAAAGGCCAG CAGCAGCCTGACCACATCTCATCCA |
| 151 | PL1 242 | MTF1_v 9 | GAATTCACTAGTGTACTCAAGTATAAGGTAAGATTTGCACACGGTACGTACTCATTT GCACACGGTACATGCGAGTTTGCACACGGTACAGCTCAGTTTGCACACGGTACGTCA GCTTTTGCACACGGTACATCAGAATTTGCACACGGTACGGTACCTATAAAAGGCCAG CAGCAGCCTGACCACATCTCATCCACCGGTG |
| 152 | PL1 243 | NFE2L2_v14 | GAATTCACTAGTTAATTGCTGAGTCATTGCTGCTATGTAATTGCTGAGTCATATGCC TATCCTAATTGCTGAGTCATAATCGAGATGTAATTGCTGAGTCATGTCCGACGCATA ATTGCTGAGTCATTCTAACTCGCTAATTGCTGAGTCATGGTACCTATAAAAGGCCAG CAGCAGCCTGACCACATCTCATCCA |

TABLE 1A-continued

Sequences of engineered promoters according to the disclosure

| SEQ ID NO: | EA RLI. ID | Name | Regulatory element sequence (nucleotide) |
|---|---|---|---|
| 153 | PL1 244 | NFKB1_ v3 | GAATTCACTAGTGCTGAGCGACAGTATAGTGCACAGTGACTGCAGCAGTCATTATAC GTAGGGGAATCCCCTCGAAGGGGAATCCCCTTTAAGGGGAATCCCCTCGCAGGGGAA TCCCCTCTCAGGGGAATCCCCTAACAGGGGAATCCCCTGGTACCTATAAAAGGCCAG CAGCAGCCTGACCACATCTCATCCA |
| 154 | PL1 245 | TP53-v5- TCF7- v2- 1x1_v1 | GAATTCACTAGTGCATCCTTTGATGTTACCTGATCAAACATGCCCGGACATGTCGTA AGACATATCCTTTGATGTCTCGCAATCTAACATGCCCGGACATGTCCTCGCAATCTT CCTTTGATGTTGCAAGCTACAACATGCCCGGACATGTCGGTACCTATAAAAGGCCAG CAGCAGCCTGACCACATCTCATCCA |
| 155 | PL1 246 | XBP1_v 19 | GAATTCACTAGTGCACCATTAGTACTTGATCAGTATGCCACGTCATCACTACTCTAT GCCACGTCATCTCCTAGATATGCCACGTCATCGTAAGACTATGCCACGTCATCTACA GCTTATGCCACGTCATCACGTACTTATGCCACGTCATCGGTACCTATAAAAGGCCAG CAGCAGCCTGACCACATCTCATCCA |
| 156 | PL5 50 | Cancript- coreBIR C5- FLUC | ggcctaactggccggtaccactagtgtccccacccacacattcctgtccccacccac acattcctgtccccacccacacattcctgtccccacccacacattcctgtccccacc cacacattcctgtccccacccacacattcctgtgcgctcccgacatgccccgcggcg cgccattaaccgccagatttgagtcgcgggacccgttggcagaggtgggctagcctc gaggatatcaagatctggcctcggcggccaagcttggcaatccggtactgttggtaa agccacc |
| 157 | PL5 51 | UAS- minB- FLUC_n o KPNI | ggcctaactggccggtaccagcttgcatgcctgcaggtcggagtactgtcctccgag cggagtactgtcctccgagcggagtactgtcctccgagcggagtactgtcctccgag cggagtactgtcctccgagcggtgcgctcccgacatgccccgcggcgcgccattaac cgccagatttgagtcgcgggacccgttggcagaggtgggctagcctcgaggatatca agatctggcctcggcggccaagcttggcaatccggtactgttggtaaagccacc |
| 158 | PL5 73 | TTF- 1_1_no space_mi nBIRC5 | ggcctaactggccggtaccactagtggttttgtggggttttgtggggttttgtgggg ttttgtggggttttgtggggttttgtggggttttgtggggttttgtggggttttgtg gggttttgtggtgcgctcccgacatgccccgcggcgcgccattaaccgccagatttg agtcgcgggacccgttggcagaggtgggctagcctcgaggatatcaagatctggcct cggcggccaagcttggcaatccggtactgttggtaaagccacc |
| 159 | PL5 74 | TTF- 1_2_no space_mi nBIRC5 | ggcctaactggccggtaccactagtagccacttgaaattagccacttgaaattagcc acttgaaattagccacttgaaattagccacttgaaattagccacttgaaattagcca cttgaaatttgcgctcccgacatgccccgcggcgcgccattaaccgccagatttgag tcgcgggacccgttggcagaggtgggctagcctcgaggatatcaagatctggcctcg gcggccaagcttggcaatccggtactgttggtaaagccacc |
| 160 | PL5 75 | TTF- 1_3_no space_mi nBIRC5 | ggcctaactggccggtaccactagtctgggaacaagtgctgggaacaagtgctggga acaagtgctgggaacaagtgctgggaacaagtgctgggaacaagtgctgggaacaag tgctgggaacaagtgtgcgctcccgacatgccccgcggcgcgccattaaccgccaga tttgagtcgcgggacccgttggcagaggtgggctagcctcgaggatatcaagatctg gcctcggcggccaagcttggcaatccggtactgttggtaaagccacc |
| 161 | PL5 76 | TTF- 1_4_no space_mi nBIRC5 | ggcctaactggccggtaccactagtgactcctcaaggggactcctcaaggggactcc tcaaggggactcctcaaggggactcctcaaggggactcctcaaggggactcctcaag gggactcctcaagggtgcgctcccgacatgccccgcggcgcgccattaaccgccaga tttgagtcgcgggacccgttggcagaggtgggctagcctcgaggatatcaagatctg gcctcggcggccaagcttggcaatccggtactgttggtaaagccacc |
| 162 | PL5 77 | TCF7_no space_mi nBIRC5 | ggcctaactggccggtaccactagtcgggctttgatctttcgggctttgatctttcg ggctttgatctttcgggctttgatctttcgggctttgatctttcgggctttgatctt tcgggctttgatctttgcgctcccgacatgccccgcggcgcgccattaaccgccag atttgagtcgcgggacccgttggcagaggtgggctagcctcgaggatatcaagatct ggcctcggcggccaagcttggcaatccggtactgttggtaaagccacc |
| 163 | PL5 78 | TCF7:L2_ no space_mi nBIRC5 | ggcctaactggccggtaccactagtgcgctttgatgtgcggggcggccctttgaagt tggcgctttgatgtgcggggcggccctttgaagttggcgctttgatgtgcggggcgg ccctttgaagttgtgcgctcccgacatgccccgcggcgcgccattaaccgccagatt tgagtcgcgggacccgttggcagaggtgggctagcctcgaggatatcaagatctggc ctcggcggccaagcttggcaatccggtactgttggtaaagccacc |
| 164 | PL5 79 | MSC_no space_mi nBIRC5 | ggcctaactggccggtaccactagtaacagctgttaacagctgttaacagctgttaa cagctgttaacagctgttaacagctgttaacagctgttaacagctgttaacagctgt ttgcgctcccgacatgccccgcggcgcgccattaaccgccagatttgagtcgcggga cccgttggcagaggtgggctagcctcgaggatatcaagatctggcctcggcggccaa gcttggcaatccggtactgttggtaaagccacc |
| 165 | PL5 80 | ZEB1_no space_mi nBIRC5 | ggcctaactggccggtaccactagtcacctgcacctgcacctgcacctgcacctgca cctgcacctgcacctgcacctgcacctgcacctgcacctgcacctgtgcgctcccgacatgcc ccgcggcgcgccattaaccgccagatttgagtcgcgggacccgttggcagaggtggg |

TABLE 1A-continued

Sequences of engineered promoters according to the disclosure

| SEQ ID NO: | EARLI. ID | Name | Regulatory element sequence (nucleotide) |
|---|---|---|---|
| | | | ctagcctcgaggatatcaagatctggcctcggcggccaagcttggcaatccggtact gttggtaaagccacc |
| 166 | PL5 81 | MAX_M YC_no space_mi nBIRC5 | ggcctaactggccggtaccactagtagttcaacacgtggtctgggagttcaacacgt ggtctgggagttcaacacgtggtctgggagttcaacacgtggtctgggagttcaaca cgtggtctgggtgcgctcccgacatgccccgcggcgcgccattaaccgccagatttg agtcgcgggacccgttggcagaggtgggctagcctcgaggatatcaagatctggcct cggcggccaagcttggcaatccggtactgttggtaaagccacc |
| 167 | PL5 82 | GATA6 no space_mi nBIRC5 | ggcctaactggccggtaccactagtgacagataagaaagacagataagaaagacaga taagaaagacagataagaaagacagataagaaagacagataagaaagacagataaga aagacagataagaaatgcgctcccgacatgccccgcggcgcgccattaaccgccaga tttgagtcgcgggacccgttggcagaggtgggctagcctcgaggatatcaagatctg gcctcggcggccaagcttggcaatccggtactgttggtaaagccacc |
| 168 | PL5 83 | GATA1-BIRC5co re | ggcctaactggccggtaccactagtttctaatctatttctaatctatttctaatcta tttctaatctatttctaatctatttctaatctatttctaatctatttctaatctatt tctaatctattgcgctcccgacatgccccgcggcgcgccattaaccgccagatttga gtcgcgggacccgttggcagaggtgggctagcctcgaggatatcaagatctggcctc ggcggccaagcttggcaatccggtactgttggtaaagccacc |
| 169 | PL5 84 | FOSL1_ no space_mi nBIRC5 | ggcctaactggccggtaccactagtggtgactcatgggtgactcatgggtgactcat gggtgactcatgggtgactcatgggtgactcatgggtgactcatgggtgactcatgg gtgactcatgtgcgctcccgacatgccccgcggcgcgccattaaccgccagatttga gtcgcgggacccgttggcagaggtgggctagcctcgaggatatcaagatctggcctc ggcggccaagcttggcaatccggtactgttggtaaagccacc |
| 170 | PL5 85 | STAT3_ no space_mi nBIRC5 | ggcctaactggccggtaccactagtcttctgggaaacttctgggaaacttctgggaa acttctgggaaacttctgggaaacttctgggaaacttctgggaaacttctgggaaac ttctgggaaatgcgctcccgacatgccccgcggcgcgccattaaccgccagatttga gtcgcgggacccgttggcagaggtgggctagcctcgaggatatcaagatctggcctc ggcggccaagcttggcaatccggtactgttggtaaagccacc |
| 171 | PL5 86 | STAT:S TAT_no space_mi nBIRC5 | ggcctaactggccggtaccactagtaattcttagaaataaattcttagaaataaatt cttagaaataaattcttagaaataaattcttagaaataaattcttagaaataaattc ttagaaatatgcgctcccgacatgccccgcggcgcgccattaaccgccagatttgag tcgcgggacccgttggcagaggtgggctagcctcgaggatatcaagatctggcctcg gcggccaagcttggcaatccggtactgttggtaaagccacc |
| 172 | PL5 87 | SOX9_no space_mi nBIRC5 | ggcctaactggccggtaccactagtaaaacaaaggatcctttgttttaaaacaaagg atcctttgttttaaaacaaaggatcctttgttttaaaacaaaggatcctttgtttta aaacaaaggatcctttgttttctgcgctcccgacatgccccgcggcgcgccattaac cgccagatttgagtcgcgggacccgttggcagaggtgggctagcctcgaggatatca agatctggcctcggcggccaagcttggcaatccggtactgttggtaaagccacc |
| 173 | PL5 88 | HNF4_no space_mi nBIRC5 | ggcctaactggccggtaccactagtaaagtccaagtccaaaagtccaagtccaaaag tccaagtccaaaagtccaagtccaaaagtccaagtccaaaagtccaagtccaaaagt ccaagtccatgcgctcccgacatgccccgcggcgcgccattaaccgccagatttgag tcgcgggacccgttggcagaggtgggctagcctcgaggatatcaagatctggcctcg gcggccaagcttggcaatccggtactgttggtaaagccacc |
| 174 | PL5 89 | TTF-1_1_3bp space_mi nBIRC5 | ggcctaactggccggtaccactagtggttttgtggagaggttttgtggtcgggtttt gtgggacggttttgtggtaggttttgtggactggttttgtggtgcggtttttgtggg taggttttgtggtgcgctcccgacatgccccgcggcgcgccattaaccgccagattt gagtcgcgggacccgttggcagaggtgggctagcctcgaggatatcaagatctggcc tcggcggccaagcttggcaatccggtactgttggtaaagccacc |
| 175 | PL5 90 | TTF-1_2_3bp space_mi nBIRC5 | ggcctaactggccggtaccactagtagccacttgaaattagaagccacttgaaattt cgagccacttgaaattgacagccacttgaaattctaagccacttgaaattactagcc acttgaaatttgcgctcccgacatgccccgcggcgcgccattaaccgccagatttga gtcgcgggacccgttggcagaggtgggctagcctcgaggatatcaagatctggcctc ggcggccaagcttggcaatccggtactgttggtaaagccacc |
| 176 | PL5 91 | TTF-1_3_3bp space_mi nBIRC5 | ggcctaactggccggtaccactagtctgggaacaagtgagactgggaacaagtgtcg ctgggaacaagtggacctgggaacaagtgctactgggaacaagtgtcgctgggaaca agtgtgcctgggaacaagtgtcgcgctcccgacatgccccgcggcgcgccattaaccg ccagatttgagtcgcgggacccgttggcagaggtgggctagcctcgaggatatcaag atctggcctcggcggccaagcttggcaatccggtactgttggtaaagccacc |
| 177 | PL5 92 | TTF-1_4_3bp space_mi nBIRC5 | ggcctaactggccggtaccactagtgactcctcaaggggagagactcctcaagggtcg gactcctcaaggggacgactcctcaagggctagactcctcaagggactgactcctca agggtgcgactcctcaagggtgcgctcccgacatgccccgcggcgcgccattaaccg ccagatttgagtcgcgggacccgttggcagaggtgggctagcctcgaggatatcaag atctggcctcggcggccaagcttggcaatccggtactgttggtaaagccacc |

TABLE 1A-continued

Sequences of engineered promoters according to the disclosure

| SEQ ID NO: | EA RLI. ID | Name | Regulatory element sequence (nucleotide) |
|---|---|---|---|
| 178 | PL5 93 | TCF7_3bp space_mi nBIRC5 | ggcctaactggccggtaccactagtccggctttgatcttttagacgggctttgatctt<br>ttcgcgggctttgatctttgaccgggctttgatctttctacgggctttgatctttac<br>tcgggctttgatcttttgcgctcccgacatgccccgcggcgcgccattaaccgccag<br>atttgagtcgcgggacccgttggcagaggtgggctagcctcgaggatatcaagatct<br>ggcctcggcggccaagcttggcaatccggtactgttggtaaagccacc |
| 179 | PL5 94 | TCF7:L2_ 3bp space_mi nBIRC5 | ggcctaactggccggtaccactagtgcgctttgatgtgcggggcggccctttgaagt<br>tgagagcgctttgatgtgcggggcggccctttgaagttgtcggcgctttgatgtgcg<br>gggcggccctttgaagttgtgcgctcccgacatgccccgcggcgcgccattaaccgc<br>cagatttgagtcgcgggacccgttggcagaggtgggctagcctcgaggatatcaaga<br>tctggcctcggcggccaagcttggcaatccggtactgttggtaaagccacc |
| 180 | PL5 95 | MSC_3bp space_mi nBIRC5 | ggcctaactggccggtaccactagtaacagctgttagaaacagctgtttcgaacagc<br>tgttgacaacagctgttctaaacagctgttactaacagctgtttgcaacagctgttg<br>taaacagctgtttgcgctcccgacatgccccgcggcgcgccattaaccgccagattt<br>gagtcgcgggacccgttggcagaggtgggctagcctcgaggatatcaagatctggcc<br>tcggcggccaagcttggcaatccggtactgttggtaaagccacc |
| 181 | PL5 96 | ZEB1_3 bp space_mi nBIRC5 | ggcctaactggccggtaccactagtcacctgagacacctgtcgcacctggaccacct<br>gctacacctgactcacctgtgccacctgagacacctgtcgcacctggaccacctgtg<br>cgctcccgacatgccccgcggcgcgccattaaccgccagatttgagtcgcgggaccc<br>gttggcagaggtgggctagcctcgaggatatcaagatctggcctcggcggccaagct<br>tggcaatccggtactgttggtaaagccacc |
| 182 | PL5 97 | MAX_M YC_3bp space_mi nBIRC5 | ggcctaactggccggtaccactagtagttcaacacgtggtctgggagaagttcaaca<br>cgtggtctgggtcgagttcaacacgtggtctggggacagttcaacacgtggtctggg<br>ctaagttcaacacgtggtctgggtgcgtcccgacatgccccgcggcgcgccattaa<br>ccgccagatttgagtcgcgggacccgttggcagaggtgggctagcctcgaggatatc<br>aagatctggcctcggcggccaagcttggcaatccggtactgttggtaaagccacc |
| 183 | PL5 98 | GATA6_ 3bp space_mi nBIRC5 | ggcctaactggccggtaccactagtgacagataagaaaagagacagataagaaatcg<br>gacagataagaaagacgacagataagaaactagacagataagaaaactgacagataa<br>gaaatgcgacagataagaaatgcgctcccgacatgccccgcggcgcgccattaaccg<br>ccagatttgagtcgcgggacccgttggcagaggtgggctagcctcgaggatatcaag<br>atctggcctcggcggccaagcttggcaatccggtactgttggtaaagccacc |
| 184 | PL5 99 | GATA1_ 3bp space_mi nBIRC5 | ggcctaactggccggtaccactagtttctaatctatagattctaatctattcgttct<br>aatctatgacttctaatctatctattctaatctatactttctaatctattgcttcta<br>atctattgcgctcccgacatgccccgcggcgcgccattaaccgccagatttgagtcg<br>cgggacccgttggcagaggtgggctagcctcgaggatatcaagatctggcctcggcg<br>gccaagcttggcaatccggtactgttggtaaagccacc |
| 185 | PL6 00 | FOSL1_ 3bp space_mi nBIRC5 | ggcctaactggccggtaccactagtggtgactcatgagaggtgactcatgtcgggtg<br>actcatggacggtgactcatgctaggtgactcatgactggtgactcatgtgcggtga<br>ctcatgctgcgctcccgacatgccccgcggcgcgccattaaccgccagatttgagtc<br>gcgggacccgttggcagaggtgggctagcctcgaggatatcaagatctggcctcggc<br>ggccaagcttggcaatccggtactgttggtaaagccacc |
| 186 | PL6 01 | STAT3_ 3bp space_mi nBIRC5 | ggcctaactggccggtaccactagtcttctgggaaaagacttctgggaaatcgcttc<br>tgggaaagaccttctgggaaactacttctgggaaaactcttctgggaaatgccttct<br>gggaaatgcgctcccgacatgccccgcggcgcgccattaaccgccagatttgagtcg<br>cgggacccgttggcagaggtgggctagcctcgaggatatcaagatctggcctcggcg<br>gccaagcttggcaatccggtactgttggtaaagccacc |
| 187 | PL6 02 | STAT:S TAT_3b p space_mi nBIRC5 | ggcctaactggccggtaccactagtaattcttagaaataagaaattcttagaaatat<br>cgaattcttagaaatagacaattcttagaaatactaaattcttagaaataactaatt<br>cttagaaatatgcgctcccgacatgccccgcggcgcgccattaaccgccagatttga<br>gtcgcgggacccgttggcagaggtgggctagcctcgaggatatcaagatctggcctc<br>ggcggccaagcttggcaatccggtactgttggtaaagccacc |
| 188 | PL6 03 | SOX9_3 bp space_mi nBIRC5 | ggcctaactggccggtaccactagtaaaacaaaggatcctttgttttagaaaaacaa<br>aggatcctttgttttcgaaaacaaaggatcctttgttttgacaaaacaaaggatcc<br>tttgttttgcgctcccgacatgccccgcggcgcgccattaaccgccagatttgagt<br>cgcgggacccgttggcagaggtgggctagcctcgaggatatcaagatctggcctcgg<br>cggccaagcttggcaatccggtactgttggtaaagccacc |
| 189 | PL6 04 | HNF4_3 bp space_mi nBIRC5 | ggcctaactggccggtaccactagtaaagtccaagtccaagaaaagtccaagtccat<br>cgaaagtccaagtccagacaaagtccaagtccactaaaagtccaagtccaactaaag<br>tccaagtccatgcgctcccgacatgccccgcggcgcgccattaaccgccagatttga<br>gtcgcgggacccgttggcagaggtgggctagcctcgaggatatcaagatctggcctc<br>ggcggccaagcttggcaatccggtactgttggtaaagccacc |

TABLE 1A-continued

Sequences of engineered promoters according to the disclosure

| SEQ ID NO: | EA RLI. ID | Name | Regulatory element sequence (nucleotide) |
|---|---|---|---|
| 190 | PL6 05 | STAT:S TAT_no space_mi nBIRC5 2 w extra insert | ggcctaactggccggtaccactagtaattcttagaaataaattcttagaaataaatt cttagaaataaattcttagaaataaattcttagaaataaattcttagaaataaattc ttagaaatatgcgctcccgacatgtcccgcggcgcgccattaaccgccagatttgag tcgcgggacccgttggcagaggtgggctagcctcgaggatatcaagatctggcctcg gcggccaagcttggcaatccggtactgttggtaaagccaccatcctcgaggatatca agatctggcctcggcggccaagcttggcaatccggtactgttggtaaagccacc |
| 191 | PL6 16 | HOXA1 3_no space_mi nB | ggcctaactggccggtaccactagtccaataaaaaccaataaaaaccaataaaaacc aataaaaaccaataaaaaccaataaaaaccaataaaaaccaataaaaaccaataaaa atgcgctcccgacatgccccgcggcgcgccattaaccgccagatttgagtcgcggga cccgttggcagaggtgggctagcctcgaggatatcaagatctggcctcggcggccaa gcttggcaatccggtactgttggtaaagccacc |
| 193 | PL6 35 | FOXM1_ no space_co reBIRC5 | ggcctaactggccggtaccactagttgtttacttatgtttacttatgtttacttatg tttacttatgtttacttatgtttacttatgtttacttatgtttacttatgtttactt atgcgctcccgacatgccccgcggcgcgccattaaccgccagatttgagtcgcggga cccgttggcagaggtgggctagcctcgaggatatcaagatctggcctcggcggccaa gcttggcaatccggtactgttggtaaagccacc |
| 194 | PL6 36 | E2F2_no space_co reBIRC5 | ggcctaactggccggtaccactagtaaaatggcgccattttaaaatggcgccatttt aaaatggcgccattttaaaatggcgccattttaaaatggcgccattttaaaatggcg ccattttttgcgctcccgacatgccccgcggcgcgccattaaccgccagatttgagtc gcgggacccgttggcagaggtgggctagcctcgaggatatcaagatctggcctcggc ggccaagcttggcaatccggtactgttggtaaagccacc |
| 195 | PL6 37 | RUNX1_ no space_co reBIRC5 | ggcctaactggccggtaccactagttattgtggttatattgtggttatattgtggtt atattgtggttatattgtggttatattgtggttatattgtggttatattgtggttat gcgctcccgacatgccccgcggcgcgccattaaccgccagatttgagtcgcgggacc cgttggcagaggtgggctagcctcgaggatatcaagatctggcctcggcggccaagc ttggcaatccggtactgttggtaaagccacc |
| 196 | PL6 38 | SOX4_no space_co reBIRC5 | ggcctaactggccggtaccactagtgaacaattgcagtgttgaacaattgcagtgtt gaacaattgcagtgttgaacaattgcagtgttgaacaattgcagtgttgaacaattg cagtgttgaacaattgcagtgtttgcgctcccgacatgccccgcggcgcgccattaa ccgccagatttgagtcgcgggacccgttggcagaggtgggctagcctcgaggatatc aagatctggcctcggcggccaagcttggcaatccggtactgttggtaaagccacc |
| 197 | PL6 39 | RREB1_ no space_co reBIRC5 | ggcctaactggccggtaccactagtccccaaaccacccccccccccccccaaaccacc cccccccccccaaaccacccccccccccccccaaaccacccccccccccccccaaacc acccccccccctgcgctcccgacatgccccgcggcgcgccattaaccgccagatttg agtcgcgggacccgttggcagaggtgggctagcctcgaggatatcaagatctggcct cggcggccaagcttggcaatccggtactgttggtaaagccacc |
| 198 | PL6 40 | ETV4_no space_co reBIRC5 | CACTAGTACCGGAAGTAACCGGAAGTAACCGGAAGTAACCGGAAGTAACCGGAAGTA ACCGGAAGTAACCGGAAGTAACCGGAAGTAACCGGAAGTAtgcgctcccgacatgcc ccgcggcgcgccattaaccgccagatttgagtcgcgggacccgttggcagaggtggg ctagcctcgaggatatcaagatctggcctcggcggccaagcttggcaatccggtact gttggtaaagccacc |
| 199 | PL6 41 | HES6_no space_co reBIRC5 | ggcctaactggccggtaccactagtggcacgtgttggcacgtgttggcacgtgttgg cacgtgttggcacgtgttggcacgtgttggcacgtgttggcacgtgttggcacgtgt ttgcgctcccgacatgccccgcggcgcgccattaaccgccagatttgagtcgcggga cccgttggcagaggtgggctagcctcgaggatatcaagatctggcctcggcggccaa gcttggcaatccggtactgttggtaaagccacc |
| 200 | PL6 42 | ASCL1_ no space_co reBIRC5 | ggcctaactggccggtaccactagtcgagcagctggtgcgagcagctggtgcgagca gctggtgcgagcagctggtgcgagcagctggtgcgagcagctggtgcgagcagctgg tgtcgcgctcccgacatgccccgcggcgcgccattaaccgccagatttgagtcgcggg acccgttggcagaggtgggctagcctcgaggatatcaagatctggcctcggcggcca agcttggcaatccggtactgttggtaaagccacc |
| 201 | PL6 43 | TWIST1_ no space_co reBIRC5 | ggcctaactggccggtaccactagttccagatgtttccagatgtttccagatgtttc cagatgtttccagatgtttccagatgtttccagatgtttccagatgtttgcgctccc gacatgccccgcggcgcgccattaaccgccagatttgagtcgcgggacccgttggca gaggtgggctagcctcgaggatatcaagatctggcctcggcggccaagcttggcaat ccggtactgttggtaaagccacc |
| 202 | PL6 44 | FOXA3_ no space_co reBIRC5 | ggcctaactggccggtaccactagtatagtaaacaatagtaaacaatagtaaacaat agtaaacaatagtaaacaatagtaaacaatagtaaacaatagtaaacatgcgctccc gacatgccccgcggcgcgccattaaccgccagatttgagtcgcgggacccgttggca gaggtgggctagcctcgaggatatcaagatctggcctcggcggccaagcttggcaat ccggtactgttggtaaagccacc |

TABLE 1A-continued

Sequences of engineered promoters according to the disclosure

| SEQ ID NO: | EARLI. ID | Name | Regulatory element sequence (nucleotide) |
|---|---|---|---|
| 203 | PL6 45 | PITX2_no space_co reBIRC5 | ggcctaactggccggtaccactagttaatccctaatccctaatccctaatccctaat ccctaatccctaatccctaatccctaatccctaatccctaatccctgcgctcccgac atgccccgcggcgcgccattaaccgccagatttgagtcgcgggacccgttggcagag gtgggctagcctcgaggatatcaagatctggcctcggcggccaagcttggcaatccg gtactgttggtaaagccacc |
| 204 | PL6 46 | HOXB2_ no space_co reBIRC5 | ggcctaactggccggtaccactagtctaattaactaattaactaattaactaattaa ctaattaactaattaactaattaactaattaactaattaactaattaatgcgctccc gacatgccccgcggcgcgccattaaccgccagatttgagtcgcgggacccgttggca gaggtgggctagcctcgaggatatcaagatctggcctcggcggccaagcttggcaat ccggtactgttggtaaagccacc |
| 205 | PL6 47 | EN2_no space_co reBIRC5 | ggcctaactggccggtaccactagtcccaattagccccaattagccccaattagccc caattagccccaattagccccaattagccccaattagctgcgctcccgacatgcccc gcggcgcgccattaaccgccagatttgagtcgcgggacccgttggcagaggtgggct agcctcgaggatatcaagatctggcctcggcggccaagcttggcaatccggtactgt tggtaaagccacc |
| 206 | PL6 48 | DLX4_no space_co reBIRC5 | ggcctaactggccggtaccactagtcaattacaattacaattacaattacaattaca attacaattacaattacaattacaattacaattatgcgctcccgacatgccccgcgg cgcgccattaaccgccagatttgagtcgcgggacccgttggcagaggtgggctagcc tcgaggatatcaagatctggcctcggcggccaagcttggcaatccggtactgttggt aaagccacc |
| 207 | PL6 49 | GRHL1_ no space_co reBIRC5 | ggcctaactggccggtaccactagtaaaaccggtttttaaaaccggtttttaaaaccgg ttttaaaaccggtttttaaaaccggtttttaaaaccggtttttaaaaccggtttttaaaac cggtttttgcgctcccgacatgccccgcggcgcgccattaaccgccagatttgagtc gcgggacccgttggcagaggtgggctagcctcgaggatatcaagatctggcctcggc ggccaagcttggcaatccggtactgttggtaaagccacc |
| 208 | PL6 50 | FOXM1_ 3bp space_co reBIRC5 | ggcctaactggccggtaccactagttgtttacttaagatgtttacttatcgtgttta cttagactgtttacttactatgtttacttacttgtttacttatgcgtgtttacttat gcgctcccgacatgccccgcggcgcgccattaaccgccagatttgagtcgcgggacc cgttggcagaggtgggctagcctcgaggatatcaagatctggcctcggcggccaagc ttggcaatccggtactgttggtaaagccacc |
| 209 | PL6 51 | E2F2_3b p space_co reBIRC5 | ggcctaactggccggtaccactagtaaaatggcgccattttcgaaaatggcgccat tttgacaaaatggcgccattttctaaaaatggcgccattttactaaaatggcgccat ttttgcaaaatggcgccattttgcgctcccgacatgccccgcggcgcgccattaac cgccagatttgagtcgcgggacccgttggcagaggtgggctagcctcgaggatatca agatctggcctcggcggccaagcttggcaatccggtactgttggtaaagccacc |
| 210 | PL6 52 | RUNX1_ 3bp space_co reBIRC5 | ggcctaactggccggtaccactagttattgtggttatcgtattgtggttagactatt gtggttactatattgtggttaacttattgtggttatgctattgtggttatgcgctcc cgacatgccccgcggcgcgccattaaccgccagatttgagtcgcgggacccgttggc agaggtgggctagcctcgaggatatcaagatctggcctcggcggccaagcttggcaa tccggtactgttggtaaagccacc |
| 211 | PL6 53 | SOX4_3 bp space_co reBIRC5 | ggcctaactggccggtaccactagtgaacaattgcagtgttgacgaacaattgcagt gttctagaacaattgcagtgttactgaacaattgcagtgtttgcgaacaattgcagt gtttgcgctcccgacatgccccgcggcgcgccattaaccgccagatttgagtcgcgg gacccgttggcagaggtgggctagcctcgaggatatcaagatctggcctcggcggcc aagcttggcaatccggtactgttggtaaagccacc |
| 212 | PL6 54 | RREB1_ 3bp space_co reBIRC5 | ggcctaactggccggtaccactagtccccaaaccaccccccccccgacccccaaacc accccccccccctaccccaaaccacccccccccactccccaaaccacccccccccc tgcgctcccgacatgccccgcggcgcgccattaaccgccagatttgagtcgcgggac ccgttggcagaggtgggctagcctcgaggatatcaagatctggcctcggcggccaag cttggcaatccggtactgttggtaaagccacc |
| 213 | PL6 55 | ETV4_3 bp space_co reBIRC5 | ggcctaactggccggtaccactagtaccggaagtaagaaccggaagtatcgaccgga agtagacaccggaagtactaaccggaagtaactaccggaagtatgcaccggaagtat gcgctcccgacatgccccgcggcgcgccattaaccgccagatttgagtcgcgggacc cgttggcagaggtgggctagcctcgaggatatcaagatctggcctcggcggccaagc ttggcaatccggtactgttggtaaagccacc |
| 214 | PL6 56 | HES6_3 bp space_co reBIRC5 | ggcctaactggccggtaccactagtggcacgtgttagaggcacgtgtttcgggcacg tgttgacggcacgtgttctaggcacgtgttactggcacgtgtttgcggcacgtgttt gcgctcccgacatgccccgcggcgcgccattaaccgccagatttgagtcgcgggacc cgttggcagaggtgggctagcctcgaggatatcaagatctggcctcggcggccaagc ttggcaatccggtactgttggtaaagccacc |

TABLE 1A-continued

Sequences of engineered promoters according to the disclosure

| SEQ ID NO: | EARLI. ID | Name | Regulatory element sequence (nucleotide) |
|---|---|---|---|
| 215 | PL6 57 | ASCL1_ 3bp space_co reBIRC5 | ggcctaactggccggtaccactagtcgagcagctggtgagacgagcagctggtgtcg cgagcagctggtggaccgagcagctggtgctacgagcagctggtgactcgagcagct ggtgtgcgctcccgacatgccccgcggcgcgccattaaccgccagatttgagtcgcg ggaccgttggcagaggtgggctagcctcgaggatatcaagatctggcctcggcggc caagcttggcaatccggtactgttggtaaagccacc |
| 216 | PL6 58 | TWIST1_ 3bp space_co reBIRC5 | ggcctaactggccggtaccactagttccagatgttagatccagatgtttcgtccaga tgttgactccagatgttctatccagatgttacttccagatgtttgctccagatgttt gcgctcccgacatgccccgcggcgcgccattaaccgccagatttgagtcgcgggacc cgttggcagaggtgggctagcctcgaggatatcaagatctggcctcggcggccaagc ttggcaatccggtactgttggtaaagccacc |
| 217 | PLE 59 | FOXA3_ 3bp space_co reBIRC5 | ggcctaactggccggtaccactagtatagtaaacaagaatagtaaacatcgatagta aacagacatagtaaacactaatagtaaacaactatagtaaacatgcatagtaaacat gcgctcccgacatgccccgcggcgcgccattaaccgccagatttgagtcgcgggacc cgttggcagaggtgggctagcctcgaggatatcaagatctggcctcggcggccaagc ttggcaatccggtactgttggtaaagccacc |
| 218 | PL6 60 | PITX2_3 bp space_co reBIRC5 | ggcctaactggccggtaccactagttaatcccagataatccctcgtaatcccgacta atccctataatcccacttaatccctgctaatcccacttaatccctgctaatccctg cgctcccgacatgccccgcggcgcgtcattaaccgccagatttgagtcgcgggaccc gttggcagaggtgggctagcctcgaggatatcaagatctggcctcggcggccaagct tggcaatccggtactgttggtaaagccacc |
| 219 | PLE 61 | HOXB2_ 3bp space_co reBIRC5 | ggcctaactggccggtaccactagtctaattaaagactaattaatcgctaattaaga cctaattaactactaattaaactctaattaatgcctaattaaactctaattaatgcg ctcccgacatgccccgcggcgcgccattaaccgccagatttgagtcgcgggacccgt tggcagaggtgggctagcctcgaggatatcaagatctggcctcggcggccaagcttg gcaatccggtactgttggtaaagccacc |
| 220 | PL6 62 | EN2_3bp space_co reBIRC5 | ggcctaactggccggtaccactagtcccaattagcagacccaattagctcgcccaat tagcgaccccaattagcctacccaattagcactcccaattagctgccccaattagct gcgctcccgacatgccctgcggcgcgccattaaccgccagatttgagtcgcgggacc cgttggcagaggtgggctagcctcgaggatatcaagatctggcctcggcggccaagc ttggcaatccggtactgttggtaaagccacc |
| 221 | PL6 63 | DLX4_3 bp space_co reBIRC5 | ggcctaactggccggtaccactagtcaattaagacaattatcgcaattagaccaatt actacaattaactcaattatgccaattaactcaattatgccaattaagacaattatg cgctcccgacatgccccgcggcgtgccattaaccgccagatttgagtcgcgggaccc gttggcagaggtgggctagcctcgaggatatcaagatctggcctcggcggccaagct tggcaatccggtactgttggtaaagccacc |
| 222 | PL6 64 | GRHL1_ 3bp space_co reBIRC5 | ggcctaactggccggtaccactagtaaaaccggtttttagaaaaaccggtttttcgaa aaccggttttgacaaaaccggttttctaaaaaccggttttactaaaaccggtttttg caaaaccggttttgcgctcccgacatgccccgcggcgcgccattaaccgccagatt tgagtcgcgggacccgttggcagaggtgggctagcctcgaggatatcaagatctggc ctcggcggccaagcttggcaatccggtactgttggtaaagccacc |
| 223 | PL6 69 | FOSL1- 5X_BIR C5core | ggcctaactggccggtaccactagtggtgactcatgggtgactcatgggtgactcat gggtgactcatgggtgactcatgtgcgctcccgacatgccccgcggcgcgccattaa ccgccagatttgagtcgcgggacccgttggcagaggtgggctagcctcgaggatatc aagatctggcctcggcggccaagcttggcaatccggtactgttggtaaagccacc |
| 224 | PL6 72 | FOSL1- 11X_BI RC5core | ggcctaactggccggtaccactagtggtgactcatgggtgactcatgggtgactcat gggtgactcatgggtgactcatgggtgactcatgggtgactcatgggtgactcatgg gtgactcatgggtgactcatgggtgactcatgtgcgctcccgacatgccccgcggcg cgccattaaccgccagatttgagtcgcgggacccgttggcagaggtgggctagcctc gaggatatcaagatctggcctcggcggccaagcttggcaatccggtactgttggtaa agccacc |
| 225 | PL6 73 | FOSL1- 7X_BIR C5core | ggcctaactggccggtaccactagtggtgactcatgggtgactcatgggtgactcat gggtgactcatgggtgactcatgggtgactcatgtgcgctcccgac atgccccgcggcgcgccattaaccgccagatttgagtcgcgggacccgttggcagag gtgggctagcctcgaggatatcaagatctggcctcggcggccaagcttggcaatccg gtactgttggtaaagccacc |
| 226 | PL6 74 | FOSL1_ no space_no p53_BIR C5core | ggcctaactggccggtaccactagtggtgactcatgggtgactcatgggtgactcat gggtgactcatgggtgactcatgggtgactcatgggtgactcatgggtgactcatgg gtgactcatgcggcgcgccattaaccgccagatttgagtcgcgggacccgttggcag aggtgggctagcctcgaggatatcaagatctggcctcggcggccaagcttggcaatc cggtactgttggtaaagccacc |

TABLE 1A-continued

Sequences of engineered promoters according to the disclosure

| SEQ ID NO: | EA RLI. ID | Name | Regulatory element sequence (nucleotide) |
|---|---|---|---|
| 227 | PL6 75 | FOSL1_ TATATS S_10bp spacing | ggcctaactggccggtaccactagtggtgactcatgggtgactcatgggtgactcat gggtgactcatgggtgactcatgggtgactcatgggtgactcatgggtgactcatgg gtgactcatgcggtgctagctataaaaggccagcagcagcctgaccacatctcatcc tcctcgaggatatcaagatctggcctcggcggccaagcttggcaatccggtactgtt ggtaaagccacc |
| 228 | PL6 76 | FOSL1_ TATATS S_no spacing | ggcctaactggccggtaccactagtggtgactcatgggtgactcatgggtgactcat gggtgactcatgggtgactcatgggtgactcatgggtgactcatgggtgactcatgg gtgactcatgtataaaaggccagcagcagcctgaccacatctcatcctcctcgagga tatcaagatctggcctcggcggccaagcttggcaatccggtactgttggtaaagcca cc |
| 229 | PL6 85 | FOSL1_ TATATS S_25bp spacing | ggcctaactggccggtaccactagtggtgactcatgggtgactcatgggtgactcat gggtgactcatgggtgactcatgggtgactcatgggtgactcatgggtgactcatgg gtgactcatgacatctttcagggaccggtgctagctataaaaggccagcagcagcct gaccacatctcatcctcctcgaggatatcaagatctggcctcggcggccaagcttgg caatccggtactgttggtaaagccacc |
| 230 | PL6 86 | FOSL1_ TATATS S_50bp spacing | ggcctaactggccggtaccactagtggtgactcatgggtgactcatgggtgactcat gggtgactcatgggtgactcatgggtgactcatgggtgactcatgggtgactcatgg gtgactcatgtggctattagcagtaccgcttagacacatctttcagggaccggtgct agctataaaaggccagcagcagcctgaccacatctcatcctcctcgaggatatcaag atctggcctcggcggccaagcttggcaatccggtactgttggtaaagccacc |
| 231 | PL6 89 | Forkhead_ 7XFOS L1_BIR C5core | ggcctaactggccggtaccactagtctgtttacctgtttacctgtttacctgtttac ctgtttacggtgactcatgggtgactcatgggtgactcatgggtgactcatgggtga ctcatgggtgactcatgggtgactcatgggtgactcatgggtgactcatgtgcgctc ccgacatgccccgcggcgcgccattaaccgccagatttgagtcgcgggacccgttgg cagaggtgggctagcctcgaggatatcaagatctggcctcggcggccaagcttggca atccggtactgttggtaaagccacc |
| 232 | PL6 90 | Forkhead_ 7XFOS L1_BIR C5core 3bp | ggcctaactggccggtaccactagtctgtttacagactgtttactcgctgtttacga cctgtttacctactgtttacggtgactcatgggtgactcatgggtgactcatgggtg actcatgggtgactcatgggtgactcatgggtgactcatgggtgactcatgggtgac tcatgtgcgctcccgacatgccccgcggcgcgccattaaccgccagatttgagtcgc gggacccgttggcagaggtgggctagcctcgaggatatcaagatctggcctcggcgg ccaagcttggcaatccggtactgttggtaaagccacc |
| 233 | PL8 25 | FOSL1_ 10bp spacer_c oreBIRC 5 | ggcctaactggccggtaccactagtggtgactcatgggtgactcatgggtgactcat gggtgactcatgggtgactcatgggtgactcatgggtgactcatgggtgactcatgg gtgactcatgcataggcctctgaacaacgcgtcccgacatgccccgcggcgcgccat taaccgccagatttgagtcgcgggacccgttggcagaggtgggctagcctcgaggat atcaagatctggcctcggcggccaagcttggcaatccggtactgttggtaaagccac c |
| 234 | PL8 26 | FOSL1_ 30bp spacer_c oreBIRC 5 | ggcctaactggccggtaccactagtggtgactcatgggtgactcatgggtgactcat gggtgactcatgggtgactcatgggtgactcatgggtgactcatgggtgactcatgg gtgactcatgcataggcctctgatagagctgcgatagaccaagacaacgcgtcccga catgccccgcggcgcgccattaaccgccagatttgagtcgcgggacccgttggcaga ggtgggctagcctcgaggatatcaagatctggcctcggcggccaagcttggcaatcc ggtactgttggtaaagccacc |
| 235 | PL8 27 | FOSL1_ 88bp spacer_c oreBIRC 5 | ggcctaactggccggtaccactagtggtgactcatgggtgactcatgggtgactcat gggtgactcatgggtgactcatgggtgactcatgggtgactcatgggtgactcatgg gtgactcatgcatagaaacgacgcaatatctccatagggttaacggcggaacttgac ggcgtccattagccacttggtcatgggacaggggggaaaacggacaacgcgtcccg acatgccccgcggcgcgccattaaccgccagatttgagtcgcgggacccgttggcag aggtgggctagcctcgaggatatcaagatctggcctcggcggccaagcttggcaatc cggtactgttggtaaagccacc |
| 236 | PL8 28 | FOSL1_ Low_cor eBIRC5 | ggcctaactggccggtaccactagtggtgactcatgggtgactcatgggtgactcat gggtgactcatgggtgactcatgggtgactcatgggtgactcatgggtgactcatgg gtgactcatgcataccggaagtacttgcgcaatgaccggaagtacaacgcgtcccga catgccccgcggcgcgccattaaccgccagatttgagtcgcgggacccgttggcaga ggtgggctagcctcgaggatatcaagatctggcctcggcggccaagcttggcaatcc ggtactgttggtaaagccacc |
| 237 | PL8 29 | FOSL1_ Medium coreBI RC5 | ggcctaactggccggtaccactagtggtgactcatgggtgactcatgggtgactcat gggtgactcatgggtgactcatgggtgactcatgggtgactcatgggtgactcatgg gtgactcatgcatttgcgcaacaggggcgggtgatgacacagcaattcgcttgcgt gagaagagaccggaagtgagggactttccacatgacacagcaatacaacgcgtcccg acatgccccgcggcgcgccattaaccgccagatttgagtcgcgggacccgttggcag aggtgggctagcctcgaggatatcaagatctggcctcggcggccaagcttggcaatc cggtactgttggtaaagccacc |

TABLE 1A-continued

Sequences of engineered promoters according to the disclosure

| SEQ ID NO: | EARLI. ID | Name | Regulatory element sequence (nucleotide) |
|---|---|---|---|
| 238 | PL8 30 | FOSL1_High_cor eBIRC5 | ggcctaactggccggtaccactagtggtgactcatgggtgactcatgggtgactcat gggtgactcatgggtgactcatgggtgactcatgggtgactcatgggtgactcatgg gtgactcatgcatggggggggtgatgacacagcaattcgggactttccacgcttgc gtgagaagagaccggaagtgaatgacacagcaattcgcttgcgtgagaagctgggac tttcctaggggcggggttgggactttccacatgacacagcaatacaacgcgtcccga catgccccgcggcgcgccattaaccgccagatttgagtcgcgggacccgttggcaga ggtgggctagcctcgaggatatcaagatctggcctcggcggccaagcttggcaatcc ggtactgttggtaaagccacc |
| 239 | PL8 31 | Low_cor eBIRC5 | ggcctaactggccggtaccactagtaccggaagtacttgcgcaatgaccggaagtac aacgcgtcccgacatgccccgcggcgcgccattaaccgccagatttgagtcgcggga cccgttggcagaggtgggctagcctcgaggatatcaagatctggcctcggcggccaa gcttggcaatccggtactgttggtaaagccacc |
| 240 | PL8 32 | Medium_ coreBI RC5 | ggcctaactggccggtaccactagtttgcgcaacaggggggggtgatgacacagca attcgcttgcgtgagaagagaccggaagtgagggactttccacatgacacagcaata caacgcgtcccgacatgccccgcggcgcgccattaaccgccagatttgagtcgcggg acccgttggcagaggtgggctagcctcgaggatatcaagatctggcctcggcggcca agcttggcaatccggtactgttggtaaagccacc |
| 241 | PL8 33 | High_cor eBIRC5 | ggcctaactggccggtaccactagtggggcggggtgatgacacagcaattcgggact ttccacgcttgcgtgagaagagaccggaagtgaatgacacagcaattcgcttgcgtg agaagctgggactttcctaggggcggggttgggactttccacatgacacagcaatac aacgcgtcccgacatgccccgcggcgcgccattaaccgccagatttgagtcgcggga cccgttggcagaggtgggctagcctcgaggatatcaagatctggcctcggcggccaa gcttggcaatccggtactgttggtaaagccacc |
| 242 | PL8 34 | FOSL1_ Tetramer p53_core BIRC5 | ggcctaactggccggtaccactagtggtgactcatgggtgactcatgggtgactcat gggtgactcatgggtgactcatgggtgactcatgggtgactcatgggtgactcatgg gtgactcatgcatacaacgcgtcccgacatgccccgacatgcccatcgacatgcccc gacatgccccgcggcgcgccattaaccgccagatttgagtcgcgggacccgttggcag aggtgggctagcctcgaggatatcaagatctggcctcggcggccaagcttggcaatc cggtactgttggtaaagccacc |
| 243 | PL8 35 | FOSL1_ p53RE_c oreBIRC 5 | ggcctaactggccggtaccactagtggtgactcatgggtgactcatgggtgactcat gggtgactcatgggtgactcatgggtgactcatgggtgactcatgggtgactcatgg gtgactcatgcatgaattcggacatgcccgggcatgtccccaggacatgcccgggc atgtccccagagacatgtccagacatgtccccaggaacatgtcccaacatgttgtcc aggagacatgtccagacatgtccccaggaacatgtcccaacatgttgtactagtaca acgcgtcccgacatgccccgcggcgcgccattaaccgccagatttgagtcgcgggac ccgttggcagaggtgggctagcctcgaggatatcaagatctggcctcggcggccaag cttggcaatccggtactgttggtaaagccacc |
| 244 | PL8 36 | EN7R_F OSL1_co reBIRC5 | ggcctaactggccggtacctgccactcaaagtggcacactccctgctcaggaggccg ggagggaggacacagccctggcaactcctcctgccccggggggtcaggaaggggtcac cccacactccagaaccctacagaatgtggccttggcttttcccatcaagagctgggg aaagccaggccccgacttcattaccccctgccccgtcccatgctcagtgggcccca tcgtgggtccatgccacactcccaactgagcagccccgcagccccgcgtgtcacaga catgggccctcctaattgctgctgaggtcccaatccctggctggacgtgcctg |
| 245 | PL8 58 | FOSL1_ CS6X- BIRC5co re | ggcctaactggccggtaccactagtggtgactcatgggtgactcatgggtgactcat gggtgactcatgggtgactcatgggtgactcatgggtgactcatgggtgactcatga ctagtgtccccacccacacattcctgtccccacccacacattcctgtccccacccac acattcctgtccccacccacacattcctgtccccacccacacattcctgtccccacc cacacattcctgtgcgctcccgacatgccccgcggcgcgccattaaccgccagattt gagtcgcgggacccgttggcagaggtgggctagcctcgaggatatcaagatctggcc tcggcggccaagcttggcaatccggtactgttggtaaagccacc |
| 246 | PL8 80 | pGL4.10- coreCEA CAM5_1 | ggcctaactggccggtaccaagacaggttgtcctcccaggggatgggggtccatcca ccttgccgaaaagatttgtctgaggaactgaaaatgaagggaaaaaagaggaggga caaaagaggcagaaatgagaggggaggggacagaggacacctgaataaagaccacac ccatgacccacgtgatgctgagaagtactcctgccctaggaagagactcagggcaga gggaggaaggacagcagaccagacagtcacagcagccttgacaaaacgttcctggaa ctaccggtgctagcctcgaggatatcaagatctggcctcggcggccaagcttggcaa tccggtactgttggtaaagccacc |
| 247 | PL8 81 | pGL4.10- coreCEA CAM5_2 | ggcctaactggccggtaccatgacccacgtgatgctgagaagtactcctgccctagg aagagactcagggcagagggaggaaggacagcagaccagacagtcacagcagccttg acaaaacgttcctggaactaccggtgctagcctcgaggatatcaagatctggcctcg gcggccaagcttggcaatccggtactgttggtaaagccacc |

TABLE 1A-continued

Sequences of engineered promoters according to the disclosure

| SEQ ID NO: | EARLI. ID | Name | Regulatory element sequence (nucleotide) |
|---|---|---|---|
| 248 | PL8 82 | pGL4.10-coreFAM111B_1 | ggcctaactggccggtaccctggatgctcatcccgccaccgtcgcccaccccgccgc tgcagaaaggcagcaactgccacacacctaagcaacttggcgggctattcgccctgc agctgccgccagcgcgcggctcccgccagcgcgctggcaatcaaaagtcggagaaag cgcgaaacctccaggcacctcccactccgcccagctaccgcgcagctcctccctagc ctccactgggagacaggggacgcccatgagcgggaaagagcagggcggtgattgctt agtttatcctgggacacgggaactggccgtggactgagtggtgccggggagggggatc actgagaccgggaagggtcatccagacaaataggggagggtgggcgggttggcgcgca gtaccctcggcccggccttcagacccacctgcgcgcgctgcgcgctcatccggtcct tcccttcaatcactgtctggagtgatgataattggcttccacagtggatgagagatg agtcatttacatccaatgagagaaaaacagcctccagagactcttcgtccattggcc agcgagagtgtcagttcccaggctcctgccgcgcacgggcgagcccttctaggcggg aaaagttcagctgagagatataaaagagcagtctttccagcacctgcaaatccagag cggcgggcactgacgggcacttgcaccgtgtggacagactctccggttctgtgagtg gttttttcttttcccgggtcggacctggagttcttaggggatggctgaaccggtgct agcctcgaggatatcaagatctggcctcggcggccaagcttggcaatccggtactgt tggtaaagccacc |
| 249 | PL8 83 | pGL4.10-coreFAM111B_2 | ggcctaactggccggtacctgagaccgggaagggtcatccagacaaatagggagggt gggcgggttggcgcgcagtaccctcggcccggccttcagacccacctgcgcgcgctg cgcgctcatccggtccttcccttcaatcactgtctggagtgatgataattggcttcc acagtggatgagagatgagtcatttacatccaatgagagaaaaacagcctccagaga ctcttcgtccattggccagcgagagtgtcagttcccaggctcctgccgcgcacgggc gagcccttctaggcgggaaaagttcagctgagagatataaaagagcagtctttccag cacctgcaaatccagagcggcgggcactgacgggcacttgcaccgtgtggacagact ctccggttctgtgagtggttttttcttttcccgggtcggacctggagttcttaggggg atggctgaaccggtgctagcctcgaggatatcaagatctggcctcggcggccaagct tggcaatccggtactgttggtaaagccacc |
| 250 | PL8 84 | pGL4.10-coreFAM111B_3 | ggcctaactggccggtaccgggaaaagttcagctgagagatataaaagagcagtctt tccagcacctgcaaatccagagcggcgggcactgacgggcacttgcaccgtgtggac agactctccggttctgtgagtggttttttcttttcccgggtcggacctggagttctta ggggatggctgaaccggtgctagcctcgaggatatcaagatctggcctcggcggcc aagcttggcaatccggtactgttggtaaagccacc |
| 251 | PL8 85 | pGL4.10-coreCEP55 | ggcctaactggccggtaccctgctcctccttcttgcgggccgcgccctgccggcagt gacgtgccccgccctgcagccgcgggattcaaactcccggaagcggcatccacacct gatggtgtgactcggccgacgcgagcgccgcgcttcgcttcagctgctaaccggtgc tagcctcgaggatatcaagatctggcctcggcggccaagcttggcaatccggtactg ttggtaaagccacc |
| 252 | PL8 86 | pGL4.10-coreKIF20A | ggcctaactggccggtaccggcccgcccctttccttacgcggattggtagctgcag gcttccctatctgattggccgaacgaacgcagcgcgtaatttaaaatattgtatctg taacaaagctgcacctcgtgggcggagttgtgctctgcggctgcgaaagtccagctt cggcgactaggtgtgagtaagccagtatcccaggaggagcaagtggcacgtcttcgg gtgagtgtgcggctgtgctggagcccgggttaccagctcttaccggtgctagcctcg aggatatcaagatctggcctcggcggccaagcttggcaatccggtactgttggtaaa gccacc |
| 253 | PL8 87 | pGL4.10-coreAGR2_1 | ggcctaactggccggtaccttgttttgacaggagcagggaagtattgtagaaaataa tttttatcataatggagtatggcaggttatatgactgcgaggatcagaattgtgaat catctcttgtgtgtcttcaagtaaataaaggcaatctgcccacggagcagaaaaaaa atctacaaactacaaactctgtccaatcatgtaaagacaaatcagccttcaggcaaa tcaaatgtcttcattcaaagtctacctggatttggcactctgcccatcgtttcaaaa cctcttaacaatacgtttcacaaatagttaaaaacatgcatactgaaaagcatactt ttgcaatgttattttttaaaaacaaggaactctttaacccagggaagataatcacttg gggaaaggaaggttcgtttctgagttagcaacaagtaaatgcagcactagtgggtgg gattgaggtgtgccctggtgcataaatagagactcagctgtgctggcacactcagaa gcttggaccgcatcctagccgccgactcacacaaggcaggtgggtgaggaaatccag gtaaggctcctgacagcagctttagaagggtacttgctggagtgaattcgggcctct gattaccggtgctagcctcgaggatatcaagatctggcctcggcggccaagcttggc aatccggtactgttggtaaagccacc |
| 254 | PL8 88 | pGL4.10-coreAGR2_2 | ggcctaactggccggtaccacctcttaacaatacgtttcacaaatagttaaaaacat gcatactgaaaagcatacttttgcaatgttattttttaaaaacaaggaactctttaac ccagggaagataatcacttgggggaaaggaaggttcgtttctgagttagcaacaagta aatgcagcactagtgggtgggattgaggtgtgccctggtgcataaatagagactcag ctgtgctggcacactcagaagcttggaccgcatcctagccgccgactcacacaaggc aggtgggtgaggaaatccaggtaaggctcctgacagcagctttagaagggtacttgc tggagtgaattcgggcctctgattaccggtgctagcctcgaggatatcaagatctgg cctcggcggccaagcttggcaatccggtactgttggtaaagccacc |

TABLE 1A-continued

Sequences of engineered promoters according to the disclosure

| SEQ ID NO: | EARLI. ID | Name | Regulatory element sequence (nucleotide) |
|---|---|---|---|
| 255 | PL8 89 | pGL4.10-coreUBE2C | ggcctaactggccggtacccagtgggtaggtctagcagtggcgcagcaatagagcgc tccggagcgtctcattggctggatcaaacccaagcgagccattgattggtcgacgcc cccagagggttacaattcaaacgcgggcgggcgggccccgcagtcctgcagttgcagt cgtgttctccgagttcctgtctctctgccgagctagcctcgaggatatcaagatctg gcctcggcggccaagcttggcaatccggtactgttggtaaagccacc |
| 256 | PL8 90 | pGL4.10-coreCST1 | ggcctaactggccggtaccagtggtgggggagtgaaaagagagatggagaaagaggg gatgggcagaaagaggaggaggagtcaggggcagggcatggaggtgggtggggctgg gctgccaaagcaggataaatgcacacctgcctgctggtctgggctccctgcctcggg ctctcaccctcctctcctgcagctccagctttgtgctctaccggtgctagcctcgag gatatcaagatctggcctcggcggccaagcttggcaatccggtactgttggtaaagc cacc |
| 257 | PL8 93 | hTERT-FLUC | ggcctaactggccggtaccactagtcgggttaccccacagcctaggccgattcgacc tctctccgctggggccctcgctggcgtccctgcaccctgggagcgcgagcggcgcgc gggcggggaagcgcggcccagacccccgggtccgcccggagcagctgcgctgtcggg gccaggccgggctcccagtggattcgcgggcacagacgcccaggaccgcgcttccca cgtggcggagggactggggacccgggcacccgtcctgccccttcaccttccagctcc gcctcctccgcgcggaccccgccccgtcccgacccctcccgggtccccggcccagcc ccctccgggccctcccagccctcccttcctttccgcggccccgccctctcctcgc ggcgcgagtttcaggcagcgctgcgtcctgctgcgcacgtgggaagccctggccccg gccaccccgcgatgccgcgcgctcctagctatcctcgaggatatcaagatctggcc tcggcggccaagcttggcaatccggtactgttggtaaagccacc |
| 258 | PL8 94 | pGL4.10-murine BIRC5-FLUC | ggcctaactggccggtaccctggcaggaagcctactgagatttattgaaaaggaaac cgaattatcagggcactcgtttgcaacgccaacctgggctgtgttcggggcatgccc agcctgctgtctgcagtgtgaagctctttagaagccactgcaaccacaggccgcccg acaggaacagagacactgaaaacgggcccgcagcaaggcaggctcagcagccaacag tcacacccaggaagcagtattttcttctgctcctggactctcttgcggtgtatggc tgcttcccttggtctgagccaggccgatggtctcagaaatagacacccattgactt tcttttccagcgctgggacatacagaccccgcctccatcccagggtgtctataggaa ggatggcggctgctgcaggaggagggtctcctgtcttcctaagggcgccctccac cagcctgtgggtgggtccgaggcacttccattccgatatctagctggccaaatcctg caaaccttgaggcaggaagaacctgcagagcacatgggacttgcagcggacatgctt taaagaggtgccccaggcccgtccaccgccctcggccaccctccgtgtcctctgggg agcagctgcggaagattcgagtcagaatagcaagaaggaaccgcagcagaaggtaca actcccagcatgccctgcgcccgccacgcccacaaggccaggcgcagatgggcgtgg ggcgggactttcccggctcgcctcgcgccgtccactcccagaaggcagcgggcgagg gcgtggggccggggctctcccggcatgctctgcggcgcgcctccgcccgcgcgattt gaatcctgcgtttgagtcgtcttggcggaggttgtggtgacgcgctagcctcgagga tatcaagatctggcctcggcggccaagcttggcaatccggtactgttggtaaagcca cc |
| 259 | PL8 95 | pGL4.10-murine coreBIRC5-FLUC | ggcctaactggccggtaccactcccagaaggcagcgggcgagggcgtggggccgggg ctctcccggcatgctctgcggcgcgcctccgcccgcgcgatttgaatcctgcgtttg agtcgtcttggcggaggttgtggtgacgcgctagctattctagcctcgaggatatca agatctggcctcggcggccaagcttggcaatccggtactgttggtaaagccacc |
| 260 | PL9 88 | PL-FOSL1-coreCEACAM5_2 | ggcctaactggccggtaccactagtggtgactcatgggtgactcatgggtgactcat gggtgactcatgggtgactcatgggtgactcatgggtgactcatgggtgactcatgg gtgactcatggtgatcatgctagcctcgaggatatcaagatcggtaccatgacccac gtgatgctgagaagtactcctgccctaggaagagactcagggcagagggaggaagga cagcagaccagacagtcacagcagccttgacaaaacgttcctggaactaccggtgct agcctcgaggatatcaagatctggcctcggcggccaagcttggcaatccggtactgt tggtaaagccacc |
| 261 | PL9 89 | PL-FOSL1-coreFAM111B_3 | ggcctaactggccggtaccactagtggtgactcatgggtgactcatgggtgactcat gggtgactcatgggtgactcatgggtgactcatgggtgactcatgggtgactcatgg gtgactcatggtgatcatcgggaaaagttcagctgagagatataaaagagcagtctt tccagcacctgcaaatccagagcggcgggcactggacccgtggcacttgaccgtgtgg ac agactctccggttctgtgagtggtttttcttttcccgggtcggacctggagttctta gggggatggctgaaccggtgctagcctcgaggatatcaagatctggcctcggcggcc aagcttggcaatccggtactgttggtaaagccacc |
| 262 | PL9 90 | PL-FOSL1-coreKIF20A | ggcctaactggccggtaccactagtggtgactcatgggtgactcatgggtgactcat gggtgactcatgggtgactcatgggtgactcatgggtgactcatgggtgactcatgg gtgactcatggtgatcatgctagcctcgaggatatcaagatcggtaccggcccgccc cctttccttacgcggattggtagctgcaggcttccctatctgattggccgaacgaac gcagcgcgtaatttaaaatattgtatctgtaacaaagctgcacctcgtgggcggagt tgtgctctgcggctgcgaaagtccagcttcggcgactaggtgtgagtaagccagtat cccaggaggagcaagtggcacgtcttcgggtgagtgtgcggctgtgctggagcccgg gttaccagctcttaccggtgctagcctcgaggatatcaagatctggcctcggcggcc aagcttggcaatccggtactgttggtaaagccacc |

TABLE 1A-continued

Sequences of engineered promoters according to the disclosure

| SEQ ID NO: | EARLI. ID | Name | Regulatory element sequence (nucleotide) |
|---|---|---|---|
| 263 | PL9 91 | PL-FOSL1-coreCST 1 | ggcctaactggccggtaccactagtggtgactcatgggtgactcatgggtgactcat gggtgactcatgggtgactcatgggtgactcatgggtgactcatgggtgactcatgg gtgactcatggtgatcatgctagcctcgaggatatcaagatcggtaccagtggtggg ggagtgaaaagagagatggagaaagaggggatgggcagaaagaggaggaggagtcag gggcagggcatggaggtgggtggggctgggctgccaaagcaggataaatgcacacct gcctgctggtctgggctccctgcctcgggctctcaccctcctctcctgcagctccag ctttgtgctctaccggtgctagcctcgaggatatcaagatctggcctcggcggccaa gcttggcaatccggtactgttggtaaagccacc |
| 264 | PL9 92 | PL-Canscript-coreCEA CAM5_2 | ggcctaactggccggtaccactagtgtccccacccacacattcctgtccccacccac acattcctgtccccacccacacattcctgtccccacccacacattcctgtccccacc cacacattcctgtccccacccacacattcctgaccggtgctagcctcgaggatatca agatcggtaccatgacccacgtgatgctgagaagtactcctgccctaggaagagact cagggcagagggaggaaggacagcagaccagacagtcacagcagccttgacaaaacg ttcctggaactaccggtgctagcctcgaggatatcaagatctggcctcggcggccaa gcttggcaatccggtactgttggtaaagccacc |
| 265 | PL9 93 | PL-Canscript-coreFA M111B_ 3 | ggcctaactggccggtaccactagtgtccccacccacacattcctgtccccacccac acattcctgtccccacccacacattcctgtccccacccacacattcctgtccccacc cacacattcctgtccccacccacacattcctgcgggaaaagttcagctgagagatat aaaagagcagtctttccagcacctgcaaatccagagcggcgggcactgacgggcact tgcaccgtgtggacagactctccggttctgtgagtggttttttcttttcccgggtcgg acctggagttcttaggggggatggctgaaccggtgctagcctcgaggatatcaagatc tggcctcggcggccaagcttggcaatccggtactgttggtaaagccacc |
| 266 | PL9 94 | PL-Canscript-coreKIF2 0A | ggcctaactggccggtaccactagtgtccccacccacacattcctgtccccacccac acattcctgtccccacccacacattcctgtccccacccacacattcctgtccccacc cacacattcctgtccccacccacacattcctgcggcccgcccccctttccttacgcgg attggtagctgcaggcttccctatctgattggccgaacgaacgcagcgcgtaattta aaatattgtatctgtaacaaagctgcacctcgtgggcggagttgtgctctgcggctg cgaaagtccagcttcggcgactaggtgtgagtaagccagtatcccaggagggagcaag tggcacgtcttcgggtgagtgtgcggctgtgctggagcccgggttaccagctcttac cggtgctagcctcgaggatatcaagatctggcctcggcggccaagcttggcaatccg gtactgttggtaaagccacc |
| 267 | PL9 95 | PL-Canscript-coreAGR 2_2 | ggcctaactggccggtaccactagtgtccccacccacacattcctgtccccacccac acattcctgtccccacccacacattcctgtccccacccacacattcctgtccccacc cacacattcctgtccccacccacacattcctgaccggtgctagcctcgaggatatca agatcggtaccacctcttaacaatacgtttcacaaatagttaaaaacatgcatactg aaaagcatacttttgcaatgttattttttaaaaacaaggaactctttaacccagggaa gataatcacttggggaaaggaaggttcgtttctgagttagcaacaagtaaatgcagc actagtgggtgggattgaggtgtgccctggtgcataaatagagactcagctgtgctg gcacactcagaagcttggaccgcatcctagccgccgactcacacaaggcaggtgggt gaggaaatccaggtaaggctcctgacagcagctttagaagggtacttgctggagtga attcgggcctctgattaccggtgctagcctcgaggatatcaagatctggcctcggcg gccaagcttggcaatccggtactgttggtaaagccacc |
| 268 | PL9 96 | PL-Canscript-coreCST 1 | ggcctaactggccggtaccactagtgtccccacccacacattcctgtccccacccac acattcctgtccccacccacacattcctgtccccacccacacattcctgtccccacc cacacattcctgtccccacccacacattcctgaccggtgctagcctcgaggatatca agatcggtaccagtggtgggggagtgaaaagagagatggagaaagaggggatgggca gaaagaggaggagtcaggggcagggcatggaggtgggtggggctgggctgggctgccaa agcaggataaatgcacacctgcctgctggtctgggctccctgcctcgggctctcacc ctcctctcctgcagctccagctttgtgctctaccggtgctagcctcgaggatatcaa gatctggcctcggcggccaagcttggcaatccggtactgttggtaaagccacc |
| 269 | PL9 99 | PL-FOSL1-coreAGR 2_2 | ggcctaactggccggtaccactagtggtgactcatgggtgactcatgggtgactcat gggtgactcatgggtgactcatgggtgactcatgggtgactcatgggtgactcatgg gtgactcatggtgatcatgctagcctcgaggatatcaagatcggtaccacctcttaa caatacgtttcacaaatagttaaaaacatgcatactgaaaagcatacttttgcaatg ttattttttaaaaacaaggaactctttaacccagggaagataatcacttggggaaagg aaggttcgtttctgagttagcaacaagtaaatgcagcactagtgggtgggattgagg tgtgccctggtgcataaatagagactcagctgtgctggcacactcagaagcttggac cgcatcctagccgccgactcacacaaggcaggtgggtgaggaaatccaggtaaggct cctgacagcagctttagaagggtacttgctggagtgaattcgggcctctgattaccg gtgctagcctcgaggatatcaagatctggcctcggcggccaagcttggcaatccggt actgttggtaaagccacc |
| 271 | NP3 30 | NP-5XFOSL 1-coreBIR C5- | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct |

TABLE 1A-continued

Sequences of engineered promoters according to the disclosure

| SEQ ID NO: | EA RLI. ID | Name | Regulatory element sequence (nucleotide) |
|---|---|---|---|
| | | FLUC | accttaacttaatgattttgataaaaatcattaggtacggccgcggtgccagggcgt gcccttgggctccccgggcgcgaCTAGTGGTGACTCATGGGTGACTCATGGGTGACT CATGGGTGACTCATGGGTGACTCATGtgcgctcccgacatgccccgcggcgcgccat taaccgccagatttgagtcgcgggacccgttggcagaggtgggaattcaccggtcga cgctagc |
| 273 | NP3 31 | NP-7XFOSL1-coreBIRC5-FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct accttaacttaatgattttgataaaaatcattaggtacggccgcggtgccagggcgt gcccttgggctccccgggcgcgaCTAGTGGTGACTCATGGGTGACTCATGGGTGACT CATGGGTGACTCATGGGTGACTCATGGGTGACTCATGGGTGACTCATGtgcgctccc gacatgccccgcggcgcgccattaaccgccagatttgagtcgcgggaccgttggca gaggtgggaattcaccggtcgacgctagc |
| 274 | NP1 03 | NP-AFP3-FLUC | TCTGTAGTTTGAGGAGAATATTTGTTATATTGCACAATAAAATAAGTTTGCAAGTTT TTTTTTTTCTGCCCCAAAGAGCTCTGTGTCCTTGAACATAAAATACAAATAACCGCTA TGCTGTTAATTATTAACAAATGTCCCATTTTCAACCTAAGGAAATACCATAAAGTAA CAGATATACCAACAAAAGGTTAATAATTAACAGGCATTGCCTGAAAAGAGTATAAAA GGCTTTCAGCATGATTTTCCATATTGTGCTTCCACCACTGCCAATAACAAAccggtc gacgctagc |
| 278 | NP1 02 | NP-AFP-FLUC | gccctccccgtgccttccttgaccctggaaggtgccactcccactgtcctttcct aataaaatgaggaaattgcatcgcattgtctgagtaggtgtcattctattctggggg gtggggtggggcaggacagcaaggggggaggattgggaagacaatagcaggcatgctg gggatgcggtgggctctatggcccgggacggccgctagcccgcctaatgagcgggct ttttttttggcttgttgtccacaaccgttaaaccttaaaagctttaaaagccttatat attcttttttttcttataaaacttaaaaccttagaggctatttaagttgctgattta tattaattttattgttcaaacatgagagcttagtacgtgaaacatgagagcttagta cgttagccatgagagcttagtacgttagccatgagggtttagttcgttaaacatgag agcttagtacgttaaacatgagagcttagtacgtactatcaacaggttgaactgctg atccacgttgtggtagaattggtaaagagagtcgtgtaaaatatcgagttcgcacat cttgttgtctgattattgattttttggcgaaaccatttgatcatatgacaagatgtgt atctaccttaacttaatgattttgataaaaatcattaggtacggccgcggtgccagg gcgtgcccttgggctccccgggcgcgaCTAGTCTCGAGTCTTGTGTGCCTGGCATAT GATAGGCATTTAATAGTTTTAAAGAATTAATGTATTTAGATGAATTGCATACCAAAT CTGCTGTCTTTTCTTTATGGCTTCATTAACTTAATTTGAGAGAAATTAATTATTCTG CAACTTAGGGACAAGTCATCTCTTTGAATATTCTGTAGTTTGAGGAGAATATTTGTT ATATTTGCAAAATAAAATAAGTTTGCAAGTTTTTTTTTTTCTGCCCCAAAGAGCTCTG TGTCCTTGAACATAAAATACAAATAACCGCTATGCTGTTAATTATTGGCAAATGTCC CATTTTCAACCTAAGGAAATACCATAAAGTAACAGATATACCAACAAAAGGTTACTA GTTAACAGGCATTGCCTGAAAAGAGTATAAAAGAATTTCAGCATGATTTTCCATATT GTGCTTCCACCACTGCCAATAACAAAATAACTAGCAGAGCTAGCCtcgaggctagc |
| 279 | NP3 88 | NP-coreAGR2-FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct accttaacttaatgattttgataaaaatcattaggtacggccgcggtgccagggcgt gcccttgggctccccgggcgcgAATGCATACTAGTaacatttctctggcctaactgg ccggtacCACCTCTTAACAATACGTTTCACAAATAGTTAAAAACATGCATACTGAA AGCATACTTTTGCAATGTTATTTTTAAAAACAAGGAACTCTTTAACCCAGGGAAGAT AATCACTTGGGGAAAGGAAGGTTCGTTTCTGAGTTAGCAACAAGTAAATGCAGCACT AGTGGGTGGGATTGAGGTgTGCCCTGGTGCATAAATAGAGACTCAGCTGTGCTGGCA CACTCAGAAGCTTGGACCGCATCCTAGCCGCCGACTCACACAAGGCAGGTGGGTGAG GAAATCCAGGTAAGGCTCCTGACAGCAGCTTTAGAAGGGTACTTGCTGGAGTGAATT CGGGCCTCTGATTAccggtcgacgctagc |
| 281 | NP3 85 | NP-coreCEACAM5-FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct accttaacttaatgattttgataaaaatcattaggtacggccgcggtgccagggcgt gcccttgggctccccgggcgcgAATGCATACTAGTaacatttctctggcctaactgg ccggtaccatgACCCACGTGATGCTGAGAAGTACTCCTGCCCTAGGAAGAGACTCAG GGCAGAGGGAGGAAGGACAGCAGACCAGACAGTCACAGCAGCCTTGACAAAACGTTC CTGGAACTaccggtcgacgctagc |

TABLE 1A-continued

Sequences of engineered promoters according to the disclosure

| SEQ ID NO: | EA RLI. ID | Name | Regulatory element sequence (nucleotide) |
|---|---|---|---|
| 282 | NP3 89 | NP-coreCST-FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttggcgaaaccatttgatcatatgacaagatgtgtatct accttaacttaatgattttgataaaaatcattaggtacggccgcggtgccagggcgt gcccttgggctccccgggcgcgAATGCATACTAGTaacatttctctggcctaactgg ccggtaccAGTGGTGGGGGAGTGAAAAGAGAGATGGAGAAAGAGGGGATGGGCAGAA AGAGGAGGAGGAGTCAGGGGCAGGGCATGGAGGTGGGTGGGGCTGGGCTGCCAAAGC AGGATAAATGCACACCTGCCTGCTGGTCTGGGCTCCCTGCCTCGGGCTCTCACCCTC CTCTCCTGCAGCTCCAGCTTTGTGCTCTccggtcgacgctagc |
| 283 | NP3 86 | NP-coreFA M111B-FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttggcgaaaccatttgatcatatgacaagatgtgtatct accttaacttaatgattttgataaaaatcattaggtacggccgcggtgccagggcgt gcccttgggctccccgggcgcgAATGCATACTAGTaacatttctctggcctaactgg ccggtacCGGGAAAAGTTCAGCTGAGAGATATAAAAGAGCAGTCTTTCCAGCACCTG CAAATCCAGAGCGGCGGGCACTGACGGGCACTTGCACCGTGTGGACAGACTCTCCGG TTCTGTGAGTGGTTTTTCTTTTCCCGGGTCGGACCTGGAGTTCTTAGGGGGATGGCT Gaaccggtcgacgctagc |
| 284 | NP3 87 | NP-coreKIF2 0A-FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttggcgaaaccatttgatcatatgacaagatgtgtatct accttaacttaatgattttgataaaaatcattaggtacggccgcggtgccagggcgt gcccttgggctccccgggcgcAATGCATACTAGTaacatttctctggcctaactggc cggtacCGGCCCGCCCCCTTTCCTTACGCGGATTGGTAGCTGCAGGCTTCCCTATCT GATTGGCCGAACGAACGCAGCGCGTAATTTAAAATATTGTATCTGTAACAAAGCTGC ACCTCGTGGGCGGAGTTGTGCTCTGCGGCTGCGAAAGTCCAGCTTCGGCGACTAGGT GTGAGTAAGCCAGTATCCCAGGAGGAGCAAGTGGCACGTCTTCGGGTGAGTGTGCGG CTGTGCTGGAGCCCGGGTTACCAGCTCTTAAccggtcgacgctagc |
| 285 | NP4 00 | NP-CREB3L 1_v6-coreBIR C5-FLUC | gagagcaactgcataaggctatgaagagatacgccctggttcctggaacaattgctt ttacagatgcacatatcgaggtggacatcacttacgctgagtacttcgaaatgtccg ttcggttggcagaagctatgaaacgatatgggctgaatacaaatcacagaatcgtcg tatgcagtgaaaactctcttcaattctttatgccggtgttgggcgcgttatttatcg gagttgcagttgcgcccgcgaacgacatttataatgaacgtgaattgctcaacagta tgggcatttcgcagcctaccgtggtgttcgtttccaaaaaggggttgcaaaaaattt tgaacgtgcaaaaaaagctcccaatcatccaaaaaattattatcatggattctaaaa cggattaccagggatttcagtcgatgtacacgttcgtcacatctcatctacctcccg gttttaatgaatacgattttgtgccagagtccttcgatagggacaagacaattgcac tgatcatgaactcctctggatctactggtctgcctaaaggtgtcgctctgcctcata gaactgcctgcgtgagattctcgcatgccagagatcctattttttggcaatcaaatca ttccggatactgcgattttaagtgttgttccattccatcacggttttggaatgtttta ctacactcggatatttgatatgtggatttcgagtcgtcttaatgtatagatttgaag aagagctgtttctgaggagccttcaggattacaagattcaaagtgcgctgctggtgc caaccctattctccttcttcgccaaaagcactctgattgacaaatacgatttatcta atttacacgaaattgcttctggtggcgctccctctctcaaggaagtcggggaagcgg ttgccaagaggttccatctgccaggtatcaggcaaggatatgggctcactgagacta catcagctattctgattacacccgaggggggatgataaaccgggcgcggtcggtaaag ttgttccattttttgaagcgaaggttgtggatctggataccgggaaaacgctgggcg ttaatcaaagaggcgaactgtgtgtgagagtcctatgattatgtccggttatgtaa acaatccggaagcgaccaacgccttgattgacaaggatggatggctacattctggag acatagcttactgggacgaagacgaacacttcttcatcgttgaccgcctgaagtctc tgattaagtacaaaggctatcaggtggctcccgctgaattggaatccatcttgctcc aacaccccaacatcttcgacgcaggtgtcgcaggtcttcccgacgatgacgccggtg aacttcccgccgccgttgttgtttttggagcacggaaagacgatgacggaaaaagaga tcgtggattacgtcgccagtcaagtaacaaccgcgaaaaagttgcgcggaggagttg tgtttgtggacgaagtaccgaaaggtcttaccggaaaactcgacgcaagaaaaatca gagagatcctcataaaggccaagaagggcggaaagatcgccgtgtaatgaatgcatg aattcctgtgccttctagttgccagccatctgttgtttgcccctcccccgtgccttc cttgaccctggaaggtgccactcccactgtcctttcctaataaaatgaggaaattgc atcgcattgtctgagtaggtgtcattctattctggggggtggggtggggcaggacag caaggggggaggattgggaagacaatagcaggcatgctggggatgcggtgggctctat ggcccgggacggccgctagcccgcctaatgagcgggcttttttttggcttgttgtcc acaaccgttaaaccttaaaaagctttaaaagccttatatattcttttttttcttataa aacttaaaaccttagaggctatttaagttgctgatttatattaattttattgttcaa acatgagagcttagtacgtgaaacatgagagcttagtacgttagccatgagagctta gtacgttagccatgagggtttagttcgttaaacatgagagcttagtacgttaaacat |

TABLE 1A-continued

Sequences of engineered promoters according to the disclosure

| SEQ ID NO: | EA RLI. ID | Name | Regulatory element sequence (nucleotide) |
|---|---|---|---|
| | | | gagagcttagtacgtactatcaacaggttgaactgctgatccacgttgtggtagaat |
| | | | tggtaaagagagtcgtgtaaaatatcgagttcgcacatcttgttgtctgattattga |
| | | | tttttggcgaaaccatttgatcatatgacaagatgtgtatctaccttaacttaatga |
| | | | ttttgataaaaatcattaggtacggccgcggtgccagggcgtgcccttgggctcccc |
| | | | gggcgcgacTAGTAACATTTCTCTGGCCTAACTGGCCGGTACCACATCGGCTATGCT |
| | | | GCTGCTAATGCCACGTCACCACATCGACATGCCACGTCACCATCATGCCATGCCACG |
| | | | TCACCACTGCAAGATGCCACGTCACCACAGTATAATGCCACGTCACCAAGTTACTAT |
| | | | GCCACGTCACCAggtacctgcgctcccgacatgccccgcggcgcgccattaaccgcc |
| | | | agatttgagtcgcgcgggacccgttggcagaggtggaccggtcgacgctagc |
| 289 | NP4 03 | NP-E4AD-AFP3-FLUC | cgttgtggtagaattggtaaagagagtcgtgtaaaatatcgagttcgcacatcttgt |
| | | | tgtctgattattgattttttggcgaaaccatttgatcatatgacaagatgtgtatcta |
| | | | ccttaacttaatgatttttgataaaaatcattaggtacCACTAGTTATTAATAGTAAT |
| | | | CAATTACGGGGTCATTAGTTCATAGCCCATATATGGAGTTCCGCGTTACATAACTTA |
| | | | CGGTAAATGGCCCGCCTTGACCGCCCAACGACCCCCGCCCATTGACGTCAATAATGA |
| | | | CGTATGTTCCCATAGTAACGCCAATAGGGACTTTCCATTGACGTCAATGGGTGGAGT |
| | | | ATTTACGGTAAACTGCCCACTTGGCAGTACATCAAGTGTATCATATGCCAAGTACGC |
| | | | CCCCTATTGACGTCAATGACGGTAAATGGCCCGCCTGGCATTATGCCCAGTACATGA |
| | | | CCTTATGGGACTTTCCTACTTGGCAGTACATCTACGTATTAGTCATCGCTATTACCA |
| | | | TGGTGATGCGGTTTTGGCAGTACATCAATGGGCGTGGATAGCGGTTTGACTCACGGG |
| | | | GATTTCCAAGTCTCCACCCCATTGACGTCAATGGGAGTTTGTTTTGGCACCAAAATC |
| | | | AACGGGACTTTCCAAAATGTCGTAACAACTCCGCCCCATGGATCTCAGATTGAATTA |
| | | | TTTGCCTGTCATACAGCTAATAATTGACCATAAGACAATTAGATTTAAATTAGTTTT |
| | | | GAATCTTTCTAATACCAAAGTTCAGTTTACTGTTCCATGTTGCTTCTGAGTGGCTTC |
| | | | ACAGACTTATGAAAAAGTAAACGGAATCAGAATTACATCAATGCAAAAGCATTGCTG |
| | | | TGAACTCTGTACTTAGGACTAAACTTTGAGCAATAACACATATAGATTGAGGATTGT |
| | | | TTGCTGTTAGTATACAAACTCTGGTTCAAAGCTCCTCTTTATTGCTTGTCTTGGAAA |
| | | | ATTTGCTGTTCTTCATGGTTTCTCTTTTCACTGCTATCTATTTTTCTCAACCACTCA |
| | | | CATGGCTACAATAACTGTCTGCAAGCTTATGATTCCCAAATATCTATCTCTAGCCTC |
| | | | AATCTTGTTCCAGAAGATAAAAAGTAGTATTCAAATGCACATCAACGTCTCCACTTG |
| | | | GAGGGCTTAAAGACGTTTCAACATACAAACCGGGGAGTTTTGCCTGGAATGTTTCCT |
| | | | AAAATGTGTCCTGTAGCACATAGGGTCCTCTTGTTCCTTAAAATCTAATTACTTTTA |
| | | | GCCCAGTGCTCATCCCACCTATGGGGAGATGAGAGTGAAAAGGGAGCCTGATTAATA |
| | | | ATTACACTAAGTCAATAGGCATAGAGCCAGGACTGTTTGGGTAAACTGGTCACTTTA |
| | | | TCTTAAACTAAATATATCCAAAACTGAACATGTACTTAGTTACTAAGTCTTTGACTT |
| | | | TATCTCATTCATACCACTCAGCTTTATCCAGGCCACTTATTTGACAGTATTATTGCG |
| | | | AAAACTTCCTACTAGTGTCATCTCTTTGAATATTCTGTAGTTTGAGGAGAATATTTG |
| | | | TTATATTGCACAATAAAATAAGTTTGCAAGTTTTTTTTTTTCTGCCCCAAAGAGCTCT |
| | | | GTGTCCTTGAACATAAAATACAAATAACCGCTATGCTGTTAATTATTAACAAATGTC |
| | | | CCATTTTCAACCTAAGGAAATACCATAAAGTAACAGATATACCAACAAAAGGTTAAT |
| | | | AATTAACAGGCATTGCCTGAAAAGAGTATAAAAGGCTTTCAGCATGATTTTCCATAT |
| | | | TGTGCTTCCACCACTGCCAATAACAAAccggtcgacgctagc |
| 290 | NP3 71 | NP-EN7R-FOS-coreBIRC5-FLUC | actggtctgcctaaaggtgtcgctctgcctcatagaactgcctgcgtgagattctcg |
| | | | catgccagagatcctatttttggcaatcaaatcattccggatactgcgatttttaagt |
| | | | gttgttccattccatcacggttttggaatgtttactacactcggatatttgatatgt |
| | | | ggatttcgagtcgtcttaatgtatagatttgaagaagagctgtttctgaggagcctt |
| | | | caggattacaagattcaaagtgcgctgctggtgccaaccctattctccttcttcgcc |
| | | | aaaagcactctgattgacaaatacgatttatctaatttacacgaaattgcttctggt |
| | | | ggcgctcccctctctaaggaagtcggggaagcggttgccaagaggttccatctgcca |
| | | | ggtatcaggcaaggatatgggctcactgagactacatcagctattctgattacaccc |
| | | | gaggggggatgataaaccgggcgcggtcggtaaagttgttccattttttgaagcgaag |
| | | | gttgtggatctggataccgggaaaacgctgggcgttaatcaaagaggcgaactgtgt |
| | | | gtgagaggtcctatgattatgtccggttatgtaaacaatccggaagcgaccaacgcc |
| | | | ttgattgacaaggatggatggctacattctggagacatagcttactgggacgaagac |
| | | | gaacacttcttcatcgttgaccgcctgaagtctctgattaagtacaaaggctatcag |
| | | | gtggctcccgctgaattggaatccatcttgctccaacaccccaacatcttcgacgca |
| | | | ggtgtcgcaggtcttcccgacgatgacgccggtgaacttcccgccgccgttgttgtt |
| | | | ttggagcacggaaagacgatgacggaaaaagagatcgtggattacgtcgccagtcaa |
| | | | gtaacaaccgcgaaaaagttgcgcggaggagttgtgtttgtggacgaagtaccgaaa |
| | | | ggtcttaccggaaaactcgacgcaagaaaaatcagagagatcctcataaaggccaag |
| | | | aagggcggaaagatcgccgtgtaatgaatgcatgaattcctgtgccttctagttgcc |
| | | | agccatctgttgtttgcccctcccccgtgccttccttgacctggaaggtgccactc |
| | | | ccactgtcctttcctaataaaatgaggaaattgcatcgcattgtctgagtaggtgtc |
| | | | attctattctgggggtggggtggggcaggacagcaaggggggaggattgggaagaca |
| | | | atagcaggcatgctgggggatgcggtgggctctatggcccgggacggccgctagcccg |
| | | | cctaatgagcgggcttttttttggcttgttgtccacaaccgttaaaccttaaaagct |
| | | | ttaaaagccttatatattctttttttttcttataaaacttaaaaccttagaggctatt |
| | | | taagttgctgatttatattaatttttattgttcaaacatgagagcttagtacgtgaaa |
| | | | catgagagcttagtacgttagccatgagagcttagtacgttagccatgagggtttag |
| | | | ttcgttaaacatgagagcttagtacgttaaacatgagagcttagtacgtactatcaa |
| | | | caggttgaactgctgatccacgttgtggtagaattggtaaagagagtcgtgtaaaat |
| | | | atcgagttcgcacatcttgttgtctgattattgattttttggcgaaaccatttgatca |
| | | | tatgacaagatgtgtatctaccttaacttaatgatttttgataaaaatcattaggtac |

TABLE 1A-continued

Sequences of engineered promoters according to the disclosure

| SEQ ID NO: | EA RLI. ID | Name | Regulatory element sequence (nucleotide) |
|---|---|---|---|
| | | | ggccgcggtgccagggcgtgcccttgggctccccgggcgcgaCTAGTAACATTTCTC TGGCCTAACTGGCCGGTACCTGCCACTCAAAGTGGCACACTCCCTGCTCAGGAGGCC GGGAGGGAGGACACAGCCCTGGCAACTCCTCTGCCCCGGGGGGTCAGGAAGGGGTCA CCCCACACTCCAGAACCCTACAGAATGTGGCCTTGGCTTTTCCCATCAAGAGCTGGG GAAAGCCAGGCCCCGACTTCATTACCCCCTGCCCCCGTCCCATGCTCAGTGGGCCCC ATCGTGGGTCCATGCCACACTCCCAACTGAGCAGCCCCGCAGCCCCGCGTGTCACAG ACATGGGGCCTCCTAATTGCTGCTGAGGTCCCAATCCCTGGCTGGACGTGCCTGATG |
| 291 | NP3 69 | NP- EN18- Canscript- FLUC | GAAGAGCCAGCTCTGGTCTCAGGGGGCTGGTTTGCAGGAGTCTCCACAGACCTGGCT CCAGCTTTGTGTCTTCAAATGAATACCCGGCCAAGATTGCAACTAAATTACCAGAAA CACTTAGGTTTCCTCACAGACTCCACAACAGGGATGGAGAAGGAAGTCAGCTGACGA GGTTACGACGCTGTTCGAGGGAGTCTTTCTTGGGTCACAAGTGGTAAACTGTGTTCC CTGAACAAAACCAGGAAGCTTTCAGTGTTTATTGTATGTACTAAGTGGAGGGAGGGG CTTCAGATTCTGATAAAAATATCTCCCCATTCCCAGTGCCCAATGTGACATGAATAG GAGGGCCCCTCCCTGAATTCCCAAGCAGATCTCCAGAGACAGCTTCAGAGAGCAGGG AGCCCACGGTGGCTGGGGCTTTAGGGACTTTCTGGGTTGTGGGGAGGCTAGAGGCTG GGCAGTCCCAGCAGGATTTGGCCTCTAGGGACCGGGCACTGTAGGGCTCAGGAGAGC AGCTGCCGTCCCAGTATATAAGCATAGGTGGAATTATCTGGAAACATATTTCTGCGT TTCACAGGCAGAGAAATCAGTCTATCCCTAAAGAATGGAAGAGCTACAGTAGCAGAC CTACCACCCTCCACCCTCCCACAGGCAAAAGCCCCTGAGATTCAGGTTTGGGAAGAA AAAGAAAATATCCCAAATATGTCATTTGAGAAAGCAGCTGCTAACCACAGGCGGCCC CAGCTTTTCTCAAGATCCAGGATGTGGGTTCAGTGCCCTTACTAGGGCAGTGGGGGA GGACGGTCAGTACCAGGACCCCAGGCACAGGCCTGGAGGACTTGCTCCCCCAAGCAA CTCAGATCCACGCAGAACCCATGGTACCACTAGTGGTGACTCATGGGTGACTCATGG GTGACTCATGGGTGACTCATGGGTGACTCATGGGTGACTCATGGGTGACTCATGGGT GACTCATGGGTGACTCATGtgcgctcccgacatgccccgcgggcgcgccattaaccgc cagatttgagtcgcgggacccgttggcagaggtggaccggtcgacgctagc cgattttgtgccagagtccttcgatagggacaagacaattgcactgatcatgaactc ctctggatctactggtctgcctaaaggtgtcgctctgcctcatagaactgcctgcgt gagattctcgcatgccagagatcctatttttggcaatcaaatcattccggatactgc gattttaagtgttgttccattccatcacggttttggaatgtttactacactcggata tttgatatgtggatttcgagtcgtcttaatgtatagatttgaagaagagctgtttct gaggagccttcaggattacaagattcaaagtgcgctgctggtgccaaccctattctc cttcttcgccaaaagcactctgattgacaaatacgatttatctaatttacacgaaat tgcttctggtggcgctcccctctctaaggaagtcggggaagcggttgccaagaggtt ccatctgccaggtatcaggcaaggatatgggctcactgagactacatcagctattct gattacacccgagggggatgataaaccgggcgcggtcggtaaagttgttccatttt tgaagcgaaggttgtggatctggataccgggaaaacgctgggcgttaatcaaagagg cgaactgtgtgtgagaggtcctatgattatgtccggttatgtaaacaatccggaagc gaccaacgccttgattgacaaggatggatggctacattctggagacatagcttactg ggacgaagacgaacacttcttcatcgttgaccgcctgaagtctctgattaagtacaa aggctatcaggtggctcccgctgaattggaatccatcttgctccaacaccccaacat cttcgacgcaggtgtcgcaggtcttcccgacgatgacgccggtgaacttcccgccgc cgttgttgttttggagcacggaaagacgatgacggaaaaagagatcgtggattacgt cgccagtcaagtaacaaccgcgaaaaagttgcgcggaggagttgtgtttgtggacga agtaccgaaaggtcttaccggaaaactcgacgcaagaaaaatcagagagatcctcat aaaggccaagaagggcggaaagatcgccgtgtaatgaatgcatgaattcctgtgcct tctagttgccagccatctgttgtttgcccctccccgtgccttccttgaccctggaa ggtgccactcccactgtcctttcctaataaaatgaggaaattgcatcgcattgtctg agtaggtgtcattctattctggggggtggggtggggcaggacagcaaggggggaggat tgggaagacaatagcaggcatgctggggatgcggtgggctctatggcccgggacggc cgctagcccgcctaatgagcgggcttttttttggcttgttgtccacaaccgttaaac cttaaaagctttaaaagccttatatattcttttttttcttataaaacttaaaacctt agaggctatttaagttgctgatttatattaattttattgttcaaacatgagagctta gtacgtgaaacatgagagcttagtacgttagccatgagagcttagtacgttagccat gagggtttagttcgttaaacatgagagcttagtacgttaaacatgagagcttagtac gtactatcaacaggttgaactgctgatccacgttgtggtagaattggtaaagagagt cgtgtaaaatatcgagttcgcacatcttgttgtctgattattgatttttggcgaaac catttgatcatatgacaagatgtgtatctaccttaacttaatgattttgataaaaat cattaggtacggccgcggtgccagggcgtgcccttgggctccccgggcgcgACTAGT CTTCTGCCCTGAGAAAGACCTATGATTGCATGACACAAAAGAGACTGTTCAAAGGGA CACCATCATTCAGCAGGGCAAGCCTCCTTGCTGGGGGCAACCTGGTAGCTCCTGAGC CTCCCTCATCTTCACTGAGCCCCTCCAACTCTCTGAGTTCCCATGCCCCTCACTGAA CCTCCCTTCCCCCATGGCGAGCCTCCGCCAGCACCTTTGCACACACTCAGCCCCTTC CCCCTACTGAGCCCCAGCACAGTCACTGAACAGCTCTTCTTCCCCTCTGACTGAGTC ATCCTCCCAAGCCCTCCCCTTCCCCTCACTGAGTCTCCACCACCCCTGGTCACTGGG CACCCTGCTTCTGACCTCCTCCCTCCCCCAACCCCTCCACCCTTCCTCTTCACTGAG CCTGGCGCCTCTCACCCACCCGCCTTCCTCTCCCAGCCGCTTCTGAGCTGCCTCTTT GGAGCCCAACTGTCTCGCCCACGAGTCCCCATCACTCAGTGGTCACTCACTCTAAGAC ACCTGAAAGCAGTTAGAGAACATGTGTTCATGGGGGGAGGATGAGGCTCTATCATCA TCCTGCAAACTAGTGTCCCCACCCACACATTCCTGTCCCCACCCACACATTCCTGTC CCCACCCACACATTCCTGTCCCCACCCACACATTCCTGTCCCCACCCACACATTCCT GTCCCCACCCACACATTCCTGAccggtcgacgctagc |

TABLE 1A-continued

Sequences of engineered promoters according to the disclosure

| SEQ ID NO: | EARLI. ID | Name | Regulatory element sequence (nucleotide) |
|---|---|---|---|
| 292 | NP3 70 | NP-EN19-Canscript-FLUC | cgattttgtgccagagtccttcgatagggacaagacaattgcactgatcatgaactc<br>ctctggatctactggtctgcctaaaggtgtcgctctgcctcatagaactgcctgcgt<br>gagattctcgcatgccagagatcctatttttggcaatcaaatcattccggatactgc<br>gattttaagtgttgttccattccatcacggttttggaatgtttactacactcggata<br>tttgatatgtggatttcgagtcgtcttaatgtatagatttgaagaagagctgtttct<br>gaggagccttcaggattacaagattcaaagtgcgctgctggtgccaaccctattctc<br>cttcttcgccaaaagcactctgattgacaaatacgatttatctaatttacacgaaat<br>tgcttctggtggcgctcccctctctaaggaagtcggggaagcggttgccaagaggtt<br>ccatctgccaggtatcaggcaaggatatgggctcactgagactacatcagctattct<br>gattacacccgaggggatgataaaccgggcgcggtcggtaaagttgttccattttt<br>tgaagcgaaggttgtggatctggataccgggaaaacgctgggcgttaatcaaagagg<br>cgaactgtgtgtgagaggtcctatgattatgtccggttatgtaaacaatccggaagc<br>gaccaacgccttgattgacaaggatggatggctacattctggagacatagcttactg<br>ggacgaagacgaacacttcttcatcgttgaccgcctgaagtctctgattaagtacaa<br>aggctatcaggtggctcccgctgaattggaatccatcttgctccaacaccccaacat<br>cttcgacgcaggtgtcgcaggtcttcccgacgatgacgccggtgaacttcccgccgc<br>cgttgttgtttggagcacggaaagacgatgacggaaaaagagatcgtggattacgt<br>cgccagtcaagtaacaaccgcgaaaaagttgcgcggaggagttgtgtttgtggacga<br>agtaccgaaaggtcttaccggaaaactcgacgcaagaaaatcagagagatcctcat<br>aaaggccaagaagggcggaaagatcgccgtgtaatgaatgcatgaattcctgtgcct<br>tctagttgccagccatctgttgtttgcccctcccccgtgccttccttgaccctggaa<br>ggtgccactcccactgtcctttcctaataaaatgaggaaattgcatcgcattgtctg<br>agtaggtgtcattctattctgggggtggggtggggcaggacagcaaggggggaggat<br>tgggaagacaatagcaggcatgctggggatgcggtgggctctatggcccgggacggc<br>cgctagcccgcctaatgagcgggcttttttttggcttgttgtccacaaccgttaaac<br>cttaaaagctttaaaagcctttatatattcttttttttcttataaaacttaaaacctt<br>agaggctatttaagttgctgatttatattaattttattgttcaaacatgagagctta<br>gtacgtgaaacatgagagcttagtacgttagccatgagagcttagtacgttagccat<br>gagggtttagttcgttaaacatgagagcttagtacgttaaacatgagagcttagtac<br>gtactatcaacaggttgaactgctgatccacgttgtggtagaattggtaaagagagt<br>cgtgtaaaatatcgagttcgcacatcttgttgtctgattattgatttttggcgaaac<br>catttgatcatatgacaagatgtgtatctaccttaacttaatgattttgataaaaat<br>cattaggtacggccgcggtgccagggcgtgcccttgggctccccgggcgcgACTAGT<br>GAACATACACACCTGTGGGGGTGTCTAAGGGGCTCCCAGGGAGTTCTGGGGGGTCCT<br>GGGGAGCAGGACCCTCTTCACTCCCTCCTCCAGGGGAAGTGGCCCTGGGGCACCCCA<br>GGCTGTTCCCCCAGCTCTGTGGGGCCGAAGCCATCCACAGGGGGCTTTCCCCACCGG<br>ATGTGGTGCGGGCCGTGGTTAATCTCACTTGAGTTAGTCACCCAGGACAAACAGCTA<br>ACCGACACAATTCCTCCCAAGTCCAGGGGGCCGGAGGCGGGGTCAGCACCTGGCGGC<br>AGGAGACAGTGCTGCCCTGGGATGTGGCCGGGCCTCCCTCCATTCCCAATCCTGTTG<br>TCTCTGTGGCAATACCTGGCTGGGAGCTCCTATCAGGCCCGTGACCCCCGCCCTTTC<br>TCCAGTGCCCTCCTGTCTGCATTCACCTGTCAGATCCCGgGGAGAGAGGGGCACTGG<br>CGGCCGCCCAGGACCAGAGCTGTGGGGCCTCCCGCACCAGAGTGCAGTGAAGGTTTG<br>TGGGCTGCTAGTGTCCCCACCCACACATTCCTGTCCCCACCCACACATTCCTGTCCC<br>CACCCACACATTCCTGTCCCCACCCACACATTCCTGTCCCCACCCACACATTCCTGT<br>CCCCACCCACACATTCCTGAccggtcgacgctagc |
| 293 | NP3 99 | NP-ETV4-coreBIRC5-FLUC | gagagcaactgcataaggctatgaagagatacgccctggttcctggaacaattgctt<br>ttacagatgcacatatcgaggtggacatccacttacgctgagtacttcgaaatgtccg<br>ttcggttggcagaagctatgaaacgatatgggctgaatacaaatcacagaatcgtcg<br>tatgcagtgaaaactctcttcaattctttatgccggtgttgggcgcgttatttatcg<br>gagttgcagttgcgcccgcgaacgacatttataatgaacgtgaattgctcaacagta<br>tgggcatttcgcagcctaccgtggtgttcgtttccaaaaaggggttgcaaaaaattt<br>tgaacgtgcaaaaaaagctcccaatcatccaaaaaattattatcatggattctaaaa<br>cggattaccagggatttcagtcgatgtacacgttcgtcacatctcatctacctcccg<br>gtttttaatgaatacgattttgtgccagagtccttcgatagggacaagacaattgcac<br>tgatcatgaactcctctggatctactggtctgcctaaaggtgtcgctctgcctcata<br>gaactgcctgcgtgagattctcgcatgccagagatcctattttggcaatcaaatca<br>ttccggatactgcgattttaagtgttgttccattccatcacggttttggaatgttta<br>ctacactcggatatttgatatgtggatttcgagtcgtcttaatgtatagatttgaag<br>aagagctgtttctgaggagccttcaggattacaagattcaaagtgcgctgctggtgc<br>caaccctattctccttcttcgccaaaagcactctgattgacaaatacgatttatcta<br>atttacacgaaattgcttctggtggcgctcccctctctaaggaagtcggggaagcgg<br>ttgccaagaggttccatctgccaggtatcaggcaaggatatgggctcactgagacta<br>catcagctattctgattacacccgaggggatgataaaccgggcgcggtcggtaaag<br>ttgttccatttttgaagcgaaggttgtggatctggataccgggaaaacgctgggcg<br>ttaatcaaagaggcgaactgtgtgtgagaggtcctatgattatgtccggttatgtaa<br>acaatccggaagcgaccaacgccttgattgacaaggatggatggctacattctggag<br>acatagcttactgggacgaagacgaacacttcttcatcgttgaccgcctgaagtctc<br>tgattaagtacaaaggctatcaggtggctcccgctgaattggaatccatcttgctcc<br>aacaccccaacatcttcgacgcaggtgtcgcaggtcttcccgacgatgacgccggtg<br>aacttcccgccgccgttgttgtttggagcacggaaagacgatgacggaaaaagaga<br>tcgtggattacgtcgccagtcaagtaacaaccgcgaaaaagttgcgcggaggagttg<br>tgtttgtggacgaagtaccgaaaggtcttaccggaaaactcgacgcaagaaaatca<br>gagagatcctcataaaggccaagaagggcggaaagatcgccgtgtaatgaatgcatg |

TABLE 1A-continued

<div align="center">Sequences of engineered promoters according to the disclosure</div>

| SEQ ID NO: | EA RLI. ID | Name | Regulatory element sequence (nucleotide) |
|---|---|---|---|
| | | | aattcctgtgccttctagttgccagccatctgttgtttgcccctcccccgtgccttc |
| | | | cttgaccctggaaggtgccactcccactgtcctttcctaataaaatgaggaaattgc |
| | | | atcgcattgtctgagtaggtgtcattctattctggggggtggggtggggcaggacag |
| | | | caaggggggaggattgggaagacaatagcaggcatgctgggggatgcggtgggctctat |
| | | | ggcccgggacggccgctagcccgcctaatgagcgggcttttttttggcttgttgtcc |
| | | | acaaccgttaaaccttaaaagctttaaaagccttatatattcttttttttcttataa |
| | | | aacttaaaaccttagaggctatttaagttgctgatttatattaattttattgttcAA |
| | | | ACATGAGAGCTTAGTACGTGaaacatgagagcttagtacgtgaaacatgagagctta |
| | | | gtacgttagccatgagagcttagtacgttagccatgagggtttagttcgttaaacat |
| | | | gagagcttagtacgttaaacatgagagcttagtacgtactatcaacaggttgaactg |
| | | | ctgatccacgttgtggtagaattggtaaagagagtcgtgtaaaatatcgagttcgca |
| | | | catcttgttgtctgattattgattttttggcgaaaccatttgatcatatgacaagatg |
| | | | tgtatctaccttaacttaatgatttttgataaaaatcattaggtacggccgcggtgcc |
| | | | agggcgtgcccttgggctccccgggcgcgaCTAGTAACATTTCTCTGGCCTAACTGG |
| | | | CCGGTACCACTAGTACCGGAAGTAAGAACCGGAAGTATCGACCGGAAGTAGACACCG |
| | | | GAAGTACTAACCGGAAGTAACTACCGGAAGTATGCACCGGAAGTAtgcgctcccgac |
| | | | atgccccgcggcgcgccattaaccgccagatttgagtcgcgggacccgttggcagag |
| | | | gtggaccggtcgacgctagc |
| 301 | NP391 | NP-FOS-coreAGR2-FLUC | tcaaacatgagagcttagtacgtgaaaCATGAGAGCTTAGTACGTTAGCcatgagag |
| | | | cttagtacgttagccatgagagcttagtacgttagccatgagggtttagttcgttaa |
| | | | acatgagagcttagtacgttaaacatgagagcttagtacgtactatcaacaggttga |
| | | | actgctgatccacgttgtggtagaattggtaaagagagtcgtgtaaaatatcgagtt |
| | | | cgcacatcttgttgtctgattattgattttttggcgaaaccatttgatcatatgacaa |
| | | | gatgtgtatctaccttaacttaatgatttttgataaaaatcattaggtacggccgcgg |
| | | | tgccagggcgtgcccttgggctccccgggcgcgaATGCATACTAGTAACATTTCTCT |
| | | | GGCCTAACTGGCCGGTACCGATCTTGATATCCTCGAGGCTAGCATGATCACCATGAG |
| | | | TCACCCATGAGTCACCCATGAGTCACCCATGAGTCACCCATGAGTCACCCATGAGTC |
| | | | ACCCATGAGTCACCCATGAGTCACCCATGAGTCACCACTAGTGGTACCACCTCTTAA |
| | | | CAATACGTTTCACAAATAGTTAAAAACATGCATACTGAAAAGCATACTTTTGCAATG |
| | | | TTATTTTTAAAAACAAGGAACTCTTTAACCCAGGGAAGATAATCACTTGGGGAAAGG |
| | | | AAGGTTCGTTTCTGAGTTAGCAACAAGTAAATGCAGCACTAGTGGGTGGGATTGAGG |
| | | | TgTGCCCTGGTGCATAAATAGAGACTCAGCTGTGCTGGCACACTCAGAAGCTTGGAC |
| | | | CGCATCCTAGCCGCCGACTCACACAAGGCAGGTGGGTGAGGAAATCCAGGTAAGGCT |
| | | | CCTGACAGCAGCTTTAGAAGGGTACTTGCTGGAGTGAATTCGGGCCTCTGATTAccg |
| | | | gtcgacgctagc |
| 302 | NP404 | NP-FOS-coreCEACAM-FLUC | aattttattgttcaaacatgagagcttagtacgtgaaacatgagagcttagtacgtt |
| | | | agccatgagagcttagtacgttagccatgagggtttagttcgttaaacatgagagct |
| | | | tagtacgttaaacatgagagcttagtacgtactatcaacaggttgaactgctgatcc |
| | | | acgttgtggtagaattggtaaagagagtcgtgtaaaatatcgagttcgcacatcttg |
| | | | ttgtctgattattgattttttggcgaaaccatttgatcatatgacaagatgtgtatct |
| | | | accttaacttaatgatttttgataaaaatcattaggtacggccgcggtgccagggcgt |
| | | | gcccttgggctccccgggcgcgAATGCATaCTAGTGGTGACTCATGGGTGACTCATG |
| | | | GGTGACTCATGGGTGACTCATGGGTGACTCATGGGTGACTCATGGGTGACTCATGGG |
| | | | TGACTCATGGGTGACTCATGGTGATCATGCTAGCCTCGAGGATATCAAGATCGGTAC |
| | | | CATGACCCACGTGATGCTGAGAAGTACTCCTGCCCTAGGAAGAGACTCAGGGCAGAG |
| | | | GGAGGAAGGACAGCAGACCAGACAGTCACAGCAGCCTTGACAAAACGTTCCTGGAAC |
| | | | Taccggtcgacgctagc |
| 303 | NP392 | NP-FOS-coreCST-FLUC | aattttattgttcaaacatgagagcttagtacgtgaaaCATGAGAGCTTAGTACGTT |
| | | | AGCcatgagagcttagtacgttagccatgagagcttagtacgttagccatgagggtt |
| | | | tagttcgttaaacatgagagcttagtacgttaaacatgagagcttagtactattat |
| | | | caacaggttgaactgctgatccacgttgtggtagaattggtaaagagagtcgtgtaa |
| | | | aatatcgagttcgcacatcttgttgtctgattattgattttttggcgaaaccatttga |
| | | | tcatatgacaagatgtgtatctaccttaacttaatgatttttgataaaaatcattagg |
| | | | tacggccgcggtgccagggcgtgcccttgggctccccgggcgcgAATGCATACTAGT |
| | | | AACATTTCTCTGGCCTAACTGGCCGGTACCGATCTTGATATCCTCGAGGCTAGCATG |
| | | | ATCACCATGAGTCACCCATGAGTCACCCATGAGTCACCCATGAGTCACCCATGAGTC |
| | | | ACCCATGAGTCACCCATGAGTCACCCATGAGTCACCCATGAGTCACCACTAGTGGTA |
| | | | CCAGTGGTGGGGGAGTGAAAAGAGAGATGGAGAAAGAGGGGATGGGCAGAAAGAGGA |
| | | | GGAGGAGTCAGGGGCAGGGCATGGAGGTGGGTGGGGCTGGGCTGCCAAAGCAGGATA |
| | | | AATGCACACCTGCCTGCTGGTCTGGGCTCCCTGCCTCGGGCTCTCACCCTCCTCTCC |
| | | | TGCAGCTCCAGCTTTGTGCTCTaccggtcgacgctagc |
| 304 | NP390 | NP-FOS-coreFAM111B-FLUC | aattttattgttcaaacatgagagcttagtacgtgaaacatgagagcttagtacgtt |
| | | | agccatgagagcttagtacgttagccatgagggtttagttcgttaaacatgagagct |
| | | | tagtacgttaaacatgagagcttagtacgtactatcaacaggttgaactgctgatcc |
| | | | acgttgtggtagaattggtaaagagagtcgtgtaaaatatcgagttcgcacatcttg |
| | | | ttgtctgattattgattttttggcgaaaccatttgatcatatgacaagatgtgtatct |
| | | | accttaacttaatgatttttgataaaaatcattaggtacggccgcggtgccagggcgt |
| | | | gcccttgggctccccgggcgcgaCTAGTAACATTTCTCTGGCCTAACTGGCCGGTAC |
| | | | CACTAGTGGTGACTCATGGGTGACTCATGGGTGACTCATGGGTGACTCATGGGTGAC |
| | | | TCATGGGTGACTCATGGGTGACTCATGGGTGACTCATGGGTGACTCATGGTGATCAT |

TABLE 1A-continued

Sequences of engineered promoters according to the disclosure

| SEQ ID NO: | EARLI. ID | Name | Regulatory element sequence (nucleotide) |
|---|---|---|---|
| | | | GCTAGCCTCGAGGATATCAAGATCGGTACCGGGAAAAGTTCAGCTGAGAGATATAAA AGAGCAGTCTTTCCAGCACCTGCAAATCCAGAGCGGCGGGCACTGACGGGCACTTGC ACCGTGTGGACAGACTCTCCGGTTCTGTGAGTGGTTTTTCTTTTCCCGGGTCGGACC TGGAGTTCTTAGGGGGATGGCTGaaccggtcgacgctagc |
| 305 | NP4 05 | NP-FOS-coreKIF-FLUC | ataccgggaaaacgctgggcgttaatcaaagaggcgaactgtgtgtgagaggtccta tgattatgtccggttatgtaaacaatccggaagcgaccaacgccttgattgacaagg atggatggctacattctggagacatagcttactgggacgaagacgaacacttcttca tcgttgaccgcctgaagtctctgattaagtacaaaggctatcaggtggctcccgctg aattggaatccatcttgctccaacaccccaacatcttcgacgcaggtgtcgcaggtc ttcccgacgatgacgccggtgaacttcccgccgccgttgttgttttggagcacggaa agacgatgacggaaaaagagatcgtggattacgtcgccagtcaagtaacaaccgcga aaaagttgcgcggaggagttgtgtttgtggacgaagtaccgaaaggtcttaccggaa aactcgacgcaagaaaatcagagagatcctcataaaggccaagaagggcggaaaga tcgccgtgtaatgaatgcatgaattcctgtgccttctagttgccagccatctgttgt ttgcccctcccccgtgccttccttgacctggaaggtgccactcccactgtccttc ctaataaaatgaggaaattgcatcgcattgtctgagtaggtgtcattctattctggg gggtgggtggggcaggacagcaaggggggaggattgggaagacaatagcaggcatgc tggggatgcggtgggctctatggcccgggacggccgctagcccgcctaatgagcggg cttttttttggcttgttgtccacaaccgttaaaccttaaaagcttttaaaagccttat atattctttttttttcttataaaacttaaaaaccttagaggctatttaagttgctgatt tatattaattttattgttcaaacatgagagcttagtacgtgaaacatgagagcttag tacgttagccatgagagcttagtacgttagccatgagggtttagttcgttaaacatg agagcttagtacgttaaacatgagagcttagtacgtactatcaacaggttgaactgc tgatccacgttgtggtagaattggtaaagagagtcgtgtaaaatatcgagttcgcac atcttgttgtctgattattgattttttggcgaaaccatttgatcatatgacaagatgt gtatctaccttaacttaatgattttgataaaaatcattaggtacggccgcggtgcca gggcgtgcccttgggctccccgggcgcgAATGCATaCTAGTGGTGACTCATGGGTGA CTCATGGGTGACTCATGGGTGACTCATGGGTGACTCATGGGTGACTCATGGGTGACT CATGGGTGACTCATGGGTGACTCATGGTGATCATGCTAGCCTCGAGGATATCAAGAT CGGTACCGGCCCGCCCCCTTTCCTTACGCGGATTGGTAGCTGCAGGCTTCCCTATCT GATTGGCCGAACGAACGCAGCGCGTAATTTAAAATATTGTATCTGTAACAAAGCTGC ACCTCGTGGGCGGAGTTGTGCTCTGCGGCTGCGAAAGTCCAGCTTCGGCGACTAGGT GTGAGTAAGCCAGTATCCCAGGAGGAGCAAGTGGCACGTCTTCGGGTGAGTGTGCGG CTGTGCTGGAGCCCGGGTTACCAGCTCTTccggtcgacgctagc |
| 310 | NP4 64 | NP-FOS-FOS-coreAGR2-FLUC | cttataaaacttaaaaccttagaggctatttaagttgctgatttatattaattttat tgttcaaacatgagagcttagtacgtgaaaCATGAGAGCTTAGTACGTTAGCcatga gagcttagtacgttagccatgagagcttagtacgttagccatgagggtttagttcgt taaacatgagagcttagtacgttaaacatgagagcttagtacgtactatcaacaggt tgaactgctgatccacgttgtggtagaattggtaaagagagtcgtgtaaaatatcga gttcgcacatcttgttgtctgattattgattttttggcgaaaccatttgatcatatga caagatgtgtatctaccttaacttaatgattttgataaaaatcattaggtacggccg cggtgccagggcgtgcccttgggctccccgggcgcgaATGCATACTAGTAACATTTC TCTGGCCTAACTGGCCGGTACCGATCTTGATATCCTCGAGGCTAGCATGATCACCAT GAGTCACCCATGAGTCACCCATGAGTCACCCATGAGTCACCCATGAGTCACCCATGA GTCACCCATGAGTCACCCATGAGTCACCCATGAGTCACCACTAGTGGTACCGATTCT TGATATCCTCGAGGCTAGCATGATCACCATGAGTCACCCATGAGTCACCCATGAGTC ACCCATGAGTCACCCATGAGTCACCCATGAGTCACCCATGAGTCACCCATGAGTCAC CCATGAGTCACCACTAGTGGTACCACCTCTTAACAATACGTTTCACAAATAGTTAAA AACATGCATACTGAAAAGCATACTTTTGCAATGTTATTTTTAAAAACAAGGAACTCT TTAACCCAGGGAAGATAATCACTTGGGGAAAGGAAGGTTCGTTTCTGAGTTAGCAAC AAGTAAATGCAGCACTAGTGGGTGGGATTGAGGTgTGCCCTGGTGCATAAATAGAGA CTCAGCTGTGCTGGCACACTCAGAAGCTTGGACCGCATCCTAGCCGCCGACTCACAC AAGGCAGGTGGGTGAGGAAATCCAGGTAAGGCTCCTGACAGCAGCTTTAGAAGGGTA CTTGCTGGAGTGAATTCGGGCCTCTGATTAccggtcgacgctagc |
| 311 | NP4 06 | NP-FOS-FOS-coreCEACAM-FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct accttaacttaatgattttgataaaaatcattaggtacggccgcggtgccagggcgt gcccttgggctccccgggcgcgAATGCATaCTAGTAACATTTCTCTGGCCTAACTGG CCGGTACCACTAGTGGTGACTCATGGGTGACTCATGGGTGACTCATGGGTGACTCAT GGGTGACTCATGGGTGACTCATGGGTGACTCATGGGTGACTCATGGGTGACTCATGG TGATCATGCTAGCCTCGAGGATATCAAGATCGGTACCACTAGTGGTGACTCATGGGT GACTCATGGGTGACTCATGGGTGACTCATGGTGATCATGCTAGCCTCGAGGATATCAAG ATCGGTACCATGACCCACGTGATGCTGAGAAGTACTCCTGCCCTAGGAAGAGACTCA GGGCAGAGGGAGGAAGGACAGCAGACCAGACAGTCACAGCAGCCTTGACAAAACGTT CCTGGAACTaccggtcgacgctagc |

TABLE 1A-continued

Sequences of engineered promoters according to the disclosure

| SEQ ID NO: | EARLI. ID | Name | Regulatory element sequence (nucleotide) |
|---|---|---|---|
| 312 | NP4 63 | NP-FOS-FOS-FOS-coreAGR2-FLUC | cttataaaacttaaaaccttagaggctatttaagttgctgatttatattaattttat tgttcaaacatgagagcttagtacgtgaaaCATGAGAGCTTAGTACGTTAGCcatga gagcttagtacgttagccatgagagcttagtacgttagccatgagggtttagttcgt taaacatgagagcttagtacgttaaacatgagagcttagtacgtactatcaacaggt tgaactgctgatccacgttgtggtagaattggtaaagagagtcgtgtaaaatatcga gttcgcacatcttgttgtctgattattgattttttggcgaaaccatttgatcatatga caagatgtgtatctaccttaacttaatgattttgataaaaatcattaggtacggccg cggtgccagggcgtgcccttgggctccccgggcgcgaATGCATACTAGTAACATTTC TCTGGCCTAACTGGCCGGTACCGATCTTGATATCCTCGAGGCTAGCATGATCACCAT GAGTCACCCATGAGTCACCCATGAGTCACCCATGAGTCACCACTAGTGGTACCGATC TTGATATCCTCGAGGCTAGCATGATCACCATGAGTCACCCATGAGTCACCCATGAGT CACCCATGAGTCACCCATGAGTCACCCATGAGTCACCCATGAGTCACCCATGAGTCA CCCATGAGTCACCACTAGTGGTACCGATTCTTGATATCCTCGAGGCTAGCATGATCA CCATGAGTCACCCATGAGTCACCCATGAGTCACCCATGAGTCACCCATGAGTCACCC ATGAGTCACCCATGAGTCACCCATGAGTCACCCATGAGTCACCACTAGTGGTACCAC CTCTTAACAATACGTTTCACAAATAGTTAAAAACATGCATACTGAAAAGCATACTTT TGCAATGTTATTTTTAAAAACAAGGAACTCTTTAACCCAGGGAAGATAATCACTTGG GGAAAGGAAGGTTCGTTTCTGAGTTAGCAACAAGTAAATGCAGCACTAGTGGGTGGG ATTGAGGTgTGCCCTGGTGCATAAATAGAGACTCAGCTGTGCTGGCACACTCAGAAG CTTGGACCGCATCCTAGCCGCCGACTCACACAAGGCAGGTGGGTGAGGAAATCCAGG TAAGGCTCCTGACAGCAGCTTTAGAAGGGTACTTGCTGGAGTGAATTCGGGCCTCTG ATTAccggtcgacgctagc |
| 315 | NP4 59 | NP-FOS-TATA-TSS-FLUC-3'OIPR | ctgggacgaagacgaacacttcttcatcgttgaccgcctgaagtctctgattaagta caaaggctatcaggtggctcccgctgaattggaatccatcttgctccaacaccccaa catcttcgacgcaggtgtcgcaggtcttcccgacgatgacgccggtgaacttcccgc cgccgttgttgtttggagcacggaaagacgatgacggaaaaagagatcgtggatta cgtcgccagtcaagtaacaaccgcgaaaaagttgcgcggaggagttgtgtttgtgga cgaagtaccgaaaggtcttaccggaaaactcgacgcaagaaaaatcagagagatcct cataaaggccaagaagggcggaaagatcgccgtgtaatgaattgggATCTTCacaca gcagGTaaggttgcGGGCCGGGCCTGGGCCGGGTCCGGGCCGGGcccgcctaatga gcgggctttttttttggcttgttgtccacaaccgttaaaccttaaaagctttaaaagc cttatatattctttttttttcttataaaacttaaaaccttagaggctatttaagttgc tgatttatattaattttattgttcaaacatgagagcttagtacgtgaaacatgagag cttagtacgttagccatgagagcttagtacgttagccatgagggtttagttcgttaa acatgagagcttagtacgttaaacatgagagcttagtacgtactatcaacaggttga actgctgatccacgttgtggtagaattggtaaagagagtcgtgtaaaatatcgagtt cgcacatcttgttgtctgattattgattttttggcgaaaccatttgatcatatgacaa gatgtgtatctaccttaacttaatgattttgataaaaatcattaccgcaCTGACccc tggtgttgcTTTTTTTTTTTAGgccgcaagCTGAAGcgtgtccctgtgcccttctagt tgccagccatctgttgtttgcccctcccccgtgccttccttgaccctggaaggtgcc actcccactgtcctttcctaataaaatgaggaaattgcatcgccattgtctgagtagg tgtcattctattctggggggtgggtggggcaggacagcaagggggaggattgggaa gacaatagcaggcatgctggggatgcggtgggctctatgggttaccatgcatactag tGGTGACTCATGGGTGACTCATGGGTGACTCATGGGTGACTCATGGGTGACTCATGG GTGACTCATGGGTGACTCATGGGTGACTCATGCGGTGCTAGCTATA AAAGGCCAGCAGCAGCCTGACCACATCTCATCCTCctcgaggatatcaagatctggc ctcggcggccagaattcaccggtcacc |
| 318 | NP3 14 | NP-FOSL1-Canscript-coreBIRC5-FLUC | ggccgctagcccgcctaatgagcgggcttttttttggcttgttgtccacaaccgtta aaccttaaaagcttaaaagccttatatattctttttttcttataaaacttaaaac cttagaggctatttaagttgctgatttatattaattttattgttcaaacatgagagc ttagtacgtgaaacatgagagcttagtacgttagccatgagagcttagtacgttagc catgagggtttagttcgttaaacatgagagcttagtacgttaaacatgagagcttag tacgtactatcaacaggttgaactgctgatccacgttgtggtagaattggtaaagag agtcgtgtaaaatatcgagttcgcacatcttgttgtctgattattgattttttggcg aaccatttgatcatatgacaagatgtgtatctaccttaacttaatgatttttgataaa aatcattaggtacCACTAGTGGTGACTCATGGGTGACTCATGGGTGACTCATGGGTG ACTCATGGGTGACTCATGGGTGACTCATGGGTGACTCATGGGTGACTCATGACTAGT GTCCCCACCCACACATTCCTGTCCCCACCCACACATTCCTGTCCCCACCCACACATT CCTGTCCCCACCCACACATTCCTGTCCCCACCCACACATTCCTGTCCCCACCCACAC ATTCCTGtgcgctcccgacatgccccgcggcgcgccattaaccgccagatttgagtc gcgggacccgttggcagaggtgggctagcctcgaggatatcaagatctggcctcggc ggccaagcttgctagc |
| 319 | NP3 08 | NP-FOSL1-coreBIRC5-FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct accttaacttaatgattttgataaaaatcattaggtacggccgcggtgccagggcgt |

TABLE 1A-continued

| Sequences of engineered promoters according to the disclosure | | | |
|---|---|---|---|
| SEQ ID NO: | EA RLI. ID | Name | Regulatory element sequence (nucleotide) |
| | | | gcccttgggctccccgggcgcgaCTAGTGGTGACTCATGGGTGACTCATGGGTGACT CATGGGTGACTCATGGGTGACTCATGGGTGACTCATGGGTGACTCATGGGTGACTCA TGGGTGACTCATGtgcgctcccgacatgccccgcggcgcgccattaaccgccagatt tgagtcgcgggacccgttggcagaggtggaccggtcgacgctagc |
| 324 | NP3 34 | NP-FOSL1-High-FLUC | gacggccgctagcccgcctaatgagcgggcttttttttggcttgttgtccacaaccg ttaaaccttaaaagctttaaaagccttatatattcttttttttcttataaaacttaa aaccttagaggctatttaagttgctgatttatattaattttattgttcAAACATGAG AGCTTAGTACGTGaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct accttaacttaatgattttgataaaaatcattaggtacggccgcggtgccagggcgt gcccttgggctccccgggcgcgaCTAGTGGTGACTCATGGGTGACTCATGGGTGACT CATGGGTGACTCATGGGTGACTCATGGGTGACTCATGGGTGACTCATGGGTGACTCA TGGGTGACTCATGcatGGGGGGGGGGtgATGACACAGCAATtcGGGACTTTCCacGCT TGCGTGAGAAGagACCGGAAGTgaATGACACAGCAATtcGCTTGCGTGAGAAGctGG GACTTTCCtaGGGGCGGGGttGGGACTTTCCacATGACACAGCAATacaAcgcGtcc cgacatgccccgcggcgcgccattaaccgccagatttgagtcgcgggacccgttggc agaggtgggaattcaccggtcgacgctagc |
| 325 | NP3 32 | NP-FOSL1-Low-FLUC | tttattgttcaaacatgagagcttagtacgtgaaacatgagagcttagtacgttagc catgagagcttagtacgttagccatgagggtttagttcgttaaacatgagagcttag tacgttaaacatgagagcttagtacgtactatcaacaggttgaactgctgatccacg ttgtggtagaattggtaaagagagtcgtgtaaaatatcgagttcgcacatcttgttg tctgattattgattttttggcgaaaccatttgatcatatgacaagatgtgtatctacc ttaacttaatgattttgataaaaatcattaggtacggccgcggtgccagggcgtgcc cttgggctccccgggcgcgaCTAGTGGTGACTCATGGGTGACTCATGGGTGACTCAT GGGTGACTCATGGGTGACTCATGGGTGACTCATGGGTGACTCATGGGTGACTCATGG GTGACTCATGcatACCGGAAGTacTTGCGCAAtgACCGGAAGTacaAcgcGtcccga catgccccgcggcgcgccattaaccgccagatttgagtcgcgggacccgttggcaga ggtgggaattcaccggtcgacgctagc |
| 326 | NP3 33 | NP-FOSL1-Med-FLUC | taattttattgttcaaacatgagagcttagtacgtgaaacatgagagcttagtacgt tagccatgagagcttagtacgttagccatgagggtttagttcgttaaacatgagagc ttagtacgttaaacatgagagcttagtacgtactatcaacaggttgaactgctgatc cacgttgtggtagaattggtaaagagagtcgtgtaaaatatcgagttcgcacatctt gttgtctgattattgattttttggcgaaaccatttgatcatatgacaagatgtgtatc taccttaacttaatgattttgataaaaatcattaggtacggccgcggtgccagggcg tgcccttgggctccccgggcgcgaCTAGTGGTGACTCATGGGTGACTCATGGGTGAC TCATGGGTGACTCATGGGTGACTCATGGGTGACTCATGGGTGACTCATGGGTGACTC ATGGGTGACTCATGcatTTGCGCAAcaGGGGGGGGGGGtgATGACACAGCAATtcGCTT GCGTGAGAAGagACCGGAAGTgaGGGACTTTCCacATGACACAGCAATacaAcgcGt cccgacatgccccgcggcgcgccattaaccgccagatttgagtcgcgggacccgttg gcagaggtgggaattcaccggtcgacgctagc |
| 328 | NP3 15 | NP-FOSL1-TATA-TSS-FLUC | gcccgcctaatgagcgggctttttttttggcttgttgtccacaaccgttaaaccttaa aagctttaaaagccttatatattcttttttttcttataaaacttaaaaccttagagg ctatttaagttgctgatttatattaattttattgttcaaacatgagagcttagtacg tgaaacatgagagcttagtacgttagccatgagagcttagtacgttagccatgaggg tttagttcgttaaacatgagagcttagtacgttaaacatgagagcttagtacgtact atcaacaggttgaactgctgatccacgttgtggtagaattggtaaagagagtcgtgt aaaatatcgagttcgcacatcttgttgtctgattattgattttttggcgaaaccattt gatcatatgacaagatgtgtatctaccttaacttaatgattttgataaaaatcatta ggtacCACTAGTGGTGACTCATGGGTGACTCATGGGTGACTCATGGGTGACTCATGG GTGACTCATGGGTGACTCATGGGTGACTCATGGGTGACTCATGCGG TGCTAGCTATAAAAGGCCAGCAGCAGCCTGACCACATCTCATCCTCctcgaggatat caagatctggcctcggcggccaagcttgctagc |
| 329 | NP3 96 | NP-HIGH-coreAGR2-FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct accttaacttaatgattttgataaaaatcattaggtacggccgcggtgccagggcgt gcccttgggctccccgggcgcgaCTAGTGGGGGGGGGGtgATGACACAGCAATtcGGG ACTTTCCacGCTTGCGTGAGAAGagACCGGAAGTgaATGACACAGCAATtcGCTTGC GTGAGAAGctGGGACTTTCCtaGGGGCGGGGttGGGACTTTCCacATGACACAGCAA TacagtacCACCTCTTAACAATACGTTTCACAAATAGTTAAAAACATGCATACTGAA AAGCATACTTTTGCAATGTTATTTTTAAAAACAAGGAACTCTTTAACCCAGGGAAGA |

TABLE 1A-continued

Sequences of engineered promoters according to the disclosure

| SEQ ID NO: | EA RLI. ID | Name | Regulatory element sequence (nucleotide) |
|---|---|---|---|
| | | | TAATCACTTGGGGAAAGGAAGGTTCGTTTCTGAGTTAGCAACAAGTAAATGCAGCAC TAGTGGGTGGGATTGAGGTgTGCCCTGGTGCATAAATAGAGACTCAGCTGTGCTGGC ACACTCAGAAGCTTGGACCGCATCCTAGCCGCCGACTCACACAAGGCAGGTGGGTGA GGAAATCCAGGTAAGGCTCCTGACAGCAGCTTTAGAAGGGTACTTGCTGGAGTGAAT TCGGGCCTCTGATTAccggtcgacgctagc |
| 330 | NP3 35 | NP- HIGH- coreBIR C5- FLUC | GGGGCGGGGtgATGACACAGCAATtcGGGACTTTCCacGCTTGCGTGAGAAGAgACC GGAAGTgaATGACACAGCAATtcGCTTGCGTGAGAAGctGGGACTTTCCtaGGGGCG GGGttGGGACTTTCCacATGACACAGCAATacaAcgcGtcccgacatgccccgcggc gcgccattaaccgccagatttgagtcgcgggacccgttggcagaggtgggaattcac cggtcgacgctagc |
| 331 | NP3 93 | NP- HIGH- coreCEA CAM- FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct accttaacttaatgattttgataaaaatcattaggtacggccgcggtgccagggcgt gcccttgggctccccgggcgcgaCTAGTGGGGGGGGGtgATGACACAGCAATtcGGG ACTTTCCacGCTTGCGTGAGAAGAgACCGGAAGTgaATGACACAGCAATtcGCTTGC GTGAGAAGctGGGACTTTCCtaGGGGCGGGGttGGGACTTTCCacATGACACAGCAA TacacTAGTAACATTTCTCTGGCCTAACTGGCCGGTACCATGACCCACGTGATGCTG AGAAGTACTCCTGCCCTAGGAAGAGACTCAGGGCAGAGGGGAGGAAGGACAGCAGACC AGACAGTCACAGCAGCCTTGACAAAACGTTCCTGGAACtaccggtcgacgctagc |
| 332 | NP3 97 | NP- HIGH- coreCST- FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct accttaacttaatgattttgataaaaatcattaggtacggccgcggtgccagggcgt gcccttgggctccccgggcgcgaCTAGTGGGGGGGGGtgATGACACAGCAATtcGGG ACTTTCCacGCTTGCGTGAGAAGAgACCGGAAGTgaATGACACAGCAATtcGCTTGC GTGAGAAGctGGGACTTTCCtaGGGGCGGGGttGGGACTTTCCacATGACACAGCAA TacactagtaacatttctctggcctaactggccggtaccAGTGGTGGGGGAGTGAAA AGAGAGATGGAGAAAGAGGGGATGGGCAGAAAGAGGAGGAGGAGTCAGGGGCAGGGC ATGGAGGTGGGTGGGGCTGGGCTGCCAAAGCAGGATAAATGCACACCTGCCTGCTGG TCTGGGCTCCCTGCCTCGGGCTCTCACCCTCCTCTCCTGCAGCTCCAGCTTTGTGCT CTaccggtcgacgctagc |
| 333 | NP3 94 | NP- HIGH- coreFA M111B- FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct accttaacttaatgattttgataaaaatcattaggtacggccgcggtgccagggcgt gcccttgggctccccgggcgcgaCTAGTGGGGGGGGGtgATGACACAGCAATtcGGG ACTTTCCacGCTTGCGTGAGAAGAgACCGGAAGTgaATGACACAGCAATtcGCTTGC GTGAGAAGctGGGACTTTCCtaGGGGGGGGGGttGGGACTTTCCacATGACACAGCAA TacacTAGTAACATTTCTCTGGCCTAACTGGCCGGTACCGGGAAAAGTTCAGCTGAG AGATATAAAAGAGCAGTCTTTCCAGCACCTGCAAATCCAGAGCGGCGGGCACTGACG GGCACTTGCACCGTGTGGACAGACTCTCCGGTTCTGTGAGTGGTTTTTCTTTTCCCG GGTCGGACCTGGAGTTCTTAGGGGGATGGCTGAaccggtcgacgctagc |
| 334 | NP4 65 | NP- High- coreFA M111B- FLUC- 3'OIPR | AGgccgcaagCTGAAGcgtgtccctgtgccttctagttgccagccatctgttgtttg cccctcccccgtgccttccttgaccctggaaggtgccactcccactgtcctttccta ataaaatgaggaaattgcatcgcattgtctgagtaggtgtcattctattctggggg tggggtggggcaggacagcaaggggggaggattgggaagacaatagcaggcatgctgg ggatgcggtgggctctatggggtaccatgcataCTAGTGGGGCGGGGtgATGACACA GCAATtcGGGACTTTCCacGCTTGCGTGAGAAGAgACCGGAAGTgaATGACACAGCA ATtcGCTTGCGTGAGAAGctGGGACTTTCCtaGGGGGGGGGttGGGACTTTCCacAT GACACAGCAATacacTAGTAACATTTCTCTGGCCTAACTGGCCGGTACCGGGAAAAG TTCAGCTGAGAGATATAAAAGAGCAGTCTTTCCAGCACCTGCAAATCCAGAGCGGCG GGCACTGACGGGCACTTGCACCGTGTGGACAGACTCTCCGGTTCTGTGAGTGGTTTT TCTTTTCCCGGGTCGGACCTGGAGTTCTTAGGGGGATGGCTGAagaattcaccggtc acc |
| 335 | NP3 95 | NP- HIGH- coreKIF2 0A- FLUC | aattttattgttcaaacatgagagcttagtacgtgaaacatgagagcttagtacgtt agccatgagagcttagtacgttagccatgagggtttagttcgttaaacatgagagct tagtacgttaaacatgagagcttagtacgtactatcaacaggttgaactgctgatcc acgttgtggtagaattggtaaagagagtcgtgtaaaatatcgagttcgcacatcttg ttgtctgattattgattttttggcgaaaccatttgatcatatgacaagatgtgtatct accttaacttaatgattttgataaaaatcattaggtacggccgcggtgccagggcgt gcccttgggctccccgggcgcgaCTAGTGGGGGGGGGtgATGACACAGCAATtcGGG |

TABLE 1A-continued

Sequences of engineered promoters according to the disclosure

| SEQ ID NO: | EA RLI. ID | Name | Regulatory element sequence (nucleotide) |
|---|---|---|---|
| | | | ACTTTCCacGCTTGCGTGAGAAGagACCGGAAGTgaATGACACAGCAATtcGCTTGC |
| | | | GTGAGAAGctGGGACTTTCCtaGGGGCGGGGttGGGACTTTCCacATGACACAGCAA |
| | | | TacactagtaacatttctctggcctaactggccggtacCGGCCCGCCCCCTTTCCTT |
| | | | ACGCGGATTGGTAGCTGCAGGCTTCCCTATCTGATTGGCCGAACGAACGCAGCGCGT |
| | | | AATTTAAAATATTGTATCTGTAACAAAGCTGCACCTCGTGGGCGGAGTTGTGCTCTG |
| | | | CGGCTGCGAAAGTCCAGCTTCGGCGACTAGGTGTGAGTAAGCCAGTATCCCAGGAGG |
| | | | AGCAAGTGGCACGTCTTCGGGTGAGTGTGCGGCTGTGCTGGAGCCCGGGTTACCAGC |
| | | | TCTTAaccggtcgacgctagc |
| 342 | NP4 01 | NP- HOXA1_ v8- coreBIR C5- FLUC | gagagcaactgcataaggctatgaagagatacgccctggttcctggaacaattgctt |
| | | | ttacagatgcacatatcgaggtggacatcacttacgctgagtacttcgaaatgtccg |
| | | | ttcggttggcagaagctatgaaacgatatgggctgaatacaaatcacagaatcgtcg |
| | | | tatgcagtgaaaactctcttcaattctttatgccggtgttgggcgcgttatttatcg |
| | | | gagttgcagttgcgcccgcgaacgacatttataatgaacgtgaattgctcaacagta |
| | | | tgggcatttcgcagcctaccgtggtgttcgtttccaaaaaggggttgcaaaaaattt |
| | | | tgaacgtgcaaaaaaagctcccaatcatccaaaaaattattatcatggattctaaaa |
| | | | cggattaccagggatttcagtcgatgtacacgttcgtcacatctcatctacctcccg |
| | | | gtttaatgaatacgattttgtgccagagtccttcgataggacaagacaattgcac |
| | | | tgatcatgaactcctctggatctactggtctgcctaaaggtgtcgctctgcctcata |
| | | | gaactgcctgcgtgagattctcgcatgccagagatcctattttggcaatcaaatca |
| | | | ttccggatactgcgattttaagtgttgttccattccatcacggttttggaatgttta |
| | | | ctacactcggatatttgatatgtggatttcgagtcgtcttaatgtatagatttgaag |
| | | | aagagctgtttctgaggagccttcaggattacaagattcaaagtgcgctgctggtgc |
| | | | caaccctattctccttcttcgccaaaagcactctgattgacaaatacgatttatcta |
| | | | atttacacgaaattgcttctggtggcgctcccctctctaaggaagtcggggaagcgg |
| | | | ttgccaagaggttccatctgccaggtatcaggcaaggatatgggctcactgagacta |
| | | | catcagctattctgattacacccgaggggggatgataaaccgggcgcggtcggtaaag |
| | | | ttgttccatttttgaagcgaaggttgtggatctggataccgggaaaacgctgggcg |
| | | | ttaatcaaagaggcgaactgtgtgtgagaggtcctatgattatgtccggttatgtaa |
| | | | acaatccggaagcgaccaacgccttgattgacaaggatggatggctacattctggag |
| | | | acatagcttactgggacgaagacgaacacttcttcatcgttgaccgcctgaagtctc |
| | | | tgattaagtacaaaggctatcaggtggctcccgctgaattggaatccatcttgctcc |
| | | | aacaccccaacatcttcgacgcaggtgtcgcaggtcttcccgacgatgacgccggtg |
| | | | aacttcccgccgccgttgttgtttttggagcacggaaagacgatgacggaaaaagaga |
| | | | tcgtggattacgtcgccagtcaagtaacaaccgcgaaaaagttgcgcggaggagttg |
| | | | tgtttgtggacgaagtaccgaaaggtcttaccggaaaactcgacgcaagaaaaatca |
| | | | gagagatcctcataaaggccaagaagggcggaaagatcgccgtgtaatgaatgcatg |
| | | | aattcctgtgccttctagttgccagccatctgttgtttgcccctcccccgtgccttc |
| | | | cttgaccctggaaggtgccactcccactgtcctttcctaataaaatgaggaaattgc |
| | | | atcgcattgtctgagtaggtgtcattctattctggggggtggggtggggcaggacag |
| | | | caaggggggaggattgggaagacaatagcaggcatgctggggatgcggtgggctctat |
| | | | ggcccgggacggcgctagcccgcctaatgagcgggcttttttttggcttgttgtcc |
| | | | acaaccgttaaaccttaaaagctttaaaagccttatatattctttttttttcttataa |
| | | | aacttaaaaccttagaggctatttaagttgctgatttatattaattttattgttcAA |
| | | | ACATGAGAGCTTAGTACGTGaaacatgagagcttagtacgtgaaacatgagagctta |
| | | | gtacgttagccatgagagcttagtacgttagccatgagggtttagttcgttaaacat |
| | | | gagagcttagtacgttaaacatgagagcttagtacgtactatcaacaggttgaactg |
| | | | ctgatccacgttgtggtagaattggtaaagagagtcgtgtaaaatatcgagttcgca |
| | | | catcttgttgtctgattattgatttttggcgaaaccatttgatcatatgacaagatg |
| | | | tgtatctaccttaacttaatgattttgataaaaatcattaggtacggccgcggtgcc |
| | | | agggcgtgcccttgggctccccgggcgcgaCTAGTAACATTTCTCTGGCCTAACTGG |
| | | | CCggtaccCGATGTAGCTGAGCGACAGTATAGTGCACAGTGACTGCAGCAGTCATTA |
| | | | TACGTCGCCTAAATCGAGATGCTGTACTGATCTATAAGGATCGGTAATGACGTAATG |
| | | | ACGTAATGACGTAATGACGTAATGACGTAATGAcggtacctgcgctcccgacatgcc |
| | | | ccgcggcgcgccattaaccgccagatttgagtcgcgggacccgttggcagaggtgga |
| | | | ccggtcgacgctagc |
| 343 | NP4 02 | NP- HOXC10_ v24- coreBIR C5- FLUC | aactgcataaggctatgaagagatacgccctggttcctggaacaattgcttttacag |
| | | | atgcacatatcgaggtggacatcacttacgctgagtacttcgaaatgtccgttcggt |
| | | | tggcagaagctatgaaacgatatgggctgaatacaaatcacagaatcgtcgtatgca |
| | | | gtgaaaactctcttcaattctttatgccggtgttgggcgcgttatttatcggagttg |
| | | | cagttgcgcccgcgaacgacatttataatgaacgtgaattgctcaacagtatgggca |
| | | | tttcgcagcctaccgtggtgttcgtttccaaaaaggggttgcaaaaaattttgaacg |
| | | | tgcaaaaaaagctcccaatcatccaaaaaattattatcatggattctaaaacggatt |
| | | | accagggatttcagtcgatgtacacgttcgtcacatctcatctacctcccggtttta |
| | | | atgaatacgattttgtgccagagtccttcgatagggacaagacaattgcactgatca |
| | | | tgaactcctctggatctactggtctgcctaaaggtgtcgctctgcctcatagaactg |
| | | | cctgcgtgagattctcgcatgccagagatcctattttggcaatcaaatcattccgg |
| | | | atactgcgattttaagtgttgttccattccatcacggttttggaatgtttactacac |
| | | | tcggatatttgatatgtggatttcgagtcgtcttaatgtatagatttgaagaagagc |
| | | | tgtttctgaggagccttcaggattacaagattcaaagtgcgctgctggtgccaaccc |
| | | | tattctccttcttcgccaaaagcactctgattgacaaatacgatttatctaatttac |
| | | | acgaaattgcttctggtggcgctcccctctctaaggaagtcggggaagcggttgcca |
| | | | agaggttccatctgccaggtatcaggcaaggatatgggctcactgagactacatcag |

TABLE 1A-continued

Sequences of engineered promoters according to the disclosure

| SEQ ID NO: | EA RLI. ID | Name | Regulatory element sequence (nucleotide) |
|---|---|---|---|
| | | | ctattctgattacacccgaggggggatgataaaccgggcgcggtcggtaaagttgttc |
| | | | catttttttgaagcgaaggttgtggatctggataccgggaaaacgctgggcgttaatc |
| | | | aaagaggcgaactgtgtgtgagaggtcctatgattatgtccggttatgtaaacaatc |
| | | | cggaagcgaccaacgccttgattgacaaggatggatggctacattctggagacatag |
| | | | cttactgggacgaagacgaacacttcttcatcgttgaccgcctgaagtctctgatta |
| | | | agtacaaaggctatcaggtggctcccgctgaattggaatccatcttgctccaacacc |
| | | | ccaacatcttcgacgcaggtgtcgcaggtcttcccgacgatgacgccggtgaacttc |
| | | | ccgccgccgttgttgttttggagcacggaaagacgatgacggaaaaagagatcgtgg |
| | | | attacgtcgccagtcaagtaacaaccgcgaaaaagttgcgcggaggagttgtgtttg |
| | | | tggacgaagtaccgaaaggtcttaccggaaaactcgacgcaagaaaaatcagagaga |
| | | | tcctcataaaggccaagaagggcggaaagatcgccgtgtaatgaatgcatgaattcc |
| | | | tgtgccttctagttgccagccatctgttgtttgcccctccccgtgccttccttgac |
| | | | cctggaaggtgccactcccactgtcctttcctaataaaatgaggaaattgcatcgca |
| | | | ttgtctgagtaggtgtcattctattctgggggggtggggtggggcaggacagcaaggg |
| | | | ggaggattgggaagacaatagcaggcatgctggggatgcggtgggctctatggcccg |
| | | | ggacggccgctagcccgcctaatgagcgggcttttttttggcttgttgtccacaacc |
| | | | gttaaaccttaaaagctttaaaagccttatatattctttttttttcttataaaactta |
| | | | aaaccttagaggctatttaagttgctgatttatattaattttattgttcaaacatga |
| | | | gagcttagtacgtgaaaCATGAGAGCTTAGTACGTTAGCcatgagagcttagtacgt |
| | | | tagccatgagagcttagtacgttagccatgagggttttagttcgttaaacatgagagc |
| | | | ttagtacgttaaacatgagagcttagtacgtactatcaacaggttgaactgctgatc |
| | | | cacgttgtggtagaattggtaaagagagtcgtgtaaaatatcgagttcgcacatctt |
| | | | gttgtctgattattgattttttggcgaaaccatttgatcatatgacaagatgtgtatc |
| | | | taccttaacttaatgattttgataaaaatcattaggtacggccgcggtgccagggcg |
| | | | tgcccttgggctccccgggcgcgaCTAGTAACATTTCTCTGGCCTAACTGGCCggta |
| | | | ccAGCTGAGCGACAGTATAGTGCACAGTGACTGCAGCAGTCATTATACGTCGCCTAA |
| | | | ATCGAGATGCTGTACTGATCTATAAGTCGTAAACTGTCGTAAACTGTCGTAAACTGT |
| | | | CGTAAACTGTCGTAAACTGTCGTAAACTggtacctgcgctcccgacatgccccgcgg |
| | | | cgcgccattaaccgccagatttgagtcgcgggacccgttggcagaggtggaccggtc |
| | | | gacgctagc |

TABLE 1B

Sequences of Synthetic Response Elements (SREs) according to the disclosure

| SEQ ID NO: | Name | Sequence |
|---|---|---|
| 377 | SRE001 | Cggagtactgtcctccgagcggagtactgtcctccgagcggagtactgtcctccgagcgga gtactgtcctccgagcggagtactgtcctccgag |
| 378 | SRE002 | GGTGACTCATGGGTGACTCATGGGTGACTCATGGGTGACTCATGGGTGACTCATGGGTGAC TCATGGGTGACTCATGGGTGACTCATGGGTGACTCATG |
| 379 | SRE003 | GGGGCGGGGtgATGACACAGCAATtcGGGACTTTCCacGCTTGCGTGAGAAGagACCGGAA GTgaATGACACAGCAATtcGCTTGCGTGAGAAGctGGGACTTTCCtaGGGGCGGGGttGGG ACTTTCCacATGACACAGCAATac |
| 380 | SRE004 | AATAGGTACCACTAGTGTCCCCACCCACACATTCCTGTCCCCACCCACACATTCCTGTCCC CACCCACACATTCCTGTCCCCACCCACACATTCCTGTCCCCACCCACACATTCCTGTCCCC ACCCACACATTCCTGACCGGTGctagcctcgag |
| 381 | SRE005 | CTGAGCGACAGTATAGTGCACAGTGACTGCAGCAGTCATTCCTTTGATGTACGCAACTCCT TTGATGTCTATGCGTCCTTTGATGTTAAGGATTCCTTTGATGTAGGTACATCCTTTGATGT CCGTAAATCCTTTGATGTGACgatcttgatatc |
| 382 | SRE006 | TACCTGATCAAACATGCCCGGACATGTCGTAAGACATAAACATGCCCGGACATGTCCTCGC AATCTAACATGCCCGGACATGTCCTCGCAATCTAACATGCCCGGACATGTCTGCAAGCTAC AACATGCCCGGACATGTC |
| 383 | SRE007 | GGGGGGGGGTGATGACACAGCAATTCGGGACTTTCCACGCTTGCGTGAGAAGAGACCGGAA GTGAATGACACAGCAAT |
| 384 | SRE008 | GCTTGCGTGAGAAGctGGGACTTTCCtaGGGGGGGGGGttGGGACTTTCCacATGACACAGC AATac |
| 385 | SRE009 | GGTGACTCATGGGTGACTCATGGGTGACTCATGCTaCgTgTgAcGGTGACTCATGGGTGAC TCATGGGTGACTCATGaagTcgcaGattGGTGACTCATGGGTGACTCATGGGTGACTCATG |

TABLE 1B-continued

Sequences of Synthetic Response Elements (SREs) according to the disclosure

| SEQ ID NO: | Name | Sequence |
|---|---|---|
| 386 | SRE010 | GGTGACTCATGATGATGCCACGTCACCAATGCCACGTCACCAGGTGACTCATGGGTGACTC ATGACGTGTGACATGCCACGTCACCAATGCCACGTCACCAGGTGACTCATGGGTGACTCAT G |
| 387 | SRE011 | GGGAGGAAGTCGTAAAACTTGGGAGGAAGTCGTAAAAAATGGGAGGAAGTCGTAAAATGCG GGAGGAAGTCGTAAAAGAAGGGAGGAAGTCGTAAAAATCGGGAGGAAGTCGTAAAA |
| 388 | SRE012 | ATGACTCAGCAATTAGCGAGTTAGAATGACTCAGCAATTATGCGTCGGACATGACTCAGCA ATTACATCTCGATTATGACTCAGCAATTAGGATAGGCATATGACTCAGCAATTACATAGCA GCAATGACTCAGCAATTA |
| 389 | SRE013 | ACATCAAAGGATTTACGGACATCAAAGGATGTACCTACATCAAAGGAATCCTTAACATCAA AGGACGCATAGACATCAAAGGAGTTGCGTACATCAAAGGA |
| 390 | SRE014 | CACTTCCGGTTTACTTCCACTTCCGGTTTACTAGCACTTCCGGTTTACGCTCACTTCCGGT TTACGATCACTTCCGGTTTACAGACACTTCCGGTTTAC |
| 391 | SRE015 | GCGTCCGCCCGAGTCCCCGCCTCGCCGCCAACGCCAAtgcTcatGCGTCCGCCCGAGTCCC CGCCTCGCCGCCAACGCCAtcatgcctGCGTCCGCCCGAGTCCCCGCCTCGCCGCCAACGC CA |
| 392 | SRE016 | CAACATGGCGGCGCCCAACATGGCGGCTACCAACATGGCGGCCTCCAACATGGCGGCAGGC AACATGGCGGCTGCCAACATGGCGGC |
| 393 | SRE017 | TGGTTGCTGACTAATTGAGATGCATGCTTTGCATACTTCTGCCTGCTGGGGAGCCTGGGGA CTTTCCACAC |
| 394 | SRE018 | GCTCACTCACTCACTCACTGAGGCCTGCAGAGCAAAGCTCTGCAGTCTGGGGACCTTTGGT CCCCAGGCCTCAGTGAGTGAGTGAGTGAGCAGAGAGGGAGTGGCCAACTCCATCACTAGGG GTTCCT |
| 395 | SRE019 | GGTGACTCATGGGTGACTCATGGGTGACTCATGGGTGACTCATGCTaCgTGGTGACTCATG GGTGACTCATGGGTGACTCATGGGTGACTCATGGGTGACTCATG |
| 396 | SRE020 | AGTATAGTGCACAGTGACTGCAGCAGGGTGACTCATGATGATGCCACGTCACCAATGCCAC GTCACCAGGTGACTCATGGGTGACTCATGATGCCACGTCACCAATGCCACGTCACCAGGTG ACTCATGGGTGACTCATG |
| 397 | SRE021 | TAATTGCTGAGTCATTGCTGCTATGTAATTGCTGAGTCATATGCCTATCCTCCTTTGATGT ACGCAACTCCTTTGATGTCTATGCGTAATTGCTGAGTCATAATCGAGATGTAATTGCTGAG TCATGTCCGACGCATCCTTTGATGTTAAGGATTCCTTTGATGTAGGTACATAATTGCTGAG TCATTCTAACTCGCTAATTGCTGAGTCATCATCTCGACCTCCTTTGATGTCCGTAAATCCT TTGATGT |

TABLE 1C

Sequences of Synthetic Response Sensors (SRSs) according to the disclosure

| SEQ ID NO: | Name | Sequence |
|---|---|---|
| 398 | SRS002 | ACTAGTGGTGACTCATGGGTGACTCATGGGTGACTCATGGGTGACTCATGGGTGACTCATG GGTGACTCATGGGTGACTCATGGGTGACTCATGGGTGACTCATGtgcgctcccgacatgcc ccgcggcgcgccattaaccgccagatttgagtcgcgggacccgttggcagaggtgg |
| 399 | SRS003 | agcttgcatgcctgcaggtcggagtactgtcctccgagcggagtactgtcctccgagcgga gtactgtcctccgagcggagtactgtcctccgagcggagtactgtcctccgagcggtgcgc tcccgacatgccccgcggcgcgccattaaccgccagatttgagtcgcgggacccgttggca gaggtggg |
| 400 | SRS004 | ctcgaggctagcATGATCACCATGAGTCACCCATGAGTCACCCATGAGTCACCCATGAGTC ACCCATGAGTCACCCATGAGTCACCCATGAGTCACCCATGAGTCACCCATGAGTCACCACT AGTGGTACCACCTCTTAACAATACGTTTCACAAATAGTTAAAAACATGCATACTGAAAAGC ATACTTTTGCAATGTTATTTTTAAAAACAAGGAACTCTTTAACCCAGGGAAGATAATCACT TGGGGAAAGGAAGGTTCGTTTCTGAGTTAGCAACAAGTAAATGCAGCACTAGTGGGTGGGA TTGAGGTGTGCCCTGGTCATAAATAGAGACTCAGCTGTGCTGGCACACTCAGAAGCTTGG ACCGCATCCTAGCCGCCGACTCACACAAGGCAGGTGGGTGAGGAAATCCAGGTAAGGCTCC TGACAGCAGCTTTAGAAGGGTACTTGCTGGAGTGAATTCGGGCCTCTGATTA |

TABLE 1C-continued

Sequences of Synthetic Response Sensors (SRSs) according to the disclosure

| SEQ ID NO: | Name | Sequence |
|---|---|---|
| 401 | SRS005 | GGTGACTCATGGGTGACTCATGGGTGACTCATGGGTGACTCATGGGTGACTCATGGGTGAC<br>TCATGGGTGACTCATGGGTGACTCATGGGTGACTCATGGTGATCATGCTAGCCTCGAGGAT<br>ATCAAGATCGGTACCGGGAAAAGTTCAGCTGAGAGATATAAAAGAGCAGTCTTTCCAGCAC<br>CTGCAAATCCAGAGCGGCGGGCACTGACGGGCACTTGCACCGTGTGGACAGACTCTCCGGT<br>TCTGTGAGTGGTTTTTCTTTTCCCGGGTCGGACCTGGAGTTCTTAGGGGGATGGCTGa |
| 402 | SRS006 | GGTGACTCATGGGTGACTCATGGGTGACTCATGGGTGACTCATGGGTGACTCATGGGTGAC<br>TCATGGGTGACTCATGGGTGACTCATGGGTGACTCATGGTGATCATGCTAGCCTCGAGGAT<br>ATCAAGATCGGTACCATGACCCACGTGATGCTGAGAAGTACTCCTGCCCTAGGAAGAGACT<br>CAGGGCAGAGGGAGGAAGGACAGCAGACCAGACAGTCACAGCAGCCTTGACAAAACGTTCC<br>TGGAACT |
| 403 | SRS007 | GGTGACTCATGGGTGACTCATGGGTGACTCATGGGTGACTCATGGGTGACTCATGGGTGAC<br>TCATGGGTGACTCATGGGTGACTCATGGGTGACTCATGGTGATCATGCTAGCCTCGAGGAT<br>ATCAAGATCGGTACCGGCCCGCCCCCTTTCCTTACGCGGATTGGTAGCTGCAGGCTTCCCT<br>ATCTGATTGGCCGAACGAACGCAGCGCGTAATTTAAAATATTGTATCTGTAACAAAGCTGC<br>ACCTCGTGGGCGGAGTTGTGCTCTGCGGCTGCGAAAGTCCAGCTTCGGCGACTAGGTGTGA<br>GTAAGCCAGTATCCCAGGAGGAGCAAGTGGCACGTCTTCGGGTGAGTGTGCGGCTGTGCTG<br>GAGCCCGGGTTACCAGCTCTT |
| 404 | SRS008 | GGTGACTCATGGGTGACTCATGGGTGACTCATGGGTGACTCATGGGTGACTCATGGGTGAC<br>TCATGGGTGACTCATGGGTGACTCATGGGTGACTCATGCGGTGCTAGCTATAAAAGGCCAG<br>CAGCAGCCTGACCACATCTCATCCTCctcgaggatatcaagatctggcctcggcggccaaa<br>ttca |
| 405 | SRS009 | GGGGCGGGGtgATGACACAGCAATtcGGGACTTTCCacGCTTGCGTGAGAAGagACCGGAA<br>GTgaATGACACAGCAATtcGCTTGCGTGAGAAGctGGGACTTTCCtaGGGGCGGGGttGGG<br>ACTTTCCacATGACACAGCAATacaAcgcGtcccgacatgccccgcggcgcgccattaacc<br>gccagatttgagtcgcgggacccgttggcagaggtgg |
| 406 | SRS010 | GGGGCGGGGtgATGACACAGCAATtcGGGACTTTCCacGCTTGCGTGAGAAGagACCGGAA<br>GTgaATGACACAGCAATtcGCTTGCGTGAGAAGctGGGACTTTCCtaGGGGCGGGGttGGG<br>ACTTTCCacATGACACAGCAATacagtacCACCTCTTAACAATACGTTTCACAAATAGTTA<br>AAAACATGCATACTGAAAAGCATACTTTTGCAATGTTATTTTTAAAAACAAGGAACTCTTT<br>AACCCAGGGAAGATAATCACTTGGGGAAAGGAAGGTTCGTTTCTGAGTTAGCAACAAGTAA<br>ATGCAGCACTAGTGGGTGGGATTGAGGTgTGCCCTGGTGCATAAATAGAGACTCAGCTGTG<br>CTGGCACACTCAGAAGCTTGGACCGCATCCTAGCCGCCGACTCACACAAGGCAGGTGGGTG<br>AGGAAATCCAGGTAAGGCTCCTGACAGCAGCTTTAGAAGGGTACTTGCTGGAGTGAATTCG<br>GGCCTCTGATT |
| 407 | SRS011 | GGGGCGGGGtgATGACACAGCAATtcGGGACTTTCCacGCTTGCGTGAGAAGagACCGGAA<br>GTgaATGACACAGCAATtcGCTTGCGTGAGAAGctGGGACTTTCCtaGGGGGGGGGttGGG<br>ACTTTCCacATGACACAGCAATacacTAGTAACATTTCTCTGGCCTAACTGGCCGGTACCG<br>GGAAAAGTTCAGCTGAGAGATATAAAAGAGCAGTCTTTCCAGCACCTGCAAATCCAGAGCG<br>GCGGGCACTGACGGGCACTTGCACCGTGTGGACAGACTCTCCGGTTCTGTGAGTGGTTTTT<br>CTTTTCCCGGGTCGGACCTGGAGTTCTTAGGGGGATGGCTGA |
| 408 | SRS012 | GGGGCGGGGtgATGACACAGCAATtcGGGACTTTCCacGCTTGCGTGAGAAGagACCGGAA<br>GTgaATGACACAGCAATtcGCTTGCGTGAGAAGctGGGACTTTCCtaGGGGCGGGGttGGG<br>ACTTTCCacATGACACAGCAATacacTAGTAACATTTCTCTGGCCTAACTGGCCGGTACCA<br>TGACCCACGTGATGCTGAGAAGTACTCCTGCCCTAGGAAGAGACTCAGGGCAGAGGGAGGA<br>AGGACAGCAGACCAGACAGTCACAGCAGCCTTGACAAAACGTTCCTGGAACt |
| 409 | SRS013 | GGGGCGGGGtgATGACACAGCAATtcGGGACTTTCCacGCTTGCGTGAGAAGagACCGGAA<br>GTgaATGACACAGCAATtcGCTTGCGTGAGAAGctGGGACTTTCCtaGGGGCGGGGttGGG<br>ACTTTCCacATGACACAGCAATacactagtaacatttctctggcctaactggccggtacCG<br>GCCCGCCCCCTTTCCTTACGCGGATTGGTAGCTGCAGGCTTCCCTATCTGATTGGCCGAAC<br>GAACGCAGCGCGTAATTTAAAATATTGTATCTGTAACAAAGCTGCACCTCGTGGGCGGAGT<br>TGTGCTCTGCGGCTGCGAAAGTCCAGCTTCGGCGACTAGGTGTGAGTAAGCCAGTATCCCA<br>GGAGGAGCAAGTGGCACGTCTTCGGGTGAGTGTGCGGCTGTGCTGGAGCCCGGGTTACCAG<br>CTCTTA |
| 410 | SRS014 | TCCCCACCCACACATTCCTGTCCCCACCCACACATTCCTGTCCCCACCCACACATTCCTGT<br>CCCCACCCACACATTCCTGTCCCCACCCACACATTCCTGTCCCCACCCACACATTCCTGtg<br>cgctcccgacatgccccgcggcgcgccattaaccgccagatttgagtcgcgggacccgttg<br>gcagaggtgg |
| 411 | SRS015 | GGTGACTCATGGGTGACTCATGGGTGACTCATGGGTGACTCATGGGTGACTCATGGGTGAC<br>TCATGGGTGACTCATGGGTGACTCATGACTAGTGTCCCCACCCACACATTCCTGTCCCCAC<br>CCACACATTCCTGTCCCCACCCACACATTCCTGTCCCCACCCACACATTCCTGTCCCCACC<br>CACACATTCCTGTCCCCACCCACACATTCCTGtgcgctcccgacatgccccgcggcgcgcc<br>attaaccgccagatttgagtcgcgggacccgttggcagaggtgg |

TABLE 1C-continued

Sequences of Synthetic Response Sensors (SRSs) according to the disclosure

| SEQ ID NO: | Name | Sequence |
|---|---|---|
| 412 | SRS016 | CTGAGCGACAGTATAGTGCACAGTGACTGCAGCAGTCATTCCTTTGATGTACGCAACTCCT<br>TTGATGTCTATGCGTCCTTTGATGTTAAGGATTCCTTTGATGTAGGTACATCCTTTGATGT<br>CCGTAAATCCTTTGATGTGACGTCTACGTACATACTGAAAAGCATACTTTTGCAATGTTAT<br>TTTTAAAAACAAGGAACTCTTTAACCCAGGGAAGATAATCACTTGGGGAAAGGAAGGTTCG<br>TTTCTGAGTTAGCAACAAGTAAATGCAGCACTAGTGGGTGGGATTGAGGTgTGCCCTGGTG<br>CATAAATAGAGACTCAGCTGTGCTGGCACACTCAGAAGCTTGGACCGCATCCTAGCCGCCG<br>ACTCACACAAGGCAGGTGGGTGAGGAAATCCAGGTAAGGCTCCTGACAGCAGCTTTAGAAG<br>GGTACTTGCTGGAGTGAATTCGGGCCTCTGATTA |
| 413 | SRS017 | CTGAGCGACAGTATAGTGCACAGTGACTGCAGCAGTCATTCCTTTGATGTACGCAACTCCT<br>TTGATGTCTATGCGTCCTTTGATGTTAAGGATTCCTTTGATGTAGGTACATCCTTTGATGT<br>CCGTAAATCCTTTGATGTGACgatcttgatatcctcgaggctagcATGATCACCATGAGTC<br>ACCCATGAGTCACCCATGAGTCACCCATGAGTCACCCATGAGTCACCCATGAGTCACCCAT<br>GAGTCACCCATGAGTCACCCATGAGTCACCACTAGTGGTACCACCTCTTAACAATACGTTT<br>CACAAATAGTTAAAAACATGCATACTGAAAAGCATACTTTTGCAATGTTATTTTTAAAAAC<br>AAGGAACTCTTTAACCCAGGGAAGATAATCACTTGGGGAAAGGAAGGTTCGTTTCTGAGTT<br>AGCAACAAGTAAATGCAGCACTAGTGGGTGGGATTGAGGTqTGCCCTGGTGCATAAATAGA<br>GACTCAGCTGTGCTGGCACACTCAGAAGCTTGGACCGCATCCTAGCCGCCGACTCACACAA<br>GGCAGGTGGGTGAGGAAATCCAGGTAAGGCTCCTGACAGCAGCTTTAGAAGGGTACTTGCT<br>GGAGTGAATTCGGGCCTCTGATTA |
| 414 | SRS018 | CTGAGCGACAGTATAGTGCACAGTGACTGCAGCAGTCATTCCTTTGATGTACGCAACTCCT<br>TTGATGTCTATGCGTCCTTTGATGTTAAGGATTCCTTTGATGTAGGTACATCCTTTGATGT<br>CCGTAAATCCTTTGATGTGACGTCTACGTATCTACCTGATCAAACATGCCCGGACATGTCG<br>TAAGACATAAACATGCCCGGACATGTCCTCGCAATCTAACATGCCCGGACATGTCCTCGCA<br>ATCTAACATGCCCGGACATGTCTGCAAGCTACAACATGCCCGGACATGTCTACAATATACG<br>TATCTACCTGATCAAACATGCCCGGACATGTCGTAAGACATAAACATGCCCGGACATGTCC<br>TCGCAATCTAACATGCCCGGACATGTCCTCGCAATCTAACATGCCCGGACATGTCTGCAAG<br>CTACAACATGCCCGGACATGTCTACGTACATACTGAAAAGCATACTTTTGCAATGTTATTT<br>TTAAAAACAAGGAACTCTTTAACCCAGGGAAGATAATCACTTGGGGAAAGGAAGGTTCGTT<br>TCTGAGTTAGCAACAAGTAAATGCAGCACTAGTGGGTGGGATTGAGGTgTGCCCTGGTGCA<br>TAAATAGAGACTCAGCTGTGCTGGCACACTCAGAAGCTTGGACCGCATCCTAGCCGCCGAC<br>TCACACAAGGCAGGTGGGTGAGGAAATCCAGGTAAGGCTCCTGACAGCAGCTTTAGAAGGG<br>TACTTGCTGGAGTGAATTCGGGCCTCTGATTA |
| 415 | SRS019 | GGGGCGGGGtgATGACACAGCAATtcGGGACTTTCCacGCTTGCGTGAGAAGagACCGGAA<br>GTgaATGACACAGCAATGGATCCGCTTGCGTGAGAAGctGGGACTTTCCtaGGGGGGGGGt<br>tGGGACTTTCCacATGACACAGCAATacCTCGAGGGTACCGGCCCGCCCCCTTTCCTTACG<br>CGGATTGGTAGCTGCAGGCTTCCCTATCTGATTGGCCGAACGAACGCAGCGCGTAATTTAA<br>AATATTGTATCTGTAACAAAGCTGCACCTCGTGGGCGGAGTTGTGCTCTGCGGCTGCGAAA<br>GTCCAGCTTCGGCGACTAGGTGTGAGTAAGCCAGTATCCCAGGAGGAGCAAGTGGCACGTC<br>TTCGGGTGAGTGTGCGGCTGTGCTGGAGCCCGGGTTACCAGCTCTT |
| 416 | SRS020 | GGGGCGGGGtgATGACACAGCAATtcGGGACTTTCCacGCTTGCGTGAGAAGagACCGGAA<br>GTgaATGACACAGCAATGGATCCGCTTGCGTGAGAAGctGGGACTTTCCtaGGGGGGGGGt<br>tGGGACTTTCCacATGACACAGCAATacCTCGAGGGTACCGGGAAAGTTCAGCTGAGAGA<br>TATAAAAGAGCAGTCTTTCCAGCACCTGCAAATCCAGAGCGGCGGGCACTGACGGGCACTT<br>GCACCGTGTGGACAGACTCTCCGGTTCTGTGAGTGGTTTTTCTTTTCCCGGGTCGGACCTG<br>GAGTTCTTAGGGGGATGGCTG |
| 417 | SRS021 | GGGGCGGGGtgATGACACAGCAATtcGGGACTTTCCacGCTTGCGTGAGAAGagACCGGAA<br>GTgaATGACACAGCAATGGATCCGCTTGCGTGAGAAGctGGGACTTTCCtaGGGGGGGGGt<br>tGGGACTTTCCacATGACACAGCAATacCTCGAGGGTGACTCATGGGTGACTCATGGGTGA<br>CTCATGCTaCgTgTgAcGGTGACTCATGGGTGACTCATGGGTGACTCATGaagTcgcaGat<br>tGGTGACTCATGGGTGACTCATGGGTGACTCATGGGTACCGGCCCGCCCCCTTTCCTTACG<br>CGGATTGGTAGCTGCAGGCTTCCCTATCTGATTGGCCGAACGAACGCAGCGCGTAATTTAA<br>AATATTGTATCTGTAACAAAGCTGCACCTCGTGGGCGGAGTTGTGCTCTGCGGCTGCGAAA<br>GTCCAGCTTCGGCGACTAGGTGTGAGTAAGCCAGTATCCCAGGAGGAGCAAGTGGCACGTC<br>TTCGGGTGAGTGTGCGGCTGTGCTGGAGCCCGGGTTACCAGCTCTT |
| 418 | SRS022 | GGGGCGGGGtgATGACACAGCAATtcGGGACTTTCCacGCTTGCGTGAGAAGagACCGGAA<br>GTgaATGACACAGCAATGGATCCGCTTGCGTGAGAAGctGGGACTTTCCtaGGGGGGGGGt<br>tGGGACTTTCCacATGACACAGCAATacCTCGAGGGTGACTCATGATGATGCCACGTCACC<br>AATGCCACGTCACCAGGTGACTCATGGGTGACTCATGaCgTgTgAcATGCCACGTCACCAA<br>TGCCACGTCACCAGGTGACTCATGGGTGACTCATGGGTACCGGCCCGCCCCCTTTCCTTAC<br>GCGGATTGGTAGCTGCAGGCTTCCCTATCTGATTGGCCGAACGAACGCAGCGCGTAATTTA<br>AAATATTGTATCTGTAACAAAGCTGCACCTCGTGGGCGGAGTTGTGCTCTGCGGCTGCGAA<br>AGTCCAGCTTCGGCGACTAGGTGTGAGTAAGCCAGTATCCCAGGAGGAGCAAGTGGCACGT<br>CTTCGGGTGAGTGTGCGGCTGTGCTGGAGCCCGGGTTACCAGCTCTT |

TABLE 1C-continued

<u>Sequences of Synthetic Response Sensors (SRSs) according to the disclosure</u>

| SEQ ID NO: | Name | Sequence |
|---|---|---|
| 419 | SRS023 | GGGGCGGGGtgATGACACAGCAATtcGGGACTTTCCacGCTTGCGTGAGAAGagACCGGAA<br>GTgaATGACACAGCAATGGATCCGCTTGCGTGAGAAGctGGGACTTTCCtaGGGGGGGGGt<br>tGGGACTTTCCacATGACACAGCAATacCTCGAGGGGAGGAAGTCGTAAAACTTGGGAGGA<br>AGTCGTAAAAAATGGGAGGAAGTCGTAAAATGCGGGAGGAAGTCGTAAAAGAAGGGAGGAA<br>GTCGTAAAAATCGGGAGGAAGTCGTAAAAGGTACCGGCCCGCCCCCTTTCCTTACGCGGAT<br>TGGTAGCTGCAGGCTTCCCTATCTGATTGGCCGAACGAACGCAGCGCGTAATTTAAAATAT<br>TGTATCTGTAACAAAGCTGCACCTCGTGGGCGGAGTTGTGCTCTGCGGCTGCGAAAGTCCA<br>GCTTCGGCGACTAGGTGTGAGTAAGCCAGTATCCCAGGAGGAGCAAGTGGCACGTCTTCGG<br>GTGAGTGTGCGGCTGTGCTGGAGCCCGGGTTACCAGCTCTT |
| 420 | SRS024 | GGGGCGGGGtgATGACACAGCAATtcGGGACTTTCCacGCTTGCGTGAGAAGagACCGGAA<br>GTgaATGACACAGCAATGGATCCGCTTGCGTGAGAAGctGGGACTTTCCtaGGGGGGGGGt<br>tGGGACTTTCCacATGACACAGCAATacCTCGAGGGTGACTCATGGGTGACTCATGGGTGA<br>CTCATGCTaCgTgTgAcGGTGACTCATGGGTGACTCATGGGTGACTCATGaagTcgcaGat<br>tGGTGACTCATGGGTGACTCATGGGTGACTCATGGGTACCGGGAAAAGTTCAGCTGAGAGA<br>TATAAAAGAGCAGTCTTTCCAGCACCTGCAAATCCAGAGCGGCGGGCACTGACGGGCACTT<br>GCACCGTGTGGACAGACTCTCCGGTTCTGTGAGTGGTTTTTCTTTTCCCGGGTCGGACCTG<br>GAGTTCTTAGGGGGATGGCTG |
| 421 | SRS025 | GGGGCGGGGtgATGACACAGCAATtcGGGACTTTCCacGCTTGCGTGAGAAGagACCGGAA<br>GTgaATGACACAGCAATGGATCCGCTTGCGTGAGAAGctGGGACTTTCCtaGGGGGGGGGt<br>tGGGACTTTCCacATGACACAGCAATacCTCGAGGGTGACTCATGATGATGCCACGTCACC<br>AATGCCACGTCACCAGGTGACTCATGGGTGACTCATGaCgTgTgAcATGCCACGTCACCAA<br>TGCCACGTCACCAGGTGACTCATGGGTGACTCATGGGTACCGGGAAAAGTTCAGCTGAGAG<br>ATATAAAAGAGCAGTCTTTCCAGCACCTGCAAATCCAGAGCGGCGGGCACTGACGGGCACT<br>TGCACCGTGTGGACAGACTCTCCGGTTCTGTGAGTGGTTTTTCTTTTCCCGGGTCGGACCT<br>GGAGTTCTTAGGGGGATGGCTG |
| 422 | SRS026 | ATGACTCAGCAATTAGCGAGTTAGAATGACTCAGCAATTATGCGTCGGACATGACTCAGCA<br>ATTACATCTCGATTATGACTCAGCAATTAGGATAGGCATATGACTCAGCAATTACATAGCA<br>GCAATGACTCAGCAATTAGCTAGTAAGCTTGGGGGGGGGtgATGACACAGCAATtcGGGAC<br>TTTCCacGCTTGCGTGAGAAGagACCGGAAGTgaATGACACAGCAATGGATCCGCTTGCGT<br>GAGAAGctGGGACTTTCCtaGGGGGGGGGttGGGACTTTCCacATGACACAGCAATacCTC<br>GAGGGTACCGGCCCGCCCCCTTTCCTTACGCGGATTGGTAGCTGCAGGCTTCCCTATCTGA<br>TTGGCCGAACGAACGCAGCGCGTAATTTAAAATATTGTATCTGTAACAAAGCTGCACCTCG<br>TGGGCGGAGTTGTGCTCTGCGGCTGCGAAAGTCCAGCTTCGGCGACTAGGTGTGAGTAAGC<br>CAGTATCCCAGGAGGAGCAAGTGGCACGTCTTCGGGTGAGTGTGCGGCTGTGCTGGAGCCC<br>GGGTTACCAGCTCTT |
| 423 | SRS027 | GGGGCGGGGtgATGACACAGCAATtcGGGACTTTCCacGCTTGCGTGAGAAGagACCGGAA<br>GTgaATGACACAGCAATGGATCCGCTTGCGTGAGAAGctGGGACTTTCCtaGGGGGGGGGt<br>tGGGACTTTCCacATGACACAGCAATacCTCGAGGGTACCCATACTGAAAAGCATACTTTT<br>GCAATGTTATTTTTAAAAACAAGGAACTCTTTAACCCAGGGAAGATAATCACTTGGGGAAA<br>GGAAGGTTCGTTTCTGAGTTAGCAACAAGTAAATGCAGCACTAGTGGGTGGGATTGAGGTA<br>TGCCCTGGTGCATAAATAGAGACTCAGCTGTGCTGGCACACTCAGAAGCTTGGACCGCATC<br>CTAGCCGCCGACTCACACAAGGCAGGTGGGTGAGGAAATCCAGGTAAGGCTCCTGACAGCA<br>GCTTTAGAAGGGTACTTGCTGGAGTGAATTCGGGCCTCTGATTA |
| 424 | SRS028 | ACATCAAAGGATTTACGGACATCAAAGGATGTACCTACATCAAAGGAATCCTTAACATCAA<br>AGGACGCATAGACATCAAAGGAGTTGCGTACATCAAAGGAGCTAGTAAGCTTGGGGCGGGG<br>tgATGACACAGCAATtcGGGACTTTCCacGCTTGCGTGAGAAGagACCGGAAGTgaATGAC<br>ACAGCAATGGATCCGCTTGCGTGAGAAGctGGGACTTTCCtaGGGGCGGGGttGGGACTTT<br>CCacATGACACAGCAATacCTCGAGGGTACCGGCCCGCCCCCTTTCCTTACGCGGATTGGT<br>AGCTGCAGGCTTCCCTATCTGATTGGCCGAACGAACGCAGCGCGTAATTTAAAATATTGTA<br>TCTGTAACAAAGCTGCACCTCGTGGGCGGAGTTGTGCTCTGCGGCTGCGAAAGTCCAGCTT<br>CGGCGACTAGGTGTGAGTAAGCCAGTATCCCAGGAGGAGCAAGTGGCACGTCTTCGGGTGA<br>GTGTGCGGCTGTGCTGGAGCCCGGGTTACCAGCTCTT |
| 425 | SRS029 | GGTGACTCATGGGTGACTCATGGGTGACTCATGCTaCgTgTgAcGGTGACTCATGGGTGAC<br>TCATGGGTGACTCATGaagTcgcaGattGGTGACTCATGGGTGACTCATGGGTGACTCATG<br>ACTAGTAAGCTTGGGGGGGGGtgATGACACAGCAATtcGGGACTTTCCacGCTTGCGTGAG<br>AAGagACCGGAAGTgaATGACACAGCAATGGATCCGCTTGCGTGAGAAGctGGGACTTTCC<br>taGGGGCGGGGttGGGACTTTCCacATGACACAGCAATacCTCGAGGGTACCGGCCCGCCC<br>CCTTTCCTTACGCGGATTGGTAGCTGCAGGCTTCCCTATCTGATTGGCCGAACGAACGCAG<br>CGCGTAATTTAAAATATTGTATCTGTAACAAAGCTGCACCTCGTGGGCGGAGTTGTGCTCT<br>GCGGCTGCGAAAGTCCAGCTTCGGCGACTAGGTGTGAGTAAGCCAGTATCCCAGGAGGAGC<br>AAGTGGCACGTCTTCGGGTGAGTGTGCGGCTGTGCTGGAGCCCGGGTTACCAGCTCTT |
| 426 | SRS030 | GGTGACTCATGATGATGCCACGTCACCAATGCCACGTCACCAGGTGACTCATGGGTGACTC<br>ATGaCgTgTgAcATGCCACGTCACCAATGCCACGTCACCAGGTGACTCATGGGTGACTCAT<br>GACTAGTAAGCTTGGGGCGGGGtgATGACACAGCAATtcGGGACTTTCCacGCTTGCGTGA<br>GAAGagACCGGAAGTgaATGACACAGCAATGGATCCGCTTGCGTGAGAAGctGGGACTTTC<br>CtaGGGGCGGGGttGGGACTTTCCacATGACACAGCAATacCTCGAGGGTACCGGCCCGCC<br>CCCTTTCCTTACGCGGATTGGTAGCTGCAGGCTTCCCTATCTGATTGGCCGAACGAACGCA |

TABLE 1C-continued

Sequences of Synthetic Response Sensors (SRSs) according to the disclosure

| SEQ ID NO: | Name | Sequence |
|---|---|---|
| | | GCGCGTAATTTAAAATATTGTATCTGTAACAAAGCTGCACCTCGTGGGCGGAGTTGTGCTC TGCGGCTGCGAAAGTCCAGCTTCGGCGACTAGGTGTGAGTAAGCCAGTATCCCAGGAGGAG CAAGTGGCACGTCTTCGGGTGAGTGTGCGGCTGTGCTGGAGCCCGGGTTACCAGCTCTT |
| 427 | SRS031 | CACTTCCGGTTTACTTCCACTTCCGGTTTACTAGCACTTCCGGTTTACGCTCACTTCCGGT TTACGATCACTTCCGGTTTACAGACACTTCCGGTTTACGCTAGTAAGCTTGGGGCGGGGTg ATGACACAGCAATtcGGGACTTTCCacGCTTGCGTGAGAAGagACCGGAAGTgaATGACAC AGCAATGGATCCGCTTGCGTGAGAAGctGGGACTTTCCtaGGGGGGGGGGttGGGACTTTCC acATGACACAGCAATacCTCGAGGGTACCGGCCCGCCCCCTTTCCTTACGCGGATTGGTAG CTGCAGGCTTCCCTATCTGATTGGCCGAACGAACGCAGCGCGTAATTTAAAATATTGTATC TGTAACAAAGCTGCACCTCGTGGGCGGAGTTGTGCTCTGCGGCTGCGAAAGTCCAGCTTCG GCGACTAGGTGTGAGTAAGCCAGTATCCCAGGAGGAGCAAGTGGCACGTCTTCGGGTGAGT GTGCGGCTGTGCTGGAGCCCGGGTTACCAGCTCTT |
| 428 | SRS032 | ATGACTCAGCAATTAGCGAGTTAGAATGACTCAGCAATTATGCGTCGGACATGACTCAGCA ATTACATCTCGATTATGACTCAGCAATTAGGATAGGCATATGACTCAGCAATTACATAGCA GCAATGACTCAGCAATTAGCTAGTAAGCTTGGGGGGGGGtgATGACACAGCAATtcGGGAC TTTCCacGCTTGCGTGAGAAGagACCGGAAGTgaATGACACAGCAATGGATCCGCTTGCGT GAGAAGctGGGACTTTCCtaGGGGGGGGGGttGGGACTTTCCacATGACACAGCAATacCTC GAGGGTACCGGGAAAAGTTCAGCTGAGAGATATAAAAGAGCAGTCTTTCCAGCACCTGCAA ATCCAGAGCGGCGGGCACTGACGGGCACTTGCACCGTGTGGACAGACTCTCCGGTTCTGTG AGTGGTTTTTCTTTTCCCGGGTCGGACCTGGAGTTCTTAGGGGGATGGCTG |
| 429 | SRS033 | ACATCAAAGGATTTACGGACATCAAAGGATGTACCTACATCAAAGGAATCCTTAACATCAA AGGACGCATAGACATCAAAGGAGTTGCGTACATCAAAGGAGCTAGTAAGCTTGGGGCGGGG tgATGACACAGCAATtcGGGACTTTCCacGCTTGCGTGAGAAGagACCGGAAGTgaATGAC ACAGCAATGGATCCGCTTGCGTGAGAAGctGGGACTTTCCtaGGGGGGGGGGttGGGACTTT CCacATGACACAGCAATacCTCGAGGGTACCGGGAAAAGTTCAGCTGAGAGATATAAAAGA GCAGTCTTTCCAGCACCTGCAAATCCAGAGCGGCGGGCACTGACGGGCACTTGCACCGTGT GGACAGACTCTCCGGTTCTGTGAGTGGTTTTTCTTTTCCCGGGTCGGACCTGGAGTTCTTA GGGGGATGGCTG |
| 430 | SRS034 | GGTGACTCATGGGTGACTCATGGGTGACTCATGCTaCgTgTgAcGGTGACTCATGGGTGAC TCATGGGTGACTCATGaagTcgcaGattGGTGACTCATGGGTGACTCATGGGTGACTCATG ACTAGTAAGCTTGGGGCGGGGtgATGACACAGCAATtcGGGACTTTCCacGCTTGCGTGAG AAGagACCGGAAGTgaATGACACAGCAATGGATCCGCTTGCGTGAGAAGctGGGACTTTCC taGGGGCGGGGttGGGACTTTCCacATGACACAGCAATacCTCGAGGGTACCGGGAAAAGT TCAGCTGAGAGATATAAAAGAGCAGTCTTTCCAGCACCTGCAAATCCAGAGCGGCGGGCAC TGACGGGCACTTGCACCGTGTGGACAGACTCTCCGGTTCTGTGAGTGGTTTTTCTTTTCCC GGGTCGGACCTGGAGTTCTTAGGGGGATGGCTG |
| 431 | SRS035 | GGTGACTCATGATGATGCCACGTCACCAATGCCACGTCACCAGGTGACTCATGGGTGACTC ATGaCgTgTgAcATGCCACGTCACCAATGCCACGTCACCAGGTGACTCATGGGTGACTCAT GACTAGTAAGCTTGGGGCGGGGtgATGACACAGCAATtcGGGACTTTCCacGCTTGCGTGA GAAGagACCGGAAGTgaATGACACAGCAATGGATCCGCTTGCGTGAGAAGctGGGACTTTC CtaGGGGCGGGGttGGGACTTTCCacATGACACAGCAATacCTCGAGGGTACCGGGAAAAG TTCAGCTGAGAGATATAAAAGAGCAGTCTTTCCAGCACCTGCAAATCCAGAGCGGCGGGCA CTGACGGGCACTTGCACCGTGTGGACAGACTCTCCGGTTCTGTGAGTGGTTTTTCTTTTCC CGGGTCGGACCTGGAGTTCTTAGGGGGATGGCTG AGTGCTAGTAAACCGGAAGTGGAAGTAAACCGGAAGTGACTAGTAAGCTTGGGGGGGGGGtg |
| 432 | SRS036 | GTAAACCGGAAGTGTCTGTAAACCGGAAGTGATCGTAAACCGGAAGTGAGCGTAAACCGGA AGTGCTAGTAAACCGGAAGTGGAAGTAAACCGGAAGTGACTAGTAAGCTTGGGGGGGGGGtg ATGACACAGCAATtcGGGACTTTCCacGCTTGCGTGAGAAGagACCGGAAGTgaATGACAC AGCAATGGATCCGCTTGCGTGAGAAGctGGGACTTTCCtaGGGGGGGGGGttGGGACTTTCC acATGACACAGCAATacCTCGAGGGTACCGGGAAAAGTTCAGCTGAGAGATATAAAAGAGC AGTCTTTCCAGCACCTGCAAATCCAGAGCGGCGGGCACTGACGGGCACTTGCACCGTGTGG ACAGACTCTCCGGTTCTGTGAGTGGTTTTTCTTTTCCCGGGTCGGACCTGGAGTTCTTAGG GGGATGGCTG |
| 433 | SRS037 | GGGGCGGGGtgATGACACAGCAATtcGGGACTTTCCacGCTTGCGTGAGAAGagACCGGAA GTgaATGACACAGCAATGGATCCGCGTCCGCCCGAGTCCCCGCCTCGCCGCCAACGCCAAt gcTcatGCGTCCGCCCGAGTCCCCGCCTCGCCGCCAACGCCAtcatgcctGCGTCCGCCCG AGTCCCCGCCTCGCCGCCAACGCCAGGATCCGCTTGCGTGAGAAGctGGGACTTTCCtaGG GGCGGGGttGGGACTTTCCacATGACACAGCAATacCTCGAGGGTGACTCATGATGATGCC ACGTCACCAATGCCACGTCACCAGGTGACTCATGGGTGACTCATGaCgTgTgAcATGCCAC GTCACCAATGCCACGTCACCAGGTGACTCATGGGTGACTCATGGGTGACTCATGGGCCCCCT TTCCTTACGCGGATTGGTAGCTGCAGGCTTCCCTATCTGATTGGCCGAACGAACGCAGCGC GTAATTTAAAATATTGTATCTGTAACAAAGCTGCACCTCGTGGGCGGAGTTGTGCTCTGCG GCTGCGAAAGTCCAGCTTCGGCGACTAGGTGTGAGTAAGCCAGTATCCCAGGAGGAGCAAG TGGCACGTCTTCGGGTGAGTGTGCGGCTGTGCTGGAGCCCGGGTTACCAGCTCTT |

TABLE 1C-continued

Sequences of Synthetic Response Sensors (SRSs) according to the disclosure

SEQ
ID
NO:   Name    Sequence

434   SRS038  ATGACTCAGCAATTAGCGAGTTAGAATGACTCAGCAATTATGCGTCGGACATGACTCAGCA
              ATTACATCTCGATTATGACTCAGCAATTAGGATAGGCATATGACTCAGCAATTACATAGCA
              GCAATGACTCAGCAATTAGCTAGTAAGCTTGGGGGGGGGGtqATGACACAGCAATtcGGGAC
              TTTCCacGCTTGCGTGAGAAGAgaACCGGAAGTgaATGACACAGCAATGGATCCGCTTGCGT
              GAGAAGctGGGACTTTCCtaGGGGGGGGGGttGGGACTTTCCacATGACACAGCAATacCTC
              GAGGGTGACTCATGATGATGCCACGTCACCAATGCCACGTCACCAGGTGACTCATGGGTGA
              CTCATGaCgTgTgAcATGCCACGTCACCAATGCCACGTCACCAGGTGACTCATGGGTGACT
              CATGGGTACCGGCCCGCCCCCTTTCCTTACGCGGATTGGTAGCTGCAGGCTTCCCTATCTG
              ATTGGCCGAACGAACGCAGCGCGTAATTTAAAATATTGTATCTGTAACAAAGCTGCACCTC
              GTGGGCGGAGTTGTGCTCTGCGGCTGCGAAAGTCCAGCTTCGGCGACTAGGTGTGAGTAAG
              CCAGTATCCCAGGAGGAGCAAGTGGCACGTCTTCGGGTGAGTGTGCGGCTGTGCTGGAGCC
              CGGGTTACCAGCTCTT

435   SRS039  ACATCAAAGGATTTACGGACATCAAAGGATGTACCTACATCAAAGGAATCCTTAACATCAA
              AGGACGCATAGACATCAAAGGAGTTGCGTACATCAAAGGAGCTAGTAAGCTTGGGGCGGGG
              tgATGACACAGCAATtcGGGACTTTCCacGCTTGCGTGAGAAGAgaACCGGAAGTgaATGAC
              ACAGCAATGGATCCGCTTGCGTGAGAAGctGGGACTTTCCtaGGGGGGGGGGttGGGACTTT
              CCacATGACACAGCAATacCTCGAGGGTGACTCATGATGATGCCACGTCACCAATGCCACG
              TCACCAGGTGACTCATGGGTGACTCATGaCgTgTgAcATGCCACGTCACCAATGCCACGTC
              ACCAGGTGACTCATGGGTGACTCATGGGTACCGGCCCGCCCCCTTTCCTTACGCGGATTGG
              TAGCTGCAGGCTTCCCTATCTGATTGGCCGAACGAACGCAGCGCGTAATTTAAAATATTGT
              ATCTGTAACAAAGCTGCACCTCGTGGGCGGAGTTGTGCTCTGCGGCTGCGAAAGTCCAGCT
              TCGGCGACTAGGTGTGAGTAAGCCAGTATCCCAGGAGGAGCAAGTGGCACGTCTTCGGGTG
              AGTGTGCGGCTGTGCTGGAGCCCGGGTTACCAGCTCTT

436   SRS040  CACTTCCGGTTTACTTCCACTTCCGGTTTACTAGCACTTCCGGTTTACGCTCACTTCCGGT
              TTACGATCACTTCCGGTTTACAGACACTTCCGGTTTACGCTAGTAAGCTTGGGGGGGGGGtg
              ATGACACAGCAATtcGGGACTTTCCacGCTTGCGTGAGAAGAgaACCGGAAGTgaATGACAC
              AGCAATGGATCCGCTTGCGTGAGAAGctGGGACTTTCCtaGGGGGGGGGGttGGGACTTTCC
              acATGACACAGCAATacCTCGAGGGTGACTCATGATGATGCCACGTCACCAATGCCACGTC
              ACCAGGTGACTCATGGGTGACTCATGaCgTgTgAcATGCCACGTCACCAATGCCACGTCAC
              CAGGTGACTCATGGGTGACTCATGGGTACCGGCCCGCCCCCTTTCCTTACGCGGATTGGTA
              GCTGCAGGCTTCCCTATCTGATTGGCCGAACGAACGCAGCGCGTAATTTAAAATATTGTAT
              CTGTAACAAAGCTGCACCTCGTGGGCGGAGTTGTGCTCTGCGGCTGCGAAAGTCCAGCTTC
              GGCGACTAGGTGTGAGTAAGCCAGTATCCCAGGAGGAGCAAGTGGCACGTCTTCGGGTGAG
              TGTGCGGCTGTGCTGGAGCCCGGGTTACCAGCTCTT

437   SRS041  GGGGCGGGGtgATGACACAGCAATtcGGGACTTTCCacGCTTGCGTGAGAAGAgACCGGAA
              GTgaATGACACAGCAATGGATCCCAACATGGCGGCGCCCAACATGGCGGCTACCAACATGG
              CGGCCTCCAACATGGCGGCAGGCAACATGGCGGCTGCCAACATGGCGGCGGATCCGCTTGC
              GTGAGAAGctGGGACTTTCCtaGGGGGGGGGGttGGGACTTTCCacATGACACAGCAATacC
              TCGAGGGTGACTCATGATGATGCCACGTCACCAATGCCACGTCACCAGGTGACTCATGGGT
              GACTCATGaCgTgTgAcATGCCACGTCACCAATGCCACGTCACCAGGTGACTCATGGGTGA
              CTCATGGGTACCGGCCCGCCCCCTTTCCTTACGCGGATTGGTAGCTGCAGGCTTCCCTATC
              TGATTGGCCGAACGAACGCAGCGCGTAATTTAAAATATTGTATCTGTAACAAAGCTGCACC
              TCGTGGGCGGAGTTGTGCTCTGCGGCTGCGAAAGTCCAGCTTCGGCGACTAGGTGTGAGTA
              AGCCAGTATCCCAGGAGGAGCAAGTGGCACGTCTTCGGGTGAGTGTGCGGCTGTGCTGGAG
              CCCGGGTTACCAGCTCTT

438   SRS042  GGGGGGGGGtgATGACACAGCAATtcGGGACTTTCCacGCTTGCGTGAGAAGAgACCGGAA
              GTgaATGACACAGCAATGGATCCTCCTTTGATGTACGCAACTCCTTTGATGTCTATGCGTC
              CTTTGATGTTAAGGATTCCTTTGATGTAGGTACATCCTTTGATGTCGTAAATCCTTTGAT
              GTGGATCCGCTTGCGTGAGAAGctGGGACTTTCCtaGGGGCGGGGttGGGACTTTCCacAT
              GACACAGCAATacCTCGAGGGTGACTCATGATGATGCCACGTCACCAATGCCACGTCACCA
              GGTGACTCATGGGTGACTCATGaCgTgTgAcATGCCACGTCACCAATGCCACGTCACCAGG
              TGACTCATGGGTGACTCATGGGTACCGGCCCGCCCCCTTTCCTTACGCGGATTGGTAGCTG
              CAGGCTTCCCTATCTGATTGGCCGAACGAACGCAGCGCGTAATTTAAAATATTGTATCTGT
              AACAAAGCTGCACCTCGTGGGCGGAGTTGTGCTCTGCGGCTGCGAAAGTCCAGCTTCGGCG
              ACTAGGTGTGAGTAAGCCAGTATCCCAGGAGGAGCAAGTGGCACGTCTTCGGGTGAGTGTG
              CGGCTGTGCTGGAGCCCGGGTTACCAGCTCTT

439   SRS043  TAATTGCTGAGTCATTGCTGCTATGTAATTGCTGAGTCATATGCCTATCCTAATTGCTGAG
              TCATAATCGAGATGTAATTGCTGAGTCATGTCCGACGCATAATTGCTGAGTCATTCTAACT
              CGCTAATTGCTGAGTCATGTCGACGCTAGCGGTGACTCATGATGATGCCACGTCACCAATG
              CCACGTCACCAGGTGACTCATGGGTGACTCATGaCgTgTgAcATGCCACGTCACCAATGCC
              ACGTCACCAGGTGACTCATGGGTGACTCATGACTAGTAAGCTTGGGGGGGGGGtgATGACAC
              AGCAATtcGGGACTTTCCacGCTTGCGTGAGAAGAgACCGGAAGTgaATGACACAGCAATG
              GATCCGCTTGCGTGAGAAGctGGGACTTTCCtaGGGGGGGGGGttGGGACTTTCCacATGAC
              ACAGCAATacCTCGAGGGTACCGGCCCGCCCCCTTTCCTTACGCGGATTGGTAGCTGCAGG
              CTTCCCTATCTGATTGGCCGAACGAACGCAGCGCGTAATTTAAAATATTGTATCTGTAACA
              AAGCTGCACCTCGTGGGCGGAGTTGTGCTCTGCGGCTGCGAAAGTCCAGCTTCGGCGACTA
              GGTGTGAGTAAGCCAGTATCCCAGGAGGAGCAAGTGGCACGTCTTCGGGTGAGTGTGCGGC
              TGTGCTGGAGCCCGGGTTACCAGCTCTT

TABLE 1C-continued

Sequences of Synthetic Response Sensors (SRSs) according to the disclosure

| SEQ ID NO: | Name | Sequence |
|---|---|---|
| 440 | SRS044 | TAATTGCTGAGTCATTGCTGCTATGTAATTGCTGAGTCATATGCCTATCCTCCTTTGATGT<br>ACGCAACTCCTTTGATGTCTATGCGTAATTGCTGAGTCATAATCGAGATGTAATTGCTGAG<br>TCATGTCCGACGCATCCTTTGATGTTAAGGATTCCTTTGATGTAGGTACATAATTGCTGAG<br>TCATTCTAACTCGCTAATTGCTGAGTCATcatCtcgAcCTCCTTTGATGTCCGTAAATCCT<br>TTGATGTGTCGACGCTAGCGGTGACTCATGATGATGCCACGTCACCAATGCCACGTCACCA<br>GGTGACTCATGGGTGACTCATGaCgTgTgAcATGCCACGTCACCAATGCCACGTCACCAGG<br>TGACTCATGGGTGACTCATGACTAGTAAGCTTGGGGGGGGGtgATGACACAGCAATtcGGG<br>ACTTTCCacGCTTGCGTGAGAAGagACCGGAAGTgaATGACACAGCAATGGATCCGCTTGC<br>GTGAGAAGctGGGACTTTCCtaGGGGCGGGGttGGGACTTTCCacATGACACAGCAATacC<br>TCGAGGGTACCGGCCCGCCCCCTTTCCTTACGCGGATTGGTAGCTGCAGGCTTCCCTATCT<br>GATTGGCCGAACGAACGCAGCGCGTAATTTAAAATATTGTATCTGTAACAAAGCTGCACCT<br>CGTGGGCGGAGTTGTGCTCTGCGGCTGCGAAAGTCCAGCTTCGGCGACTAGGTGTGAGTAA<br>GCCAGTATCCCAGGAGGAGCAAGTGGCACGTCTTCGGGTGAGTGTGCGGCTGTGCTGGAGC<br>CCGGGTTACCAGCTCTT |
| 441 | SRS045 | TAATTGCTGAGTCATTGCTGCTATGTAATTGCTGAGTCATATGCCTATCCTAATTGCTGAG<br>TCATAATCGAGATGTAATTGCTGAGTCATGTCCGACGCATAATTGCTGAGTCATTCTAACT<br>CGCTAATTGCTGAGTCATGTCGACACTAGTAAGCTTGGGGGGGGGtgATGACACAGCAATt<br>CGGGACTTTCCacGCTTGCGTGAGAAGagACCGGAAGTgaATGACACAGCAATGGATCCGC<br>TTGCGTGAGAAGctGGGACTTTCCtaGGGGGGGGGttGGGACTTTCCacATGACACAGCAA<br>TacCTCGAGGGTACCGGCCCGCCCCCTTTCCTTACGCGGATTGGTAGCTGCAGGCTTCCCT<br>ATCTGATTGGCCGAACGAACGCAGCGCGTAATTTAAAATATTGTATCTGTAACAAAGCTGC<br>ACCTCGTGGGCGGAGTTGTGCTCTGCGGCTGCGAAAGTCCAGCTTCGGCGACTAGGTGTGA<br>GTAAGCCAGTATCCCAGGAGGAGCAAGTGGCACGTCTTCGGGTGAGTGTGCGGCTGTGCTG<br>GAGCCCGGGTTACCAGCTCTT |
| 442 | SRS046 | GGTGACTCATGATGATGCCACGTCACCAATGCCACGTCACCAGGTGACTCATGGGTGACTC<br>ATGaCgTgTgAcATGCCACGTCACCAATGCCACGTCACCAGGTGACTCATGGGTGACTCAT<br>GACTAGTGAATTCTAATTGCTGAGTCATTGCTGCTATGTAATTGCTGAGTCATATGCCTAT<br>CCTCCTTTGATGTACGCAACTCCTTTGATGTCTATGCGTAATTGCTGAGTCATAATCGAGA<br>TGTAATTGCTGAGTCATGTCCGACGCATCCTTTGATGTTAAGGATTCCTTTGATGTAGGTA<br>CATAATTGCTGAGTCATTCTAACTCGCTAATTGCTGAGTCATcatCtcgAcCTCCTTTGAT<br>GTCCGTAAATCCTTTGATGTGTCGACACTAGTAAGCTTGGGGCGGGGtgATGACACAGCAA<br>TtcGGGACTTTCCacGCTTGCGTGAGAAGagACCGGAAGTgaATGACACAGCAATGGATCC<br>GCTTGCGTGAGAAGctGGGACTTTCCtaGGGGGGGGGGttGGGACTTTCCacATGACACAGC<br>AATacCTCGAGGGTACCGGCCCGCCCCCTTTCCTTACGCGGATTGGTAGCTGCAGGCTTCC<br>CTATCTGATTGGCCGAACGAACGCAGCGCGTAATTTAAAATATTGTATCTGTAACAAAGCT<br>GCACCTCGTGGGCGGAGTTGTGCTCTGCGGCTGCGAAAGTCCAGCTTCGGCGACTAGGTGT<br>GAGTAAGCCAGTATCCCAGGAGGAGCAAGTGGCACGTCTTCGGGTGAGTGTGCGGCTGTGC<br>TGGAGCCCGGGTTACCAGCTCTT |
| 443 | SRS047 | TCCTTTGATGTACGCAACTCCTTTGATGTCTATGCGTCCTTTGATGTTAAGGATTCCTTTG<br>ATGTAGGTACATCCTTTGATGTCCGTAAATCCTTTGATGTGTCGACGCTAGCGGTGACTCA<br>TGATGATGCCACGTCACCAATGCCACGTCACCAGGTGACTCATGGGTGACTCATGaCgTgT<br>gAcATGCCACGTCACCAATGCCACGTCACCAGGTGACTCATGGGTGACTCATGACTAGTAA<br>GCTTGGGGCGGGGtgATGACACAGCAATtcGGGACTTTCCacGCTTGCGTGAGAAGagACC<br>GGAAGTgaATGACACAGCAATGGATCCGCTTGCGTGAGAAGctGGGACTTTCCtaGGGGCG<br>GGGttGGGACTTTCCacATGACACAGCAATacCTCGAGGGTACCGGCCCGCCCCCTTTCCT<br>TACGCGGATTGGTAGCTGCAGGCTTCCCTATCTGATTGGCCGAACGAACGCAGCGCGTAAT<br>TTAAAATATTGTATCTGTAACAAAGCTGCACCTCGTGGGCGGAGTTGTGCTCTGCGGCTGC<br>GAAAGTCCAGCTTCGGCGACTAGGTGTGAGTAAGCCAGTATCCCAGGAGGAGCAAGTGGCA<br>CGTCTTCGGGTGAGTGTGCGGCTGTGCTGGAGCCCGGGTTACCAGCTCTT |
| 444 | SRS048 | GGTGACTCATGATGATGCCACGTCACCAATGCCACGTCACCAGGTGACTCATGGGTGACTC<br>ATGaCgTgTgAcATGCCACGTCACCAATGCCACGTCACCAGGTGACTCATGGGTGACTCAT<br>GACTAGTGAATTCGACTCCTTTGATGTACGCAACTCCTTTGATGTCTATGCGTCCTTTGAT<br>GTTAAGGATTCCTTTGATGTAGGTACATCCTTTGATGTCCGTAAATCCTTTGATGTGTCGA<br>CACTAGTAAGCTTGGGGCGGGGtgATGACACAGCAATtcGGGACTTTCCacGCTTGCGTGA<br>GAAGagACCGGAAGTgaATGACACAGCAATGGATCCGCTTGCGTGAGAAGctGGGACTTTC<br>CtaGGGGCGGGGttGGGACTTTCCacATGACACAGCAATacCTCGAGGGTACCGGCCCGCC<br>CCCTTTCCTTACGCGGATTGGTAGCTGCAGGCTTCCCTATCTGATTGGCCGAACGAACGCA<br>GCGCGTAATTTAAAATATTGTATCTGTAACAAAGCTGCACCTCGTGGGCGGAGTTGTGCTC<br>TGCGGCTGCGAAAGTCCAGCTTCGGCGACTAGGTGTGAGTAAGCCAGTATCCCAGGAGGAG<br>CAAGTGGCACGTCTTCGGGTGAGTGTGCGGCTGTGCTGGAGCCCGGGTTACCAGCTCTT |
| 445 | SRS049 | ATGACTCAGCAATTAGCGAGTTAGAATGACTCAGCAATTATGCGTCGGACATGACTCAGCA<br>ATTACATCTCGATTATGACTCAGCAATTAGGATAGGCATATGACTCAGCAATTACATAGCA<br>GCAATGACTCAGCAATTAGCTAGTAAGCTTGGGGGGGGGtgATGACACAGCAATtcGGGAC<br>TTTCCacGCTTGCGTGAGAAGagACCGGAAGTgaATGACACAGCAATGGATCCGCTTGCGT<br>GAGAAGctGGGACTTTCCtaGGGGGGGGGGttGGGACTTTCCacATGACACAGCAATacCTC<br>GAGGGTACCGGGAAAAGTTCAGCTGAGAGATATAAAAGAGCAGTCTTTCCAGCACCTGCGT<br>ATCCCAGGAGGAGCAAGTGGCACGTCTTCGGGTGAGTGTGCGGCTGTGCTGGAGCCCGGGT<br>TACCAGCTCTTA |

TABLE 1C-continued

Sequences of Synthetic Response Sensors (SRSs) according to the disclosure

| SEQ ID NO: | Name | Sequence |
|---|---|---|
| 446 | SRS050 | ATGACTCAGCAATTAGCGAGTTAGAATGACTCAGCAATTATGCGTCGGACATGACTCAGCA<br>ATTACATCTCGATTATGACTCAGCAATTAGGATAGGCATATGACTCAGCAATTACATAGCA<br>GCAATGACTCAGCAATTAGCTAGTAAGCTTGGGGGGGGGGtgATGACACAGCAATtcGGGAC<br>TTTCCacGCTTGCGTGAGAAGagACCGGAAGTgaATGACACAGCAATGGATCCGCTTGCGT<br>GAGAAGctGGGACTTTCCtaGGGGCGGGGttGGGACTTTCCacATGACACAGCAATacCTC<br>GAGGGTACCtgcgctcccgacatgccccgcggcgcgccattaaccgccagatttgagtcgc<br>gggacccgttggcagaggtgg |
| 447 | SRS051 | GGTGACTCATGATGATGCCACGTCACCAATGCCACGTCACCAGGTGACTCATGGGTGACTC<br>ATGACgTgTgAcATGCCACGTCACCAATGCCACGTCACCAGGTGACTCATGGGTGACTCAT<br>GACTAGTAAGCTTGGGGCGGGGtgATGACACAGCAATtcGGGACTTTCCacGCTTGCGTGA<br>GAAGagACCGGAAGTgaATGACACAGCAATGGATCCGCTTGCGTGAGAAGctGGGACTTTC<br>CtaGGGGCGGGGttGGGACTTTCCacATGACACAGCAATacCTCGAGGGTACCGGGAAAAG<br>TTCAGCTGAGAGATATAAAAGAGCAGTCTTTCCAGCACCTGCGTATCCCAGGAGGAGCAAG<br>TGGCACGTCTTCGGGTGAGTGTGCGGCTGTGCTGGAGCCCGGGTTACCAGCTCTTA |
| 448 | SRS052 | GGTGACTCATGATGATGCCACGTCACCAATGCCACGTCACCAGGTGACTCATGGGTGACTC<br>ATGACgTgTgAcATGCCACGTCACCAATGCCACGTCACCAGGTGACTCATGGGTGACTCAT<br>GACTAGTAAGCTTGGGGCGGGGtgATGACACAGCAATtcGGGACTTTCCacGCTTGCGTGA<br>GAAGagACCGGAAGTgaATGACACAGCAATGGATCCGCTTGCGTGAGAAGctGGGACTTTC<br>CtaGGGGGGGGGttGGGACTTTCCacATGACACAGCAATacCTCGAGGGTACCtgcgctcc<br>cgacatgccccgcggcgcgccattaaccgccagatttgagtcgcgggacccgttggcagag<br>gtgg |
| 449 | SRS053 | ATGACTCAGCAATTAGCGAGTTAGAATGACTCAGCAATTATGCGTCGGACATGACTCAGCA<br>ATTACATCTCGATTATGACTCAGCAATTAGGATAGGCATATGACTCAGCAATTACATAGCA<br>GCAATGACTCAGCAATTAGCTAGTAAGCTTGGGGGGGGGGtgATGACACAGCAATtcGGGAC<br>TTTCCacGCTTGCGTGAGAAGagACCGGAAGTgaATGACACAGCAATGGATCCGGGAGGAA<br>GTCGTAAAACTTGGGAGGAAGTCGTAAAAAATGGGAGGAAGTCGTAAAATGCGGGAGGAAG<br>TCGTAAAAGAAGGGAGGAAGTCGTAAAAATCGGGAGGAAGTCGTAAAAGGATCCGCTTGCG<br>TGAGAAGctGGGACTTTCCtaGGGGGGGGGGttGGGACTTTCCacATGACACAGCAATacCT<br>CGAGGGTACCGGCCCGCCCCCTTTCCTTACGCGGATTGGTAGCTGCAGGCTTCCCTATCTG<br>ATTGGCCGAACGAACGCAGCGCGTAATTTAAAATATTGTATCTGTAACAAAGCTGCACCTC<br>GTGGGCGGAGTTGTGCTCTGCGGCTGCGAAAGTCCAGCTTCGGCGACTAGGTGTGAGTAAG<br>CCAGTATCCCAGGAGGAGCAAGTGGCACGTCTTCGGGTGAGTGTGCGGCTGTGCTGGAGCC<br>CGGGTTACCAGCTCTT |
| 450 | SRS054 | ATGACTCAGCAATTAGCGAGTTAGAATGACTCAGCAATTATGCGTCGGACATGACTCAGCA<br>ATTACATCTCGATTATGACTCAGCAATTAGGATAGGCATATGACTCAGCAATTACATAGCA<br>GCAATGACTCAGCAATTAGCTAGTAAGCTTGGGGCGGGGtgATGACACAGCAATtcGGGAC<br>TTTCCacGCTTGCGTGAGAAGagACCGGAAGTgaATGACACAGCAATGGATCCTCCTTTGA<br>TGTACGCAACTCCTTTGATGTCTATGCGTCCTTTGATGTTAAGGATTCCTTTGATGTAGGT<br>ACATCCTTTGATGTCCGTAAATCCTTTGATGTGGATCCGCTTGCGTGAGAAGctGGGACTT<br>TCCtaGGGGCGGGGttGGGACTTTCCacATGACACAGCAATacCTCGAGGGTACCGGCCCG<br>CCCCCTTTCCTTACGCGGATTGGTAGCTGCAGGCTTCCCTATCTGATTGGCCGAACGAACG<br>CAGCGCGTAATTTAAAATATTGTATCTGTAACAAAGCTGCACCTCGTGGGCGGAGTTGTGC<br>TCTGCGGCTGCGAAAGTCCAGCTTCGGCGACTAGGTGTGAGTAAGCCAGTATCCCAGGAGG<br>AGCAAGTGGCACGTCTTCGGGTGAGTGTGCGGCTGTGCTGGAGCCCGGGTTACCAGCTCTT |
| 451 | SRS055 | GGTGACTCATGATGATGCCACGTCACCAATGCCACGTCACCAGGTGACTCATGGGTGACTC<br>ATGACgTgTgAcATGCCACGTCACCAATGCCACGTCACCAGGTGACTCATGGGTGACTCAT<br>GACTAGTAAGCTTGGGGCGGGGtgATGACACAGCAATtcGGGACTTTCCacGCTTGCGTGA<br>GAAGagACCGGAAGTgaATGACACAGCAATGGATCCTTTTACGACTTCCTCCCGATTTTTA<br>CGACTTCCTCCCTTCTTTTACGACTTCCTCCCGCATTTTACGACTTCCTCCCATTTTTTAC<br>GACTTCCTCCCAAGTTTTACGACTTCCTCCCGGATCCGCTTGCGTGAGAAGctGGGACTTT<br>CCtaGGGGCGGGGttGGGACTTTCCacATGACACAGCAATacCTCGAGGGTACCGGCCCGC<br>CCCCTTTCCTTACGCGGATTGGTAGCTGCAGGCTTCCCTATCTGATTGGCCGAACGAACGC<br>AGCGCGTAATTTAAAATATTGTATCTGTAACAAAGCTGCACCTCGTGGGCGGAGTTGTGCT<br>CTGCGGCTGCGAAAGTCCAGCTTCGGCGACTAGGTGTGAGTAAGCCAGTATCCCAGGAGGA<br>GCAAGTGGCACGTCTTCGGGTGAGTGTGCGGCTGTGCTGGAGCCCGGGTTACCAGCTCTT |
| 452 | SRS056 | GGTGACTCATGATGATGCCACGTCACCAATGCCACGTCACCAGGTGACTCATGGGTGACTC<br>ATGACgTgTgAcATGCCACGTCACCAATGCCACGTCACCAGGTGACTCATGGGTGACTCAT<br>GACTAGTAAGCTTGGGGCGGGGtgATGACACAGCAATtcGGGACTTTCCacGCTTGCGTGA<br>GAAGagACCGGAAGTgaATGACACAGCAATGGATCCTCCTTTGATGTACGCAACTCCTTTG<br>ATGTCTATGCGTCCTTTGATGTTAAGGATTCCTTTGATGTAGGTACATCCTTTGATGTCCG<br>TAAATCCTTTGATGTGGATCCGCTTGCGTGAGAAGctGGGACTTTCCtaGGGGCGGGGttG<br>GGACTTTCCacATGACACAGCAATacCTCGAGGGTACCGGCCCGCCCCCTTTCCTTACGCG<br>GATTGGTAGCTGCAGGCTTCCCTATCTGATTGGCCGAACGAACGCAGCGCGTAATTTAAAA<br>TATTGTATCTGTAACAAAGCTGCACCTCGTGGGCGGAGTTGTGCTCTGCGGCTGCGAAAGT<br>CCAGCTTCGGCGACTAGGTGTGAGTAAGCCAGTATCCCAGGAGGAGCAAGTGGCACGTCTT<br>CGGGTGAGTGTGCGGCTGTGCTGGAGCCCGGGTTACCAGCTCTT |

TABLE 1C-continued

Sequences of Synthetic Response Sensors (SRSs) according to the disclosure

| SEQ ID NO: | Name | Sequence |
|---|---|---|
| 453 | SRS057 | ATGACTCAGCAATTAGCGAGTTAGAATGACTCAGCAATTATGCGTCGGACATGACTCAGCA<br>ATTACATCTCGATTATGACTCAGCAATTAGGATAGGCATATGACTCAGCAATTACATAGCA<br>GCAATGACTCAGCAATTAGCTAGTAAGCTTGGGGCGGGGtgATGACACAGCAATtcGGGAC<br>TTTCCacGCTTGCGTGAGAAGAgaCCGGAAGTgaATGACACAGCAATGGATCCGCTTGCGT<br>GAGAAGctGGGACTTTCCtaGGGGGGGGGttGGGACTTTCCacATGACACAGCAATacCTC<br>GAGGGTACCTATAAAAGGCCAGCAGCAGCCTGACCACATCTCATCC |
| 454 | SRS058 | GGTGACTCATGATGATGCCACGTCACCAATGCCACGTCACCAGGTGACTCATGGGTGACTC<br>ATGaCgTgTgAcATGCCACGTCACCAATGCCACGTCACCAGGTGACTCATGGGTGACTCAT<br>GACTAGTAAGCTTGGGGCGGGGtgATGACACAGCAATtcGGGACTTTCCacGCTTGCGTGA<br>GAAGagACCGGAAGTgaATGACACAGCAATGGATCCGCTTGCGTGAGAAGctGGGACTTTC<br>CtaGGGGCGGGGttGGGACTTTCCacATGACACAGCAATacCTCGAGGGTACCTATAAAAG<br>GCCAGCAGCAGCCTGACCACATCTCATCC |
| 455 | SRS059 | ATGACTCAGCAATTAGCGAGTTAGAATGACTCAGCAATTATGCGTCGGACATGACTCAGCA<br>ATTACATCTCGATTATGACTCAGCAATTAGGATAGGCATATGACTCAGCAATTACATAGCA<br>GCAATGACTCAGCAATTAGCTAGTAAGCTTGGGGGGGGGtgATGACACAGCAATtcGGGAC<br>TTTCCacGCTTGCGTGAGAAGAgaCCGGAAGTgaATGACACAGCAATGGATCCGCTTGCGT<br>GAGAAGctGGGACTTTCCtaGGGGGGGGGttGGGACTTTCCacATGACACAGCAATacCTC<br>GAGGGTACCACCTCTTAACAATACGTTTCACAAATAGTTAAAAACATGCATACTGAAAAGC<br>ATACTTTTGCAATGTTATTTTTAAAAACAAGGAACTCTTTAACCCAGGGAAGATAATCACT<br>TGGGGAAAGGAAGGTTCGTTTCTGAGTTAGCAACAAGTAAATGCAGCACTAGTGGGTGGGA<br>TTGAGGTgTGCCCTGGTGCATAAATAGAGACTCAGCTGTGCTGGCACACTCAAGAAGCTTG<br>GACCGCATCCTAGCCGCCGACTCACACAAGGCAGGTGGGTGAGGAAATCCAGGTAAGGCTC<br>CTGACAGCAGCTTTAGAAGGGTACTTGCTGGAGTGAATTCGGGCCTCTGATT |
| 456 | SRS060 | GGTGACTCATGATGATGCCACGTCACCAATGCCACGTCACCAGGTGACTCATGGGTGACTC<br>ATGaCgTgTgAcATGCCACGTCACCAATGCCACGTCACCAGGTGACTCATGGGTGACTCAT<br>GACTAGTAAGCTTGGGGCGGGGtgATGACACAGCAATtcGGGACTTTCCacGCTTGCGTGA<br>GAAGagACCGGAAGTgaATGACACAGCAATGGATCCGCTTGCGTGAGAAGctGGGACTTTC<br>CtaGGGGCGGGGttGGGACTTTCCacATGACACAGCAATacCTCGAGGGTACCACCTCTTA<br>ACAATACGTTTCACAAATAGTTAAAAACATGCATACTGAAAAGCATACTTTTGCAATGTTA<br>TTTTTAAAAACAAGGAACTCTTTAACCCAGGGAAGATAATCACTTGGGGAAAGGAAGGTTC<br>GTTTCTGAGTTAGCAACAAGTAAATGCAGCACTAGTGGGTGGGATTGAGGTgTGCCCTGGT<br>GCATAAATAGAGACTCAGCTGTGCTGGCACACTCAAGAAGCTTGGACCGCATCCTAGCCGC<br>CGACTCACACAAGGCAGGTGGGTGAGGAAATCCAGGTAAGGCTCCTGACAGCAGCTTTAGA<br>AGGGTACTTGCTGGAGTGAATTCGGGCCTCTGATT |
| 457 | SRS061 | TAATTGCTGAGTCATTGCTGCTATGTAATTGCTGAGTCATATGCCTATCCTAATTGCTGAG<br>TCATAATCGAGATGTAATTGCTGAGTCATGTCCGACGCATAATTGCTGAGTCATTCTAACT<br>CGCTAATTGCTGAGTCATGTCGACGCTAGCGGTGACTCATGATGATGCCACGTCACCAATG<br>CCACGTCACCAGGTGACTCATGGGTGACTCATGaCgTgTgAcATGCCACGTCACCAATGCC<br>ACGTCACCAGGTGACTCATGGGTGACTCATGACTAGTTCCTTTGATGTACGCAACTCCTTT<br>GATGTCTATGCGTCCTTTGATGTTAAGGATTCCTTTGATGTAGGTACATCCTTTGATGTCC<br>GTAAATCCTTTGATGTCTCGAGGGTACCGGCCCGCCCCCTTTCCTTACGCGGATTGGTAGC<br>TGCAGGCTTCCCTATCTGATTGGCCGAACGAACGCAGCGCGTAATTTAAAATATTGTATCT<br>GTAACAAAGCTGCACCTCGTGGGCGGAGTTGTGCTCTGCGGCTGCGAAAGTCCAGCTTCGG<br>CGACTAGGTGTGAGTAAGCCAGTATCCCAGGAGGAGCAAGTGGCACGTCTTCGGGTGAGTG<br>TGCGGCTGTGCTGGAGCCCGGGTTACCAGCTCTT |
| 458 | SRS062 | TAATTGCTGAGTCATTGCTGCTATGTAATTGCTGAGTCATATGCCTATCCTAATTGCTGAG<br>TCATAATCGAGATGTAATTGCTGAGTCATGTCCGACGCATAATTGCTGAGTCATTCTAACT<br>CGCTAATTGCTGAGTCATGTCGACGCTAGCGGTGACTCATGATGATGCCACGTCACCAATG<br>CCACGTCACCAGGTGACTCATGGGTGACTCATGaCgTgTgAcATGCCACGTCACCAATGCC<br>ACGTCACCAGGTGACTCATGGGTGACTCATGACTAGTCAACATGGCGGCGCCCAACATGGC<br>GGCTACCAACATGGCGGCCTCCAACATGGCGGCAGGCAACATGGCGGCTGCCAACATGGCG<br>GCCTCGAGGGTACCGGCCCGCCCCCTTTCCTTACGCGGATTGGTAGCTGCAGGCTTCCCTA<br>TCTGATTGGCCGAACGAACGCAGCGCGTAATTTAAAATATTGTATCTGTAACAAAGCTGCA<br>CCTCGTGGGCGGAGTTGTGCTCTGCGGCTGCGAAAGTCCAGCTTCGGCGACTAGGTGTGAG<br>TAAGCCAGTATCCCAGGAGGAGCAAGTGGCACGTCTTCGGGTGAGTGTGCGGCTGTGCTGG<br>AGCCCGGGTTACCAGCTCTT |
| 459 | SRS063 | TCCTTTGATGTACGCAACTCCTTTGATGTCTATGCGTCCTTTGATGTTAAGGATTCCTTTG<br>ATGTAGGTACATCCTTTGATGTCCGTAAATCCTTTGATGTGTCGACGCTAGCGGTGACTCA<br>TGATGATGCCACGTCACCAATGCCACGTCACCAGGTGACTCATGGGTGACTCATGaCgTgT<br>gAcATGCCACGTCACCAATGCCACGTCACCAGGTGACTCATGGGTGACTCATGACTAGTTA<br>ATTGCTGAGTCATTGCTGCTATGTAATTGCTGAGTCATATGCCTATCCTAATTGCTGAGTC<br>ATAATCGAGATGTAATTGCTGAGTCATGTCCGACGCATAATTGCTGAGTCATTCTAACTCG<br>CTAATTGCTGAGTCATCTCGAGGGTACCGGCCCGCCCCCTTTCCTTACGCGGATTGGTAGC<br>TGCAGGCTTCCCTATCTGATTGGCCGAACGAACGCAGCGCGTAATTTAAAATATTGTATCT<br>GTAACAAAGCTGCACCTCGTGGGCGGAGTTGTGCTCTGCGGCTGCGAAAGTCCAGCTTCGG<br>CGACTAGGTGTGAGTAAGCCAGTATCCCAGGAGGAGCAAGTGGCACGTCTTCGGGTGAGTG<br>TGCGGCTGTGCTGGAGCCCGGGTTACCAGCTCTT |

TABLE 1C-continued

Sequences of Synthetic Response Sensors (SRSs) according to the disclosure

SEQ
ID
NO:  Name    Sequence

460  SRS064  AcgcGtcccgacatgccccgcggcgcgccattaaccgccagatttgagtcgcgggacccgt
             tggcagaggtgg 461  SRS065  GGGGCGGGGtgATGACACAGCAATtcGGGACTTTCCacGCTTGCGTGAGAAGagACCGGAA
             GTgaATGACACAGCAATGGATCCGCTTGCGTGAGAAGctGGGACTTTCCtaGGGGCGGGGt
             tGGGACTTTCCacATGACACAGCAATacCTCGAGGGTGACTCATGATGATGCCACGTCACC
             AATGCCACGTCACCAGGTGACTCATGGGTGACTCATGaCgTgTgAcATGCCACGTCACCAA
             TGCCACGTCACCAGGTGACTCATGGGTGACTCATGGGTACCACCTCTTAACAATACGTTTC
             ACAAATAGTTAAAAACATGCATACTGAAAAGCATACTTTTGCAATGTTATTTTTAAAAACA
             AGGAACTCTTTAACCCAGGGAAGATAATCACTTGGGGAAAGGAAGGTTCGTTTCTGAGTTA
             GCAACAAGTAAATGCAGCACTAGTGGGTGGGATTGAGGTgTGCCCTGGTGCATAAATAGAG
             ACTCAGCTGTGCTGGCACACTCAAAAATCCAGAGCGGCGGGCACTGACGGGCACTTGCACC
             GTGTGGACAGACTCTCCGGTTCTGTGAGTGGTTTTTCTTTTCCCGGGTCGGACCTGGAGTT
             CTTAGGGGGATGGCTGAAgaattcA 462  SRS066  GGGGCGGGGtgATGACACAGCAATtcGGGACTTTCCacGCTTGCGTGAGAAGagACCGGAA
             GTgaATGACACAGCAATGGATCCGCTTGCGTGAGAAGctGGGACTTTCCtaGGGGGGGGGt
             tGGGACTTTCCacATGACACAGCAATacCTCGAGGGTGACTCATGATGATGCCACGTCACC
             AATGCCACGTCACCAGGTGACTCATGGGTGACTCATGaCgTgTgAcATGCCACGTCACCAA
             TGCCACGTCACCAGGTGACTCATGGGTGACTCATGGGTACCACCTCTTAACAATACGTTTC
             ACAAATAGTTAAAAACATGCATACTGAAAAGCATACTTTTGCAATGTTATTTTTAAAAACA
             AGGAACTCTTTAACCCAGGGAAGATAATCACTTGGGGAAAGGAAGGTTCGTTTCTGAGTTA
             GCAACAAGTAAATGCAGCACTAGTGGGTGGGATTGAGGTgTGCCCTGGTGCATAAATAGAG
             ACTCAGCTGTGCTGGCACACTCAAGAAGCTTGGACCGCATCCTAGCCGCCGACTCACACAA
             GGCAGGTGGGTGAGGAAATCCAGGTAAGGCTCCTGACAGCAGCTTTAGAAGGGTACTTGCT
             GGAGTGAATTCGGGCCTCTGATTA 463  SRS067  GGGGCGGGGtgATGACACAGCAATtcGGGACTTTCCacGCTTGCGTGAGAAGagACCGGAA
             GTgaATGACACAGCAATGGATCCGCTTGCGTGAGAAGctGGGACTTTCCtaGGGGGGGGGt
             tGGGACTTTCCacATGACACAGCAATacCTCGAGGGTGACTCATGATGATGCCACGTCACC
             AATGCCACGTCACCAGGTGACTCATGGGTGACTCATGaCgTgTgAcATGCCACGTCACCAA
             TGCCACGTCACCAGGTGACTCATGGGTGACTCATGGGTACCACCTCTTAACAATACGTTTC
             ACAAATAGTTAAAAACATGCATACTGAAAAGCATACTTTTGCAATGTTATTTTTAAAAACA
             AGGAACTCTTTAACCCAGGGAAGATAATCACTTGGGGAAAGGAAGGTTCGTTTCTGAGTTA
             GCAACAAGTAAATGCAGCACTAGTGGGTGGGATTGAGGTgTGCCCTGGTGCATAAATAGAG
             ACTCAGCTGTGCTGGCACACTCAAGTATCCCAGGAGGAGCAAGTGGCACGTCTTCGGGTGA
             GTGTGCGGCTGTGCTGGAGCCCGGGTTACCAGCTCTTAA 464  SRS068  GGGGCGGGGtgATGACACAGCAATtcGGGACTTTCCacGCTTGCGTGAGAAGagACCGGAA
             GTgaATGACACAGCAATGGATCCGCTTGCGTGAGAAGctGGGACTTTCCtaGGGGGGGGGt
             tGGGACTTTCCacATGACACAGCAATacCTCGAGGGTGACTCATGATGATGCCACGTCACC
             AATGCCACGTCACCAGGTGACTCATGGGTGACTCATGaCgTgTgAcATGCCACGTCACCAA
             TGCCACGTCACCAGGTGACTCATGGGTGACTCATGGGTACCACCTCTTAACAATACGTTTC
             ACAAATAGTTAAAAACATGCATACTGAAAAGCATACTTTTGCAATGTTATTTTTAAAAACA
             AGGAACTCTTTAACCCAGGGAAGATAATCACTTGGGGAAAGGAAGGTTCGTTTCTGAGTTA
             GCAACAAGTAAATGCAGCACTAGTGGGTGGGATTGAGGTgTGCCCTGGTGCATAAATAGAG
             ACTCAGCTGTGCTGGCACACTCAACACTCGCGCTGCCATCACTCTTCCGCCGTCTTCGCCG
             CCATCCTCGGCGCGACTCGCTTCTTTCGGTTCTACCAGGTAGAGTCCGCCGCCATCCTCA 465  SRS069  GGGGCGGGGtgATGACACAGCAATtcGGGACTTTCCacGCTTGCGTGAGAAGagACCGGAA
             GTgaATGACACAGCAATGGATCCGCTTGCGTGAGAAGctGGGACTTTCCtaGGGGGGGGGt
             tGGGACTTTCCacATGACACAGCAATacCTCGAGGGTGACTCATGATGATGCCACGTCACC
             AATGCCACGTCACCAGGTGACTCATGGGTGACTCATGaCgTqTqAcATGCCACGTCACCAA
             TGCCACGTCACCAGGTGACTCATGGGTGACTCATGGGTACCACCTCTTAACAATACGTTTC
             ACAAATAGTTAAAAACATGCATACTGAAAAGCATACTTTTGCAATGTTATTTTTAAAAACA
             AGGAACTCTTTAACCCAGGGAAGATAATCACTTGGGGAAAGGAAGGTTCGTTTCTGAGTTA
             GCAACAAGTAAATGCAGCACTAGTGGGTGGGATTGAGGTgTGCCCTGGTGCATAAATAGAG
             ACTCAGCTGTGCTGGCACACTCAACtttttccgtgctacctgcagaggggtccatacggcg
             ttgttctggattca 466  SRS070  GGGGCGGGGtgATGACACAGCAATtcGGGACTTTCCacGCTTGCGTGAGAAGagACCGGAA
             GTgaATGACACAGCAATGGATCCGCTTGCGTGAGAAGctGGGACTTTCCtaGGGGGGGGGt
             tGGGACTTTCCacATGACACAGCAATacCTCGAGGGTGACTCATGATGATGCCACGTCACC
             AATGCCACGTCACCAGGTGACTCATGGGTGACTCATGaCgTgTgAcATGCCACGTCACCAA
             TGCCACGTCACCAGGTGACTCATGGGTGACTCATGGGTACCACCTCTTAACAATACGTTTC
             ACAAATAGTTAAAAACATGCATACTGAAAAGCATACTTTTGCAATGTTATTTTTAAAAACA
             AGGAACTCTTTAACCCAGGGAAGATAATCACTTGGGGAAAGGAAGGTTCGTTTCTGAGTTA
             GCAACAAGTAAATGCAGCACTAGTGGGTGGGATTGAGGTgTGCCCTGGTGCATAAATAGAG
             ACTCAGCTGTGCTGGCACACTCAAcggcggcgcagatcgcccggcgcggctccgccccctg
             cgccggtcacgtgggggcgccggctgcgcctgcggagaagcggtggccgccgagcgggatc
             tgtgcggggagccggaaatggttgtggactacgtctgtgcggctgcgtggggctcggccgc
             gcggactgaaggagactgaaggtgctggggggaccctgatgtggA TABLE 1C-continued Sequences of Synthetic Response Sensors (SRSs) according to the disclosure

| SEQ ID NO: | Name | Sequence |
|---|---|---|
| 467 | SRS071 | GGGGCGGGGtgATGACACAGCAATtcGGGACTTTCCacGCTTGCGTGAGAAGagACCGGAA GTgaATGACACAGCAATGGATCCGCTTGCGTGAGAAGctGGGACTTTCCtaGGGGGGGGGt tGGGACTTTCCacATGACACAGCAATacCTCGAGGGTGACTCATGATGATGCCACGTCACC AATGCCACGTCACCAGGTGACTCATGGGTGACTCATGaCgTgTgAcATGCCACGTCACCAA TGCCACGTCACCAGGTGACTCATGGGTGACTCATGGGTACCGGGAAAAGTTCAGCTGAGAG ATATAAAAGAGCAGTCTTTCCAGCACCTGCGAAGCTTGGACCGCATCCTAGCCGCCGACTC ACACAAGGCAGGTGGGTGAGGAAATCCAGGTAAGGCTCCTGACAGCAGCTTTAGAAGGGTA CTTGCTGGAGTGAATTCGGGCCTCTGATTA |
| 468 | SRS072 | GGGGGGGGGGTGATGACACAGCAATTCGGGACTTTCCACGCTTGCGTGAGAAGAGACCGGAA GTGAATGACACAGCAATGGATCCGCTTGCGTGAGAAGCTGGGACTTTCCTAGGGGGGGGGT TGGGACTTTCCACATGACACAGCAATACCTCGAGGGTGACTCATGATGATGCCACGTCACC AATGCCACGTCACCAGGTGACTCATGGGTGACTCATGACGTGTGACATGCCACGTCACCAA TGCCACGTCACCAGGTGACTCATGGGTGACTCATGGGTACCGGGAAAAGTTCAGCTGAGAG ATATAAAAGAGCAGTCTTTCCAGCACCTGCGTATCCCAGGAGGAGCAAGTGGCACGTCTTC GGGTGAGTGTGCGGCTGTGCTGGAGCCCGGGTTACCAGCTCTTAA |
| 469 | SRS073 | GGGGGGGGGGTGATGACACAGCAATTCGGGACTTTCCACGCTTGCGTGAGAAGAGACCGGAA GTGAATGACACAGCAATGGATCCGCTTGCGTGAGAAGCTGGGACTTTCCTAGGGGGGGGGT TGGGACTTTCCACATGACACAGCAATACCTCGAGGGTGACTCATGATGATGCCACGTCACC AATGCCACGTCACCAGGTGACTCATGGGTGACTCATGACGTGTGACATGCCACGTCACCAA TGCCACGTCACCAGGTGACTCATGGGTGACTCATGGGTACCGGGAAAAGTTCAGCTGAGAG ATATAAAAGAGCAGTCTTTCCAGCACCTGCCACTCGCGCTGCCATCACTCTTCCGCCGTCT TCGCCGCCATCCTCGGCGCGACTCGCTTCTTTCGGTTCTACCAGGTAGAGTCCGCCGCCAT CCTCA |
| 470 | SRS074 | GGGGCGGGGtgATGACACAGCAATtcGGGACTTTCCacGCTTGCGTGAGAAGagACCGGAA GTgaATGACACAGCAATGGATCCGCTTGCGTGAGAAGctGGGACTTTCCtaGGGGGGGGGt tGGGACTTTCCacATGACACAGCAATacCTCGAGGGTGACTCATGATGATGCCACGTCACC AATGCCACGTCACCAGGTGACTCATGGGTGACTCATGaCgTgTgAcATGCCACGTCACCAA TGCCACGTCACCAGGTGACTCATGGGTGACTCATGGGTACCGGGAAAAGTTCAGCTGAGAG ATATAAAAGAGCAGTCTTTCCAGCACCTGCCtttttccgtgctacctgcagaggggtccat acggcgttgttctggattc |
| 471 | SRS075 | GGGGCGGGGtgATGACACAGCAATtcGGGACTTTCCacGCTTGCGTGAGAAGagACCGGAA GTgaATGACACAGCAATGGATCCGCTTGCGTGAGAAGctGGGACTTTCCtaGGGGGGGGGt tGGGACTTTCCacATGACACAGCAATacCTCGAGGGTGACTCATGATGATGCCACGTCACC AATGCCACGTCACCAGGTGACTCATGGGTGACTCATGaCgTgTgAcATGCCACGTCACCAA TGCCACGTCACCAGGTGACTCATGGGTGACTCATGGGTACCGGGAAAAGTTCAGCTGAGAG ATATAAAAGAGCAGTCTTTCCAGCACCTGCcggcggcgcagatcgcccggcgcggctccgc cccctgcgccggtcacgtgggggcgccggctgcgcctgcggagaagcggtggccgccgagc gggatctgtgcggggagccggaaatggttgtggactacgtctgtgcggctgcgtggggctc ggccgcgcggactgaaggagactgaaggtgctgggggggaccctgatgtgg |
| 472 | SRS076 | GGGGCGGGGtgATGACACAGCAATtcGGGACTTTCCacGCTTGCGTGAGAAGagACCGGAA GTgaATGACACAGCAATGGATCCGCTTGCGTGAGAAGctGGGACTTTCCtaGGGGGGGGGt tGGGACTTTCCacATGACACAGCAATacCTCGAGGGTGACTCATGATGATGCCACGTCACC AATGCCACGTCACCAGGTGACTCATGGGTGACTCATGaCgTgTgAcATGCCACGTCACCAA TGCCACGTCACCAGGTGACTCATGGGTGACTCATGGGTACCCGGCCCGCCCCCTTTCCTTA CGCGGATTGGTAGCTGCAGGCTTCCCTATCTGATTGGCCGAACGAACGCAGCGCGTAATTT AAAATATTGTATCTGTAACAAAGCTGCACCTCGTGGGCGGAGTTGTGCTCTGCGGCTGCGA AGTCCAGCTTCGGCGACTAGGTGTGAGTAAGCCAAAATCCAGAGCGGCGGGCACTGACGG GCACTTGCACCGTGTGGACAGACTCTCCGGTTCTGTGAGTGGTTTTTCTTTTCCCGGGTCG GACCTGGAGTTCTTAGGGGGATGGCTGAAgaattc |
| 473 | SRS077 | GGGGCGGGGtgATGACACAGCAATtcGGGACTTTCCacGCTTGCGTGAGAAGagACCGGAA GTgaATGACACAGCAATGGATCCGCTTGCGTGAGAAGctGGGACTTTCCtaGGGGGGGGGt tGGGACTTTCCacATGACACAGCAATacCTCGAGGGTGACTCATGATGATGCCACGTCACC AATGCCACGTCACCAGGTGACTCATGGGTGACTCATGaCgTgTgAcATGCCACGTCACCAA TGCCACGTCACCAGGTGACTCATGGGTGACTCATGGGTACCCGGCCCGCCCCCTTTCCTTA CGCGGATTGGTAGCTGCAGGCTTCCCTATCTGATTGGCCGAACGAACGCAGCGCGTAATTT AAAATATTGTATCTGTAACAAAGCTGCACCTCGTGGGCGGAGTTGTGCTCTGCGGCTGCGA AGTCCAGCTTCGGCGACTAGGTGTGAGTAAGCCAGAAGCTTGGACCGCATCCTAGCCGCC GACTCACACAAGGCAGGTGGGTGAGGAAATCCAGGTAAGGCTCCTGACAGCAGCTTTAGAA GGGTACTTGCTGGAGTGAATTCGGGCCTCTGATT |
| 474 | SRS078 | GGGGGGGGGtgATGACACAGCAATtcGGGACTTTCCacGCTTGCGTGAGAAGagACCGGAA GTgaATGACACAGCAATGGATCCGCTTGCGTGAGAAGctGGGACTTTCCtaGGGGGGGGGt tGGGACTTTCCacATGACACAGCAATacCTCGAGGGTGACTCATGATGATGCCACGTCACC AATGCCACGTCACCAGGTGACTCATGGGTGACTCATGaCgTgTgAcATGCCACGTCACCAA TGCCACGTCACCAGGTGACTCATGGGTGACTCATGGGTACCCGGCCCGCCCCCTTTCCTTA CGCGGATTGGTAGCTGCAGGCTTCCCTATCTGATTGGCCGAACGAACGCAGCGCGTAATTT AAAATATTGTATCTGTAACAAAGCTGCACCTCGTGGGCGGAGTTGTGCTCTGCGGCTGCGA AGTCCAGCTTCGGCGACTAGGTGTGAGTAAGCCACACTCGCGCTGCCATCACTCTTCCGC |

TABLE 1C-continued

Sequences of Synthetic Response Sensors (SRSs) according to the disclosure

| SEQ ID NO: | Name | Sequence |
|---|---|---|

CGTCTTCGCCGCCATCCTCGGCGCGACTCGCTTCTTTCGGTTCTACCAGGTAGAGTCCGCC
GCCATCCTC

475 SRS079 GGGGCGGGGtgATGACACAGCAATtcGGGACTTTCCacGCTTGCGTGAGAAGagACCGGAA
GTgaATGACACAGCAATGGATCCGCTTGCGTGAGAAGctGGGACTTTCCtaGGGGGCGGGGt
tGGGACTTTCCacATGACACAGCAATacCTCGAGGGTGACTCATGATGATGCCACGTCACC
AATGCCACGTCACCAGGTGACTCATGGGTGACTCATGaCgTgTgAcATGCCACGTCACCAA
TGCCACGTCACCAGGTGACTCATGGGTGACTCATGGGTACCCGGCCCGCCCCCTTTCCTTA
CGCGGATTGGTAGCTGCAGGCTTCCCTATCTGATTGGCCGAACGAACGCAGCGCGTAATTT
AAAATATTGTATCTGTAACAAAGCTGCACCTCGTGGGCGGAGTTGTGCTCTGCGGCTGCGA
AAGTCCAGCTTCGGCGACTAGGTGTGAGTAAGCCACtttttccgtgctacctgcagaggggg
tccatacggcgttgttctggattc 476 SRS080 GGGGCGGGGtgATGACACAGCAATtcGGGACTTTCCacGCTTGCGTGAGAAGagACCGGAA
GTgaATGACACAGCAATGGATCCGCTTGCGTGAGAAGctGGGACTTTCCtaGGGGGCGGGGt
tGGGACTTTCCacATGACACAGCAATacCTCGAGGGTGACTCATGATGATGCCACGTCACC
AATGCCACGTCACCAGGTGACTCATGGGTGACTCATGaCgTgTgAcATGCCACGTCACCAA
TGCCACGTCACCAGGTGACTCATGGGTGACTCATGGGTACCCGGCCCGCCCCCTTTCCTTA
CGCGGATTGGTAGCTGCAGGCTTCCCTATCTGATTGGCCGAACGAACGCAGCGCGTAATTT
AAAATATTGTATCTGTAACAAAGCTGCACCTCGTGGGCGGAGTTGTGCTCTGCGGCTGCGA
AAGTCCAGCTTCGGCGACTAGGTGTGAGTAAGCCAcggcggcgcagatcgcccggcgcggc
tccgcccctgcgccggtcacgtgggggcgccggctgcgcctgcggagaagcggtggccgc
cgagcgggatctgtgcggggagccggaaatggttgtggactacgtctgtgcggctgcgtgg
ggctcggccgcgcggactgaaggagactgaaggtgctgggggggaccctgatgtgg 477 SRS081 AGTATAGTGCACAGTGACTGCAGCAGGGTGACTCATGATGATGCCACGTCACCAATGCCAC
GTCACCAGGTGACTCATGGGTGACTCATGATGCCACGTCACCAATGCCACGTCACCAGGTG
ACTCATGGGTGACTCATGGGTACCTATAAAAGGCCAGCAGCAGCCTGACCACATCTCATCC 478 SRS082 TCCTTTGATGTACGCAACTCCTTTGATGTCTATGCGTCCTTTGATGTTAAGGATTCCTTTG
ATGTAGGTACATCCTTTGATGTCCGTAAATCCTTTGATGTAAGCTTAACTCGCAATCTAGC
ATCGTCCGACGCAACGCCTTACACCATCAGAATCTGCTAGCGGTGACTCATGGGTGACTCA
TGGGTGACTCATGGGTGACTCATGCTaCgTGGTGACTCATGGGTGACTCATGGGTGACTCA
TGGGTGACTCATGGGTGACTCATGGGTACCGGGAAAAGTTCAGCTGAGAGATATAAAAGAG
CAGTCTTTCCAGCACCTGCAAATCCAGAGCGGCGGGCACTGACGGGCACTTGCACCGTGTG
GACAGACTCTCCGGTTCTGTGAGTGGTTTTTCTTTTCCCGGGTCGGACCTGGAGTTCTTAG
GGGGATGGCTGa 479 SRS083 TCCTTTGATGTACGCAACTCCTTTGATGTCTATGCGTCCTTTGATGTTAAGGATTCCTTTG
ATGTAGGTACATCCTTTGATGTCCGTAAATCCTTTGATGTAAGCTTGGTACAACTTCTCAC
GGAGGCTTCTAACTCGCAATCTAGCATCGTCCGACGCAACGCCTTACACCATCAGAATCTG
CTAGCGGTGACTCATGGGTGACTCATGGGTGACTCATGGGTGACTCATGCTaCgTGGTGAC
TCATGGGTGACTCATGGGTGACTCATGGGTGACTCATGGGTGACTCATGGGTACCGGGAAA
AGTTCAGCTGAGAGATATAAAAGAGCAGTCTTTCCAGCACCTGCAAATCCAGAGCGGCGGG
CACTGACGGGCACTTGCACCGTGTGGACAGACTCTCCGGTTCTGTGAGTGGTTTTTCTTTT
CCCGGGTCGGACCTGGAGTTCTTAGGGGGATGGCTGa 480 SRS084 TCCTTTGATGTACGCAACTCCTTTGATGTCTATGCGTCCTTTGATGTTAAGGATTCCTTTG
ATGTAGGTACATCCTTTGATGTCCGTAAATCCTTTGATGTGACgattcttgatatcctcga
ggctagcATGATCACCATGAGTCACCCATGAGTCACCCATGAGTCACCCATGAGTCACCCA
TGAGTCACCCATGAGTCACCCATGAGTCACCCATGAGTCACCCATGAGTCACCACTAGTGG
TACCACCTCTTAACAATACGTTTCACAAATAGTTAAAAACATGCATACTGAAAAGCATACT
TTTGCAATGTTATTTTTAAAAACAAGGAACTCTTTAACCCAGGGAAGATAATCACTTGGGG
AAAGGAAGGTTCGTTTCTGAGTTAGCAACAAGTAAATGCAGCACTAGTGGGTGGGATTGAG
GTgTGCCCTGGTGCATAAATAGAGACTCAGCTGTGCTGGCACACTCAGAAGCTTGGACCGC
ATCCTAGCCGCCGACTCACACAAGGCAGGTGGGTGAGGAAATCCAGGTAAGGCTCCTGACA
GCAGCTTTAGAAGGGTACTTGCTGGAGTGAATTCGGGCCTCTGATTA 481 SRS085 TCCTTTGATGTACGCAACTCCTTTGATGTCTATGCGTCCTTTGATGTTAAGGATTCCTTTG
ATGTAGGTACATCCTTTGATGTCCGTAAATCCTTTGATGTGACgatcttgatatcctcgag
gctagcATGATCACCATGAGTCACCCATGAGTCACCCATGAGTCACCCATGAGTCACCCAT
GAGTCACCCATGAGTCACCCATGAGTCACCCATGAGTCACCCATGAGTCACCACTAGTGGT
ACCACCTCTTAACAATACGTTTCACAAATAGTTAAAAACATGCAtACTAGTGGGGGGGGGt
gATGACACAGCAATtcGGGACTTTCCacGCTTGCGTGAGAAGagACCGGAAGTgaATGACA
CAGCAATtcGCTTGCGTGAGAAGctGGGACTTTCCtaGGGGGGGGGGttGGGACTTTCCacA
TGACACAGCAATacacTAGTAACATTTCTCTGGCCTAACTGGCCGGTACCGGGAAAAGTTC
AGCTGAGAGATATAAAAGAGCAGTCTTTCCAGCACCTGCAAATCCAGAGCGGCGGGCACTG
ACGGGCACTTGCACCGTGTGGACAGACTCTCCGGTTCTGTGAGTGGTTTTTCTTTTCCCGG
GTCGGACCTGGAGTTCTTAGGGGGATGGCTG 482 SRS086 TCCTTTGATGTACGCAACTCCTTTGATGTCTATGCGTCCTTTGATGTTAAGGATTCCTTTG
ATGTAGGTACATCCTTTGATGTCCGTAAATCCTTTGATGTGACgatcttgatatcctcgag
gctagcATGATCACCATGAGTCACCCATGAGTCACCCATGAGTCACCCATGAGTCACCCAT
GAGTCACCCATGAGTCACCCATGAGTCACCCATGAGTCACCCATGAGTCACCACTAGTGGT TABLE 1C-continued _Sequences of Synthetic Response Sensors (SRSs) according to the disclosure_

SEQ
ID
NO: Name    Sequence

ACCACCTCTTAACAATACGTTTCACAAATAGTTAAAAACATGCAtACTAGTGGGGGGGGGt
gATGACACAGCAATtcGGGACTTTCCacGCTTGCGTGAGAAGagACCGGAAGTgaATGACA
CAGCAATtcGCTTGCGTGAGAAGctGGGACTTTCCtaGGGGGGGGGttGGGACTTTCCacA
TGACACAGCAATacacTAGTAACATTTCTCTGGCCTAACTGGCCGGTACCGGGAAAAGTTC
AGCTGAGAGATATAAAAGAGCAGTCTTTCCAGCACCTGCAAATCCAGAGCGGCGGGCACTG
ACGGGCACTTGCACCGTGTGGACAGACTCTCCGGTTCTGTGAGTGGTTTTTCTTTTCCCGG
GTCGGACCTGGAGTTCTTAGGGGGATGGCTGAA 483  SRS087  ATGACTCAGCAATTAGCGAGTTAGAATGACTCAGCAATTATGCGTCGGACATGACTCAGCA
ATTACATCTCGATTATGACTCAGCAATTAGGATAGGCATATGACTCAGCAATTACATAGCA
GCAATGACTCAGCAATTAGCTAGTAAGCTTGGGGCGGGGtgATGACACAGCAATtcGGGAC
TTTCCacGCTTGCGTGAGAAGagACCGGAAGTgaATGACACAGCAATGGATCCGCTTGCGT
GAGAAGctGGGACTTTCCtaGGGGCGGGGttGGGACTTTCCacATGACACAGCAATacCTC
GAGGGTACcatgcataCTAGTCTGAGCGACAGTATAGTGCACAGTGACTGCAGCAGTCATT
CCTTTGATGTACGCAACTCCTTTGATGTCTATGCGTCCTTTGATGTTAAGGATTCCTTTGA
TGTAGGTACATCCTTTGATGTCCGTAAATCCTTTGATGTGACGTCTACGTATCTACCTGAT
CAAACATGCCCGGACATGTCGTAAGACATAAACATGCCCGGACATGTCCTCGCAATCTAAC
ATGCCCGGACATGTCCTCGCAATCTAACATGCCCGGACATGTCTGCAAGCTACAACATGCC
CGGACATGTCTACAATATACGTATCTACCTGATCAAACATGCCCGGACATGTCGTAAGACA
TAAACATGCCCGGACATGTCCTCGCAATCTAACATGCCCGGACATGTCCTCGCAATCTAAC
ATGCCCGGACATGTCTGCAAGCTACAACATGCCCGGACATGTCTACGTACATACTGAAAAG
CATACTTTTGCAATGTTATTTTTAAAAACAAGGAACTCTTTAACCCAGGGAAGATAATCAC
TTGGGGAAAGGAAGGTTCGTTTCTGAGTTAGCAACAAGTAAATGCACTAGTGGGTGGG
ATTGAGGTgTGCCCTGGTGCATAAATAGAGACTCAGCTGTGCTGGCACACTCAGAAGCTTG
GACCGCATCCTAGCCGCCGACTCACACAAGGCAGGTGGGTGAGGAAATCCAGGTAAGGCTC
CTGACAGCAGCTTTAGAAGGGTACTTGCTGGAGTGAATTCGGGCCTCTGATTA 484  SRS088  ATGACTCAGCAATTAGCGAGTTAGAATGACTCAGCAATTATGCGTCGGACATGACTCAGCA
ATTACATCTCGATTATGACTCAGCAATTAGGATAGGCATATGACTCAGCAATTACATAGCA
GCAATGACTCAGCAATTAGCTAGTAAGCTTGGGGGGGGGtgATGACACAGCAATtcGGGAC
TTTCCacGCTTGCGTGAGAAGagACCGGAAGTgaATGACACAGCAATGGATCCGCTTGCGT
GAGAAGctGGGACTTTCCtaGGGGGGGGGttGGGACTTTCCacATGACACAGCAATacCTC
GAGGGTACCACTAGTGTCATCTCTTTGAATATTCTGTAGTTTGAGGAGAATATTTGTTATA
TTGCACAATAAAATAAGTTTGCAAGTTTTTTTTTTCTGCCCCAAAGAGCTCTGTGTCCTTG
AACATAAAATACAAATAACCGCTATGCTGTTAATTATTAACAAATGTCCCATTTTCAACCT
AAGGAAATACCATAAAGTAACAGATATACCAACAAAAGGTTAATAATTAACAGGCATTGCC
TGAAAAGAGTATAAAAGGCTTTCAGCATGATTTTCCATATTGTGCTTCCACCACTGCCAAT
AACAAA 485  SRS089  ATGACTCAGCAATTAGCGAGTTAGAATGACTCAGCAATTATGCGTCGGACATGACTCAGCA
ATTACATCTCGATTATGACTCAGCAATTAGGATAGGCATATGACTCAGCAATTACATAGCA
GCAATGACTCAGCAATTAGCTAGTAAGCTTGGGGGGGGGtgATGACACAGCAATtcGGGAC
TTTCCacGCTTGCGTGAGAAGagACCGGAAGTgaATGACACAGCAATGGATCCGCTTGCGT
GAGAAGctGGGACTTTCCtaGGGGCGGGGttGGGACTTTCCacATGACACAGCAATacCTC
GAGGGTACcagcttgcatgcctgcaggtcggagtactgtcctccgagcggagtactgtcct
ccgagcggagtactgtcctccgagcggagtactgtcctccgagcggagtactgtcctccga
gcggagactctagagggtatataatggatcc 486  SRS090  TCTGTAGTTTGAGGAGAATATTTGTTATATTGCACAATAAAATAAGTTTGCAAGTTTTTTT
TTTCTGCCCCAAAGAGCTCTGTGTCCTTGAACATAAAATACAAATAACCGCTATGCTGTTA
ATTATTAACAAATGTCCCATTTTCAACCTAAGGAAATACCATAAAGTAACAGATATACCAA
CAAAAGGTTAATAATTAACAGGCATTGCCTGAAAAGAGTATAAAAGGCTTTCAGCATGATT
TTCCATATTGTGCTTCCACCACTGCCAATAACAAA 556  SRS091  GGTGACTCATGATGATGCCACGTCACCAATGCCACGTCACCAGGTGACTCATGGGTGACTC
ATGACGTGTGACATGCCACGTCACCAATGCCACGTCACCAGGTGACTCATGGGTGACTCAT
GACTAGTGAATTCTAATTGCTGAGTCATTGCTGCTATGTAATTGCTGAGTCATATGCCTAT
CCTAATTGCTGAGTCATAATCGAGATGTAATTGCTGAGTCATGTCCGACGCATAATTGCTG
AGTCATTCTAACTCGCTAATTGCTGAGTCATGTCGACACTAGTAAGCTTGGGGGGGGGTGA
TGACACAGCAATTCGGGACTTTCCACGCTTGCGTGAGAAGAGACCGGAAGTGAATGACACA
GCAATGGATCCGCTTGCGTGAGAAGCTGGGACTTTCCTAGGGGGGGGGGTTGGGACTTTCCA
CATGACACAGCAATACCTCGAGGGTACCGGGAAAAGTTCAGCTGAGAGATATAAAAGAGCA
GTCTTTCCAGCACCTGCTATCCCAGGAGGAGCAAGTGGCACGTCTTCGGGTGAGTGTGCG
GCTGTGCTGGAGCCCGGGTTACCAGCTCTTAA 557  SRS092  GGTGACTCATGATGATGCCACGTCACCAATGCCACGTCACCAGGTGACTCATGGGTGACTC
ATGACGTGTGACATGCCACGTCACCAATGCCACGTCACCAGGTGACTCATGGGTGACTCAT
GACTAGTGAATTCTAATTGCTGAGTCATTGCTGCTATGTAATTGCTGAGTCATATGCCTAT
CCTAATTGCTGAGTCATAATCGAGATGTAATTGCTGAGTCATGTCCGACGCATAATTGCTG
AGTCATTCTAACTCGCTAATTGCTGAGTCATGTCGACACTAGTAAGCTTGGGGGGGGGTGA
TGACACAGCAATTCGGGACTTTCCACGCTTGCGTGAGAAGAGACCGGAAGTGAATGACACA
GCAATGGATCCGCTTGCGTGAGAAGCTGGGACTTTCCTAGGGGGGGGGGTTGGGACTTTCCA
CATGACACAGCAATACCTCGAGGGTACGGCCCGCCCCCTTTCCTTACGCGGATTGGTAGCT
GCAGGCTTCCCTATCTGATTGGCCGAACGAACGCAGCGCGTAATTTAAAATATTGTATCTG TABLE 1C-continued Sequences of Synthetic Response Sensors (SRSs) according to the disclosure SEQ
ID
NO:  Name    Sequence TAACAAAGCTGCACCTCGTGGGCGGAGTTGTGCTCTGCGGCTGCGAAAGTCCAGCTTCGGC
           GACTAGGTGTGAGTAAGCCAGTATCCCAGGAGGAGCAAGTGGCACGTCTTCGGGTGCAGTG
           TGCGGCTGTGCTGGAGCCCGGGTTACCAGCTCTT

TABLE 1D coreBIRC5_H1299

| Construct | Expression Score | Fold Change | Barcode Support | Motif | SEQ ID NO: | Spacer |
|---|---|---|---|---|---|---|
| TRPS1_v22 | 2.20 | 1.95 | 5 | TATTTTATCTTT | 129 | 7 |
| MNX1_v18 | 2.05 | 1.81 | 5 | GTCATTAT | | 7 |
| TWIST1_v3 | 1.87 | 1.66 | 5 | ATTCCAGATGTTT | 131 | 3 |
| Control-1_FOSL1_v1 | 1.64 | 1.45 | 27 | | | |
| HOXAI_v10 | 1.47 | 1.30 | 5 | GTCATTAC | | 7 |
| TWIST1_v4 | 1.41 | 1.25 | 5 | ATTCCAGATGTTT | 131 | 0 |
| ETV4_v2 | 1.40 | 1.24 | 6 | ACCGGAAGTG | 132 | 7 |
| GATAI_v1 | 1.39 | 1.23 | 6 | TTCTAATCTAT | 133 | 10 |
| ETV4_v14 | 1.38 | 1.22 | 6 | ACCGGAAATG | 134 | 7 |
| FOSL2_v1 | 1.37 | 1.21 | 5 | GGATGACTCAT | 135 | 10 |
| NFIC_v15 | 1.33 | 1.18 | 6 | TTCTTGGCAGA | 136 | 3 |
| EN2_v7 | 1.33 | 1.18 | 5 | CGCAATTA | | 3 |
| ETV4_v6 | 1.33 | 1.18 | 6 | ACCGGAAGCG | 137 | 7 |
| SOX11_v2 | 1.32 | 1.17 | 6 | GAGAACAAAGGA | 138 | 7 |
| ETV6_v6 | 1.32 | 1.17 | 5 | ACCGGAAGTG | 132 | 7 |
| TRPS1_v20 | 1.31 | 1.16 | 6 | TAACTTATCTTT | 139 | 0 |
| TFDP1_v6 | 1.31 | 1.16 | 6 | GGGCGGGAACG | 140 | 7 |
| TCF7_v9 | 1.30 | 1.15 | 5 | TCCTTTGATAT | 141 | 10 |
| TRPS1_v10 | 1.29 | 1.14 | 6 | TAGCTTATCTTT | 142 | 7 |
| PITX2_v22 | 1.29 | 1.14 | 5 | TTAATCCA | | 7 |
| TCF7L1_v8 | 1.26 | 1.12 | 6 | AAACATCAAAGG | 143 | 0 |
| CREB3L1_v6 | 1.25 | 1.11 | 6 | ATGCCACGTCACCA | 144 | 7 |
| E2F8_v21 | 1.24 | 1.10 | 5 | TTCGCGCTAAAA | 146 | 10 |
| ZBTB7B_v6 | 1.23 | 1.09 | 6 | GCGACCACCAAA | 192 | 7 |
| ZBTB7B_v21 | 1.23 | 1.09 | 5 | GCAACCACCGAA | 270 | 10 |
| TCF7_v23 | 1.22 | 1.08 | 6 | TCCTTTGAACT | 272 | 3 |
| HOXC10_v10 | 1.22 | 1.08 | 6 | GTCGTTAAAT | 275 | 7 |
| ETV6_v15 | 1.22 | 1.08 | 6 | AGAGGAAGTG | 276 | 3 |
| VENTX_v9 | 1.22 | 1.08 | 6 | AGCGATTAG | | 10 |
| NFIC_v1 | 1.22 | 1.08 | 6 | TACTTGGCAGA | 277 | 10 |

TABLE 1D-continued

| coreBIRC5 H1299 | | | | | | |
|---|---|---|---|---|---|---|
| Construct | Expression Score | Fold Change | Barcode Support | Motif | SEQ ID NO: | Spacer |
| NFIC_v21 | 1.21 | 1.07 | 5 | TACTTGGCAAA | 280 | 10 |
| FOXN1_v17 | 1.21 | 1.07 | 6 | AGAAGC | | 10 |
| PITX2_v24 | 1.21 | 1.07 | 5 | TTAATCCA | | 0 |
| E2F4_v7 | 1.21 | 1.07 | 6 | TTTTGGCGCCCTTT | 286 | 3 |
| TCF7_v14 | 1.20 | 1.07 | 6 | TCCTTTGATTT | 287 | 7 |
| EN2_v16 | 1.20 | 1.07 | 6 | CTCAATTA | | 0 |
| DMBX1_v19 | 1.20 | 1.06 | 6 | TGAACAGGATTAATGTA | 288 | 3 |
| CREB3L1_v18 | 1.20 | 1.06 | 5 | ATGCCACGTAATCA | 294 | 7 |
| SOX11_v7 | 1.20 | 1.06 | 6 | GAGAACAAAGAA | 295 | 3 |
| ETV6_v10 | 1.20 | 1.06 | 6 | ATCGGAAGTG | 296 | 7 |
| FOSL2_v9 | 1.20 | 1.06 | 5 | GGGTGACTCAT | 297 | 10 |
| ZBTB7B_v4 | 1.20 | 1.06 | 5 | GCGACCACCGAA | 298 | 0 |
| FOXNI_v6 | 1.19 | 1.06 | 5 | GGAAGC | | 7 |
| SIX4_v16 | 1.19 | 1.06 | 5 | GAAATCTGAGC | 299 | 0 |
| TCF7_v3 | 1.19 | 1.05 | 5 | TCCTTTGATGT | 300 | 3 |
| NFIC_v9 | 1.19 | 1.05 | 6 | TACTTGGCATA | 306 | 10 |
| ETV4_v5 | 1.19 | 1.05 | 6 | ACCGGAAGCG | 137 | 10 |
| FOSL2_v17 | 1.19 | 1.05 | 6 | GGATGACTCAC | 307 | 10 |
| ETV6_v14 | 1.19 | 1.05 | 5 | AGAGGAAGTG | 276 | 7 |
| GATA1_v13 | 1.19 | 1.05 | 6 | TTCTAATCTCT | 308 | 10 |

TABLE 1E

| TATA-TSS H1299 | | | | | | |
|---|---|---|---|---|---|---|
| Construct | Expression Score | Fold Change | Barcode Support | Motif | SEQ ID NO: | Spacer |
| Control-1_FOSL1_v1 | 3.19 | 4.84 | 27 | | | |
| FOSL2_v4 | 2.22 | 3.37 | 5 | GGATGACTCAT | 135 | 0 |
| CREB3L1_v18 | 1.87 | 2.85 | 5 | ATGCCACGTAATCA | 294 | 7 |
| Control-1_FOSL1_v2 | 1.52 | 2.31 | 24 | | | |
| FOSL2_v22 | 1.46 | 2.22 | 6 | GGGTGACTCAC | 309 | 7 |
| CREB3L1_v6 | 1.46 | 2.22 | 6 | ATGCCACGTCACCA | 144 | 7 |
| FOSL2_v17 | 1.35 | 2.04 | 6 | GGATGACTCAC | 307 | 10 |
| Control-1_FOSL1_v3 | 1.32 | 2.00 | 26 | | | |
| FOSL2_v7 | 1.28 | 1.94 | 6 | GGATGACTCAG | 313 | 3 |
| FOSL2_v1 | 1.28 | 1.94 | 6 | GGATGACTCAT | 135 | 10 |
| NPAS2_v11 | 1.21 | 1.84 | 6 | GACACGTGTC | 314 | 3 |

TABLE 1E-continued

| | | | | | SEQ ID | |
|---|---|---|---|---|---|---|
| Construct | Expression Score | Fold Change | Barcode Support | Motif | NO: | Spacer |
| FOSL2_v11 | 1.20 | 1.82 | 5 | GGGTGACTCAT | 297 | 3 |
| HES6_v11 | 1.11 | 1.69 | 6 | GGCACGTGTA | 316 | 3 |
| HES6_v7 | 1.09 | 1.66 | 5 | GGCACGTGTC | 317 | 3 |
| CREB3L1_v14 | 1.03 | 1.57 | 6 | ATGCCACGTCAACA | 320 | 7 |
| HES6_v3 | 0.98 | 1.49 | 6 | GGCACGTGTT | 321 | 3 |
| ASCL1_v23 | 0.96 | 1.45 | 5 | GGCACGTGCC | 322 | 3 |
| TWIST1_v3 | 0.95 | 1.43 | 5 | ATTCCAGATGTTT | 131 | 3 |
| FOSL2_v8 | 0.94 | 1.43 | 5 | GGATGACTCAG | 313 | 0 |
| TRPS1_v22 | 0.92 | 1.40 | 5 | TATTTTATCTTT | 129 | 7 |
| GRHL1_v10 | 0.90 | 1.36 | 6 | AAAACCGGTTCT | 323 | 7 |
| FOSL2_v9 | 0.87 | 1.32 | 6 | GGGTGACTCAT | 297 | 10 |
| ETV4_v14 | 0.83 | 1.27 | 6 | ACCGGAAATG | 134 | 7 |
| TWIST1_v2 | 0.82 | 1.25 | 6 | ATTCCAGATGTTT | 131 | 7 |
| SOX11_v2 | 0.82 | 1.24 | 6 | GAGAACAAAGGA | 138 | 7 |
| ZNF354A_v15 | 0.80 | 1.21 | 5 | ATAAATAAAAATGGACTAATT | 327 | 3 |
| ZBTB7B_v4 | 0.79 | 1.20 | 5 | GCGACCACCGAA | 298 | 0 |
| ZBTB7B_v21 | 0.78 | 1.18 | 5 | GCAACCACCGAA | 270 | 10 |
| ETV6_v6 | 0.78 | 1.18 | 5 | ACCGGAAGTG | 132 | 7 |
| ETV4_v12 | 0.77 | 1.18 | 5 | ACCGGATGTG | 336 | 0 |
| ETV4_v6 | 0.77 | 1.17 | 6 | ACCGGAAGCG | 137 | 7 |
| TFDP1_v21 | 0.76 | 1.16 | 6 | GGGCGGGACCG | 337 | 10 |
| SOX11_v7 | 0.76 | 1.15 | 6 | GAGAACAAAGAA | 295 | 3 |
| FOSL2_v18 | 0.75 | 1.14 | 6 | GGATGACTCAC | 307 | 7 |
| ETV6_v10 | 0.74 | 1.13 | 6 | ATCGGAAGTG | 296 | 7 |
| FOSL2_v14 | 0.74 | 1.12 | 6 | GGGTGACTCAG | 338 | 7 |
| NFIC_v2 | 0.74 | 1.12 | 5 | TACTTGGCAGA | 277 | 7 |
| MGA_v17 | 0.73 | 1.11 | 5 | AGGTGCGA | | 10 |
| TRPS1_v20 | 0.73 | 1.11 | 6 | TAACTTATCTTT | 139 | 0 |
| IRF6_v23 | 0.73 | 1.10 | 6 | GCCGATACT | | 3 |
| ETV4_v10 | 0.72 | 1.10 | 5 | ACCGGATGTG | 336 | 7 |
| ETV4_v7 | 0.72 | 1.10 | 6 | ACCGGAAGCG | 137 | 3 |
| ZBTB7B_v24 | 0.72 | 1.09 | 6 | GCAACCACCGAA | 270 | 0 |
| SIX2_v17 | 0.72 | 1.09 | 6 | AACTGAAACTTGATAC | 339 | 10 |
| TWIST1_v23 | 0.72 | 1.09 | 6 | ATTGCAGATGTTT | 340 | 3 |
| SIX2_v5 | 0.71 | 1.08 | 5 | AACTGTAACCTGATAC | 341 | 10 |
| ETV4_v2 | 0.71 | 1.08 | 6 | ACCGGAAGTG | 132 | 7 |
| E2F7_v3 | 0.71 | 1.08 | 5 | TTTTCCCGCCAAAA | 487 | 3 |

TABLE 1E-continued

| | | | | | SEQ | |
| Construct | Expression Score | Fold Change | Barcode Support | Motif | ID NO: | Spacer |
|---|---|---|---|---|---|---|
| CUX1_v21 | 0.71 | 1.07 | 5 | TGATCAATAA | 488 | 10 |
| SIX_4_v6 | 0.71 | 1.07 | 5 | GAAACATGAGC | 489 | 7 |

TABLE 1F coreBIRC5 PDX430

| | | | | | SEQ | |
| Construct | Expression Score | Fold Change | Barcode Support | Motif | ID NO: | Spacer |
|---|---|---|---|---|---|---|
| TCF7_v2 | 4.37 | 3.90 | 6 | TCCTTTGATGT | 300 | 7 |
| TCF7_v3 | 3.76 | 3.35 | 5 | TCCTTTGATGT | 300 | 3 |
| TCF7L1_v19 | 3.61 | 3.22 | 6 | AGACATCAAAGG | 490 | 3 |
| ETV4_v14 | 3.58 | 3.19 | 6 | ACCGGAAATG | 134 | 7 |
| TCF7L1_v5 | 3.10 | 2.76 | 6 | AAACATCAAAGG | 143 | 10 |
| TCF7L1_v8 | 3.06 | 2.73 | 6 | AAACATCAAAGG | 143 | 0 |
| ETV4_v2 | 3.01 | 2.68 | 6 | ACCGGAAGTG | 132 | 7 |
| ETV4_v6 | 2.96 | 2.64 | 6 | ACCGGAAGCG | 137 | 7 |
| ETV4_v10 | 2.92 | 2.61 | 5 | ACCGGATGTG | 336 | 7 |
| ETV4_v13 | 2.73 | 2.43 | 6 | ACCGGAAATG | 134 | 10 |
| TWIST1_v3 | 2.67 | 2.38 | 5 | ATTCCAGATGTTT | 131 | 3 |
| TCF7L1_v24 | 2.61 | 2.33 | 6 | AAACTTCAAAGG | 491 | 0 |
| TCF7_v23 | 2.54 | 2.27 | 6 | TCCTTTGAACT | 272 | 3 |
| ETV4_v8 | 2.53 | 2.26 | 5 | ACCGGAAGCG | 137 | 0 |
| DLX1_v24 | 2.47 | 2.20 | 6 | GTCATTAC | | 0 |
| TCF7_v7 | 2.41 | 2.15 | 5 | TCCTTTGATCT | 492 | 3 |
| ETV6_v6 | 2.29 | 2.04 | 5 | ACCGGAAGTG | 132 | 7 |
| ETV4_v5 | 2.29 | 2.04 | 6 | ACCGGAAGCG | 137 | 10 |
| ETV4_v7 | 2.14 | 1.91 | 6 | ACCGGAAGCG | 137 | 3 |
| TWIST1_v2 | 2.10 | 1.88 | 6 | ATTCCAGATGTTT | 131 | 7 |
| TRPS1_v22 | 2.05 | 1.83 | 5 | TATTTTATCTTT | 129 | 7 |
| SIX2_v5 | 2.05 | 1.83 | 5 | AACTGTAACCTGATAC | 341 | 10 |
| HOXA1_v8 | 2.01 | 1.79 | 6 | GTAATGAC | | 0 |
| HOXC10_v24 | 1.97 | 1.75 | 6 | GTCGTAAACT | 493 | 0 |
| HOXA1_v12 | 1.95 | 1.74 | 6 | GTCATTAC | | 0 |
| HOXB9_v18 | 1.94 | 1.73 | 6 | GTCGTAAAGT | 494 | 7 |
| ETV4_v16 | 1.90 | 1.70 | 5 | ACCGGAAATG | 134 | 0 |
| HOXC10_v14 | 1.85 | 1.65 | 6 | GTCGTAAATT | 495 | 7 |
| ETV6_v8 | 1.84 | 1.64 | 6 | ACCGGAAGTG | 132 | 0 |
| ETV4_v1 | 1.82 | 1.63 | 6 | ACCGGAAGTG | 132 | 10 |

TABLE 1F-continued

| | | | | | SEQ | |
|---|---|---|---|---|---|---|
| Construct | Expression Score | Fold Change | Barcode Support | Motif | ID NO: | Spacer |
| MYCN_v22 | 1.80 | 1.60 | 5 | GTCCACGTGGCC | 496 | 7 |
| SP3_v8 | 1.79 | 1.59 | 5 | GGCCCCGCCCACC | 497 | 0 |
| HOXC10_v15 | 1.78 | 1.58 | 6 | GTCGTAAATT | 495 | 3 |
| TCF7_v18 | 1.72 | 1.54 | 5 | TCCTTTGAAGT | 498 | 7 |
| TCF7_v22 | 1.72 | 1.53 | 5 | TCCTTTGAACT | 272 | 7 |
| ETV4_v23 | 1.72 | 1.53 | 6 | AGCGGAAGTG | 499 | 3 |
| ZNF281_v13 | 1.71 | 1.52 | 5 | GGGGGAAGGGAG | 500 | 10 |
| HOXC10_v4 | 1.71 | 1.52 | 6 | GTCGTAAAAT | 501 | 0 |
| FOSL2_v1 | 1.70 | 1.51 | 5 | GGATGACTCAT | 135 | 10 |
| PAX8_v19 | 1.64 | 1.46 | 5 | GTCATGCATGACTGC | 502 | 3 |
| E2F2_v23 | 1.62 | 1.45 | 6 | GTTTGGGCGCCATTTC | 503 | 3 |
| SP3_v19 | 1.61 | 1.43 | 5 | GGACCCGCCCACC | 504 | 3 |
| SIX4_v4 | 1.60 | 1.43 | 5 | GAAACCTGAGC | 505 | 0 |
| SIX4_v10 | 1.58 | 1.41 | 5 | GAAACTTGAGC | 506 | 7 |
| NFIC_v10 | 1.56 | 1.39 | 5 | TACTTGGCATA | 306 | 7 |
| HOXC9_v15 | 1.56 | 1.39 | 6 | GTCGTAAACT | 493 | 3 |
| PAX7_v15 | 1.55 | 1.38 | 5 | ATTAATCGATTATTT | 507 | 3 |
| RUNX1_v17 | 1.52 | 1.36 | 5 | GTCTGTGGCTT | 508 | 10 |
| DLX1_v8 | 1.52 | 1.36 | 6 | GTAATTAC | | 0 |
| RREB1_v14 | 1.52 | 1.35 | 6 | CCCCAAACCACCACCCCCC | 509 | 7 |

TABLE 1G

TATA-TSS PDX430

| | | | | | SEQ | |
|---|---|---|---|---|---|---|
| construct | Expression Score | Fold Change | Barcode Support | Motif | ID NO: | Spacer |
| TCF7_v2 | 5.12 | 11.18 | 6 | TCCTTTGATGT | 300 | 7 |
| TCF7L1_v19 | 4.35 | 9.49 | 6 | AGACATCAAAGG | 490 | 3 |
| TCF7_v7 | 3.21 | 7.00 | 5 | TCCTTTGATCT | 492 | 3 |
| TCF7_v19 | 2.78 | 6.07 | 5 | TCCTTTGAAGT | 498 | 3 |
| TCF7_v3 | 2.78 | 6.06 | 5 | TCCTTTGATGT | 300 | 3 |
| ETV4_v14 | 2.54 | 5.54 | 6 | ACCGGAAATG | 134 | 7 |
| TCF7L1_v5 | 2.44 | 5.32 | 6 | AAACATCAAAGG | 143 | 10 |
| ETV4_v2 | 2.37 | 5.17 | 6 | ACCGGAAGTG | 132 | 7 |
| ETV4_v6 | 2.36 | 5.15 | 6 | ACCGGAAGCG | 137 | 7 |
| ETV4_v10 | 2.29 | 5.00 | 5 | ACCGGATGTG | 336 | 7 |
| ETV6_v6 | 2.18 | 4.75 | 5 | ACCGGAAGTG | 132 | 7 |

TABLE 1G-continued

TATA-TSS PDX430

| construct | Expression Score | Fold Change | Barcode Support | Motif | SEQ ID NO: | Spacer |
|---|---|---|---|---|---|---|
| HOXC10_v24 | 2.07 | 4.51 | 6 | GTCGTAAACT | 493 | 0 |
| HOXC10_v4 | 2.01 | 4.38 | 6 | GTCGTAAAAT | 501 | 0 |
| ETV4_v8 | 1.94 | 4.23 | 5 | ACCGGAAGCG | 137 | 0 |
| TCF7L1_v4 | 1.91 | 4.16 | 5 | AAAGATCAAAGG | 510 | 0 |
| TCF7_v23 | 1.87 | 4.09 | 6 | TCCTTTGAACT | 272 | 3 |
| ZNF354A_v7 | 1.80 | 3.94 | 5 | ATAAATATAAAAGGACTAATT | 511 | 3 |
| TCF7_v18 | 1.80 | 3.93 | 5 | TCCTTTGAAGT | 498 | 7 |
| TCF7L1_v11 | 1.69 | 3.70 | 6 | AGAGATCAAAGG | 512 | 3 |
| DLX1_v24 | 1.65 | 3.61 | 6 | GTCATTAC | | 0 |
| FOSL2_v4 | 1.64 | 3.58 | 5 | GGATGACTCAT | 135 | 0 |
| ZNF384_v14 | 1.63 | 3.55 | 5 | TTGAAAAAAAA | 513 | 7 |
| HNF1A_v13 | 1.62 | 3.54 | 5 | AGTTAATTATTAACT | 514 | 10 |
| SIX4_v6 | 1.59 | 3.48 | 5 | GAAACATGAGC | 489 | 7 |
| ETV4_v13 | 1.58 | 3.46 | 6 | ACCGGAAATG | 134 | 10 |
| PAX7_v3 | 1.54 | 3.37 | 5 | ATTAATCAATTATTT | 515 | 3 |
| TCF7L1_v24 | 1.53 | 3.35 | 6 | AAACTTCAAAGG | 491 | 0 |
| SP3_v24 | 1.50 | 3.28 | 6 | GGCCCCGCCTACC | 516 | 0 |
| HOXB9_v4 | 1.47 | 3.21 | 5 | GTCGTAAAAT | 501 | 0 |
| TCF7L1_v23 | 1.44 | 3.14 | 6 | AAACTTCAAAGG | 491 | 3 |
| TCF7L1_v8 | 1.44 | 3.13 | 6 | AAACATCAAAGG | 143 | 0 |
| E2F3_v20 | 1.43 | 3.12 | 5 | ATTTTGGCGCGAAAAT | 517 | 0 |
| HOXA1_v8 | 1.42 | 3.09 | 6 | GTAATGAC | | 0 |
| RORB_v4 | 1.38 | 3.00 | 6 | AATTAGGTCAC | 518 | 0 |
| PAX7_v12 | 1.37 | 3.00 | 5 | ATTAATCAATTTTTT | 519 | 0 |
| HOXB9_v13 | 1.37 | 2.99 | 6 | GTCGTAAACT | 493 | 10 |
| TCF7_v22 | 1.36 | 2.97 | 5 | TCCTTTGAACT | 272 | 7 |
| SP3_v12 | 1.35 | 2.95 | 6 | GGACACGCCCACC | 520 | 0 |
| HOXA1_v4 | 1.35 | 2.95 | 6 | GTAATTAC | | 0 |
| HOXB9_v17 | 1.34 | 2.92 | 6 | GTCGTAAAGT | 494 | 10 |
| HOXB9_v18 | 1.34 | 2.92 | 6 | GTCGTAAAGT | 494 | 7 |
| HOXC10_v15 | 1.33 | 2.91 | 6 | GTCGTAAATT | 495 | 3 |
| HOXC9_v15 | 1.33 | 2.91 | 6 | GTCGTAAACT | 493 | 3 |
| ETV4_v1 | 1.32 | 2.89 | 6 | ACCGGAAGTG | 132 | 10 |
| SP3_v11 | 1.32 | 2.89 | 6 | GGACACGCCCACC | 520 | 3 |
| ETV4_v19 | 1.32 | 2.88 | 5 | ACCGGAAGGG | 521 | 3 |
| ETV4_v16 | 1.32 | 2.88 | 5 | ACCGGAAATG | 134 | 0 |
| HOXC10_v14 | 1.31 | 2.87 | 6 | GTCGTAAATT | 495 | 7 |

TABLE 1G-continued

| | | | | | SEQ | |
|---|---|---|---|---|---|---|
| | Expression | | Barcode | | ID | |
| construct | Score | Fold Change | Support | Motif | NO: | Spacer |
| TWIST1_v3 | 1.31 | 2.85 | 5 | ATTCCAGATGTTT | 131 | 3 |
| DLX4_v3 | 1.29 | 2.82 | 6 | CCAATTAC | | 3 |

TATA-TSS PDX430

TABLE 1H coreBIRC5 PDX586

| | | | | | SEQ | |
|---|---|---|---|---|---|---|
| | Expression | Fold | Barcode | | ID | |
| Construct | Score | Change | Support | Motif | NO: | Spacer |
| TRPS1_v22 | 2.22 | 1.85 | 5 | TATTTTATCTTT | 129 | 7 |
| TP53_v21 | 1.80 | 1.50 | 5 | AACATGCCTGGGCATGTC | 522 | 10 |
| TP53_v5 | 1.76 | 1.47 | 6 | AACATGCCCGGACATGTC | 523 | 10 |
| TWIST1_v3 | 1.75 | 1.46 | 5 | ATTCCAGATGTTT | 131 | 3 |
| MYCN_v13 | 1.70 | 1.42 | 5 | GCCCACGTGGCC | 524 | 10 |
| MNX1_v18 | 1.66 | 1.38 | 5 | GTCATTAT | | 7 |
| TP53_v1 | 1.65 | 1.37 | 6 | AACATGCCCGGGCATGTC | 525 | 10 |
| TP53_v10 | 1.59 | 1.32 | 5 | AACATGTCCGGGCATGTC | 526 | 7 |
| HOXB9_v5 | 1.57 | 1.31 | 6 | GTCGTAAATT | 495 | 10 |
| SIX2_v5 | 1.57 | 1.31 | 5 | AACTGTAACCTGATAC | 341 | 10 |
| TP63_v3 | 1.56 | 1.30 | 5 | AACATGTTGGGACATGTC | 527 | 3 |
| SIX4_v16 | 1.55 | 1.29 | 5 | GAAATCTGAGC | 299 | 0 |
| HOXB9_v15 | 1.51 | 1.26 | 6 | GTCGTAAACT | 493 | 3 |
| SOX11_v16 | 1.50 | 1.25 | 5 | GAGAACAAAGCA | 528 | 0 |
| E2F8_v21 | 1.50 | 1.25 | 5 | TTCGCGCTAAAA | 146 | 10 |
| HOXA1_v12 | 1.49 | 1.24 | 6 | GTCATTAC | | 0 |
| TP53_v6 | 1.48 | 1.23 | 6 | AACATGCCCGGACATGTC | 523 | 7 |
| CREB3L1_v1 | 1.46 | 1.22 | 5 | ATGCCACGTCATCA | 529 | 10 |
| TFDP1_v6 | 1.45 | 1.21 | 6 | GGGCGGGAACG | 140 | 7 |
| ETV4_v14 | 1.44 | 1.20 | 6 | ACCGGAAATG | 134 | 7 |
| SURV_v9 | 1.43 | 1.20 | 6 | GGGCGTGCGCTCCCGACAAGCCC | 530 | 0 |
| TP53_v16 | 1.41 | 1.18 | 6 | AACATGCCCAGGCATGTC | 531 | 0 |
| TP53_v8 | 1.41 | 1.18 | 5 | AACATGCCCGGACATGTC | 523 | 0 |
| FOXE1_v3 | 1.40 | 1.17 | 5 | CCTAAATAAACAAA | 532 | 3 |
| EN1_v23 | 1.40 | 1.17 | 6 | GCAATTAG | | 3 |
| ZBTB7B_v21 | 1.40 | 1.17 | 5 | GCAACCACCGAA | 270 | 10 |
| TRPS1_v20 | 1.40 | 1.16 | 6 | TAACTTATCTTT | 139 | 0 |
| TP53_v22 | 1.39 | 1.16 | 6 | AACATGCCTGGGCATGTC | 522 | 7 |
| SP3_v8 | 1.39 | 1.16 | 5 | GGCCCCGCCCACC | 497 | 0 |
| SIX2_v20 | 1.38 | 1.15 | 5 | AACTGAAACTTGATAC | 339 | 0 |

TABLE 1H-continued coreBIRC5 PDX586

| Construct | Expression Score | Fold Change | Barcode Support | Motif | SEQ ID NO: | Spacer |
|---|---|---|---|---|---|---|
| TP53_v7 | 1.38 | 1.15 | 5 | AACATGCCCGGACATGTC | 523 | 3 |
| TWIST1_v1 | 1.37 | 1.15 | 5 | ATTCCAGATGTTT | 131 | 10 |
| MYBL2_v4 | 1.37 | 1.15 | 5 | AACCGTTAAACGGTC | 533 | 0 |
| SIX2_v17 | 1.37 | 1.14 | 6 | AACTGAAACTTGATAC | 339 | 10 |
| TP53_v24 | 1.36 | 1.14 | 6 | AACATGCCTGGGCATGTC | 522 | 0 |
| TRPS1_v11 | 1.36 | 1.13 | 5 | TAGCTTATCTTT | 142 | 3 |
| Control-0_Filler_v3 | 1.36 | 1.13 | 26 | | | |
| TP53_v20 | 1.35 | 1.13 | 6 | AACATGTCCGGACATGTC | 534 | 0 |
| GATA1_v1 | 1.35 | 1.12 | 6 | TTCTAATCTAT | 133 | 10 |
| SHOX2_v16 | 1.34 | 1.12 | 5 | CCAATTAG | | 0 |
| TP53_v9 | 1.33 | 1.11 | 6 | AACATGTCCGGGCATGTC | 526 | 10 |
| HOXB7_v16 | 1.33 | 1.11 | 6 | GGTAATTGAC | 535 | 0 |
| E2F4_v9 | 1.32 | 1.10 | 5 | TTTTGGCGCCTTTT | 536 | 10 |
| E2F2_v12 | 1.31 | 1.09 | 5 | GTTTTGGCGCCTTTTC | 537 | 0 |
| SIX4_v21 | 1.30 | 1.09 | 5 | GAAATTTGAGC | 538 | 10 |
| SURV_v3 | 1.30 | 1.09 | 5 | GGGCAAGCGCTCCCGACATGCCC | 539 | 0 |
| DLX4_v12 | 1.30 | 1.08 | 6 | CAAATTAC | | 0 |
| BARX1_v11 | 1.29 | 1.08 | 6 | GCGATTAG | | 3 |
| NR2F6_v4 | 1.29 | 1.08 | 5 | GAGGTCAAAGGTCA | 540 | 0 |
| TFDP1_v7 | 1.29 | 1.07 | 5 | GGGCGGGAACG | 140 | 3 |

TABLE 1I

TATA-TSS PDX586

| Construct | Expression Score | Fold Change | Barcode Support | Motif | SEQ ID NO: | Spacer |
|---|---|---|---|---|---|---|
| TP53_v5 | 2.73 | 5.63 | 6 | AACATGCCCGGACATGTC | 523 | 10 |
| NPAS2_v11 | 2.59 | 5.34 | 6 | GACACGTGTC | 314 | 3 |
| HES6_v11 | 2.52 | 5.21 | 6 | GGCACGTGTA | 316 | 3 |
| SURV_v3 | 2.41 | 4.97 | 6 | GGGCAAGCGCTCCCGACATGCCC | 539 | 0 |
| TP53_v22 | 1.93 | 3.97 | 6 | AACATGCCTGGGCATGTC | 522 | 7 |
| HES6_v3 | 1.82 | 3.76 | 6 | GGCACGTGTT | 321 | 3 |
| TP53_v10 | 1.79 | 3.69 | 6 | AACATGTCCGGGCATGTC | 526 | 7 |
| TP53_v13 | 1.79 | 3.69 | 5 | AACATGCCCAGGCATGTC | 531 | 10 |
| TP53_v18 | 1.74 | 3.60 | 5 | AACATGTCCGGACATGTC | 534 | 7 |
| TP53_v16 | 1.74 | 3.59 | 6 | AACATGCCCAGGCATGTC | 531 | 0 |
| SURV_v15 | 1.73 | 3.57 | 6 | GGGCTAGCGCTCCCGACATGCCC | 541 | 0 |

TABLE 1I-continued

| | | | | | SEQ | |
| --- | --- | --- | --- | --- | --- | --- |
| | | | TATA-TSS PDX586 | | | |
| Construct | Expression Score | Fold Change | Barcode Support | Motif | ID NO: | Spacer |
| HES6_v7 | 1.71 | 3.53 | 5 | GGCACGTGTC | 317 | 3 |
| ASCL1_v23 | 1.66 | 3.43 | 5 | GGCACGTGCC | 322 | 3 |
| TFDP1_v4 | 1.59 | 3.27 | 6 | GGGCGGGAAGG | 542 | 0 |
| FOSL2_v4 | 1.57 | 3.25 | 5 | GGATGACTCAT | 135 | 0 |
| TFDP1_v19 | 1.57 | 3.23 | 5 | GGGCGGGACGG | 543 | 3 |
| TP53_v1 | 1.55 | 3.19 | 6 | AACATGCCCGGGCATGTC | 525 | 10 |
| Control-1_FOSL1_v1 | 1.54 | 3.18 | 27 | | | |
| MYC_v22 | 1.46 | 3.01 | 6 | GGACACGTGCCC | 544 | 7 |
| TP53_v6 | 1.45 | 2.99 | 6 | AACATGCCCGGACATGTC | 523 | 7 |
| SP3_v24 | 1.45 | 2.98 | 6 | GGCCCCGCCTACC | 516 | 0 |
| CREB3L1_v18 | 1.42 | 2.92 | 5 | ATGCCACGTAATCA | 294 | 7 |
| ETV4_v10 | 1.41 | 2.90 | 5 | ACCGGATGTG | 336 | 7 |
| CREB3L1_v6 | 1.37 | 2.82 | 6 | ATGCCACGTCACCA | 144 | 7 |
| SOX11_v17 | 1.33 | 2.75 | 6 | GGGAACAAAGAA | 545 | 10 |
| SP3_v12 | 1.32 | 2.73 | 6 | GGACACGCCCACC | 520 | 0 |
| TP53_v24 | 1.31 | 2.70 | 6 | AACATGCCTGGGCATGTC | 522 | 0 |
| SP3_v20 | 1.30 | 2.69 | 6 | GGACCCGCCCACC | 504 | 0 |
| HOXC9_v15 | 1.30 | 2.68 | 6 | GTCGTAAACT | 493 | 3 |
| ETV4_v14 | 1.28 | 2.65 | 6 | ACCGGAAATG | 134 | 7 |
| HOXC10_v14 | 1.28 | 2.64 | 6 | GTCGTAAATT | 495 | 7 |
| SP3_v22 | 1.28 | 2.64 | 5 | GGCCCCGCCTACC | 516 | 7 |
| HES6_v6 | 1.27 | 2.61 | 6 | GGCACGTGTC | 317 | 7 |
| CREB3L1_v14 | 1.26 | 2.61 | 6 | ATGCCACGTCAACA | 320 | 7 |
| SURV_v6 | 1.25 | 2.58 | 6 | GGGCATGCGCTCCCGACATGCCC | 546 | 0 |
| FOSL2_v7 | 1.25 | 2.57 | 6 | GGATGACTCAG | 313 | 3 |
| HOXC10_v15 | 1.24 | 2.57 | 6 | GTCGTAAATT | 495 | 3 |
| HOXA1_v8 | 1.23 | 2.54 | 6 | GTAATGAC | | 0 |
| BARX1_v7 | 1.23 | 2.53 | 5 | GCCATTAG | | 3 |
| HES6_v10 | 1.22 | 2.51 | 5 | GGCACGTGTA | 316 | 7 |
| ETV6_v6 | 1.21 | 2.50 | 5 | ACCGGAAGTG | 132 | 7 |
| CREB3L1_v12 | 1.21 | 2.50 | 5 | ATGCCACGTCAGCA | 547 | 0 |
| DLX1_v24 | 1.21 | 2.50 | 6 | GTCATTAC | | 0 |
| TP53_v8 | 1.20 | 2.48 | 6 | AACATGCCCGGACATGTC | 523 | 0 |
| SP3_v1 | 1.20 | 2.48 | 6 | GGCCACGCCCACC | 548 | 10 |
| ZNF281_v15 | 1.20 | 2.48 | 5 | GGGGGAAGGGAG | 500 | 3 |
| RREB1_v21 | 1.19 | 2.46 | 5 | CCCCAAAACAACCCCCCCC | 549 | 10 |
| MYCN_v3 | 1.19 | 2.45 | 5 | GGCCACGTGGCC | 550 | 3 |

TABLE 1I-continued

TATA-TSS PDX586

| Construct | Expression Score | Fold Change | Barcode Support | Motif | SEQ ID NO: | Spacer |
|-----------|------------------|-------------|-----------------|-------|------------|--------|
| TWIST1_v22 | 1.18 | 2.44 | 5 | ATTGCAGATGTTT | 340 | 7 |
| NPAS2_v1 | 1.17 | 2.41 | 5 | GGCACGTGTC | 317 | 10 |

TABLE 1J

Core Promoter Sequences

| SEQ ID NO: | Name | Sequence |
|------------|------|----------|
| 558 | PR181 | CATACTGAAAAGCATACTTTTGCAATGTTATTTTTAAAAACAAGGAA CTCTTTAACCCAGGGAAGATAATCACTTGGGGAAAGGAAGGTTCGTT TCTGAGTTAGCAACAAGTAAATGCAGCACTAGTGGGTGGGATTGAGG TATGCCCTGGTGCATAAATAGAGACTCAGCTGTGCTGGCACACTCAG AAGCTTGGACCGCATCCTAGCCGCCGACTCACACAAGGCAGGTGGGT GAGGAAATCCAGGTAAGGCTCCTGACAGCAGCTTTAGAAGGGTACTT GCTGGAGTGAATTCGGGCCTCTGATTA |
| 559 | PR180 | ACCTCTTAACAATACGTTTCACAAATAGTTAAAAACATGCATACTGA AAAGCATACTTTTGCAATGTTATTTTTAAAAACAAGGAACTCTTTAAC CCAGGGAAGATAATCACTTGGGGAAAGGAAGGTTCGTTTCTGAGTTA GCAACAAGTAAATGCAGCACTAGTGGGTGGGATTGAGGTgTGCCCTG GTGCATAAATAGAGACTCAGCTGTGCTGGCACACTCAAGAAGCTTGG ACCGCATCCTAGCCGCCGACTCACACAAGGCAGGTGGGTGAGGAAAT CCAGGTAAGGCTCCTGACAGCAGCTTTAGAAGGGTACTTGCTGGAGT GAATTCGGGCCTCTGATT |
| 560 | PR179 | CCGGCCCGCCCCCTTTCCTTACGCGGATTGGTAGCTGCAGGCTTCCCT ATCTGATTGGCCGAACGAACGCAGCGCGTAATTTAAAATATTGTATC TGTAACAAAGCTGCACCTCGTGGGCGGAGTTGTGCTCTGCGGCTGCG AAAGTCCAGCTTCGGCGACTAGGTGTGAGTAAGCCAcggcggcgcagatcgc ccggcgcggctccgccccctgcgccggtcacgtggggcgccggctgcgcctgcggagaagcggtggccgc cgagcgggatctgtgcggggagccggaaatggttgtggactacgtctgtgcggctgcgtggggctcggccgcgc ggactgaaggagactgaaggtgctgggggggaccctgatgtggA |
| 561 | PR178 | CCGGCCCGCCCCCTTTCCTTACGCGGATTGGTAGCTGCAGGCTTCCCT ATCTGATTGGCCGAACGAACGCAGCGCGTAATTTAAAATATTGTATC TGTAACAAAGCTGCACCTCGTGGGCGGAGTTGTGCTCTGCGGCTGCG AAAGTCCAGCTTCGGCGACTAGGTGTGAGTAAGCCACtttttccgtgctacctgc agaggggtccatacggcgttgttctggattcACCGGTa |
| 562 | PR177 | CCGGCCCGCCCCCTTTCCTTACGCGGATTGGTAGCTGCAGGCTTCCCT ATCTGATTGGCCGAACGAACGCAGCGCGTAATTTAAAATATTGTATC TGTAACAAAGCTGCACCTCGTGGGCGGAGTTGTGCTCTGCGGCTGCG AAAGTCCAGCTTCGGCGACTAGGTGTGAGTAAGCCACACTCGCGCTG CCATCACTCTTCCGCCGTCTTCGCCGCCATCCTCGGCGCGACTCGCTT CTTTCGGTTCTACCAGGTAGAGTCCGCCGCCATCCTCA |
| 563 | PR176 | CCGGCCCGCCCCCTTTCCTTACGCGGATTGGTAGCTGCAGGCTTCCCT ATCTGATTGGCCGAACGAACGCAGCGCGTAATTTAAAATATTGTATC TGTAACAAAGCTGCACCTCGTGGGCGGAGTTGTGCTCTGCGGCTGCG AAAGTCCAGCTTCGGCGACTAGGTGTGAGTAAGCCAGAAGCTTGGAC CGCATCCTAGCCGCCGACTCACACAAGGCAGGTGGGTGAGGAAATCC AGGTAAGGCTCCTGACAGCAGCTTTAGAAGGGTACTTGCTGGAGTGA ATTCGGGCCTCTGATTA |
| 564 | PR175 | CCGGCCCGCCCCCTTTCCTTACGCGGATTGGTAGCTGCAGGCTTCCCT ATCTGATTGGCCGAACGAACGCAGCGCGTAATTTAAAATATTGTATC TGTAACAAAGCTGCACCTCGTGGGCGGAGTTGTGCTCTGCGGCTGCG AAAGTCCAGCTTCGGCGACTAGGTGTGAGTAAGCCAAAATCCAGAGC GGCGGGCACTGACGGGCACTTGCACCGTGTGGACAGACTCTCCGGTT CTGTGAGTGGTTTTTCTTTTCCCGGGTCGGACCTGGAGTTCTTAGGGG GATGGCTGAAgaattcA |
| 565 | PR174 | CACCTCTTAACAATACGTTTCACAAATAGTTAAAAACATGCATACTG AAAAGCATACTTTTGCAATGTTATTTTTAAAAACAAGGAACTCTTTAA CCCAGGGAAGATAATCACTTGGGGAAAGGAAGGTTCGTTTCTGAGTT AGCAACAAGTAAATGCAGCACTAGTGGGTGGGATTGAGGTgTGCCCT GGTGCATAAATAGAGACTCAGCTGTGCTGGCACACTCAAcggcggcgcaga tcgcccggcgcggctccgccccctgcgccggtcacgtggggcgccggctgcgcctgcggagaagcggtggc |

TABLE 1J-continued

Core Promoter Sequences

| SEQ ID NO: | Name | Sequence |
|---|---|---| cgccgagcgggatctgtgcggggagccggaaatggttgtggactacgtctgtgcggctgcgtggggctcggccg
cgcggactgaaggagactgaaggtgctggggggaccctgatgtggA 566 PR173 CACCTCTTAACAATACGTTTCACAAATAGTTAAAAACATGCATACTG
AAAAGCATACTTTTGCAATGTTATTTTTAAAAACAAGGAACTCTTTAA
CCCAGGGAAGATAATCACTTGGGGAAAGGAAGGTTCGTTTCTGAGTT
AGCAACAAGTAAATGCAGCACTAGTGGGTGGGATTGAGGTgTGCCCT
GGTGCATAAATAGAGACTCAGCTGTGCTGGCACACTCAACttttttccgtgcta
cctgcagaggggtccatacggogttgttctggattca 567 PR172 CACCTCTTAACAATACGTTTCACAAATAGTTAAAAACATGCATACTG
AAAAGCATACTTTTGCAATGTTATTTTTAAAAACAAGGAACTCTTTAA
CCCAGGGAAGATAATCACTTGGGGAAAGGAAGGTTCGTTTCTGAGTT
AGCAACAAGTAAATGCAGCACTAGTGGGTGGGATTGAGGTgTGCCCT
GGTGCATAAATAGAGACTCAGCTGTGCTGGCACACTCAACACTCGCG
CTGCCATCACTCTTCCGCCGTCTTCGCCGCCATCCTCGGCGCGACTCG
CTTCTTTCGGTTCTACCAGGTAGAGTCCGCCGCCATCCTCA 568 PR171 CACCTCTTAACAATACGTTTCACAAATAGTTAAAAACATGCATACTG
AAAAGCATACTTTTGCAATGTTATTTTTAAAAACAAGGAACTCTTTAA
CCCAGGGAAGATAATCACTTGGGGAAAGGAAGGTTCGTTTCTGAGTT
AGCAACAAGTAAATGCAGCACTAGTGGGTGGGATTGAGGTgTGCCCT
GGTGCATAAATAGAGACTCAGCTGTGCTGGCACACTCAAGTATCCCA
GGAGGAGCAAGTGGCACGTCTTCGGGTGAGTGTGCGGCTGTGCTGGA
GCCCGGGTTACCAGCTCTTAA 569 PR170 CACCTCTTAACAATACGTTTCACAAATAGTTAAAAACATGCATACTG
AAAAGCATACTTTTGCAATGTTATTTTTAAAAACAAGGAACTCTTTAA
CCCAGGGAAGATAATCACTTGGGGAAAGGAAGGTTCGTTTCTGAGTT
AGCAACAAGTAAATGCAGCACTAGTGGGTGGGATTGAGGTgTGCCCT
GGTGCATAAATAGAGACTCAGCTGTGCTGGCACACTCAAAAATCCAG
AGCGGCGGGCACTGACGGGCACTTGCACCGTGTGGACAGACTCTCCG
GTTCTGTGAGTGGTTTTTCTTTTCCCGGGTCGGACCTGGAGTTCTTAG
GGGGATGGCTGAAgaattcA 570 PR169 CGGGAAAAGTTCAGCTGAGAGATATAAAAGAGCAGTCTTTCCAGCAC
CTGCcggcggcgcagatcgcccggcgcggctccgcccctgcgccggtcacgtgggggcgccggctgcg
cctgcgggagaagcggtggccgccgagcgggatctgtgcggggagccggaaatggttgtggactacgtctgtgc
ggctgcgtggggctcggccgcgcgactgaaggagactgaaggtgctggggggaccctgatgtggA 571 PR168 CGGGAAAAGTTCAGCTGAGAGATATAAAAGAGCAGTCTTTCCAGCAC
CTGCCttttttccgtgctacctgcagaggggtccatacggcgttgttctggattca 572 PR167 CGGGAAAAGTTCAGCTGAGAGATATAAAAGAGCAGTCTTTCCAGCAC
CTGCCACTCGCGCTGCCATCACTCTTCCGCCGTCTTCGCCGCCATCCT
CGGCGCGACTCGCTTCTTTCGGTTCTACCAGGTAGAGTCCGCCGCCAT
CCTCA 573 PR166 CGGGAAAAGTTCAGCTGAGAGATATAAAAGAGCAGTCTTTCCAGCAC
CTGCGTATCCCAGGAGGAGCAAGTGGCACGTCTTCGGGTGAGTGTGC
GGCTGTGCTGGAGCCCGGGTTACCAGCTCTTAA 574 PR165 CGGGAAAAGTTCAGCTGAGAGATATAAAAGAGCAGTCTTTCCAGCAC
CTGCGAAGCTTGGACCGCATCCTAGCCGCCGACTCACACAAGGCAGG
TGGGTGAGGAAATCCAGGTAAGGCTCCTGACAGCAGCTTTAGAAGGG
TACTTGCTGGAGTGAATTCGGGCCTCTGATTA 575 PR159 agcttgcatgcctgcaggtcggagtactgtcctccgagcggagtactgtcctccgagcggagtactgtcctccgag
cggagtactgtcctccgagcggagtactgtcctccgagcggtgcgctcccgacatgccccgcggcgcgccattaa
ccgccagatttgagtcgcgggacccgttggcagaggtggg 576 PR156 AGTGGTGGGGGAGTGAAAAGAGAGATGGAGAAAGAGGGGATGGGC
AGAAAGAGGAGGAGGAGTCAGGGGCAGGGCATGGAGGTGGGTGGG
GCTGGGCTGCCAAAGCAGGATAAATGCACACCTGCCTGCTGGTCTGG
GCTCCCTGCCTCGGGCTCTCACCCTCCTCCTGCAGCTCCAGCTTTG
TGCTCT 577 PR155 CATACTGAAAAGCATACTTTTGCAATGTTATTTTTAAAAACAAGGAA
CTCTTTAACCCAGGGAAGATAATCACTTGGGGAAAGGAAGGTTCGTT
TCTGAGTTAGCAACAAGTAAATGCAGCACTAGTGGGTGGGATTGAGG
TGTGCCCTGGTGCATAAATAGAGACTCAGCTGTGCTGGCACACTCAG
AAGCTTGGACCGCATCCTAGCCGCCGACTCACACAAGGCAGGTGGGT
GAGGAAATCCAGGTAAGGCTCCTGACAGCAGCTTTAGAAGGGTACTT
GCTGGAGTG TABLE 1J-continued Core Promoter Sequences

| SEQ ID NO: | Name | Sequence |
|---|---|---|
| 578 | PR154 | GGCCCGCCCCCTTTCCTTACGCGGATTGGTAGCTGCAGGCTTCCCTAT CTGATTGGCCGAACGAACGCAGCGCGTAATTTAAAATATTGTATCTG TAACAAAGCTGCACCTCGTGGGCGGAGTTGTGCTCTGCGGCTGCGAA AGTCCAGCTTCGGCGACTAGGTGTGAGTAAGCCAGTATCCCAGGAGG AGCAAGTGGCACGTCTTCGGGTGAGTGTGCGGCTGTGCTGGAGCCCG GGTTACCAGCTCTT |
| 579 | PR153 | GGGAAAAGTTCAGCTGAGAGATATAAAAGAGCAGTCTTTCCAGCACC TGCAAATCCAGAGCGGCGGGCACTGACGGGCACTTGCACCGTGTGGA CAGACTCTCCGGTTCTGTGAGTGGTTTTTCTTTTCCCGGGTCGGACCT GGAGTTCTTAGGGGGATGGCTGa |
| 580 | PR152 | ACCCACGTGATGCTGAGAAGTACTCCTGCCCTAGGAAGAGACTCAGG GCAGAGGGAGGAAGGACAGCAGACCAGACAGTCACAGCAGCCTTGA CAAAACGTTCCTGGAAC |
| 581 | PR151 | TATAAAAGGCCAGCAGCAGCCTGACCACATCTCATCC |
| 582 | PR150 | CACTCCCAGAAGGCAGCGGGCGAGGGCGTGGGGCCGGGGCTCTCCC GGCATGCTCTGCGGCGCGCCTCCGCCCGCGCGATTTGAATCCTGCGTT TGAGTCGTCTTGGCGGAGGTTGTGGTGACGC |
| 583 | PR131 | tcccgacatgccccgcggcgcgccattaaccgccagatttgagtcgcgggacccgttggcagaggtg |
| 584 | | GTATCCCAGGAGGAGCAAGTGGCACGTCTTCGGGT |
| 585 | | CGGGAAAAGTTCAGCTGAGAGATATAAAAGAGCAGTCTTTCCAGCAC CTGC |
| 586 | | GTATCCCAGGAGGAGCAAGTGGCACGTCTTCGGGTGAGTGTGCGGCT GTGCTGGAGCCCGGGTTACCAGCTCTTAA |
| 587 | | CAGTGTGCGGCTGTGCTGGAGCCCGGGTTACCAGCTCTT |

In some embodiments, the sequence of any of the core promoters listed in Table 1J can further comprise, at the 5' end, any of SEQ ID NOs: 377-397 listed in Table 1B, or reverse complements thereof. In some embodiments, the sequence of any of the core promoters listed in Table 1J can further comprise, at the 5' end, any of SEQ ID NOs: 377-397 listed in Table 1B, or reverse complements thereof, in a vector. In some embodiments, the sequence of any of the core promoters listed in Table UJ can further comprise, at the 5' end, any of SEQ ID NOs: 377-397 listed in Table 1B, or reverse complements thereof, in a nanoplasmid. In some embodiments, the sequence of any of the core promoters listed in Table UJ can further comprise, at the 5' end, any of SEQ ID NOs: 377-397 listed in Table 1B, or reverse complements thereof, in a linked double-stranded DNA.

In an embodiment, PR181 can further comprise, at the 5' end, a sequence comprising SRE010, SRE012, SRE007, and SRE008, or a reverse complement thereof, in a vector. In some embodiments, PR180 can further comprise, at the 5' end, a sequence comprising SRE010, SRE012, SRE007, and SRE008, or a reverse complement thereof, in a vector. In some embodiments, PR179 can further comprise, at the 5' end, a sequence comprising SRE010, SRE012, SRE007, and SRE008, or a reverse complement thereof, in a vector. In some embodiments, PR178 can further comprise, at the 5' end, a sequence comprising SRE010, SRE012, SRE007, and SRE008, or a reverse complement thereof, in a vector. In some embodiments, PR177 can further comprise, at the 5' end, a sequence comprising SRE010, SRE012, SRE007, and SRE008, or a reverse complement thereof, in a vector. In some embodiments, PR176 can further comprise, at the 5' end, a sequence comprising SRE010, SRE012, SRE007, and SRE008, or a reverse complement thereof, in a vector. In some embodiments, PR175 can further comprise, at the 5' end, a sequence comprising SRE010, SRE012, SRE007, and SRE008, or a reverse complement thereof, in a vector. In some embodiments, PR174 can further comprise, at the 5' end, a sequence comprising SRE010, SRE012, SRE007, and SRE008, or a reverse complement thereof, in a vector. In some embodiments, PR173 can further comprise, at the 5' end, a sequence comprising SRE010, SRE012, SRE007, and SRE008, or a reverse complement thereof, in a vector. In some embodiments, PR172 can further comprise, at the 5' end, a sequence comprising SRE010, SRE012, SRE007, and SRE008, or a reverse complement thereof, in a vector. In some embodiments, PR171 can further comprise, at the 5' end, a sequence comprising SRE010, SRE012, SRE007, and SRE008, or a reverse complement thereof, in a vector. In some embodiments, PR170 can further comprise, at the 5' end, a sequence comprising SRE010, SRE012, SRE007, and SRE008, or a reverse complement thereof, in a vector. In some embodiments, PR169 can further comprise, at the 5' end, a sequence comprising SRE010, SRE012, SRE007, and SRE008, or a reverse complement thereof, in a vector. In some embodiments, PR168 can further comprise, at the 5' end, a sequence comprising SRE010, SRE012, SRE007, and SRE008, or a reverse complement thereof, in a vector. In some embodiments, PR167 can further comprise, at the 5' end, a sequence comprising SRE010, SRE012, SRE007, and SRE008, or a reverse complement thereof, in a vector. In some embodiments, PR166 can further comprise, at the 5' end, a sequence comprising SRE010, SRE012, SRE007, and SRE008, or a reverse complement thereof, in a vector. In some embodiments, PR165 can further comprise, at the 5' end, a sequence comprising SRE010, SRE012, SRE007, and SRE008, or a reverse complement thereof, in a vector. In some embodiments, PR159 can further comprise, at the 5' end, a sequence comprising SRE010, SRE012, SRE007, and SRE008, or a reverse complement thereof, in a vector. In some embodiments, PR156 can further comprise, at the 5' end, a sequence comprising SRE010, SRE012, SRE007, and SRE008, or a reverse complement thereof, in a vector. In some embodiments, PR155 can further comprise, at the 5' end, a sequence comprising SRE010, SRE012, SRE007, and SRE008, or a reverse complement thereof, in a vector. In some embodiments, PR154 can further comprise, at the 5' end, a sequence comprising SRE010, SRE012, SRE007, and SRE008, or a reverse complement thereof, in a vector. In some embodiments, PR153 can further comprise, at the 5' end, a sequence comprising SRE010, SRE012, SRE007, and SRE008, or a reverse complement thereof, in a vector. In some embodiments, PR152 can further comprise, at the 5' end, a sequence comprising SRE010, SRE012, SRE007, and SRE008, or a reverse complement thereof, in a vector. In some embodiments, PR151 can further comprise, at the 5' end, a sequence comprising SRE010, SRE012, SRE007, and SRE008, or a reverse complement thereof, in a vector. In some embodiments, PR150 can further comprise, at the 5' end, a sequence comprising SRE010, SRE012, SRE007, and SRE008, or a reverse complement thereof, in a vector. In some embodiments, PR131 can further comprise, at the 5' end, a sequence comprising SRE010, SRE012, SRE007, and SRE008, or a reverse complement thereof, in a vector. In some embodiments, SEQ ID NO: 584 can further comprise, at the 5' end, a sequence comprising SRE010, SRE012, SRE007, and SRE008, or a reverse complement thereof, in a vector. In some embodiments, SEQ ID NO: 585 can further comprise, at the 5' end, a sequence comprising SRE010, SRE012, SRE007, and SRE008, or a reverse complement thereof, in a vector. In some embodiments, SEQ ID NO: 586 can further comprise, at the 5' end, a sequence comprising SRE010, SRE012, SRE007, and SRE008, or a reverse complement thereof, in a vector. In some embodiments, SEQ ID NO: 587 can further comprise, at the 5' end, a sequence comprising SRE010, SRE012, SRE007, and SRE008, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In an embodiment, PR181 can further comprise, at the 5' end, a sequence comprising SRE010, SRE012, SRE007, and SRE008, or a reverse complement thereof, in a nanoplasmid. In some embodiments, PR180 can further comprise, at the 5' end, a sequence comprising SRE010, SRE012, SRE007, and SRE008, or a reverse complement thereof, in a nanoplasmid. In some embodiments, PR179 can further comprise, at the 5' end, a sequence comprising SRE010, SRE012, SRE007, and SRE008, or a reverse complement thereof, in a nanoplasmid. In some embodiments, PR178 can further comprise, at the 5' end, a sequence comprising SRE010, SRE012, SRE007, and SRE008, or a reverse complement thereof, in a nanoplasmid. In some embodiments, PR177 can further comprise, at the 5' end, a sequence comprising SRE010, SRE012, SRE007, and SRE008, or a reverse complement thereof, in a nanoplasmid.

In some embodiments, PR176 can further comprise, at the 5' end, a sequence comprising SRE010, SRE012, SRE007, and SRE008, or a reverse complement thereof, in a nanoplasmid. In some embodiments, PR175 can further comprise, at the 5' end, a sequence comprising SRE010, SRE012, SRE007, and SRE008, or a reverse complement thereof, in a nanoplasmid. In some embodiments, PR174 can further comprise, at the 5' end, a sequence comprising SRE010, SRE012, SRE007, and SRE008, or a reverse complement thereof, in a nanoplasmid. In some embodiments, PR173 can further comprise, at the 5' end, a sequence comprising SRE010, SRE012, SRE007, and SRE008, or a reverse complement thereof, in a nanoplasmid. In some embodiments, PR172 can further comprise, at the 5' end, a sequence comprising SRE010, SRE012, SRE007, and SRE008, or a reverse complement thereof, in a nanoplasmid. In some embodiments, PR171 can further comprise, at the 5' end, a sequence comprising SRE010, SRE012, SRE007, and SRE008, or a reverse complement thereof, in a nanoplasmid. In some embodiments, PR170 can further comprise, at the 5' end, a sequence comprising SRE010, SRE012, SRE007, and SRE008, or a reverse complement thereof, in a nanoplasmid. In some embodiments, PR169 can further comprise, at the 5' end, a sequence comprising SRE010, SRE012, SRE007, and SRE008, or a reverse complement thereof, in a nanoplasmid. In some embodiments, PR168 can further comprise, at the 5' end, a sequence comprising SRE010, SRE012, SRE007, and SRE008, or a reverse complement thereof, in a nanoplasmid. In some embodiments, PR167 can further comprise, at the 5' end, a sequence comprising SRE010, SRE012, SRE007, and SRE008, or a reverse complement thereof, in a nanoplasmid. In some embodiments, PR166 can further comprise, at the 5' end, a sequence comprising SRE010, SRE012, SRE007, and SRE008, or a reverse complement thereof, in a nanoplasmid. In some embodiments, PR165 can further comprise, at the 5' end, a sequence comprising SRE010, SRE012, SRE007, and SRE008, or a reverse complement thereof, in a nanoplasmid. In some embodiments, PR159 can further comprise, at the 5' end, a sequence comprising SRE010, SRE012, SRE007, and SRE008, or a reverse complement thereof, in a nanoplasmid. In some embodiments, PR156 can further comprise, at the 5' end, a sequence comprising SRE010, SRE012, SRE007, and SRE008, or a reverse complement thereof, in a nanoplasmid. In some embodiments, PR155 can further comprise, at the 5' end, a sequence comprising SRE010, SRE012, SRE007, and SRE008, or a reverse complement thereof, in a nanoplasmid. In some embodiments, PR154 can further comprise, at the 5' end, a sequence comprising SRE010, SRE012, SRE007, and SRE008, or a reverse complement thereof, in a nanoplasmid. In some embodiments, PR153 can further comprise, at the 5' end, a sequence comprising SRE010, SRE012, SRE007, and SRE008, or a reverse complement thereof, in a nanoplasmid. In some embodiments, PR152 can further comprise, at the 5' end, a sequence comprising SRE010, SRE012, SRE007, and SRE008, or a reverse complement thereof, in a nanoplasmid. In some embodiments, PR151 can further comprise, at the 5' end, a sequence comprising SRE010, SRE012, SRE007, and SRE008, or a reverse complement thereof, in a nanoplasmid. In some embodiments, PR150 can further comprise, at the 5' end, a sequence comprising SRE010, SRE012, SRE007, and SRE008, or a reverse complement thereof, in a nanoplasmid. In some embodiments, PR131 can further comprise, at the 5' end, a sequence comprising SRE010, SRE012, SRE007, and SRE008, or a reverse complement thereof, in a nanoplasmid. In some embodiments, SEQ ID NO: 584 can further comprise, at the 5' end, a sequence comprising SRE010, SRE012, SRE007, and SRE008, or a reverse complement thereof, in a nanoplasmid. In some embodiments, SEQ ID NO: 585 can further comprise, at the 5' end, a sequence comprising SRE010, SRE012, SRE007, and SRE008, or a reverse complement thereof, in a nanoplasmid. In some embodiments, SEQ ID NO: 586 can further comprise, at the 5' end, a sequence comprising SRE010, SRE012, SRE007, and SRE008, or a reverse complement thereof, in a nanoplasmid. In some embodiments, SEQ ID NO: 587 can further comprise, at the 5' end, a sequence comprising SRE010, SRE012, SRE007, and SRE008, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In an embodiment, PR181 can further comprise, at the 5' end, a sequence comprising SRE010, SRE012, SRE007, and SRE008, or a reverse complement thereof, in a linked double-stranded DNA. In some embodiments, PR180 can further comprise, at the 5' end, a sequence comprising SRE010, SRE012, SRE007, and SRE008, optionally in a vector, further optionally, in a nanoplasmid or linked double-stranded DNA. In some embodiments, PR179 can further comprise, at the 5' end, a sequence comprising SRE010, SRE012, SRE007, and SRE008, or a reverse complement thereof, in a linked double-stranded DNA. In some embodiments, PR178 can further comprise, at the 5' end, a sequence comprising SRE010, SRE012, SRE007, and SRE008, or a reverse complement thereof, in a linked double-stranded DNA. In some embodiments, PR177 can further comprise, at the 5' end, a sequence comprising SRE010, SRE012, SRE007, and SRE008, or a reverse complement thereof, in a linked double-stranded DNA. In some embodiments, PR176 can further comprise, at the 5' end, a sequence comprising SRE010, SRE012, SRE007, and SRE008, or a reverse complement thereof, in a linked double-stranded DNA. In some embodiments, PR175 can further comprise, at the 5' end, a sequence comprising SRE010, SRE012, SRE007, and SRE008, or a reverse complement thereof, in a linked double-stranded DNA. In some embodiments, PR174 can further comprise, at the 5' end, a sequence comprising SRE010, SRE012, SRE007, and SRE008, or a reverse complement thereof, in a linked double-stranded DNA. In some embodiments, PR173 can further comprise, at the 5' end, a sequence comprising SRE010, SRE012, SRE007, and SRE008, or a reverse complement thereof, in a linked double-stranded DNA. In some embodiments, PR172 can further comprise, at the 5' end, a sequence comprising SRE010, SRE012, SRE007, and SRE008, or a reverse complement thereof, in a linked double-stranded DNA. In some embodiments, PR171 can further comprise, at the 5' end, a sequence comprising SRE010, SRE012, SRE007, and SRE008, or a reverse complement thereof, in a linked double-stranded DNA. In some embodiments, PR170 can further comprise, at the 5' end, a sequence comprising SRE010, SRE012, SRE007, and SRE008, or a reverse complement thereof, in a linked double-stranded DNA. In some embodiments, PR169 can further comprise, at the 5' end, a sequence comprising SRE010, SRE012, SRE007, and SRE008, or a reverse complement thereof, in a linked double-stranded DNA. In some embodiments, PR168 can further comprise, at the 5' end, a sequence comprising SRE010, SRE012, SRE007, and SRE008, or a reverse complement thereof, in a linked double-stranded DNA. In some embodiments, PR167 can further comprise, at the 5' end, a sequence comprising SRE010, SRE012, SRE007, and SRE008, or a reverse complement thereof, in a linked double-stranded DNA. In some embodiments, PR166 can further comprise, at the 5' end, a sequence comprising SRE010, SRE012, SRE007, and SRE008, or a reverse complement thereof, in a linked double-stranded DNA. In some embodiments, PR165 can further comprise, at the 5' end, a sequence comprising SRE010, SRE012, SRE007, and SRE008, or a reverse complement thereof, in a linked double-stranded DNA. In some embodiments, PR159 can further comprise, at the 5' end, a sequence comprising SRE010, SRE012, SRE007, and SRE008, or a reverse complement thereof, in a linked double-stranded DNA. In some embodiments, PR156 can further comprise, at the 5' end, a sequence comprising SRE010, SRE012, SRE007, and SRE008, or a reverse complement thereof, in a linked double-stranded DNA. In some embodiments, PR155 can further comprise, at the 5' end, a sequence comprising SRE010, SRE012, SRE007, and SRE008, or a reverse complement thereof, in a linked double-stranded DNA. In some embodiments, PR154 can further comprise, at the 5' end, a sequence comprising SRE010, SRE012, SRE007, and SRE008, or a reverse complement thereof, in a linked double-stranded DNA. In some embodiments, PR153 can further comprise, at the 5' end, a sequence comprising SRE010, SRE012, SRE007, and SRE008, or a reverse complement thereof, in a linked double-stranded DNA. In some embodiments, PR152 can further comprise, at the 5' end, a sequence comprising SRE010, SRE012, SRE007, and SRE008, or a reverse complement thereof, in a linked double-stranded DNA. In some embodiments, PR151 can further comprise, at the 5' end, a sequence comprising SRE010, SRE012, SRE007, and SRE008, or a reverse complement thereof, in a linked double-stranded DNA. In some embodiments, PR150 can further comprise, at the 5' end, a sequence comprising SRE010, SRE012, SRE007, and SRE008, or a reverse complement thereof, in a linked double-stranded DNA. In some embodiments, PR131 can further comprise, at the 5' end, a sequence comprising SRE010, SRE012, SRE007, and SRE008, or a reverse complement thereof, in a linked double-stranded DNA. In some embodiments, SEQ ID NO: 584 can further comprise, at the 5' end, a sequence comprising SRE010, SRE012, SRE007, and SRE008, or a reverse complement thereof, in a linked double-stranded DNA. In some embodiments, SEQ ID NO: 585 can further comprise, at the 5' end, a sequence comprising SRE010, SRE012, SRE007, and SRE008, or a reverse complement thereof, in a linked double-stranded DNA. In some embodiments, SEQ ID NO: 586 can further comprise, at the 5' end, a sequence comprising SRE010, SRE012, SRE007, and SRE008, or a reverse complement thereof, in a linked double-stranded DNA. In some embodiments, SEQ ID NO: 587 can further comprise, at the 5' end, a sequence comprising SRE010, SRE012, SRE007, and SRE008, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In an embodiment, PR181 can further comprise, at the 5' end, a sequence comprising SRE010, SRE007, and SRE008, or a reverse complement thereof, in a vector. In some embodiments, PR180 can further comprise, at the 5' end, a sequence comprising SRE010, SRE007, and SRE008, or a reverse complement thereof, in a vector. In some embodiments, PR179 can further comprise, at the 5' end, a sequence comprising SRE010, SRE007, and SRE008, or a reverse complement thereof, in a vector. In some embodiments, PR178 can further comprise, at the 5' end, a sequence comprising SRE010, SRE007, and SRE008, or a reverse complement thereof, in a vector. In some embodiments, PR177 can further comprise, at the 5' end, a sequence comprising SRE010, SRE007, and SRE008, or a reverse complement thereof, in a vector. In some embodiments, PR176 can further comprise, at the 5' end, a sequence comprising SRE010, SRE007, and SRE008, or a reverse complement thereof, in a vector. In some embodiments, PR175 can further comprise, at the 5' end, a sequence comprising SRE010, SRE007, and SRE008, or a reverse complement thereof, in a vector. In some embodiments, PR174 can further comprise, at the 5' end, a sequence comprising SRE010, SRE007, and SRE008, or a reverse complement thereof, in a vector. In some embodiments, PR173 can further comprise, at the 5' end, a sequence comprising SRE010, SRE007, and SRE008, or a reverse complement thereof, in a vector. In some embodiments, PR172 can further comprise, at the 5' end, a sequence comprising SRE010, SRE007, and SRE008, or a reverse complement thereof, in a vector. In some embodiments, PR171 can further comprise, at the 5' end, a sequence comprising SRE010, SRE007, and SRE008, or a reverse complement thereof, in a vector. In some embodiments, PR170 can further comprise, at the 5' end, a sequence comprising SRE010, SRE007, and SRE008, or a reverse complement thereof, in a vector. In some embodiments, PR169 can further comprise, at the 5' end, a sequence comprising SRE010, SRE007, and SRE008, or a reverse complement thereof, in a vector. In some embodiments, PR168 can further comprise, at the 5' end, a sequence comprising SRE010, SRE007, and SRE008, or a reverse complement thereof, in a vector. In some embodiments, PR167 can further comprise, at the 5' end, a sequence comprising SRE010, SRE007, and SRE008, or a reverse complement thereof, in a vector. In some embodiments, PR166 can further comprise, at the 5' end, a sequence comprising SRE010, SRE007, and SRE008, or a reverse complement thereof, in a vector. In some embodiments, PR165 can further comprise, at the 5' end, a sequence comprising SRE010, SRE007, and SRE008, or a reverse complement thereof, in a vector. In some embodiments, PR159 can further comprise, at the 5' end, a sequence comprising SRE010, SRE007, and SRE008, or a reverse complement thereof, in a vector. In some embodiments, PR156 can further comprise, at the 5' end, a sequence comprising SRE010, SRE007, and SRE008, or a reverse complement thereof, in a vector. In some embodiments, PR155 can further comprise, at the 5' end, a sequence comprising SRE010, SRE007, and SRE008, or a reverse complement thereof, in a vector. In some embodiments, PR154 can further comprise, at the 5' end, a sequence comprising SRE010, SRE007, and SRE008, or a reverse complement thereof, in a vector. In some embodiments, PR153 can further comprise, at the 5' end, a sequence comprising SRE010, SRE007, and SRE008, or a reverse complement thereof, in a vector. In some embodiments, PR152 can further comprise, at the 5' end, a sequence comprising SRE010, SRE007, and SRE008, or a reverse complement thereof, in a vector. In some embodiments, PR151 can further comprise, at the 5' end, a sequence comprising SRE010, SRE007, and SRE008, or a reverse complement thereof, in a vector. In some embodiments, PR150 can further comprise, at the 5' end, a sequence comprising SRE010, SRE007, and SRE008, or a reverse complement thereof, in a vector. In some embodiments, PR131 can further comprise, at the 5' end, a sequence comprising SRE010, SRE007, and SRE008, or a reverse complement thereof, in a vector. In some embodiments, SEQ ID NO: 584 can further comprise, at the 5' end, a sequence comprising SRE010, SRE007, and SRE008, or a reverse complement thereof, in a vector. In some embodiments, SEQ ID NO: 585 can further comprise, at the 5' end, a sequence comprising SRE010, SRE007, and SRE008, or a reverse complement thereof, in a vector. In some embodiments, SEQ ID NO: 586 can further comprise, at the 5' end, a sequence comprising SRE010, SRE007, and SRE008, or a reverse complement thereof, in a vector. In some embodiments, SEQ ID NO: 587 can further comprise, at the 5' end, a sequence comprising SRE010, SRE007, and SRE008, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In an embodiment, PR181 can further comprise, at the 5' end, a sequence comprising SRE010, SRE007, and SRE008, or a reverse complement thereof, in a nanoplasmid. In some embodiments, PR180 can further comprise, at the 5' end, a sequence comprising SRE010, SRE007, and SRE008, or a reverse complement thereof, in a nanoplasmid. In some embodiments, PR179 can further comprise, at the 5' end, a sequence comprising SRE010, SRE007, and SRE008, or a reverse complement thereof, in a nanoplasmid. In some embodiments, PR178 can further comprise, at the 5' end, a sequence comprising SRE010, SRE007, and SRE008, or a reverse complement thereof, in a nanoplasmid. In some embodiments, PR177 can further comprise, at the 5' end, a sequence comprising SRE010, SRE007, and SRE008, or a reverse complement thereof, in a nanoplasmid. In some embodiments, PR176 can further comprise, at the 5' end, a sequence comprising SRE010, SRE007, and SRE008, or a reverse complement thereof, in a nanoplasmid. In some embodiments, PR175 can further comprise, at the 5' end, a sequence comprising SRE010, SRE007, and SRE008, or a reverse complement thereof, in a nanoplasmid. In some embodiments, PR174 can further comprise, at the 5' end, a sequence comprising SRE010, SRE007, and SRE008, or a reverse complement thereof, in a nanoplasmid. In some embodiments, PR173 can further comprise, at the 5' end, a sequence comprising SRE010, SRE007, and SRE008, or a reverse complement thereof, in a nanoplasmid. In some embodiments, PR172 can further comprise, at the 5' end, a sequence comprising SRE010, SRE007, and SRE008, or a reverse complement thereof, in a nanoplasmid. In some embodiments, PR171 can further comprise, at the 5' end, a sequence comprising SRE010, SRE007, and SRE008, or a reverse complement thereof, in a nanoplasmid. In some embodiments, PR170 can further comprise, at the 5' end, a sequence comprising SRE010, SRE007, and SRE008, or a reverse complement thereof, in a nanoplasmid. In some embodiments, PR169 can further comprise, at the 5' end, a sequence comprising SRE010, SRE007, and SRE008, or a reverse complement thereof, in a nanoplasmid. In some embodiments, PR168 can further comprise, at the 5' end, a sequence comprising SRE010, SRE007, and SRE008, or a reverse complement thereof, in a nanoplasmid. In some embodiments, PR167 can further comprise, at the 5' end, a sequence comprising SRE010, SRE007, and SRE008, or a reverse complement thereof, in a nanoplasmid. In some embodiments, PR166 can further comprise, at the 5' end, a sequence comprising SRE010, SRE007, and SRE008, or a reverse complement thereof, in a nanoplasmid. In some embodiments, PR165 can further comprise, at the 5' end, a sequence comprising SRE010, SRE007, and SRE008, or a reverse complement thereof, in a nanoplasmid. In some embodiments, PR159 can further comprise, at the 5' end, a sequence comprising SRE010, SRE007, and SRE008, or a reverse complement thereof, in a nanoplasmid. In some embodiments, PR156 can further comprise, at the 5' end, a sequence comprising SRE010, SRE007, and SRE008, or a reverse complement thereof, in a nanoplasmid. In some embodiments, PR155 can further comprise, at the 5' end, a sequence comprising SRE010, SRE007, and SRE008, or a reverse complement thereof, in a nanoplasmid. In some embodiments, PR154 can further comprise, at the 5' end, a sequence comprising SRE010, SRE007, and SRE008, or a reverse complement thereof, in a nanoplasmid. In some embodiments, PR153 can further comprise, at the 5' end, a sequence comprising SRE010, SRE007, and SRE008, or a reverse complement thereof, in a nanoplasmid. In some embodiments, PR152 can further comprise, at the 5' end, a sequence comprising SRE010, SRE007, and SRE008, or a reverse complement thereof, in a nanoplasmid. In some embodiments, PR151 can further comprise, at the 5' end, a sequence comprising SRE010, SRE007, and SRE008, or a reverse complement thereof, in a nanoplasmid. In some embodiments, PR150 can further comprise, at the 5' end, a sequence comprising SRE010, SRE007, and SRE008, or a reverse complement thereof, in a nanoplasmid. In some embodiments, PR131 can further comprise, at the 5' end, a sequence comprising SRE010, SRE007, and SRE008, or a reverse complement thereof, in a nanoplasmid. In some embodiments, SEQ ID NO: 584 can further comprise, at the 5' end, a sequence comprising SRE010, SRE007, and SRE008, or a reverse complement thereof, in a nanoplasmid. In some embodiments, SEQ ID NO: 585 can further comprise, at the 5' end, a sequence comprising SRE010, SRE007, and SRE008, or a reverse complement thereof, in a nanoplasmid. In some embodiments, SEQ ID NO: 586 can further comprise, at the 5' end, a sequence comprising SRE010, SRE007, and SRE008, or a reverse complement thereof, in a nanoplasmid. In some embodiments, SEQ ID NO: 587 can further comprise, at the 5' end, a sequence comprising SRE010, SRE007, and SRE008, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In an embodiment, PR181 can further comprise, at the 5' end, a sequence comprising SRE010, SRE007, and SRE008, or a reverse complement thereof, in a linked double-stranded DNA. In some embodiments, PR180 can further comprise, at the 5' end, a sequence comprising SRE010, SRE007, and SRE008, or a reverse complement thereof, in a linked double-stranded DNA. In some embodiments, PR179 can further comprise, at the 5' end, a sequence comprising SRE010, SRE007, and SRE008, or a reverse complement thereof, in a linked double-stranded DNA. In some embodiments, PR178 can further comprise, at the 5' end, a sequence comprising SRE010, SRE007, and SRE008, or a reverse complement thereof, in a linked double-stranded DNA. In some embodiments, PR177 can further comprise, at the 5' end, a sequence comprising SRE010, SRE007, and SRE008, or a reverse complement thereof, in a linked double-stranded DNA. In some embodiments, PR176 can further comprise, at the 5' end, a sequence comprising SRE010, SRE007, and SRE008, or a reverse complement thereof, in a linked double-stranded DNA. In some embodiments, PR175 can further comprise, at the 5' end, a sequence comprising SRE010, SRE007, and SRE008, or a reverse complement thereof, in a linked double-stranded DNA. In some embodiments, PR174 can further comprise, at the 5' end, a sequence comprising SRE010, SRE007, and SRE008, or a reverse complement thereof, in a linked double-stranded DNA. In some embodiments, PR173 can further comprise, at the 5' end, a sequence comprising SRE010, SRE007, and SRE008, or a reverse complement thereof, in a linked double-stranded DNA. In some embodiments, PR172 can further comprise, at the 5' end, a sequence comprising SRE010, SRE007, and SRE008, or a reverse complement thereof, in a linked double-stranded DNA. In some embodiments, PR171 can further comprise, at the 5' end, a sequence comprising SRE010, SRE007, and SRE008, or a reverse complement thereof, in a linked double-stranded DNA. In some embodiments, PR170 can further comprise, at the 5' end, a sequence comprising SRE010, SRE007, and SRE008, or a reverse complement thereof, in a linked double-stranded DNA. In some embodiments, PR169 can further comprise, at the 5' end, a sequence comprising SRE010, SRE007, and SRE008, or a reverse complement thereof, in a linked double-stranded DNA. In some embodiments, PR168 can further comprise, at the 5' end, a sequence comprising SRE010, SRE007, and SRE008, or a reverse complement thereof, in a linked double-stranded DNA. In some embodiments, PR167 can further comprise, at the 5' end, a sequence comprising SRE010, SRE007, and SRE008, or a reverse complement thereof, in a linked double-stranded DNA. In some embodiments, PR166 can further comprise, at the 5' end, a sequence comprising SRE010, SRE007, and SRE008, or a reverse complement thereof, in a linked double-stranded DNA. In some embodiments, PR165 can further comprise, at the 5' end, a sequence comprising SRE010, SRE007, and SRE008, or a reverse complement thereof, in a linked double-stranded DNA. In some embodiments, PR159 can further comprise, at the 5' end, a sequence comprising SRE010, SRE007, and SRE008, or a reverse complement thereof, in a linked double-stranded DNA. In some embodiments, PR156 can further comprise, at the 5' end, a sequence comprising SRE010, SRE007, and SRE008, or a reverse complement thereof, in a linked double-stranded DNA. In some embodiments, PR155 can further comprise, at the 5' end, a sequence comprising SRE010, SRE007, and SRE008, or a reverse complement thereof, in a linked double-stranded DNA. In some embodiments, PR154 can further comprise, at the 5' end, a sequence comprising SRE010, SRE007, and SRE008, or a reverse complement thereof, in a linked double-stranded DNA. In some embodiments, PR153 can further comprise, at the 5' end, a sequence comprising SRE010, SRE007, and SRE008, or a reverse complement thereof, in a linked double-stranded DNA. In some embodiments, PR152 can further comprise, at the 5' end, a sequence comprising SRE010, SRE007, and SRE008, or a reverse complement thereof, in a linked double-stranded DNA. In some embodiments, PR151 can further comprise, at the 5' end, a sequence comprising SRE010, SRE007, and SRE008, or a reverse complement thereof, in a linked double-stranded DNA. In some embodiments, PR150 can further comprise, at the 5' end, a sequence comprising SRE010, SRE007, and SRE008, or a reverse complement thereof, in a linked double-stranded DNA. In some embodiments, PR131 can further comprise, at the 5' end, a sequence comprising SRE010, SRE007, and SRE008, or a reverse complement thereof, in a linked double-stranded DNA. In some embodiments, SEQ ID NO: 584 can further comprise, at the 5' end, a sequence comprising SRE010, SRE007, and SRE008, or a reverse complement thereof, in a linked double-stranded DNA. In some embodiments, SEQ ID NO: 585 can further comprise, at the 5' end, a sequence comprising SRE010, SRE007, and SRE008, or a reverse complement thereof, in a linked double-stranded DNA. In some embodiments, SEQ ID NO: 586 can further comprise, at the 5' end, a sequence comprising SRE010, SRE007, and SRE008, or a reverse complement thereof, in a linked double-stranded DNA. In some embodiments, SEQ ID NO: 587 can further comprise, at the 5' end, a sequence comprising SRE010, SRE007, and SRE008, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In an embodiment, PR181 can further comprise, at the 5' end, a sequence comprising SRE010, SRE012, and SRE007, or a reverse complement thereof, in a vector. In some embodiments, PR180 can further comprise, at the 5' end, a sequence comprising SRE010, SRE012, and SRE007, or a reverse complement thereof, in a vector. In some embodiments, PR179 can further comprise, at the 5' end, a sequence comprising SRE010, SRE012, and SRE007, or a reverse complement thereof, in a vector. In some embodiments, PR178 can further comprise, at the 5' end, a sequence comprising SRE010, SRE012, and SRE007, or a reverse complement thereof, in a vector. In some embodiments, PR177 can further comprise, at the 5' end, a sequence comprising SRE010, SRE012, and SRE007, or a reverse complement thereof, in a vector. In some embodiments, PR176 can further comprise, at the 5' end, a sequence comprising SRE010, SRE012, and SRE007, or a reverse complement thereof, in a vector. In some embodiments, PR175 can further comprise, at the 5' end, a sequence comprising SRE010, SRE012, and SRE007, or a reverse complement thereof, in a vector. In some embodiments, PR174 can further comprise, at the 5' end, a sequence comprising SRE010, SRE012, and SRE007, or a reverse complement thereof, in a vector. In some embodiments, PR173 can further comprise, at the 5' end, a sequence comprising SRE010, SRE012, and SRE007, or a reverse complement thereof, in a vector. In some embodiments, PR172 can further comprise, at the 5' end, a sequence comprising SRE010, SRE012, and SRE007, or a reverse complement thereof, in a vector. In some embodiments, PR171 can further comprise, at the 5' end, a sequence comprising SRE010, SRE012, and SRE007, or a reverse complement thereof, in a vector. In some embodiments, PR170 can further comprise, at the 5' end, a sequence comprising SRE010, SRE012, and SRE007, or a reverse complement thereof, in a vector. In some embodiments, PR169 can further comprise, at the 5' end, a sequence comprising SRE010, SRE012 and SRE007, or a reverse complement thereof, in a vector. In some embodiments, PR168 can further comprise, at the 5' end, a sequence comprising SRE010, SRE012, and SRE007, or a reverse complement thereof, in a vector. In some embodiments, PR167 can further comprise, at the 5' end, a sequence comprising SRE010, SRE012, and SRE007, or a reverse complement thereof, in a vector. In some embodiments, PR166 can further comprise, at the 5' end, a sequence comprising SRE010, SRE012, and SRE007, or a reverse complement thereof, in a vector. In some embodiments, PR165 can further comprise, at the 5' end, a sequence comprising SRE010, SRE012, and SRE007, or a reverse complement thereof, in a vector. In some embodiments, PR159 can further comprise, at the 5' end, a sequence comprising SRE010, SRE012, and SRE007, or a reverse complement thereof, in a vector. In some embodiments, PR156 can further comprise, at the 5' end, a sequence comprising SRE010, SRE012, and SRE007, or a reverse complement thereof, in a vector. In some embodiments, PR155 can further comprise, at the 5' end, a sequence comprising SRE010, SRE012, and SRE007, or a reverse complement thereof, in a vector. In some embodiments, PR154 can further comprise, at the 5' end, a sequence comprising SRE010, SRE012, and SRE007, or a reverse complement thereof, in a vector. In some embodiments, PR153 can further comprise, at the 5' end, a sequence comprising SRE010, SRE012, and SRE007, or a reverse complement thereof, in a vector. In some embodiments, PR152 can further comprise, at the 5' end, a sequence comprising SRE010, SRE012, and SRE007, or a reverse complement thereof, in a vector. In some embodiments, PR151 can further comprise, at the 5' end, a sequence comprising SRE010, SRE012, and SRE007, or a reverse complement thereof, in a vector. In some embodiments, PR150 can further comprise, at the 5' end, a sequence comprising SRE010, SRE012, and SRE007, or a reverse complement thereof, in a vector. In some embodiments, PR131 can further comprise, at the 5' end, a sequence comprising SRE010, SRE012, and SRE007, or a reverse complement thereof, in a vector. In some embodiments, SEQ ID NO: 584 can further comprise, at the 5' end, a sequence comprising SRE010, SRE012, and SRE007, or a reverse complement thereof, in a vector. In some embodiments, SEQ ID NO: 585 can further comprise, at the 5' end, a sequence comprising SRE010, SRE012, and SRE007, or a reverse complement thereof, in a vector. In some embodiments, SEQ ID NO: 586 can further comprise, at the 5' end, a sequence comprising SRE010, SRE012, and SRE007, or a reverse complement thereof, in a vector. In some embodiments, SEQ ID NO: 587 can further comprise, at the 5' end, a sequence comprising SRE010, SRE012, and SRE007, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In an embodiment, PR181 can further comprise, at the 5' end, a sequence comprising SRE010, SRE012, and SRE007, or a reverse complement thereof, in a nanoplasmid. In some embodiments, PR180 can further comprise, at the 5' end, a sequence comprising SRE010, SRE012, and SRE007, or a reverse complement thereof, in a nanoplasmid. In some embodiments, PR179 can further comprise, at the 5' end, a sequence comprising SRE010, SRE012, and SRE007, or a reverse complement thereof, in a nanoplasmid. In some embodiments, PR178 can further comprise, at the 5' end, a sequence comprising SRE010, SRE012, and SRE007, or a reverse complement thereof, in a nanoplasmid. In some embodiments, PR177 can further comprise, at the 5' end, a sequence comprising SRE010, SRE012, and SRE007, or a reverse complement thereof, in a nanoplasmid. In some embodiments, PR176 can further comprise, at the 5' end, a sequence comprising SRE010, SRE012, and SRE007, or a reverse complement thereof, in a nanoplasmid. In some embodiments, PR175 can further comprise, at the 5' end, a sequence comprising SRE010, SRE012, and SRE007, or a reverse complement thereof, in a nanoplasmid. In some embodiments, PR174 can further comprise, at the 5' end, a sequence comprising SRE010, SRE012, and SRE007, or a reverse complement thereof, in a nanoplasmid. In some embodiments, PR173 can further comprise, at the 5' end, a sequence comprising SRE010, SRE012, and SRE007, or a reverse complement thereof, in a nanoplasmid. In some embodiments, PR172 can further comprise, at the 5' end, a sequence comprising SRE010, SRE012, and SRE007, or a reverse complement thereof, in a nanoplasmid. In some embodiments, PR171 can further comprise, at the 5' end, a sequence comprising SRE010, SRE012, and SRE007, or a reverse complement thereof, in a nanoplasmid. In some embodiments, PR170 can further comprise, at the 5' end, a sequence comprising SRE010, SRE012, and SRE007, or a reverse complement thereof, in a nanoplasmid. In some embodiments, PR169 can further comprise, at the 5' end, a sequence comprising SRE010, SRE012 and SRE007, or a reverse complement thereof, in a nanoplasmid. In some embodiments, PR168 can further comprise, at the 5' end, a sequence comprising SRE010, SRE012, and SRE007, or a reverse complement thereof, in a nanoplasmid. In some embodiments, PR167 can further comprise, at the 5' end, a sequence comprising SRE010, SRE012, and SRE007, or a reverse complement thereof, in a nanoplasmid. In some embodiments, PR166 can further comprise, at the 5' end, a sequence comprising SRE010, SRE012, and SRE007, or a reverse complement thereof, in a nanoplasmid. In some embodiments, PR165 can further comprise, at the 5' end, a sequence comprising SRE010, SRE012, and SRE007, or a reverse complement thereof, in a nanoplasmid. In some embodiments, PR159 can further comprise, at the 5' end, a sequence comprising SRE010, SRE012, and SRE007, or a reverse complement thereof, in a nanoplasmid. In some embodiments, PR156 can further comprise, at the 5' end, a sequence comprising SRE010, SRE012, and SRE007, or a reverse complement thereof, in a nanoplasmid. In some embodiments, PR155 can further comprise, at the 5' end, a sequence comprising SRE010, SRE012, and SRE007, or a reverse complement thereof, in a nanoplasmid. In some embodiments, PR154 can further comprise, at the 5' end, a sequence comprising SRE010, SRE012, and SRE007, or a reverse complement thereof, in a nanoplasmid. In some embodiments, PR153 can further comprise, at the 5' end, a sequence comprising SRE010, SRE012, and SRE007, or a reverse complement thereof, in a nanoplasmid. In some embodiments, PR152 can further comprise, at the 5' end, a sequence comprising SRE010, SRE012, and SRE007, or a reverse complement thereof, in a nanoplasmid. In some embodiments, PR151 can further comprise, at the 5' end, a sequence comprising SRE010, SRE012, and SRE007, or a reverse complement thereof, in a nanoplasmid. In some embodiments, PR150 can further comprise, at the 5' end, a sequence comprising SRE010, SRE012, and SRE007, or a reverse complement thereof, in a nanoplasmid. In some embodiments, PR131 can further comprise, at the 5' end, a sequence comprising SRE010, SRE012, and SRE007, or a reverse complement thereof, in a nanoplasmid. In some embodiments, SEQ ID NO: 584 can further comprise, at the 5' end, a sequence comprising SRE010, SRE012, and SRE007, or a reverse complement thereof, in a nanoplasmid. In some embodiments, SEQ ID NO: 585 can further comprise, at the 5' end, a sequence comprising SRE010, SRE012, and SRE007, or a reverse complement thereof, in a nanoplasmid. In some embodiments, SEQ ID NO: 586 can further comprise, at the 5' end, a sequence comprising SRE010, SRE012, and SRE007, or a reverse complement thereof, in a nanoplasmid. In some embodiments, SEQ ID NO: 587 can further comprise, at the 5' end, a sequence comprising SRE010, SRE012, and SRE007, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In an embodiment, PR181 can further comprise, at the 5' end, a sequence comprising SRE010, SRE012, and SRE007, or a reverse complement thereof, in a linked double-stranded DNA. In some embodiments, PR180 can further comprise, at the 5' end, a sequence comprising SRE010, SRE012, and SRE007, or a reverse complement thereof, in a linked double-stranded DNA. In some embodiments, PR179 can further comprise, at the 5' end, a sequence comprising SRE010, SRE012, and SRE007, or a reverse complement thereof, in a linked double-stranded DNA. In some embodiments, PR178 can further comprise, at the 5' end, a sequence comprising SRE010, SRE012, and SRE007, or a reverse complement thereof, in a linked double-stranded DNA. In some embodiments, PR177 can further comprise, at the 5' end, a sequence comprising SRE010, SRE012, and SRE007, or a reverse complement thereof, in a linked double-stranded DNA. In some embodiments, PR176 can further comprise, at the 5' end, a sequence comprising SRE010, SRE012, and SRE007, or a reverse complement thereof, in a linked double-stranded DNA. In some embodiments, PR175 can further comprise, at the 5' end, a sequence comprising SRE010, SRE012, and SRE007, or a reverse complement thereof, in a linked double-stranded DNA. In some embodiments, PR174 can further comprise, at the 5' end, a sequence comprising SRE010, SRE012, and SRE007, or a reverse complement thereof, in a linked double-stranded DNA. In some embodiments, PR173 can further comprise, at the 5' end, a sequence comprising SRE010, SRE012, and SRE007, or a reverse complement thereof, in a linked double-stranded DNA. In some embodiments, PR172 can further comprise, at the 5' end, a sequence comprising SRE010, SRE012, and SRE007, or a reverse complement thereof, in a linked double-stranded DNA. In some embodiments, PR171 can further comprise, at the 5' end, a sequence comprising SRE010, SRE012, and SRE007, or a reverse complement thereof, in a linked double-stranded DNA. In some embodiments, PR170 can further comprise, at the 5' end, a sequence comprising SRE010, SRE012, and SRE007, or a reverse complement thereof, in a linked double-stranded DNA. In some embodiments, PR169 can further comprise, at the 5' end, a sequence comprising SRE010, SRE012 and SRE007, or a reverse complement thereof, in a linked double-stranded DNA. In some embodiments, PR168 can further comprise, at the 5' end, a sequence comprising SRE010, SRE012, and SRE007, or a reverse complement thereof, in a linked double-stranded DNA. In some embodiments, PR167 can further comprise, at the 5' end, a sequence comprising SRE010, SRE012, and SRE007, or a reverse complement thereof, in a linked double-stranded DNA. In some embodiments, PR166 can further comprise, at the 5' end, a sequence comprising SRE010, SRE012, and SRE007, or a reverse complement thereof, in a linked double-stranded DNA. In some embodiments, PR165 can further comprise, at the 5' end, a sequence comprising SRE010, SRE012, and SRE007, or a reverse complement thereof, in a linked double-stranded DNA. In some embodiments, PR159 can further comprise, at the 5' end, a sequence comprising SRE010, SRE012, and SRE007, or a reverse complement thereof, in a linked double-stranded DNA. In some embodiments, PR156 can further comprise, at the 5' end, a sequence comprising SRE010, SRE012, and SRE007, or a reverse complement thereof, in a linked double-stranded DNA. In some embodiments, PR155 can further comprise, at the 5' end, a sequence comprising SRE010, SRE012, and SRE007, or a reverse complement thereof, in a linked double-stranded DNA. In some embodiments, PR154 can further comprise, at the 5' end, a sequence comprising SRE010, SRE012, and SRE007, or a reverse complement thereof, in a linked double-stranded DNA. In some embodiments, PR153 can further comprise, at the 5' end, a sequence comprising SRE010, SRE012, and SRE007, or a reverse complement thereof, in a linked double-stranded DNA. In some embodiments, PR152 can further comprise, at the 5' end, a sequence comprising SRE010, SRE012, and SRE007, or a reverse complement thereof, in a linked double-stranded DNA. In some embodiments, PR151 can further comprise, at the 5' end, a sequence comprising SRE010, SRE012, and SRE007, or a reverse complement thereof, in a linked double-stranded DNA. In some embodiments, PR150 can further comprise, at the 5' end, a sequence comprising SRE010, SRE012, and SRE007, or a reverse complement thereof, in a linked double-stranded DNA. In some embodiments, PR131 can further comprise, at the 5' end, a sequence comprising SRE010, SRE012, and SRE007, or a reverse complement thereof, in a linked double-stranded DNA. In some embodiments, SEQ ID NO: 584 can further comprise, at the 5' end, a sequence comprising SRE010, SRE012, and SRE007, or a reverse complement thereof, in a linked double-stranded DNA. In some embodiments, SEQ ID NO: 585 can further comprise, at the 5' end, a sequence comprising SRE010, SRE012, and SRE007, or a reverse complement thereof, in a linked double-stranded DNA. In some embodiments, SEQ ID NO: 586 can further comprise, at the 5' end, a sequence comprising SRE010, SRE012, and SRE007, or a reverse complement thereof, in a linked double-stranded DNA. In some embodiments, SEQ ID NO: 587 can further comprise, at the 5' end, a sequence comprising SRE010, SRE012, and SRE007, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In an embodiment, PR181 can further comprise, at the 5' end, a sequence comprising SRE010, SRE012, and SRE008, or a reverse complement thereof, in a vector. In some embodiments, PR180 can further comprise, at the 5' end, a sequence comprising SRE010, SRE012, and SRE008, or a reverse complement thereof, in a vector. In some embodiments, PR179 can further comprise, at the 5' end, a sequence comprising SRE010, SRE012, and SRE008, or a reverse complement thereof, in a vector. In some embodiments, PR178 can further comprise, at the 5' end, a sequence comprising SRE010, SRE012, and SRE008, or a reverse complement thereof, in a vector. In some embodiments, PR177 can further comprise, at the 5' end, a sequence comprising SRE010, SRE012, and SRE008, or a reverse complement thereof, in a vector. In some embodiments, PR176 can further comprise, at the 5' end, a sequence comprising SRE010, SRE012, and SRE008, or a reverse complement thereof, in a vector. In some embodiments, PR175 can further comprise, at the 5' end, a sequence comprising SRE010, SRE012, and SRE008, or a reverse complement thereof, in a vector. In some embodiments, PR174 can further comprise, at the 5' end, a sequence comprising SRE010, SRE012, and SRE008, or a reverse complement thereof, in a vector. In some embodiments, PR173 can further comprise, at the 5' end, a sequence comprising SRE010, SRE012, and SRE008, or a reverse complement thereof, in a vector. In some embodiments, PR172 can further comprise, at the 5' end, a sequence comprising SRE010, SRE012, and SRE008, or a reverse complement thereof, in a vector. In some embodiments, PR171 can further comprise, at the 5' end, a sequence comprising SRE010, SRE012, and SRE008, or a reverse complement thereof, in a vector. In some embodiments, PR170 can further comprise, at the 5' end, a sequence comprising SRE010, SRE012, and SRE008, or a reverse complement thereof, in a vector. In some embodiments, PR169 can further comprise, at the 5' end, a sequence comprising SRE010, SRE012 and SRE008, or a reverse complement thereof, in a vector. In some embodiments, PR168 can further comprise, at the 5' end, a sequence comprising SRE010, SRE012, and SRE008, or a reverse complement thereof, in a vector. In some embodiments, PR167 can further comprise, at the 5' end, a sequence comprising SRE010, SRE012, and SRE008, or a reverse complement thereof, in a vector. In some embodiments, PR166 can further comprise, at the 5' end, a sequence comprising SRE010, SRE012, and SRE008, or a reverse complement thereof, in a vector. In some embodiments, PR165 can further comprise, at the 5' end, a sequence comprising SRE010, SRE012, and SRE008, or a reverse complement thereof, in a vector. In some embodiments, PR159 can further comprise, at the 5' end, a sequence comprising SRE010, SRE012, and SRE008, or a reverse complement thereof, in a vector. In some embodiments, PR156 can further comprise, at the 5' end, a sequence comprising SRE010, SRE012, and SRE008, or a reverse complement thereof, in a vector. In some embodiments, PR155 can further comprise, at the 5' end, a sequence comprising SRE010, SRE012, and SRE008, or a reverse complement thereof, in a vector. In some embodiments, PR154 can further comprise, at the 5' end, a sequence comprising SRE010, SRE012, and SRE008, or a reverse complement thereof, in a vector. In some embodiments, PR153 can further comprise, at the 5' end, a sequence comprising SRE010, SRE012, and SRE008, or a reverse complement thereof, in a vector. In some embodiments, PR152 can further comprise, at the 5' end, a sequence comprising SRE010, SRE012, and SRE008, or a reverse complement thereof, in a vector. In some embodiments, PR151 can further comprise, at the 5' end, a sequence comprising SRE010, SRE012, and SRE008, or a reverse complement thereof, in a vector. In some embodiments, PR150 can further comprise, at the 5' end, a sequence comprising SRE010, SRE012, and SRE008, or a reverse complement thereof, in a vector. In some embodiments, PR131 can further comprise, at the 5' end, a sequence comprising SRE010, SRE012, and SRE008, or a reverse complement thereof, in a vector. In some embodiments, SEQ ID NO: 584 can further comprise, at the 5' end, a sequence comprising SRE010, SRE012, and SRE008, or a reverse complement thereof, in a vector. In some embodiments, SEQ ID NO: 585 can further comprise, at the 5' end, a sequence comprising SRE010, SRE012, and SRE008, or a reverse complement thereof, in a vector. In some embodiments, SEQ ID NO: 586 can further comprise, at the 5' end, a sequence comprising SRE010, SRE012, and SRE008, or a reverse complement thereof, in a vector. In some embodiments, SEQ ID NO: 587 can further comprise, at the 5' end, a sequence comprising SRE010, SRE012, and SRE008, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In an embodiment, PR181 can further comprise, at the 5' end, a sequence comprising SRE010, SRE012, and SRE008, or a reverse complement thereof, in a nanoplasmid. In some embodiments, PR180 can further comprise, at the 5' end, a sequence comprising SRE010, SRE012, and SRE008, or a reverse complement thereof, in a nanoplasmid. In some embodiments, PR179 can further comprise, at the 5' end, a sequence comprising SRE010, SRE012, and SRE008, or a reverse complement thereof, in a nanoplasmid. In some embodiments, PR178 can further comprise, at the 5' end, a sequence comprising SRE010, SRE012, and SRE008, or a reverse complement thereof, in a nanoplasmid. In some embodiments, PR177 can further comprise, at the 5' end, a sequence comprising SRE010, SRE012, and SRE008, or a reverse complement thereof, in a nanoplasmid. In some embodiments, PR176 can further comprise, at the 5' end, a sequence comprising SRE010, SRE012, and SRE008, or a reverse complement thereof, in a nanoplasmid. In some embodiments, PR175 can further comprise, at the 5' end, a sequence comprising SRE010, SRE012, and SRE008, or a reverse complement thereof, in a nanoplasmid. In some embodiments, PR174 can further comprise, at the 5' end, a sequence comprising SRE010, SRE012, and SRE008, or a reverse complement thereof, in a nanoplasmid. In some embodiments, PR173 can further comprise, at the 5' end, a sequence comprising SRE010, SRE012, and SRE008, or a reverse complement thereof, in a nanoplasmid. In some embodiments, PR172 can further comprise, at the 5' end, a sequence comprising SRE010, SRE012, and SRE008, or a reverse complement thereof, in a nanoplasmid. In some embodiments, PR171 can further comprise, at the 5' end, a sequence comprising SRE010, SRE012, and SRE008, or a reverse complement thereof, in a nanoplasmid. In some embodiments, PR170 can further comprise, at the 5' end, a sequence comprising SRE010, SRE012, and SRE008, or a reverse complement thereof, in a nanoplasmid. In some embodiments, PR169 can further comprise, at the 5' end, a sequence comprising SRE010, SRE012 and SRE008, or a reverse complement thereof, in a nanoplasmid. In some embodiments, PR168 can further comprise, at the 5' end, a sequence comprising SRE010, SRE012, and SRE008, or a reverse complement thereof, in a nanoplasmid. In some embodiments, PR167 can further comprise, at the 5' end, a sequence comprising SRE010, SRE012, and SRE008, or a reverse complement thereof, in a nanoplasmid. In some embodiments, PR166 can further comprise, at the 5' end, a sequence comprising SRE010, SRE012, and SRE008, or a reverse complement thereof, in a nanoplasmid. In some embodiments, PR165 can further comprise, at the 5' end, a sequence comprising SRE010, SRE012, and SRE008, or a reverse complement thereof, in a nanoplasmid. In some embodiments, PR159 can further comprise, at the 5' end, a sequence comprising SRE010, SRE012, and SRE008, or a reverse complement thereof, in a nanoplasmid. In some embodiments, PR156 can further comprise, at the 5' end, a sequence comprising SRE010, SRE012, and SRE008, or a reverse complement thereof, in a nanoplasmid. In some embodiments, PR155 can further comprise, at the 5' end, a sequence comprising SRE010, SRE012, and SRE008, or a reverse complement thereof, in a nanoplasmid. In some embodiments, PR154 can further comprise, at the 5' end, a sequence comprising SRE010, SRE012, and SRE008, or a reverse complement thereof, in a nanoplasmid. In some embodiments, PR153 can further comprise, at the 5' end, a sequence comprising SRE010, SRE012, and SRE008, or a reverse complement thereof, in a nanoplasmid. In some embodiments, PR152 can further comprise, at the 5' end, a sequence comprising SRE010, SRE012, and SRE008, or a reverse complement thereof, in a nanoplasmid. In some embodiments, PR151 can further comprise, at the 5' end, a sequence comprising SRE010, SRE012, and SRE008, or a reverse complement thereof, in a nanoplasmid. In some embodiments, PR150 can further comprise, at the 5' end, a sequence comprising SRE010, SRE012, and SRE008, or a reverse complement thereof, in a nanoplasmid. In some embodiments, PR131 can further comprise, at the 5' end, a sequence comprising SRE010, SRE012, and SRE008, or a reverse complement thereof, in a nanoplasmid. In some embodiments, SEQ ID NO: 584 can further comprise, at the 5' end, a sequence comprising SRE010, SRE012, and SRE008, or a reverse complement thereof, in a nanoplasmid. In some embodiments, SEQ ID NO: 585 can further comprise, at the 5' end, a sequence comprising SRE010, SRE012, and SRE008, or a reverse complement thereof, in a nanoplasmid. In some embodiments, SEQ ID NO: 586 can further comprise, at the 5' end, a sequence comprising SRE010, SRE012, and SRE008, or a reverse complement thereof, in a nanoplasmid. In some embodiments, SEQ ID NO: 587 can further comprise, at the 5' end, a sequence comprising SRE010, SRE012, and SRE008, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In an embodiment, PR181 can further comprise, at the 5' end, a sequence comprising SRE010, SRE012, and SRE008, or a reverse complement thereof, in a linked double-stranded DNA. In some embodiments, PR180 can further comprise, at the 5' end, a sequence comprising SRE010, SRE012, and SRE008, or a reverse complement thereof, in a linked double-stranded DNA. In some embodiments, PR179 can further comprise, at the 5' end, a sequence comprising SRE010, SRE012, and SRE008, or a reverse complement thereof, in a linked double-stranded DNA. In some embodiments, PR178 can further comprise, at the 5' end, a sequence comprising SRE010, SRE012, and SRE008, or a reverse complement thereof, in a linked double-stranded DNA. In some embodiments, PR177 can further comprise, at the 5' end, a sequence comprising SRE010, SRE012, and SRE008, or a reverse complement thereof, in a linked double-stranded DNA. In some embodiments, PR176 can further comprise, at the 5' end, a sequence comprising SRE010, SRE012, and SRE008, or a reverse complement thereof, in a linked double-stranded DNA. In some embodiments, PR175 can further comprise, at the 5' end, a sequence comprising SRE010, SRE012, and SRE008, or a reverse complement thereof, in a linked double-stranded DNA. In some embodiments, PR174 can further comprise, at the 5' end, a sequence comprising SRE010, SRE012, and SRE008, or a reverse complement thereof, in a linked double-stranded DNA. In some embodiments, PR173 can further comprise, at the 5' end, a sequence comprising SRE010, SRE012, and SRE008, or a reverse complement thereof, in a linked double-stranded DNA. In some embodiments, PR172 can further comprise, at the 5' end, a sequence comprising SRE010, SRE012, and SRE008, or a reverse complement thereof, in a linked double-stranded DNA. In some embodiments, PR171 can further comprise, at the 5' end, a sequence comprising SRE010, SRE012, and SRE008, or a reverse complement thereof, in a linked double-stranded DNA. In some embodiments, PR170 can further comprise, at the 5' end, a sequence comprising SRE010, SRE012, and SRE008, or a reverse complement thereof, in a linked double-stranded DNA. In some embodiments, PR169 can further comprise, at the 5' end, a sequence comprising SRE010, SRE012 and SRE008, or a reverse complement thereof, in a linked double-stranded DNA. In some embodiments, PR168 can further comprise, at the 5' end, a sequence comprising SRE010, SRE012, and SRE008, or a reverse complement thereof, in a linked double-stranded DNA. In some embodiments, PR167 can further comprise, at the 5' end, a sequence comprising SRE010, SRE012, and SRE008, or a reverse complement thereof, in a linked double-stranded DNA. In some embodiments, PR166 can further comprise, at the 5' end, a sequence comprising SRE010, SRE012, and SRE008, or a reverse complement thereof, in a linked double-stranded DNA. In some embodiments, PR165 can further comprise, at the 5' end, a sequence comprising SRE010, SRE012, and SRE008, or a reverse complement thereof, in a linked double-stranded DNA. In some embodiments, PR159 can further comprise, at the 5' end, a sequence comprising SRE010, SRE012, and SRE008, or a reverse complement thereof, in a linked double-stranded DNA. In some embodiments, PR156 can further comprise, at the 5' end, a sequence comprising SRE010, SRE012, and SRE008, or a reverse complement thereof, in a linked double-stranded DNA. In some embodiments, PR155 can further comprise, at the 5' end, a sequence comprising SRE010, SRE012, and SRE008, or a reverse complement thereof, in a linked double-stranded DNA. In some embodiments, PR154 can further comprise, at the 5' end, a sequence comprising SRE010, SRE012, and SRE008, or a reverse complement thereof, in a linked double-stranded DNA. In some embodiments, PR153 can further comprise, at the 5' end, a sequence comprising SRE010, SRE012, and SRE008, or a reverse complement thereof, in a linked double-stranded DNA. In some embodiments, PR152 can further comprise, at the 5' end, a sequence comprising SRE010, SRE012, and SRE008, or a reverse complement thereof, in a linked double-stranded DNA. In some embodiments, PR151 can further comprise, at the 5' end, a sequence comprising SRE010, SRE012, and SRE008, or a reverse complement thereof, in a linked double-stranded DNA. In some embodiments, PR150 can further comprise, at the 5' end, a sequence comprising SRE010, SRE012, and SRE008, or a reverse complement thereof, in a linked double-stranded DNA. In some embodiments, PR131 can further comprise, at the 5' end, a sequence comprising SRE010, SRE012, and SRE008, or a reverse complement thereof, in a linked double-stranded DNA. In some embodiments, SEQ ID NO: 584 can further comprise, at the 5' end, a sequence comprising SRE010, SRE012, and SRE008, or a reverse complement thereof, in a linked double-stranded DNA. In some embodiments, SEQ ID NO: 585 can further comprise, at the 5' end, a sequence comprising SRE010, SRE012, and SRE008, or a reverse complement thereof, in a linked double-stranded DNA. In some embodiments, SEQ ID NO: 586 can further comprise, at the 5' end, a sequence comprising SRE010, SRE012, and SRE008, or a reverse complement thereof, in a linked double-stranded DNA. In some embodiments, SEQ ID NO: 587 can further comprise, at the 5' end, a sequence comprising SRE010, SRE012, and SRE008, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012, SRE007, and SRE008, or a reverse complement thereof, in a vector. In some embodiments, PR180 can further comprise, at the 5' end, a sequence comprising SRE012, SRE007, and SRE008, or a reverse complement thereof, in a vector. In some embodiments, PR179 can further comprise, at the 5' end, a sequence comprising SRE012, SRE007, and SRE008, or a reverse complement thereof, in a vector. In some embodiments, PR178 can further comprise, at the 5' end, a sequence comprising SRE012, SRE007, and SRE008, or a reverse complement thereof, in a vector. In some embodiments, PR177 can further comprise, at the 5' end, a sequence comprising SRE012, SRE007, and SRE008, or a reverse complement thereof, in a vector. In some embodiments, PR176 can further comprise, at the 5' end, a sequence comprising SRE012, SRE007, and SRE008, or a reverse complement thereof, in a vector. In some embodiments, PR175 can further comprise, at the 5' end, a sequence comprising SRE012, SRE007, and SRE008, or a reverse complement thereof, in a vector. In some embodiments, PR174 can further comprise, at the 5' end, a sequence comprising SRE012, SRE007, and SRE008, or a reverse complement thereof, in a vector. In some embodiments, PR173 can further comprise, at the 5' end, a sequence comprising SRE012, SRE007, and SRE008, or a reverse complement thereof, in a vector. In some embodiments, PR172 can further comprise, at the 5' end, a sequence comprising SRE012, SRE007, and SRE008, or a reverse complement thereof, in a vector. In some embodiments, PR171 can further comprise, at the 5' end, a sequence comprising SRE012, SRE007, and SRE008, or a reverse complement thereof, in a vector. In some embodiments, PR170 can further comprise, at the 5' end, a sequence comprising SRE012, SRE007, and SRE008, or a reverse complement thereof, in a vector. In some embodiments, PR169 can further comprise, at the 5' end, a sequence comprising SRE012, SRE007, and SRE008, or a reverse complement thereof, in a vector. In some embodiments, PR168 can further comprise, at the 5' end, a sequence comprising SRE012, SRE007, and SRE008, or a reverse complement thereof, in a vector. In some embodiments, PR167 can further comprise, at the 5' end, a sequence comprising SRE012, SRE007, and SRE008, or a reverse complement thereof, in a vector. In some embodiments, PR166 can further comprise, at the 5' end, a sequence comprising SRE012, SRE007, and SRE008, or a reverse complement thereof, in a vector. In some embodiments, PR165 can further comprise, at the 5' end, a sequence comprising SRE012, SRE007, and SRE008, or a reverse complement thereof, in a vector. In some embodiments, PR159 can further comprise, at the 5' end, a sequence comprising SRE012, SRE007, and SRE008, or a reverse complement thereof, in a vector. In some embodiments, PR156 can further comprise, at the 5' end, a sequence comprising SRE012, SRE007, and SRE008, or a reverse complement thereof, in a vector. In some embodiments, PR155 can further comprise, at the 5' end, a sequence comprising SRE012, SRE007, and SRE008, or a reverse complement thereof, in a vector. In some embodiments, PR154 can further comprise, at the 5' end, a sequence comprising SRE012, SRE007, and SRE008, or a reverse complement thereof, in a vector. In some embodiments, PR153 can further comprise, at the 5' end, a sequence comprising SRE012, SRE007, and SRE008, or a reverse complement thereof, in a vector. In some embodiments, PR152 can further comprise, at the 5' end, a sequence comprising SRE012, SRE007, and SRE008, or a reverse complement thereof, in a vector. In some embodiments, PR151 can further comprise, at the 5' end, a sequence comprising SRE012, SRE007, and SRE008, or a reverse complement thereof, in a vector. In some embodiments, PR150 can further comprise, at the 5' end, a sequence comprising SRE012, SRE007, and SRE008, or a reverse complement thereof, in a vector. In some embodiments, PR131 can further comprise, at the 5' end, a sequence comprising SRE012, SRE007, and SRE008, or a reverse complement thereof, in a vector. In some embodiments, SEQ ID NO: 584 can further comprise, at the 5' end, a sequence comprising SRE012, SRE007, and SRE008, or a reverse complement thereof, in a vector. In some embodiments, SEQ ID NO: 585 can further comprise, at the 5' end, a sequence comprising SRE012, SRE007, and SRE008, or a reverse complement thereof, in a vector. In some embodiments, SEQ ID NO: 586 can further comprise, at the 5' end, a sequence comprising SRE012, SRE007, and SRE008, or a reverse complement thereof, in a vector. In some embodiments, SEQ ID NO: 587 can further comprise, at the 5' end, a sequence comprising SRE012, SRE007, and SRE008, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012, SRE007, and SRE008, or a reverse complement thereof, in a nanoplasmid. In some embodiments, PR180 can further comprise, at the 5' end, a sequence comprising SRE012, SRE007, and SRE008, or a reverse complement thereof, in a nanoplasmid. In some embodiments, PR179 can further comprise, at the 5' end, a sequence comprising SRE012, SRE007, and SRE008, or a reverse complement thereof, in a nanoplasmid. In some embodiments, PR178 can further comprise, at the 5' end, a sequence comprising SRE012, SRE007, and SRE008, or a reverse complement thereof, in a nanoplasmid. In some embodiments, PR177 can further comprise, at the 5' end, a sequence comprising SRE012, SRE007, and SRE008, or a reverse complement thereof, in a nanoplasmid. In some embodiments, PR176 can further comprise, at the 5' end, a sequence comprising SRE012, SRE007, and SRE008, or a reverse complement thereof, in a nanoplasmid. In some embodiments, PR175 can further comprise, at the 5' end, a sequence comprising SRE012, SRE007, and SRE008, or a reverse complement thereof, in a nanoplasmid. In some embodiments, PR174 can further comprise, at the 5' end, a sequence comprising SRE012, SRE007, and SRE008, or a reverse complement thereof, in a nanoplasmid. In some embodiments, PR173 can further comprise, at the 5' end, a sequence comprising SRE012, SRE007, and SRE008, or a reverse complement thereof, in a nanoplasmid. In some embodiments, PR172 can further comprise, at the 5' end, a sequence comprising SRE012, SRE007, and SRE008, or a reverse complement thereof, in a nanoplasmid. In some embodiments, PR171 can further comprise, at the 5' end, a sequence comprising SRE012, SRE007, and SRE008, or a reverse complement thereof, in a nanoplasmid. In some embodiments, PR170 can further comprise, at the 5' end, a sequence comprising SRE012, SRE007, and SRE008, or a reverse complement thereof, in a nanoplasmid. In some embodiments, PR169 can further comprise, at the 5' end, a sequence comprising SRE012, SRE007, and SRE008, or a reverse complement thereof, in a nanoplasmid. In some embodiments, PR168 can further comprise, at the 5' end, a sequence comprising SRE012, SRE007, and SRE008, or a reverse complement thereof, in a nanoplasmid. In some embodiments, PR167 can further comprise, at the 5' end, a sequence comprising SRE012, SRE007, and SRE008, or a reverse complement thereof, in a nanoplasmid. In some embodiments, PR166 can further comprise, at the 5' end, a sequence comprising SRE012, SRE007, and SRE008, or a reverse complement thereof, in a nanoplasmid. In some embodiments, PR165 can further comprise, at the 5' end, a sequence comprising SRE012, SRE007, and SRE008, or a reverse complement thereof, in a nanoplasmid. In some embodiments, PR159 can further comprise, at the 5' end, a sequence comprising SRE012, SRE007, and SRE008, or a reverse complement thereof, in a nanoplasmid. In some embodiments, PR156 can further comprise, at the 5' end, a sequence comprising SRE012, SRE007, and SRE008, or a reverse complement thereof, in a nanoplasmid. In some embodiments, PR155 can further comprise, at the 5' end, a sequence comprising SRE012, SRE007, and SRE008, or a reverse complement thereof, in a nanoplasmid. In some embodiments, PR154 can further comprise, at the 5' end, a sequence comprising SRE012, SRE007, and SRE008, or a reverse complement thereof, in a nanoplasmid. In some embodiments, PR153 can further comprise, at the 5' end, a sequence comprising SRE012, SRE007, and SRE008, or a reverse complement thereof, in a nanoplasmid. In some embodiments, PR152 can further comprise, at the 5' end, a sequence comprising SRE012, SRE007, and SRE008, or a reverse complement thereof, in a nanoplasmid. In some embodiments, PR151 can further comprise, at the 5' end, a sequence comprising SRE012, SRE007, and SRE008, or a reverse complement thereof, in a nanoplasmid. In some embodiments, PR150 can further comprise, at the 5' end, a sequence comprising SRE012, SRE007, and SRE008, or a reverse complement thereof, in a nanoplasmid. In some embodiments, PR131 can further comprise, at the 5' end, a sequence comprising SRE012, SRE007, and SRE008, or a reverse complement thereof, in a nanoplasmid. In some embodiments, SEQ ID NO: 584 can further comprise, at the 5' end, a sequence comprising SRE012, SRE007, and SRE008, or a reverse complement thereof, in a nanoplasmid. In some embodiments, SEQ ID NO: 585 can further comprise, at the 5' end, a sequence comprising SRE012, SRE007, and SRE008, or a reverse complement thereof, in a nanoplasmid. In some embodiments, SEQ ID NO: 586 can further comprise, at the 5' end, a sequence comprising SRE012, SRE007, and SRE008, or a reverse complement thereof, in a nanoplasmid. In some embodiments, SEQ ID NO: 587 can further comprise, at the 5' end, a sequence comprising SRE012, SRE007, and SRE008, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012, SRE007, and SRE008, or a reverse complement thereof, in a linked double-stranded DNA. In some embodiments, PR180 can further comprise, at the 5' end, a sequence comprising SRE012, SRE007, and SRE008, or a reverse complement thereof, in a linked double-stranded DNA. In some embodiments, PR179 can further comprise, at the 5' end, a sequence comprising SRE012, SRE007, and SRE008, or a reverse complement thereof, in a linked double-stranded DNA. In some embodiments, PR178 can further comprise, at the 5' end, a sequence comprising SRE012, SRE007, and SRE008, or a reverse complement thereof, in a linked double-stranded DNA. In some embodiments, PR177 can further comprise, at the 5' end, a sequence comprising SRE012, SRE007, and SRE008, or a reverse complement thereof, in a linked double-stranded DNA. In some embodiments, PR176 can further comprise, at the 5' end, a sequence comprising SRE012, SRE007, and SRE008, or a reverse complement thereof, in a linked double-stranded DNA. In some embodiments, PR175 can further comprise, at the 5' end, a sequence comprising SRE012, SRE007, and SRE008, or a reverse complement thereof, in a linked double-stranded DNA. In some embodiments, PR174 can further comprise, at the 5' end, a sequence comprising SRE012, SRE007, and SRE008, or a reverse complement thereof, in a linked double-stranded DNA. In some embodiments, PR173 can further comprise, at the 5' end, a sequence comprising SRE012, SRE007, and SRE008, or a reverse complement thereof, in a linked double-stranded DNA. In some embodiments, PR172 can further comprise, at the 5' end, a sequence comprising SRE012, SRE007, and SRE008, or a reverse complement thereof, in a linked double-stranded DNA. In some embodiments, PR171 can further comprise, at the 5' end, a sequence comprising SRE012, SRE007, and SRE008, or a reverse complement thereof, in a linked double-stranded DNA. In some embodiments, PR170 can further comprise, at the 5' end, a sequence comprising SRE012, SRE007, and SRE008, or a reverse complement thereof, in a linked double-stranded DNA. In some embodiments, PR169 can further comprise, at the 5' end, a sequence comprising SRE012, SRE007, and SRE008, or a reverse complement thereof, in a linked double-stranded DNA. In some embodiments, PR168 can further comprise, at the 5' end, a sequence comprising SRE012, SRE007, and SRE008, or a reverse complement thereof, in a linked double-stranded DNA. In some embodiments, PR167 can further comprise, at the 5' end, a sequence comprising SRE012, SRE007, and SRE008, or a reverse complement thereof, in a linked double-stranded DNA. In some embodiments, PR166 can further comprise, at the 5' end, a sequence comprising SRE012, SRE007, and SRE008, or a reverse complement thereof, in a linked double-stranded DNA. In some embodiments, PR165 can further comprise, at the 5' end, a sequence comprising SRE012, SRE007, and SRE008, or a reverse complement thereof, in a linked double-stranded DNA. In some embodiments, PR159 can further comprise, at the 5' end, a sequence comprising SRE012, SRE007, and SRE008, or a reverse complement thereof, in a linked double-stranded DNA. In some embodiments, PR156 can further comprise, at the 5' end, a sequence comprising SRE012, SRE007, and SRE008, or a reverse complement thereof, in a linked double-stranded DNA. In some embodiments, PR155 can further comprise, at the 5' end, a sequence comprising SRE012, SRE007, and SRE008, or a reverse complement thereof, in a linked double-stranded DNA. In some embodiments, PR154 can further comprise, at the 5' end, a sequence comprising SRE012, SRE007, and SRE008, or a reverse complement thereof, in a linked double-stranded DNA. In some embodiments, PR153 can further comprise, at the 5' end, a sequence comprising SRE012, SRE007, and SRE008, or a reverse complement thereof, in a linked double-stranded DNA. In some embodiments, PR152 can further comprise, at the 5' end, a sequence comprising SRE012, SRE007, and SRE008, or a reverse complement thereof, in a linked double-stranded DNA. In some embodiments, PR151 can further comprise, at the 5' end, a sequence comprising SRE012, SRE007, and SRE008, or a reverse complement thereof, in a linked double-stranded DNA. In some embodiments, PR150 can further comprise, at the 5' end, a sequence comprising SRE012, SRE007, and SRE008, or a reverse complement thereof, in a linked double-stranded DNA. In some embodiments, PR131 can further comprise, at the 5' end, a sequence comprising SRE012, SRE007, and SRE008, or a reverse complement thereof, in a linked double-stranded DNA. In some embodiments, SEQ ID NO: 584 can further comprise, at the 5' end, a sequence comprising SRE012, SRE007, and SRE008, or a reverse complement thereof, in a linked double-stranded DNA. In some embodiments, SEQ ID NO: 585 can further comprise, at the 5' end, a sequence comprising SRE012, SRE007, and SRE008, or a reverse complement thereof, in a linked double-stranded DNA. In some embodiments, SEQ ID NO: 586 can further comprise, at the 5' end, a sequence comprising SRE012, SRE007, and SRE008, or a reverse complement thereof, in a linked double-stranded DNA. In some embodiments, SEQ ID NO: 587 can further comprise, at the 5' end, a sequence comprising SRE012, SRE007, and SRE008, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007 and SRE008, or a reverse complement thereof, in a vector. In some embodiments, PR180 can further comprise, at the 5' end, a sequence comprising SRE007 and SRE008, or a reverse complement thereof, in a vector. In some embodiments, PR179 can further comprise, at the 5' end, a sequence comprising SRE007 and SRE008, or a reverse complement thereof, in a vector. In some embodiments, PR178 can further comprise, at the 5' end, a sequence comprising SRE007 and SRE008, or a reverse complement thereof, in a vector. In some embodiments, PR177 can further comprise, at the 5' end, a sequence comprising SRE007 and SRE008, or a reverse complement thereof, in a vector. In some embodiments, PR176 can further comprise, at the 5' end, a sequence comprising SRE007 and SRE008, or a reverse complement thereof, in a vector. In some embodiments, PR175 can further comprise, at the 5' end, a sequence comprising SRE007 and SRE008, or a reverse complement thereof, in a vector. In some embodiments, PR174 can further comprise, at the 5' end, a sequence comprising SRE007 and SRE008, or a reverse complement thereof, in a vector. In some embodiments, PR173 can further comprise, at the 5' end, a sequence comprising SRE007 and SRE008, or a reverse complement thereof, in a vector. In some embodiments, PR172 can further comprise, at the 5' end, a sequence comprising SRE007 and SRE008, or a reverse complement thereof, in a vector. In some embodiments, PR171 can further comprise, at the 5' end, a sequence comprising SRE007 and SRE008, or a reverse complement thereof, in a vector. In some embodiments, PR170 can further comprise, at the 5' end, a sequence comprising SRE007 and SRE008, or a reverse complement thereof, in a vector. In some embodiments, PR169 can further comprise, at the 5' end, a sequence comprising SRE007 and SRE008, or a reverse complement thereof, in a vector. In some embodiments, PR168 can further comprise, at the 5' end, a sequence comprising SRE007 and SRE008, or a reverse complement thereof, in a vector. In some embodiments, PR167 can further comprise, at the 5' end, a sequence comprising SRE007 and SRE008, or a reverse complement thereof, in a vector. In some embodiments, PR166 can further comprise, at the 5' end, a sequence comprising SRE007 and SRE008, or a reverse complement thereof, in a vector. In some embodiments, PR165 can further comprise, at the 5' end, a sequence comprising SRE007 and SRE008, or a reverse complement thereof, in a vector. In some embodiments, PR159 can further comprise, at the 5' end, a sequence comprising SRE007 and SRE008, or a reverse complement thereof, in a vector. In some embodiments, PR156 can further comprise, at the 5' end, a sequence comprising SRE007 and SRE008, or a reverse complement thereof, in a vector. In some embodiments, PR155 can further comprise, at the 5' end, a sequence comprising SRE007 and SRE008, or a reverse complement thereof, in a vector. In some embodiments, PR154 can further comprise, at the 5' end, a sequence comprising SRE007 and SRE008, or a reverse complement thereof, in a vector. In some embodiments, PR153 can further comprise, at the 5' end, a sequence comprising SRE007 and SRE008, or a reverse complement thereof, in a vector. In some embodiments, PR152 can further comprise, at the 5' end, a sequence comprising SRE007 and SRE008, or a reverse complement thereof, in a vector. In some embodiments, PR151 can further comprise, at the 5' end, a sequence comprising SRE007 and SRE008, or a reverse complement thereof, in a vector. In some embodiments, PR150 can further comprise, at the 5' end, a sequence comprising SRE007 and SRE008, or a reverse complement thereof, in a vector. In some embodiments, PR131 can further comprise, at the 5' end, a sequence comprising SRE007 and SRE008, or a reverse complement thereof, in a vector. In some embodiments, SEQ ID NO: 584 can further comprise, at the 5' end, a sequence comprising SRE007 and SRE008, or a reverse complement thereof, in a vector. In some embodiments, SEQ ID NO: 585 can further comprise, at the 5' end, a sequence comprising SRE007 and SRE008, or a reverse complement thereof, in a vector. In some embodiments, SEQ ID NO: 586 can further comprise, at the 5' end, a sequence comprising SRE007 and SRE008, or a reverse complement thereof, in a vector. In some embodiments, SEQ ID NO: 587 can further comprise, at the 5' end, a sequence comprising SRE007 and SRE008, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007 and SRE008, or a reverse complement thereof, in a nanoplasmid. In some embodiments, PR180 can further comprise, at the 5' end, a sequence comprising SRE007 and SRE008, or a reverse complement thereof, in a nanoplasmid. In some embodiments, PR179 can further comprise, at the 5' end, a sequence comprising SRE007 and SRE008, or a reverse complement thereof, in a nanoplasmid. In some embodiments, PR178 can further comprise, at the 5' end, a sequence comprising SRE007 and SRE008, or a reverse complement thereof, in a nanoplasmid. In some embodiments, PR177 can further comprise, at the 5' end, a sequence comprising SRE007 and SRE008, or a reverse complement thereof, in a nanoplasmid. In some embodiments, PR176 can further comprise, at the 5' end, a sequence comprising SRE007 and SRE008, or a reverse complement thereof, in a nanoplasmid. In some embodiments, PR175 can further comprise, at the 5' end, a sequence comprising SRE007 and SRE008, or a reverse complement thereof, in a nanoplasmid. In some embodiments, PR174 can further comprise, at the 5' end, a sequence comprising SRE007 and SRE008, or a reverse complement thereof, in a nanoplasmid. In some embodiments, PR173 can further comprise, at the 5' end, a sequence comprising SRE007 and SRE008, or a reverse complement thereof, in a nanoplasmid. In some embodiments, PR172 can further comprise, at the 5' end, a sequence comprising SRE007 and SRE008, or a reverse complement thereof, in a nanoplasmid. In some embodiments, PR171 can further comprise, at the 5' end, a sequence comprising SRE007 and SRE008, or a reverse complement thereof, in a nanoplasmid. In some embodiments, PR170 can further comprise, at the 5' end, a sequence comprising SRE007 and SRE008, or a reverse complement thereof, in a nanoplasmid. In some embodiments, PR169 can further comprise, at the 5' end, a sequence comprising SRE007 and SRE008, or a reverse complement thereof, in a nanoplasmid. In some embodiments, PR168 can further comprise, at the 5' end, a sequence comprising SRE007 and SRE008, or a reverse complement thereof, in a nanoplasmid. In some embodiments, PR167 can further comprise, at the 5' end, a sequence comprising SRE007 and SRE008, or a reverse complement thereof, in a nanoplasmid. In some embodiments, PR166 can further comprise, at the 5' end, a sequence comprising SRE007 and SRE008, or a reverse complement thereof, in a nanoplasmid. In some embodiments, PR165 can further comprise, at the 5' end, a sequence comprising SRE007 and SRE008, or a reverse complement thereof, in a nanoplasmid. In some embodiments, PR159 can further comprise, at the 5' end, a sequence comprising SRE007 and SRE008, or a reverse complement thereof, in a nanoplasmid. In some embodiments, PR156 can further comprise, at the 5' end, a sequence comprising SRE007 and SRE008, or a reverse complement thereof, in a nanoplasmid. In some embodiments, PR155 can further comprise, at the 5' end, a sequence comprising SRE007 and SRE008, or a reverse complement thereof, in a nanoplasmid. In some embodiments, PR154 can further comprise, at the 5' end, a sequence comprising SRE007 and SRE008, or a reverse complement thereof, in a nanoplasmid. In some embodiments, PR153 can further comprise, at the 5' end, a sequence comprising SRE007 and SRE008, or a reverse complement thereof, in a nanoplasmid. In some embodiments, PR152 can further comprise, at the 5' end, a sequence comprising SRE007 and SRE008, or a reverse complement thereof, in a nanoplasmid. In some embodiments, PR151 can further comprise, at the 5' end, a sequence comprising SRE007 and SRE008, or a reverse complement thereof, in a nanoplasmid. In some embodiments, PR150 can further comprise, at the 5' end, a sequence comprising SRE007 and SRE008, or a reverse complement thereof, in a nanoplasmid. In some embodiments, PR131 can further comprise, at the 5' end, a sequence comprising SRE007 and SRE008, or a reverse complement thereof, in a nanoplasmid. In some embodiments, SEQ ID NO: 584 can further comprise, at the 5' end, a sequence comprising SRE007 and SRE008, or a reverse complement thereof, in a nanoplasmid. In some embodiments, SEQ ID NO: 585 can further comprise, at the 5' end, a sequence comprising SRE007 and SRE008, or a reverse complement thereof, in a nanoplasmid. In some embodiments, SEQ ID NO: 586 can further comprise, at the 5' end, a sequence comprising SRE007 and SRE008, or a reverse complement thereof, in a nanoplasmid. In some embodiments, SEQ ID NO: 587 can further comprise, at the 5' end, a sequence comprising SRE007 and SRE008, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007 and SRE008, or a reverse complement thereof, in a linked double-stranded DNA. In some embodiments, PR180 can further comprise, at the 5' end, a sequence comprising SRE007 and SRE008, or a reverse complement thereof, in a linked double-stranded DNA. In some embodiments, PR179 can further comprise, at the 5' end, a sequence comprising SRE007 and SRE008, or a reverse complement thereof, in a linked double-stranded DNA. In some embodiments, PR178 can further comprise, at the 5' end, a sequence comprising SRE007 and SRE008, or a reverse complement thereof, in a linked double-stranded DNA. In some embodiments, PR177 can further comprise, at the 5' end, a sequence comprising SRE007 and SRE008, or a reverse complement thereof, in a linked double-stranded DNA. In some embodiments, PR176 can further comprise, at the 5' end, a sequence comprising SRE007 and SRE008, or a reverse complement thereof, in a linked double-stranded DNA. In some embodiments, PR175 can further comprise, at the 5' end, a sequence comprising SRE007 and SRE008, or a reverse complement thereof, in a linked double-stranded DNA. In some embodiments, PR174 can further comprise, at the 5' end, a sequence comprising SRE007 and SRE008, or a reverse complement thereof, in a linked double-stranded DNA. In some embodiments, PR173 can further comprise, at the 5' end, a sequence comprising SRE007 and SRE008, or a reverse complement thereof, in a linked double-stranded DNA. In some embodiments, PR172 can further comprise, at the 5' end, a sequence comprising SRE007 and SRE008, or a reverse complement thereof, in a linked double-stranded DNA. In some embodiments, PR171 can further comprise, at the 5' end, a sequence comprising SRE007 and SRE008, or a reverse complement thereof, in a linked double-stranded DNA. In some embodiments, PR170 can further comprise, at the 5' end, a sequence comprising SRE007 and SRE008, or a reverse complement thereof, in a linked double-stranded DNA. In some embodiments, PR169 can further comprise, at the 5' end, a sequence comprising SRE007 and SRE008, or a reverse complement thereof, in a linked double-stranded DNA. In some embodiments, PR168 can further comprise, at the 5' end, a sequence comprising SRE007 and SRE008, or a reverse complement thereof, in a linked double-stranded DNA. In some embodiments, PR167 can further comprise, at the 5' end, a sequence comprising SRE007 and SRE008, or a reverse complement thereof, in a linked double-stranded DNA. In some embodiments, PR166 can further comprise, at the 5' end, a sequence comprising SRE007 and SRE008, or a reverse complement thereof, in a linked double-stranded DNA. In some embodiments, PR165 can further comprise, at the 5' end, a sequence comprising SRE007 and SRE008, or a reverse complement thereof, in a linked double-stranded DNA. In some embodiments, PR159 can further comprise, at the 5' end, a sequence comprising SRE007 and SRE008, or a reverse complement thereof, in a linked double-stranded DNA. In some embodiments, PR156 can further comprise, at the 5' end, a sequence comprising SRE007 and SRE008, or a reverse complement thereof, in a linked double-stranded DNA. In some embodiments, PR155 can further comprise, at the 5' end, a sequence comprising SRE007 and SRE008, or a reverse complement thereof, in a linked double-stranded DNA. In some embodiments, PR154 can further comprise, at the 5' end, a sequence comprising SRE007 and SRE008, or a reverse complement thereof, in a linked double-stranded DNA. In some embodiments, PR153 can further comprise, at the 5' end, a sequence comprising SRE007 and SRE008, or a reverse complement thereof, in a linked double-stranded DNA. In some embodiments, PR152 can further comprise, at the 5' end, a sequence comprising SRE007 and SRE008, or a reverse complement thereof, in a linked double-stranded DNA. In some embodiments, PR151 can further comprise, at the 5' end, a sequence comprising SRE007 and SRE008, or a reverse complement thereof, in a linked double-stranded DNA. In some embodiments, PR150 can further comprise, at the 5' end, a sequence comprising SRE007 and SRE008, or a reverse complement thereof, in a linked double-stranded DNA. In some embodiments, PR131 can further comprise, at the 5' end, a sequence comprising SRE007 and SRE008, or a reverse complement thereof, in a linked double-stranded DNA. In some embodiments, SEQ ID NO: 584 can further comprise, at the 5' end, a sequence comprising SRE007 and SRE008, or a reverse complement thereof, in a linked double-stranded DNA. In some embodiments, SEQ ID NO: 585 can further comprise, at the 5' end, a sequence comprising SRE007 and SRE008, or a reverse complement thereof, in a linked double-stranded DNA. In some embodiments, SEQ ID NO: 586 can further comprise, at the 5' end, a sequence comprising SRE007 and SRE008, or a reverse complement thereof, in a linked double-stranded DNA. In some embodiments, SEQ ID NO: 587 can further comprise, at the 5' end, a sequence comprising SRE007 and SRE008, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007 and SRE010, or a reverse complement thereof, in a vector. In some embodiments, PR180 can further comprise, at the 5' end, a sequence comprising SRE007 and SRE010, or a reverse complement thereof, in a vector. In some embodiments, PR179 can further comprise, at the 5' end, a sequence comprising SRE007 and SRE010, or a reverse complement thereof, in a vector. In some embodiments, PR178 can further comprise, at the 5' end, a sequence comprising SRE007 and SRE010, or a reverse complement thereof, in a vector. In some embodiments, PR177 can further comprise, at the 5' end, a sequence comprising SRE007 and SRE010, or a reverse complement thereof, in a vector. In some embodiments, PR176 can further comprise, at the 5' end, a sequence comprising SRE007 and SRE010, or a reverse complement thereof, in a vector. In some embodiments, PR175 can further comprise, at the 5' end, a sequence comprising SRE007 and SRE010, or a reverse complement thereof, in a vector. In some embodiments, PR174 can further comprise, at the 5' end, a sequence comprising SRE007 and SRE010, or a reverse complement thereof, in a vector. In some embodiments, PR173 can further comprise, at the 5' end, a sequence comprising SRE007 and SRE010, or a reverse complement thereof, in a vector. In some embodiments, PR172 can further comprise, at the 5' end, a sequence comprising SRE007 and SRE010, or a reverse complement thereof, in a vector. In some embodiments, PR171 can further comprise, at the 5' end, a sequence comprising SRE007 and SRE010, or a reverse complement thereof, in a vector. In some embodiments, PR170 can further comprise, at the 5' end, a sequence comprising SRE007 and SRE010, or a reverse complement thereof, in a vector. In some embodiments, PR169 can further comprise, at the 5' end, a sequence comprising SRE007 and SRE010, or a reverse complement thereof, in a vector. In some embodiments, PR168 can further comprise, at the 5' end, a sequence comprising SRE007 and SRE010, or a reverse complement thereof, in a vector. In some embodiments, PR167 can further comprise, at the 5' end, a sequence comprising SRE007 and SRE010, or a reverse complement thereof, in a vector. In some embodiments, PR166 can further comprise, at the 5' end, a sequence comprising SRE007 and SRE010, or a reverse complement thereof, in a vector. In some embodiments, PR165 can further comprise, at the 5' end, a sequence comprising SRE007 and SRE010, or a reverse complement thereof, in a vector. In some embodiments, PR159 can further comprise, at the 5' end, a sequence comprising SRE007 and SRE010, or a reverse complement thereof, in a vector. In some embodiments, PR156 can further comprise, at the 5' end, a sequence comprising SRE007 and SRE010, or a reverse complement thereof, in a vector. In some embodiments, PR155 can further comprise, at the 5' end, a sequence comprising SRE007 and SRE010, or a reverse complement thereof, in a vector. In some embodiments, PR154 can further comprise, at the 5' end, a sequence comprising SRE007 and SRE010, or a reverse complement thereof, in a vector. In some embodiments, PR153 can further comprise, at the 5' end, a sequence comprising SRE007 and SRE010, or a reverse complement thereof, in a vector. In some embodiments, PR152 can further comprise, at the 5' end, a sequence comprising SRE007 and SRE010, or a reverse complement thereof, in a vector. In some embodiments, PR151 can further comprise, at the 5' end, a sequence comprising SRE007 and SRE010, or a reverse complement thereof, in a vector. In some embodiments, PR150 can further comprise, at the 5' end, a sequence comprising SRE007 and SRE010, or a reverse complement thereof, in a vector. In some embodiments, PR131 can further comprise, at the 5' end, a sequence comprising SRE007 and SRE010, or a reverse complement thereof, in a vector. In some embodiments, SEQ ID NO: 584 can further comprise, at the 5' end, a sequence comprising SRE007 and SRE010, or a reverse complement thereof, in a vector. In some embodiments, SEQ ID NO: 585 can further comprise, at the 5' end, a sequence comprising SRE007 and SRE010, or a reverse complement thereof, in a vector. In some embodiments, SEQ ID NO: 586 can further comprise, at the 5' end, a sequence comprising SRE007 and SRE010, or a reverse complement thereof, in a vector. In some embodiments, SEQ ID NO: 587 can further comprise, at the 5' end, a sequence comprising SRE007 and SRE010, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007 and SRE010, or a reverse complement thereof, in a nanoplasmid. In some embodiments, PR180 can further comprise, at the 5' end, a sequence comprising SRE007 and SRE010, or a reverse complement thereof, in a nanoplasmid. In some embodiments, PR179 can further comprise, at the 5' end, a sequence comprising SRE007 and SRE010, or a reverse complement thereof, in a nanoplasmid. In some embodiments, PR178 can further comprise, at the 5' end, a sequence comprising SRE007 and SRE010, or a reverse complement thereof, in a nanoplasmid. In some embodiments, PR177 can further comprise, at the 5' end, a sequence comprising SRE007 and SRE010, or a reverse complement thereof, in a nanoplasmid. In some embodiments, PR176 can further comprise, at the 5' end, a sequence comprising SRE007 and SRE010, or a reverse complement thereof, in a nanoplasmid. In some embodiments, PR175 can further comprise, at the 5' end, a sequence comprising SRE007 and SRE010, or a reverse complement thereof, in a nanoplasmid. In some embodiments, PR174 can further comprise, at the 5' end, a sequence comprising SRE007 and SRE010, or a reverse complement thereof, in a nanoplasmid. In some embodiments, PR173 can further comprise, at the 5' end, a sequence comprising SRE007 and SRE010, or a reverse complement thereof, in a nanoplasmid. In some embodiments, PR172 can further comprise, at the 5' end, a sequence comprising SRE007 and SRE010, or a reverse complement thereof, in a nanoplasmid. In some embodiments, PR171 can further comprise, at the 5' end, a sequence comprising SRE007 and SRE010, or a reverse complement thereof, in a nanoplasmid. In some embodiments, PR170 can further comprise, at the 5' end, a sequence comprising SRE007 and SRE010, or a reverse complement thereof, in a nanoplasmid. In some embodiments, PR169 can further comprise, at the 5' end, a sequence comprising SRE007 and SRE010, or a reverse complement thereof, in a nanoplasmid. In some embodiments, PR168 can further comprise, at the 5' end, a sequence comprising SRE007 and SRE010, or a reverse complement thereof, in a nanoplasmid. In some embodiments, PR167 can further comprise, at the 5' end, a sequence comprising SRE007 and SRE010, or a reverse complement thereof, in a nanoplasmid. In some embodiments, PR166 can further comprise, at the 5' end, a sequence comprising SRE007 and SRE010, or a reverse complement thereof, in a nanoplasmid. In some embodiments, PR165 can further comprise, at the 5' end, a sequence comprising SRE007 and SRE010, or a reverse complement thereof, in a nanoplasmid. In some embodiments, PR159 can further comprise, at the 5' end, a sequence comprising SRE007 and SRE010, or a reverse complement thereof, in a nanoplasmid. In some embodiments, PR156 can further comprise, at the 5' end, a sequence comprising SRE007 and SRE010, or a reverse complement thereof, in a nanoplasmid. In some embodiments, PR155 can further comprise, at the 5' end, a sequence comprising SRE007 and SRE010, or a reverse complement thereof, in a nanoplasmid. In some embodiments, PR154 can further comprise, at the 5' end, a sequence comprising SRE007 and SRE010, or a reverse complement thereof, in a nanoplasmid. In some embodiments, PR153 can further comprise, at the 5' end, a sequence comprising SRE007 and SRE010, or a reverse complement thereof, in a nanoplasmid. In some embodiments, PR152 can further comprise, at the 5' end, a sequence comprising SRE007 and SRE010, or a reverse complement thereof, in a nanoplasmid. In some embodiments, PR151 can further comprise, at the 5' end, a sequence comprising SRE007 and SRE010, or a reverse complement thereof, in a nanoplasmid. In some embodiments, PR150 can further comprise, at the 5' end, a sequence comprising SRE007 and SRE010, or a reverse complement thereof, in a nanoplasmid. In some embodiments, PR131 can further comprise, at the 5' end, a sequence comprising SRE007 and SRE010, or a reverse complement thereof, in a nanoplasmid. In some embodiments, SEQ ID NO: 584 can further comprise, at the 5' end, a sequence comprising SRE007 and SRE010, or a reverse complement thereof, in a nanoplasmid. In some embodiments, SEQ ID NO: 585 can further comprise, at the 5' end, a sequence comprising SRE007 and SRE010, or a reverse complement thereof, in a nanoplasmid. In some embodiments, SEQ ID NO: 586 can further comprise, at the 5' end, a sequence comprising SRE007 and SRE010, or a reverse complement thereof, in a nanoplasmid. In some embodiments, SEQ ID NO: 587 can further comprise, at the 5' end, a sequence comprising SRE007 and SRE010, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007 and SRE010, or a reverse complement thereof, in a linked double-stranded DNA. In some embodiments, PR180 can further comprise, at the 5' end, a sequence comprising SRE007 and SRE010, or a reverse complement thereof, in a linked double-stranded DNA. In some embodiments, PR179 can further comprise, at the 5' end, a sequence comprising SRE007 and SRE010, or a reverse complement thereof, in a linked double-stranded DNA. In some embodiments, PR178 can further comprise, at the 5' end, a sequence comprising SRE007 and SRE010, or a reverse complement thereof, in a linked double-stranded DNA. In some embodiments, PR177 can further comprise, at the 5' end, a sequence comprising SRE007 and SRE010, or a reverse complement thereof, in a linked double-stranded DNA. In some embodiments, PR176 can further comprise, at the 5' end, a sequence comprising SRE007 and SRE010, or a reverse complement thereof, in a linked double-stranded DNA. In some embodiments, PR175 can further comprise, at the 5' end, a sequence comprising SRE007 and SRE010, or a reverse complement thereof, in a linked double-stranded DNA. In some embodiments, PR174 can further comprise, at the 5' end, a sequence comprising SRE007 and SRE010, or a reverse complement thereof, in a linked double-stranded DNA. In some embodiments, PR173 can further comprise, at the 5' end, a sequence comprising SRE007 and SRE010, or a reverse complement thereof, in a linked double-stranded DNA. In some embodiments, PR172 can further comprise, at the 5' end, a sequence comprising SRE007 and SRE010, or a reverse complement thereof, in a linked double-stranded DNA. In some embodiments, PR171 can further comprise, at the 5' end, a sequence comprising SRE007 and SRE010, or a reverse complement thereof, in a linked double-stranded DNA. In some embodiments, PR170 can further comprise, at the 5' end, a sequence comprising SRE007 and SRE010, or a reverse complement thereof, in a linked double-stranded DNA. In some embodiments, PR169 can further comprise, at the 5' end, a sequence comprising SRE007 and SRE010, or a reverse complement thereof, in a linked double-stranded DNA. In some embodiments, PR168 can further comprise, at the 5' end, a sequence comprising SRE007 and SRE010, or a reverse complement thereof, in a linked double-stranded DNA. In some embodiments, PR167 can further comprise, at the 5' end, a sequence comprising SRE007 and SRE010, or a reverse complement thereof, in a linked double-stranded DNA. In some embodiments, PR166 can further comprise, at the 5' end, a sequence comprising SRE007 and SRE010, or a reverse complement thereof, in a linked double-stranded DNA. In some embodiments, PR165 can further comprise, at the 5' end, a sequence comprising SRE007 and SRE010, or a reverse complement thereof, in a linked double-stranded DNA. In some embodiments, PR159 can further comprise, at the 5' end, a sequence comprising SRE007 and SRE010, or a reverse complement thereof, in a linked double-stranded DNA. In some embodiments, PR156 can further comprise, at the 5' end, a sequence comprising SRE007 and SRE010, or a reverse complement thereof, in a linked double-stranded DNA. In some embodiments, PR155 can further comprise, at the 5' end, a sequence comprising SRE007 and SRE010, or a reverse complement thereof, in a linked double-stranded DNA. In some embodiments, PR154 can further comprise, at the 5' end, a sequence comprising SRE007 and SRE010, or a reverse complement thereof, in a linked double-stranded DNA. In some embodiments, PR153 can further comprise, at the 5' end, a sequence comprising SRE007 and SRE010, or a reverse complement thereof, in a linked double-stranded DNA. In some embodiments, PR152 can further comprise, at the 5' end, a sequence comprising SRE007 and SRE010, or a reverse complement thereof, in a linked double-stranded DNA. In some embodiments, PR151 can further comprise, at the 5' end, a sequence comprising SRE007 and SRE010, or a reverse complement thereof, in a linked double-stranded DNA. In some embodiments, PR150 can further comprise, at the 5' end, a sequence comprising SRE007 and SRE010, or a reverse complement thereof, in a linked double-stranded DNA. In some embodiments, PR131 can further comprise, at the 5' end, a sequence comprising SRE007 and SRE010, or a reverse complement thereof, in a linked double-stranded DNA. In some embodiments, SEQ ID NO: 584 can further comprise, at the 5' end, a sequence comprising SRE007 and SRE010, or a reverse complement thereof, in a linked double-stranded DNA. In some embodiments, SEQ ID NO: 585 can further comprise, at the 5' end, a sequence comprising SRE007 and SRE010, or a reverse complement thereof, in a linked double-stranded DNA. In some embodiments, SEQ ID NO: 586 can further comprise, at the 5' end, a sequence comprising SRE007 and SRE010, or a reverse complement thereof, in a linked double-stranded DNA. In some embodiments, SEQ ID NO: 587 can further comprise, at the 5' end, a sequence comprising SRE007 and SRE010, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007 and SRE012, or a reverse complement thereof, in a vector. In some embodiments, PR180 can further comprise, at the 5' end, a sequence comprising SRE007 and SRE012, or a reverse complement thereof, in a vector. In some embodiments, PR179 can further comprise, at the 5' end, a sequence comprising SRE007 and SRE012, or a reverse complement thereof, in a vector. In some embodiments, PR178 can further comprise, at the 5' end, a sequence comprising SRE007 and SRE012, or a reverse complement thereof, in a vector. In some embodiments, PR177 can further comprise, at the 5' end, a sequence comprising SRE007 and SRE012, or a reverse complement thereof, in a vector. In some embodiments, PR176 can further comprise, at the 5' end, a sequence comprising SRE007 and SRE012, or a reverse complement thereof, in a vector. In some embodiments, PR175 can further comprise, at the 5' end, a sequence comprising SRE007 and SRE012, or a reverse complement thereof, in a vector. In some embodiments, PR174 can further comprise, at the 5' end, a sequence comprising SRE007 and SRE012, or a reverse complement thereof, in a vector. In some embodiments, PR173 can further comprise, at the 5' end, a sequence comprising SRE007 and SRE012, or a reverse complement thereof, in a vector. In some embodiments, PR172 can further comprise, at the 5' end, a sequence comprising SRE007 and SRE012, or a reverse complement thereof, in a vector. In some embodiments, PR171 can further comprise, at the 5' end, a sequence comprising SRE007 and SRE012, or a reverse complement thereof, in a vector. In some embodiments, PR170 can further comprise, at the 5' end, a sequence comprising SRE007 and SRE012, or a reverse complement thereof, in a vector. In some embodiments, PR169 can further comprise, at the 5' end, a sequence comprising SRE007 and SRE012, or a reverse complement thereof, in a vector. In some embodiments, PR168 can further comprise, at the 5' end, a sequence comprising SRE007 and SRE012, or a reverse complement thereof, in a vector. In some embodiments, PR167 can further comprise, at the 5' end, a sequence comprising SRE007 and SRE012, or a reverse complement thereof, in a vector. In some embodiments, PR166 can further comprise, at the 5' end, a sequence comprising SRE007 and SRE012, or a reverse complement thereof, in a vector. In some embodiments, PR165 can further comprise, at the 5' end, a sequence comprising SRE007 and SRE012, or a reverse complement thereof, in a vector. In some embodiments, PR159 can further comprise, at the 5' end, a sequence comprising SRE007 and SRE012, or a reverse complement thereof, in a vector. In some embodiments, PR156 can further comprise, at the 5' end, a sequence comprising SRE007 and SRE012, or a reverse complement thereof, in a vector. In some embodiments, PR155 can further comprise, at the 5' end, a sequence comprising SRE007 and SRE012, or a reverse complement thereof, in a vector. In some embodiments, PR154 can further comprise, at the 5' end, a sequence comprising SRE007 and SRE012, or a reverse complement thereof, in a vector. In some embodiments, PR153 can further comprise, at the 5' end, a sequence comprising SRE007 and SRE012, or a reverse complement thereof, in a vector. In some embodiments, PR152 can further comprise, at the 5' end, a sequence comprising SRE007 and SRE012, or a reverse complement thereof, in a vector. In some embodiments, PR151 can further comprise, at the 5' end, a sequence comprising SRE007 and SRE012, or a reverse complement thereof, in a vector. In some embodiments, PR150 can further comprise, at the 5' end, a sequence comprising SRE007 and SRE012, or a reverse complement thereof, in a vector. In some embodiments, PR131 can further comprise, at the 5' end, a sequence comprising SRE007 and SRE012, or a reverse complement thereof, in a vector. In some embodiments, SEQ ID NO: 584 can further comprise, at the 5' end, a sequence comprising SRE007 and SRE012, or a reverse complement thereof, in a vector. In some embodiments, SEQ ID NO: 585 can further comprise, at the 5' end, a sequence comprising SRE007 and SRE012, or a reverse complement thereof, in a vector. In some embodiments, SEQ ID NO: 586 can further comprise, at the 5' end, a sequence comprising SRE007 and SRE012, or a reverse complement thereof, in a vector. In some embodiments, SEQ ID NO: 587 can further comprise, at the 5' end, a sequence comprising SRE007 and SRE012, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007 and SRE012, or a reverse complement thereof, in a nanoplasmid. In some embodiments, PR180 can further comprise, at the 5' end, a sequence comprising SRE007 and SRE012, or a reverse complement thereof, in a nanoplasmid. In some embodiments, PR179 can further comprise, at the 5' end, a sequence comprising SRE007 and SRE012, or a reverse complement thereof, in a nanoplasmid. In some embodiments, PR178 can further comprise, at the 5' end, a sequence comprising SRE007 and SRE012, or a reverse complement thereof, in a nanoplasmid. In some embodiments, PR177 can further comprise, at the 5' end, a sequence comprising SRE007 and SRE012, or a reverse complement thereof, in a nanoplasmid. In some embodiments, PR176 can further comprise, at the 5' end, a sequence comprising SRE007 and SRE012, or a reverse complement thereof, in a nanoplasmid. In some embodiments, PR175 can further comprise, at the 5' end, a sequence comprising SRE007 and SRE012, or a reverse complement thereof, in a nanoplasmid. In some embodiments, PR174 can further comprise, at the 5' end, a sequence comprising SRE007 and SRE012, or a reverse complement thereof, in a nanoplasmid. In some embodiments, PR173 can further comprise, at the 5' end, a sequence comprising SRE007 and SRE012, or a reverse complement thereof, in a nanoplasmid. In some embodiments, PR172 can further comprise, at the 5' end, a sequence comprising SRE007 and SRE012, or a reverse complement thereof, in a nanoplasmid.

In some embodiments, PR171 can further comprise, at the 5' end, a sequence comprising SRE007 and SRE012, or a reverse complement thereof, in a nanoplasmid. In some embodiments, PR170 can further comprise, at the 5' end, a sequence comprising SRE007 and SRE012, or a reverse complement thereof, in a nanoplasmid. In some embodiments, PR169 can further comprise, at the 5' end, a sequence comprising SRE007 and SRE012, or a reverse complement thereof, in a nanoplasmid. In some embodiments, PR168 can further comprise, at the 5' end, a sequence comprising SRE007 and SRE012, or a reverse complement thereof, in a nanoplasmid. In some embodiments, PR167 can further comprise, at the 5' end, a sequence comprising SRE007 and SRE012, or a reverse complement thereof, in a nanoplasmid. In some embodiments, PR166 can further comprise, at the 5' end, a sequence comprising SRE007 and SRE012, or a reverse complement thereof, in a nanoplasmid. In some embodiments, PR165 can further comprise, at the 5' end, a sequence comprising SRE007 and SRE012, or a reverse complement thereof, in a nanoplasmid. In some embodiments, PR159 can further comprise, at the 5' end, a sequence comprising SRE007 and SRE012, or a reverse complement thereof, in a nanoplasmid. In some embodiments, PR156 can further comprise, at the 5' end, a sequence comprising SRE007 and SRE012, or a reverse complement thereof, in a nanoplasmid. In some embodiments, PR155 can further comprise, at the 5' end, a sequence comprising SRE007 and SRE012, or a reverse complement thereof, in a nanoplasmid. In some embodiments, PR154 can further comprise, at the 5' end, a sequence comprising SRE007 and SRE012, or a reverse complement thereof, in a nanoplasmid. In some embodiments, PR153 can further comprise, at the 5' end, a sequence comprising SRE007 and SRE012, or a reverse complement thereof, in a nanoplasmid. In some embodiments, PR152 can further comprise, at the 5' end, a sequence comprising SRE007 and SRE012, or a reverse complement thereof, in a nanoplasmid. In some embodiments, PR151 can further comprise, at the 5' end, a sequence comprising SRE007 and SRE012, or a reverse complement thereof, in a nanoplasmid. In some embodiments, PR150 can further comprise, at the 5' end, a sequence comprising SRE007 and SRE012, or a reverse complement thereof, in a nanoplasmid. In some embodiments, PR131 can further comprise, at the 5' end, a sequence comprising SRE007 and SRE012, or a reverse complement thereof, in a nanoplasmid. In some embodiments, SEQ ID NO: 584 can further comprise, at the 5' end, a sequence comprising SRE007 and SRE012, or a reverse complement thereof, in a nanoplasmid. In some embodiments, SEQ ID NO: 585 can further comprise, at the 5' end, a sequence comprising SRE007 and SRE012, or a reverse complement thereof, in a nanoplasmid. In some embodiments, SEQ ID NO: 586 can further comprise, at the 5' end, a sequence comprising SRE007 and SRE012, or a reverse complement thereof, in a nanoplasmid. In some embodiments, SEQ ID NO: 587 can further comprise, at the 5' end, a sequence comprising SRE007 and SRE012, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007 and SRE012, or a reverse complement thereof, in a linked double-stranded DNA. In some embodiments, PR180 can further comprise, at the 5' end, a sequence comprising SRE007 and SRE012, or a reverse complement thereof, in a linked double-stranded DNA. In some embodiments, PR179 can further comprise, at the 5' end, a sequence comprising SRE007 and SRE012, or a reverse complement thereof, in a linked double-stranded DNA. In some embodiments, PR178 can further comprise, at the 5' end, a sequence comprising SRE007 and SRE012, or a reverse complement thereof, in a linked double-stranded DNA. In some embodiments, PR177 can further comprise, at the 5' end, a sequence comprising SRE007 and SRE012, or a reverse complement thereof, in a linked double-stranded DNA. In some embodiments, PR176 can further comprise, at the 5' end, a sequence comprising SRE007 and SRE012, or a reverse complement thereof, in a linked double-stranded DNA. In some embodiments, PR175 can further comprise, at the 5' end, a sequence comprising SRE007 and SRE012, or a reverse complement thereof, in a linked double-stranded DNA. In some embodiments, PR174 can further comprise, at the 5' end, a sequence comprising SRE007 and SRE012, or a reverse complement thereof, in a linked double-stranded DNA. In some embodiments, PR173 can further comprise, at the 5' end, a sequence comprising SRE007 and SRE012, or a reverse complement thereof, in a linked double-stranded DNA. In some embodiments, PR172 can further comprise, at the 5' end, a sequence comprising SRE007 and SRE012, or a reverse complement thereof, in a linked double-stranded DNA. In some embodiments, PR171 can further comprise, at the 5' end, a sequence comprising SRE007 and SRE012, or a reverse complement thereof, in a linked double-stranded DNA. In some embodiments, PR170 can further comprise, at the 5' end, a sequence comprising SRE007 and SRE012, or a reverse complement thereof, in a linked double-stranded DNA. In some embodiments, PR169 can further comprise, at the 5' end, a sequence comprising SRE007 and SRE012, or a reverse complement thereof, in a linked double-stranded DNA. In some embodiments, PR168 can further comprise, at the 5' end, a sequence comprising SRE007 and SRE012, or a reverse complement thereof, in a linked double-stranded DNA. In some embodiments, PR167 can further comprise, at the 5' end, a sequence comprising SRE007 and SRE012, or a reverse complement thereof, in a linked double-stranded DNA. In some embodiments, PR166 can further comprise, at the 5' end, a sequence comprising SRE007 and SRE012, or a reverse complement thereof, in a linked double-stranded DNA. In some embodiments, PR165 can further comprise, at the 5' end, a sequence comprising SRE007 and SRE012, or a reverse complement thereof, in a linked double-stranded DNA. In some embodiments, PR159 can further comprise, at the 5' end, a sequence comprising SRE007 and SRE012, or a reverse complement thereof, in a linked double-stranded DNA. In some embodiments, PR156 can further comprise, at the 5' end, a sequence comprising SRE007 and SRE012, or a reverse complement thereof, in a linked double-stranded DNA. In some embodiments, PR155 can further comprise, at the 5' end, a sequence comprising SRE007 and SRE012, or a reverse complement thereof, in a linked double-stranded DNA. In some embodiments, PR154 can further comprise, at the 5' end, a sequence comprising SRE007 and SRE012, or a reverse complement thereof, in a linked double-stranded DNA. In some embodiments, PR153 can further comprise, at the 5' end, a sequence comprising SRE007 and SRE012, or a reverse complement thereof, in a linked double-stranded DNA. In some embodiments, PR152 can further comprise, at the 5' end, a sequence comprising SRE007 and SRE012, or a reverse complement thereof, in a linked double-stranded DNA. In some embodiments, PR151 can further comprise, at the 5' end, a sequence comprising SRE007 and SRE012, or a reverse complement thereof, in a linked double-stranded DNA. In some embodiments, PR150 can further comprise, at the 5' end, a sequence comprising SRE007 and SRE012, or a reverse complement thereof, in a linked double-stranded DNA. In some embodiments, PR131 can further comprise, at the 5' end, a sequence comprising SRE007 and SRE012, or a reverse complement thereof, in a linked double-stranded DNA. In some embodiments, SEQ ID NO: 584 can further comprise, at the 5' end, a sequence comprising SRE007 and SRE012, or a reverse complement thereof, in a linked double-stranded DNA. In some embodiments, SEQ ID NO: 585 can further comprise, at the 5' end, a sequence comprising SRE007 and SRE012, or a reverse complement thereof, in a linked double-stranded DNA. In some embodiments, SEQ ID NO: 586 can further comprise, at the 5' end, a sequence comprising SRE007 and SRE012, or a reverse complement thereof, in a linked double-stranded DNA. In some embodiments, SEQ ID NO: 587 can further comprise, at the 5' end, a sequence comprising SRE007 and SRE012, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE010 and SRE008, or a reverse complement thereof, in a vector. In some embodiments, PR180 can further comprise, at the 5' end, a sequence comprising SRE010 and SRE008, or a reverse complement thereof, in a vector. In some embodiments, PR179 can further comprise, at the 5' end, a sequence comprising SRE010 and SRE008, or a reverse complement thereof, in a vector. In some embodiments, PR178 can further comprise, at the 5' end, a sequence comprising SRE010 and SRE008, or a reverse complement thereof, in a vector. In some embodiments, PR177 can further comprise, at the 5' end, a sequence comprising SRE010 and SRE008, or a reverse complement thereof, in a vector. In some embodiments, PR176 can further comprise, at the 5' end, a sequence comprising SRE010 and SRE008, or a reverse complement thereof, in a vector. In some embodiments, PR175 can further comprise, at the 5' end, a sequence comprising SRE010 and SRE008, or a reverse complement thereof, in a vector. In some embodiments, PR174 can further comprise, at the 5' end, a sequence comprising SRE010 and SRE008, or a reverse complement thereof, in a vector. In some embodiments, PR173 can further comprise, at the 5' end, a sequence comprising SRE010 and SRE008, or a reverse complement thereof, in a vector. In some embodiments, PR172 can further comprise, at the 5' end, a sequence comprising SRE010 and SRE008, or a reverse complement thereof, in a vector. In some embodiments, PR171 can further comprise, at the 5' end, a sequence comprising SRE010 and SRE008, or a reverse complement thereof, in a vector. In some embodiments, PR170 can further comprise, at the 5' end, a sequence comprising SRE010 and SRE008, or a reverse complement thereof, in a vector. In some embodiments, PR169 can further comprise, at the 5' end, a sequence comprising SRE010 and SRE008, or a reverse complement thereof, in a vector. In some embodiments, PR168 can further comprise, at the 5' end, a sequence comprising SRE010 and SRE008, or a reverse complement thereof, in a vector. In some embodiments, PR167 can further comprise, at the 5' end, a sequence comprising SRE010 and SRE008, or a reverse complement thereof, in a vector. In some embodiments, PR166 can further comprise, at the 5' end, a sequence comprising SRE010 and SRE008, or a reverse complement thereof, in a vector. In some embodiments, PR165 can further comprise, at the 5' end, a sequence comprising SRE010 and SRE008, or a reverse complement thereof, in a vector. In some embodiments, PR159 can further comprise, at the 5' end, a sequence comprising SRE010 and SRE008, or a reverse complement thereof, in a vector. In some embodiments, PR156 can further comprise, at the 5' end, a sequence comprising SRE010 and SRE008, or a reverse complement thereof, in a vector. In some embodiments, PR155 can further comprise, at the 5' end, a sequence comprising SRE010 and SRE008, or a reverse complement thereof, in a vector. In some embodiments, PR154 can further comprise, at the 5' end, a sequence comprising SRE010 and SRE008, or a reverse complement thereof, in a vector. In some embodiments, PR153 can further comprise, at the 5' end, a sequence comprising SRE010 and SRE008, or a reverse complement thereof, in a vector. In some embodiments, PR152 can further comprise, at the 5' end, a sequence comprising SRE010 and SRE008, or a reverse complement thereof, in a vector. In some embodiments, PR151 can further comprise, at the 5' end, a sequence comprising SRE010 and SRE008, or a reverse complement thereof, in a vector. In some embodiments, PR150 can further comprise, at the 5' end, a sequence comprising SRE010 and SRE008, or a reverse complement thereof, in a vector. In some embodiments, PR131 can further comprise, at the 5' end, a sequence comprising SRE010 and SRE008, or a reverse complement thereof, in a vector. In some embodiments, SEQ ID NO: 584 can further comprise, at the 5' end, a sequence comprising SRE010 and SRE008, or a reverse complement thereof, in a vector.

In some embodiments, SEQ ID NO: 585 can further comprise, at the 5' end, a sequence comprising SRE010 and SRE008, or a reverse complement thereof, in a vector. In some embodiments, SEQ ID NO: 586 can further comprise, at the 5' end, a sequence comprising SRE010 and SRE008, or a reverse complement thereof, in a vector. In some embodiments, SEQ ID NO: 587 can further comprise, at the 5' end, a sequence comprising SRE010 and SRE008, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE010 and SRE008, or a reverse complement thereof, in a nanoplasmid. In some embodiments, PR180 can further comprise, at the 5' end, a sequence comprising SRE010 and SRE008, or a reverse complement thereof, in a nanoplasmid. In some embodiments, PR179 can further comprise, at the 5' end, a sequence comprising SRE010 and SRE008, or a reverse complement thereof, in a nanoplasmid. In some embodiments, PR178 can further comprise, at the 5' end, a sequence comprising SRE010 and SRE008, or a reverse complement thereof, in a nanoplasmid. In some embodiments, PR177 can further comprise, at the 5' end, a sequence comprising SRE010 and SRE008, or a reverse complement thereof, in a nanoplasmid. In some embodiments, PR176 can further comprise, at the 5' end, a sequence comprising SRE010 and SRE008, or a reverse complement thereof, in a nanoplasmid. In some embodiments, PR175 can further comprise, at the 5' end, a sequence comprising SRE010 and SRE008, or a reverse complement thereof, in a nanoplasmid. In some embodiments, PR174 can further comprise, at the 5' end, a sequence comprising SRE010 and SRE008, or a reverse complement thereof, in a nanoplasmid. In some embodiments, PR173 can further comprise, at the 5' end, a sequence comprising SRE010 and SRE008, or a reverse complement thereof, in a nanoplasmid. In some embodiments, PR172 can further comprise, at the 5' end, a sequence comprising SRE010 and SRE008, or a reverse complement thereof, in a nanoplasmid. In some embodiments, PR171 can further comprise, at the 5' end, a sequence comprising SRE010 and SRE008, or a reverse complement thereof, in a nanoplasmid. In some embodiments, PR170 can further comprise, at the 5' end, a sequence comprising SRE010 and SRE008, or a reverse complement thereof, in a nanoplasmid. In some embodiments, PR169 can further comprise, at the 5' end, a sequence comprising SRE010 and SRE008, or a reverse complement thereof, in a nanoplasmid. In some embodiments, PR168 can further comprise, at the 5' end, a sequence comprising SRE010 and SRE008, or a reverse complement thereof, in a nanoplasmid. In some embodiments, PR167 can further comprise, at the 5' end, a sequence comprising SRE010 and SRE008, or a reverse complement thereof, in a nanoplasmid. In some embodiments, PR166 can further comprise, at the 5' end, a sequence comprising SRE010 and SRE008, or a reverse complement thereof, in a nanoplasmid. In some embodiments, PR165 can further comprise, at the 5' end, a sequence comprising SRE010 and SRE008, or a reverse complement thereof, in a nanoplasmid. In some embodiments, PR159 can further comprise, at the 5' end, a sequence comprising SRE010 and SRE008, or a reverse complement thereof, in a nanoplasmid. In some embodiments, PR156 can further comprise, at the 5' end, a sequence comprising SRE010 and SRE008, or a reverse complement thereof, in a nanoplasmid. In some embodiments, PR155 can further comprise, at the 5' end, a sequence comprising SRE010 and SRE008, or a reverse complement thereof, in a nanoplasmid. In some embodiments, PR154 can further comprise, at the 5' end, a sequence comprising SRE010 and SRE008, or a reverse complement thereof, in a nanoplasmid. In some embodiments, PR153 can further comprise, at the 5' end, a sequence comprising SRE010 and SRE008, or a reverse complement thereof, in a nanoplasmid. In some embodiments, PR152 can further comprise, at the 5' end, a sequence comprising SRE010 and SRE008, or a reverse complement thereof, in a nanoplasmid. In some embodiments, PR151 can further comprise, at the 5' end, a sequence comprising SRE010 and SRE008, or a reverse complement thereof, in a nanoplasmid. In some embodiments, PR150 can further comprise, at the 5' end, a sequence comprising SRE010 and SRE008, or a reverse complement thereof, in a nanoplasmid. In some embodiments, PR131 can further comprise, at the 5' end, a sequence comprising SRE010 and SRE008, or a reverse complement thereof, in a nanoplasmid. In some embodiments, SEQ ID NO: 584 can further comprise, at the 5' end, a sequence comprising SRE010 and SRE008, or a reverse complement thereof, in a nanoplasmid. In some embodiments, SEQ ID NO: 585 can further comprise, at the 5' end, a sequence comprising SRE010 and SRE008, or a reverse complement thereof, in a nanoplasmid. In some embodiments, SEQ ID NO: 586 can further comprise, at the 5' end, a sequence comprising SRE010 and SRE008, or a reverse complement thereof, in a nanoplasmid. In some embodiments, SEQ ID NO: 587 can further comprise, at the 5' end, a sequence comprising SRE010 and SRE008, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE010 and SRE008, or a reverse complement thereof, in a linked double-stranded DNA. In some embodiments, PR180 can further comprise, at the 5' end, a sequence comprising SRE010 and SRE008, or a reverse complement thereof, in a linked double-stranded DNA. In some embodiments, PR179 can further comprise, at the 5' end, a sequence comprising SRE010 and SRE008, or a reverse complement thereof, in a linked double-stranded DNA. In some embodiments, PR178 can further comprise, at the 5' end, a sequence comprising SRE010 and SRE008, or a reverse complement thereof, in a linked double-stranded DNA. In some embodiments, PR177 can further comprise, at the 5' end, a sequence comprising SRE010 and SRE008, or a reverse complement thereof, in a linked double-stranded DNA. In some embodiments, PR176 can further comprise, at the 5' end, a sequence comprising SRE010 and SRE008, or a reverse complement thereof, in a linked double-stranded DNA. In some embodiments, PR175 can further comprise, at the 5' end, a sequence comprising SRE010 and SRE008, or a reverse complement thereof, in a linked double-stranded DNA. In some embodiments, PR174 can further comprise, at the 5' end, a sequence comprising SRE010 and SRE008, or a reverse complement thereof, in a linked double-stranded DNA. In some embodiments, PR173 can further comprise, at the 5' end, a sequence comprising SRE010 and SRE008, or a reverse complement thereof, in a linked double-stranded DNA. In some embodiments, PR172 can further comprise, at the 5' end, a sequence comprising SRE010 and SRE008, or a reverse complement thereof, in a linked double-stranded DNA. In some embodiments, PR171 can further comprise, at the 5' end, a sequence comprising SRE010 and SRE008, or a reverse complement thereof, in a linked double-stranded DNA. In some embodiments, PR170 can further comprise, at the 5' end, a sequence comprising SRE010 and SRE008, or a reverse complement thereof, in a linked double-stranded DNA. In some embodiments, PR169 can further comprise, at the 5' end, a sequence comprising SRE010 and SRE008, or a reverse complement thereof, in a linked double-stranded DNA. In some embodiments, PR168 can further comprise, at the 5' end, a sequence comprising SRE010 and SRE008, or a reverse complement thereof, in a linked double-stranded DNA. In some embodiments, PR167 can further comprise, at the 5' end, a sequence comprising SRE010 and SRE008, or a reverse complement thereof, in a linked double-stranded DNA. In some embodiments, PR166 can further comprise, at the 5' end, a sequence comprising SRE010 and SRE008, or a reverse complement thereof, in a linked double-stranded DNA. In some embodiments, PR165 can further comprise, at the 5' end, a sequence comprising SRE010 and SRE008, or a reverse complement thereof, in a linked double-stranded DNA. In some embodiments, PR159 can further comprise, at the 5' end, a sequence comprising SRE010 and SRE008, or a reverse complement thereof, in a linked double-stranded DNA. In some embodiments, PR156 can further comprise, at the 5' end, a sequence comprising SRE010 and SRE008, or a reverse complement thereof, in a linked double-stranded DNA. In some embodiments, PR155 can further comprise, at the 5' end, a sequence comprising SRE010 and SRE008, or a reverse complement thereof, in a linked double-stranded DNA. In some embodiments, PR154 can further comprise, at the 5' end, a sequence comprising SRE010 and SRE008, or a reverse complement thereof, in a linked double-stranded DNA. In some embodiments, PR153 can further comprise, at the 5' end, a sequence comprising SRE010 and SRE008, or a reverse complement thereof, in a linked double-stranded DNA. In some embodiments, PR152 can further comprise, at the 5' end, a sequence comprising SRE010 and SRE008, or a reverse complement thereof, in a linked double-stranded DNA. In some embodiments, PR151 can further comprise, at the 5' end, a sequence comprising SRE010 and SRE008, or a reverse complement thereof, in a linked double-stranded DNA. In some embodiments, PR150 can further comprise, at the 5' end, a sequence comprising SRE010 and SRE008, or a reverse complement thereof, in a linked double-stranded DNA. In some embodiments, PR131 can further comprise, at the 5' end, a sequence comprising SRE010 and SRE008, or a reverse complement thereof, in a linked double-stranded DNA. In some embodiments, SEQ ID NO: 584 can further comprise, at the 5' end, a sequence comprising SRE010 and SRE008, or a reverse complement thereof, in a linked double-stranded DNA. In some embodiments, SEQ ID NO: 585 can further comprise, at the 5' end, a sequence comprising SRE010 and SRE008, or a reverse complement thereof, in a linked double-stranded DNA. In some embodiments, SEQ ID NO: 586 can further comprise, at the 5' end, a sequence comprising SRE010 and SRE008, or a reverse complement thereof, in a linked double-stranded DNA. In some embodiments, SEQ ID NO: 587 can further comprise, at the 5' end, a sequence comprising SRE010 and SRE008, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012 and SRE008, or a reverse complement thereof, in a vector. In some embodiments, PR180 can further comprise, at the 5' end, a sequence comprising SRE012 and SRE008, or a reverse complement thereof, in a vector. In some embodiments, PR179 can further comprise, at the 5' end, a sequence comprising SRE012 and SRE008, or a reverse complement thereof, in a vector. In some embodiments, PR178 can further comprise, at the 5' end, a sequence comprising SRE012 and SRE008, or a reverse complement thereof, in a vector. In some embodiments, PR177 can further comprise, at the 5' end, a sequence comprising SRE012 and SRE008, or a reverse complement thereof, in a vector. In some embodiments, PR176 can further comprise, at the 5' end, a sequence comprising SRE012 and SRE008, or a reverse complement thereof, in a vector. In some embodiments, PR175 can further comprise, at the 5' end, a sequence comprising SRE012 and SRE008, or a reverse complement thereof, in a vector. In some embodiments, PR174 can further comprise, at the 5' end, a sequence comprising SRE012 and SRE008, or a reverse complement thereof, in a vector. In some embodiments, PR173 can further comprise, at the 5' end, a sequence comprising SRE012 and SRE008, or a reverse complement thereof, in a vector. In some embodiments, PR172 can further comprise, at the 5' end, a sequence comprising SRE012 and SRE008, or a reverse complement thereof, in a vector. In some embodiments, PR171 can further comprise, at the 5' end, a sequence comprising SRE012 and SRE008, or a reverse complement thereof, in a vector. In some embodiments, PR170 can further comprise, at the 5' end, a sequence comprising SRE012 and SRE008, or a reverse complement thereof, in a vector. In some embodiments, PR169 can further comprise, at the 5' end, a sequence comprising SRE012 and SRE008, or a reverse complement thereof, in a vector. In some embodiments, PR168 can further comprise, at the 5' end, a sequence comprising SRE012 and SRE008, or a reverse complement thereof, in a vector. In some embodiments, PR167 can further comprise, at the 5' end, a sequence comprising SRE012 and SRE008, or a reverse complement thereof, in a vector. In some embodiments, PR166 can further comprise, at the 5' end, a sequence comprising SRE012 and SRE008, or a reverse complement thereof, in a vector. In some embodiments, PR165 can further comprise, at the 5' end, a sequence comprising SRE012 and SRE008, or a reverse complement thereof, in a vector. In some embodiments, PR159 can further comprise, at the 5' end, a sequence comprising SRE012 and SRE008, or a reverse complement thereof, in a vector. In some embodiments, PR156 can further comprise, at the 5' end, a sequence comprising SRE012 and SRE008, or a reverse complement thereof, in a vector. In some embodiments, PR155 can further comprise, at the 5' end, a sequence comprising SRE012 and SRE008, or a reverse complement thereof, in a vector. In some embodiments, PR154 can further comprise, at the 5' end, a sequence comprising SRE012 and SRE008, or a reverse complement thereof, in a vector. In some embodiments, PR153 can further comprise, at the 5' end, a sequence comprising SRE012 and SRE008, or a reverse complement thereof, in a vector. In some embodiments, PR152 can further comprise, at the 5' end, a sequence comprising SRE012 and SRE008, or a reverse complement thereof, in a vector. In some embodiments, PR151 can further comprise, at the 5' end, a sequence comprising SRE012 and SRE008, or a reverse complement thereof, in a vector. In some embodiments, PR150 can further comprise, at the 5' end, a sequence comprising SRE012 and SRE008, or a reverse complement thereof, in a vector. In some embodiments, PR131 can further comprise, at the 5' end, a sequence comprising SRE012 and SRE008, or a reverse complement thereof, in a vector. In some embodiments, SEQ ID NO: 584 can further comprise, at the 5' end, a sequence comprising SRE012 and SRE008, or a reverse complement thereof, in a vector. In some embodiments, SEQ ID NO: 585 can further comprise, at the 5' end, a sequence comprising SRE012 and SRE008, or a reverse complement thereof, in a vector. In some embodiments, SEQ ID NO: 586 can further comprise, at the 5' end, a sequence comprising SRE012 and SRE008, or a reverse complement thereof, in a vector. In some embodiments, SEQ ID NO: 587 can further comprise, at the 5' end, a sequence comprising SRE012 and SRE008, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012 and SRE008, or a reverse complement thereof, in a nanoplasmid. In some embodiments, PR180 can further comprise, at the 5' end, a sequence comprising SRE012 and SRE008, or a reverse complement thereof, in a nanoplasmid. In some embodiments, PR179 can further comprise, at the 5' end, a sequence comprising SRE012 and SRE008, or a reverse complement thereof, in a nanoplasmid. In some embodiments, PR178 can further comprise, at the 5' end, a sequence comprising SRE012 and SRE008, or a reverse complement thereof, in a nanoplasmid. In some embodiments, PR177 can further comprise, at the 5' end, a sequence comprising SRE012 and SRE008, or a reverse complement thereof, in a nanoplasmid. In some embodiments, PR176 can further comprise, at the 5' end, a sequence comprising SRE012 and SRE008, or a reverse complement thereof, in a nanoplasmid. In some embodiments, PR175 can further comprise, at the 5' end, a sequence comprising SRE012 and SRE008, or a reverse complement thereof, in a nanoplasmid. In some embodiments, PR174 can further comprise, at the 5' end, a sequence comprising SRE012 and SRE008, or a reverse complement thereof, in a nanoplasmid. In some embodiments, PR173 can further comprise, at the 5' end, a sequence comprising SRE012 and SRE008, or a reverse complement thereof, in a nanoplasmid. In some embodiments, PR172 can further comprise, at the 5' end, a sequence comprising SRE012 and SRE008, or a reverse complement thereof, in a nanoplasmid. In some embodiments, PR171 can further comprise, at the 5' end, a sequence comprising SRE012 and SRE008, or a reverse complement thereof, in a nanoplasmid. In some embodiments, PR170 can further comprise, at the 5' end, a sequence comprising SRE012 and SRE008, or a reverse complement thereof, in a nanoplasmid. In some embodiments, PR169 can further comprise, at the 5' end, a sequence comprising SRE012 and SRE008, or a reverse complement thereof, in a nanoplasmid. In some embodiments, PR168 can further comprise, at the 5' end, a sequence comprising SRE012 and SRE008, or a reverse complement thereof, in a nanoplasmid. In some embodiments, PR167 can further comprise, at the 5' end, a sequence comprising SRE012 and SRE008, or a reverse complement thereof, in a nanoplasmid. In some embodiments, PR166 can further comprise, at the 5' end, a sequence comprising SRE012 and SRE008, or a reverse complement thereof, in a nanoplasmid. In some embodiments, PR165 can further comprise, at the 5' end, a sequence comprising SRE012 and SRE008, or a reverse complement thereof, in a nanoplasmid. In some embodiments, PR159 can further comprise, at the 5' end, a sequence comprising SRE012 and SRE008, or a reverse complement thereof, in a nanoplasmid. In some embodiments, PR156 can further comprise, at the 5' end, a sequence comprising SRE012 and SRE008, or a reverse complement thereof, in a nanoplasmid. In some embodiments, PR155 can further comprise, at the 5' end, a sequence comprising SRE012 and SRE008, or a reverse complement thereof, in a nanoplasmid. In some embodiments, PR154 can further comprise, at the 5' end, a sequence comprising SRE012 and SRE008, or a reverse complement thereof, in a nanoplasmid. In some embodiments, PR153 can further comprise, at the 5' end, a sequence comprising SRE012 and SRE008, or a reverse complement thereof, in a nanoplasmid. In some embodiments, PR152 can further comprise, at the 5' end, a sequence comprising SRE012 and SRE008, or a reverse complement thereof, in a nanoplasmid. In some embodiments, PR151 can further comprise, at the 5' end, a sequence comprising SRE012 and SRE008, or a reverse complement thereof, in a nanoplasmid. In some embodiments, PR150 can further comprise, at the 5' end, a sequence comprising SRE012 and SRE008, or a reverse complement thereof, in a nanoplasmid. In some embodiments, PR131 can further comprise, at the 5' end, a sequence comprising SRE012 and SRE008, or a reverse complement thereof, in a nanoplasmid. In some embodiments, SEQ ID NO: 584 can further comprise, at the 5' end, a sequence comprising SRE012 and SRE008, or a reverse complement thereof, in a nanoplasmid. In some embodiments, SEQ ID NO: 585 can further comprise, at the 5' end, a sequence comprising SRE012 and SRE008, or a reverse complement thereof, in a nanoplasmid. In some embodiments, SEQ ID NO: 586 can further comprise, at the 5' end, a sequence comprising SRE012 and SRE008, or a reverse complement thereof, in a nanoplasmid. In some embodiments, SEQ ID NO: 587 can further comprise, at the 5' end, a sequence comprising SRE012 and SRE008, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012 and SRE008, or a reverse complement thereof, in a linked double-stranded DNA. In some embodiments, PR180 can further comprise, at the 5' end, a sequence comprising SRE012 and SRE008, or a reverse complement thereof, in a linked double-stranded DNA. In some embodiments, PR179 can further comprise, at the 5' end, a sequence comprising SRE012 and SRE008, or a reverse complement thereof, in a linked double-stranded DNA. In some embodiments, PR178 can further comprise, at the 5' end, a sequence comprising SRE012 and SRE008, or a reverse complement thereof, in a linked double-stranded DNA. In some embodiments, PR177 can further comprise, at the 5' end, a sequence comprising SRE012 and SRE008, or a reverse complement thereof, in a linked double-stranded DNA. In some embodiments, PR176 can further comprise, at the 5' end, a sequence comprising SRE012 and SRE008, or a reverse complement thereof, in a linked double-stranded DNA. In some embodiments, PR175 can further comprise, at the 5' end, a sequence comprising SRE012 and SRE008, or a reverse complement thereof, in a linked double-stranded DNA. In some embodiments, PR174 can further comprise, at the 5' end, a sequence comprising SRE012 and SRE008, or a reverse complement thereof, in a linked double-stranded DNA. In some embodiments, PR173 can further comprise, at the 5' end, a sequence comprising SRE012 and SRE008, or a reverse complement thereof, in a linked double-stranded DNA. In some embodiments, PR172 can further comprise, at the 5' end, a sequence comprising SRE012 and SRE008, or a reverse complement thereof, in a linked double-stranded DNA. In some embodiments, PR171 can further comprise, at the 5' end, a sequence comprising SRE012 and SRE008, or a reverse complement thereof, in a linked double-stranded DNA. In some embodiments, PR170 can further comprise, at the 5' end, a sequence comprising SRE012 and SRE008, or a reverse complement thereof, in a linked double-stranded DNA. In some embodiments, PR169 can further comprise, at the 5' end, a sequence comprising SRE012 and SRE008, or a reverse complement thereof, in a linked double-stranded DNA. In some embodiments, PR168 can further comprise, at the 5' end, a sequence comprising SRE012 and SRE008, or a reverse complement thereof, in a linked double-stranded DNA. In some embodiments, PR167 can further comprise, at the 5' end, a sequence comprising SRE012 and SRE008, or a reverse complement thereof, in a linked double-stranded DNA. In some embodiments, PR166 can further comprise, at the 5' end, a sequence comprising SRE012 and SRE008, or a reverse complement thereof, in a linked double-stranded DNA. In some embodiments, PR165 can further comprise, at the 5' end, a sequence comprising SRE012 and SRE008, or a reverse complement thereof, in a linked double-stranded DNA. In some embodiments, PR159 can further comprise, at the 5' end, a sequence comprising SRE012 and SRE008, or a reverse complement thereof, in a linked double-stranded DNA. In some embodiments, PR156 can further comprise, at the 5' end, a sequence comprising SRE012 and SRE008, or a reverse complement thereof, in a linked double-stranded DNA. In some embodiments, PR155 can further comprise, at the 5' end, a sequence comprising SRE012 and SRE008, or a reverse complement thereof, in a linked double-stranded DNA. In some embodiments, PR154 can further comprise, at the 5' end, a sequence comprising SRE012 and SRE008, or a reverse complement thereof, in a linked double-stranded DNA. In some embodiments, PR153 can further comprise, at the 5' end, a sequence comprising SRE012 and SRE008, or a reverse complement thereof, in a linked double-stranded DNA. In some embodiments, PR152 can further comprise, at the 5' end, a sequence comprising SRE012 and SRE008, or a reverse complement thereof, in a linked double-stranded DNA. In some embodiments, PR151 can further comprise, at the 5' end, a sequence comprising SRE012 and SRE008, or a reverse complement thereof, in a linked double-stranded DNA. In some embodiments, PR150 can further comprise, at the 5' end, a sequence comprising SRE012 and SRE008, or a reverse complement thereof, in a linked double-stranded DNA. In some embodiments, PR131 can further comprise, at the 5' end, a sequence comprising SRE012 and SRE008, or a reverse complement thereof, in a linked double-stranded DNA. In some embodiments, SEQ ID NO: 584 can further comprise, at the 5' end, a sequence comprising SRE012 and SRE008, or a reverse complement thereof, in a linked double-stranded DNA. In some embodiments, SEQ ID NO: 585 can further comprise, at the 5' end, a sequence comprising SRE012 and SRE008, or a reverse complement thereof, in a linked double-stranded DNA. In some embodiments, SEQ ID NO: 586 can further comprise, at the 5' end, a sequence comprising SRE012 and SRE008, or a reverse complement thereof, in a linked double-stranded DNA. In some embodiments, SEQ ID NO: 587 can further comprise, at the 5' end, a sequence comprising SRE012 and SRE008, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012 and SRE010, or a reverse complement thereof, in a vector. In some embodiments, PR180 can further comprise, at the 5' end, a sequence comprising SRE012 and SRE010, or a reverse complement thereof, in a vector. In some embodiments, PR179 can further comprise, at the 5' end, a sequence comprising SRE012 and SRE010, or a reverse complement thereof, in a vector. In some embodiments, PR178 can further comprise, at the 5' end, a sequence comprising SRE012 and SRE010, or a reverse complement thereof, in a vector. In some embodiments, PR177 can further comprise, at the 5' end, a sequence comprising SRE012 and SRE010, or a reverse complement thereof, in a vector. In some embodiments, PR176 can further comprise, at the 5' end, a sequence comprising SRE012 and SRE010, or a reverse complement thereof, in a vector. In some embodiments, PR175 can further comprise, at the 5' end, a sequence comprising SRE012 and SRE010, or a reverse complement thereof, in a vector. In some embodiments, PR174 can further comprise, at the 5' end, a sequence comprising SRE012 and SRE010, or a reverse complement thereof, in a vector. In some embodiments, PR173 can further comprise, at the 5' end, a sequence comprising SRE012 and SRE010, or a reverse complement thereof, in a vector. In some embodiments, PR172 can further comprise, at the 5' end, a sequence comprising SRE012 and SRE010, or a reverse complement thereof, in a vector. In some embodiments, PR171 can further comprise, at the 5' end, a sequence comprising SRE012 and SRE010, or a reverse complement thereof, in a vector. In some embodiments, PR170 can further comprise, at the 5' end, a sequence comprising SRE012 and SRE010, or a reverse complement thereof, in a vector. In some embodiments, PR169 can further comprise, at the 5' end, a sequence comprising SRE012 and SRE010, or a reverse complement thereof, in a vector. In some embodiments, PR168 can further comprise, at the 5' end, a sequence comprising SRE012 and SRE010, or a reverse complement thereof, in a vector. In some embodiments, PR167 can further comprise, at the 5' end, a sequence comprising SRE012 and SRE010, or a reverse complement thereof, in a vector. In some embodiments, PR166 can further comprise, at the 5' end, a sequence comprising SRE012 and SRE010, or a reverse complement thereof, in a vector. In some embodiments, PR165 can further comprise, at the 5' end, a sequence comprising SRE012 and SRE010, or a reverse complement thereof, in a vector. In some embodiments, PR159 can further comprise, at the 5' end, a sequence comprising SRE012 and SRE010, or a reverse complement thereof, in a vector. In some embodiments, PR156 can further comprise, at the 5' end, a sequence comprising SRE012 and SRE010, or a reverse complement thereof, in a vector. In some embodiments, PR155 can further comprise, at the 5' end, a sequence comprising SRE012 and SRE010, or a reverse complement thereof, in a vector. In some embodiments, PR154 can further comprise, at the 5' end, a sequence comprising SRE012 and SRE010, or a reverse complement thereof, in a vector. In some embodiments, PR153 can further comprise, at the 5' end, a sequence comprising SRE012 and SRE010, or a reverse complement thereof, in a vector. In some embodiments, PR152 can further comprise, at the 5' end, a sequence comprising SRE012 and SRE010, or a reverse complement thereof, in a vector. In some embodiments, PR151 can further comprise, at the 5' end, a sequence comprising SRE012 and SRE010, or a reverse complement thereof, in a vector. In some embodiments, PR150 can further comprise, at the 5' end, a sequence comprising SRE012 and SRE010, or a reverse complement thereof, in a vector. In some embodiments, PR131 can further comprise, at the 5' end, a sequence comprising SRE012 and SRE010, or a reverse complement thereof, in a vector. In some embodiments, SEQ ID NO: 584 can further comprise, at the 5' end, a sequence comprising SRE012 and SRE010, or a reverse complement thereof, in a vector.

In some embodiments, SEQ ID NO: 585 can further comprise, at the 5' end, a sequence comprising SRE012 and SRE010, or a reverse complement thereof, in a vector. In some embodiments, SEQ ID NO: 586 can further comprise, at the 5' end, a sequence comprising SRE012 and SRE010, or a reverse complement thereof, in a vector. In some embodiments, SEQ ID NO: 587 can further comprise, at the 5' end, a sequence comprising SRE012 and SRE010, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012 and SRE010, or a reverse complement thereof, in a nanoplasmid. In some embodiments, PR180 can further comprise, at the 5' end, a sequence comprising SRE012 and SRE010, or a reverse complement thereof, in a nanoplasmid. In some embodiments, PR179 can further comprise, at the 5' end, a sequence comprising SRE012 and SRE010, or a reverse complement thereof, in a nanoplasmid. In some embodiments, PR178 can further comprise, at the 5' end, a sequence comprising SRE012 and SRE010, or a reverse complement thereof, in a nanoplasmid. In some embodiments, PR177 can further comprise, at the 5' end, a sequence comprising SRE012 and SRE010, or a reverse complement thereof, in a nanoplasmid. In some embodiments, PR176 can further comprise, at the 5' end, a sequence comprising SRE012 and SRE010, or a reverse complement thereof, in a nanoplasmid. In some embodiments, PR175 can further comprise, at the 5' end, a sequence comprising SRE012 and SRE010, or a reverse complement thereof, in a nanoplasmid. In some embodiments, PR174 can further comprise, at the 5' end, a sequence comprising SRE012 and SRE010, or a reverse complement thereof, in a nanoplasmid. In some embodiments, PR173 can further comprise, at the 5' end, a sequence comprising SRE012 and SRE010, or a reverse complement thereof, in a nanoplasmid. In some embodiments, PR172 can further comprise, at the 5' end, a sequence comprising SRE012 and SRE010, or a reverse complement thereof, in a nanoplasmid. In some embodiments, PR171 can further comprise, at the 5' end, a sequence comprising SRE012 and SRE010, or a reverse complement thereof, in a nanoplasmid. In some embodiments, PR170 can further comprise, at the 5' end, a sequence comprising SRE012 and SRE010, or a reverse complement thereof, in a nanoplasmid. In some embodiments, PR169 can further comprise, at the 5' end, a sequence comprising SRE012 and SRE010, or a reverse complement thereof, in a nanoplasmid. In some embodiments, PR168 can further comprise, at the 5' end, a sequence comprising SRE012 and SRE010, or a reverse complement thereof, in a nanoplasmid. In some embodiments, PR167 can further comprise, at the 5' end, a sequence comprising SRE012 and SRE010, or a reverse complement thereof, in a nanoplasmid. In some embodiments, PR166 can further comprise, at the 5' end, a sequence comprising SRE012 and SRE010, or a reverse complement thereof, in a nanoplasmid. In some embodiments, PR165 can further comprise, at the 5' end, a sequence comprising SRE012 and SRE010, or a reverse complement thereof, in a nanoplasmid. In some embodiments, PR159 can further comprise, at the 5' end, a sequence comprising SRE012 and SRE010, or a reverse complement thereof, in a nanoplasmid. In some embodiments, PR156 can further comprise, at the 5' end, a sequence comprising SRE012 and SRE010, or a reverse complement thereof, in a nanoplasmid. In some embodiments, PR155 can further comprise, at the 5' end, a sequence comprising SRE012 and SRE010, or a reverse complement thereof, in a nanoplasmid. In some embodiments, PR154 can further comprise, at the 5' end, a sequence comprising SRE012 and SRE010, or a reverse complement thereof, in a nanoplasmid. In some embodiments, PR153 can further comprise, at the 5' end, a sequence comprising SRE012 and SRE010, or a reverse complement thereof, in a nanoplasmid. In some embodiments, PR152 can further comprise, at the 5' end, a sequence comprising SRE012 and SRE010, or a reverse complement thereof, in a nanoplasmid. In some embodiments, PR151 can further comprise, at the 5' end, a sequence comprising SRE012 and SRE010, or a reverse complement thereof, in a nanoplasmid. In some embodiments, PR150 can further comprise, at the 5' end, a sequence comprising SRE012 and SRE010, or a reverse complement thereof, in a nanoplasmid. In some embodiments, PR131 can further comprise, at the 5' end, a sequence comprising SRE012 and SRE010, or a reverse complement thereof, in a nanoplasmid. In some embodiments, SEQ ID NO: 584 can further comprise, at the 5' end, a sequence comprising SRE012 and SRE010, or a reverse complement thereof, in a nanoplasmid. In some embodiments, SEQ ID NO: 585 can further comprise, at the 5' end, a sequence comprising SRE012 and SRE010, or a reverse complement thereof, in a nanoplasmid. In some embodiments, SEQ ID NO: 586 can further comprise, at the 5' end, a sequence comprising SRE012 and SRE010, or a reverse complement thereof, in a nanoplasmid. In some embodiments, SEQ ID NO: 587 can further comprise, at the 5' end, a sequence comprising SRE012 and SRE010, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012 and SRE010, or a reverse complement thereof, in a linked double-stranded DNA. In some embodiments, PR180 can further comprise, at the 5' end, a sequence comprising SRE012 and SRE010, or a reverse complement thereof, in a linked double-stranded DNA. In some embodiments, PR179 can further comprise, at the 5' end, a sequence comprising SRE012 and SRE010, or a reverse complement thereof, in a linked double-stranded DNA. In some embodiments, PR178 can further comprise, at the 5' end, a sequence comprising SRE012 and SRE010, or a reverse complement thereof, in a linked double-stranded DNA. In some embodiments, PR177 can further comprise, at the 5' end, a sequence comprising SRE012 and SRE010, or a reverse complement thereof, in a linked double-stranded DNA. In some embodiments, PR176 can further comprise, at the 5' end, a sequence comprising SRE012 and SRE010, or a reverse complement thereof, in a linked double-stranded DNA. In some embodiments, PR175 can further comprise, at the 5' end, a sequence comprising SRE012 and SRE010, or a reverse complement thereof, in a linked double-stranded DNA. In some embodiments, PR174 can further comprise, at the 5' end, a sequence comprising SRE012 and SRE010, or a reverse complement thereof, in a linked double-stranded DNA. In some embodiments, PR173 can further comprise, at the 5' end, a sequence comprising SRE012 and SRE010, or a reverse complement thereof, in a linked double-stranded DNA. In some embodiments, PR172 can further comprise, at the 5' end, a sequence comprising SRE012 and SRE010, or a reverse complement thereof, in a linked double-stranded DNA. In some embodiments, PR171 can further comprise, at the 5' end, a sequence comprising SRE012 and SRE010, or a reverse complement thereof, in a linked double-stranded DNA. In some embodiments, PR170 can further comprise, at the 5' end, a sequence comprising SRE012 and SRE010, or a reverse complement thereof, in a linked double-stranded DNA. In some embodiments, PR169 can further comprise, at the 5' end, a sequence comprising SRE012 and SRE010, or a reverse complement thereof, in a linked double-stranded DNA. In some embodiments, PR168 can further comprise, at the 5' end, a sequence comprising SRE012 and SRE010, or a reverse complement thereof, in a linked double-stranded DNA. In some embodiments, PR167 can further comprise, at the 5' end, a sequence comprising SRE012 and SRE010, or a reverse complement thereof, in a linked double-stranded DNA. In some embodiments, PR166 can further comprise, at the 5' end, a sequence comprising SRE012 and SRE010, or a reverse complement thereof, in a linked double-stranded DNA. In some embodiments, PR165 can further comprise, at the 5' end, a sequence comprising SRE012 and SRE010, or a reverse complement thereof, in a linked double-stranded DNA. In some embodiments, PR159 can further comprise, at the 5' end, a sequence comprising SRE012 and SRE010, or a reverse complement thereof, in a linked double-stranded DNA. In some embodiments, PR156 can further comprise, at the 5' end, a sequence comprising SRE012 and SRE010, or a reverse complement thereof, in a linked double-stranded DNA. In some embodiments, PR155 can further comprise, at the 5' end, a sequence comprising SRE012 and SRE010, or a reverse complement thereof, in a linked double-stranded DNA. In some embodiments, PR154 can further comprise, at the 5' end, a sequence comprising SRE012 and SRE010, or a reverse complement thereof, in a linked double-stranded DNA. In some embodiments, PR153 can further comprise, at the 5' end, a sequence comprising SRE012 and SRE010, or a reverse complement thereof, in a linked double-stranded DNA. In some embodiments, PR152 can further comprise, at the 5' end, a sequence comprising SRE012 and SRE010, or a reverse complement thereof, in a linked double-stranded DNA. In some embodiments, PR151 can further comprise, at the 5' end, a sequence comprising SRE012 and SRE010, or a reverse complement thereof, in a linked double-stranded DNA. In some embodiments, PR150 can further comprise, at the 5' end, a sequence comprising SRE012 and SRE010, or a reverse complement thereof, in a linked double-stranded DNA. In some embodiments, PR131 can further comprise, at the 5' end, a sequence comprising SRE012 and SRE010, or a reverse complement thereof, in a linked double-stranded DNA. In some embodiments, SEQ ID NO: 584 can further comprise, at the 5' end, a sequence comprising SRE012 and SRE010, or a reverse complement thereof, in a linked double-stranded DNA. In some embodiments, SEQ ID NO: 585 can further comprise, at the 5' end, a sequence comprising SRE012 and SRE010, or a reverse complement thereof, in a linked double-stranded DNA. In some embodiments, SEQ ID NO: 586 can further comprise, at the 5' end, a sequence comprising SRE012 and SRE010, or a reverse complement thereof, in a linked double-stranded DNA. In some embodiments, SEQ ID NO: 587 can further comprise, at the 5' end, a sequence comprising SRE012 and SRE010, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007, or a reverse complement thereof, in a vector. In some embodiments, PR180 can further comprise, at the 5' end, a sequence comprising SRE007, or a reverse complement thereof, in a vector. In some embodiments, PR179 can further comprise, at the 5' end, a sequence comprising SRE007, or a reverse complement thereof, in a vector. In some embodiments, PR178 can further comprise, at the 5' end, a sequence comprising SRE007, or a reverse complement thereof, in a vector. In some embodiments, PR177 can further comprise, at the 5' end, a sequence comprising SRE007, or a reverse complement thereof, in a vector. In some embodiments, PR176 can further comprise, at the 5' end, a sequence comprising SRE007, or a reverse complement thereof, in a vector. In some embodiments, PR175 can further comprise, at the 5' end, a sequence comprising SRE007, or a reverse complement thereof, in a vector. In some embodiments, PR174 can further comprise, at the 5' end, a sequence comprising SRE007, or a reverse complement thereof, in a vector. In some embodiments, PR173 can further comprise, at the 5' end, a sequence comprising SRE007, or a reverse complement thereof, in a vector. In some embodiments, PR172 can further comprise, at the 5' end, a sequence comprising SRE007, or a reverse complement thereof, in a vector. In some embodiments, PR171 can further comprise, at the 5' end, a sequence comprising SRE007, or a reverse complement thereof, in a vector. In some embodiments, PR170 can further comprise, at the 5' end, a sequence comprising SRE007, or a reverse complement thereof, in a vector. In some embodiments, PR169 can further comprise, at the 5' end, a sequence comprising SRE007, or a reverse complement thereof, in a vector. In some embodiments, PR168 can further comprise, at the 5' end, a sequence comprising SRE007, or a reverse complement thereof, in a vector. In some embodiments, PR167 can further comprise, at the 5' end, a sequence comprising SRE007, or a reverse complement thereof, in a vector. In some embodiments, PR166 can further comprise, at the 5' end, a sequence comprising SRE007, or a reverse complement thereof, in a vector. In some embodiments, PR165 can further comprise, at the 5' end, a sequence comprising SRE007, or a reverse complement thereof, in a vector. In some embodiments, PR159 can further comprise, at the 5' end, a sequence comprising SRE007, or a reverse complement thereof, in a vector. In some embodiments, PR156 can further comprise, at the 5' end, a sequence comprising SRE007 and SRE010, or a reverse complement thereof, in a vector. In some embodiments, PR155 can further comprise, at the 5' end, a sequence comprising SRE007, or a reverse complement thereof, in a vector. In some embodiments, PR154 can further comprise, at the 5' end, a sequence comprising SRE007, or a reverse complement thereof, in a vector. In some embodiments, PR153 can further comprise, at the 5' end, a sequence comprising SRE007, or a reverse complement thereof, in a vector. In some embodiments, PR152 can further comprise, at the 5' end, a sequence comprising SRE007, or a reverse complement thereof, in a vector. In some embodiments, PR151 can further comprise, at the 5' end, a sequence comprising SRE007, or a reverse complement thereof, in a vector. In some embodiments, PR150 can further comprise, at the 5' end, a sequence comprising SRE007, or a reverse complement thereof, in a vector. In some embodiments, PR131 can further comprise, at the 5' end, a sequence comprising SRE007, or a reverse complement thereof, in a vector. In some embodiments, SEQ ID NO: 584 can further comprise, at the 5' end, a sequence comprising SRE007, or a reverse complement thereof, in a vector. In some embodiments, SEQ ID NO: 585 can further comprise, at the 5' end, a sequence comprising SRE007, or a reverse complement thereof, in a vector. In some embodiments, SEQ ID NO: 586 can further comprise, at the 5' end, a sequence comprising SRE007, or a reverse complement thereof, in a vector. In some embodiments, SEQ ID NO: 587 can further comprise, at the 5' end, a sequence comprising SRE007, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007, or a reverse complement thereof, in a nanoplasmid. In some embodiments, PR180 can further comprise, at the 5' end, a sequence comprising SRE007, or a reverse complement thereof, in a nanoplasmid. In some embodiments, PR179 can further comprise, at the 5' end, a sequence comprising SRE007, or a reverse complement thereof, in a nanoplasmid. In some embodiments, PR178 can further comprise, at the 5' end, a sequence comprising SRE007, or a reverse complement thereof, in a nanoplasmid. In some embodiments, PR177 can further comprise, at the 5' end, a sequence comprising SRE007, or a reverse complement thereof, in a nanoplasmid. In some embodiments, PR176 can further comprise, at the 5' end, a sequence comprising SRE007, or a reverse complement thereof, in a nanoplasmid. In some embodiments, PR175 can further comprise, at the 5' end, a sequence comprising SRE007, or a reverse complement thereof, in a nanoplasmid. In some embodiments, PR174 can further comprise, at the 5' end, a sequence comprising SRE007, or a reverse complement thereof, in a nanoplasmid. In some embodiments, PR173 can further comprise, at the 5' end, a sequence comprising SRE007, or a reverse complement thereof, in a nanoplasmid. In some embodiments, PR172 can further comprise, at the 5' end, a sequence comprising SRE007, or a reverse complement thereof, in a nanoplasmid. In some embodiments, PR171 can further comprise, at the 5' end, a sequence comprising SRE007, or a reverse complement thereof, in a nanoplasmid. In some embodiments, PR170 can further comprise, at the 5' end, a sequence comprising SRE007, or a reverse complement thereof, in a nanoplasmid. In some embodiments, PR169 can further comprise, at the 5' end, a sequence comprising SRE007, or a reverse complement thereof, in a nanoplasmid. In some embodiments, PR168 can further comprise, at the 5' end, a sequence comprising SRE007, or a reverse complement thereof, in a nanoplasmid. In some embodiments, PR167 can further comprise, at the 5' end, a sequence comprising SRE007, or a reverse complement thereof, in a nanoplasmid. In some embodiments, PR166 can further comprise, at the 5' end, a sequence comprising SRE007, or a reverse complement thereof, in a nanoplasmid. In some embodiments, PR165 can further comprise, at the 5' end, a sequence comprising SRE007, or a reverse complement thereof, in a nanoplasmid. In some embodiments, PR159 can further comprise, at the 5' end, a sequence comprising SRE007, or a reverse complement thereof, in a nanoplasmid. In some embodiments, PR156 can further comprise, at the 5' end, a sequence comprising SRE007 and SRE010, or a reverse complement thereof, in a nanoplasmid. In some embodiments, PR155 can further comprise, at the 5' end, a sequence comprising SRE007, or a reverse complement thereof, in a nanoplasmid. In some embodiments, PR154 can further comprise, at the 5' end, a sequence comprising SRE007, or a reverse complement thereof, in a nanoplasmid. In some embodiments, PR153 can further comprise, at the 5' end, a sequence comprising SRE007, or a reverse complement thereof, in a nanoplasmid. In some embodiments, PR152 can further comprise, at the 5' end, a sequence comprising SRE007, or a reverse complement thereof, in a nanoplasmid. In some embodiments, PR151 can further comprise, at the 5' end, a sequence comprising SRE007, or a reverse complement thereof, in a nanoplasmid. In some embodiments, PR150 can further comprise, at the 5' end, a sequence comprising SRE007, or a reverse complement thereof, in a nanoplasmid. In some embodiments, PR131 can further comprise, at the 5' end, a sequence comprising SRE007, or a reverse complement thereof, in a nanoplasmid. In some embodiments, SEQ ID NO: 584 can further comprise, at the 5' end, a sequence comprising SRE007, or a reverse complement thereof, in a nanoplasmid. In some embodiments, SEQ ID NO: 585 can further comprise, at the 5' end, a sequence comprising SRE007, or a reverse complement thereof, in a nanoplasmid. In some embodiments, SEQ ID NO: 586 can further comprise, at the 5' end, a sequence comprising SRE007, or a reverse complement thereof, in a nanoplasmid. In some embodiments, SEQ ID NO: 587 can further comprise, at the 5' end, a sequence comprising SRE007, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE007, or a reverse complement thereof, in a linked double-stranded DNA. In some embodiments, PR180 can further comprise, at the 5' end, a sequence comprising SRE007, or a reverse complement thereof, in a linked double-stranded DNA. In some embodiments, PR179 can further comprise, at the 5' end, a sequence comprising SRE007, or a reverse complement thereof, in a linked double-stranded DNA.

In some embodiments, PR178 can further comprise, at the 5' end, a sequence comprising SRE007, or a reverse complement thereof, in a linked double-stranded DNA. In some embodiments, PR177 can further comprise, at the 5' end, a sequence comprising SRE007, or a reverse complement thereof, in a linked double-stranded DNA. In some embodiments, PR176 can further comprise, at the 5' end, a sequence comprising SRE007, or a reverse complement thereof, in a linked double-stranded DNA. In some embodiments, PR175 can further comprise, at the 5' end, a sequence comprising SRE007, or a reverse complement thereof, in a linked double-stranded DNA. In some embodiments, PR174 can further comprise, at the 5' end, a sequence comprising SRE007, or a reverse complement thereof, in a linked double-stranded DNA. In some embodiments, PR173 can further comprise, at the 5' end, a sequence comprising SRE007, or a reverse complement thereof, in a linked double-stranded DNA. In some embodiments, PR172 can further comprise, at the 5' end, a sequence comprising SRE007, or a reverse complement thereof, in a linked double-stranded DNA. In some embodiments, PR171 can further comprise, at the 5' end, a sequence comprising SRE007, or a reverse complement thereof, in a linked double-stranded DNA. In some embodiments, PR170 can further comprise, at the 5' end, a sequence comprising SRE007, or a reverse complement thereof, in a linked double-stranded DNA. In some embodiments, PR169 can further comprise, at the 5' end, a sequence comprising SRE007, or a reverse complement thereof, in a linked double-stranded DNA. In some embodiments, PR168 can further comprise, at the 5' end, a sequence comprising SRE007, or a reverse complement thereof, in a linked double-stranded DNA. In some embodiments, PR167 can further comprise, at the 5' end, a sequence comprising SRE007, or a reverse complement thereof, in a linked double-stranded DNA. In some embodiments, PR166 can further comprise, at the 5' end, a sequence comprising SRE007, or a reverse complement thereof, in a linked double-stranded DNA. In some embodiments, PR165 can further comprise, at the 5' end, a sequence comprising SRE007, or a reverse complement thereof, in a linked double-stranded DNA. In some embodiments, PR159 can further comprise, at the 5' end, a sequence comprising SRE007, or a reverse complement thereof, in a linked double-stranded DNA. In some embodiments, PR156 can further comprise, at the 5' end, a sequence comprising SRE007 and SRE010, or a reverse complement thereof, in a linked double-stranded DNA. In some embodiments, PR155 can further comprise, at the 5' end, a sequence comprising SRE007, or a reverse complement thereof, in a linked double-stranded DNA. In some embodiments, PR154 can further comprise, at the 5' end, a sequence comprising SRE007, or a reverse complement thereof, in a linked double-stranded DNA. In some embodiments, PR153 can further comprise, at the 5' end, a sequence comprising SRE007, or a reverse complement thereof, in a linked double-stranded DNA. In some embodiments, PR152 can further comprise, at the 5' end, a sequence comprising SRE007, or a reverse complement thereof, in a linked double-stranded DNA. In some embodiments, PR151 can further comprise, at the 5' end, a sequence comprising SRE007, or a reverse complement thereof, in a linked double-stranded DNA. In some embodiments, PR150 can further comprise, at the 5' end, a sequence comprising SRE007, or a reverse complement thereof, in a linked double-stranded DNA. In some embodiments, PR131 can further comprise, at the 5' end, a sequence comprising SRE007, or a reverse complement thereof, in a linked double-stranded DNA. In some embodiments, SEQ ID NO: 584 can further comprise, at the 5' end, a sequence comprising SRE007, or a reverse complement thereof, in a linked double-stranded DNA. In some embodiments, SEQ ID NO: 585 can further comprise, at the 5' end, a sequence comprising SRE007, or a reverse complement thereof, in a linked double-stranded DNA. In some embodiments, SEQ ID NO: 586 can further comprise, at the 5' end, a sequence comprising SRE007, or a reverse complement thereof, in a linked double-stranded DNA. In some embodiments, SEQ ID NO: 587 can further comprise, at the 5' end, a sequence comprising SRE007, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE008, or a reverse complement thereof, in a vector. In some embodiments, PR180 can further comprise, at the 5' end, a sequence comprising SRE008, or a reverse complement thereof, in a vector. In some embodiments, PR179 can further comprise, at the 5' end, a sequence comprising SRE008, or a reverse complement thereof, in a vector. In some embodiments, PR178 can further comprise, at the 5' end, a sequence comprising SRE008, or a reverse complement thereof, in a vector. In some embodiments, PR177 can further comprise, at the 5' end, a sequence comprising SRE008, or a reverse complement thereof, in a vector. In some embodiments, PR176 can further comprise, at the 5' end, a sequence comprising SRE008, or a reverse complement thereof, in a vector. In some embodiments, PR175 can further comprise, at the 5' end, a sequence comprising SRE008, or a reverse complement thereof, in a vector. In some embodiments, PR174 can further comprise, at the 5' end, a sequence comprising SRE008, or a reverse complement thereof, in a vector. In some embodiments, PR173 can further comprise, at the 5' end, a sequence comprising SRE008, or a reverse complement thereof, in a vector. In some embodiments, PR172 can further comprise, at the 5' end, a sequence comprising SRE008, or a reverse complement thereof, in a vector. In some embodiments, PR171 can further comprise, at the 5' end, a sequence comprising SRE008, or a reverse complement thereof, in a vector. In some embodiments, PR170 can further comprise, at the 5' end, a sequence comprising SRE008, or a reverse complement thereof, in a vector. In some embodiments, PR169 can further comprise, at the 5' end, a sequence comprising SRE008, or a reverse complement thereof, in a vector. In some embodiments, PR168 can further comprise, at the 5' end, a sequence comprising SRE008, or a reverse complement thereof, in a vector. In some embodiments, PR167 can further comprise, at the 5' end, a sequence comprising SRE008, or a reverse complement thereof, in a vector. In some embodiments, PR166 can further comprise, at the 5' end, a sequence comprising SRE008, or a reverse complement thereof, in a vector. In some embodiments, PR165 can further comprise, at the 5' end, a sequence comprising SRE008, or a reverse complement thereof, in a vector. In some embodiments, PR159 can further comprise, at the 5' end, a sequence comprising SRE008, or a reverse complement thereof, in a vector. In some embodiments, PR156 can further comprise, at the 5' end, a sequence comprising SRE008 and SRE010, or a reverse complement thereof, in a vector. In some embodiments, PR155 can further comprise, at the 5' end, a sequence comprising SRE008, or a reverse complement thereof, in a vector. In some embodiments, PR154 can further comprise, at the 5' end, a sequence comprising SRE008, or a reverse complement thereof, in a vector. In some embodiments, PR153 can further comprise, at the 5' end, a sequence comprising SRE008, or a reverse complement thereof, in a vector. In some embodiments, PR152 can further comprise, at the 5' end, a sequence comprising SRE008, or a reverse complement thereof, in a vector. In some embodiments, PR151 can further comprise, at the 5' end, a sequence comprising SRE008, or a reverse complement thereof, in a vector. In some embodiments, PR150 can further comprise, at the 5' end, a sequence comprising SRE008, or a reverse complement thereof, in a vector. In some embodiments, PR131 can further comprise, at the 5' end, a sequence comprising SRE008, or a reverse complement thereof, in a vector. In some embodiments, SEQ ID NO: 584 can further comprise, at the 5' end, a sequence comprising SRE008, or a reverse complement thereof, in a vector. In some embodiments, SEQ ID NO: 585 can further comprise, at the 5' end, a sequence comprising SRE008, or a reverse complement thereof, in a vector. In some embodiments, SEQ ID NO: 586 can further comprise, at the 5' end, a sequence comprising SRE008, or a reverse complement thereof, in a vector. In some embodiments, SEQ ID NO: 587 can further comprise, at the 5' end, a sequence comprising SRE008, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE008, or a reverse complement thereof, in a nanoplasmid. In some embodiments, PR180 can further comprise, at the 5' end, a sequence comprising SRE008, or a reverse complement thereof, in a nanoplasmid. In some embodiments, PR179 can further comprise, at the 5' end, a sequence comprising SRE008, or a reverse complement thereof, in a nanoplasmid. In some embodiments, PR178 can further comprise, at the 5' end, a sequence comprising SRE008, or a reverse complement thereof, in a nanoplasmid. In some embodiments, PR177 can further comprise, at the 5' end, a sequence comprising SRE008, or a reverse complement thereof, in a nanoplasmid. In some embodiments, PR176 can further comprise, at the 5' end, a sequence comprising SRE008, or a reverse complement thereof, in a nanoplasmid. In some embodiments, PR175 can further comprise, at the 5' end, a sequence comprising SRE008, or a reverse complement thereof, in a nanoplasmid. In some embodiments, PR174 can further comprise, at the 5' end, a sequence comprising SRE008, or a reverse complement thereof, in a nanoplasmid. In some embodiments, PR173 can further comprise, at the 5' end, a sequence comprising SRE008, or a reverse complement thereof, in a nanoplasmid. In some embodiments, PR172 can further comprise, at the 5' end, a sequence comprising SRE008, or a reverse complement thereof, in a nanoplasmid. In some embodiments, PR171 can further comprise, at the 5' end, a sequence comprising SRE008, or a reverse complement thereof, in a nanoplasmid. In some embodiments, PR170 can further comprise, at the 5' end, a sequence comprising SRE008, or a reverse complement thereof, in a nanoplasmid. In some embodiments, PR169 can further comprise, at the 5' end, a sequence comprising SRE008, or a reverse complement thereof, in a nanoplasmid. In some embodiments, PR168 can further comprise, at the 5' end, a sequence comprising SRE008, or a reverse complement thereof, in a nanoplasmid. In some embodiments, PR167 can further comprise, at the 5' end, a sequence comprising SRE008, or a reverse complement thereof, in a nanoplasmid. In some embodiments, PR166 can further comprise, at the 5' end, a sequence comprising SRE008, or a reverse complement thereof, in a nanoplasmid. In some embodiments, PR165 can further comprise, at the 5' end, a sequence comprising SRE008, or a reverse complement thereof, in a nanoplasmid. In some embodiments, PR159 can further comprise, at the 5' end, a sequence comprising SRE008, or a reverse complement thereof, in a nanoplasmid. In some embodiments, PR156 can further comprise, at the 5' end, a sequence comprising SRE008 and SRE010, or a reverse complement thereof, in a nanoplasmid. In some embodiments, PR155 can further comprise, at the 5' end, a sequence comprising SRE008, or a reverse complement thereof, in a nanoplasmid. In some embodiments, PR154 can further comprise, at the 5' end, a sequence comprising SRE008, or a reverse complement thereof, in a nanoplasmid. In some embodiments, PR153 can further comprise, at the 5' end, a sequence comprising SRE008, or a reverse complement thereof, in a nanoplasmid. In some embodiments, PR152 can further comprise, at the 5' end, a sequence comprising SRE008, or a reverse complement thereof, in a nanoplasmid. In some embodiments, PR151 can further comprise, at the 5' end, a sequence comprising SRE008, or a reverse complement thereof, in a nanoplasmid. In some embodiments, PR150 can further comprise, at the 5' end, a sequence comprising SRE008, or a reverse complement thereof, in a nanoplasmid. In some embodiments, PR131 can further comprise, at the 5' end, a sequence comprising SRE008, or a reverse complement thereof, in a nanoplasmid. In some embodiments, SEQ ID NO: 584 can further comprise, at the 5' end, a sequence comprising SRE008, or a reverse complement thereof, in a nanoplasmid. In some embodiments, SEQ ID NO: 585 can further comprise, at the 5' end, a sequence comprising SRE008, or a reverse complement thereof, in a nanoplasmid. In some embodiments, SEQ ID NO: 586 can further comprise, at the 5' end, a sequence comprising SRE008, or a reverse complement thereof, in a nanoplasmid. In some embodiments, SEQ ID NO: 587 can further comprise, at the 5' end, a sequence comprising SRE008, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE008, or a reverse complement thereof, in a linked double-stranded DNA. In some embodiments, PR180 can further comprise, at the 5' end, a sequence comprising SRE008, or a reverse complement thereof, in a linked double-stranded DNA. In some embodiments, PR179 can further comprise, at the 5' end, a sequence comprising SRE008, or a reverse complement thereof, in a linked double-stranded DNA. In some embodiments, PR178 can further comprise, at the 5' end, a sequence comprising SRE008, or a reverse complement thereof, in a linked double-stranded DNA. In some embodiments, PR177 can further comprise, at the 5' end, a sequence comprising SRE008, or a reverse complement thereof, in a linked double-stranded DNA. In some embodiments, PR176 can further comprise, at the 5' end, a sequence comprising SRE008, or a reverse complement thereof, in a linked double-stranded DNA. In some embodiments, PR175 can further comprise, at the 5' end, a sequence comprising SRE008, or a reverse complement thereof, in a linked double-stranded DNA. In some embodiments, PR174 can further comprise, at the 5' end, a sequence comprising SRE008, or a reverse complement thereof, in a linked double-stranded DNA. In some embodiments, PR173 can further comprise, at the 5' end, a sequence comprising SRE008, or a reverse complement thereof, in a linked double-stranded DNA. In some embodiments, PR172 can further comprise, at the 5' end, a sequence comprising SRE008, or a reverse complement thereof, in a linked double-stranded DNA. In some embodiments, PR171 can further comprise, at the 5' end, a sequence comprising SRE008, or a reverse complement thereof, in a linked double-stranded DNA. In some embodiments, PR170 can further comprise, at the 5' end, a sequence comprising SRE008, or a reverse complement thereof, in a linked double-stranded DNA. In some embodiments, PR169 can further comprise, at the 5' end, a sequence comprising SRE008, or a reverse complement thereof, in a linked double-stranded DNA. In some embodiments, PR168 can further comprise, at the 5' end, a sequence comprising SRE008, or a reverse complement thereof, in a linked double-stranded DNA. In some embodiments, PR167 can further comprise, at the 5' end, a sequence comprising SRE008, or a reverse complement thereof, in a linked double-stranded DNA. In some embodiments, PR166 can further comprise, at the 5' end, a sequence comprising SRE008, or a reverse complement thereof, in a linked double-stranded DNA. In some embodiments, PR165 can further comprise, at the 5' end, a sequence comprising SRE008, or a reverse complement thereof, in a linked double-stranded DNA. In some embodiments, PR159 can further comprise, at the 5' end, a sequence comprising SRE008, or a reverse complement thereof, in a linked double-stranded DNA. In some embodiments, PR156 can further comprise, at the 5' end, a sequence comprising SRE008 and SRE010, or a reverse complement thereof, in a linked double-stranded DNA. In some embodiments, PR155 can further comprise, at the 5' end, a sequence comprising SRE008, or a reverse complement thereof, in a linked double-stranded DNA. In some embodiments, PR154 can further comprise, at the 5' end, a sequence comprising SRE008, or a reverse complement thereof, in a linked double-stranded DNA. In some embodiments, PR153 can further comprise, at the 5' end, a sequence comprising SRE008, or a reverse complement thereof, in a linked double-stranded DNA. In some embodiments, PR152 can further comprise, at the 5' end, a sequence comprising SRE008, or a reverse complement thereof, in a linked double-stranded DNA. In some embodiments, PR151 can further comprise, at the 5' end, a sequence comprising SRE008, or a reverse complement thereof, in a linked double-stranded DNA. In some embodiments, PR150 can further comprise, at the 5' end, a sequence comprising SRE008, or a reverse complement thereof, in a linked double-stranded DNA. In some embodiments, PR131 can further comprise, at the 5' end, a sequence comprising SRE008, or a reverse complement thereof, in a linked double-stranded DNA. In some embodiments, SEQ ID NO: 584 can further comprise, at the 5' end, a sequence comprising SRE008, or a reverse complement thereof, in a linked double-stranded DNA. In some embodiments, SEQ ID NO: 585 can further comprise, at the 5' end, a sequence comprising SRE008, or a reverse complement thereof, in a linked double-stranded DNA. In some embodiments, SEQ ID NO: 586 can further comprise, at the 5' end, a sequence comprising SRE008, or a reverse complement thereof, in a linked double-stranded DNA. In some embodiments, SEQ ID NO: 587 can further comprise, at the 5' end, a sequence comprising SRE008, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE010, or a reverse complement thereof, in a vector. In some embodiments, PR180 can further comprise, at the 5' end, a sequence comprising SRE010, or a reverse complement thereof, in a vector. In some embodiments, PR179 can further comprise, at the 5' end, a sequence comprising SRE010, or a reverse complement thereof, in a vector. In some embodiments, PR178 can further comprise, at the 5' end, a sequence comprising SRE010, or a reverse complement thereof, in a vector. In some embodiments, PR177 can further comprise, at the 5' end, a sequence comprising SRE010, or a reverse complement thereof, in a vector. In some embodiments, PR176 can further comprise, at the 5' end, a sequence comprising SRE010, or a reverse complement thereof, in a vector. In some embodiments, PR175 can further comprise, at the 5' end, a sequence comprising SRE010, or a reverse complement thereof, in a vector. In some embodiments, PR174 can further comprise, at the 5' end, a sequence comprising SRE010, or a reverse complement thereof, in a vector. In some embodiments, PR173 can further comprise, at the 5' end, a sequence comprising SRE010, or a reverse complement thereof, in a vector. In some embodiments, PR172 can further comprise, at the 5' end, a sequence comprising SRE010, or a reverse complement thereof, in a vector. In some embodiments, PR171 can further comprise, at the 5' end, a sequence comprising SRE010, or a reverse complement thereof, in a vector. In some embodiments, PR170 can further comprise, at the 5' end, a sequence comprising SRE010, or a reverse complement thereof, in a vector. In some embodiments, PR169 can further comprise, at the 5' end, a sequence comprising SRE010, or a reverse complement thereof, in a vector. In some embodiments, PR168 can further comprise, at the 5' end, a sequence comprising SRE010, or a reverse complement thereof, in a vector. In some embodiments, PR167 can further comprise, at the 5' end, a sequence comprising SRE010, or a reverse complement thereof, in a vector. In some embodiments, PR166 can further comprise, at the 5' end, a sequence comprising SRE010, or a reverse complement thereof, in a vector. In some embodiments, PR165 can further comprise, at the 5' end, a sequence comprising SRE010, or a reverse complement thereof, in a vector. In some embodiments, PR159 can further comprise, at the 5' end, a sequence comprising SRE010, or a reverse complement thereof, in a vector. In some embodiments, PR156 can further comprise, at the 5' end, a sequence comprising SRE010 and SRE010, or a reverse complement thereof, in a vector. In some embodiments, PR155 can further comprise, at the 5' end, a sequence comprising SRE010, or a reverse complement thereof, in a vector. In some embodiments, PR154 can further comprise, at the 5' end, a sequence comprising SRE010, or a reverse complement thereof, in a vector. In some embodiments, PR153 can further comprise, at the 5' end, a sequence comprising SRE010, or a reverse complement thereof, in a vector. In some embodiments, PR152 can further comprise, at the 5' end, a sequence comprising SRE010, or a reverse complement thereof, in a vector. In some embodiments, PR151 can further comprise, at the 5' end, a sequence comprising SRE010, or a reverse complement thereof, in a vector. In some embodiments, PR150 can further comprise, at the 5' end, a sequence comprising SRE010, or a reverse complement thereof, in a vector. In some embodiments, PR131 can further comprise, at the 5' end, a sequence comprising SRE010, or a reverse complement thereof, in a vector. In some embodiments, SEQ ID NO: 584 can further comprise, at the 5' end, a sequence comprising SRE010, or a reverse complement thereof, in a vector. In some embodiments, SEQ ID NO: 585 can further comprise, at the 5' end, a sequence comprising SRE010, or a reverse complement thereof, in a vector.. In some embodiments, SEQ ID NO: 586 can further comprise, at the 5' end, a sequence comprising SRE010, or a reverse complement thereof, in a vector. In some embodiments, SEQ ID NO: 587 can further comprise, at the 5' end, a sequence comprising SRE010, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE010, or a reverse complement thereof, in a nanoplasmid. In some embodiments, PR180 can further comprise, at the 5' end, a sequence comprising SRE010, or a reverse complement thereof, in a nanoplasmid. In some embodiments, PR179 can further comprise, at the 5' end, a sequence comprising SRE010, or a reverse complement thereof, in a nanoplasmid. In some embodiments, PR178 can further comprise, at the 5' end, a sequence comprising SRE010, or a reverse complement thereof, in a nanoplasmid. In some embodiments, PR177 can further comprise, at the 5' end, a sequence comprising SRE010, or a reverse complement thereof, in a nanoplasmid. In some embodiments, PR176 can further comprise, at the 5' end, a sequence comprising SRE010, or a reverse complement thereof, in a nanoplasmid. In some embodiments, PR175 can further comprise, at the 5' end, a sequence comprising SRE010, or a reverse complement thereof, in a nanoplasmid. In some embodiments, PR174 can further comprise, at the 5' end, a sequence comprising SRE010, or a reverse complement thereof, in a nanoplasmid. In some embodiments, PR173 can further comprise, at the 5' end, a sequence comprising SRE010, or a reverse complement thereof, in a nanoplasmid. In some embodiments, PR172 can further comprise, at the 5' end, a sequence comprising SRE010, or a reverse complement thereof, in a nanoplasmid. In some embodiments, PR171 can further comprise, at the 5' end, a sequence comprising SRE010, or a reverse complement thereof, in a nanoplasmid. In some embodiments, PR170 can further comprise, at the 5' end, a sequence comprising SRE010, or a reverse complement thereof, in a nanoplasmid. In some embodiments, PR169 can further comprise, at the 5' end, a sequence comprising SRE010, or a reverse complement thereof, in a nanoplasmid. In some embodiments, PR168 can further comprise, at the 5' end, a sequence comprising SRE010, or a reverse complement thereof, in a nanoplasmid. In some embodiments, PR167 can further comprise, at the 5' end, a sequence comprising SRE010, or a reverse complement thereof, in a nanoplasmid. In some embodiments, PR166 can further comprise, at the 5' end, a sequence comprising SRE010, or a reverse complement thereof, in a nanoplasmid. In some embodiments, PR165 can further comprise, at the 5' end, a sequence comprising SRE010, or a reverse complement thereof, in a nanoplasmid. In some embodiments, PR159 can further comprise, at the 5' end, a sequence comprising SRE010, or a reverse complement thereof, in a nanoplasmid. In some embodiments, PR156 can further comprise, at the 5' end, a sequence comprising SRE010 and SRE010, or a reverse complement thereof, in a nanoplasmid. In some embodiments, PR155 can further comprise, at the 5' end, a sequence comprising SRE010, or a reverse complement thereof, in a nanoplasmid. In some embodiments, PR154 can further comprise, at the 5' end, a sequence comprising SRE010, or a reverse complement thereof, in a nanoplasmid. In some embodiments, PR153 can further comprise, at the 5' end, a sequence comprising SRE010, or a reverse complement thereof, in a nanoplasmid. In some embodiments, PR152 can further comprise, at the 5' end, a sequence comprising SRE010, or a reverse complement thereof, in a nanoplasmid. In some embodiments, PR151 can further comprise, at the 5' end, a sequence comprising SRE010, or a reverse complement thereof, in a nanoplasmid. In some embodiments, PR150 can further comprise, at the 5' end, a sequence comprising SRE010, or a reverse complement thereof, in a nanoplasmid. In some embodiments, PR131 can further comprise, at the 5' end, a sequence comprising SRE010, or a reverse complement thereof, in a nanoplasmid. In some embodiments, SEQ ID NO: 584 can further comprise, at the 5' end, a sequence comprising SRE010, or a reverse complement thereof, in a nanoplasmid. In some embodiments, SEQ ID NO: 585 can further comprise, at the 5' end, a sequence comprising SRE010, or a reverse complement thereof, in a nanoplasmid. In some embodiments, SEQ ID NO: 586 can further comprise, at the 5' end, a sequence comprising SRE010, or a reverse complement thereof, in a nanoplasmid. In some embodiments, SEQ ID NO: 587 can further comprise, at the 5' end, a sequence comprising SRE010, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE010, or a reverse complement thereof, in a linked double-stranded DNA. In some embodiments, PR180 can further comprise, at the 5' end, a sequence comprising SRE010, or a reverse complement thereof, in a linked double-stranded DNA. In some embodiments, PR179 can further comprise, at the 5' end, a sequence comprising SRE010, or a reverse complement thereof, in a linked double-stranded DNA. In some embodiments, PR178 can further comprise, at the 5' end, a sequence comprising SRE010, or a reverse complement thereof, in a linked double-stranded DNA. In some embodiments, PR177 can further comprise, at the 5' end, a sequence comprising SRE010, or a reverse complement thereof, in a linked double-stranded DNA. In some embodiments, PR176 can further comprise, at the 5' end, a sequence comprising SRE010, or a reverse complement thereof, in a linked double-stranded DNA. In some embodiments, PR175 can further comprise, at the 5' end, a sequence comprising SRE010, or a reverse complement thereof, in a linked double-stranded DNA. In some embodiments, PR174 can further comprise, at the 5' end, a sequence comprising SRE010, or a reverse complement thereof, in a linked double-stranded DNA. In some embodiments, PR173 can further comprise, at the 5' end, a sequence comprising SRE010, or a reverse complement thereof, in a linked double-stranded DNA. In some embodiments, PR172 can further comprise, at the 5' end, a sequence comprising SRE010, or a reverse complement thereof, in a linked double-stranded DNA. In some embodiments, PR171 can further comprise, at the 5' end, a sequence comprising SRE010, or a reverse complement thereof, in a linked double-stranded DNA. In some embodiments, PR170 can further comprise, at the 5' end, a sequence comprising SRE010, or a reverse complement thereof, in a linked double-stranded DNA. In some embodiments, PR169 can further comprise, at the 5' end, a sequence comprising SRE010, or a reverse complement thereof, in a linked double-stranded DNA. In some embodiments, PR168 can further comprise, at the 5' end, a sequence comprising SRE010, or a reverse complement thereof, in a linked double-stranded DNA. In some embodiments, PR167 can further comprise, at the 5' end, a sequence comprising SRE010, or a reverse complement thereof, in a linked double-stranded DNA. In some embodiments, PR166 can further comprise, at the 5' end, a sequence comprising SRE010, or a reverse complement thereof, in a linked double-stranded DNA. In some embodiments, PR165 can further comprise, at the 5' end, a sequence comprising SRE010, or a reverse complement thereof, in a linked double-stranded DNA. In some embodiments, PR159 can further comprise, at the 5' end, a sequence comprising SRE010, or a reverse complement thereof, in a linked double-stranded DNA. In some embodiments, PR156 can further comprise, at the 5' end, a sequence comprising SRE010 and SRE010, or a reverse complement thereof, in a linked double-stranded DNA. In some embodiments, PR155 can further comprise, at the 5' end, a sequence comprising SRE010, or a reverse complement thereof, in a linked double-stranded DNA. In some embodiments, PR154 can further comprise, at the 5' end, a sequence comprising SRE010, or a reverse complement thereof, in a linked double-stranded DNA. In some embodiments, PR153 can further comprise, at the 5' end, a sequence comprising SRE010, or a reverse complement thereof, in a linked double-stranded DNA. In some embodiments, PR152 can further comprise, at the 5' end, a sequence comprising SRE010, or a reverse complement thereof, in a linked double-stranded DNA. In some embodiments, PR151 can further comprise, at the 5' end, a sequence comprising SRE010, or a reverse complement thereof, in a linked double-stranded DNA. In some embodiments, PR150 can further comprise, at the 5' end, a sequence comprising SRE010, or a reverse complement thereof, in a linked double-stranded DNA. In some embodiments, PR131 can further comprise, at the 5' end, a sequence comprising SRE010, or a reverse complement thereof, in a linked double-stranded DNA. In some embodiments, SEQ ID NO: 584 can further comprise, at the 5' end, a sequence comprising SRE010, or a reverse complement thereof, in a linked double-stranded DNA. In some embodiments, SEQ ID NO: 585 can further comprise, at the 5' end, a sequence comprising SRE010, or a reverse complement thereof, in a linked double-stranded DNA. In some embodiments, SEQ ID NO: 586 can further comprise, at the 5' end, a sequence comprising SRE010, or a reverse complement thereof, in a linked double-stranded DNA. In some embodiments, SEQ ID NO: 587 can further comprise, at the 5' end, a sequence comprising SRE010, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012, or a reverse complement thereof, in a vector. In some embodiments, PR180 can further comprise, at the 5' end, a sequence comprising SRE012, or a reverse complement thereof, in a vector. In some embodiments, PR179 can further comprise, at the 5' end, a sequence comprising SRE012, or a reverse complement thereof, in a vector. In some embodiments, PR178 can further comprise, at the 5' end, a sequence comprising SRE012, or a reverse complement thereof, in a vector. In some embodiments, PR177 can further comprise, at the 5' end, a sequence comprising SRE012, or a reverse complement thereof, in a vector. In some embodiments, PR176 can further comprise, at the 5' end, a sequence comprising SRE012, or a reverse complement thereof, in a vector. In some embodiments, PR175 can further comprise, at the 5' end, a sequence comprising SRE012, or a reverse complement thereof, in a vector. In some embodiments, PR174 can further comprise, at the 5' end, a sequence comprising SRE012, or a reverse complement thereof, in a vector. In some embodiments, PR173 can further comprise, at the 5' end, a sequence comprising SRE012, or a reverse complement thereof, in a vector. In some embodiments, PR172 can further comprise, at the 5' end, a sequence comprising SRE012, or a reverse complement thereof, in a vector. In some embodiments, PR171 can further comprise, at the 5' end, a sequence comprising SRE012, or a reverse complement thereof, in a vector. In some embodiments, PR170 can further comprise, at the 5' end, a sequence comprising SRE012, or a reverse complement thereof, in a vector. In some embodiments, PR169 can further comprise, at the 5' end, a sequence comprising SRE012, or a reverse complement thereof, in a vector. In some embodiments, PR168 can further comprise, at the 5' end, a sequence comprising SRE012, or a reverse complement thereof, in a vector. In some embodiments, PR167 can further comprise, at the 5' end, a sequence comprising SRE012, or a reverse complement thereof, in a vector. In some embodiments, PR166 can further comprise, at the 5' end, a sequence comprising SRE012, or a reverse complement thereof, in a vector. In some embodiments, PR165 can further comprise, at the 5' end, a sequence comprising SRE012, or a reverse complement thereof, in a vector. In some embodiments, PR159 can further comprise, at the 5' end, a sequence comprising SRE012, or a reverse complement thereof, in a vector. In some embodiments, PR156 can further comprise, at the 5' end, a sequence comprising SRE012, or a reverse complement thereof, in a vector. In some embodiments, PR155 can further comprise, at the 5' end, a sequence comprising SRE012, or a reverse complement thereof, in a vector. In some embodiments, PR154 can further comprise, at the 5' end, a sequence comprising SRE012, or a reverse complement thereof, in a vector. In some embodiments, PR153 can further comprise, at the 5' end, a sequence comprising SRE012, or a reverse complement thereof, in a vector. In some embodiments, PR152 can further comprise, at the 5' end, a sequence comprising SRE012, or a reverse complement thereof, in a vector. In some embodiments, PR151 can further comprise, at the 5' end, a sequence comprising SRE012, or a reverse complement thereof, in a vector. In some embodiments, PR150 can further comprise, at the 5' end, a sequence comprising SRE012, or a reverse complement thereof, in a vector. In some embodiments, PR131 can further comprise, at the 5' end, a sequence comprising SRE012, or a reverse complement thereof, in a vector. In some embodiments, SEQ ID NO: 584 can further comprise, at the 5' end, a sequence comprising SRE012, or a reverse complement thereof, in a vector. In some embodiments, SEQ ID NO: 585 can further comprise, at the 5' end, a sequence comprising SRE012, or a reverse complement thereof, in a vector. In some embodiments, SEQ ID NO: 586 can further comprise, at the 5' end, a sequence comprising SRE012, or a reverse complement thereof, in a vector. In some embodiments, SEQ ID NO: 587 can further comprise, at the 5' end, a sequence comprising SRE012, or a reverse complement thereof, in a vector. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012, or a reverse complement thereof, in a nanoplasmid. In some embodiments, PR180 can further comprise, at the 5' end, a sequence comprising SRE012, or a reverse complement thereof, in a nanoplasmid. In some embodiments, PR179 can further comprise, at the 5' end, a sequence comprising SRE012, or a reverse complement thereof, in a nanoplasmid. In some embodiments, PR178 can further comprise, at the 5' end, a sequence comprising SRE012, or a reverse complement thereof, in a nanoplasmid. In some embodiments, PR177 can further comprise, at the 5' end, a sequence comprising SRE012, or a reverse complement thereof, in a nanoplasmid. In some embodiments, PR176 can further comprise, at the 5' end, a sequence comprising SRE012, or a reverse complement thereof, in a nanoplasmid. In some embodiments, PR175 can further comprise, at the 5' end, a sequence comprising SRE012, or a reverse complement thereof, in a nanoplasmid. In some embodiments, PR174 can further comprise, at the 5' end, a sequence comprising SRE012, or a reverse complement thereof, in a nanoplasmid. In some embodiments, PR173 can further comprise, at the 5' end, a sequence comprising SRE012, or a reverse complement thereof, in a nanoplasmid. In some embodiments, PR172 can further comprise, at the 5' end, a sequence comprising SRE012, or a reverse complement thereof, in a nanoplasmid. In some embodiments, PR171 can further comprise, at the 5' end, a sequence comprising SRE012, or a reverse complement thereof, in a nanoplasmid. In some embodiments, PR170 can further comprise, at the 5' end, a sequence comprising SRE012, or a reverse complement thereof, in a nanoplasmid. In some embodiments, PR169 can further comprise, at the 5' end, a sequence comprising SRE012, or a reverse complement thereof, in a nanoplasmid. In some embodiments, PR168 can further comprise, at the 5' end, a sequence comprising SRE012, or a reverse complement thereof, in a nanoplasmid. In some embodiments, PR167 can further comprise, at the 5' end, a sequence comprising SRE012, or a reverse complement thereof, in a nanoplasmid. In some embodiments, PR166 can further comprise, at the 5' end, a sequence comprising SRE012, or a reverse complement thereof, in a nanoplasmid. In some embodiments, PR165 can further comprise, at the 5' end, a sequence comprising SRE012, or a reverse complement thereof, in a nanoplasmid. In some embodiments, PR159 can further comprise, at the 5' end, a sequence comprising SRE012, or a reverse complement thereof, in a nanoplasmid. In some embodiments, PR156 can further comprise, at the 5' end, a sequence comprising SRE012, or a reverse complement thereof, in a nanoplasmid. In some embodiments, PR155 can further comprise, at the 5' end, a sequence comprising SRE012, or a reverse complement thereof, in a nanoplasmid. In some embodiments, PR154 can further comprise, at the 5' end, a sequence comprising SRE012, or a reverse complement thereof, in a nanoplasmid. In some embodiments, PR153 can further comprise, at the 5' end, a sequence comprising SRE012, or a reverse complement thereof, in a nanoplasmid. In some embodiments, PR152 can further comprise, at the 5' end, a sequence comprising SRE012, or a reverse complement thereof, in a nanoplasmid. In some embodiments, PR151 can further comprise, at the 5' end, a sequence comprising SRE012, or a reverse complement thereof, in a nanoplasmid. In some embodiments, PR150 can further comprise, at the 5' end, a sequence comprising SRE012, or a reverse complement thereof, in a nanoplasmid. In some embodiments, PR131 can further comprise, at the 5' end, a sequence comprising SRE012, or a reverse complement thereof, in a nanoplasmid. In some embodiments, SEQ ID NO: 584 can further comprise, at the 5' end, a sequence comprising SRE012, or a reverse complement thereof, in a nanoplasmid. In some embodiments, SEQ ID NO: 585 can further comprise, at the 5' end, a sequence comprising SRE012, or a reverse complement thereof, in a nanoplasmid. In some embodiments, SEQ ID NO: 586 can further comprise, at the 5' end, a sequence comprising SRE012, or a reverse complement thereof, in a nanoplasmid. In some embodiments, SEQ ID NO: 587 can further comprise, at the 5' end, a sequence comprising SRE012, or a reverse complement thereof, in a nanoplasmid. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, PR181 can further comprise, at the 5' end, a sequence comprising SRE012, or a reverse complement thereof, in a linked double-stranded DNA. In some embodiments, PR180 can further comprise, at the 5' end, a sequence comprising SRE012, or a reverse complement thereof, in a linked double-stranded DNA. In some embodiments, PR179 can further comprise, at the 5' end, a sequence comprising SRE012, or a reverse complement thereof, in a linked double-stranded DNA. In some embodiments, PR178 can further comprise, at the 5' end, a sequence comprising SRE012, or a reverse complement thereof, in a linked double-stranded DNA. In some embodiments, PR177 can further comprise, at the 5' end, a sequence comprising SRE012, or a reverse complement thereof, in a linked double-stranded DNA. In some embodiments, PR176 can further comprise, at the 5' end, a sequence comprising SRE012, or a reverse complement thereof, in a linked double-stranded DNA. In some embodiments, PR175 can further comprise, at the 5' end, a sequence comprising SRE012, or a reverse complement thereof, in a linked double-stranded DNA. In some embodiments, PR174 can further comprise, at the 5' end, a sequence comprising SRE012, or a reverse complement thereof, in a linked double-stranded DNA. In some embodiments, PR173 can further comprise, at the 5' end, a sequence comprising SRE012, or a reverse complement thereof, in a linked double-stranded DNA. In some embodiments, PR172 can further comprise, at the 5' end, a sequence comprising SRE012, or a reverse complement thereof, in a linked double-stranded DNA. In some embodiments, PR171 can further comprise, at the 5' end, a sequence comprising SRE012, or a reverse complement thereof, in a linked double-stranded DNA. In some embodiments, PR170 can further comprise, at the 5' end, a sequence comprising SRE012, or a reverse complement thereof, in a linked double-stranded DNA. In some embodiments, PR169 can further comprise, at the 5' end, a sequence comprising SRE012, or a reverse complement thereof, in a linked double-stranded DNA. In some embodiments, PR168 can further comprise, at the 5' end, a sequence comprising SRE012, or a reverse complement thereof, in a linked double-stranded DNA. In some embodiments, PR167 can further comprise, at the 5' end, a sequence comprising SRE012, or a reverse complement thereof, in a linked double-stranded DNA. In some embodiments, PR166 can further comprise, at the 5' end, a sequence comprising SRE012, or a reverse complement thereof, in a linked double-stranded DNA. In some embodiments, PR165 can further comprise, at the 5' end, a sequence comprising SRE012, or a reverse complement thereof, in a linked double-stranded DNA. In some embodiments, PR159 can further comprise, at the 5' end, a sequence comprising SRE012, or a reverse complement thereof, in a linked double-stranded DNA. In some embodiments, PR156 can further comprise, at the 5' end, a sequence comprising SRE012, or a reverse complement thereof, in a linked double-stranded DNA. In some embodiments, PR155 can further comprise, at the 5' end, a sequence comprising SRE012, or a reverse complement thereof, in a linked double-stranded DNA. In some embodiments, PR154 can further comprise, at the 5' end, a sequence comprising SRE012, or a reverse complement thereof, in a linked double-stranded DNA. In some embodiments, PR153 can further comprise, at the 5' end, a sequence comprising SRE012, or a reverse complement thereof, in a linked double-stranded DNA. In some embodiments, PR152 can further comprise, at the 5' end, a sequence comprising SRE012, or a reverse complement thereof, in a linked double-stranded DNA. In some embodiments, PR151 can further comprise, at the 5' end, a sequence comprising SRE012, or a reverse complement thereof, in a linked double-stranded DNA. In some embodiments, PR150 can further comprise, at the 5' end, a sequence comprising SRE012, or a reverse complement thereof, in a linked double-stranded DNA. In some embodiments, PR131 can further comprise, at the 5' end, a sequence comprising SRE012, or a reverse complement thereof, in a linked double-stranded DNA. In some embodiments, SEQ ID NO: 584 can further comprise, at the 5' end, a sequence comprising SRE012, or a reverse complement thereof, in a linked double-stranded DNA. In some embodiments, SEQ ID NO: 585 can further comprise, at the 5' end, a sequence comprising SRE012, or a reverse complement thereof, in a linked double-stranded DNA. In some embodiments, SEQ ID NO: 586 can further comprise, at the 5' end, a sequence comprising SRE012, or a reverse complement thereof, in a linked double-stranded DNA. In some embodiments, SEQ ID NO: 587 can further comprise, at the 5' end, a sequence comprising SRE012, or a reverse complement thereof, in a linked double-stranded DNA. In some embodiments, any of these named elements can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a nucleic acid having any of these named elements and any of SEQ ID NOs: 584-587 can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

In some embodiments, the disclosure provides for a nucleic acid comprising any of the sequences described herein separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, the nucleic acid can comprise any of the sequences listed in Table 1B or any one of the sequences listed in Table 1J separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some embodiments, a sequence comprising any of nucleic acid sequences listed in Table 1B and any one of the core promoter sequences listed in Table 1J can be separated by a linker of variable length, wherein the linker can comprise a sequence of 1, 2, 5, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides.

EXAMPLES

These examples are provided for illustrative purposes only and not to limit the scope of the claims provided herein.

Example 1: Development of a High-Throughput Screening Platform for Novel Cancer-Activated Promoters In this example, a high-throughput screening (HTS) platform to design and test synthetic sequence elements that can drive cancer specific expression of a report gene or a gene of interest. Synthetic promoters described herein comprise a core promoter and one or more response elements. Response elements can be designed by tiling binding sites for putative transcription factor candidates identified through transcriptomics and proteomics. Using Massively Parallel Reporter Assay (MPRA) method, 1,800 unique synthetic response elements placed in front of (5' end of) the two different core promoters were screened. Synthetic promoters were able to drive expression up to 80 times higher than the previously described FOS-coreBIRC5 synthetic promoter. In addition, TF tiles for TCF7 (a downstream target of the WNT signaling pathway) and TPS3 (a tumor suppressor that is mutated in many cancers) that can drive expression 100 times or more within a specific lung cancer cell line that represents a specific pathway dysregulation were identified. The MPRA platform allows simultaneously testing thousands of hypotheses from the multi-omics identification of key transcription factors in cancer combined with different design strategies for a functioning response element, as demonstrated in this example. Low-throughput validation demonstrated that the MPRA accurately identifies winning candidates from thousands of test sequences. This MPRA pipeline is a key component of the workflow to develop and test hypotheses for cancer-regulated gene expression at a massive, highly parallelized scale. The MPRA can be performed by assembling a pooled library of reporter plasmids that interrogate the function of a candidate DNA sequence through an expressed barcode. The pool of reporter plasmids can be transfected into mammalian cell lines and then harvested for RNA. The barcodes from the mRNA and the input DNA can be sequenced using Next Generation sequencing techniques. The input DNA barcode can be used to normalize the mRNA barcode to get the final expression level for each candidate DNA sequence.

Genes are highly regulated by a complex collaboration between the transcription factors downstream of signaling pathways and the DNA regulatory elements they interact with. These DNA regulatory elements include promoters, 5' and 3'UTRs, and distal and proximal enhancers. Cancer is marked by aberrant molecular signaling leading to highly active transcription factors and functional signaling cascades that might normally only be found in early development or in other disease states, leading to hallmark cancer phonotypes such as uncontrolled growth and invasion/metastasis. The regulatory elements of these dysregulated genes can be re-used in exogenous vectors to drive expression that is restricted to cancer cells. For example, the promoters for Survivin and hTERT have been used exogenously to drive tumor specific expression. Although endogenous promoters can be used as cancer-activated regulatory elements, by having highly complex logic and interplay of multiple transcription factor binding sites, they can be unpredictable and have higher basal activity than desired. Endogenous promoters also rarely drive very high signal even in the correct cell-state or genomic profile to activate TFs, as few natural promoters have been naturally evolved to have the high level of expression observed in the constitutive viral-origin promoters often used in gene therapy.

A stronger, and more predictably activated promoter can be engineered by bringing together diverse regulatory elements that respond to a variety of signaling pathways that might not be found in a single regulatory element. For these reasons, a synthetic approach has been developed to construct novel cancer-activated promoters, as further described in Example 2.

Synthetic promoters were constructed by combining a small core promoter from a gene upregulated in cancer with synthetic response elements to particular dysregulated TFs. These response elements comprise a series of repeated binding sites for the desired TFs. Various "-omics" based approaches have been used to identify TFs that are enriched in tumor targets, and hundreds of possible candidate TFs have been identified. Each of those TFs has many possible binding sites and configurations that can create the most efficacious response element. As testing each individual candidate element in series can be costly in labor and time, a high-throughput approach was used to test thousands of synthetic promoter elements simultaneously.

The screening assay that most closely aligns with the vector design and transient delivery platform described herein is the MPRA (Massively Parallel Reporter Assay). In this assay, short oligos containing a sequence of interest coupled with a unique barcode was synthesized and cloned as a pool into a reporter plasmid. This plasmid pool was transfected into a cell line and the expression of each sequence of interest was measured in parallel through targeted barcode sequencing of the RNA and plasmid DNA. MPRAs have been used to identify endogenous human enhancers, determine the role of genetic variation on gene expression, and characterize sequence determinants of gene regulation. This screening assay is an ideal method to simultaneously test and identify synthetic promoters that drive strong expression in relevant cancer models.

A high-throughput screening platform (MPRA) to identify novel synthetic promoters that can drive cancer-activated expression is described in this example.

High-Throughput Screening (HTS) Methodology Overview

The MPRA was performed by assembling a pooled library of reporter plasmids that interrogate the function of a candidate DNA sequence through an expressed barcode. The pool of reporter plasmids was transfected into mammalian cell lines and then harvested for RNA. The barcodes from the mRNA and the input DNA were sequenced using Next Generation sequencing (NGS) techniques. The input DNA barcode was used to normalize the mRNA barcode to get the final expression level for each candidate DNA sequence.

Homotypic TF Tile Library Design

A computational pipeline that systematically creates synthetic DNA sequences that contain repeated TF binding sites (TF tiles) was developed using the following parameters:

1. Total Length: The full length of the synthetic DNA sequence. A length of 140 bp was used.
2. Total Number of Binding Sites in a Tile: The number of repeated binding sites that make up the homotypic TF tile. 6 repeated binding sites were used.
3. Spacing: The number of nucleotides between each of the TF binding sites. 0, 3, 7, and 10 bp spacing were used.
4. Binding Site Sequence: The binding site sequences for each tile were chosen using the TF's position frequency matrix (PFM) from either the HOMER or JASPAR database. The pipeline used the frequency of each nucleotide at each position and chose the most frequent nucleotide or nucleotides based on a user defined frequency cut off. Once a nucleotide was chosen for one position all other positions were assigned the most frequent nucleotide. The pipeline used a 10% cut off and focused on the positions at the core of the motif. For example, if at the center position the frequency of A, T, C, G is 5%, 5%, 30%, 60%, respectively, then two binding sites were chosen. One would have a C and the other would have a G and all other positions would have the highest frequency nucleotide.

In addition, the pipeline has the following features:

1. Length Consistency: For TF tiles that were shorter than the total length, a small filler sequence was added to the 5' end. This short sequence was randomly chosen from a 1 kb filler sequence that was manually curated to reduce strong binding site for characterized TFs. This created synthetic DNA sequences that were the same length with little to no effect on the overall expression.
2. Restriction Enzyme Check: Each synthetic DNA sequence was checked for restriction enzyme cut sites used in the cloning method. In this example, the KpnI and XbaI cut sites were used and checked.
3. Addition of Cloning Sequences: Primer sites and restriction enzyme sites were added to facilitate the cloning workflow.
4. Addition of Barcodes: A unique barcode was added to each synthetic DNA sequence. These barcodes were created using the DNABarcodes R package. This package created large numbers of barcodes that were different enough from each other that when mutations were introduced during the sequencing and library preparation the barcodes were still distinguishable.

Using the pipeline described above, homotypic TF Tiles for 77 Lung adenocarcinoma (LUAD) specific TFs were designed. These TF were computationally identified using various multiomic data sets, including RNA-seq and proteomics (see Example 2). A full list of TFs can be found in Table 1D-1I. 24 TF tiles were designed for each TF (6 binding site variations each with 4 different spacing variants: 0, 3, 7, 10 bp). Each tile was assigned 6 barcodes for a total of 144 DNA sequences for each TF. Additionally, positive expression controls and controls for the baseline core promoter expression were included. The positive expression controls include FOSL and Canscript (see Example 2), and 90 barcodes were assigned to each. Baseline expression controls comprised 5 different 140 bp segments of the filler sequence (curated to remove all strong TF binding sites) that were assigned 30 barcodes for a total of 150. An oligo pool of ~12,000 oligos containing the synthetic TF tile, the assigned barcode, and necessary sequences for cloning was ordered from a vendor (TWIST BIOSICENCES).

FIG. 13 (top) shows each synthetic DNA sequence that was designed as a series of repeated transcription factor (TF) binding sites derived from the consensus binding motif for the TF of interest (blue). To test the impact of the different relative positioning of these sites around the helical nature of the double stranded DNA (one helical turn is equivalent to ~10.5 base pairs), the repeated binding sites were separated by a variable length of nucleic acid spacer sequences (FIG. 13, yellow). Lastly, the synthetic DNA sequence contained a short filler sequence (FIG. 13, grey) to maintain consistent total length of the candidate enhancer sequence block.

Building the MPRA Library

Base Plasmid

A base plasmid that contains the key features necessary for cloning, mammalian expression, and transfection efficiency monitoring was constructed. The plasmid has SfiI restriction enzyme sites for cloning in synthetic oligos, and a reverse selection cassette for removing undesired cloning products. For mammalian expression, the plasmid has a strong polyA termination site downstream of (or 3' to) where the final expression cassette will be located. There is an additional polyA termination site upstream of (or 5' to) the final expression cassette that reduces errant transcripts that might be produced by the bacterial components of the plasmid. Lastly, a constitutively expressed GFP cassette was added to monitor the transfection efficiency either visually under a fluorescent microscope or using FACS.

Cloning Round 1: Oligo Pool

The single stranded oligo pool was PCR amplified to create a pool of double stranded DNA fragments. To maintain the integrity of the library (size and complexity), an emulsion PCR with a limited number of cycles ranging from 12-20 cycles was used. Next the base plasmid and double stranded DNA pool were digested with the SfiI restriction enzyme. The base plasmid was gel extracted using the QIAGEN® II Gel Extraction Kit, a standard gel extraction kit. The double stranded DNA pool was purified using the Monarch® PCR and DNA Cleanup Kit, a standard DNA cleanup kit. The digested products were ligated overnight using a T4 DNA ligase and electroporated into bacteria at a recovery efficiency of at least 100 times the complexity (number of unique DNA sequences) of the oligo library. The integrity of the library was validated by performing Sanger sequencing on 40 individual clones. All clones that were Sanger sequenced contained a unique sequence from the oligo pool, indicating that the library's complexity was maintained. In addition, there was only 1 sequenced clone that contained a large variation in the sequence, indicating an estimated error rate of less than 3%, which met the tolerated criteria. The bacteria pool was cultured overnight at 30° C., and a plasmid prep was done using the ZymoPURE™ II Plasmid Maxiprep Kit, a standard plasmid purification kit. The product was a plasmid pool containing the library of synthetic sequences. Each of these sequences contained the XbaI and KpnI restriction enzyme sites. These sites were used in the next round of cloning to add in the core promoter and luciferase expression.

Cloning Round 2:

The plasmid pool from the Round 1 cloning was serially digested with KpnI and XbaI. Each digestion was purified using the Monarch® PCR and DNA Cleanup Kit, a standard DNA cleanup kit. The final digested product was treated with CIP to dephosphorylate the overhangs. Additionally, plasmids containing the coreBIRC5-Fluc or the TATA-TSS- Fluc cassette were digested with KpnI and XbaI, and gel extracted using a standard kit. The digested plasmid pool and core promoters were ligated overnight and electroporated into bacteria at a recovery efficiency of at least 100 times the complexity of the oligo library. 10 single clones were Sangar sequenced to validate the integrity of the library and expression cassette. Each of the clones sequenced had an intact core promoter-luciferase expression cassette and the expected TF tile-barcode combination. The pools of bacteria were cultured, and the plasmid libraries were extracted using a standard maxiprep kit.

Transfections and Library Preparation

Cell Line Transfections

Each library was transfected independently at least 3 times (3 replicates) in various lung cancer model cell lines, including the well-studied H1299 and several patient-derived xenografts (PDXs) from human lung tumors. Cells for each line were seeded at appropriate densities on 6-well plates. The total number of cells seeded was at least 100 times the complexity of the library and scaled for the typical transfection efficiency of the relevant cell line. For example, with the library complexity of 12,000 and a cell line of a transfection efficiency of 75%, 1.6e6 cells total were seeded for each replicate. Cells were transfected using the commercial product Lipofectamine™ 3000, a transfection agent comprising DOSPA (2,3-dioleoyloxy-N-[2(sperminecarbox-amido)ethyl]-N,N-dimethyl-1-propaniminium trifluoroacetate) and DOPE (dioleoyl phosphatidylethanolamine), and harvested after 24 or 48 hours depending on the cell viability. Before harvesting, the transfection efficiency was evaluated by visual inspection of GFP expression using a fluorescent microscope. If the transfection efficiency was lower than expected, it was repeated.

NGS Tag-Seq Library Prep

Total RNA was extracted using a standard Trizol™ (a standard nucleic acid isolation reagent) prep method. Briefly, cells from each replicate were resuspended in Trizol™, chloroform was added, and the mixtures were phase-separated using centrifugation. Then, the aqueous layer was removed, and total RNA was recovered using ethanol precipitation. Next, mRNA was isolated using a commercial polyA magnet bead kit (Dynabeads™ mRNA Purification Kit), followed by a commercially available Turbo DNase treatment to remove all DNA fragments, including the transfected plasmid. To ensure that samples did not contain residual plasmid DNA, a pre-NGS PCR was performed using 30-50 ng of mRNA for 26 cycles and the result was visualized on a gel. Samples that had a visual band underwent additional DNase treatments. Next, cDNA production was done using the commercially available Superscript IV™, a standard reverse transcriptase. 400-600 ng of mRNA was used with a poly-dT primer. Targeted PCR amplification was performed to produce an Illumina compatible NGS sequencing library that contained the TF tile associated barcodes. In parallel, NGS sequencing libraries was also produced from the input plasmid DNA library. Indexed libraries were pooled, and paired end sequenced on an Illumina sequencing platform.

Data Processing and Analysis

Barcodes were matched to their respective synthetic TF tiles using the DNABarcodes R package. All libraries had greater than 95% of the sequenced barcodes matched to it synthetic TF tile. To determine the expression scores for our screens, the MPRAnalyze R package was used. Briefly, this package uses a graphical model to relate the barcode counts from the RNA to barcode counts from the input plasmid DNA. It supports the use of multiple barcodes per sequence, multiple replicates, and multiple conditions (i.e., cell line).

Luciferase Assay

For the low throughput validation, cells were transfected using Lipofectamine™ 3000, a transfection agent comprising DOSPA (2,3-dioleoyloxy-N-[2(sperminecarboxamido) ethyl]-N,N-dimethyl-1-propaniminium trifluoroacetate) and DOPE (dioleoyl phosphatidylethanolamine), according to the manufacturer's instructions. Briefly, for each well, 100 ng of plasmid DNA was mixed with 0.2 μL of P3000™ reagent, a neutral/helper co-lipid, and 0.2 μL of Lipofectamine™ 3000 and 2 ng of control DNA in 100 μL Opti-MEM™ medium, a serum-reduced minimal essential medium, and the mixture was incubated at room temperature for 20 minutes. The transfection mixture was added to the cells in a 96-well plate and incubated for 24 hours. Approximately 24 hours after transfection, the firefly luciferase and *renilla* luciferase levels were measured from each well using the Promega Dual-Glo® Luciferase System (E2940) with a working volume of 50 μL.

Results

Study Design and Synthetic TF Tile Construction

A high-throughput MPRA screen for identifying synthetic regulatory elements that drive strong expression in lung cancer has been developed and validated. In the first high-throughput screen, the focus was on screening synthetic enhancer elements intended to serve as response elements to TFs that play a role in non-small cell lung cancer (NSCLC). A multi-omics approach to NSCLC identified more than 100 TFs that are dysregulated in lung adenocarcinoma (LUAD). Based on the strength of the multi-omics and evidence, and with the filter of DNA binding site characterization, 77 TFs were selected for this library. For each TF, 24,140 bp homotypic tiles that varied in the binding site motif and the spacing between the binding sites were designed. Each binding site motif was tiled 6 times. 6 different binding site motifs with 4 spacing variants (0, 3, 7, and 10 bp) were chosen. 6 barcodes were assigned, and 4 different control TF tiles were also included (FOSL1, TTF, MYC-MAX, Cansript). As a result, a total of 1,850 unique synthetic sequences were designed and constructed.

These unique enhancer sequences were placed in front of (e.g., upstream of or 5' end of) two core promoters and screened. The two core promoters included the minimal TATA-TSS that drives little to no expression of a reporter gene or a gene of interest, and coreBIRC5 that drives cancer specific expression of a reporter gene or a gene of interest (see Example 1). Additionally, 5 control sequences were included. The control sequences were selected from random sequences and known not to contain TF binding sites and served as negative control, when combined with the core promoters, and the measurement of expression from control sequences were used as the baseline expression. Several positive control TF tiles were also used. These positive control TF tiles had been previously characterized (i.e., FOSL2) (see Example 2). To add redundancy and allow for statistical significance, each TF tile was assigned 6 barcodes for a total screening library size of 12,000.

The coreBIRC5 and TATA-TSS libraries were screened in four lung cancer cell line models: H1299 and three human patient derived xenograft (PDX) tumor cell lines (LXFA586, LXFL1121, and LXFL430). At least 3 biological replicates were performed for each cell line. To measure the activity of the synthetic TF tiles, the detected barcode levels in the RNA were normalized to the DNA input, to calculate an expression score (as described in the Methods above).

High-Throughput Screen Identifies Active Synthetic TF Tiles

Figure 14:
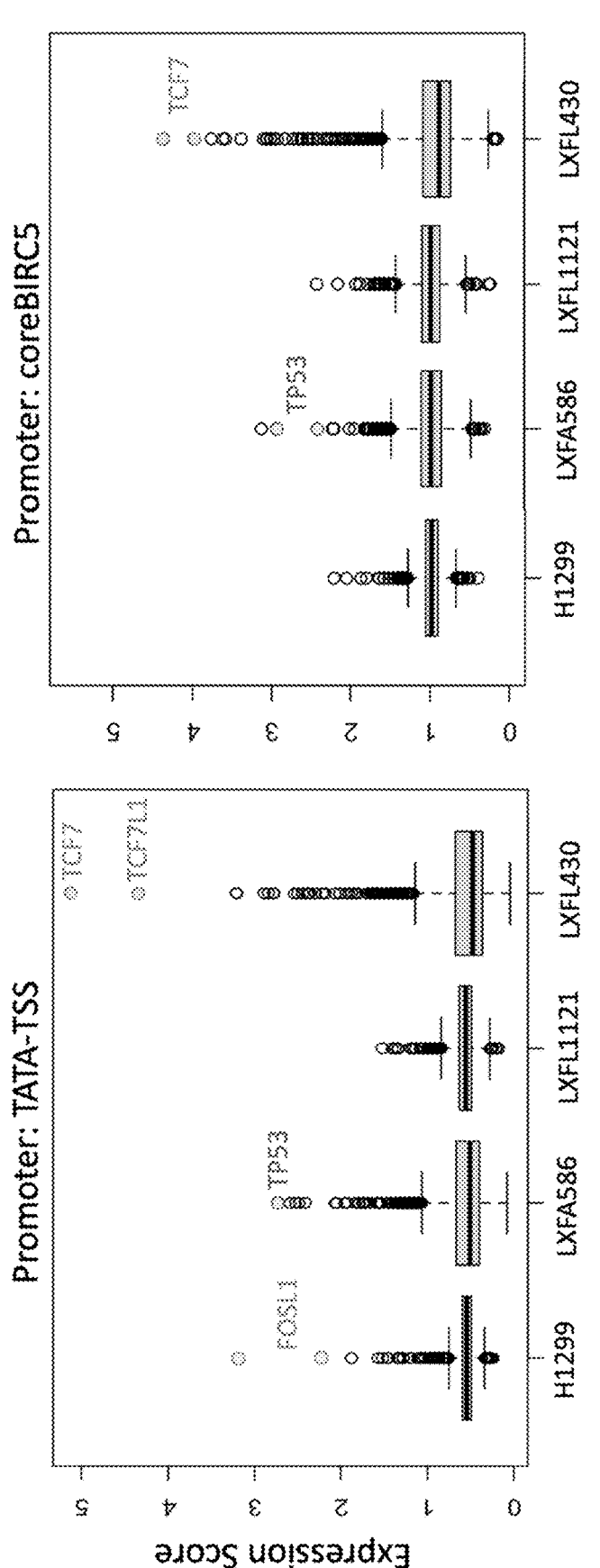
FIG. 14 shows Expression Score Distribution Across Lung Cancer Models. The expression score distribution varies across different lung cancer models. The PDX cell line LXFL430 had the widest distribution and outliers with the highest expression scores.

In both first two screening libraries, synthetic enhancers were found to drive expression in cancer cell line models with both the TATA-TSS and coreBIRC5 core promoters. The expression score distribution varied between cell lines, with the PDX LXFL430 having the widest distribution and the highest expression scores (FIG. 14).

Next, the fold change for each unique synthetic sequence was calculated using the baseline core promoter expression score to normalize. With the TATA-TSS core promoter driving low levels of expression, these TF tiles had a higher fold change compared to the coreBIRC5 promoter. The positive control FOSL2 tile was strongly active in the H1299 cell line for both core promoters tested, suggesting that there are no candidates that are stronger than the FOS motif for H1299s in this library of dysregulated TFs. Other synthetic response elements were discovered in this approach that were highly active in all cell lines. These include CREB3L1, TWIST, and a set of HOX variants (MNX1, HOXC10, HOXB9).

Other tiles were much more specific for particular genetic backgrounds across different cell lines. For example, the TCF7 and TCF7L1 TF tiles ranked at the top of the list in the LXFL430 cell line but not in any other cell lines. Similarly, the TP53 TF tiles rank highly only in the LXFA586 cell line.

Some TF tiles were found to have a core promoter preference. For example, the TWIST_v3 tile is at the top of the ranked list for the coreBIRC5 promoter but is not highly ranked for the TATA-TSS promoter. Additionally, this TWIST_v3 tile is ranked highly in all cell lines. HOXC10, MNX1, and CREB3L1 tile variants were also ranked higher for two or more cell lines (Table 1D-1I).

Synthetic TF Tile Validation

Figure 29:
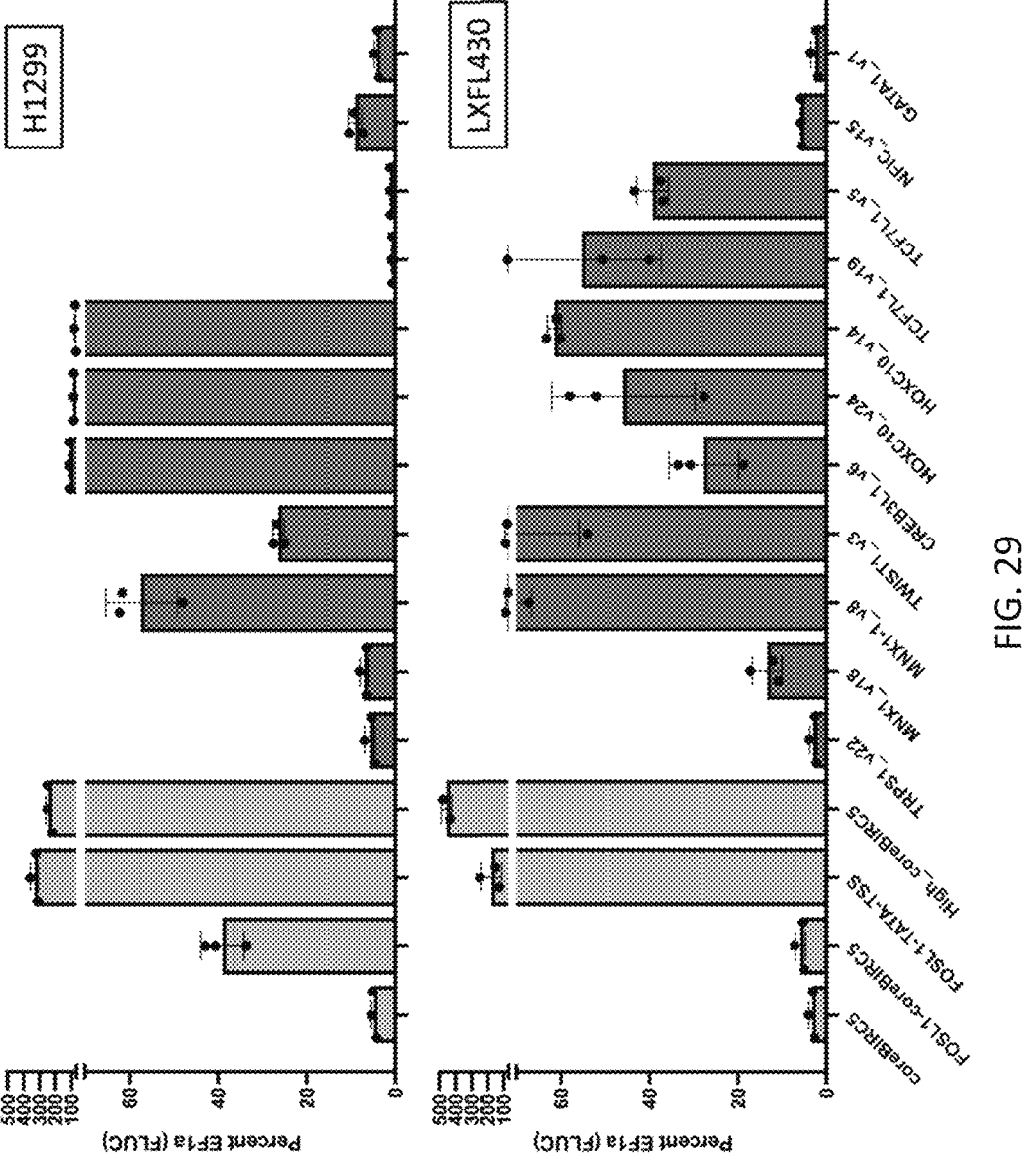
FIG. 29 shows validation of top ranked TF tiles with the coreBIRC5 promoter. Using a luciferase reporter assay various TF tiles that were highly ranked in the MPRA screens for H1299 and LXFL430 were tested. Many of the TF tiles showed stronger expression than the base expression of the coreBIRC5 and the FOSL-coreBIRC5. The TCF7L1 TF tiles showed specific expression in the LXFL430 cell line.

To establish the validity of the screening strategy and qualify candidates for further testing, a set of high-scoring and low-scoring candidates from the screen was constructed using the coreBIRC5 core sequence in the PDX430 lung cancer cell line. The candidates were cloned into the luciferase reporter plasmid and the expression of the luciferase was measured. Most of the high-scoring enhancer sequences were also found to have expression level that is higher than the core sequence alone, with some candidates approaching levels of internal positive control promoters, FOS-TATA-TSS and High-coreBIRC5 (FIG. 29). In PDX-derived cell line LXFL430, 10 out of 11 TF tiles tested from the top of the list drove significantly higher expression than coreBIRC5 alone (FIG. 29), while only 1 out of 9 sequences tested from the bottom of the list drove expression higher than coreBIRC5.

In summary, more than seven unique TFs were identified as candidates for synthetic enhancers that can drive cancer-regulated gene expression through the two screens described in this example. Some of the candidates appear to be stronger than the previous favorite FOSL2-enhancer element and will be studied further. As shown in FIG. 15, new synthetic promoters comprising coreBIRC5, that responds to HOXC10, MNX1, and CREB3L1, drive stronger expression of the reporter gene than the FOS-coreBIRC5 promoter.

Conclusion

MPRA high-throughput has been successfully implemented to screen 1,800 unique TF tiles in combination with two separate TF tile libraries, one using the TATA-TSS promoter and the other using the coreBIRC5 promoter. These libraries were screened in five different lung cancer cell lines. As expected, most candidate response elements drove expression of a reporter gene similar to the baseline expression of the core promoter alone, supporting the importance of approaching this testing in a highly parallel manner. However, a subset of synthetic promoter elements that drive expression well above the core promoter baseline was identified, as demonstrated by the screening data and low-throughput validation. Synthetic response elements particularly responding to HOXC10, CREB3L1 and MNX1 were found to drive expression across multiple lung cancer cell lines. For example, the HOXC10 element drove the expression of a reporter gene up to 80 times higher than FOS-coreBIRC5 synthetic promoter.

In addition, synthetic response elements that uniquely drive expression in only specific genetic contexts were identified. The screen identified that multiple variations of elements responding to TCF7 or TP53 drove strong expression in only LXFL430 or LXFA586, respectively. Low-throughput validation confirmed the results and have led to designing and testing of combining multiple pathway-sensitive synthetic promoter elements into a single regulatory element. TCF7 is the downstream target of the B-cat/Wnt signaling pathway, which is well-studied in primary & metastatic lung cancer. TP53 is also a well-studied for its role, particularly in mutated form, within non-small cell lung cancer.

Overall, the screening platform successfully identified synthetic promoters that (1) drive expression of a gene broadly across lung cancer models due to universal changes in proliferation and de-differentiation and (2) are downstream of signaling pathways and drive expression in specific lung cancer models. The MPRA developed is a core feature in designing and constructing synthetic promoters, given the vast amount of sequence space to cover when designing completely new promoter sequences from scratch. As demonstrated here, it allows simultaneously testing thousands of hypotheses from the multi-omics identification of key TFs in cancer combined with different design strategies for a functioning response element. The MPRA accurately brings the best candidates to the top, as demonstrated by the low-throughput validation results, and thus can greatly accelerate designing novel synthetic promoters. This MPRA platform, now optimized and fully-developed, can also be applied to test any series of large hypotheses that can result in stronger expression of a gene in any models of choice, such as mutations to UTR sequences, ideal codon optimization, or screening a library of endogenous enhancer sequences.

Example 2: Design and Construction of Synthetic Promoters

In this example, the general strategy of synthetic promoter engineering to combine specific response elements in dysregulated pathways in cancer is described. The modular components (response element, signal element and core promoter) can be individually and synchronously engineered for improved sensitivity, specificity and signal strength in both low-throughput and high-throughput approaches. Response of synthetic promoters to distinct TF upregulation is demonstrated, which indicates that synthetic promoters described herein can establish highly predictable activity in new cell lines.

The cancer-activated promoter is a key component within cancer-activated DNA constructs to drive expression of a synthetic biomarker in cancer cells. Cancer is notably characterized by aberrant molecular signaling, which is a result of dysregulated expression of highly active transcription factors (TFs) and functional signaling cascades that can normally only be found in early development or in other disease states. Synthetic promoters described herein can function directly as response elements or sensors for known dysregulated transcription factors. Synthetic promoters can perform as protein sensors by responding predictably to the presence of phosphorylated TF in the nucleus. This can allow estimating sensitivity and specificity using available in silico data for cancer and normal patients, without having to create and test in empirical models. Empirical testing can follow to demonstrate the responsiveness of a synthetic promoter comprising TF binding sequences to the TF, which allows extrapolating known expression data for that TF in large datasets like The Cancer Genome Atlas (TCGA) or Clinical Proteomic Tumor Analysis Consortium (CPTAC). In addition, as there are no common models for benign tissues, proteomics and transcriptomics of benign lung disease can be studied to determine whether a TF is present, which can be helpful for predicting whether a synthetic promoter comprising the TF binding sequence can activate in those cell states.

Figures 21A, 21B, 21C:
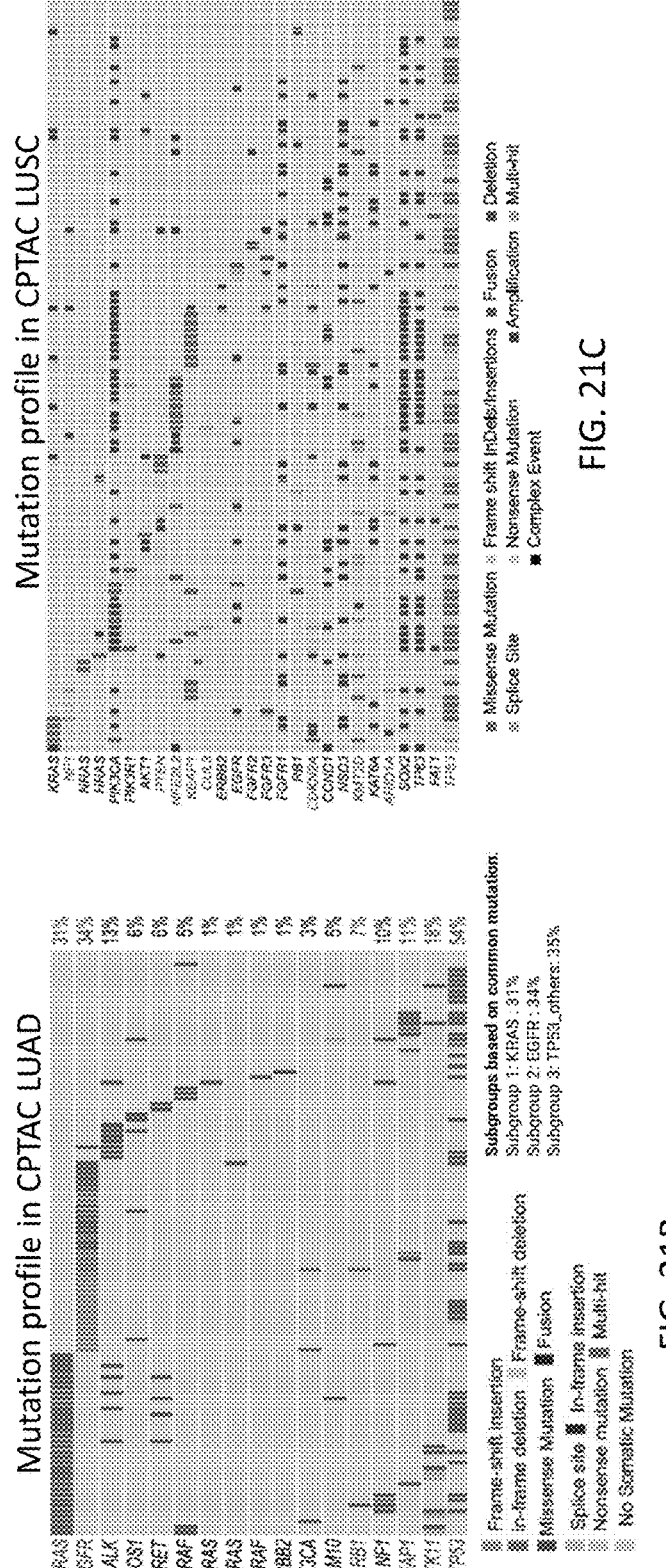
FIG. 21A shows a table comparing mutation status of P53, key gene set expression, and TP63 expression in different cancer cell lines.
FIGS. 21B and 21C show mutation profile in Clinical Proteomic Tumor Analysis Consortium (CPTAC) Lung adenocarcinoma (LUAD) and lung squamous cell carcinoma (LUSC), respectively.
Figure 22:
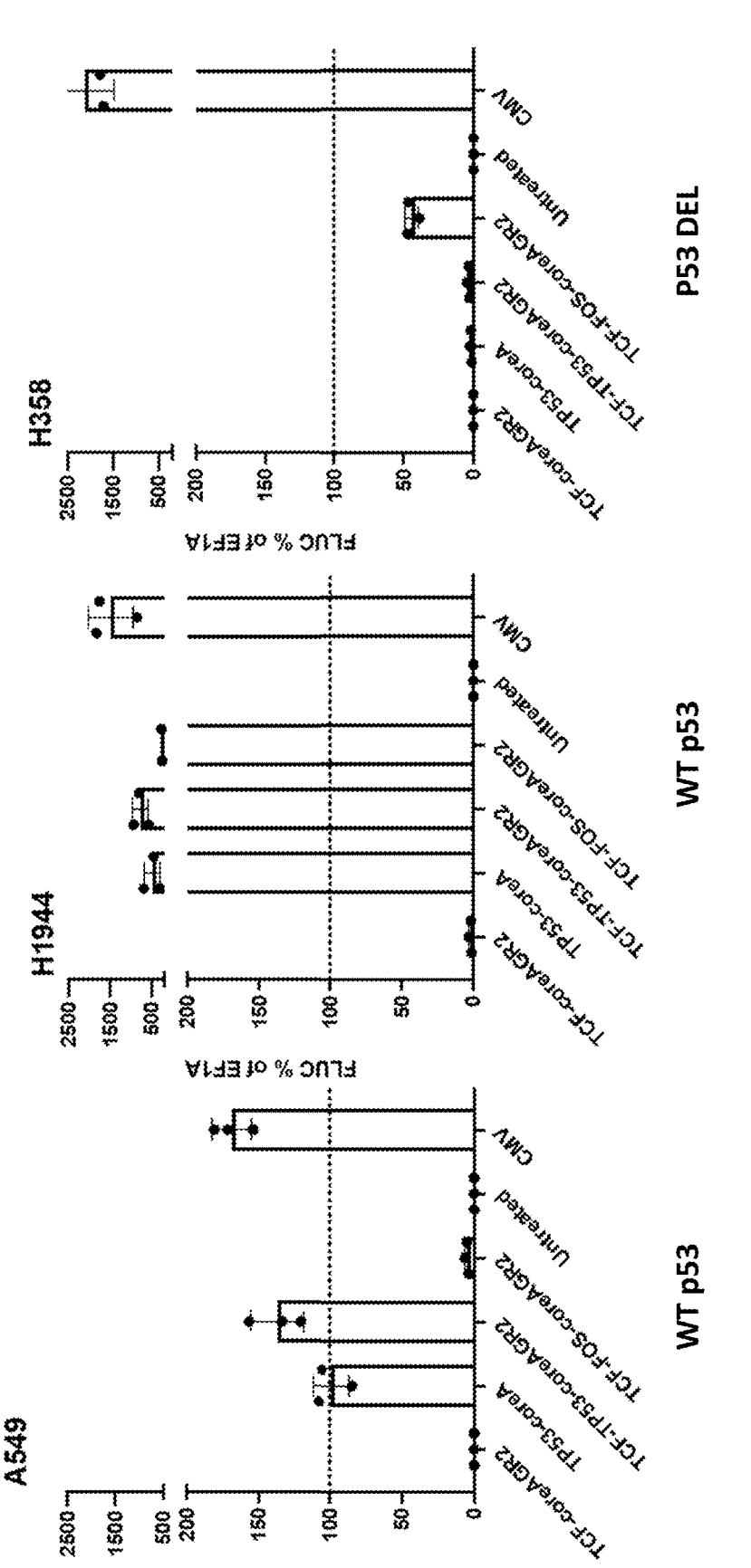
FIG. 22 shows the reporter gene expression by p53 in A549, H1944, and H358 cell lines.

The approach to designing cancer-specific promoters starts with identifying the key response elements that bind the TFs. These TFs were identified by a multi-omics approach that utilizes transcriptomics, proteomics and phospho-proteomics to identify TFs that are highly upregulated in cancer cells or tissues, compared to normal cells or tissues. TFs identified using the multi-omics approach in non-small cell lung cancer (NSCLC) were categorized by major driver mutations and signaling pathways (FIG. 21B). TFs identified are downstream of major NSCLC driver mutations (e.g., EGFR, KRAS, TP53, etc.) and signaling pathways. Combining specific elements across multiple pathways can ensure broad cancer coverage of cancer specific expression of a reporter gene or a gene of interest. For example, based on the above analysis, a synthetic promoter can be designed to include elements to ensure coverage of LUAD and LUSC dysregulated pathways by combining elements and probing various signaling pathways.

To build a synthetic promoter, one can use the known DNA binding site (TFBS) as a sequence element to "sense" that TF's presence, and if present, that TF upon binding to the promoter, will recruit additional transcriptional machinery and co-factors such as RNA polymerase. There are also additional signal-based elements that are not cancer-specific, but generally can attract more transcriptional machinery to a promoter that has been activated.

The transcription start site (TSS) is the driving component of the core promoter. Two approaches have been used to design the core: (1) using a minimal basal promoter, which is frequently used to create response elements and (2) using the core region of a cancer-specific promoter, which adds additional specificity to the construct. The three components—cancer-activated response elements, signal elements, and cancer-specific cores—are each modular and highly engineerable.

Synthetic Construct Design and Cloning

Core Promoters

A minimal cancer-specific core promoter can comprise a short DNA sequence within the promoter region of a gene that is specifically activated or repressed in cancer cells compared to normal cells. The core promoter region is a critical regulatory element that controls the initiation of transcription by RNA polymerase II. The coreBIRC5 element comprises a 74 bp element from the 3' end of the promoter consisting of a TP53 half-site, and 33 bp after the transcriptional start site (TSS).

Equivalent types of core promoter sequences were also created for endogenous promoters AGR2, CST1, and FAM111B by evaluating candidate sequences in the UCSC Genome Browser and limiting assessment from –300 bp to +100 bp relative to the predicted TSS of the endogenous promoter. Boundaries of the core sequences were further trimmed based on a combination of the following: presence of ChIP-Seq peaks (including general TFs and indicators of active promoter regions such as RNA Pol II, DNAse I, H3K4me1, H3K4me3 peaks), TFs that may indicate cancer specificity by presence in cancer cell lines and absence in non-cancerous cell lines, abundance of predicted TFBS via JASPAR or HOMER motif analysis, and/or retaining regions of high species conservation.

The TATA-TSS minimal core (37 bp) comprises a canonical TATA site with a 23 bp GC-rich spacer 5' end to or upstream of the TSS, which can mediate high expression.
Tiled Transcription Factor Binding Sites JASPAR (open-access database of curated and non-redundant transcription factor (TF) binding profiles from six different taxonomic groups) consensus sequences were used as the DNA binding domain and tiled consecutively or with a 3 bp spacer between the DNA binding domains to fill a size of 125 bp. Ultramers were ordered from Integrated DNA Technologies (IDT) with a common sequence at the 3' end. Single-stranded ultramers were PCR-amplified using a common reverse primer to add appropriate restriction enzyme digestion sites as described below. Ultramer sequences are listed in Table 2.

TABLE 2

Ultramer sequences

| SEQ ID NO. | Reference | Sequence Name | Sequence |
|---|---|---|---|
| 344 | 312398676 | TTF-1_1_no space | AAT AGG TAC CAC TAG TGG TTT TGT GGG GTT TTG TGG GGT TTT GTG GGG TTT TGT GGG GTT TTG TGG GGT TTT GTG GGG TTT TGT GGG GTT TTG TGG GGT TTT GTG GGG TTT TGT GGT GCG CTC CCG ACA TGC CCC GC |
| 345 | 312398677 | MAX MYC_no space | AAT AGG TAC CAC TAG TAG TTC AAC ACG TGG TCT GGG AGT TCA ACA CGT GGT CTG GGA GTT CAA CAC GTG GTC TGG GAG TTC AAC ACG TGG TCT GGG AGT TCA ACA CGT GGT CTG GGT GCG CTC CCG ACA TGC CCC GC |
| 346 | 312398678 | TTF-1_1_3bp space | AAT AGG TAC CAC TAG TGG TTT TGT GGA GAG GTT TTG TGG TCG GGT TTT GTG GGA CGG TTT TGT GGC TAG GTT TTG TGG ACT GGT TTT GTG GTG CGG TTT TGT GGG TAG GTT TTG TGG TGC GCT CCC GAC ATG CCC CGC |
| 347 | 312398679 | MAX_MYC_3bp space | AAT AGG TAC CAC TAG TAG TTC AAC ACG TGG TCT GGG AGA AGT TCA ACA CGT GGT CTG GGT CGA GTT CAA CAC GTG GTC TGG GGA CAG TTC AAC ACG TGG TCT GGG CTA AGT TCA ACA CGT GGT CTG GGT GCG CTC CCG ACA TGC CCC GC |
| 348 | 312398680 | TTF-1_2_no space | AAT AGG TAC CAC TAG TAG CCA CTT GAA ATT AGC CAC TTG AAA TTA GCC ACT TGA AAT TAG CCA CTT GAA ATT AGC CAC TTG AAA TTA GCC ACT TGA AAT TAG CCA CTT GAA ATT GCG CTC CCG ACA TGC CCC GC |
| 349 | 312398681 | GATA6_no space | AAT AGG TAC CAC TAG TGA CAG ATA AGA AAG ACA GAT AAG AAA GAC AGA TAA GAA AGA CAG ATA AGA AAG ACA GAT AAG AAA GAC AGA TAA GAA AGA CAG ATA AGA AAG ACA GAT AAG AAA TGC GCT CCC GAC ATG CCC CGC |
| 350 | 312398682 | TTF-1_2_3bp space | AAT AGG TAC CAC TAG TAG CCA CTT GAA ATT AGA AGC CAC TTG AAA TTT CGA GCC ACT TGA AAT TGA CAG CCA CTT GAA ATT CTA AGC CAC TTG AAA TTA CTA GCC ACT TGA AAT TTG CGC TCC CGA CAT GCC CCG C |
| 351 | 312398683 | GATA6_3bp space | AAT AGG TAC CAC TAG TGA CAG ATA AGA AAA GAG ACA GAT AAG AAA TCG GAC AGA TAA GAA AGA CGA CAG ATA AGA AAC TAG ACA GAT AAG AAA ACT GAC AGA TAA GAA ATG CGA CAG ATA AGA AAT GCG CTC CCG ACA TGC CCC GC |

TABLE 2-continued

| Ultramer sequences | | | |
|---|---|---|---|
| SEQ ID NO. | Reference | Sequence Name | Sequence |
| 352 | 312398684 | TTF-1_3_no space | AAT AGG TAC CAC TAG TCT GGG AAC AAG TGC TGG GAA CAA GTG CTG GGA ACA AGT GCT GGG AAC AAG TGC TGG GAA CAA GTG CTG GGA ACA AGT GCT GGG AAC AAG TGC TGG GAA CAA GTG TGC GCT CCC GAC ATG CCC CGC |
| 353 | 312398685 | GATAI_no space | AAT AGG TAC CAC TAG TTT CTA ATC TAT TTC TAA TCT ATT TCT AAT CTA TTT CTA ATC TAT TTC TAA TCT ATT TCT AAT CTA TTT CTA ATC TAT TTC TAA TCT ATT TCT AAT CTA TTG CGC TCC CGA CAT GCC CCG C |
| 354 | 312398686 | TTF-1_3_3bp space | AAT AGG TAC CAC TAG TCT GGG AAC AAG TGA GAC TGG GAA CAA GTG TCG CTG GGA ACA AGT GGA CCT GGG AAC AAG TGC TAC TGG GAA CAA GTG ACT CTG GGA ACA AGT GTG CCT GGG AAC AAG TGT GCG CTC CCG ACA TGC CCC GC |
| 355 | 312398687 | GATA1_3bp space | AAT AGG TAC CAC TAG TTT CTA ATC TAT AGA TTC TAA TCT ATT CGT TCT AAT CTA TGA CTT CTA ATC TAT CTA TTC TAA TCT ATA CTT TCT AAT CTA TTG CTT CTA ATC TAT TGC GCT CCC GAC ATG CCC CGC |
| 356 | 312398688 | TTF-1_4_no space | AAT AGG TAC CAC TAG TGA CTC CTC AAG GGG ACT CCT CAA GGG GAC TCC TCA AGG GGA CTC CTC AAG GGG ACT CCT CAA GGG GAC TCC TCA AGG GGA CTC CTC AAG GGG ACT CCT CAA GGG TGC GCT CCC GAC ATG CCC CGC |
| 357 | 312398689 | FOSL1_no space | AAT AGG TAC CAC TAG TGG TGA CTC ATG GGT GAC TCA TGG GTG ACT CAT GGG TGA CTC ATG GGT GAC TCA TGG GTG ACT CAT GGG TGA CTC ATG GGT GAC TCA TGG GTG ACT CAT GTG CGC TCC CGA CAT GCC CCG C |
| 358 | 312398690 | TTF-1_4_3bp space | AAT AGG TAC CAC TAG TGA CTC CTC AAG GGA GAG ACT CCT CAA GGG TCG GAC TCC TCA AGG GGA CGA CTC CTC AAG GGC TAG ACT CCT CAA GGG ACT GAC TCC TCA AGG GTG CGA CTC CTC AAG GGT GCG CTC CCG ACA TGC CCC GC |
| 359 | 312398691 | FOSL1_3bp space | AAT AGG TAC CAC TAG TGG TGA CTC ATG AGA GGT GAC TCA TGT CGG GTG ACT CAT GGA CGG TGA CTC ATG CTA GGT GAC TCA TGA CTG GTG ACT CAT GTG CGG TGA CTC ATG TGC GCT CCC GAC ATG CCC CGC |
| 360 | 312398692 | TCF7_no space | AAT AGG TAC CAC TAG TCG GGC TTT GAT CTT TCG GGC TTT GAT CTT TCG GGC TTT GAT CTT TCG GGC TTT GAT CTT TCG GGC TTT GAT CTT TCG GGC TTT GAT CTT TTG CGC TCC CGA CAT GCC CCG C |
| 361 | 312398693 | STAT3_no space | AAT AGG TAC CAC TAG TCT TCT GGG AAA CTT CTG GAA ACT TCT GGG AAA CTT CTG GAA ACT TCT GGG AAA CTT CTG GAA ACT TCT GGG AAA CTT CTG GAA ACT TCT GGG AAA CTT CTG GAA ACT TCT GGG AAA CTT CTG GAA ACT TCT GGG AAA CTT CTG GAA AAA CTT CTG GAA AAT GCG CTC CGA CAT GCC CCG C |
| 362 | 312398694 | TCF7_3bp space | AAT AGG TAC CAC TAG TCG GGC TTT GAT CTT TAG ACG GGC TTT GAT CTT TTC GCG GGC TTT GAT CTT TGA CCG GGC TTT GAT CTT TCT ACG GGC TTT GAT CTT TAC TCG GGC TTT GAT CTT TTG CGC TCC CGA CAT GCC CCG C |
| 363 | 312398695 | STAT3_3bp space | AAT AGG TAC CAC TAG TCT TCT GGG AAA AGA CTT CTG GAA AAT CGC TTC TGG GAA AGA CCT CTG GGA AAA CTA CTT CTG GGA |

TABLE 2-continued

| Ultramer sequences | | | |
|---|---|---|---|
| SEQ ID NO. | Reference | Sequence Name | Sequence |
| | | | AAA CTC TTC TGG GAA ATG CCT TCT GGG AAA TGC GCT CCC GAC ATG CCC CGC |
| 364 | 312398696 | TCF7:L2_no space | AAT AGG TAC CAC TAG TGC GCT TTG ATG TGC GGG GCG GCC CTT TGA AGT TGG CGC TTT GAT GTG CGG GGC GGC CCT TTG AAG TTG GCG CTT TGA TGT GCG GGG CGG CCC TTT GAA GTT GTG CGC TCC CGA CAT GCC CCG C |
| 365 | 312398697 | STAT:STAT no space | AAT AGG TAC CAC TAG TAA TTC TTA GAA ATA AAT TCT TAG AAA TAA ATT CTT AGA AAT AAA TTC TTA GAA ATA AAT TCT TAG AAA TAA ATT CTT AGA AAT AAA TTC TTA GAA ATA TGC GCT CCC GAC ATG CCC CGC |
| 366 | 312398698 | TCF7:L2_3bp space | AAT AGG TAC CAC TAG TGC GCT TTG ATG TGC GGG GCG GCC CTT TGA AGT TGA GAG CGC TTT GAT GTG CGG GGC GGC CCT TTG AAG TTG TCG CGC TTT GAT GTG CGG GGC GGC CCT TTG AAG TTG TCG CGC TTT GA TGT GCG GGG CGG CCC TTT GAA GTT GTG CGC TCC CGA CAT GCC CCG C |
| 367 | 312398699 | STAT:STAT_3bp space | AAT AGG TAC CAC TAG TAA TTC TTA GAA ATA AGA AAT TCT TAG AAA TAT CGA ATT CTT AGA AAT AGA CAA TTC TTA GAA ATA CTA AAT TCT TAG AAA TAA CTA ATT CTT AGA AAT ATG CGC TCC CGA CAT GCC CCG C |
| 368 | 312398700 | MSC_no space | AAT AGG TAC CAC TAG TAA CAG CTG TTA ACA GCT GTT AAC AGC TGT TAA CAG CTG TTA ACA GCT GTT AAC AGC TGT TAA CAG CTG TTA ACA GCT GTT AAC AGC TGT TTG CGC TCC CGA CAT GCC CCG C |
| 369 | 312398701 | SOX9_no space | AAT AGG TAC CAC TAG TAA AAC AAA GGA TCC TTT GTT TTA AAA CAA AGG ATC CTT TGT TTT AAA ACA AAG GAT CCT TTG TTT TAA AAC AAA GGA TCC TTT GTT TTA AAA CAA AGG ATC CTT TGT TTT TGC GCT CCC GAC ATG CCC CGC |
| 370 | 312398702 | MSC_3bp space | AAT AGG TAC CAC TAG TAA CAG CTG TTA GAA ACA GCT GTT TCG AAC AGC TGT TGA CAA CAG CTG TTC TAA ACA GCT GTT ACT AAC AGC TGT TTG CAA CAG CTG TTG TAA ACA GCT GTT TGC GCT CCC GAC ATG CCC CGC |
| 371 | 312398703 | SOX9_3bp space | AAT AGG TAC CAC TAG TAA AAC AAA GGA TCC TTT GTT TTA GAA AAA CAA AGG ATC CTT TGT TTT TCG AAA ACA AAG GAT CCT TTG TTT TGA CAA AAC AAA GGA TCC TTT GTT TTT GCG CTC CGA CAT GCC CCG C |
| 372 | 312398704 | ZEB1_no space | AAT AGG TAC CAC TAG TCA CCT GCA CCT GCA CCT GCA CCT GCA CCT GCA CCT GCA CCT GCA CCT GCA CCT GCA CCT GCA CCT GCA CCT GCA CCT GTG CGC TCC CGA CAT GCC CCG C |
| 373 | 312398705 | HNF4_no space | AAT AGG TAC CAC TAG TAA AGT CCA AGT CCA AAA GTC CAA GTC CAA AAG TCC AAG TCC AAA AGT CCA AGT CCA AAA GTC CAA GTC CAA AAG TCC AAG TCC AAA AGT CCA AGT CCA TGC GCT CCC GAC ATG CCC CGC |
| 374 | 312398706 | ZEB1_3bp space | AAT AGG TAC CAC TAG TCA CCT GAG ACA CCT GTC GCA CCT GGA CCA CCT GCT ACA CCT GAC TCA CCT GTG CCA CCT GAG ACA CCT GTC GCA CCT GGA CCA CCT GTG CGC TCC CGA CAT GCC CCG C |
| 375 | 312398707 | HNF4_3bp space | AAT AGG TAC CAC TAG TAA AGT CCA AGT CCA AGA AAA GTC CAA GTC CAT CGA AAG TCC AAG TCC AGA CAA AGT CCA AGT CCA |

TABLE 2-continued

Ultramer sequences

| SEQ ID NO. | Reference | Sequence Name | Sequence |
|---|---|---|---|
| | | | CTA AAA GTC CAA GTC CAA CTA AAG TCC AAG TCC ATG CGC TCC CGA CAT GCC CCG C |
| 376 | 312398708 | BIRC5_core REV | CCA TGG TGG CTT TAC CAA CAG TAC CGG ATT GCC AAG CTT GGC CGC CGA GGC CAG ATC TTG ATA TCC TCG AGG CTA GCC CAC CTC TGC CAA CGG GTC CCG CGA CTC AAA TCT GGC GGT TAA TGG CGC GCC GCG GGG CAT GTC GGG AGC GCA GGT ACC G |

Cloning into Firefly Reporter Vector

To generate a reporter construct for use in measuring promoter activity, DNA fragments of interest were cloned into a standard Firefly Luciferase (FLUC) reporter vector from Promega (pGL4.10[luc2] Promega E6651). Two cloning methods were used: restriction enzyme cloning and Gibson assembly.

For restriction enzyme cloning, DNA fragments containing promoter sequences were amplified by PCR using primers designed to incorporate KpnI and NheI restriction enzyme recognition sites in the PCR products. The PCR products were then digested with the appropriate restriction enzymes, purified using gel extraction kits (Zymo Cat #D4001), and ligated into the FLUC vector that had been digested with the same enzymes using NEB Quick Ligation™ Kit (Cat #M2200), a standard DNA ligation kit. The ligation mixture was transformed into E. coli Stable cells (C3040H), and clones were screened by restriction enzyme digestion and DNA sequencing to confirm the correct insert.

For Gibson assembly, Gibson Assembly® Master Mix (NEB E2611), a standard PCR master mix, was used. Briefly, PCR products containing the promoter of interest and the FLUC vector were generated using primers designed to create overlapping regions between the two fragments. The PCR products were then mixed with Gibson Assembly® Master Mix and incubated at 50° C. for 1 hour. The resulting mixture was then transformed into E. coli Stable cells, and clones were screened by DNA sequencing to confirm the correct assembly.

DNA was scaled up and purified using QIAGEN® Plasmid Plus Midi (Cat #12945), a standard plasmid purification kit, or equivalent. Briefly, larger cultures were prepared from bacterial glycerol stocks containing the plasmid DNA. A 2 mL culture was started in the morning and larger cultures inoculated for overnight growth at 37° C. Purified DNA was used for subsequent in vitro and in vivo transfections.

Cell Lines

Cells were maintained according to standard protocols with recommended media described below and incubated at 37° C. and 5% CO$_2$. H1299 (human non-small cell lung carcinoma cell line derived from the lymph node), H520 (squamous cell carcinoma), and LK-2 (squamous cell carcinoma) cells were cultured in standard RPMI1640 medium supplemented with 10% (v/v) fetal bovine serum. IMR90 (normal lung fibroblast cell line) cells were cultured in standard EMEM supplemented with 10% (v/v) fetal bovine serum. A549 (pulmonary adenocarcinoma) cells were cultured in standard F-12K medium supplemented with 10% (v/v) fetal bovine serum.

Patient-derived xenograft (PDX) cell lines licensed from Charles River Laboratories (CRL) were cultured in standard RPMI1640 medium with 25 mM HEPES and L-glutamine (#FG1385, Biochrom, Berlin, Germany), supplemented with 10% (v/v) fetal calf serum (Sigma, Tauflkirchen, Germany) and 0.1 mg/ml Gentamycin (Life Technologies, Karlsruhe, Germany).

Lonza primary-like cell line SAEC-1 were cultured using the Lonza SAGM™ Small Airway Epithelial Cell Growth Medium BulletKit® (CC-3118). Lonza Normal Human Bronchial Epithelial (NHBE) and Chronic Obstructive Pulmonary Disease (COPD) primary-like cell lines were cultured using Lonza Bronchial Epithelial Cell Growth Medium BulletKit® (CC-3170).

Approximately 24 hours prior to conducting experimentations, cells were plated to achieve a confluence of 70-80/on the day of transfection.

Transfections

For transient transfections, Lipofectamine™ 3000 (Thermo Fisher), a transfection agent comprising DOSPA (2,3-dioleoyloxy-N-[2(sperminecarboxamido)ethyl]-N,N-dimethyl-1-propaniminium trifluoroacetate) and DOPE (dioleoyl phosphatidylethanolamine), was used according to the manufacturer's instructions. Briefly, for each well, 100 ng of plasmid DNA was mixed with 0.2 µL of P3000™ reagent, a neutral/helper co-lipid, and 0.2 µL of Lipofectamine™ 3000 and 2 ng of control DNA in 100 µL Opti-MEM™ medium, a serum-reduced minimal essential medium, and the mixture was incubated at room temperature for 20 minutes. The transfection mixture was then added to the cells in a 96-well plate and the cells were incubated for 24 hours.

Luciferase Assays and Analysis

Approximately 24 hours after the transfection, firefly luciferase and Renilla luciferase levels were measured from each well using the Promega Dual-Glo® Luciferase System (E2940) with a working volume of 50 µL.

Data are presented as raw output of Firefly Luciferase Relative Light Units (FLUC RLUs) relative to constitutively active promoters, % of EF1A or % of CMV or relative to another strong, constitutive promoter. A plasmid encoding for Renilla luciferase was added into transfection mixtures at a low ratio to control for variance in transfection efficiency between parallel wells of cells. Normalization for transfection and well-to-well variability was performed by dividing the FLUC RLU output by the Renilla luciferase (RLUC) RLU output from the CMV-RLUC co-transfection control. Normalized FLUC/RLUC may also be presented as % of expression relative to EF1A.

Chromatin Immunoprecipitation (ChIP)—Quantitative PCR (qPCR)

24 hours after transfection, cells (10-cm dish) were fixed with 1% formaldehyde for 10 minutes at room temperature. Cells were then washed twice with ice-cold PBS. Then, cells were harvested using cell scraper in 2 ml of ice-cold PBS with protease inhibitors and centrifuged at 2000 rpm at 4° C. for 5 minutes. The cell pellets were lysed in 200 µL (per 100 µL cell pellet) of 1% SDS lysis buffer (1% SDS, 10 mM EDTA, 50 mM Tris-HCl, pH 8.1) with protease inhibitors, and the extracts were sonicated using a Misonix Sonicator® 3000 instrument and a microtip probe (use 1 second on, 0.5 second pulse for 15 seconds at power setting of 2; put on ice for 15 seconds to chill the tube; 6-9 cycles were performed). Samples were then centrifuged at 12,000×g at 4° C. for 10 minutes, and supernatant was collected. Samples were diluted to 2 ml in ChIP dilution buffer (1% Triton™ X-100, a non-ionic surfactant, 2 mM EDTA, 20 mM Tris-HCl, pH 8, 150 mM NaCl) with protease inhibitors. 40 µL of the diluted sample was kept aside as the input fraction before preclearing with non-blocked 75 µL ProteinA Agarose/ Salmon Sperm DNA (50% Slurry) for 30 minutes at 4° C. with agitation. Agarose was pelleted by centrifugation (10, 000×g-15,000×g) and the supernatant fraction was collected. 60 µL blocked agarose beads were added to the supernatant fraction per reaction with control rabbit IgG, anti-c-Jun, or anti-FRA2 rabbit antibodies (purchased from CellSignaling) and incubated at 4° C. overnight with rotation. Immune complexes were washed once with low salt wash buffer, once with high salt wash buffer, once with LiCl wash buffer with 0.1% SDS, and two times with Tris-EDTA buffer. DNA-protein complex was eluted in ChIP elution buffer (1% SDS, 0.1M NaHCO$_3$). Cross-links were reversed at 65° C. for 2 hours. DNA was purified by QIAquick® Spin Miniprep Kit following the manufacturer's protocol (Qiagen). For all quantitative PCR (qPCR) analyses, Taqman primer/probe assay for target gene promoter binding was performed using QuantStudio 6 Flex machine.

RNA-Seq and Principal Component Analysis

Briefly, raw sequencing data was aligned to GRCh38/ hg38 using Spliced Transcripts Alignment to a Reference (STAR). The resulting Binary Alignment Map (BAM) files were analyzed using feature counts against a transcriptomic reference based on Gencode 36 (gencodegenes.org/human/ release_36). The resulting gene-level counts for protein-coding genes were upper-quartile normalized, transformed into Fragments Per Kilobase of transcript per Million mapped reads (FPKM-UQ), and log 2 transformed. Clinical Proteomic Tumor Analysis Consortium (CPTAC) RNA-seq data in FPKM-UQ unit was directly downloaded from linkedOmics data portal.

PCA (R package PCAtools version 2.6.0), a dimensionality reduction method, was used to cluster the samples using the RNA-seq profiles. PCA was either performed on all genes, expression-quantified as FPKM-UQ, or on genes restricted to the relevant gene sets downloaded from MSigDB (gsea-msigdb.org/gsea/msigdb/).

Results

Synthetic Promoters Dependent on Dysregulated FOS and a Core-Cancer Specific Promoter are Highly Active The use of synthetic promoters composed of tiled transcription factor binding sites (TFBSs) and a minimal core promoter to improve gene expression in cancer cells was investigated. The expression of a reporter gene expressed from a panel of synthetic promoter constructs was tested and the expression levels were compared to the expression levels of the reporter expressed from the endogenous BIRC5 (Survivin) promoter, a combination of three endogenous cancer-activated promoters, or constitutive controls such as EF1a and CMV promoters.

Figures 30A, 30B:
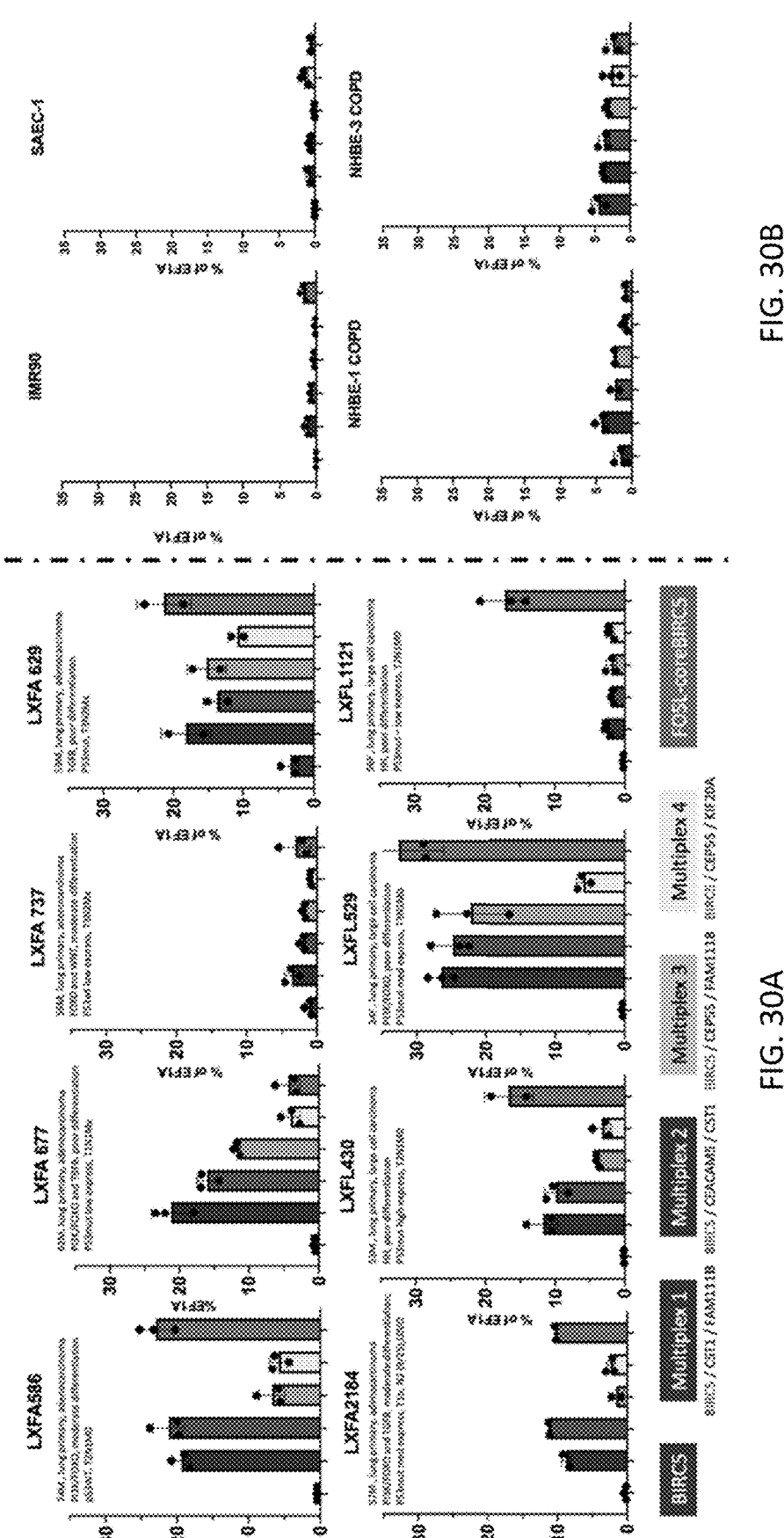
FIGS. 30A and 30B show expression of synthetic promoter FOS-coreBIRC5 in PDX cell lines and normal lung cell lines. Compared to endogenous promoters, including the Survivin (BIRC5) promoter and other first-generation endogenous promoters used in multiplexes, the synthetic promoter FOS-coreBIRC5 outperformed in terms of strength and sensitivity in 8 PDX cell lines that represent different patients' genomic profiles (FIG. 30A).

FIG. 30A demonstrates that the synthetic constructs generated (FOS-coreBIRC5) outperformed the individual or multiplexed endogenous promoters in terms of both strength and sensitivity across PDX cell lines, having up to 10-fold more signal than the endogenous BIRC5 (Survivin) promoter and equivalent or better signal than the multiplexed endogenous promoters. The FOS-coreBIRC5 promoter also showed sensitivity capturing patient LXFL1121, which was missed by all other multiplexed endogenous promoters. The FOS-coreBIRC5 promoter had similar expression level as the endogenous BIRC5 promoter in normal lung fibroblast, bronchial epithelial (NHBE), and small airway epithelial cells (SAEC) (FIG. 30B).

Figure 31:
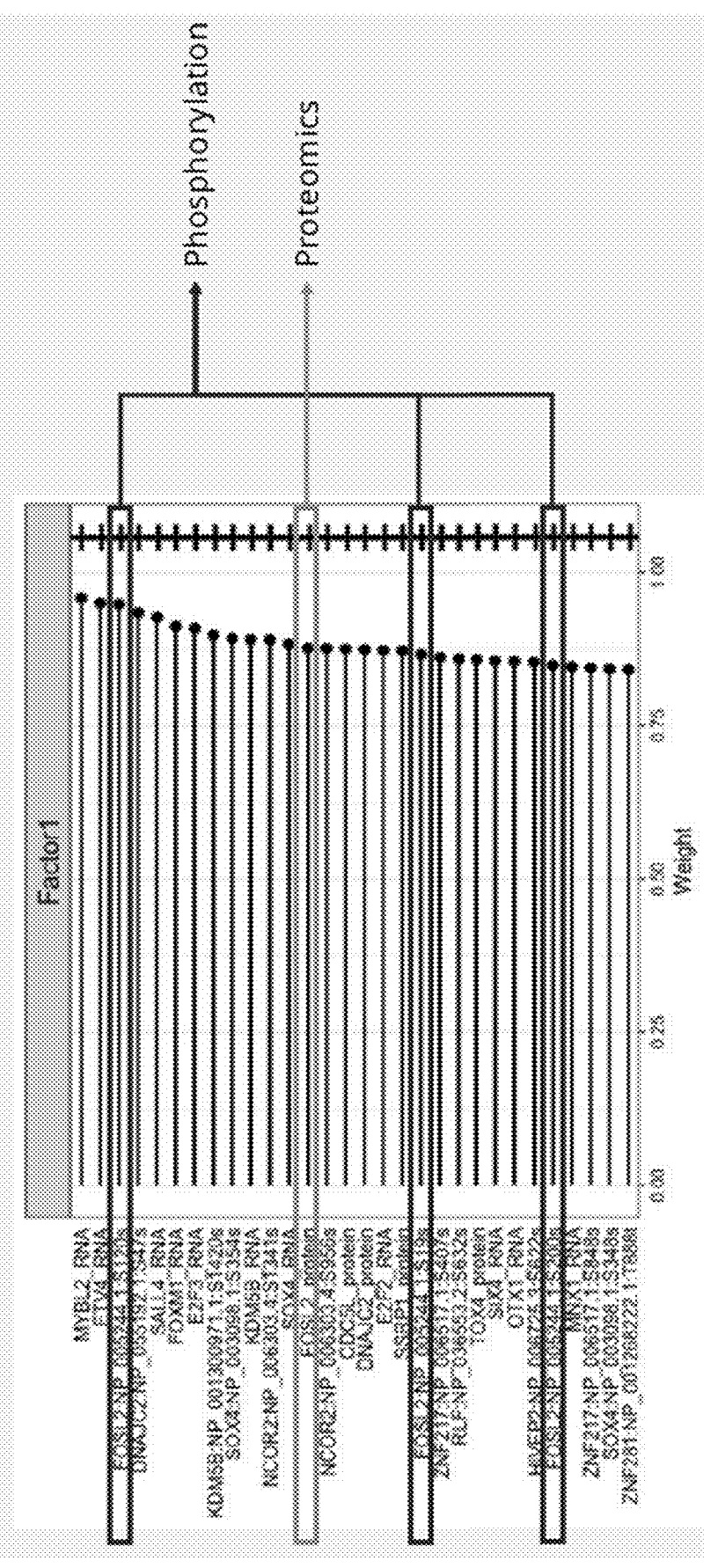
FIG. 31 shows the top 30 contributing features that make up a factor of MOFA analysis.
Figure 32:
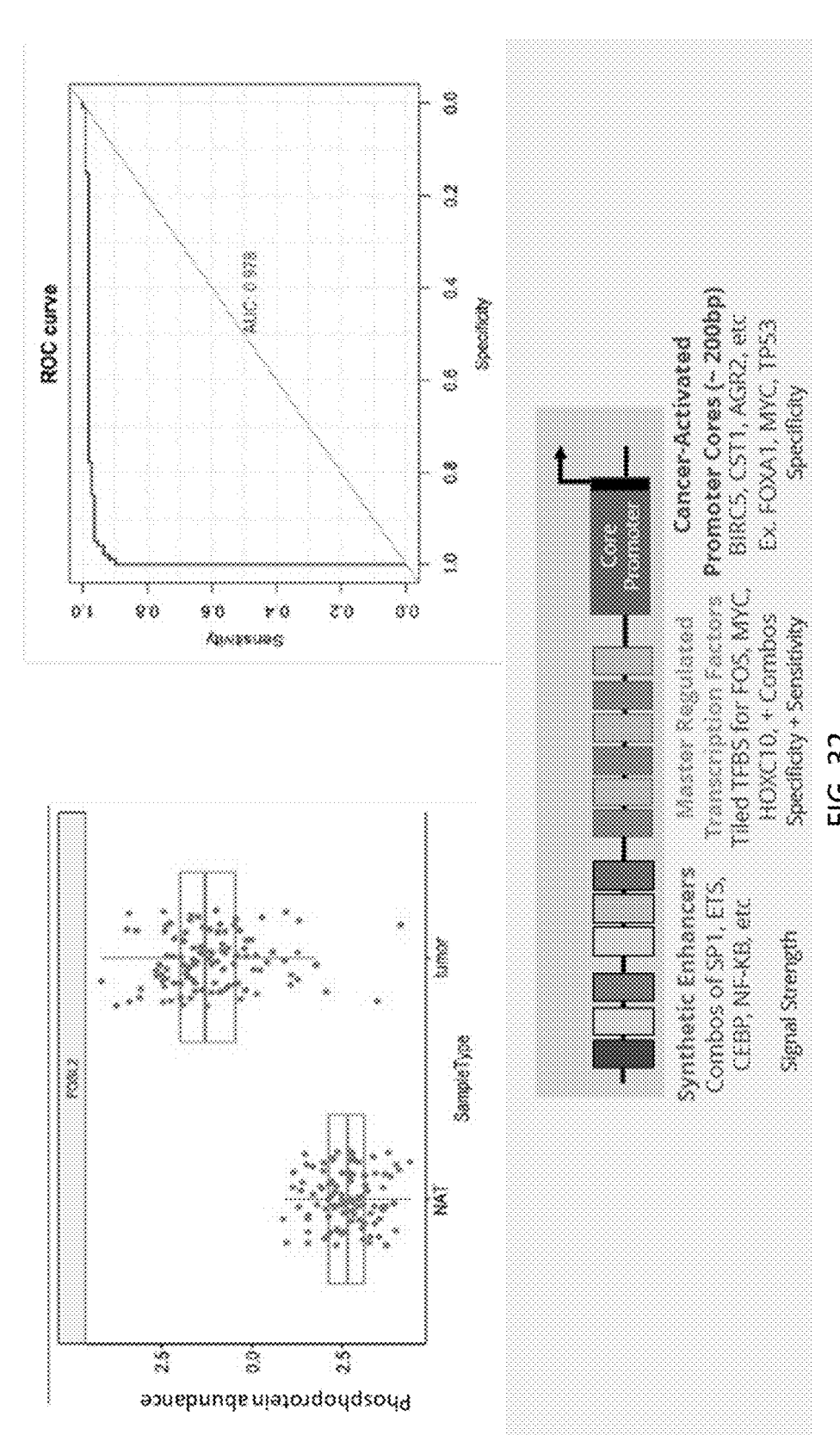
FIG. 32 shows comparison of reporter gene expression by FOSL2 in Normal Adjacent Tissues (NAT) and tumor.

While the FOS binding site used is the DNA binding motif for a variety of bZIP-like transcription factors, including Jun and FOS family (FOS, FOSB, FOSL1, and FOSL2), cancer-activated upregulation of FOSL2 is expected and is primarily driving the differential expression of this promoter, as FOSL2 was identified as one of the top candidates in the multi-omics analysis performed as a part of Multi-Omics Factor Analysis (MOFA) for NSCLC specific transcription factor identification (FIGS. 31-32). This MOFA utilized an unsupervised integration of different -omics data available from CPTAC's LUAD and lung squamous cell carcinoma (LUSQ) tumor and patient matched Normal Adjacent Tissues (NAT) samples and restricted gene analysis to TFs and phosphorylation sites of those TFs. The initial analysis of NSCLC patients consistently showed FOSL2 as one of the top activated transcription factors in NSCLC, especially by protein abundance and phosphorylation abundance (FIGS. 31-32). However, based on the literature evidence, other various FOS family members can be also used, as high FOSL1 expression has been shown in KRAS driven lung and pancreatic cancers, and gross upregulation of c-Fos and its binding partner c-Jun has been shown in NSCLC.

To prove the hypothesis that FOS-coreBIRC5 activity is directly responsive to varying levels of FOSL2, a chromatin immunoprecipitation (ChIP) assay was performed to determine whether the FOSL2 protein binds directly to the FOS-coreBIRC5 in cell lines where the FOS-coreBIRC5 promoter is active. The results showed that the FOS-core-BIRC5 sequence is 14 times more enriched in the FOSL2 pulldown versus the non-specific pulldown of the same construct (FIG. 33). The coreBIRC5 promoter alone construct that does not contain the putative FOSL2 binding sequences serves as a negative control, demonstrating that there is no enrichment of the DNA sequence upon a pull-down of the FOSL2 or c-Jun proteins. This mechanistically proves that the response element binds directly the FOSL2 transcription factor as well as its dimerization partner, c-Jun.

Additional TF Response Element Promoters Using core-BIRC5

Figure 34:
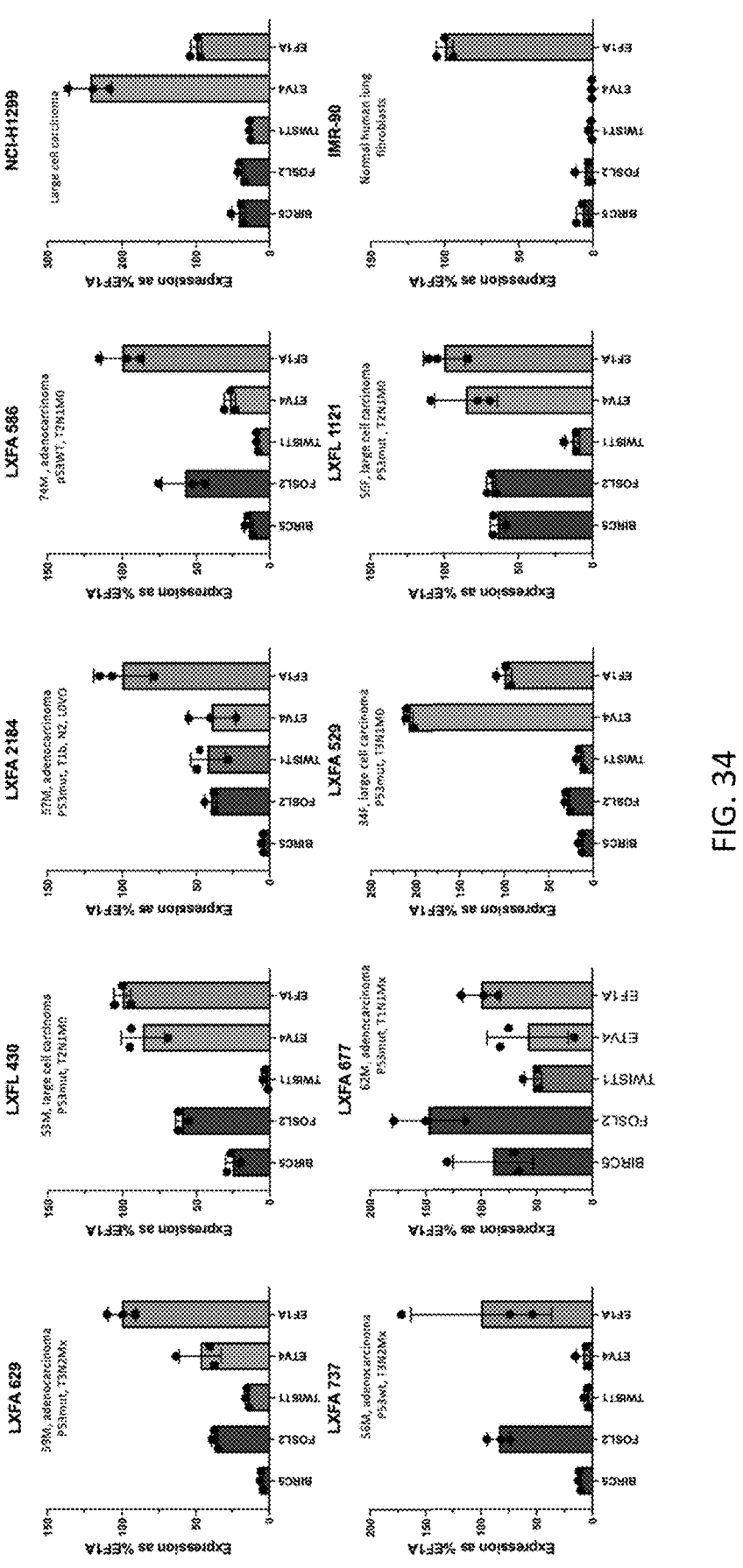
FIG. 34 shows demonstration of high sensitivity and specificity in primary-derived and commercial cell lines by chimeric promoters using core-BIRC5. Response elements for different TFs (FOSL2, TWIST1, ETV4) in combination with the coreBIRC5 promoter showed variable sensitivity across different PDX cell lines, H1299 NSCLC cell line, and a lack of expression in IMR-90 (normal human fibroblast) cell line.

In addition to the FOS response element, more than 20-30 working response elements to transcription factors dysregulated in NSCLC were engineered. A high-throughput screening approach was implemented to test and design thousands of unique response elements at a time. FIG. 34 shows a small subset of these transcription factors (FOSL2, ETV4, TWIST1) across a panel of eight different lung cancer PDX cell lines, as well as NSCLC cell line H1299 and control normal fibroblast cell line IMR-90, demonstrating that several of these chimeric promoters can drive fairly high expression in a variety of cancer cell lines, especially compared to the initial endogenous (1000 bp) BIRC5 promoter, while still maintaining high specificity.

Predictability of Synthetic Promoters: B-Cat/Wnt Pathway Synthetic Promoter

Figure 35:
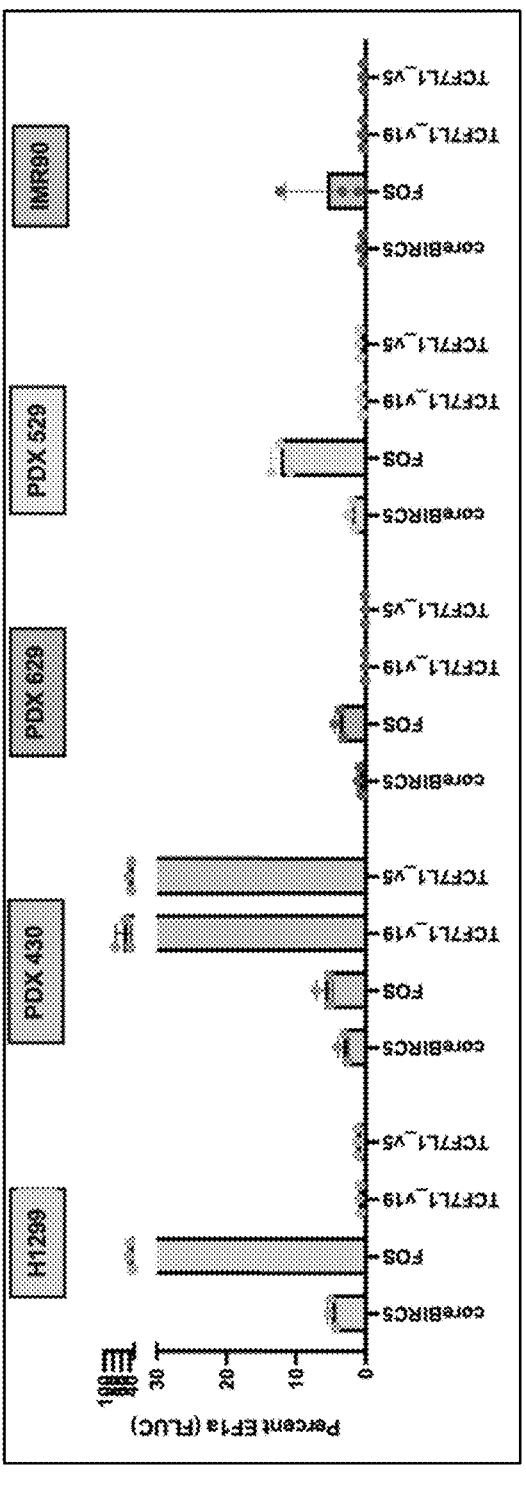
FIG. 35 shows the activity of TCF7 & TCFL1 variants in different cell lines. TCF7 & TCFL1 variants were only active in PDX LXFL430 among cell lines tested. Two variants of the TCF7-response element promoter, as compared to the minimal coreBIRC5 and positive control FOS-coreBIRC5 promoter, demonstrated extremely high levels of expression in the large cell lung cancer PDX430.

While many of the synthetic TFBS constructs tested had increased sensitivity and specificity relative to endogenous promoters, it was also found that synthetic promoters containing binding sites for the TCF/LEF family of transcription factors showed significant activity in only one of the primary models (PDX430, FIG. 35), while maintaining high specificity as evidenced by a lack of signal in normal cell lines such as IMR-90 fibroblasts. As TCF7 is a well-studied acting transcription factor in the B-catenin/Wnt signaling pathway, it was postulated that this cell line uniquely represented a Wnt-dependent tumor.

A principal component analysis (PCA) was performed on the transcriptome data from Charles River on all NSCLC PDX tumors, as well as CCLE, the Cancer Cell Line Encyclopedia. The primary differentiator (PC1) was driven by inherent transcriptomic differences between the PDX cell lines (blue) and the immortalized traditional cell lines (red), likely due to similar genetic drift in the immortalized cell lines due to many generations of adjustment to plastic. However, by PC2, PDX430 was uniquely situated in PC2, and within the CCLE cell lines, NCI-H520 and LK2 plot similarly by PC2. This is driven by nearly identical profiles in key Wnt pathway genes Wnt7B, CCND1, FZD3, AXIN2, and NKD1.

Figure 17:
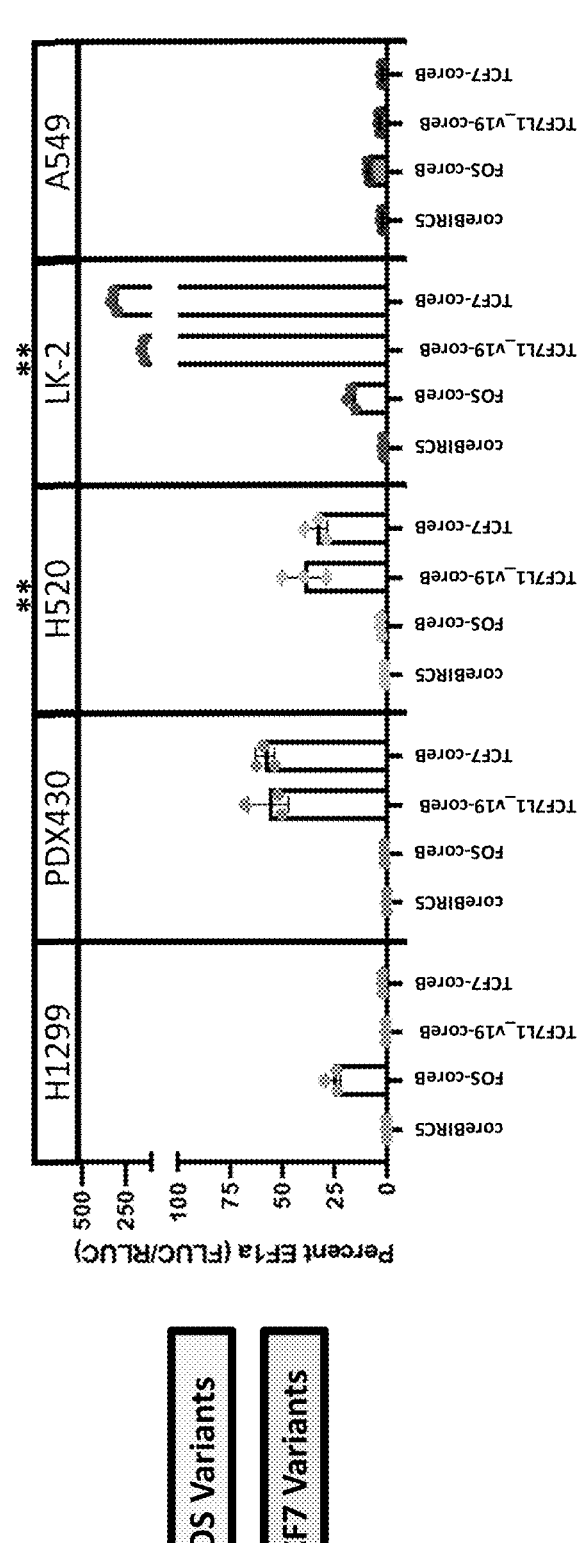
FIG. 17 shows Wnt-driven cell lines identified by PCA (LK2 and NCI-H520) driving the expression by TCF7 and TCF7L1 promoters. In a transient transfection of two TCF7 variant promoters across five cell lines, H520 and LK-2 show the same high levels of activation as PDX430, which was predicted by the PCA analysis. As expected, H1299 and A549 cell lines do not show substantial expression by the TCF7 promoters, and are much better represented by the FOS-coreBIRC5 promoter.
Figure 18:
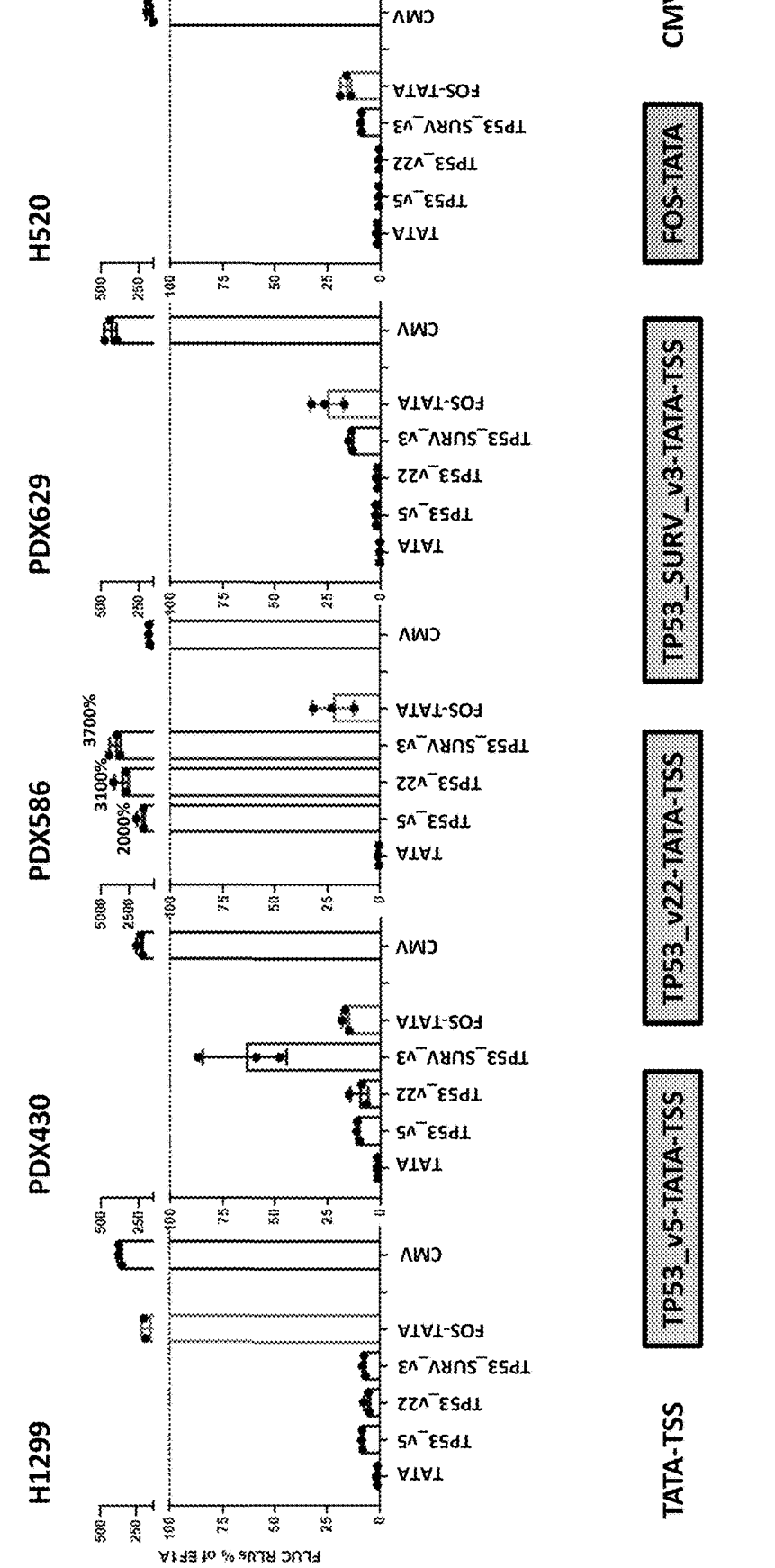
FIG. 18 shows the expression of the reporter gene by TP53 elements. Addition of TP53 elements to TATA-TSS core results in significantly increased expression of the reporter gene in PDX586 as predicted by HTS-002.
Figure 19:
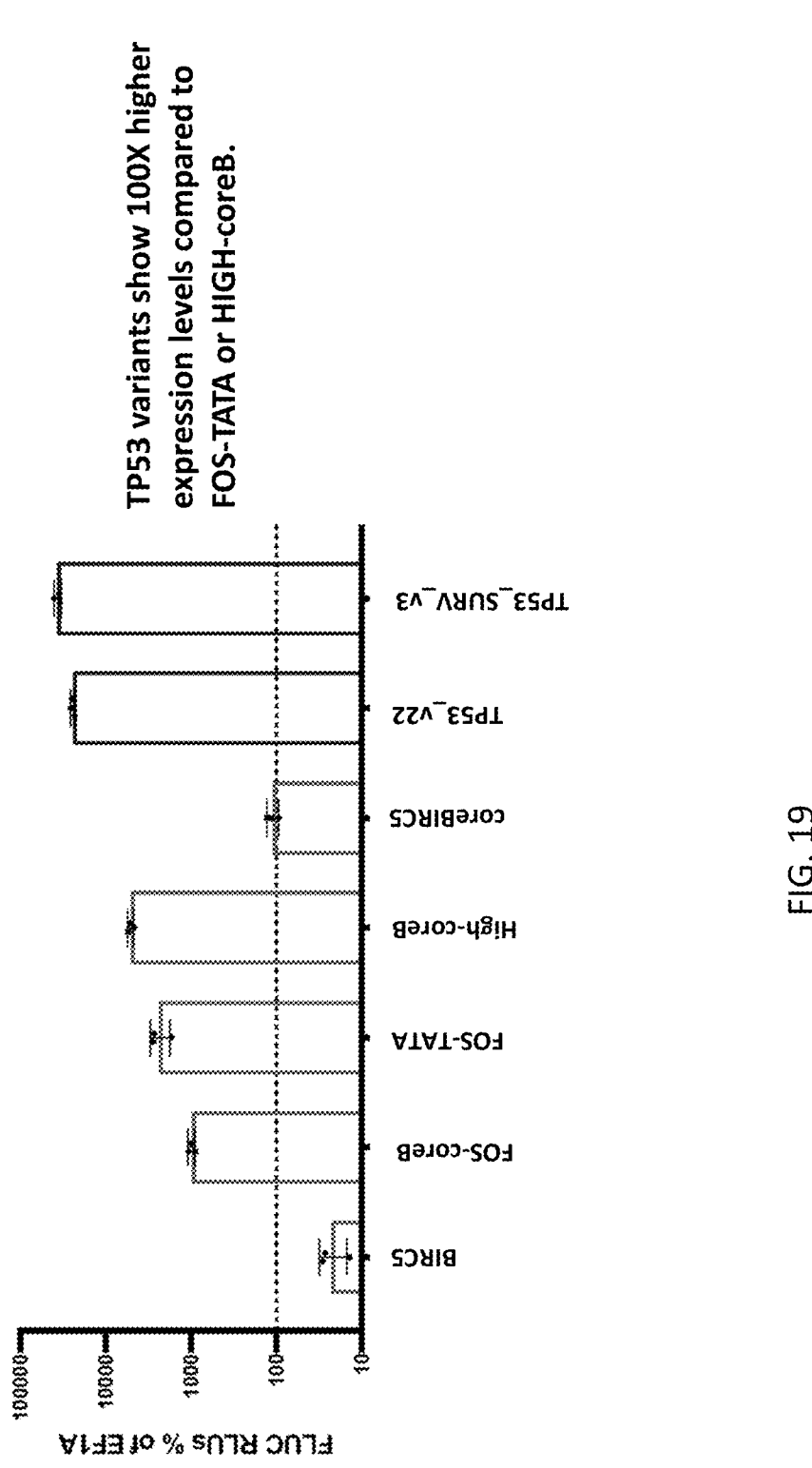
FIG. 19 shows the expression of the reporter gene by TP53 variants in A549 cells.
Figure 20:
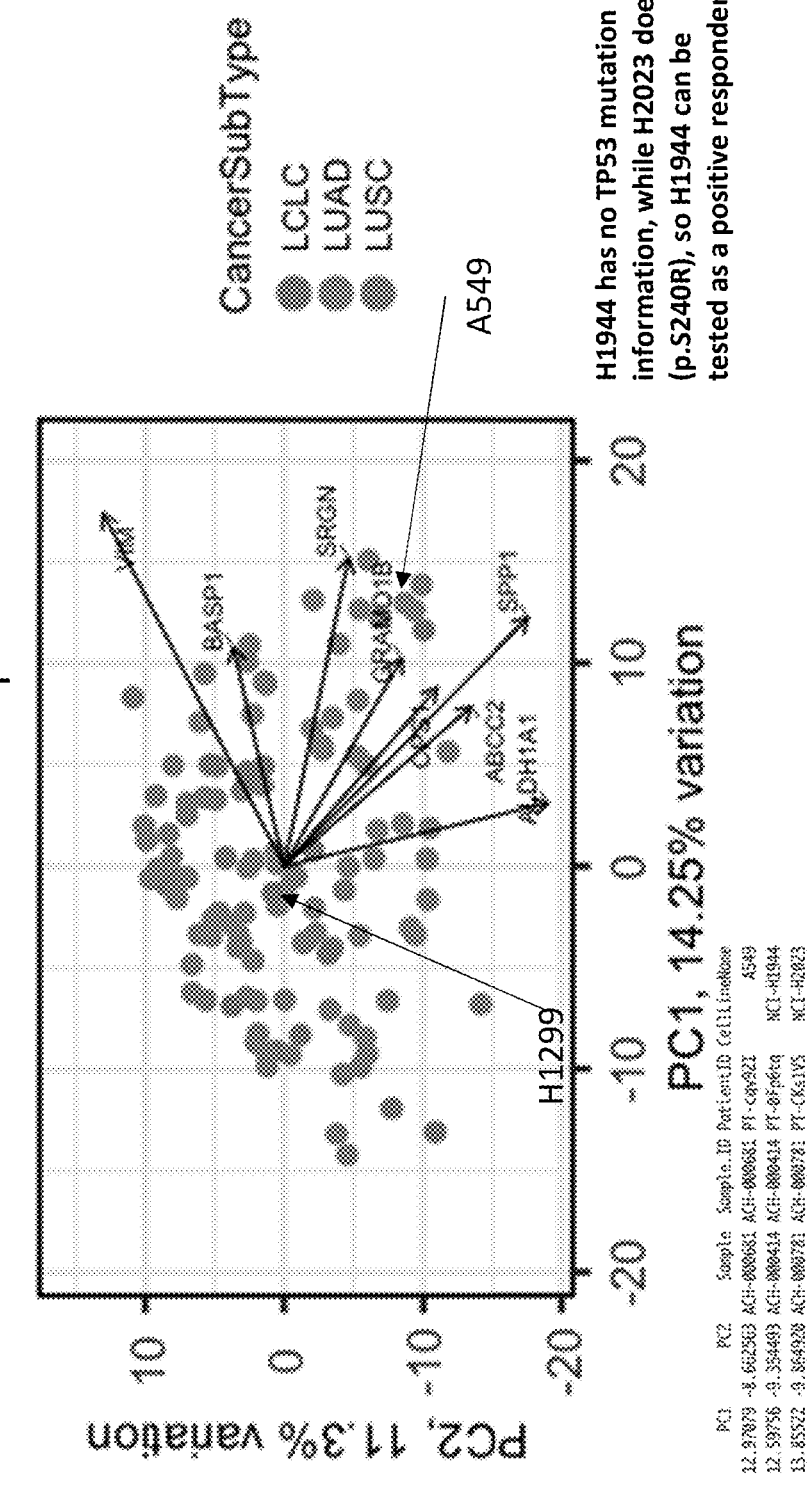
FIG. 20 shows PCA analysis in H1944 and H2023 cells.

These similarly profiled cell lines were purchased and transfected with a panel of synthetic constructs including the TCF7 and TCF7L1 variants, and as shown in FIG. 17, H520 and LK-2 predictably activated the TCF7 promoter, while KRAS-driven cell lines H1299 and A549 did not show any activation of the Wnt-pathway promoter, especially as compared to the FOS driven promoter.

Core Promoter Signal Elements

In addition to cancer-specific response elements, synthetic promoters can also be engineered with general activating elements comprising transcriptional factor binding sites and elements, GC-Box, antioxidant response elements (ARE). These can be combined with minimal core promoters or with synthetic promoter constructs containing TFBS such as FOSL-core BIRC5.

The "Low," "Medium," and "High" expressing elements were added to core promoters. Addition of activating elements resulted in increased signal strength of the promoters.

New Cancer-Specific Core Promoters

In addition to modifying proximal promoter regions, alternative core promoters from endogenous promoters beyond BIRC5 can be combined with synthetic enhancer sequences to increase signal strength while maintaining specificity. Based on the analysis of coreBIRC5 element, it was hypothesized that other "core" regions of endogenous cancer-dysregulated promoters could also serve as the core element in the synthetically engineered promoters and it was sought to understand whether they also maintain the specificity driven by coreBIRC5 while increasing sensitivity or signal strength.

Figure 36:
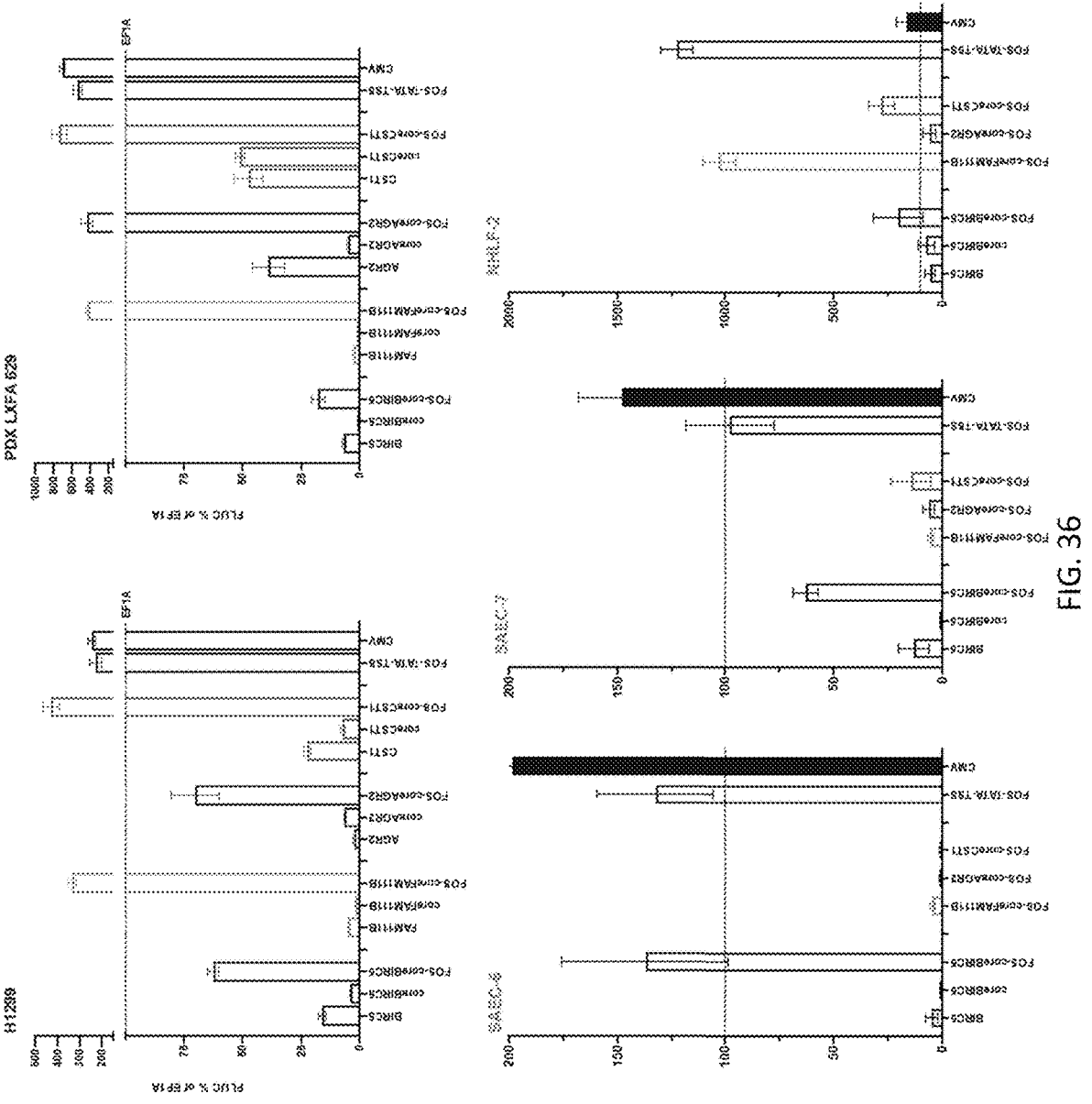
FIG. 36 shows that alternative core promoters to core-BIRC5 demonstrate high utility in synthetic promoter constructs. The full-length endogenous promoters, core promoters, and FOS-core promoters using BIRC5, FAM111B, AGR2 and CST1 were tested in two lung cancer cell lines—H1299 and PDX629. The use of the new cores with FOS demonstrated up to 20-fold improvement in signal compared to the original FOS-coreBIRC5 promoter described previously. On the bottom, experiments using three primary normal lung cell lines (small airway epithelial cells from two donors and normal human lung fibroblasts) demonstrated the FOS-coreAGR2 and FOS-coreCST1 constructs still maintain high specificity for cancer, while FOS-coreFAM111B appears to have significant noise in lung fibroblasts.
Figure 37:
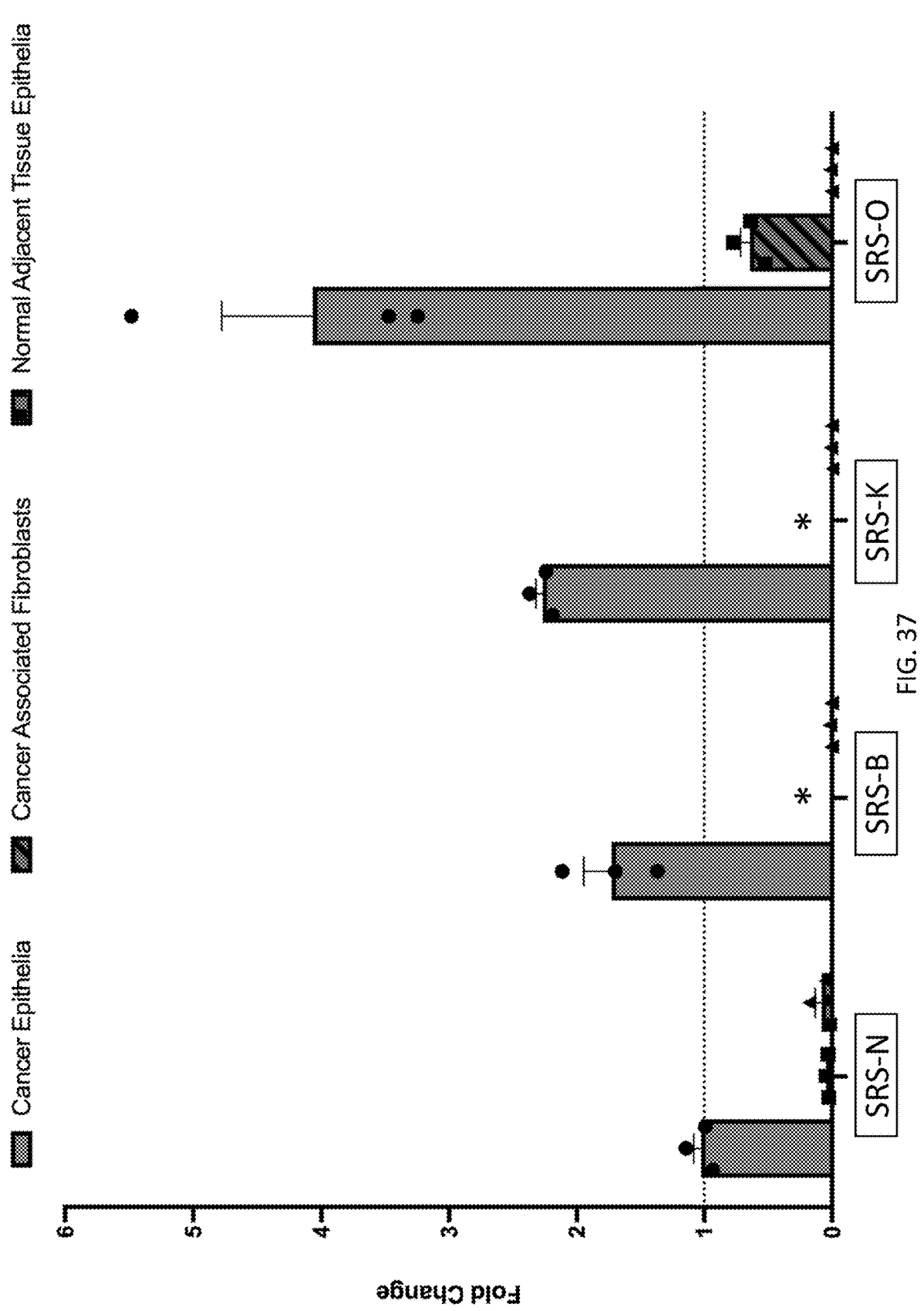
FIG. 37 shows reporter gene expression derived by different synthetic promoters in cancer epithelial cells, cancer associated fibroblast cells, and normal adjacent tissue (NAT) cells from patient derived cell lines (LU057: 63/F/White, Stage IIIB Adeno-squamous pT4, N2). *: not tested. dotted line: CAG, constitutive promoter.

Based on the previous positive results with the FAM111B, AGR2 and CST1 promoters, the use of the core elements isolated from these were first explored. Increasingly short variants of the core were tested and the 165 bp (FAM111B), 360 bp (AGR2), and 191 bp (CST1) version of these cores were further chosen. As shown in FIG. 36, new chimeric promoters FOS-coreFAM111B, FOS-coreAGR2, FOS-coreCST1 led to dramatic improvements in signal strength (up to 20-fold) as compared to FOS-coreBIRC5. As previously suggested, these constructs had improvements over the full-length version of the respective endogenous promoters as well. The new cores also maintained high specificity compared to the completely permissive core TATA-TSS (gray) in normal lung models of human small airway epithelial cells (SAEC-6, SAEC-7) and normal human lung fibroblasts (NHLF-2), although core-FAM111B may not maintain as much specificity in fibroblasts.

Figure 24:
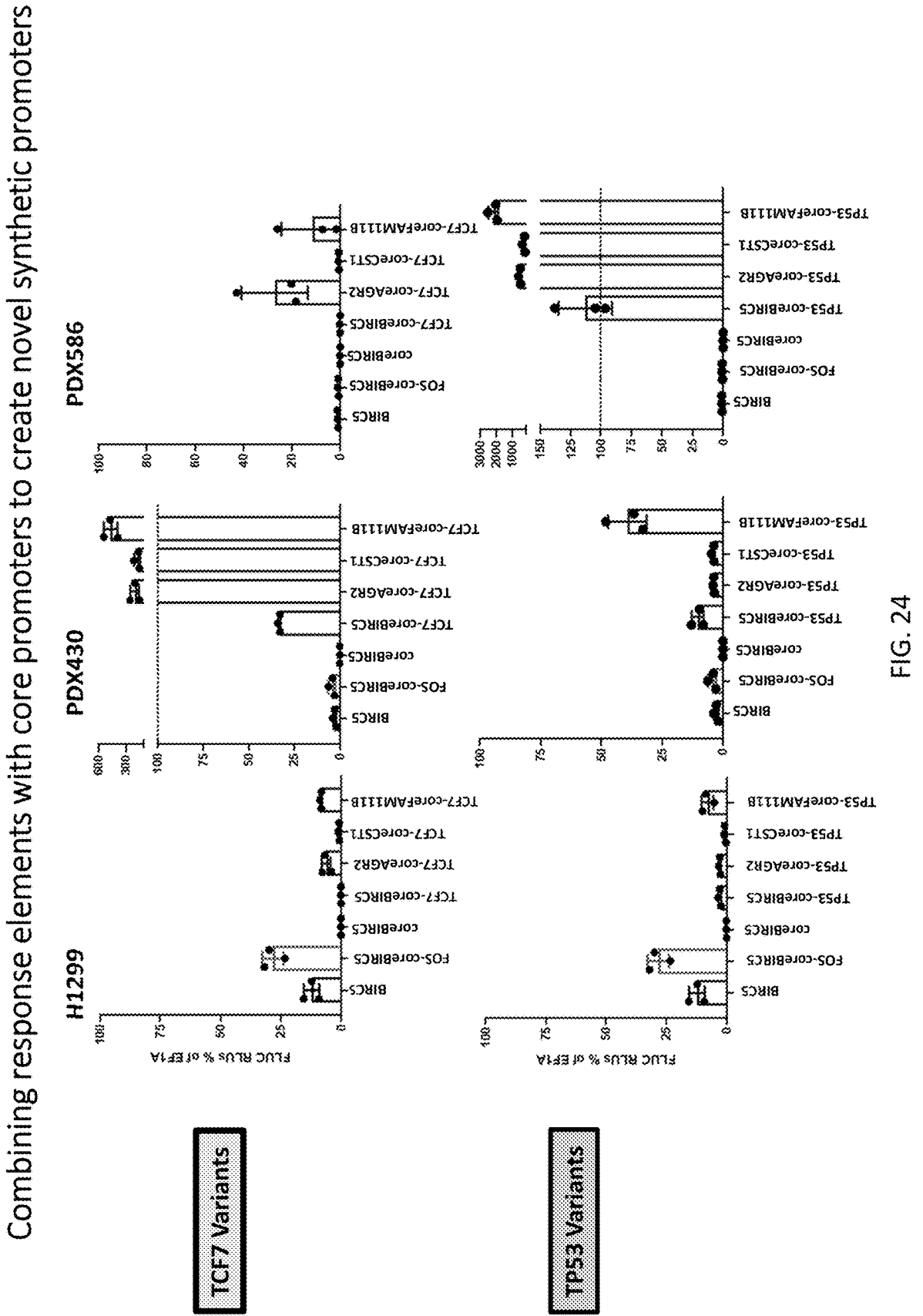
FIG. 24 shows the reporter gene expression by TP53 and TCF7. Pathway specific TP53 and TCF7 response elements pair well and get higher signal using new non-coreBIRC5 cores. As observed with the FOS response element, TP53 and TCF7 response elements combined with coreCST1, coreAGR2, and coreFAM111B show up to a 10-fold signal increase compared to the same promoters constructed with coreBIRC5.
Figure 25:
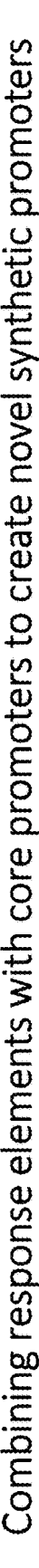
FIG. 25 shows the reporter gene expression by coreBIRC5 and coreAGR2 combined with different response elements in H1299, PDX430, and PDX586 cell lines.
Figure 26:
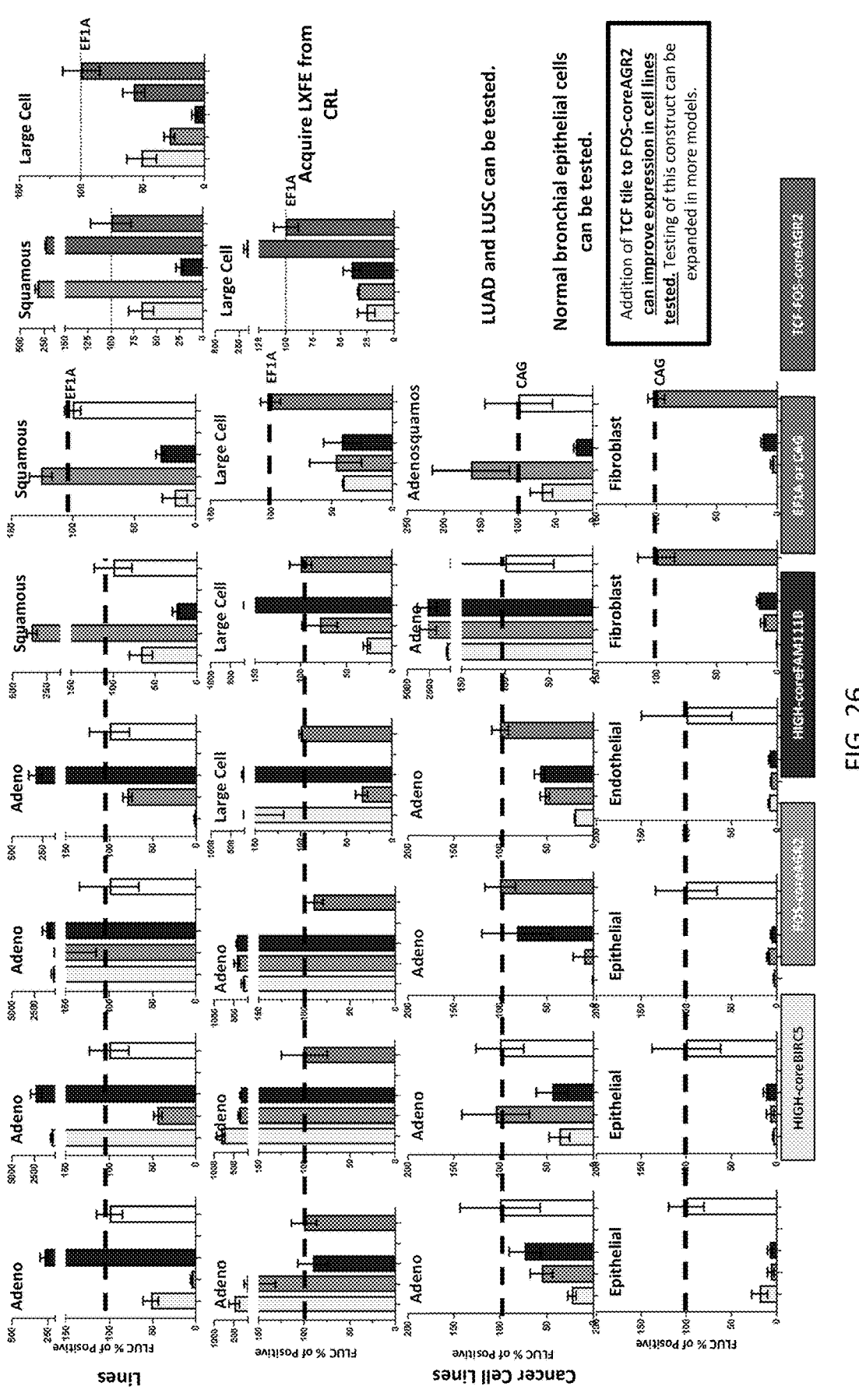
FIG. 26 shows the reporter gene expression by coreBIRC5, coreAGR2, coreFAM111B combined with different response elements in different cell lines.
Figure 27:
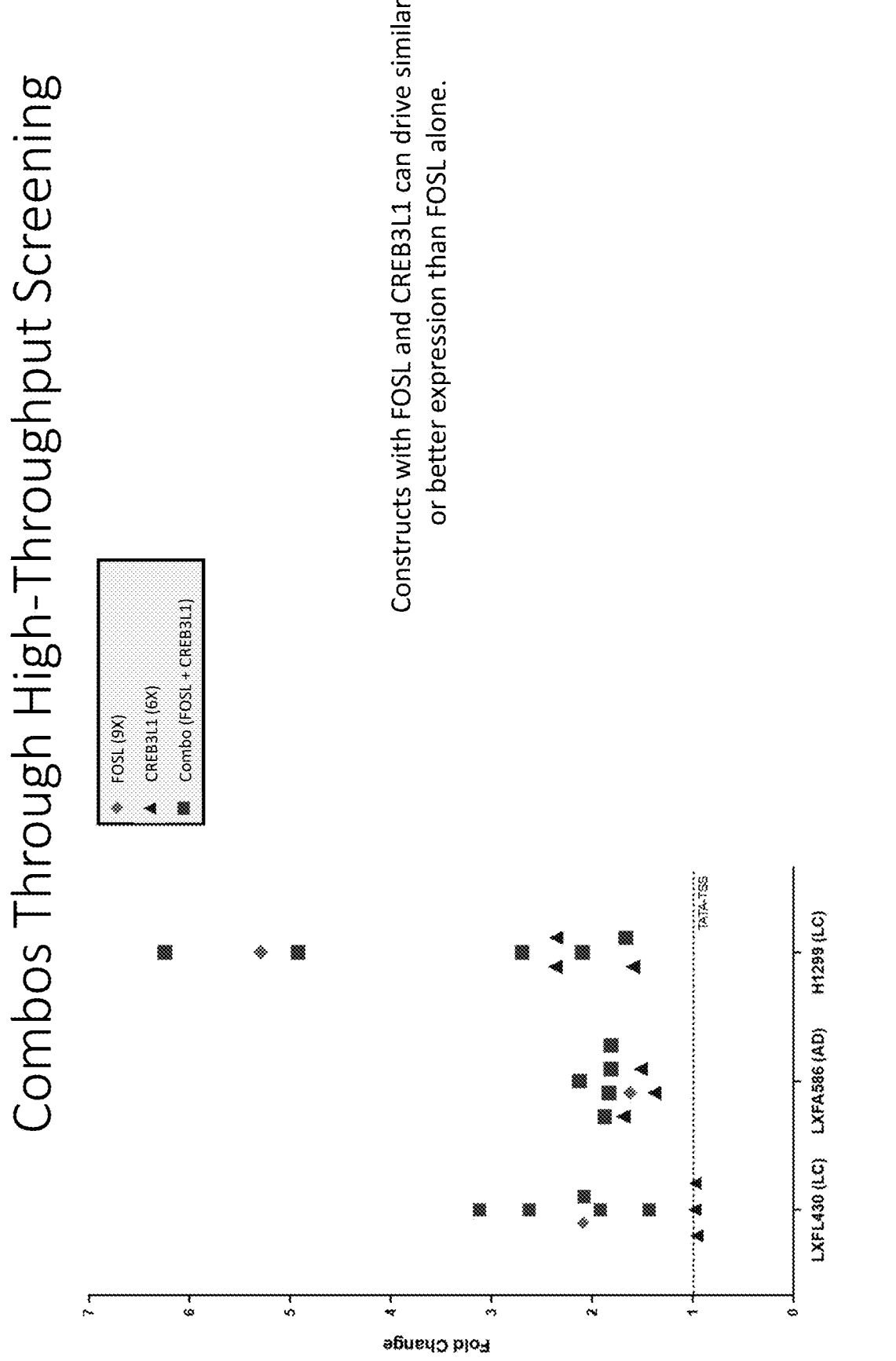
FIG. 27 shows fold change in expression of reporter genes from constructs comprising combination of FOSL and CREB3L1.
Figure 28:
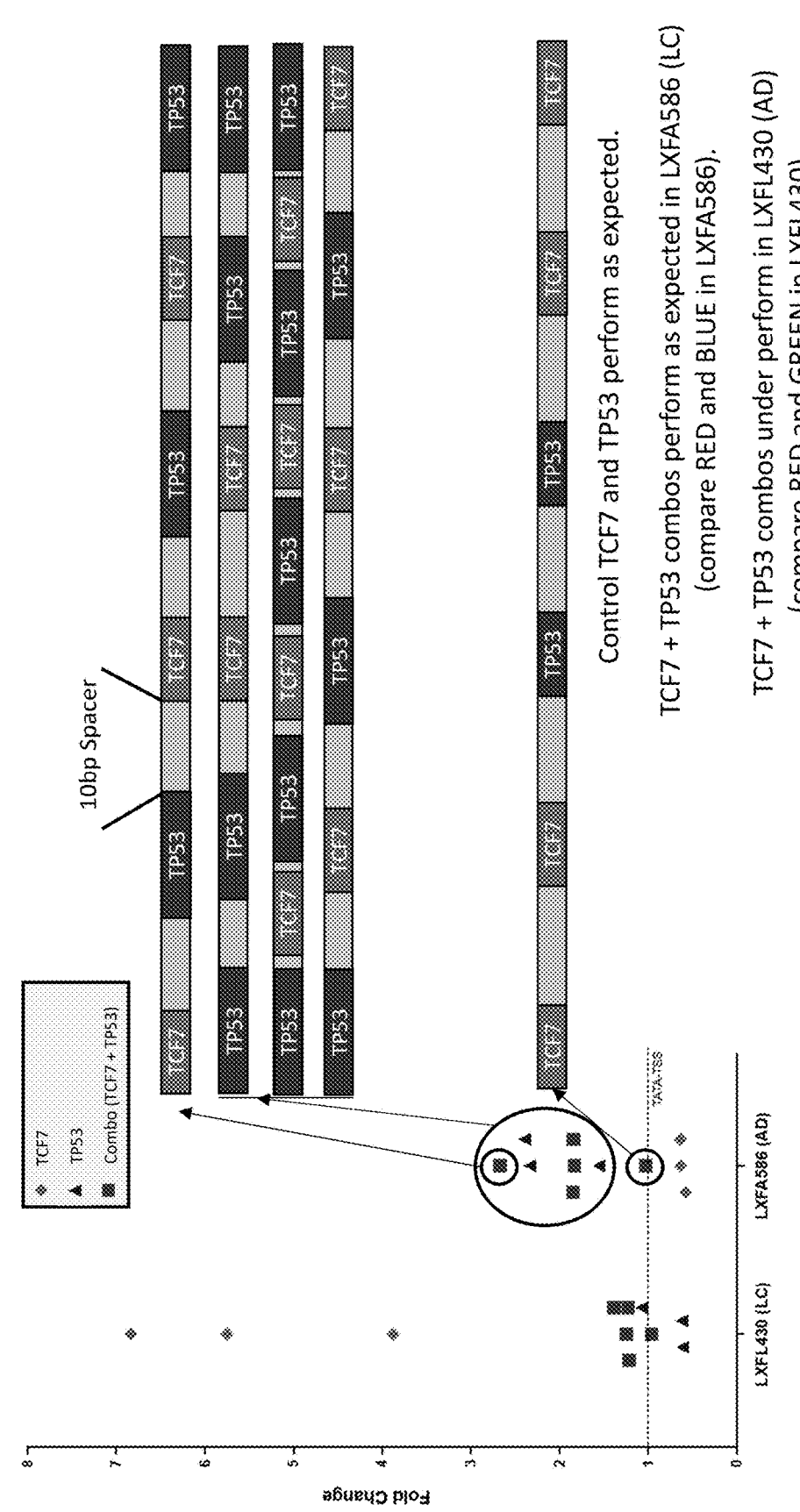
FIG. 28 shows fold change in expression of reporter genes from constructs comprising combination of TCF7 and TP53.

Additional experiments have similarly shown that alternative core promoters coreAGR2 and coreCST1 can partner well with TFs besides FOS to drive higher signal while maintaining cancer specificity (FIGS. 24-26). FIG. 24 shows that response elements for TCF7 and TP53 which are particularly active in cell lines PDX430 and PDX586, respectively, gained additional strength without loss in specificity by using alternate core promoters AGR2, CST1 and FAM111B. Furthermore, addition of TCF tiles to FOS-coreAGR2 improved expression of the reporter gene in various cell lines tested, including cancer cell lines, CRL PDX cell lines, and primary normal lung cells (FIG. 26).

Conclusion

By creating synthetic response elements that are bound by the presence of transcription factors whose expression is dysregulated in cancer, chimeric promoters with high sensitivity and specificity have been engineered to drive cancer specific expression of a reporter gene or a gene of interest. Engineered synthetic promoters can drive substantially higher expression of a reporter gene or a gene of interest than the endogenous promoter of the BIRC5 gene. Furthermore, synthetic promoters can maintain cancer specificity when comparing lung cancer models to normal small airway epithelial cells or lung fibroblasts. Most importantly, the activation of synthetic promoters as opposed to endogenous promoters is highly predictable, as demonstrated by the analysis of the TCF7 chimeric promoter.

Example 3: Detection of Hepatocellular Carcinoma in an Orthotopic Mouse Model Synthetic promoters designed for highly specific cancer-activated expression of a gene in tumors is applicable to malignancies beyond the non-small cell lung cancer (NSCLC). In this example, the utility of a rational-based sequence engineered approach of a highly specific and strong liver cancer promoter is demonstrated. For example, a known alpha-fetoprotein (AFP) promoter drove the expression of a gene up to 200-fold higher in liver cancer cell lines without any increase in basal activity in non-liver and normal cell lines. The promoter-mediated strong cancer-activated expression, when combined with the reporter and delivery aspects of the platform, was demonstrated by blood-based biomarkers and imaging markers (assayed by staining) in an in vivo model of liver cancer.

Hepatocellular carcinoma can greatly benefit from additional technologies in the early detection and diagnostic space. Risk of HCC is highly elevated in patients with chronic liver disease, including those with chronic Hepatitis B (HBV) or with cirrhosis from other severe liver diseases such as HBV, HCV, or NASH. At-risk patients are closely monitored for disease progression into a malignancy, but the tools currently available are highly limited. Semi-annual abdominal ultrasounds and the AFP blood marker test are the only two surveillance tests in clinical guidelines and with broad adoption, but their performance has been quite poor in detecting early-stage malignancies, which are much more likely to be cured & treated effectively than later stage cancers.

Both abdominal ultrasound and AFP blood tests have less than optimal sensitivities, with the AFP test shown to detect HCC with only 63% sensitivity. In particular, ultrasound effectiveness is highly variable based on operator, and is markedly difficult in obese patients and patients with NASH. A novel diagnostic modality described herein could bridge the gap between these screens and diagnosis, either bypassing physical biopsies or further reducing the population that is subjected to them. These patients include those for whom ultrasounds can be inconclusive due to high levels of cirrhosis or indeterminate liver nodules that simply don't have the hallmark radiological features of HCC. Additionally, for patients with small liver nodules (<2 cm), it is difficult to distinguish HCC from benign dysplastic nodules or intrahepatic cholangiocarcinoma (bile duct cancer).

From a scientific perspective, lipid nanoparticles (LNPs) have traditionally been known for their ability to mediate highly effective delivery in the liver, which can be a benefit to liver cancer diagnostics platform, provided that the reporter expression post-delivery is still highly cancer-specific to avoid noise from normal liver. This example provides a strong example of a rational engineering approach applied to endogenous promoters to create a unique liver cancer promoter (named AFP-3) and show that when coupled with a LNP formulation, the platform can provide strong cancer-activated synthetic biomarker expression in primary liver tumors.

The goal is to assess the signal-to-noise response of a liver-tropic formulation using an engineered promoter specific to liver cancer in the Hep3B orthotopic liver tumor model in mice.

Engineering & Testing of the AFP-3 Promoter

Cloning

To generate a reporter construct for use in measuring promoter activity, DNA fragments of interest were cloned into a standard Firefly Luciferase (FLuc) reporter vector from Promega (pGL4.10[luc2] Promega E6651) using the KpnI and NheI restriction enzymes.

The promoter region of interest was amplified using PCR primers with flanking restriction enzyme sites, and the PCR product was purified and digested with the appropriate restriction enzymes. BIRC5 promoter was amplified from approximately −1000 bp to +33 bp relative to the predicted transcriptional start site (TSS) of the endogenous promoter. The AFP promoter was amplified from approximately −250 bp to +28 bp relative to the TSS. AFP-3 was subcloned from AFP using mutagenic primers containing the desired point mutations. Ligated vectors were transformed into E. coli Stable cells, and clones were screened by DNA sequencing to confirm the correct assembly.

DNA was scaled up and purified using QIAGEN® Plasmid Plus Midi (Cat #12945)-), a standard plasmid purification kit, or equivalent. Purified DNA was used for subsequent in vitro and in vivo transfections. Promoters were transferred into Nanoplasmid vectors utilizing restriction enzyme cloning with restriction enzymes flanking the promoter region.

Cell Culture & Transfections

Cells were maintained according to standard protocols with recommended media listed below and incubated at 37° C. and 5% $CO_2$.

SNU-449, H1299 cells were cultured in standard RPMI1640 medium supplemented with 10% (v/v) fetal bovine serum. HepG2 (human hepatocellular carcinoma), Hep3B (human hepatocellular adenocarcinoma), PLC/PRF/5 (human hepatocellular carcinoma), C3A (clonal derivative of HepG2), MRC-9 (fibroblast) and IMR-90 (control normal fibroblast cell line) cells were cultured in standard EMEM supplemented with 10% (v/v) fetal bovine serum. MeWo (human melanoma cell line) cells were cultured in standard DMEM supplemented with 10% (v/v) fetal bovine serum.

Approximately 24 hours prior to transfections, cells were plated to achieve a confluence of 70-80% on the day of transfections. For transient transfections, Lipofectamine™ 3000, a transfection agent comprising DOSPA (2,3-dioleoy-loxy-N-[2(sperminecarboxamido)ethyl]-N,N-dimethyl-1-propaniminium trifluoroacetate) and DOPE (dioleoyl phosphatidylethanolamine), was used according to the manufacturer's instructions. Briefly, for each well, 100 ng of plasmid DNA was mixed with 0.2 μL of P3000™ reagent, a neutral/helper co-lipid, and 0.2 μL of Lipofectamine™ 3000 and 2 ng of control DNA in 100 μL Opti-MEM™ medium, a serum-reduced minimal essential medium, and the mixture was incubated at room temperature for 20 minutes. The transfection mixture was added to the cells in a 96-well plate and incubated for 24 hours.

Luciferase Readouts

Approximately 24 hours after transfection, firefly luciferase and renilla luciferase levels were measured from each well using the Promega Dual-Glo® Luciferase System (E2940) with a working volume of 50 μL.

Hep3B Murine Experiment

Cell Culture

The Hep3B-luc tumor cells (ATCC, Manassas, VA, cat #HB-8064) were maintained in vitro as a monolayer culture in EMEM medium supplemented with 10% fetal bovine serum, 100 U/mL penicillin and 100 μg/mL streptomycin, at 37° C. in an atmosphere of 5% $CO_2$ in air. The tumor cells were routinely sub-cultured twice weekly by trypsin-EDTA treatment. The cells growing in an exponential growth phase were harvested and counted for tumor inoculation.

Orthotopic Tumor Implantation

The female BALB/c nude mice were anesthetized with 20 μL/g Avertin (2,2,2-tribromoethanol). For pain relief, the animals were dosed with 10 mg/kg of Carprofen 30 minutes before surgery and 6 hours post-surgery.

Each of the anesthetized mice was properly positioned. The abdomen skin was sterilized with 70% ethanol and the surgical site was prepared in a sterile condition. A small incision was across the abdominal wall. The left lobe of the liver was identified and exposed. Approximately $3 \times 10^6$ Hep3B-luc cells with BD Matrigel®, a standard mix of extracellular matrix proteins, in 20 μL (PBS: Matrigel®=1:1) were injected into the left lobe of the liver. The injection site was monitored for leakage of cells and after confirmation of no leakage of cells, the left lobe of the liver was placed back to the abdominal cavity. The abdominal wall was then closed, and the skin was closed with surgical suture. These mice were continuously monitored for their complete recovery from anesthesia.

Bioluminescence Measurements

The surgically inoculated mice were weighted and intraperitoneally injected luciferin at 150 mg/kg. After 10 minutes of the luciferin administration, the animals were pre-anesthetized with the mixture gas of oxygen and isoflurane. When the animals were in a complete anesthetic state, they were moved into the imaging chamber for bioluminescence measurements with IVIS (Lumina III). The bioluminescence of the whole animal body, including primary and metastatic tumors, was measured and images were recorded.

Assignment to Groups

Bioluminescence from the Hep3B-luc tumor cells were measured on all tumor bearing mice at Day 7, Day 14, and Day 20 post implantation. Randomization of animals for tumor bearing mice was based on the imaging at Day 20 post implantation, and randomization of non-tumor bearing mice was based on the body weight taken at Day 20 post implantation. Mice were selected at Day 21 post implantation, and mice bearing established tumors were assigned to 9 groups (1, 4, or 5 mice/group) using an Excel-based randomization procedure performing stratified randomization based upon the intensity of bioluminescence. Normal mice (no tumors) were also assigned to 5 groups (2 or 5 mice/group) using the same method. Administration of test article was started at Day 21 post implantation.

Observations

All the procedures related to animal handling, care and the treatment in the study were performed according to the guidelines approved by the Institutional Animal Care and Use Committee (IACUC) of WuXi AppTec following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured twice a week and at Day 20 post implantation as well as every occurrence prior to bleed), eye/hair matting and any other abnormal effect as stated in the protocol. Death and observed clinical signs were recorded on the basis of the numbers of animals within each subset.

Sample Collection and Endpoints

Serum Collection:

For Groups 1, 2, 9, 13 and 14: Bleed 1 day before testing of test article, and at 48 hours after dosing (terminal).

Tissue Collection:

For all non-tumored mice Groups 3-14: collect left lobe and right lobe separately and snap frozen at 48 hours after dosing.

For all tumored-mice Groups 3-13: collect tumor, left lobe and right lobe separately, bisect each of them and snap frozen half, then the other half into FFPE at 48 hours after dosing.

Animals & Housing Conditions

Species: *Mus musculus*

Strain: BALB/c nude

Age: 6-8 weeks

Sex: female

Body weight: 18-22 g

Number of animals: 56 mice plus spare

Animal supplier: Beijing Vital River Laboratory Animal Co. LTD

Animal quality certificate number: 20221208Abzz0619000836, 20221208Abzz0619000874, 20221212Abzz0619000183

Housing Condition

The mice were kept in individual ventilation cages at constant temperature (20-26° C.) and humidity (40-70%). Cages were made of polycarbonate with a size of 375 mm×215 mm×180 mm. The bedding material was corn cob, which was changed twice per week. Animals had free access to irradiation sterilized dry granule food during the entire study period. Animals had free access to sterile drinking water.

Results

Design and Validation of AFP-3 Promoter for Activation in Liver Cancer

The alpha-fetoprotein (AFP) promoter has been extensively studied and shown to confer selective expression of transgenes in hepatocellular carcinoma (HCC) in vitro and in vivo. The AFP transcript is normally expressed in normal fetal livers but not adult livers, and then is known to be re-activated in about 70% of liver cancers. Thus, circulating AFP protein is a well-known marker for liver cancer, but the promoter is also well studied to drive specific expression in liver cancer models proportional to the level of AFP expression in the HCC studied.

Figures 38A, 38B:
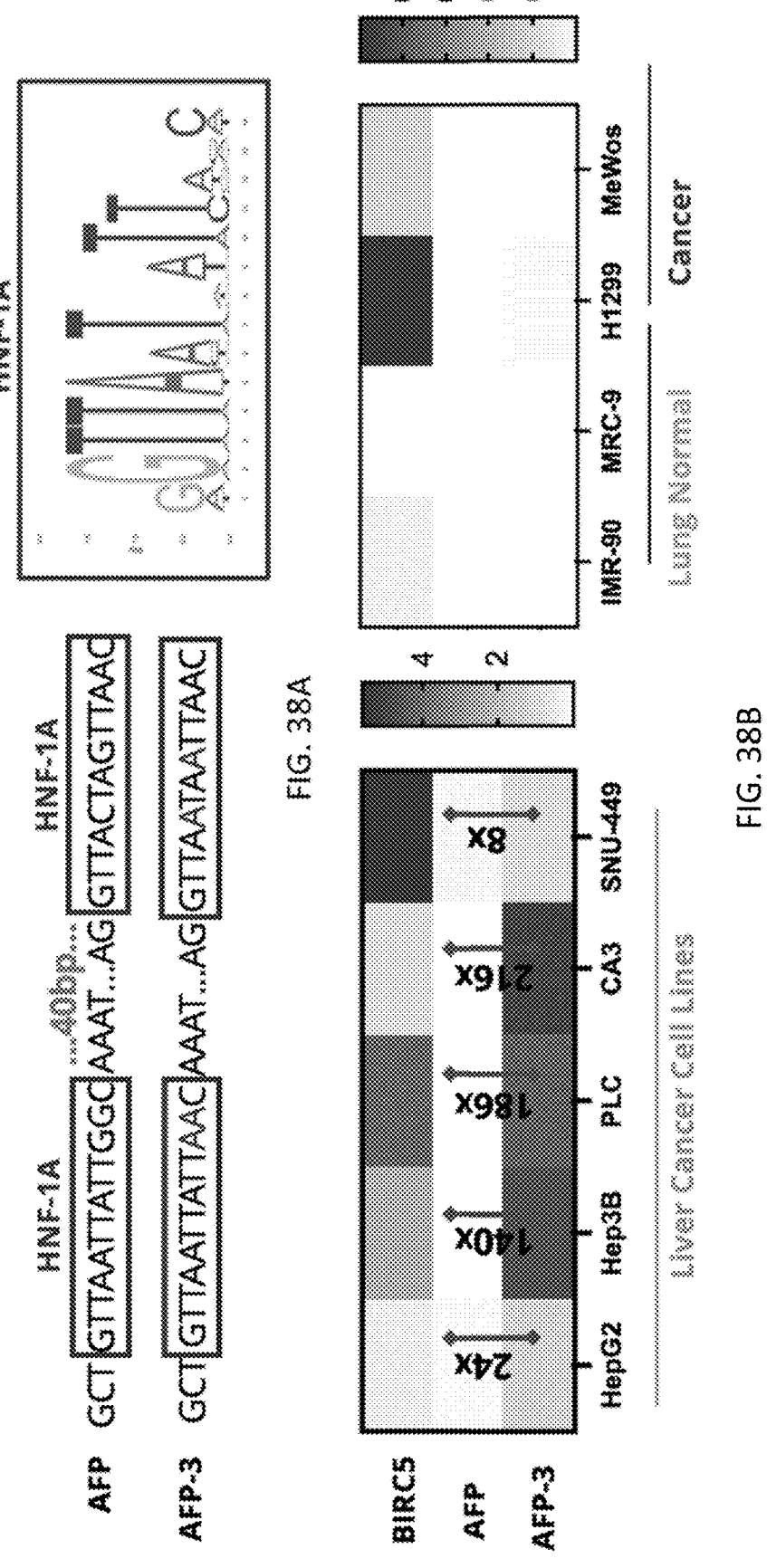
FIGS. 38A and 38B show AFP-3, an engineered variant of the human alpha-fetoprotein (AFP) promoter that can drive strong and highly specific expression in HCC.

However, as with most endogenous promoters, the level of expression from the AFP promoter is remarkably low, gating its effectiveness in previous applications of liver activated expression. In an effort to create a stronger and more robust activating promoter, a bioinformatic analysis was performed and it was found that there were suboptimal binding sequences for TFs. To boost transcription level, the promoter was rationally engineered by strengthening the dimerized binding sites for HNF-1A, TF binding sites within the AFP promoter, to be closer to the known consensus site for HNF-1A from other promoters (FIG. 38A). Modification of these sequences to have a greater consensus with the ideal binding site can create a more durable and longer interaction of the HNF1A with the AFP promoter, allowing this TF to drive more expression from the TSS in the promoter. These small, rational edits to the base pairs in the promoter led to the reporter construct expressing firefly luciferase to increase expression between 20 to 200-fold in liver cancer cell lines HepG2, Hep3B, PLC, CA3 and SNU-449 (FIG. 38B) while continuing to maintain highly specific liver expression, as shown by continued lack of activity in lung normal cell lines IMR-90, MRC-9, as well as lung cancer H1299 and melanoma MeWo cell lines.

In Vivo Experimental Design and Groups

Figure 42:
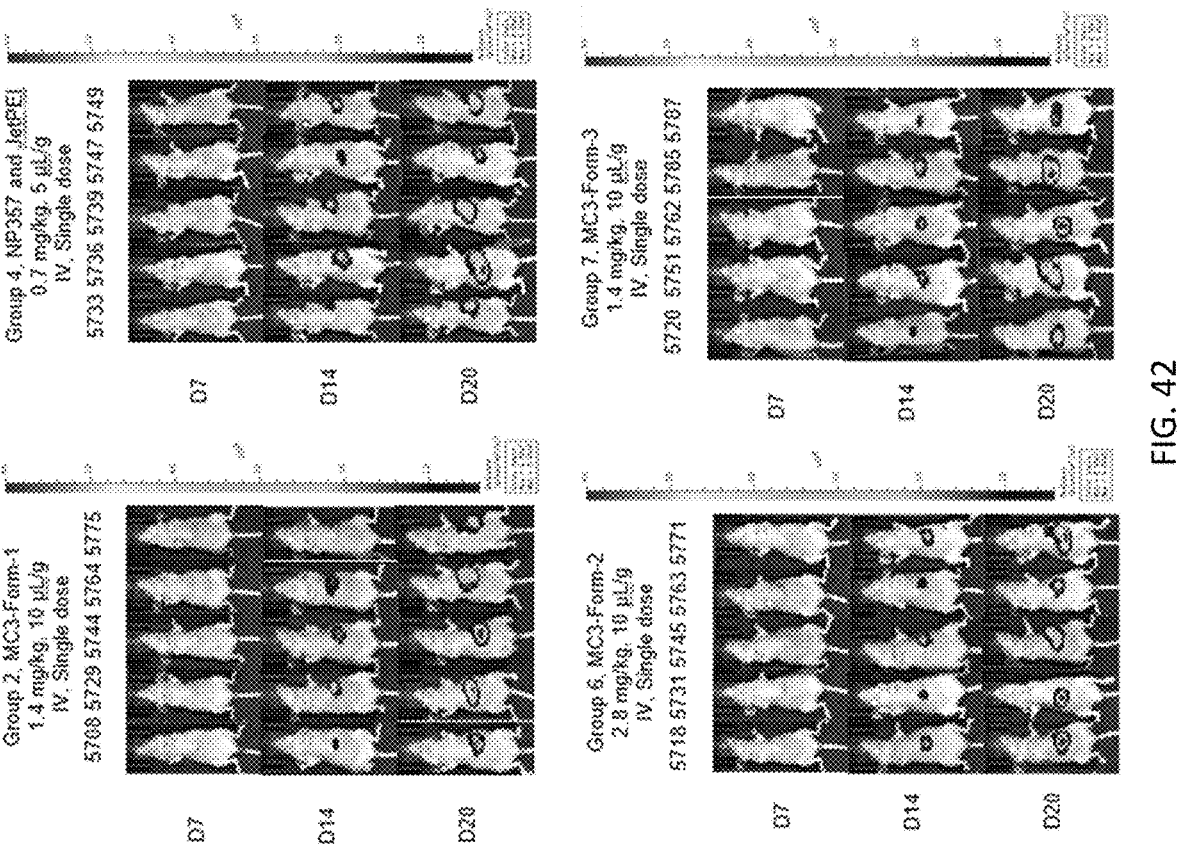
FIG. 42 shows images of animal bioluminescence.

In orthotopic models of HCC, cancer cells are directly inoculated into the liver parenchyma, which allows the tumor to be studied within the correct target organ. In this study, the Hep3B human HCC cell line was orthotopically implanted into the left lobe of the liver for tumor-bearing mice. The cell line used includes a luciferase-based marker to track tumor growth over time and allow for fair assignment of groups based on tumor size. Luciferase and body weight data are shown in Tables 3 & 4 and FIG. 42, demonstrating appropriate tumor growth over 20 days before the mice were randomized and assigned experimental groups in Table 5.

TABLE 3

| Raw Data of Body Weight Measurements | | | | |
|---|---|---|---|---|
| BW | Tumor | Animal No. | 0[a] | 2 |
| Group 1 | N | 5797 | 23.36 | 21.05 |
| MC3-Form-1 | | 5798 | 23.66 | 20.96 |
| 1.4 mg/kg | | 5800 | 21.02 | 19.67 |
| 10 μL/g | | 5801 | 22.90 | 20.54 |
| IV, Single dose | | 5806 | 24.14 | 22.89 |
| | | Mean | 23.02 | 21.02 |
| | | SEM | 0.54 | 0.53 |
| Group 2 | Y | 5708 | 23.41 | 20.87 |
| MC3-Form-1 | | 5729 | 20.85 | 18.99 |
| 1.4 mg/kg | | 5744 | 23.32 | 21.01 |
| 10 μL/g | | 5764 | 20.32 | 17.89 |
| IV, Single dose | | 5775 | 20.62 | 18.03 |
| | | Mean | 21.70 | 19.36 |
| | | SEM | 0.68 | 0.67 |
| Group 3 | N | 5795 | 23.02 | 21.48 |
| NP357 and JetPEI | | 5805 | 23.02 | 21.48 |
| 0.7 mg/kg | | | | |
| 5 μL/g | | | | |
| IV, Single dose | | | | |
| | | Mean | 23.02 | 21.48 |
| | | SEM | 0.00 | 0.00 |
| Group 4 | Y | 5733 | 20.97 | 20.76 |
| NP357 and JetPEI | | 5736 | 22.32 | 20.81 |
| 0.7 mg/kg | | 5739 | 20.13 | 17.84 |
| 5 μL/g | | 5747 | 24.00 | 21.31 |
| IV, Single dose | | 5749 | 21.53 | 19.84 |

TABLE 3-continued

Raw Data of Body Weight Measurements

| BW | Tumor | Animal No. | 0[a] | 2 |
|---|---|---|---|---|
|  |  | Mean | 21.79 | 20.11 |
|  |  | SEM | 0.66 | 0.62 |
| Group 5 MC3-Form-2 2.8 mg/kg 10 µL/g IV, Single dose | N | 5799 | 23.39 | 21.09 |
|  |  | 5804 | 22.26 | 20.55 |
|  |  | Mean | 22.83 | 20.82 |
|  |  | SEM | 0.57 | 0.27 |
| Group 6 MC3-Form-2 2.8 mg/kg 10 µL/g IV, Single dose | Y | 5718 | 21.20 | 17.81 |
|  |  | 5731 | 23.74 | 19.57 |
|  |  | 5745 | 23.42 | 18.67 |
|  |  | 5763 | 22.43 | 16.96 |
|  |  | 5771 | 23.17 | 18.88 |
|  |  | Mean | 22.79 | 18.38 |
|  |  | SEM | 0.45 | 0.45 |
| Group 7 MC3-Form-3 1.4 mg/kg 10 µL/g IV, Single dose | Y | 5720 | 24.82 | 22.41 |
|  |  | 5751 | 22.02 | 19.09 |
|  |  | 5762 | 22.42 | 20.10 |
|  |  | 5785 | 22.04 | 19.55 |
|  |  | 5787 | 22.59 | 20.40 |
|  |  | Mean | 22.78 | 20.31 |
|  |  | SEM | 0.52 | 0.57 |
| Group 8 MC3-Form-4 0.7 mg/kg 10 µL/g IV, Single dose | Y | 5709 | 22.56 | 19.84 |
|  |  | 5754 | 22.20 | 20.64 |
|  |  | 5756 | 22.45 | 20.25 |
|  |  | 5761 | 22.28 | 20.39 |
|  |  | 5772 | 23.92 | 20.73 |
|  |  | Mean | 22.68 | 20.37 |
|  |  | SEM | 0.32 | 0.16 |
| Group 9 MC3-Form-5 diluted 1:2 0.7 mg/kg 10 µL/g IV, Single dose | Y | 5704 | 23.30 | 20.68 |
|  |  | 5721 | 22.65 | 20.57 |
|  |  | 5724 | 24.74 | 22.36 |
|  |  | 5782 | 21.96 | 19.42 |
|  |  | 5788 | 20.09 | 18.21 |
|  |  | Mean | 22.55 | 20.25 |
|  |  | SEM | 0.77 | 0.69 |
| Group 10 MC3-Form-6 1.4 mg/kg 10 µL/g IV, Single dose | Y | 5702 | 21.86 | 18.23 |
|  |  | 5726 | 23.15 | 19.10 |
|  |  | 5769 | 22.05 | 17.21 |
|  |  | 5774 | 20.91 | 17.19 |
|  |  | 5781 | 22.84 | 18.99 |
|  |  | Mean | 22.16 | 18.14 |
|  |  | SEM | 0.39 | 0.41 |
| Group 11 MC3-Form-7 2.8 mg/kg 10 µL/g IV, Single dose | N | 5794 | 23.76 | 21.79 |
|  |  | 5802 | 22.40 | 19.66 |
|  |  | Mean | 23.08 | 20.73 |
|  |  | SEM | 0.68 | 1.07 |
| Group 12 MC3-Form-7 2.8 mg/kg 10 µL/g IV, Single dose | Y | 5703 | 25.38 | 22.75 |
|  |  | 5711 | 22.00 | 20.73 |
|  |  | 5730 | 21.71 | 19.26 |
|  |  | 5789 | 20.93 | 18.48 |
|  |  | Mean | 22.51 | 20.31 |
|  |  | SEM | 0.98 | 0.94 |
| Group 13 PBS 10 µL/g IV, Single dose | Y | 5719 | 22.11 | 21.66 |
|  |  | Mean | 22.11 | 21.66 |
|  |  | SEM | — | — |
| Group 14 MC3-Form-5 diluted 1:2 0.7 mg/kg 10 µL/g IV, Single dose | N | 5791 | 27.22 | 25.08 |
|  |  | 5792 | 21.17 | 19.75 |
|  |  | 5793 | 21.84 | 19.94 |
|  |  | 5796 | 23.19 | 21.27 |
|  |  | 5803 | 21.79 | 20.53 |
|  |  | Mean | 23.04 | 21.31 |
|  |  | SEM | 1.10 | 0.98 |

Note:
adays after the start of treatment.

TABLE 4

Bioluminescence

| TV | Tumor | Animal No. | 0[a] |
|---|---|---|---|
| Group 2 MC3-Form-1 1.4 mg/kg 10 µL/g IV, Single dose | Y | 5708 | 3.367E+09 |
|  |  | 5729 | 7.370E+09 |
|  |  | 5744 | 8.847E+09 |
|  |  | 5764 | 7.500E+09 |
|  |  | 5775 | 4.111E+09 |
|  |  | Mean | 6.239E+09 |
|  |  | SEM | 1.059E+09 |
| Group 4 NP357 and JetPEI 0.7 mg/kg 5 µL/g IV, Single dose | Y | 5733 | 4.683E+09 |
|  |  | 5736 | 9.999E+09 |
|  |  | 5739 | 8.016E+09 |
|  |  | 5747 | 2.125E+09 |
|  |  | 5749 | 6.586E+09 |
|  |  | Mean | 6.282E+09 |
|  |  | SEM | 1.356E+09 |
| Group 6 MC3-Form-2 2.8 mg/kg 10 µL/g IV, Single dose | Y | 5718 | 7.971E+09 |
|  |  | 5731 | 4.694E+09 |
|  |  | 5745 | 6.386E+09 |
|  |  | 5763 | 2.822E+09 |
|  |  | 5771 | 9.288E+09 |
|  |  | Mean | 6.232E+09 |
|  |  | SEM | 1.148E+09 |
| Group 7 MC3-Form-3 1.4 mg/kg 10 µL/g IV, Single dose | Y | 5720 | 3.778E+09 |
|  |  | 5751 | 8.746E+09 |
|  |  | 5762 | 6.683E+09 |
|  |  | 5785 | 9.662E+09 |
|  |  | 5787 | 2.267E+09 |
|  |  | Mean | 6.227E+09 |
|  |  | SEM | 1.415E+09 |
| Group 8 MC3-Form-4 0.7 mg/kg 10 µL/g IV, Single dose | Y | 5709 | 9.165E+09 |
|  |  | 5754 | 2.435E+09 |
|  |  | 5756 | 4.592E+09 |
|  |  | 5761 | 7.135E+09 |
|  |  | 5772 | 7.896E+09 |
|  |  | Mean | 6.245E+09 |
|  |  | SEM | 1.210E+09 |
| Group 9 MC3-Form-5 diluted 1:2 0.7 mg/kg 10 µL/g IV, Single dose | Y | 5704 | 8.262E+09 |
|  |  | 5721 | 3.337E+09 |
|  |  | 5724 | 8.483E+09 |
|  |  | 5782 | 7.793E+09 |
|  |  | 5788 | 3.307E+09 |
|  |  | Mean | 6.236E+09 |
|  |  | SEM | 1.195E+09 |
| Group 10 MC3-Form-6 1.4 mg/kg 10 µL/g IV, Single dose | Y | 5702 | 3.083E+09 |
|  |  | 5726 | 6.548E+09 |
|  |  | 5769 | 8.508E+09 |
|  |  | 5774 | 7.457E+09 |
|  |  | 5781 | 5.539E+09 |
|  |  | Mean | 6.227E+09 |
|  |  | SEM | 9.267E+08 |
| Group 12 MC3-Form-7 2.8 mg/kg 10 µL/g IV, Single dose | Y | 5703 | 2.731E+09 |
|  |  | 5711 | 4.297E+09 |
|  |  | 5730 | 8.090E+09 |
|  |  | 5789 | 9.780E+09 |
|  |  | Mean | 6.225E+09 |
|  |  | SEM | 1.634E+09 |
| Group 13 PBS 10 µL/g IV, Single dose | Y | 5719 | 6.283E+09 |
|  |  | Mean | 6.283E+09 |
|  |  | SEM | — |

Note:
adays after the start of treatment.

This study was designed to assess the cancer-activated gene expression using different delivery formulations, with an LNP shown to be highly effective at delivery in the liver. One cohort (Table 5, Groups 1, 2, 9, and 14) used a secreted embryonic alkaline phosphatase (SEAP) reporter protein to study the activation of the AFP-3 promoter versus the Survivin (BIRC5) promoter. The other groups contained a lead imaging reporter, HSV-sr39tk with a 9-amino acid epitope tag (hemagglutinin) fused to the terminus, a modification that is commonly used to study the expression levels of proteins. The hemagglutinin (HA) tag allows for the use of high affinity anti-HA antibodies to study the protein expression of sr39tk through immunohistochemistry (IHC).

Mice were implanted with liver orthotopic tumors of Hep3B as previously described. EM-040 formulated DNA nanoplasmids that are comprised of the modified AFP-3 promoter to drive the expression of the HA-tagged sr39Tk

TABLE 5

Experimental Groups in Hep3B Orthotopic Liver Tumor Study

| Group | N | Tumor | Treatment | Delivery | Dose (mg/kg) | Dosing Route | Dosing Volume (mL/kg) | Schedule |
|---|---|---|---|---|---|---|---|---|
| 1 | 5 | N | NP003 (BIRC5-SEAP) | LNP | 1.4 | IV | 10 | single dose |
| 2 | 5 | Y | NP003 (BIRC5-SEAP) | LNP | 1.4 | IV | 10 | single dose |
| 3 | 2 | N | NP357 (AFP-3-sr39tk) | LNP | 0.7 | IV | 5 | single dose |
| 4 | 5 | Y | NP357 | LNP | 0.7 | IV | 5 | single dose |
| 5 | 2 | N | NP357 | LNP | 2.8 | IV | 10 | single dose |
| 6 | 5 | Y | NP357 | LNP | 2.8 | IV | 10 | single dose |
| 7 | 5 | Y | NP357 | LNP | 1.4 | IV | 10 | single dose |
| 8 | 5 | Y | NP357 | LNP | 0.7 | IV | 10 | single dose |
| 9 | 5 | Y | NP041 (AFP-3-SEAP) | LNP | 1.4 | IV | 10 | single dose |
| 10 | 5 | Y | NP355 (CAG-sr39tk) | LNP | 1.4 | IV | 10 | single dose |
| 11 | 2 | N | NP357 | LNP | 2.8 | IV | 10 | single dose |
| 12 | 4 | Y | NP357 | LNP | 2.8 | IV | 10 | single dose |
| 13 | 1 | Y | NA | LNP | NA | IV | 10 | single dose |
| 14 | 5 | N | NP041 (AFP-3-SEAP) | LNP | 1.4 | IV | 10 | single dose |

SEAP Results

Figure 39:
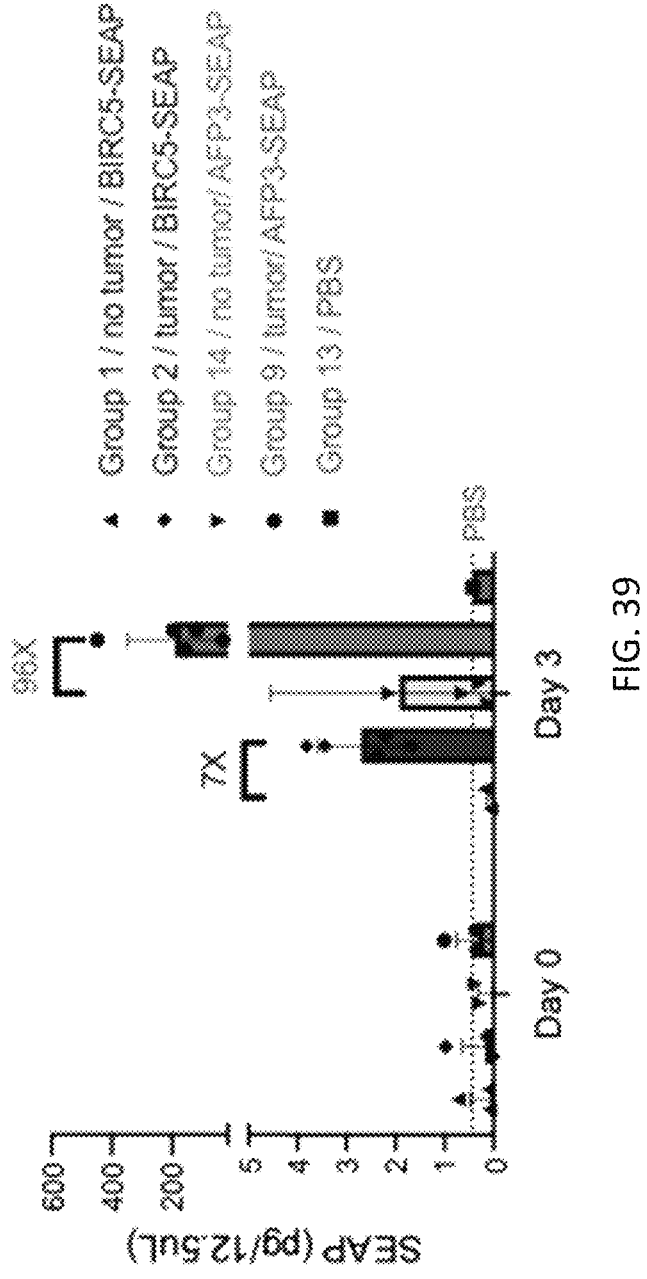
FIG. 39 shows signal-to-noise ratio of SEAP in Hep3B orthotopic tumor model. Secreted alkaline phosphatase (SEAP) was measured from the serum of tumor-bearing and normal animals dosed with the BIRC5-SEAP construct versus the AFP-3-SEAP construct. At the day 0 bleed (pre-dosing), background levels of SEAP in all mice were below the lower limit of quantification (LLOQ) of the assay (0.4 pg/12.5 uL), as expected. At 3 days post-dose, the BIRC5-SEAP construct dosed animals showed a 7-fold increase of SEAP reporter in the serum over the LLOQ, with no background expression at all in non-tumored animals. The AFP-3 construct promoted expression in tumored animals approximately 97-fold higher than non-tumored animals.

Mice were IV-dosed with EM-40 formulated reporter constructs containing the SEAP reporter, as described in the previous section. Two different DNA nanoplasmids were used; one was comprised with the Survivin (BIRC5) cancer-activated promoter driving SEAP expression and one with the AFP-3 promoter to drive liver cancer activated expression. Once expressed in cancer cells, SEAP is secreted into the blood and a simple blood draw can be collected to reveal the presence of cancer. As expected, SEAP is secreted into the serum by the construct. Control blood draws from all animals before dosing (Day 0 in FIG. 39) showed undetectable background/basal activity in serum from tumor-bearing and normal mice (below the assay's LLOQ of 0.4 pg/12.5 μL serum). At the day 3 bleed, there was a significant difference in the SEAP biomarker availability in serum between non-tumor and tumor mice dosed with the same formulation. For mice dosed with Survivin, the non-tumor animals still showed undetectable background levels of SEAP, and a 7-fold increase over background expression in tumor-bearing mice. While there was a small amount of the reporter SEAP in the non-tumor mice dosed with AFP-3-SEAP, the fold-activation in tumor-bearing mice was higher, at nearly 100-fold the average SEAP expression in the non-tumor background.

IHC Results

Additional experiments were performed to determine which cells from a target organ contributed to the strong SEAP signal driven from the modified AFP3 promoter in the DNA nanoplasmids. The sequences encoding for SEAP were removed from the DNA nanoplasmid and replaced with sequences encoding for a version of the sr39TK PET Reporter Gene that had been modified with a HA (hemagglutinin) tag—a 9 bp epitope tag. Using antibodies against HA, IHC was performed on formalin fixed paraffin embedded (FFPE) liver tissues using a commonly available anti-HA antibody.

PET Reporter Gene were injected systemically into the mice. Following 3 days of expression, the mice were sacrificed, their livers were harvested and then processed for IHC staining using the anti-HA antibody. H&E staining which can help distinguish different tissue structures and cell types within a sample, and correlate with expression by IHC to structural location and cell type was also performed. Control-stained sections of tumors and normal left & right lobes of the liver from mice dosed with a non-HA tag expressing construct (in this case BIRC5-SEAP) showed no non-specific staining, demonstrating that the method used specifically and accurately detected only the sr39tk-HA reporter from the construct.

Tumor sections from AFP-3-sr39tk dosed mice (FIGS. 40A-40C) showed strong expression of the construct in a significant portion of cells within the tumor, at both the 2.8 and 1.4 mg/kg dose levels, with no detected expression in left lobe cells bordering the tumor, or the non-tumor right lobe of the liver within the same mice.

Figures 41A, 41B, 41C, 41D, 41E, 41F:
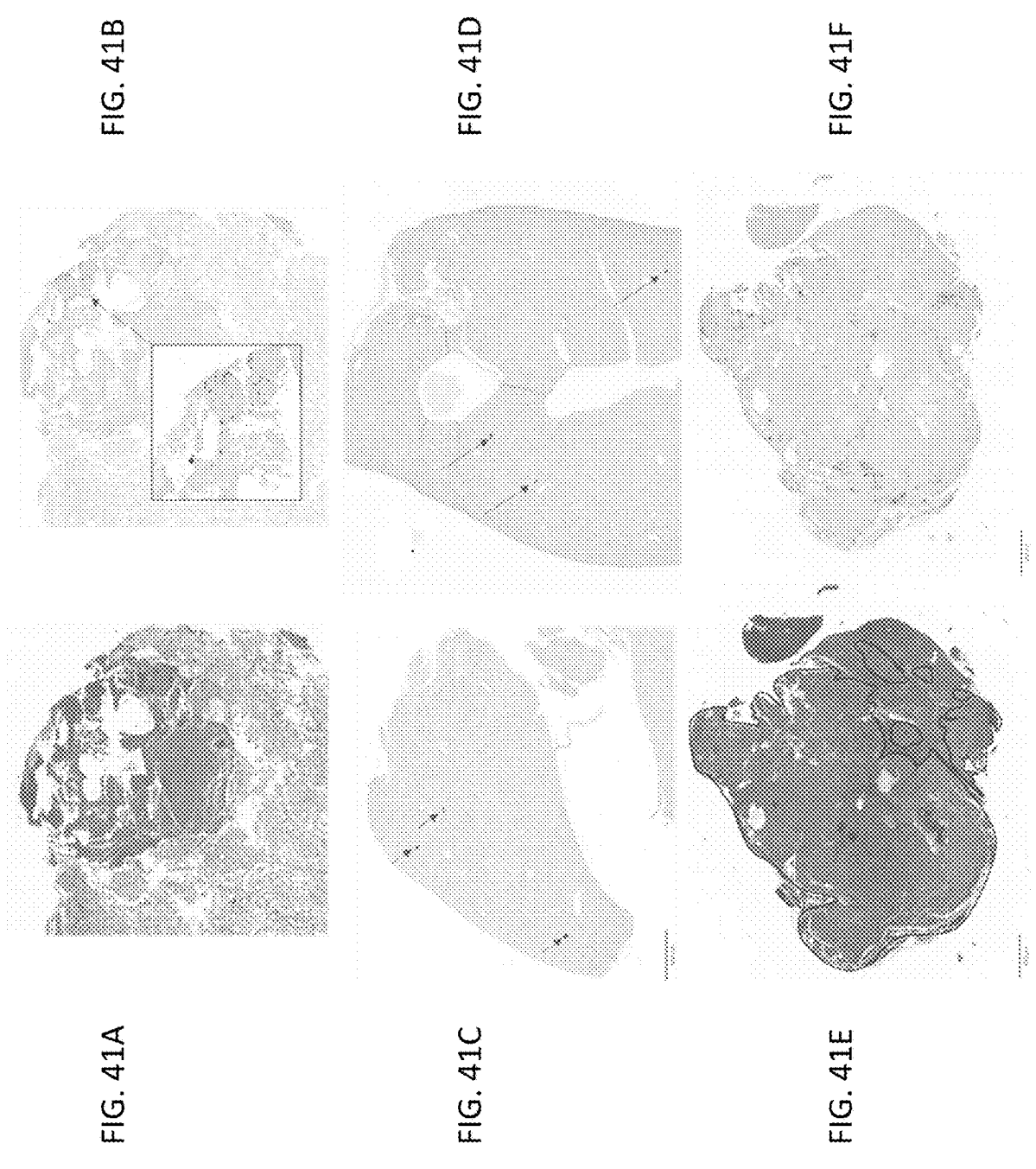
FIGS. 41A, 41B, 41C, 41D, 41E, and 41F show IHC results for positive control CAG-sr39tk. Serial sections of the tumor-containing left lobe from a mouse in Group 10 show positive staining in the tumor (FIGS. 41A and 41B; stained dark purple by H&E). Left and right lobe sections from the same mouse show occasional disperse signal from individual cells (FIGS. 41C and 41D). Serial sections stained by H&E and by IHC for the -HA tag for a second mouse's tumor also show many positive-stained cells throughout the tumor tissue, as outlined in the H&E figure (FIGS. 41E and 41F).

The mice dosed with CAG-sr39tk was similarly studied. Because CAG is a very strong and constitutive promoter, it should accurately exhibit where delivery and expression is possible. While IHC is not quantitative by nature, the qualitative assessment of the tumors (as shown in FIGS. 41A-41F) showed that the CAG-driven construct exhibited equivalent levels of expression in tumors to the AFP-3 promoter, which was remarkable given that that CAG is considered one of the strongest constitutive promoters available in gene therapy. CAG expression was also preferentially localized to the tumor tissue as opposed to normal hepatocytes in the left or right lobe of the liver (possibly indicating that the nature of the highly vascularized tissue helps distribute the vector preferentially to the tumor tissues versus normal), but did show strong expression in disperse single cells in representative left and right lobe sections which were not observed with the more specific AFP-3 (FIGS. 41C and 41D).

Conclusion

These series of experiments demonstrate the utility of the cancer-specific gene expression in an orthotopic liver tumor model, demonstrating delivery to primary liver tumors as well as activation in the context of a human liver cancer cell. The LNP formulation demonstrates highly effective delivery to tumor cells upon IV dosing.

The AFP-3 promoter showed a nearly 100-fold higher activation in the blood marker SEAP than the BIRC5 promoter in the Hep3B-model, and IHC analysis also showed highly specific and strong expression in tumor cells and not in normal liver cells. The highly qualitative IHC data demonstrated strong levels of activation of the AFP-3 promoter and the ability of the combined components to deliver and express in a cancer-specific manner.

Example 4: Benign Versus Malignant, Inflammation and Specificity

Figures 43A, 43B, 43C, 43D:
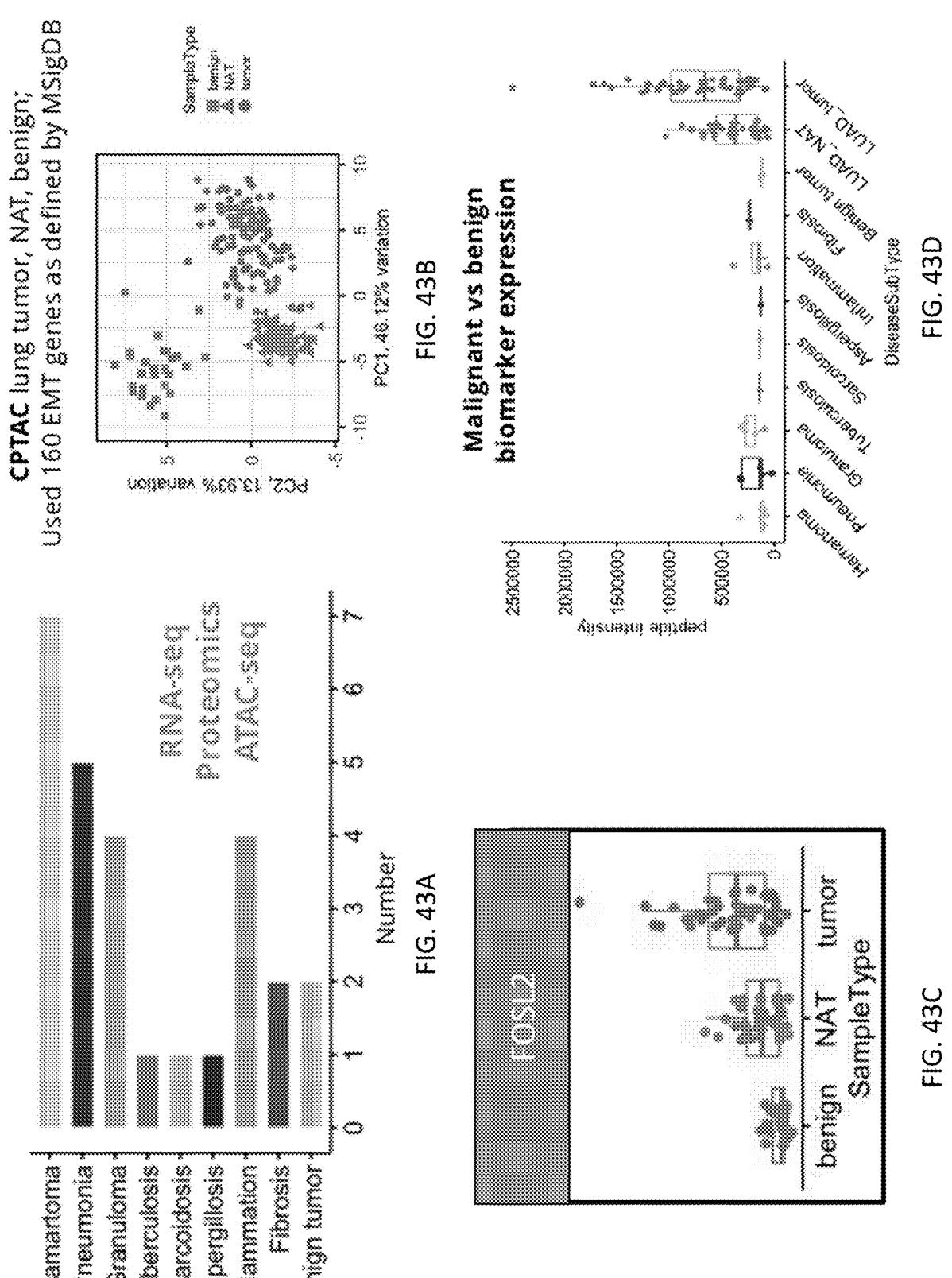
FIGS. 43A, 43B, 43C, and 43D show muti-omics data on benign cell lines.

Multi-omics (RNA-seq, proteomics, and ATAC-seq) methodology was used to analyze benign tissue/cell samples. FIG. 43A shows number of different benign tissue/cell samples used for multi-omics analysis. Details of multi-omics methodology was described in Examples 1 and 2. Analysis of 160 Epithelial-Mesenchymal Transition (EMT) genes defined by the Molecular Signatures Database (MsigDB; see Liberzon A., et al. The Molecular Signatures Database hallmark gene set collection. Cell Syst. 2015 Dec. 23; 1(6):417-425) using multi-omics and principal component analysis (PCA) demonstrated a transcriptomic difference between malignant human lung cancer (Clinical Proteomic Tumor Analysis Consortium (CPTAC) lung tumor) and benign lesions (NAT), and internal benign) (FIGS. 43B-43D).

Figure 44:
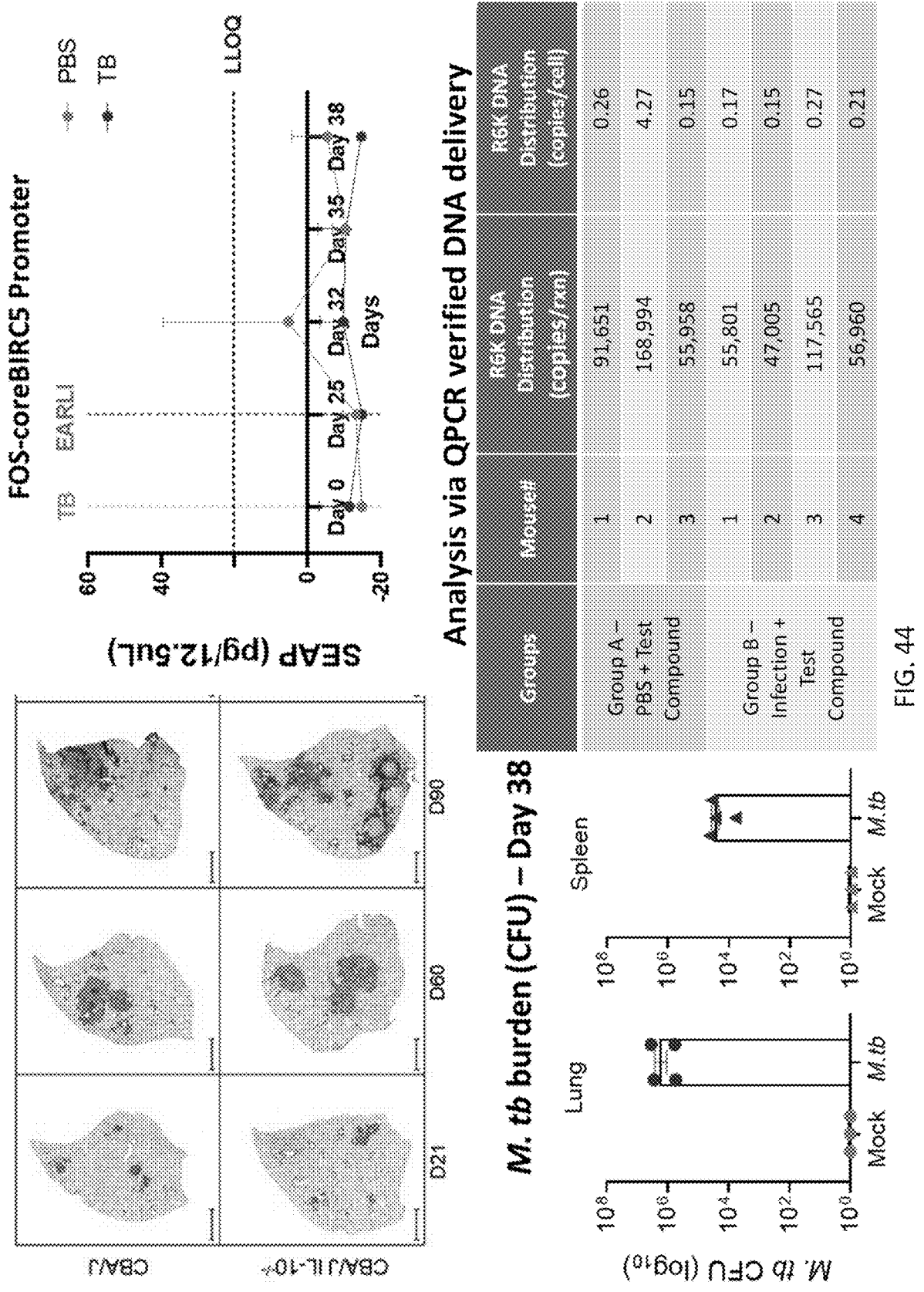
FIG. 44 shows that there is no reporter expression by synthetic promoter constructs in granulomatous lesions caused by *Mycobacterium tuberculosis* (M. tb) infection in CBA/J mice despite high disease burden.
Figure 45:
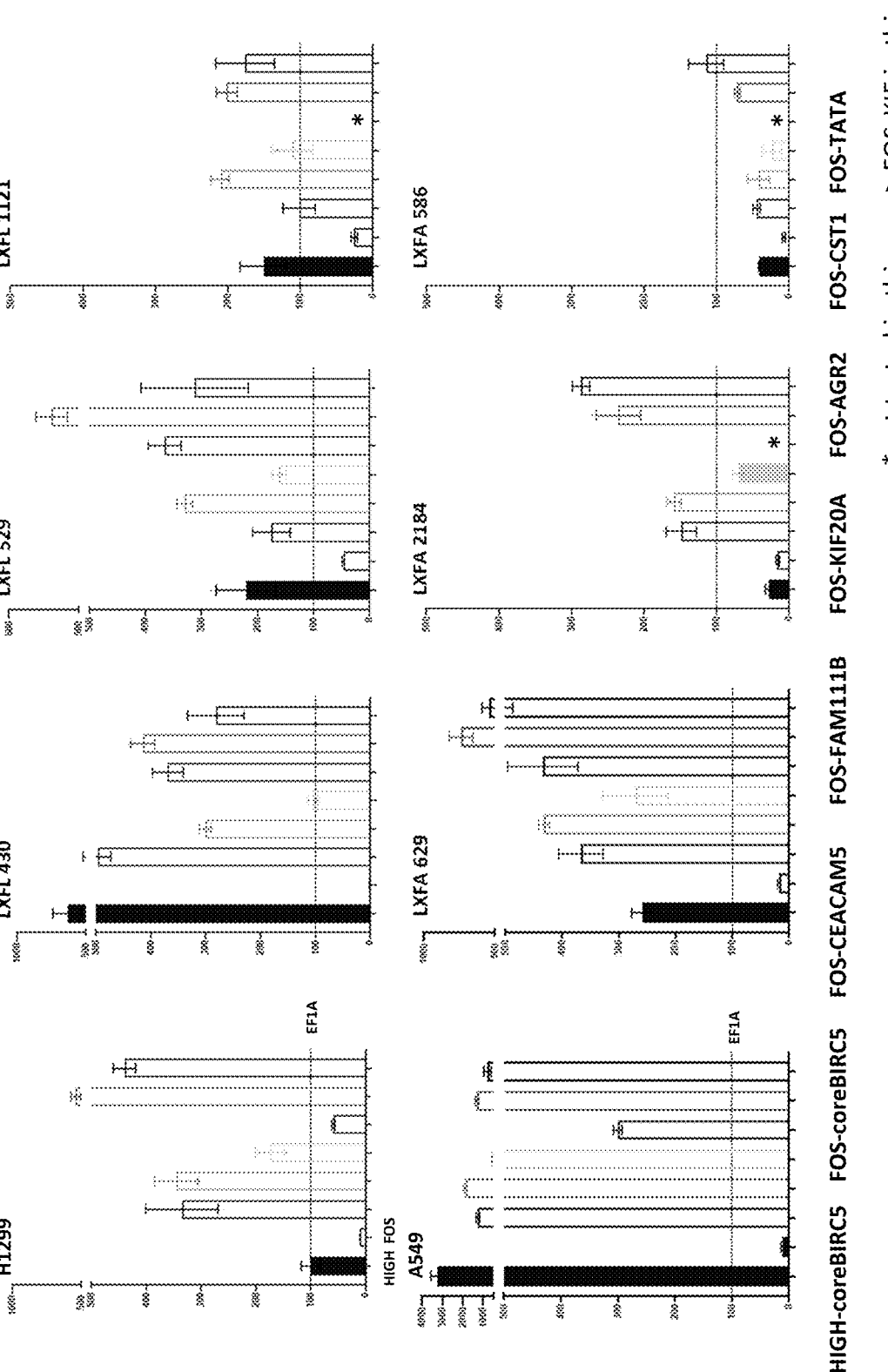
FIG. 45 shows the reporter gene expression performance by different synthetic promoters in various cancer and non-cancer cell lines. Combining the FOS element with new core promoters resulted in significant increases in expression across NSCLC cell lines & PDX CL models. Bar graphs from left to right: HIGH-coreBIRC5, FOS-coreBIRC5, FOS-CEACAM5, FOS-FAM111B, FOS-KIF20A, FOS-AGR2, FOS-CST, and FOS-TATA, respectively.
Figure 46:
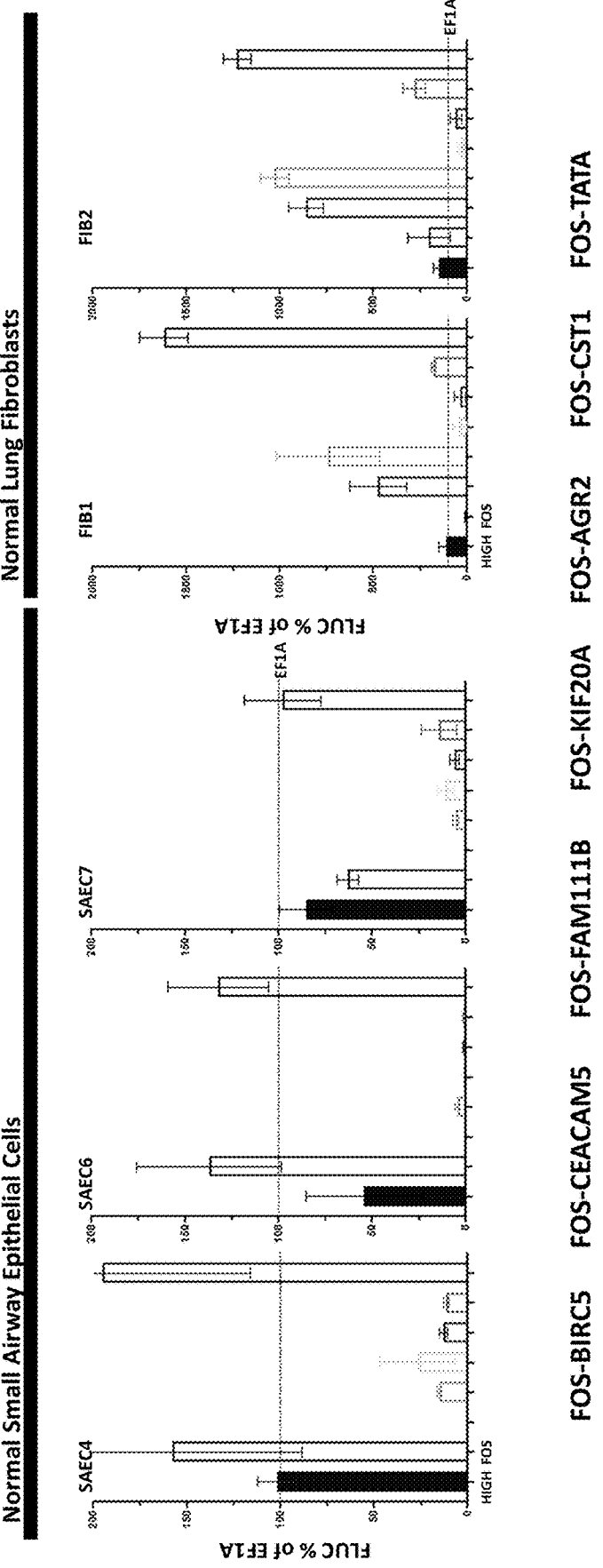
FIG. 46 shows the reporter gene expression performance by different synthetic promoters in various cancer and non-cancer cell lines. Some FOS-newCores combinations had elevated noise in Normal Lung Fibroblasts. Bar graphs from left to right: FOS-BIRC5, FOS-CEACAM5, FOS-FAM111B, FOS-KIF20A, FOS-AGR2, FOS-CST1, and FOS-TATA, respectively.
Figure 48:
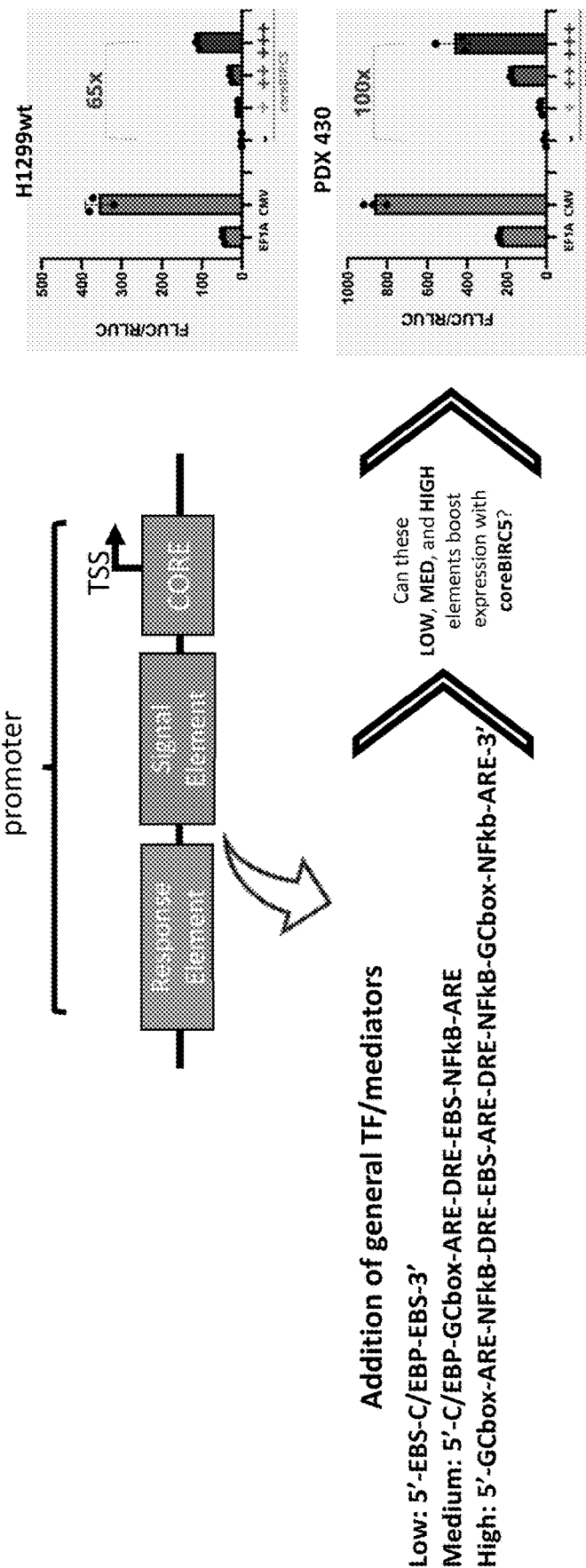
FIG. 48 shows a schematic of adding activating elements to the new core promoters.
Figure 49:
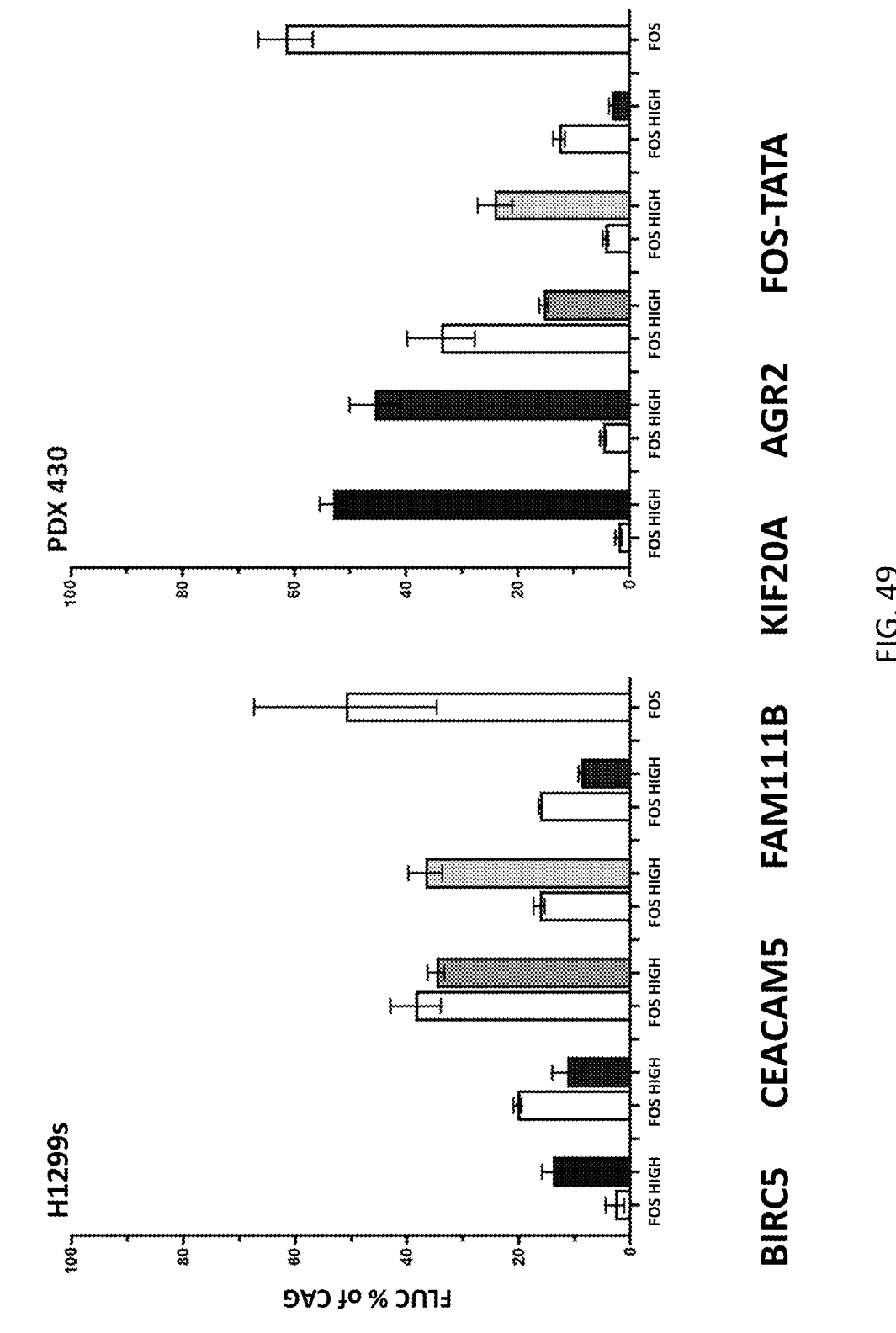
FIG. 49 shows the reporter gene expression performance by different synthetic promoters in H1299 and PDX430 cell lines. HIGH element was observed to be functional in vitro when combined with alternate core promoters. Bar graphs from left to right: BIRC5, CEACAM5, FAM111B, KIF20A, AGR2, and FOS-TATA, respectively.
Figure 50:
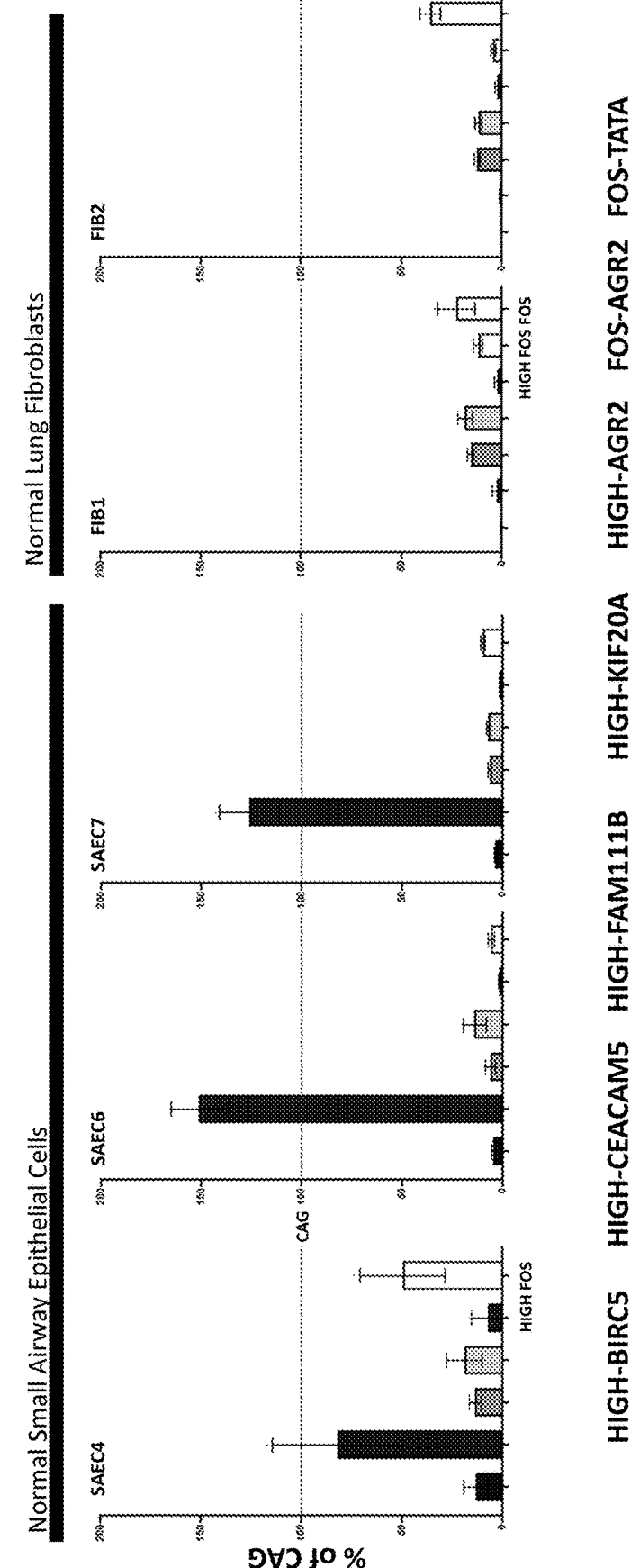
FIG. 50 shows the reporter gene expression performance by different synthetic promoters in normal small airway epithelial cells and normal lung fibroblasts. In vitro specificity models were predictive of lung noise with HIGH-CEACAM5, HIGH-FAM111B and HIGH-KIF20A. Bar graphs from left to right: HIGH-BIRC5, HIGH-CEACAM5, HIGH-FAM111B, HIGH-KIF20A, HIGH-AGR2, FOS-AGR2, and FOS-TATA, respectively.
Figure 51:
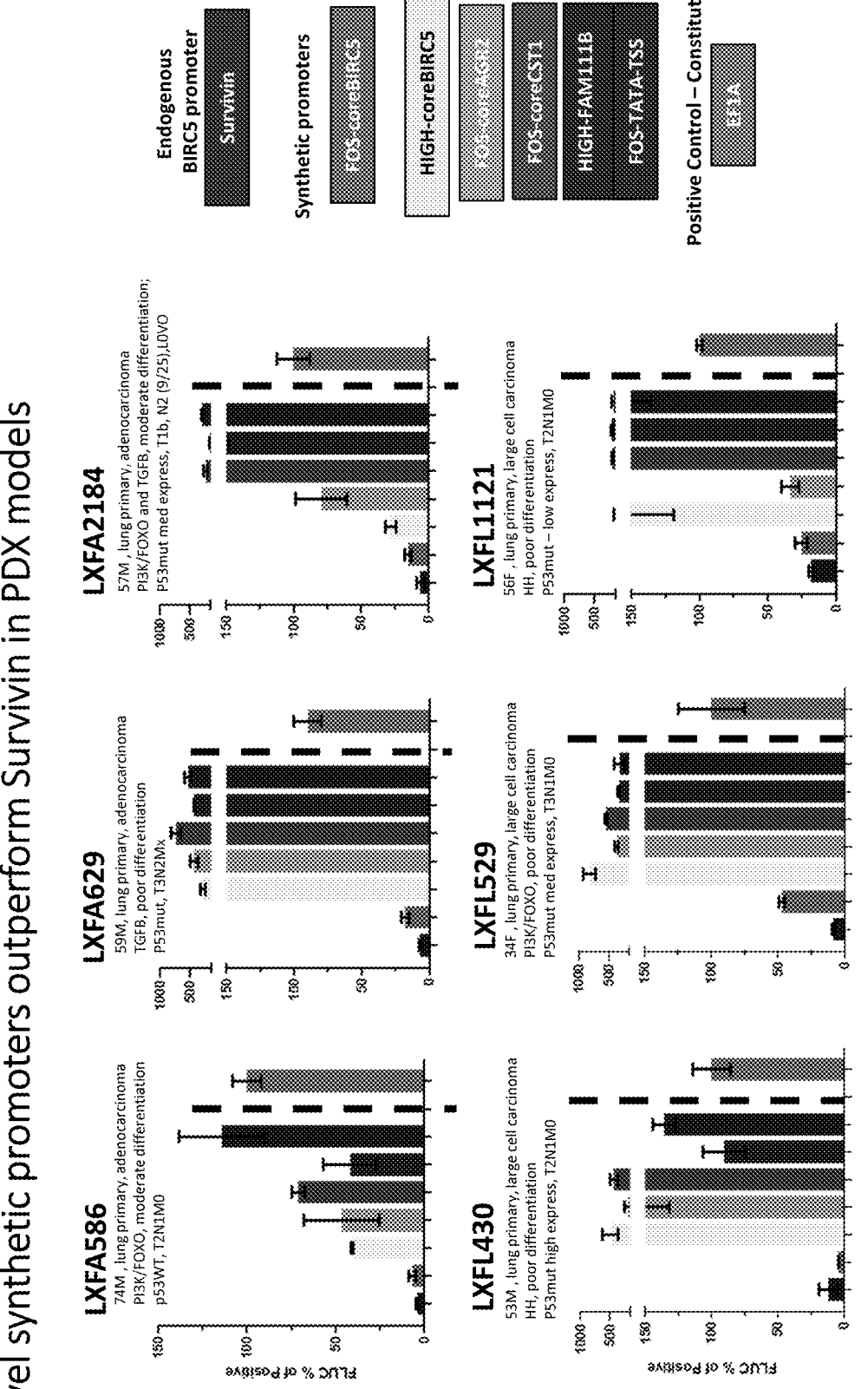
FIG. 51 shows the reporter gene expression performance by different synthetic promoters in various PDX cell lines. Synthetic promoters described herein outperform endogenous promoter in PDX cell lines. Bar graphs from left to right: Survivin (endogenous BIRC5 promoter), FOS-core-BIRC5, HIGH-coreBIRC5, FOS-coreAGR2, FOS-coreCST1, HIGH-FAM111B, FOS-TATA-TSS, and EF1A (positive control), respectively.
Figure 52:
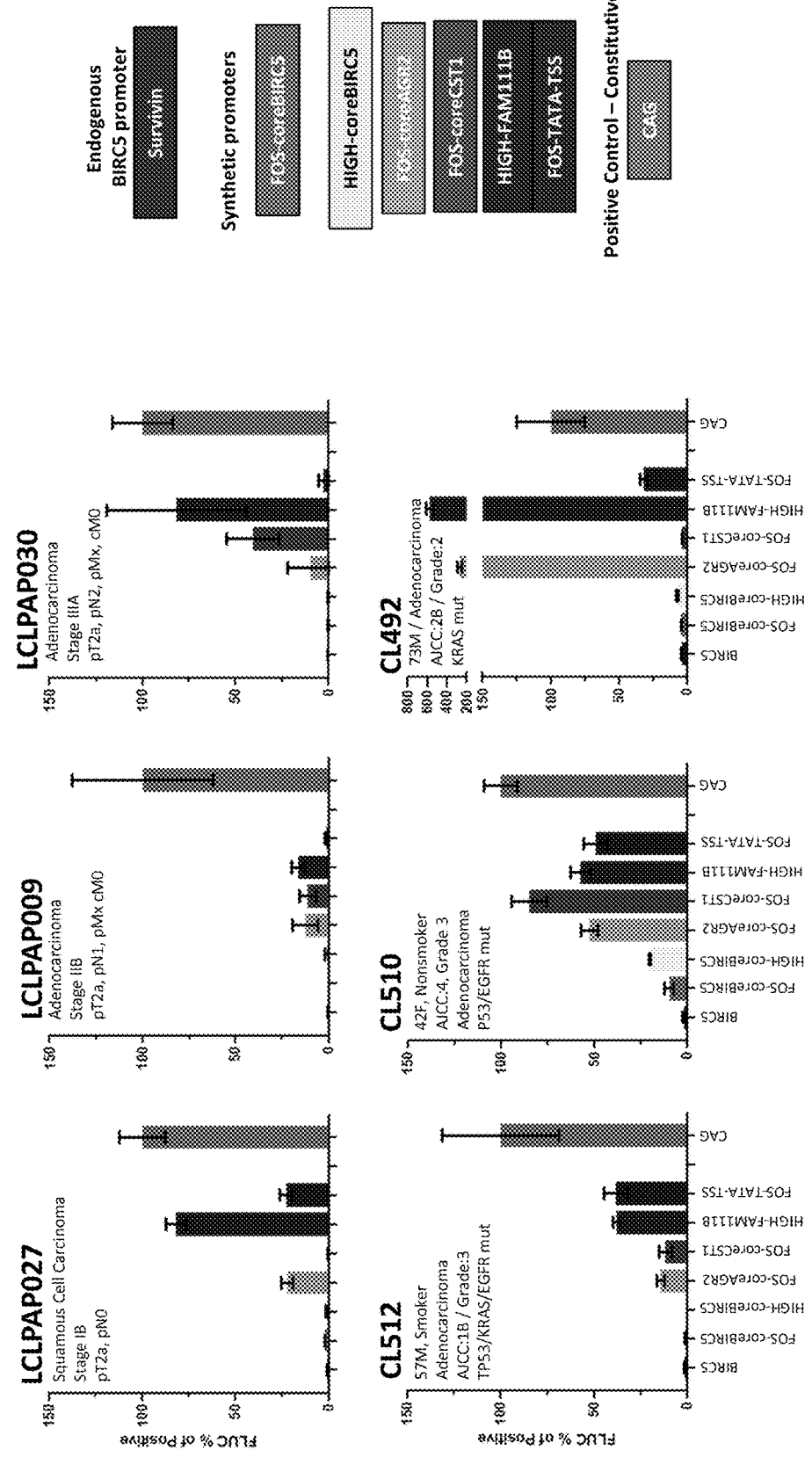
FIG. 52 shows the reporter gene expression performance by different synthetic promoters in various primary cell lines derived from PDX or primary tissue. Bar graphs from left to right: Survivin (endogenous BIRC5 promoter), FOS-core-BIRC5, HIGH-coreBIRC5, FOS-coreAGR2, FOS-coreCST1, HIGH-FAM111B, FOS-TATA-TSS, and CAG (positive control), respectively.
Figure 53:
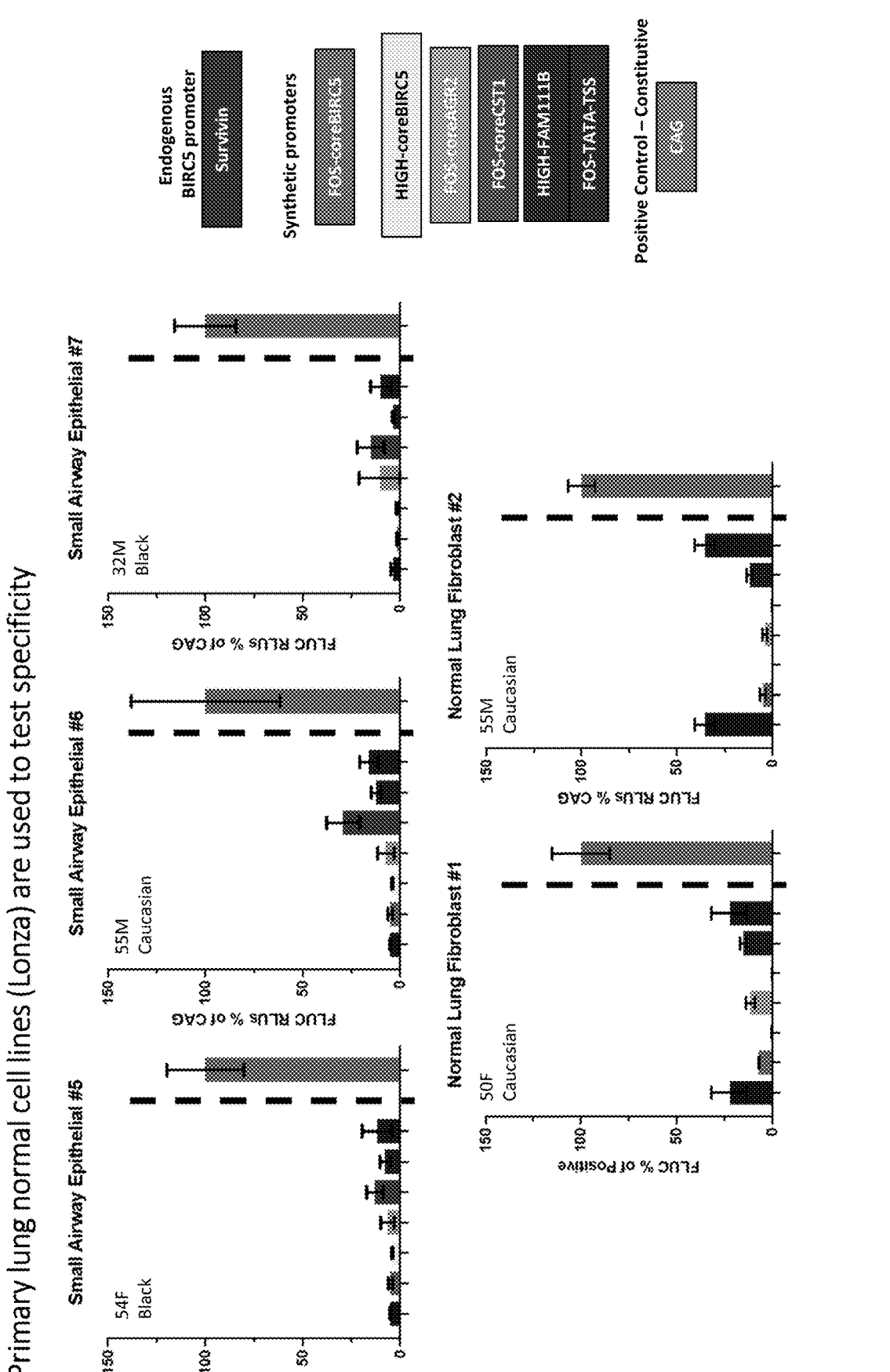
FIG. 53 shows the reporter gene expression performance by different synthetic promoters in primary lung normal cells (Lonza). Bar graphs from left to right: Survivin (endogenous BIRC5 promoter), FOS-coreBIRC5, HIGH-core-BIRC5, FOS-coreAGR2, FOS-coreCST1, HIGH-FAM111B, FOS-TATA-TSS, and EF1A (positive control), respectively.
Figure 54:
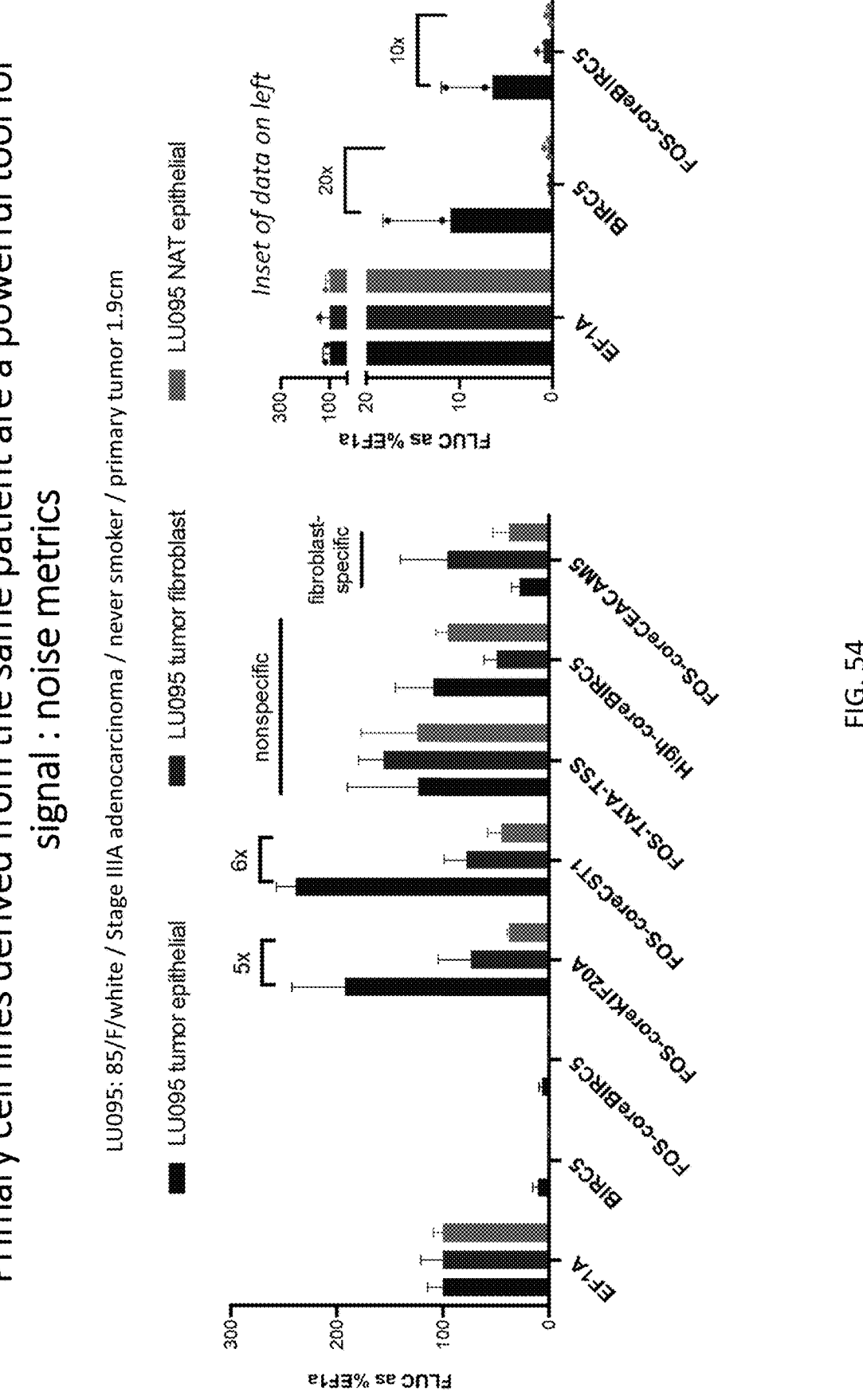
FIG. 54 shows the reporter gene expression performance by different synthetic promoters in different primary lung normal cells derived from the same patient.
Figure 55:
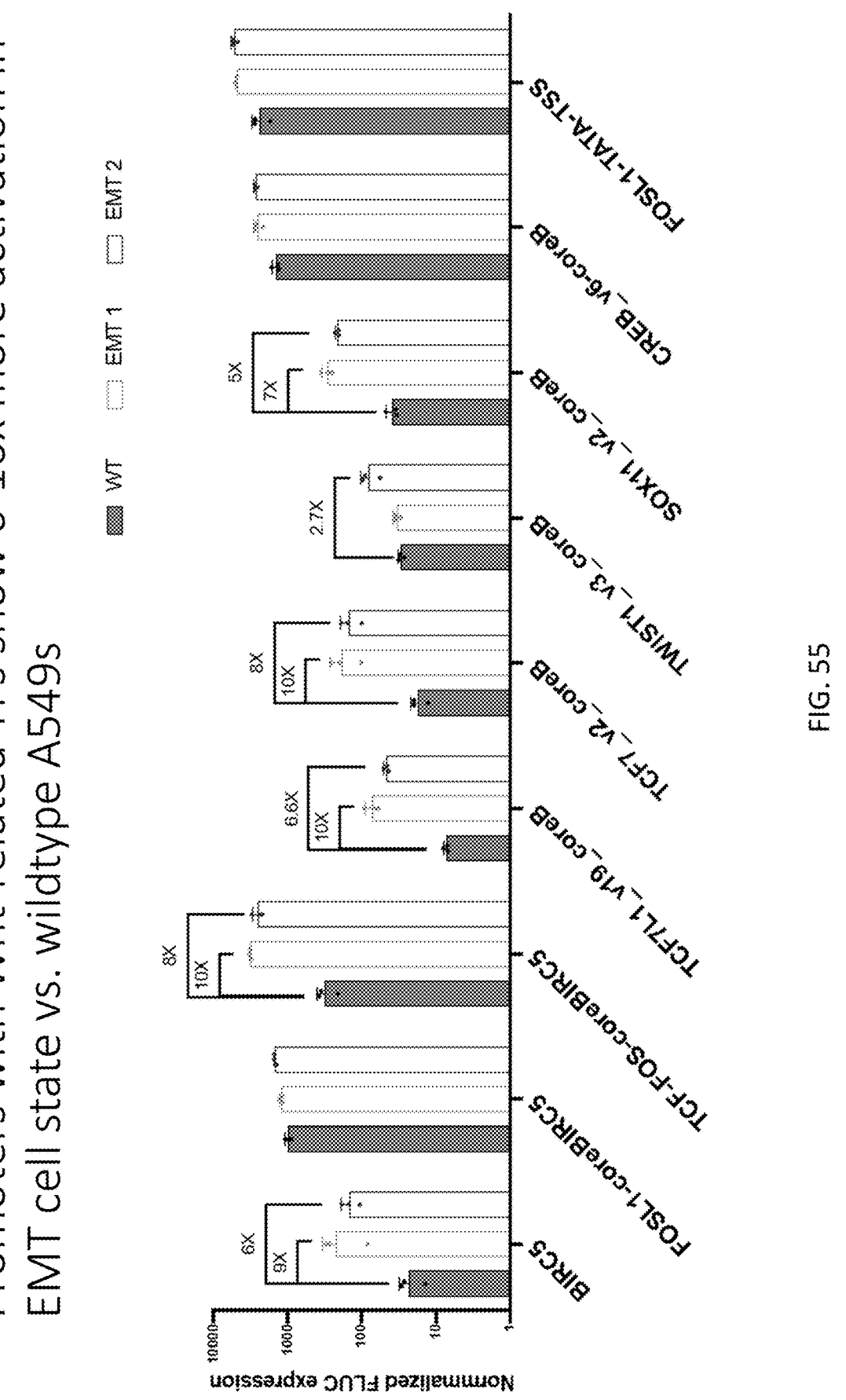
FIG. 55 shows the comparison of the reporter gene expression performance by synthetic promoters in EMT state cells and wild type A549 cells.
Figure 57:
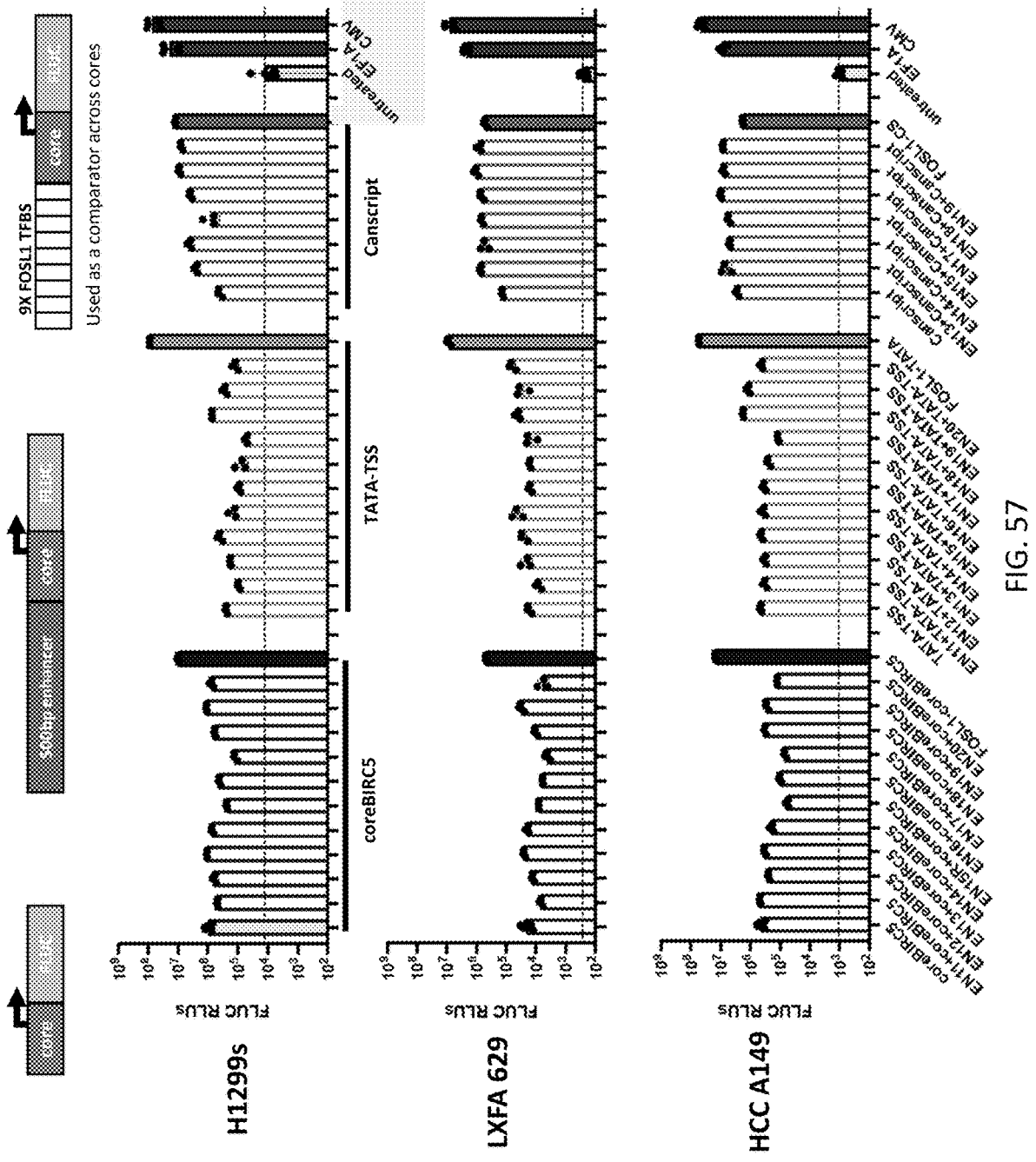
FIG. 57 shows the reporter gene expression performance by synthetic promoters comprising enhancer elements in various cancer and non-cancer cells. Constructs were tested in vitro across panel of 5 LUAD cell lines, 3 HCC cell lines, and IMR90 lung normal cells for expression profiles of enhancer elements paired with each core promoter (including 7× CRL PDX cell lines and 2× Lonza normal cells).
Figure 59:
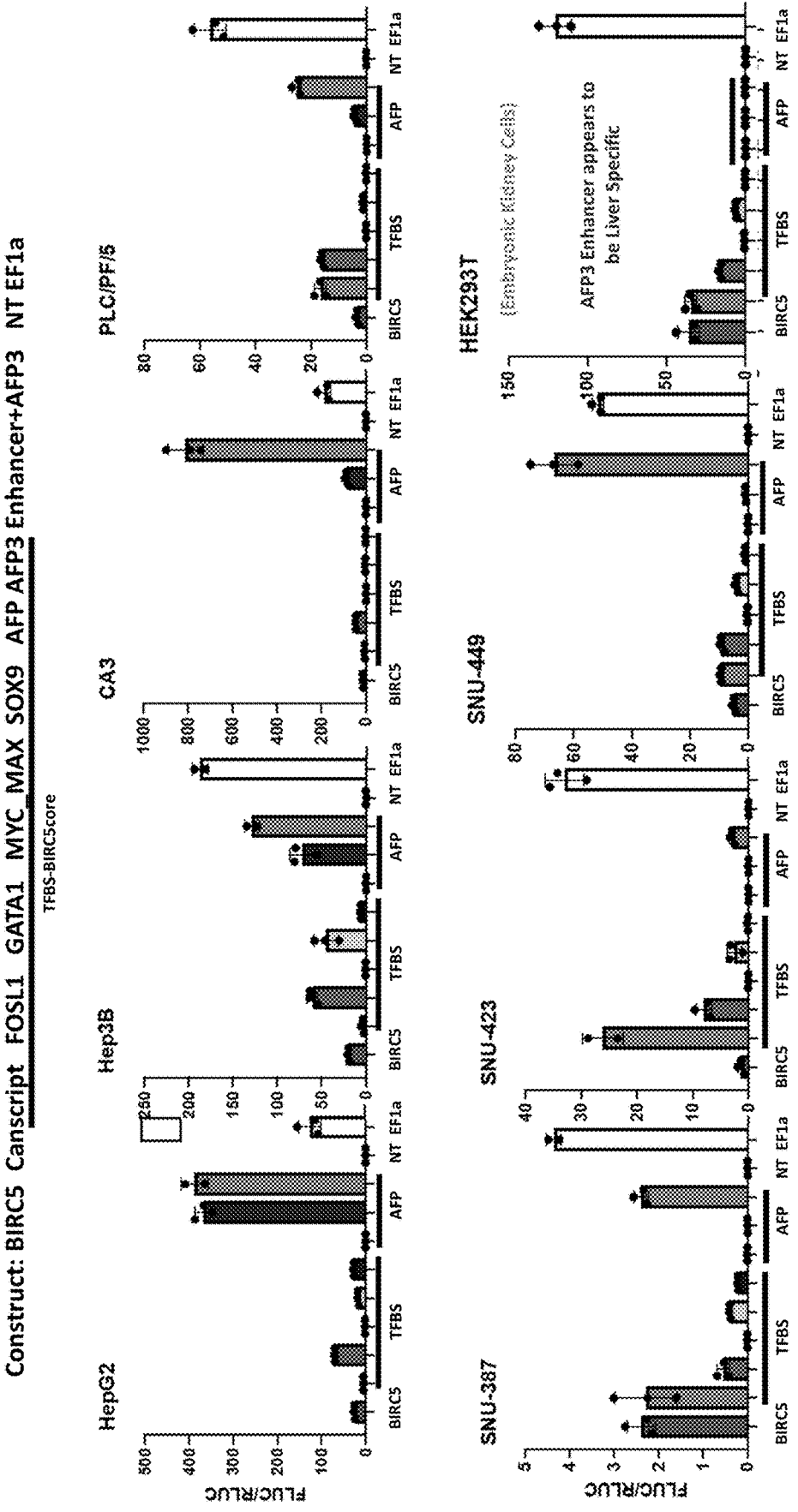
FIG. 59 shows the reporter gene expression performance by different synthetic promoters in various cell lines. Bar graphs from left to right: BIRC5, Canscript, FOSL1, GATA1, MYC_MAX, SOX9, AFP, AFP3, Enhancer+AFP3, and NT EF1a, respectively.
Figure 60:
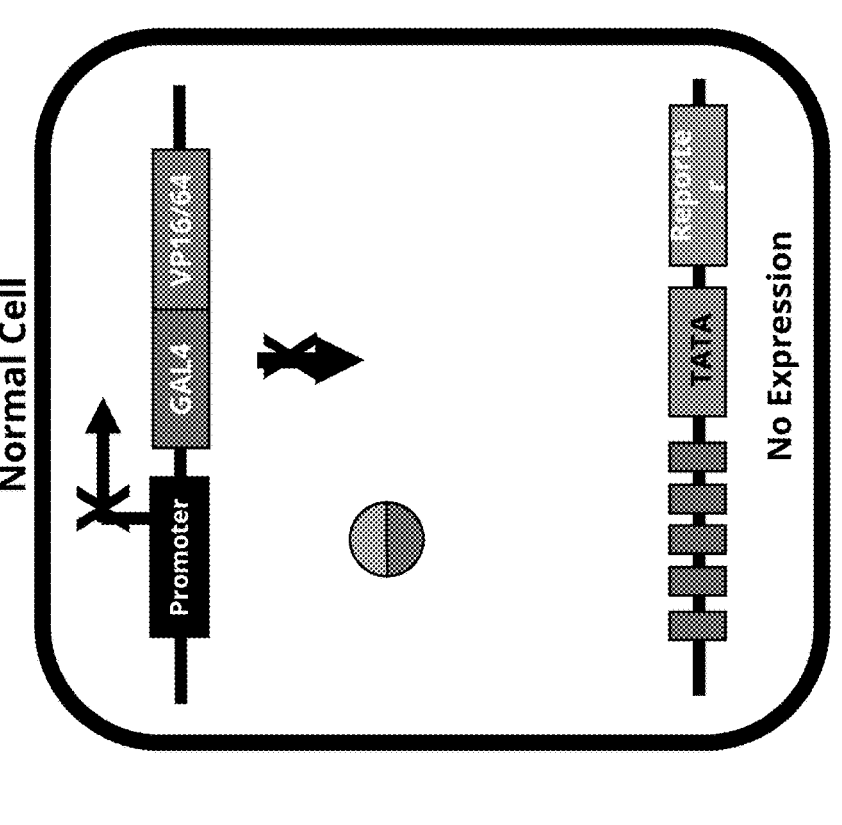
FIG. 60 shows a two-step promoter amplification utilizing the yeast GAL4-VP system.
Figure 61:
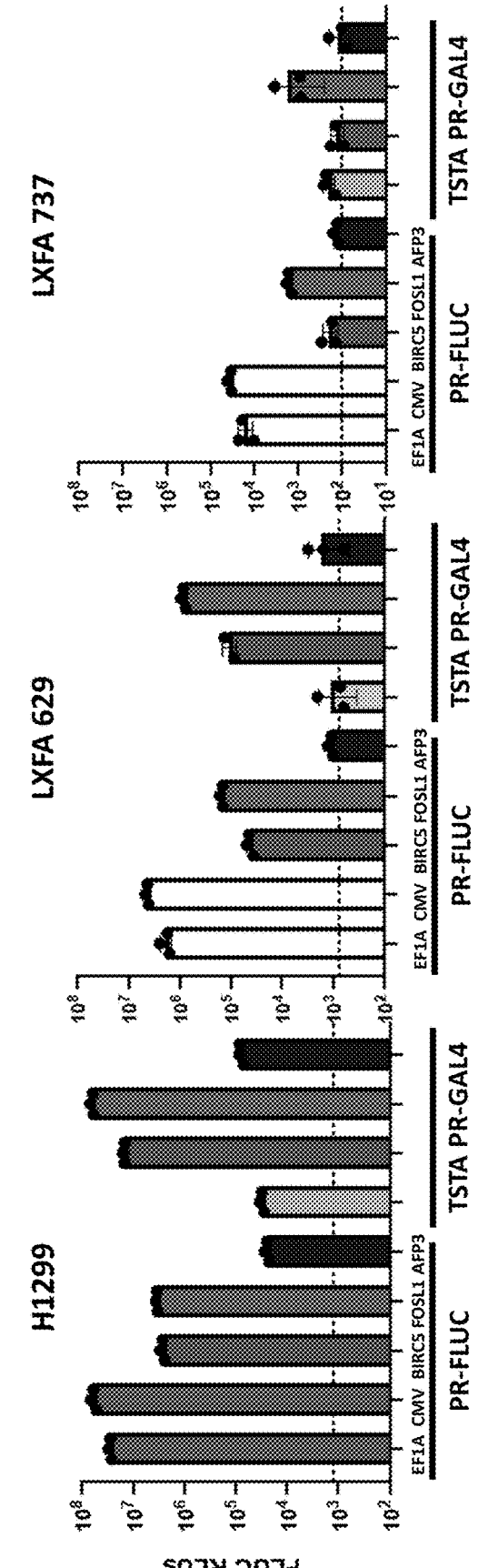
FIG. 61 shows comparison of the reporter gene expression performance by different synthetic promoters and the yeast GAL4-VP system in H1299, LXFA629, and LXFA 737 cell lines. TSTA: two-step transcriptional activation. Bar graphs from left to right: EF1A, CMV, BIRC5, FOSL1, AFP3, TSTA PR-GAL4 only, BIRC5, FOSL1, AFP3, respectively.
Figure 62:
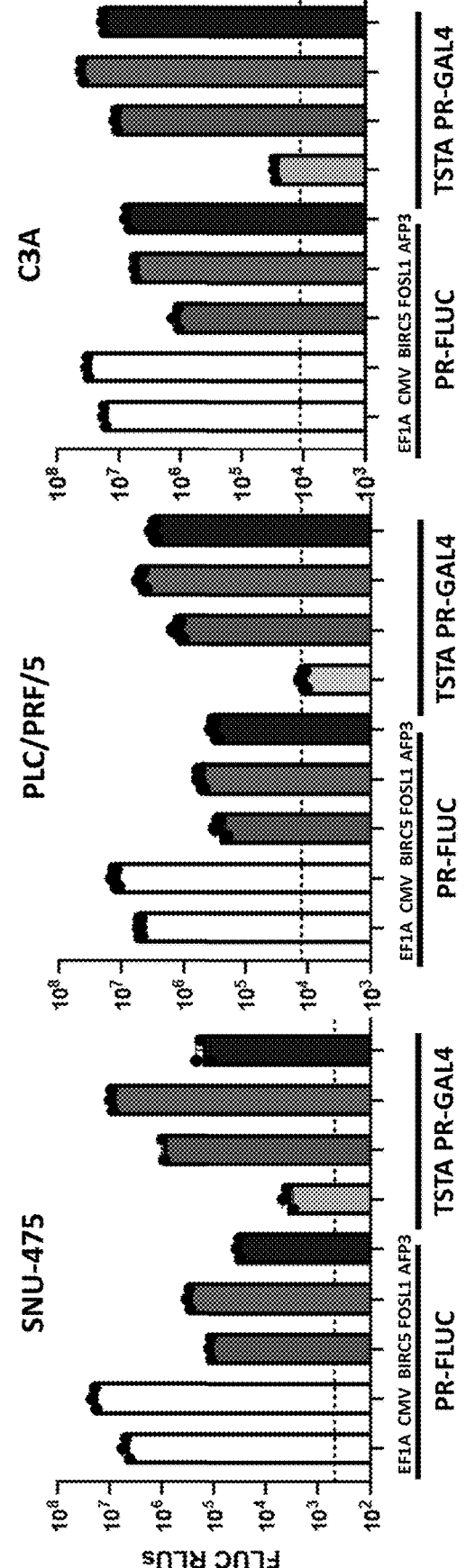
FIG. 62 shows comparison of the reporter gene expression performance by different synthetic promoters and the yeast GAL4-VP system in SNU-475, PLC/PRF/5, and C3A cell lines. TSTA: two-step transcriptional activation. Bar graphs from left to right: EF1A, CMV, BIRC5, FOSL1, AFP3, TSTA PR-GAL4 only, BIRC5, FOSL1, AFP3, respectively.
Figure 65:
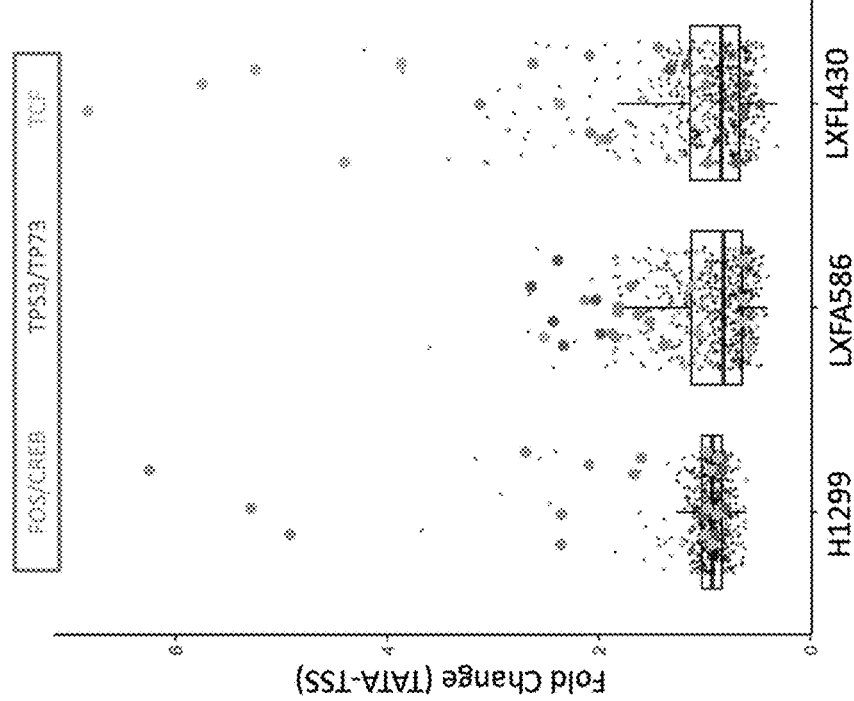
FIG. 65 shows top 10 ranked response elements from H1299 (Large Cell Carcinoma), LXFA586 (Adenocarcinoma), and LXFL430 (Large Cell Carcinoma). Control response elements containing FOS/CREB (H1299), TP53/TP73 (LXFA586), or TCF (LXFL430) drive strong expression of reporter gene in H1299, LXFA586, and LXFL430 cell lines respectively, and there are several additional hits.
Figure 66A:
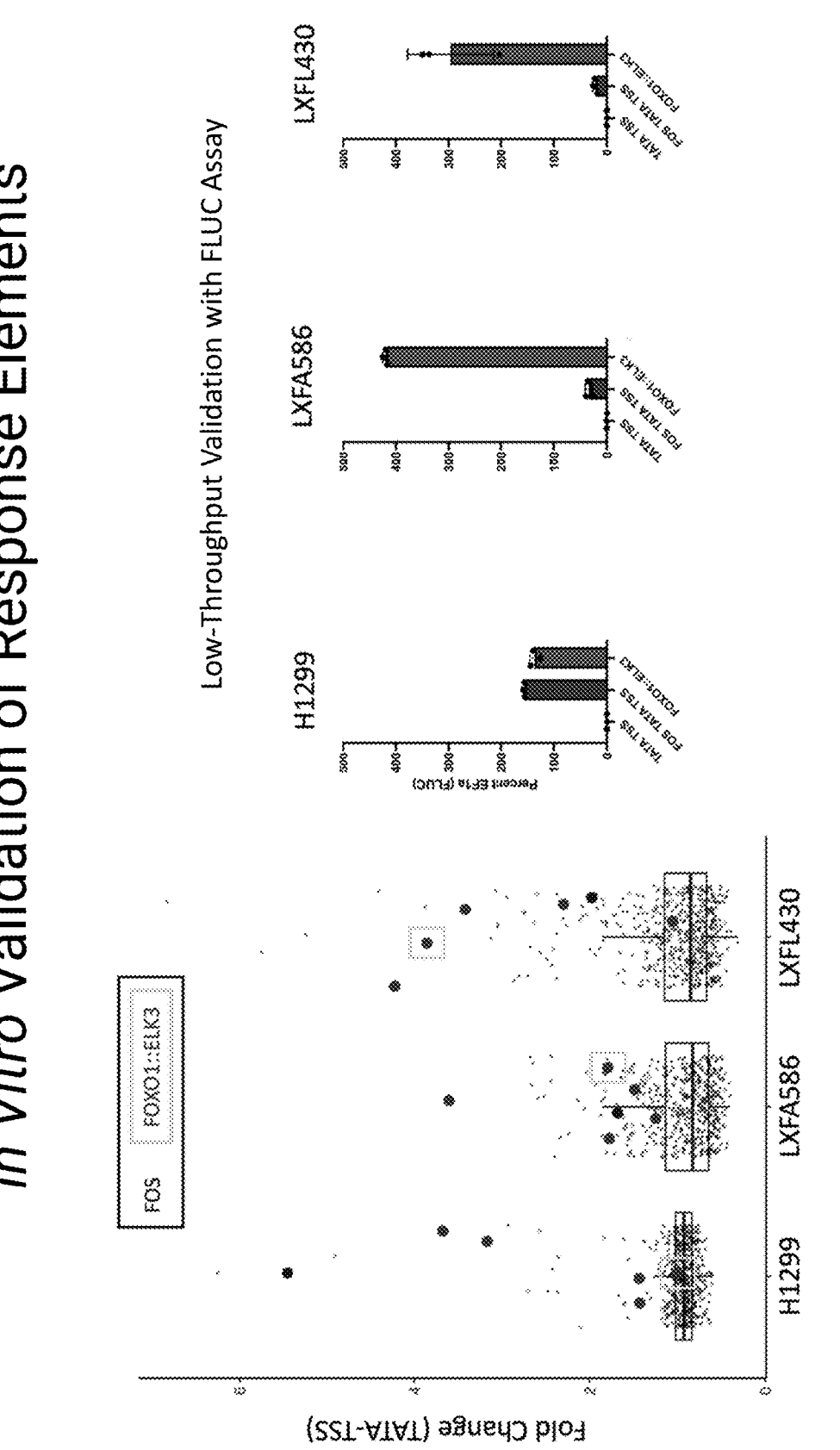
FIGS. 66A, 66B, 66C, and 66D show in vitro low throughput validation of response elements from FIG. 112 using Firefly luciferase (FLuc) assay.
Figure 66B:
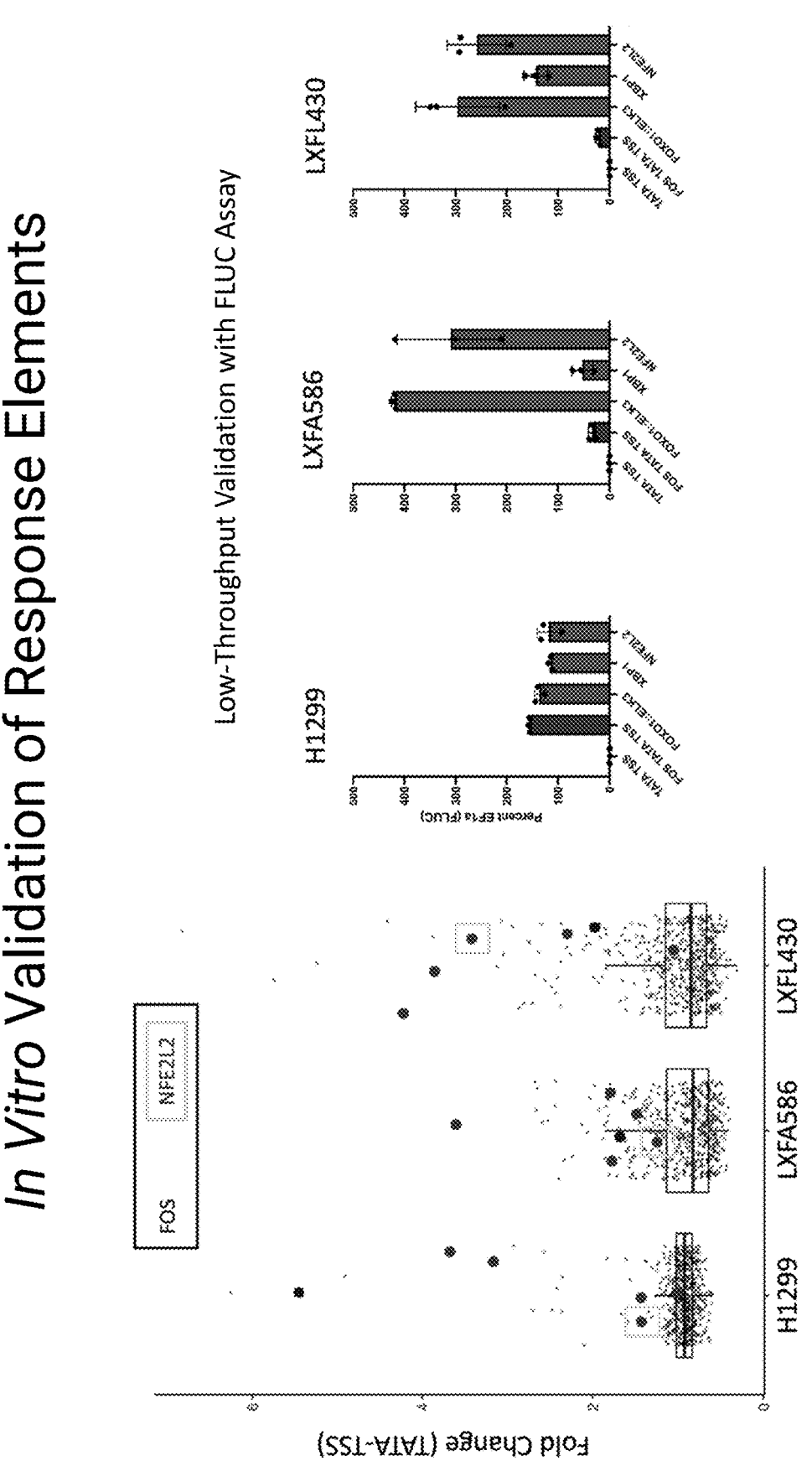
Figure 66C:
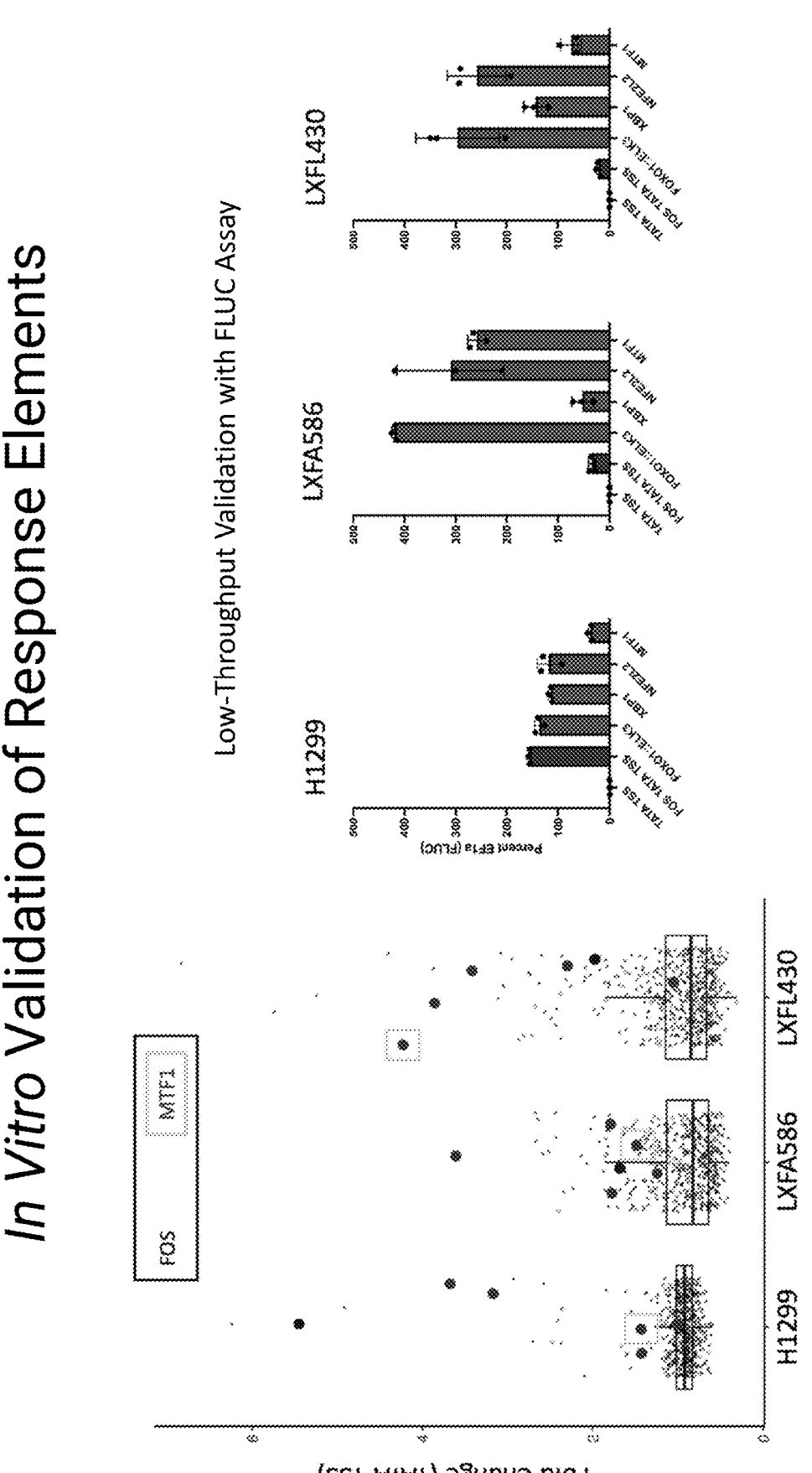
Figure 66D:
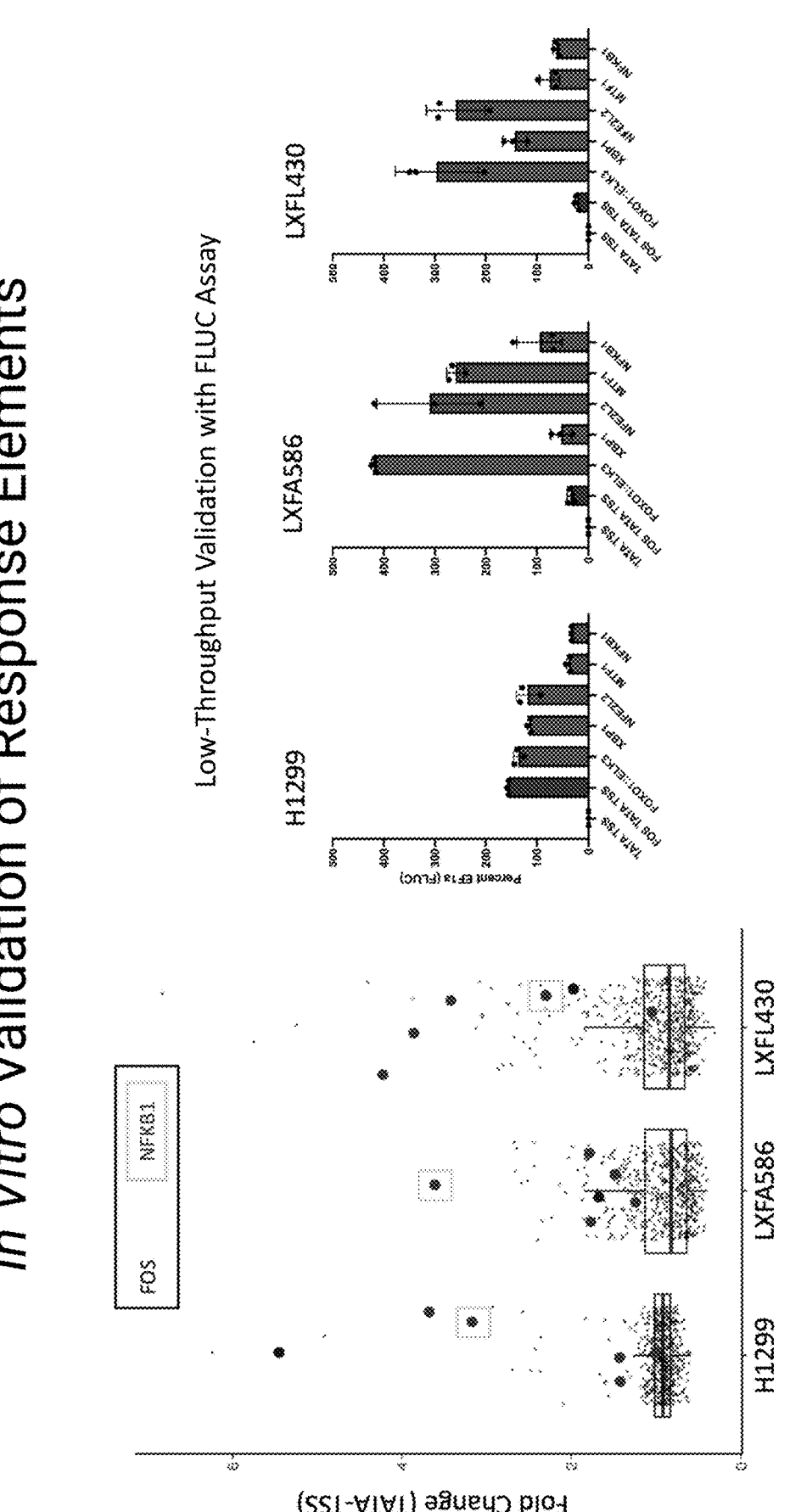
Figures 67, 68:
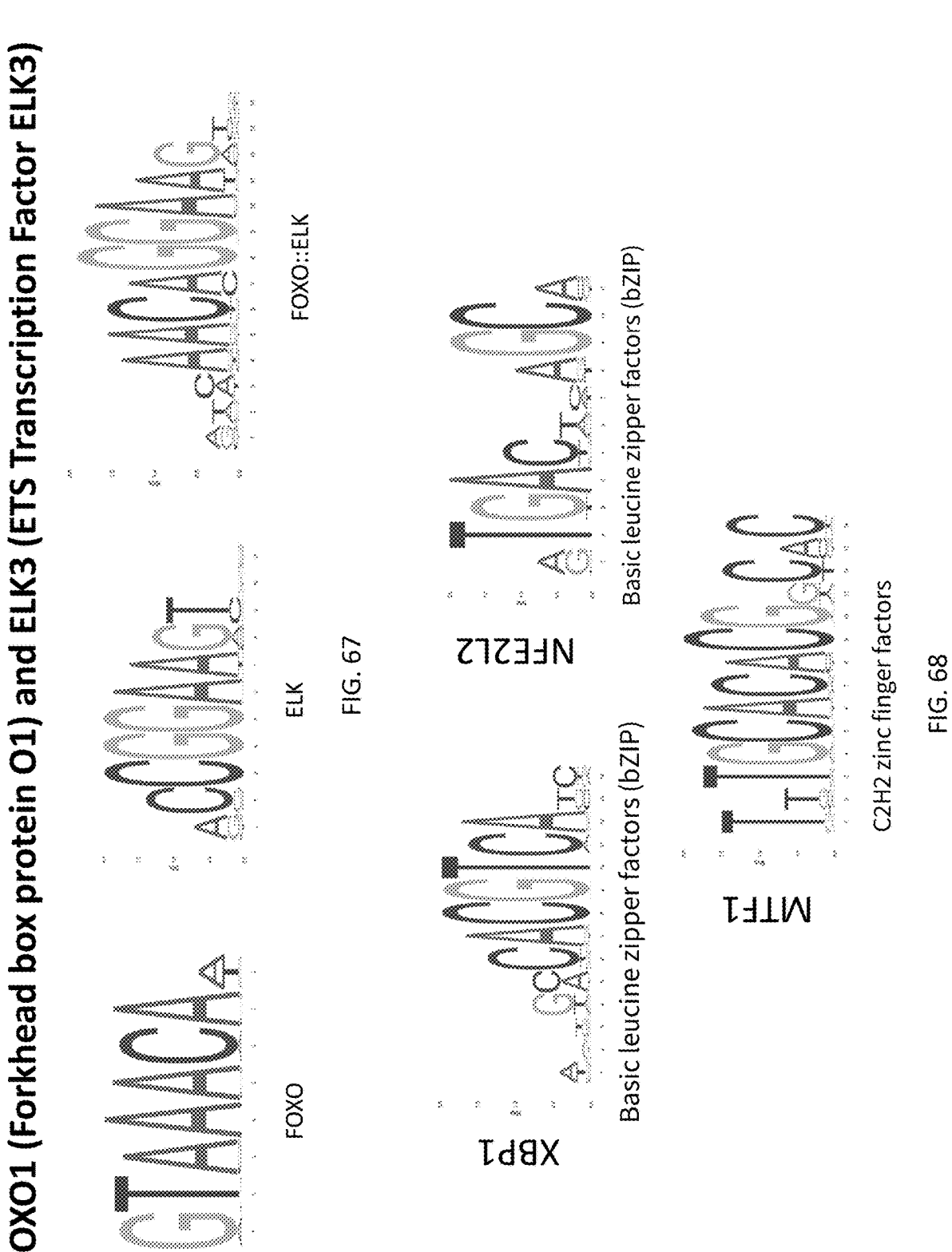
FIGS. 67-68 show a DNA binding consensus sequence of Forkhead Box Protein 01 (FOXO1.
Figure 69:
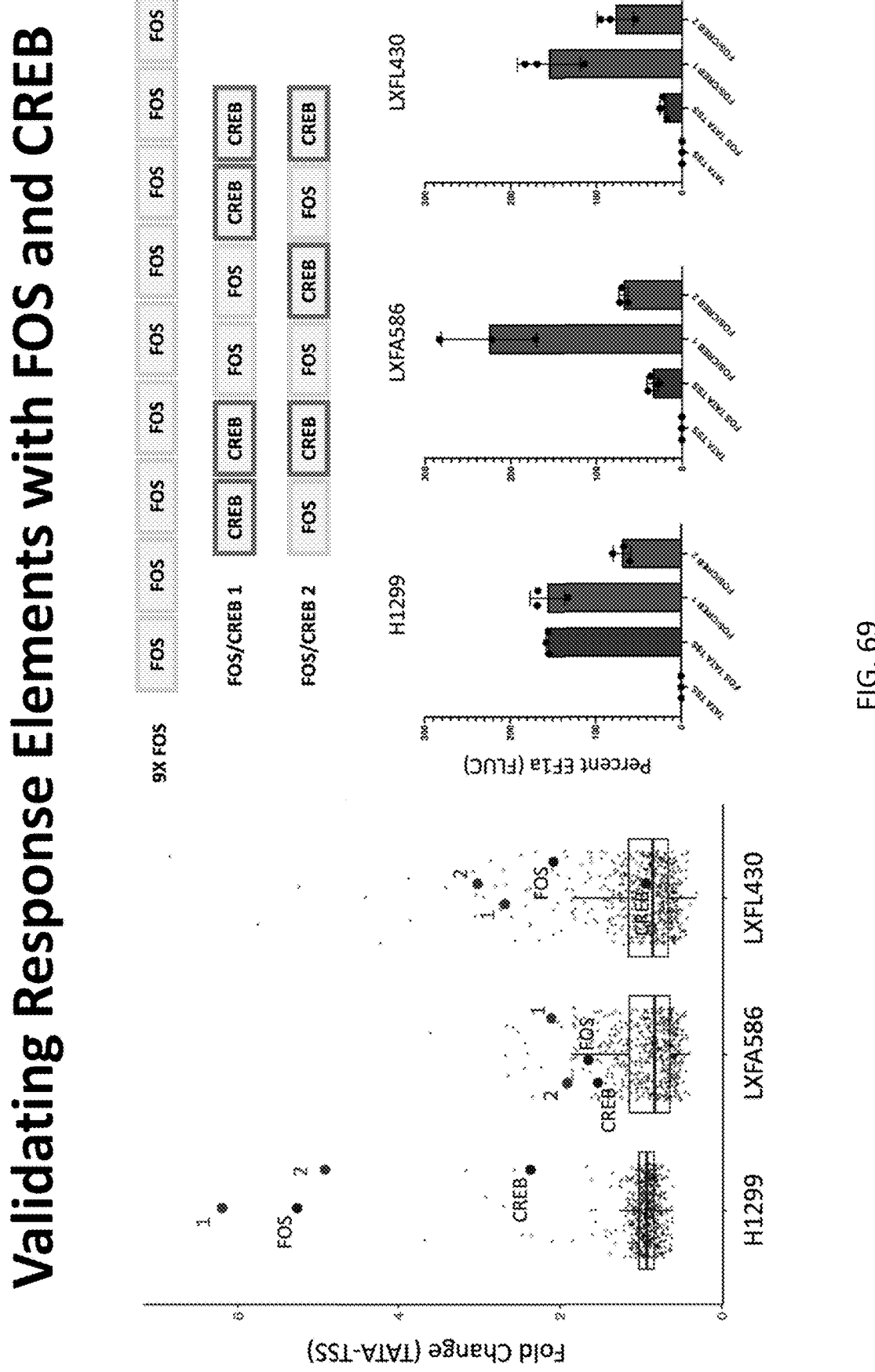
FIG. 69 shows validation of response elements with FOS and CREB using Firefly luciferase (FLuc) assay.
Figure 70:
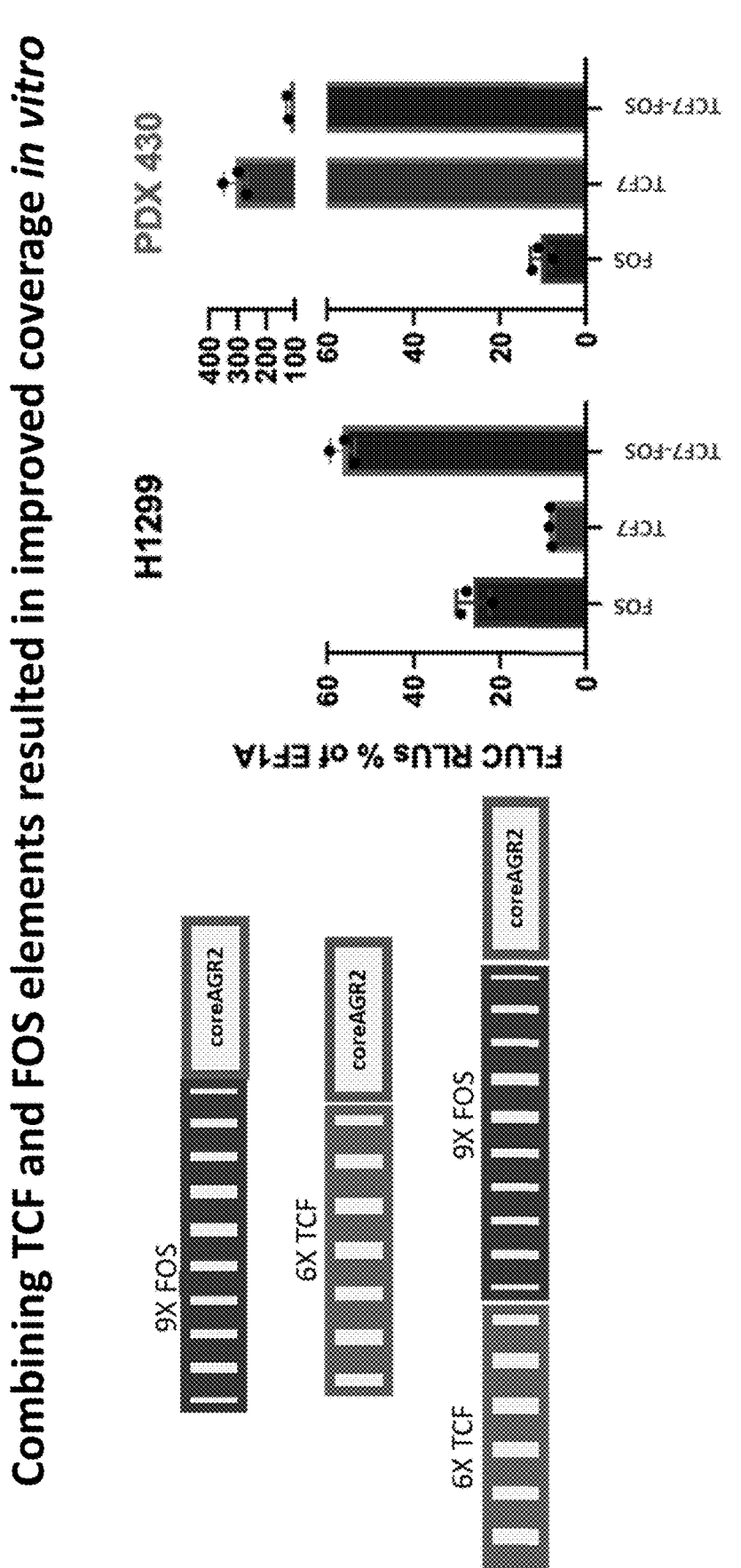
FIG. 70 shows Firefly luciferase (FLuc) assay results of combination of TCF and FOS elements.
Figure 71:
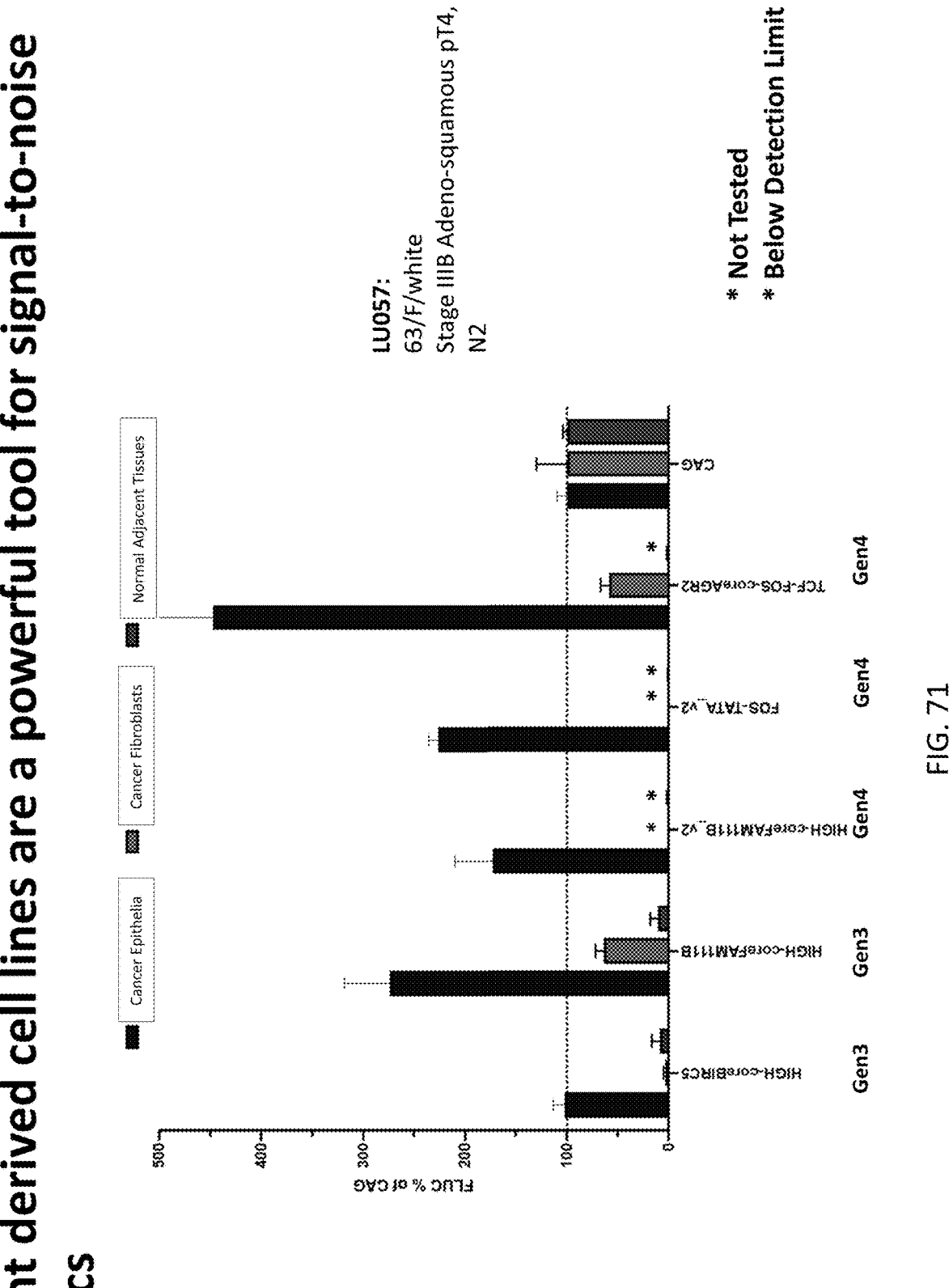
FIG. 71 shows Firefly luciferase (FLuc) assay results of different elements in patient-derived cancer cells (cancer epithelia and cancer fibroblasts) and normal adjacent tissues. Bar graphs from left to right: Cancer Epithelia, Cancer Fibroblasts, and Normal Adjacent Tissues, respectively.

Next, using CBA/J mice model infected with *Mycobacterium tuberculosis* (M. tb; S. Major, J. Turner, and G. Beamer. Tuberculosis in CBA/J Mice. Veterinary Pathology 2013 50:6, 1016-1021), reporter gene expression driven by FOS-core-BIRC5 synthetic promoter was analyzed. There was no expression of reporter gene in granulomatous lesions caused by M.tb infection in CBA/J mice despite high disease burden (FIG. 44), suggesting there is no cancer-activated expression in granulomas, which is a model of benign tissue lesions.

The examples and embodiments described herein are for illustrative purposes only and various modifications or changes suggested to persons skilled in the art are to be included within the spirit and purview of this application and scope of the appended claims.

EMBODIMENTS

The following embodiments are not intended to be limiting in any way.

Embodiment 1: A recombinant polynucleotide comprising:

(a) a core promoter comprising a transcription start site (TSS), wherein the core promoter is derived from one or more cancer-responsive genes that are either expressed at a higher level or are more active in cancer cells compared to non-cancer cells and operably linked to an open reading frame (ORF) and (b) a plurality of binding sites for one or more transcription factors (TFs), wherein said one or more TFs are expressed at higher levels or more active in cancer cells compared to non-cancer cells.

Embodiment 2: A recombinant polynucleotide comprising:

(a) a core promoter comprising a transcription start site (TSS) and two or more promoter elements derived from two or more cancer-responsive genes that are either expressed at a higher level or are more active in cancer cells compared to non-cancer cells and operably linked to an open reading frame (ORF) and (b) a plurality of binding sites for one or more transcription factors (TFs), wherein said one or more TFs are expressed at higher levels or more active in cancer cells compared to non-cancer cells.

Embodiment 3: The recombinant polynucleotide of Embodiment 1 or 2, further comprising a plurality of enhancers.

Embodiment 4: A recombinant polynucleotide comprising:

(a) a core promoter comprising a transcription start site (TSS), wherein the core promoter is derived from one or more cancer-responsive genes that are either expressed at a higher level or are more active in cancer cells compared to non-cancer cells and operably linked to an open reading frame (ORF) and (b) a plurality of enhancers.

Embodiment 5: A recombinant polynucleotide comprising:

(a) a core promoter comprising a transcription start site (TSS), wherein the core promoter is derived from one or more cancer-responsive genes that are either expressed at a higher level or are more active in cancer cells compared to non-cancer cells and operably linked to an open reading frame (ORF), (b) a plurality of binding sites for one or more transcription factors (TFs), wherein said one or more TFs are expressed at higher levels or more active in cancer cells compared to non-cancer cells, and (c) a plurality of enhancers.

Embodiment 6: The recombinant polynucleotide of any one of embodiments 3-5, wherein said plurality of enhancers are derived from one or more cancer-responsive genes that are either expressed at a higher level or are more active in cancer cells compared to non-cancer cells.

Embodiment 7: The recombinant polynucleotide of any one of embodiments 3-6, wherein the plurality of enhancers are derived from two or more cancer-responsive genes that are either expressed at a higher level or are more active in cancer cells compared to non-cancer cells, wherein one of said plurality of enhancers comprises:

(i) a transcription regulatory element with at least 90% sequence homology to an enhancer consensus sequence of two or more homologous cancer-responsive genes, and/or (ii) a sequence capable of binding a transcription associated protein as determined by chromatin immunoprecipitation (ChIP) or an in vitro transfection reporter assay.

Embodiment 8: The recombinant polynucleotide of any one of embodiments 1-7, wherein said core promoter further comprises two or more promoter elements derived from two or more cancer-responsive genes that are either expressed at a higher level or are more active in cancer cells compared to non-cancer cells and operably linked to an open reading frame (ORF).

Embodiment 9: The recombinant polynucleotide of any one of embodiments 1-8, wherein said one or more cancer-responsive genes are derived from a human subject.

Embodiment 10: The recombinant polynucleotide of any one of embodiments 6-9, wherein: (a) said core promoter, and (b) said plurality of binding sites for one or more TFs or said plurality of enhancers derived from one or more cancer-responsive genes are not derived from a same cancer-responsive gene.

Embodiment 11: The recombinant polynucleotide of any one of embodiments 7-10, wherein said enhancer consensus sequence of two or more homologous cancer-responsive genes is a consensus sequence of an enhancer sequence derived from two or more cancer-responsive genes that has at least 90% sequence identity between two or more human cancer-responsive genes.

Embodiment 12: The recombinant polynucleotide of any one of embodiments 3-11, wherein at least one of the plurality of enhancers comprises a CpG island.

Embodiment 13: The recombinant polynucleotide of any one of embodiments 3-11, wherein at least one of the plurality of enhancers does not comprise a CpG island.

Embodiment 14: The recombinant polynucleotide of any one of embodiments 1-13, wherein said higher levels of TF expression in cancer cells compared to non-cancer cells is determined by chromatin immunoprecipitation (ChIP).

Embodiment 15: The recombinant polynucleotide of any one of embodiments 1-14, further comprising an open reading frame (ORF), wherein said core promoter is operably linked to said ORF.

Embodiment 16: The recombinant polynucleotide of any one of embodiments 1-15, wherein said plurality of binding sites for one or more TFs are 5' to said core promoter.

Embodiment 17: The recombinant polynucleotide of any one of embodiments 3-16, wherein said plurality of enhancers are 5' to said core promoter and 3' to said plurality of binding sites for one or more TFs, if present.

Embodiment 18: The recombinant polynucleotide of any one of embodiments 1-17, wherein said plurality of binding sites for one or more TFs comprises two or more binding sites for one TF, wherein each of the plurality of binding sites for one or more TFs is sequentially arranged at 5' to said core promoter in the recombinant polynucleotide.

Embodiment 19: The recombinant polynucleotide of any one of embodiments 1-17, wherein said plurality of binding sites for one or more TFs comprises two or more binding sites for two or more TFs, wherein each of the plurality of binding sites for one or more TFs is non-sequentially arranged at 5' to said core promoter in the recombinant polynucleotide.

Embodiment 20: The recombinant polynucleotide of any one of embodiments 1-19, wherein said plurality of binding sites for one or more TFs comprise a plurality of TRPS1, MNX1, TWIST1, ETV4, FOSL2, NFIC, EN2, TFDP1, PITX2, TCF7L1, VENTX, HOXB9, DLX1, MYCN, SIX4, TP63, SOX11, E2F8, TFDP1, SURV, TOXE, EN1, ZBTB7B, SP3, SIX2, XBP1, HIF-1A, CREB3L1, HSF-1, MTF1, NFE2L2, USF2, TP73, USF2, POU2F2, HOXA1, FOXO1, TFAP4, BACH1, E2F4, HOXC10, KLF11, FOXM1, E2F2, RUNX1, SOX4, RREB1, ETV4, HES6, ASCL1, TWIST1, FOXA3, PITX2, HOXB2, EN2, DLX4, GRHL1, FOXA, HIF, E2F6, FOSL1, NF-1, RFX6, EL4, or NFκB TF binding sites.

Embodiment 21: The recombinant polynucleotide of any one of embodiments 1-20, further comprising a spacer element comprising 1-10 nucleotides between each of plurality of binding sites for one or more TFs.

Embodiment 22: The recombinant polynucleotide of any one of embodiments 1-21, wherein said one or more cancer-responsive genes from which said core promoter is derived comprise TCF7, MNX1, HOXC10, TP53, CEACAM5, CEP55, FAM111B, CST1, BIRC5, FOS, TWIST1, E2F2, KIF20A, or ETV4.

Embodiment 23: The recombinant polynucleotide of any one of embodiments 1-22, wherein said one or more cancer-responsive genes from which said core promoter is derived comprise two or more of TCF7, MNX1, HOXC10, TPS3, CEACAM5, CEP55, FAM111B, CST1, BIRC5, FOS, TWIST1, E2F2, KIF20A, or ETV4.

Embodiment 24: The recombinant polynucleotide of any one of embodiments 1-22, wherein said one or more cancer-responsive genes from which said core promoter is derived comprise TCF7 and HOXC10.

Embodiment 25: The recombinant polynucleotide of any one of embodiments 1-22, wherein said one or more cancer-responsive genes from which said core promoter is derived comprise TP53 and CEP55.

Embodiment 26: The recombinant polynucleotide of any one of embodiments 1-22, wherein said one or more cancer-responsive genes from which said core promoter is derived comprise FAM111B and KIF20A.

Embodiment 27: The recombinant polynucleotide of any one of embodiments 1-22, wherein said one or more cancer-responsive genes from which said core promoter is derived comprise BIRC5 and E2F2.

Embodiment 28: The recombinant polynucleotide of any one of embodiments 1-22, wherein said one or more cancer-responsive genes from which said core promoter is derived comprise CEACAM5 and TWIST1.

Embodiment 29: The recombinant polynucleotide of any one of embodiments 1-28, wherein said core promoter comprises a region from about −300 bp to +100 bp relative to said TSS.

Embodiment 30: The recombinant polynucleotide of any one of embodiments 3-29, wherein said plurality of enhancers comprises at least two enhancer sequences, wherein each of said at least two enhancer sequences comprises (i) the same enhancer sequences, (ii) different enhancer sequences, or (iii) a combination thereof.

Embodiment 31: The recombinant polynucleotide of embodiment 30, wherein each of said at least two enhancer sequences is sequentially arranged at 5' to said core promoter in the recombinant polynucleotide.

Embodiment 32: The recombinant polynucleotide of embodiment 30, wherein each of said at least two enhancer sequences is sequentially arranged at 5' to said core promoter and at 3' to said plurality of binding sites of one or more TFs, if present, in the recombinant polynucleotide.

Embodiment 33: The recombinant polynucleotide of embodiment 30, wherein each of said at least two enhancer sequences comprises (ii), wherein each of said plurality of enhancers comprising different enhancer sequences is non-sequentially arranged at 5' to said core promoter in the recombinant polynucleotide.

Embodiment 34: The recombinant polynucleotide of embodiment 30, wherein each of said at least two enhancer sequences comprises (ii), wherein each of said plurality of enhancers is non-sequentially arranged at 5' to said core promoter and at 3' to said plurality of binding sites for one or more TFs, if present, in the recombinant polynucleotide.

Embodiment 35: The recombinant polynucleotide of embodiment 30, wherein each of said at least two enhancer sequences comprises (iii), wherein each of said plurality of enhancers comprising a combination of the same and different enhancer sequences is non-sequentially arranged at 5' to said core promoter in the recombinant polynucleotide.

Embodiment 36: The recombinant polynucleotide of embodiment 30, wherein each of said at least two enhancer sequences comprises (iii), wherein each of said plurality of enhancers comprising a combination of the same and different enhancer sequences is non-sequentially arranged at 5' to said core promoter and at 3' to said plurality of binding sites for one or more TFs, if present, in the recombinant polynucleotide.

Embodiment 37: The recombinant polynucleotide of any one of embodiments 3-36, wherein said plurality of enhancers comprises at least two EBS, C/EBP, ARE, DRE, NFκB, GC-box, UN5CL, BOP1, RTN4RL2, ARNTL2, AGR2, LHX2, TRNP1, MU5AC, or DOK4 enhancer sequences.

Embodiment 38: The recombinant polynucleotide of any one of embodiments 1-37, wherein expression of said ORF is increased when said recombinant polynucleotide is introduced to cancer cells compared to non-cancer cells.

Embodiment 39: The recombinant polynucleotide of any one of embodiments 1-37, wherein expression of said ORF is increased in a first plurality of cancer cells when said recombinant polynucleotide is introduced to said first plurality of cancer cells compared to a second plurality of cancer cells, wherein said first plurality of cancer cells and said second plurality of cancer cells are different types of cancer cells.

Embodiment 40: The recombinant polynucleotide of embodiment 38 or 39, wherein said cancer cells comprise malignant cancer cells.

Embodiment 41: The recombinant polynucleotide of any one of embodiments 38-40, wherein said cancer cells comprise lung cancer cells, colorectal cancer cells, breast cancer cells, or hepatocellular carcinoma cells.

Embodiment 42: The recombinant polynucleotide of any one of embodiments 38-40, wherein said cancer cells comprise cells associated with colorectal cancer, hepatocellular carcinoma, lung cancer, liver cancer, breast cancer, prostate cancer, cervix cancer, uterus cancer, pancreas cancer, kidney cancer, stomach cancer, bladder cancer, ovary cancer, brain cancer, head and neck cancer, eye cancer, mouth cancer, throat cancer, esophagus cancer, chest cancer, bone cancer, rectum or other gastrointestinal tract organ cancer, spleen cancer, skeletal muscle cancer, subcutaneous tissue cancer, testicles or other reproductive organ cancer, skin cancer, thyroid cancer, blood cancer, or lymph nodes cancer.

Embodiment 43: The recombinant polynucleotide of embodiment 42, wherein said cancer cells comprise cells associated with two or more cancers comprising colorectal cancer, hepatocellular carcinoma, lung cancer, liver cancer, breast cancer, prostate cancer, cervix cancer, uterus cancer, pancreas cancer, kidney cancer, stomach cancer, bladder cancer, ovary cancer, brain cancer, head and neck cancer, eye cancer, mouth cancer, throat cancer, esophagus cancer, chest cancer, bone cancer, rectum or other gastrointestinal tract organ cancer, spleen cancer, skeletal muscle cancer, subcutaneous tissue cancer, testicles or other reproductive organ cancer, skin cancer, thyroid cancer, blood cancer, or lymph nodes cancer.

Embodiment 44: The recombinant polynucleotide of any one of embodiments 3-43, wherein said core promoter, said plurality of binding sites for one or more transcription factors (TFs), said plurality of enhancers, or said recombinant polynucleotide comprises a sequence from Table 1A, Table 1B, or Table 1C.

Embodiment 45: A recombinant polynucleotide comprising any of the sequences from Table 1A, Table 1B, or Table 1C.

Embodiment 46: A recombinant polynucleotide comprising a human alpha-fetoprotein (AFP) promoter sequence comprising a plurality of HNF-1A TF binding sites, wherein each HNF-1A binding site comprises the sequence 5'-GT-TAATTATTAAC-3' (SEQ ID NO: 128).

Embodiment 47: A vector comprising the recombinant polynucleotide of any one of embodiments 1-46.

Embodiment 48: A pharmaceutical composition comprising the recombinant polynucleotide of any one of embodiments 1-46 or the vector of embodiment 47 and a pharmaceutically acceptable excipient, carrier, or diluents.

Embodiment 49: A lipid nanoparticle (LNP) comprising the recombinant polynucleotide of any one of embodiments 1-46, the vector of embodiment 47, or the pharmaceutical composition of embodiment 48.

Embodiment 50: A cell comprising the recombinant polynucleotide of any one of embodiments 1-46, the vector of embodiment 47, the pharmaceutical composition of embodiment 48, or the LNP of embodiment 49.

Embodiment 51: A method of selectively expressing a reporter protein in a cancer or tumor cell, comprising contacting said tumor cell the recombinant polynucleotide according to any one of embodiments 1-46, the vector of embodiment 47, the pharmaceutical composition of embodiment 48, or the LNP of embodiment 49, wherein the recombinant polynucleotide further comprises an open reading frame (ORF) encoding said reporter protein, wherein said ORF is operatively linked to said synthetic promoter.

Embodiment 52: A method comprising:

(a) administering to a subject the pharmaceutical composition of embodiment 48; or a composition comprising the recombinant polynucleotide of any one of embodiments 1-46, the vector of embodiment 47, or the LNP of embodiment 49; wherein the recombinant polynucleotide further comprises an open reading frame (ORF) encoding a reporter protein, wherein said ORF is operatively linked to a synthetic promoter in said recombinant polynucleotide, and (b) detecting said reporter protein, wherein said pharmaceutical composition or said composition induces expression of said reporter protein preferentially in diseased cells in said subject compared to in non-disease cells, and wherein a relative ratio of said reporter protein expressed in said diseased cells over said non-diseased cells is greater than 1.0.

Embodiment 53: The method of embodiment 52, wherein said relative ratio of said reporter protein expressed in said diseased cells over said non-diseased cells is greater than 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, or about 15.0, 20.0, 25.0, 30.0, 35.0, 40.0, 45.0, 50.0, 55.0, 60.0, 65.0, 70.0, 75.0, 80.0, 85.0, 90.0, 95.0, or about 100.0.

Embodiment 54: A method for treating a subject having or suspected of having a disease, comprising administering to said subject the pharmaceutical composition of embodiment 48; or a composition comprising the recombinant polynucleotide of any one of embodiments 1-46, the vector of embodiment 47, or the LNP of embodiment 49;

wherein the recombinant polynucleotide further comprises an open reading frame (ORF) encoding a therapeutic protein, wherein said ORF is operatively linked to a synthetic promoter in said recombinant polynucleotide, wherein said pharmaceutical composition or said composition induces expression of said therapeutic protein preferentially in diseased cells in said subject compared to in non-disease cells, and wherein a relative ratio of said therapeutic protein expressed in said diseased cells over said non-diseased cells is greater than 1.0.

Embodiment 55: The method of any one of embodiments 52-54, wherein said diseased cells comprise a cancer or tumor cell.

Embodiment 56: The method of embodiment 51 or 55, wherein said cancer or tumor cell is associated with colorectal cancer (CRC), hepatocellular carcinoma, lung cancer, liver cancer, breast cancer, prostate cancer, cervix cancer, uterus cancer, pancreas cancer, kidney cancer, stomach cancer, bladder cancer, ovary cancer, brain cancer, head and neck cancer, eye cancer, mouth cancer, throat cancer, esophagus cancer, chest cancer, bone cancer, rectum or other gastrointestinal tract organ cancer, spleen cancer, skeletal muscle cancer, subcutaneous tissue cancer, testicles or other reproductive organ cancer, skin cancer, thyroid cancer, blood cancer, or lymph nodes cancer.

Embodiment 57: A method comprising:

(a) administering to a subject the pharmaceutical composition of embodiment 48; or a composition comprising the recombinant polynucleotide of any one of embodiments 1-46, the vector of embodiment 47, or the LNP of embodiment 49; wherein said recombinant polynucleotide further comprises an open reading frame (ORF) encoding a reporter protein, wherein said ORF is operatively linked to a synthetic promoter in said recombinant polynucleotide, and (b) localizing a tumor or an absence thereof in a body of said subject via expression of said reporter protein using an imaging technique performed on said body of said subject.

Embodiment 58: A method comprising:

(a) introducing to a subject suspected of having a cancer via intravenous administration the pharmaceutical composition of embodiment 48; or a composition comprising the recombinant polynucleotide of any one of embodiments 1-46, the vector of embodiment 47, or the LNP of embodiment 49; wherein said recombinant polynucleotide further comprises an open reading frame (ORF) encoding a reporter protein, wherein said ORF is operatively linked to a synthetic promoter in said recombinant polynucleotide, and (b) detecting said reporter protein from said subject.

Embodiment 59: A method comprising:

(a) introducing to a subject suspected of having a cancer via intravenous administration a plurality of recombinant polynucleotides, wherein: said plurality of recombinant polynucleotides comprises a plurality of different promoters of genes overexpressed in a tumor cell versus a normal tissue or functional fragments thereof operably linked to genes encoding reporter proteins, wherein said plurality of different promoters of genes overexpressed in said tumor cell versus said normal tissue drive expression of said corresponding reporter proteins in a cell affected by said cancer, wherein said DNA molecules are selected from the group consisting of nanoplasmids and linear double-stranded DNA molecules; and (b) detecting said reporter proteins from said subject.

What is claimed is:

1. A method for increasing expression of a gene in a cancer cell as compared with a non-cancer cell, the method comprising, administering a recombinant polynucleotide to a subject with cancer, wherein said recombinant polynucleotide comprises:

a) one or more synthetic response elements comprising one or more enhancers and a plurality of transcription factor binding sites;

b) a core promoter operably linked to an open reading frame (ORF) comprising said gene, wherein said core promoter comprises a promoter element obtained from one or more cancer-responsive genes; and c) a transcription start site (TSS) upstream of said ORF, wherein said one or more synthetic response elements and said core promoter increase transcription of said gene in said cancer cell of said subject as compared with a non-cancer cell.

2. The method of claim 1, wherein said one or more cancer-responsive genes has at least a 10-fold increase in expression in cancer cells compared to non-cancer cells.

3. The method of claim 1, wherein said gene encodes a therapeutic protein.

4. The method of claim 1, wherein said gene encodes a biomarker protein.

5. The method of claim 1, wherein said gene is transcribed at a higher level in said cancer cell compared to said non-cancer cell as determined by chromatin immunoprecipitation (ChIP).

6. The method of claim 1, wherein said one or more cancer-responsive genes is a *Homo sapiens* cancer-responsive gene.

7. The method of claim 1, wherein said recombinant polynucleotide further comprises a spacer element disposed between two enhancers of said one or more enhancers, wherein said spacer element comprises 1-20 contiguous nucleotides.

8. The method of claim 1, wherein said one or more cancer-responsive genes comprises FAM111B or KIF20A.

9. The method of claim 1, wherein said one or more cancer-responsive genes comprises KIF20A.

10. The method of claim 1, wherein said one or more cancer-responsive genes comprises FAM111B.

11. The method of claim 1, wherein said core promoter comprises two or more promoter elements, wherein at least two promoter elements of said two or more promoter elements are obtained from different cancer-responsive genes of said one or more cancer-responsive genes.

12. The method of claim 1, wherein said core promoter comprises a first promoter element and a second promoter element, wherein said first promoter element is obtained from FAM111B, and said second promoter element is obtained from KIF20A.

13. The method of claim 1, wherein said recombinant polynucleotide is a circular nucleic acid molecule.

14. The method of claim 1, wherein said administering is systemic administration.

15. The method of claim 1, wherein said administering is regional administration.

16. The method of claim 1, wherein said administering is intravenous (i.v.) administration.

17. A method comprising: administering a recombinant polynucleotide to a subject, wherein said recombinant polynucleotide comprises:

a) one or more synthetic response elements comprising one or more enhancers and a plurality of transcription factor binding sites, wherein said one or more enhancers comprises a sequence having at least 80% sequence identity to at least one of:

i. bases 1-11, 15-64, and 74-123 of SEQ ID NO: 386,
ii. bases 1-15, 26-40, 51-65, 76-90, 101-115, and 126-140 of SEQ ID NO: 388, or
iii. bases 1-14, 17-26, 29-37, 40-49, and 52-64 of SEQ ID NO: 384, or a reverse complement thereof;
b) a core promoter operably linked to an open reading frame (ORF) comprising a gene, wherein said core promoter comprises a promoter element obtained from one or more cancer-responsive genes; and
c) a transcription start site (TSS) upstream of said ORF.

18. The method of claim 17, wherein said administering is systemic administration.

19. The method of claim 17, wherein said administering is regional administration.

20. The method of claim 17, wherein said administering is intravenous (i.v.) administration.

21. The method of claim 17, wherein said recombinant polynucleotide is a circular nucleic acid molecule.

22. The method of claim 17, wherein said gene is expressed at a higher level in a cancer cell of said subject compared to a non-cancer cell as determined by chromatin immunoprecipitation (ChIP).

23. The method of claim 17, wherein said core promoter comprises two or more promoter elements, wherein at least two promoter elements of said two or more promoter elements are obtained from different cancer-responsive genes of said one or more cancer-responsive genes.

24. The method of claim 17, wherein said core promoter comprises a first promoter element and a second promoter element, wherein said first promoter element is obtained from FAM111B, and said second promoter element is obtained from KIF20A.

25. The method of claim 17, wherein said gene encodes a therapeutic protein.

26. The method of claim 17, wherein said one or more synthetic response elements and said core promoter increase transcription of said gene in a cancer cell of said subject as compared with a non-cancer cell.

27. The method of claim 26, wherein said increase in said transcription is a 10-fold increase.

28. The method of claim 17, wherein said sequence is at least 95% identical to at least one of:
i. bases 1-11, 15-64, and 74-123 of SEQ ID NO: 386,
ii. bases 1-15, 26-40, 51-65, 76-90, 101-115, and 126-140 of SEQ ID NO: 388, or
iii. bases 1-14, 17-26, 29-37, 40-49, and 52-64 of SEQ ID NO: 384, or a reverse 29 complement thereof.

29. The method of claim 17, wherein said sequence comprises SEQ ID NOs: 386, 388, or 384.

30. A method comprising administering a recombinant polynucleotide to a subject, wherein said recombinant polynucleotide comprises:
(a) a sequence that is at least 85% identical to bases 1-123, 136-275, 294-371, 378-443, and 455-581 of SEQ ID NO: 556 encoding a synthetic response sensor (SRS); and (b) an open reading frame (ORF) comprising a gene, wherein said ORF is operably linked to said SRS.

31. The method of claim 30, wherein said recombinant polynucleotide is a circular nucleic acid molecule.

32. The method of claim 30, wherein said administering is systemic administration.

33. The method of claim 30, wherein said administering is regional administration.

34. The method of claim 30, wherein said administering is intravenous (i.v.) administration.

35. The method of claim 30, wherein said gene is transcribed at a higher level in a cancer cell of said subject compared to a non-cancer cell as determined by chromatin immunoprecipitation (ChIP).

36. The method of claim 30, wherein said sequence is at least 95% identical to bases 1-123, 136-275, 294-371, 378-443, and 455-581 of SEQ ID NO: 556.

37. The method of claim 30, wherein said sequence comprises SEQ ID NOs: 445, 447, 453, 454, 468, 470, or 556.

38. The method of claim 30, wherein said sequence comprises SEQ ID NO: 556.

39. A method comprising administering a recombinant polynucleotide to a subject, wherein said recombinant polynucleotide comprises:
(a) a sequence that is at least 85% identical to bases 1-123, 136-275, 294-371, 378-443, and 455-705 of SEQ ID NO: 557 encoding a synthetic response sensor (SRS); and
(b) an open reading frame (ORF) comprising a gene, wherein said ORF is operably linked to said SRS.

40. The method of claim 39, wherein said recombinant polynucleotide is a circular nucleic acid molecule.

41. The method of claim 36, wherein said administering is systemic administration.

42. The method of claim 39, wherein said administering is regional administration.

43. The method of claim 39, wherein said administering is intravenous (i.v.) administration.

44. The method of claim 39, wherein said gene is transcribed at a higher level in a cancer cell of said subject compared to a non-cancer cell as determined by chromatin immunoprecipitation (ChIP).

45. The method of claim 39, wherein said sequence is at least 95% identical to bases 1-123, 136-275, 294-371, 378-443, and 455-705 of SEQ ID NO: 557.

46. The method of claim 39, wherein said sequence comprises 445, 447, 450, 452, 453, 454, 458, 468, 470, 475, or 556.

47. The method of claim 39, wherein said sequence comprises SEQ ID NO: 557.

* * * * *